United States Patent
Zhang et al.

(10) Patent No.: US 11,013,757 B2
(45) Date of Patent: May 25, 2021

(54) OLIGONUCLEOTIDES, COMPOSITIONS AND METHODS THEREOF

(71) Applicant: WAVE LIFE SCIENCES LTD., Singapore (SG)

(72) Inventors: Jason Jingxin Zhang, Walpole, MA (US); Naoki Iwamoto, Brighton, MA (US); Christopher J. Francis, Arlington, MA (US); Chandra Vargeese, Schwenksville, PA (US); David Charles Donnell Butler, Medford, MA (US); Sethumadhavan Divakaramenon, Lexington, MA (US); Genliang Lu, Winchester, MA (US); Subramanian Marappan, Acton, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 14 days.

(21) Appl. No.: 16/305,937

(22) PCT Filed: Jun. 2, 2017

(86) PCT No.: PCT/US2017/035837
§ 371 (c)(1),
(2) Date: Nov. 30, 2018

(87) PCT Pub. No.: WO2017/210647
PCT Pub. Date: Dec. 7, 2017

(65) Prior Publication Data
US 2019/0209604 A1 Jul. 11, 2019

Related U.S. Application Data

(60) Provisional application No. 62/405,816, filed on Oct. 7, 2016, provisional application No. 62/345,709, filed on Jun. 3, 2016.

(51) Int. Cl.
*A61K 31/7125* (2006.01)
*C12N 15/117* (2010.01)
*A61K 31/7088* (2006.01)
*A61P 21/00* (2006.01)

(52) U.S. Cl.
CPC ...... *A61K 31/7125* (2013.01); *A61K 31/7088* (2013.01); *A61P 21/00* (2018.01); *C12N 15/117* (2013.01); *C12N 2310/17* (2013.01); *C12N 2310/31* (2013.01); *C12N 2310/315* (2013.01); *C12N 2310/351* (2013.01); *C12N 2310/3515* (2013.01)

(58) Field of Classification Search
None
See application file for complete search history.

(56) References Cited

U.S. PATENT DOCUMENTS

| | | | |
|---|---|---|---|
| 5,883,237 A  * | 3/1999 | Stec | C07F 9/6564 536/23.1 |
| 6,440,943 B1 * | 8/2002 | Cook | C07H 19/04 435/7.2 |
| 6,867,294 B1 | 3/2005 | Sanghvi et al. | |
| 8,470,987 B2 | 6/2013 | Wada et al. | |
| 8,729,036 B2 | 5/2014 | Zamore et al. | |
| 8,822,671 B2 | 9/2014 | Shimizu et al. | |
| 8,859,755 B2 | 10/2014 | Wada et al. | |
| 9,394,333 B2 | 7/2016 | Wada et al. | |
| 9,476,044 B2 | 10/2016 | Tuschl et al. | |
| 9,598,458 B2 | 3/2017 | Shimizu et al. | |
| 9,605,019 B2 | 3/2017 | Verdine et al. | |

(Continued)

FOREIGN PATENT DOCUMENTS

| | | |
|---|---|---|
| EP | 1220684 B1 | 7/2006 |
| JP | 2011-184318 A | 9/2011 |

(Continued)

OTHER PUBLICATIONS

U.S. Appl. No. 16/618,003, filed Nov. 27, 2019, Vargeese et al.

(Continued)

*Primary Examiner* — Tracy Vivlemore
(74) *Attorney, Agent, or Firm* — Choate, Hall & Stewart LLP; Brenda Herschbach Jarrell; Xiaodong Li

(57) ABSTRACT

The present disclosure pertains to the recognition that immune responses mediated by CpG oligonucleotides can be affected by the stereochemistry of modified internucleotidic linkages such as phosphorothioates. In some embodiments, the present disclosure relates to chirally controlled CpG oligonucleotide compositions comprising CpG oligonucleotides comprising multiple modified internucleotidic linkages such as phosphorothioate linkages, wherein the oligonucleotides comprise one or more CpG region motifs having defined stereochemistry patterns of chiral internucleotidic linkages. In some embodiments, CpG oligonucleotides comprising one or more CpG region motifs are capable of agonizing an immune response. In some embodiments, CpG oligonucleotides comprising one or more CpG region motifs are antagonistic. Methods for making and using chirally controlled CpG oligonucleotide compositions are also described. In some embodiments, no immune modulation is desired, and the present disclosure provides methods of identifying chirally controlled oligonucleotide compositions which have decreased immune modulation.

20 Claims, 26 Drawing Sheets
Specification includes a Sequence Listing.

(56) References Cited

U.S. PATENT DOCUMENTS

| | | | |
|---|---|---|---|
| 9,617,547 B2 | 4/2017 | Gemba | |
| 9,695,211 B2 | 7/2017 | Wada et al. | |
| 9,744,183 B2 | 8/2017 | Verdine et al. | |
| 9,982,257 B2 | 5/2018 | Butler et al. | |
| 10,144,933 B2 | 12/2018 | Gemba et al. | |
| 10,149,905 B2 | 12/2018 | Gemba et al. | |
| 10,160,969 B2 | 12/2018 | Meena et al. | |
| 10,167,309 B2 | 1/2019 | Shimizu et al. | |
| 10,280,192 B2 | 5/2019 | Verdine et al. | |
| 10,307,434 B2 | 6/2019 | Verdine et al. | |
| 10,322,173 B2 | 6/2019 | Gemba et al. | |
| 10,329,318 B2 | 6/2019 | Wada et al. | |
| 10,428,019 B2 | 10/2019 | Wada et al. | |
| 10,450,568 B2 | 10/2019 | Butler et al. | |
| 10,479,995 B2 | 11/2019 | Vargeese et al. | |
| 10,590,413 B2 | 3/2020 | Butler et al. | |
| 10,696,711 B2 | 6/2020 | Shimizu et al. | |
| 10,724,035 B2 | 7/2020 | Vargeese et al. | |
| 2005/0059619 A1* | 3/2005 | Krieg | C12N 15/117 514/44 A |
| 2015/0211006 A1* | 7/2015 | Butler | C12N 15/113 514/44 A |
| 2017/0029457 A1 | 2/2017 | Verdine et al. | |
| 2018/0216107 A1 | 8/2018 | Frank-Kamenetsky et al. | |
| 2019/0077817 A1 | 3/2019 | Butler et al. | |
| 2019/0106696 A1 | 4/2019 | Meena et al. | |
| 2019/0127733 A1 | 5/2019 | Butler et al. | |
| 2019/0249173 A1 | 8/2019 | Vargeese et al. | |
| 2019/0264267 A1 | 8/2019 | Yang et al. | |
| 2019/0375774 A1 | 12/2019 | Butler et al. | |
| 2019/0390197 A1 | 12/2019 | Butler et al. | |
| 2020/0080083 A1 | 3/2020 | Vargeese et al. | |
| 2020/0157545 A1 | 5/2020 | Vargeese et al. | |
| 2020/0190515 A1 | 6/2020 | Vargeese et al. | |
| 2020/0231620 A1 | 7/2020 | Bowman et al. | |

FOREIGN PATENT DOCUMENTS

| | | |
|---|---|---|
| WO | WO-00/06588 A1 | 2/2000 |
| WO | WO-2004/007718 A2 | 1/2004 |
| WO | WO-2004/016805 A2 | 2/2004 |
| WO | WO-2005/014609 A2 | 2/2005 |
| WO | WO-2005/023828 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2010/064146 A2 | 6/2010 |
| WO | WO-2010/067262 A1 | 6/2010 |
| WO | WO-2011/005761 A1 | 1/2011 |
| WO | WO-2011/034072 A1 | 3/2011 |
| WO | WO-2011/108682 A1 | 9/2011 |
| WO | WO-2012/039448 A1 | 3/2012 |
| WO | WO-2012/073857 A1 | 6/2012 |
| WO | WO-2013/012758 A1 | 1/2013 |
| WO | WO-2014/010250 A1 | 1/2014 |
| WO | WO-2014/010718 A1 | 1/2014 |
| WO | WO-2014/012081 A2 | 1/2014 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2017/015555 A1 | 1/2017 |
| WO | WO-2017/015575 A1 | 1/2017 |
| WO | WO-2017/062862 A2 | 4/2017 |
| WO | WO-2017/160741 A1 | 9/2017 |
| WO | WO-2017/192664 A1 | 11/2017 |
| WO | WO-2017/192679 A1 | 11/2017 |
| WO | WO-2017/210647 A1 | 12/2017 |
| WO | WO-2018/022473 A1 | 2/2018 |
| WO | WO-2018/067973 A1 | 4/2018 |
| WO | WO-2018/098264 A1 | 5/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/032607 A1 | 2/2019 |
| WO | WO-2019/032612 A1 | 2/2019 |
| WO | WO-2019/055951 A1 | 3/2019 |
| WO | WO-2019/075357 A1 | 4/2019 |
| WO | WO-2019/200185 A1 | 10/2019 |
| WO | WO-2019/217784 A1 | 11/2019 |
| WO | WO-2020/118246 A1 | 6/2020 |
| WO | WO-2020/160336 A1 | 8/2020 |

OTHER PUBLICATIONS

U.S. Appl. No. 16/624,896, filed Dec. 19, 2019, Butler et al.
U.S. Appl. No. 16/636,900, filed Feb. 5, 2020, Dodart et al.
U.S. Appl. No. 16/636,902, filed Feb. 5, 2020, Vargeese et al.
U.S. Appl. No. 16/717,986, filed Dec. 17, 2019, Butler et al.
U.S. Appl. No. 16/755,544, filed Apr. 10, 2020, Zhang et al.
U.S. Appl. No. 16/782,021, filed Feb. 4, 2020, Frank-Kamenetsky et al.
U.S. Appl. No. 16/869,126, filed May 7, 2020, Vargeese et al.
U.S. Appl. No. 16/878,461, filed May 19, 2020, Shimizu et al.
Ballas, Z.K. et al., Induction of NK Activity in Murine and Human Cells by CpG Motifs in Oligodeoxynucleotides and Bacterial DNA, J. Immunoll., 57: 1840-1845 (1996).
Bartz, H. et al., Poly-guanosine strings improve cellular uptake and stimulatory activity of phosphodiester CpG oligonucleotides in human leukocytes, Vaccine, 23: 148-155 (2004).
Bode, C. et al. CpG DNA as a vaccine adjuvant, Expert Rev. Vaccines, 10(4): 499-511 (2011).
Grajkowski, A. et al., Thermolytic CpG-containing DNA oligonucleotides as potential immunotherapeutic prodrugs, Nucleic Acids Research, 33(11):3550-3560 (2005).
Hanagata, N., Structure-dependent immunostimulatory effect of CpG oligodeoxynucleoties and their delivery system, Int. J. Nanomedicine, 7: 2181-95 (2012).
Hartmann, G. et al., Delineation of a CpG Phosphorothioate Oligodeoxynucleotide for Activating Primate Immune Responses In Vitro and In Vivo, The Journal of Immunology, 164(3): 1617-1624 (2000).
International Search Report for PCT/US2017/035837, 4 pages (dated Aug. 24, 2017).
Kim, D. et al., Immunostimulation and anti-DNA antibody production by backbone modified CpG-DNA, Biochemical and Biophysical Research Communications, 379(2): 362-367 (2009).
Krieg, A.M. et al., CpG motifs in bacterial DNA trigger direct B-cell activation, Nature, 374: 546-549 (1995).
Krieg, A.M. et al., P-Chirality-Dependent Immune Activiation by Phosphorothioate CpG Oligodeoxynucleotides, Oligonucleotides, 13:491-499 (2003).
Krieg, A.M., Development of TLR9 agonists for cancer therapy, The Journal of Clinical Investigation, 117(5): 1184-1194 (2007).
Krieg, A.M., Therapeutic potential of Toll-like receptor 9 activation, Nature Reviews, 471-484 (2006).
Kuramoto, Y. et al., Mannosylated cationic liposomes/CpG DNA complex for the treatment of hepatic metastasis after intravenous administration in mice, Journal of Pharmaceutical Science, 98(3): 1193-1197 (2009).
Kwon, H-J. et al., NF-kappaB-dependent regulation of tumor necrosis factor-alpha gene expression by CpG-oligodeoxynucleotides, Biochem. Biophys. Res. Commun., 311(1): 129-138 (2003).
Lee, K-W et al., CG sequence- and phosphorothioate backbone modification-dependent activation of the NF-κB-responsive gene expression by CpG-oligodeoxynucleotides in human RPMI 8226 B cells, Molecular Immonulogy, 41: 955-964 (2004).
Liu, S. et al., Evaluation of protective effect of multi-epitope DNA vaccine encoding six antigen segments of Toxoplasma gondii in mice Parasitol Res, 105:267-274 (2009).
Molenkamp, B.G. et al., Local Administration of PF-3512676 CpG-B Instigates Tumor-Specific CD8+ T-Cell Reactivity in Melanoma Patients , Clin. Cancer Res., 14(14): 4532-4542 (2008).

(56) References Cited

OTHER PUBLICATIONS

O'Connell, D. et al., Calcium-dependent oligonucleotide antagonists specific for L-selectin, Proc. Natl. Acad. Sci. USA, 93: 5883-5887 (1996).

Pontarollo, R.A. et al., Monocytes are required for optimum in vitro stimulation of bovine peripheral blood mononuclear cells by non-methylated CpG motifs, Veterinary Immunology and Immunopathology, 84(1-2): 43-59 (2002).

Robinson, D.S. et al., Predominant TH2-Like Bronchoalveolar T-Lymphocyte Population in Atopic Asthma, The New England Journal of Medicine, 326: 298-304 (1992).

Senn, J.J. et al., Non-CpG-Containing Antisense 2'-Methoxyethyl Oligonucleotides Activate a Proinflammatory Response Independent of Toll-Like Receptor 9 or Myeloid DifferentiationFactor 88, The Journal of Pharmacology and Experimental Therapeutics, 314: 972-979 (2005).

Tam, Immunostimulatory oligonucleotides: ready for immunotherapy prime time!, Journal of Hematotherapy & Stem Cell Research, 12(5): 467-471 (2003).

Tulic, M.K. et al Amb a 1-immunostimulatory oligodeoxynucleotide conjugate immunotherapy decreases the nasal inflammatory response, J. Allergy Clin. Immunol., 235-241 (2004).

Weiner, G. J. et al., Immunostimulatory oligodeoxynucleotides containing the CpG motif are effective as immune adjuvants in tumor antigen immunization, 94(20): 10833-10837 (1997).

Written Opinion for PCT/US2017/035837, 15 pages (dated Aug. 24, 2017).

Yamamoto, S. et al., Unique Palindromic Sequences in Synthetic Oligonucleotides are Required to Induce INF and Augment INF-Mediated Natural Killer Activity, J. Immunol., 148(12): 4072-4076 (1992).

Yanai, H. et al., Suppression of immune responses by nonimmunogenic oligodeoxynucleotides with high affinity for high-mobility group box proteins (HMGBs), PNAS Early Edition, 1-6 (2011).

Yasuda, K. et al., CpG motif-independent activation of TLR9 upon endosomal translocation of "natural" phosphodiester DNA, European Journal of Immunology, 431-436 (2006).

Yu, D. et al., Accessible 5'-end of CpGcontaining phosphorothioate oligodeoxynucleotides is essential for immunostimulatory activity, Bioorganic & Medicinal Chemistry Letters, 10: 2585-2588 (2000).

Zhang, J. et al., Potency, stability, and immune system effects of WVE-210201, an investigational stereopure oligonucleotide for the treatment of Duchenne muscular dystrophy. Poster presented at: Action Duchenne 16th International Conference, Birmingham, UK (Nov. 9-11, 2017).

Zon, Automated synthesis of phosphorus-sulfur analogs of nucleic acids-25 years on: potential therapeutic agents and proven utility in biotechnology, New J. Chem., 34(5): 795-804 (2010).

\* cited by examiner

OLIGONUCLEOTIDES, COMPOSITIONS AND METHODS THEREOF

CROSS-REFERENCE TO RELATED APPLICATIONS

This application is a U.S. National Stage Application of PCT Application No. PCT/US2017/035837, filed Jun. 2, 2017 and published as WO 2017/210647, which claims priority to United States Provisional Application Nos. 62/345,709, filed Jun. 3, 2016, and 62/405,816, filed Oct. 7, 2016, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Jun. 29, 2017, is named SL.txt and is 458,011 bytes in size.

BACKGROUND

Oligonucleotides are valuable therapeutic, diagnostic and analytical agents, with many important applications.

SUMMARY

Among other things, the present disclosure encompasses the recognition that oligonucleotides, including those comprising any of various CpG region motifs, are useful and valuable as immunomodulatory agents. The present disclosure also encompasses, inter alia, methods of identifying oligonucleotides and compositions thereof which have improved immunomodulatory activity, stability, utility and/or effectiveness.

In some embodiments, the present disclosure encompasses the recognition that structural elements of oligonucleotides, such as base sequence, chemical modifications (e.g., modifications of sugar, base, and/or internucleotidic linkages, and patterns thereof), and/or stereochemistry (e.g., stereochemistry of backbone chiral centers (chiral internucleotidic linkages), and/or patterns thereof), can have significant impact on properties, e.g., activity, stability, etc., of oligonucleotides. In some embodiments, the present disclosure demonstrates that oligonucleotide compositions comprising oligonucleotides with controlled structural elements, e.g., controlled chemical modification and/or controlled backbone stereochemistry patterns, provide unexpected properties, including but not limited to those described herein. In some embodiments, the present disclosure provides methods for modulating properties (e.g., activity, stability, etc.) of oligonucleotides through chemical modifications (e.g., chemical modification of bases, sugars, and internucleotidic linkages) and/or stereochemistry (e.g., stereochemistry of chiral internucleotidic linkages and patterns thereof). In some embodiments, the present disclosure provides chirally controlled oligonucleotide compositions which provide improved properties, e.g., enhanced TLR9 agonist activities, reduced TLR9 agonist activities, enhanced TLR9 antagonist activities, reduced TLR9 antagonist activities, etc. when compared to a reference oligonucleotide composition, e.g., a chirally uncontrolled (stereorandom) oligonucleotide composition.

In some embodiments, the present disclosure encompasses the recognition that conjugation with lipids, which incorporates lipid moieties into oligonucleotides, is unexpectedly effective in improving oligonucleotide properties, e.g., their TLR9-related activities, delivery, pharmacokinetics properties, etc. For example, in some embodiments, the present disclosure surprisingly demonstrated that oligonucleotides comprising lipid moieties have unexpected high hTLR9 antagonist activities compared to oligonucleotides absent the lipid moieties. In some embodiments, oligonucleotides comprising lipid moieties demonstrate not only improved hTLR9 antagonist activities, but also surprisingly improved other properties, e.g., activities toward their complementary nucleic acid targets, improved delivery, pharmacokinetic properties, etc. In some embodiments, lipid conjugation is utilized together with other structural elements, such as base sequence, chemical modifications (e.g., sugar modifications, base modifications, internucleotidic linkage modifications), and/or stereochemistry, to improve oligonucleotide properties, e.g., TLR9-related properties. In some embodiments, a provided oligonucleotide comprises a lipid moiety, and a base sequence, pattern of chemical modifications, pattern of backbone linkages, pattern or backbone chiral centers, and/or pattern of backbone phosphorus modifications described herein, for example, those described for CpG oligonucleotides.

In some embodiments, the present disclosure encompasses the recognition that immune responses mediated by CpG oligonucleotides (oligonucleotides comprising one or more CpG motif region wherein the linkage between C and G is optionally modified) can be modulated by stereochemistry of chiral internucleotidic linkages. According to some embodiments of the disclosure, when oligonucleotides comprise a CpG region motif having one or more chiral centers (e.g., within or adjacent to the CpG region motif), different stereoforms of such oligonucleotides can have different immunomodulatory activity, stability, biological activity, characteristics and/or other activities, one or more of which can impact their utility and/or effectiveness. In some embodiments, chiral centers that can impact oligonucleotide characteristics and/or activities are found in modified internucleotidic linkages, e.g., involving one or more phosphorothioate (PS) or other modified phosphodiester linkages. In some embodiments, the present disclosure provides technologies comprising chirally controlled oligonucleotide compositions of oligonucleotides comprising one or more CpG region motifs with designed stereochemistry of chiral internucleotidic linkages within and/or adjacent to the CpG region motifs.

Among other things, the present disclosure demonstrates that provided chirally controlled CpG oligonucleotide compositions can have very different immunomodulatory activities when compared to stereorandom compositions which are uncontrolled mixtures of many stereoisomers, e.g., those previously reported stereorandom compositions of CpG oligonucleotides comprising phosphorothioate linkages. The present disclosure pertains, inter alia, to chirally controlled oligonucleotide compositions comprising CpG oligonucleotides which are chirally pure, in that the stereochemistry of each (or at least one) chiral internucleotidic linkage is controlled and not random.

In some embodiments, oligonucleotides of provided chirally controlled oligonucleotide compositions comprise one or more CpG region motifs, wherein the internucleotidic linkage between C and G is Rp. In some embodiments, oligonucleotides of provided chirally controlled oligonucleotide compositions comprise one or more CpG region motifs, wherein the internucleotidic linkage between C and G is Rp, and the oligonucleotides further comprise one or more Sp internucleotidic linkages. In some embodiments, oligonucleotides of provided chirally controlled oligonucleotide compositions comprise one or more CpG region motifs, wherein the internucleotidic linkage between C and G is Rp, and the oligonucleotides further comprise Sp internucleotidic linkages immediately to the 5'- and 3'-ends of the CpG (i.e., Sp internucleotidic linkage—C-Rp internucleotidic linkage—G-Sp internucleotidic linkage). In some embodiments, oligonucleotides comprising such motifs are agonists for, e.g., mouse TLR9 and provide increased agonist activity when compared to a reference oligonucleotide. In some embodiments, oligonucleotides of provided chirally controlled oligonucleotide compositions comprise one or more CpG region motifs, wherein one or both of the internucleotidic linkages immediately to the 5'- and 3'-ends of the CpG are Rp. In some embodiments, such oligonucleotides provide reduced agonist activities, or provide increased antagonist activities, for e.g., mouse TLR9.

In some embodiments, oligonucleotides of provided chirally controlled oligonucleotide compositions comprise one or more CpG region motifs, wherein the internucleotidic linkage between C and G is Rp. In some embodiments, oligonucleotides of provided chirally controlled oligonucleotide compositions comprise one or more CpG region motifs, wherein the internucleotidic linkage between C and G is Rp, and the oligonucleotides further comprise one or more Sp internucleotidic linkages. In some embodiments, oligonucleotides of provided chirally controlled oligonucleotide compositions comprise one or more CpG region motifs, wherein the internucleotidic linkage between C and G is Sp, and the oligonucleotides further comprise Rp internucleotidic linkages immediately to the 5'-end of the CpG (i.e., Rp internucleotidic linkage—C-Rp internucleotidic linkage—G). In some embodiments, oligonucleotides of provided chirally controlled oligonucleotide compositions comprise one or more CpG region motifs, wherein the internucleotidic linkage between C and G is Rp, and the oligonucleotides further comprise an Rp internucleotidic linkage immediately to the 5'-end of the CpG (i.e., Rp internucleotidic linkage—C-Rp internucleotidic linkage—G). In some embodiments, oligonucleotides of provided chirally controlled oligonucleotide compositions comprise one or more CpG region motifs, wherein the internucleotidic linkage between C and G is Rp, and the oligonucleotides further comprise an Sp internucleotidic linkage immediately to the 3'-end of the CpG (i.e., C-Rp internucleotidic linkage—G-Sp internucleotidic linkage). In some embodiments, oligonucleotides comprising such motifs are agonists for, e.g., human TLR9 and provide increased agonist activity when compared to a reference oligonucleotide. In some embodiments, oligonucleotides of provided chirally controlled oligonucleotide compositions comprise one or more CpG region motifs, wherein the internucleotidic linkages immediately to the 3'-end of the CpG is Sp. In some embodiments, such oligonucleotides provide reduced agonist activities, or provide increased antagonist activities, for e.g., human TLR9.

In some embodiments, beyond the CpG region motifs provided oligonucleotides are predominately Sp (e.g., more than about 50%, 55%, 60%, 65%, 70%, 75%, 80%, 85%, 90% or 95%) to provide enhanced agonist activities. In some embodiments, beyond the CpG region motifs provided oligonucleotides are predominately Sp (e.g., more than about 50%, 55%, 60%, 65%, 70%, 75%, 80%, 85%, 90% or 95%) to reduce agonist activities, and/or to provide enhanced antagonist activities.

In some embodiments, the present disclosure pertains to compositions and methods related to CpG oligonucleotides which comprise a strand comprising one or more of any of various CpG region motifs disclosed herein. In some embodiments, various CpG region motifs, which are defined at least in part by the stereochemistry of the modified internucleotidic linkages, such as phosphorothioates, in the CpG region, can, depending on the motif, either agonize or antagonize an immunostimulatory effect. In some embodiments, the CpG region motif comprises at least one phosphorothioate in the Rp conformation and at least one phosphorothioate in the Sp conformation. In some embodiments, if no immune modulation is desired, the present disclosure also provides oligonucleotides and compositions thereof, and methods of identifying oligonucleotides and compositions thereof which have decreased immune modulation, e.g., those lacking CpG region motifs which agonize or antagonize an immune response.

Among other things, the present disclosure encompasses the recognition that chemical modifications such as cytosine methylation and/or sugar modifications (e.g., 5-methylcytosine, 2'-modification of sugards, etc.), which were widely accepted as effective for removing TLR9 agonist activities prior to the present disclosure, cannot eliminate or reduce TLR9 agonist activities in certain circumstances. In some embodiments, the present disclosure provides chirally controlled oligonucleotide compositions comprising predetermined level of oligonucleotides of a particular type, wherein the oligonucleotides comprise one or more CpG region motifs, wherein the C is methylated. In some embodiments, the present disclosure provides chirally controlled oligonucleotide compositions comprising predetermined level of oligonucleotides of a particular type, wherein the oligonucleotides comprise one or more modified sugars. In some embodiments, the present disclosure provides chirally controlled oligonucleotide compositions comprising predetermined level of oligonucleotides of a particular type, wherein the oligonucleotides comprise one or more modified sugars and one or more CpG region motifs, wherein the C is methylated. In some embodiments, a modified sugar comprises 2'-modification. In some embodiments, the present disclosure demonstrates that such oligonucleotides and chirally controlled oligonucleotide compositions thereof provide unexpected TLR9 agonist activity. Among other things, the present disclosure demonstrates that TLR9 agonist and antagonist activities of oligonucleotides and compositions thereof can be effectively modulated through stereochemistry (including patterns thereof) of chiral internucleotidic linkages and/or chemical modifications.

A CpG oligonucleotide composition comprising a CpG oligonucleotide comprising phosphorothioates can be either chirally controlled (e.g., chirally controlled or stereopure), or stereorandom (e.g., a stereomixture). In some embodiments, the present disclosure pertains to a chirally controlled CpG oligonucleotide composition, which is chirally controlled in that the composition comprises a predetermined level of oligonucleotides of an individual oligonucleotide type, wherein an oligonucleotide type is defined by: 1) base sequence; 2) pattern of backbone (internucleotidic) linkages; 3) pattern of backbone (internucleotidic linkage) chiral centers; and 4) pattern of backbone (internucleotidic linkage) phosphorus modifications; wherein each oligonucleotide of the individual oligonucleotide type independently comprises at least one common CpG region motif. In some embodiments, in provided methods and/or compositions CpG oligonucleotides comprise two or more CpG region motifs described herein. In some embodiments, the present disclosure pertains to a chirally controlled CpG oligonucleotide composition, which is chirally controlled in that the composition comprises a predetermined level of oligonucleotides of an individual oligonucleotide type, wherein an oligonucleotide type is defined by: 1) base sequence; 2) pattern of backbone (internucleotidic) linkages; 3) pattern of backbone (internucleotidic linkage) chiral centers; and 4) pattern of backbone (internucleotidic linkage) phosphorus modifications; wherein each oligonucleotide of the individual oligonucleotide type independently comprises at least one common CpG region motif: $N_1$-(*R/S)—C—(*R/S)-G-(*R/S)—$N_2$; wherein each (*R/S) is independently a chiral internucleotidic linkage, and N) and $N_2$ are any nucleoside. In some embodiments, the present disclosure pertains to a chirally controlled CpG oligonucleotide composition comprising a plurality of oligonucleotides, each of which: (a) hybridizes with a particular target sequence; (b) has a base sequence that includes at least one C residue in a CpG region motif that is present in all oligonucleotides of the plurality (a "common C residue") and that is modified, a modified sugar moiety, or both; and (c) includes one or more chiral internucleotidic linkages, so that each oligonucleotide is a particular stereoform, characterized by its stereoidentity at each of the one or more chiral internucleotidic linkages, wherein stereoidentity identifies which stereoisomer is present at a particular chiral internucleotidic linkage, wherein the composition is chirally controlled in that it contains a predetermined level of each stereoform. In some embodiments, the present disclosure pertains to a chirally controlled CpG oligonucleotide composition comprising a plurality of oligonucleotides, each of which: (a) hybridizes with a particular target sequence; (b) has a base sequence that includes at least one C residue in a CpG region motif that is present in all oligonucleotides of the plurality (a "common C residue") and that has a 5-methyl group, a modified sugar moiety, or both; and (c) includes one or more chiral internucleotidic linkages, so that each oligonucleotide is a particular stereoform, characterized by its stereoidentity at each of the one or more chiral internucleotidic linkages, wherein stereoidentity identifies which stereoisomer is present at a particular chiral internucleotidic linkage, wherein the composition is chirally controlled in that it contains a predetermined level of each stereoform. In some embodiments, provided chirally controlled oligonucleotide compositions provide modulated (e.g., enhanced or reduced) TLR9 agonist and/or antagonist activities when compared to a reference composition. In some embodiments, the present disclosure provides methods of modulating TLR9 agonist and/or antagonist activities comprising providing a provided chirally controlled oligonucleotide composition. In some embodiments, in provided methods and/or compositions CpG oligonucleotides comprise two or more CpG region motifs described herein.

A non-limiting example of a chirally controlled CpG oligonucleotide composition is T*RC*RG*ST*RC*RG*ST*ST*ST*ST*SG*ST*RC*RG*ST*ST*ST*ST*SG*ST*RC*RG*S T*ST (WV-1698) (SEQ ID NO: 1). *R is a phosphorothioate in the Rp configuration; and *S is a phosphorothioate in the Sp configuration. A preparation of WV-1698 is stereopure or mostly stereopure; most or all of the oligonucleotide have not only the same sequence of base (a base sequence of each molecule or most molecules is TCGTCGTTTTGTCGTTTTGTCGTT (SEQ ID NO: 2)) but also the same pattern of configuration of the phosphorothioates (each molecule is or most of the molecules are *R*R*S*R*R*S*S*S*S*S*R*R*S*S*S*S*S*R*R*S*S). Unlike a stereopure (or chirally controlled) preparation, a stereomixture preparation comprises a variety of different stereoisomers. A non-limiting example of a CpG oligonucleotide composition which is a stereomixture of stereoisomers is T*C*G*T*C*G*T*T*T*T*G*T*C*G*T*T*T*T*G* T*C*G*T*T (ODN-2006) (SEQ ID NO: 3). * indicates a phosphorothioate which is not stereocontrolled; it can randomly be either Rp or Sp for individual stereoisomers in the composition. The stereorandom (chirally uncontrolled) ODN-2006 and the chirally controlled WV-1698 oligonucleotide compositions share the same base sequence. However, they differ in stereochemistry: ODN-2006 is a random mixture (uncontrolled from e.g., oligonucleotide synthesis using no technologies to effectively control stereochemistry of chiral internucleotidic linkages) of many stereoisomers; WV-1698 contains a predetermined level of the stereoisomer T*RC*RG*ST*RC*RG*ST*ST*ST*ST*SG*ST*RC*RG* ST*ST*ST*ST*SG*ST*RC*RG*S T*ST (SEQ ID NO: 1). For example, a stereopure preparation (e.g., a chirally controlled oligonucleotide composition) only contains oligonucleotides of the following stereochemistry (or mostly only, or with a predetermined level): *R*R*S*R*R*S*S*S*S*S*R*R*S*S*S*S*S*R*R* S*S. In contrast, a stereomixture is a random combination of stereoisomers which can include $2^{23}$ ($2^n$) stereoisomers, for example: *R*S*S*R*R*S*R*S*S*S*S*R*R*S*S*R* S*S*S*R*R*S*S *R*R*S*R*R*S*R*R*S*S*R*R*S* S*S*S*S*R*R*S*S *S*R*S*R*R*S*S*R*S*S* S*R*R*S*S*S*R*R*S*R*R*S *R*R*S*R*R*S*S* S*S*R*S*R*R*S*S*S*S*S*R*R*S*S *S*R*S*R*R*R*R*S*S*S*S*R*S*R*R*S*S*S*S*R*R* S*S and millions of other stereoisomers. The number of stereoisomers in a stereomixture is determined by the number of chiral internucleotidic linkages; when there are n chiral internucleotidic linkages, there can be $2^n$ stereoisomers. For ODN-2006 which comprises 23 phosphorothioates, a stereorandom ODN-2006 oligonucleotide composition is a stereomixture of $2^{23}$ or 8,388,608 different molecules. In contrast, a preparation of the stereopure molecule WV-1698 (e.g., a chirally controlled oligonucleotide composition) is a pure (or mostly pure or with a predetermined level) preparation of one stereoisomer.

In some chirally controlled oligonucleotide compositions, each chiral modified internucleotidic linkage (including but not limited to a phosphorothioate) is chirally controlled.

In some embodiments, in a chirally controlled oligonucleotide composition, at least one chiral modified internucleotidic linkage (including but not limited to a phosphorothioate) is chirally controlled. In some embodiments, in a chirally controlled oligonucleotide composition, at least one chiral modified internucleotidic linkage (including but not limited to a phosphorothioate) is chirally controlled and at least one chiral modified internucleotidic linkage (including but not limited to a phosphorothioate) is not chirally controlled.

A non-limiting example of a chirally controlled CpG oligonucleotide composition is a CpG oligonucleotide comprising a CpG region motif:
C—(*X)-G-(*S)—N, wherein N is any nucleotide.
*S indicates a phosphorothioate in the Sp conformation;
*X or (*X) indicates that, in a population of oligonucleotides or an oligonucleotide composition, some of the individual oligonucleotides have a phosphorothioate in the Rp conformation and some have a phosphorothioate in the Sp conformation at this position.

In some embodiments, even if one position (e.g., *X) is not chirally controlled, if any one or more other position is chirally controlled, the oligonucleotide composition is chirally controlled. In some embodiments, C—(*X)-G-(*S)—N represents, in a chirally controlled oligonucleotide composition, a CpG oligonucleotide comprising a CpG region motif C—(*R)-G-(*S)—N and a CpG oligonucleotide comprising a CpG region motif C—(*S)-G-(*S)—N. In some embodiments, C—(*R/S)-G-(*S)—N represents, in a chirally controlled oligonucleotide composition, a CpG oligonucleotide comprising a CpG region motif C—(*R)-G-(*S)—N or a CpG oligonucleotide comprising a CpG region motif C—(*S)-G-(*S)—N.

In some embodiments, the present disclosure provides chirally controlled oligonucleotide compositions of CpG oligonucleotides comprising a sequence of N—(*X)—C—(*R/S)-G-(*R/S)—N, N—(*R/S)—C—(*X)-G-(*R/S)—N, N—(*R/S)—C—(*R/S)-G-(*X)—N, N—(*X)—C*R)-G-(*R)—N, N—(*X)—C—(*R)-G-(*S)—N, N—(*X)—C—(*S)-G-(*R)—N, N—(*X)—C—(*S)-G-(*S)—N, N—(*R)—C—(*X)-G-(*R)—N, N—(*R)—C—(*X)-G-(*S)—N, N—(*S)—C—(*X)-G-(*R)—N, N—(*S)—C—(*X)-G-(*S)—N, N—(*R)—C—(*R)-G-(*X)—N, N—(*R)—C—(*S)-G-(*X)—N, N—(*S)—C—(*S)-G-(*X)—N, N—(*S)—C—(*R)-G-(*X)—N, N—(*X)—C—(*R)-G-(*X)—N, N—(*X)—C—(*S)-G-(*X)—N, N—(*R)—C—(*X)-G-(*X)—N, N—(*S)—C—(*X)-G-(*X)—N, N—(*X)—C—(*X)-G-(*R)—N, or N—(*X)—C—(*X)-G-(*S)—N.

A non-limiting example of a chirally controlled CpG oligonucleotide composition is a CpG oligonucleotide comprising a CpG region motif:
C-(*D)-G-(*R)—N, wherein N is any nucleotide.
*R indicates a phosphorothioate in the Rp conformation;
*D indicates a phosphorodithioate, wherein both of the non-bridging phosphorus atoms in a phosphodiester have been replaced by sulfur.

Additional CpG oligonucleotides comprise a CpG region motif comprising a sequence of N-(*D)-C—(*R/S)-G-(*R/S)—N, N—(*R/S)—C-(*D)-G-(*R/S)—N, N—(*R/S)—C—(*R/S)-G-(*D)-N, N-(*D)-C—(*R)-G-(*R)—N, N-(*D)-C—(*R)-G-(*S)—N, N-(*D)-C—(*S)-G-(*R)—N, N-(*D)-C—(*S)-G-(*S)—N, N—(*R)—C-(*D)-G-(*R)—N, N—(*R)—C-(*D)-G-(*S)—N, N—(*S)—C-(*D)-G-(*R)—N, N—(*S)—C-(*D)-G-(*S)—N, N—(*R)—C—(*R)-G-(*D)-N, N—(*R)—C—(*S)-G-(*D)-N, N—(*S)—C—(*S)-G-(*D)-N, N—(*S)—C—(*R)-G-(*D)-N, N-(*D)-C—(*R)-G-(*D)-N, N-(*D)-C—(*S)-G-(*D)-N, N—(*R)—C-(*D)-G-(*D)-N, N—(*S)—C-(*D)-G-(*D)-N, N-(*D)-C-(*D)-G-(*R)—N, or N-(*D)-C-(*D)-G-(*S)—N.

The terms N, *R, *S, *R/S, *X and *D as used herein can be used to define the characteristics of any oligonucleotide or oligonucleotide composition.

In some embodiments, a chirally controlled CpG oligonucleotide composition comprises a CpG oligonucleotide comprising a *X in a CpG region motif. In some embodiments, a chirally controlled CpG oligonucleotide composition comprises a CpG oligonucleotide comprising a *X outside a CpG region motif. In some embodiments, a chirally controlled CpG oligonucleotide composition comprises a CpG oligonucleotide comprising a *D in a CpG region motif. In some embodiments, a chirally controlled CpG oligonucleotide composition comprises a CpG oligonucleotide comprising a *D outside a CpG region motif. In some embodiments, a chirally controlled CpG oligonucleotide can comprise a *X (either inside or outside of a CpG region motif) and a *D (either inside or outside of a CpG region motif). In some embodiments, a chirally controlled CpG oligonucleotide can comprise at least one *X (either inside or outside of a CpG region motif) and at least one *D (either inside or outside of a CpG region motif). In some embodiments, a chirally controlled CpG oligonucleotide comprises a CpG oligonucleotide comprising at least one *R and/or at least one *S in a CpG region motif, and, optionally, at least one *X (either inside or outside of a CpG region motif) and at least one *D (either inside or outside of a CpG region motif). In some embodiments, a chirally controlled CpG oligonucleotide comprises a CpG oligonucleotide comprising at least one *R and/or at least one *S in a CpG region motif, and, optionally, at least one *X (either inside or outside of a CpG region motif) and/or at least one *D (either inside or outside of a CpG region motif).

While researchers have previously reported CpG oligonucleotides which are stereomixtures, the present disclosure pertains to CpG oligonucleotides which are chirally controlled. In some embodiments, chirally controlled CpG oligonucleotides provide unique insights into CpG region motifs, including the elucidation of various CpG region motifs, defined at least in part by the stereochemistry of the phosphorothioates, variants of which are able to agonize or antagonize an immune response.

In some embodiments, the present disclosure demonstrates in both mouse models and human PBMCs that a stereorandom oligonucleotide composition and a corresponding chirally controlled oligonucleotide composition can display very different activities against TLR9. In some embodiments, the present disclosure demonstrates that for mouse TLR9, some stereopure CpG-oligos with all-Sp backbone are strong agonists, whose activities are further modulated by the chirality of the PS bonds in and adjacent to the CpG motifs (CpG regions). In some embodiments, human TLR9 (hTLR9) activities are affected very differently, in several cases, with agonists preferring Sp chirality on the 3' of CpG motif. In some embodiments, the present disclosure demonstrates that 2'-modifications on the ribose ring completely eliminate agonist activity on mouse TLR9, but not on human TLR9, which is more relevant to drug discovery for human diseases. In some embodiments, the present disclosure demonstrates that mouse and human TLR9 respond differently to stereopure CpG oligonucleotide compositions with 2'-modifications and CpG methylations. In some embodiments, the present disclosure surprisingly demonstrates that phosphorothioate chirality is an important determinant of TLR9 activity.

In addition, while the present disclosure showed that, in at least some chirally controlled CpG oligonucleotide compositions, some CpG region motifs had greater immunomodulatory activity (e.g., greater agonistic or greater antagonistic activity), the present disclosure encompasses any chirally controlled CpG oligonucleotide composition, wherein the CpG region motif comprises a stereodefined phosphorothioate or other chiral internucleotidic linkage, wherein the CpG oligonucleotide demonstrates a greater agonistic or antagonistic activity than a negative control (e.g., in the absence of the oligonucleotide composition).

Thus, in some embodiments, the present disclosure presents the surprising recognition that stereochemistry of chiral modified internucleotidic linkages such phosphorothioates in the CpG region motif can greatly affect the agonistic and/or antagonist effects of a CpG oligonucleotide. In some embodiments, various motifs, defined at least in part by the stereochemistry of the phosphorothioates, can either agonize or antagonize an immune response.

In some embodiments, the present disclosure pertains, inter alia, to compositions and methods comprising a CpG oligonucleotide comprising a strand comprising one or more copies of a CpG region motif, wherein the motif comprises stereodefined (Rp or Sp) phosphorothioates (or other chiral internucleotidic linkages).

In some embodiments, if no immune modulation is desired, the present disclosure provides methods of identifying oligonucleotides which have decreased immune modulation (e.g., those lacking CpG region motifs which agonize or antagonize an immune response). In many cases, oligonucleotides intended for therapeutic use comprise phosphorothioates or other chiral internucleotic linkages which are not chirally controlled. In some embodiments of the present disclosure, oligonucleotides intended for therapeutic use can thus be screened for immune modulation, and modified variants of these oligonucleotides (e.g., chirally controlled oligonucleotides) can be identified which have less or greater immunomodulation (agonism or antagonism), and/or greater stability, increased biological activity, shorter length, or other improved characteristics, as desired. A person having ordinary skill in the art appreciates that designs (e.g., chemical modifications and/or stereochemistry) identified by the present disclosure for enhanced activities (e.g., TLR9 agonist or antagonist activities) are also useful for preparing oligonucleotide compositions with reduced such activities; when such activities are not desired, designs identified for enhanced activities are reduced or eliminated from oligonucleotides.

In some embodiments, the present disclosure provides methods for modulating immune response, comprising providing a provided chirally controlled oligonucleotide composition. In some embodiments, the present disclosure provides methods for modulating TLR9 activities, comprising providing a provided chirally controlled oligonucleotide composition. In some embodiments, the present disclosure provides methods for treating a disease, comprising providing a provided chirally controlled oligonucleotide composition. In some embodiments, the present disclosure provides methods for treating cancer, comprising administering to a subject a provided chirally controlled oligonucleotide composition. In some embodiments, the present disclosure provides methods for treating cancer, comprising administering to a subject a provided chirally controlled oligonucleotide composition and a cancer therapeutic agent. In some embodiments, a cancer therapeutic agent is a vaccine. In some embodiments, a cancer therapeutic agent is an antibody, such anti-EGFR, anti-PD1, etc. In some embodiments, a cancer therapeutic agent is an immune checkpoint antibody. In some embodiments, a provided chirally controlled oligonucleotide composition provides enhanced TLR9 agonist activities. In some embodiments, a provided chirally controlled oligonucleotide composition provides enhanced TLR9 antagonist activities.

In some embodiments, the present disclosure provides methods for assaying TLR9 agonist and/or antagonist activities, comprising providing a provided chirally controlled oligonucleotide composition. In some embodiments, the present disclosure provides assay systems for accessing TLR9 agonist and/or antagonist activities, comprising a provided chirally controlled oligonucleotide composition. In some embodiments, a provided method and/or assay system is based on a method and/or assay system widely known and applied in the art, by replacing a stereorandom oligonucleotide composition in the method and/or assay system with a provided chirally controlled oligonucleotide composition in accordance with the present disclosure.

In some embodiments, the present disclosure pertains to a chirally controlled oligonucleotide composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a modified internucleotidic linkage in the Rp conformation and at least one (*R/S) is a modified internucleotidic linkage in the Sp conformation, and each of $N_1$ and $N_2$ is independently any nucleoside.

In some embodiments, the present disclosure pertains to a chirally controlled oligonucleotide composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and each of $N_1$ and $N_2$ is independently any nucleoside.

In some embodiments, the present disclosure pertains to a composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and each of $N_1$ and $N_2$ is independently any nucleoside.

In some embodiments, the present disclosure pertains to a composition comprising a plurality of oligonucleotides, each of which: (a) hybridizes with a particular target sequence; and (b) comprises a sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, and each of N) and $N_2$ is independently any nucleoside.

In some embodiments, the present disclosure pertains to a composition comprising a plurality of oligonucleotides, each of which: (a) consists of a particular base sequence; and (b) comprises a sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein at least one (*R/S) is a phosphorothioate in the Rp conformation and at least one (*R/S) is a phosphorothioate in the Sp conformation, and each of N) and $N_2$ is independently any nucleoside.

In some embodiments, the present disclosure pertains to a composition comprising a plurality of oligonucleotides, each of which: (a) hybridizes with a particular target sequence; and (b) has a sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, wherein the composition is chirally controlled in that it contains a predetermined level of each of stereoisomers 1-8 (S1-S8) for each common CpG region motif: S1: $N_1$-(*R)—C—(*R)-G-(*R)—$N_2$; S2: $N_1$-(*R)—C—(*R)-G-(*S)—$N_2$; S3: $N_1$-(*R)—C—(*S)-G-(*R)—$N_2$; S4: $N_1$-(*R)—C—(*S)-G-(*S)—$N_2$; S5: $N_1$-(*S)—C—(*R)-G-(*R)—$N_2$; S6: $N_1$-(*S)—C—(*R)-G-(*S)—$N_2$; S7: $N_1$-(*S)—C—(*S)-G-(*R)—$N_2$; S8: $N_1$-(*S)—C—(*S)-G-(*S)—$N_2$.

In some embodiments, the present disclosure pertains to an oligonucleotide composition that is chirally controlled in that the composition comprises a predetermined level of oligonucleotides of an individual oligonucleotide type, wherein an oligonucleotide type is defined by: 1) base sequence; 2) pattern of backbone linkages; 3) pattern of backbone chiral centers; and 4) pattern of backbone phosphorus modifications; wherein each oligonucleotide of the individual oligonucleotide type independently comprises at least one common CpG region motif: $N_1$-(*R/S)—C—(*R/S)-G-(*R/S)—$N_2$; wherein each (*R/S) is independently a chiral internucleotidic linkage, and each of N) and $N_2$ is independently any nucleoside.

In some embodiments, the present disclosure pertains to a composition comprising a plurality of oligonucleotides, each of which: (a) hybridizes with a particular target sequence; (b) has a base sequence that includes at least one C residue in a CpG region motif that is present in all oligonucleotides of the plurality (a "common C residue") and that has a 5-methyl group, a modified sugar moiety, or both; and (c) includes one or more chiral internucleotidic linkages, so that each oligonucleotide is a particular stereoform, characterized by its stereoidentity at each of the one or more chiral internucleotidic linkages, wherein stereoidentity identifies which stereoisomer is present at a particular chiral internucleotidic linkage, wherein the composition is chirally controlled in that it contains a predetermined level of each stereoform.

In some embodiments, the present disclosure pertains to an oligonucleotide composition that is chirally controlled in that the composition comprises a predetermined level of oligonucleotides of an individual oligonucleotide type, wherein an oligonucleotide type is defined by: 1) base sequence; 2) pattern of backbone linkages; 3) pattern of backbone chiral centers; and 4) pattern of backbone phosphorus modifications; wherein the base sequence includes at least one C residue in a CpG region motif that has a 5-methyl group, a modified sugar moiety, or both; and the composition has a reduced ability to activate a TLR9-mediated and/or TLR9-associated immune response relative to the ability of a composition that is not chirally controlled in that the composition comprises a random level of oligonucleotides of an individual oligonucleotide type.

In some embodiments, the present disclosure pertains to a chirally controlled oligonucleotide composition comprising a CpG oligonucleotide comprising a strand comprising about 14 to about 49 nucleotides, wherein the strand comprises at least one copy of any CpG region motif disclosed herein.

In some embodiments, the present disclosure pertains to a chirally controlled oligonucleotide composition comprising a CpG oligonucleotide comprising a strand comprising about 14 to about 49 nucleotides, wherein the strand comprises at least one copy of any CpG region motif of any CpG oligonucleotide disclosed herein.

In some embodiments, the present disclosure pertains to a chirally controlled oligonucleotide composition comprising a CpG oligonucleotide comprising a strand comprising about 14 to about 49 nucleotides, wherein the strand comprises or consists of the sequence of any oligonucleotide disclosed herein.

In some embodiments, the present disclosure pertains to a chirally controlled oligonucleotide composition comprising a CpG oligonucleotide comprising a strand comprising 14 to 49 nucleotides, wherein the strand comprises at least one copy of any CpG region motif disclosed herein.

In some embodiments, the present disclosure pertains to a chirally controlled oligonucleotide composition comprising a CpG oligonucleotide comprising a strand comprising 14 to 49 nucleotides, wherein the strand comprises at least one copy of any CpG region motif of any CpG oligonucleotide disclosed herein.

In some embodiments, the present disclosure pertains to a chirally controlled oligonucleotide composition comprising a CpG oligonucleotide comprising a strand comprising at least one copy of the CpG region motif T-(*R)—C—(*R)-G-(*R)-T, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif T-(*R)—C—(*R)-G-(*R)-T-(*R)-Py, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least two non-adjacent copies of the CpG region motif of $N_1$-(*R)—C—(*R)-G-(*R)—$N_2$, wherein at least one phosphorothioate between the CpG region motifs is in the Sp conformation, and wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif T-(*S)—C—(*S)-G-(*S)-T-(*S)-T, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein at least one (*R/S) is (*R) and at least one (*R/S) is (*S), wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein at least one (*R/S) is (*R) and at least one (*R/S) is (*S), and wherein C is unmethylated, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif $N_1$-(*R)—C—(*R)-G-(*S)—$N_2$, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif $N_1$-(*R)—C—(*S)-G-(*S)—$N_2$, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif $N_1$-(*R)—C—

(*S)-G-(*R)—N₂, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*S)—C—(*R)-G-(*S)—N₂, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*S)—C—(*R)-G-(*R)—N₂, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*S)—C—(*S)-G-(*R)—N₂, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif Py-(*R/S)—C—(*R/S)-G-(*R/S)-Py, wherein at least one (*R/S) is (*R) and at least one (*R/S) is (*S), and wherein C is unmethylated, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif m5C—(*R)-m5C—(*R)-G-(*R)—N₁, where all the nucleosides are 2'-MOE, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif m5C—(*R)-m5C—(*R)-G-(*R)-Py, where all the nucleosides are 2'-MOE, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*R)-m5C—(*R)-G-(*R)—N₂, wherein N₁ is methylated or not methylated, and all the nucleosides are 2'-MOE, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*R)-m5C—(*R)-G-(*R)-Py, wherein N₁ is methylated or not methylated, and all the nucleosides are 2'-MOE, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*R/S)-m5C—(*R/S)-G-(*R/S)—N₂, wherein at least 2 of the (*R/S) are (*R), all the nucleosides are 2'-MOE, and N₁ and N₂ are methylated or not methylated, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*R/S)-m5C—(*R/S)-G-(*R/S)—N₂, wherein at least 2 of the (*R/S) are (*R), all the nucleosides are 2'-MOE; and N₁ and N₂ are methylated or not methylated, wherein the CpG oligonucleotide is capable of agonizing an immune response in the human.

In some embodiments, the present disclosure pertains to a chirally controlled oligonucleotide composition comprising a CpG oligonucleotide comprising a strand comprising at least one copy of the CpG region motif N₁-(*S)—[C]-(*R)-[G]-(*S)—N₂, where N₁ is 2'H, 2'-MOE or 2'-OMe; [C] is C, m5C, 2'-MOE C, or 2'-MOE m5C; [G] is G, 2'-Ome G, or 2'-MOE G; and N₂ is 2'H, 2'-MOE or 2'-OMe, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif N₁-(*S)—[C]-(*R)-[G]-(*S)—N₂, where N₁ is 2'H; [C] is C, m5C, 2'-MOE C, or 2'-MOE m5C; [G] is G, 2'-Ome G, or 2'-MOE G; and N₂ is 2'H, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif N₁-(*R)—[C]-(*R)-[G]-(*R)-Py, where N₁ and Py are 2'H, 2'-MOE or 2'OMe; and [C] is C or 2'-MOE C; and [G] is G or 2'-MOE G; and Py is 2'-H or 2'-MOE, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif N₁-(*R)—[C]-(*R)-[G]-(*R)—N₂, where N₁ and N₂ are 2'H, 2'-MOE or 2'OMe; and [C] is 2'-MOE m5C; N₂ is 2'-H or 2'-MOE, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—C—(*R)-G-(*R)-Py, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—C—(*R)-G-(*R)-Py, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*S)—C—(*R)-G-(*S)-Py.

In some embodiments, the present disclosure pertains to a chirally controlled oligonucleotide composition comprising a CpG oligonucleotide comprising a strand comprising at least one copy of the CpG region motif Py-(*S)—C—(*S)-G-(*S)-Py, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where [C] is 2'-MOE C; and [G] is 2'-MOE G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*S)-Py, where [C] is 2'-MOE C; and [G] is 2'-MOE G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—[C]-(*R)-G-(*R)-Py, where [C] is C, 2'-OMe m5C, or 2'-MOE C, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)—$N_1$, where [C] is 2'-OMe m5C, and [G] is 2'-OMe G, and $N_1$ is 2'-OMe, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe m5C, and [G] is 2'-OMe G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe C and [G] is 2'-OMe G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE C and [G] is 2'-MOE G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)-m5C—(*R)-G-(*R)-Py, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)-m5C—(*R)-G-(*R)-Py, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*S)-m5C—(*R)-G-(*S)-Py, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE m5C and [G] is 2'-MOE G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe m5C and [G] is 2'-OMe G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe C and [G] is 2'-OMe G, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where both [C] and [G] are 2'-modified, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif $N_1$-(*R)—[C]-(*R)-[G]-(*R)—$N_2$, where both [C] and [G] are 2'-modified, wherein the CpG oligonucleotide is capable of antagonizing an immune response in the human.

In some embodiments, the present disclosure pertains to a chirally controlled oligonucleotide composition comprising a CpG oligonucleotide comprising a strand comprising at least one copy of the CpG region motif T-(*R)—C—(*R)-G-(*R)-T.

In some embodiments, the present disclosure pertains to a chirally controlled oligonucleotide composition comprising a CpG oligonucleotide comprising a strand comprising at least one copy of the CpG region motif T-(*R)—C—(*R)-G-(*R)-T-(*R)-Py.

In some embodiments, the present disclosure pertains to a chirally controlled oligonucleotide composition comprising a CpG oligonucleotide comprising a strand comprising at least two non-adjacent copies of the CpG region motif of $N_1$-(*R)—C—(*R)-G-(*R)—$N_2$, wherein at least one phosphorothioate between the CpG region motifs is in the Sp conformation.

In some embodiments, the present disclosure pertains to a chirally controlled oligonucleotide composition comprising a CpG oligonucleotide comprising a strand comprising at least one copy of the CpG region motif T-(*S)—C—(*S)-G-(*S)-T-(*S)-T.

In some embodiments, the present disclosure pertains to a chirally controlled oligonucleotide composition comprising a CpG oligonucleotide comprising a strand comprising at least one copy of the CpG region motif $N_1$-(*R/S)—C—(*R/S)-G-(*R/S)—$N_2$.

In some embodiments, the present disclosure pertains to a chirally controlled oligonucleotide composition comprising a CpG oligonucleotide comprising a strand comprising at least one copy of the CpG region motif N$_1$-(*R/S)—C—(*R/S)-G-(*R/S)—N$_2$, wherein at least one (*R/S) is (*R) and at least one (*R/S) is (*S).

In some embodiments, the present disclosure pertains to a chirally controlled oligonucleotide composition comprising a CpG oligonucleotide comprising a strand comprising at least one copy of the CpG region motif N$_1$-(*R/S)—C—(*R/S)-G-(*R/S)—N$_2$, wherein at least one (*R/S) is (*R) and at least one (*R/S) is (*S), and wherein C is unmethylated.

In some embodiments, the present disclosure pertains to a chirally controlled oligonucleotide composition comprising a CpG oligonucleotide comprising a strand comprising at least one copy of the CpG region motif N$_1$-(*R)—C—(*R)-G-(*S)—N$_2$.

In some embodiments, the present disclosure pertains to a chirally controlled oligonucleotide composition comprising a CpG oligonucleotide comprising a strand comprising at least one copy of the CpG region motif N$_1$-(*R)—C—(*S)-G-(*S)—N$_2$.

In some embodiments, the present disclosure pertains to a chirally controlled oligonucleotide composition comprising a CpG oligonucleotide comprising a strand comprising at least one copy of the CpG region motif N$_1$-(*R)—C—(*S)-G-(*R)—N$_2$.

In some embodiments, the present disclosure pertains to a chirally controlled oligonucleotide composition comprising a CpG oligonucleotide comprising a strand comprising at least one copy of the CpG region motif N$_1$-(*S)—C—(*R)-G-(*S)—N$_2$.

In some embodiments, the present disclosure pertains to a chirally controlled oligonucleotide composition comprising a CpG oligonucleotide comprising a strand comprising at least one copy of the CpG region motif N$_1$-(*S)—C—(*R)-G-(*R)—N$_2$.

In some embodiments, the present disclosure pertains to a chirally controlled oligonucleotide composition comprising a CpG oligonucleotide comprising a strand comprising at least one copy of the CpG region motif N$_1$-(*S)—C—(*S)-G-(*R)—N$_2$.

In some embodiments, the present disclosure pertains to a chirally controlled oligonucleotide composition comprising a CpG oligonucleotide comprising a strand comprising at least one copy of the CpG region motif Py-(*R/S)—C—(*R/S)-G-(*R/S)-Py, wherein at least one (*R/S) is (*R) and at least one (*R/S) is (*S), and wherein C is unmethylated.

In some embodiments, the present disclosure pertains to a chirally controlled oligonucleotide composition comprising a CpG oligonucleotide comprising a strand comprising at least one copy of the CpG region motif m5C—(*R)-m5C—(*R)-G-(*R)—N$_1$, where all the nucleosides are 2'-MOE.

In some embodiments, the present disclosure pertains to a chirally controlled oligonucleotide composition comprising a CpG oligonucleotide comprising a strand comprising at least one copy of the CpG region motif m5C—(*R)-m5C—(*R)-G-(*R)-Py, where all the nucleosides are 2'-MOE.

In some embodiments, the present disclosure pertains to a chirally controlled oligonucleotide composition comprising a CpG oligonucleotide comprising a strand comprising at least one copy of the CpG region motif N$_1$-(*R)-m5C—(*R)-G-(*R)—N$_2$, wherein N$_1$ is methylated or not methylated, and all the nucleosides are 2'-MOE.

In some embodiments, the present disclosure pertains to a chirally controlled oligonucleotide composition comprising a CpG oligonucleotide comprising a strand comprising at least one copy of the CpG region motif N$_1$-(*R)-m5C—(*R)-G-(*R)-Py, wherein N$_1$ is methylated or not methylated, and all the nucleosides are 2'-MOE.

In some embodiments, the present disclosure pertains to a chirally controlled oligonucleotide composition comprising a CpG oligonucleotide comprising a strand comprising at least one copy of the CpG region motif N$_1$-(*R/S)-m5C—(*R/S)-G-(*R/S)—N$_2$, wherein at least 2 of the (*R/S) are (*R), all the nucleosides are 2'-MOE, and N$_1$ and N$_2$ are methylated or not methylated.

In some embodiments, the present disclosure pertains to a chirally controlled oligonucleotide composition comprising a CpG oligonucleotide comprising a strand comprising at least one copy of the CpG region motif N$_1$-(*R/S)-m5C—(*R/S)-G-(*R/S)—N$_2$, wherein at least 2 of the (*R/S) are (*R), all the nucleosides are 2'-MOE; and N$_1$ and N$_2$ are methylated or not methylated.

In some embodiments, the present disclosure pertains to a chirally controlled oligonucleotide composition comprising a CpG oligonucleotide comprising a strand comprising at least one copy of the CpG region motif N$_1$-(*S)—[C]-(*R)-[G]-(*S)—N$_2$, where N$_1$ is 2'H, 2'-MOE or 2'-OMe; [C] is C, m5C, 2'-MOE C, or 2'-MOE m5C; [G] is G, 2'-Ome G, or 2'-MOE G; and N$_2$ is 2'H, 2'-MOE or 2'-OMe.

In some embodiments, the present disclosure pertains to a chirally controlled oligonucleotide composition comprising a CpG oligonucleotide comprising a strand comprising at least one copy of the CpG region motif N$_1$-(*S)—[C]-(*R)-[G]-(*S)—N$_2$, where N$_1$ is 2'H; [C] is C, m5C, 2'-MOE C, or 2'-MOE m5C; [G] is G, 2'-Ome G, or 2'-MOE G; and N$_2$ is 2'H.

In some embodiments, the present disclosure pertains to a chirally controlled oligonucleotide composition comprising a CpG oligonucleotide comprising a strand comprising at least one copy of the CpG region motif N$_1$-(*R)—[C]-(*R)-[G]-(*R)-Py, where N$_1$ and Py are 2'H, 2'-MOE or 2'OMe; and [C] is C or 2'-MOE C; and [G] is G or 2'-MOE G; and Py is 2'-H or 2'-MOE.

In some embodiments, the present disclosure pertains to a chirally controlled oligonucleotide composition comprising a CpG oligonucleotide comprising a strand comprising at least one copy of the CpG region motif N$_1$-(*R)—[C]-(*R)-[G]-(*R)—N$_2$, where N$_1$ and N$_2$ are 2'H, 2'-MOE or 2'OMe; and [C] is 2'-MOE m5C; N$_2$ is 2'-H or 2'-MOE.

In some embodiments, the present disclosure pertains to a chirally controlled oligonucleotide composition comprising a CpG oligonucleotide comprising a strand comprising at least one copy of the CpG region motif Py-(*R)—C—(*R)-G-(*R)-Py.

In some embodiments, the present disclosure pertains to a chirally controlled oligonucleotide composition comprising a CpG oligonucleotide comprising a strand comprising at least one copy of the CpG region motif Py-(*R)—C—(*R)-G-(*R)-Py.

In some embodiments, the present disclosure pertains to a chirally controlled oligonucleotide composition comprising a CpG oligonucleotide comprising a strand comprising at least one copy of the CpG region motif Py-(*S)—C—(*R)-G-(*S)-Py.

In some embodiments, the present disclosure pertains to a chirally controlled oligonucleotide composition comprising a CpG oligonucleotide comprising a strand comprising at least one copy of the CpG region motif Py-(*S)—C—(*S)-G-(*S)-Py.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where [C] is 2'-MOE C; and [G] is 2'-MOE G.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*S)-Py, where [C] is 2'-MOE C; and [G] is 2'-MOE G.

In some embodiments, the present disclosure pertains to a chirally controlled oligonucleotide composition comprising a CpG oligonucleotide comprising a strand comprising at least one copy of the CpG region motif Py-(*R)—[C]-(*R)-G-(*R)-Py, where [C] is C, 2'-OMe m5C, or 2'-MOE C.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)—N₁, where [C] is 2'-OMe m5C, and [G] is 2'-OMe G, and N₁ is 2'-OMe.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe m5C, and [G] is 2'-OMe G.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe C and [G] is 2'-OMe G.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE C and [G] is 2'-MOE G.

In some embodiments, the present disclosure pertains to a chirally controlled oligonucleotide composition comprising a CpG oligonucleotide comprising a strand comprising at least one copy of the CpG region motif Py-(*R)-m5C—(*R)-G-(*R)-Py.

In some embodiments, the present disclosure pertains to a chirally controlled oligonucleotide composition comprising a CpG oligonucleotide comprising a strand comprising at least one copy of the CpG region motif Py-(*R)-m5C—(*R)-G-(*R)-Py.

In some embodiments, the present disclosure pertains to a chirally controlled oligonucleotide composition comprising a CpG oligonucleotide comprising a strand comprising at least one copy of the CpG region motif Py-(*S)-m5C—(*R)-G-(*S)-Py.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE m5C and [G] is 2'-MOE G.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe m5C and [G] is 2'-OMe G.

In some embodiments, the present disclosure pertains to a chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe C and [G] is 2'-OMe G.

In some embodiments, the present disclosure pertains to a chirally controlled oligonucleotide composition comprising a CpG oligonucleotide comprising a strand comprising at least one copy of the CpG region motif Py-(*R)—[C]-(*R)-[G]-(*R)-Py, where both [C] and [G] are 2'-modified.

In some embodiments, the present disclosure pertains to a chirally controlled oligonucleotide composition comprising a CpG oligonucleotide comprising a strand comprising at least one copy of the CpG region motif N₁-(*R)—[C]-(*R)-[G]-(*R)—N₂, where both [C] and [G] are 2'-modified.

In some embodiments of the methods and compositions of the present disclosure, a CpG oligonucleotide comprises two or more CpG region motifs described herein.

In some embodiments, the present disclosure pertains to the composition of any one of the preceding embodiments, wherein at least one internucleotidic linkage is a phosphorodithioate.

In some embodiments, the present disclosure pertains to the composition of any one of the preceding embodiments, wherein at least one internucleotidic linkage is selected from: phosphorodithioate, phosphoramidate, boranophosphonoate, an amide linker, or a compound of formula (I):

$$R^3-\underset{\underset{R^4}{|}}{\overset{\overset{O}{\|}}{P}}=O,$$ (I)

where $R^3$ is selected from OH, SH, NH₂, BH₃, CH₃, C₁₋₆ alkyl, C₆₋₁₀ aryl, C₁₋₆ alkoxy and C₆₋₁₀ aryl-oxy, wherein C₁₋₆ alkyl and C₆₋₁₀ aryl are unsubstituted or optionally independently substituted with 1 to 3 groups independently selected from halo, hydroxyl and NH₂, and applicable salts thereof; and $R^4$ is selected from O, S, NH, or CH₂.

In some embodiments, the present disclosure pertains to the composition of any one of the preceding embodiments, wherein at least one internucleotidic linkage is selected from:

| Symbol | Modified Internucleotidic Linkage |
|---|---|
| s | phosphorothioate  |
| s1 | |

| Symbol | Modified Internucleotidic Linkage |
|---|---|
| s2 | |
| s3 | |
| s4 | |
| s5 | |
| s6 | |
| s7 | |
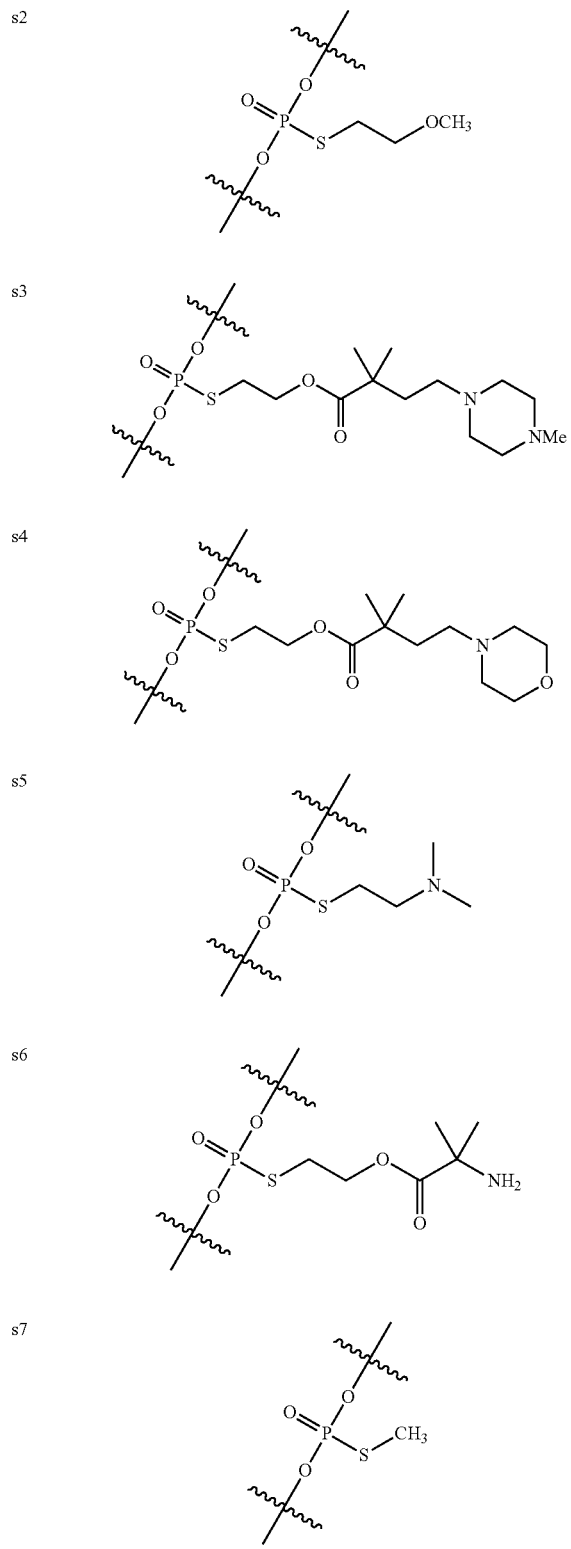
| Symbol | Modified Internucleotidic Linkage |
|---|---|
| s8 | |
| s9 | |
| s10 | |
| s11 | |
| s12 | |
| s13 | |
| s14 | |
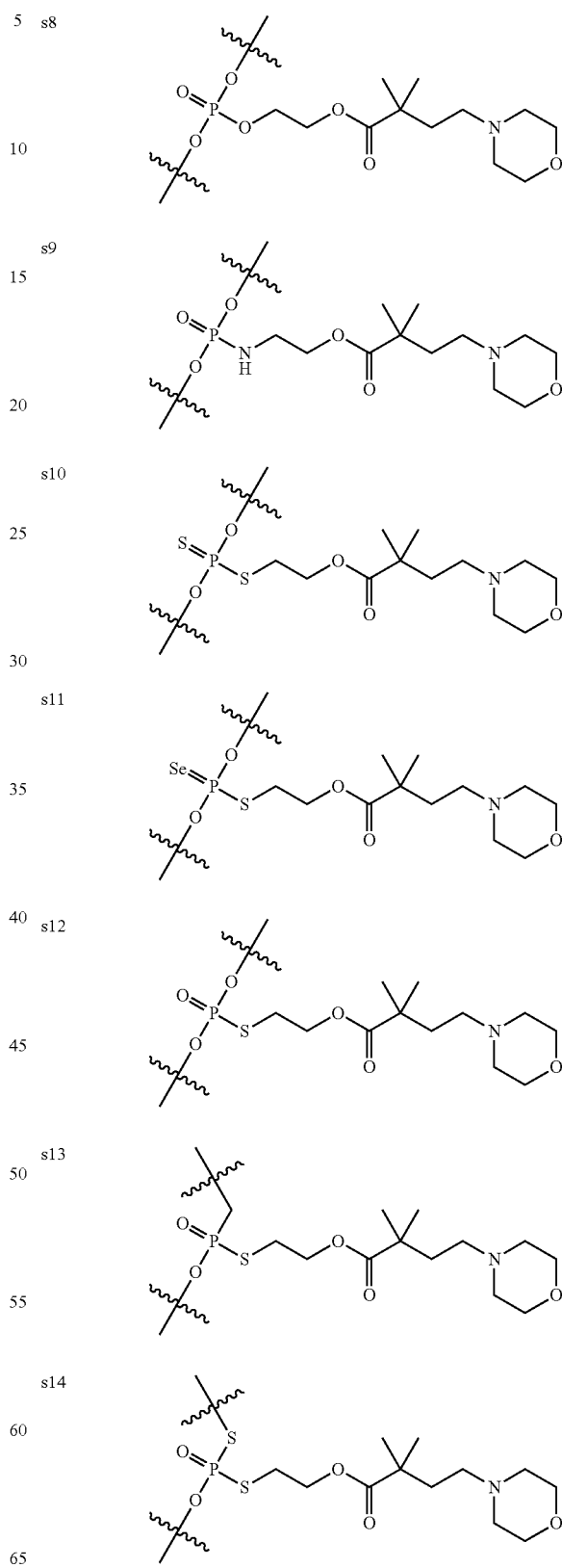

| Symbol | Modified Internucleotidic Linkage |
|---|---|
| s15 | (structure) |
| s16 | (structure) |
| s17 | (structure) |
| s18 | (structure) |

In some embodiments, the present disclosure pertains to a method of agonizing an immune response in a human cell, the method comprising the step of contacting the human cell with a CpG oligonucleotide composition of any one of the preceding embodiments, wherein the CpG oligonucleotide is capable of agonizing a TLR9-mediated or TLR9-associated immune response.

In some embodiments, the present disclosure pertains to a method of antagonizing an immune response in a human cell, the method comprising the step of contacting the human cell with a CpG oligonucleotide composition of any one of the preceding embodiments, wherein the CpG oligonucleotide is capable of antagonizing a TLR9-mediated or TLR9-associated immune response.

In some embodiments, the present disclosure pertains to a method of modulating an immune response in a subject, the method comprising the step of administering a composition of any one of preceding embodiments, wherein the CpG oligonucleotide is capable of modulating a TLR9-mediated or TLR9-associated immune response.

In some embodiments, the present disclosure pertains to a method of agonizing an immune response in a human being in need thereof, the method comprising the step of contacting the human with an immunologically effective amount of CpG oligonucleotide composition of any one of the preceding embodiments.

In some embodiments, the present disclosure pertains to the method of any one of the preceding embodiments, wherein the human has a disease.

In some embodiments, the present disclosure pertains to the method of any one of the preceding embodiments, wherein the human has a disease amenable to treatment with an agonized immune response.

In some embodiments, the present disclosure pertains to the method of any one of the preceding embodiments, wherein the human has a disease selected from an infectious disease, a genetic disease, and cancer.

In some embodiments, the present disclosure pertains to a method of increasing an immune response to an immunologically active component in a subject, comprising administering an immunologically effective amount of (a) a composition of any one of the preceding embodiments and (b) the immunologically active component.

In some embodiments, the present disclosure pertains to the composition of any one of the preceding embodiments, wherein the immunologically active component is selected from: an immunogen, an antigen, a toxin, a virus, a bacterium, a fungus, an infectious agent, a cancer antigen, a pathogen, and a component thereof.

In some embodiments, the present disclosure pertains to a method of identifying a second oligonucleotide composition with decreased immune stimulation in a subject compared to a first oligonucleotide composition, the method comprising steps of: (a) measuring the immune stimulation mediated by the first oligonucleotide composition, wherein the first oligonucleotide composition comprising oligonucleotides that have a common base sequence comprising at least one CpG region; (b) measuring the immune stimulation mediated by a second oligonucleotide composition, wherein the second oligonucleotide composition has the same common base sequence as the first oligonucleotide composition, and wherein the CpG region of oligonucleotides of the second composition differs in its pattern of chiral centers from the corresponding region of oligonucleotides of the first oligonucleotide composition; (c) optionally repeating step (b), each repeat with a different second oligonucleotide composition, and selecting a second oligonucleotide composition which mediates less immune stimulation than the first oligonucleotide composition. In some embodiments of the methods and compositions of the present disclosure, a CpG oligonucleotide comprises two or more CpG region motifs described herein.

In some embodiments, the present disclosure pertains to the method of any one of the preceding embodiments, wherein the first oligonucleotide is immunostimulatory in a human cell.

In some embodiments, the present disclosure pertains to the method of any one of the preceding embodiments, wherein the second oligonucleotide comprises at least one phosphorothioate in the Sp conformation and at least one phosphorothioate in the Rp conformation in the CpG region motif.

In some embodiments, the present disclosure pertains to the method of any one of the preceding embodiments, wherein the second oligonucleotide does not comprise an agonistic CpG region motif described herein.

In some embodiments, the present disclosure pertains to the method of any one of the preceding embodiments, wherein the second oligonucleotide does not comprise an antagonistic CpG region motif described herein.

In some embodiments, the present disclosure pertains to the method of any one of the preceding embodiments, wherein the second oligonucleotide does not comprise an agonistic or antagonistic CpG region motif described herein.

In some embodiments, the present disclosure pertains to a method of improving a characteristic of a CpG oligonucleotide composition comprising at least two CpG oligonucleotides, wherein the method comprises a step of: decreasing the amount in the composition of at least one of the at least two CpG oligonucleotides, wherein each of the at least two CpG oligonucleotides is defined by the stereochemistry of a CpG region motif, and wherein the at least one of the at least two CpG oligonucleotides is determined to have an inferior characteristic relative to the CpG oligonucleotide composition.

In some embodiments, the present disclosure pertains to a method of improving a characteristic of a stereorandom CpG oligonucleotide composition, wherein the method comprises a step of: decreasing the amount in the composition of at least one of the at least two CpG oligonucleotides, wherein each of the at least two CpG oligonucleotides is defined by the stereochemistry of a CpG region motif, and wherein the at least one of the at least two CpG oligonucleotides is determined to have an inferior characteristic relative to the CpG oligonucleotide composition, wherein the characteristic is increased activity, improved efficacy, reduced toxicity, increased stability, increased delivery, or increased biological half-life.

In some embodiments, the present disclosure pertains to a method of designing a second oligonucleotide mediating decreased immune stimulation in a human cell relative to the immune stimulation mediated by a first oligonucleotide, the method comprising the steps of: (a) measuring the immune stimulation mediated by a first oligonucleotide, wherein the first oligonucleotide has a defined base sequence comprising at least one CpG region; (b) measuring the immune stimulation mediated by one or more second oligonucleotides, wherein the second oligonucleotides have the same base sequence as the first oligonucleotide and further comprise one or more phosphorothioates in the CpG region motif, wherein the stereochemistry of the phosphorothioates in the CpG region motif of the second oligonucleotides differs from the stereochemistry of any phosphoroates in the CpG region motif of the first oligonucleotides, wherein steps (a) and (b) can be performed in any order; (c) selecting a second oligonucleotide which mediates less immune stimulation than the first oligonucleotide.

In some embodiments, the present disclosure pertains to the method of any one of the preceding embodiments, wherein the first oligonucleotide is immunostimulatory in a human cell.

In some embodiments, the present disclosure pertains to the method of any one of the preceding embodiments, wherein the second oligonucleotide comprises at least one phosphorothioate in the Sp conformation and at least one phosphorothioate in the Rp conformation in the CpG region motif.

In some embodiments, the present disclosure pertains to the method of any one of the preceding embodiments, wherein the second oligonucleotide does not comprise an agonistic CpG region motif described herein.

In some embodiments, the present disclosure pertains to the method of any one of the preceding embodiments, wherein the second oligonucleotide does not comprise an antagonistic CpG region motif described herein.

In some embodiments, the present disclosure pertains to the method of any one of the preceding embodiments, wherein the second oligonucleotide does not comprise an agonistic or antagonistic CpG region motif described herein.

In some embodiments, the present disclosure pertains to a method of decreasing the immune stimulation in a human cell mediated by a first oligonucleotide, the method comprising the steps of: (a) providing the first oligonucleotide, wherein the first oligonucleotide has a defined base sequence comprising at least one CpG region; and measuring the immune stimulation in a human cell mediated by the first oligonucleotide; (b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order; (c) selecting a second oligonucleotide which mediates less immune stimulation than the first oligonucleotide; and (d) contacting the cell with the second oligonucleotide.

In some embodiments, the present disclosure pertains to the method of any one of the preceding embodiments, wherein the first oligonucleotide is immunostimulatory in a human cell.

In some embodiments, the present disclosure pertains to the method of any one of the preceding embodiments, wherein the second oligonucleotide comprises at least one phosphorothioate in the Sp conformation and at least one phosphorothioate in the Rp conformation in the CpG region motif.

In some embodiments, the present disclosure pertains to the method of any one of the preceding embodiments, wherein the second oligonucleotide does not comprise an agonistic CpG region motif described herein.

In some embodiments, the present disclosure pertains to the method of any one of the preceding embodiments, wherein the second oligonucleotide does not comprise an antagonistic CpG region motif described herein.

In some embodiments, the present disclosure pertains to the method of any one of the preceding embodiments, wherein the second oligonucleotide does not comprise an agonistic or antagonistic CpG region motif described herein.

In some embodiments, the present disclosure pertains to a composition comprising an oligonucleotide, wherein the oligonucleotide mediates less immune stimulation than a reference oligonucleotide, wherein the second oligonucleotide is selected using a method comprising the steps of: (a) providing the reference oligonucleotide, wherein the reference oligonucleotide has a defined base sequence comprising at least one CpG region; and measuring the immune stimulation in a human cell mediated by the reference oligonucleotide; (b) providing one or more second oligonucleotides, wherein the second oligonucleotides have the same base sequence as the reference oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the reference oligonucleotides; and measuring the immune stimulation in a human cell of the second oligonucleotides, wherein steps (a) and (b) can be performed in any order; (c) selecting a second oligonucleotide which mediates less immune stimulation than the reference oligonucleotide.

In some embodiments, the present disclosure pertains to the method of any one of the preceding embodiments, wherein the reference oligonucleotide is immunostimulatory in a human cell.

In some embodiments, the present disclosure pertains to the method of any one of the preceding embodiments, wherein the second oligonucleotide comprises at least one phosphorothioate in the Sp conformation and at least one phosphorothioate in the Rp conformation in the CpG region motif.

In some embodiments, the present disclosure pertains to the method of any one of the preceding embodiments, wherein the second oligonucleotide does not comprise an agonistic CpG region motif described herein.

In some embodiments, the present disclosure pertains to the method of any one of the preceding embodiments, wherein the second oligonucleotide does not comprise an antagonistic CpG region motif described herein.

In some embodiments, the present disclosure pertains to the method of any one of the preceding embodiments, wherein the second oligonucleotide does not comprise an agonistic or antagonistic CpG region motif described herein.

In some embodiments, the present disclosure pertains to a method of administering a therapeutic oligonucleotide to a patient, wherein the therapeutic oligonucleotide mediates less immune stimulation than a first oligonucleotide, wherein the therapeutic oligonucleotide is selected using a method comprising the steps of: (a) providing the first oligonucleotide, wherein the first oligonucleotide has a defined base sequence comprising at least one CpG region; and measuring the immune stimulation in a human cell mediated by the first oligonucleotide; (b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order; (c) selecting a second oligonucleotide which mediates less immune stimulation than the first oligonucleotide as the therapeutic oligonucleotide.

In some embodiments, the present disclosure pertains to the method of any one of the preceding embodiments, wherein the first oligonucleotide is immunostimulatory in a human cell.

In some embodiments, the present disclosure pertains to the method of any one of the preceding embodiments, wherein the second oligonucleotide comprises at least one phosphorothioate in the Sp conformation and at least one phosphorothioate in the Rp conformation in the CpG region motif.

In some embodiments, the present disclosure pertains to the method of any one of the preceding embodiments, wherein the second oligonucleotide does not comprise an agonistic CpG region motif described herein.

In some embodiments, the present disclosure pertains to the method of any one of the preceding embodiments, wherein the second oligonucleotide does not comprise an antagonistic CpG region motif described herein.

In some embodiments, the present disclosure pertains to the method of any one of the preceding embodiments, wherein the second oligonucleotide does not comprise an agonistic or antagonistic CpG region motif described herein.

In some embodiments, the present disclosure pertains to a method, comprising administering a composition comprising a first plurality of oligonucleotides, each of which: (a) hybridizes with a particular target sequence; and (b) has base sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, wherein the composition is chirally controlled in that it contains a predetermined level of each of stereoisomers 1-8 (S1-S8) for each common CpG region motif: S1: $N_1$-(*R)—C—(*R)-G-(*R)—$N_2$; S2: $N_1$-(*R)—C—(*R)-G-(*S)—$N_2$; S3: $N_1$-(*R)—C—(*S)-G-(*R)—$N_2$; S4: $N_1$-(*R)—C—(*S)-G-(*S)—$N_2$; S5: $N_1$-(*S)—C—(*R)-G-(*R)—$N_2$; S6: $N_1$-(*S)—C—(*R)-G-(*S)—$N_2$; S7: $N_1$-(*S)—C—(*S)-G-(*R)—$N_2$; S8: $N_1$-(*S)—C—(*S)-G-(*S)—$N_2$; wherein the composition is characterized by reduced immune stimulation relative to a reference composition, which differs from the composition in that it is stereorandom with respect to internucleotidic linkages of at least one CpG region motif.

In some embodiments, the present disclosure pertains to, in some embodiments, the present disclosure pertains to, in a method of administering an oligonucleotide composition comprising a plurality of oligonucleotides having a common base sequence, the improvement that comprises: administering a composition comprising a first plurality of oligonucleotides, each of which: (a) hybridizes with a particular target sequence; and (b) has base sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, wherein the composition is chirally controlled in that it contains a predetermined level of each of stereoisomers 1-8 (S1-S8) for each common CpG region motif: S1: $N_1$-(*R)—C—(*R)-G-(*R)—$N_2$; S2: $N_1$-(*R)—C—(*R)-G-(*S)—$N_2$; S3: $N_1$-(*R)—C—(*S)-G-(*R)—$N_2$; S4: $N_1$-(*R)—C—(*S)-G-(*S)—$N_2$; S5: $N_1$-(*S)—C—(*R)-G-(*R)—$N_2$; S6: $N_1$-(*S)—C—(*R)-G-(*S)—$N_2$; S7: $N_1$-(*S)—C—(*S)-G-(*R)—$N_2$; S8: $N_1$-(*S)—C—(*S)-G-(*S)—$N_2$; wherein the composition is characterized by reduced immune stimulation relative to a reference composition, which differs from the composition in that it is stereorandom with respect to internucleotidic linkages of at least one CpG region motif.

In some embodiments, the present disclosure pertains to a method, comprising administering a chirally controlled oligonucleotide composition that is chirally controlled in that the composition comprises a predetermined level of oligonucleotides of an individual oligonucleotide type, wherein an oligonucleotide type is defined by: 1) base sequence; 2) pattern of backbone linkages; 3) pattern of backbone chiral centers; and 4) pattern of backbone phosphorus modifications; wherein each oligonucleotide of the individual oligonucleotide type independently comprises at least one copy of a CpG region motif: $N_1$-(*R/S)—C—(*R/S)-G-(*R/S)—$N_2$; wherein: each (*R/S) is independently a chiral internucleotidic linkage; oligonucleotides of the individual oligonucleotide have the common base sequence; and the chirally controlled oligonucleotide composition displays reduced immune stimulation relative to a reference oligonucleotide composition, which reference oligonucleotide composition is a stereorandom oligonucleotide composition comprising oligonucleotides having the same common base sequence, or a chirally controlled oligonucleotide composition of oligonucleotides having the same common base sequence but of a different oligonucleotide type.

In some embodiments, the present disclosure pertains to, in a method of administering an oligonucleotide composition comprising a plurality of oligonucleotides having a common base sequence, the improvement that comprises: administering a chirally controlled oligonucleotide composition that is chirally controlled in that the composition comprises a predetermined level of oligonucleotides of an individual oligonucleotide type, wherein an oligonucleotide type is defined by: 1) base sequence; 2) pattern of backbone linkages; 3) pattern of backbone chiral centers; and 4) pattern of backbone phosphorus modifications; wherein each oligonucleotide of the individual oligonucleotide type independently comprises at least one copy of a CpG region motif: $N_1$-(*R/S)—C—(*R/S)-G-(*R/S)—$N_2$; wherein: each (*R/S) is independently a chiral internucleotidic linkage; oligonucleotides of the individual oligonucleotide type have the common base sequence; and the chirally controlled oligonucleotide composition displays reduced immune stimulation relative to a reference oligonucleotide composition, which reference oligonucleotide composition is a stereorandom oligonucleotide composition comprising oligonucleotides having the same common base sequence, or a chirally controlled oligonucleotide composition of oligonucleotides having the same common base sequence but of a different oligonucleotide type.

In some embodiments, the present disclosure pertains to the method of any one of the preceding embodiments, wherein the reference oligonucleotide composition is a chirally controlled oligonucleotide composition of oligonucleotides having the same common base sequence but a different pattern of backbone chiral centers.

In some embodiments, the present disclosure pertains to the method of any one of the preceding embodiments, wherein the reference oligonucleotide composition is a chirally controlled oligonucleotide composition of oligonucleotides having the same common base sequence but a different pattern of backbone chiral centers.

In some embodiments, the present disclosure pertains to a method, comprising administering a chirally controlled oligonucleotide composition, wherein the composition comprises a plurality of oligonucleotides, each of which: (a) hybridizes with a particular target sequence; (b) has base sequence that includes at least one C residue in a CpG that is present in all oligonucleotides of the plurality (a "common C residue") and that has a 5-methyl group, a T-OMe group in its sugar moiety, or both; and (c) includes one or more chiral internucleotidic linkages, so that each oligonucleotide is a particular stereoform, characterized by its stereoidentity [stereoidentity=which stereoisomer is present at a particular chiral linkage] at each of the one or more chiral internucleotidic linkages, wherein the composition is chirally controlled in that it contains a predetermined level of each stereoform, and the composition is substantially free of those stereoforms that individually, and in the absence of other stereoforms, activate TLR9.

In some embodiments, the present disclosure pertains to, in a method comprising administering a chirally controlled oligonucleotide composition, wherein the composition comprises a plurality of oligonucleotides, each of which: (a) hybridizes with a particular target sequence; (b) has base sequence that includes at least one C residue in a CpG region motif that is present in all oligonucleotides of the plurality (a "common C residue") and that has a 5-methyl group, a T-OMe group in its sugar moiety, or both; and (c) includes one or more chiral internucleotidic linkages; the improvement that comprises administering a composition comprising a plurality of oligonucleotides, each of which: (a) hybridizes with the same target sequence; (b) has base sequence that includes the same common C residue in a CpG region motif that has a 5-methyl group, a 2'-OMe group in its sugar moiety, or both; and (c) includes one or more chiral internucleotidic linkages, so that each oligonucleotide is a particular stereoform, characterized by its stereoidentity [stereoidentity=which stereoisomer is present at a particular chiral linkage] at each of the one or more chiral internucleotidic linkages, wherein the composition is chirally controlled in that it contains a predetermined level of each stereoform, and the composition is substantially free of those stereoforms that individually, and in the absence of other stereoforms, activate TLR9.

In some embodiments, the present disclosure pertains to a method, comprising administering a composition that is chirally controlled in that the composition comprises a predetermined level of oligonucleotides of an individual oligonucleotide type, wherein an oligonucleotide type is defined by: 1) base sequence; 2) pattern of backbone linkages; 3) pattern of backbone chiral centers; and 4) pattern of backbone phosphorus modifications; wherein the base sequence includes at least one C residue in a CpG region motif that has a 5-methyl group, a 2'-OMe group in its sugar moiety, or both; and the composition is substantially free of oligonucleotides of a different oligonucleotide type having the same sequence that individually, and in the absence of other stereoforms, activate TLR9.

In some embodiments, the present disclosure pertains to, in a method comprising administering a composition of oligonucleotides of a common base sequence, wherein the common base sequence includes at least one C residue in a CpG region motif that has a 5-methyl group, a 2'-OMe group in its sugar moiety, or both; the improvement comprises administering a composition that is chirally controlled in that the composition comprises a predetermined level of oligonucleotides of an individual oligonucleotide type, wherein an oligonucleotide type is defined by: 1) base sequence; 2) pattern of backbone linkages; 3) pattern of backbone chiral centers; and 4) pattern of backbone phosphorus modifications; wherein oligonucleotides of the individual oligonucleotide type has the same common sequence, the base sequence includes the same at least one C residue in a CpG region motif that has a 5-methyl group, a 2'-OMe group in its sugar moiety, or both; and the composition is substantially free of oligonucleotides of a different oligonucleotide type having the same sequence that individually, and in the absence of other stereoforms, activate TLR9.

In some embodiments, the present disclosure pertains to a method comprising a step of administering to a subject a composition of any one of preceding embodiments.

In some embodiments, the present disclosure pertains to, in a method of agonizing an immune response in a subject, the improvement comprises: administering to the subject a composition of any one of the preceding embodiments.

In some embodiments, the present disclosure pertains to, in a method of agonizing an immune response in a human subject, the improvement comprises: administering to the subject a composition of any one of the preceding embodiments.

In some embodiments, the present disclosure pertains to the composition or method of any of the preceding embodiments, wherein the oligonucleotides are structurally identical.

In some embodiments, the present disclosure pertains to the composition or method of any of the preceding embodiments, wherein each (*R/S) is independently a phosphorothioate linkage.

In some embodiments, the present disclosure pertains to the composition or method of any of the preceding embodiments, wherein the oligonucleotides comprises an Rp phosphorothioate linkage within a CpG region motif, and an Sp phosphorothioate linkage within a CpG region motif.

In some embodiments, the present disclosure pertains to the composition or method of any of the preceding embodiments, wherein the at least one CpG region motif comprises at least comprises an Rp phosphorothioate linkage and at least one Sp phosphorothioate linkage within a CpG region motif.

In some embodiments, the present disclosure pertains to the composition or method of any of the preceding embodiments, wherein the oligonucleotides comprise at least 5 nucleotides.

In some embodiments, the present disclosure pertains to the composition or method of any of the preceding embodiments, wherein the oligonucleotides comprise no more than 49 nucleotides.

In some embodiments, the present disclosure pertains to the composition or method of any of the preceding embodiments, wherein the oligonucleotides comprise 5 or more chiral internucleotidic linkages;

In some embodiments, the present disclosure pertains to the composition or method of any of the preceding embodiments, wherein the oligonucleotides comprise 10 or more chiral internucleotidic linkages;

In some embodiments, the present disclosure pertains to the composition or method of any of the preceding embodiments, wherein the oligonucleotides comprise 15 or more chiral internucleotidic linkages.

In some embodiments, the present disclosure pertains to the composition or method of any one of the preceding embodiments, wherein one or more nucleotides in the CpG region is an RNA or DNA nucleotide.

In some embodiments, the present disclosure pertains to the composition or method of any one of the preceding embodiments, wherein at least one sugar is not modified.

In some embodiments, the present disclosure pertains to the composition or method of any one of the preceding embodiments, wherein at least one sugar is modified.

In some embodiments, the present disclosure pertains to the composition or method of any one of the preceding embodiments, wherein at least one sugar is modified, wherein the modification is 2'-OMe, 2'-MOE, 2'-F, or 2'-OR, wherein R is optionally substituted $C_{1-6}$ alkyl.

In some embodiments, the present disclosure pertains to the composition or method of any of the preceding embodiments, wherein the modification is 2'-OR, wherein R is optionally substituted $C_{1-6}$ alkyl.

In some embodiments, the present disclosure pertains to the composition or method of any one of the preceding embodiments, wherein at least five sugars are modified.

In some embodiments, the present disclosure pertains to the composition or method of any one of the preceding embodiments, wherein at least five sugars are modified, wherein the modification is 2'-OMe, 2'-MOE, 2'-F, or 2'-OR, wherein R is optionally substituted $C_{1-6}$ alkyl.

In some embodiments, the present disclosure pertains to the composition or method of any one of the preceding embodiments, wherein at least ten sugars are modified.

In some embodiments, the present disclosure pertains to the composition or method of any one of the preceding embodiments, wherein at least ten sugars are modified, wherein the modification is 2'-OMe, 2'-MOE, 2'-F, or 2'-OR, wherein R is optionally substituted $C_{1-6}$ alkyl.

In some embodiments, the present disclosure pertains to the composition or method of any one of the preceding embodiments, wherein the strand further comprises a nucleotide substitute.

In some embodiments, the present disclosure pertains to the composition or method of any one of the preceding embodiments, wherein the strand further comprises a Morpholino, PNA, LNA, BNA, TNA, GNA, ANA, FANA, CeNa, HNA or UNA.

In some embodiments, the present disclosure pertains to the composition or method of any one of the preceding embodiments, wherein at least one internucleotidic linkage is modified.

In some embodiments, the present disclosure pertains to the composition or method of any one of the preceding embodiments, wherein at least one internucleotidic linkage is selected from: phosphorodithioate, phosphoramidate, boranophosphonoate, an amide linker, or a compound of formula (I): (I), where R3 is selected from O", S", NH$_2$, BH$_3$, CH$_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and NH2; and R4 is selected from O, S, NH, or CH$_2$.

In some embodiments, the present disclosure pertains to the composition or method of any one of the preceding embodiments, wherein at least one internucleotidic linkage is phosphorodithioate.

In some embodiments, the present disclosure pertains to the composition or method of any one of the preceding embodiments, wherein the CpG oligonucleotide further comprises a second strand.

In some embodiments, the present disclosure pertains to the composition or method of any one of the preceding embodiments, wherein the CpG oligonucleotide is capable of agonizing an immune response.

In some embodiments, the present disclosure pertains to the composition or method of any one of the preceding embodiments, wherein the CpG oligonucleotide is capable of agonizing an immune response in human cells.

In some embodiments, the present disclosure pertains to the composition or method of any one of the preceding embodiments, wherein the immune response is agonized in a human cell or human.

In some embodiments, the present disclosure pertains to the composition or method of any one of the preceding embodiments, wherein the CpG oligonucleotide further comprises a second strand.

In some embodiments, the present disclosure pertains to the composition or method of any one of the preceding embodiments, wherein each oligonucleotide in the plurality/composition has the same base sequence In some embodiments, the present disclosure pertains to the composition or method of any one of the preceding embodiments, wherein, for at least one common CpG region motif, the composition is substantially free of at least stereoisomer S8, so that the predetermined level is considered to be substantially zero.

In some embodiments, the present disclosure pertains to the composition or method of any one of the preceding embodiments, wherein, for at least one common CpG region motif, the composition is substantially free of at least seven of the stereoisomers, so that the predetermined level is considered to be substantially zero for seven of the stereoisomers.

In some embodiments, the present disclosure pertains to the composition or method of any one of the preceding embodiments, wherein each oligonucleotide in the composition includes at least one non-chiral internucleosidic linkage outside of the CpG region motif.

In some embodiments, the present disclosure pertains to the composition or method of any one of the preceding embodiments, wherein the composition is substantially racemic for at least one chiral internucleosidic linkage outside of the CpG region motif.

In some embodiments, the present disclosure pertains to the composition or method of any one of the preceding embodiments, wherein the CpG region motifs "C" residue is methylated and the composition is substantially free of at least stereoisomers.

In some embodiments, the present disclosure pertains to the composition or method of any one of the preceding embodiments, wherein the composition is capable of activating an TLR9-associated or TLR9-mediated immune response less than a stereorandom composition of oligonucleotides having the same sequence.

In some embodiments, the present disclosure pertains to the composition or method of any one of the preceding embodiments, wherein the C residue in the CpG region motif comprises a 2'-OMe group in its sugar moiety . . . .

In some embodiments, the present disclosure pertains to the composition or method of any one of the preceding embodiments, wherein the C residue in the CpG region motif is a 5-methyl-2'-OMe C residue In some embodiments, the present disclosure pertains to the composition or method of any one of the preceding embodiments, wherein one or more nucleotides in the CpG region is RNA or DNA.

In some embodiments, the present disclosure pertains to the composition or method of any one of the preceding embodiments, wherein at least one sugar is not modified.

In some embodiments, the present disclosure pertains to the composition or method of any one of the preceding embodiments, wherein at least one sugar is modified.

In some embodiments, the present disclosure pertains to the composition or method of any one of the preceding embodiments, wherein at least one sugar is modified, wherein the modification is 2'-OMe, 2'-MOE, 2'-F, or 2'-OR, wherein R is optionally substituted $C_{1-6}$ alkyl.

In some embodiments, the present disclosure pertains to the composition or method of any one of the preceding embodiments, wherein at least five sugars are modified.

In some embodiments, the present disclosure pertains to the composition or method of any one of the preceding embodiments, wherein at least five sugars are modified, wherein the modification is 2'-OMe, 2'-MOE, 2'-F, or 2'-OR, wherein R is optionally substituted $C_{1-6}$ alkyl.

In some embodiments, the present disclosure pertains to the composition or method of any one of the preceding embodiments, wherein at least ten sugars are modified.

In some embodiments, the present disclosure pertains to the composition or method of any one of the preceding embodiments, wherein at least ten sugars are modified, wherein the modification is 2'-OMe, 2'-MOE, 2'-F, or 2'-OR, wherein R is optionally substituted $C_{1-6}$ alkyl.

In some embodiments, the present disclosure pertains to the composition or method of any one of the preceding embodiments, wherein the strand comprises a nucleotide substitute.

In some embodiments, the present disclosure pertains to the composition or method of any one of the preceding embodiments, wherein the strand further comprises a Morpholino, PNA, LNA, BNA, TNA, GNA, ANA, FANA, CeNa, HNA or UNA.

In some embodiments, the present disclosure pertains to the composition or method of any one of the preceding embodiments, wherein at least one internucleotidic linkage is modified.

In some embodiments, the present disclosure pertains to the composition or method of any one of the preceding embodiments, wherein at least one internucleotidic linkage is selected from: phosphorodithioate, phosphoramidate, boranophosphonate, an amide linker, or a compound of formula (I): (I), where R3 is selected from O", S", $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and NH2; and R4 is selected from O, S, NH, or $CH_2$.

In some embodiments, the present disclosure pertains to the composition or method of any one of the preceding embodiments, further comprising a immunologically active component.

In some embodiments, the present disclosure pertains to the composition or method of any one of the preceding embodiments, further comprising a immunologically active component selected from: an immunogen, an antigen, a toxin, a virus, a bacterium, a fungus, an infectious agent, a cancer antigen, a pathogen, and a component thereof.

In some embodiments, the present disclosure pertains to the composition or method of any one of the preceding embodiments, further comprising a immunologically active component, wherein the CpG oligonucleotide is conjugated to the immunologically active component.

In some embodiments, the present disclosure pertains to the composition or method of any one of the preceding embodiments, further comprising a immunologically active component selected from: an immunogen, an antigen, a toxin, a virus, a bacterium, a fungus, an infectious agent, a cancer antigen, a pathogen, and a component thereof, wherein the CpG oligonucleotide is conjugated to the immunologically active component.

In some embodiments, the present disclosure pertains to the composition or method of any one of the preceding embodiments, further comprising an additional adjuvant, a stabilizer, a preservative, or an antibiotic.

In some embodiments, the present disclosure pertains to the composition or method of any one of the preceding embodiments, wherein *R is a modified internucleotidic linkage in the Rp conformation, *S is a modified internucleotidic linkage in the Sp conformation, and *R/S is a modified internucleotidic linkage in the Rp or Sp conformation.

In some embodiments, the present disclosure pertains to the composition or method of any one of the preceding embodiments, wherein *R is a phosphorothioate in the Rp conformation, *S is a phosphorothioate in the Sp conformation, and *R/S is phosphorothioate in the Rp or Sp conformation.

In some embodiments, the present disclosure pertains to a chirally controlled oligonucleotide composition comprising a CpG oligonucleotide comprising a strand comprising about 14 to about 49 nucleotides, wherein the strand comprises at least two copies of CpG region motif $N_1$-(*R/S)—C—(*R/S)-G-(*R/S)—$N_2$, wherein at least one (*R/S) is a modified internucleotidic linkage in the Rp conformation and at least one (*R/S) is a modified internucleotidic linkage in the Sp conformation, and each of $N_1$ and $N_2$ is independently any nucleoside.

In some embodiments, the present disclosure pertains to a chirally controlled oligonucleotide composition comprising a CpG oligonucleotide comprising a strand comprising about 14 to about 49 nucleotides, wherein the strand comprises at least two copies of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and each of $N_1$ and $N_2$ is independently any nucleoside.

In some embodiments, the present disclosure pertains to a composition comprising a CpG oligonucleotide comprising a strand comprising about 14 to about 49 nucleotides, wherein the strand comprises at least two copies of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and each of $N_1$ and $N_2$ is independently any nucleoside.

In some embodiments, the present disclosure pertains to the method or composition of any of the preceding embodiments, wherein the CpG oligonucleotide comprises two or more copies of a CpG region motif.

In some embodiments, the present disclosure pertains to the method or composition of any of the preceding embodiments, wherein the CpG oligonucleotide comprises two or more copies of a CpG region motif disclosed herein.

In some embodiments, the present disclosure pertains to the method or composition of any of the preceding embodiments, wherein the CpG oligonucleotide comprises two or more CpG region motifs disclosed herein.

In some embodiments, the present disclosure pertains to the method or composition of any of the preceding embodiments, wherein the CpG oligonucleotide comprises two or more CpG region motifs disclosed herein, wherein the motifs are different from each other.

In some embodiments, the present disclosure pertains to the method or composition of any of the preceding embodiments, wherein the CpG oligonucleotide comprises two or more CpG region motifs disclosed herein, wherein the motifs are the same as each other.

In some embodiments, the present disclosure pertains to the method or composition of any of the preceding embodiments, wherein the CpG oligonucleotide is agonistic.

In some embodiments, the present disclosure pertains to the method or composition of any of the preceding embodiments, wherein the CpG oligonucleotide is agonistic in human cells.

In some embodiments, the present disclosure pertains to the method or composition of any of the preceding embodiments, wherein the CpG oligonucleotide is agonistic, as measured by an increase in secretion of a cytokine, interferon-alpha, interferon-gamma, IL-4, IL-6, IL-8, IL-10, IL-12, and/or TNF-alpha, and/or an increase in NF-κβ activity.

In some embodiments, the present disclosure pertains to the method or composition of any of the preceding embodiments, wherein the CpG oligonucleotide is antagonistic.

In some embodiments, the present disclosure pertains to the method or composition of any of the preceding embodiments, wherein the CpG oligonucleotide is antagonistic in human cells.

In some embodiments, the present disclosure pertains to the method or composition of any of the preceding embodiments, wherein the CpG oligonucleotide is antagonistic, as measured by a decrease in secretion of a cytokine, interferon-alpha, interferon-gamma, IL-4, IL-6, IL-8, IL-10, IL-12, and/or TNF-alpha, and/or an increase in NF-κβ activity.

BRIEF DESCRIPTION OF THE DRAWING

In FIG. 1 and various other figures, agonistic activity of CpG oligonucleotides was measured as an increase in NF-κβ activity. In various figures, antagonistic activity of CpG oligonucleotides was measured as a decrease in NF-κβ activity (in competition with a TLR9 agonist, e.g. ODN2006 for human studies, or ODN1826 for mouse studies). FIG. 1 discloses SEQ ID NOS 1768 and 1770, respectively, in order of appearance.

FIG. 2 discloses SEQ ID NOS 1757, 1759 and 1768, respectively, in order of appearance.

FIG. 3 discloses SEQ ID NOS 1759, 1758, 1768 and 1777, respectively, in order of appearance.

FIG. 4 discloses SEQ ID NOS 1775, 1777 and 1776, respectively, in order of appearance.

FIG. 6 discloses SEQ ID NOS 1759, 1761, 1760, 1764 and 1765, respectively, in order of appearance.

FIG. 7 discloses SEQ ID NOS 1781-1788, respectively, in order of appearance.

FIG. 8 discloses SEQ ID NOS 1789-1791, 1793 and 1795, respectively, in order of appearance.

FIG. 9 discloses SEQ ID NOS 1768 and 1770, respectively, in order of appearance.

FIG. 10 discloses SEQ ID NOS 1805 and 1808-1812, respectively, in order of appearance.

FIG. 11 discloses SEQ ID NOS 1805 and 1807, respectively, in order of appearance.

FIG. 12 discloses SEQ ID NOS 1806 and 1809, respectively, in order of appearance.

FIG. 13 discloses SEQ ID NOS 1806 and 1809, respectively, in order of appearance.

FIG. 14 discloses SEQ ID NOS 1799, 1800, 1815 and 1816, respectively, in order of appearance.

FIG. 15 discloses SEQ ID NOS 1799-1804, respectively, in order of appearance.

FIG. 16 discloses SEQ ID NOS 1817 and 1818, respectively, in order of appearance.

FIG. 17 discloses SEQ ID NOS 1796 and 1798-1800, respectively, in order of appearance.

FIG. 18 discloses SEQ ID NOS 1796, 1798-1800, 1817 and 1818, respectively, in order of appearance.

FIG. 21 discloses SEQ ID NOS 1797, 1834, 1796 and 1798-1800, respectively, in order of appearance.

DETAILED DESCRIPTION OF CERTAIN EMBODIMENTS

Terms and Definitions

Figure 1:
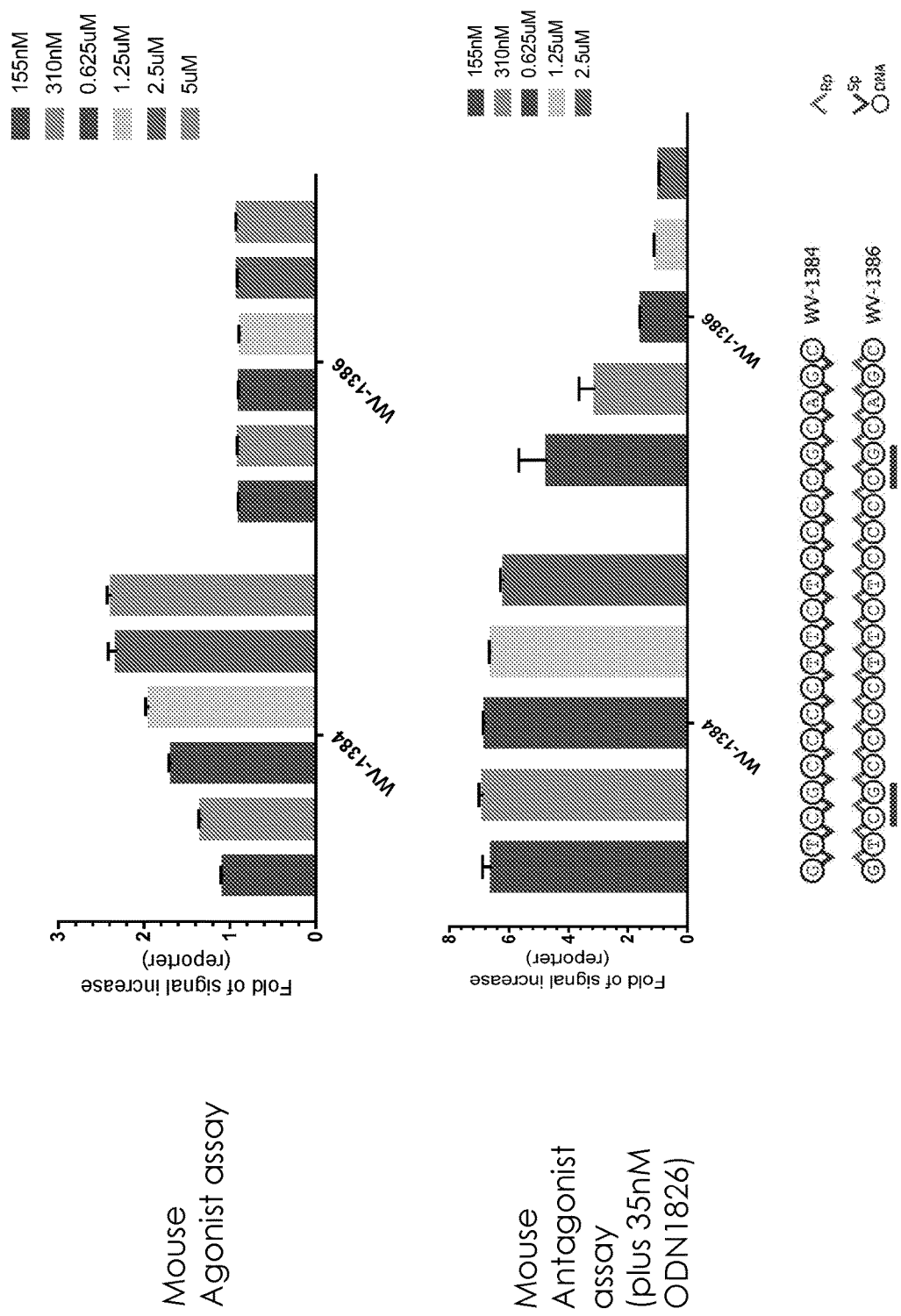
FIG. 1 shows that stereochemistry of the backbone of the CpG oligonucleotide affects mouse TLR9 activities in agonist and antagonist assays; data from SMAD7 series. The CpG dinucleotide is underlined.

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Nucleic acid. The term "nucleic acid", as used herein, includes any dimer, trimer, tetramer or polymer comprising nucleotides, modified nucleotides and/or nucleotide analogs. The term "polynucleotide" as used herein refers to a polymeric form of any length of nucleotides, modified nucleotides and/or nucleotide analogs, including ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges or internucleotidic linkage. The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. In some embodiments, the prefix poly- refers to a nucleic acid containing 2 to about 10,000 nucleotide monomer units and wherein the prefix oligo- refers to a nucleic acid containing 2 to about 200 nucleotide monomer units. In some embodiments, a nucleic acid includes, but is not limited to, deoxyribonucleotides or ribonucleotides and polymers thereof, for example, in at least partially single- or double-stranded form. In some embodiments, a nucleic acid includes any nucleotides, modified nucleotides, and/or nucleotide analogs, and polymers thereof. In some embodiments, a polynucleotide includes a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. Analogs of RNA and DNA (e.g., nucleotide analogs) include, but are not limited to: Morpholino, PNA, LNA, BNA, TNA, GNA, ANA, FANA, CeNa, HNA and UNA. Modified nucleotides include those which are modified in the phosphate, sugar, and/or base. Such modifications include sugar modifications at the 2' carbon, such as 2'-MOE, 2'-OMe, and 2'-F. In some embodiments, a nucleic acid includes a poly- or oligo-ribonucleotide (RNA) and poly- or oligo-deoxyribonucleotide (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges or internucleotidic linkage. The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. In some embodiments, a nucleic acid is an oligonucleotide, an antisense oligonucleotide, an RNAi agent, a miRNA, splice switching oligonucleotide (SSO), immunomodulatory nucleic acid, an aptamer, a ribozyme, a Piwi-interacting RNA (piRNA), a small nucleolar RNA (snoRNA), a mRNA, a lncRNA, a ncRNA, an antigomir (e.g., an antagonist to a miRNA, lncRNA, ncRNA or other nucleic acid), a plasmid, a vector, or a portion thereof. In some embodiments, a nucleic acid is a chirally controlled nucleic acid composition. In some embodiments, a nucleic acid is a chirally controlled oligonucleotide composition, or a chirally controlled nucleic acid composition. In some embodiments, a base, nucleobase, nitrogenous base, heterocyclic base and the like includes a part (or a modified variant thereof) of a nucleic acid that is involved in the hydrogen-bonding that binds one nucleic acid strand to another complementary strand in a sequence-specific manner. The naturally occurring bases, [guanine, (G), adenine, (A), cytosine, (C), thymine, (T), and uracil (U)] are derivatives of purine (Pu) or pyrimidine (Py), though it should be understood that naturally and non-naturally occurring base analogs are also included. In some embodiments, the nucleobases are modified adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. Various additional modifications of the bases are known in the art. In some cases, a nucleic acid sequence can be defined as a sequence of bases, generally presented in the 5' to 3' direction. While in the context of a nucleic acid, a base is normally conjugated to a sugar which forms the backbone along with an internucleotidic linkage (e.g., a phosphate or phosphorothioate or other modified internucleotidic linkage); however, as used herein, the term "base" does not comprise a sugar or an internucleotidic linkage. In some embodiments, a nucleoside includes a unit consisting of: (a) a base covalently bound to (b) a sugar. The base and/or sugar can be modified or not modified. In some embodiments, a sugar, as referenced herein in the context of referencing a nucleic acid, includes a monosaccharide in closed and/or open form. The naturally occurring sugar is the pentose (five-carbon sugar) deoxyribose (which forms DNA) or ribose (which forms RNA), though it should be understood that naturally and non-naturally occurring sugar analogs are also included. Sugars include, but are not limited to, ribose, deoxyribose, pentofuranose, pentopyranose, and hexopyranose moieties. As used herein, the term also encompasses structural analogs used in lieu of conventional sugar molecules, such as glycol, polymer of which forms the backbone of the nucleic acid analog, glycol nucleic acid ("GNA"). A deoxynucleoside comprises a deoxyribose. In some cases, a nucleic acid sequence can be defined as a sequence of bases and sugar modifications. In some embodiments, a sugar includes a modified sugar or unmodified sugar. In some embodiments, a modified sugar includes, as referenced in the context of a nucleic acid, a sugar which has been modified or a moiety that can functionally replace a sugar in a nucleic acid or modified nucleic acid. The modified sugar mimics the spatial arrangement, electronic properties, or some other physicochemical property of a sugar. A modified sugar, as a non-limiting example, can have a modification at the 2' carbon. Various modifications include 2'-MOE, 2'-OMe and 2'-F. Various additional modifications of the sugar are known in the art. In some embodiments, a nucleotide includes a monomeric unit of a polynucleotide that consists of: (a) a heterocyclic base, a sugar, and one or more phosphate groups or phosphorus-containing internucleotidic linkages; a nucleotide is a subunit of a polynucleotide, nucleic acid or oligonucleotide. Each base, sugar and phosphate or internucleoside linker can be independently modified or not modified. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. In some embodiments, an internucleotidic linkage includes linkage between nucleoside units of an oligonucleotide; in most cases the linkage comprises a phosphorus or linkage phosphorus; in some embodiments, the linkage is referred to as "p". In some embodiments, an internucleotidic linkage is a phosphodiester linkage, as found in naturally occurring DNA and RNA molecules. In some embodiments, the linkage is a phosphorothioate. In some embodiments, the backbone of an oligonucleotide or a nucleic acid includes the alternating sugars and internucleotidic linkages (e.g., a phosphodiester or phosphorothioate). Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Also included are molecules having naturally occurring phosphodiester linkages as well as those having non-naturally occurring linkages, e.g., for stabilization purposes. The nucleic acid can be in any physical form, e.g., linear, circular, nicked, or supercoiled. The term nucleic acid is used interchangeably with oligonucleotide, gene, cDNA, and mRNA encoded by a gene. In various embodiments, one or more nucleotides is modified or is substituted with one or more DNA, a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), constrained ethyl (cEt), tricyclo-DNA (tc-DNA), xeno nucleic acid (XNA), and/or unlocked nucleic acid (UNA). In various embodiments, the nucleic acid comprises a modified internucleoside linker.

Nucleotide: The term "nucleotide" as used herein refers to a monomeric unit of a polynucleotide that consists of a heterocyclic base, a sugar, and one or more phosphate groups or phosphorus-containing internucleotidic linkages. The naturally occurring bases, (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. As described herein, in some embodiments, a nucleotide is a natural nucleotide; in some embodiments, a nucleotide is modified.

Nucleoside: The term "nucleoside", as used herein, refers to a moiety wherein a nucleobase or a modified nucleobase is covalently bound to a sugar or modified sugar.

Sugar: The term "sugar", as used herein, refers to a saccharide, in some embodiments, a monosaccharide in closed and/or open form. Sugars include, but are not limited to, ribose, deoxyribose, pentofuranose, pentopyranose, and hexopyranose moieties. As used herein, the term also encompasses structural analogs used in lieu of conventional sugar molecules, such as glycol, polymer of which forms the backbone of the nucleic acid analog, glycol nucleic acid ("GNA").

Modified sugar: The term "modified sugar", as used herein, refers to a moiety that can replace a sugar, in some embodiments, in oligonucleotides. The modified sugar mimics the spatial arrangement, electronic properties, or some other physicochemical property of a sugar. In some embodiments, a modified sugar comprises a modification at a 2' carbon. In some embodiments, a modified sugar comprises a 2'-F, 2'-OMe or 2'-MOE.

Nucleobase: The term "nucleobase", as used herein, refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex.

DNA and other terms: The terms "DNA", "DNA molecule" and the like, as used herein, refer to a polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

Chiral ligand: The term "chiral ligand" or "chiral auxiliary", as used herein, refers to a moiety that is chiral and can be incorporated into a reaction so that the reaction can be carried out with certain stereoselectivity.

Condensing reagent: In a condensation reaction, the term "condensing reagent", as used herein, refers to a reagent that activates a less reactive site and renders it more susceptible to attack by another reagent. In some embodiments, such another reagent is a nucleophile.

Blocking group: The term "blocking group", as used herein, refers to a group that masks the reactivity of a functional group. The functional group can be subsequently unmasked by removal of the blocking group. In some embodiments, a blocking group is a protecting group.

Moiety: The term "moiety", as used herein, refers to a specific segment or functional group of a molecule. Chemical moieties are often recognized chemical entities embedded in or appended to a molecule.

Solid support: The term "solid support", as used herein, refers to any support which enables synthesis of nucleic acids. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Coding sequence: A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence is, usually, be located 3' to the coding sequence. The term "non-coding sequence" or "non-coding region" refers to regions of a polynucleotide sequence that are not translated into amino acids (e.g. 5' and 3' un-translated regions).

Reading frame: The term "reading frame", as used herein, refers to one of the six possible reading frames, three in each direction, of the double stranded DNA molecule. The reading frame that is used determines which codons are used to encode amino acids within the coding sequence of a DNA molecule.

Antisense: The term "antisense", as used herein, for example, in reference to a nucleic acid, refers to a nucleic acid molecule which comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can associate via hydrogen bonds to a sense nucleic acid molecule. In some embodiments, an antisense oligonucleotide is capable of annealing to a target mRNA in a sequence-specific manner and mediating degradation of the mRNA via a RNaseH-dependent mechanism. In some embodiments, an antisense nucleic acid includes, as a non-limiting example, an antisense strand of a siRNA or other RNAi agent, which is capable of anneal to a target mRNA in a sequence-specific manner and mediating degradation of the mRNA via a RISC (RNA inhibition silencing complex)-mediated mechanism. In some embodiments, an antisense strand of a siRNA or other RNAi agent is annealed to a corresponding sense strand; in some embodiments, an antisense strand of a siRNA or other RNAi agent is not annealed to a corresponding sense strand.

Homology: The terms "Homology" or "identity" or "similarity", as used herein, refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity. In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, wordlength=12 to obtain nucleotide sequences homologous to nucleic acid molecules of the disclosure. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

Heterologous: A "heterologous" region of a DNA sequence is an identifiable segment of DNA within a larger DNA sequence that is not found in association with the larger sequence in nature. Thus, when the heterologous region encodes a mammalian gene, the gene can usually be flanked by DNA that does not flank the mammalian genomic DNA in the genome of the source organism. Another example of a heterologous coding sequence is a sequence where the coding sequence itself is not found in nature (e.g., a cDNA where the genomic coding sequence contains introns or synthetic sequences having codons or motifs different than the unmodified gene). Allelic variations or naturally-occurring mutational events do not give rise to a heterologous region of DNA as defined herein.

Oligonucleotide: The term "oligonucleotide", as used herein, refers to a polymer or oligomer of nucleotide monomers, containing any combination of nucleobases, modified nucleobases, sugars, modified sugars, phosphate bridges, or modified phosphorus atom bridges (also referred to herein as "internucleotidic linkage", defined further herein).

Oligonucleotides can be single-stranded or double-stranded. As used herein, the term "oligonucleotide strand" encompasses a single-stranded oligonucleotide. A single-stranded oligonucleotide can have double-stranded regions and a double-stranded oligonucleotide can have single-stranded regions. Example oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, aptamers, antimirs, antagomirs, U1 adaptors, triplex-forming oligonucleotides, G-quadruplex oligonucleotides, RNA activators, immuno-stimulatory oligonucleotides, and decoy oligonucleotides.

Double-stranded and single-stranded oligonucleotides that are effective in inducing RNA interference are also referred to as siRNA, RNAi agent, or iRNA agent, herein. In some embodiments, these RNA interference inducing oligonucleotides associate with a cytoplasmic multi-protein complex known as RNAi-induced silencing complex (RISC). In many embodiments, single-stranded and double-stranded RNAi agents are sufficiently long that they can be cleaved by an endogenous molecule, e.g., by Dicer, to produce smaller oligonucleotides that can enter the RISC machinery and participate in RISC mediated cleavage of a target sequence, e.g. a target mRNA.

Oligonucleotides of the present disclosure can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length. In some embodiments, a sequence of a nucleic acid or an oligonucleotide comprises or consists of a common base sequence hybridizes with a transcript of dystrophin, myostatin, Huntingtin, a myostatin receptor, ActRIIB, ActRIIA, DMPK, SMN2, dystrophia myotonica protein kinase (DMPK), Proprotein convertase subtilisin/kexin type 9 (PCSK9), SMAD7 or KRT14 (Keratin 14). In some embodiments, a sequence of a nucleic acid or an oligonucleotide comprises or consists of a common base sequence hybridizes with a transcript of a gene related to Huntington's disease, spinal muscular atrophy, spinal muscular atrophy type 1, amyotrophic lateral sclerosis, Duchenne muscular dystrophy, myotonic dystrophy, myotonic dystrophy type 1, a genetic disease of the liver, a metabolic disease of the liver, epidermolysis bullosa simplex, a genetic disease of the skin, a genetic disease of the skin, or irritable bowel syndrome, or a genetic disease, or a metabolic disease.

Internucleotidic linkage: As used herein, the phrase "internucleotidic linkage", "internucleotidic linker" and the like refer generally to a linkage, including but not limited to a phosphorus-containing linkage, between nucleotide units of an oligonucleotide, and is interchangeable with "inter-sugar linkage" and "phosphorus atom bridge," as used above and herein. In some embodiments, an internucleotidic linkage is a phosphodiester linkage, as found in naturally occurring DNA and RNA molecules. In some embodiments, a modified internucleotidic linkage is an internucleotidic linkage which is not phosphorodiester. In some embodiments, an internucleotidic linkage is a "modified internucleotidic linkage", wherein the internucleotidic linkage is not phosphodiester. In some embodiments of a modified internucleotidic linkage, each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —N(R')$_2$, B(R')$_3$—S—, —Se—, and —N(R')—, wherein each R' is independently as defined and described below. In some embodiments, a modified internucleotidic linkage is a phosphotriester linkage, phosphorothioate diester linkage

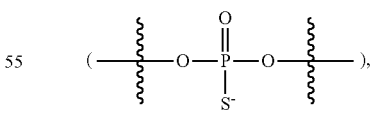

or modified phosphorothioate triester linkage. It is understood by a person of ordinary skill in the art that the internucleotidic linkage can exist as an anion or cation at a given pH due to the existence of acid or base moieties in the linkage.

Unless otherwise specified, when used with an oligonucleotide sequence, each of s, s1, s2, s3, s4, s5, s6 and s7 independently represents the following modified internucleotidic linkage as illustrated below:

Example Modified Internucleotidic Linkage.
| Symbol | Modified Internucleotidic Linkage |
|---|---|
| s | |
| s1 | |
| s2 | |
| s3 | |
| s4 | |
| s5 | |
| s6 | |
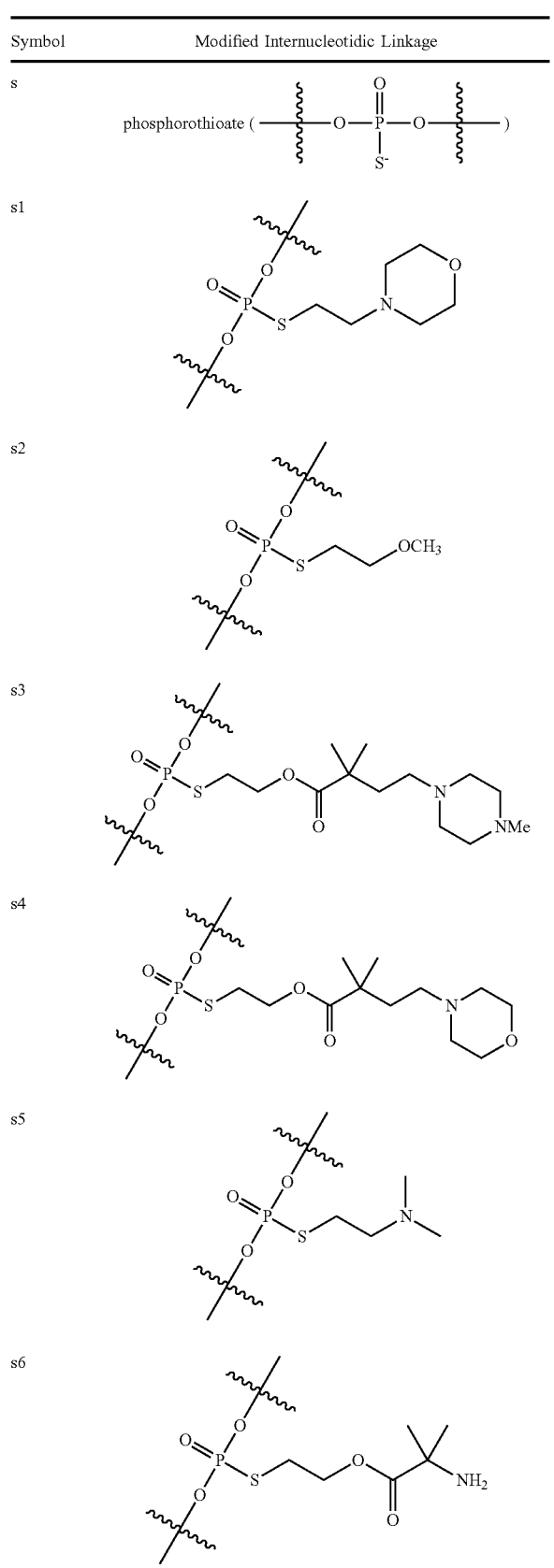
-continued
| Symbol | Modified Internucleotidic Linkage |
|---|---|
| s7 | |
| s8 | |
| s9 | |
| s10 | |
| s11 | |
| s12 | |
| s13 | |
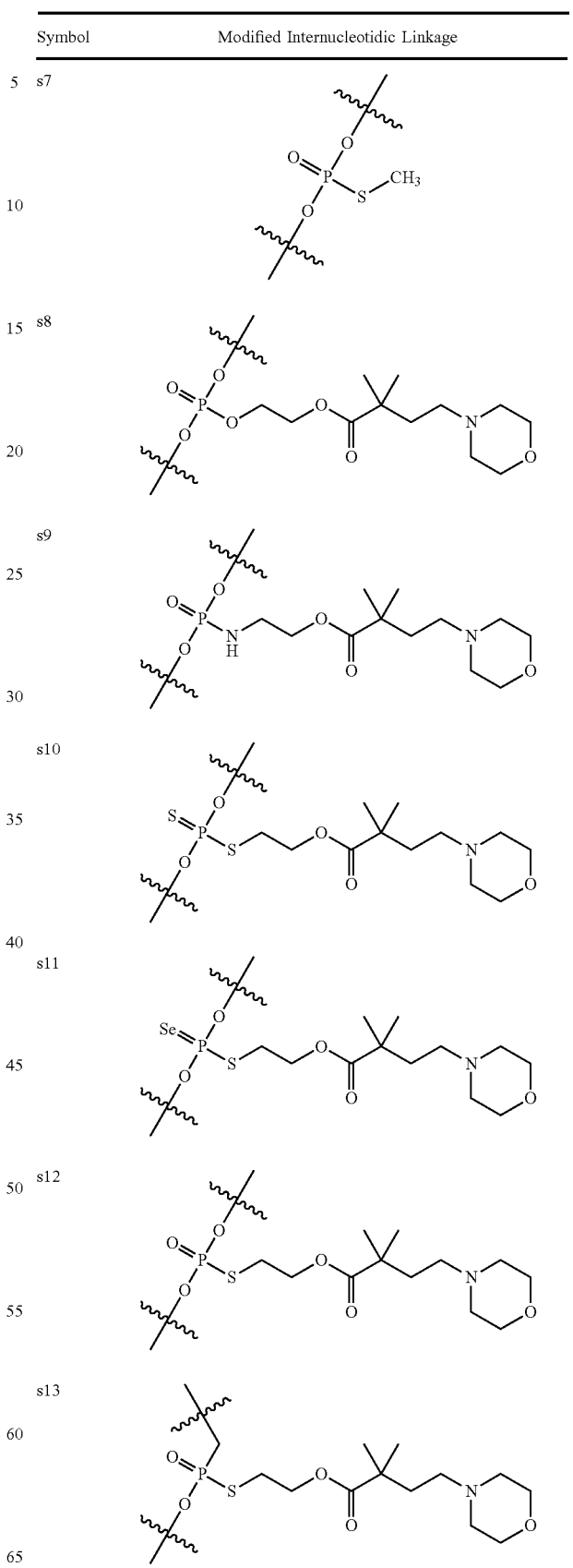

| Symbol | Modified Internucleotidic Linkage |
|---|---|
| s14 | 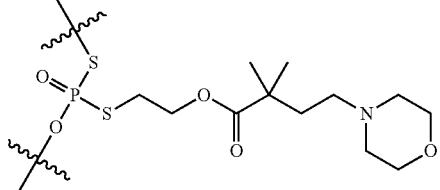 [SMILES: *CP(=O)(O*)SCCOC(=O)C(C)(C)CCN1CCOCC1] |
| s15 | 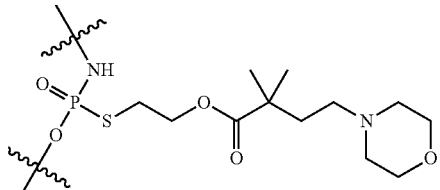 |
| s16 | 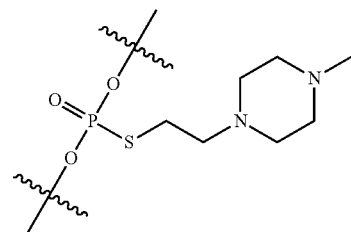 [SMILES: *OP(=O)(O*)SCCN1CCN(C)CC1] |
| s17 | 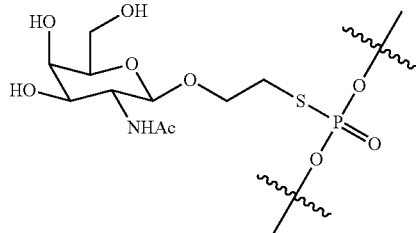 [SMILES: *OP(=O)(O*)SCCOC1OC(CO)C(O)C(O)C1NC(C)=O] |
| s18 | 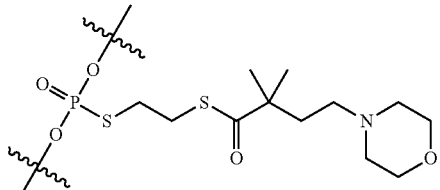 |

Additional modified internucleotidic linkages are described by formula I.

As a non-limiting example, (Rp, Sp)-ATsCs1GA has 1) a phosphorothioate internucleotidic linkage

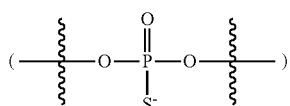

between T and C; and 2) a phosphorothioate triester internucleotidic linkage having the structure of

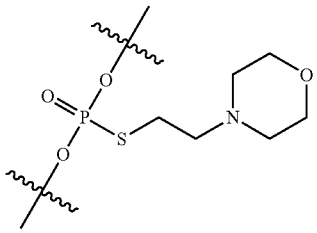 [SMILES: *OP(=O)(O*)SCCN1CCOCC1]

between C and G. Unless otherwise specified, the Rp/Sp designations preceding an oligonucleotide sequence describe the configurations of chiral linkage phosphorus atoms in the internucleotidic linkages sequentially from 5' to 3' of the oligonucleotide sequence. For instance, in (Rp, Sp)-ATsCs1GA, the phosphorus in the "s" linkage between T and C has Rp configuration and the phosphorus in "s1" linkage between C and G has Sp configuration. In some embodiments, "All-(Rp)" or "All-(Sp)" is used to indicate that all chiral linkage phosphorus atoms in oligonucleotide have the same Rp or Sp configuration, respectively. For instance, All-(Rp)-GsCsCsTsCsAsGsTsCsTsGsCsTsT-sCsGsCsAsCsC (SEQ ID NO: 4) indicates that all the chiral linkage phosphorus atoms in the oligonucleotide have Rp configuration; All-(Sp)-GsCsCsTsCsAsGsTsCsTsGsCsTsT-sCsGsCsAsCsC (SEQ ID NO: 5) indicates that all the chiral linkage phosphorus atoms in the oligonucleotide have Sp configuration. In some embodiments, in a modified internucleotidic linkage, a non-bridging oxygen in a phosphodiester is replaced by sulfur. In some embodiments, a modified internucleotidic linkage is a phosphorothioate. In some embodiments, in a modified internucleotidic linkage, both non-bridging oxygens in a phosphodiester are replaced by sulfur. In some embodiments, a modified internucleotidic linkage is a phosphorodithioate. In some embodiments, in a modified internucleotidic linkage, a bridging oxygen of the phosphodiester is replaced by sulfur. In some embodiments, a modified internucleotidic linkage is a phosphorothioic ether. In some embodiments, in a modified internucleotidic linkage, both bridging oxygens of the phosphodiester are replaced by sulfur. In some embodiments, in a modified internucleotidic linkage, a non-bridging oxygen in the phosphodiester is replaced by carbon. In some embodiments, in a modified internucleotidic linkage, any one or more oxygen is replaced by another atom which is not oxygen. In some embodiments, in a modified internucleotidic linkage, the phosphorus is replaced by another atom which is not phosphorus. In some embodiments, in a modified internucleotidic linkage, any one or more oxygens and the phosphorus are replaced by atoms which are not oxygen or phosphorus, respectively.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "—XLR[1]" groups in formula I). In some embodiments, oligonucleotides of a common designated "type" are structurally identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. The present disclosure provides compositions comprising or consisting of a plurality of oligonucleotide molecules (e.g., chirally controlled oligonucleotide compositions). In some embodiments, all of most of such molecules are of the same type. In some embodiments, provided compositions comprise a plurality of oligonucleotides of different types, typically in pre-determined relative amounts.

Chiral control: As used herein, "chiral control" refers to an ability to control the stereochemical designation of a chiral modified internucleotidic linkage, e.g., a linkage phosphorus, in a chiral internucleotidic linkage within an oligonucleotide. In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure.

Chirally controlled oligonucleotide composition: The terms "chirally controlled oligonucleotide composition", "chirally controlled nucleic acid composition", "chirally controlled oligonucleotide composition" and the like, as used herein, refers to a composition that comprising a plurality of oligonucleotides (or nucleic acids) which share 1) a common base sequence, 2) a common pattern of backbone linkages, and 3) a common pattern of backbone phosphorus modifications, wherein the plurality of oligonucleotides share the same stereochemistry at one or more chiral internucleotidic linkages (chirally controlled internucleotidic linkages), and the level of the plurality of oligonucleotides in the composition is pre-determined. In some embodiments, each chiral internucleotidic linkage is a chiral controlled internucleotidic linkage, and the composition is a completely chirally controlled oligonucleotide composition. In some embodiments, not all of most of chiral internucleotidic linkages are chiral controlled internucleotidic linkages, and the composition is a partially chirally controlled oligonucleotide composition. In some embodiments, a chirally controlled oligonucleotide composition comprises predetermined levels of individual oligonucleotide type or nucleic acids types. For instance, in some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises multiple oligonucleotide types. In some embodiments, in a chirally controlled oligonucleotide composition, the conformation (e.g., Rp or Sp) of each phosphorothioate or other internucleotidic linkage is defined. In some embodiments, in a chirally controlled oligonucleotide composition, the conformation (Rp or Sp) of at least one phosphorothioate or other internucleotidic linkage is defined, but the conformation of at least one phosphorothioate or other internucleotidic linkage is not defined. As a non-limiting example, in some embodiments, in a chirally controlled oligonucleotide composition, the conformation of the phosphorothioate or other internucleotidic linkage at one or more position can be defined (e.g., as Rp or rip); however, at one or more other positions, the conformation of the phosphorothioate or other internucleotidic linkage is not defined (e.g., the composition comprises a mixture of molecules wherein some have a phosphorothioate or other internucleotidic linkage in the Rp conformation and some in the rip conformation at that position).

Chirally pure: As used herein, the phrase "chirally pure" is used to describe a chirally controlled oligonucleotide composition, or a plurality of oligonucleotides, in which all or most of the oligonucleotides exist in a single diastereomeric form with respect to the linkage phosphorus.

Chirally uniform: As used herein, the phrase "chirally uniform" is used to describe an oligonucleotide molecule or type in which all of most of nucleotide units have the same stereochemistry at the linkage phosphorus. For instance, an oligonucleotide whose nucleotide units all have Rp stereochemistry at the linkage phosphorus is chirally uniform. Likewise, an oligonucleotide whose nucleotide units all have rip stereochemistry at the linkage phosphorus is chirally uniform.

Predetermined: By predetermined (or pre-determined) is meant deliberately selected, for example as opposed to randomly occurring or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. Compositions that may contain certain oligonucleotides because they happen to have been generated through a process that cannot be controlled to intentionally generate the particular chemistry and/or stereochemistry features is not a "predetermined" composition. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled.

Linkage phosphorus: As defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester of an internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is P* of formula I. In some embodiments, a linkage phosphorus atom is chiral. In some embodiments, a chiral linkage phosphorus atom is P* of formula I.

P-modification: As used herein, the term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X-L-R$^1$ wherein each of X, L and R$^1$ is independently as defined and described herein and below.

Blockmer: The term "blockmer," as used herein, refers to an oligonucleotide strand whose pattern of structural features characterizing each individual nucleotide unit is characterized by the presence of at least two consecutive nucleotide units sharing a common structural feature at the internucleotidic phosphorus linkage. By common structural feature is meant common stereochemistry at the linkage phosphorus or a common modification at the linkage phosphorus. In some embodiments, the at least two consecutive nucleotide units sharing a common structure feature at the internucleotidic phosphorus linkage are referred to as a "block".

In some embodiments, a blockmer is a "stereoblockmer," e.g., at least two consecutive nucleotide units have the same stereochemistry at the linkage phosphorus. Such at least two consecutive nucleotide units form a "stereoblock." For instance, (Sp, Sp)-ATsCs1GA is a stereoblockmer because at least two consecutive nucleotide units, the Ts and the Cs1, have the same stereochemistry at the linkage phosphorus (both Sp). In the same oligonucleotide (Sp, Sp)-ATsCs1GA, TsCs1 forms a block, and it is a stereoblock.

In some embodiments, a blockmer is a "P-modification blockmer," e.g., at least two consecutive nucleotide units have the same modification at the linkage phosphorus. Such at least two consecutive nucleotide units form a "P-modification block". For instance, (Rp, Sp)-ATsCsGA is a P-modification blockmer because at least two consecutive nucleotide units, the Ts and the Cs, have the same P-modification (i.e., both are a phosphorothioate diester). In the same oligonucleotide of (Rp, Sp)-ATsCsGA, TsCs forms a block, and it is a P-modification block.

In some embodiments, a blockmer is a "linkage blockmer," e.g., at least two consecutive nucleotide units have identical stereochemistry and identical modifications at the linkage phosphorus. At least two consecutive nucleotide units form a "linkage block". For instance, (Rp, Rp)-ATsCsGA is a linkage blockmer because at least two consecutive nucleotide units, the Ts and the Cs, have the same stereochemistry (both Rp) and P-modification (both phosphorothioate). In the same oligonucleotide of (Rp, Rp)-ATsCsGA, TsCs forms a block, and it is a linkage block.

In some embodiments, a blockmer comprises one or more blocks independently selected from a stereoblock, a P-modification block and a linkage block. In some embodiments, a blockmer is a stereoblockmer with respect to one block, and/or a P-modification blockmer with respect to another block, and/or a linkage blockmer with respect to yet another block. For instance, (Rp, Rp, Rp, Rp, Rp, Sp, Sp, Sp)-AAsTsCsGsAs1Ts1Cs1Gs1ATCG (SEQ ID NO: 6) is a stereoblockmer with respect to the stereoblock AsTsCsGsAs1 (all Rp at linkage phosphorus) or Ts1Cs1Gs1 (all Sp at linkage phosphorus), a P-modification blockmer with respect to the P-modification block AsTsCsGs (all s linkage) or As 1 Ts1Cs1Gs1 (all s1 linkage), or a linkage blockmer with respect to the linkage block AsTsCsGs (all Rp at linkage phosphorus and all s linkage) or Ts1Cs1Gs1 (all Sp at linkage phosphorus and all s1 linkage).

Altmer: The term "altmer," as used herein, refers to an oligonucleotide strand whose pattern of structural features characterizing each individual nucleotide unit is characterized in that no two consecutive nucleotide units of the oligonucleotide strand share a particular structural feature at the internucleotidic phosphorus linkage. In some embodiments, an altmer is designed such that it comprises a repeating pattern. In some embodiments, an altmer is designed such that it does not comprise a repeating pattern.

In some embodiments, an altmer is a "stereoaltmer," e.g., no two consecutive nucleotide units have the same stereochemistry at the linkage phosphorus. For instance, (Rp, Sp, Rp, Sp, Rp, Sp, Rp, Sp, Rp, Sp Rp, Sp, Rp, Sp, Rp, Sp, Rp)-GsCsCsTsCsAsGsTsCsTsGsCsTsTsCsGsCsAsCsC (SEQ ID NO: 7).

In some embodiments, an altmer is a "P-modification altmer" e.g., no two consecutive nucleotide units have the same modification at the linkage phosphorus. For instance, All-(Sp)-CAs1GsT, in which each linkage phosphorus has a different P-modification than the others.

In some embodiments, an altmer is a "linkage altmer," e.g., no two consecutive nucleotide units have identical stereochemistry or identical modifications at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCs1CsTs1CsAs1GsTs1CsTs1GsCs1TsTs2CsGs3CsAs4 CsC (SEQ ID NO: 8).

Sequence: As used herein, the term "sequence" refers to any arrangement of molecules or atoms characteristic of a particular molecule. In some embodiments, in referencing a nucleic acid, a "sequence" refers to any of: base sequence (including length), the pattern of chemical modifications to sugar and base moieties, the pattern of backbone linkages (e.g., pattern of natural phosphate linkages, phosphorothioate linkages, phosphorothioate triester linkages, and combinations thereof), the pattern of backbone chiral centers (e.g., pattern of stereochemistry (Rp/Sp) of chiral internucleotidic linkages), and the pattern of backbone phosphorus modifications (e.g., pattern of modifications on the internucleotidic phosphorus atom, such as —S$^-$, and -L-R$^1$ of formula I). In some embodiments, in referencing a nucleic acid or oligonucleotide, a "sequence" refers to the sequence of bases or base sequence. In some embodiments, in reference to a peptide or protein, a sequence refers to a sequence of amino acids.

Unimer: The term "unimer," as used herein, refers to an oligonucleotide strand whose pattern of structural features characterizing each individual nucleotide unit is such that all nucleotide units within the strand share at least one common structural feature at the internucleotidic phosphorus linkage. By common structural feature is meant common stereochemistry at the linkage phosphorus or a common modification at the linkage phosphorus.

In some embodiments, a unimer is a "stereounimer," e.g., all nucleotide units have the same stereochemistry at the linkage phosphorus. For instance, All-(Sp)-CsAs1GsT, in which all the linkages have Sp phosphorus.

In some embodiments, a unimer is a "P-modification unimer", e.g., all nucleotide units have the same modification at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCsCsTsCsAsGsTsCsTsGsCsTsTsCsGsCsAsCsC (SEQ ID NO: 7), in which all the internucleotidic linkages are phosphorothioate diester.

In some embodiments, a unimer is a "linkage unimer," e.g., all nucleotide units have the same stereochemistry and the same modifications at the linkage phosphorus. For instance, All-(Sp)-GsCsCsTsCsAsGsTsCsTsGsCsTsTsCsGsCsAsCsC (SEQ ID NO: 5), in which all the internucleotidic linkages are phosphorothioate diester having Sp linkage phosphorus.

Gapmer: As used herein, the term "gapmer" refers to an oligonucleotide or oligonucleotide strand comprising two or more chemically distinct segments or regions. In some embodiments, a segment or region is characterized by modifications to the base, sugar and/or internucleotidic linkage, or comprises one or more nucleotide analogs. In some embodiments, a segment or region is characterized in that at least one internucleotidic phosphorus linkage of the oligonucleotide strand is a phosphate diester linkage, for example such as those found in naturally occurring DNA or RNA. In some embodiments, more than one internucleotidic phosphorus linkage of the oligonucleotide strand is a phosphate diester linkage such as those found in naturally occurring DNA or RNA. For instance, All-(Sp)-CAs1GsT, in which the internucleotidic linkage between C and A is a phosphate diester linkage.

Skipmer: As used herein, the term "skipmer" refers to a type of gapmer in which every other internucleotidic phosphorus linkage of the oligonucleotide strand is a phosphate diester linkage, for example such as those found in naturally occurring DNA or RNA, and every other internucleotidic phosphorus linkage of the oligonucleotide strand is a modified internucleotidic linkage.

CpG: The terms "CpG", "CpG dinucleotide", "CpG motif" and the like, as used herein, refer to the dinucleotide comprising, in 5' to 3' order: a nucleoside cytidine (C); a phosphate, phosphorothioate or other internucleoside linkage (p); and a nucleoside guanosine (G). In various CpG oligonucleotides, (p) is phosphorothioate. In some embodiments, the C residue in the CpG comprises modifications of the base and/or the sugar, e.g., 5-methyl C, T-modified 5mC (e.g., 2'-OMe 5-methyl C; or 2'-MOE m5C, etc.), etc. In some embodiments, immunomodulatory CpG oligonucleotides comprise base and/or sugar modifications, e.g., 5-methyl C, 2'-modified 5mC (e.g., 2'-OMe 5-methyl C; or 2'-MOE m5C, etc.), etc.

CpG region motif: The term "CpG region motif", as used herein, refers to a particular motif, comprising the CpG dinucleotide, plus one or more of the positions flanking (immediately 5' and/or 3' of) the CpG, wherein the motif is defined by the base sequence, the chemistry of the base, sugar and internucleotidic linkages (e.g., chemical modifications of bases, sugars and/or internucleotidic linkages, etc.), and stereochemistry of chiral internucleotidic linkages (e.g., if the phosphorothioate at a particular position is in the Rp or Sp configuration). Various CpG region motifs are presented herein, which can agonize or antagonize an immunostimulatory effect. In some embodiments, the C residue in the CpG comprises base and/or sugar modifications, e.g., 5-methyl C, 2'-modified 5mC (e.g., 2'-OMe 5-methyl C; or 2'-MOE m5C, etc.), etc. In some embodiments, immunomodulatory CpG oligonucleotides comprise base and/or sugar modifications, e.g., 5-methyl C, 2'-modified 5mC (e.g., 2'-OMe 5-methyl C; or 2'-MOE m5C, etc.), etc.

CpG oligonucleotide: The term "CpG oligonucleotide", as used herein, refers to an oligonucleotide which comprises at least one CpG or CpG region motif. In some embodiments, a CpG oligonucleotide comprises at least two CpG dinucleotides or CpG region motifs. Some CpG oligonucleotides are capable of agonizing an immune response in at least one assay; others are capable of antagonizing an immune response in at least one assay. Others do neither. In some embodiments, a CpG oligonucleotide optionally comprises modifications of sugars, bases and/or internucleotidic linkages, as well as secondary and tertiary structures. See, for example, Vollmer et al. 2009 Adv. Drug. Del. Rev. 61: 195-204. One example of a modified internucleotidic linkage is phosphorothioate. For example, a CpG oligonucleotide can comprise all phosphodiesters in the backbone; or a mixture of phosphodiesters and internucleoside linkers in the backbone; or all internucleoside linkers in the backbone. In various embodiments, a CpG oligonucleotide comprises a phosphorothioate which is in the Rp or Sp conformation. An immunomodulatory CpG oligonucleotide is capable of modulating an immune response, including agonizing or antagonizing an immune response. In some embodiments, an "immunostimulatory" CpG oligonucleotide is capable of agonizing an immune response. Oligonucleotides, including CpG oligonucleotides, can be single-stranded or, in some embodiments, at least partially double-stranded. As used herein, the term "oligonucleotide strand" encompasses a single-stranded oligonucleotide. A single-stranded oligonucleotide can have double-stranded regions and a double-stranded oligonucleotide can have single-stranded regions. Oligonucleotides can also form one or two single-stranded loops with one or more double-stranded regions. See, for example, Schmidt et al. 2015 Nucl. Acid Therp. 25: 130-140. Example oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, aptamers, antimirs, antagomirs, Ul adaptors, triplex-forming oligonucleotides, G-quadruplex oligonucleotides, RNA activators, immuno-stimulatory oligonucleotides, and decoy oligonucleotides. A CpG oligonucleotide, in some embodiments, can comprise a strand having (1) a single-stranded region and (2) another region or regions which is double stranded. Such structures are reported in, as a non-limiting example, Schmidt et al. 2015 Nucl. Acid Therp. 25: 130-140. In some embodiments, CpG oligonucleotides have the structure of a covalently closed DNA molecule, comprising one single-stranded loop and a double-stranded stem, or two single-stranded loops connected through a double-stranded stem, wherein the stem and/or one or both loops can comprise one or more CpG region motifs. In some embodiments, a CpG oligonucleotide of the present disclosure can comprise any novel CpG region motif disclosed herein and have the structure of a covalently closed DNA molecule, comprising one single-stranded loop and a double-stranded stem, or two single-stranded loops connected through a double-stranded stem, wherein the stem and/or one or both loops can comprise one or more CpG region motifs. In some embodiments, the present disclosure pertains to a CpG oligonucleotide comprising a first strand comprising one or more novel CpG region motifs, optionally further comprising a second strand. In some embodiments, the C residue in the CpG comprises base and/or sugar modifications, e.g., 5-methyl C, 2'-modified 5mC (e.g., 2'-OMe 5-methyl C; or 2'-MOE m5C, etc.), etc. In some embodiments, immunomodulatory CpG oligonucleotides comprise base and/or sugar modifications, e.g., 5-methyl C, 2'-modified 5mC (e.g., 2'-OMe 5-methyl C; or 2'-MOE m5C, etc.), etc.

A CpG oligonucleotide can comprise one strand; or, optionally, it can further comprise a second or other additional strands. A CpG oligonucleotide can further comprise or be conjugated to other components which are not nucleotides.

Adjuvant: An "adjuvant" is an immunological agent that can enhance the magnitude, breadth, quality and/or longevity of a specific immune response generated against a co-administered antigen. Among other things, adjuvants can be used to reduce the dose and frequency of immunizations required to achieve protective immunity. In some embodiments, provided CpG oligonucleotide technologies (e.g., oligonucleotides, compositions, methods, etc.) can be used as adjuvants. See, for example, Shirota et al. 2015 Vaccines 3: 390-407, and references cited therein.

Agonism: By "agonism", "agonizing", "induction", "stimulation", "immunostimulation", and the like, of the immune response, as used herein, is meant full or at least partial activation or increase in activity, or the capability of activating or decreasing activity, of an immune response (e.g., a response mediated by immune cells), for example, in a mammal such as a mouse or human; such activation can be measured by any method known in the art. Methods include, but are not limited to, measurement of change in secretion of a cytokine, e.g., interferon-alpha, interferon-gamma, IL-4, IL-6, IL-8, IL-10, IL-12, TNF-alpha, etc. Such methods include, as non-limiting examples, ELISPOT assay, use of peripheral blood mononuclear cells, other assays involving measurements of immune activity in animals and cells, etc. The amount of production of cytokinins in the cell can be determined, for example, using specific antibodies. In this way, it is possible to measure the number of immune cells in the cells, and assess the immunity-inducing activity. In various embodiments, agonism of an immune response is mediated by a CpG oligonucleotide. In various embodiments, if the CpG oligonucleotide is administered with an immunologically active agent such as a vaccine, agonism can be measured by a change in the level of antibodies produced to the agent. In various embodiments, the mammal includes, as non-limiting examples, mouse and human.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkenyl: As used herein, the term "alkenyl" refers to an alkyl group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkynyl: As used herein, the term "alkynyl" refers to an alkyl group, as defined herein, having one or more triple bonds.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, a bovine, a horse, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Antagonism: By "antagonism", "antagonizing", and the like, of the immune response, as used herein is meant a full or at least partial inactivation or decrease in activity, or capability of inactivating or decreasing activity, of an immune response (e.g., a response mediated by immune cells), for example, in a mammal; such inactivation or decrease in activity can be measured by any method known in the art. Methods include, but are not limited to, measurement of change in secretion of a cytokine, e.g., interferon-alpha, interferon-gamma, IL-4, IL-6, IL-8, IL-10, IL-12, TNF-alpha, etc. Such methods include, as non-limiting examples, ELISPOT assay, use of peripheral blood mononuclear cells, other assays involving measurements of immune activity in animals and cells, etc. In various embodiments, antagonism of an immune response is mediated by a CpG oligonucleotide. In various embodiments, the mammal includes, as non-limiting examples, mouse and human.

Antibody: The terms "antibody", "immunoglobulin" and related terms, as used herein, refer to a protein (or fragment thereof, or biologically active fragment thereof), e.g., produced mainly by plasma cells that is used by the immune system to recognize, identify and/or neutralize specific antigens, epitopes, structures, pathogens, nucleic acids and other molecules. In some embodiments, an antibody recognizes a unique molecule of the harmful agent, called an antigen, via the variable region. In some embodiments, antibodies include, without limitation: monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. In some embodiments, an antibody is a monoclonal antibody, for example, an antibody obtained from a population of substantially homogeneous antibodies. In some embodiments, an antibody is a chimeric antibody, in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity. Chimeric antibodies of interest herein include, but are not limited to, "primatized" antibodies comprising variable domain antigen-binding sequences derived from a non-human primate (e.g., Old World Monkey, Ape etc.) and human constant region sequences. In some embodiments, an antibody fragment comprises a portion of an intact antibody, preferably the antigen binding and/or the variable region of the intact antibody. Non-limiting examples of antibody fragments include Fab, Fab', F(ab')$_2$ and Fv fragments; diabodies; linear antibodies; nanobodies; single-chain antibody molecules and multispecific antibodies formed from antibody fragments. In some embodiments, an antibody can be of any of five classes, IgA, IgD, IgE, IgG and IgM, and can be encoded by a mRNA, including the heavy chains designated alpha, delta, epsilon, gamma and mu, respectively. In some embodiments, any of the subclasses of antibodies can be encoded in part or in whole and include the following subclasses: IgG1, IgG2, IgG3, IgG4, IgA1 and IgA2. In various embodiments, an antibody can be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, respiratory, sensory and anti-infective. In some embodiments, an antibody is any of antibody variants, including, but not limited to, substitutional variants, conservative amino acid substitution, insertional variants, deletional variants and/or covalent derivatives. In one embodiment, the primary construct and/or mmRNA disclosed herein can encode an immunoglobulin Fc region. In another embodiment, the primary constructs and/or mmRNA can encode a variant immunoglobulin Fc region. In some embodiments, the primary constructs and/or mmRNA can encode an antibody having a variant immunoglobulin Fc region as described in U.S. Pat. No. 8,217,147.

Antisense oligonucleotide: The terms "antisense oligonucleotide" or "ASO", as used herein, refer to an oligonucleotide or the like having, comprising, or consisting of a sequence of bases or the like which allow the oligonucleotide or the like to hybridize to a target molecule, such as another nucleic acid, modified nucleic acid or nucleic acid analog, e.g., by base-pairing, such as Watson-Crick basepairing or non-Watson-Crick basepairing. In some embodiments, an antisense oligonucleotide is fully complementary or nearly fully complementary to the target molecule. In some embodiments, any olignucleotide of any type described herein or known in the art can be used as an antisense oligonucleotide. In various embodiments, an antisense oligonucleotide can perform or participate in any of various biological functions, including RNA interference, RNaseH-mediated cleavage, exon skipping, the prevention of exon skipping, the enhancement or blocking of an agent (e.g., a protein, RNA, protein-RNA complex, or any other molecule) from binding to another nucleic acid, or any other biological function performed by an antisense oligonucleotide, as described herein or known in the art. In some embodiments, an antisense oligonucleotide is an oligonucleotide which participates in RNaseH-mediated cleavage; for example, an antisense oligonucleotide hybridizes in a sequence-specific manner to a portion of a target mRNA, thus targeting the mRNA for cleavage my RNase H. In some embodiments, an antisense oligonucleotide is able to differentiate between a wild-type and a mutant allele of a target. In some embodiments, an antisense oligonucleotide significantly participates in RNaseH-mediated cleavage of a mutant allele but participates in RNaseH-mediated cleavage of a wild-type allele to a much less degree (e.g., does not significantly participate in RNaseH-mediated cleavage of the wild-type allele of the target).

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aptamer: The term "aptamer", as used herein, refers to a nucleic acid molecule, e.g., a molecule comprising a RNA, DNA or nucleotide analog, that is capable of binding to a specific molecule with high affinity and specificity (Ellington et al., Nature 346, 818-22 (1990); and Tuerk et al., Science 249, 505-10 (1990)). In various embodiments, a ligand that binds to an aptamer includes, without limitation, small molecules, such as drugs, metabolites, intermediates, cofactors, transition state analogs, ions, metals, nucleic acids, and toxins. In some embodiments, an aptamer can also bind natural and synthetic polymers, including proteins, peptides, nucleic acids, polysaccharides, glycoproteins, hormones, receptors and cell surfaces such as cell walls and cell membranes. In some embodiments, an aptamer is between about 10 and about 300 nucleotides in length. In some embodiments, an aptamer is between about 30 and about 100 nucleotides in length. In some embodiments, an aptamer can bind to a wide variety of molecules. Each of these molecules can be used as a modulator of gene expression. In some embodiments, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have reportedly been used as target ligands in vitro aptamer selections (Werstuck and Green, Science 282:296-298 (1998)). Other small organic molecules like dopamine, theophylline, sulforhodamine B, and cellobiose have also been reported as ligands in the isolation of aptamers. In some embodiments, an aptamers is been isolated for antibiotics such as kanamycin A, lividomycin, tobramycin, neomycin B, viomycin, chloramphenicol and streptomycin. For a review of aptamers that recognize small molecules, see Famulok, Science 9:324-9 (1999). In some embodiments, a ligand of the aptamer of an aptamer-regulated nucleic acid of the disclosure is a cell-permeable, small organic molecule. Small organic molecules which do not have a general inhibitory effect on translation can be used as ligands. The small molecule can also exhibit in vivo persistence sufficient for achieving a desired level of inhibition of translation. The molecules also can be screened to identify those that are bioavailable after, for example, oral administration. In some embodiments, the ligand is nontoxic. The ligand can optionally be a drug, including, for example, a steroid. In some embodiments, in some of the methods of controlling gene expression, a ligand can be pharmacologically inert. In some embodiments, a ligand is a polypeptide whose presence in the cell is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand can be a metal ion. In a specific embodiment, the aptamer domain of an aptamer-regulated nucleic acid responds to binding to caffeine. In some embodiments, an aptamers is developed to bind particular ligands by employing known in vivo or in vitro (most typically, in vitro) selection techniques known as SELEX (Ellington et al., Nature 346, 818-22 (1990); and Tuerk et al., Science 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291. In some embodiments, aptamers include those that target any of: VEGF, tissue factor pathway inhibitor (TFPI), Factor IXa, complement component 5 (C5), HIV Tat protein, and HIV Rev protein.

Aryl: The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" can be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which can bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. In some embodiments, an aryl group has a radical or point of attachment on an aromatic ring.

Biologically active agent: The term "biologically active agent", as used herein, refers to any agent (including, but not limited to, an active compound) which has, mediates, or participates, or is capable of having, mediating, or participating in a biological activity. In various embodiments, a biologically active agent can be organic or in-organic. Non-limiting examples of biologically active agents include: a small molecule, a peptide, a protein, a component of a CRISPR-Cas system, a carbohydrate, a therapeutic agent, a chemotherapeutic agent, a vaccine, a nucleic acid, and a lipid. In some embodiments, a biologically active agent includes an inorganic or organic molecule including a small molecule, peptide (e.g. cell penetrating peptides), carbohydrate (including monosaccharides, oligosaccharides, and polysaccharides), protein (including nucleoprotein, mucoprotein, lipoprotein, synthetic polypeptide, or a small molecule linked to a protein, glycoprotein), steroid, nucleic acid, lipid, hormone, or combination thereof, that causes a biological effect when administered in vivo to an animal, including but not limited to birds and mammals, including humans. In some embodiments, the biologically active agent is charged. In some embodiments, the biologically active agent is positively charged. In some embodiments, the biologically active agent is negatively charged. In some embodiments, a biologically active agent is a nucleic acid. In some embodiments, a biologically active agent is a CpG oligonucleotide.

Carbohydrate: The term "carbohydrate", as used herein, refers to a biological molecule comprising carbon, oxygen and hydrogen; in some embodiments, a carbohydrate includes a saccharide, a sugar, a starch or cellulose. In some embodiments, saccharides include monosaccharides, disaccharides, oligosaccharides and polysaccharides. In some embodiments, a polysaccharide acts as a structural component or for energy storage. In some embodiments, a carbohydrate is involved in the immune system, fertilization, preventing pathogenesis, blood clotting and/or development. In some embodiments, a biologically active agent comprises a carbohydrate.

Cell penetrating peptide: The terms "cell penetrating peptide", "cell penetrating protein", "CPP" and the like, as used herein, refer to a peptide or protein having an ability to pass through cellular membranes. In various embodiments, a CPP is conjugated to a biologically active agent to facilitate transport of the agent across the membrane. In some embodiments, the CPP is useful in facilitating the uptake of such agents across cell membranes, such as the plasma membrane of a mammalian cell and/or the nuclear membrane of a mammalian cell. In some embodiments, a CPP is capable of being internalized into a cell and passing cellular membranes (including, inter alia, the outer "limiting" cell membrane (also commonly referred to as "plasma membrane"), endosomal membranes, and membranes of the endoplasmatic reticulum) and/or directing the passage of a given agent or cargo through these cellular membranes. In some embodiments, any possible mechanism of internalization is envisaged including both energy-dependent (i.e. active) transport mechanisms (e.g., endocytosis) and energy-independent (i.e. passive) transport mechanism (e.g., diffusion). In various embodiments, internalization includes involving the localization of at least a part of the peptides that passed through the plasma cellular membrane into the cytoplasma (in contrast to localization in different cellular compartments such as vesicles, endosomes or in the nucleus). A non-limiting example of a CPP is a peptide having amino acid sequence GRKKRRQRRRPPQ (SEQ ID NO: 9) (Vives; E. et al. (1997), supra). Non-limiting examples of CPPs include the HIV-1 TAT translocation domain (Green; M. and Loewenstein, P. M. (1988) Cell 55, 1179-1188) and the homeodomain of the Antennapedia protein from *Drosophila* (Joliot; A. et al. (1991) Proc. Natl. Acad. Sci. USA 88, 1864-1868); a sequence of 16 amino acids called penetratin or pAntp of the Antennapedia protein (Derossi, D. et al. (1994) J. Biol. Chem. 269, 10444-10450); a basic sequence of the HIV-1 Tat protein (Vives, E. et al. (1997) J. Biol. Chem. 272, 16010-16017); and a synthetic peptide developed from the amphipathic model peptide MAP (Oehlke, J. et al. (1998) Biochim. Biophys. Acta 1414, 127-139). Additional non-limiting examples of CPPs are described in U.S. Pat. Nos. 9,303,076; and 9,302,014.

Characteristic portion: As used herein, the phrase a "characteristic portion" or "characteristic sequence", and the like, of a protein or polypeptide (or nucleic acid) is one that contains a continuous stretch of amino acids (or nucleotides, modified nucleotides or nucleotide analogs), or a collection of continuous stretches of amino acids (or nucleotides, modified nucleotides or nucleotide analogs), that together are characteristic of a protein or polypeptide (or nucleic acid). Each such continuous stretch generally will contain at least two amino acids. Furthermore, those of ordinary skill in the art will appreciate that typically at least 5, 10, 15, 20 or more amino acids (or nucleotides, modified nucleotides or nucleotide analogs) are required to be characteristic of a protein (or nucleic acid). In general, a characteristic portion is one that, in addition to the sequence identity specified above, shares at least one functional characteristic with the relevant intact protein. In some embodiments, a characteristic sequence is a sequence that is found in all members of a family of polypeptides or nucleic acids, and therefore can be used by those of ordinary skill in the art to define members of the family.

Characteristic structural element: The term "characteristic structural element", as used herein, refers to a distinctive structural element (e.g., core structure, collection of pendant moieties, sequence element, etc.) that is found in all members of a family of polypeptides, small molecules, or nucleic acids, and therefore can be used by those of ordinary skill in the art to define members of the family.

Chemotherapeutic agent: The term "chemotherapeutic agent", as used herein, refers to a drug or agent capable of killing growing cells, including cancer cells. Chemotherapeutic agents are frequently used to treat various forms of cancer. In some embodiments, non-limiting examples of chemotherapeutic agents include adriamycin, paclitaxel (Taxol), docetaxel (Taxotere), actinomycin D, doxorubicin, daunorubicin, valrubicin, idarubicin, epirubicin, bleomycin, plicamycin, camptothecin and derivatives, bleomycin, etoposide, teniposide, mitomycin, vinca alkaloids, such as vinblastine and vincristine, and platinum-based compounds such as cisplatin, gemcitabine. In some embodiments, a composition comprises a lipid and a portion of a chemotherapeutic agent capable of mediating at least one function of a chemotherapeutic agent.

Comparable: The term "comparable", as used herein, is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Conjugate: The term "conjugate", as used herein, refers to a composition comprising two or more components, moieties or molecules which are physically linked together, e.g., by a covalent bond, either directly or indirectly (as a non-limiting example, with one or more linkers interposed between two adjacent components, moieties or molecules). The term "conjugated", as used herein, in reference to a composition comprising two or more components, moieties or molecules, references the state the two or more components, moieties or molecules are physically linked together. In some embodiments, a composition comprises a lipid and a biologically active agent, wherein the lipid and the biologically active agent are conjugated.

CRISPR: The term "CRISPR", "CRISPR/Cas system" and the like, as used herein, refers to a biologically active system involving clustered regularly-interspaced short palindromic repeats (CRISPR), which are segments of prokaryotic DNA containing short repetitions of base sequences, or various artificial systems derived from or inspired by the naturally-occurring prokaryotic system. In some embodiments, a biologically active agent comprises a component of a CRISPR/Cas system. In some embodiments, a component of a CRISPR/Cas system includes, without limitation: a gene encoding a Cas protein (including, as non-limiting examples, Cas9, dCas9, and variants thereof, both naturally-occurring and artificial) or the protein itself; a guide RNA; any component of a CAS crRNA complex; a cas (CRISPR-associated) gene or gene product; and any other biologically active molecule involved in a naturally-occurring or artificial CRISPR/Cas system. See, for example, Jinek et al. 2012 Science 337: 816-821; Cong et al. 2013 Science 339: 819-823; U.S. Pat. App. 20140234972; DiCarlo 2013 Nucl. Acids Res. 41: 4336-43; Hwang et al. 2013 Nat. Biotech. 31: 227-9; and Flowers et al. 2014 Development 141: 2165-71.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" can also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic C3-C6 hydrocarbon, or a C8-C10 bicyclic hydrocarbon that is completely saturated or that contains one or more units of unsaturation, but which is not aromatic, that has a single point of attachment to the rest of the molecule, or a C9-C16 tricyclic hydrocarbon that is completely saturated or that contains one or more units of unsaturation, but which is not aromatic, that has a single point of attachment to the rest of the molecule.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which can involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Equivalent agents: The term "equivalent agent", as used herein," refers to a molecule, compound or other agent which is capable of functionally substituting for another molecule, compound or agent, even if the structures of the molecules, compounds or agents are not similar, identical or related. Those of ordinary skill in the art, reading the present disclosure, will appreciate that the scope of useful agents in the context of the present disclosure is not limited to those specifically mentioned or exemplified herein. In particular, those skilled in the art will recognize that active agents typically have a structure that consists of a core and attached pendant moieties, and furthermore will appreciate that simple variations of such core and/or pendant moieties may not significantly alter activity of the agent. For example, in some embodiments, substitution of one or more pendant moieties with groups of comparable three-dimensional structure and/or chemical reactivity characteristics can generate a substituted compound or portion equivalent to a parent reference compound or portion. In some embodiments, addition or removal of one or more pendant moieties can generate a substituted compound equivalent to a parent reference compound. In some embodiments, alteration of core structure, for example by addition or removal of a small number of bonds (typically not more than 5, 4, 3, 2, or 1 bonds, and often only a single bond) can generate a substituted compound equivalent to a parent reference compound. In many embodiments, equivalent compounds can be prepared by methods illustrated in general reaction schemes as, for example, described below, or by modifications thereof, using readily available starting materials, reagents and conventional or provided synthesis procedures. In these reactions, it is also possible to make use of variants, which are in themselves known, but are not mentioned here.

Equivalent Dosage: The term "equivalent dosage", as used herein, is used herein to compare dosages of different pharmaceutically active agents that effect the same biological result. Dosages of two different agents are considered to be "equivalent" to one another in accordance with the present disclosure if they achieve a comparable level or extent of the biological result. In some embodiments, equivalent dosages of different pharmaceutical agents for use in accordance with the present disclosure are determined using in vitro and/or in vivo assays as described herein. In some embodiments, one or more lysosomal activating agents for use in accordance with the present disclosure is utilized at a dose equivalent to a dose of a reference lysosomal activating agent; in some such embodiments, the reference lysosomal activating agent for such purpose is selected from the group consisting of small molecule allosteric activators (e.g., pyrazolpyrimidines), imminosugars (e.g., isofagomine), antioxidants (e.g., n-acetyl-cysteine), and regulators of cellular trafficking (e.g., Rab1a polypeptide).

Halogen: The term "halogen", as used herein, means F, Cl, Br, or I.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, or $CH_3$ are independently replaced by one or more heteroatoms (including oxidized and/or substituted form thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one ore more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 pi electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group can be monocyclic, bicyclic or polycyclic. The term "heteroaryl" can be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom", as used herein, means an atom that is not carbon or hydrogen. In some embodiments, a heteroatom is oxygen, sulfur, nitrogen, phosphorus, or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.).

Heterocyclyl: As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen can be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group can be monocyclic, bicyclic or polycyclic. The term "heterocyclylalkyl" refers to an alkyl group substituted by a heterocyclyl, wherein the alkyl and heterocyclyl portions independently are optionally substituted.

Immunomodulatory nucleic acid and CpG oligonucleotide and related terms: The term "immunomodulatory nucleic acid", as used herein, refers to a nucleic acid which is capable of modulating an immune response, e.g., in a mammal, e.g., in a human subject. In various embodiments, the immunomodulatory nucleic acid is capable of stimulating (agonizing) an immune response; in other embodiments, different immunomodulatory nucleic acids are capable of decreasing (antagonizing) an immune response. In non-limiting examples, an immunomodulatory nucleic acid includes a CpG oligonucleotide. The term "CpG oligonucleotide", as used herein, refers to an oligonucleotide or other nucleic acid comprising a CpG motif, wherein the oligonucleotide can comprise nucleotides, modified nucleotides and/or nucleotide analogs. In some embodiments, a CpG oligonucleotide is capable of agonizing a TLR9-mediated and/or TLR9-associated immune response in at least one assay; in some embodiments, a CpG oligonucleotide is capable of antagonizing an immune response in at least one assay. Others do neither. In some embodiments, a CpG oligonucleotide can optionally comprise modifications of the sugar, base or phosphate (phosphodiester), as well as secondary and tertiary structures. See, for example, Vollmer et al. 2009 Adv. Drug. Del. Rev. 61: 195-204. In some embodiments, an example of a modified phosphodiester is a phosphorothioate. In some embodiments, one or more phosphorothioates (PS) is incorporated into the backbone of a CpG oligonucleotide (in place of a phosphodiester or PO); the PS can reportedly reduce nuclease degradation and, in at least some cases, enhance the immunogenic activity of the CpG oligonucleotide 10- to 100-fold. Vollmer et al. 2009 Adv. Drug Del. Rev. 61: 195-204. In some embodiments, a CpG oligonucleotide can comprise all phosphodiesters in the backbone; or a mixture of phosphodiesters and internucleoside linkers in the backbone; or all internucleoside linkers in the backbone. For example, WO 2015/108047 reports CpG oligonucleotides with a mixture of phosphodiester and internucleoside (e.g., phosphorothioate) linkages; in this case, the CpG region motif comprises phosphodiesters, with phosphorothioates flanking the CpG region motif. In various embodiments, the CpG oligonucleotide can comprise a phosphorothioate which is in the Rp or Sp conformation. The terms "CpG ODN" or "CpG oligodeoxynucleotide" as used in the literature, and as used herein, are not strictly limited to oligonucleotides wherein "p" is a phosphate; these terms have previously been used in the literature and are used herein to encompass oligonucleotides which comprise one or more phosphorothioates in place of phosphodiesters, or even comprise all phosphorothioates in their backbones, and/or other modifications. In some embodiments, an "immunostimulatory" CpG oligonucleotide is capable of agonizing an immune response. In some embodiments, a CpG oligonucleotide can comprise one strand; or, optionally, it can further comprise a second or other additional strands. In some embodiments, a CpG oligonucleotide can further comprise or be conjugated to other components which are not nucleotides. In some embodiments, a composition comprises a lipid and a portion of an immunomodulatory nucleic acid capable of mediating at least one function of an immunomodulatory nucleic acid. In some embodiments, an immunomodulatory activity is the activity of a molecule, including but not limited to an oligonucleotide, to agonize or antagonize an immune response.

Immunostimulatory: The term "immunostimulatory", as used herein, refers to a biologically active agent, as a non-limiting example, a CpG oligonucleotide, which has or is capable of having an agonistic effect on at least one immune response.

Intraperitoneal: The phrases "intraperitoneal administration" and "administered intraperitonealy" as used herein have their art-understood meaning referring to administration of a compound or composition into the peritoneum of a subject.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Linker: The term "linker", as used herein, refers to a moiety that connects two parts of a composition; as a non-limiting example, a linker physically connects a nucleic acid (including, but not limited to, a CpG oligonucleotide) to a lipid. Non-limiting examples of suitable linkers include: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group. Other non-limiting examples of linkers are described herein, or detailed in FIG. 7.

Linking moiety: The term "linking moiety", as used herein, refers to a moiety which links one molecule to another. In some embodiments, a linking moiety is a moiety optionally positioned between the terminal nucleoside and the solid support or between the terminal nucleoside and another nucleoside, nucleotide, or nucleic acid.

Lower alkyl: The term "lower alkyl", as used herein, refers to a $C_{1-4}$ straight or branched alkyl group. Example lower alkyl groups are methyl, ethyl, propyl, isopropyl, butyl, isobutyl, and tert-butyl.

Lipid: The term "lipid", as used herein, refers to any member of a large group of molecules which are generally at least partially hydrophobic or amphiphilic, and include, inter alia, phospholipids, triglycerides, diglycerides, monoglycerides, fat-soluble vitamins, sterols, fats and waxes. In some embodiments, lipids include fatty acids, glycerolipids, glycerophospholipids, sphingolipids, sterol lipids, prenol lipids, saccharolipids, polyketides, and other molecules. In some embodiments, a lipid comprises a linear, saturated or partially unsaturated aliphatic chain, for example having a length within the range of $C_{10}$-$C_{80}$, or $C_{10}$-$C_{60}$, or $C_{10}$-$C_{40}$. In some embodiments, a lipid may comprise such a linear, saturated or partially unsaturated aliphatic chain that is optionally substituted with one or more $C_{1-4}$ aliphatic groups. In some embodiments, a lipid includes, without limitation, lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. In some embodiments, a lipid includes, without limitation: an amino lipid; an amphipathic lipid; an anionic lipid; an apolipoprotein; a cationic lipid; a low molecular weight cationic lipid; a cationic lipid such as CLinDMA and DLinDMA; an ionizable cationic lipid; a cloaking component; a helper lipid; a lipopeptide; a neutral lipid; a neutral zwitterionic lipid; a hydrophobic small molecule; a hydrophobic vitamin; a PEG-lipid; an uncharged lipid modified with one or more hydrophilic polymers; phospholipid; a phospholipid such as 1,2-dioleoyl-sn-glycero-3-phosphoethanolamine; a stealth lipid; a sterol; a cholesterol; and a targeting lipid; and any other lipid described herein or reported in the art. In some embodiments, a composition comprises a lipid and a portion of another lipid capable of mediating at least one function of another lipid. In various embodiments, a composition of the present disclosure comprises any one or more of any lipid described herein or known in the art.

lncRNA: The terms "Long non-coding RNA" and "lncRNA", as used herein, refer to non-protein coding RNA transcripts longer than about 200 nucleotides. This numerical limit distinguishes long ncRNAs from small regulatory RNAs such as microRNAs (miRNAs), short interfering RNAs (siRNAs), Piwi-interacting RNAs (piRNAs), small nucleolar RNAs (snoRNAs), and other short RNAs. In some embodiments, a lncRNA bears one or more signatures of mRNAs, including 5' capping, splicing, and poly-adenylation, but has little or no open reading frame (ORF). In some embodiments, a lncRNA is Air or Xist. In some embodiments, a lncRNA functions in regulating expression of another gene. In some embodiments, a lncRNA is a lncRNA listed in any lncRNA database, including, but not limited to: ChIPBase, C-It-Loci, LNCipedia, lncRNABase, lncRNAdb, lncRNome, MONOCLdb, NONCODE, and NRED. In some embodiments, a composition comprises a lipid and a portion of a lncRNA capable of mediating at least one function of a lncRNA.

mKNA: The terms "Messenger RNA", "mRNA" and the like, as used herein, refer to any of a large family of RNA molecules that convey genetic information from DNA to the ribosome, where they specify the amino acid sequence of the protein products of gene expression. In various embodiments, following transcription of primary transcript mRNA (known as pre-mRNA) by RNA polymerase, processed, mature mRNA is translated into a polymer of amino acids: a protein, as summarized in the central dogma of molecular biology. In some embodiments, the mRNA includes a modified mRNA or mmRNA. U.S. Pat. No. 9,220,792. In some embodiments, a mRNA encodes any of: an allergen, a blood component, a gene therapy product, a human tissue or cellular product used in transplantation, a vaccine, an antibody, a cytokine, a growth factor, an enzyme, a thrombolytic, or an immunomodulator. In some embodiments, a composition comprises a lipid and a portion of a mRNA capable of mediating at least one function of a mRNA.

ncRNA: The term "ncRNA", as used herein, refers to non-coding RNA, of which there are several types, including, but not limited to lncRNA (long non-coding RNA). In some embodiments, a ncRNA participates in regulating the expression of a gene or protein or gene product. Wahlestedt 2013 Nat. Rev. Drug Disc. 12: 433-446. Antagonists to ncRNAs have been reported. Meng et al. 2015 Nature 518: 409-412; and Ling et al. 2013 Nature Rev. Drug Discov. 12: 847-865. In some embodiments, a composition comprises a nucleic acid (including, but not limited to, a CpG oligonucleotide) and a lipid.

Optionally Substituted: As described herein, compounds, e.g., oligonucleotides, of the disclosure can contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group can have a suitable substituent at each substitutable position of the group, and when more than one position in any given structure can be substituted with more than one substituent selected from a specified group, the substituent can be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents include halogen, $-(CH_2)_{0-4}R^\circ$, $-(CH_2)_{0-4}OR^\circ$, $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which can be substituted with $R^\circ$; $-(CH_2)_{0-4}O(CH_2)_{0-1}Ph$ which can be substituted with $R^\circ$; $-CH=CHPh$, which can be substituted with $R^\circ$; $-(CH_2)_{0-4}O(CH_2)_{0-1}$-pyridyl which can be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR$, $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-OSiR^\circ_3$; $-(C_{1-4}$ straight or branched alkylene$)O-N(R^\circ)_2$; or $-(C_{1-4}$ straight or branched alkylene$)C(O)O-N(R^\circ)_2$, wherein each $R^\circ$ can be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which can be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$—(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which can be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which can be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R$^\bullet$ include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

In some embodiments, suitable substituents on a substitutable nitrogen include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R')S(O)$_2$R$^\dagger$; wherein each R$^\dagger$ is independently hydrogen, C$_{1-6}$ aliphatic which can be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Peptide: The term "peptide", as used herein, refers to a molecule comprising a plurality of amino acids joined together via peptide bonds. In some embodiments, a peptide includes a dipeptide, tripeptide, oligopeptide and polypeptide. In some embodiments, a dipeptide contains two amino acids; a tripeptide contains three amino acids; and an oligopeptide comprises about 2 to about 50 or more amino acids. In some embodiments, peptides comprise more than about 50 amino acids. In some embodiments, a polypeptide and a protein are also molecules comprising a plurality of amino acids joined together via peptide bonds. In some embodiments, a peptide includes any therapeutic peptide listed in the SATPdb database of therapeutic peptides. Singh et al. 2015 Nucl. Acids Res. doi: 10.1093/nar/gkv1114. In some embodiments, a composition comprises a lipid and a portion of a peptide capable of mediating at least one function of a peptide.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. In some embodiments, a pharmaceutically acceptable carrier includes: any compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A carrier can enable a composition comprising a CpG oligonucleotide to be formulated as tablets to be taken orally by a subject to be targeted, pills, dragees, capsules, liquids, gels, syrups, slurries, suspensions and the like. The pharmaceutical preparations for oral administration can be obtained as solid excipient by adding suitable auxiliaries if necessary, subsequently grounding the resulting mixture and forming the tablet cores or the dragee cores by processing the mixture of granules. In particular, suitable excipients are fillers [for example, sugar (lactose, sucrose, mannitol and sorbitol, etc.); cellulose preparations (for example, corn starch, wheat starch, Rice starch, potato starch, gelatin, tragacanth gum, methyl cellulose, hydroxypropyl methyl-cellulose, sodium carboxymethyl-cellulose, etc.) and/or polyvinylpyrrolidone (PVP)]. If necessary, a disintegrating agent [for example, cross-linked polyvinyl pyrrolidone, agar, alginic acid or a salt thereof (for example, sodium alginate), etc.] can be added. If necessary, the oral formulations can also be administered in saline or buffer solution to neutralize the acidic internal state. In addition, the oral formulations can be administered without any carriers. A dragee core can be provided with suitable coatings. For this purpose, concentrated sugar solutions can be used. If necessary, the concentrated sugar solutions can contain gum arabic, talc, polyvinyl pyrrolidone, carbopol gel, polyethylene glycol and/or titanium dioxide, lacquer solutions, suitable organic solvents or solvent mixtures. In order to identify or characterize different combinations of active compound doses, dyestuffs or pigments can be added to the tablets or the dragee coatings. A pharmaceutically acceptable carrier can comprise a pharmaceutically acceptable salt. The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Plasmid: The term "plasmid", as used herein, refers to an extra-chromosomal (apart from a chromosome) length of DNA; plasmids are generally circular and generally capable of independent replication, though exceptions exist such as linear plasmids and plasmids which are not capable of independent replication (including, but not limited to, suicide vectors). In some embodiments, a plasmid can be extra-chromosomal under some conditions (e.g., in a laboratory), but capable of integrating into a chromosome (e.g., acting as a suicide vector capable of integrating into a chromosome in a cell or subject). Plasmids naturally exist in many organisms, including bacteria and some eukaryotic organisms, and are commonly engineered and produced artificially to carry genes into an organism. A plasmid is generally double-stranded, or can alternatively be single-stranded or partially single- and double-stranded, or have other strandedness. Artificial plasmids are commonly used in genetic engineering. Plasmids include plasmids encoding or capable of expressing a nucleic acid, including, without limitation, a mRNA, a RNAi agent or precursor thereof, an antagonist to another nucleic acid (including, without limitation, an antagonist to a miRNA, RNAi agent, mRNA, etc.) or precursor thereof, or other nucleic acids of therapeutic benefit. Additional parts of a plasmid can optionally include one or more copies of any one or more component selected from: a gene encoding a protein related to replication, an origin or replication, a gene encoding a replication initiator protein, an origin of replication enhancer, a gene encoding a nucleic acid of therapeutic benefit (or a precursor thereof), one or multiple promoters, one or multiple transcription enhancers, one or multiple transcription terminators, one or more marker genes (e.g., a gene encoding resistance to an antibiotic or encoding an enzyme required for survival and/or growth under certain laboratory conditions). In some embodiments, a plasmid is a suicide vector, which can lack any of: an origin of replication, a gene encoding a DNA replication initiator protein, or any other component required for independent replication. In some embodiments, two plasmids can be physically separate, but produce products which work in concert; for example, one plasmid can encode a gene for a transcriptional enhancer which enhances transcription of a gene encoded on another plasmid; for another example, one plasmid can comprise a gene encoding a DNA replication initiator protein which initiates replication at a DNA replication origin on another plasmid. Various plasmids are known in the art. In some embodiments, a composition comprises a lipid and a portion of a plasmid capable of mediating at least one function of a plasmid.

Protecting group: The term "protecting group," as used herein, is well known in the art and includes those described in detail in *Protecting Groups in Organic Synthesis*, T. W. Greene and P. G. M. Wuts, 3$^{rd}$ edition, John Wiley & Sons, 1999, the entirety of which is incorporated herein by reference. Also included are those protecting groups specially adapted for nucleoside and nucleotide chemistry described in *Current Protocols in Nucleic Acid Chemistry*, edited by Serge L. Beaucage et al. 06/2012, the entirety of Chapter 2 is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl) 1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), w-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonyl aminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenyl methyl amino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N,N'dimethylaminomethylene)amine, N, N isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonyl chromium- or tungsten)carbonyl] amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Suitably protected carboxylic acids further include, but are not limited to, silyl-, alkyl-, alkenyl-, aryl-, and arylalkyl-protected carboxylic acids. Examples of suitable silyl groups include trimethyl silyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl. Suitable hydroxyl protecting groups include methyl, methoxylmethyl (MOM), methylthiomethyl (MTM), t-butylthiomethyl, (phenyldimethylsilyl)methoxymethyl (SMOM), benzyloxy methyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyl diphenyl methyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethyl silyl (DPMS), t-butylmethoxyphenyl silyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxy acetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(l, 1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N' tetramethylphosphorodiamidate, alkyl N-phenyl carbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxy methylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethyl amino)ethylidene derivative, α-(N,N'-dimethyl amino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris (benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group. In some embodiments, a phosphorous protecting group is a group attached to the internucleotide phosphorous linkage throughout oligonucleotide synthesis. In some embodiments, the phosphorous protecting group is attached to the sulfur atom of the internucleotide phosphorothioate linkage. In some embodiments, the phosphorous protecting group is attached to the oxygen atom of the internucleotide phosphorothioate linkage. In some embodiments, the phosphorous protecting group is attached to the oxygen atom of the internucleotide phosphate linkage. In some embodiments the phosphorous protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methyl aminobutyl, 3-(2-pyridyl)-1-propyl, 2-[N-methyl-N-(2-pyridyl)]aminoethyl, 2-(N-formyl,N-methyl) aminoethyl, 4-[N-methyl-N-(2,2,2-trifluoroacetyl)amino] butyl.

Protein: As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc.). In some embodiments, a protein includes more than one polypeptide chain, for example linked by one or more disulfide bonds or associated by other means. In some embodiments, proteins contain L-amino acids, D-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Ribozymes: The term "ribozyme", as used herein, refers to a catalytic RNA that functions as an enzyme and does not require proteins for catalysis. In some embodiments, a ribozyme is a self-processing RNA that catalyzes RNA cleavage and ligation reactions. In some embodiments, a substrate recognition domain of a ribozyme is artificially engineered to stimulate site-specific cleavage in cis (the same nucleic acid strand) or trans (a non-covalently linked nucleic acid). Scherer et al. 2003 Nat Biotechnol. 21:1457-1465. In some embodiments, a ribozyme is subject to in vitro selection and directed evolution to generate improved properties and new functions for therapeutic and diagnostic reagents. In some embodiments, a ribozyme is engineered to be allosterically activated by effector molecules, which has led to the development of artificial "riboswitches" as biosensors and synthetic biological tools. Wieland et al. 2010 Chem Biol. 17:236-242; Liang et al. 2011 Mol Cell. 43:915-926. In some embodiments, a ribozyme is derived from a "hammerhead" or "hairpin/paperclip" motifs. In some embodiments, a ribozyme is delivered to the target cells in RNA form or can be transcribed from therapeutic genes. In some embodiments, a ribozyme is chemically modified with any one or more of the following modifications: 5'-PS backbone linkage, 2'-O-Me, 2'-deoxy-2'-C-allyl uridine, and terminal inverted 3'-3' deoxyabasic nucleotides. A non-limiting example of a ribozyme is Angiozyme (RPI.4610), which targets the mRNA of the vascular endothelial growth factor receptor-1 (VEGFR-1) to block angiogenesis and tumor growth. Kobayashi et al. 2005 Cancer Chemother Pharmacol. 56:329-336; Weng et al. 2005 Mol Cancer Ther. 4:948-955. Another non-limiting example of a ribozyme is Heptazyme, a synthetic ribozyme against hepatitis C virus (HCV). Sandberg et al. 2001 Hepatology 34:333a-333a; Tong et al. 2002 Hepatology 36:360a-360a; Berk 2006 Hepatology 43:S13-S30. In some embodiments, Ribozymes include those that target any of: VEGFR-1, HCV IRES, HIV U5 and pol, HIV Tat and Vpr, CCR5, HIV Tat and Rev. In some embodiments, a composition comprises a lipid and a portion of a ribozyme capable of mediating at least one function of a ribozyme.

RNAi agent: The term "RNAi agent", as used herein, refers to a molecule capable of mediating RNA interference. The term encompasses a variety of structures and formats, including, as a non-limiting example, siRNAs (including but not limited to those of the "canonical" structure), in addition to various natural and artificial structures capable of mediating RNA interference. The term "RNA interference" or "RNAi", as used herein, refers to a post-transcriptional, targeted gene-silencing technique mediated by the RISC (RNA interference silencing complex) that uses a RNAi agent to degrade messenger RNA (mRNA) containing a sequence which is the same as or very similar to the RNAi agent. See: Zamore and Haley, 2005, Science, 309, 1519-1524; Zamore et al., 2000, Cell, 101, 25-33; Elbashir et al., 2001, Nature, 41 1, 494-498; and Kreutzer et al., PCT Publication WO 00/44895; Fire, PCT Publication WO 99/32619; Mello and Fire, PCT Publication WO 01/29058; and the like. The process of RNAi occurs naturally when long dsRNA is introduced into a cell and cleaved by ribonuclease III (Dicer) into shorter fragments called siRNAs. Naturally produced siRNAs are typically about 21 nucleotides long and comprise about 19 base pair duplexes with two 2-nt overhangs (the "canonical" structure). One strand of the siRNA is reportedly incorporated into the RNA-induced silencing complex (RISC). This strand (known as the anti-sense or guide strand strand) guides RISC to a complementary mRNA. One or more nucleases in the RISC then reportedly mediates cleavage of the target mRNA to induce silencing. Cleavage of the target RNA reportedly takes place in the middle of the region complementary to the anti-sense strand. See: Nykanen, et al. 2001 Cell 107:309; Sharp et al. 2001 Genes Dev. 15:485; Bernstein, et al. 2001 Nature 409:363; Elbashir, et al. 2001 Genes Dev. 15:188. As various non-limiting examples, a RNAi agent includes: siRNAs (including but not limited to those of the canonical structure), shRNAs, miRNAs, sisiRNAs, meroduplex RNAs (mdRNAs), DNA-RNA chimeras, siRNAs comprising two mismatches (or more mismatches), neutral siRNAs, aiR-NAs, or a siRNA comprising a terminal or internal spacer (e.g., an 18-mer format siRNA). In various non-limiting examples, the RNAi agent is a shRNA (small hairpin RNA or short hairpin RNA), which reportedly comprises a sequence of RNA that makes a tight hairpin turn and, like siRNAs, silences targets via RISC. The antisense and sense strand are thus reportedly connected by a hairpin. shRNAs reportedly can be expressed, for example, via delivery of plasmids or through viral or bacterial vectors. Various varieties of shRNAs have been reported in the art. See, for example: Xiang et al. 2006. Nature Biotech. 24: 697-702; Macrae et al. 2006 Science 31 1: 195-8. Lombardo et al. 2007. Nature Biotech. 25: 1298-1306; Wang et al. 2011. Pharm. Res. 28: 2983-2995; Senzer et al. 2011 Mol. Ther. 20: 679-686. In various non-limiting examples, the RNAi agent is a miRNA (microRNA), which reportedly is a small RNA molecule (ca. 22 nt) that, like siRNAs, also silences targets via RISC. Naturally-occurring miRNAs are encoded by eukaryotic nuclear DNA; miRNAs are generated by post-transcriptional RNA processing, and function via base-pairing with complementary sequences within mRNA molecules, usually resulting in translational repression or target degradation and gene silencing. The human genome can reportedly encode over 1000 miRNAs, which can target about 60% of mammalian genes and are abundant in many human cell types. Various varieties of naturally-occurring and artificial derivatives of miRNAs have been reported in the art. See, for example: Lewis et al. 2003. Cell 1 15: 787-798; Lim et al. 2003. Genes Dev. 17: 991-1008; He et al. 2004. Nat. Rev. Genet. 5: 522-31; Bentwich et al. 2005. Nat. Genet. 37: 766-70; Lewis et al. 2005. Cell 120: 15-20; Kusenda et al. 2006. Biomed Pap Med Fac Univ Palacky Olomouc Czech Repub 150: 205-15; Zhang et al. 2006. J. Gen. Gen. 36: 1-6; Brodersen et al. 2008. Science 320: 1 185-90; Friedman et al. 2009. Genome Res. 19 (1): 92-105; Bartel 2009. Cell 136 (2): 215-33. In various non-limiting examples, the RNAi agent is a sisiRNA (small internally segmented interfering RNA), wherein the sense strand comprises at least one single-stranded nick. This nick decreases the incorporation of the sense strand into the RISC complex and thus reduces off-target effects. See: WO 2007/107162. In various non-limiting examples, a DNA-RNA chimera, wherein the seed portion of each strand is DNA, while the remainder of each strand is RNA. See: Yamato et al. 2011 Cancer Gene Ther. 18: 587-597. In various non-limiting examples, the RNAi agent is a siRNA comprising two mismatches, wherein that the molecule reportedly comprises three short double-stranded regions. In one embodiment of this RNAi agent, the guide (antisense) strand is a 22-mer, while the sense strand is a 20-mer (producing only a single 2-nt overhang on the 3' end of the anti-sense strand; and two mismatches reportedly produce double-stranded regions of 6, 8 and 4 bp. See: U.S. Pat. App. 2009/0209626. In various embodiments, the RNAi agent is a neutral siRNA, in which the negative charges of the phosphate backbone are reversibly masked; Meade et al. 2014 Nat. Biotech. 32: 1256-1261. In various non-limiting examples, the RNAi agent is a aiRNA (assymetrical interfering RNA) which comprises a sense strand is shorter than 19-nt long, so that the anti-sense strand is reportedly preferentially loaded into RISC, and thus off-target effects are reduced. In various embodiments of this RNAi agent, the anti-sense strand is 21-nt long, but the sense strand is only 15 or 16 nt long. See: Sun et al. 2008 Nature Biotech. 26: 1379-1382; and Chu and Rana. 2008 RNA 14: 1714-1719. In various non-limiting examples, the RNAi agent is a siRNA comprising a terminal or internal spacer (e.g., an 18-mer format siRNA), which reportedly comprises a strand which is shorter than that of a canonical siRNA, wherein the strand comprises an internal or terminal spacer such as a ribitol or other type of non-nucleotidic spacer. See: WO2015/051366. In some embodiments, RNAi agents include those that target any of: miR-122, VEGF, VEGF-R1, RTP801, Caspase 2, KRT6A(N171K), ADRB2, TRPV1, Syk kinase, RSV Nucleocapsid, Beta catenin, KRASG12D, Apo B, PLK1, KSP and VEGF, TTR, Bcr-Abl, PKN3, P53, RRM2, Furin and GM-CSF, LMP2, LMP7, MECL1, HIV Tat and Rev. In some embodiments, a composition comprises a lipid and a portion of a RNAi agent capable of mediating at least one function of a RNAi agent.

Small molecule: The terms "small molecule" or "low molecular weight molecule" or "LMW molecule" and the like, as used herein, refer to molecules which have a relatively low molecular weight. As a non-limiting example, small molecules include molecules that are less than about 7500, 7000, 6000, 5000, 4000, 3000, 2500, 2000, 1500, 1000, 900, 800, 700, 600, 500, 400, 300, 200, or 100 molecular weight. In some embodiments, a small molecule is a biologically active agent, and inhibits or decreases target gene or target gene product level, product, and/or activity. Example small molecules include, but are not limited to, small organic molecules (e.g., Cane et al. 1998. Science 282: 63), and natural product extract libraries. In another embodiment, small molecules are small, organic non-peptidic compounds. In some embodiments, small molecule inhibitors indirectly or directly inhibit or decrease target gene or target gene product level, product, and/or activity. In some embodiments, a composition comprises a lipid and a portion of a small molecule capable of mediating at least one function of a small molecule.

Small nucleolar RNAs (snoRNAs): The terms "small nucleolar RNA", "snoRNA" and the like, as used herein, refer to any of a class of small RNA molecules that, for example, guide chemical modifications of other RNAs. In some embodiments, snoRNAs are capable of guiding chemical modifications of other RNAs, including ribosomal RNAs, transfer RNAs and small nuclear RNAs. In some embodiments, there are reportedly two main classes of snoRNA, the C/D box snoRNAs, which are associated with methylation, and the H/ACA box snoRNAs, which are associated with pseudouridylation.

Splice switching oligonucleotide (SSO): The term "Splice switching oligonucleotide" or "SSO", as used herein, refers to an oligonucleotide capable of altering the splicing of a pre-mRNA. In a non-limiting example, a SSO can bind to a 5' or 3' splicing junction or to exonic splicing enhancer or silencing sites. In doing so, a SSO can modify splicing in various ways, such as promoting alternative use of exons, exon exclusion, or exon inclusion. In various embodiments, a SSO can cause an exon to be skipped; or, in other cases, prevent the skipping of an exon. Crooke 2004 Curr. Mol. Med. 4: 465-487; Bennett et al. 2010 Ann. Rev. Pharmacol. Toxicol. 50: 259-293; and Kole et al. 2012 Nat. Rev. Drug Discov. 11: 125-140. A non-limiting example of a SSO is an oligonucleotide which is reportedly capable of mediating skipping of an exon in dystrophin pre-mRNA. A non-limiting example of a SSO is WV-942. A non-limiting example of a SSO is an oligonucleotide which is capable of preventing the skipping of an exon in the SMN2 pre-mRNA; see Rigo et al. 2012 J. Cell Biol. 199: 21-25; and Kaczmarek et al. 2015 Exp. Opin. Exp. Drugs 24: 867-881. In some embodiments, a SSO switches splicing in a gene related to a muscle-related disorder. In some embodiments, a SSO is capable of skipping or mediating the skipping of an exon, wherein a mutation in the exon is related to a muscle-related disorder. In some embodiments, a SSO is capable of preventing the skipping or mediating the prevent of skipping of an exon, wherein a mutation in the exon is related to a muscle-related disorder. In some embodiments, a SSO is capable of skipping or mediates skipping of an exon in the dystrophin gene. In some embodiments, a SSO is capable of skipping or mediates skipping of exon 51, 45, 53 or 44 in the dystrophin gene. In some embodiments, a SSO is capable of preventing or mediating the prevention of skipping of an exon in a gene related to SMA. In some embodiments, a SSO is capable of preventing or mediating the prevention of skipping of an exon in the SMN2 gene. In some embodiments, a SSO is capable of preventing or mediating the prevention of skipping of exon 7 in the SMN2 gene.

Stereochemically isomeric forms, stereoforms, stereoisomers: The phrases "stereochemically isomeric forms", "stereoforms", "stereoisoforms", "stereoisomers", and the like, as used herein, refers to different compounds made up of the same atoms bonded by the same sequence of bonds but having different three-dimensional structures which are not interchangeable. In some embodiments of the disclosure, provided chemical compositions can be or include pure preparations of individual stereochemically isomeric forms of a compound; in some embodiments, provided chemical compositions can be or include mixtures of two or more stereochemically isomeric forms of the compound. In certain embodiments, such mixtures contain equal amounts of different stereochemically isomeric forms; in certain embodiments, such mixtures contain different amounts of at least two different stereochemically isomeric forms. In some embodiments, a chemical composition can contain all diastereomers and/or enantiomers of the compound. In some embodiments, a chemical composition can contain less than all diastereomers and/or enantiomers of a compound. In some embodiments, if a particular enantiomer of a compound of the present disclosure is desired, it can be prepared, for example, by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, diastereomeric salts are formed with an appropriate optically-active acid, and resolved, for example, by fractional crystallization. In some embodiments, a composition which is stereorandom comprises two or more stereoisomers.

Subject. As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject can be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition can not have been diagnosed with the disease, disorder, and/or condition. In some embodiments, an individual who is susceptible to a disease, disorder, and/or condition can exhibit symptoms of the disease, disorder, and/or condition. In some embodiments, an individual who is susceptible to a disease, disorder, and/or condition can not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Targeting compound or moiety or component: The term "targeting moiety", "targeting compound or moiety", "targeting compound", "target component", and the like, as used herein, is a structure capable of targeting a compound or composition to a particular cell or tissue or subset of cells or tissues. In some embodiments, a targeting moiety is designed to take advantage of cell- or tissue-specific expression of particular targets, receptors, proteins, or other subcellular components; In some embodiments, a targeting moiety is a ligand (e.g., a small molecule, antibody, peptide, protein, carbohydrate, aptamer, etc.) that targets a compound or a composition to a cell or tissue, and/or binds to a target, receptor, protein, or other subcellular component. In some embodiments, a targeting moiety targets a composition comprising a lipid and a nucleic acid (including, but not limited to a CpG oligonucleotide) to a muscle cell or tissue. In some embodiments, a targeting moiety comprises a compound that targets a muscle cell or tissue. In some embodiments, a targeting moiety comprises fetuin, epidermal growth factor, fibroblast growth factor, insulin, and/or dexamethasone, or a component or fragment or combination thereof. In some embodiments, a targeting moiety targets a composition comprising a lipid and a nucleic acid (including, but not limited to a CpG oligonucleotide) to a neuron or other cell or tissue in the neuromuscular system. In some embodiments, a targeting moiety comprises a rabies virus peptide (see Kumar et al. 2007 Nature 448: 39-43; and Hwang do et al. 2011 Biomaterials 32: 4968-4975). In some embodiments, a targeting moiety is a moiety capable of binding to a neurotransmitter transporter, a dopamine transporter, a serotonin transporter, or norepinephrine transporter, or alpha-synuclein, or a mRNA encoding any of these components (see U.S. Pat. No. 9,084,825). In some embodiments, a targeting moiety is a transferrin receptor ligand or alpha-transferrin antibody, thus reportedly making use of a transferrin receptor-mediated route across the vascular endothelium. Clark et al. 2015 Proc. Natl. Acad. Sci. USA 112: 12486-12491; Bien-Ly et al. 2014 J. Exp. Med. 211: 233-244; and Youn et al. 2014 Mol. Pharm. 11: 486-495. In some embodiments, a targeting moiety binds to an integrin. In some embodiments, a targeting moiety binds to alphaII-beta3, e.g., on platelets. In some embodiments, a targeting moiety binds to a beta2 integrin, e.g., on a leukocyte. In some embodiments, a targeting moiety binds to an alphav-beta3, e.g., on a tumor cell. In some embodiments, a targeting moiety binds to a GPCR (G protein-coupled receptor) (see Hanyaloglu et al. 2008 Ann. Rev. Pharm. Tox. 48: 537-568). In some embodiments, a targeting moiety binds to a gastrin releasing peptide receptor, e.g., on a cancer cell (see Cornelio et al. 2007 Ann. Oncol. 18: 1457-1466). In some embodiments, a targeting moiety comprises a carbonic anhydrase inhibitor.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the invention, chemical compositions may be provided that are or include pure preparations of a single tautomeric form of a compound. In some embodiments of the invention, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the invention, chemical compositions may contain all tautomeric forms of a compound. In some embodiments of the invention, chemical compositions may contain less than all tautomeric forms of a compound. In some embodiments of the invention, chemical compositions may contain one or more tautomeric forms of a compound in amounts that vary over time as a result of interconversion. In some embodiments of the invention, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts to provide an enol derivative that may subsequently be isolated using one or more suitable techniques known in the art. Unless otherwise indicated, the present disclosure encompasses all tautomeric forms of relevant compounds, whether in pure form or in admixture with one another.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance can vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment can be administered to a subject who does not exhibit signs of a disease, disorder, and/or condition. In some embodiments, treatment can be administered to a subject who exhibits only early signs of the disease, disorder, and/or condition, for example for the purpose of decreasing the risk of developing pathology associated with the disease, disorder, and/or condition.

Unsaturated: The term "unsaturated" as used herein, means that a moiety has one or more units of unsaturation.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose can be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose can be present in a formulation that includes any of a variety of components in addition to the therapeutic agent(s). For example, acceptable carriers (e.g., pharmaceutically acceptable carriers), diluents, stabilizers, buffers, preservatives, etc., can be included as described infra. The carrier can be a solvent such as water or alcohol. The carrier can optionally comprise any one or more of: excipients, diluents, fillers, salts, buffers, stabilizers, solubilizers, lipids or other substance which is well reported for medicine compositions in the art. This oligonucleotide can be administrated to a subject directly or with a nucleic acid delivery complex. A nucleic acid delivery complex can be, as a non-limiting example, a nucleic acid which is associated (e.g., ionic bond or covalent bond, or encapsulated in the way) with a targeting moiety (e.g., a molecule which generates high affinity bond to target cells (e.g., surface of B cell) and/or increase cellular uptake by target cells.). Non-limiting examples of the nucleic acid delivery complex include nucleic acid associated with sterols such as cholesterol, lipids (e.g., cationic lipids, virosomes or liposomes) or target cell specific bonding factors (egg, ligands recognized by target cell specific receptor).

Preferred complex can be enough stable in vivo to prevent from significant de-coupling before the internalization by the target cell. But the complex can be cleavage under appropriate conditions in the cells so that the nucleic acid is released in a functional form.

Vaccine: The term "vaccine", as used herein, refers to a molecule that improves immunity to a particular disease or infectious agent. Vaccines encoded in the polynucleotides, primary constructs or mmRNA of the disclosure can be utilized to treat conditions or diseases in many therapeutic areas such as, but not limited to, cardiovascular, CNS, dermatology, endocrinology, oncology, immunology, respiratory, and anti-infective. In some embodiments, a vaccine comprises an agent that immunologically resembles a disease-causing micro-organism or fragment thereof; In some embodiments, a vaccine is made from weakened or killed forms of the virus, microbe, parasite or other pathogen, or a fragment thereof. In some embodiments, a vaccine stimulates the body's immune system to recognize the agent as a threat, destroy it, and keep a record of it, so that the immune system can more easily recognize and destroy any of these micro-organisms that it later encounters. In some embodiments, a vaccine is prophylactic or therapeutic. In various embodiments, a vaccine can be to a virus, a bacterium, a parasite, or another pathogen. In some embodiments, a vaccine is to a virus selected from: common cold virus, Hepatitis A virus, Hepatitis B virus, Hepatitis E virus, Human papillomavirus, Influenza virus, Japanese encephalitis virus, Measles virus, Mumps virus, Polio virus, Rabies virus, Rhinovirus, Rotavirus, Rubella virus, Varicella zoster virus, Variola virus, and Yellow fever virus. In various embodiments, a vaccine is a vaccine selected from: a virus vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, Epstein-Barr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans, and Zika virus vaccine. In some embodiments, a vaccine is to a bacterium selected from: *Bacillus anthracis*, *Vibrio cholerae*, *Bordetella pertussis*, *Clostridium tetani*, *Corynebacterium diphtheriae*, *Haemophilus influenzae* type B (Hib), *Neisseria meningitidis*, *Streptococcus pneumoniae*, *Coxiella burnetii*, *Mycobacterium tuberculosis*, and *Salmonella typhi*. In various embodiments, a vaccine is a vaccine selected from: a Bacterial disease vaccine, Caries vaccine, Ehrlichiosis vaccine, Leprosy vaccine, Lyme disease vaccine, *Staphylococcus aureus* vaccine, *Streptococcus pyogenes* vaccine, Syphilis vaccine, Tularemia vaccine, and *Yersinia pestis* vaccine. In various embodiments, a vaccine is a vaccine selected from: A parasitic disease vaccine, Malaria vaccine, Schistosomiasis vaccine, Chagas disease vaccine, Hookworm vaccine, Onchocerciasis river blindness vaccine for humans, Trypanosomiasis vaccine, and Visceral leishmaniasis vaccine. In various embodiments, a vaccine is selected from: a non-infectious disease vaccine, Alzheimer's disease amyloid protein vaccine, Breast cancer vaccine, Ovarian cancer vaccine, Prostate cancer vaccine, and Talimogene laherparepvec (T-VEC). In some embodiments, a composition comprises a lipid and a portion of a vaccine capable of mediating at least one function of a vaccine.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

The methods and structures described herein relating to compounds and compositions of the disclosure also apply to the pharmaceutically acceptable acid or base addition salts and all stereoisomeric forms of these compounds and compositions.

In general, properties of CpG oligonucleotides, including the ability to agonize or antagonize an immune response, can be assayed using any method or technique described herein or known in the art.

Certain Embodiments

In some embodiments, the present disclosure pertains to the recognition that an immune response mediated by a CpG oligonucleotide can be affected by stereochemistry of chiral internucleotidic linkages, such as phosphorothioates, in a CpG region motif in the oligonucleotide.

In some embodiments, the present disclosure encompasses an insight that immune responses mediated by CpG oligonucleotides can be affected by stereochemistry. In some embodiments, the present disclosure presents data showing that stereorandom and stereopure CpG oligonucleotide compositions can display different immunomodulatory activities. Different stereopure CpG oligonucleotide compositions can also display different immunomodulatory activities.

According to some embodiments of the disclosure, when oligonucleotides comprising a CpG region motif have one or more chiral centers (e.g., within the CpG region motif), different stereoforms of such oligonucleotides can have different characteristics and/or activities, one or more of which can impact their utility and/or effectiveness. In some embodiments, chiral centers that can impact oligonucleotide characteristics and/or activities are found in internucleotidic linkages, e.g., involving one or more phosphorothioate or otherwise modified phosphodiester linkages.

In some embodiments, the present disclosure pertains to a chirally controlled CpG oligonucleotide composition, which is chirally controlled in that the composition comprises a predetermined level of oligonucleotides of an individual oligonucleotide type, wherein an oligonucleotide type is defined by: 1) base sequence; 2) pattern of backbone (internucleotidic) linkages; 3) pattern of backbone (internucleotidic linkage) chiral centers; and 4) pattern of backbone (internucleotidic linkage) phosphorus modifications; wherein each oligonucleotide of the individual oligonucleotide type independently comprises at least one common CpG region motif. In some embodiments, provided oligonucleotides of an individual oligonucleotide type further comprise one or more chemical modifications of one or more bases and/or sugars. In some embodiments, provided oligonucleotides comprise one or more modified sugars. In some embodiments, provided oligonucleotides comprise one or more 2'-modified sugars. In some embodiments, a 2'-modification is 2'-OR, wherein R is optionally substituted $C_{1-6}$ aliphatic. In some embodiments, provided oligonucleotides comprise one or more modified bases. In some embodiments, provided oligonucleotides comprise one or more modified 5mC. In some embodiments, provided oligonucleotides comprise one or more modified sugars and one or more modified bases.

In some embodiments, while the present disclosure provides data showing that, in at least some chirally controlled CpG oligonucleotide compositions, some CpG region motifs had greater immunomodulatory activity (e.g., greater agonistic or greater antagonistic activity) than others, the present disclosure encompasses any chirally controlled CpG oligonucleotide composition, wherein the CpG region motif comprises a stereodefined phosphorothioate or other internucleotidic linkage, wherein the CpG oligonucleotide demonstrates a greater agonistic or antagonistic activity than a negative control (e.g., in the absence of the oligonucleotide composition) or a reference composition (e.g., a stereorandom composition of oligonucleotides having the same base sequence and/or chemical modifications, another chirally controlled oligonucleotide composition of oligonucleotides having the same base sequence and/or chemical modifications, etc.). In some embodiments, the present disclosure provides a chirally controlled oligonucleotide composition comprising any CpG region motif disclosed herein.

In some embodiments, the present disclosure pertains to a chirally controlled CpG oligonucleotide composition, which is chirally controlled in that the composition comprises a predetermined level of oligonucleotides of an individual oligonucleotide type, wherein an oligonucleotide type is defined by: 1) base sequence; 2) pattern of backbone (internucleotidic) linkages; 3) pattern of backbone (internucleotidic linkage) chiral centers; and 4) pattern of backbone (internucleotidic linkage) phosphorus modifications; wherein each oligonucleotide of the individual oligonucleotide type independently comprises at least one common CpG region motif, which is any CpG region motif disclosed herein.

In some embodiments, the present disclosure pertains to a chirally controlled CpG oligonucleotide composition, which is chirally controlled in that the composition comprises a predetermined level of oligonucleotides of an individual oligonucleotide type, wherein an oligonucleotide type is defined by: 1) base sequence; 2) pattern of backbone (internucleotidic) linkages; 3) pattern of backbone (internucleotidic linkage) chiral centers; and 4) pattern of backbone (internucleotidic linkage) phosphorus modifications; wherein each oligonucleotide of the individual oligonucleotide type independently comprises at least one common CpG region motif: $N_1$-(*R/S)—C—(*R/S)-G-(*R/S)—$N_2$; wherein each (*R/S) is independently a chiral internucleotidic linkage, and N) and $N_2$ are any nucleoside. In some embodiments, the present disclosure pertains to a chirally controlled CpG oligonucleotide composition comprising a plurality of oligonucleotides, each of which: (a) hybridizes with a particular target sequence; (b) has a base sequence that includes at least one C residue in a CpG region motif that is present in all oligonucleotides of the plurality (a "common C residue") and that has a 5-methyl group, a modified sugar moiety, or both; and (c) includes one or more chiral internucleotidic linkages, so that each oligonucleotide is a particular stereoform, characterized by its stereoidentity at each of the one or more chiral internucleotidic linkages, wherein stereoidentity identifies which stereoisomer is present at a particular chiral internucleotidic linkage, wherein the composition is chirally controlled in that it contains a predetermined level of each stereoform.

In some embodiments, the present disclosure pertains to a chirally controlled oligonucleotide composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a phosphorothioate in the Rp conformation and at least one (*R/S) is a modified internucleotidic linkage in the Sp conformation, and each of $N_1$ and $N_2$ is independently any nucleoside.

In some embodiments, the present disclosure pertains to a chirally controlled oligonucleotide composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and each of $N_1$ and $N_2$ is independently any nucleoside.

In some embodiments, the present disclosure pertains to a composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and $N_1$ and $N_2$ are any nucleoside.

In some embodiments, the present disclosure pertains to a composition comprising a plurality of oligonucleotides, each of which: (a) hybridizes with a particular target sequence; and (b) comprises a sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, and $N_1$ and $N_2$ are any nucleoside.

In some embodiments, the present disclosure pertains to a composition comprising a plurality of oligonucleotides, each of which: (a) consists of a particular base sequence; and (b) comprises a sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein at least one (*R/S) is a phosphorothioate in the Rp conformation and at least one (*R/S) is a phosphorothioate in the Sp conformation, and each of $N_1$ and $N_2$ is independently any nucleoside.

In some embodiments, the present disclosure pertains to a composition comprising a plurality of oligonucleotides, each of which: (a) hybridizes with a particular target sequence; and (b) has a sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, wherein the composition is chirally controlled in that it contains a predetermined level of each of stereoisomers 1-8 (S1-S8) for each common CpG region motif: S1: $N_1$-(*R)—C—(*R)-G-(*R)—$N_2$; S2: $N_1$-(*R)—C—(*R)-G-(*S)—$N_2$; S3: $N_1$-(*R)—C—(*S)-G-(*R)—$N_2$; S4: $N_1$-(*R)—C—(*S)-G-(*S)—$N_2$; S5: $N_1$-(*S)—C—(*R)-G-(*R)—$N_2$; S6: $N_1$-(*S)—C—(*R)-G-(*S)—$N_2$; S7: $N_1$-(*S)—C—(*S)-G-(*R)—$N_2$; S8: $N_1$-(*S)—C—(*S)-G-(*S)—$N_2$.

In some embodiments, the present disclosure pertains to an oligonucleotide composition that is chirally controlled in that the composition comprises a predetermined level of oligonucleotides of an individual oligonucleotide type, wherein an oligonucleotide type is defined by: (1) base sequence; (2) pattern of backbone linkages; (3) pattern of backbone chiral centers; and (4) pattern of backbone phosphorus modifications; wherein each oligonucleotide of the individual oligonucleotide type independently comprises at least one common CpG region motif: $N_1$-(*R/S)—C—(*R/

S)-G-(*R/S)—N₂; wherein each (*R/S) is independently a chiral internucleotidic linkage, and each of N₁ and N₂ is independently any nucleoside.

In some embodiments, the present disclosure pertains to a composition comprising a plurality of oligonucleotides, each of which: (a) hybridizes with a particular target sequence; (b) has a base sequence that includes at least one C residue in a CpG region motif that is present in all oligonucleotides of the plurality (a "common C residue") and that has a 5-methyl group, a modified sugar moiety, or both; and (c) includes one or more chiral internucleotidic linkages, so that each oligonucleotide is a particular stereoform, characterized by its stereoidentity at each of the one or more chiral internucleotidic linkages, wherein stereoidentity identifies which stereoisomer is present at a particular chiral internucleotidic linkage, wherein the composition is chirally controlled in that it contains a predetermined level of each stereoform.

In some embodiments, the present disclosure pertains to an oligonucleotide composition that is chirally controlled in that the composition comprises a predetermined level of oligonucleotides of an individual oligonucleotide type, wherein an oligonucleotide type is defined by: (1) base sequence; (2) pattern of backbone linkages; (3) pattern of backbone chiral centers; and (4) pattern of backbone phosphorus modifications; wherein the base sequence includes at least one C residue in a CpG region motif that has a 5-methyl group, a modified sugar moiety, or both; and the composition has a reduced ability to activate a TLR9-mediated and/or TLR9-associated immune response relative to the ability of a composition that is not chirally controlled in that the composition comprises a random level of oligonucleotides of an individual oligonucleotide type.

In some embodiments, the present disclosure pertains to a composition comprising a CpG oligonucleotide comprising a strand comprising about 14 to about 49 nucleotides, wherein the strand comprises at least one copy of any CpG region motif disclosed herein.

In some embodiments, the present disclosure pertains to a composition comprising a CpG oligonucleotide comprising a strand comprising about 14 to about 49 nucleotides, wherein the strand comprises at least one copy of any CpG region motif of any CpG oligonucleotide disclosed herein.

In some embodiments, the present disclosure pertains to a composition comprising a CpG oligonucleotide comprising a strand comprising about 14 to about 49 nucleotides, wherein the strand comprises or consists of the sequence of any oligonucleotide disclosed herein.

In some embodiments, the present disclosure pertains to a composition comprising a CpG oligonucleotide comprising a strand comprising 14 to 49 nucleotides, wherein the strand comprises at least one copy of any CpG region motif disclosed herein.

In some embodiments, the present disclosure pertains to a composition comprising a CpG oligonucleotide comprising a strand comprising 14 to 49 nucleotides, wherein the strand comprises at least one copy of any CpG region motif of any CpG oligonucleotide disclosed herein.

In some embodiments, the present disclosure pertains to a composition comprising CpG oligonucleotides comprising a strand comprising 14 to 49 nucleotides, wherein the strand comprises at least two copies of any CpG region motif disclosed herein.

In some embodiments, the present disclosure pertains to a method of agonizing an immune response in a human cell, the method comprising the step of contacting the human cell with a CpG oligonucleotide of any one of the preceding embodiments, wherein the CpG oligonucleotide is capable of agonizing a TLR9-mediated or TLR9-associated immune response.

In some embodiments, the present disclosure pertains to a method of antagonizing an immune response in a human cell, the method comprising the step of contacting the human cell with a CpG oligonucleotide of any one of the preceding embodiments, wherein the CpG oligonucleotide is capable of antagonizing a TLR9-mediated or TLR9-associated immune response.

In some embodiments, the present disclosure pertains to a method of modulating an immune response in a subject, the method comprising the step of administering a composition of any one of preceding embodiments, wherein the CpG oligonucleotide is capable of modulating a TLR9-mediated or TLR9-associated immune response.

In some embodiments, the present disclosure pertains to a method of agonizing an immune response in a human being in need thereof, the method comprising the step of contacting the human with an immunologically effective amount of CpG oligonucleotide of any one of the preceding embodiments.

In some embodiments, the present disclosure pertains to a method of increasing an immune response to an immunologically active component in a subject, comprising administering an immunologically effective amount of (a) a composition of any one of the preceding embodiments and (b) the immunologically active component.

In some embodiments, the present disclosure pertains to a method of identifying a second oligonucleotide composition with decreased immune stimulation in a subject compared to a first oligonucleotide composition, the method comprising steps of: (a) measuring the immune stimulation mediated by the first oligonucleotide composition, wherein the first oligonucleotide composition comprising oligonucleotides that have a common base sequence comprising at least one CpG region; (b) measuring the immune stimulation mediated by a second oligonucleotide composition, wherein the second oligonucleotide composition has the same common base sequence as the first oligonucleotide composition, and wherein the CpG region of oligonucleotides of the second composition differs in its pattern of chiral centers from the corresponding region of oligonucleotides of the first oligonucleotide composition; optionally repeating step (b), each repeat with a different second oligonucleotide composition, and selecting a second oligonucleotide composition which mediates less immune stimulation than the first oligonucleotide composition.

In some embodiments, the present disclosure pertains to a method of improving a characteristic of a CpG oligonucleotide composition comprising at least two CpG oligonucleotides, wherein the method comprises a step of: decreasing the amount in the composition of at least one of the at least two CpG oligonucleotides, wherein each of the at least two CpG oligonucleotides is defined by the stereochemistry of a CpG region motif, and wherein the at least one of the at least two CpG oligonucleotides is determined to have an inferior characteristic relative to the CpG oligonucleotide composition.

In some embodiments, the present disclosure pertains to a method of improving a characteristic of a stereorandom CpG oligonucleotide composition at least two CpG oligonucleotides, wherein the method comprises a step of: decreasing the amount in the composition of at least one of the at least two CpG oligonucleotides, wherein each of the at least two CpG oligonucleotides is defined by the stereochemistry of a CpG region motif, and wherein the at least one of the at least two CpG oligonucleotides is determined to have an inferior characteristic relative to the CpG oligonucleotide composition, wherein the characteristic is increased activity, improved efficacy, reduced toxicity, increased stability, increased delivery, or increased biological half-life.

In some embodiments, the present disclosure pertains to a method of designing a second oligonucleotide mediating decreased immune stimulation in a human cell relative to the immune stimulation mediated by a first oligonucleotide, the method comprising the steps of: (a) measuring the immune stimulation mediated by a first oligonucleotide, wherein the first oligonucleotide has a defined base sequence comprising at least one CpG region; (b) measuring the immune stimulation mediated by one or more second oligonucleotides, wherein the second oligonucleotides have the same base sequence as the first oligonucleotide and further comprise one or more phosphorothioates in the CpG region motif, wherein the stereochemistry of the phosphorothioates in the CpG region motif of the second oligonucleotides differs from the stereochemistry of any phosphorothioates in the CpG region motif of the first oligonucleotides, wherein steps (a) and (b) can be performed in any order; selecting a second oligonucleotide which mediates less immune stimulation than the first oligonucleotide.

In some embodiments, the present disclosure pertains to a method of decreasing the immune stimulation in a human cell mediated by a first oligonucleotide, the method comprising the steps of: (a) providing the first oligonucleotide, wherein the first oligonucleotide has a defined base sequence comprising at least one CpG region; and measuring the immune stimulation in a human cell mediated by the first oligonucleotide; (b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order; selecting a second oligonucleotide which mediates less immune stimulation than the first oligonucleotide; and contacting the cell with the second oligonucleotide.

In some embodiments, the present disclosure pertains to a composition comprising an oligonucleotide, wherein the oligonucleotide mediates less immune stimulation than a reference oligonucleotide, wherein the second oligonucleotide is selected using a method comprising the steps of: providing the reference oligonucleotide, wherein the reference oligonucleotide has a defined base sequence comprising at least one CpG region; and measuring the immune stimulation in a human cell mediated by the reference oligonucleotide; providing one or more second oligonucleotides, wherein the second oligonucleotides have the same base sequence as the reference oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the reference oligonucleotides; and measuring the immune stimulation in a human cell of the second oligonucleotides, wherein steps can be performed in any order; selecting a second oligonucleotide which mediates less immune stimulation than the reference oligonucleotide.

In some embodiments, the present disclosure pertains to a method of administering a therapeutic oligonucleotide to a subject, wherein the therapeutic oligonucleotide mediates less immune stimulation than a first oligonucleotide. In some embodiments, the therapeutic oligonucleotide is selected using a method comprising the steps of: providing the first oligonucleotide, wherein the first oligonucleotide has a defined base sequence comprising at least one CpG region; and measuring the immune stimulation in a human cell mediated by the first oligonucleotide; providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps can be performed in any order; selecting a second oligonucleotide which mediates less immune stimulation than the first oligonucleotide as the therapeutic oligonucleotide.

In some embodiments, the present disclosure pertains to a method, comprising administering a composition comprising a first plurality of oligonucleotides, each of which: (a) hybridizes with a particular target sequence; and (b) has base sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, wherein the composition is chirally controlled in that it contains a predetermined level of each of stereoisomers 1-8 (S1-S8) for each common CpG region motif: S1: $N_1$-(*R)—C—(*R)-G-(*R)—$N_2$; S2: $N_1$-(*R)—C—(*R)-G-(*S)—$N_2$; S3: $N_1$-(*R)—C—(*S)-G-(*R)—$N_2$; S4: $N_1$-(*R)—C—(*S)-G-(*S)—$N_2$; S5: $N_1$-(*S)—C—(*R)-G-(*R)—$N_2$; S6: $N_1$-(*S)—C—(*R)-G-(*S)—$N_2$; S7: $N_1$-(*S)—C—(*S)-G-(*R)—$N_2$; S8: $N_1$-(*S)—C—(*S)-G-(*S)—$N_2$; wherein the composition is characterized by reduced immune stimulation relative to a reference composition, which differs from the composition in that it is stereorandom with respect to internucleotidic linkages of at least one CpG region motif.

In some embodiments, the present disclosure pertains to: In a method of administering an oligonucleotide composition comprising a plurality of oligonucleotides having a common base sequence, the improvement that comprises: administering a composition comprising a first plurality of oligonucleotides, each of which: (a) hybridizes with a particular target sequence; and (b) has base sequence that includes at least one CpG region motif present in all oligonucleotides of the plurality (a "common CpG region motif"), which CpG region motif has a structure: $N_1$-(*R/S)—C—(*R/S)-G-(*R/S)—$N_2$; wherein each (*R/S) is independently a chiral internucleotidic linkage, wherein the composition is chirally controlled in that it contains a predetermined level of each of stereoisomers 1-8 (S1-S8) for each common CpG region motif: S1: $N_1$-(*R)—C—(*R)-G-(*R)—$N_2$; S2: $N_1$-(*R)—C—(*R)-G-(*S)—$N_2$; S3: $N_1$-(*R)—C—(*S)-G-(*R)—$N_2$; S4: $N_1$-(*R)—C—(*S)-G-(*S)—$N_2$; S5: $N_1$-(*S)—C—(*R)-G-(*R)—$N_2$; S6: $N_1$-(*S)—C—(*R)-G-(*S)—$N_2$; S7: $N_1$-(*S)—C—(*S)-G-(*R)—$N_2$; S8: $N_1$-(*S)—C—(*S)-G-(*S)—$N_2$; wherein the composition is characterized by reduced immune stimulation relative to a reference composition, which differs from the composition in that it is stereorandom with respect to internucleotidic linkages of at least one CpG region motif.

In some embodiments, the present disclosure pertains to a method, comprising administering a chirally controlled oligonucleotide composition that is chirally controlled in that the composition comprises a predetermined level of oligonucleotides of an individual oligonucleotide type, wherein an oligonucleotide type is defined by: (1) base sequence; (2) pattern of backbone linkages; (3) pattern of backbone chiral centers; and (4) pattern of backbone phosphorus modifications; wherein each oligonucleotide of the individual oligonucleotide type independently comprises at least one copy of a CpG region motif: $N_1$-(*R/S)—C—(*R/S)-G-(*R/S)—$N_2$; wherein: each (*R/S) is independently a chiral internucleotidic linkage; oligonucleotides of the individual oligonucleotide type have the common base sequence; and the chirally controlled oligonucleotide composition displays reduced immune stimulation relative to a reference oligonucleotide composition, which reference oligonucleotide composition is a stereorandom oligonucleotide composition comprising oligonucleotides having the same common base sequence, or a chirally controlled oligonucleotide composition of oligonucleotides having the same common base sequence but of a different oligonucleotide type.

In some embodiments, the present disclosure pertains to:
In a method of administering an oligonucleotide composition comprising a plurality of oligonucleotides having a common base sequence, the improvement that comprises: administering a chirally controlled oligonucleotide composition that is chirally controlled in that the composition comprises a predetermined level of oligonucleotides of an individual oligonucleotide type, wherein an oligonucleotide type is defined by: (1) base sequence; (2) pattern of backbone linkages; (3) pattern of backbone chiral centers; and (4) pattern of backbone phosphorus modifications; wherein each oligonucleotide of the individual oligonucleotide type independently comprises at least one copy of a CpG region motif: $N_1$-(*R/S)—C—(*R/S)-G-(*R/S)—$N_2$; wherein: each (*R/S) is independently a chiral internucleotidic linkage; oligonucleotides of the individual oligonucleotide type have the common base sequence; and the chirally controlled oligonucleotide composition displays reduced immune stimulation relative to a reference oligonucleotide composition, which reference oligonucleotide composition is a stereorandom oligonucleotide composition comprising oligonucleotides having the same common base sequence, or a chirally controlled oligonucleotide composition of oligonucleotides having the same common base sequence but of a different oligonucleotide type.

In some embodiments, the present disclosure pertains to a method, comprising administering a chirally controlled oligonucleotide composition, wherein the composition comprises a plurality of oligonucleotides, each of which: (a) hybridizes with a particular target sequence; (b) has base sequence that includes at least one C residue in a CpG that is present in all oligonucleotides of the plurality (a "common C residue") and that has a 5-methyl group, a T-OMe group in its sugar moiety, or both; and (c) includes one or more chiral internucleotidic linkages, so that each oligonucleotide is a particular stereoform, characterized by its stereoidentity [stereoidentity=which stereoisomer is present at a particular chiral linkage] at each of the one or more chiral internucleotidic linkages, wherein the composition is chirally controlled in that it contains a predetermined level of each stereoform, and the composition is substantially free of those stereoforms that individually, and in the absence of other stereoforms, activate TLR9.

In a method comprising administering a chirally controlled oligonucleotide composition, wherein the composition comprises a plurality of oligonucleotides, each of which: (a) hybridizes with a particular target sequence; (b) has base sequence that includes at least one C residue in a CpG region motif that is present in all oligonucleotides of the plurality (a "common C residue") and that has a 5-methyl group, a 2'-OMe group in its sugar moiety, or both; and (c) includes one or more chiral internucleotidic linkages; the improvement that comprises administering a composition comprising a plurality of oligonucleotides, each of which: (a) hybridizes with the same target sequence; (b) has base sequence that includes the same common C residue in a CpG region motif that has a 5-methyl group, a 2'-OMe group in its sugar moiety, or both; and (c) includes one or more chiral internucleotidic linkages, so that each oligonucleotide is a particular stereoform, characterized by its stereoidentity [stereoidentity=which stereoisomer is present at a particular chiral linkage] at each of the one or more chiral internucleotidic linkages, wherein the composition is chirally controlled in that it contains a predetermined level of each stereoform, and the composition is substantially free of those stereoforms that individually, and in the absence of other stereoforms, activate TLR9.

In some embodiments, the present disclosure pertains to a method, comprising administering a composition that is chirally controlled in that the composition comprises a predetermined level of oligonucleotides of an individual oligonucleotide type, wherein an oligonucleotide type is defined by: (1) base sequence; (2) pattern of backbone linkages; (3) pattern of backbone chiral centers; and (4) pattern of backbone phosphorus modifications; wherein the base sequence includes at least one C residue in a CpG region motif that has a 5-methyl group, a 2'-OMe group in its sugar moiety, or both; and the composition is substantially free of oligonucleotides of a different oligonucleotide type having the same sequence that individually, and in the absence of other stereoforms, activate TLR9.

In some embodiments, the present disclosure pertains to:
In a method comprising administering a composition of oligonucleotides of a common base sequence, wherein the common base sequence includes at least one C residue in a CpG region motif that has a 5-methyl group, a 2'-OMe group in its sugar moiety, or both; the improvement comprises administering a composition that is chirally controlled in that the composition comprises a predetermined level of oligonucleotides of an individual oligonucleotide type, wherein an oligonucleotide type is defined by: (1) base sequence; (2) pattern of backbone linkages; (3) pattern of backbone chiral centers; and (4) pattern of backbone phosphorus modifications; wherein oligonucleotides of the individual oligonucleotide type has the same common sequence, the base sequence includes the same at least one C residue in a CpG region motif that has a 5-methyl group, a 2'-OMe group in its sugar moiety, or both; and the composition is substantially free of oligonucleotides of a different oligonucleotide type having the same sequence that individually, and in the absence of other stereoforms, activate TLR9.

Provided CpG oligonucleotides can have various patterns of backbone chiral centers including those extensively described in the present disclosure, for example, percentage of Sp, percentage of Rp, specific combinations of Sp and Rp, etc. In some embodiments, provided CpG oligonucleotides have high percentage of Sp, for example, more than above 50%, 55%, 60%, 65%, 70%, 75%, 80%, 85%, 90%, 95%, etc. as described in the present disclosure. In some embodiments, oligonucleotides having high percentage of Sp provide enhanced agonist activities, for example, toward mouse TLR9. In some embodiments, to avoid agonist activities and/or to provide antagonist activities, percentage of Sp is controlled in oligonucleotides. In some embodiments, the internucleotidic linkage of CpG is Rp. In some embodiments, oligonucleotides comprising such Rp-CpG provide enhanced agonist activities, for example, toward mouse TLR9. In some embodiments, to avoid agonist activities and/or to provide antagonist activities, one or more Rp-CpG are eliminated from oligonucleotides. In some embodiments, Sp adjacent to CpG, including those immediately to the 5'- and/or 3'-ends of CpG, enhances agonist activity. In some embodiments, Sp adjacent to CpG, including those immediately to the 5'- and/or 3'-ends of CpG, reduces agonist activities and/or enhances antagonist activities. In some embodiments, provided agonist oligonucleotides comprise a Sp-C-Rp-G-Sp motif. In some embodiments, provided antagonist oligonucleotides comprise a Rp-CpG-Sp motif, wherein the CpG can be either modified or unmodified, and the p, if modified, can be either Rp or Sp. In some embodiments, provided antagonist oligonucleotides comprise a Rp-C-Rp-G-Rp motif. In some embodiments, provided oligonucleotides comprise Sp to the 3' of CpG. In some embodiments, provided oligonucleotides comprise one or more -CpG-Sp motifs. In some embodiments, such oligonucleotides provide enhanced agonist activities, for example, toward human TLR9. In some embodiments, provided oligonucleotides comprise Rp to the 5' of CpG. In some embodiments, provided oligonucleotides comprise one or more Rp-CpG- motifs. In some embodiments, such oligonucleotides provide enhanced agonist activities, for example, toward human TLR9. In some embodiments, provided oligonucleotides comprise one or more Rp-CpG-Sp motifs. In some embodiments, provided oligonucleotides comprise one or more Rp-C-Rp-G-Sp motifs. In some embodiments, provided oligonucleotides comprise one or more Rp-C-Sp-G-Sp motifs. In some embodiments, such oligonucleotides provide enhanced agonist activities, for example, toward human TLR9. In some embodiments, CpG and/or its two neighboring nucleosides do not all contain 2'-modifications. In some embodiments, CpG and/or its two neighboring nucleosides do not all contain 2'-MOE. In some embodiments, CpG and/or its two neighboring nucleosides do not contain 2'-modifications. In some embodiments, CpG and/or its two neighboring nucleosides do not contain 2'-MOE. In some embodiments, provided oligonucleotides comprise one or more -CpG-Sp motifs wherein the CpG and/or its two neighboring nucleosides do not all contain 2'-modifications. In some embodiments, provided oligonucleotides comprise one or more Rp-CpG- motifs wherein the CpG and/or its two neighboring nucleosides do not all contain 2'-modifications. In some embodiments, provided oligonucleotides comprise one or more Rp-CpG-Sp motifs wherein the CpG and/or its two neighboring nucleosides do not all contain 2'-modifications. In some embodiments, provided oligonucleotides comprise one or more Rp-C-Sp-G-Sp motifs wherein the CpG and/or its two neighboring nucleosides do not all contain 2'-modifications. In some embodiments, provided oligonucleotides comprise one or more Rp-C-Sp-G-Sp motifs wherein the CpG and/or its two neighboring nucleosides do not all contain 2'-modifications. In some embodiments, provided oligonucleotides comprise Rp to the 3' of CpG. In some embodiments, provided oligonucleotides comprise one or more -CpG-Rp motifs. In some embodiments, such oligonucleotides provide enhanced agonist activities, for example, toward human TLR9. In some embodiments, provided oligonucleotides comprise Rp to the 5' of CpG. In some embodiments, provided oligonucleotides comprise one or more Rp-CpG- motifs. In some embodiments, such oligonucleotides provide enhanced agonist activities, for example, toward human TLR9. In some embodiments, provided oligonucleotides comprise one or more Rp-CpG-Rp motifs. In some embodiments, provided oligonucleotides comprise one or more Rp-C-Rp-G-Rp motifs. In some embodiments, provided oligonucleotides comprise one or more Rp-C-Sp-G-Rp motifs. In some embodiments, such oligonucleotides provide enhanced agonist activities, for example, toward human TLR9. In some embodiments, CpG and/or its two neighboring nucleosides contain one or more modified sugars. In some embodiments, CpG and/or its two neighboring nucleosides contain one or more 2'-modifications. In some embodiments, CpG and/or its two neighboring nucleosides contain one or more 2'-MOE. In some embodiments, CpG and/or its two neighboring nucleosides contain one or more modified C. In some embodiments, CpG and/or its two neighboring nucleosides contain one or more 5mC. In some embodiments, provided oligonucleotides comprise one or more -CpG-Rp motifs wherein the CpG and/or its two neighboring nucleosides contain one or more modified sugars. In some embodiments, provided oligonucleotides comprise one or more Rp-CpG- motifs wherein the CpG and/or its two neighboring nucleosides contain one or more modified sugars. In some embodiments, provided oligonucleotides comprise one or more Rp-CpG-Rp motifs wherein the CpG and/or its two neighboring nucleosides contain one or more modified sugars. In some embodiments, provided oligonucleotides comprise one or more Rp-C-Rp-G-Rp motifs wherein the CpG and/or its two neighboring nucleosides contain one or more modified sugars. In some embodiments, provided oligonucleotides comprise one or more -Rp-C-Sp-G-Rp motifs wherein the CpG and/or its two neighboring nucleosides contain one or more modified sugars. In some embodiments, provided oligonucleotides comprise one or more -CpG-Rp motifs wherein the CpG and/or its two neighboring nucleosides contain one or more 2'-modifications. In some embodiments, provided oligonucleotides comprise one or more Rp-CpG- motifs wherein the CpG and/or its two neighboring nucleosides contain one or more 2'-modifications. In some embodiments, provided oligonucleotides comprise one or more Rp-CpG-Rp motifs wherein the CpG and/or its two neighboring nucleosides contain one or more 2'-modifications. In some embodiments, provided oligonucleotides comprise one or more Rp-C-Rp-G-Rp motifs wherein the CpG and/or its two neighboring nucleosides contain one or more 2'-modifications. In some embodiments, provided oligonucleotides comprise one or more -Rp-C-Sp-G-Rp motifs wherein the CpG and/or its two neighboring nucleosides contain one or more 2'-modifications. In some embodiments, provided oligonucleotides comprise one or more -CpG-Rp motifs wherein the CpG and/or its two neighboring nucleosides contain one or more 2'-MOE. In some embodiments, provided oligonucleotides comprise one or more Rp-CpG- motifs wherein the CpG and/or its two neighboring nucleosides contain one or more 2'-MOE. In some embodiments, provided oligonucleotides comprise one or more Rp-CpG-Rp motifs wherein the CpG and/or its two neighboring nucleosides contain one or more 2'-MOE. In some embodiments, provided oligonucleotides comprise one or more Rp-C-Rp-G-Rp motifs wherein the CpG and/or its two neighboring nucleosides contain one or more 2'-MOE. In some embodiments, provided oligonucleotides comprise one or more -Rp-C-Sp-G-Rp motifs wherein the CpG and/or its two neighboring nucleosides contain one or more 2'-MOE. In some embodiments, provided oligonucleotides comprise one or more -CpG-Rp motifs wherein the CpG and/or its two neighboring nucleosides contain one or more modified bases. In some embodiments, provided oligonucleotides comprise one or more Rp-CpG- motifs wherein the CpG and/or its two neighboring nucleosides contain one or more modified bases. In some embodiments, provided oligonucleotides comprise one or more Rp-CpG-Rp motifs wherein the CpG and/or its two neighboring nucleosides contain one or more modified bases. In some embodiments, provided oligonucleotides comprise one or more Rp-C-Rp-G-Rp motifs wherein the CpG and/or its two neighboring nucleosides contain one or more modified bases. In some embodiments, provided oligonucleotides comprise one or more -Rp-C-Sp-G-Rp motifs wherein the CpG and/or its two neighboring nucleosides contain one or more modified bases. In some embodiments, provided oligonucleotides comprise one or more -CpG-Rp motifs wherein the CpG and/or its two neighboring nucleosides contain one or more 5mC. In some embodiments, provided oligonucleotides comprise one or more Rp-CpG- motifs wherein the CpG and/or its two neighboring nucleosides contain one or more 5mC. In some embodiments, provided oligonucleotides comprise one or more Rp-CpG-Rp motifs wherein the CpG and/or its two neighboring nucleosides contain one or more 5mC. In some embodiments, provided oligonucleotides comprise one or more Rp-C-Rp-G-Rp motifs wherein the CpG and/or its two neighboring nucleosides contain one or more 5mC. In some embodiments, provided oligonucleotides comprise one or more -Rp-C-Sp-G-Rp motifs wherein the CpG and/or its two neighboring nucleosides contain one or more 5mC. In some embodiments, provided oligonucleotides comprise one or more -CpG-Rp motifs wherein the CpG and/or its two neighboring nucleosides contain one or more modified sugars and modified bases. In some embodiments, provided oligonucleotides comprise one or more Rp-CpG- motifs wherein the CpG and/or its two neighboring nucleosides contain one or more modified sugars and modified bases. In some embodiments, provided oligonucleotides comprise one or more Rp-CpG-Rp motifs wherein the CpG and/or its two neighboring nucleosides contain one or more modified sugars and modified bases. In some embodiments, provided oligonucleotides comprise one or more Rp-C-Rp-G-Rp motifs wherein the CpG and/or its two neighboring nucleosides contain one or more modified sugars and modified bases. In some embodiments, provided oligonucleotides comprise one or more -Rp-C-Sp-G-Rp motifs wherein the CpG and/or its two neighboring nucleosides contain one or more modified sugars and modified bases. In some embodiments, a modified sugar is a 2'-modified sugar. In some embodiments, a 2'-modification is 2'-OR wherein R is optionally substituted $C_{1-6}$ aliphatic. In some embodiments, a T-modification is 2'-MOE. In some embodiments, a modified base is 5mC. In some embodiments, a modified base is within CpG. In some embodiments, a modified sugar is within CpG. In some embodiments, a modified sugar and a modified base is within CpG. In some embodiments, the C of the CpG comprise a modified sugar. In some embodiments, the C of the CpG comprise a modified base. In some embodiments, the C of the CpG comprise a modified sugar and a modified base. In some embodiments, provided oligonucleotides comprise combinations of CpG motifs described in the present disclosure. A person of ordinary skill in the art appreciates that in accordance with the present disclosure, provided designs of CpG that enhance agonist activities will be avoided when such agonist activities are not desired, and/or or antagonist activities, are desired.

In some embodiments, to provide antagonist oligonucleotides and compositions thereof, stereochemistry designs for agonist oligonucleotides, particularly the CpG motifs, may be partially or completely reversed. For example, in some embodiments, provided CpG oligonucleotides have high percentage of Rp, for example, more than above 50%, 55%, 60%, 65%, 70%, 75%, 80%, 85%, 90%, 95%, etc. as described in the present disclosure. In some embodiments, oligonucleotides having high percentage of Rp provide enhanced antagonist activities, for example, toward mouse TLR9. Examples include but are not limited to all-Rp (e.g., WV-1386) and Rp-CpG-Rp (e.g., WV-1373).

The present disclosure pertains to, inter alia, chirally controlled CpG oligonucleotides compositions and methods related to CpG oligonucleotides which comprise one or more copies of a CpG region motif disclosed herein. Various motifs, which are defined at least in part by the stereochemistry of the phosphorothioates in the CpG region, can either agonize or antagonize an immunostimulatory effect. In various embodiments, the CpG region comprises at least one phosphorothioate in the Rp conformation and at least one in the Sp conformation.

Chirally controlled CpG oligonucleotides compositions comprising agonistic CpG oligonucleotides can be used as immunostimulatory agents, e.g., vaccines, adjuvants or mono-therapies. Chirally controlled CpG oligonucleotides compositions comprising antagonistic CpG oligonucleotides can be used to antagonize an immune response.

If no immune stimulation is desired, the present disclosure also provides methods of identifying oligonucleotides which have decreased immune stimulation, e.g., those lacking immunostimulatory CpG region motifs. Therapeutic oligonucleotides can thus be screened for immune stimulation, or modified or stereopure versions of these oligonucleotides can be prepared with have less immune stimulation.

Naturally-occurring nucleotides, as found in RNA and DNA, comprise three components: a phosphate (a phosphodiester linkage), a sugar, and a base. In many synthetic CpG oligonucleotides, the phosphodiester has been replaced by phosphorothioate linkage. In a phosphorothioate, one of the non-bridging oxygen atoms in the phosphodiester linkage is substituted with sulfur. A phosphorothioate reportedly increases stability (e.g., against nucleases). Phosphorothioates reportedly can also increase solubility and membrane penetration. Fiset et al. 2001 Rev. Biol. Biotech. 1: 27-33. Phosphorothioates reportedly also increase affinity of a CpG oligonucleotide to TLR9 and alter the sequence specificity for TLR-mediated responses. Roberts et al. 2011 Mol. Immun. 48: 1027-1034; Haas et al. 2008 Immunity 28: 315-323; Roberts et al. 2005 J. Immun. 174: 605-608.

Unlike phosphodiester linkages, phosphorothioates are chiral centers and can exist in either an Rp or Sp conformation. The present disclosure shows the surprising result that the conformation of the phosphorothioate in a CpG region motif can greatly alter the agonistic or antagonistic capability of a CpG oligonucleotide. Various of the novel CpG region motifs disclosed herein define particular sequences of phosphorothioate conformations which are agonistic or antagonistic.

In various other embodiments, the present disclosure pertains to a chirally controlled CpG oligonucleotide composition comprising an agonistic CpG oligonucleotide comprising a strand comprising 15 to 49 nucleotides, wherein the strand comprises one or more copies of any agonistic CpG region motif disclosed herein.

In various other embodiments, the present disclosure pertains to a chirally controlled CpG oligonucleotide composition comprising an antagonistic CpG oligonucleotide comprising a strand comprising 15 to 49 nucleotides, wherein the strand comprises one or more copies of any antagonistic CpG region motif disclosed herein.

If no agonism is desired, or if no antagonism is desired, or if neither agonism nor antagonism is desired of a particular oligonucleotide: In various embodiments, the present disclosure pertains to methods of identifying oligonucleotides which have decreased agonism, decreased antagonism, or decreased agonism and antagonism. Oligonucleotides can be screened for agonism or antagonism mediated by CpG region motifs, and modified variants of those oligonucleotides can be prepared which have decreased agonism, decreased antagonism, or decreased agonism and antagonism. The CpG region motifs can comprise, as a non-limiting example, at least one phosphorothioate in the Rp conformation and at least one phosphorothioate in the rip conformation. In some embodiments, modified variants of those oligonucleotides can be, for example, a stereopure or chirally controlled oligonucleotide composition. In some embodiments, modified variants can also, for example, have higher stability, a shorter length, improved biological activity (e.g., if the oligonucleotide of which the variant is made has a desirable biological activity), etc.

The present disclosure pertains to, inter alia, chirally controlled CpG oligonucleotides compositions and methods related to CpG oligonucleotides which comprise one or more copies of a CpG region motif disclosed herein.

In some embodiments, a provided composition is a CpG oligonucleotide composition comprising a plurality of CpG oligonucleotides, which share:
1) a common base sequence;
2) a common pattern of backbone linkages; and
3) a common pattern of backbone phosphorus modifications.

In some embodiments, a provided composition is a chirally controlled CpG oligonucleotide composition comprising a plurality of CpG oligonucleotides, which share:
1) a common base sequence;
2) a common pattern of backbone linkages; and
3) a common pattern of backbone phosphorus modifications;
wherein:
the composition is chirally controlled in that the plurality of CpG oligonucleotides share the same stereochemistry at one or more chiral internucleotidic linkages, and level of the plurality of CpG oligonucleotides in the composition is pre-determined.

In some embodiments, a provided composition is a partially chirally controlled CpG oligonucleotide composition comprising a plurality of CpG oligonucleotides, which share:
1) a common base sequence;
2) a common pattern of backbone linkages; and
3) a common pattern of backbone phosphorus modifications;
wherein:
the composition is partially chirally controlled in that the plurality of CpG oligonucleotides share the same stereochemistry at one or more chiral internucleotidic linkages in the CpG region motif and do not share the same stereochemistry at one or more chiral internucleotidic linkages outside the CpG region motif, and level of the plurality of CpG oligonucleotides in the composition is pre-determined.

In some embodiments, a provided chirally controlled oligonucleotide composition is a completely chirally controlled oligonucleotide composition.

In some embodiments, provided oligonucleotides in provided chirally controlled oligonucleotide compositions comprise one or more modified sugars. In some embodiments, a modified sugar comprises a 2'-modification. In some embodiments, a 2'-modification is 2'-OR, wherein R is optionally substituted $C_{1-6}$ aliphatic. In some embodiments, a 2'-modification is T-OMe. In some embodiments, a 2'-modification is 2'-MOE. In some embodiments, a 2'-modification is 2'-F. In some embodiments, a modified sugar is comprises a bicyclic modification. In some embodiments, a modified sugar is a sugar in LNA. In some embodiments, a modification is within a CpG.

In some embodiments, provided oligonucleotides in provided chirally controlled oligonucleotide composition comprise one or more modified bases. In some embodiments, a modified base is 5mC. In some embodiments, a modification is within a CpG.

In some embodiments, oligonucleotides in provided chirally controlled oligonucleotide compositions comprise one or more modified sugars and one or more modified bases, for example, those described herein. In some embodiments, the present disclosure surprisingly demonstrates that, despite the widely accepted belief prior to the present disclosure that such sugar and/or base modifications dramatically reduce or completely eliminate TLR9 agonist activities, chirally controlled oligonucleotide compositions of oligonucleotides comprising such modified sugars and bases can provide strong TLR9 agonist activities. In some embodiments, the present disclosure provides chirally controlled oligonucleotide compositions of oligonucleotides comprising one or more modified sugars and one or more modified bases, for example, those described herein, wherein the oligonucleotides provide TLR9 agonist activities. A person having ordinary skill in the art appreciates that various assays, including those described herein, can be utilized to measure TLR9 activities, both in vivo and in vitro, in accordance with the present disclosure for various species. In some embodiments, provided oligonucleotides of such provided chirally controlled oligonucleotide composition comprise modified sugars. In some embodiments, a 2'-modification is T-OR, wherein R is optionally substituted $C_{1-6}$ aliphatic. In some embodiments, a 2'-modification is 2'-OMe. In some embodiments, a 2'-modification is 2'-MOE. In some embodiments, a 2'-modification is 2'-F. In some embodiments, a modified sugar is comprises a bicyclic modification. In some embodiments, a modified sugar is a sugar in LNA. In some embodiments, provided oligonucleotides comprise one or more modified bases. In some embodiments, a modified base is 5mC. In some embodiments, a modification is within a CpG of provided CpG oligonucleotides.

In some embodiments, a CpG oligonucleotide is selected from: an antisense oligonucleotide, an RNAi agent, a miRNA, splice switching oligonucleotide (SSO), immunomodulatory nucleic acid, an aptamer, a ribozyme, a Piwi-interacting RNA (piRNA), a small nucleolar RNA (snoRNA), a mRNA, a lncRNA, a ncRNA, an antigomir (e.g., an antagonist to a miRNA, lncRNA, ncRNA or other nucleic acid), a plasmid, a vector, or a portion thereof.

In some embodiments, a common base sequence of a CpG oligonucleotide in a CpG oligonucleotide composition hybridizes with a transcript of dystrophin, Huntingtin, myostatin, a myostatin receptor, ActRIIA, ActRIIB, DMPK, SMN2, dystrophia myotonica protein kinase (DMPK), Proprotein convertase subtilisin/kexin type 9 (PCSK9), SMAD7, transthyretin (TTR), alpha-1 antitrypsin (AAT), aminolevulinate synthase 1 (ALAS1), antithrombin 3 (ATIII), factor VII (FVII), factor XI (FXI), factor XII (FXII), hepcidin antimicrobial peptide (HAMP), a gene of hepatitis B (HBV), hepatitis C (HCV) or hepatitis D (HDV), programmed death-ligand 1 (PD-L1), complement component 5 (C5), transmembrane protease, serine 6 (TMPRSS6), or KRT14 (Keratin 14). In some embodiments, a CpG oligonucleotide is capable of reducing the level and/or activity of a mutant form of any of: dystrophin, Huntingtin, myostatin, a myostatin receptor, ActRIIA, ActRIIB, DMPK, SMN2, dystrophia myotonica protein kinase (DMPK), Proprotein convertase subtilisin/kexin type 9 (PCSK9), SMAD7, transthyretin (TTR), alpha-1 antitrypsin (AAT), aminolevulinate synthase 1 (ALAS1), antithrombin 3 (ATIII), factor VII (FVII), factor XI (FXI), factor XII (FXII), hepcidin antimicrobial peptide (HAMP), a gene of hepatitis B (HBV), hepatitis C (HCV) or hepatitis D (HDV), programmed death-ligand 1 (PD-L1), complement component 5 (C5), transmembrane protease, serine 6 (TMPRSS6), or KRT14 (Keratin 14). In some embodiments, a CpG oligonucleotide is capable of increasing the level and/or activity of a wild-type and/or functional form of any of: dystrophin, Huntingtin, myostatin, a myostatin receptor, ActRIIA, ActRIIB, DMPK, SMN2, dystrophia myotonica protein kinase (DMPK), Proprotein convertase subtilisin/kexin type 9 (PCSK9), SMAD7, transthyretin (TTR), alpha-1 antitrypsin (AAT), aminolevulinate synthase 1 (ALAS1), antithrombin 3 (ATIII), factor VII (FVII), factor XI (FXI), factor XII (FXII), hepcidin antimicrobial peptide (HAMP), a gene of hepatitis B (HBV), hepatitis C (HCV) or hepatitis D (HDV), programmed death-ligand 1 (PD-L1), complement component 5 (C5), transmembrane protease, serine 6 (TMPRSS6), or KRT14 (Keratin 14).

In some embodiments of a chirally controlled oligonucleotide composition, all chiral internucleotidic linkages are chirally controlled.

In some embodiments of a chirally controlled oligonucleotide composition, not all chiral internucleotidic linkages are chirally controlled, and a CpG oligonucleotide composition is a partially chirally controlled CpG oligonucleotide composition. In some embodiments, all chiral internucleotidic linkage are chirally controlled, and a CpG oligonucleotide composition is a completely chirally controlled CpG oligonucleotide composition.

In some embodiments, a chiral internucleoside linkage is a phosphorothioate. In some embodiments, a phosphorothioate can exist in a Rp or Sp conformation. Various other internucleotidic linkages, which can be chiral, are described herein.

In some embodiments, a CpG oligonucleotide is a nucleic acid described in or produced by a method described in Patent Application Publications US20120316224, US20140194610, US20150211006, WO2015107425, and U.S. Patent Application No. 62/307,542, which CpG oligonucleotides are incorporated herein by reference. In some embodiments, stereoselectivity and/or purity of provided oligonucleotides and compositions thereof can be assessed by stereoselectivity for the formation of each chiral internucleotidic linkage, which can be assessed by stereoselectivity for the formation of a chiral internucleotidic linkage in a model dimer who has the same nucleosides at the 5'- and the 3'-sides of the chiral internucleotidic linkage. Stereoselectivity is typically greater than 95:5, 96:4, 97:3, 98:2 or 99:1 in preparation of provided oligonucleotides and compositions thereof. In some embodiments, solid chemistry is utilized for preparing provided oligonucleotides and compositions. Typically after synthesis, the product is cleaved from the solid support and deprotected, and the product is purified by, for example, anion exchange chromatography, and desired fractions are pooled based on HPLC analysis. In some embodiments, purified pooled fractions are concentrated and diafiltered against water for injection (WFI) and passed through a 0.2 μm filter prior to lyophilization.

In some embodiments, the sequence of the CpG oligonucleotide in the CpG oligonucleotide composition comprises or consists of the sequence of any CpG oligonucleotide described herein. In some embodiments, the sequence of the CpG region motif in the CpG oligonucleotide in the CpG oligonucleotide composition comprises the sequence of the CpG region motif of any CpG oligonucleotide described, listed or referenced herein. In some embodiments, the CpG oligonucleotide in the CpG oligonucleotide composition is a splice-switching oligonucleotide. In some embodiments, the CpG oligonucleotide in the CpG oligonucleotide composition is capable of skipping or mediating skipping of an exon in the dystrophin gene. In some embodiments, the CpG oligonucleotide in the CpG oligonucleotide composition is capable of skipping or mediating skipping of exon 51 in the dystrophin gene. In some embodiments, the present disclosure pertains to a CpG oligonucleotide composition or chirally controlled CpG oligonucleotide composition, wherein the sequence of the CpG oligonucleotide comprises or consists of the sequence of a CpG oligonucleotide capable of skipping or mediating skipping of exon 51, 45, 53 or 44 in the dystrophin gene.

In some embodiments, a sequence of a CpG oligonucleotide includes any one or more of: base sequence (including length), pattern of chemical modifications to sugar and base moieties, pattern of backbone linkages (e.g., pattern of natural phosphate linkages, phosphorothioate linkages, phosphorothioate triester linkages, and combinations thereof), pattern of backbone chiral centers (e.g., pattern of stereochemistry (Rp/Sp) of chiral internucleotidic linkages), and pattern of backbone phosphorus modifications (e.g., pattern of modifications on the internucleotidic phosphorus atom, such as S, and -L-R$^1$ of formula I). In some embodiments, a CpG oligonucleotide or CpG oligonucleotide composition of any sequence of any CpG oligonucleotide listed herein can be used in combination with any composition and/or method described herein, including, but not limited to, any combination with any lipid described herein, any additional component described herein, or any other composition (or component thereof) or method described herein.

In some embodiments, a CpG oligonucleotide comprises one or more chiral internucleotidic linkages. In some embodiments, for CpG oligonucleotides comprising one or more chiral internucleotidic linkages, a provided composition is a chirally controlled CpG oligonucleotide composition of such CpG oligonucleotides in that stereochemistry of at least one of the chiral internucleotidic linkages is controlled. In some embodiments, stereochemistry of each of the chiral internucleotidic linkages is independently controlled, and a provided composition is a completely chirally controlled CpG oligonucleotide composition. In some embodiments, stereochemistry of one or more chiral internucleotidic linkages is controlled (chiral controlled internucleotidic linkages) while stereochemistry of one or more chiral internucleotidic linkages is not controlled (stereorandom/non-chirally controlled internucleotidic linkages), and a provided composition is a partially chirally controlled CpG oligonucleotide composition. In some embodiments, a chirally controlled CpG oligonucleotide composition can be prepared by oligonucleotide synthesis comprising stereoselective formation of one or more or all chiral internucleotidic linkages using, for example, technologies described in Patent Application Publications US20120316224, US20140194610, US20150211006, and WO2015107425.

In some embodiments, provided oligonucleotides comprise 1 or more chirally controlled internucleotidic linkages. In some embodiments, provided oligonucleotides comprise 2 or more chirally controlled internucleotidic linkages. In some embodiments, provided oligonucleotides comprise 3 or more chirally controlled internucleotidic linkages. In some embodiments, provided oligonucleotides comprise 4 or more chirally controlled internucleotidic linkages. In some embodiments, provided oligonucleotides comprise 5 or more chirally controlled internucleotidic linkages. In some embodiments, provided oligonucleotides comprise 6 or more chirally controlled internucleotidic linkages. In some embodiments, provided oligonucleotides comprise 7 or more chirally controlled internucleotidic linkages. In some embodiments, provided oligonucleotides comprise 8 or more chirally controlled internucleotidic linkages. In some embodiments, provided oligonucleotides comprise 9 or more chirally controlled internucleotidic linkages. In some embodiments, provided oligonucleotides comprise 10 or more chirally controlled internucleotidic linkages. In some embodiments, provided oligonucleotides comprise 11 or more chirally controlled internucleotidic linkages. In some embodiments, provided oligonucleotides comprise 12 or more chirally controlled internucleotidic linkages. In some embodiments, provided oligonucleotides comprise 13 or more chirally controlled internucleotidic linkages. In some embodiments, provided oligonucleotides comprise 14 or more chirally controlled internucleotidic linkages. In some embodiments, provided oligonucleotides comprise 15 or more chirally controlled internucleotidic linkages. In some embodiments, provided oligonucleotides comprise 16 or more chirally controlled internucleotidic linkages. In some embodiments, provided oligonucleotides comprise 17 or more chirally controlled internucleotidic linkages. In some embodiments, provided oligonucleotides comprise 18 or more chirally controlled internucleotidic linkages. In some embodiments, provided oligonucleotides comprise 19 or more chirally controlled internucleotidic linkages. In some embodiments, provided oligonucleotides comprise 20 or more chirally controlled internucleotidic linkages. In some embodiments, provided oligonucleotides comprise 21 or more chirally controlled internucleotidic linkages. In some embodiments, provided oligonucleotides comprise 22 or more chirally controlled internucleotidic linkages. In some embodiments, provided oligonucleotides comprise 23 or more chirally controlled internucleotidic linkages. In some embodiments, provided oligonucleotides comprise 24 or more chirally controlled internucleotidic linkages. In some embodiments, provided oligonucleotides comprise 25 or more chirally controlled internucleotidic linkages.

In some embodiments, the present disclosure provides a CpG oligonucleotide composition comprising a first plurality of CpG oligonucleotides which have a common base sequence, and comprise one or more modified sugar moieties, one or more natural phosphate linkages, or combinations thereof. In some embodiments, the present disclosure provides a CpG oligonucleotide composition comprising a first plurality of CpG oligonucleotides which have a common base sequence, comprise one or more modified internucleotidic linkages, and comprise one or more modified sugar moieties, one or more natural phosphate linkages, or combinations thereof. In some embodiments, CpG oligonucleotides of a first plurality have a wing-core-wing structure, wherein a wing and a core are different segments or portions of an oligonucleotide or other nucleic acid which have distinct chemistry. In some embodiments, CpG oligonucleotides of a first plurality have a wing-core or core-wing structure (e.g., a hemimer structure). In some embodiments, a wing is also designated a wing region. In some embodiments, a core is also designated a core region. In some embodiments wherein the CpG oligonucleotides of a first plurality have a wing-core-wing structure, the two wings can be chemically identical or distinct (e.g., they can optionally match or differ in any of: sugar modification, internucleotidic linkage, stereochemistry, etc.). In some embodiments, the wings can be the same or different. In some embodiments, a wing comprises a CpG region motif. In some embodiments, two wings comprise a CpG region motif. In some embodiments, a core comprises a CpG region motif. In some embodiments, a wing and a core comprise a CpG region motif. In some embodiments, two wings and a core comprise a CpG region motif. In some embodiments, a wing and/or a core and/or a second wing can each independently comprise one or more CpG region motifs. In some embodiments, each wing region independently comprises one or more natural phosphate linkages and optionally one or more modified internucleotidic linkages, and the core comprises one or more modified internucleotidic linkages and optionally one or more natural phosphate linkages. In some embodiments, each wing region independently comprises one or more natural phosphate linkages and one or more modified internucleotidic linkages, and the core comprises one or more modified internucleotidic linkages and no natural phosphate linkages. In some embodiments, a wing comprises modified sugar moieties. In some embodiments, a modified internucleotidic linkage is phosphorothioate. In some embodiments, a modified internucleotidic linkage is substituted phosphorothioate. In some embodiments, a modified internucleotidic linkage has the structure of formula I described in this disclosure. In some embodiments, a modified sugar moiety is 2'-modified. In some embodiments, a 2'-modification is 2'-OR$^1$. In some embodiments, such provided compositions have lower toxicity. In some embodiments, provided compositions have lower complement activation.

In some embodiments, a provided composition is a chirally controlled CpG oligonucleotide composition. In some embodiments, a provided CpG oligonucleotide composition comprising a first plurality of CpG oligonucleotides is chirally controlled, and CpG oligonucleotides of the first plurality comprise a combination of 2'-modification of one or more sugar moieties, one or more natural phosphate linkages, and one or more chiral internucleotidic linkages. In some embodiments, a provided CpG oligonucleotide composition comprising a first plurality of CpG oligonucleotides is chirally controlled, and CpG oligonucleotides of the first plurality comprise a combination of 2'-modification of one or more sugar moieties, one or more natural phosphate linkages, one or more chiral internucleotidic linkages, wherein the 5'- and/or the 3'-end internucleotidic linkages are chiral. In some embodiments, both the 5'- and the 3'-end internucleotidic linkages are chiral. In some embodiments, both the 5'- and the 3'-end internucleotidic linkages are chiral and Sp. In some embodiments, a provided CpG oligonucleotide composition comprising a first plurality of CpG oligonucleotides is chirally controlled, and CpG oligonucleotides of the first plurality comprise a combination of 2'-modification of one or more sugar moieties, one or more natural phosphate linkages, one or more chiral internucleotidic linkages, and a stereochemistry pattern of (Rp)

n(Sp)m, (Np)t(Rp)n(Sp)m, or (Sp)t(Rp)n(Sp)m, wherein m>2. In some embodiments, a chiral internucleotidic linkage has the structure of formula I. In some embodiments, a chiral internucleotidic linkage is a phosphorothioate linkage. In some embodiments, a chiral internucleotidic linkage is a substituted phosphorothioate linkage.

In some embodiments, provided CpG oligonucleotides in provided technologies comprise a wing region and a core region; in some embodiments, such a format is designated a hemimer or hemi-mer. In some embodiments, provided CpG oligonucleotides have a wing-core-wing structure, wherein the core region comprises one or more sugar moieties and/or internucleotidic linkages not in the wing regions. In some embodiments, provided CpG oligonucleotides have a wing-core-wing structure, wherein the core region comprises one or more sugar moieties and internucleotidic linkages not in the wing regions. In some embodiments, provided CpG oligonucleotides have a wing-core-wing structure, wherein the core region comprises one or more sugar moieties not in the wing regions. In some embodiments, provided CpG oligonucleotides have a wing-core-wing structure, wherein the core region comprises one or more internucleotidic linkages not in the wing regions. In some embodiments, a core region comprises a modified sugar moiety. In some embodiments, each sugar moiety in a core region is modified. Example sugar modifications are widely known in the art including but not limited to those described in this disclosure. In some embodiments, each wing region comprises no modified sugar moieties. In some embodiments, a core region comprises one or more natural phosphate linkages. In some embodiments, each internucleotidic linkage following a core nucleoside is natural phosphate linkage. In some embodiments, a wing comprises one or more modified internucleotidic linkages. In some embodiments, each internucleotidic linkage following a core nucleoside is a modified internucleotidic linkage.

In some embodiments, provided CpG oligonucleotides are blockmers. In some embodiments, provided CpG oligonucleotide are altmers. In some embodiments, provided CpG oligonucleotides are altmers comprising alternating blocks. In some embodiments, a blockmer or an altmer can be defined by chemical modifications (including presence or absence), e.g., base modifications, sugar modification, internucleotidic linkage modifications, stereochemistry, etc.

In some embodiments, provided CpG oligonucleotides comprise blocks comprising different internucleotidic linkages. In some embodiments, provided CpG oligonucleotides comprise blocks comprising modified internucleotidic linkages and natural phosphate linkages. In some embodiments, provided CpG oligonucleotides comprise blocks comprising different modified internucleotidic linkages. In some embodiments, provided CpG oligonucleotides comprise alternating blocks comprising different internucleotidic linkages. In some embodiments, provided CpG oligonucleotides comprise alternating blocks comprising modified internucleotidic linkages and natural phosphate linkages. In some embodiments, provided CpG oligonucleotides comprise alternating blocks comprising different modified internucleotidic linkages. In some embodiments, a block comprising modified internucleotidic linkages have pattern of backbone chiral centers as described herein. In some embodiments, each block comprising modified internucleotidic linkages has the same pattern of backbone chiral centers. In some embodiments, blocks comprising modified internucleotidic linkages have different patterns of backbone chiral centers. In some embodiments, blocks comprising modified internucleotidic linkages have different length and/or modifications. In some embodiments, blocks comprising modified internucleotidic linkages have the same length and/or modifications. In some embodiments, blocks comprising modified internucleotidic linkages have the same length. In some embodiments, blocks comprising modified internucleotidic linkages have the same internucleotidic linkages.

In some embodiments, provided CpG oligonucleotides comprise alternating blocks comprising modified sugar moieties and unmodified sugar moieties. In some embodiments, modified sugar moieties comprise 2'-modifications. In some embodiments, provided CpG oligonucleotides comprise alternating 2'-OMe modified sugar moieties and unmodified sugar moieties.

In some embodiments, provided CpG oligonucleotides comprise alternating blocks comprising different modified sugar moieties and/or unmodified sugar moieties. In some embodiments, provided CpG oligonucleotides comprise alternating blocks comprising different modified sugar moieties and unmodified sugar moieties. In some embodiments, provided CpG oligonucleotides comprise alternating blocks comprising different modified sugar moieties. In some embodiments, provided CpG oligonucleotides comprise alternating blocks comprising different modified sugar moieties, wherein the modified sugar moieties comprise different T-modifications. For example, in some embodiments, provided CpG oligonucleotide comprises alternating blocks comprising 2'-OMe and 2'-F, respectively.

In some embodiments, a type of nucleoside in a region or a CpG oligonucleotide is modified, optionally with a different modification compared to another type of nucleoside. In some embodiments, a type of nucleoside in a region or a CpG oligonucleotide is modified with a different modification compared to another type of nucleoside. For example, in some embodiments, a pyrimidine nucleoside comprises a 2'-F modification, and a purine nucleoside comprises a 2'-OMe modification. In some other embodiments, a pyrimidine nucleoside comprises a 2'-OMe modification, and a purine nucleoside comprises a 2'-F modification.

In some embodiments, an internucleotidic linkage following an unmodified sugar moiety is a modified internucleotidic linkage. In some embodiments, an internucleotidic linkage after an unmodified sugar moiety is a phosphorothioate linkage. In some embodiments, each internucleotidic linkage after an unmodified sugar moiety is a modified internucleotidic linkage. In some embodiments, each internucleotidic linkage after an unmodified sugar moiety is a phosphorothioate linkage. In some embodiments, an internucleotidic linkage following a modified sugar moiety is a natural phosphate linkage. In some embodiments, each internucleotidic linkage following a modified sugar moiety is a natural phosphate linkage.

In some embodiments, a provided pattern of backbone chiral centers comprises repeating (Sp)m(Rp)n, (Rp)n(Sp)m, (Np)t(Rp)n(Sp)m, or (Sp)t(Rp)n(Sp)m units. In some embodiments, a repeating unit is (Sp)m(Rp)n. In some embodiments, a repeating unit is SpRp. In some embodiments, a repeating unit is SpSpRp. In some embodiments, a repeating unit is SpRpRp. In some embodiments, a repeating unit is RpRpSp. In some embodiments, a repeating unit is (Rp)n(Sp)m. In some embodiments, a repeating unit is (Np)t(Rp)n(Sp)m. In some embodiments, a repeating unit is (Sp)t(Rp)n(Sp)m.

In some embodiments, a provided pattern of backbone chiral centers comprises a (Sp)m(Rp)n, (Rp)n(Sp)m, (Np)t(Rp)n(Sp)m, or (Sp)t(Rp)n(Sp)m unit. In some embodiments, a unit is (Sp)m(Rp)n. In some embodiments, a unit is SpRp. In some embodiments, a unit is SpSpRp. In some embodiments, a unit is SpRpRp. In some embodiments, a unit is RpRpSp. In some embodiments, a unit is (Rp)n(Sp)m. In some embodiments, a unit is (Sp)m(Rp)n. In some embodiments, a unit is (Rp)n(Sp)m. In some embodiments, a unit is (Np)t(Rp)n(Sp)m. In some embodiments, a unit is (Sp)t(Rp)n(Sp)m.

In some embodiments, a provided pattern of backbone chiral centers comprises (Rp/Sp)-(All Rp or All Sp)-(Rp/Sp). In some embodiments, a provided pattern of backbone chiral centers comprises (Rp)-(All Sp)-(Rp). In some embodiments, a provided pattern of backbone chiral centers comprises (Sp)-(All Rp)-(Sp). In some embodiments, a provided pattern of backbone chiral centers comprises (Rp/Sp)-(repeating (Sp)m(Rp)n)-(Rp/Sp). In some embodiments, a provided pattern of backbone chiral centers comprises (Rp/Sp)-(repeating SpSpRp)-(Rp/Sp).

In some embodiments, a provided pattern of backbone chiral centers is (Rp/Sp)-(All Rp or All Sp)-(Rp/Sp). In some embodiments, a provided pattern of backbone chiral centers is (Sp)-(All Sp)-(Sp). In some embodiments, each chiral internucleotidic linkage is Sp. In some embodiments, a provided pattern of backbone chiral centers is (Rp)-(All Sp)-(Rp). In some embodiments, a provided pattern of backbone chiral centers is (Sp)-(All Rp)-(Sp). In some embodiments, a provided pattern of backbone chiral centers is (Rp/Sp)-(repeating (Sp)m(Rp)n)-(Rp/Sp). In some embodiments, a provided pattern of backbone chiral centers is (Rp/Sp)-(repeating SpSpRp)-(Rp/Sp).

In some embodiments, the present disclosure provides CpG oligonucleotide compositions having low toxicity. In some embodiments, the present disclosure provides CpG oligonucleotide compositions having improved protein binding profile. In some embodiments, the present disclosure provides CpG oligonucleotide compositions having improved binding to albumin. In some embodiments, provided CpG oligonucleotide compositions have low toxicity and improved binding to certain desired proteins. In some embodiments, provided CpG oligonucleotide compositions have low toxicity and improved binding to certain desired proteins. In some embodiments, provided CpG oligonucleotide compositions at the same time provides the same level of, or greatly enhanced, stability and/or activities, e.g., better target-cleavage pattern, better target-cleavage efficiency, better target specificity, etc.

In some embodiments, a CpG oligonucleotide composition has at least one improved characteristic or quality related to a reference composition. Example reference compositions comprising a reference plurality of CpG oligonucleotides have been reported in this disclosure. In some embodiments, CpG oligonucleotides of the reference plurality have a different structural elements (chemical modifications, stereochemistry, etc.) compared with chirally controlled CpG oligonucleotides of the first plurality in a provided composition. In some embodiments, a reference composition is a stereorandom preparation of CpG oligonucleotides having the same chemical modifications. In some embodiments, a reference composition is a mixture of stereoisomers while a provided composition is a chirally controlled CpG oligonucleotide composition of one stereoisomer. In some embodiments, CpG oligonucleotides of the reference plurality have the same base sequence as a CpG oligonucleotide of the first plurality in a provided composition. In some embodiments, CpG oligonucleotides of the reference plurality have the same chemical modifications as a CpG oligonucleotide of the first plurality in a provided composition. In some embodiments, CpG oligonucleotides of the reference plurality have the same sugar modifications as a CpG oligonucleotide of the first plurality in a provided composition. In some embodiments, CpG oligonucleotides of the reference plurality have the same base modifications as a CpG oligonucleotide of the first plurality in a provided composition. In some embodiments, CpG oligonucleotides of the reference plurality have the same internucleotidic linkage modifications as a CpG oligonucleotide of the first plurality in a provided composition. In some embodiments, CpG oligonucleotides of the reference plurality have the same stereochemistry as a CpG oligonucleotide of the first plurality in a provided composition but different chemical modifications, e.g., base modification, sugar modification, internucleotidic linkage modifications, etc.

In some embodiments, the present disclosure provides a CpG oligonucleotide composition comprising a first plurality of CpG oligonucleotides of a particular CpG oligonucleotide type defined by:
1) base sequence;
2) pattern of backbone linkages;
3) pattern of backbone chiral centers; and
4) pattern of backbone phosphorus modifications;
wherein the level of CpG oligonucleotides of the plurality is predetermined.

In some embodiments, the present disclosure provides a CpG oligonucleotide composition comprising a first plurality of CpG oligonucleotides of a particular CpG oligonucleotide type defined by:
1) base sequence;
2) pattern of backbone linkages;
3) pattern of backbone chiral centers; and
4) pattern of backbone phosphorus modifications,
which composition is chirally controlled in that it is enriched, relative to a substantially racemic preparation of CpG oligonucleotides having the same base sequence, for CpG oligonucleotides of the particular CpG oligonucleotide type.

In some embodiments, the present disclosure provides a CpG oligonucleotide composition comprising a first plurality of CpG oligonucleotides comprising one or more wing regions and a core region, wherein:
CpG oligonucleotides of the first plurality have the same base sequence; and
each wing region independently comprises one or more modified internucleotidic linkages and optionally one or more natural phosphate linkages, and the core region independently comprises one or more modified internucleotidic linkages; or
each wing region independently comprises one or more modified sugar moieties, and the core region comprises one or more un-modified sugar moieties.

In some embodiments, the present disclosure provides a CpG oligonucleotide composition comprising a first plurality of CpG oligonucleotides comprising one or more wing regions and a core region, wherein:
CpG oligonucleotides of the first plurality have the same base sequence;
each wing region independently has a length of two or more bases, and independently comprises one or more modified internucleotidic linkages and one or more natural phosphate linkages; and
the core region independently has a length of two or more bases and independently comprises one or more modified internucleotidic linkages.

In some embodiments, the present disclosure provides a CpG oligonucleotide composition comprising a first plurality of CpG oligonucleotides comprising two wing regions and a core region, wherein:

CpG oligonucleotides of the first plurality have the same base sequence;

each wing region independently has a length of two or more bases, and independently comprises one or more modified internucleotidic linkages and one or more natural phosphate linkages; and the core region independently has a length of two or more bases and independently comprises one or more modified internucleotidic linkages.

In some embodiments, the present disclosure provides a CpG oligonucleotide composition comprising a first plurality of CpG oligonucleotides comprising two wing regions and a core region, wherein:

CpG oligonucleotides of the first plurality have the same base sequence;

each wing region independently has a length of two or more bases, and independently comprises one or more modified internucleotidic linkages and one or more natural phosphate linkages;

the wing region to the 5'-end of the core region comprises at least one modified internucleotidic linkage followed by a natural phosphate linkage in the wing; and the wing region to the 3'-end of the core region comprises at least one modified internucleotidic linkage preceded by a natural phosphate linkage in the wing;

the core region independently has a length of two or more bases and independently comprises one or more modified internucleotidic linkages.

In some embodiments, the present disclosure provides a CpG oligonucleotide composition comprising a first plurality of CpG oligonucleotides comprising a wing region and a core region, wherein:

CpG oligonucleotides of the first plurality have the same base sequence;

the wing region has a length of two or more bases, and comprises one or more modified internucleotidic linkages and one or more natural phosphate linkages;

the wing region is to the 5'-end of the core region and comprises a natural phosphate linkage between the two nucleosides at its 3'-end, or the wing region to the 3'-end of the core region and comprises a natural phosphate linkage between the two nucleosides at its 5'-end; and the core region independently has a length of two or more bases and independently comprises one or more modified internucleotidic linkages.

In some embodiments, the present disclosure provides a CpG oligonucleotide composition comprising a first plurality of CpG oligonucleotides comprising two wing regions and a core region, wherein:

CpG oligonucleotides of the first plurality have the same base sequence; each wing region independently has a length of two or more bases, and independently comprises one or more modified internucleotidic linkages and one or more natural phosphate linkages;

the wing region to the 5'-end of the core region comprises a natural phosphate linkage between the two nucleosides at its 3'-end;

the wing region to the 3'-end of a core region comprises a natural phosphate linkage between the two nucleosides at its 5'-end; and the core region independently has a length of two or more bases and independently comprises one or more modified internucleotidic linkages.

In some embodiments, the present disclosure provides a CpG oligonucleotide composition comprising a first plurality of CpG oligonucleotides comprising one or more wing regions and a core region, wherein:

CpG oligonucleotides of the first plurality have the same base sequence; and each wing region independently comprises one or more modified internucleotidic linkages and optionally one or more natural phosphate linkages, and the core region independently comprises one or more modified internucleotidic linkages; and each wing region independently comprises one or more modified sugar moieties, and the core region comprises one or more un-modified sugar moieties.

In some embodiments, the present disclosure provides a CpG oligonucleotide composition comprising a first plurality of CpG oligonucleotides which:

1) have a common base sequence; and
2) comprise one or more wing regions and a core region;

wherein:

each wing region comprises at least one modified sugar moiety; and each core region comprises at least one un-modified sugar moiety.

In some embodiments, the present disclosure provides a chirally controlled CpG oligonucleotide composition, a CpG oligonucleotide being defined by having:

1) a common base sequence and length;
2) a common pattern of backbone linkages; and
3) a common pattern of backbone chiral centers, which composition is a substantially pure preparation of a single CpG oligonucleotide in that a predetermined level of the CpG oligonucleotides in the composition have the common base sequence and length, the common pattern of backbone linkages, and the common pattern of backbone chiral centers.

In some embodiments, the present disclosure provides a chirally controlled CpG oligonucleotide composition comprising CpG oligonucleotides of a particular CpG oligonucleotide type characterized by:

1) a common base sequence and length;
2) a common pattern of backbone linkages; and
3) a common pattern of backbone chiral centers;

which composition is chirally controlled in that it is enriched, relative to a substantially racemic preparation of CpG oligonucleotides having the same base sequence and length, for CpG oligonucleotides of the particular CpG oligonucleotide type.

In some embodiments, the present disclosure provides a chirally controlled CpG oligonucleotide composition, wherein a CpG oligonucleotide of a particular CpG oligonucleotide type is characterized by:

1) a common base sequence and length;
2) a common pattern of backbone linkages; and
3) a common pattern of backbone chiral centers, which composition is a substantially pure preparation of a single CpG oligonucleotide in that at least about 10% of the CpG oligonucleotides in the composition have the common base sequence and length, the common pattern of backbone linkages, and the common pattern of backbone chiral centers.

In some embodiments, the present disclosure provides a CpG oligonucleotide composition comprising a predetermined level of CpG oligonucleotides which comprise one or more wing regions and a common core region, wherein:

each wing region independently has a length of two or more bases, and independently and optionally comprises one or more chiral internucleotidic linkages;

the core region independently has a length of two or more bases, and independently comprises one or more chiral internucleotidic linkages, and the common core region has:
  1) a common base sequence and length;
  2) a common pattern of backbone linkages; and
  3) a common pattern of backbone chiral centers.

In some embodiments, levels of defined CpG oligonucleotides in provided compositions (e.g., CpG oligonucleotides of a plurality; CpG oligonucleotides of a CpG oligonucleotide type, CpG oligonucleotides defined by sequence, backbone linkages, and/or backbone chiral centers, etc.) are predetermined. In some embodiments, levels of defined CpG oligonucleotides are predetermined in that their absolute or relative (e.g., ratio, percentage, etc.) amounts within a composition is controlled.

A wing and core can be defined by any structural elements. In some embodiments, a wing and core is defined by nucleoside modifications, wherein a wing comprises a nucleoside modification that the core region does not have. In some embodiments, CpG oligonucleotides in provided compositions have a wing-core structure of nucleoside modification. In some embodiments, CpG oligonucleotides in provided compositions have a core-wing structure of nucleoside modification. In some embodiments, CpG oligonucleotides in provided compositions have a wing-core-wing structure of nucleoside modification. In some embodiments, a wing and core is defined by modifications of the sugar moieties. In some embodiments, a wing and core is defined by modifications of the base moieties. In some embodiments, each sugar moiety in the wing region has the same 2'-modification which is not found in the core region. In some embodiments, each sugar moiety in the wing region has the same 2'-modification which is different than any sugar modifications in the core region. In some embodiments, each sugar moiety in the wing region has the same 2'-modification, and the core region has no 2'-modifications. In some embodiments, when two or more wings are present, each sugar moiety in a wing region has the same 2'-modification, yet the common T-modification in a first wing region can either be the same as or different from the common T-modification in a second wing region. In some embodiments, a wing and core is defined by pattern of backbone internucleotidic linkages. In some embodiments, a wing comprises a type of internucleotidic linkage, and/or a pattern of internucleotidic linkages, that are not found in a core. In some embodiments, a wing region comprises both a modified internucleotidic linkage and a natural phosphate linkage. In some embodiments, the internucleotidic linkage at the 5'-end of a wing to the 5'-end of the core region is a modified internucleotidic linkage. In some embodiments, the internucleotidic linkage at the 3'-end of a wing to the 3'-end of the core region is a modified internucleotidic linkage. In some embodiments, a modified internucleotidic linkage is a chiral internucleotidic linkage.

In some embodiments, each wing comprises at least one chiral internucleotidic linkage and at least one natural phosphate linkage. In some embodiments, each wing comprises at least one modified sugar moiety. In some embodiments, each wing sugar moiety is modified. In some embodiments, a wing sugar moiety is modified by a modification that is absent from the core region. In some embodiments, a wing region only has modified internucleotidic linkages at one or both of its ends. In some embodiments, a wing region only has a modified internucleotidic linkage at its 5'-end. In some embodiments, a wing region only has a modified internucleotidic linkage at its 3'-end. In some embodiments, a wing region only has modified internucleotidic linkages at its 5'- and 3'-ends. In some embodiments, a wing is to the 5'-end of a core, and the wing only has a modified internucleotidic linkage at its 5'-end. In some embodiments, a wing is to the 5'-end of a core, and the wing only has a modified internucleotidic linkage at its 3'-end. In some embodiments, a wing is to the 5'-end of a core, and the wing only has modified internucleotidic linkages at both its 5'- and 3'-ends. In some embodiments, a wing is to the 3'-end of a core, and the wing only has a modified internucleotidic linkage at its 5'-end. In some embodiments, a wing is to the 3'-end of a core, and the wing only has a modified internucleotidic linkage at its 3'-end. In some embodiments, a wing is to the 3'-end of a core, and the wing only has modified internucleotidic linkages at both its 5'- and 3'-ends.

In some embodiments, each internucleotidic linkage within a core region is modified. In some embodiments, each internucleotidic linkage within a core region is chiral. In some embodiments, a core region comprises a pattern of backbone chiral centers of (Sp)m(Rp)n, (Rp)n(Sp)m, (Np)t(Rp)n(Sp)m, or (Sp)t(Rp)n(Sp)m. In some embodiments, the pattern of backbone chiral centers of a core region is (Sp)m(Rp)n, (Rp)n(Sp)m, (Np)t(Rp)n(Sp)m, or (Sp)t(Rp)n(Sp)m. In some embodiments, a core region comprises a pattern of backbone chiral centers of (Rp)n(Sp)m, (Np)t(Rp)n(Sp)m, or (Sp)t(Rp)n(Sp)m, wherein m>2. In some embodiments, the pattern of backbone chiral centers of a core region is (Sp)m(Rp)n, (Rp)n(Sp)m, (Np)t(Rp)n(Sp)m, or (Sp)t(Rp)n(Sp)m, wherein m>2. Among other things, in some embodiments such patterns can provide or enhance controlled cleavage of a target sequence, e.g., an RNA sequence.

In some embodiments, CpG oligonucleotides in provided compositions have a common pattern of backbone phosphorus modifications. In some embodiments, a provided composition is a CpG oligonucleotide composition that is chirally controlled in that the composition contains a predetermined level of CpG oligonucleotides of an individual CpG oligonucleotide type, wherein a CpG oligonucleotide type is defined by:
  1) base sequence;
  2) pattern of backbone linkages;
  3) pattern of backbone chiral centers; and
  4) pattern of backbone phosphorus modifications.

As noted above and understood in the art, in some embodiments, base sequence of a CpG oligonucleotide can refer to the identity and/or modification status of nucleoside residues (e.g., of sugar and/or base components, relative to standard naturally occurring nucleotides such as adenine, cytosine, guanosine, thymine, and uracil) in the CpG oligonucleotide and/or to the hybridization character (i.e., the ability to hybridize with particular complementary residues) of such residues.

In some embodiments, a particular CpG oligonucleotide type can be defined by
  1A) base identity;
  1B) pattern of base modification;
  1C) pattern of sugar modification;
  2) pattern of backbone linkages;
  3) pattern of backbone chiral centers; and
  4) pattern of backbone phosphorus modifications.
Thus, in some embodiments, CpG oligonucleotides of a particular type can share identical bases but differ in their pattern of base modifications and/or sugar modifications. In some embodiments, CpG oligonucleotides of a particular type can share identical bases and pattern of base modifications (including, e.g., absence of base modification), but differ in pattern of sugar modifications.

In some embodiments, the present disclosure provides chirally controlled CpG oligonucleotide compositions of CpG oligonucleotides comprising multiple (e.g., more than 5, 6, 7, 8, 9, or 10) internucleotidic linkages, and particularly for CpG oligonucleotides comprising multiple (e.g., more than 5, 6, 7, 8, 9, or 10) chiral internucleotidic linkages. In some embodiments, for a stereoselective or chirally controlled preparation of CpG oligonucleotides, each chiral internucleotidic linkage is formed with greater than 90:10, 95:5, 96:4, 97:3, or 98:2 diastereoselectivity. In some embodiments, for a stereoselective or chirally controlled preparation of CpG oligonucleotides, each chiral internucleotidic linkage is formed with greater than 95:5 diastereoselectivity. In some embodiments, for a stereoselective or chirally controlled preparation of CpG oligonucleotides, each chiral internucleotidic linkage is formed with greater than 96:4 diastereoselectivity. In some embodiments, for a stereoselective or chirally controlled preparation of CpG oligonucleotides, each chiral internucleotidic linkage is formed with greater than 97:3 diastereoselectivity. In some embodiments, for a stereoselective or chirally controlled preparation of CpG oligonucleotides, each chiral internucleotidic linkage is formed with greater than 98:2 diastereoselectivity. In some embodiments, for a stereoselective or chirally controlled preparation of CpG oligonucleotides, each chiral internucleotidic linkage is formed with greater than 99:1 diastereoselectivity. In some embodiments, diastereoselectivity of a chiral internucleotidic linkage in a CpG oligonucleotide can be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage.

In some embodiments, the present disclosure provides methods for modulating levels of target nucleic acids in a system comprising administering a provided CpG oligonucleotide composition. In some embodiments, a system is an in vitro system. In some embodiments, a system is a cell. In some embodiments, a system is a tissue. In some embodiments, a system is an organ. In some embodiments, a system is a subject. In some embodiments, a target nucleic acid is genomic DNA. In some embodiments, a target nucleic acid is a transcript. In some embodiments, a target nucleic acid is a primary transcript. In some embodiments, a target nucleic acid is a processed transcript. In some embodiments, a target nucleic acid is a spliced transcript. In some embodiments, a target nucleic acid is RNA. In some embodiments, a target nucleic acid is mRNA. In some embodiments, a target nucleic acid is pre-mRNA.

In some embodiments, the present disclosure provides a method for treating or preventing a disease, comprising administering to a subject a CpG oligonucleotide composition described herein.

In some embodiments, the present disclosure provides a method for treating or preventing a disease, comprising administering to a subject a provided CpG oligonucleotide composition.

In general, properties of CpG oligonucleotide compositions as described herein can be assessed using any appropriate assay. Relative toxicity and/or protein binding properties and/or activity and/or delivery for different compositions (e.g., stereocontrolled vs non-stereocontrolled, and/or different stereocontrolled compositions) are typically desirably determined in the same assay, in some embodiments substantially simultaneously and in some embodiments with reference to historical results.

Those of skill in the art will be aware of and/or will readily be able to develop appropriate assays for particular CpG oligonucleotide compositions. The present disclosure provides descriptions of certain particular assays, for example that can be useful in assessing one or more features of CpG oligonucleotide composition behavior e.g., complement activation, injection site inflammation, protein biding, etc.

Among other things, the present disclosure encompasses the recognition that stereorandom CpG oligonucleotide preparations contain a plurality of distinct chemical entities that differ from one another, e.g., in the stereochemical structure of individual backbone chiral centers within the CpG oligonucleotide chain. Without control of stereochemistry of backbone chiral centers, stereorandom CpG oligonucleotide preparations provide uncontrolled compositions comprising undetermined levels of CpG oligonucleotide stereoisomers. Even though these stereoisomers can have the same base sequence, they are different chemical entities at least due to their different backbone stereochemistry, and they can have, as demonstrated herein, different properties, e.g., activities, toxicities, etc. Among other things, the present disclosure provides new compositions that are or contain particular stereoisomers of CpG oligonucleotides of interest. In some embodiments, a particular stereoisomer can be defined, for example, by its base sequence, its length, its pattern of backbone linkages, and its pattern of backbone chiral centers. As is understood in the art, in some embodiments, base sequence can refer to the identity and/or modification status of nucleoside residues (e.g., of sugar and/or base components, relative to standard naturally occurring nucleotides such as adenine, cytosine, guanosine, thymine, and uracil) in a CpG oligonucleotide and/or to the hybridization character (i.e., the ability to hybridize with particular complementary residues) of such residues. In some embodiments, CpG oligonucleotides in provided compositions comprise sugar modifications, e.g., 2'-modifications, at e.g., a wing region. In some embodiments, CpG oligonucleotides in provided compositions comprise a region in the middle, e.g., a core region, that has no sugar modifications. In some embodiments, the present disclosure provide a CpG oligonucleotide composition comprising a predetermined level of CpG oligonucleotides of an individual CpG oligonucleotide type which are chemically identical, e.g., they have the same base sequence, the same pattern of nucleoside modifications (modifications to sugar and base moieties, if any), the same pattern of backbone chiral centers, and the same pattern of backbone phosphorus modifications. The present disclosure demonstrates, among other things, that individual stereoisomers of a particular CpG oligonucleotide can show different stability and/or activity (e.g., functional and/or toxicity properties) from each other. In some embodiments, property improvements achieved through inclusion and/or location of particular chiral structures within a CpG oligonucleotide can be comparable to, or even better than those achieved through use of particular backbone linkages, residue modifications, etc. (e.g., through use of certain types of modified phosphates [e.g., phosphorothioate, substituted phosphorothioate, etc.], sugar modifications [e.g., 2'-modifications, etc.], and/or base modifications [e.g., methylation, etc.]). Among other things, the present disclosure recognizes that, in some embodiments, properties (e.g., activities, toxicities, etc.) of a CpG oligonucleotide can be adjusted by optimizing its pattern of backbone chiral centers, optionally in combination with adjustment/optimization of one or more other features (e.g., linkage pattern, nucleoside modification pattern, etc.) of the CpG oligonucleotide. As exemplified by various examples in the present disclosure, provided chirally controlled CpG oligonucleotide compositions can demonstrate improved properties, such as lower toxicity, improved protein binding profile, improved delivery, etc.

In some embodiments, CpG oligonucleotide properties can be adjusted by optimizing stereochemistry (pattern of backbone chiral centers) and chemical modifications (modifications of base, sugar, and/or internucleotidic linkage). Among other things, the present disclosure demonstrates that stereochemistry can further improve properties of CpG oligonucleotides comprising chemical modifications. In some embodiments, the present disclosure provides CpG oligonucleotide compositions wherein the CpG oligonucleotides comprise nucleoside modifications, chiral internucleotidic linkages and natural phosphate linkages.

In some embodiments, the present disclosure provides CpG oligonucleotide compositions which, unexpectedly, greatly improve properties of CpG oligonucleotides. In some embodiments, provided CpG oligonucleotide compositions provides surprisingly low toxicity. In some embodiments, provided CpG oligonucleotide compositions provides surprisingly improved protein binding profile. In some embodiments, provided CpG oligonucleotide compositions provides surprisingly enhanced delivery. In some embodiments, certain property improvement, such as lower toxicity, improved protein binding profile, and/or enhanced delivery, etc., are achieved without sacrificing other properties, e.g., activities, specificity, etc. In some embodiments, provided compositions provides lower toxicity, improved protein binding profile, and/or enhanced delivery, and improved activity, stability, and/or specificity (e.g., target-specificity, cleavage site specificity, etc.). Example improved activities (e.g., enhanced cleavage rates, increased target-specificity, cleavage site specificity, etc.) include but are not limited to those produced by a method described in WO/2014/012081 and WO/2015/107425.

In some embodiments, a pattern of backbone chiral centers provides increased stability. In some embodiments, a pattern of backbone chiral centers provides surprisingly increased activity. In some embodiments, a pattern of backbone chiral centers provides increased stability and activity. In some embodiments, a pattern of backbone chiral centers provides surprisingly low toxicity. In some embodiments, a pattern of backbone chiral centers provides surprisingly low immune response. In some embodiments, a pattern of backbone chiral centers provides surprisingly low complement activation. In some embodiments, a pattern of backbone chiral centers provides surprisingly low complement activation via the alternative pathway. In some embodiments, a pattern of backbone chiral centers provides surprisingly improved protein binding profile. In some embodiments, a pattern of backbone chiral centers provides surprisingly increased binding to certain proteins. In some embodiments, a pattern of backbone chiral centers provides surprisingly enhanced delivery.

In some embodiments, a pattern of backbone chiral centers comprises or is (Sp)m(Rp)n, (Rp)n(Sp)m, (Np)t(Rp)n(Sp)m, or (Sp)t(Rp)n(Sp)m. In some embodiments, a pattern of backbone chiral centers comprises or is (Rp)n(Sp)m, (Np)t(Rp)n(Sp)m, or (Sp)t(Rp)n(Sp)m, wherein m>2. In some embodiments, a pattern of backbone chiral centers comprises or is (Rp)n(Sp)m, (Np)t(Rp)n(Sp)m, or (Sp)t(Rp)n(Sp)m, wherein n is 1, t>1, and m>2. In some embodiments, m>3. In some embodiments, m>4. In some embodiments, a pattern of backbone chiral centers comprises one or more achiral natural phosphate linkages.

In some embodiments, the present disclosure recognizes that chemical modifications, such as modifications of nucleosides and internucleotidic linkages, can provide enhanced properties. In some embodiments, the present disclosure demonstrates that combinations of chemical modifications and stereochemistry can provide unexpected, greatly improved properties (e.g., bioactivity, selectivity, etc.). In some embodiments, chemical combinations, such as modifications of sugars, bases, and/or internucleotidic linkages, are combined with stereochemistry patterns, e.g., (Rp)n(Sp)m, (Np)t(Rp)n(Sp)m, or (Sp)t(Rp)n(Sp)m, to provide CpG oligonucleotides and compositions thereof with surprisingly enhanced properties. In some embodiments, a provided CpG oligonucleotide composition is chirally controlled, and comprises a combination of 2'-modification of one or more sugar moieties, one or more natural phosphate linkages, one or more phosphorothioate linkages, and a stereochemistry pattern of (Rp)n(Sp)m, (Np)t(Rp)n(Sp)m, or (Sp)t(Rp)n(Sp)m, wherein m>2. In some embodiments, n is 1, t>1, and m>2. In some embodiments, m>3. In some embodiments, m>4.

In some embodiments, a pattern of backbone chiral centers comprises or is (Rp)n(Sp)m, (Sp)t(Rp)n, (Np)t(Rp)n(Sp)m, or (Sp)t(Rp)n(Sp)m. In some embodiments, a pattern of backbone chiral centers comprises or is (Rp)n(Sp)m. In some embodiments, a pattern of backbone chiral centers comprises or is (Sp)t(Rp)n. In some embodiments, a pattern of backbone chiral centers comprises or is (Np)t(Rp)n(Sp)m. In some embodiments, a pattern of backbone chiral centers comprises or is (Sp)t(Rp)n(Sp)m. In some embodiments, each of t and m is independently greater than 1, 2, 3, 4, 5, 6, 7, 8, 9, 10, 11, 12, 13, 14, 15, 16, 17, 18, 19 or 20. In some embodiments, each of t and m is independently greater than 1. In some embodiments, each of t and m is independently greater than 2. In some embodiments, each of t and m is independently greater than 2. In some embodiments, each of t and m is independently greater than 3. In some embodiments, each of t and m is independently greater than 4. In some embodiments, each of t and m is independently greater than 5. In some embodiments, each of t and m is independently greater than 6. In some embodiments, each of t and m is independently greater than 7. In some embodiments, each of t and m is independently greater than 8. In some embodiments, each of t and m is independently greater than 9. In some embodiments, each of t and m is independently greater than 10. In some embodiments, each of t and m is independently greater than 11. In some embodiments, each of t and m is independently greater than 12. In some embodiments, each of t and m is independently greater than 13. In some embodiments, each of t and m is independently greater than 14. In some embodiments, each of t and m is independently greater than 15. In some embodiments, t is greater than 1, 2, 3, 4, 5, 6, 7, 8, 9, 10, 11, 12, 13, 14, 15, 16, 17, 18, 19 or 20. In some embodiments, t is greater than 1. In some embodiments, t is greater than 2. In some embodiments, t is greater than 2. In some embodiments, t is greater than 3. In some embodiments, t is greater than 4. In some embodiments, t is greater than 5. In some embodiments, t is greater than 6. In some embodiments, t is greater than 7. In some embodiments, t is greater than 8. In some embodiments, t is greater than 9. In some embodiments, t is greater than 10. In some embodiments, t is greater than 11.

In some embodiments, t is greater than 12. In some embodiments, t is greater than 13. In some embodiments, t is greater than 14. In some embodiments, t is greater than 15. In some embodiments, t is 1, 2, 3, 4, 5, 6, 7, 8, 9, 10, 11, 12, 13, 14, 15, 16, 17, 18, 19 or 20. In some embodiments, t is 1. In some embodiments, t is 2. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, m is greater than 1, 2, 3, 4, 5, 6, 7, 8, 9, 10, 11, 12, 13, 14, 15, 16, 17, 18, 19 or 20. In some embodiments, m is greater than 1. In some embodiments, m is greater than 2. In some embodiments, m is greater than 2. In some embodiments, m is greater than 3. In some embodiments, m is greater than 4. In some embodiments, m is greater than 5. In some embodiments, m is greater than 6. In some embodiments, m is greater than 7. In some embodiments, m is greater than 8. In some embodiments, m is greater than 9. In some embodiments, m is greater than 10. In some embodiments, m is greater than 11. In some embodiments, m is greater than 12. In some embodiments, m is greater than 13. In some embodiments, m is greater than 14. In some embodiments, m is greater than 15. In some embodiments, m is 1, 2, 3, 4, 5, 6, 7, 8, 9, 10, 11, 12, 13, 14, 15, 16, 17, 18, 19 or 20. In some embodiments, m is 1. In some embodiments, m is 2. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, t=m. In some embodiments, n is greater than 1, 2, 3, 4, 5, 6, 7, 8, 9, 10, 11, 12, 13, 14, 15, 16, 17, 18, 19 or 20. In some embodiments, n is greater than 1. In some embodiments, n is greater than 2. In some embodiments, n is greater than 2. In some embodiments, n is greater than 3. In some embodiments, n is greater than 4. In some embodiments, n is greater than 5. In some embodiments, n is greater than 6. In some embodiments, n is greater than 7. In some embodiments, n is greater than 8. In some embodiments, n is greater than 9. In some embodiments, n is greater than 10. In some embodiments, n is greater than 11. In some embodiments, n is greater than 12. In some embodiments, n is greater than 13. In some embodiments, n is greater than 14. In some embodiments, n is greater than 15. In some embodiments, n is 1, 2, 3, 4, 5, 6, 7, 8, 9, 10, 11, 12, 13, 14, 15, 16, 17, 18, 19 or 20. In some embodiments, n is 1. In some embodiments, n is 2. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15.

In some embodiments, provided CpG oligonucleotides comprise one or more modified sugar moieties. In some embodiments, provided CpG oligonucleotides comprise one or more modified sugar moieties. In some embodiments, provided CpG oligonucleotides comprise 2 or more modified sugar moieties. In some embodiments, provided CpG oligonucleotides comprise 3 or more modified sugar moieties. In some embodiments, provided CpG oligonucleotides comprise 4 or more modified sugar moieties. In some embodiments, provided CpG oligonucleotides comprise 5 or more modified sugar moieties. In some embodiments, provided CpG oligonucleotides comprise 6 or more modified sugar moieties. In some embodiments, provided CpG oligonucleotides comprise 7 or more modified sugar moieties. In some embodiments, provided CpG oligonucleotides comprise 8 or more modified sugar moieties. In some embodiments, provided CpG oligonucleotides comprise 9 or more modified sugar moieties. In some embodiments, provided CpG oligonucleotides comprise 10 or more modified sugar moieties. In some embodiments, provided CpG oligonucleotides comprise 15 or more modified sugar moieties. In some embodiments, provided CpG oligonucleotides comprise 20 or more modified sugar moieties. In some embodiments, provided CpG oligonucleotides comprise 25 or more modified sugar moieties. In some embodiments, provided CpG oligonucleotides comprise 30 or more modified sugar moieties.

Provided CpG oligonucleotides can comprise various number of chiral internucleotidic linkages. In some embodiments, provided CpG oligonucleotides comprise no chiral internucleotidic linkages. In some embodiments, provided CpG oligonucleotides comprise one chiral internucleotidic linkage. In some embodiments, provided CpG oligonucleotides comprise 2 or more chiral internucleotidic linkages. In some embodiments, provided CpG oligonucleotides comprise 3 or more chiral internucleotidic linkages. In some embodiments, provided CpG oligonucleotides comprise 4 or more chiral internucleotidic linkages. In some embodiments, provided CpG oligonucleotides comprise 5 or more chiral internucleotidic linkages. In some embodiments, provided CpG oligonucleotides comprise 6 or more chiral internucleotidic linkages. In some embodiments, provided CpG oligonucleotides comprise 7 or more chiral internucleotidic linkages. In some embodiments, provided CpG oligonucleotides comprise 8 or more chiral internucleotidic linkages. In some embodiments, provided CpG oligonucleotides comprise 9 or more chiral internucleotidic linkages. In some embodiments, provided CpG oligonucleotides comprise 10 or more chiral internucleotidic linkages. In some embodiments, provided CpG oligonucleotides comprise 15 or more chiral internucleotidic linkages. In some embodiments, provided CpG oligonucleotides comprise 20 or more chiral internucleotidic linkages. In some embodiments, provided CpG oligonucleotides comprise 25 or more chiral internucleotidic linkages. In some embodiments, provided CpG oligonucleotides comprise 30 or more chiral internucleotidic linkages.

Provided CpG oligonucleotides can comprise various number of achiral internucleotidic linkages. In some embodiments, provided CpG oligonucleotides comprise no achiral internucleotidic linkages. In some embodiments, provided CpG oligonucleotides comprise one achiral internucleotidic linkage. In some embodiments, provided CpG oligonucleotides comprise 2 or more achiral internucleotidic linkages. In some embodiments, provided CpG oligonucleotides comprise 3 or more achiral internucleotidic linkages. In some embodiments, provided CpG oligonucleotides comprise 4 or more achiral internucleotidic linkages. In some embodiments, provided CpG oligonucleotides comprise 5 or more achiral internucleotidic linkages. In some embodiments, provided CpG oligonucleotides comprise 6 or more achiral internucleotidic linkages. In some embodiments, provided CpG oligonucleotides comprise 7 or more achiral internucleotidic linkages. In some embodiments, provided CpG oligonucleotides comprise 8 or more achiral internucleotidic linkages. In some embodiments, provided CpG oligonucleotides comprise 9 or more achiral internucleotidic linkages. In some embodiments, provided CpG oligonucleotides comprise 10 or more achiral internucleotidic linkages. In some embodiments, provided CpG oligonucleotides comprise 15 or more achiral internucleotidic linkages. In some embodiments, provided CpG oligonucleotides comprise 20 or more achiral internucleotidic linkages. In some embodiments, provided CpG oligonucleotides comprise 25 or more achiral internucleotidic linkages. In some embodiments, provided CpG oligonucleotides comprise 30 or more achiral internucleotidic linkages.

In some embodiments, 5% or more of the sugar moieties of provided CpG oligonucleotides are modified. In some embodiments, 10% or more of the sugar moieties of provided CpG oligonucleotides are modified. In some embodiments, 15% or more of the sugar moieties of provided CpG oligonucleotides are modified. In some embodiments, 20% or more of the sugar moieties of provided CpG oligonucleotides are modified. In some embodiments, 25% or more of the sugar moieties of provided CpG oligonucleotides are modified. In some embodiments, 30% or more of the sugar moieties of provided CpG oligonucleotides are modified. In some embodiments, 35% or more of the sugar moieties of provided CpG oligonucleotides are modified. In some embodiments, 40% or more of the sugar moieties of provided CpG oligonucleotides are modified. In some embodiments, 45% or more of the sugar moieties of provided CpG oligonucleotides are modified. In some embodiments, 50% or more of the sugar moieties of provided CpG oligonucleotides are modified. In some embodiments, 55% or more of the sugar moieties of provided CpG oligonucleotides are modified. In some embodiments, 60% or more of the sugar moieties of provided CpG oligonucleotides are modified. In some embodiments, 65% or more of the sugar moieties of provided CpG oligonucleotides are modified. In some embodiments, 70% or more of the sugar moieties of provided CpG oligonucleotides are modified. In some embodiments, 75% or more of the sugar moieties of provided CpG oligonucleotides are modified. In some embodiments, 80% or more of the sugar moieties of provided CpG oligonucleotides are modified. In some embodiments, 85% or more of the sugar moieties of provided CpG oligonucleotides are modified. In some embodiments, 90% or more of the sugar moieties of provided CpG oligonucleotides are modified. In some embodiments, 95% or more of the sugar moieties of provided CpG oligonucleotides are modified. In some embodiments, each sugar moiety of provided CpG oligonucleotides is modified.

In some embodiments, provided CpG oligonucleotides comprise one or more T-F. In some embodiments, provided CpG oligonucleotides comprise two or more 2'-F. In some embodiments, provided CpG oligonucleotides comprise three or more 2'-F. In some embodiments, provided CpG oligonucleotides comprise four or more 2'-F. In some embodiments, provided CpG oligonucleotides comprise five or more 2'-F. In some embodiments, provided CpG oligonucleotides comprise six or more 2'-F. In some embodiments, provided CpG oligonucleotides comprise seven or more 2'-F. In some embodiments, provided CpG oligonucleotides comprise eight or more 2'-F. In some embodiments, provided CpG oligonucleotides comprise nine or more 2'-F. In some embodiments, provided CpG oligonucleotides comprise ten or more 2'-F. In some embodiments, provided CpG oligonucleotides comprise 11 or more 2'-F. In some embodiments, provided CpG oligonucleotides comprise 12 or more 2'-F. In some embodiments, provided CpG oligonucleotides comprise 13 or more 2'-F. In some embodiments, provided CpG oligonucleotides comprise 14 or more 2'-F. In some embodiments, provided CpG oligonucleotides comprise 15 or more 2'-F. In some embodiments, provided CpG oligonucleotides comprise 16 or more 2'-F. In some embodiments, provided CpG oligonucleotides comprise 17 or more 2'-F. In some embodiments, provided CpG oligonucleotides comprise 18 or more 2'-F. In some embodiments, provided CpG oligonucleotides comprise 19 or more 2'-F. In some embodiments, provided CpG oligonucleotides comprise 20 or more 2'-F. In some embodiments, provided CpG oligonucleotides comprise 21 or more 2'-F. In some embodiments, provided CpG oligonucleotides comprise 22 or more 2'-F. In some embodiments, provided CpG oligonucleotides comprise 23 or more 2'-F. In some embodiments, provided CpG oligonucleotides comprise 24 or more 2'-F. In some embodiments, provided CpG oligonucleotides comprise 25 or more 2'-F. In some embodiments, provided CpG oligonucleotides comprise 30 or more 2'-F. In some embodiments, provided CpG oligonucleotides comprise 35 or more 2'-F.

In some embodiments, provided CpG oligonucleotides comprise one or more consecutive 2'-F. In some embodiments, provided CpG oligonucleotides comprise two or more consecutive 2'-F. In some embodiments, provided CpG oligonucleotides comprise three or more consecutive 2'-F. In some embodiments, provided CpG oligonucleotides comprise four or more consecutive 2'-F. In some embodiments, provided CpG oligonucleotides comprise five or more consecutive 2'-F. In some embodiments, provided CpG oligonucleotides comprise six or more consecutive 2'-F. In some embodiments, provided CpG oligonucleotides comprise seven or more consecutive 2'-F. In some embodiments, provided CpG oligonucleotides comprise eight or more consecutive 2'-F. In some embodiments, provided CpG oligonucleotides comprise nine or more consecutive 2'-F. In some embodiments, provided CpG oligonucleotides comprise ten or more consecutive 2'-F. In some embodiments, provided CpG oligonucleotides comprise 11 or more consecutive 2'-F. In some embodiments, provided CpG oligonucleotides comprise 12 or more consecutive 2'-F. In some embodiments, provided CpG oligonucleotides comprise 13 or more consecutive 2'-F. In some embodiments, provided CpG oligonucleotides comprise 14 or more consecutive 2'-F. In some embodiments, provided CpG oligonucleotides comprise 15 or more consecutive 2'-F. In some embodiments, provided CpG oligonucleotides comprise 16 or more consecutive 2'-F. In some embodiments, provided CpG oligonucleotides comprise 17 or more consecutive 2'-F. In some embodiments, provided CpG oligonucleotides comprise 18 or more consecutive 2'-F. In some embodiments, provided CpG oligonucleotides comprise 19 or more consecutive 2'-F. In some embodiments, provided CpG oligonucleotides comprise 20 or more consecutive 2'-F. In some embodiments, provided CpG oligonucleotides comprise 21 or more consecutive 2'-F. In some embodiments, provided CpG oligonucleotides comprise 22 or more consecutive 2'-F. In some embodiments, provided CpG oligonucleotides comprise 23 or more consecutive 2'-F. In some embodiments, provided CpG oligonucleotides comprise 24 or more consecutive 2'-F. In some embodiments, provided CpG oligonucleotides comprise 25 or more consecutive 2'-F. In some embodiments, provided CpG oligonucleotides comprise 30 or more consecutive 2'-F. In some embodiments, provided CpG oligonucleotides comprise 35 or more consecutive 2'-F.

In some embodiments, a nucleoside comprising a 2'-modification is followed by a modified internucleotidic linkage. In some embodiments, a nucleoside comprising a 2'-modification is preceded by a modified internucleotidic linkage. In some embodiments, a modified internucleotidic linkage is a chiral internucleotidic linkage. In some embodiments, a modified internucleotidic linkage is a phosphorothioate. In some embodiments, a chiral internucleotidic linkage is Sp. In some embodiments, a nucleoside comprising a 2'-modification is followed by an Sp chiral internucleotidic linkage. In some embodiments, a nucleoside comprising a 2'-F is followed by an Sp chiral internucleotidic linkage. In some embodiments, a nucleoside comprising a 2'-modification is preceded by an Sp chiral internucleotidic linkage. In some embodiments, a nucleoside comprising a 2'-F is preceded by an Sp chiral internucleotidic linkage. In some embodiments, a chiral internucleotidic linkage is Rp. In some embodiments, a nucleoside comprising a 2'-modification is followed by an Rp chiral internucleotidic linkage. In some embodiments, a nucleoside comprising a 2'-F is followed by an Rp chiral internucleotidic linkage. In some embodiments, a nucleoside comprising a 2'-modification is preceded by an Rp chiral internucleotidic linkage. In some embodiments, a nucleoside comprising a 2'-F is preceded by an Rp chiral internucleotidic linkage.

In some embodiments, provided CpG oligonucleotides comprise one or more natural phosphate linkages and one or more modified internucleotidic linkages.

Provided CpG oligonucleotides can comprise various number of natural phosphate linkages. In some embodiments, provided CpG oligonucleotides comprise no natural phosphate linkages. In some embodiments, provided CpG oligonucleotides comprise one natural phosphate linkage. In some embodiments, provided CpG oligonucleotides comprise 2 or more natural phosphate linkages. In some embodiments, provided CpG oligonucleotides comprise 3 or more natural phosphate linkages. In some embodiments, provided CpG oligonucleotides comprise 4 or more natural phosphate linkages. In some embodiments, provided CpG oligonucleotides comprise 5 or more natural phosphate linkages. In some embodiments, provided CpG oligonucleotides comprise 6 or more natural phosphate linkages. In some embodiments, provided CpG oligonucleotides comprise 7 or more natural phosphate linkages. In some embodiments, provided CpG oligonucleotides comprise 8 or more natural phosphate linkages. In some embodiments, provided CpG oligonucleotides comprise 9 or more natural phosphate linkages. In some embodiments, provided CpG oligonucleotides comprise 10 or more natural phosphate linkages. In some embodiments, provided CpG oligonucleotides comprise 15 or more natural phosphate linkages. In some embodiments, provided CpG oligonucleotides comprise 20 or more natural phosphate linkages. In some embodiments, provided CpG oligonucleotides comprise 25 or more natural phosphate linkages. In some embodiments, provided CpG oligonucleotides comprise 30 or more natural phosphate linkages.

In some embodiments, 5% or more of the internucleotidic linkages of provided CpG oligonucleotides are natural phosphate linkages. In some embodiments, 10% or more of the internucleotidic linkages of provided CpG oligonucleotides are natural phosphate linkages. In some embodiments, 15% or more of the internucleotidic linkages of provided CpG oligonucleotides are natural phosphate linkages. In some embodiments, 20% or more of the internucleotidic linkages of provided CpG oligonucleotides are natural phosphate linkages. In some embodiments, 25% or more of the internucleotidic linkages of provided CpG oligonucleotides are natural phosphate linkages. In some embodiments, 30% or more of the internucleotidic linkages of provided CpG oligonucleotides are natural phosphate linkages. In some embodiments, 35% or more of the internucleotidic linkages of provided CpG oligonucleotides are natural phosphate linkages. In some embodiments, 40% or more of the internucleotidic linkages of provided CpG oligonucleotides are natural phosphate linkages. In some embodiments, 45% or more of the internucleotidic linkages of provided CpG oligonucleotides are natural phosphate linkages. In some embodiments, 50% or more of the internucleotidic linkages of provided CpG oligonucleotides are natural phosphate linkages. In some embodiments, 55% or more of the internucleotidic linkages of provided CpG oligonucleotides are natural phosphate linkages. In some embodiments, 60% or more of the internucleotidic linkages of provided CpG oligonucleotides are natural phosphate linkages. In some embodiments, 65% or more of the internucleotidic linkages of provided CpG oligonucleotides are natural phosphate linkages. In some embodiments, 70% or more of the internucleotidic linkages of provided CpG oligonucleotides are natural phosphate linkages. In some embodiments, 75% or more of the internucleotidic linkages of provided CpG oligonucleotides are natural phosphate linkages. In some embodiments, 80% or more of the internucleotidic linkages of provided CpG oligonucleotides are natural phosphate linkages. In some embodiments, 85% or more of the internucleotidic linkages of provided CpG oligonucleotides are natural phosphate linkages. In some embodiments, 90% or more of the internucleotidic linkages of provided CpG oligonucleotides are natural phosphate linkages. In some embodiments, 95% or more of the internucleotidic linkages of provided CpG oligonucleotides are natural phosphate linkages.

In some embodiments, provided CpG oligonucleotides comprise no more than about 25 consecutive unmodified sugar moieties. In some embodiments, provided CpG oligonucleotides comprise no more than about 20 consecutive unmodified sugar moieties. In some embodiments, provided CpG oligonucleotides comprise no more than about 15 consecutive unmodified sugar moieties. In some embodiments, provided CpG oligonucleotides comprise no more than about 10 consecutive unmodified sugar moieties. In some embodiments, provided CpG oligonucleotides comprise no more than about 9 consecutive unmodified sugar moieties. In some embodiments, provided CpG oligonucleotides comprise no more than about 8 consecutive unmodified sugar moieties. In some embodiments, provided CpG oligonucleotides comprise no more than about 7 consecutive unmodified sugar moieties. In some embodiments, provided CpG oligonucleotides comprise no more than about 6 consecutive unmodified sugar moieties. In some embodiments, provided CpG oligonucleotides comprise no more than about 5 consecutive unmodified sugar moieties. In some embodiments, provided CpG oligonucleotides comprise no more than about 4 consecutive unmodified sugar moieties. In some embodiments, provided CpG oligonucleotides comprise no more than about 3 consecutive unmodified sugar moieties. In some embodiments, provided CpG oligonucleotides comprise no more than about 2 consecutive unmodified sugar moieties. In some embodiments, provided CpG oligonucleotides comprise no more than about 25 unmodified sugar moieties. In some embodiments, provided CpG oligonucleotides comprise no more than about 20 unmodified sugar moieties. In some embodiments, provided CpG oligonucleotides comprise no more than about 15 unmodified sugar moieties. In some embodiments, provided CpG oligonucleotides comprise no more than about 10 unmodified sugar moieties. In some embodiments, provided CpG oligonucleotides comprise no more than about 5 unmodified sugar moieties.

In some embodiments, provided CpG oligonucleotides comprise no more than about 95% unmodified sugar moieties. In some embodiments, provided CpG oligonucleotides comprise no more than about 90% unmodified sugar moieties. In some embodiments, provided CpG oligonucleotides comprise no more than about 85% unmodified sugar moieties. In some embodiments, provided CpG oligonucleotides comprise no more than about 80% unmodified sugar moieties. In some embodiments, provided CpG oligonucleotides comprise no more than about 70% unmodified sugar moieties. In some embodiments, provided CpG oligonucleotides comprise no more than about 60% unmodified sugar moieties. In some embodiments, provided CpG oligonucleotides comprise no more than about 50% unmodified sugar moieties. In some embodiments, provided CpG oligonucleotides comprise no more than about 40% unmodified sugar moieties. In some embodiments, provided CpG oligonucleotides comprise no more than about 30% unmodified sugar moieties. In some embodiments, provided CpG oligonucleotides comprise no more than about 20% unmodified sugar moieties. In some embodiments, provided CpG oligonucleotides comprise no more than about 10% unmodified sugar moieties. In some embodiments, provided CpG oligonucleotides comprise no more than about 5% unmodified sugar moieties. In some embodiments, provided CpG oligonucleotides comprise no more than about 15 consecutive unmodified sugar moieties. In some embodiments, provided CpG oligonucleotides comprise no more than about 10 consecutive unmodified sugar moieties. In some embodiments, provided CpG oligonucleotides comprise no more than about 9 consecutive unmodified sugar moieties. In some embodiments, provided CpG oligonucleotides comprise no more than about 8 consecutive unmodified sugar moieties. In some embodiments, provided CpG oligonucleotides comprise no more than about 7 consecutive unmodified sugar moieties. In some embodiments, provided CpG oligonucleotides comprise no more than about 6 consecutive unmodified sugar moieties. In some embodiments, provided CpG oligonucleotides comprise no more than about 5 consecutive unmodified sugar moieties. In some embodiments, provided CpG oligonucleotides comprise no more than about 4 consecutive unmodified sugar moieties. In some embodiments, provided CpG oligonucleotides comprise no more than about 3 consecutive unmodified sugar moieties. In some embodiments, provided CpG oligonucleotides comprise no more than about 2 consecutive unmodified sugar moieties. In some embodiments, provided CpG oligonucleotides comprise no more than about 25 unmodified sugar moieties. In some embodiments, provided CpG oligonucleotides comprise no more than about 20 unmodified sugar moieties. In some embodiments, provided CpG oligonucleotides comprise no more than about 15 unmodified sugar moieties. In some embodiments, provided CpG oligonucleotides comprise no more than about 10 unmodified sugar moieties. In some embodiments, provided CpG oligonucleotides comprise no more than about 5 unmodified sugar moieties.

In some embodiments, provided CpG oligonucleotides comprise no more than about 95% unmodified sugar moieties. In some embodiments, provided CpG oligonucleotides comprise no more than about 90% unmodified sugar moieties. In some embodiments, provided CpG oligonucleotides comprise no more than about 85% unmodified sugar moieties. In some embodiments, provided CpG oligonucleotides comprise no more than about 80% unmodified sugar moieties. In some embodiments, provided CpG oligonucleotides comprise no more than about 70% unmodified sugar moieties. In some embodiments, provided CpG oligonucleotides comprise no more than about 60% unmodified sugar moieties. In some embodiments, provided CpG oligonucleotides comprise no more than about 50% unmodified sugar moieties. In some embodiments, provided CpG oligonucleotides comprise no more than about 40% unmodified sugar moieties. In some embodiments, provided CpG oligonucleotides comprise no more than about 30% unmodified sugar moieties. In some embodiments, provided CpG oligonucleotides comprise no more than about 20% unmodified sugar moieties. In some embodiments, provided CpG oligonucleotides comprise no more than about 10% unmodified sugar moieties. In some embodiments, provided CpG oligonucleotides comprise no more than about 5% unmodified sugar moieties. In some embodiments, each sugar moiety of the CpG oligonucleotides of the first plurality is independently modified.

In some embodiments, provided CpG oligonucleotides comprise two or more modified internucleotidic linkages. In some embodiments, provided CpG oligonucleotides comprise three or more modified internucleotidic linkages. In some embodiments, provided CpG oligonucleotides comprise four or more modified internucleotidic linkages. In some embodiments, provided CpG oligonucleotides comprise five or more modified internucleotidic linkages. In some embodiments, provided CpG oligonucleotides comprise ten or more modified internucleotidic linkages. In some embodiments, provided CpG oligonucleotides comprise about 15 or more modified internucleotidic linkages. In some embodiments, provided CpG oligonucleotides comprise about 20 or more modified internucleotidic linkages. In some embodiments, provided CpG oligonucleotides comprise about 25 or more modified internucleotidic linkages.

In some embodiments, about 5% of the internucleotidic linkages in provided CpG oligonucleotides are modified internucleotidic linkages. In some embodiments, about 10% of the internucleotidic linkages in provided CpG oligonucleotides are modified internucleotidic linkages. In some embodiments, about 20% of the internucleotidic linkages in provided CpG oligonucleotides are modified internucleotidic linkages. In some embodiments, about 30% of the internucleotidic linkages in provided CpG oligonucleotides are modified internucleotidic linkages. In some embodiments, about 40% of the internucleotidic linkages in provided CpG oligonucleotides are modified internucleotidic linkages. In some embodiments, about 50% of the internucleotidic linkages in provided CpG oligonucleotides are modified internucleotidic linkages. In some embodiments, about 60% of the internucleotidic linkages in provided CpG oligonucleotides are modified internucleotidic linkages. In some embodiments, about 70% of the internucleotidic linkages in provided CpG oligonucleotides are modified internucleotidic linkages. In some embodiments, about 80% of the internucleotidic linkages in provided CpG oligonucleotides are modified internucleotidic linkages. In some embodiments, about 85% of the internucleotidic linkages in provided CpG oligonucleotides are modified internucleotidic linkages. In some embodiments, about 90% of the internucleotidic linkages in provided CpG oligonucleotides are modified internucleotidic linkages. In some embodiments, about 95% of the internucleotidic linkages in provided CpG oligonucleotides are modified internucleotidic linkages.

In some embodiments, provided CpG oligonucleotides comprise no more than about 25 consecutive natural phosphate linkages. In some embodiments, provided CpG oligonucleotides comprise no more than about 20 consecutive natural phosphate linkages. In some embodiments, provided CpG oligonucleotides comprise no more than about 15 consecutive natural phosphate linkages. In some embodiments, provided CpG oligonucleotides comprise no more than about 10 consecutive natural phosphate linkages. In some embodiments, provided CpG oligonucleotides comprise no more than about 9 consecutive natural phosphate linkages. In some embodiments, provided CpG oligonucleotides comprise no more than about 8 consecutive natural phosphate linkages. In some embodiments, provided CpG oligonucleotides comprise no more than about 7 consecutive natural phosphate linkages. In some embodiments, provided CpG oligonucleotides comprise no more than about 6 consecutive natural phosphate linkages. In some embodiments, provided CpG oligonucleotides comprise no more than about 5 consecutive natural phosphate linkages. In some embodiments, provided CpG oligonucleotides comprise no more than about 4 consecutive natural phosphate linkages. In some embodiments, provided CpG oligonucleotides comprise no more than about 3 consecutive natural phosphate linkages. In some embodiments, provided CpG oligonucleotides comprise no more than about 2 consecutive natural phosphate linkages. In some embodiments, provided CpG oligonucleotides comprise no more than about 25 natural phosphate linkages. In some embodiments, provided CpG oligonucleotides comprise no more than about 20 natural phosphate linkages. In some embodiments, provided CpG oligonucleotides comprise no more than about 15 natural phosphate linkages. In some embodiments, provided CpG oligonucleotides comprise no more than about 10 natural phosphate linkages. In some embodiments, provided CpG oligonucleotides comprise no more than about 5 natural phosphate linkages. In some embodiments, provided CpG oligonucleotides comprise no more than about 95% natural phosphate linkages. In some embodiments, provided CpG oligonucleotides comprise no more than about 90% natural phosphate linkages. In some embodiments, provided CpG oligonucleotides comprise no more than about 85% natural phosphate linkages. In some embodiments, provided CpG oligonucleotides comprise no more than about 80% natural phosphate linkages. In some embodiments, provided CpG oligonucleotides comprise no more than about 70% natural phosphate linkages. In some embodiments, provided CpG oligonucleotides comprise no more than about 60% natural phosphate linkages. In some embodiments, provided CpG oligonucleotides comprise no more than about 50% natural phosphate linkages. In some embodiments, provided CpG oligonucleotides comprise no more than about 40% natural phosphate linkages. In some embodiments, provided CpG oligonucleotides comprise no more than about 30% natural phosphate linkages. In some embodiments, provided CpG oligonucleotides comprise no more than about 20% natural phosphate linkages. In some embodiments, provided CpG oligonucleotides comprise no more than about 10% natural phosphate linkages. In some embodiments, provided CpG oligonucleotides comprise no more than about 5% natural phosphate linkages.

In some embodiments, provided CpG oligonucleotides comprise no DNA nucleotide. A DNA nucleotide is a nucleotide in which the sugar moiety is an unmodified DNA sugar moiety, and the internucleotidic linkage is a natural phosphate linkage. In some embodiments, provided CpG oligonucleotides comprise no more than 2 DNA nucleotides. In some embodiments, provided CpG oligonucleotides comprise no more than 3 DNA nucleotides. In some embodiments, provided CpG oligonucleotides comprise no more than 4 DNA nucleotides. In some embodiments, provided CpG oligonucleotides comprise no more than 5 DNA nucleotides. In some embodiments, provided CpG oligonucleotides comprise no more than 6 DNA nucleotides. In some embodiments, provided CpG oligonucleotides comprise no more than 7 DNA nucleotides. In some embodiments, provided CpG oligonucleotides comprise no more than 8 DNA nucleotides. In some embodiments, provided CpG oligonucleotides comprise no more than 9 DNA nucleotides. In some embodiments, provided CpG oligonucleotides comprise no more than 10 DNA nucleotides. In some embodiments, provided CpG oligonucleotides comprise no more than 11 DNA nucleotides. In some embodiments, provided CpG oligonucleotides comprise no more than 12 DNA nucleotides. In some embodiments, provided CpG oligonucleotides comprise no more than 13 DNA nucleotides. In some embodiments, provided CpG oligonucleotides comprise no more than 14 DNA nucleotides. In some embodiments, provided CpG oligonucleotides comprise no more than 15 DNA nucleotides. In some embodiments, provided CpG oligonucleotides comprise no more than 20 DNA nucleotides. In some embodiments, provided CpG oligonucleotides comprise no more than 25 DNA nucleotides. In some embodiments, provided CpG oligonucleotides comprise no more than 30 DNA nucleotides.

In some embodiments, provided CpG oligonucleotides comprise no more than 2 consecutive DNA nucleotides. In some embodiments, provided CpG oligonucleotides comprise no more than 3 consecutive DNA nucleotides. In some embodiments, provided CpG oligonucleotides comprise no more than 4 consecutive DNA nucleotides. In some embodiments, provided CpG oligonucleotides comprise no more than 5 consecutive DNA nucleotides. In some embodiments, provided CpG oligonucleotides comprise no more than 6 consecutive DNA nucleotides. In some embodiments, provided CpG oligonucleotides comprise no more than 7 consecutive DNA nucleotides. In some embodiments, provided CpG oligonucleotides comprise no more than 8 consecutive DNA nucleotides. In some embodiments, provided CpG oligonucleotides comprise no more than 9 consecutive DNA nucleotides. In some embodiments, provided CpG oligonucleotides comprise no more than 10 consecutive DNA nucleotides. In some embodiments, provided CpG oligonucleotides comprise no more than 11 consecutive DNA nucleotides. In some embodiments, provided CpG oligonucleotides comprise no more than 12 consecutive DNA nucleotides. In some embodiments, provided CpG oligonucleotides comprise no more than 13 consecutive DNA nucleotides. In some embodiments, provided CpG oligonucleotides comprise no more than 14 consecutive DNA nucleotides. In some embodiments, provided CpG oligonucleotides comprise no more than 15 consecutive DNA nucleotides. In some embodiments, provided CpG oligonucleotides comprise no more than 20 consecutive DNA nucleotides. In some embodiments, provided CpG oligonucleotides comprise no more than 25 consecutive DNA nucleotides. In some embodiments, provided CpG oligonucleotides comprise no more than 30 consecutive DNA nucleotides.

In some embodiments, provided CpG oligonucleotides comprise two wing and one core regions. In some embodiments, provided CpG oligonucleotides comprises a 5'-wing-core-wing-3' structure. In some embodiments, provided CpG oligonucleotides are of a 5'-wing-core-wing-3' gapmer structure. In some embodiments, the two wing regions are identical. In some embodiments, the two wing regions are different. In some embodiments, the two wing regions are identical in chemical modifications. In some embodiments, the two wing regions are identical in 2'-modifications. In some embodiments, the two wing regions are identical in internucleotidic linkage modifications. In some embodiments, the two wing regions are identical in patterns of backbone chiral centers. In some embodiments, the two wing regions are identical in pattern of backbone linkages. In some embodiments, the two wing regions are identical in pattern of backbone linkage types. In some embodiments, the two wing regions are identical in pattern of backbone phosphorus modifications.

In some embodiments, provided CpG oligonucleotides comprise one wing and one core regions. In some embodiments, provided CpG oligonucleotides comprises a 5'-wing-core-3' hemimer structure. In some embodiments, provided CpG oligonucleotides are of a 5'-wing-core-3' hemimer structure. In some embodiments, provided CpG oligonucleotides comprises a 5'-core-wing-3' hemimer structure. In some embodiments, provided CpG oligonucleotides are of a 5'-core-wing-3' hemimer structure.

A wing region can be differentiated from a core region in that a wing region contains a different structure feature than a core region. For example, in some embodiments, a wing region differs from a core region in that they have different sugar modifications, base modifications, internucleotidic linkages, internucleotidic linkage stereochemistry, etc. In some embodiments, a wing region differs from a core region in that they have different 2'-modifications of the sugars.

In some embodiments, an internucleotidic linkage between a wing region and a core region is considered part of the wing region. In some embodiments, an internucleotidic linkage between a 5'-wing region and a core region is considered part of the wing region. In some embodiments, an internucleotidic linkage between a 3'-wing region and a core region is considered part of the wing region. In some embodiments, an internucleotidic linkage between a wing region and a core region is considered part of the core region. In some embodiments, an internucleotidic linkage between a 5'-wing region and a core region is considered part of the core region. In some embodiments, an internucleotidic linkage between a 3'-wing region and a core region is considered part of the core region.

In some embodiments, an internucleotidic linkage between a wing region and a core region is considered part of the wing region. In some embodiments, an internucleotidic linkage between a 5'-wing region and a core region is considered part of the wing region. In some embodiments, an internucleotidic linkage between a 3'-wing region and a core region is considered part of the wing region. In some embodiments, an internucleotidic linkage between a wing region and a core region is considered part of the core region. In some embodiments, an internucleotidic linkage between a 5'-wing region and a core region is considered part of the core region. In some embodiments, an internucleotidic linkage between a 3'-wing region and a core region is considered part of the core region.

In some embodiments, a wing region comprises 2 or more nucleosides. In some embodiments, a wing region comprises 3 or more nucleosides. In some embodiments, a wing region comprises 4 or more nucleosides. In some embodiments, a wing region comprises 5 or more nucleosides. In some embodiments, a wing region comprises 6 or more nucleosides. In some embodiments, a wing region comprises 7 or more nucleosides. In some embodiments, a wing region comprises 8 or more nucleosides. In some embodiments, a wing region comprises 9 or more nucleosides. In some embodiments, a wing region comprises 10 or more nucleosides. In some embodiments, a wing region comprises 11 or more nucleosides. In some embodiments, a wing region comprises 12 or more nucleosides. In some embodiments, a wing region comprises 13 or more nucleosides. In some embodiments, a wing region comprises 14 or more nucleosides. In some embodiments, a wing region comprises 15 or more nucleosides.

In some embodiments, a wing region comprises 2 or more modified internucleotidic linkages. In some embodiments, a wing region comprises 3 or more modified internucleotidic linkages. In some embodiments, a wing region comprises 4 or more modified internucleotidic linkages. In some embodiments, a wing region comprises 5 or more modified internucleotidic linkages. In some embodiments, a wing region comprises 6 or more modified internucleotidic linkages. In some embodiments, a wing region comprises 7 or more modified internucleotidic linkages. In some embodiments, a wing region comprises 8 or more modified internucleotidic linkages. In some embodiments, a wing region comprises 9 or more modified internucleotidic linkages. In some embodiments, a wing region comprises 10 or more modified internucleotidic linkages. In some embodiments, a wing region comprises 11 or more modified internucleotidic linkages. In some embodiments, a wing region comprises 12 or more modified internucleotidic linkages. In some embodiments, a wing region comprises 13 or more modified internucleotidic linkages. In some embodiments, a wing region comprises 14 or more modified internucleotidic linkages. In some embodiments, a wing region comprises 15 or more modified internucleotidic linkages.

In some embodiments, a chiral internucleotidic linkage or a modified internucleotidic linkage has the structure of formula I. In some embodiments, a chiral internucleotidic linkage or a modified internucleotidic linkage is phosphorothioate. In some embodiments, each chiral internucleotidic linkage or a modified internucleotidic linkage independently has the structure of formula I. In some embodiments, each chiral internucleotidic linkage or a modified internucleotidic linkage is phosphorothioate.

In some embodiments, a wing region comprises 2 or consecutive modified internucleotidic linkages. In some embodiments, a wing region comprises 3 or consecutive modified internucleotidic linkages. In some embodiments, a wing region comprises 4 or consecutive modified internucleotidic linkages. In some embodiments, a wing region comprises 5 or consecutive modified internucleotidic linkages. In some embodiments, a wing region comprises 6 or consecutive modified internucleotidic linkages. In some embodiments, a wing region comprises 7 or consecutive modified internucleotidic linkages. In some embodiments, a wing region comprises 8 or consecutive modified internucleotidic linkages. In some embodiments, a wing region comprises 9 or consecutive modified internucleotidic linkages. In some embodiments, a wing region comprises 10 or consecutive modified internucleotidic linkages. In some embodiments, a wing region comprises 11 or consecutive modified internucleotidic linkages. In some embodiments, a wing region comprises 12 or consecutive modified internucleotidic linkages. In some embodiments, a wing region comprises 13 or consecutive modified internucleotidic linkages. In some embodiments, a wing region comprises 14 or consecutive modified internucleotidic linkages. In some embodiments, a wing region comprises 15 or consecutive modified internucleotidic linkages. In some embodiments, each internucleotidic linkage in a wing region is independently a modified internucleotidic linkage.

In some embodiments, 5% or more of the internucleotidic linkages of provided CpG oligonucleotides are modified internucleotidic linkages. In some embodiments, 10% or more of the internucleotidic linkages of provided CpG oligonucleotides are modified internucleotidic linkages. In some embodiments, 15% or more of the internucleotidic linkages of provided CpG oligonucleotides are modified internucleotidic linkages. In some embodiments, 20% or more of the internucleotidic linkages of provided CpG oligonucleotides are modified internucleotidic linkages. In some embodiments, 25% or more of the internucleotidic linkages of provided CpG oligonucleotides are modified internucleotidic linkages. In some embodiments, 30% or more of the internucleotidic linkages of provided CpG oligonucleotides are modified internucleotidic linkages. In some embodiments, 35% or more of the internucleotidic linkages of provided CpG oligonucleotides are modified internucleotidic linkages. In some embodiments, 40% or more of the internucleotidic linkages of provided CpG oligonucleotides are modified internucleotidic linkages. In some embodiments, 45% or more of the internucleotidic linkages of a wing region are modified internucleotidic linkages. In some embodiments, 50% or more of the internucleotidic linkages of a wing region are modified internucleotidic linkages. In some embodiments, 55% or more of the internucleotidic linkages of a wing region are modified internucleotidic linkages. In some embodiments, 60% or more of the internucleotidic linkages of a wing region are modified internucleotidic linkages. In some embodiments, 65% or more of the internucleotidic linkages of a wing region are modified internucleotidic linkages. In some embodiments, 70% or more of the internucleotidic linkages of a wing region are modified internucleotidic linkages. In some embodiments, 75% or more of the internucleotidic linkages of a wing region are modified internucleotidic linkages. In some embodiments, 80% or more of the internucleotidic linkages of a wing region are modified internucleotidic linkages. In some embodiments, 85% or more of the internucleotidic linkages of a wing region are modified internucleotidic linkages. In some embodiments, 90% or more of the internucleotidic linkages of a wing region are modified internucleotidic linkages. In some embodiments, 95% or more of the internucleotidic linkages of a wing region are modified internucleotidic linkages. In some embodiments, each internucleotidic linkage of a wing region is a modified internucleotidic linkage.

In some embodiments, a wing region comprises 2 or more natural phosphate linkages. In some embodiments, a wing region comprises 3 or more natural phosphate linkages. In some embodiments, a wing region comprises 4 or more natural phosphate linkages. In some embodiments, a wing region comprises 5 or more natural phosphate linkages. In some embodiments, a wing region comprises 6 or more natural phosphate linkages. In some embodiments, a wing region comprises 7 or more natural phosphate linkages. In some embodiments, a wing region comprises 8 or more natural phosphate linkages. In some embodiments, a wing region comprises 9 or more natural phosphate linkages. In some embodiments, a wing region comprises 10 or more natural phosphate linkages. In some embodiments, a wing region comprises 11 or more natural phosphate linkages. In some embodiments, a wing region comprises 12 or more natural phosphate linkages. In some embodiments, a wing region comprises 13 or more natural phosphate linkages. In some embodiments, a wing region comprises 14 or more natural phosphate linkages. In some embodiments, a wing region comprises 15 or more natural phosphate linkages. In some embodiments, a wing region comprises 2 or consecutive natural phosphate linkages. In some embodiments, a wing region comprises 3 or consecutive natural phosphate linkages. In some embodiments, a wing region comprises 4 or consecutive natural phosphate linkages. In some embodiments, a wing region comprises 5 or consecutive natural phosphate linkages. In some embodiments, a wing region comprises 6 or consecutive natural phosphate linkages. In some embodiments, a wing region comprises 7 or consecutive natural phosphate linkages. In some embodiments, a wing region comprises 8 or consecutive natural phosphate linkages. In some embodiments, a wing region comprises 9 or consecutive natural phosphate linkages. In some embodiments, a wing region comprises 10 or consecutive natural phosphate linkages. In some embodiments, a wing region comprises 11 or consecutive natural phosphate linkages. In some embodiments, a wing region comprises 12 or consecutive natural phosphate linkages. In some embodiments, a wing region comprises 13 or consecutive natural phosphate linkages. In some embodiments, a wing region comprises 14 or consecutive natural phosphate linkages. In some embodiments, a wing region comprises 15 or consecutive natural phosphate linkages. In some embodiments, each internucleotidic linkage in a wing region is independently a natural phosphate linkage.

In some embodiments, 5% or more of the internucleotidic linkages of provided CpG oligonucleotides are natural phosphate linkages. In some embodiments, 10% or more of the internucleotidic linkages of provided CpG oligonucleotides are natural phosphate linkages. In some embodiments, 15% or more of the internucleotidic linkages of provided CpG oligonucleotides are natural phosphate linkages. In some embodiments, 20% or more of the internucleotidic linkages of provided CpG oligonucleotides are natural phosphate linkages. In some embodiments, 25% or more of the internucleotidic linkages of provided CpG oligonucleotides are natural phosphate linkages. In some embodiments, 30% or more of the internucleotidic linkages of provided CpG oligonucleotides are natural phosphate linkages. In some embodiments, 35% or more of the internucleotidic linkages of provided CpG oligonucleotides are natural phosphate linkages. In some embodiments, 40% or more of the internucleotidic linkages of provided CpG oligonucleotides are natural phosphate linkages. In some embodiments, 45% or more of the internucleotidic linkages of a wing region are natural phosphate linkages. In some embodiments, 50% or more of the internucleotidic linkages of a wing region are natural phosphate linkages. In some embodiments, 55% or more of the internucleotidic linkages of a wing region are natural phosphate linkages. In some embodiments, 60% or more of the internucleotidic linkages of a wing region are natural phosphate linkages. In some embodiments, 65% or more of the internucleotidic linkages of a wing region are natural phosphate linkages. In some embodiments, 70% or more of the internucleotidic linkages of a wing region are natural phosphate linkages. In some embodiments, 75% or more of the internucleotidic linkages of a wing region are natural phosphate linkages. In some embodiments, 80% or more of the internucleotidic linkages of a wing region are natural phosphate linkages. In some embodiments, 85% or more of the internucleotidic linkages of a wing region are natural phosphate linkages. In some embodiments, 90% or more of the internucleotidic linkages of a wing region are natural phosphate linkages. In some embodiments, 95% or more of the internucleotidic linkages of a wing region are natural phosphate linkages. In some embodiments, each internucleotidic linkage of a wing region is a natural phosphate linkage.

In some embodiments, a core region comprises 2 or more modified internucleotidic linkages. In some embodiments, a core region comprises 3 or more modified internucleotidic linkages. In some embodiments, a core region comprises 4 or more modified internucleotidic linkages. In some embodiments, a core region comprises 5 or more modified internucleotidic linkages. In some embodiments, a core region comprises 6 or more modified internucleotidic linkages. In some embodiments, a core region comprises 7 or more modified internucleotidic linkages. In some embodiments, a core region comprises 8 or more modified internucleotidic linkages. In some embodiments, a core region comprises 9 or more modified internucleotidic linkages. In some embodiments, a core region comprises 10 or more modified internucleotidic linkages. In some embodiments, a core region comprises 11 or more modified internucleotidic linkages. In some embodiments, a core region comprises 12 or more modified internucleotidic linkages. In some embodiments, a core region comprises 13 or more modified internucleotidic linkages. In some embodiments, a core region comprises 14 or more modified internucleotidic linkages. In some embodiments, a core region comprises 15 or more modified internucleotidic linkages. In some embodiments, a core region comprises 2 or consecutive modified internucleotidic linkages. In some embodiments, a core region comprises 3 or consecutive modified internucleotidic linkages. In some embodiments, a core region comprises 4 or consecutive modified internucleotidic linkages. In some embodiments, a core region comprises 5 or consecutive modified internucleotidic linkages. In some embodiments, a core region comprises 6 or consecutive modified internucleotidic linkages. In some embodiments, a core region comprises 7 or consecutive modified internucleotidic linkages. In some embodiments, a core region comprises 8 or consecutive modified internucleotidic linkages. In some embodiments, a core region comprises 9 or consecutive modified internucleotidic linkages. In some embodiments, a core region comprises 10 or consecutive modified internucleotidic linkages. In some embodiments, a core region comprises 11 or consecutive modified internucleotidic linkages. In some embodiments, a core region comprises 12 or consecutive modified internucleotidic linkages. In some embodiments, a core region comprises 13 or consecutive modified internucleotidic linkages. In some embodiments, a core region comprises 14 or consecutive modified internucleotidic linkages. In some embodiments, a core region comprises 15 or consecutive modified internucleotidic linkages. In some embodiments, each internucleotidic linkage in a core region is independently a modified internucleotidic linkage.

In some embodiments, 5% or more of the internucleotidic linkages of provided CpG oligonucleotides are modified internucleotidic linkages. In some embodiments, 10% or more of the internucleotidic linkages of provided CpG oligonucleotides are modified internucleotidic linkages. In some embodiments, 15% or more of the internucleotidic linkages of provided CpG oligonucleotides are modified internucleotidic linkages. In some embodiments, 20% or more of the internucleotidic linkages of provided CpG oligonucleotides are modified internucleotidic linkages. In some embodiments, 25% or more of the internucleotidic linkages of provided CpG oligonucleotides are modified internucleotidic linkages. In some embodiments, 30% or more of the internucleotidic linkages of provided CpG oligonucleotides are modified internucleotidic linkages. In some embodiments, 35% or more of the internucleotidic linkages of provided CpG oligonucleotides are modified internucleotidic linkages. In some embodiments, 40% or more of the internucleotidic linkages of provided CpG oligonucleotides are modified internucleotidic linkages. In some embodiments, 45% or more of the internucleotidic linkages of a core region are modified internucleotidic linkages. In some embodiments, 50% or more of the internucleotidic linkages of a core region are modified internucleotidic linkages. In some embodiments, 55% or more of the internucleotidic linkages of a core region are modified internucleotidic linkages. In some embodiments, 60% or more of the internucleotidic linkages of a core region are modified internucleotidic linkages. In some embodiments, 65% or more of the internucleotidic linkages of a core region are modified internucleotidic linkages. In some embodiments, 70% or more of the internucleotidic linkages of a core region are modified internucleotidic linkages. In some embodiments, 75% or more of the internucleotidic linkages of a core region are modified internucleotidic linkages. In some embodiments, 80% or more of the internucleotidic linkages of a core region are modified internucleotidic linkages. In some embodiments, 85% or more of the internucleotidic linkages of a core region are modified internucleotidic linkages. In some embodiments, 90% or more of the internucleotidic linkages of a core region are modified internucleotidic linkages. In some embodiments, 95% or more of the internucleotidic linkages of a core region are modified internucleotidic linkages. In some embodiments, each internucleotidic linkage of a core region is a modified internucleotidic linkage.

Provided CpG oligonucleotides can comprise various number of modified internucleotidic linkages. In some embodiments, provided CpG oligonucleotides comprise one modified internucleotidic linkage. In some embodiments, provided CpG oligonucleotides comprise 2 or more modified internucleotidic linkages. In some embodiments, provided CpG oligonucleotides comprise 3 or more modified internucleotidic linkages. In some embodiments, provided CpG oligonucleotides comprise 4 or more modified internucleotidic linkages. In some embodiments, provided CpG oligonucleotides comprise 5 or more modified internucleotidic linkages. In some embodiments, provided CpG oligonucleotides comprise 6 or more modified internucleotidic linkages. In some embodiments, provided CpG oligonucleotides comprise 7 or more modified internucleotidic linkages. In some embodiments, provided CpG oligonucleotides comprise 8 or more modified internucleotidic linkages. In some embodiments, provided CpG oligonucleotides comprise 9 or more modified internucleotidic linkages. In some embodiments, provided CpG oligonucleotides comprise 10 or more modified internucleotidic linkages. In some embodiments, provided CpG oligonucleotides comprise 15 or more modified internucleotidic linkages. In some embodiments, provided CpG oligonucleotides comprise 20 or more modified internucleotidic linkages. In some embodiments, provided CpG oligonucleotides comprise 25 or more modified internucleotidic linkages. In some embodiments, provided CpG oligonucleotides comprise 30 or more modified internucleotidic linkages.

In some embodiments, 5% or more of the internucleotidic linkages of provided CpG oligonucleotides are modified internucleotidic linkages. In some embodiments, 10% or more of the internucleotidic linkages of provided CpG oligonucleotides are modified internucleotidic linkages. In some embodiments, 15% or more of the internucleotidic linkages of provided CpG oligonucleotides are modified internucleotidic linkages. In some embodiments, 20% or more of the internucleotidic linkages of provided CpG oligonucleotides are modified internucleotidic linkages. In some embodiments, 25% or more of the internucleotidic linkages of provided CpG oligonucleotides are modified internucleotidic linkages. In some embodiments, 30% or more of the internucleotidic linkages of provided CpG oligonucleotides are modified internucleotidic linkages. In some embodiments, 35% or more of the internucleotidic linkages of provided CpG oligonucleotides are modified internucleotidic linkages. In some embodiments, 40% or more of the internucleotidic linkages of provided CpG oligonucleotides are modified internucleotidic linkages. In some embodiments, 45% or more of the internucleotidic linkages of provided CpG oligonucleotides are modified internucleotidic linkages. In some embodiments, 50% or more of the internucleotidic linkages of provided CpG oligonucleotides are modified internucleotidic linkages. In some embodiments, 55% or more of the internucleotidic linkages of provided CpG oligonucleotides are modified internucleotidic linkages. In some embodiments, 60% or more of the internucleotidic linkages of provided CpG oligonucleotides are modified internucleotidic linkages. In some embodiments, 65% or more of the internucleotidic linkages of provided CpG oligonucleotides are modified internucleotidic linkages. In some embodiments, 70% or more of the internucleotidic linkages of provided CpG oligonucleotides are modified internucleotidic linkages. In some embodiments, 75% or more of the internucleotidic linkages of provided CpG oligonucleotides are modified internucleotidic linkages. In some embodiments, 80% or more of the internucleotidic linkages of provided CpG oligonucleotides are modified internucleotidic linkages. In some embodiments, 85% or more of the internucleotidic linkages of provided CpG oligonucleotides are modified internucleotidic linkages. In some embodiments, 90% or more of the internucleotidic linkages of provided CpG oligonucleotides are modified internucleotidic linkages. In some embodiments, 95% or more of the internucleotidic linkages of provided CpG oligonucleotides are modified internucleotidic linkages. In some embodiments, each internucleotidic linkage of provided CpG oligonucleotides is a modified internucleotidic linkage.

As understood by a person having ordinary skill in the art, a stereorandom or racemic preparation of CpG oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of CpG oligonucleotides, all or most coupling steps are not chirally controlled in that the coupling steps are not specifically conducted to provide enhanced stereoselectivity. An example substantially racemic preparation of CpG oligonucleotides is the preparation of phosphorothioate CpG oligonucleotides through sulfurizing phosphite triesters from commonly used phosphoramidite oligonucleotide synthesis with either tteraethylthiuram disulfide or (TETD) or 3H-1, 2-bensodithiol-3-one 1, 1-dioxide (BDTD), a well-known process in the art. In some embodiments, substantially racemic preparation of CpG oligonucleotides provides substantially racemic oligonucleotide compositions (or chirally uncontrolled CpG oligonucleotide compositions). In some embodiments, at least one coupling of a nucleotide monomer has a diastereoselectivity lower than about 60:40, 70:30, 80:20, 85:15, 90:10, 91:9, 92:8, 97:3, 98:2, or 99:1. In some embodiments, at least two couplings of a nucleotide monomer have a diastereoselectivity lower than about 60:40, 70:30, 80:20, 85:15, 90:10, 91:9, 92:8, 97:3, 98:2, or 99:1. In some embodiments, at least three couplings of a nucleotide monomer have a diastereoselectivity lower than about 60:40, 70:30, 80:20, 85:15, 90:10, 91:9, 92:8, 97:3, 98:2, or 99:1. In some embodiments, at least four couplings of a nucleotide monomer have a diastereoselectivity lower than about 60:40, 70:30, 80:20, 85:15, 90:10, 91:9, 92:8, 97:3, 98:2, or 99:1. In some embodiments, at least five couplings of a nucleotide monomer have a diastereoselectivity lower than about 60:40, 70:30, 80:20, 85:15, 90:10, 91:9, 92:8, 97:3, 98:2, or 99:1. In some embodiments, each coupling of a nucleotide monomer independently has a diastereoselectivity lower than about 60:40, 70:30, 80:20, 85:15, 90:10, 91:9, 92:8, 97:3, 98:2, or 99:1. In some embodiments, at least two internucleotidic linkages have a diastereoselectivity lower than about 60:40, 70:30, 80:20, 85:15, 90:10, 91:9, 92:8, 97:3, 98:2, or 99:1. In some embodiments, at least three internucleotidic linkages have a diastereoselectivity lower than about 60:40, 70:30, 80:20, 85:15, 90:10, 91:9, 92:8, 97:3, 98:2, or 99:1. In some embodiments, at least four internucleotidic linkages have a diastereoselectivity lower than about 60:40, 70:30, 80:20, 85:15, 90:10, 91:9, 92:8, 97:3, 98:2, or 99:1. In some embodiments, at least five internucleotidic linkages have a diastereoselectivity lower than about 60:40, 70:30, 80:20, 85:15, 90:10, 91:9, 92:8, 97:3, 98:2, or 99:1. In some embodiments, each internucleotidic linkage independently has a diastereoselectivity lower than about 60:40, 70:30, 80:20, 85:15, 90:10, 91:9, 92:8, 97:3, 98:2, or 99:1. In some embodiments, a diastereoselectivity is lower than about 60:40. In some embodiments, a diastereoselectivity is lower than about 70:30. In some embodiments, a diastereoselectivity is lower than about 80:20. In some embodiments, a diastereoselectivity is lower than about 90:10. In some embodiments, a diastereoselectivity is lower than about 91:9. In some embodiments, a diastereoselectivity is lower than about 92:8. In some embodiments, a diastereoselectivity is lower than about 93:7. In some embodiments, a diastereoselectivity is lower than about 94:6. In some embodiments, a diastereoselectivity is lower than about 95:5. In some embodiments, a diastereoselectivity is lower than about 96:4. In some embodiments, a diastereoselectivity is lower than about 97:3. In some embodiments, a diastereoselectivity is lower than about 98:2. In some embodiments, a diastereoselectivity is lower than about 99:1. In some embodiments, at least one coupling has a diastereoselectivity lower than about 90:10. In some embodiments, at least two couplings have a diastereoselectivity lower than about 90:10. In some embodiments, at least three couplings have a diastereoselectivity lower than about 90:10. In some embodiments, at least four couplings have a diastereoselectivity lower than about 90:10. In some embodiments, at least five couplings have a diastereoselectivity lower than about 90:10. In some embodiments, each coupling independently has a diastereoselectivity lower than about 90:10. In some embodiments, at least one internucleotidic linkage has a diastereoselectivity lower than about 90:10. In some embodiments, at least two internucleotidic linkages have a diastereoselectivity lower than about 90:10. In some embodiments, at least three internucleotidic linkages have a diastereoselectivity lower than about 90:10. In some embodiments, at least four internucleotidic linkages have a diastereoselectivity lower than about 90:10. In some embodiments, at least five internucleotidic linkages have a diastereoselectivity lower than about 90:10. In some embodiments, each internucleotidic linkage independently has a diastereoselectivity lower than about 90:10. In some embodiments, a diastereoselectivity corresponding to an internucleotidic linkage is utilized as diastereopurity of the internucleotidic linkage.

As understood by a person having ordinary skill in the art, in some embodiments, diastereoselectivity of a coupling or a linkage can be assessed through the diastereoselectivity of a dimer formation under the same or comparable conditions, wherein the dimer has the same 5'- and 3'-nucleosides and internucleotidic linkage. For example, diastereoselectivity of the underlined coupling or linkage in NNNNNNNG*SGNNNNNNN can be assessed from coupling two G moieties under the same or comparable conditions, e.g., monomers, chiral auxiliaries, solvents, activators, temperatures, etc.

In some embodiments, a plurality of oligonucleotides, e.g., provided oligonucleotides comprising CpG and/or lipid moieties, share the same stereochemistry at one or more chiral internucleotidic linkages (chirally controlled internucleotidic linkages). In some embodiments, they share the same stereochemistry at two or more chiral internucleotidic linkages. In some embodiments, they share the same stereochemistry at three or more chiral internucleotidic linkages. In some embodiments, they share the same stereochemistry at four or more chiral internucleotidic linkages. In some embodiments, they share the same stereochemistry at five or more chiral internucleotidic linkages. In some embodiments, they share the same stereochemistry at six or more chiral internucleotidic linkages. In some embodiments, they share the same stereochemistry at seven or more chiral internucleotidic linkages. In some embodiments, they share the same stereochemistry at eight or more chiral internucleotidic linkages. In some embodiments, they share the same stereochemistry at nine or more chiral internucleotidic linkages. In some embodiments, they share the same stereochemistry at ten or more chiral internucleotidic linkages. In some embodiments, they share the same stereochemistry at 11 or more chiral internucleotidic linkages. In some embodiments, they share the same stereochemistry at 12 or more chiral internucleotidic linkages. In some embodiments, they share the same stereochemistry at 13 or more chiral internucleotidic linkages. In some embodiments, they share the same stereochemistry at 14 or more chiral internucleotidic linkages. In some embodiments, they share the same stereochemistry at 15 or more chiral internucleotidic linkages. In some embodiments, they share the same stereochemistry at 10% or more of the chiral internucleotidic linkages. In some embodiments, they share the same stereochemistry at 20% or more of the chiral internucleotidic linkages. In some embodiments, they share the same stereochemistry at 30% or more of the chiral internucleotidic linkages. In some embodiments, they share the same stereochemistry at 40% or more of the chiral internucleotidic linkages. In some embodiments, they share the same stereochemistry at 50% or more of the chiral internucleotidic linkages. In some embodiments, they share the same stereochemistry at 60% or more of the chiral internucleotidic linkages. In some embodiments, they share the same stereochemistry at 70% or more of the chiral internucleotidic linkages. In some embodiments, they share the same stereochemistry at 80% or more of the chiral internucleotidic linkages. In some embodiments, they share the same stereochemistry at 90% or more of the chiral internucleotidic linkages. In some embodiments, they share the same stereochemistry at 95% or more of the chiral internucleotidic linkages. In some embodiments, they share the same stereochemistry at 96% or more of the chiral internucleotidic linkages. In some embodiments, they share the same stereochemistry at 97% or more of the chiral internucleotidic linkages. In some embodiments, they share the same stereochemistry at 98% or more of the chiral internucleotidic linkages. In some embodiments, they share the same stereochemistry at each of the chiral internucleotidic linkages. As readily appreciated by a person having ordinary skill in the art and illustrated the examples, chiral internucleotidic linkages where a plurality of oligonucleotides share the same stereochemistry can independently be either Rp or Sp, e.g., at a first chiral internucleotidic linkage a plurality of oligonucleotides are all Rp while at a second position they are all Sp (RpSp; can also be RpRp, SpSp, or SpRp as desired).

In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99% of oligonucleotides in a provided composition that share the common base sequence, the common pattern of backbone linkages; and the common pattern of backbone phosphorus modifications share the same stereochemistry at the one or more chiral internucleotidic linkages. In some embodiments, the percentage is at least 0.5%. In some embodiments, the percentage is at least 1%. In some embodiments, the percentage is at least 2%. In some embodiments, the percentage is at least 3%. In some embodiments, the percentage is at least 4%. In some embodiments, the percentage is at least 5%. In some embodiments, the percentage is at least 6%. In some embodiments, the percentage is at least 7%. In some embodiments, the percentage is at least 8%. In some embodiments, the percentage is at least 9%. In some embodiments, the percentage is at least 10%. In some embodiments, the percentage is at least 20%. In some embodiments, the percentage is at least 30%. In some embodiments, the percentage is at least 40%. In some embodiments, the percentage is at least 50%. In some embodiments, the percentage is at least 60%. In some embodiments, the percentage is at least 70%. In some embodiments, the percentage is at least 75%. In some embodiments, the percentage is at least 80%. In some embodiments, the percentage is at least 81%. In some embodiments, the percentage is at least 82%. In some embodiments, the percentage is at least 83%. In some embodiments, the percentage is at least 84%. In some embodiments, the percentage is at least 85%. In some embodiments, the percentage is at least 86%. In some embodiments, the percentage is at least 87%. In some embodiments, the percentage is at least 88%. In some embodiments, the percentage is at least 89%. In some embodiments, the percentage is at least 90%. In some embodiments, the percentage is at least 91%. In some embodiments, the percentage is at least 92%. In some embodiments, the percentage is at least 93%. In some embodiments, the percentage is at least 94%. In some embodiments, the percentage is at least 95%. In some embodiments, the percentage is at least 96%. In some embodiments, the percentage is at least 97%. In some embodiments, the percentage is at least 98%. In some embodiments, the percentage is at least 99%.

In some embodiments, oligonucleotides that share the common base sequence, the common pattern of backbone linkages, the common pattern of backbone phosphorus modifications and the same stereochemistry at the one or more chiral internucleotidic linkages are enriched, for example, relative to oligonucleotides that share the common base sequence, the common pattern of backbone linkages, the common pattern of backbone phosphorus modifications but not the same stereochemistry at the one or more chiral internucleotidic linkages. In some embodiments, as understood by a person having ordinary skill in the art, the enrichment is from the use of one or more provided technologies that enable stereoselective (chirally controlled) formation of each of the internucleotidic linkages where the oligonucleotides share the same stereochemistry.

In some embodiments, oligonucleotides that share the common base sequence, the common pattern of backbone linkages, the common pattern of backbone phosphorus modifications and the same stereochemistry at the one or more chiral internucleotidic linkages are enriched at least 5 fold (such oligonucleotides have a fraction of $5*(\frac{1}{2}^n)$ of oligonucleotides that share the common base sequence, the common pattern of backbone linkages, and the common pattern of backbone phosphorus modifications, wherein n is the number of internucleotidic linkages where such oligonucleotides share the same stereochemistry; or oligonucleotides that share the common base sequence, the common pattern of backbone linkages, the common pattern of backbone phosphorus modifications but not the same stereochemistry at the one or more chiral internucleotidic linkages are no more than $[1-(\frac{1}{2}^n)]/5$ of oligonucleotides that share the common base sequence, the common pattern of backbone linkages, and the common pattern of backbone phosphorus modifications) compared to a stereorandom preparation of the oligonucleotides wherein none of the internucleotidic linkages are chirally controlled (oligonucleotides that share the common base sequence, the common pattern of backbone linkages, the common pattern of backbone phosphorus modifications, and the same stereochemistry at the one or more chiral internucleotidic linkages are typically considered to have a fraction of $\frac{1}{2}^n$ of oligonucleotides that share the common base sequence, the common pattern of backbone linkages, and the common pattern of backbone phosphorus modifications, wherein n is the number of chiral internucleotidic linkages wherein the oligonucleotides share the same stereochemistry, and oligonucleotides that share the common base sequence, the common pattern of backbone linkages, the common pattern of backbone phosphorus modifications but are not of the particular oligonucleotide type are typically considered to have a fraction of $[1-(\frac{1}{2}^n)]$ of oligonucleotides that share the common base sequence, the common pattern of backbone linkages, and the common pattern of backbone phosphorus modifications). In some embodiments, the enrichment is at least 20 fold. In some embodiments, the enrichment is at least 30 fold. In some embodiments, the enrichment is at least 40 fold. In some embodiments, the enrichment is at least 50 fold. In some embodiments, the enrichment is at least 60 fold. In some embodiments, the enrichment is at least 70 fold. In some embodiments, the enrichment is at least 80 fold. In some embodiments, the enrichment is at least 90 fold. In some embodiments, the enrichment is at least 100 fold. In some embodiments, the enrichment is at least 200 fold. In some embodiments, the enrichment is at least 300 fold. In some embodiments, the enrichment is at least 400 fold. In some embodiments, the enrichment is at least 500 fold. In some embodiments, the enrichment is at least 600 fold. In some embodiments, the enrichment is at least 700 fold. In some embodiments, the enrichment is at least 800 fold. In some embodiments, the enrichment is at least 900 fold. In some embodiments, the enrichment is at least 1,000 fold. In some embodiments, the enrichment is at least 2,000 fold. In some embodiments, the enrichment is at least 4,000 fold. In some embodiments, the enrichment is at least 8,000 fold. In some embodiments, the enrichment is at least 10,000 fold. In some embodiments, the enrichment is at least 20,000 fold. In some embodiments, the enrichment is at least $(1.5)^n$. In some embodiments, the enrichment is at least $(1.6)^n$. In some embodiments, the enrichment is at least $(1.7)^n$. In some embodiments, the enrichment is at least $(1.1)^n$. In some embodiments, the enrichment is at least $(1.8)^n$. In some embodiments, the enrichment is at least $(1.9)^n$. In some embodiments, the enrichment is at least $2^n$. In some embodiments, the enrichment is at least $3^n$. In some embodiments, the enrichment is at least $4^n$. In some embodiments, the enrichment is at least $5^n$. In some embodiments, the enrichment is at least $6^n$. In some embodiments, the enrichment is at least $7^n$. In some embodiments, the enrichment is at least $8^n$. In some embodiments, the enrichment is at least $9^n$. In some embodiments, the enrichment is at least $10^n$. In some embodiments, the enrichment is at least $15^n$. In some embodiments, the enrichment is at least $20^n$. In some embodiments, the enrichment is at least $25^n$. In some embodiments, the enrichment is at least $30^n$. In some embodiments, the enrichment is at least $40^n$. In some embodiments, the enrichment is at least $50^n$. In some embodiments, the enrichment is at least $100^n$. In some embodiments, enrichment is measured by increase of the fraction of oligonucleotides that share the common base sequence, the common pattern of backbone linkages, the common pattern of backbone phosphorus modifications and the same stereochemistry at the one or more chiral internucleotidic linkages. In some embodiments, an enrichment is measured by decrease of the fraction of oligonucleotides that share the common base sequence, the common pattern of backbone linkages, the common pattern of backbone phosphorus modifications but not the same stereochemistry at the one or more chiral internucleotidic linkages.

In some embodiments, oligonucleotides of a particular type in a chirally controlled oligonucleotide composition are structurally identical (including stereochemically) and are enriched at least 5 fold (oligonucleotides of the particular type have a fraction of $5*(\frac{1}{2}^n)$ of oligonucleotides that have the base sequence, the pattern of backbone linkages, and the pattern of backbone phosphorus modifications of the particular oligonucleotide type, wherein n is the number of chiral internucleotidic linkages; or oligonucleotides that have the base sequence, the pattern of backbone linkages, and the pattern of backbone phosphorus modifications of the particular oligonucleotide type but are not of the particular oligonucleotide type are no more than $[1-(\frac{1}{2}^n)]/5$ of oligonucleotides that have the base sequence, the pattern of backbone linkages, and the pattern of backbone phosphorus modifications of the particular oligonucleotide type) compared to a stereorandom preparation of the oligonucleotides (oligonucleotides of the particular type are typically considered to have a fraction of $\frac{1}{2}^n$ of oligonucleotides that have the base sequence, the pattern of backbone linkages, and the pattern of backbone phosphorus modifications of the particular oligonucleotide type, wherein n is the number of chiral internucleotidic linkages, and oligonucleotides that have the base sequence, the pattern of backbone linkages, and the pattern of backbone phosphorus modifications of the particular oligonucleotide type but are not of the particular oligonucleotide type are typically considered to have a fraction of $[1-(\frac{1}{2}^n)]$ of oligonucleotides that have the base sequence, the pattern of backbone linkages, and the pattern of backbone phosphorus modifications of the particular oligonucleotide type). In some embodiments, the enrichment is at least 20 fold. In some embodiments, the enrichment is at least 30 fold. In some embodiments, the enrichment is at least 40 fold. In some embodiments, the enrichment is at least 50 fold. In some embodiments, the enrichment is at least 60 fold. In some embodiments, the enrichment is at least 70 fold. In some embodiments, the enrichment is at least 80 fold. In some embodiments, the enrichment is at least 90 fold. In some embodiments, the enrichment is at least 100 fold. In some embodiments, the enrichment is at least 200 fold. In some embodiments, the enrichment is at least 300 fold. In some embodiments, the enrichment is at least 400 fold. In some embodiments, the enrichment is at least 500 fold. In some embodiments, the enrichment is at least 600 fold. In some embodiments, the enrichment is at least 700 fold. In some embodiments, the enrichment is at least 800 fold. In some embodiments, the enrichment is at least 900 fold. In some embodiments, the enrichment is at least 1,000 fold. In some embodiments, the enrichment is at least 2,000 fold. In some embodiments, the enrichment is at least 4,000 fold. In some embodiments, the enrichment is at least 8,000 fold. In some embodiments, the enrichment is at least 10,000 fold. In some embodiments, the enrichment is at least 20,000 fold. In some embodiments, the enrichment is at least $(1.5)^n$. In some embodiments, the enrichment is at least $(1.6)^n$. In some embodiments, the enrichment is at least $(1.7)^n$. In some embodiments, the enrichment is at least $(1.1)^n$. In some embodiments, the enrichment is at least $(1.8)^n$. In some embodiments, the enrichment is at least $(1.9)^n$. In some embodiments, the enrichment is at least $2^n$. In some embodiments, the enrichment is at least $3^n$. In some embodiments, the enrichment is at least $4^n$. In some embodiments, the enrichment is at least $5^n$. In some embodiments, the enrichment is at least $6^n$. In some embodiments, the enrichment is at least $7^n$. In some embodiments, the enrichment is at least $8^n$. In some embodiments, the enrichment is at least $9^n$. In some embodiments, the enrichment is at least $10^n$. In some embodiments, the enrichment is at least $15^n$. In some embodiments, the enrichment is at least $20^n$. In some embodiments, the enrichment is at least $25^n$. In some embodiments, the enrichment is at least $30^n$. In some embodiments, the enrichment is at least $40^n$. In some embodiments, the enrichment is at least $50^n$. In some embodiments, the enrichment is at least $100^n$. In some embodiments, enrichment is measured by increase of the fraction of oligonucleotides of the particular oligonucleotide type in oligonucleotides that have the base sequence, the pattern of backbone linkages, and the pattern of backbone phosphorus modifications of the particular oligonucleotide type. In some embodiments, an enrichment is measured by decrease of the fraction of oligonucleotides that have the base sequence, the pattern of backbone linkages, and the pattern of backbone phosphorus modifications of the particular oligonucleotide type but are not of the particular oligonucleotide type in oligonucleotides that have the base sequence, the pattern of backbone linkages, and the pattern of backbone phosphorus modifications of the particular oligonucleotide type.

In some embodiments, CpG oligonucleotides having a common base sequence and length, a common pattern of backbone linkages, and a common pattern of backbone chiral centers have a common pattern of backbone phosphorus modifications and a common pattern of base modifications. In some embodiments, CpG oligonucleotides having a common base sequence and length, a common pattern of backbone linkages, and a common pattern of backbone chiral centers have a common pattern of backbone phosphorus modifications and a common pattern of nucleoside modifications. In some embodiments, CpG oligonucleotides having a common base sequence and length, a common pattern of backbone linkages, and a common pattern of backbone chiral centers have identical structures.

In some embodiments, CpG oligonucleotides of a CpG oligonucleotide type have a common pattern of backbone phosphorus modifications and a common pattern of sugar modifications. In some embodiments, CpG oligonucleotides of a CpG oligonucleotide type have a common pattern of backbone phosphorus modifications and a common pattern of base modifications. In some embodiments, CpG oligonucleotides of a CpG oligonucleotide type have a common pattern of backbone phosphorus modifications and a common pattern of nucleoside modifications. In some embodiments, CpG oligonucleotides of a CpG oligonucleotide type are identical.

In some embodiments, a chirally controlled CpG oligonucleotide composition is a substantially pure preparation of a CpG oligonucleotide type in that CpG oligonucleotides in the composition that are not of the CpG oligonucleotide type are impurities form the preparation process of said CpG oligonucleotide type, in some case, after certain purification procedures.

In some embodiments, at least about 20% of the CpG oligonucleotides in the composition have a common base sequence and length, a common pattern of backbone linkages, and a common pattern of backbone chiral centers. In some embodiments, at least about 25% of the CpG oligonucleotides in the composition have a common base sequence and length, a common pattern of backbone linkages, and a common pattern of backbone chiral centers. In some embodiments, at least about 30% of the CpG oligonucleotides in the composition have a common base sequence and length, a common pattern of backbone linkages, and a common pattern of backbone chiral centers. In some embodiments, at least about 35% of the CpG oligonucleotides in the composition have a common base sequence and length, a common pattern of backbone linkages, and a common pattern of backbone chiral centers. In some embodiments, at least about 40% of the CpG oligonucleotides in the composition have a common base sequence and length, a common pattern of backbone linkages, and a common pattern of backbone chiral centers. In some embodiments, at least about 45% of the CpG oligonucleotides in the composition have a common base sequence and length, a common pattern of backbone linkages, and a common pattern of backbone chiral centers. In some embodiments, at least about 50% of the CpG oligonucleotides in the chirally controlled oligonucleotide composition have a common base sequence and length, a common pattern of backbone linkages, and a common pattern of backbone chiral centers. In some embodiments, at least about 55% of the CpG oligonucleotides in the chirally controlled oligonucleotide composition have a common base sequence and length, a common pattern of backbone linkages, and a common pattern of backbone chiral centers. In some embodiments, at least about 60% of the CpG oligonucleotides in the chirally controlled oligonucleotide composition have a common base sequence and length, a common pattern of backbone linkages, and a common pattern of backbone chiral centers. In some embodiments, at least about 65% of the CpG oligonucleotides in the chirally controlled oligonucleotide composition have a common base sequence and length, a common pattern of backbone linkages, and a common pattern of backbone chiral centers. In some embodiments, at least about 70% of the CpG oligonucleotides in the chirally controlled oligonucleotide composition have a common base sequence and length, a common pattern of backbone linkages, and a common pattern of backbone chiral centers. In some embodiments, at least about 75% of the CpG oligonucleotides in the chirally controlled oligonucleotide composition have a common base sequence and length, a common pattern of backbone linkages, and a common pattern of backbone chiral centers. In some embodiments, at least about 80% of the CpG oligonucleotides in the chirally controlled oligonucleotide composition have a common base sequence and length, a common pattern of backbone linkages, and a common pattern of backbone chiral centers. In some embodiments, at least about 85% of the CpG oligonucleotides in the chirally controlled oligonucleotide composition have a common base sequence and length, a common pattern of backbone linkages, and a common pattern of backbone chiral centers. In some embodiments, at least about 90% of the CpG oligonucleotides in the chirally controlled oligonucleotide composition have a common base sequence and length, a common pattern of backbone linkages, and a common pattern of backbone chiral centers. In some embodiments, at least about 92% of the CpG oligonucleotides in the chirally controlled oligonucleotide composition have a common base sequence and length, a common pattern of backbone linkages, and a common pattern of backbone chiral centers. In some embodiments, at least about 94% of the CpG oligonucleotides in the chirally controlled oligonucleotide composition have a common base sequence and length, a common pattern of backbone linkages, and a common pattern of backbone chiral centers. In some embodiments, at least about 95% of the CpG oligonucleotides in the chirally controlled oligonucleotide composition have a common base sequence and length, a common pattern of backbone linkages, and a common pattern of backbone chiral centers. In some embodiments, at least about 91%, 92%, 93%, 94%, 95%, 96%, 97%, 98%, or 99% of the CpG oligonucleotides in the chirally controlled oligonucleotide composition have a common base sequence and length, a common pattern of backbone linkages, and a common pattern of backbone chiral centers. In some embodiments, greater than about 99% of the CpG oligonucleotides in the chirally controlled oligonucleotide composition have a common base sequence and length, a common pattern of backbone linkages, and a common pattern of backbone chiral centers. In some embodiments, purity of a chirally controlled CpG oligonucleotide composition of a CpG oligonucleotide can be expressed as the percentage of CpG oligonucleotides in the composition that have a common base sequence and length, a common pattern of backbone linkages, and a common pattern of backbone chiral centers.

In some embodiments, CpG oligonucleotides having a common base sequence and length, a common pattern of backbone linkages, and a common pattern of backbone chiral centers have a common pattern of backbone phosphorus modifications. In some embodiments, CpG oligonucleotides having a common base sequence and length, a common pattern of backbone linkages, and a common pattern of backbone chiral centers have a common pattern of backbone phosphorus modifications and a common pattern of nucleoside modifications. In some embodiments, CpG oligonucleotides having a common base sequence and length, a common pattern of backbone linkages, and a common pattern of backbone chiral centers have a common pattern of backbone phosphorus modifications and a common pattern of sugar modifications. In some embodiments, CpG oligonucleotides having a common base sequence and length, a common pattern of backbone linkages, and a common pattern of backbone chiral centers have a common pattern of backbone phosphorus modifications and a common pattern of base modifications. In some embodiments, CpG oligonucleotides having a common base sequence and length, a common pattern of backbone linkages, and a common pattern of backbone chiral centers have a common pattern of backbone phosphorus modifications and a common pattern of nucleoside modifications. In some embodiments, CpG oligonucleotides having a common base sequence and length, a common pattern of backbone linkages, and a common pattern of backbone chiral centers are identical.

In some embodiments, CpG oligonucleotides in provided compositions have a common pattern of backbone phosphorus modifications. In some embodiments, a common base sequence is a base sequence of a CpG oligonucleotide type.

As noted above and understood in the art, in some embodiments, base sequence of a CpG oligonucleotide can refer to the identity and/or modification status of nucleoside residues (e.g., of sugar and/or base components, relative to standard naturally occurring nucleotides such as adenine, cytosine, guanosine, thymine, and uracil) in the CpG oligonucleotide and/or to the hybridization character (i.e., the ability to hybridize with particular complementary residues) of such residues.

In some embodiments, a particular CpG oligonucleotide type can be defined by
  1A) base identity;
  1B) pattern of base modification;
  1C) pattern of sugar modification;
  2) pattern of backbone linkages;
  3) pattern of backbone chiral centers; and
  4) pattern of backbone phosphorus modifications.

Thus, in some embodiments, CpG oligonucleotides of a particular type can share identical bases but differ in their pattern of base modifications and/or sugar modifications. In some embodiments, CpG oligonucleotides of a particular type can share identical bases and pattern of base modifications (including, e.g., absence of base modification), but differ in pattern of sugar modifications.

In some embodiments, CpG oligonucleotides of a particular type are identical in that they have the same base sequence (including length), the same pattern of chemical modifications to sugar and base moieties, the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications (e.g., pattern of modifications on the internucleotidic phosphorus atom, such as —S$^-$, and -L-R$^1$ of formula I).

In some embodiments, purity of a chirally controlled CpG oligonucleotide composition of a CpG oligonucleotide type is expressed as the percentage of CpG oligonucleotides in the composition that are of the CpG oligonucleotide type. In some embodiments, at least about 10% of the CpG oligonucleotides in a chirally controlled CpG oligonucleotide composition are of the same CpG oligonucleotide type. In some embodiments, at least about 20% of the CpG oligonucleotides in a chirally controlled CpG oligonucleotide composition are of the same CpG oligonucleotide type. In some embodiments, at least about 30% of the CpG oligonucleotides in a chirally controlled CpG oligonucleotide composition are of the same CpG oligonucleotide type. In some embodiments, at least about 40% of the CpG oligonucleotides in a chirally controlled CpG oligonucleotide composition are of the same CpG oligonucleotide type. In some embodiments, at least about 50% of the CpG oligonucleotides in a chirally controlled CpG oligonucleotide composition are of the same CpG oligonucleotide type. In some embodiments, at least about 60% of the CpG oligonucleotides in a chirally controlled CpG oligonucleotide composition are of the same CpG oligonucleotide type. In some embodiments, at least about 70% of the CpG oligonucleotides in a chirally controlled CpG oligonucleotide composition are of the same CpG oligonucleotide type. In some embodiments, at least about 80% of the CpG oligonucleotides in a chirally controlled CpG oligonucleotide composition are of the same CpG oligonucleotide type. In some embodiments, at least about 90% of the CpG oligonucleotides in a chirally controlled CpG oligonucleotide composition are of the same CpG oligonucleotide type. In some embodiments, at least about 92% of the CpG oligonucleotides in a chirally controlled CpG oligonucleotide composition are of the same CpG oligonucleotide type. In some embodiments, at least about 94% of the CpG oligonucleotides in a chirally controlled CpG oligonucleotide composition are of the same CpG oligonucleotide type. In some embodiments, at least about 95% of the CpG oligonucleotides in a chirally controlled CpG oligonucleotide composition are of the same CpG oligonucleotide type. In some embodiments, at least about 96% of the CpG oligonucleotides in a chirally controlled CpG oligonucleotide composition are of the same CpG oligonucleotide type. In some embodiments, at least about 97% of the CpG oligonucleotides in a chirally controlled CpG oligonucleotide composition are of the same CpG oligonucleotide type. In some embodiments, at least about 98% of the CpG oligonucleotides in a chirally controlled CpG oligonucleotide composition are of the same CpG oligonucleotide type. In some embodiments, at least about 99% of the CpG oligonucleotides in a chirally controlled CpG oligonucleotide composition are of the same CpG oligonucleotide type.

In some embodiments, purity of a chirally controlled CpG oligonucleotide composition can be controlled by stereoselectivity of each coupling step in its preparation process. In some embodiments, a coupling step has a stereoselectivity (e.g., diastereoselectivity) of 60% (60% of the new internucleotidic linkage formed from the coupling step has the intended stereochemistry). After such a coupling step, the new internucleotidic linkage formed can be referred to have a 60% purity. In some embodiments, each coupling step has a stereoselectivity of at least 60%. In some embodiments, each coupling step has a stereoselectivity of at least 70%. In some embodiments, each coupling step has a stereoselectivity of at least 80%. In some embodiments, each coupling step has a stereoselectivity of at least 85%. In some embodiments, each coupling step has a stereoselectivity of at least 90%. In some embodiments, each coupling step has a stereoselectivity of at least 91%. In some embodiments, each coupling step has a stereoselectivity of at least 92%. In some embodiments, each coupling step has a stereoselectivity of at least 93%. In some embodiments, each coupling step has a stereoselectivity of at least 94%. In some embodiments, each coupling step has a stereoselectivity of at least 95%. In some embodiments, each coupling step has a stereoselectivity of at least 96%. In some embodiments, each coupling step has a stereoselectivity of at least 97%. In some embodiments, each coupling step has a stereoselectivity of at least 98%. In some embodiments, each coupling step has a stereoselectivity of at least 99%. In some embodiments, each coupling step has a stereoselectivity of at least 99.5%. In some embodiments, each coupling step has a stereoselectivity of virtually 100%. In some embodiments, a coupling step has a stereoselectivity of virtually 100% in that all detectable products from the coupling step by an analytical method (e.g., NMR, HPLC, etc.) have the intended stereoselectivity. In some embodiments, stereoselectivity of a chiral internucleotidic linkage in an oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage (e.g., for fU*SfU*SfC*SfU. through the dimer of fU*SfC). As appreciated by a person having ordinary skill in the art, percentage of oligonucleotides of a particular type having n internucleotidic linkages in a preparation may be calculated as $SE^1*SE^2*SE^3* \ldots SE^n$, wherein $SE^1, SE^2, SE^3, \ldots, SE^n$ is independently the stereoselectivity of the $1^{st}, 2^{nd}, 3^{rd}, \ldots,$ and $n^{th}$ chiral internucleotidic linkage.

In some embodiments, in provided compositions, at least 0.5%, 1%, 2%, 3%, 4%, 5%, 6%, 7%, 8%, 9%, 10%, 20%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 97% or 99% of oligonucleotides that have the base sequence of a particular oligonucleotide type (defined by 1) base sequence; 2) pattern of backbone linkages; 3) pattern of backbone chiral centers; and 4) pattern of backbone phosphorus modifications) are oligonucleotides of the particular oligonucleotide type. In some embodiments, at least 0.5%, 1%, 2%, 3%, 4%, 5%, 6%, 7%, 8%, 9%, 10%, 20%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 97% or 99% of oligonucleotides that have the base sequence, the pattern of backbone linkages, and the pattern of backbone phosphorus modifications of a particular oligonucleotide type are oligonucleotides of the particular oligonucleotide type. In some embodiments, the percentage is at least 0.5%. In some embodiments, the percentage is at least 1%. In some embodiments, the percentage is at least 2%. In some embodiments, the percentage is at least 3%. In some embodiments, the percentage is at least 4%. In some embodiments, the percentage is at least 5%. In some embodiments, the percentage is at least 6%. In some embodiments, the percentage is at least 7%. In some embodiments, the percentage is at least 8%. In some embodiments, the percentage is at least 9%. In some embodiments, the percentage is at least 10%. In some embodiments, the percentage is at least 20%. In some embodiments, the percentage is at least 30%. In some embodiments, the percentage is at least 40%. In some embodiments, the percentage is at least 50%. In some embodiments, the percentage is at least 60%. In some embodiments, the percentage is at least 70%. In some embodiments, the percentage is at least 75%. In some embodiments, the percentage is at least 80%. In some embodiments, the percentage is at least 81%. In some embodiments, the percentage is at least 82%. In some embodiments, the percentage is at least 83%. In some embodiments, the percentage is at least 84%. In some embodiments, the percentage is at least 85%. In some embodiments, the percentage is at least 86%. In some embodiments, the percentage is at least 87%. In some embodiments, the percentage is at least 88%. In some embodiments, the percentage is at least 89%. In some embodiments, the percentage is at least 90%. In some embodiments, the percentage is at least 91%. In some embodiments, the percentage is at least 92%. In some embodiments, the percentage is at least 93%. In some embodiments, the percentage is at least 94%. In some embodiments, the percentage is at least 95%. In some embodiments, the percentage is at least 96%. In some embodiments, the percentage is at least 97%. In some embodiments, the percentage is at least 98%. In some embodiments, the percentage is at least 99%.

In some embodiments, a stereopure CpG oligonucleotide composition is highly pure. As a non-limiting example, a chirally controlled composition of CpG oligonucleotide WV-1512, described herein, is 94.00% pure (batch 2), as determined by analytical anion exchange chromatography. The purity of other chirally controlled oligonucleotide compositions described herein include: WV1698 (batch 1), 88.10%; WV1696.01: 79.79%; and WV1701 (batch 1), 94.41%.

In some embodiments, a chirally controlled CpG oligonucleotide composition is at least 30% pure. In some embodiments, a chirally controlled CpG oligonucleotide composition is at least 40% pure. In some embodiments, a chirally controlled CpG oligonucleotide composition is at least 50% pure. In some embodiments, a chirally controlled CpG oligonucleotide composition is at least 60% pure. In some embodiments, a chirally controlled CpG oligonucleotide composition is at least 70% pure. In some embodiments, a chirally controlled CpG oligonucleotide composition is at least 80% pure. In some embodiments, a chirally controlled CpG oligonucleotide composition is at least 90% pure. In some embodiments, a chirally controlled CpG oligonucleotide composition is at least 30% pure as determined by analytical anion exchange chromatography. In some embodiments, a chirally controlled CpG oligonucleotide composition is at least 40% pure as determined by analytical anion exchange chromatography. In some embodiments, a chirally controlled CpG oligonucleotide composition is at least 50% pure as determined by analytical anion exchange chromatography. In some embodiments, a chirally controlled CpG oligonucleotide composition is at least 60% pure as determined by analytical anion exchange chromatography. In some embodiments, a chirally controlled CpG oligonucleotide composition is at least 70% pure as determined by analytical anion exchange chromatography. In some embodiments, a chirally controlled CpG oligonucleotide composition is at least 80% pure as determined by analytical anion exchange chromatography. In some embodiments, a chirally controlled CpG oligonucleotide composition is at least 90% pure as determined by analytical anion exchange chromatography.

As described herein, in some embodiments, provided CpG oligonucleotides comprises one or more wing regions and a core region. In some embodiments, a wing region comprises a structural feature that is not in a core region. In some embodiments, a wing and core can be defined by any structural elements, e.g., base modifications (e.g., methylated/non-methylated, methylation at position 1/methylation at position 2, etc.), sugar modifications (e.g., modified/non-modified, 2'-modification/another type of modification, one type of T-modification/another type of 2'-modification, etc.), backbone linkage types (e.g., phosphate/phosphorothioate, phosphorothioate/substituted phosphorothioate, etc.), backbone chiral center stereochemistry (e.g., all Sp/all Rp, (SpRp) repeats/all Rp, etc.), backbone phosphorus modification types (e.g., s1/s2, s1/s3, etc.), etc.

In some embodiments, a wing and core is defined by nucleoside modifications, wherein a wing comprises a nucleoside modification that the core region does not have. In some embodiments, a wing and core is defined by sugar modifications, wherein a wing comprises a sugar modification that the core region does not have. In some embodiments, a sugar modification is a 2'-modification. In some embodiments, a sugar modification is 2'-OR$^1$. In some embodiments, a sugar modification is 2'-MOE. In some embodiments, a sugar modification is 2'-OMe. Additionally example sugar modifications are described in the present disclosure. In some embodiments, a wing and core is defined by internucleotidic linkages, wherein a wing comprises a internucleotidic linkage type (e.g., natural phosphate linkage, a type of modified internucleotidic linkage, etc.) that the core region does not have. In some embodiments, a wing and core is defined by internucleotidic linkages, wherein a wing has a pattern of backbone linkage that is different from that of the core.

In some embodiments, CpG oligonucleotides in provided compositions have a wing-core or core-wing structure (hemimer). In some embodiments, CpG oligonucleotides in provided compositions have a wing-core structure of nucleoside modifications. In some embodiments, CpG oligonucleotides in provided compositions have a core-wing structure (another type of hemimer). In some embodiments, CpG oligonucleotides in provided compositions have a core-wing structure of nucleoside modifications. In some embodiments, CpG oligonucleotides in provided compositions have a wing-core-wing structure (gapmer). In some embodiments, CpG oligonucleotides in provided compositions have a wing-core-wing structure of nucleoside modifications. In some embodiments, a wing and core is defined by modifications of the sugar moieties. In some embodiments, a wing and core is defined by modifications of the base moieties. In some embodiments, each sugar moiety in the wing region has the same 2'-modification which is not found in the core region. In some embodiments, each sugar moiety in the wing region has the same 2'-modification which is different than any sugar modifications in the core region. In some embodiments, a core region has no sugar modification. In some embodiments, each sugar moiety in the wing region has the same 2'-modification, and the core region has no 2'-modifications. In some embodiments, when two or more wings are present, each wing is defined by its own modifications. In some embodiments, each wing has its own characteristic sugar modification. In some embodiments, each wing has the same characteristic sugar modification differentiating it from a core. In some embodiments, each wing sugar moiety has the same modification. In some embodiments, each wing sugar moiety has the same 2'-modification. In some embodiments, each sugar moiety in a wing region has the same 2'-modification, yet the common 2'-modification in a first wing region can either be the same as or different from the common 2'-modification in a second wing region. In some embodiments, each sugar moiety in a wing region has the same 2'-modification, and the common 2'-modification in a first wing region is the same as the common 2'-modification in a second wing region. In some embodiments, each sugar moiety in a wing region has the same 2'-modification, and the common 2'-modification in a first wing region is different from the common 2'-modification in a second wing region.

In some embodiments, provided chirally controlled (and/or stereochemically pure) preparations are antisense CpG oligonucleotides (e.g., chiromersen). In some embodiments, provided chirally controlled (and/or stereochemically pure) preparations are siRNA CpG oligonucleotides. In some embodiments, a provided chirally controlled CpG oligonucleotide composition is of CpG oligonucleotides that can be antisense oligonucleotide, antagomir, microRNA, premicroRNs, antimir, supermir, ribozyme, U1 adaptor, RNA activator, RNAi agent, decoy oligonucleotide, triplex forming oligonucleotide, aptamer or adjuvant. In some embodiments, a chirally controlled CpG oligonucleotide composition is of antisense CpG oligonucleotides. In some embodiments, a chirally controlled CpG oligonucleotide composition is of antagomir CpG oligonucleotides. In some embodiments, a chirally controlled CpG oligonucleotide composition is of microRNA CpG oligonucleotides. In some embodiments, a chirally controlled CpG oligonucleotide composition is of pre-microRNA CpG oligonucleotides. In some embodiments, a chirally controlled CpG oligonucleotide composition is of antimir CpG oligonucleotides. In some embodiments, a chirally controlled CpG oligonucleotide composition is of supermir CpG oligonucleotides. In some embodiments, a chirally controlled CpG oligonucleotide composition is of ribozyme CpG oligonucleotides. In some embodiments, a chirally controlled CpG oligonucleotide composition is of U1 adaptor CpG oligonucleotides. In some embodiments, a chirally controlled CpG oligonucleotide composition is of RNA activator CpG oligonucleotides. In some embodiments, a chirally controlled CpG oligonucleotide composition is of RNAi agent CpG oligonucleotides. In some embodiments, a chirally controlled CpG oligonucleotide composition is of decoy CpG oligonucleotides. In some embodiments, a chirally controlled CpG oligonucleotide composition is of triplex forming CpG oligonucleotides. In some embodiments, a chirally controlled CpG oligonucleotide composition is of aptamer CpG oligonucleotides. In some embodiments, a chirally controlled CpG oligonucleotide composition is of adjuvant CpG oligonucleotides.

In some embodiments, provided chirally controlled (and/or stereochemically pure) preparations are of CpG oligonucleotides that include one or more modified backbone linkages, bases, and/or sugars.

In some embodiments, a provided CpG oligonucleotide comprises one or more chiral, modified phosphate linkages. In some embodiments, a provided CpG oligonucleotide comprises two or more chiral, modified phosphate linkages. In some embodiments, a provided CpG oligonucleotide comprises three or more chiral, modified phosphate linkages. In some embodiments, a provided CpG oligonucleotide comprises four or more chiral, modified phosphate linkages. In some embodiments, a provided CpG oligonucleotide comprises five or more chiral, modified phosphate linkages. In some embodiments, a provided CpG oligonucleotide comprises 1, 2, 3, 4, 5, 6, 7, 8, 9, 10, 11, 12, 13, 14, 15, 16, 17, 18, 19, 20, 21, 22, 23, 24, or 25 chiral, modified phosphate linkages. In some embodiments, a provided CpG oligonucleotide type comprises 5 or more chiral, modified phosphate linkages. In some embodiments, a provided CpG oligonucleotide type comprises 6 or more chiral, modified phosphate linkages. In some embodiments, a provided CpG oligonucleotide type comprises 7 or more chiral, modified phosphate linkages. In some embodiments, a provided CpG oligonucleotide type comprises 8 or more chiral, modified phosphate linkages. In some embodiments, a provided CpG oligonucleotide type comprises 9 or more chiral, modified phosphate linkages. In some embodiments, a provided CpG oligonucleotide type comprises 10 or more chiral, modified phosphate linkages. In some embodiments, a provided CpG oligonucleotide type comprises 11 or more chiral, modified phosphate linkages. In some embodiments, a provided CpG oligonucleotide type comprises 12 or more chiral, modified phosphate linkages. In some embodiments, a provided CpG oligonucleotide type comprises 13 or more chiral, modified phosphate linkages. In some embodiments, a provided CpG oligonucleotide type comprises 14 or more chiral, modified phosphate linkages. In some embodiments, a provided CpG oligonucleotide type comprises 15 or more chiral, modified phosphate linkages. In some embodiments, a provided CpG oligonucleotide type comprises 16 or more chiral, modified phosphate linkages. In some embodiments, a provided CpG oligonucleotide type comprises 17 or more chiral, modified phosphate linkages. In some embodiments, a provided CpG oligonucleotide type comprises 18 or more chiral, modified phosphate linkages. In some embodiments, a provided CpG oligonucleotide type comprises 19 or more chiral, modified phosphate linkages. In some embodiments, a provided CpG oligonucleotide type comprises 20 or more chiral, modified phosphate linkages. In some embodiments, a provided CpG oligonucleotide type comprises 21 or more chiral, modified phosphate linkages. In some embodiments, a provided CpG oligonucleotide type comprises 22 or more chiral, modified phosphate linkages. In some embodiments, a provided CpG oligonucleotide type comprises 23 or more chiral, modified phosphate linkages. In some embodiments, a provided CpG oligonucleotide type comprises 24 or more chiral, modified phosphate linkages. In some embodiments, a provided CpG oligonucleotide type comprises 25 or more chiral, modified phosphate linkages.

In some embodiments, a provided CpG oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages. Example such chiral, modified phosphate linkages are described above and herein. In some embodiments, a provided CpG oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages in the Sp configuration. In some embodiments, a provided CpG oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages in the Rp configuration.

In some embodiments, provided chirally controlled (and/or stereochemically pure) preparations are of a stereochemical purity of greater than about 80%. In some embodiments, provided chirally controlled (and/or stereochemically pure) preparations are of a stereochemical purity of greater than about 85%. In some embodiments, provided chirally controlled (and/or stereochemically pure) preparations are of a stereochemical purity of greater than about 90%. In some embodiments, provided chirally controlled (and/or stereochemically pure) preparations are of a stereochemical purity of greater than about 91%. In some embodiments, provided chirally controlled (and/or stereochemically pure) preparations are of a stereochemical purity of greater than about 92%. In some embodiments, provided chirally controlled (and/or stereochemically pure) preparations are of a stereochemical purity of greater than about 93%. In some embodiments, provided chirally controlled (and/or stereochemically pure) preparations are of a stereochemical purity of greater than about 94%. In some embodiments, provided chirally controlled (and/or stereochemically pure) preparations are of a stereochemical purity of greater than about 95%. In some embodiments, provided chirally controlled (and/or stereochemically pure) preparations are of a stereochemical purity of greater than about 96%. In some embodiments, provided chirally controlled (and/or stereochemically pure) preparations are of a stereochemical purity of greater than about 97%. In some embodiments, provided chirally controlled (and/or stereochemically pure) preparations are of a stereochemical purity of greater than about 98%. In some embodiments, provided chirally controlled (and/or stereochemically pure) preparations are of a stereochemical purity of greater than about 99%. In some embodiments, such a provided purity can be of one or more chiral internucleotidic linkage is a composition is partially chirally controlled.

In some embodiments, a chiral, modified phosphate linkage is a chiral phosphorothioate linkage, i.e., phosphorothioate internucleotidic linkage. In some embodiments, a provided CpG oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10, 20, 30, 40, 50, 60, 70, 80, or 90% chiral phosphorothioate internucleotidic linkages of a provided CpG oligonucleotide are of the Sp conformation. In some embodiments, at least about 10% chiral phosphorothioate internucleotidic linkages of a provided CpG oligonucleotide are of the Sp conformation. In some embodiments, at least about 20% chiral phosphorothioate internucleotidic linkages of a provided CpG oligonucleotide are of the Sp conformation. In some embodiments, at least about 30% chiral phosphorothioate internucleotidic linkages of a provided CpG oligonucleotide are of the Sp conformation. In some embodiments, at least about 40% chiral phosphorothioate internucleotidic linkages of a provided CpG oligonucleotide are of the Sp conformation. In some embodiments, at least about 50% chiral phosphorothioate internucleotidic linkages of a provided CpG oligonucleotide are of the Sp conformation. In some embodiments, at least about 60% chiral phosphorothioate internucleotidic linkages of a provided CpG oligonucleotide are of the Sp conformation. In some embodiments, at least about 70% chiral phosphorothioate internucleotidic linkages of a provided CpG oligonucleotide are of the Sp conformation. In some embodiments, at least about 80% chiral phosphorothioate internucleotidic linkages of a provided CpG oligonucleotide are of the Sp conformation. In some embodiments, at least about 90% chiral phosphorothioate internucleotidic linkages of a provided CpG oligonucleotide are of the Sp conformation. In some embodiments, at least about 95% chiral phosphorothioate internucleotidic linkages of a provided CpG oligonucleotide are of the Sp conformation.

In some embodiments, at least about 10, 20, 30, 40, 50, 60, 70, 80, or 90% chiral phosphorothioate internucleotidic linkages of a provided CpG oligonucleotide are of the Rp conformation. In some embodiments, at least about 10% chiral phosphorothioate internucleotidic linkages of a provided CpG oligonucleotide are of the Rp conformation. In some embodiments, at least about 20% chiral phosphorothioate internucleotidic linkages of a provided CpG oligonucleotide are of the Rp conformation. In some embodiments, at least about 30% chiral phosphorothioate internucleotidic linkages of a provided CpG oligonucleotide are of the Rp conformation. In some embodiments, at least about 40% chiral phosphorothioate internucleotidic linkages of a provided CpG oligonucleotide are of the Rp conformation. In some embodiments, at least about 50% chiral phosphorothioate internucleotidic linkages of a provided CpG oligonucleotide are of the Rp conformation. In some embodiments, at least about 60% chiral phosphorothioate internucleotidic linkages of a provided CpG oligonucleotide are of the Rp conformation. In some embodiments, at least about 70% chiral phosphorothioate internucleotidic linkages of a provided CpG oligonucleotide are of the Rp conformation. In some embodiments, at least about 80% chiral phosphorothioate internucleotidic linkages of a provided CpG oligonucleotide are of the Rp conformation. In some embodiments, at least about 90% chiral phosphorothioate internucleotidic linkages of a provided CpG oligonucleotide are of the Rp conformation. In some embodiments, at least about 95% chiral phosphorothioate internucleotidic linkages of a provided CpG oligonucleotide are of the Rp conformation.

In some embodiments, less than about 10, 20, 30, 40, 50, 60, 70, 80, or 90% chiral phosphorothioate internucleotidic linkages of a provided CpG oligonucleotide are of the Rp conformation. In some embodiments, less than about 10% chiral phosphorothioate internucleotidic linkages of a provided CpG oligonucleotide are of the Rp conformation. In some embodiments, less than about 20% chiral phosphorothioate internucleotidic linkages of a provided CpG oligonucleotide are of the Rp conformation. In some embodiments, less than about 30% chiral phosphorothioate internucleotidic linkages of a provided CpG oligonucleotide are of the Rp conformation. In some embodiments, less than about 40% chiral phosphorothioate internucleotidic linkages of a provided CpG oligonucleotide are of the Rp conformation. In some embodiments, less than about 50% chiral phosphorothioate internucleotidic linkages of a provided CpG oligonucleotide are of the Rp conformation. In some embodiments, less than about 60% chiral phosphorothioate internucleotidic linkages of a provided CpG oligonucleotide are of the Rp conformation. In some embodiments, less than about 70% chiral phosphorothioate internucleotidic linkages of a provided CpG oligonucleotide are of the Rp conformation. In some embodiments, less than about 80% chiral phosphorothioate internucleotidic linkages of a provided CpG oligonucleotide are of the Rp conformation. In some embodiments, less than about 90% chiral phosphorothioate internucleotidic linkages of a provided CpG oligonucleotide are of the Rp conformation. In some embodiments, less than about 95% chiral phosphorothioate internucleotidic linkages of a provided CpG oligonucleotide are of the Rp conformation. In some embodiments, a provided CpG oligonucleotide has only one Rp chiral phosphorothioate internucleotidic linkages. In some embodiments, a provided CpG oligonucleotide has only one Rp chiral phosphorothioate internucleotidic linkages, wherein all internucleotide linkages are chiral phosphorothioate internucleotidic linkages.

In some embodiments, a chiral phosphorothioate internucleotidic linkage is a chiral phosphorothioate diester linkage. In some embodiments, each chiral phosphorothioate internucleotidic linkage is independently a chiral phosphorothioate diester linkage. In some embodiments, each internucleotidic linkage is independently a chiral phosphorothioate diester linkage. In some embodiments, each internucleotidic linkage is independently a chiral phosphorothioate diester linkage, and only one is Rp.

In some embodiments, provided chirally controlled (and/or stereochemically pure) preparations are of CpG oligonucleotides that contain one or more modified bases. In some embodiments, provided chirally controlled (and/or stereochemically pure) preparations are of CpG oligonucleotides that contain no modified bases. Example such modified bases are described above and herein.

In some embodiments, CpG oligonucleotides of provided compositions comprise at least 2, 3, 4, 5, 6, 7, 8, 9 or 10 natural phosphate linkages. In some embodiments, CpG oligonucleotides of provided compositions comprise at least one natural phosphate linkage. In some embodiments, CpG oligonucleotides of provided compositions comprise at least two natural phosphate linkages. In some embodiments, CpG oligonucleotides of provided compositions comprise at least three natural phosphate linkages. In some embodiments, CpG oligonucleotides of provided compositions comprise at least four natural phosphate linkages. In some embodiments, CpG oligonucleotides of provided compositions comprise at least five natural phosphate linkages. In some embodiments, CpG oligonucleotides of provided compositions comprise at least six natural phosphate linkages. In some embodiments, CpG oligonucleotides of provided compositions comprise at least seven natural phosphate linkages. In some embodiments, CpG oligonucleotides of provided compositions comprise at least eight natural phosphate linkages. In some embodiments, CpG oligonucleotides of provided compositions comprise at least nine natural phosphate linkages. In some embodiments, CpG oligonucleotides of provided compositions comprise at least ten natural phosphate linkages.

In some embodiments, CpG oligonucleotides of provided compositions comprise 2, 3, 4, 5, 6, 7, 8, 9 or 10 natural phosphate linkages. In some embodiments, CpG oligonucleotides of provided compositions comprise one natural phosphate linkage. In some embodiments, CpG oligonucleotides of provided compositions comprise two natural phosphate linkages. In some embodiments, CpG oligonucleotides of provided compositions comprise three natural phosphate linkages. In some embodiments, CpG oligonucleotides of provided compositions comprise four natural phosphate linkages. In some embodiments, CpG oligonucleotides of provided compositions comprise five natural phosphate linkages. In some embodiments, CpG oligonucleotides of provided compositions comprise six natural phosphate linkages. In some embodiments, CpG oligonucleotides of provided compositions comprise seven natural phosphate linkages. In some embodiments, CpG oligonucleotides of provided compositions comprise eight natural phosphate linkages. In some embodiments, CpG oligonucleotides of provided compositions comprise nine natural phosphate linkages. In some embodiments, CpG oligonucleotides of provided compositions comprise ten natural phosphate linkages.

In some embodiments, CpG oligonucleotides of provided compositions comprise at least 2, 3, 4, 5, 6, 7, 8, 9 or 10 consecutive natural phosphate linkages. In some embodiments, CpG oligonucleotides of provided compositions comprise at least two consecutive natural phosphate linkages. In some embodiments, CpG oligonucleotides of provided compositions comprise at least three consecutive natural phosphate linkages. In some embodiments, CpG oligonucleotides of provided compositions comprise at least four consecutive natural phosphate linkages. In some embodiments, CpG oligonucleotides of provided compositions comprise at least five consecutive natural phosphate linkages. In some embodiments, CpG oligonucleotides of provided compositions comprise at least six consecutive natural phosphate linkages. In some embodiments, CpG oligonucleotides of provided compositions comprise at least seven consecutive natural phosphate linkages. In some embodiments, CpG oligonucleotides of provided compositions comprise at least eight consecutive natural phosphate linkages. In some embodiments, CpG oligonucleotides of provided compositions comprise at least nine consecutive natural phosphate linkages. In some embodiments, CpG oligonucleotides of provided compositions comprise at least ten consecutive natural phosphate linkages.

In some embodiments, CpG oligonucleotides of provided compositions comprise 2, 3, 4, 5, 6, 7, 8, 9 or 10 consecutive natural phosphate linkages. In some embodiments, CpG oligonucleotides of provided compositions comprise two consecutive natural phosphate linkages. In some embodiments, CpG oligonucleotides of provided compositions comprise three consecutive natural phosphate linkages. In some embodiments, CpG oligonucleotides of provided compositions comprise four consecutive natural phosphate linkages. In some embodiments, CpG oligonucleotides of provided compositions comprise five consecutive natural phosphate linkages. In some embodiments, CpG oligonucleotides of provided compositions comprise six consecutive natural phosphate linkages. In some embodiments, CpG oligonucleotides of provided compositions comprise seven consecutive natural phosphate linkages. In some embodiments, CpG oligonucleotides of provided compositions comprise eight consecutive natural phosphate linkages. In some embodiments, CpG oligonucleotides of provided compositions comprise nine consecutive natural phosphate linkages. In some embodiments, CpG oligonucleotides of provided compositions comprise ten consecutive natural phosphate linkages.

In some embodiments, provided chirally controlled (and/or stereochemically pure) preparations are of CpG oligonucleotides having a common base sequence of at least 8 bases. In some embodiments, provided chirally controlled (and/or stereochemically pure) preparations are of CpG oligonucleotides having a common base sequence of at least 9 bases. In some embodiments, provided chirally controlled (and/or stereochemically pure) preparations are of CpG oligonucleotides having a common base sequence of at least 10 bases. In some embodiments, provided chirally controlled (and/or stereochemically pure) preparations are of CpG oligonucleotides having a common base sequence of at least 11 bases. In some embodiments, provided chirally controlled (and/or stereochemically pure) preparations are of CpG oligonucleotides having a common base sequence of at least 12 bases. In some embodiments, provided chirally controlled (and/or stereochemically pure) preparations are of CpG oligonucleotides having a common base sequence of at least 13 bases. In some embodiments, provided chirally controlled (and/or stereochemically pure) preparations are of CpG oligonucleotides having a common base sequence of at least 14 bases. In some embodiments, provided chirally controlled (and/or stereochemically pure) preparations are of CpG oligonucleotides having a common base sequence of at least 15 bases. In some embodiments, provided chirally controlled (and/or stereochemically pure) preparations are of CpG oligonucleotides having a common base sequence of at least 16 bases. In some embodiments, provided chirally controlled (and/or stereochemically pure) preparations are of CpG oligonucleotides having a common base sequence of at least 17 bases. In some embodiments, provided chirally controlled (and/or stereochemically pure) preparations are of CpG oligonucleotides having a common base sequence of at least 18 bases. In some embodiments, provided chirally controlled (and/or stereochemically pure) preparations are of CpG oligonucleotides having a common base sequence of at least 19 bases. In some embodiments, provided chirally controlled (and/or stereochemically pure) preparations are of CpG oligonucleotides having a common base sequence of at least 20 bases. In some embodiments, provided chirally controlled (and/or stereochemically pure) preparations are of CpG oligonucleotides having a common base sequence of at least 21 bases. In some embodiments, provided chirally controlled (and/or stereochemically pure) preparations are of CpG oligonucleotides having a common base sequence of at least 22 bases. In some embodiments, provided chirally controlled (and/or stereochemically pure) preparations are of CpG oligonucleotides having a common base sequence of at least 23 bases. In some embodiments, provided chirally controlled (and/or stereochemically pure) preparations are of CpG oligonucleotides having a common base sequence of at least 24 bases. In some embodiments, provided chirally controlled (and/or stereochemically pure) preparations are of CpG oligonucleotides having a common base sequence of at least 25 bases. In some embodiments, provided chirally controlled (and/or stereochemically pure) preparations are of CpG oligonucleotides having a common base sequence of at least 30, 35, 40, 45, 50, 55, 60, 65, 70, or 75 bases.

In some embodiments, provided compositions comprise CpG oligonucleotides containing one or more residues which are modified at the sugar moiety. In some embodiments, provided compositions comprise CpG oligonucleotides containing one or more residues which are modified at the 2' position of the sugar moiety (referred to herein as a "2'-modification"). Example such modifications are described above and herein and include, but are not limited to, 2'-OMe, 2'-MOE, 2'-LNA, 2'-F, FRNA, FANA, S-cEt, etc. In some embodiments, provided compositions comprise CpG oligonucleotides containing one or more residues which are 2'-modified. For example, in some embodiments, provided CpG oligonucleotides contain one or more residues which are 2'-O-methoxyethyl (2'-MOE)-modified residues. In some embodiments, provided compositions comprise CpG oligonucleotides which do not contain any 2'-modifications. In some embodiments, provided compositions are CpG oligonucleotides which do not contain any 2'-MOE residues. That is, in some embodiments, provided CpG oligonucleotides are not MOE-modified. Additional example sugar modifications are described in the present disclosure.

In some embodiments, provided CpG oligonucleotides are of a general motif of wing-core or core-wing (hemimer, also represented herein generally as X-Y or Y—X, respectively). In some embodiments, provided CpG oligonucleotides are of a general motif of wing-core-wing (gapmer, also represented herein generally as X—Y—X). In some embodiments, each wing region independently contains one or more residues having a particular modification, which modification is absent from the core "Y" portion. In some embodiments, each wing region independently contains one or more residues having a particular nucleoside modification, which modification is absent from the core "Y" portion. In some embodiments, each wing region independently contains one or more residues having a particular base modification, which modification is absent from the core "Y" portion. In some embodiments, each wing region independently contains one or more residues having a particular sugar modification, which modification is absent from the core "Y" portion. Example sugar modifications are widely known in the art. In some embodiments, a sugar modification is a modification selected from those modifications described in U.S. Pat. No. 9,006,198, which sugar modifications are incorporated herein by references. Additional example sugar modifications are described in the present disclosure. In some embodiment, each wing contains one or more residues having a 2' modification that is not present in the core portion. In some embodiments, a 2'-modification is 2'-OR$^1$, wherein R$^1$ is as defined and described in the present disclosure.

In some embodiments, provided CpG oligonucleotides have a wing-core motif represented as X-Y, or a core-wing motif represented as Y—X, wherein the residues at the "X" portion are sugar modified residues of a particular type and the residues in the core "Y" portion are not sugar modified residues of the same particular type. In some embodiments, provided CpG oligonucleotides have a wing-core-wing motif represented as X—Y—X, wherein the residues at each "X" portion are sugar modified residues of a particular type and the residues in the core "Y" portion are not sugar modified residues of the same particular type. In some embodiments, provided CpG oligonucleotides have a wing-core motif represented as X-Y, or a core-wing motif represented as Y—X, wherein the residues at the "X" portion are 2'-modified residues of a particular type and the residues in the core "Y" portion are not 2'-modified residues of the same particular type. In some embodiments, provided CpG oligonucleotides have a wing-core motif represented as X-Y, wherein the residues at the "X" portion are 2'-modified residues of a particular type and the residues in the core "Y" portion are not 2'-modified residues of the same particular type. In some embodiments, provided CpG oligonucleotides have a core-wing motif represented as Y—X, wherein the residues at the "X" portion are 2'-modified residues of a particular type and the residues in the core "Y" portion are not 2'-modified residues of the same particular type. In some embodiments, provided CpG oligonucleotides have a wing-core-wing motif represented as X—Y—X, wherein the residues at each "X" portion are 2'-modified residues of a particular type and the residues in the core "Y" portion are not 2'-modified residues of the same particular type. In some embodiments, provided CpG oligonucleotides have a wing-core motif represented as X-Y, wherein the residues at the "X" portion are 2'-modified residues of a particular type and the residues in the core "Y" portion are 2'-deoxyribonucleoside. In some embodiments, provided CpG oligonucleotides have a core-wing motif represented as Y—X, wherein the residues at the "X" portion are 2'-modified residues of a particular type and the residues in the core "Y" portion are 2'-deoxyribonucleoside. In some embodiments, provided CpG oligonucleotides have a wing-core-wing motif represented as X—Y—X, wherein the residues at each "X" portion are 2'-modified residues of a particular type and the residues in the core "Y" portion are 2'-deoxyribonucleoside. In some embodiments, provided CpG oligonucleotides have a wing-core-wing motif represented as X—Y—X, wherein the residues at each "X" portion are 2'-modified residues of a particular type and the residues in the core "Y" portion are 2'-deoxyribonucleoside. For instance, in some embodiments, provided CpG oligonucleotides have a wing-core-wing motif represented as X—Y—X, wherein the residues at each "X" portion are 2'-MOE-modified residues and the residues in the core "Y" portion are not 2'-MOE-modified residues. In some embodiments, provided CpG oligonucleotides have a wing-core-wing motif represented as X—Y—X, wherein the residues at each "X" portion are 2'-MOE-modified residues and the residues in the core "Y" portion are 2'-deoxyribonucleoside. One of skill in the relevant arts will recognize that all such 2'-modifications described above and herein are contemplated in the context of such X—Y, Y—X and/or X—Y—X motifs.

In some embodiments, a wing has a length of one or more bases. In some embodiments, a wing has a length of two or more bases. In some embodiments, a wing has a length of three or more bases. In some embodiments, a wing has a length of four or more bases. In some embodiments, a wing has a length of five or more bases. In some embodiments, a wing has a length of six or more bases. In some embodiments, a wing has a length of seven or more bases. In some embodiments, a wing has a length of eight or more bases. In some embodiments, a wing has a length of nine or more bases. In some embodiments, a wing has a length of ten or more bases. In some embodiments, a wing has a length of 11 or more bases. In some embodiments, a wing has a length of 12 or more bases. In some embodiments, a wing has a length of 13 or more bases. In some embodiments, a wing has a length of 14 or more bases. In some embodiments, a wing has a length of 15 or more bases. In some embodiments, a wing has a length of 16 or more bases. In some embodiments, a wing has a length of 17 or more bases. In some embodiments, a wing has a length of 18 or more bases. In some embodiments, a wing has a length of 19 or more bases. In some embodiments, a wing has a length of ten or more bases.

In some embodiments, a wing has a length of one base. In some embodiments, a wing has a length of two bases. In some embodiments, a wing has a length of three bases. In some embodiments, a wing has a length of four bases. In some embodiments, a wing has a length of five bases. In some embodiments, a wing has a length of six bases. In some embodiments, a wing has a length of seven bases. In some embodiments, a wing has a length of eight bases. In some embodiments, a wing has a length of nine bases. In some embodiments, a wing has a length of ten bases. In some embodiments, a wing has a length of 11 bases. In some embodiments, a wing has a length of 12 bases. In some embodiments, a wing has a length of 13 bases. In some embodiments, a wing has a length of 14 bases. In some embodiments, a wing has a length of 15 bases. In some embodiments, a wing has a length of 16 bases. In some embodiments, a wing has a length of 17 bases. In some embodiments, a wing has a length of 18 bases. In some embodiments, a wing has a length of 19 bases. In some embodiments, a wing has a length of ten bases.

In some embodiments, a wing comprises one or more chiral internucleotidic linkages. In some embodiments, a wing comprises one or more natural phosphate linkages. In some embodiments, a wing comprises one or more chiral internucleotidic linkages and one or more natural phosphate linkages. In some embodiments, a wing comprises one or more chiral internucleotidic linkages and two or more natural phosphate linkages. In some embodiments, a wing comprises one or more chiral internucleotidic linkages and two or more natural phosphate linkages, wherein two or more natural phosphate linkages are consecutive. In some embodiments, a wing comprises no chiral internucleotidic linkages. In some embodiments, each wing linkage is a natural phosphate linkage. In some embodiments, a wing comprises no phosphate linkages. In some embodiments, each wing is independently a chiral internucleotidic linkage.

In some embodiments, each wing region independently comprises one or more chiral internucleotidic linkages. In some embodiments, each wing region independently comprises one or more natural phosphate linkages. In some embodiments, each wing region independently comprises one or more chiral internucleotidic linkages and one or more natural phosphate linkages. In some embodiments, each wing region independently comprises one or more chiral internucleotidic linkages and two or more natural phosphate linkages. In some embodiments, each wing region independently comprises one or more chiral internucleotidic linkages and two or more natural phosphate linkages, wherein two or more natural phosphate linkages are consecutive.

In some embodiments, each wing region independently comprises at least one chiral internucleotidic linkage. In some embodiments, each wing region independently comprises at least two chiral internucleotidic linkages. In some embodiments, each wing region independently comprises at least three chiral internucleotidic linkages. In some embodiments, each wing region independently comprises at least four chiral internucleotidic linkages. In some embodiments, each wing region independently comprises at least five chiral internucleotidic linkages. In some embodiments, each wing region independently comprises at least six chiral internucleotidic linkages. In some embodiments, each wing region independently comprises at least seven chiral internucleotidic linkages. In some embodiments, each wing region independently comprises at least eight chiral internucleotidic linkages. In some embodiments, each wing region independently comprises at least nine chiral internucleotidic linkages. In some embodiments, each wing region independently comprises at least ten chiral internucleotidic linkages. In some embodiments, each wing region independently comprises at least 11 chiral internucleotidic linkages. In some embodiments, each wing region independently comprises at least 12 chiral internucleotidic linkages. In some embodiments, each wing region independently comprises at least 13 chiral internucleotidic linkages. In some embodiments, each wing region independently comprises at least 14 chiral internucleotidic linkages. In some embodiments, each wing region independently comprises at least 15 chiral internucleotidic linkages. In some embodiments, each wing region independently comprises at least 16 chiral internucleotidic linkages. In some embodiments, each wing region independently comprises at least 17 chiral internucleotidic linkages. In some embodiments, each wing region independently comprises at least 18 chiral internucleotidic linkages. In some embodiments, each wing region independently comprises at least 19 chiral internucleotidic linkages. In some embodiments, each wing region independently comprises at least 20 chiral internucleotidic linkages.

In some embodiments, each wing region independently comprises one chiral internucleotidic linkage. In some embodiments, each wing region independently comprises two chiral internucleotidic linkages. In some embodiments, each wing region independently comprises three chiral internucleotidic linkages. In some embodiments, each wing region independently comprises four chiral internucleotidic linkages. In some embodiments, each wing region independently comprises five chiral internucleotidic linkages. In some embodiments, each wing region independently comprises six chiral internucleotidic linkages. In some embodiments, each wing region independently comprises seven chiral internucleotidic linkages. In some embodiments, each wing region independently comprises eight chiral internucleotidic linkages. In some embodiments, each wing region independently comprises nine chiral internucleotidic linkages. In some embodiments, each wing region independently comprises ten chiral internucleotidic linkages. In some embodiments, each wing region independently comprises 11 chiral internucleotidic linkages. In some embodiments, each wing region independently comprises 12 chiral internucleotidic linkages. In some embodiments, each wing region independently comprises 13 chiral internucleotidic linkages. In some embodiments, each wing region independently comprises 14 chiral internucleotidic linkages. In some embodiments, each wing region independently comprises 15 chiral internucleotidic linkages. In some embodiments, each wing region independently comprises 16 chiral internucleotidic linkages. In some embodiments, each wing region independently comprises 17 chiral internucleotidic linkages. In some embodiments, each wing region independently comprises 18 chiral internucleotidic linkages. In some embodiments, each wing region independently comprises 19 chiral internucleotidic linkages. In some embodiments, each wing region independently comprises 20 chiral internucleotidic linkages.

In some embodiments, each wing region independently comprises at least one consecutive natural phosphate linkage. In some embodiments, each wing region independently comprises at least two consecutive chiral internucleotidic linkages. In some embodiments, each wing region independently comprises at least three consecutive chiral internucleotidic linkages. In some embodiments, each wing region independently comprises at least four consecutive chiral internucleotidic linkages. In some embodiments, each wing region independently comprises at least five consecutive chiral internucleotidic linkages. In some embodiments, each wing region independently comprises at least six consecutive chiral internucleotidic linkages. In some embodiments, each wing region independently comprises at least seven consecutive chiral internucleotidic linkages. In some embodiments, each wing region independently comprises at least eight consecutive chiral internucleotidic linkages. In some embodiments, each wing region independently comprises at least nine consecutive chiral internucleotidic linkages. In some embodiments, each wing region independently comprises at least ten consecutive chiral internucleotidic linkages. In some embodiments, each wing region independently comprises at least 11 consecutive chiral internucleotidic linkages. In some embodiments, each wing region independently comprises at least 12 consecutive chiral internucleotidic linkages. In some embodiments, each wing region independently comprises at least 13 consecutive chiral internucleotidic linkages. In some embodiments, each wing region independently comprises at least 14 consecutive chiral internucleotidic linkages. In some embodiments, each wing region independently comprises at least 15 consecutive chiral internucleotidic linkages. In some embodiments, each wing region independently comprises at least 16 consecutive chiral internucleotidic linkages. In some embodiments, each wing region independently comprises at least 17 consecutive chiral internucleotidic linkages. In some embodiments, each wing region independently comprises at least 18 consecutive chiral internucleotidic linkages. In some embodiments, each wing region independently comprises at least 19 consecutive chiral internucleotidic linkages. In some embodiments, each wing region independently comprises at least 20 consecutive chiral internucleotidic linkages.

In some embodiments, each wing region independently comprises one consecutive natural phosphate linkage. In some embodiments, each wing region independently comprises two consecutive chiral internucleotidic linkages. In some embodiments, each wing region independently comprises three consecutive chiral internucleotidic linkages. In some embodiments, each wing region independently comprises four consecutive chiral internucleotidic linkages. In some embodiments, each wing region independently comprises five consecutive chiral internucleotidic linkages. In some embodiments, each wing region independently comprises six consecutive chiral internucleotidic linkages. In some embodiments, each wing region independently comprises seven consecutive chiral internucleotidic linkages. In some embodiments, each wing region independently comprises eight consecutive chiral internucleotidic linkages. In some embodiments, each wing region independently comprises nine consecutive chiral internucleotidic linkages. In some embodiments, each wing region independently comprises ten consecutive chiral internucleotidic linkages. In some embodiments, each wing region independently comprises 11 consecutive chiral internucleotidic linkages. In some embodiments, each wing region independently comprises 12 consecutive chiral internucleotidic linkages. In some embodiments, each wing region independently comprises 13 consecutive chiral internucleotidic linkages. In some embodiments, each wing region independently comprises 14 consecutive chiral internucleotidic linkages. In some embodiments, each wing region independently comprises 15 consecutive chiral internucleotidic linkages. In some embodiments, each wing region independently comprises 16 consecutive chiral internucleotidic linkages. In some embodiments, each wing region independently comprises 17 consecutive chiral internucleotidic linkages. In some embodiments, each wing region independently comprises 18 consecutive chiral internucleotidic linkages. In some embodiments, each wing region independently comprises 19 consecutive chiral internucleotidic linkages. In some embodiments, each wing region independently comprises 20 consecutive chiral internucleotidic linkages.

In some embodiments, each wing region independently comprises at least one natural phosphate linkage. In some embodiments, each wing region independently comprises at least two natural phosphate linkages. In some embodiments, each wing region independently comprises at least three natural phosphate linkages. In some embodiments, each wing region independently comprises at least four natural phosphate linkages. In some embodiments, each wing region independently comprises at least five natural phosphate linkages. In some embodiments, each wing region independently comprises at least six natural phosphate linkages. In some embodiments, each wing region independently comprises at least seven natural phosphate linkages. In some embodiments, each wing region independently comprises at least eight natural phosphate linkages. In some embodiments, each wing region independently comprises at least nine natural phosphate linkages. In some embodiments, each wing region independently comprises at least ten natural phosphate linkages. In some embodiments, each wing region independently comprises at least 11 natural phosphate linkages. In some embodiments, each wing region independently comprises at least 12 natural phosphate linkages. In some embodiments, each wing region independently comprises at least 13 natural phosphate linkages. In some embodiments, each wing region independently comprises at least 14 natural phosphate linkages. In some embodiments, each wing region independently comprises at least 15 natural phosphate linkages. In some embodiments, each wing region independently comprises at least 16 natural phosphate linkages. In some embodiments, each wing region independently comprises at least 17 natural phosphate linkages. In some embodiments, each wing region independently comprises at least 18 natural phosphate linkages. In some embodiments, each wing region independently comprises at least 19 natural phosphate linkages. In some embodiments, each wing region independently comprises at least 20 natural phosphate linkages.

In some embodiments, each wing region independently comprises one natural phosphate linkage. In some embodiments, each wing region independently comprises two natural phosphate linkages. In some embodiments, each wing region independently comprises three natural phosphate linkages. In some embodiments, each wing region independently comprises four natural phosphate linkages. In some embodiments, each wing region independently comprises five natural phosphate linkages. In some embodiments, each wing region independently comprises six natural phosphate linkages. In some embodiments, each wing region independently comprises seven natural phosphate linkages. In some embodiments, each wing region independently comprises eight natural phosphate linkages. In some embodiments, each wing region independently comprises nine natural phosphate linkages. In some embodiments, each wing region independently comprises ten natural phosphate linkages. In some embodiments, each wing region independently comprises 11 natural phosphate linkages. In some embodiments, each wing region independently comprises 12 natural phosphate linkages. In some embodiments, each wing region independently comprises 13 natural phosphate linkages. In some embodiments, each wing region independently comprises 14 natural phosphate linkages. In some embodiments, each wing region independently comprises 15 natural phosphate linkages. In some embodiments, each wing region independently comprises 16 natural phosphate linkages. In some embodiments, each wing region independently comprises 17 natural phosphate linkages. In some embodiments, each wing region independently comprises 18 natural phosphate linkages. In some embodiments, each wing region independently comprises 19 natural phosphate linkages. In some embodiments, each wing region independently comprises 20 natural phosphate linkages.

In some embodiments, each wing region independently comprises at least one consecutive natural phosphate linkage. In some embodiments, each wing region independently comprises at least two consecutive natural phosphate linkages. In some embodiments, each wing region independently comprises at least three consecutive natural phosphate linkages. In some embodiments, each wing region independently comprises at least four consecutive natural phosphate linkages. In some embodiments, each wing region independently comprises at least five consecutive natural phosphate linkages. In some embodiments, each wing region independently comprises at least six consecutive natural phosphate linkages. In some embodiments, each wing region independently comprises at least seven consecutive natural phosphate linkages. In some embodiments, each wing region independently comprises at least eight consecutive natural phosphate linkages. In some embodiments, each wing region independently comprises at least nine consecutive natural phosphate linkages. In some embodiments, each wing region independently comprises at least ten consecutive natural phosphate linkages. In some embodiments, each wing region independently comprises at least 11 consecutive natural phosphate linkages. In some embodiments, each wing region independently comprises at least 12 consecutive natural phosphate linkages. In some embodiments, each wing region independently comprises at least 13 consecutive natural phosphate linkages. In some embodiments, each wing region independently comprises at least 14 consecutive natural phosphate linkages. In some embodiments, each wing region independently comprises at least 15 consecutive natural phosphate linkages. In some embodiments, each wing region independently comprises at least 16 consecutive natural phosphate linkages. In some embodiments, each wing region independently comprises at least 17 consecutive natural phosphate linkages. In some embodiments, each wing region independently comprises at least 18 consecutive natural phosphate linkages. In some embodiments, each wing region independently comprises at least 19 consecutive natural phosphate linkages. In some embodiments, each wing region independently comprises at least 20 consecutive natural phosphate linkages.

In some embodiments, each wing region independently comprises one consecutive natural phosphate linkage. In some embodiments, each wing region independently comprises two consecutive natural phosphate linkages. In some embodiments, each wing region independently comprises three consecutive natural phosphate linkages. In some embodiments, each wing region independently comprises four consecutive natural phosphate linkages. In some embodiments, each wing region independently comprises five consecutive natural phosphate linkages. In some embodiments, each wing region independently comprises six consecutive natural phosphate linkages. In some embodiments, each wing region independently comprises seven consecutive natural phosphate linkages. In some embodiments, each wing region independently comprises eight consecutive natural phosphate linkages. In some embodiments, each wing region independently comprises nine consecutive natural phosphate linkages. In some embodiments, each wing region independently comprises ten consecutive natural phosphate linkages. In some embodiments, each wing region independently comprises 11 consecutive natural phosphate linkages. In some embodiments, each wing region independently comprises 12 consecutive natural phosphate linkages. In some embodiments, each wing region independently comprises 13 consecutive natural phosphate linkages. In some embodiments, each wing region independently comprises 14 consecutive natural phosphate linkages. In some embodiments, each wing region independently comprises 15 consecutive natural phosphate linkages. In some embodiments, each wing region independently comprises 16 consecutive natural phosphate linkages. In some embodiments, each wing region independently comprises 17 consecutive natural phosphate linkages. In some embodiments, each wing region independently comprises 18 consecutive natural phosphate linkages. In some embodiments, each wing region independently comprises 19 consecutive natural phosphate linkages. In some embodiments, each wing region independently comprises 20 consecutive natural phosphate linkages.

In some embodiments, a wing is to the 5'-end of a core (5'-end wing). In some embodiments, a wing is to the 3'-end of a core (3'-end wing). A CpG can be at any position of an oligonucleotide, for example, in a wing, in a core, or at a span of a wing and a core.

In some embodiments, a 5'-end wing comprises one or more modified internucleotidic linkages and one or more natural phosphate internucleotidic linkages. In some embodiments, a 3'-end wing comprises one or more modified internucleotidic linkages and one or more natural phosphate internucleotidic linkages. In some embodiments, each wing independently comprises one or more modified internucleotidic linkages and one or more natural phosphate internucleotidic linkages.

In some embodiments, a 5'-end wing comprises a modified internucleotidic linkage having one or more natural phosphate linkages connecting two or more nucleosides after (to the 3'-end) the modified internucleotidic linkage in the 5'-end wing. For example, a 5'-end wing mG*SmGmCmAmC comprises a modified internucleotidic linkage (mG*SmG) which has three natural phosphate linkages connecting four nucleosides (mGmCmAmC) after the modified internucleotidic linkage in the 5'-end wing. In some embodiments, a 5'-end wing comprises a modified internucleotidic linkages followed by one or more natural phosphate linkages and/or one or more modified internucleotidic linkages, which are followed by one or more natural phosphate linkages in the 5'-end wing (for example, mG*SmG and mG*SmC in mG*SmG*SmCmAmC). In some embodiments, a 5'-end wing comprises a modified internucleotidic linkages followed by one or more natural phosphate linkages in the 5'-end wing. In some embodiments, a 5'-end wing comprises a modified internucleotidic linkages followed by one or more consecutive natural phosphate linkages in the 5'-end wing. In some embodiments, a 5'-end wing comprises a natural phosphate linkage between the two nucleosides at its 3'-end. For example, a 5'-end wing mG*SmGmCmAmC has a natural phosphate linkage between the two nucleosides at its 3'-end (mG*SmGmCmAmC).

In some embodiments, a 3'-end wing comprises a modified internucleotidic linkage having one or more natural phosphate linkages connecting two or more nucleosides before (to the 5'-end) the modified internucleotidic linkage in the 3'-end wing. For example, a 3'-end wing mAmCmUmU*SmC comprises a modified internucleotidic linkage (mU*SmC) which has three natural phosphate linkages connecting four nucleosides (mAmCmUmU) before the modified internucleotidic linkage in the 3'-end wing. In some embodiments, a 3'-end wing comprises a modified internucleotidic linkages preceded by one or more natural phosphate linkages and/or one or more modified internucleotidic linkages, which are preceded by one or more natural phosphate linkages in the 3'-end wing (for example, mU*SmU and mU*SmC in mAmCmU*SmU*SmC). In some embodiments, a 3'-end wing comprises a modified internucleotidic linkages preceded by one or more natural phosphate linkages in the 3'-end wing. In some embodiments, a 3'-end wing comprises a modified internucleotidic linkages preceded by one or more consecutive natural phosphate linkages in the 3'-end wing. In some embodiments, a 3'-end wing comprises a natural phosphate linkage between the two nucleosides at its 5'-end. For example, a 3'-end wing having the structure of mAmCmUmU*SmC has a natural phosphate linkage between the two nucleosides at its 5'-end (mAmCmUmU*SmC).

In some embodiments, one or more is one. In some embodiments, one or more is two. In some embodiments, one or more is three. In some embodiments, one or more is four. In some embodiments, one or more is five. In some embodiments, one or more is six. In some embodiments, one or more is seven. In some embodiments, one or more is eight. In some embodiments, one or more is nine. In some embodiments, one or more is ten. In some embodiments, one or more is at least one. In some embodiments, one or more is at least two. In some embodiments, one or more is at least three. In some embodiments, one or more is at least four. In some embodiments, one or more is at least five. In some embodiments, one or more is at least six. In some embodiments, one or more is at least seven. In some embodiments, one or more is at least eight. In some embodiments, one or more is at least nine. In some embodiments, one or more is at least ten.

In some embodiments, a wing comprises only one chiral internucleotidic linkage. In some embodiments, a 5'-end wing comprises only one chiral internucleotidic linkage. In some embodiments, a 5'-end wing comprises only one chiral internucleotidic linkage at the 5'-end of the wing. In some embodiments, a 5'-end wing comprises only one chiral internucleotidic linkage at the 5'-end of the wing, and the chiral internucleotidic linkage is Rp. In some embodiments, a 5'-end wing comprises only one chiral internucleotidic linkage at the 5'-end of the wing, and the chiral internucleotidic linkage is Sp. In some embodiments, a 3'-end wing comprises only one chiral internucleotidic linkage at the 3'-end of the wing. In some embodiments, a 3'-end wing comprises only one chiral internucleotidic linkage at the 3'-end of the wing, and the chiral internucleotidic linkage is Rp. In some embodiments, a 3'-end wing comprises only one chiral internucleotidic linkage at the 3'-end of the wing, and the chiral internucleotidic linkage is Sp.

In some embodiments, a wing comprises two or more natural phosphate linkages. In some embodiments, all phosphate linkages within a wing are consecutive, and there are no non-phosphate linkages between any two phosphate linkages within a wing.

In some embodiments, a linkage connecting a wing and a core is considered part of the core when describing linkages, e.g., linkage chemistry, linkage stereochemistry, etc.

In some embodiments, a 5'-internucleotidic linkage connected to a sugar moiety without a 2'-modification is a modified linkage. In some embodiments, a 5'-internucleotidic linkage connected to a sugar moiety without a 2'-modification is a linkage having the structure of formula I. In some embodiments, a 5'-internucleotidic linkage connected to a sugar moiety without a 2'-modification is phosphorothioate linkage. In some embodiments, a 5'-internucleotidic linkage connected to a sugar moiety without a 2'-modification is a substituted phosphorothioate linkage. In some embodiments, a 5'-internucleotidic linkage connected to a sugar moiety without a 2'-modification is a phosphorothioate triester linkage. In some embodiments, each 5'-internucleotidic linkage connected to a sugar moiety without a 2'-modification is a modified linkage. In some embodiments, each 5'-internucleotidic linkage connected to a sugar moiety without a 2'-modification is a linkage having the structure of formula I. In some embodiments, each 5'-internucleotidic linkage connected to a sugar moiety without a 2'-modification is phosphorothioate linkage. In some embodiments, each 5'-internucleotidic linkage connected to a sugar moiety without a 2'-modification is a substituted phosphorothioate linkage. In some embodiments, each 5'-internucleotidic linkage connected to a sugar moiety without a 2'-modification is a phosphorothioate triester linkage.

In some embodiments, a 3'-internucleotidic linkage connected to a sugar moiety without a 2'-modification is a modified linkage. In some embodiments, a 3'-internucleotidic linkage connected to a sugar moiety without a 2'-modification is a linkage having the structure of formula I. In some embodiments, a 3'-internucleotidic linkage connected to a sugar moiety without a 2'-modification is phosphorothioate linkage. In some embodiments, a 3'-internucleotidic linkage connected to a sugar moiety without a 2'-modification is a substituted phosphorothioate linkage. In some embodiments, a 3'-internucleotidic linkage connected to a sugar moiety without a 2'-modification is a phosphorothioate triester linkage. In some embodiments, each 3'-internucleotidic linkage connected to a sugar moiety without a 2'-modification is a modified linkage. In some embodiments, each 3'-internucleotidic linkage connected to a sugar moiety without a 2'-modification is a linkage having the structure of formula I. In some embodiments, each 3'-internucleotidic linkage connected to a sugar moiety without a 2'-modification is phosphorothioate linkage. In some embodiments, each 3'-internucleotidic linkage connected to a sugar moiety without a 2'-modification is a substituted phosphorothioate linkage. In some embodiments, each 3'-internucleotidic linkage connected to a sugar moiety without a 2'-modification is a phosphorothioate triester linkage.

In some embodiments, both internucleotidic linkages connected to a sugar moiety without a 2'-modification are modified linkages. In some embodiments, both internucleotidic linkages connected to a sugar moiety without a 2'-modification are linkage having the structure of formula I. In some embodiments, both internucleotidic linkages connected to a sugar moiety without a 2'-modification are phosphorothioate linkages. In some embodiments, both internucleotidic linkages connected to a sugar moiety without a 2'-modification are substituted phosphorothioate linkages. In some embodiments, both internucleotidic linkages connected to a sugar moiety without a 2'-modification are phosphorothioate triester linkages. In some embodiments, each internucleotidic linkage connected to a sugar moiety without a T-modification is a modified linkage. In some embodiments, each internucleotidic linkage connected to a sugar moiety without a 2'-modification is a linkage having the structure of formula I. In some embodiments, each internucleotidic linkage connected to a sugar moiety without a 2'-modification is phosphorothioate linkage. In some embodiments, each internucleotidic linkage connected to a sugar moiety without a 2'-modification is a substituted phosphorothioate linkage. In some embodiments, each internucleotidic linkage connected to a sugar moiety without a 2'-modification is a phosphorothioate triester linkage.

In some embodiments, a sugar moiety without a 2'-modification is a sugar moiety found in a natural DNA nucleoside.

In some embodiments, for a wing-core-wing structure, the 5'-end wing comprises only one chiral internucleotidic linkage. In some embodiments, for a wing-core-wing structure, the 5'-end wing comprises only one chiral internucleotidic linkage at the 5'-end of the wing. In some embodiments, for a wing-core-wing structure, the 3'-end wing comprises only one chiral internucleotidic linkage. In some embodiments, for a wing-core-wing structure, the 3'-end wing comprises only one chiral internucleotidic linkage at the 3'-end of the wing. In some embodiments, for a wing-core-wing structure, each wing comprises only one chiral internucleotidic linkage. In some embodiments, for a wing-core-wing structure, each wing comprises only one chiral internucleotidic linkage, wherein the 5'-end wing comprises only one chiral internucleotidic linkage at its 5'-end; and the 3'-end wing comprises only one chiral internucleotidic linkage at its 3'-end. In some embodiments, the only chiral internucleotidic linkage in the 5'-wing is Rp. In some embodiments, the only chiral internucleotidic linkage in the 5'-wing is Sp. In some embodiments, the only chiral internucleotidic linkage in the 3'-wing is Rp. In some embodiments, the only chiral internucleotidic linkage in the 3'-wing is Sp. In some embodiments, the only chiral internucleotidic linkage in both the 5'- and the 3'-wings are Sp. In some embodiments, the only chiral internucleotidic linkage in both the 5'- and the 3'-wings are Rp. In some embodiments, the only chiral internucleotidic linkage in the 5'-wing is Sp, and the only chiral internucleotidic linkage in the 3'-wing is Rp. In some embodiments, the only chiral internucleotidic linkage in the 5'-wing is Rp, and the only chiral internucleotidic linkage in the 3'-wing is Sp.

In some embodiments, a wing comprises two chiral internucleotidic linkages. In some embodiments, a wing comprises only two chiral internucleotidic linkages, and one or more natural phosphate linkages. In some embodiments, a wing comprises only two chiral internucleotidic linkages, and two or more natural phosphate linkages. In some embodiments, a wing comprises only two chiral internucleotidic linkages, and two or more consecutive natural phosphate linkages. In some embodiments, a wing comprises only two chiral internucleotidic linkages, and two consecutive natural phosphate linkages. In some embodiments, a wing comprises only two chiral internucleotidic linkages, and three consecutive natural phosphate linkages. In some embodiments, a 5'-wing (to a core) comprises only two chiral internucleotidic linkages, one at its 5'-end and the other at its 3'-end, with one or more natural phosphate linkages in between. In some embodiments, a 5'-wing (to a core) comprises only two chiral internucleotidic linkages, one at its 5'-end and the other at its 3'-end, with two or more natural phosphate linkages in between. In some embodiments, a 3'-wing (to a core) comprises only two chiral internucleotidic linkages, one at its 3'-end and the other at its 3'-end, with one or more natural phosphate linkages in between. In some embodiments, a 3'-wing (to a core) comprises only two chiral internucleotidic linkages, one at its 3'-end and the other at its 3'-end, with two or more natural phosphate linkages in between.

In some embodiments, a 5'-wing comprises only two chiral internucleotidic linkages, one at its 5'-end and the other at its 3'-end, with one or more natural phosphate linkages in between, and the 3'-wing comprise only one internucleotidic linkage at its 3'-end. In some embodiments, a 5'-wing (to a core) comprises only two chiral internucleotidic linkages, one at its 5'-end and the other at its 3'-end, with two or more natural phosphate linkages in between, and the 3'-wing comprise only one internucleotidic linkage at its 3'-end. In some embodiments, each chiral internucleotidic linkage independently has its own stereochemistry. In some embodiments, both chiral internucleotidic linkages in the 5'-wing have the same stereochemistry. In some embodiments, both chiral internucleotidic linkages in the 5'-wing have different stereochemistry. In some embodiments, both chiral internucleotidic linkages in the 5'-wing are Rp. In some embodiments, both chiral internucleotidic linkages in the 5'-wing are Sp. In some embodiments, chiral internucleotidic linkages in the 5'- and 3'-wings have the same stereochemistry. In some embodiments, chiral internucleotidic linkages in the 5'- and 3'-wings are Rp. In some embodiments, chiral internucleotidic linkages in the 5'- and 3'-wings are Sp. In some embodiments, chiral internucleotidic linkages in the 5'- and 3'-wings have different stereochemistry.

In some embodiments, a chiral, modified phosphate linkage is a chiral phosphorothioate linkage, i.e., phosphorothioate internucleotidic linkage. In some embodiments, a wing region comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10%, 20%, 30%, 40%, 50%, 60%, 70%, 80%, or 90% chiral phosphorothioate internucleotidic linkages of a wing region are of the Sp conformation. In some embodiments, at least about 10% chiral phosphorothioate internucleotidic linkages of a wing region are of the Sp conformation. In some embodiments, at least about 20% chiral phosphorothioate internucleotidic linkages of a wing region are of the Sp conformation. In some embodiments, at least about 30% chiral phosphorothioate internucleotidic linkages of a wing region are of the Sp conformation. In some embodiments, at least about 40% chiral phosphorothioate internucleotidic linkages of a wing region are of the Sp conformation. In some embodiments, at least about 50% chiral phosphorothioate internucleotidic linkages of a wing region are of the Sp conformation. In some embodiments, at least about 60% chiral phosphorothioate internucleotidic linkages of a wing region are of the Sp conformation. In some embodiments, at least about 70% chiral phosphorothioate internucleotidic linkages of a wing region are of the Sp conformation. In some embodiments, at least about 80% chiral phosphorothioate internucleotidic linkages of a wing region are of the Sp conformation. In some embodiments, at least about 90% chiral phosphorothioate internucleotidic linkages of a wing region are of the Sp conformation. In some embodiments, at least about 95% chiral phosphorothioate internucleotidic linkages of a wing region are of the Sp conformation.

In some embodiments, at least about 1 chiral phosphorothioate internucleotidic linkage of a wing region is of the Sp conformation. In some embodiments, at least about 2 chiral phosphorothioate internucleotidic linkages of a wing region are of the Sp conformation. In some embodiments, at least about 3 chiral phosphorothioate internucleotidic linkages of a wing region are of the Sp conformation. In some embodiments, at least about 4 chiral phosphorothioate internucleotidic linkages of a wing region are of the Sp conformation. In some embodiments, at least about 5 chiral phosphorothioate internucleotidic linkages of a wing region are of the Sp conformation. In some embodiments, at least about 6 chiral phosphorothioate internucleotidic linkages of a wing region are of the Sp conformation. In some embodiments, at least about 7 chiral phosphorothioate internucleotidic linkages of a wing region are of the Sp conformation. In some embodiments, at least about 8 chiral phosphorothioate internucleotidic linkages of a wing region are of the Sp conformation. In some embodiments, at least about 9 chiral phosphorothioate internucleotidic linkages of a wing region are of the Sp conformation.

In some embodiments, at least about 2 consecutive chiral phosphorothioate internucleotidic linkages of a wing region are of the Sp conformation. In some embodiments, at least about 3 consecutive chiral phosphorothioate internucleotidic linkages of a wing region are of the Sp conformation. In some embodiments, at least about 4 consecutive chiral phosphorothioate internucleotidic linkages of a wing region are of the Sp conformation. In some embodiments, at least about 5 consecutive chiral phosphorothioate internucleotidic linkages of a wing region are of the Sp conformation. In some embodiments, at least about 6 consecutive chiral phosphorothioate internucleotidic linkages of a wing region are of the Sp conformation. In some embodiments, at least about 7 consecutive chiral phosphorothioate internucleotidic linkages of a wing region are of the Sp conformation. In some embodiments, at least about 8 consecutive chiral phosphorothioate internucleotidic linkages of a wing region are of the Sp conformation. In some embodiments, at least about 9 consecutive chiral phosphorothioate internucleotidic linkages of a wing region are of the Sp conformation.

In some embodiments, at least about 10%, 20%, 30%, 40%, 50%, 60%, 70%, 80%, or 90% chiral phosphorothioate internucleotidic linkages of a wing region are of the Rp conformation. In some embodiments, at least about 10% chiral phosphorothioate internucleotidic linkages of a wing region are of the Rp conformation. In some embodiments, at least about 20% chiral phosphorothioate internucleotidic linkages of a wing region are of the Rp conformation. In some embodiments, at least about 30% chiral phosphorothioate internucleotidic linkages of a wing region are of the Rp conformation. In some embodiments, at least about 40% chiral phosphorothioate internucleotidic linkages of a wing region are of the Rp conformation. In some embodiments, at least about 50% chiral phosphorothioate internucleotidic linkages of a wing region are of the Rp conformation. In some embodiments, at least about 60% chiral phosphorothioate internucleotidic linkages of a wing region are of the Rp conformation. In some embodiments, at least about 70% chiral phosphorothioate internucleotidic linkages of a wing region are of the Rp conformation. In some embodiments, at least about 80% chiral phosphorothioate internucleotidic linkages of a wing region are of the Rp conformation. In some embodiments, at least about 90% chiral phosphorothioate internucleotidic linkages of a wing region are of the Rp conformation. In some embodiments, at least about 95% chiral phosphorothioate internucleotidic linkages of a wing region are of the Rp conformation.

In some embodiments, less than about 10%, 20%, 30%, 40%, 50%, 60%, 70%, 80%, or 90% chiral phosphorothioate internucleotidic linkages of a wing region are of the Rp conformation. In some embodiments, less than about 10% chiral phosphorothioate internucleotidic linkages of a wing region are of the Rp conformation. In some embodiments, less than about 20% chiral phosphorothioate internucleotidic linkages of a wing region are of the Rp conformation. In some embodiments, less than about 30% chiral phosphorothioate internucleotidic linkages of a wing region are of the Rp conformation. In some embodiments, less than about 40% chiral phosphorothioate internucleotidic linkages of a wing region are of the Rp conformation. In some embodiments, less than about 50% chiral phosphorothioate internucleotidic linkages of a wing region are of the Rp conformation. In some embodiments, less than about 60% chiral phosphorothioate internucleotidic linkages of a wing region are of the Rp conformation. In some embodiments, less than about 70% chiral phosphorothioate internucleotidic linkages of a wing region are of the Rp conformation. In some embodiments, less than about 80% chiral phosphorothioate internucleotidic linkages of a wing region are of the Rp conformation. In some embodiments, less than about 90% chiral phosphorothioate internucleotidic linkages of a wing region are of the Rp conformation. In some embodiments, less than about 95% chiral phosphorothioate internucleotidic linkages of a wing region are of the Rp conformation. In some embodiments, a wing region has only one Rp chiral phosphorothioate internucleotidic linkages. In some embodiments, a wing region has only one Rp chiral phosphorothioate internucleotidic linkages, wherein all internucleotide linkages are chiral phosphorothioate internucleotidic linkages.

In some embodiments, at least about 1 chiral phosphorothioate internucleotidic linkage of a wing region is of the Rp conformation. In some embodiments, at least about 2 chiral phosphorothioate internucleotidic linkages of a wing region are of the Rp conformation. In some embodiments, at least about 3 chiral phosphorothioate internucleotidic linkages of a wing region are of the Rp conformation. In some embodiments, at least about 4 chiral phosphorothioate internucleotidic linkages of a wing region are of the Rp conformation. In some embodiments, at least about 5 chiral phosphorothioate internucleotidic linkages of a wing region are of the Rp conformation. In some embodiments, at least about 6 chiral phosphorothioate internucleotidic linkages of a wing region are of the Rp conformation. In some embodiments, at least about 7 chiral phosphorothioate internucleotidic linkages of a wing region are of the Rp conformation. In some embodiments, at least about 8 chiral phosphorothioate internucleotidic linkages of a wing region are of the Rp conformation. In some embodiments, at least about 9 chiral phosphorothioate internucleotidic linkages of a wing region are of the Rp conformation.

In some embodiments, at least about 2 consecutive chiral phosphorothioate internucleotidic linkages of a wing region are of the Rp conformation. In some embodiments, at least about 3 consecutive chiral phosphorothioate internucleotidic linkages of a wing region are of the Rp conformation. In some embodiments, at least about 4 consecutive chiral phosphorothioate internucleotidic linkages of a wing region are of the Rp conformation. In some embodiments, at least about 5 consecutive chiral phosphorothioate internucleotidic linkages of a wing region are of the Rp conformation. In some embodiments, at least about 6 consecutive chiral phosphorothioate internucleotidic linkages of a wing region are of the Rp conformation. In some embodiments, at least about 7 consecutive chiral phosphorothioate internucleotidic linkages of a wing region are of the Rp conformation. In some embodiments, at least about 8 consecutive chiral phosphorothioate internucleotidic linkages of a wing region are of the Rp conformation. In some embodiments, at least about 9 consecutive chiral phosphorothioate internucleotidic linkages of a wing region are of the Rp conformation.

In some embodiments, a wing comprises one or more modified sugar moieties. In some embodiments, a wing comprises two or more modified sugar moieties. In some embodiments, a wing comprises three or more modified sugar moieties. In some embodiments, a wing comprises four or more modified sugar moieties. In some embodiments, a wing comprises five or more modified sugar moieties. In some embodiments, a wing comprises six or more modified sugar moieties. In some embodiments, a wing comprises seven or more modified sugar moieties. In some embodiments, a wing comprises eight or more modified sugar moieties. In some embodiments, a wing comprises nine or more modified sugar moieties. In some embodiments, a wing comprises ten or more modified sugar moieties. In some embodiments, a wing comprises 11 or more modified sugar moieties. In some embodiments, a wing comprises 12 or more modified sugar moieties. In some embodiments, a wing comprises 13 or more modified sugar moieties. In some embodiments, a wing comprises 14 or more modified sugar moieties. In some embodiments, a wing comprises 15 or more modified sugar moieties. In some embodiments, a wing comprises 16 or more modified sugar moieties. In some embodiments, a wing comprises 17 or more modified sugar moieties. In some embodiments, a wing comprises 18 or more modified sugar moieties. In some embodiments, a wing comprises 19 or more modified sugar moieties. In some embodiments, a wing comprises 20 or more modified sugar moieties. In some embodiments, a wing comprises 21 or more modified sugar moieties. In some embodiments, a wing comprises 22 or more modified sugar moieties. In some embodiments, a wing comprises 23 or more modified sugar moieties. In some embodiments, a wing comprises 24 or more modified sugar moieties. In some embodiments, a wing comprises 25 or more modified sugar moieties. In some embodiments, a wing comprises 30 or more modified sugar moieties. In some embodiments, a wing comprises 35 or more modified sugar moieties.

In some embodiments, a wing comprises one or more 2'-modified sugar moieties. In some embodiments, a wing comprises two or more 2'-modified sugar moieties. In some embodiments, a wing comprises three or more 2'-modified sugar moieties. In some embodiments, a wing comprises four or more 2'-modified sugar moieties. In some embodiments, a wing comprises five or more 2'-modified sugar moieties. In some embodiments, a wing comprises six or more 2'-modified sugar moieties. In some embodiments, a wing comprises seven or more 2'-modified sugar moieties. In some embodiments, a wing comprises eight or more 2'-modified sugar moieties. In some embodiments, a wing comprises nine or more 2'-modified sugar moieties. In some embodiments, a wing comprises ten or more 2'-modified sugar moieties. In some embodiments, a wing comprises 11 or more 2'-modified sugar moieties. In some embodiments, a wing comprises 12 or more 2'-modified sugar moieties. In some embodiments, a wing comprises 13 or more 2'-modified sugar moieties. In some embodiments, a wing comprises 14 or more 2'-modified sugar moieties. In some embodiments, a wing comprises 15 or more 2'-modified sugar moieties. In some embodiments, a wing comprises 16 or more 2'-modified sugar moieties. In some embodiments, a wing comprises 17 or more T-modified sugar moieties. In some embodiments, a wing comprises 18 or more 2'-modified sugar moieties. In some embodiments, a wing comprises 19 or more 2'-modified sugar moieties. In some embodiments, a wing comprises 20 or more 2'-modified sugar moieties. In some embodiments, a wing comprises 21 or more 2'-modified sugar moieties. In some embodiments, a wing comprises 22 or more 2'-modified sugar moieties. In some embodiments, a wing comprises 23 or more 2'-modified sugar moieties. In some embodiments, a wing comprises 24 or more 2'-modified sugar moieties. In some embodiments, a wing comprises 25 or more T-modified sugar moieties. In some embodiments, a wing comprises 30 or more 2'-modified sugar moieties. In some embodiments, a wing comprises 35 or more 2'-modified sugar moieties.

In some embodiments, a wing comprises one or more 2'-F. In some embodiments, a wing comprises two or more 2'-F. In some embodiments, a wing comprises three or more 2'-F. In some embodiments, a wing comprises four or more 2'-F. In some embodiments, a wing comprises five or more 2'-F. In some embodiments, a wing comprises six or more 2'-F. In some embodiments, a wing comprises seven or more 2'-F. In some embodiments, a wing comprises eight or more 2'-F. In some embodiments, a wing comprises nine or more 2'-F. In some embodiments, a wing comprises ten or more 2'-F. In some embodiments, a wing comprises 11 or more 2'-F. In some embodiments, a wing comprises 12 or more 2'-F. In some embodiments, a wing comprises 13 or more 2'-F. In some embodiments, a wing comprises 14 or more 2'-F. In some embodiments, a wing comprises 15 or more 2'-F. In some embodiments, a wing comprises 16 or more 2'-F. In some embodiments, a wing comprises 17 or more 2'-F. In some embodiments, a wing comprises 18 or more 2'-F. In some embodiments, a wing comprises 19 or more 2'-F. In some embodiments, a wing comprises 20 or more 2'-F. In some embodiments, a wing comprises 21 or more 2'-F. In some embodiments, a wing comprises 22 or more 2'-F. In some embodiments, a wing comprises 23 or more 2'-F. In some embodiments, a wing comprises 24 or more 2'-F. In some embodiments, a wing comprises 25 or more 2'-F. In some embodiments, a wing comprises 30 or more 2'-F. In some embodiments, a wing comprises 35 or more 2'-F.

In some embodiments, a wing comprises one 2'-F. In some embodiments, a wing comprises two 2'-F. In some embodiments, a wing comprises three 2'-F. In some embodiments, a wing comprises four 2'-F. In some embodiments, a wing comprises five 2'-F. In some embodiments, a wing comprises six 2'-F. In some embodiments, a wing comprises seven 2'-F. In some embodiments, a wing comprises eight 2'-F. In some embodiments, a wing comprises nine 2'-F. In some embodiments, a wing comprises ten 2'-F. In some embodiments, a wing comprises 11 2'-F. In some embodiments, a wing comprises 12 2'-F. In some embodiments, a wing comprises 13 2'-F. In some embodiments, a wing comprises 14 2'-F. In some embodiments, a wing comprises 15 2'-F. In some embodiments, a wing comprises 16 2'-F. In some embodiments, a wing comprises 17 2'-F. In some embodiments, a wing comprises 18 T-F. In some embodiments, a wing comprises 19 2'-F. In some embodiments, a wing comprises 20 2'-F. In some embodiments, a wing comprises 21 2'-F. In some embodiments, a wing comprises 22 2'-F. In some embodiments, a wing comprises 23 2'-F. In some embodiments, a wing comprises 24 2'-F. In some embodiments, a wing comprises 25 2'-F. In some embodiments, a wing comprises 30 2'-F. In some embodiments, a wing comprises 35 2'-F.

In some embodiments, a wing comprises one or more consecutive 2'-F. In some embodiments, a wing comprises two or more consecutive 2'-F. In some embodiments, a wing comprises three or more consecutive 2'-F. In some embodiments, a wing comprises four or more consecutive 2'-F. In some embodiments, a wing comprises five or more consecutive 2'-F. In some embodiments, a wing comprises six or more consecutive 2'-F. In some embodiments, a wing comprises seven or more consecutive 2'-F. In some embodiments, a wing comprises eight or more consecutive 2'-F. In some embodiments, a wing comprises nine or more consecutive T-F. In some embodiments, a wing comprises ten or more consecutive 2'-F. In some embodiments, a wing comprises 11 or more consecutive 2'-F. In some embodiments, a wing comprises 12 or more consecutive 2'-F. In some embodiments, a wing comprises 13 or more consecutive 2'-F. In some embodiments, a wing comprises 14 or more consecutive 2'-F. In some embodiments, a wing comprises 15 or more consecutive 2'-F. In some embodiments, a wing comprises 16 or more consecutive 2'-F. In some embodiments, a wing comprises 17 or more consecutive 2'-F. In some embodiments, a wing comprises 18 or more consecutive 2'-F. In some embodiments, a wing comprises 19 or more consecutive 2'-F. In some embodiments, a wing comprises 20 or more consecutive 2'-F. In some embodiments, a wing comprises 21 or more consecutive 2'-F. In some embodiments, a wing comprises 22 or more consecutive 2'-F. In some embodiments, a wing comprises 23 or more consecutive 2'-F. In some embodiments, a wing comprises 24 or more consecutive 2'-F. In some embodiments, a wing comprises 25 or more consecutive 2'-F. In some embodiments, a wing comprises 30 or more consecutive 2'-F. In some embodiments, a wing comprises 35 or more consecutive 2'-F.

In some embodiments, a wing comprises one consecutive 2'-F. In some embodiments, a wing comprises two consecutive 2'-F. In some embodiments, a wing comprises three consecutive 2'-F. In some embodiments, a wing comprises four consecutive 2'-F. In some embodiments, a wing comprises five consecutive 2'-F. In some embodiments, a wing comprises six consecutive 2'-F. In some embodiments, a wing comprises seven consecutive 2'-F. In some embodiments, a wing comprises eight consecutive 2'-F. In some embodiments, a wing comprises nine consecutive 2'-F. In some embodiments, a wing comprises ten consecutive 2'-F. In some embodiments, a wing comprises 11 consecutive 2'-F. In some embodiments, a wing comprises 12 consecutive 2'-F. In some embodiments, a wing comprises 13 consecutive 2'-F. In some embodiments, a wing comprises 14 consecutive 2'-F. In some embodiments, a wing comprises 15 consecutive 2'-F. In some embodiments, a wing comprises 16 consecutive 2'-F. In some embodiments, a wing comprises 17 consecutive 2'-F. In some embodiments, a wing comprises 18 consecutive 2'-F. In some embodiments, a wing comprises 19 consecutive 2'-F. In some embodiments, a wing comprises 20 consecutive 2'-F. In some embodiments, a wing comprises 21 consecutive 2'-F. In some embodiments, a wing comprises 22 consecutive 2'-F. In some embodiments, a wing comprises 23 consecutive 2'-F. In some embodiments, a wing comprises 24 consecutive 2'-F. In some embodiments, a wing comprises 25 consecutive 2'-F. In some embodiments, a wing comprises 30 consecutive 2'-F. In some embodiments, a wing comprises 35 consecutive 2'-F.

In some embodiments, a core region has a length of one or more bases. In some embodiments, a core region has a length of two or more bases. In some embodiments, a core region has a length of three or more bases. In some embodiments, a core region has a length of four or more bases. In some embodiments, a core region has a length of five or more bases. In some embodiments, a core region has a length of six or more bases. In some embodiments, a core region has a length of seven or more bases. In some embodiments, a core region has a length of eight or more bases. In some embodiments, a core region has a length of nine or more bases. In some embodiments, a core region has a length of ten or more bases. In some embodiments, a core region has a length of 11, 12, 13, 14, 15, 16, 17, 18, 19, 20, 25, or more bases. In certain embodiments, a core region has a length of 11 or more bases. In certain embodiments, a core region has a length of 12 or more bases. In certain embodiments, a core region has a length of 13 or more bases. In certain embodiments, a core region has a length of 14 or more bases. In certain embodiments, a core region has a length of 15 or more bases. In certain embodiments, a core region has a length of 16 or more bases. In certain embodiments, a core region has a length of 17 or more bases. In certain embodiments, a core region has a length of 18 or more bases. In certain embodiments, a core region has a length of 19 or more bases. In certain embodiments, a core region has a length of 20 or more bases. In certain embodiments, a core region has a length of more than 20 bases. In certain embodiments, a core region has a length of 2 bases. In certain embodiments, a core region has a length of 3 bases. In certain embodiments, a core region has a length of 4 bases. In certain embodiments, a core region has a length of 5 bases. In certain embodiments, a core region has a length of 6 bases. In certain embodiments, a core region has a length of 7 bases. In certain embodiments, a core region has a length of 8 bases. In certain embodiments, a core region has a length of 9 bases. In certain embodiments, a core region has a length of 10 bases. In certain embodiments, a core region has a length of 11 bases. In certain embodiments, a core region has a length of 12 bases. In certain embodiments, a core region has a length of 13 bases. In certain embodiments, a core region has a length of 14 bases. In certain embodiments, a core region has a length of 15 bases. In certain embodiments, a core region has a length of 16 bases. In certain embodiments, a core region has a length of 17 bases. In certain embodiments, a core region has a length of 18 bases. In certain embodiments, a core region has a length of 19 bases. In certain embodiments, a core region has a length of 20 bases.

In some embodiments, a core comprises one or more modified internucleotidic linkages. In some embodiments, a core comprises one or more natural phosphate linkages. In some embodiments, a core independently comprises one or more modified internucleotidic linkages and one or more natural phosphate linkages. In some embodiments, a core comprises no natural phosphate linkages. In some embodiments, each core linkage is a modified internucleotidic linkage.

In some embodiments, a core comprises at least one natural phosphate linkage. In some embodiments, a core comprises at least two modified internucleotidic linkages. In some embodiments, a core comprises at least three modified internucleotidic linkages. In some embodiments, a core comprises at least four modified internucleotidic linkages. In some embodiments, a core comprises at least five modified internucleotidic linkages. In some embodiments, a core comprises at least six modified internucleotidic linkages. In some embodiments, a core comprises at least seven modified internucleotidic linkages. In some embodiments, a core comprises at least eight modified internucleotidic linkages. In some embodiments, a core comprises at least nine modified internucleotidic linkages. In some embodiments, a core comprises at least ten modified internucleotidic linkages. In some embodiments, a core comprises at least 11 modified internucleotidic linkages. In some embodiments, a core comprises at least 12 modified internucleotidic linkages. In some embodiments, a core comprises at least 13 modified internucleotidic linkages. In some embodiments, a core comprises at least 14 modified internucleotidic linkages. In some embodiments, a core comprises at least 15 modified internucleotidic linkages. In some embodiments, a core comprises at least 16 modified internucleotidic linkages. In some embodiments, a core comprises at least 17 modified internucleotidic linkages. In some embodiments, a core comprises at least 18 modified internucleotidic linkages. In some embodiments, a core comprises at least 19 modified internucleotidic linkages. In some embodiments, a core comprises at least 20 modified internucleotidic linkages.

In some embodiments, a core comprises one or more chiral internucleotidic linkages. In some embodiments, a core comprises one or more natural phosphate linkages. In some embodiments, a core independently comprises one or more chiral internucleotidic linkages and one or more natural phosphate linkages. In some embodiments, a core comprises no natural phosphate linkages. In some embodiments, each core linkage is a chiral internucleotidic linkage.

In some embodiments, a core comprises at least one natural phosphate linkage. In some embodiments, a core comprises at least two chiral internucleotidic linkages. In some embodiments, a core comprises at least three chiral internucleotidic linkages. In some embodiments, a core comprises at least four chiral internucleotidic linkages. In some embodiments, a core comprises at least five chiral internucleotidic linkages. In some embodiments, a core comprises at least six chiral internucleotidic linkages. In some embodiments, a core comprises at least seven chiral internucleotidic linkages. In some embodiments, a core comprises at least eight chiral internucleotidic linkages. In some embodiments, a core comprises at least nine chiral internucleotidic linkages. In some embodiments, a core comprises at least ten chiral internucleotidic linkages. In some embodiments, a core comprises at least 11 chiral internucleotidic linkages. In some embodiments, a core comprises at least 12 chiral internucleotidic linkages. In some embodiments, a core comprises at least 13 chiral internucleotidic linkages. In some embodiments, a core comprises at least 14 chiral internucleotidic linkages. In some embodiments, a core comprises at least 15 chiral internucleotidic linkages. In some embodiments, a core comprises at least 16 chiral internucleotidic linkages. In some embodiments, a core comprises at least 17 chiral internucleotidic linkages. In some embodiments, a core comprises at least 18 chiral internucleotidic linkages. In some embodiments, a core comprises at least 19 chiral internucleotidic linkages. In some embodiments, a core comprises at least 20 chiral internucleotidic linkages.

In some embodiments, a core comprises one natural phosphate linkage. In some embodiments, a core comprises two chiral internucleotidic linkages. In some embodiments, a core comprises three chiral internucleotidic linkages. In some embodiments, a core comprises four chiral internucleotidic linkages. In some embodiments, a core comprises five chiral internucleotidic linkages. In some embodiments, a core comprises six chiral internucleotidic linkages. In some embodiments, a core comprises seven chiral internucleotidic linkages. In some embodiments, a core comprises eight chiral internucleotidic linkages. In some embodiments, a core comprises nine chiral internucleotidic linkages. In some embodiments, a core comprises ten chiral internucleotidic linkages. In some embodiments, a core comprises 11 chiral internucleotidic linkages. In some embodiments, a core comprises 12 chiral internucleotidic linkages. In some embodiments, a core comprises 13 chiral internucleotidic linkages. In some embodiments, a core comprises 14 chiral internucleotidic linkages. In some embodiments, a core comprises 15 chiral internucleotidic linkages. In some embodiments, a core comprises 16 chiral internucleotidic linkages. In some embodiments, a core comprises 17 chiral internucleotidic linkages. In some embodiments, a core comprises 18 chiral internucleotidic linkages. In some embodiments, a core comprises 19 chiral internucleotidic linkages. In some embodiments, a core comprises 20 chiral internucleotidic linkages.

In some embodiments, a core region has a pattern of backbone chiral centers comprising (Sp)m(Rp)n, (Rp)n(Sp)m, (Np)t(Rp)n(Sp)m, or (Sp)t(Rp)n(Sp)m, wherein each of m, n, t and Np is independently as defined and described in the present disclosure. In some embodiments, a core region has a pattern of backbone chiral centers comprising (Sp)m(Rp)n, (Rp)n(Sp)m, (Np)t(Rp)n(Sp)m, or (Sp)t(Rp)n(Sp)m. In some embodiments, a core region has a pattern of backbone chiral centers comprising (Sp)m(Rp)n. In some embodiments, a core region has a pattern of backbone chiral centers comprising (Sp)m(Rp)n, wherein m>2 and n is 1. In some embodiments, a core region has a pattern of backbone chiral centers comprising (Rp)n(Sp)m. In some embodiments, a core region has a pattern of backbone chiral centers comprising (Rp)n(Sp)m, wherein m>2 and n is 1. In some embodiments, a core region has a pattern of backbone chiral centers comprising (Np)t(Rp)n(Sp)m. In some embodiments, a core region has a pattern of backbone chiral centers comprising (Np)t(Rp)n(Sp)m, wherein m>2 and n is 1. In some embodiments, a core region has a pattern of backbone chiral centers comprising (Np)t(Rp)n(Sp)m, wherein t>2, m>2 and n is 1. In some embodiments, a core region has a pattern of backbone chiral centers comprising (Sp)t(Rp)n(Sp)m. In some embodiments, a core region has a pattern of backbone chiral centers comprising (Sp)t(Rp)n(Sp)m, wherein m>2 and n is 1. In some embodiments, a core region has a pattern of backbone chiral centers comprising (Sp)t(Rp)n(Sp)m, wherein t>2, m>2 and n is 1. Among other things, the present disclosure demonstrates that, in some embodiments, such patterns can provide and/or enhance controlled cleavage, improved cleavage rate, selectivity, etc., of a target sequence, e.g., an RNA sequence. Example patterns of backbone chiral centers are described in the present disclosure.

In some embodiments, at least 60% of the chiral internucleotidic linkages in the core region are Sp. In some embodiments, at least 65% of the chiral internucleotidic linkages in the core region are Sp. In some embodiments, at least 66% of the chiral internucleotidic linkages in the core region are Sp. In some embodiments, at least 67% of the chiral internucleotidic linkages in the core region are Sp. In some embodiments, at least 70% of the chiral internucleotidic linkages in the core region are Sp. In some embodiments, at least 75% of the chiral internucleotidic linkages in the core region are Sp. In some embodiments, at least 80% of the chiral internucleotidic linkages in the core region are Sp. In some embodiments, at least 85% of the chiral internucleotidic linkages in the core region are Sp. In some embodiments, at least 90% of the chiral internucleotidic linkages in the core region are Sp. In some embodiments, at least 95% of the chiral internucleotidic linkages in the core region are Sp. In some embodiments, each chiral internucleotidic linkages in the core region is Sp.

In some embodiments, at least 1 core region internucleotidic linkage is Sp. In some embodiments, at least 2 core region internucleotidic linkages are Sp. In some embodiments, at least 3 core region internucleotidic linkages are Sp. In some embodiments, at least 4 core region internucleotidic linkages are Sp. In some embodiments, at least 5 core region internucleotidic linkages are Sp. In some embodiments, at least 6 core region internucleotidic linkages are Sp. In some embodiments, at least 7 core region internucleotidic linkages are Sp. In some embodiments, at least 8 core region internucleotidic linkages are Sp. In some embodiments, at least 9 core region internucleotidic linkages are Sp. In some embodiments, at least 10 core region internucleotidic linkages are Sp. In some embodiments, at least 11 core region internucleotidic linkages are Sp. In some embodiments, at least 12 core region internucleotidic linkages are Sp. In some embodiments, at least 13 core region internucleotidic linkages are Sp. In some embodiments, at least 14 core region internucleotidic linkages are Sp. In some embodiments, at least 15 core region internucleotidic linkages are Sp. In some embodiments, at least 16 core region internucleotidic linkages are Sp. In some embodiments, at least 17 core region internucleotidic linkages are Sp. In some embodiments, at least 18 core region internucleotidic linkages are Sp. In some embodiments, at least 19 core region internucleotidic linkages are Sp. In some embodiments, at least 20 core region internucleotidic linkages are Sp. In some embodiments, at least 21 core region internucleotidic linkages are Sp. In some embodiments, at least two core region internucleotidic linkages are Sp. In some embodiments, the Sp internucleotidic linkages are consecutive.

In some embodiments, at least 60% of the chiral internucleotidic linkages in the core region are Rp. In some embodiments, at least 65% of the chiral internucleotidic linkages in the core region are Rp. In some embodiments, at least 66% of the chiral internucleotidic linkages in the core region are Rp. In some embodiments, at least 67% of the chiral internucleotidic linkages in the core region are Rp. In some embodiments, at least 70% of the chiral internucleotidic linkages in the core region are Rp. In some embodiments, at least 75% of the chiral internucleotidic linkages in the core region are Rp. In some embodiments, at least 80% of the chiral internucleotidic linkages in the core region are Rp. In some embodiments, at least 85% of the chiral internucleotidic linkages in the core region are Rp. In some embodiments, each chiral internucleotidic linkages in the core region is Rp.

In some embodiments, at least 1 core region internucleotidic linkage is Rp. In some embodiments, at least 2 core region internucleotidic linkages are Rp. In some embodiments, at least 3 core region internucleotidic linkages are Rp. In some embodiments, at least 4 core region internucleotidic linkages are Rp. In some embodiments, at least 5 core region internucleotidic linkages are Rp. In some embodiments, at least 6 core region internucleotidic linkages are Rp. In some embodiments, at least 7 core region internucleotidic linkages are Rp. In some embodiments, at least 8 core region internucleotidic linkages are Rp. In some embodiments, at least 9 core region internucleotidic linkages are Rp. In some embodiments, at least 10 core region internucleotidic linkages are Rp. In some embodiments, at least 11 core region internucleotidic linkages are Rp. In some embodiments, at least 12 core region internucleotidic linkages are Rp. In some embodiments, at least 13 core region internucleotidic linkages are Rp. In some embodiments, at least 14 core region internucleotidic linkages are Rp. In some embodiments, at least 15 core region internucleotidic linkages are Rp. In some embodiments, at least 16 core region internucleotidic linkages are Rp. In some embodiments, at least 17 core region internucleotidic linkages are Rp. In some embodiments, at least 18 core region internucleotidic linkages are Rp. In some embodiments, at least 19 core region internucleotidic linkages are Rp. In some embodiments, at least 20 core region internucleotidic linkages are Rp. In some embodiments, at least 21 core region internucleotidic linkages are Rp. In some embodiments, at least two core region internucleotidic linkages are Rp. In some embodiments, the Rp internucleotidic linkages are consecutive.

In some embodiments, a core comprises one or more modified sugar moieties. In some embodiments, a core comprises two or more modified sugar moieties. In some embodiments, a core comprises three or more modified sugar moieties. In some embodiments, a core comprises four or more modified sugar moieties. In some embodiments, a core comprises five or more modified sugar moieties. In some embodiments, a core comprises six or more modified sugar moieties. In some embodiments, a core comprises seven or more modified sugar moieties. In some embodiments, a core comprises eight or more modified sugar moieties. In some embodiments, a core comprises nine or more modified sugar moieties. In some embodiments, a core comprises ten or more modified sugar moieties. In some embodiments, a core comprises 11 or more modified sugar moieties. In some embodiments, a core comprises 12 or more modified sugar moieties. In some embodiments, a core comprises 13 or more modified sugar moieties. In some embodiments, a core comprises 14 or more modified sugar moieties. In some embodiments, a core comprises 15 or more modified sugar moieties. In some embodiments, a core comprises 16 or more modified sugar moieties. In some embodiments, a core comprises 17 or more modified sugar moieties. In some embodiments, a core comprises 18 or more modified sugar moieties. In some embodiments, a core comprises 19 or more modified sugar moieties. In some embodiments, a core comprises 20 or more modified sugar moieties. In some embodiments, a core comprises 21 or more modified sugar moieties. In some embodiments, a core comprises 22 or more modified sugar moieties. In some embodiments, a core comprises 23 or more modified sugar moieties. In some embodiments, a core comprises 24 or more modified sugar moieties. In some embodiments, a core comprises 25 or more modified sugar moieties. In some embodiments, a core comprises 30 or more modified sugar moieties. In some embodiments, a core comprises 35 or more modified sugar moieties. In some embodiments, a 2'-modification is 2'-$OR^1$. In some embodiments, a 2'-modification is 2'-OMe.

In some embodiments, a core comprises one or more 2'-modified sugar moieties. In some embodiments, a core comprises two or more 2'-modified sugar moieties. In some embodiments, a core comprises three or more 2'-modified sugar moieties. In some embodiments, a core comprises four or more 2'-modified sugar moieties. In some embodiments, a core comprises five or more 2'-modified sugar moieties. In some embodiments, a core comprises six or more 2'-modified sugar moieties. In some embodiments, a core comprises seven or more 2'-modified sugar moieties. In some embodiments, a core comprises eight or more 2'-modified sugar moieties. In some embodiments, a core comprises nine or more T-modified sugar moieties. In some embodiments, a core comprises ten or more 2'-modified sugar moieties. In some embodiments, a core comprises 11 or more 2'-modified sugar moieties. In some embodiments, a core comprises 12 or more 2'-modified sugar moieties. In some embodiments, a core comprises 13 or more 2'-modified sugar moieties. In some embodiments, a core comprises 14 or more 2'-modified sugar moieties. In some embodiments, a core comprises 15 or more 2'-modified sugar moieties. In some embodiments, a core comprises 16 or more T-modified sugar moieties. In some embodiments, a core comprises 17 or more 2'-modified sugar moieties. In some embodiments, a core comprises 18 or more 2'-modified sugar moieties. In some embodiments, a core comprises 19 or more 2'-modified sugar moieties. In some embodiments, a core comprises 20 or more 2'-modified sugar moieties. In some embodiments, a core comprises 21 or more 2'-modified sugar moieties. In some embodiments, a core comprises 22 or more 2'-modified sugar moieties. In some embodiments, a core comprises 23 or more T-modified sugar moieties. In some embodiments, a core comprises 24 or more 2'-modified sugar moieties. In some embodiments, a core comprises 25 or more 2'-modified sugar moieties. In some embodiments, a core comprises 30 or more 2'-modified sugar moieties. In some embodiments, a core comprises 35 or more 2'-modified sugar moieties. In some embodiments, a 2'-modification is 2'-OR$^1$. In some embodiments, a 2'-modification is 2'-OMe.

In some embodiments, a wing-core-wing (i.e., X—Y—X) motif is represented numerically as, e.g., 5-10-4, meaning the wing to the 5'-end of the core is 5 bases in length, the core region is 10 bases in length, and the wing region to the 3'-end of the core is 4-bases in length. In some embodiments, a wing-core-wing motif is any of, e.g. 2-16-2, 3-14-3, 4-12-4, 5-10-5, 2-9-6, 3-9-3, 3-9-4, 3-9-5, 4-7-4, 4-9-3, 4-9-4, 4-9-5, 4-10-5, 4-11-4, 4-11-5, 5- 7-5, 5-8-6, 8-7-5, 7-7-6, 5-9-3, 5-9-5, 5-10-4, 5-10-5, 6-7-6, 6-8-5, and 6-9-2, etc. In certain embodiments, a wing-core-wing motif is 5-10-5. In certain embodiments, a wing-core-wing motif is 7-7-6. In certain embodiments, a wing-core-wing motif is 8-7-5.

In some embodiments, a wing-core motif is 5-15, 6-14, 7-13, 8-12, 9-12, etc. In some embodiments, a core-wing motif is 5-15, 6-14, 7-13, 8-12, 9-12, etc.

In some embodiments, the internucleosidic linkages of provided CpG oligonucleotides of such wing-core-wing (i.e., X—Y—X) motifs are all chiral, modified phosphate linkages. In some embodiments, the internucleosidic linkages of provided CpG oligonucleotides of such wing-core-wing (i.e., X—Y—X) motifs are all chiral phosphorothioate internucleotidic linkages. In some embodiments, chiral internucleotidic linkages of provided CpG oligonucleotides of such wing-core-wing motifs are at least about 10, 20, 30, 40, 50, 50, 70, 80, or 90% chiral, modified phosphate internucleotidic linkages. In some embodiments, chiral internucleotidic linkages of provided CpG oligonucleotides of such wing-core-wing motifs are at least about 10, 20, 30, 40, 50, 60, 70, 80, or 90% chiral phosphorothioate internucleotidic linkages. In some embodiments, chiral internucleotidic linkages of provided CpG oligonucleotides of such wing-core-wing motifs are at least about 10, 20, 30, 40, 50, 50, 70, 80, or 90% chiral phosphorothioate internucleotidic linkages of the Sp conformation.

In some embodiments, each wing region of a wing-core-wing motif optionally contains chiral, modified phosphate internucleotidic linkages. In some embodiments, each wing region of a wing-core-wing motif optionally contains chiral phosphorothioate internucleotidic linkages. In some embodiments, each wing region of a wing-core-wing motif contains chiral phosphorothioate internucleotidic linkages. In some embodiments, the two wing regions of a wing-core-wing motif have the same internucleotidic linkage stereochemistry. In some embodiments, the two wing regions have different internucleotidic linkage stereochemistry. In some embodiments, each internucleotidic linkage in the wings is independently a chiral internucleotidic linkage.

In some embodiments, the core region of a wing-core-wing motif optionally contains chiral, modified phosphate internucleotidic linkages. In some embodiments, the core region of a wing-core-wing motif optionally contains chiral phosphorothioate internucleotidic linkages. In some embodiments, the core region of a wing-core-wing motif comprises a repeating pattern of internucleotidic linkage stereochemistry. In some embodiments, the core region of a wing-core-wing motif has a repeating pattern of internucleotidic linkage stereochemistry. In some embodiments, the core region of a wing-core-wing motif comprises repeating pattern of internucleotidic linkage stereochemistry, wherein the repeating pattern is (Sp)mRp or Rp(Sp)m, wherein m is 1-50. In some embodiments, the core region of a wing-core-wing motif comprises repeating pattern of internucleotidic linkage stereochemistry, wherein the repeating pattern is (Sp)mRp or Rp(Sp)m, wherein m is 1-50. In some embodiments, the core region of a wing-core-wing motif comprises repeating pattern of internucleotidic linkage stereochemistry, wherein the repeating pattern is (Sp)mRp, wherein m is 1-50. In some embodiments, the core region of a wing-core-wing motif comprises repeating pattern of internucleotidic linkage stereochemistry, wherein the repeating pattern is Rp(Sp)m, wherein m is 1-50. In some embodiments, the core region of a wing-core-wing motif has repeating pattern of internucleotidic linkage stereochemistry, wherein the repeating pattern is (Sp)mRp or Rp(Sp)m, wherein m is 1-50. In some embodiments, the core region of a wing-core-wing motif has repeating pattern of internucleotidic linkage stereochemistry, wherein the repeating pattern is (Sp)mRp, wherein m is 1-50. In some embodiments, the core region of a wing-core-wing motif has repeating pattern of internucleotidic linkage stereochemistry, wherein the repeating pattern is Rp(Sp)m, wherein m is 1-50. In some embodiments, the core region of a wing-core-wing motif has repeating pattern of internucleotidic linkage stereochemistry, wherein the repeating pattern is a motif comprising at least 33% of internucleotidic linkage in the S conformation. In some embodiments, the core region of a wing-core-wing motif has repeating pattern of internucleotidic linkage stereochemistry, wherein the repeating pattern is a motif comprising at least 50% of internucleotidic linkage in the S conformation. In some embodiments, the core region of a wing-core-wing motif has repeating pattern of internucleotidic linkage stereochemistry, wherein the repeating pattern is a motif comprising at least 66% of internucleotidic linkage in the S conformation. In some embodiments, the core region of a wing-core-wing motif has repeating pattern of internucleotidic linkage stereochemistry, wherein the repeating pattern is a repeating triplet motif selected from RpRpSp and SpSpRp. In some embodiments, the core region of a wing-core-wing motif has repeating pattern of internucleotidic linkage stereochemistry, wherein the repeating pattern is a repeating RpRpSp. In some embodiments, the core region of a wing-core-wing motif has repeating pattern of internucleotidic linkage stereochemistry, wherein the repeating pattern is a repeating SpSpRp.

In some embodiments, the present disclosure provides a chirally controlled CpG oligonucleotide composition of a CpG oligonucleotide type whose pattern of backbone chiral centers in the core region comprises (Sp)mRp or Rp(Sp)m. In some embodiments, the present disclosure provides a chirally controlled CpG oligonucleotide composition of a CpG oligonucleotide type whose pattern of backbone chiral centers in the core region comprises Rp(Sp)m. In some embodiments, the present disclosure provides a chirally controlled CpG oligonucleotide composition of a CpG oligonucleotide type whose pattern of backbone chiral centers in the core region comprises (Sp)mRp. In some embodiments, m is 2. In some embodiments, the present disclosure provides a chirally controlled CpG oligonucleotide composition of a CpG oligonucleotide type whose pattern of backbone chiral centers in the core region comprises Rp(Sp)$_2$. In some embodiments, the present disclosure provides a chirally controlled CpG oligonucleotide composition of a CpG oligonucleotide type whose pattern of backbone chiral centers in the core region comprises (Sp)$_2$Rp(Sp)$_2$. In some embodiments, the present disclosure provides a chirally controlled CpG oligonucleotide composition of a CpG oligonucleotide type whose pattern of backbone chiral centers in the core region comprises (Rp)$_2$Rp(Sp)$_2$. In some embodiments, the present disclosure provides a chirally controlled CpG oligonucleotide composition of a CpG oligonucleotide type whose pattern of backbone chiral centers in the core region comprises RpSpRp(Sp)$_2$. In some embodiments, the present disclosure provides a chirally controlled CpG oligonucleotide composition of a CpG oligonucleotide type whose pattern of backbone chiral centers in the core region comprises SpRpRp(Sp)$_2$. In some embodiments, the present disclosure provides a chirally controlled CpG oligonucleotide composition of a CpG oligonucleotide type whose pattern of backbone chiral centers in the core region comprises (Sp)$_2$Rp.

In some embodiments, the present disclosure provides a chirally controlled CpG oligonucleotide composition of a CpG oligonucleotide type whose pattern of backbone chiral centers comprises (Sp)mRp or Rp(Sp)m. In some embodiments, the present disclosure provides a chirally controlled CpG oligonucleotide composition of a CpG oligonucleotide type whose pattern of backbone chiral centers comprises Rp(Sp)m. In some embodiments, the present disclosure provides a chirally controlled CpG oligonucleotide composition of a CpG oligonucleotide type whose pattern of backbone chiral centers comprises (Sp)mRp. In some embodiments, m is 2, In some embodiments, the present disclosure provides a chirally controlled CpG oligonucleotide composition of a CpG oligonucleotide type whose pattern of backbone chiral centers comprises Rp(Sp)$_2$. In some embodiments, the present disclosure provides a chirally controlled CpG oligonucleotide composition of a CpG oligonucleotide type whose pattern of backbone chiral centers comprises (Sp)$_2$Rp(Sp)$_2$. In some embodiments, the present disclosure provides a chirally controlled CpG oligonucleotide composition of a CpG oligonucleotide type whose pattern of backbone chiral centers comprises (Rp)$_2$Rp(Sp)$_2$. In some embodiments, the present disclosure provides a chirally controlled CpG oligonucleotide composition of a CpG oligonucleotide type whose pattern of backbone chiral centers comprises RpSpRp(Sp)$_2$. In some embodiments, the present disclosure provides a chirally controlled CpG oligonucleotide composition of a CpG oligonucleotide type whose pattern of backbone chiral centers comprises SpRpRp(Sp)$_2$. In some embodiments, the present disclosure provides a chirally controlled CpG oligonucleotide composition of a CpG oligonucleotide type whose pattern of backbone chiral centers comprises (Sp)$_2$Rp.

As defined herein, m is 1-50. In some embodiments, m is 1. In some embodiments, m is 2-50. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12, In some embodiments, m is 13. In some embodiments, m is 14. In some embodiments, m is 15. In some embodiments, m is 16. In some embodiments, m is 17. In some embodiments, m is 18, In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is greater than 25.

In some embodiments, a repeating pattern is (Sp)m(Rp)n, wherein n is 1-10, and m is independently as defined above and described herein. In some embodiments, the present disclosure provides a chirally controlled CpG oligonucleotide composition of a CpG oligonucleotide type whose pattern of backbone chiral centers comprises (Sp)m(Rp)n. In some embodiments, the present disclosure provides a chirally controlled CpG oligonucleotide composition of a CpG oligonucleotide type whose pattern of backbone chiral centers in the core region comprises (Sp)m(Rp)n. In some embodiments, a repeating pattern is (Rp)n(Sp)m, wherein n is 1-10, and m is independently as defined above and described herein. In some embodiments, the present disclosure provides a chirally controlled CpG oligonucleotide composition of a CpG oligonucleotide type whose pattern of backbone chiral centers comprises (Rp)n(Sp)m. In some embodiments, the present disclosure provides a chirally controlled CpG oligonucleotide composition of a CpG oligonucleotide type whose pattern of backbone chiral centers in the core region comprises (Rp)n(Sp)m. In some embodiments, (Rp)n(Sp)m is (Rp)(Sp)$_2$. In some embodiments, (Sp)n(Rp)m is (Sp)$_2$(Rp).

In some embodiments, the present disclosure provides a chirally controlled CpG oligonucleotide composition of a CpG oligonucleotide type whose pattern of backbone chiral centers comprises (Sp)m(Rp)n(Sp)t. In some embodiments, a repeating pattern is (Sp)m(Rp)n(Sp)t, wherein n is 1-10, t is 1-50, and m is as defined above and described herein. In some embodiments, the present disclosure provides a chirally controlled CpG oligonucleotide composition of a CpG oligonucleotide type whose pattern of backbone chiral centers in the core region comprises (Sp)m(Rp)n(Sp)t. In some embodiments, a repeating pattern is (Sp)t(Rp)n(Sp)m, wherein n is 1-10, t is 1-50, and m is as defined above and described herein. In some embodiments, the present disclosure provides a chirally controlled CpG oligonucleotide composition of a CpG oligonucleotide type whose pattern of backbone chiral centers comprises (Sp)t(Rp)n(Sp)m. In some embodiments, the present disclosure provides a chirally controlled CpG oligonucleotide composition of a CpG oligonucleotide type whose pattern of backbone chiral centers in the core region comprises (Sp)t(Rp)n(Sp)m.

In some embodiments, a repeating pattern is (Np)t(Rp)n(Sp)m, wherein n is 1-10, t is 1-50, Np is independently Rp or Sp, and m is as defined above and described herein. In some embodiments, the present disclosure provides a chirally controlled CpG oligonucleotide composition of a CpG oligonucleotide type whose pattern of backbone chiral centers comprises (Np)t(Rp)n(Sp)m. In some embodiments, the present disclosure provides a chirally controlled CpG oligonucleotide composition of a CpG oligonucleotide type whose pattern of backbone chiral centers in the core region comprises (Np)t(Rp)n(Sp)m. In some embodiments, a repeating pattern is (Np)m(Rp)n(Sp)t, wherein n is 1-10, t is 1-50, Np is independently Rp or Sp, and m is as defined above and described herein. In some embodiments, the present disclosure provides a chirally controlled CpG oligonucleotide composition of a CpG oligonucleotide type whose pattern of backbone chiral centers comprises (Np)m(Rp)n(Sp)t. In some embodiments, the present disclosure provides a chirally controlled CpG oligonucleotide composition of a CpG oligonucleotide type whose pattern of backbone chiral centers in the core region comprises (Np)m(Rp)n(Sp)t. In some embodiments, Np is Rp. In some embodiments, Np is Sp. In some embodiments, all Np are the same. In some embodiments, all Np are Sp. In some embodiments, at least one Np is different from the other Np. In some embodiments, t is 2.

As defined herein, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

As defined herein, t is 1-50. In some embodiments, t is 1. In some embodiments, t is 2-50. In some embodiments, t is 2, 3, 4, 5, 6, 7 or 8. In some embodiments, t is 3, 4, 5, 6, 7 or 8. In some embodiments, t is 4, 5, 6, 7 or 8. In some embodiments, t is 5, 6, 7 or 8. In some embodiments, t is 6, 7 or 8. In some embodiments, t is 7 or 8. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20. In some embodiments, t is 21. In some embodiments, t is 22. In some embodiments, t is 23. In some embodiments, t is 24. In some embodiments, t is 25. In some embodiments, t is greater than 25.

In some embodiments, at least one of m and t is greater than 2. In some embodiments, at least one of m and t is greater than 3. In some embodiments, at least one of m and t is greater than 4. In some embodiments, at least one of m and t is greater than 5. In some embodiments, at least one of m and t is greater than 6. In some embodiments, at least one of m and t is greater than 7. In some embodiments, at least one of m and t is greater than 8. In some embodiments, at least one of m and t is greater than 9. In some embodiments, at least one of m and t is greater than 10. In some embodiments, at least one of m and t is greater than 11. In some embodiments, at least one of m and t is greater than 12. In some embodiments, at least one of m and t is greater than 13. In some embodiments, at least one of m and t is greater than 14. In some embodiments, at least one of m and t is greater than 15. In some embodiments, at least one of m and t is greater than 16. In some embodiments, at least one of m and t is greater than 17. In some embodiments, at least one of m and t is greater than 18. In some embodiments, at least one of m and t is greater than 19. In some embodiments, at least one of m and t is greater than 20. In some embodiments, at least one of m and t is greater than 21. In some embodiments, at least one of m and t is greater than 22. In some embodiments, at least one of m and t is greater than 23. In some embodiments, at least one of m and t is greater than 24, In some embodiments, at least one of m and t is greater than 25.

In some embodiments, each one of m and t is greater than 2. In some embodiments, each one of m and t is greater than 3. In some embodiments, each one of m and t is greater than 4. In some embodiments, each one of m and t is greater than 5. In some embodiments, each one of m and t is greater than 6. In some embodiments, each one of m and t is greater than 7. In some embodiments, each one of m and t is greater than 8. In some embodiments, each one of m and t is greater than 9. In some embodiments, each one of m and t is greater than 10. In some embodiments, each one of m and t is greater than 11. In some embodiments, each one of m and t is greater than 12. In some embodiments, each one of m and t is greater than 13. In some embodiments, each one of m and t is greater than 14. In some embodiments, each one of m and t is greater than 15. In some embodiments, each one of m and t is greater than 16. In some embodiments, each one of m and t is greater than 17. In some embodiments, each one of m and t is greater than 18. In some embodiments, each one of m and t is greater than 19, In some embodiments, each one of m and t is greater than 20.

In some embodiments, the sum of m and t is greater than 3. In some embodiments, the sum of m and t is greater than 4. In some embodiments, the sum of m and t is greater than 5. In some embodiments, the sum of m and t is greater than 6. In some embodiments, the sum of m and t is greater than 7. In some embodiments, the sum of m and t is greater than 8. In some embodiments, the sum of m and t is greater than 9. In some embodiments, the sum of m and t is greater than 10. In some embodiments, the sum of m and t is greater than 11. In some embodiments, the sum of m and t is greater than 12. In some embodiments, the sum of m and t is greater than 13. In some embodiments, the sum of m and t is greater than 14. In some embodiments, the sum of m and t is greater than 15. In some embodiments, the sum of m and t is greater than 16. In some embodiments, the sum of m and t is greater than 17. In some embodiments, the sum of m and t is greater than 18. In some embodiments, the sum of m and t is greater than 19. In some embodiments, the sum of m and t is greater than 20. In some embodiments, the sum of m and t is greater than 21. In some embodiments, the sum of m and t is greater than 22. In some embodiments, the sum of m and t is greater than 23. In some embodiments, the sum of m and t is greater than 24. In some embodiments, the sum of m and t is greater than 25.

In some embodiments, n is 1, and at least one of m and t is greater than 1. In some embodiments, n is 1 and each of m and t is independently greater than 1. In some embodiments, m>n and t>n. In some embodiments, (Sp)m(Rp)n(Sp)t is (Sp)$_2$Rp(Sp)$_2$. In some embodiments, (Sp)t(Rp)n(Sp)m is (Sp)$_2$Rp(Sp)$_2$. In some embodiments, (Sp)t(Rp)n(Sp)m is SpRp(Sp)$_2$. In some embodiments, (Np)t(Rp)n (Sp)m is (Np)tRp(Sp)m. In some embodiments, (Np)t(Rp)n(Sp)m is (Np)$_2$Rp(Sp)m. In some embodiments, (Np)t(Rp)n(Sp)m is (Rp)$_2$Rp(Sp)m. In some embodiments, (Np)t(Rp)n(Sp)m is (Sp)$_2$Rp(Sp)m. In some embodiments, (Np)t(Rp)n(Sp)m is RpSpRp(Sp)m. In some embodiments, (Np)t(Rp)n(Sp)m is SpRpRp(Sp)m.

In some embodiments, (Sp)t(Rp)n(Sp)m is SpRpSpSp. In some embodiments, (Sp)t(Rp)n(Sp)m is (Sp)$_2$Rp(Sp)$_2$. In some embodiments, (Sp)t(Rp)n(Sp)m is (Sp)$_3$Rp(Sp)$_3$. In some embodiments, (Sp)t(Rp)n(Sp)m is (Sp)$_4$Rp(Sp)$_4$. In some embodiments, (Sp)t(Rp)n(Sp)m is (Sp)tRp(Sp)$_5$. In some embodiments, (Sp)t(Rp)n(Sp)m is SpRp(Sp)$_5$. In some embodiments, (Sp)t(Rp)n(Sp)m is (Sp)$_2$Rp(Sp)$_5$. In some embodiments, (Sp)t(Rp)n(Sp)m is (Sp)$_3$Rp(Sp)$_5$. In some embodiments, (Sp)t(Rp)n(Sp)m is (Sp)$_4$Rp(Sp)$_5$. In some embodiments, (Sp)t(Rp)n(Sp)m is (Sp)$_5$Rp(Sp)$_5$.

In some embodiments, (Sp)m(Rp)n(Sp)t is (Sp)$_2$Rp(Sp)$_2$. In some embodiments, (Sp)m(Rp)n(Sp)t is (Sp)$_3$Rp(Sp)$_3$. In some embodiments, (Sp)m(Rp)n(Sp)t is (Sp)$_4$Rp(Sp)$_4$. In some embodiments, (Sp)m(Rp)n(Sp)t is (Sp)mRp(Sp)$_5$. In some embodiments, (Sp)m(Rp)n(Sp)t is (Sp)$_2$Rp(Sp)$_5$. In some embodiments, (Sp)m(Rp)n(Sp)t is (Sp)$_3$Rp(Sp)$_5$. In some embodiments, (Sp)m(Rp)n(Sp)t is (Sp)$_4$Rp(Sp)$_5$. In some embodiments, (Sp)m(Rp)n(Sp)t is (Sp)$_5$Rp(Sp)$_5$.

In some embodiments, a core region comprises at least one Rp internucleotidic linkage, in some embodiments, a core region of a wing-core-wing motif comprises at least one Rp internucleotidic linkage. In some embodiments, a core region comprises at least one Rp phosphorothioate internucleotidic linkage. In some embodiments, a core region of a wing-core-wing motif comprises at least one Rp phosphorothioate internucleotidic linkage. In some embodiments, a core region of a wing-core-wing motif comprises only one Rp phosphorothioate internucleotidic linkage. In some embodiments, a core region motif comprises at least two Rp internucleotidic linkages. In some embodiments, a core region of a wing-core-wing motif comprises at least two Rp internucleotidic linkages. In some embodiments, a core region of a wing-core-wing motif comprises at least two Rp phosphorothioate internucleotidic linkages. In some embodiments, a core region comprises at least three Rp internucleotidic linkages. In some embodiments, a core region of a wing-core-wing motif comprises at least three Rp internucleotidic linkages. In some embodiments, a core region comprises at least three Rp phosphorothioate internucleotidic linkages. In some embodiments, a core region of a wing-core-wing motif comprises at least three Rp phosphorothioate internucleotidic linkages. In some embodiments, a core region comprises at least 4, 5, 6, 7, 8, 9, or 10 Rp internucleotidic linkages. In some embodiments, a core region of a wing-core-wing motif comprises at least 4, 5, 6, 7, 8, 9, or 10 Rp internucleotidic linkages. In some embodiments, a core region comprises at least 4, 5, 6, 7, 8, 9, or 10 Rp phosphorothioate internucleotidic linkages. In some embodiments, a core region of a wing-core-wing motif comprises at least 4, 5, 6, 7, 8, 9, or 10 Rp phosphorothioate internucleotidic linkages.

In some embodiments, a wing region comprises 2'-modifications of sugar moieties that differ from a core region. In some embodiments, a wing region comprises the same type of 2'-modifications that differ from a core region. In some embodiments, a wing region comprises 2'-F which is absent from a core region. In some embodiments, a wing region comprises a pattern of 2'-F which is absent from a core region. In some embodiments, a wing region comprises a level of 2'-F which differs from a core region. In some embodiments, a level is absolute as measured by the number of 2'-F modifications. In some embodiments, a level is relative as measured by the percentage of 2'-F modifications. In some embodiments, a wing region differs from a core region in that it contains less of a 2'-modification presented in a core region, as measured by the number and/or percentage of such 2'-modifications. In some embodiments, a wing region contains less of a 2'-OR$^1$ modification in a core region. In some embodiments, a wing region contains less of a 2'-OMe modification in a core region. In some embodiments, a wing region differs from a core region in that it contains less of unmodified sugar moieties presented in a core region, as measured by the number and/or percentage of such 2'-modifications.

In some embodiments, provided CpG oligonucleotides comprise two or more wing regions and a core region, for example, provided CpG oligonucleotides can comprise a wing-core-wing structure. In some embodiments, each wing region comprises 2'-modifications of sugar moieties that differ from a core region. In some embodiments, each wing region comprises the same type of 2'-modifications that differ from a core region. In some embodiments, each wing region comprises 2'-F which is absent from a core region. In some embodiments, each wing region comprises a pattern of 2'-F which is absent from a core region. In some embodiments, each wing region comprises a level of 2'-F which differs from a core region. In some embodiments, a level is absolute as measured by the number of 2'-F modifications. In some embodiments, a level is relative as measured by the percentage of 2'-F modifications. In some embodiments, each wing region differs from a core region in that it contains less of a 2'-modification presented in a core region, as measured by the number and/or percentage of such 2'-modifications. In some embodiments, each wing region contains less of a 2'-OR$^1$ modification in a core region. In some embodiments, each wing region contains less of a 2'-OMe modification in a core region. In some embodiments, each wing region differs from a core region in that it contains less of unmodified sugar moieties presented in a core region, as measured by the number and/or percentage of such 2'-modifications.

In certain embodiments, a wing-core-wing motif is a 5-10-5 motif wherein the residues at each wing region are 2'-modified residues. In certain embodiments, a wing-core-wing motif is a 5-10-5 motif wherein the residues at each wing region are 2'-OR$^1$-modified residues. In certain embodiments, a wing-core-wing motif is a 5-10-5 motif wherein the residues at each wing region are 2'-MOE-modified residues. In certain embodiments, a wing-core-wing motif is a 5-10-5 motif wherein the residues at each wing region are 2'-OMe-modified residues. In certain embodiments, a wing-core-wing motif is a 5-10-5 motif wherein the residues at each wing region are 2'-F-modified residues. In certain embodiments, a wing-core-wing motif is a 5-10-5 motif wherein the residues in the core region are 2'-deoxyribonucleoside residues. In certain embodiments, a wing-core-wing motif is a 5-10-5 motif, wherein all internucleotidic linkages are phosphorothioate linkages. In certain embodiments, a wing-core-wing motif is a 5-10-5 motif, wherein all internucleotidic linkages are chiral phosphorothioate linkages. In certain embodiments, a wing-core-wing motif is a 5-10-5 motif wherein the residues at each wing region are 2'-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-OR$^1$-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-MOE-modified residues, the residues in the core region are T-deoxyribonucleoside residues, and all internucleotidic linkages in the core region are chiral phosphorothioate linkages. In certain embodiments, a wing-core-wing motif is a 5-10-5 motif wherein the residues at each wing region are 2'-OMe-modified residues, the residues in the core region are 2'-deoxyribonucleoside residues, and all internucleotidic linkages in the core region are chiral phosphorothioate linkages.

In some embodiments, residues at the "X" wing region are not 2'-MOE-modified residues. In certain embodiments, a wing-core motif is a motif wherein the residues at the "X" wing region are not 2'-MOE-modified residues. In certain embodiments, a core-wing motif is a motif wherein the residues at the "X" wing region are not 2'-MOE-modified residues. In certain embodiments, a wing-core-wing motif is a motif wherein the residues at each "X" wing region are not 2'-MOE-modified residues. In certain embodiments, a wing-core-wing motif is a 5-10-5 motif wherein the residues at each "X" wing region are not 2'-MOE-modified residues. In certain embodiments, a wing-core-wing motif is a 5-10-5 motif wherein the residues in the core "Y" region are 2'-deoxyribonucleoside residues. In certain embodiments, a wing-core-wing motif is a 5-10-5 motif, wherein all internucleotidic linkages are phosphorothioate internucleotidic linkages. In certain embodiments, a wing-core-wing motif is a 5-10-5 motif, wherein all internucleotidic linkages are chiral phosphorothioate internucleotidic linkages. In certain embodiments, a wing-core-wing motif is a 5-10-5 motif wherein the residues at each "X" wing region are not 2'-MOE-modified residues, the residues in the core "Y" region are T-deoxyribonucleoside, and all internucleotidic linkages are chiral phosphorothioate internucleotidic linkages.

In some embodiments, a chiral, modified phosphate linkage is a chiral phosphorothioate linkage, i.e., phosphorothioate internucleotidic linkage. In some embodiments, a core region comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10%, 20%, 30%, 40%, 50%, 60%, 70%, 80%, or 90% chiral phosphorothioate internucleotidic linkages of a core region are of the Sp conformation. In some embodiments, at least about 10% chiral phosphorothioate internucleotidic linkages of a core region are of the Sp conformation. In some embodiments, at least about 20% chiral phosphorothioate internucleotidic linkages of a core region are of the Sp conformation. In some embodiments, at least about 30% chiral phosphorothioate internucleotidic linkages of a core region are of the Sp conformation. In some embodiments, at least about 40% chiral phosphorothioate internucleotidic linkages of a core region are of the Sp conformation. In some embodiments, at least about 50% chiral phosphorothioate internucleotidic linkages of a core region are of the Sp conformation. In some embodiments, at least about 60% chiral phosphorothioate internucleotidic linkages of a core region are of the Sp conformation. In some embodiments, at least about 70% chiral phosphorothioate internucleotidic linkages of a core region are of the Sp conformation. In some embodiments, at least about 80% chiral phosphorothioate internucleotidic linkages of a core region are of the Sp conformation. In some embodiments, at least about 90% chiral phosphorothioate internucleotidic linkages of a core region are of the Sp conformation. In some embodiments, at least about 95% chiral phosphorothioate internucleotidic linkages of a core region are of the Sp conformation.

In some embodiments, at least about 10%, 20%, 30%, 40%, 50%, 60%, 70%, 80%, or 90% chiral phosphorothioate internucleotidic linkages of a core region are of the Rp conformation. In some embodiments, at least about 10% chiral phosphorothioate internucleotidic linkages of a core region are of the Rp conformation. In some embodiments, at least about 20% chiral phosphorothioate internucleotidic linkages of a core region are of the Rp conformation. In some embodiments, at least about 30% chiral phosphorothioate internucleotidic linkages of a core region are of the Rp conformation. In some embodiments, at least about 40% chiral phosphorothioate internucleotidic linkages of a core region are of the Rp conformation. In some embodiments, at least about 50% chiral phosphorothioate internucleotidic linkages of a core region are of the Rp conformation. In some embodiments, at least about 60% chiral phosphorothioate internucleotidic linkages of a core region are of the Rp conformation. In some embodiments, at least about 70% chiral phosphorothioate internucleotidic linkages of a core region are of the Rp conformation. In some embodiments, at least about 80% chiral phosphorothioate internucleotidic linkages of a core region are of the Rp conformation. In some embodiments, at least about 90% chiral phosphorothioate internucleotidic linkages of a core region are of the Rp conformation. In some embodiments, at least about 95% chiral phosphorothioate internucleotidic linkages of a core region are of the Rp conformation.

In some embodiments, less than about 10%, 20%, 30%, 40%, 50%, 60%, 70%, 80%, or 90% chiral phosphorothioate internucleotidic linkages of a core region are of the Rp conformation. In some embodiments, less than about 10% chiral phosphorothioate internucleotidic linkages of a core region are of the Rp conformation. In some embodiments, less than about 20% chiral phosphorothioate internucleotidic linkages of a core region are of the Rp conformation. In some embodiments, less than about 30% chiral phosphorothioate internucleotidic linkages of a core region are of the Rp conformation. In some embodiments, less than about 40% chiral phosphorothioate internucleotidic linkages of a core region are of the Rp conformation. In some embodiments, less than about 50% chiral phosphorothioate internucleotidic linkages of a core region are of the Rp conformation. In some embodiments, less than about 60% chiral phosphorothioate internucleotidic linkages of a core region are of the Rp conformation. In some embodiments, less than about 70% chiral phosphorothioate internucleotidic linkages of a core region are of the Rp conformation. In some embodiments, less than about 80% chiral phosphorothioate internucleotidic linkages of a core region are of the Rp conformation. In some embodiments, less than about 90% chiral phosphorothioate internucleotidic linkages of a core region are of the Rp conformation. In some embodiments, less than about 95% chiral phosphorothioate internucleotidic linkages of a core region are of the Rp conformation. In some embodiments, a core region has only one Rp chiral phosphorothioate internucleotidic linkages. In some embodiments, a core region has only one Rp chiral phosphorothioate internucleotidic linkages, wherein all internucleotide linkages are chiral phosphorothioate internucleotidic linkages.

In some embodiments, provided CpG oligonucleotides are blockmers. In some embodiments, provided CpG oligonucleotide are altmers. In some embodiments, provided CpG oligonucleotides are altmers comprising alternating blocks. In some embodiments, a blockmer or an altmer can be defined by chemical modifications (including presence or absence), e.g., base modifications, sugar modification, internucleotidic linkage modifications, stereochemistry, etc. Example chemical modifications, stereochemistry and patterns thereof for a block and/or an alternating unit include but are not limited to those described in this disclosure, such as those described for a wing, a core, a CpG oligonucleotide, etc. In some embodiments, a blockmer comprises a pattern of ..SS..RR..SS..RR... In some embodiments, an altmer comprises a pattern of SRSRSRSR.

In some embodiments, a pattern of backbone chiral center, e.g., of a wing, a core, a block, comprises one or more (Rp)p(Sp)x(Rp)q(Sp)y, wherein each of p, x, q, y is independently 0-50, p+q>0, and x+y>0.

In some embodiments, a provided pattern of backbone chiral centers comprises repeating (Sp)m(Rp)n, (Rp)n(Sp)m, (Np)t(Rp)n(Sp)m, or (Sp)t(Rp)n(Sp)m units. In some embodiments, a repeating unit is (Sp)m(Rp)n. In some embodiments, a repeating unit is SpRp. In some embodiments, a repeating unit is SpSpRp. In some embodiments, a repeating unit is SpRpRp. In some embodiments, a repeating unit is RpRpSp. In some embodiments, a repeating unit is (Rp)n(Sp)m. In some embodiments, a repeating unit is (Np)t(Rp)n(Sp)m. In some embodiments, a repeating unit is (Sp)t(Rp)n(Sp)m.

In some embodiments, a provided pattern of backbone chiral centers comprises (Rp/Sp)x-(All Rp or All Sp)-(Rp/Sp)y. In some embodiments, a provided pattern of backbone chiral centers comprises (Rp/Sp)-(All Rp or All Sp)-(Rp/Sp). In some embodiments, a provided pattern of backbone chiral centers comprises (Rp)x-(All Sp)-(Rp)y. In some embodiments, a provided pattern of backbone chiral centers comprises (Rp)-(All Sp)-(Rp). In some embodiments, a provided pattern of backbone chiral centers comprises (Sp)x-(All Rp)-(Sp)y. In some embodiments, a provided pattern of backbone chiral centers comprises (Sp)-(All Rp)-(Sp). In some embodiments, a provided pattern of backbone chiral centers comprises (Rp/Sp)x-(repeating (Sp)m(Rp)n)-(Rp/Sp)y. In some embodiments, a provided pattern of backbone chiral centers comprises (Rp/Sp)-(repeating (Sp)m(Rp)n)-(Rp/Sp). In some embodiments, a provided pattern of backbone chiral centers comprises (Rp/Sp)x-(repeating SpSpRp)-(Rp/Sp)y. In some embodiments, a provided pattern of backbone chiral centers comprises (Rp/Sp)-(repeating SpSpRp)-(Rp/Sp).

In some embodiments, a provided pattern of backbone chiral centers is (Rp/Sp)x-(All Rp or All Sp)-(Rp/Sp)y. In some embodiments, a provided pattern of backbone chiral centers is (Rp/Sp)-(All Rp or All Sp)-(Rp/Sp). In some embodiments, a provided pattern of backbone chiral centers is (Rp)x-(All Sp)-(Rp)y. In some embodiments, a provided pattern of backbone chiral centers is (Rp)-(All Sp)-(Rp). In some embodiments, a provided pattern of backbone chiral centers is (Sp)x-(All Rp)-(Sp)y. In some embodiments, a provided pattern of backbone chiral centers is (Sp)-(All Rp)-(Sp). In some embodiments, a provided pattern of backbone chiral centers is (Rp/Sp)x-(repeating (Sp)m(Rp)n)-(Rp/Sp)y. In some embodiments, a provided pattern of backbone chiral centers is (Rp/Sp)-(repeating (Sp)m(Rp)n)-(Rp/Sp). In some embodiments, a provided pattern of backbone chiral centers is (Rp/Sp)x-(repeating SpSpRp)-(Rp/Sp)y. In some embodiments, a provided pattern of backbone chiral centers is (Rp/Sp)-(repeating SpSpRp)-(Rp/Sp).

A person of ordinary skill in the art understands that various regions of a target transcript can be targeted by provided compositions and methods. In some embodiments, a base sequence of provided CpG oligonucleotides comprises an intron sequence. In some embodiments, a base sequence of provided CpG oligonucleotides comprises an exon sequence. In some embodiments, a base sequence of provided CpG oligonucleotides comprises an intron and an exon sequence. In some embodiments, a base sequence of provided CpG oligonucleotides comprises a sequence spanning a splicing site. In some embodiments, a base sequence of provided CpG oligonucleotides comprises a sequence found in or comprising a 5' splice site, a branch point sequence (BPS), a polypyrimidine tact (py tact), a 3' splice site, an intronic splicing silencer (ISS), an exonic splicing silencer (ESS), an intronic splicing enhancer (ISE), and/or an exonic splicing enhancer. In some embodiments, a base sequence of provided CpG oligonucleotides is an intron sequence. In some embodiments, a base sequence of provided CpG oligonucleotides is an exon sequence. In some embodiments, a base sequence of provided CpG oligonucleotides is a sequence spanning a splicing site. In some embodiments, a base sequence of provided CpG oligonucleotides is a sequence found in or comprising a 5' splice site, a branch point sequence (BPS), a polypyrimidine tact (py tact), a 3' splice site, an intronic splicing silencer (ISS), an exonic splicing silencer (ESS), an intronic splicing enhancer (ISE), and/or an exonic splicing enhancer. In some embodiments, a base sequence of provided CpG oligonucleotides is a sequence found in a branch point sequence (BPS), a polypyrimidine tact (py tact), an intronic splicing silencer (ISS), an exonic splicing silencer (ESS), an intronic splicing enhancer (ISE), and/or an exonic splicing enhancer.

As understood by a person having ordinary skill in the art, provided CpG oligonucleotides and compositions, among other things, can target a great number of nucleic acid polymers. For instance, in some embodiments, provided CpG oligonucleotides and compositions can target a transcript of a nucleic acid sequence, wherein a common base sequence of CpG oligonucleotides (e.g., a base sequence of a CpG oligonucleotide type) comprises or is a sequence complementary to a sequence of the transcript. In some embodiments, a common base sequence comprises a sequence complimentary to a sequence of a target. In some embodiments, a common base sequence is a sequence complimentary to a sequence of a target. In some embodiments, a common base sequence comprises or is a sequence 100% complimentary to a sequence of a target. In some embodiments, a common base sequence comprises a sequence 100% complimentary to a sequence of a target. In some embodiments, a common base sequence is a sequence 100% complimentary to a sequence of a target. In some embodiments, a common base sequence in a core comprises or is a sequence complimentary to a sequence of a target. In some embodiments, a common base sequence in a core comprises a sequence complimentary to a sequence of a target. In some embodiments, a common base sequence in a core is a sequence % complimentary to a sequence of a target. In some embodiments, a common base sequence in a core comprises or is a sequence 100% complimentary to a sequence of a target. In some embodiments, a common base sequence in a core comprises a sequence 100% complimentary to a sequence of a target. In some embodiments, a common base sequence in a core is a sequence 100% complimentary to a sequence of a target.

In some embodiments, as described in this disclosure, provided CpG oligonucleotides and compositions can provide new cleavage patterns, higher cleavage rate, higher cleavage degree, higher cleavage selectivity, etc. In some embodiments, provided compositions can selectively suppress (e.g., cleave) a transcript from a target nucleic acid sequence which has one or more similar sequences exist within a subject or a population, each of the target and its similar sequences contains a specific nucleotidic characteristic sequence element that defines the target sequence relative to the similar sequences. In some embodiments, for example, a target sequence is a wild-type allele or copy of a gene, and a similar sequence is a sequence has very similar base sequence, e.g., a sequence having SNP, mutations, etc.

In some embodiments, a similar sequence has greater than 60%, 65%, 70%, 75%, 80%, 85%, 90%, 91%, 92%, 93%, 94%, 95%, 96%, 97%, 98% or 99% sequence homology with a target sequence. In some embodiments, a target sequence is a disease-causing copy of a nucleic acid sequence comprising one or more mutations and/or SNPs, and a similar sequence is a copy not causing the disease (wild type). In some embodiments, a target sequence comprises a mutation, wherein a similar sequence is the corresponding wild-type sequence. In some embodiments, a target sequence is a mutant allele, while a similar sequence is a wild-type allele. In some embodiments, a target sequence comprises an SNP that is associated with a disease-causing allele, while a similar sequence comprises the same SNP that is not associates with the disease-causing allele. In some embodiments, the region of a target sequence that is complementary to a common base sequence of a provided CpG oligonucleotide composition has greater than 60%, 65%, 70%, 75%, 80%, 85%, 90%, 91%, 92%, 93%, 94%, 95%, 96%, 97%, 98% or 99% sequence homology with the corresponding region of a similar sequence. In some embodiments, the region of a target sequence that is complementary to a common base sequence of a provided CpG oligonucleotide composition differs from the corresponding region of a similar sequence at less than 5, less than 4, less than 3, less than 2, or only 1 base pairs. In some embodiments, the region of a target sequence that is complementary to a common base sequence of a provided CpG oligonucleotide composition differs from the corresponding region of a similar sequence only at a mutation site or SNP site. In some embodiments, the region of a target sequence that is complementary to a common base sequence of a provided CpG oligonucleotide composition differs from the corresponding region of a similar sequence only at a mutation site. In some embodiments, the region of a target sequence that is complementary to a common base sequence of a provided CpG oligonucleotide composition differs from the corresponding region of a similar sequence only at an SNP site.

In some embodiments, a common base sequence comprises or is a sequence complementary to a characteristic sequence element. In some embodiments, a common base sequence comprises a sequence complementary to a characteristic sequence element. In some embodiments, a common base sequence is a sequence complementary to a characteristic sequence element. In some embodiments, a common base sequence comprises or is a sequence 100% complementary to a characteristic sequence element. In some embodiments, a common base sequence comprises a sequence 100% complementary to a characteristic sequence element. In some embodiments, a common base sequence is a sequence 100% complementary to a characteristic sequence element. In some embodiments, a common base sequence in a core comprises or is a sequence complementary to a characteristic sequence element. In some embodiments, a common base sequence in a core comprises a sequence complementary to a characteristic sequence element. In some embodiments, a common base sequence in a core is a sequence complementary to a characteristic sequence element. In some embodiments, a common base sequence in a core comprises or is a sequence 100% complementary to a characteristic sequence element. In some embodiments, a common base sequence in a core comprises a sequence 100% complementary to a characteristic sequence element. In some embodiments, a common base sequence in a core is a sequence 100% complementary to a characteristic sequence element.

Among other things, the present disclosure recognizes that a base sequence can have impact on oligonucleotide properties. In some embodiments, a base sequence can have impact on cleavage pattern of a target when CpG oligonucleotides having the base sequence are utilized for suppressing a target, e.g., through a pathway involving RNase H. In some embodiments, a common base sequence of a non-stereorandom CpG oligonucleotide compositions (e.g., certain oligonucleotide compositions provided in the present disclosure) is a base sequence that when applied to a DNA oligonucleotide composition or a stereorandom all-phosphorothioate oligonucleotide composition, cleavage pattern of the DNA (DNA cleavage pattern) and/or the stereorandom all-phosphorothioate (stereorandom cleavage pattern) composition has a cleavage site within or in the vicinity of a characteristic sequence element. In some embodiments, a cleavage site within or in the vicinity is within a sequence complementary to a core region of a common sequence. In some embodiments, a cleavage site within or in the vicinity is within a sequence 100% complementary to a core region of a common sequence.

In some embodiments, a common base sequence is a base sequence that has a cleavage site within or in the vicinity of a characteristic sequence element in its DNA cleavage pattern. In some embodiments, a common base sequence is a base sequence that has a cleavage site within a characteristic sequence element in its DNA cleavage pattern. In some embodiments, a common base sequence is a base sequence that has a cleavage site in the vicinity of a characteristic sequence element in its DNA cleavage pattern. In some embodiments, a common base sequence is a base sequence that has a cleavage site in the vicinity of a mutation or SNP of a characteristic sequence element in its DNA cleavage pattern. In some embodiments, a common base sequence is a base sequence that has a cleavage site in the vicinity of a mutation in its DNA cleavage pattern. In some embodiments, a common base sequence is a base sequence that has a cleavage site in the vicinity of an SNP in its DNA cleavage pattern.

In some embodiments, a common base sequence is a base sequence that has a cleavage site within or in the vicinity of a characteristic sequence element in its stereorandom cleavage pattern. In some embodiments, a common base sequence is a base sequence that has a cleavage site within a characteristic sequence element in its stereorandom cleavage pattern. In some embodiments, a common base sequence is a base sequence that has a cleavage site in the vicinity of a characteristic sequence element in its stereorandom cleavage pattern. In some embodiments, a common base sequence is a base sequence that has a cleavage site in the vicinity of a mutation or SNP of a characteristic sequence element in its stereorandom cleavage pattern. In some embodiments, a common base sequence is a base sequence that has a cleavage site in the vicinity of a mutation in its stereorandom cleavage pattern. In some embodiments, a common base sequence is a base sequence that has a cleavage site in the vicinity of an SNP in its stereorandom cleavage pattern.

In some embodiments, a common base sequence comprises or is a sequence complementary to a nucleic acid sequence. In some embodiments, a common base sequence comprises or is a sequence 100% complementary to a nucleic acid sequence. In some embodiments, a common base sequence comprises or is a sequence complementary to a disease-causing nucleic acid sequence. In some embodiments, a common base sequence comprises or is a sequence 100% complementary to a disease-causing nucleic acid sequence. In some embodiments, a common base sequence comprises or is a sequence complementary to a characteristic sequence element of disease-causing nucleic acid sequence, which characteristic sequences differentiate a disease-causing nucleic acid sequence from a non-diseasing-causing nucleic acid sequence. In some embodiments, a common base sequence comprises or is a sequence 100% complementary to a characteristic sequence element of disease-causing nucleic acid sequence, which characteristic sequences differentiate a disease-causing nucleic acid sequence from a non-diseasing-causing nucleic acid sequence. In some embodiments, a common base sequence comprises or is a sequence complementary to a disease-associated nucleic acid sequence. In some embodiments, a common base sequence comprises or is a sequence 100% complementary to a disease-associated nucleic acid sequence. In some embodiments, a common base sequence comprises or is a sequence complementary to a characteristic sequence element of disease-associated nucleic acid sequence, which characteristic sequences differentiate a disease-associated nucleic acid sequence from a non-diseasing-associated nucleic acid sequence. In some embodiments, a common base sequence comprises or is a sequence 100% complementary to a characteristic sequence element of disease-associated nucleic acid sequence, which characteristic sequences differentiate a disease-associated nucleic acid sequence from a non-diseasing-associated nucleic acid sequence.

In some embodiments, a common base sequence comprises or is a sequence complementary to a gene. In some embodiments, a common base sequence comprises or is a sequence 100% complementary to a gene. In some embodiments, a common base sequence comprises or is a sequence complementary to a characteristic sequence element of a gene, which characteristic sequences differentiate the gene from a similar sequence sharing homology with the gene. In some embodiments, a common base sequence comprises or is a sequence 100% complementary to a characteristic sequence element of a gene, which characteristic sequences differentiate the gene from a similar sequence sharing homology with the gene. In some embodiments, a common base sequence comprises or is a sequence complementary to characteristic sequence element of a target gene, which characteristic sequences comprises a mutation that is not found in other copies of the gene, e.g., the wild-type copy of the gene, another mutant copy the gene, etc. In some embodiments, a common base sequence comprises or is a sequence 100% complementary to characteristic sequence element of a target gene, which characteristic sequences comprises a mutation that is not found in other copies of the gene, e.g., the wild-type copy of the gene, another mutant copy the gene, etc.

In some embodiments, a common base sequence comprises or is a sequence complementary to a sequence comprising an SNP. In some embodiments, a common base sequence comprises or is a sequence complementary to a sequence comprising an SNP, and the common base sequence is 100% complementary to the SNP that is associated with a disease.

In some embodiments, a chiral internucleotidic linkage in provided CpG oligonucleotides has the structure of formula I. In some embodiments, a chiral internucleotidic linkage is phosphorothioate. In some embodiments, each chiral internucleotidic linkage in a single CpG oligonucleotide of a provided composition independently has the structure of formula I. In some embodiments, each chiral internucleotidic linkage in a single CpG oligonucleotide of a provided composition is a phosphorothioate.

In some embodiments, CpG oligonucleotides of the present disclosure comprise one or more modified sugar moieties. In some embodiments, CpG oligonucleotides of the present disclosure comprise one or more modified base moieties. As known by a person of ordinary skill in the art and described in the disclosure, various modifications can be introduced to a sugar and/or moiety. For example, in some embodiments, a modification is a modification described in U.S. Pat. No. 9,006,198, WO2014/012081 and WO/2015/107425, the sugar and base modifications of each of which are incorporated herein by reference.

In some embodiments, a sugar modification is a 2'-modification. Commonly used 2'-modifications include but are not limited to 2'-OR$^1$, wherein R$^1$ is not hydrogen. In some embodiments, a modification is 2'-OR, wherein R is optionally substituted aliphatic. In some embodiments, a modification is 2'-OMe. In some embodiments, a modification is 2'-O-MOE. In some embodiments, the present disclosure demonstrates that inclusion and/or location of particular chirally pure internucleotidic linkages can provide stability improvements comparable to or better than those achieved through use of modified backbone linkages, bases, and/or sugars. In some embodiments, a provided single CpG oligonucleotide of a provided composition has no modifications on the sugars. In some embodiments, a provided single CpG oligonucleotide of a provided composition has no modifications on 2'-positions of the sugars (i.e., the two groups at the 2'-position are either —H/—H or —H/—OH). In some embodiments, a provided single CpG oligonucleotide of a provided composition does not have any 2'-MOE modifications.

In some embodiments, a 2'-modification is —O-L- or L which connects the T-carbon of a sugar moiety to another carbon of a sugar moiety. In some embodiments, a 2'-modification is —O-L- or L which connects the 2'-carbon of a sugar moiety to the 4'-carbon of a sugar moiety. In some embodiments, a 2'-modification is S-cEt. In some embodiments, a modified sugar moiety is an LNA moiety.

In some embodiments, a 2'-modification is —F. In some embodiments, a T-modification is FANA. In some embodiments, a 2'-modification is FRNA.

In some embodiments, a sugar modification is a 5'-modification, e.g., R-5'-Me, S-5'-Me, etc.

In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Example such moieties are widely known in the art, including but not limited to those used in morpholio (optionally with its phosphorodiamidate linkage), glycol nucleic acids, etc.

In some embodiments, a provided CpG oligonucleotide in a provided composition has at least about 25% of its internucleotidic linkages in Sp configuration. In some embodiments, a provided CpG oligonucleotide in a provided composition has at least about 30% of its internucleotidic linkages in Sp configuration. In some embodiments, a provided CpG oligonucleotide in a provided composition has at least about 35% of its internucleotidic linkages in Sp configuration. In some embodiments, a provided CpG oligonucleotide in a provided composition has at least about 40% of its internucleotidic linkages in Sp configuration. In some embodiments, a provided CpG oligonucleotide in a provided composition has at least about 45% of its internucleotidic linkages in Sp configuration. In some embodiments, a provided CpG oligonucleotide in a provided composition has at least about 50% of its internucleotidic linkages in Sp configuration. In some embodiments, a provided CpG oligonucleotide in a provided composition has at least about 55% of its internucleotidic linkages in Sp configuration. In some embodiments, a provided CpG oligonucleotide in a provided composition has at least about 60% of its internucleotidic linkages in Sp configuration. In some embodiments, a provided CpG oligonucleotide in a provided composition has at least about 65% of its internucleotidic linkages in Sp configuration. In some embodiments, a provided CpG oligonucleotide in a provided composition has at least about 70% of its internucleotidic linkages in Sp configuration. In some embodiments, a provided CpG oligonucleotide in a provided composition has at least about 75% of its internucleotidic linkages in Sp configuration. In some embodiments, a provided CpG oligonucleotide in a provided composition has at least about 80% of its internucleotidic linkages in Sp configuration. In some embodiments, a provided CpG oligonucleotide in a provided composition has at least about 85% of its internucleotidic linkages in Sp configuration. In some embodiments, a provided CpG oligonucleotide in a provided composition has at least about 90% of its internucleotidic linkages in Sp configuration.

In some embodiments, the present disclosure provides chirally controlled CpG oligonucleotide compositions which are of high crude purity and of high diastereomeric purity. In some embodiments, the present disclosure provides and chirally controlled CpG oligonucleotide compositions which are of high crude purity. In some embodiments, the present disclosure provides chirally controlled CpG oligonucleotide compositions which are of high diastereomeric purity.

In some embodiments, a chirally controlled CpG oligonucleotide composition is a substantially pure preparation of a CpG oligonucleotide type in that CpG oligonucleotides in the composition that are not of the CpG oligonucleotide type are impurities form the preparation process of said CpG oligonucleotide type, in some case, after certain purification procedures.

In some embodiments, the present disclosure provides a compound of formula O-I:

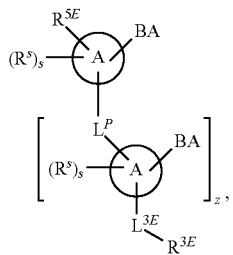

O-I or a salt thereof, wherein:

each BA is independently an optionally substituted group selected from $C_{1-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{5E}$ and $R^s$ is independently —H, —F, —Cl, —Br, —I, —CN, —N$_3$, —NO, —NO$_2$, -L-R', -L-OR', -L-SR', -L-N(R')$_2$, —O-L-OR', —O-L-SR', or —O-L-N(R')$_2$; s is 0-20;

each L is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Ring A is independently an optionally substituted 3-20 membered monocyclic, bicyclic or polycyclic ring having 0-10 heteroatoms;

each $L^P$ is independently an internucleotidic linkage;

z is 1-1000;

$L^{3E}$ is -L- or -L-L-;

$R^{3E}$ is —R', -L-R', —OR', or a solid support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

In some embodiments, a heteroatom is independently selected from oxygen, nitrogen, sulfur, phosphorus, boron and silicon. In some embodiments, a heteroatom is independently selected from oxygen, nitrogen, sulfur, and phosphorus. In some embodiments, a heteroatom is independently selected from oxygen, nitrogen, and sulfur.

In some embodiments, provided oligonucleotides, e.g., oligonucleotides of a type, oligonucleotide of a plurality, etc., are compounds having the structure of formula O-I or salts thereof. In some embodiments, an internucleotidic linkage has the structure of formula L-I:

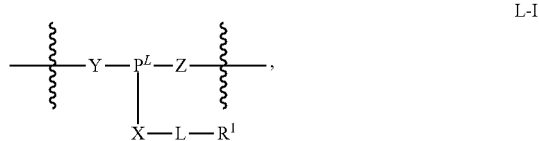

L-I or a salt form thereof, wherein:
$P^L$ is P(=W), P, or P→B(R')$_3$;
W is O, S or Se;
$R^1$ is -L-R, halogen, —CN, —NO$_2$, —Si(R)$_3$, —OR, —SR, or —N(R)$_2$;
each of X, Y and Z is independently —O—, —S—, —N(-L-R$^3$)—, or L.

In some embodiments, a modified internucleotidic linkage has the structure of formula L-1. In some embodiments, a modified internucleotidic linkage of formula L-I has the structure of formula I.

In some embodiments, the present disclosure provides CpG oligonucleotides comprising one or more diastereomerically pure internucleotidic linkages with respect to the chiral linkage phosphorus within the composition. In some embodiments, the present disclosure provides CpG oligonucleotides comprising one or more diastereomerically pure internucleotidic linkages having the structure of formula I. In some embodiments, the present disclosure provides CpG oligonucleotides comprising one or more diastereomerically pure internucleotidic linkages with respect to the chiral linkage phosphorus, and one or more phosphate diester linkages. In some embodiments, the present disclosure provides CpG oligonucleotides comprising one or more diastereomerically pure internucleotidic linkages having the structure of formula I, and one or more phosphate diester linkages. In some embodiments, the present disclosure provides CpG oligonucleotides comprising one or more diastereomerically pure internucleotidic linkages having the structure of formula I-c, and one or more phosphate diester linkages. In some embodiments, such CpG oligonucleotides are prepared by using stereoselective oligonucleotide synthesis, as described in this application, to form pre-designed diastereomerically pure internucleotidic linkages with respect to the chiral linkage phosphorus.

In certain embodiments, a modified internucleotidic linkages has the structure of formula I:

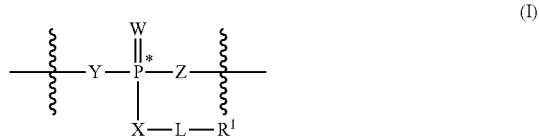

(I)

wherein each variable is as defined and described below. In some embodiments, a linkage of formula I is chiral. In some embodiments, the present disclosure provides CpG oligonucleotides comprising one or more modified internucleotidic linkages of formula I. In some embodiments, the present disclosure provides a CpG oligonucleotide comprising one or more modified internucleotidic linkages of formula I, and wherein individual internucleotidic linkages of formula I within the CpG oligonucleotide have different P-modifications relative to one another. In some embodiments, the present disclosure provides a CpG oligonucleotide comprising one or more modified internucleotidic linkages of formula I, and wherein individual internucleotidic linkages of formula I within the CpG oligonucleotide have different —X-L-R$^1$ relative to one another. In some embodiments, the present disclosure provides a CpG oligonucleotide comprising one or more modified internucleotidic linkages of formula I, and wherein individual internucleotidic linkages of formula I within the CpG oligonucleotide have different X relative to one another. In some embodiments, the present disclosure provides a CpG oligonucleotide comprising one or more modified internucleotidic linkages of formula I, and wherein individual internucleotidic linkages of formula I within the CpG oligonucleotide have different -L-R$^1$ relative to one another.

In some embodiments, a chirally controlled CpG oligonucleotide is a CpG oligonucleotide in a chirally controlled composition that is of the particular CpG oligonucleotide type, and the chirally controlled CpG oligonucleotide is of the type. In some embodiments, a chirally controlled CpG oligonucleotide is a CpG oligonucleotide in a provided composition that comprises a predetermined level of a plurality of CpG oligonucleotides that share a common base sequence, a common pattern of backbone linkages, and a common pattern of backbone chiral centers, and the chirally controlled CpG oligonucleotide shares the common base sequence, the common pattern of backbone linkages, and the common pattern of backbone chiral centers.

In some embodiments, the present disclosure provides a chirally controlled CpG oligonucleotide, wherein at least two of the individual internucleotidic linkages within the CpG oligonucleotide have different stereochemistry and/or different P-modifications relative to one another. In some embodiments, the present disclosure provides a chirally controlled CpG oligonucleotide, wherein at least two of the individual internucleotidic linkages within the CpG oligonucleotide have different stereochemistry relative to one another, and wherein at least a portion of the structure of the chirally controlled CpG oligonucleotide is characterized by a repeating pattern of alternating stereochemistry.

In some embodiments, the present disclosure provides a chirally controlled CpG oligonucleotide, wherein at least two of the individual internucleotidic linkages within the CpG oligonucleotide have different P-modifications relative to one another, in that they have different X atoms in their -XLR$^1$ moieties, and/or in that they have different L groups in their -XLR$^1$ moieties, and/or that they have different R$^1$ atoms in their -XLR$^1$ moieties.

In some embodiments, the present disclosure provides a chirally controlled CpG oligonucleotide, wherein at least two of the individual internucleotidic linkages within the CpG oligonucleotide have different stereochemistry and/or different P-modifications relative to one another and the CpG oligonucleotide has a structure represented by the following formula:

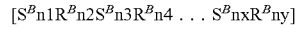

wherein:
each R$^B$ independently represents a block of nucleotide units having the R configuration at the linkage phosphorus;
each S$^B$ independently represents a block of nucleotide units having the S configuration at the linkage phosphorus;
each of n1-ny is zero or an integer, with the requirement that at least one odd n and at least one even n must be non-zero so that the CpG oligonucleotide includes at least two individual internucleotidic linkages with different stereochemistry relative to one another; and wherein the sum of n1-ny is between 2 and 200, and in some embodiments is between a lower limit selected from the group consisting of 2, 3, 4, 5, 6, 7, 8, 9, 10, 11, 12, 13, 14, 15, 16, 17, 18, 19, 20, 21, 22, 23, 24, 25 or more and an upper limit selected from the group consisting of 5, 10, 15, 20, 25, 30, 35, 40, 45, 50, 55, 60, 65, 70, 75, 80, 85, 90, 95, 100, 110, 120, 130, 140, 150, 160, 170, 180, 190, and 200, the upper limit being larger than the lower limit.

In some embodiments, y is 1-200. In some embodiments, each of n1 to ny is independently 0-200, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc.

In some such embodiments, each n has the same value; in some embodiments, each even n has the same value as each other even n; in some embodiments, each odd n has the same value each other odd n; in some embodiments, at least two even ns have different values from one another; in some embodiments, at least two odd ns have different values from one another.

In some embodiments, at least two adjacent ns are equal to one another, so that a provided CpG oligonucleotide includes adjacent blocks of S stereochemistry linkages and R stereochemistry linkages of equal lengths. In some embodiments, provided CpG oligonucleotides include repeating blocks of S and R stereochemistry linkages of equal lengths. In some embodiments, provided CpG oligonucleotides include repeating blocks of S and R stereochemistry linkages, where at least two such blocks are of different lengths from one another; in some such embodiments each S stereochemistry block is of the same length, and is of a different length from each R stereochemistry length, which can optionally be of the same length as one another.

In some embodiments, at least two skip-adjacent ns are equal to one another, so that a provided CpG oligonucleotide includes at least two blocks of linkages of a first stereochemistry that are equal in length to one another and are separated by a block of linkages of the other stereochemistry, which separating block can be of the same length or a different length from the blocks of first stereochemistry.

In some embodiments, ns associated with linkage blocks at the ends of a provided CpG oligonucleotide are of the same length. In some embodiments, provided CpG oligonucleotides have terminal blocks of the same linkage stereochemistry. In some such embodiments, the terminal blocks are separated from one another by a middle block of the other linkage stereochemistry.

In some embodiments, a provided CpG oligonucleotide of formula [S$^B$n1R$^B$n2S$^B$n3R$^B$n4 . . . S$^B$nxR$^B$ny] is a stereoblockmer. In some embodiments, a provided CpG oligonucleotide of formula [S$^B$n1R$^B$n2S$^B$n3R$^B$n4 . . . S$^B$nxR$^B$ny] is a stereoskipmer. In some embodiments, a provided CpG oligonucleotide of formula [S$^B$n1R$^B$n2S$^B$n3R$^B$n4 . . . S$^B$nxR$^B$ny] is a stereoaltmer. In some embodiments, a provided CpG oligonucleotide of formula [S$^B$n1R$^B$n2S$^B$n3R$^B$n4 . . . S$^B$nxR$^B$ny] is a gapmer.

In some embodiments, a provided CpG oligonucleotide of formula [S$^B$n1R$^B$n2S$^B$n3R$^B$n4 . . . S$^B$nxR$^B$ny] is of any of the above described patterns and further comprises patterns of P-modifications. For instance, in some embodiments, a provided CpG oligonucleotide of formula [S$^B$n1R$^B$n2S$^B$n3R$^B$n4 . . . S$^B$nxR$^B$ny] and is a stereoskipmer and P-modification skipmer. In some embodiments, a provided CpG oligonucleotide of formula [S$^B$n1R$^B$n2S$^B$n3R$^B$n4 . . . S$^B$nxR$^B$ny] and is a stereoblockmer and P-modification altmer. In some embodiments, a provided CpG oligonucleotide of formula [S$^B$n1R$^B$n2S$^B$n3R$^B$n4 . . . S$^B$nxR$^B$ny] and is a stereoaltmer and P-modification blockmer.

In some embodiments, a provided CpG oligonucleotide, for example, a CpG oligonucleotide of formula [S$^B$n1R$^B$n2S$^B$n3R$^B$n4 . . . S$^B$nxR$^B$ny], is a chirally controlled CpG oligonucleotide comprising one or more modified internucleotidic linkages independently having the structure of formula I:

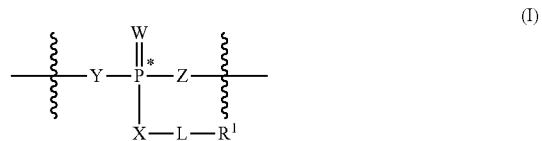

wherein:

P* is an asymmetric phosphorus atom and is either Rp or Sp;

W is O, S or Se;

each of X, Y and Z is independently —O—, —S—, —N(-L-R$^1$)—, or L;

L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;

R$^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O— each R' is independently —R, —C(O)R, —CO$_2$R, or —SO$_2$R, or:

two R' are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, and heterocyclylene;

each R is independently hydrogen, or an optionally substituted group selected from $C_1$-$C_6$ aliphatic, carbocyclyl, aryl, heteroaryl, and heterocyclyl; and each

independently represents a connection to a nucleoside.

In some embodiments, a chirally controlled CpG oligonucleotide comprises one or more modified internucleotidic phosphorus linkages. In some embodiments, a chirally controlled CpG oligonucleotide comprises, e.g., a phosphorothioate or a phosphorothioate triester linkage. In some embodiments, a chirally controlled CpG oligonucleotide comprises a phosphorothioate triester linkage. In some embodiments, a chirally controlled CpG oligonucleotide comprises at least two phosphorothioate triester linkages. In some embodiments, a chirally controlled CpG oligonucleotide comprises at least three phosphorothioate triester linkages. In some embodiments, a chirally controlled CpG oligonucleotide comprises at least four phosphorothioate triester linkages. In some embodiments, a chirally controlled CpG oligonucleotide comprises at least five phosphorothioate triester linkages. Example such modified internucleotidic phosphorus linkages are described further herein.

In some embodiments, a chirally controlled CpG oligonucleotide comprises different internucleotidic phosphorus linkages. In some embodiments, a chirally controlled CpG oligonucleotide comprises at least one phosphate diester internucleotidic linkage and at least one modified internucleotidic linkage. In some embodiments, a chirally controlled CpG oligonucleotide comprises at least one phosphate diester internucleotidic linkage and at least one phosphorothioate triester linkage. In some embodiments, a chirally controlled CpG oligonucleotide comprises at least one phosphate diester internucleotidic linkage and at least two phosphorothioate triester linkages. In some embodiments, a chirally controlled CpG oligonucleotide comprises at least one phosphate diester internucleotidic linkage and at least three phosphorothioate triester linkages. In some embodiments, a chirally controlled CpG oligonucleotide comprises at least one phosphate diester internucleotidic linkage and at least four phosphorothioate triester linkages. In some embodiments, a chirally controlled CpG oligonucleotide comprises at least one phosphate diester internucleotidic linkage and at least five phosphorothioate triester linkages. Example such modified internucleotidic phosphorus linkages are described further herein.

In some embodiments, a phosphorothioate triester linkage comprises a chiral auxiliary, which, for example, is used to control the stereoselectivity of a reaction. In some embodiments, a phosphorothioate triester linkage does not comprise a chiral auxiliary. In some embodiments, a phosphorothioate triester linkage is intentionally maintained until and/or during the administration to a subject.

In some embodiments, a chirally controlled CpG oligonucleotide is linked to a solid support. In some embodiments, a chirally controlled CpG oligonucleotide is cleaved from a solid support.

In some embodiments, a chirally controlled CpG oligonucleotide comprises at least one phosphate diester internucleotidic linkage and at least two consecutive modified internucleotidic linkages. In some embodiments, a chirally controlled CpG oligonucleotide comprises at least one phosphate diester internucleotidic linkage and at least two consecutive phosphorothioate triester internucleotidic linkages.

In some embodiments, a chirally controlled CpG oligonucleotide is a blockmer. In some embodiments, a chirally controlled CpG oligonucleotide is a stereoblockmer. In some embodiments, a chirally controlled CpG oligonucleotide is a P-modification blockmer. In some embodiments, a chirally controlled CpG oligonucleotide is a linkage blockmer.

In some embodiments, a chirally controlled CpG oligonucleotide is an altmer. In some embodiments, a chirally controlled CpG oligonucleotide is a stereoaltmer. In some embodiments, a chirally controlled CpG oligonucleotide is a P-modification altmer. In some embodiments, a chirally controlled CpG oligonucleotide is a linkage altmer.

In some embodiments, a chirally controlled CpG oligonucleotide is a unimer. In some embodiments, a chirally controlled CpG oligonucleotide is a stereounimer. In some embodiments, a chirally controlled CpG oligonucleotide is a P-modification unimer. In some embodiments, a chirally controlled CpG oligonucleotide is a linkage unimer.

In some embodiments, a chirally controlled CpG oligonucleotide is a gapmer.

In some embodiments, a chirally controlled CpG oligonucleotide is a skipmer.

In some embodiments, the present disclosure provides CpG oligonucleotides comprising one or more modified internucleotidic linkages independently having the structure of formula I:

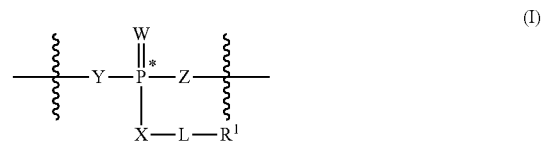

wherein:
P* is an asymmetric phosphorus atom and is either Rp or Sp;
W is O, S or Se;
each of X, Y and Z is independently —O—, —S—, —N(-L-R$^1$)—, or L;
L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;
R$^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—
each R' is independently —R, —C(O)R, —CO$_2$R, or —SO$_2$R, or:
  two R' are taken together with their intervening atoms to form an optionally substituted aryl, carbocyclic, heterocyclic, or heteroaryl ring;
-Cy- is an optionally substituted bivalent ring selected from phenylene, carbocyclylene, arylene, heteroarylene, and heterocyclylene;
each R is independently hydrogen, or an optionally substituted group selected from $C_1$-$C_6$ aliphatic, carbocyclyl, aryl, heteroaryl, and heterocyclyl; and each ⁓ independently represents a connection to a nucleoside.

In some embodiments, P* is an asymmetric phosphorus atom and is either Rp or Sp. In some embodiments, P* is Rp. In other embodiments, P* is Sp. In some embodiments, a CpG oligonucleotide comprises one or more internucleotidic linkages of formula I wherein each P* is independently Rp or Sp. In some embodiments, a CpG oligonucleotide comprises one or more internucleotidic linkages of formula I wherein each P* is Rp. In some embodiments, a CpG oligonucleotide comprises one or more internucleotidic linkages of formula I wherein each P* is Sp. In some embodiments, a CpG oligonucleotide comprises at least one internucleotidic linkage of formula I wherein P* is Rp. In some embodiments, a CpG oligonucleotide comprises at least one internucleotidic linkage of formula I wherein P* is Sp. In some embodiments, a CpG oligonucleotide comprises at least one internucleotidic linkage of formula I wherein P* is Rp, and at least one internucleotidic linkage of formula I wherein P* is Sp.

In some embodiments, BA is optionally substituted $C_{1-30}$ cycloaliphatic. In some embodiments, BA is optionally substituted $C_{6-30}$ aryl. In some embodiments, BA is optionally substituted $C_{3-30}$ heterocyclyl. In some embodiments, BA is optionally substituted $C_{5-30}$ heteroaryl. In some embodiments, BA is an optionally substituted natural base moiety. In some embodiments, BA is an optionally substituted modified base moiety. BA is an optionally substituted group selected from $C_{1-30}$ cycloaliphatic, $C_{6-30}$ aryl, $C_{3-30}$ heterocyclyl, and $C_{5-30}$ heteroaryl. In some embodiments, BA is an optionally substituted group selected from $C_{1-30}$ cycloaliphatic, $C_{6-30}$ aryl, $C_{3-30}$ heterocyclyl, $C_{5-30}$ heteroaryl, and a natural nucleobase moiety.

In some embodiments, BA is connected to a sugar ring, e.g., Ring A, through an aromatic ring. In some embodiments, BA is connected to a sugar ring through a heteroatom. In some embodiments, BA is connected to a sugar ring through a ring heteroatom of an aromatic ring. In some embodiments, BA is connected to a sugar ring through a ring nitrogen atom of an aromatic ring.

In some embodiments, BA is a natural nucleobase moiety. In some embodiments, BA is an optionally substituted natural nucleobase moiety. In some embodiments, BA is a substituted natural nucleobase moiety. In some embodiments, BA is natural nucleobase A, T, U, C, or G. In some embodiments, BA is an optionally substituted group selected from natural nucleobases A, T, U, C, and G.

In some embodiments, $R^{5E}$ is —H, —F, —Cl, —Br, —I, —CN, —N$_3$, —NO, —NO$_2$, -L-R', -L-OR', -L-SR', -L-N(R')$_2$, —O-L-OR', —O-L-SR', or —O-L-N(R')$_2$. In some embodiments, $R^{5E}$ is —H. In some embodiments, $R^{5E}$ is —R. In some embodiments, $R^{5E}$ is —CH$_2$OR. In some embodiments, $R^{5E}$ is —CH$_2$OH. In some embodiments, $R^{5E}$ is —CH$_2$OR, wherein R is a hydroxyl protecting group. In some embodiments, R is DMTr-.

In some embodiments, $R^s$ is —H. In some embodiments, each $R^s$ is independently —F, —Cl, —Br, —I, —CN, —N$_3$, —NO, —NO$_2$, -L-R', -L-OR', -L-SR', -L-N(R')$_2$, —O-L-OR', —O-L-SR', or —O-L-N(R')$_2$. In some embodiments, $R^s$ is —F. In some embodiments, $R^s$ is —Cl. In some embodiments, $R^s$ is —Br. In some embodiments, $R^s$ is —I. In some embodiments, $R^s$ is —CN. In some embodiments, $R^s$ is —N$_3$. In some embodiments, $R^s$ is —NO. In some embodiments, $R^s$ is —NO$_2$. In some embodiments, $R^s$ is -L-R'. In some embodiments, $R^s$ is —R'. In some embodiments, $R^s$ is -L-OR'. In some embodiments, $R^s$ is —OR'. In some embodiments, $R^s$ is -L-SR'. In some embodiments, $R^s$ is —SR'. In some embodiments, $R^s$ is L-L-N(R')$_2$. In some embodiments, $R^s$ is —N(R')$_2$.

In some embodiments, $R^{2s}$ is $R^s$, and $R^s$ is a 2'-modification as described in the present disclosure.

In some embodiments, $R^s$ at a 2'-position (BA is at 1'-position) is —F. In some embodiments, $R^s$ at a 2'-position is —Cl. In some embodiments, $R^s$ at a 2'-position is —Br. In some embodiments, $R^s$ at a 2'-position is —I. In some embodiments, $R^s$ at a 2'-position is —CN. In some embodiments, $R^s$ at a 2'-position is —N$_3$. In some embodiments, $R^s$ at a 2'-position is —NO. In some embodiments, $R^s$ at a 2'-position is —NO$_2$. In some embodiments, $R^s$ at a 2'-position is -L-R'. In some embodiments, $R^s$ at a 2'-position is —R'. In some embodiments, $R^s$ at a 2'-position is -L-OR'. In some embodiments, $R^s$ at a 2'-position is —OR'. In some embodiments, $R^s$ at a 2'-position is -L-SR'. In some embodiments, $R^s$ at a 2'-position is —SR'. In some embodiments, $R^s$ at a 2'-position is L-L-N(R')$_2$. In some embodiments, $R^s$ at a T-position is —N(R')$_2$. In some embodiments, $R^s$ at a 2'-position is —OR', wherein R' is optionally substituted $C_{1-6}$ aliphatic. In some embodiments, $R^s$ at a 2'-position is —OR', wherein R' is optionally substituted $C_{1-6}$ alkyl. In some embodiments, $R^s$ at a 2'-position is —OMe. In some embodiments, $R^s$ at a 2'-position is -MOE. In some embodiments, $R^s$ at a 2'-position is hydrogen. In some embodiments, $R^s$ at one T-position is hydrogen, and $R^s$ at the other 2'-position is not hydrogen as described herein. In some embodiments, $R^s$ at both T-positions are hydrogen. In some embodiments, $R^s$ at one T-position is hydrogen, and the other T-position is connected to an internucleotidic linkage.

In some embodiments, $R^s$ at a 3'-position (BA is at 1'-position) is —F. In some embodiments, $R^s$ at a 3'-position is —Cl. In some embodiments, $R^s$ at a 3'-position is —Br. In some embodiments, $R^s$ at a 3'-position is —I. In some embodiments, $R^s$ at a 3'-position is —CN. In some embodiments, $R^s$ at a 3'-position is —N$_3$. In some embodiments, $R^s$ at a 3'-position is —NO. In some embodiments, $R^s$ at a 3'-position is —NO$_2$. In some embodiments, $R^s$ at a 3'-position is -L-R'. In some embodiments, $R^s$ at a 3'-position is —R'. In some embodiments, $R^s$ at a 3'-position is -L-OR'. In some embodiments, $R^s$ at a 3'-position is —OR'. In some embodiments, $R^s$ at a 3'-position is -L-SR'. In some embodiments, $R^s$ at a 3'-position is —SR'. In some embodiments, $R^s$ at a 3'-position is L-L-N(R')$_2$. In some embodiments, $R^s$ at a 3'-position is —N(R')$_2$. In some embodiments, $R^s$ at a 3'-position is —OR', wherein R' is optionally substituted $C_{1-6}$ aliphatic. In some embodiments, $R^s$ at a 3'-position is —OR', wherein R' is optionally substituted $C_{1-6}$ alkyl. In some embodiments, $R^s$ at a 3'-position is —OMe. In some embodiments, $R^s$ at a 3'-position is -MOE. In some embodiments, $R^s$ at a 3'-position is hydrogen. In some embodiments, $R^s$ at one 3'-position is hydrogen, and $R^s$ at the other 3'-position is not hydrogen as described herein. In some embodiments, $R^s$ at both 3'-positions are hydrogen. In some embodiments, $R^s$ at one 3'-position is hydrogen, and the other 3'-position is connected to an internucleotidic linkage.

In some embodiments, $R^s$ at a 4'-position (BA is at 1'-position) is —F. In some embodiments, $R^s$ at a 4'-position is —Cl. In some embodiments, $R^s$ at a 4'-position is —Br. In some embodiments, $R^s$ at a 4'-position is —I. In some embodiments, $R^s$ at a 4'-position is —CN. In some embodiments, $R^s$ at a 4'-position is —N$_3$. In some embodiments, $R^s$ at a 4'-position is —NO. In some embodiments, $R^s$ at a 4'-position is —NO$_2$. In some embodiments, $R^s$ at a 4'-position is -L-R'. In some embodiments, $R^s$ at a 4'-position is —R'. In some embodiments, $R^s$ at a 4'-position is -L-OR'. In some embodiments, $R^s$ at a 4'-position is —OR'. In some embodiments, $R^s$ at a 4'-position is -L-SR'. In some embodiments, $R^s$ at a 4'-position is —SR'. In some embodiments, $R^s$ at a 4'-position is L-L-N(R')$_2$. In some embodiments, R$^s$ at a 4'-position is —N(R')$_2$. In some embodiments, R$^s$ at a 4'-position is —OR', wherein R' is optionally substituted C$_{1-6}$ aliphatic. In some embodiments, R$^s$ at a 4'-position is —OR', wherein R' is optionally substituted C$_{1-6}$ alkyl. In some embodiments, R$^s$ at a 4'-position is —OMe. In some embodiments, R$^s$ at a 4'-position is -MOE. In some embodiments, R$^s$ at a 4'-position is hydrogen. In some embodiments, R$^s$ at one 4'-position is hydrogen, and R$^s$ at the other 4'-position is not hydrogen as described herein. In some embodiments, R$^s$ at both 4'-positions are hydrogen. In some embodiments, R$^s$ at one 4'-position is hydrogen, and the other 4'-position is connected to an internucleotidic linkage.

In some embodiments, s is 0-20. In some embodiments, s is 1-20. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11. In some embodiments, s is 12. In some embodiments, s is 13. In some embodiments, s is 14. In some embodiments, s is 15. In some embodiments, s is 16. In some embodiments, s is 17. In some embodiments, s is 18. In some embodiments, s is 19. In some embodiments, s is 20.

In some embodiments, Cy$^L$ is an optionally substituted tetravalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon (in addition to the four connections it already has). In some embodiments, Cy$^L$ is an optionally substituted C$_{3-20}$ cycloaliphatic ring. In some embodiments, Cy$^L$ is an optionally substituted C$_{6-20}$ aryl ring. In some embodiments, Cy$^L$ is an optionally substituted 5-20 membered heteroaryl ring having 1-10 heteroatoms independently selected from oxygen, nitrogen, sulfur, phosphorus and silicon. In some embodiments, Cy$^L$ is an optionally substituted 3-20 membered heterocyclyl ring having 1-10 heteroatoms independently selected from oxygen, nitrogen, sulfur, phosphorus, boron and silicon. In some embodiments, heteroatoms are selected from oxygen, nitrogen, sulfur and phosphorus. In some embodiments, heteroatoms are selected from oxygen, nitrogen and sulfur. In some embodiments, heteroatoms are selected from oxygen and nitrogen.

In some embodiments, Cy$^L$ is Ring A as described herein. In some embodiments, -Cy- is bivalent Ring A. In some embodiments, Cy is a bivalent Cy$^L$ group.

In some embodiments, Ring A is an optionally substituted 3-20 membered monocyclic, bicyclic or polycyclic ring having 0-10 heteroatoms independently selected from independently selected from oxygen, nitrogen, sulfur, phosphorus and silicon (in addition to the one or more connections as shown in a structure). In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0-10 heteroatoms independently selected from oxygen, nitrogen, and sulfur.

In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0 heteroatom.

In some embodiments, Ring A is an optionally substituted multivalent monocyclic saturated 5-7 membered ring having the intervening nitrogen, phosphorus and oxygen atoms and no additional heteroatoms. In some embodiments, Ring A is an optionally substituted multivalent monocyclic saturated 5-membered ring having the intervening nitrogen, phosphorus and oxygen atoms and no additional heteroatoms. In some embodiments, Ring A is an optionally substituted multivalent monocyclic saturated 6-membered ring having the intervening nitrogen, phosphorus and oxygen atoms and no additional heteroatoms. In some embodiments, Ring A is an optionally substituted multivalent monocyclic saturated 7-membered ring having the intervening nitrogen, phosphorus and oxygen atoms and no additional heteroatoms.

In some embodiments, Ring A is an optionally substituted multivalent, bicyclic, saturated, partially unsaturated, or aryl 5-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, bicyclic, saturated, partially unsaturated, or aryl 5-30 membered ring having, in addition to the intervening nitrogen, phosphorus and oxygen atoms, 0-10 heteroatoms independently selected from oxygen, nitrogen, and sulfur. In some embodiments, Ring A is a multivalent, bicyclic and saturated 8-10 membered bicyclic ring having the intervening nitrogen, phosphorus and oxygen atoms and no additional heteroatoms. In some embodiments, Ring A is a multivalent, bicyclic and saturated 8-membered bicyclic ring having the intervening nitrogen, phosphorus and oxygen atoms and no additional heteroatoms. In some embodiments, Ring A is a multivalent, bicyclic and saturated 9-membered bicyclic ring having the intervening nitrogen, phosphorus and oxygen atoms and no additional heteroatoms. In some embodiments, Ring A is a multivalent, bicyclic and saturated 10-membered bicyclic ring having the intervening nitrogen, phosphorus and oxygen atoms and no additional heteroatoms. In some embodiments, Ring A is bicyclic and comprises a 5-membered ring fused to a 5-membered ring. In some embodiments, Ring A is bicyclic and comprises a 5-membered ring fused to a 6-membered ring. In some embodiments, the 5-membered ring comprises the intervening nitrogen, phosphorus and oxygen atoms as ring atoms. In some embodiments, Ring A comprises a ring system having the backbone structure of

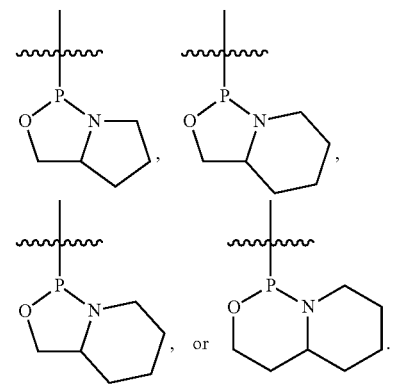

In some embodiments, Ring A is an optionally substituted multivalent, polycyclic, saturated, partially unsaturated, or aryl 3-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, polycyclic, saturated, partially unsaturated, or aryl 3-30 membered ring having, in addition to the intervening nitrogen, phosphorus and oxygen atoms, 0-10 heteroatoms independently selected from oxygen, nitrogen, and sulfur.

In some embodiments, Ring A is monocyclic, bicyclic or polycyclic and comprises an optionally substituted 5-10 membered monocyclic ring whose ring atoms comprise the intervening nitrogen, phosphorus and oxygen atoms. In some embodiments, Ring A is monocyclic, bicyclic or polycyclic and comprises an optionally substituted 5-9 membered monocyclic ring whose ring atoms comprise the intervening nitrogen, phosphorus and oxygen atoms. In some embodiments, Ring A is monocyclic, bicyclic or polycyclic and comprises an optionally substituted 5-8 membered monocyclic ring whose ring atoms comprise the intervening nitrogen, phosphorus and oxygen atoms. In some embodiments, Ring A is monocyclic, bicyclic or polycyclic and comprises an optionally substituted 5-7 membered monocyclic ring whose ring atoms comprise the intervening nitrogen, phosphorus and oxygen atoms. In some embodiments, Ring A is monocyclic, bicyclic or polycyclic and comprises an optionally substituted 5-6 membered monocyclic ring whose ring atoms comprise the intervening nitrogen, phosphorus and oxygen atoms.

In some embodiments, Ring A is monocyclic, bicyclic or polycyclic and comprises an optionally substituted 5-membered monocyclic ring whose ring atoms comprise the intervening nitrogen, phosphorus and oxygen atoms. In some embodiments, Ring A is monocyclic, bicyclic or polycyclic and comprises an optionally substituted 6-membered monocyclic ring whose ring atoms comprise the intervening nitrogen, phosphorus and oxygen atoms. In some embodiments, Ring A is monocyclic, bicyclic or polycyclic and comprises an optionally substituted 7-membered monocyclic ring whose ring atoms comprise the intervening nitrogen, phosphorus and oxygen atoms. In some embodiments, Ring A is monocyclic, bicyclic or polycyclic and comprises an optionally substituted 8-membered monocyclic ring whose ring atoms comprise the intervening nitrogen, phosphorus and oxygen atoms. In some embodiments, Ring A is monocyclic, bicyclic or polycyclic and comprises an optionally substituted 9-membered monocyclic ring whose ring atoms comprise the intervening nitrogen, phosphorus and oxygen atoms. In some embodiments, Ring A is monocyclic, bicyclic or polycyclic and comprises an optionally substituted 10-membered monocyclic ring whose ring atoms comprise the intervening nitrogen, phosphorus and oxygen atoms.

In some embodiments, Ring A is monocyclic, bicyclic or polycyclic and comprises an optionally substituted 5-membered ring whose ring atoms consist of the intervening nitrogen, phosphorus and oxygen atoms and carbon atoms. In some embodiments, Ring A is monocyclic, bicyclic or polycyclic and comprises an optionally substituted 6-membered ring whose ring atoms consist of the intervening nitrogen, phosphorus and oxygen atoms and carbon atoms. In some embodiments, Ring A is monocyclic, bicyclic or polycyclic and comprises an optionally substituted 7-membered ring whose ring atoms consist of the intervening nitrogen, phosphorus and oxygen atoms and carbon atoms. In some embodiments, Ring A is monocyclic, bicyclic or polycyclic and comprises an optionally substituted 8-membered ring whose ring atoms consist of the intervening nitrogen, phosphorus and oxygen atoms and carbon atoms. In some embodiments, Ring A is monocyclic, bicyclic or polycyclic and comprises an optionally substituted 9-membered ring whose ring atoms consist of the intervening nitrogen, phosphorus and oxygen atoms and carbon atoms. In some embodiments, Ring A is monocyclic, bicyclic or polycyclic and comprises an optionally substituted 10-membered ring whose ring atoms consist of the intervening nitrogen, phosphorus and oxygen atoms and carbon atoms.

In some embodiments, Ring A comprises a ring system having the backbone structure of

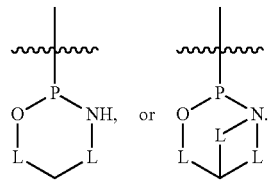

In some embodiments, Ring A is optionally substituted

In some embodiments, Ring A is optionally substituted

In some embodiments, Ring A is

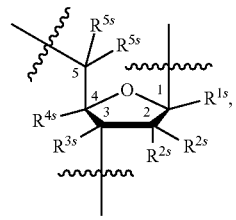

BA is connected at C1, and each of $R^{1s}$, $R^{2s}$, $R^{3s}$, $R^{4s}$ and $R^{5s}$ is independently $R^s$. In some embodiments, Ring A is

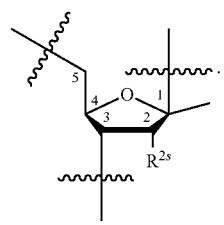

In some embodiments, Ring A is

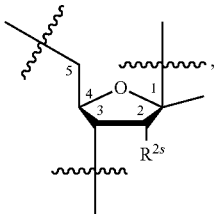

wherein $R^{2s}$ is not —OH. In some embodiments, Ring A is

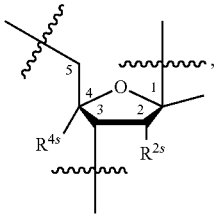

wherein $R^{2s}$ and $R^{4s}$ are R, and the two R groups are taken together with their intervening atoms to form a ring. In some embodiments, Ring A is optionally substituted

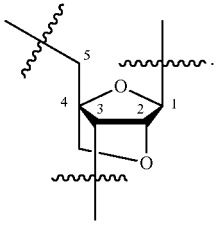 [SMILES: *C[C@]12CO[C@@H](C1*)[C@H](*)O2]

In some embodiments, Ring A is

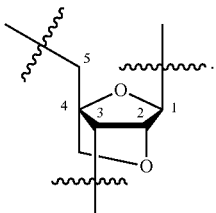

In some embodiments, Ring A is

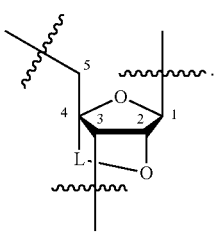

In some embodiments, $R^{2s}$ is a 2'-modification described in the present disclosure.

In some embodiments, $L^P$ is an link. In some embodiments, each $L^P$ independently has the structure of formula L-I. In some embodiments, each $L^P$ independently has the structure of formula I. In some embodiments, $L^P$ is a natural phosphate linkage. In some embodiments, $L^P$ is a modified internucleotidic linkage. In some embodiments, $L^P$ is chiral. In some embodiments, $L^P$ is a phosphorothioate diester linkage.

In some embodiments, $P^L$ is P(=W). In some embodiments, $P^L$ is P(=O). In some embodiments, $P^L$ is P(=S). In some embodiments, $P^L$ is P(=Se). In some embodiments, $P^L$ is P. In some embodiments, $P^L$ is P→B(R')$_3$.

In some embodiments, W, O or S or Se. In some embodiments, W is O or S. In some embodiments, W is O. In some embodiments, W is S. In some embodiments, W is Se.

In some embodiments, z is 1-1000. In some embodiments, z is 1-200. In some embodiments, z is 1-100. In some embodiments, z is 1-90. In some embodiments, z is 1-80. In some embodiments, z is 1-70. In some embodiments, z is 1-60. In some embodiments, z is 1-50. In some embodiments, z is 1-40. In some embodiments, z is 1-35. In some embodiments, z is 1-30. In some embodiments, z is 1-29. In some embodiments, z is 1-28. In some embodiments, z is 1-27. In some embodiments, z is 1-26. In some embodiments, z is 1-25. In some embodiments, z is 1-24. In some embodiments, z is 1-23. In some embodiments, z is 1-22. In some embodiments, z is 1-21. In some embodiments, z is 1-20. In some embodiments, z is 1-19. In some embodiments, z is 1-18. In some embodiments, z is 1-17. In some embodiments, z is 1-16. In some embodiments, z is 1-15. In some embodiments, z is 1-14. In some embodiments, z is 1-13. In some embodiments, z is 1-12. In some embodiments, z is 1-11. In some embodiments, z is 1-10. In some embodiments, z is 1-9. In some embodiments, z is 1-8. In some embodiments, z is 1-7. In some embodiments, z is 1-6. In some embodiments, z is 1-5. In some embodiments, z is 1-4. In some embodiments, z is 1-3. In some embodiments, z is 1-2. In some embodiments, z is 4-30. In some embodiments, z is 4-29. In some embodiments, z is 4-28. In some embodiments, z is 4-27. In some embodiments, z is 4-26. In some embodiments, z is 4-25. In some embodiments, z is 4-24. In some embodiments, z is 4-23. In some embodiments, z is 4-22. In some embodiments, z is 4-21. In some embodiments, z is 4-20. In some embodiments, z is 4-19. In some embodiments, z is 4-18. In some embodiments, z is 4-17. In some embodiments, z is 4-16. In some embodiments, z is 4-15. In some embodiments, z is 4-14. In some embodiments, z is 9-30. In some embodiments, z is 9-29. In some embodiments, z is 9-28. In some embodiments, z is 9-27. In some embodiments, z is 9-26. In some embodiments, z is 9-25. In some embodiments, z is 9-24. In some embodiments, z is 9-23. In some embodiments, z is 9-22. In some embodiments, z is 9-21. In some embodiments, z is 9-20. In some embodiments, z is 9-19. In some embodiments, z is 9-18. In some embodiments, z is 9-17. In some embodiments, z is 9-16. In some embodiments, z is 9-15. In some embodiments, z is 9-14. In some embodiments, z is 14-30. In some embodiments, z is 14-29. In some embodiments, z is 14-28. In some embodiments, z is 14-27. In some embodiments, z is 14-26. In some embodiments, z is 14-25. In some embodiments, z is 14-24. In some embodiments, z is 14-23. In some embodiments, z is 14-22. In some embodiments, z is 14-21. In some embodiments, z is 14-20. In some embodiments, z is 14-19. In some embodiments, z is 14-18. In some embodiments, z is 14-17. In some embodiments, z is 14-16. In some embodiments, z is 14-15.

In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 8. In some embodiments, z is 9. In some embodiments, z is 10. In some embodiments, z is 11. In some embodiments, z is 12. In some embodiments, z is 13. In some embodiments, z is 14. In some embodiments, z is 15. In some embodiments, z is 16. In some embodiments, z is 17. In some embodiments, z is 18. In some embodiments, z is 19. In some embodiments, z is 20. In some embodiments, z is 21. In some embodiments, z is 22. In some embodiments, z is 23. In some embodiments, z is 24. In some embodiments, z is 25. In some embodiments, z is 26. In some embodiments, z is 27. In some embodiments, z is 28. In some embodiments, z is 29. In some embodiments, z is 30. In some embodiments, z is at least 2. In some embodiments, z is at least 3. In some embodiments, z is at least 4. In some embodiments, z is at least 5. In some embodiments, z is at least 6. In some embodiments, z is at least 7. In some embodiments, z is at least 8. In some embodiments, z is at least 9. In some embodiments, z is at least 10. In some embodiments, z is at least 11. In some embodiments, z is at least 12. In some embodiments, z is at least 13. In some embodiments, z is at least 14. In some embodiments, z is at least 15. In some embodiments, z is at least 16. In some embodiments, z is at least 17. In some embodiments, z is at least 18. In some embodiments, z is at least 19. In some embodiments, z is at least 20. In some embodiments, z is at least 21. In some embodiments, z is at least 22. In some embodiments, z is at least 23. In some embodiments, z is at least 24. In some embodiments, z is at least 25. In some embodiments, z is at least 26. In some embodiments, z is at least 27. In some embodiments, z is at least 28. In some embodiments, z is at least 29. In some embodiments, z is at least 30.

In some embodiments, $L^{3E}$ is L. In some embodiments, $L^{3E}$ is -L-L-. In some embodiments, $L^{3E}$ is a covalent bond. In some embodiments, $L^{3E}$ is —O—.

In some embodiments, $R^{3E}$ is —R'. In some embodiments, $R^{3E}$ is -L-R'. In some embodiments, $R^{3E}$ is —OR'. In some embodiments, $R^{3E}$ is a solid support.

In some embodiments, $R^{3E}$ is —H. In some embodiments, $-L^3-R^{3E}$ is —H. In some embodiments, $-L^3-R^{3E}$ is —OH.

In some embodiments, $R^{3E}$ is optionally substituted $C_{1-6}$ aliphatic. In some embodiments, $R^{3E}$ is optionally substituted $C_{1-6}$ alkyl.

In some embodiments, $R^{3E}$ is —OR'. In some embodiments, $R^{3E}$ is-OH. In some embodiments, $R^{3E}$ is —OR', wherein R' is not hydrogen. In some embodiments, $R^{3E}$ is —OR', wherein R' is optionally substituted $C_{1-6}$ alkyl.

In some embodiments, $R^{3E}$ is a solid support. In some embodiments, $R^{3E}$ is a solid support for oligonucleotide synthesis. In some embodiments, $R^{3E}$ is for delivery.

In some embodiments, W is O, S, or Se. In some embodiments, W is O. In some embodiments, W is S. In some embodiments, W is Se. In some embodiments, a CpG oligonucleotide comprises at least one internucleotidic linkage of formula I wherein W is O. In some embodiments, a CpG oligonucleotide comprises at least one internucleotidic linkage of formula I wherein W is S. In some embodiments, a CpG oligonucleotide comprises at least one internucleotidic linkage of formula I wherein W is Se.

In some embodiments, each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

In some embodiments, each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms.

In some embodiments, two R groups are optionally and independently taken together to form a covalent bond.

In some embodiments, two or more R groups on the same atom are optionally and independently taken together with the atom to form an optionally substituted, 3-30 membered monocyclic, bicyclic or polycyclic ring having, in addition to the atom, 0-10 heteroatoms.

In some embodiments, two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

In some embodiments, each R is independently hydrogen, or an optionally substituted group selected from $C_1$-$C_6$ aliphatic, carbocyclyl, aryl, heteroaryl, and heterocyclyl. In some embodiments, each R is independently hydrogen, or an optionally substituted group selected from $C_1$-$C_6$ aliphatic, phenyl, carbocyclyl, aryl, heteroaryl, and heterocyclyl.

In some embodiments, R is hydrogen. In some embodiments, R is an optionally substituted group selected from $C_1$-$C_6$ aliphatic, phenyl, carbocyclyl, aryl, heteroaryl, or heterocyclyl.

In some embodiments, R is an optionally substituted $C_1$-$C_6$ aliphatic. In some embodiments, R is an optionally substituted $C_1$-$C_6$ alkyl. In some embodiments, R is optionally substituted, linear or branched hexyl. In some embodiments, R is optionally substituted, linear or branched pentyl. In some embodiments, R is optionally substituted, linear or branched butyl. In some embodiments, R is optionally substituted, linear or branched propyl. In some embodiments, R is optionally substituted ethyl. In some embodiments, R is optionally substituted methyl.

In some embodiments, R is optionally substituted phenyl. In some embodiments, R is substituted phenyl. In some embodiments, R is phenyl.

In some embodiments, R is optionally substituted carbocyclyl. In some embodiments, R is optionally substituted $C_3$-$C_{10}$ carbocyclyl. In some embodiments, R is optionally substituted monocyclic carbocyclyl. In some embodiments, R is optionally substituted cycloheptyl. In some embodiments, R is optionally substituted cyclohexyl. In some embodiments, R is optionally substituted cyclopentyl. In some embodiments, R is optionally substituted cyclobutyl.

In some embodiments, R is an optionally substituted cyclopropyl. In some embodiments, R is optionally substituted bicyclic carbocyclyl.

In some embodiments, R is an optionally substituted aryl. In some embodiments, R is an optionally substituted bicyclic aryl ring.

In some embodiments, R is an optionally substituted heteroaryl. In some embodiments, R is an optionally substituted 5-6 membered monocyclic heteroaryl ring having 1-3 heteroatoms independently selected from nitrogen, sulfur, or oxygen. In some embodiments, R is a substituted 5-6 membered monocyclic heteroaryl ring having 1-3 heteroatoms independently selected from nitrogen, oxygen, or sulfur. In some embodiments, R is an unsubstituted 5-6 membered monocyclic heteroaryl ring having 1-3 heteroatoms independently selected from nitrogen, sulfur, or oxygen.

In some embodiments, R is an optionally substituted 5 membered monocyclic heteroaryl ring having 1-3 heteroatoms independently selected from nitrogen, oxygen or sulfur. In some embodiments, R is an optionally substituted 6 membered monocyclic heteroaryl ring having 1-3 heteroatoms independently selected from nitrogen, oxygen, or sulfur.

In some embodiments, R is an optionally substituted 5-membered monocyclic heteroaryl ring having 1 heteroatom selected from nitrogen, oxygen, or sulfur. In some embodiments, R is selected from pyrrolyl, furanyl, or thienyl.

In some embodiments, R is an optionally substituted 5-membered heteroaryl ring having 2 heteroatoms independently selected from nitrogen, oxygen, or sulfur. In certain embodiments, R is an optionally substituted 5-membered heteroaryl ring having 1 nitrogen atom, and an additional heteroatom selected from sulfur or oxygen. Example R groups include optionally substituted pyrazolyl, imidazolyl, thiazolyl, isothiazolyl, oxazolyl or isoxazolyl.

In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having 2 nitrogen atoms. In certain embodiments, R is an optionally substituted 6-membered heteroaryl ring having 1 nitrogen. Example R groups include optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having 1 heteroatom independently selected from nitrogen, oxygen, or sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, or sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, or sulfur.

In certain embodiments, R is an optionally substituted 6,6-fused heteroaryl ring having 1-4 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having 1 heteroatom independently selected from nitrogen, oxygen, or sulfur. In some embodiments, R is an optionally substituted quinolinyl. In some embodiments, R is an optionally substituted isoquinolinyl. According to one aspect, R is an optionally substituted 6,6-fused heteroaryl ring having 2 heteroatoms independently selected from nitrogen, oxygen, or sulfur. In some embodiments, R is a quinazoline or a quinoxaline.

In some embodiments, R is an optionally substituted heterocyclyl. In some embodiments, R is an optionally substituted 3-7 membered saturated or partially unsaturated heterocyclic ring having 1-2 heteroatoms independently selected from nitrogen, oxygen, or sulfur. In some embodiments, R is a substituted 3-7 membered saturated or partially unsaturated heterocyclic ring having 1-2 heteroatoms independently selected from nitrogen, oxygen, or sulfur. In some embodiments, R is an unsubstituted 3-7 membered saturated or partially unsaturated heterocyclic ring having 1-2 heteroatoms independently selected from nitrogen, oxygen, or sulfur.

In some embodiments, R is an optionally substituted heterocyclyl. In some embodiments, R is an optionally substituted 6 membered saturated or partially unsaturated heterocyclic ring having 1-2 heteroatoms independently selected from nitrogen, oxygen, or sulfur. In some embodiments, R is an optionally substituted 6 membered partially unsaturated heterocyclic ring having 2 heteroatoms independently selected from nitrogen, oxygen, or sulfur. In some embodiments, R is an optionally substituted 6 membered partially unsaturated heterocyclic ring having 2 oxygen atom.

In certain embodiments, R is an optionally substituted 3-7 membered saturated or partially unsaturated heterocyclic ring having 1-2 heteroatoms independently selected from nitrogen, oxygen, or sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, R is an optionally substituted 5 membered saturated or partially unsaturated heterocyclic ring having 1-2 heteroatoms independently selected from nitrogen, oxygen, or sulfur.

In certain embodiments, R is an optionally substituted 5-6 membered partially unsaturated monocyclic ring having 1-2 heteroatoms independently selected from nitrogen, oxygen, or sulfur. In certain embodiments, R is an optionally substituted tetrahydropyridinyl, dihydrothiazolyl, dihydrooxazolyl, or oxazolinyl group.

In some embodiments, R is an optionally substituted 8-10 membered bicyclic saturated or partially unsaturated heterocyclic ring having 1-4 heteroatoms independently selected from nitrogen, oxygen, or sulfur. In some embodiments, R is an optionally substituted indolinyl. In some embodiments, R is an optionally substituted isoindolinyl. In some embodiments, R is an optionally substituted 1, 2, 3, 4-tetrahydroquinoline. In some embodiments, R is an optionally substituted 1, 2, 3, 4-tetrahydroisoquinoline.

In some embodiments, each R' is independently —R, —C(O)R, —CO$_2$R, or —SO$_2$R, or:
  two R' on the same nitrogen are taken together with their intervening atoms to form an optionally substituted heterocyclic or heteroaryl ring, or
  two R' on the same carbon are taken together with their intervening atoms to form an optionally substituted aryl, carbocyclic, heterocyclic, or heteroaryl ring.

In some embodiments, R' is —R, —C(O)R, —CO$_2$R, or —SO$_2$R, wherein R is as defined above and described herein.

In some embodiments, R' is —R, wherein R is as defined and described above and herein. In some embodiments, R' is hydrogen.

In some embodiments, R' is —C(O)R, wherein R is as defined above and described herein. In some embodiments, R' is —CO$_2$R, wherein R is as defined above and described herein. In some embodiments, R' is —SO$_2$R, wherein R is as defined above and described herein.

In some embodiments, two R' on the same nitrogen are taken together with their intervening atoms to form an optionally substituted heterocyclic or heteroaryl ring. In some embodiments, two R' on the same carbon are taken together with their intervening atoms to form an optionally substituted aryl, carbocyclic, heterocyclic, or heteroaryl ring.

In some embodiments, -Cy- is an optionally substituted bivalent ring selected from carbocyclylene, arylene, heteroarylene, or heterocyclylene.

In some embodiments, -Cy- is optionally substituted phenylene. In some embodiments, -Cy- is optionally substituted carbocyclylene. In some embodiments, -Cy- is optionally substituted arylene. In some embodiments, -Cy- is optionally substituted heteroaryl ene. In some embodiments, -Cy- is optionally substituted heterocyclylene.

In some embodiments, each of X, Y and Z is independently —O—, —S—, —N(-L-R$^1$)—, or L, wherein each of L and R$^1$ is independently as defined above and described below.

In some embodiments, X is —O—. In some embodiments, X is —S—. In some embodiments, X is —O— or —S—. In some embodiments, a CpG oligonucleotide comprises at least one internucleotidic linkage of formula I wherein X is —O—. In some embodiments, a CpG oligonucleotide comprises at least one internucleotidic linkage of formula I wherein X is —S—. In some embodiments, a CpG oligonucleotide comprises at least one internucleotidic linkage of formula I wherein X is —O—, and at least one internucleotidic linkage of formula I wherein X is —S—. In some embodiments, a CpG oligonucleotide comprises at least one internucleotidic linkage of formula I wherein X is —O—, and at least one internucleotidic linkage of formula I wherein X is —S—, and at least one internucleotidic linkage of formula I wherein L is an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—.

In some embodiments, X is —N(-L-R$^1$)—. In some embodiments, X is —N(R')—, In some embodiments, X is —N(R')—. In some embodiments, X is —N(R)—. In some embodiments, X is —NH—.

In some embodiments, X is L. In some embodiments, X is a covalent bond. In some embodiments, X is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, X is an optionally substituted C$_1$-C$_{10}$ alkylene or C$_1$-C$_{10}$ alkenylene. In some embodiments, X is methylene.

In some embodiments, Y is —O—. In some embodiments, Y is —S—.

In some embodiments, Y is —N(-L-R$^1$)—, In some embodiments, Y is —N(R')—, In some embodiments, Y is —N(R')—. In some embodiments, Y is —N(R)—. In some embodiments, Y is —NH—.

In some embodiments, Y is L. In some embodiments, Y is a covalent bond. In some embodiments, Y is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Y is an optionally substituted C$_1$-C$_{10}$ alkylene or C$_1$-C$_{10}$ alkenylene. In some embodiments, Y is methylene.

In some embodiments, Z is —O—. In some embodiments, Z is —S—.

In some embodiments, Z is —N(-L-R$^1$)—, In some embodiments, Z is —N(R')—, In some embodiments, Z is —N(R')—. In some embodiments, Z is —N(R)—. In some embodiments, Z is —NH—.

In some embodiments, Z is L. In some embodiments, Z is a covalent bond. In some embodiments, Z is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Z is an optionally substituted C$_1$-C$_{10}$ alkylene or C$_1$-C$_{10}$ alkenylene. In some embodiments, Z is methylene.

In some embodiments, L is a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$. In some embodiments, L is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus, boron and silicon, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$. In some embodiments, L is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus, boron and silicon, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—. In some embodiments, L is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus, boron and silicon, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—; and one or more carbon atoms are optionally and independently replaced with Cy$^L$. In some embodiments, L is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus, boron and silicon, wherein one or more methylene units are optionally and independently replaced with C$_{1-6}$ alkylene, C$_{1-6}$ alkenylene, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—. In some embodiments, L is a covalent bond or an optionally substituted, linear or branched C$_1$-C$_{10}$ alkylene, wherein one or more methylene units of L are optionally and independently replaced by an optionally substituted group selected from C$_1$-C$_6$ alkylene, C$_1$-C$_6$ alkenylene, —C≡C—, a C$_1$-C$_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—. In some embodiments, the aliphatic and/or the heteroaliphatic group is C$_{1-30}$. In some embodiments, the aliphatic and the heteroaliphatic group are independently C$_{1-30}$, C$_{1-25}$, C$_{1-20}$, C$_{1-15}$, C$_{1-10}$, C$_{1-9}$, C$_{1-8}$, C$_{1-7}$, C$_{1-6}$, C$_{1-5}$, C$_{1-4}$, C$_{1-3}$, C$_{1-2}$, or C$_1$. In some embodiments, the aliphatic group or the heteroaliphatic group is independently C$_{1-30}$, C$_{1-25}$, C$_{1-20}$, C$_{1-15}$, C$_{1-10}$, C$_{1-9}$, C$_{1-8}$, C$_{1-7}$, C$_{1-6}$, C$_{1-5}$, C$_{1-4}$, C$_{1-3}$, C$_{1-2}$, or C$_1$. In some embodiments, it is C$_1$. In some embodiments, it is C$_2$. In some embodiments, it is C$_3$. In some embodiments, it is C$_4$. In some embodiments, it is C$_5$. In some embodiments, it is C$_6$. In some embodiments, it is C$_7$. In some embodiments, it is C$_8$. In some embodiments, it is C$_9$. In some embodiments, it is C$_{10}$. In some embodiments, it is C$_{15}$. In some embodiments, it is C$_{20}$. In some embodiments, it is C$_{25}$. In some embodiments, L is a covalent bond.

In some embodiments, L is a covalent bond or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, L is a covalent bond. In some embodiments, L is an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, L has the structure of -L$^1$-V—, wherein:

$L^1$ is an optionally substituted group selected from

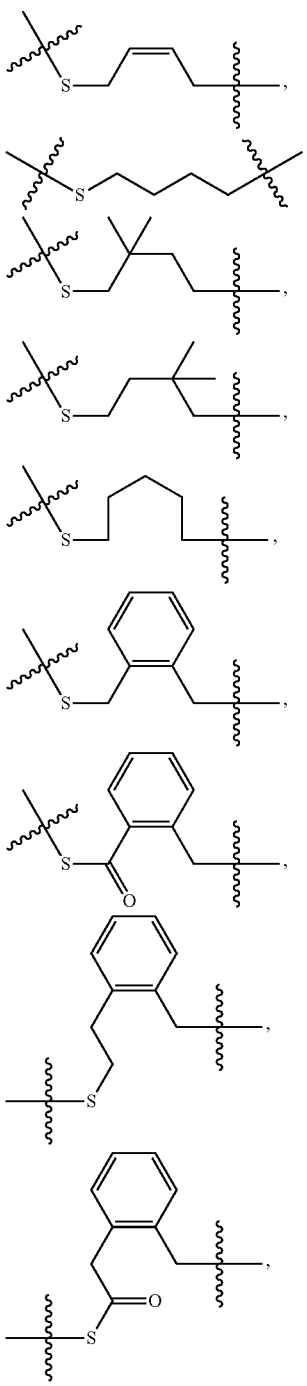

$C_1$-$C_6$ alkylene, $C_1$-$C_6$ alkenylene, carbocyclylene, arylene, $C_1$-$C_6$ heteroalkylene, heterocyclylene, and heteroarylene;
V is selected from —O—, —S—, —NR'—, C(R')$_2$, —S—S—, —B—S—S—C—,

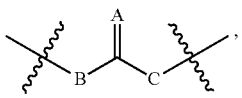

or an optionally substituted group selected from $C_1$-$C_6$ alkylene, arylene, $C_1$-$C_6$ heteroalkylene, heterocyclylene, and heteroarylene;
A is =O, =S, =NR', or =C(R')$_2$;
each of B and C is independently —O—, —S—, —NR'—, —C(R')$_2$—, or an optionally substituted group selected from $C_1$-$C_6$ alkylene, carbocyclylene, arylene, heterocyclylene, or heteroarylene; and
each R' is independently as defined above and described herein.

In some embodiments, $L^1$ is

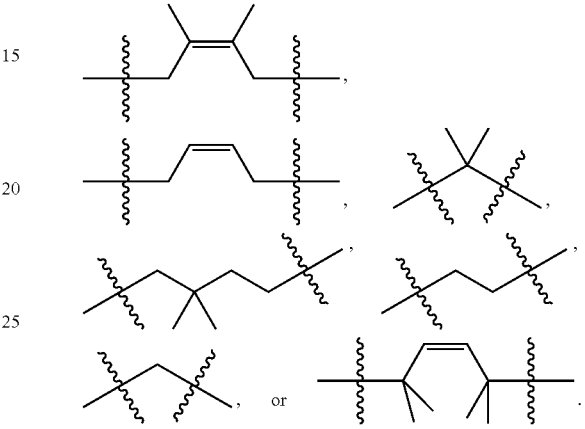

In some embodiments, $L^1$ is

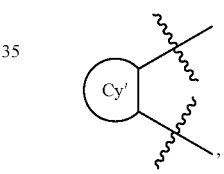

wherein Ring Cy' is an optionally substituted arylene, carbocyclylene, heteroarylene, or heterocyclylene. In some embodiments, $L^1$ is optionally substituted

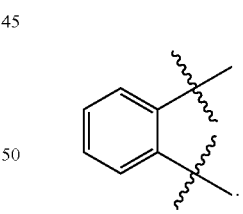

In some embodiments, $L^1$ is

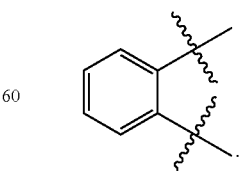

In some embodiments, $L^1$ is connected to X. In some embodiments, $L^1$ is an optionally substituted group selected from

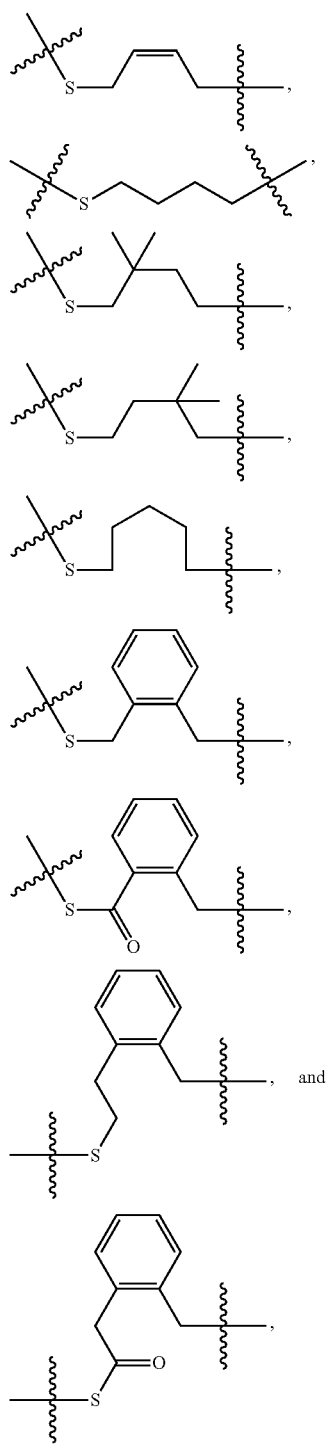

and the sulfur atom is connect to V. In some embodiments, $L^1$ is an optionally substituted group selected from

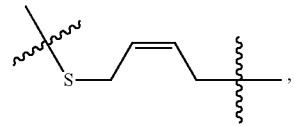

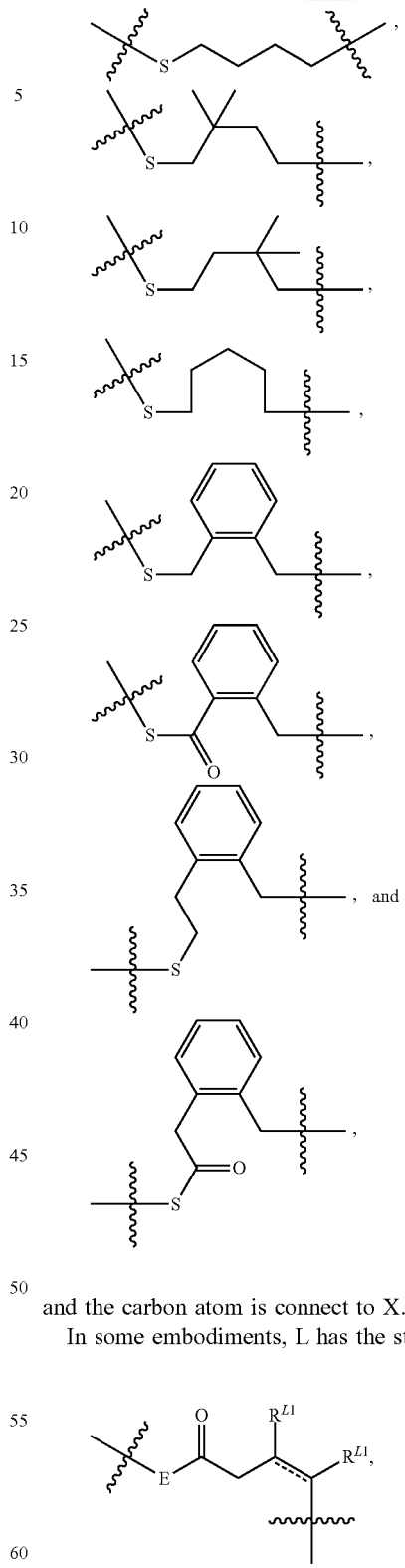

and the carbon atom is connect to X.

In some embodiments, L has the structure of:

wherein:
E is —O—, —S—, —NR'— or —C(R')$_2$—;
===== is a single or double bond;
the two $R^{L1}$ are taken together with the two carbon atoms to which they are bound to form an optionally substituted aryl, carbocyclic, heteroaryl or heterocyclic ring; and each R' is independently as defined above and described herein.

In some embodiments, L has the structure of:

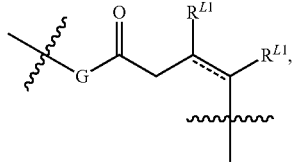

wherein:

G is —O—, —S—, or —NR';

----- is a single or double bond; and the two $R^{L1}$ are taken together with the two carbon atoms to which they are bound to form an optionally substituted aryl, $C_3$-$C_{10}$ carbocyclic, heteroaryl or heterocyclic ring.

In some embodiments, L has the structure of:

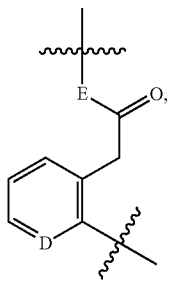

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

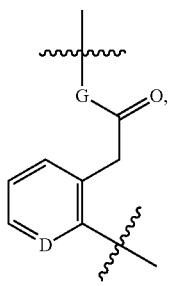

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—.

In some embodiments, L has the structure of:

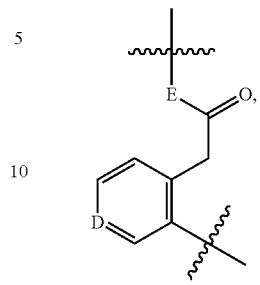

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

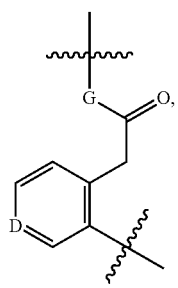

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—.

In some embodiments, L has the structure of:

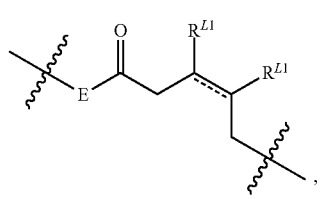

wherein:

E is —O—, —S—, —NR'— or —C(R')$_2$—;

----- is a single or double bond;

the two $R^{L1}$ are taken together with the two carbon atoms to which they are bound to form an optionally substituted aryl, $C_3$-$C_{10}$ carbocyclic, heteroaryl or heterocyclic ring; and each R' is independently as defined above and described herein.

In some embodiments, L has the structure of:

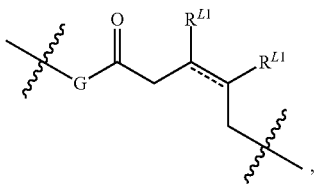

wherein:
G is —O—, —S—, or —NR';
----- is a single or double bond;
the two $R^{L1}$ are taken together with the two carbon atoms to which they are bound to form an optionally substituted aryl, $C_3$-$C_{10}$ carbocyclic, heteroaryl or heterocyclic ring; and each R' is independently as defined above and described herein.

In some embodiments, L has the structure of:

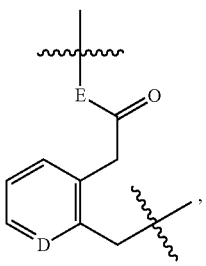

wherein:
E is —O—, —S—, —NR'— or —C(R')$_2$—;
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

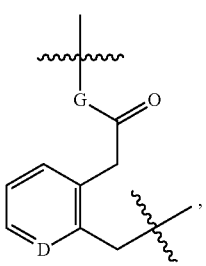

wherein:
G is —O—, —S—, or —NR';
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

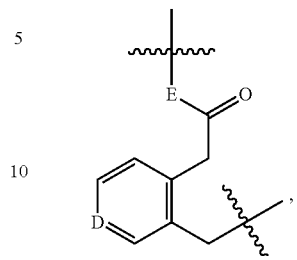

wherein:
E is —O—, —S—, —NR'— or —C(R')$_2$—;
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

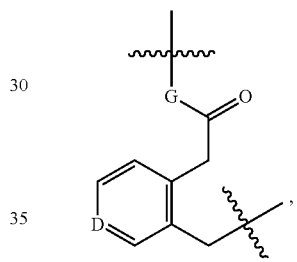

wherein:
G is —O—, —S—, or —NR';
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

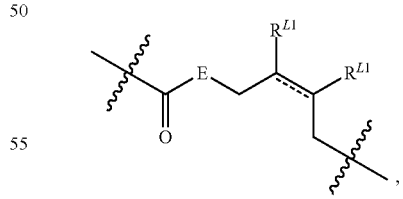

wherein:
E is —O—, —S—, —NR'— or —C(R')$_2$—;
----- is a single or double bond;
the two $R^{L1}$ are taken together with the two carbon atoms to which they are bound to form an optionally substituted aryl, $C_3$-$C_{10}$ carbocyclic, heteroaryl or heterocyclic ring; and each R' is independently as defined above and described herein.

In some embodiments, L has the structure of:

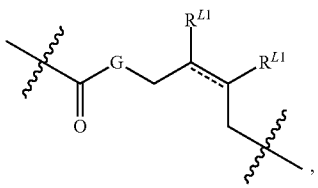

wherein:

G is —O—, —S—, or —NR';

----- is a single or double bond;

the two $R^{L1}$ are taken together with the two carbon atoms to which they are bound to form an optionally substituted aryl, $C_3$-$C_{10}$ carbocyclic, heteroaryl or heterocyclic ring; and each R' is independently as defined above and described herein.

In some embodiments, L has the structure of:

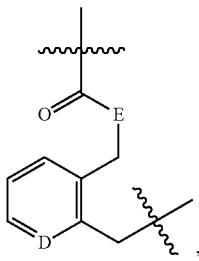

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

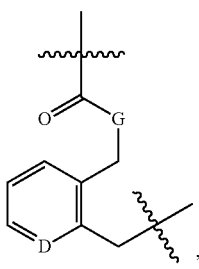

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and R' is as defined above and described herein.

In some embodiments, L has the structure of:

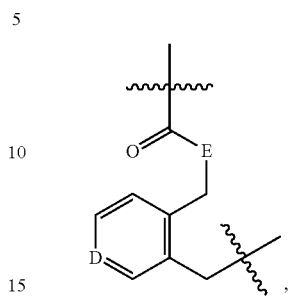

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

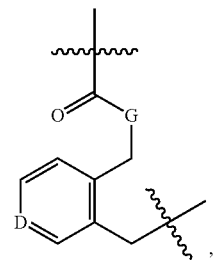

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and R' is as defined above and described herein.

In some embodiments, L has the structure of:

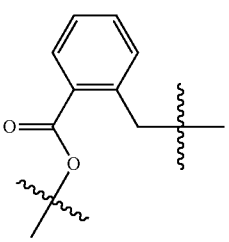

wherein the phenyl ring is optionally substituted. In some embodiments, the phenyl ring is not substituted. In some embodiments, the phenyl ring is substituted.

In some embodiments, L has the structure of:

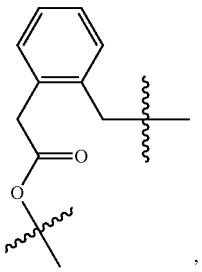 [SMILES: *Cc1ccccc1CC(=O)O*]

wherein the phenyl ring is optionally substituted. In some embodiments, the phenyl ring is not substituted. In some embodiments, the phenyl ring is substituted.

In some embodiments, L has the structure of:

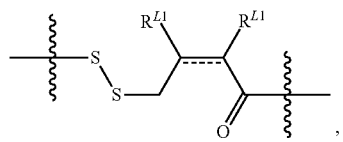

wherein:
----- is a single or double bond; and
the two $R^{L1}$ are taken together with the two carbon atoms to which they are bound to form an optionally substituted aryl, $C_3$-$C_{10}$ carbocyclic, heteroaryl or heterocyclic ring.

In some embodiments, L has the structure of:

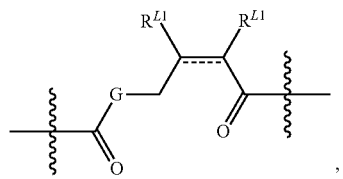

wherein:
G is —O—, —S—, or —NR';
----- is a single or double bond; and
the two $R^{L1}$ are taken together with the two carbon atoms to which they are bound to form an optionally substituted aryl, $C_3$-$C_{10}$ carbocyclic, heteroaryl or heterocyclic ring.

In some embodiments, E is —O—, —S—, —NR'— or —C(R')$_2$—, wherein each R' independently as defined above and described herein. In some embodiments, E is —O—, —S—, or —NR'—. In some embodiments, E is —O—, —S—, or —NH—. In some embodiments, E is —O—. In some embodiments, E is —S—. In some embodiments, E is —NH—.

In some embodiments, G is —O—, —S—, or —NR', wherein each R' independently as defined above and described herein. In some embodiments, G is —O—, —S—, or —NH—. In some embodiments, G is —O—. In some embodiments, G is —S—. In some embodiments, G is —NH—.

In some embodiments, L is -L$^3$-G-, wherein:
L$^3$ is an optionally substituted $C_1$-$C_5$ alkylene or alkenylene, wherein one or more methylene units are optionally and independently replaced by —O—, —S—N(R')—, —C(O)—, —C(S)—, —C(NR')—, —S(O)—, —S(O)$_2$—, or

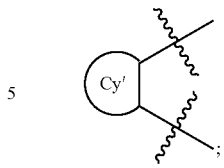

and
wherein each of G, R' and Ring Cy' is independently as defined above and described herein.

In some embodiments, L is -L$^3$-S—, wherein L$^3$ is as defined above and described herein. In some embodiments, L is -L$^3$-O—, wherein L$^3$ is as defined above and described herein. In some embodiments, L is -L$^3$-N(R')—, wherein each of L$^3$ and R' is independently as defined above and described herein. In some embodiments, L is -L$^3$-NH—, wherein each of L$^3$ and R' is independently as defined above and described herein.

In some embodiments, L$^3$ is an optionally substituted $C_5$ alkylene or alkenylene, wherein one or more methylene units are optionally and independently replaced by —O—, —S—, —N(R')—, —C(O)—, —C(S)—, —C(NR')—, —S(O)—, —S(O)$_2$—. or

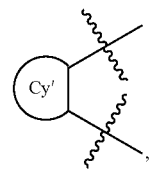 [SMILES: *CC*]

and each of R' and Ring Cy' is independently as defined above and described herein. In some embodiments, L$^3$ is an optionally substituted $C_5$ alkylene. In some embodiments, -L$^3$-G- is

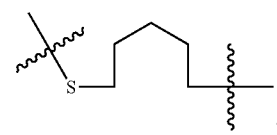

In some embodiments, L$^3$ is an optionally substituted $C_4$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

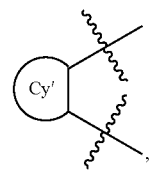

and each of R' and Cy' is independently as defined above and described herein.

229

In some embodiments, -L³-G- is

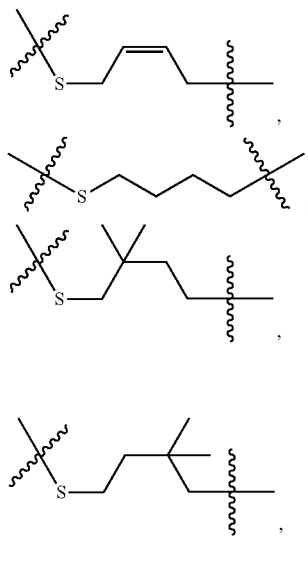

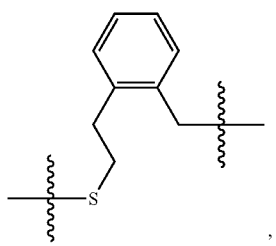

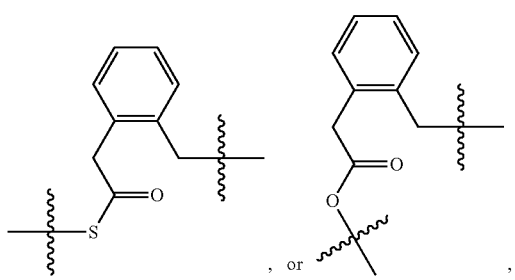

In some embodiments, L³ is an optionally substituted C₃ alkylene or alkenylene, wherein one or more methylene units are optionally and independently replaced by —O—, —S—, —N(R')—, —C(O)—, —C(S)—, —C(NR')—, —S(O)—, —S(O)₂—, or

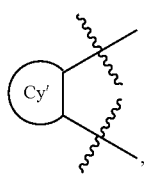

and each of R' and Cy' is independently as defined above and described herein,

230

In some embodiments, -L³-G- is

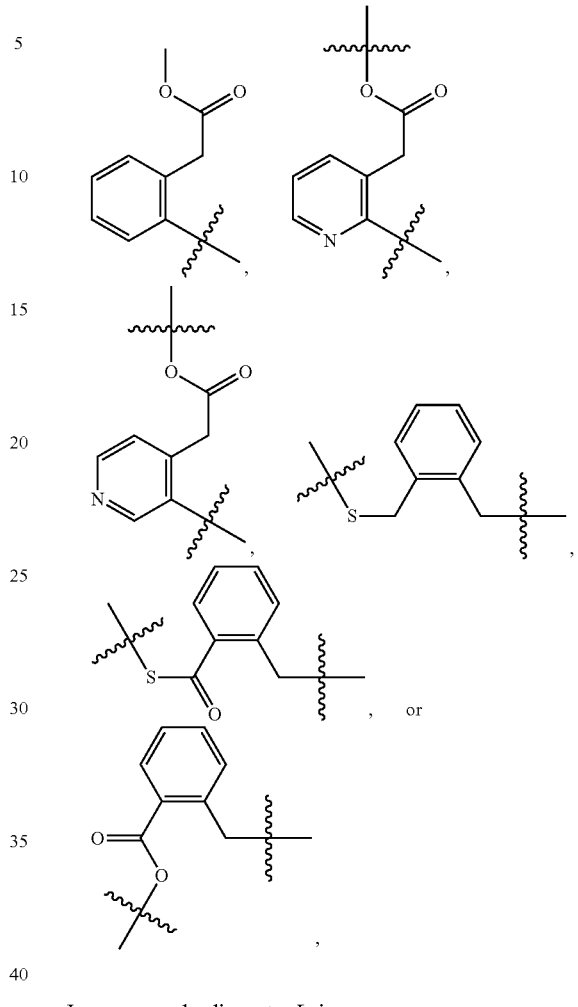

In some embodiments, L is

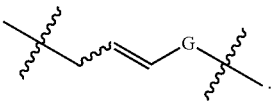

In some embodiments, L is

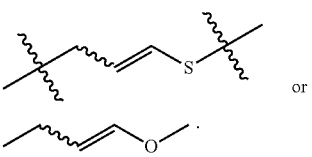

In some embodiments, L is

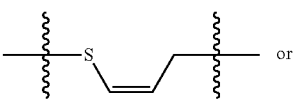 or

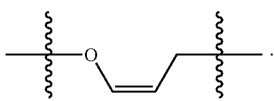

In some embodiments, $L^3$ is an optionally substituted $C_2$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

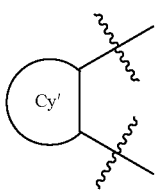

and each of R' and Cy' is independently as defined above and described herein.

In some embodiments, -$L^3$-G- is

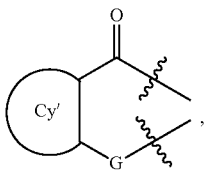

wherein each of G and Cy' is independently as defined above and described herein. In some embodiments, L is

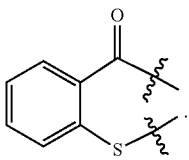 [SMILES: *Sc1ccccc1C(*)=O]

In some embodiments, L is -$L^4$-G-, wherein $L^4$ is an optionally substituted $C_1$-$C_2$ alkylene; and G is as defined above and described herein. In some embodiments, L is -$L^4$-G-, wherein $L^4$ is an optionally substituted $C_1$-$C_2$ alkylene; G is as defined above and described herein; and G is connected to $R^1$. In some embodiments, L is -$L^4$-G-, wherein $L^4$ is an optionally substituted methylene; G is as defined above and described herein; and G is connected to $R^1$. In some embodiments, L is -$L^4$-G-, wherein $L^4$ is methylene; G is as defined above and described herein; and G is connected to $R^1$. In some embodiments, L is -$L^4$-G-, wherein $L^4$ is an optionally substituted —(CH$_2$)$_2$—; G is as defined above and described herein; and G is connected to $R^1$. In some embodiments, L is -$L^4$-G-, wherein $L^4$ is —(CH$_2$)$_2$—; G is as defined above and described herein; and G is connected to $R^1$.

In some embodiments, L is

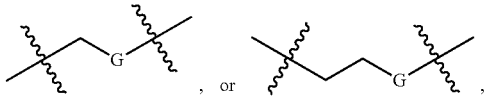

wherein G is as defined above and described herein, and G is connected to $R^1$. In some embodiments, L is

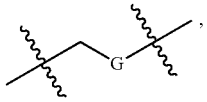

wherein G is as defined above and described herein, and G is connected to $R^1$. In some embodiments, L is

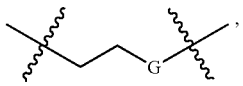

wherein G is as defined above and described herein, and G is connected to $R^1$. In some embodiments, L is

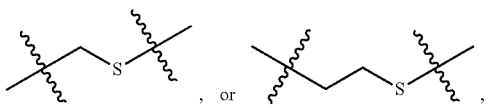

wherein the sulfur atom is connected to $R^1$. In some embodiments, L is

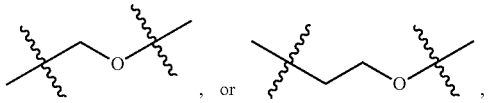

wherein the oxygen atom is connected to $R^1$.

In some embodiments, L is

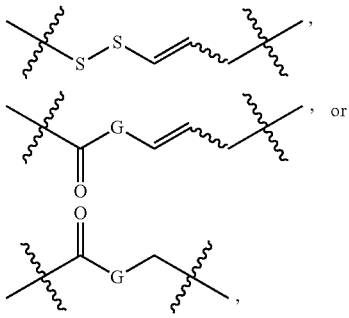

wherein G is as defined above and described herein.

In some embodiments, L is —S—$R^{L3}$— or —S—C(O)—$R^{L3}$—, wherein $R^{L3}$ is an optionally substituted, linear or branched, $C_1$-$C_9$ alkylene, wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each of R' and -Cy- is independently as defined above and described herein. In some embodiments, L is —S—R$^{L3}$— or —S—C(O)—R$^{L3}$—, wherein R$^{L3}$ is an optionally substituted $C_1$-$C_6$ alkylene. In some embodiments, L is —S—R$^{L3}$— or —S—C(O)—R$^{L3}$—, wherein R$^{L3}$ is an optionally substituted $C_1$-$C_6$ alkenylene. In some embodiments, L is —S—R$^{L3}$— or —S—C(O)—R$^{L3}$—, wherein R$^{L3}$ is an optionally substituted $C_1$-$C_6$ alkylene wherein one or more methylene units are optionally and independently replaced by an optionally substituted $C_1$-$C_6$ alkenylene, arylene, or heteroarylene. In some embodiments, R$^{L3}$ is an optionally substituted —S—($C_1$-$C_6$ alkenylene)-, —S—($C_1$-$C_6$ alkylene)-, —S—($C_1$-$C_6$ alkylene)-arylene-($C_1$-$C_6$ alkylene)-, —S—CO-arylene-($C_1$-$C_6$ alkylene)-, or —S—CO—($C_1$-$C_6$ alkylene)-arylene-($C_1$-$C_6$ alkylene)-.

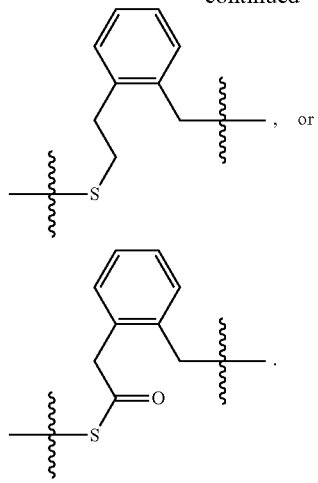

In some embodiments, L is

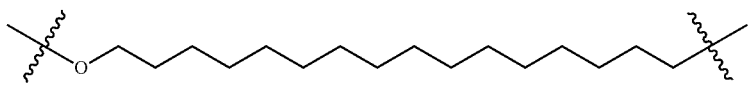

In some embodiments, L is

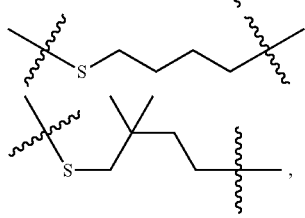

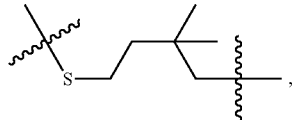

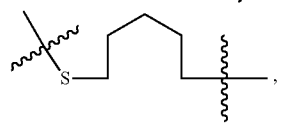

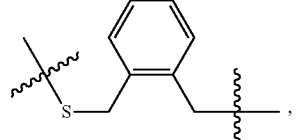

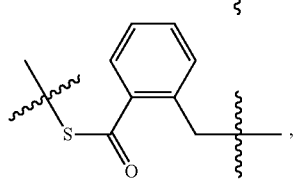

In some embodiments, L is

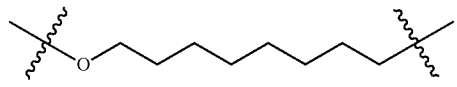

In some embodiments,

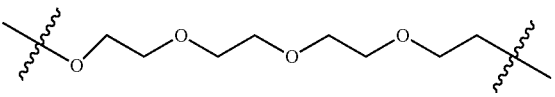

In some embodiments, the sulfur atom in the L embodiments described above and herein is connected to X. In some embodiments, the sulfur atom in the L embodiments described above and herein is connected to R$^1$.

In some embodiments, R$^1$ is -L-R, halogen, —CN, —NO$_2$, —Si(R)$_3$, —OR, —SR, or —N(R)$_2$. In some embodiments, R$^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, R$^1$ is halogen, R, or an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)₂—, —S(O)₂N(R')—, —N(R')S(O)₂—, —SC(O)—, —C(O)S—, —OC(O)—, or —C(O)O—, wherein each variable is independently as defined above and described herein.

In some embodiments, R¹ is hydrogen. In some embodiments, R¹ is halogen. In some embodiments, R¹ is —F. In some embodiments, R¹ is —Cl. In some embodiments, R¹ is —Br. In some embodiments, R¹ is —I.

In some embodiments, R¹ is R wherein R is as defined above and described herein.

In some embodiments, R¹ is hydrogen. In some embodiments, R¹ is an optionally substituted group selected from C₁-C₅₀ aliphatic, phenyl, carbocyclyl, aryl, heteroaryl, or heterocyclyl.

In some embodiments, R¹ is an optionally substituted C₁-C₅₀ aliphatic. In some embodiments, R¹ is an optionally substituted C₁-C₁₀ aliphatic. In some embodiments, R¹ is an optionally substituted C₁-C₆ aliphatic. In some embodiments, R¹ is an optionally substituted C₁-C₆ alkyl. In some embodiments, R¹ is optionally substituted, linear or branched hexyl. In some embodiments, R¹ is optionally substituted, linear or branched pentyl. In some embodiments, R¹ is optionally substituted, linear or branched butyl. In some embodiments, R¹ is optionally substituted, linear or branched propyl. In some embodiments, R¹ is optionally substituted ethyl. In some embodiments, R¹ is optionally substituted methyl.

In some embodiments, R¹ is optionally substituted phenyl. In some embodiments, R¹ is substituted phenyl. In some embodiments, R¹ is phenyl.

In some embodiments, R¹ is optionally substituted carbocyclyl. In some embodiments, R¹ is optionally substituted C₃-C₁₀ carbocyclyl. In some embodiments, R¹ is optionally substituted monocyclic carbocyclyl. In some embodiments, R¹ is optionally substituted cycloheptyl. In some embodiments, R¹ is optionally substituted cyclohexyl. In some embodiments, R¹ is optionally substituted cyclopentyl. In some embodiments, R¹ is optionally substituted cyclobutyl. In some embodiments, R¹ is an optionally substituted cyclopropyl. In some embodiments, R¹ is optionally substituted bicyclic carbocyclyl.

In some embodiments, R¹ is an optionally substituted C₁-C₅₀ polycyclic hydrocarbon. In some embodiments, R¹ is an optionally substituted C₁-C₅₀ polycyclic hydrocarbon wherein one or more methylene units are optionally and independently replaced by an optionally substituted C₁-C₆ alkylene, C₁-C₆ alkenylene, —C≡C—, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)₂—, —S(O)₂N(R')—, —N(R')S(O)₂—, —SC(O)—, —C(O)S—, —OC(O)—, or —C(O)O—, wherein each variable is independently as defined above and described herein. In some embodiments, R¹ is optionally substituted

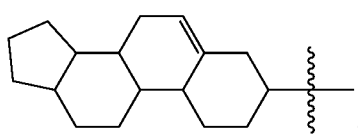

In some embodiments, R¹ is

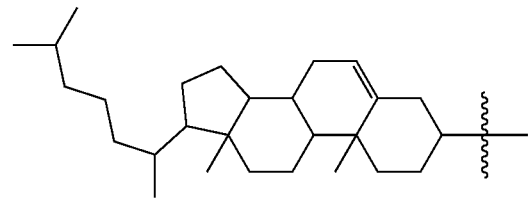

In some embodiments, R¹ is optionally substituted

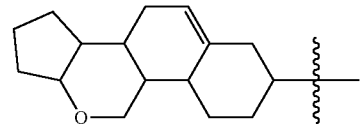

In some embodiments, R¹ is an optionally substituted C₁-C₅₀ aliphatic comprising one or more optionally substituted polycyclic hydrocarbon moieties. In some embodiments, R¹ is an optionally substituted C₁-C₅₀ aliphatic comprising one or more optionally substituted polycyclic hydrocarbon moieties, wherein one or more methylene units are optionally and independently replaced by an optionally substituted C₁-C₆ alkylene, C₁-C₆ alkenylene, —C≡C—, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)₂—, —S(O)₂N(R')—, —N(R')S(O)₂—, —SC(O)—, —C(O)S—, —OC(O)—, or —C(O)O—, wherein each variable is independently as defined above and described herein. In some embodiments, R¹ is an optionally substituted C₁-C₅₀ aliphatic comprising one or more optionally substituted

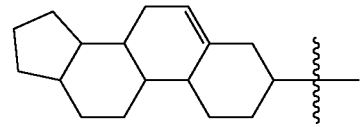

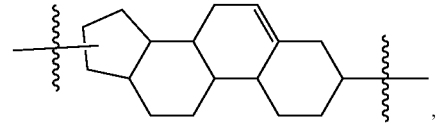

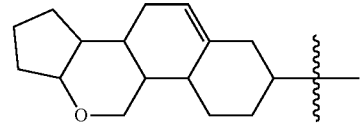

, or

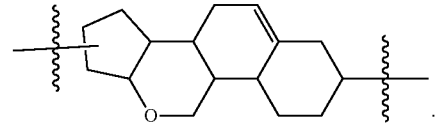

In some embodiments, R¹ is

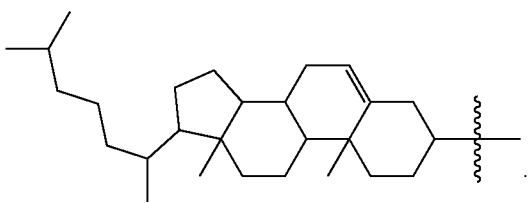 [SMILES: *C1CCC2(C)C(=CCC3C2CCC2(C)C(C(C)CCCC(C)C)CCC32)C1]

In some embodiments, R¹ is

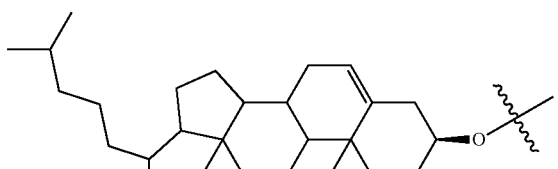

In some embodiments, R¹ is

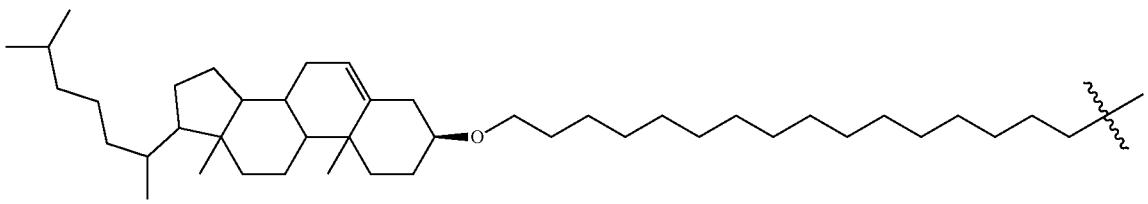 [SMILES: *CCCCCCCCCCCCCCCCO[C@H]1CCC2(C)C(=CCC3C2CCC2(C)C(C(C)CCCC(C)C)CCC32)C1]

In some embodiments, R¹ is

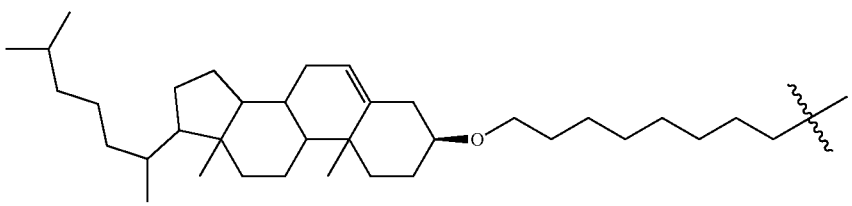 [SMILES: *CCCCCCCCO[C@H]1CCC2(C)C(=CCC3C2CCC2(C)C(C(C)CCCC(C)C)CCC32)C1]

In some embodiments, R¹ is

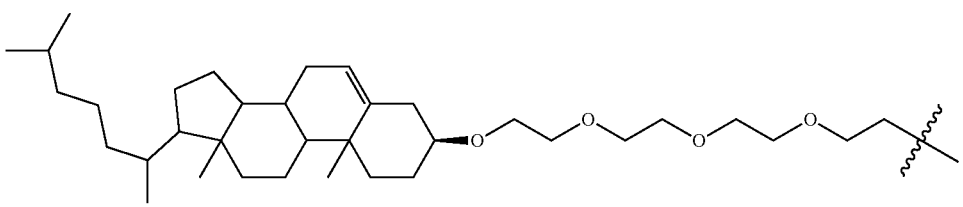 [SMILES: *CCOCCOCCOCCO[C@H]1CCC2(C)C(=CCC3C2CCC2(C)C(C(C)CCCC(C)C)CCC32)C1]

In some embodiments, R¹ is an optionally substituted aryl. In some embodiments, R¹ is an optionally substituted bicyclic aryl ring.

In some embodiments, R¹ is an optionally substituted heteroaryl. In some embodiments, R¹ is an optionally substituted 5-6 membered monocyclic heteroaryl ring having 1-3 heteroatoms independently selected from nitrogen, sulfur, or oxygen. In some embodiments, R¹ is a substituted 5-6 membered monocyclic heteroaryl ring having 1-3 heteroatoms independently selected from nitrogen, oxygen, or sulfur. In some embodiments, R¹ is an unsubstituted 5-6 membered monocyclic heteroaryl ring having 1-3 heteroatoms independently selected from nitrogen, sulfur, or oxygen.

In some embodiments, R¹ is an optionally substituted 5 membered monocyclic heteroaryl ring having 1-3 heteroatoms independently selected from nitrogen, oxygen or sulfur. In some embodiments, R¹ is an optionally substituted 6 membered monocyclic heteroaryl ring having 1-3 heteroatoms independently selected from nitrogen, oxygen, or sulfur.

In some embodiments, R¹ is an optionally substituted 5-membered monocyclic heteroaryl ring having 1 heteroatom selected from nitrogen, oxygen, or sulfur. In some embodiments, R¹ is selected from pyrrolyl, furanyl, or thienyl.

In some embodiments, R¹ is an optionally substituted 5-membered heteroaryl ring having 2 heteroatoms independently selected from nitrogen, oxygen, or sulfur. In certain embodiments, R¹ is an optionally substituted 5-membered heteroaryl ring having 1 nitrogen atom, and an additional heteroatom selected from sulfur or oxygen. Example R¹ groups include optionally substituted pyrazolyl, imidazolyl, thiazolyl, isothiazolyl, oxazolyl or isoxazolyl.

In some embodiments, R¹ is a 6-membered heteroaryl ring having 1-3 nitrogen atoms. In other embodiments, R¹ is an optionally substituted 6-membered heteroaryl ring having 1-2 nitrogen atoms. In some embodiments, R¹ is an optionally substituted 6-membered heteroaryl ring having 2 nitrogen atoms. In certain embodiments, R¹ is an optionally substituted 6-membered heteroaryl ring having 1 nitrogen. Example $R^1$ groups include optionally substituted pyridinyl, pyrimidinyl, pyrazinyl, pyridazinyl, triazinyl, or tetrazinyl.

In certain embodiments, $R^1$ is an optionally substituted 8-10 membered bicyclic heteroaryl ring having 1-4 heteroatoms independently selected from nitrogen, oxygen, or sulfur. In some embodiments, $R^1$ is an optionally substituted 5,6-fused heteroaryl ring having 1-4 heteroatoms independently selected from nitrogen, oxygen, or sulfur. In other embodiments, $R^1$ is an optionally substituted 5,6-fused heteroaryl ring having 1-2 heteroatoms independently selected from nitrogen, oxygen, or sulfur. In certain embodiments, $R^1$ is an optionally substituted 5,6-fused heteroaryl ring having 1 heteroatom independently selected from nitrogen, oxygen, or sulfur. In some embodiments, $R^1$ is an optionally substituted indolyl. In some embodiments, $R^1$ is an optionally substituted azabicyclo[3.2.1]octanyl. In certain embodiments, $R^1$ is an optionally substituted 5,6-fused heteroaryl ring having 2 heteroatoms independently selected from nitrogen, oxygen, or sulfur. In some embodiments, $R^1$ is an optionally substituted azaindolyl. In some embodiments, $R^1$ is an optionally substituted benzimidazolyl. In some embodiments, $R^1$ is an optionally substituted benzothiazolyl. In some embodiments, $R^1$ is an optionally substituted benzoxazolyl. In some embodiments, $R^1$ is an optionally substituted indazolyl. In certain embodiments, $R^1$ is an optionally substituted 5,6-fused heteroaryl ring having 3 heteroatoms independently selected from nitrogen, oxygen, or sulfur.

In certain embodiments, $R^1$ is an optionally substituted 6,6-fused heteroaryl ring having 1-4 heteroatoms independently selected from nitrogen, oxygen, or sulfur. In some embodiments, $R^1$ is an optionally substituted 6,6-fused heteroaryl ring having 1-2 heteroatoms independently selected from nitrogen, oxygen, or sulfur. In other embodiments, $R^1$ is an optionally substituted 6,6-fused heteroaryl ring having 1 heteroatom independently selected from nitrogen, oxygen, or sulfur. In some embodiments, $R^1$ is an optionally substituted quinolinyl. In some embodiments, $R^1$ is an optionally substituted isoquinolinyl. According to one aspect, $R^1$ is an optionally substituted 6,6-fused heteroaryl ring having 2 heteroatoms independently selected from nitrogen, oxygen, or sulfur. In some embodiments, $R^1$ is a quinazoline or a quinoxaline.

In some embodiments, $R^1$ is an optionally substituted heterocyclyl. In some embodiments, $R^1$ is an optionally substituted 3-7 membered saturated or partially unsaturated heterocyclic ring having 1-2 heteroatoms independently selected from nitrogen, oxygen, or sulfur. In some embodiments, $R^1$ is a substituted 3-7 membered saturated or partially unsaturated heterocyclic ring having 1-2 heteroatoms independently selected from nitrogen, oxygen, or sulfur. In some embodiments, $R^1$ is an unsubstituted 3-7 membered saturated or partially unsaturated heterocyclic ring having 1-2 heteroatoms independently selected from nitrogen, oxygen, or sulfur.

In some embodiments, $R^1$ is an optionally substituted heterocyclyl. In some embodiments, $R^1$ is an optionally substituted 6 membered saturated or partially unsaturated heterocyclic ring having 1-2 heteroatoms independently selected from nitrogen, oxygen, or sulfur. In some embodiments, $R^1$ is an optionally substituted 6 membered partially unsaturated heterocyclic ring having 2 heteroatoms independently selected from nitrogen, oxygen, or sulfur. In some embodiments, $R^1$ is an optionally substituted 6 membered partially unsaturated heterocyclic ring having 2 oxygen atoms.

In certain embodiments, $R^1$ is a 3-7 membered saturated or partially unsaturated heterocyclic ring having 1-2 heteroatoms independently selected from nitrogen, oxygen, or sulfur. In certain embodiments, $R^1$ is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, $R^1$ is an optionally substituted 5 membered saturated or partially unsaturated heterocyclic ring having 1-2 heteroatoms independently selected from nitrogen, oxygen, or sulfur.

In certain embodiments, $R^1$ is an optionally substituted 5-6 membered partially unsaturated monocyclic ring having 1-2 heteroatoms independently selected from nitrogen, oxygen, or sulfur. In certain embodiments, $R^1$ is an optionally substituted tetrahydropyridinyl, dihydrothiazolyl, dihydrooxazolyl, or oxazolinyl group.

In some embodiments, $R^1$ is an optionally substituted 8-10 membered bicyclic saturated or partially unsaturated heterocyclic ring having 1-4 heteroatoms independently selected from nitrogen, oxygen, or sulfur. In some embodiments, $R^1$ is an optionally substituted indolinyl. In some embodiments, $R^1$ is an optionally substituted isoindolinyl. In some embodiments, $R^1$ is an optionally substituted 1, 2, 3, 4-tetrahydroquinoline. In some embodiments, $R^1$ is an optionally substituted 1, 2, 3, 4-tetrahydroisoquinoline.

In some embodiments, $R^1$ is an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is an optionally substituted $C_1$-$C_{10}$ aliphatic wherein one or more methylene units are optionally and independently replaced by an optionally-Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —OC(O)—, or —C(O)O—, wherein each R' is independently as defined above and described herein. In some embodiments, $R^1$ is an optionally substituted $C_1$-$C_{10}$ aliphatic wherein one or more methylene units are optionally and independently replaced by an optionally-Cy-, —O—, —S—, —S—S—, —N(R')—, —C(O)—, —OC(O)—, or —C(O)O—, wherein each R' is independently as defined above and described herein.
In some embodiments, R is,
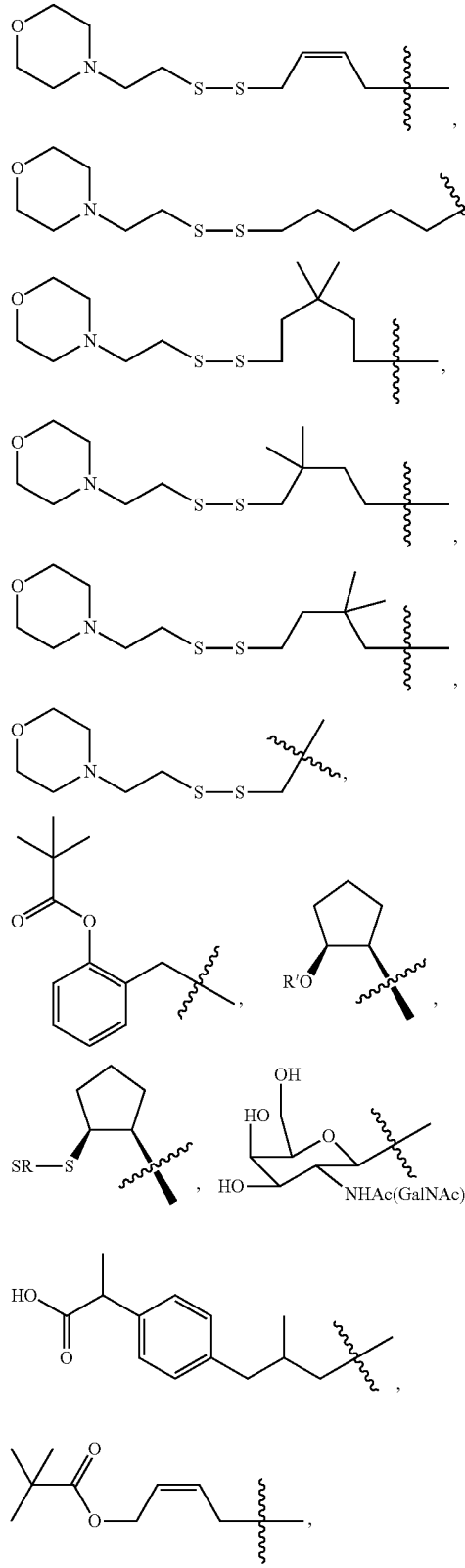
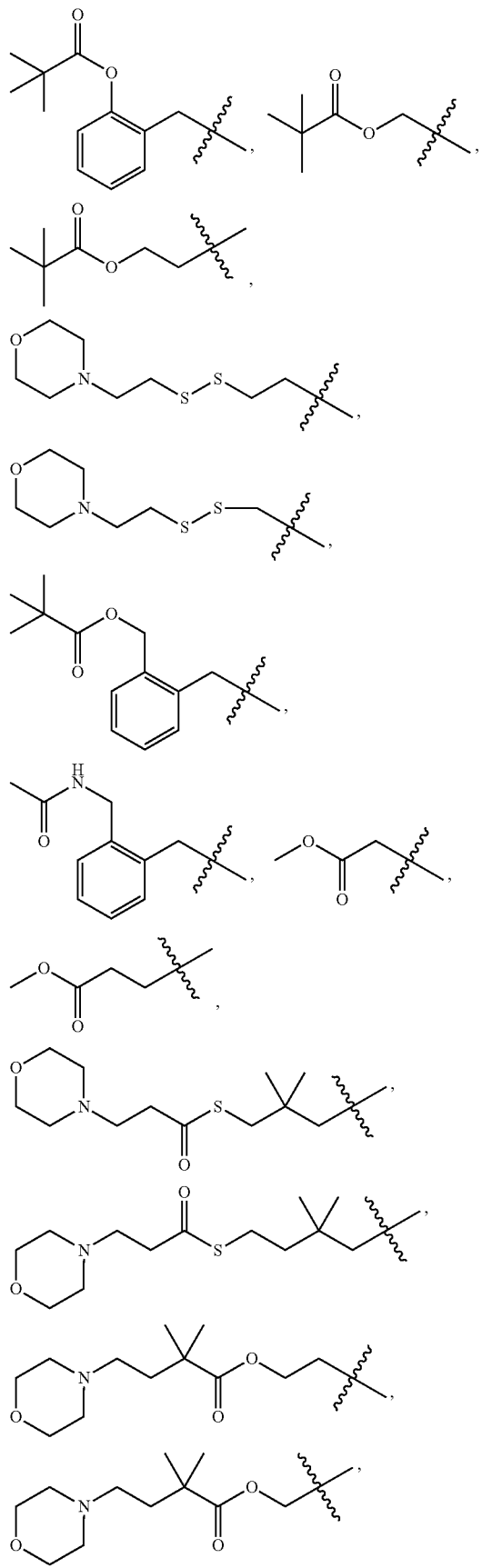

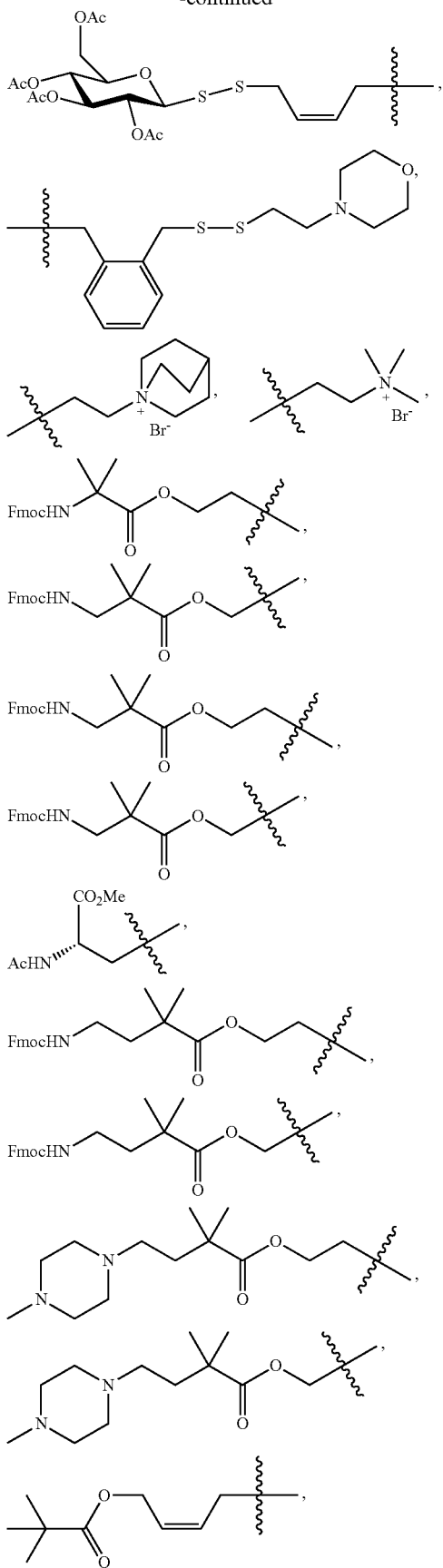
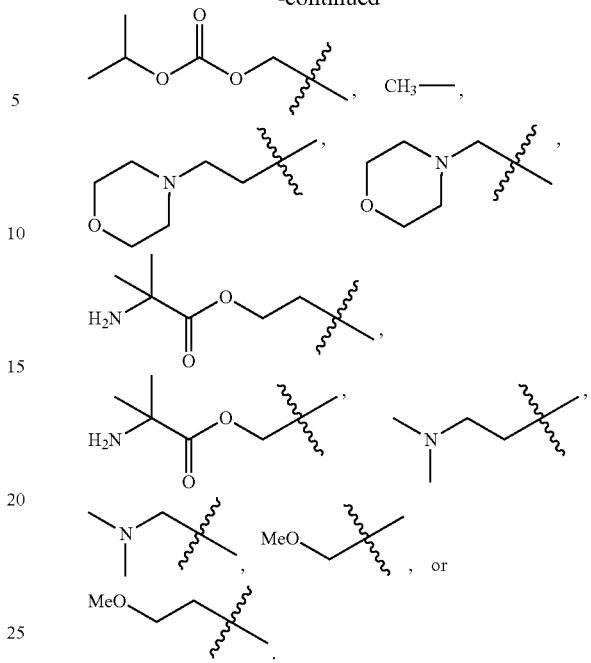
In some embodiments, $R^1$ is $CH_3-$,
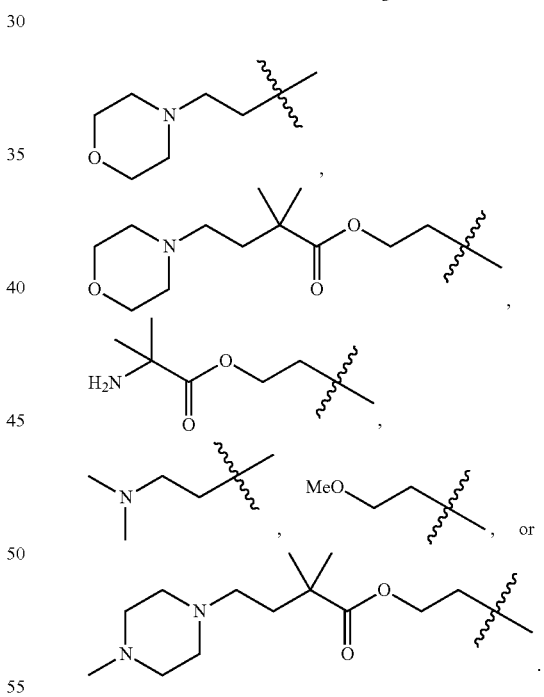
In some embodiments, $R^1$ comprises a terminal optionally substituted $-(CH_2)_2-$ moiety which is connected to L. Example such $R^1$ groups are depicted below:
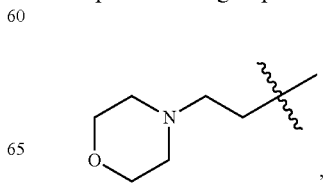

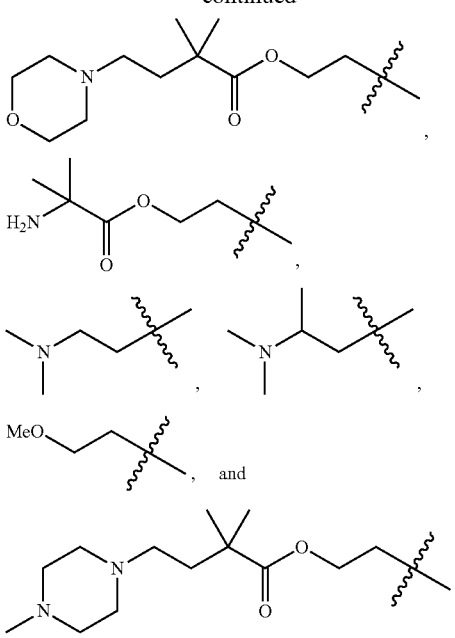

In some embodiments, $R^1$ comprises a terminal optionally substituted —(CH$_2$)— moiety which is connected to L. Exemplary such $R^1$ groups are depicted below:

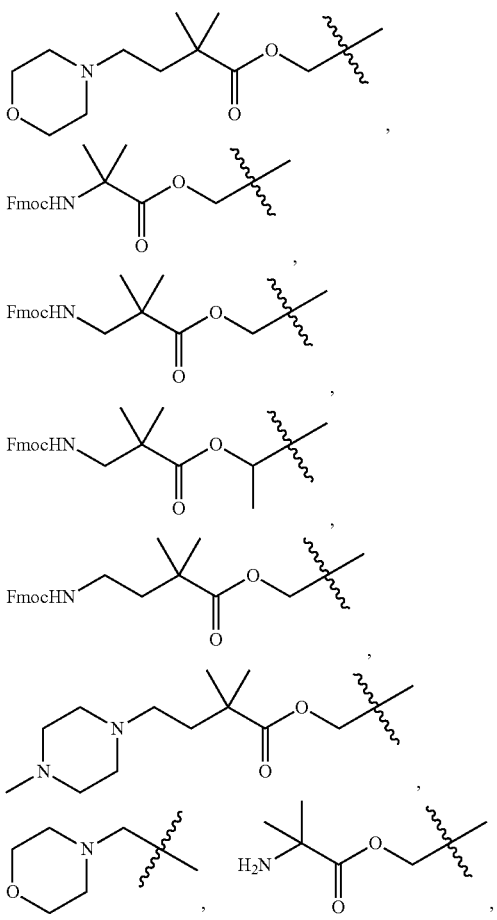

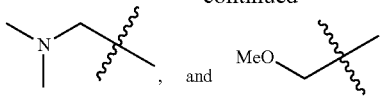

In some embodiments, $R^1$ is —S—$R^{L2}$, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, and each of R' and -Cy- is independently as defined above and described herein. In some embodiments, $R^1$ is —S—$R^{L2}$, wherein the sulfur atom is connected with the sulfur atom in L group.

In some embodiments, $R^1$ is —C(O)—$R^{L2}$, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O— and each of R' and -Cy- is independently as defined above and described herein. In some embodiments, $R^1$ is —C(O)—$R^{L2}$, wherein the carbonyl group is connected with G in L group. In some embodiments, $R^1$ is —C(O)—$R^{L2}$, wherein the carbonyl group is connected with the sulfur atom in L group.

In some embodiments, $R^{L2}$ is optionally substituted $C_1$-$C_3$ aliphatic. In some embodiments, $R^{L2}$ is optionally substituted $C_1$-$C_3$ alkyl. In some embodiments, $R^{L2}$ is optionally substituted $C_1$-$C_9$ alkenyl. In some embodiments, $R^{L2}$ is optionally substituted $C_1$-$C_3$ alkynyl. In some embodiments, $R^{L2}$ is an optionally substituted $C_1$-$C_3$ aliphatic wherein one or more methylene units are optionally and independently replaced by -Cy- or —C(O)—. In some embodiments, $R^{L2}$ is an optionally substituted $C_1$-$C_3$ aliphatic wherein one or more methylene units are optionally and independently replaced by -Cy-. In some embodiments, $R^{L2}$ is an optionally substituted $C_1$-$C_9$ aliphatic wherein one or more methylene units are optionally and independently replaced by an optionally substituted heterocycylene. In some embodiments, $R^{L2}$ is an optionally substituted $C_1$-$C_3$ aliphatic wherein one or more methylene units are optionally and independently replaced by an optionally substituted arylene. In some embodiments, $R^{L2}$ is an optionally substituted $C_1$-$C_3$ aliphatic wherein one or more methylene units are optionally and independently replaced by an optionally substituted heteroarylene. In some embodiments, $R^{L2}$ is an optionally substituted $C_1$-$C_3$ aliphatic wherein one or more methylene units are optionally and independently replaced by an optionally substituted $C_3$-$C_{10}$ carbocyclylene. In some embodiments, $R^{L2}$ is an optionally substituted $C_1$-$C_3$ aliphatic wherein two methylene units are optionally and independently replaced by -Cy- or —C(O)—. In some embodiments, $R^{L2}$ is an optionally substituted $C_1$-$C_3$ aliphatic wherein two methylene units are optionally and independently replaced by -Cy- or —C(O)—. Example $R^{L2}$ groups are depicted below:

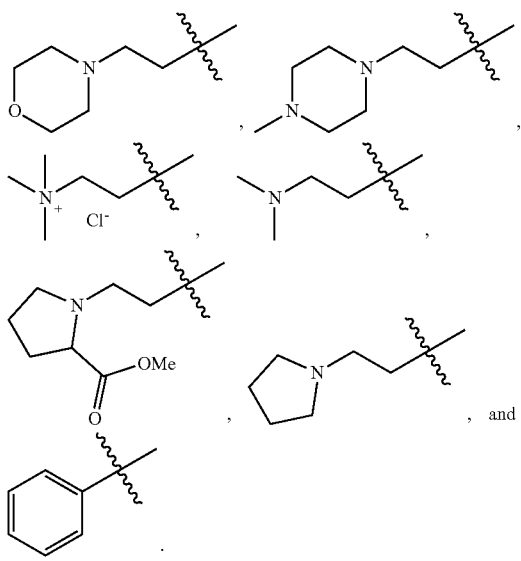

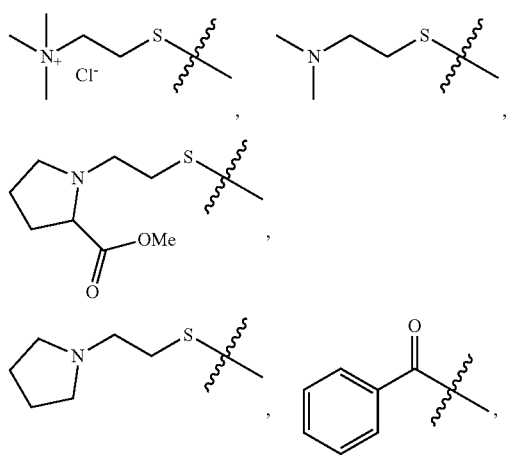

In some embodiments, $R^1$ is hydrogen, or an optionally substituted group selected

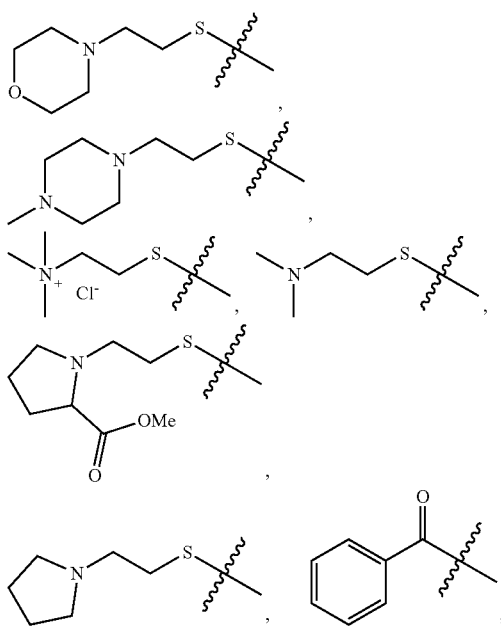

—S—($C_1$-$C_{10}$ aliphatic), $C_1$-$C_{10}$ aliphatic, aryl, $C_1$-$C_6$ heteroalkyl, heteroaryl and heterocyclyl. In some embodiments, $R^1$ is

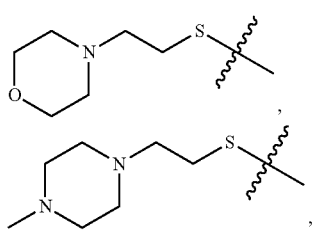

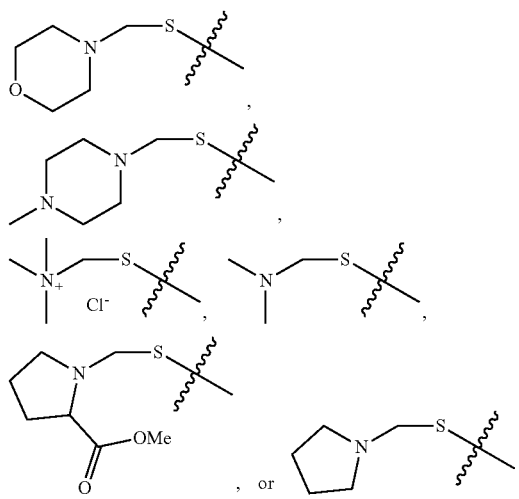

or —S—($C_1$-$C_{10}$ aliphatic). In some embodiments, $R^1$ is

In some embodiments, $R^1$ is an optionally substituted group selected from —S—($C_1$-$C_6$ aliphatic), $C_1$-$C_{10}$ aliphatic, $C_1$-$C_6$ heteroaliphatic, aryl, heterocyclyl and heteroaryl.

In some embodiments, $R^1$ is

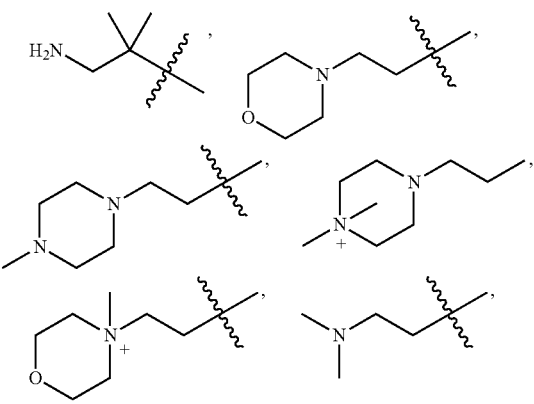

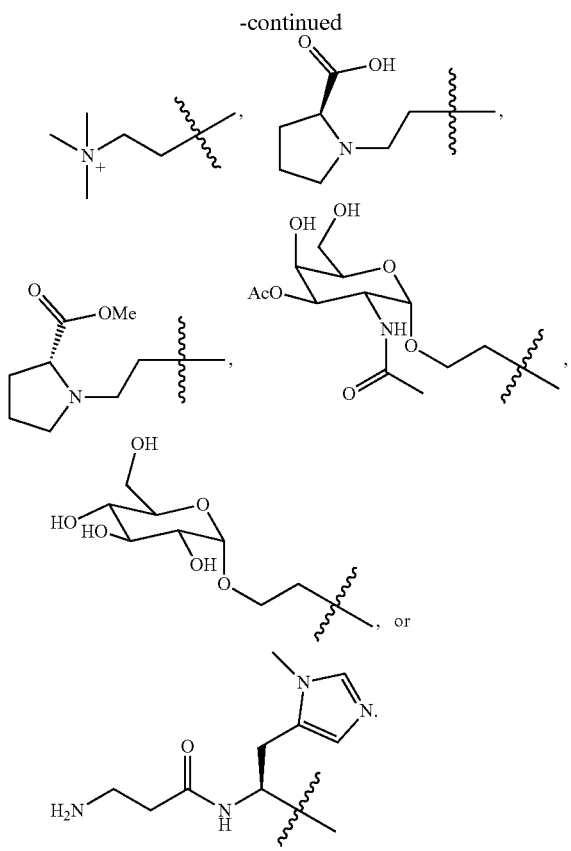

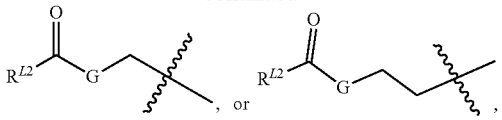, or 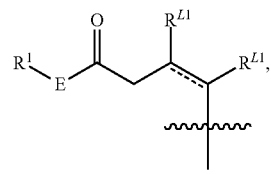, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, and each G is independently as defined above and described herein.

In some embodiments, -L-$R^1$ is —$R^{L3}$—S—S—$R^{L2}$, wherein each variable is independently as defined above and described herein. In some embodiments, -L-$R^1$ is —$R^{L3}$—C(O)—S—S—$R^{L2}$, wherein each variable is independently as defined above and described herein.

In some embodiments, -L-$R^1$ has the structure of:

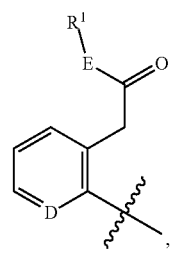

wherein each variable is independently as defined above and described herein.

In some embodiments, -L-$R^1$ has the structure of:

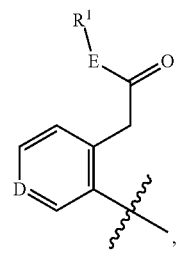

In some embodiments, the sulfur atom in the $R^1$ embodiments described above and herein is connected with the sulfur atom, G, E, or —C(O)— moiety in the L embodiments described above and herein. In some embodiments, the —C(O)— moiety in the $R^1$ embodiments described above and herein is connected with the sulfur atom, G, E, or —C(O)— moiety in the L embodiments described above and herein.

In some embodiments, -L-$R^1$ is any combination of the L embodiments and $R^1$ embodiments described above and herein.

In some embodiments, -L-$R^1$ is -L-G-$R^1$ wherein each variable is independently as defined above and described herein.

In some embodiments, -L-$R^1$ is -L$^4$-G-$R^1$ wherein each variable is independently as defined above and described herein.

In some embodiments, -L-$R^1$ is -L$^3$-G-S—$R^{L2}$, wherein each variable is independently as defined above and described herein.

In some embodiments, -L-$R^1$ is -L$^3$-G-C(O)—$R^{L2}$, wherein each variable is independently as defined above and described herein.

In some embodiments, -L-$R^1$ is

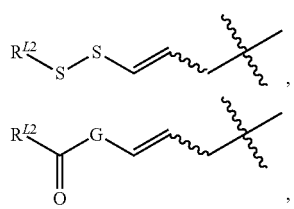

wherein each variable is independently as defined above and described herein.

In some embodiments, -L-$R^1$ has the structure of:

In some embodiments, -L-R$^1$ has the structure of:

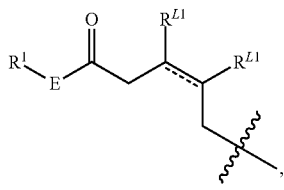

wherein each variable is independently as defined above and described herein.

In some embodiments, -L-R$^1$ has the structure of:

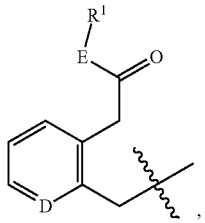

wherein each variable is independently as defined above and described herein.

In some embodiments, -L-R$^1$ has the structure of:

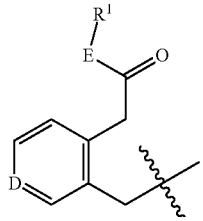

wherein each variable is independently as defined above and described herein.

In some embodiments, -L-R$^1$ has the structure of:

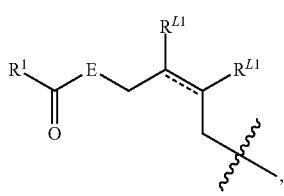

wherein each variable is independently as defined above and described herein.

In some embodiments, -L-R$^1$ has the structure of:

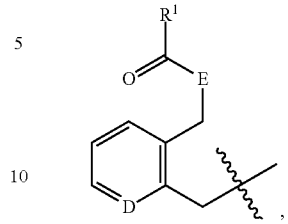

wherein each variable is independently as defined above and described herein.

In some embodiments, -L-R$^1$ has the structure of:

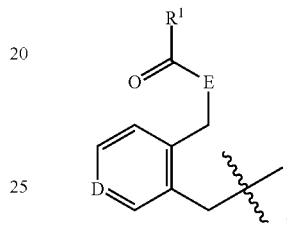

wherein each variable is independently as defined above and described herein.

In some embodiments, -L-R$^1$ has the structure of:

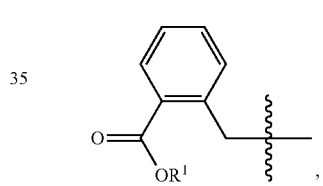

wherein each variable is independently as defined above and described herein.

In some embodiments, -L-R$^1$ has the structure of:

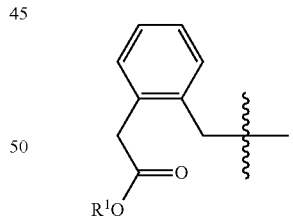

wherein each variable is independently as defined above and described herein.

In some embodiments, -L-R$^1$ has the structure of:

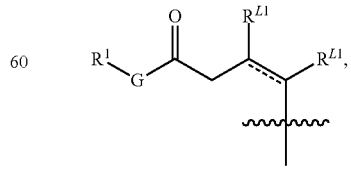

wherein each variable is independently as defined above and described herein.

In some embodiments, -L-R¹ has the structure of:

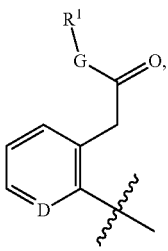

wherein each variable is independently as defined above and described herein.

In some embodiments, -L-R¹ has the structure of:

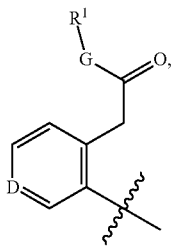

wherein each variable is independently as defined above and described herein.

In some embodiments, -L-R¹ has the structure of:

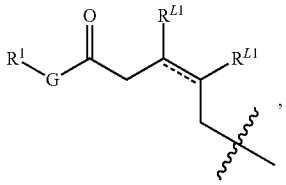

wherein each variable is independently as defined above and described herein.

In some embodiments, -L-R¹ has the structure of:

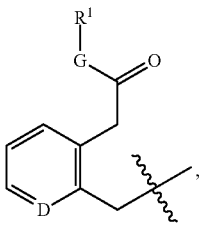

wherein each variable is independently as defined above and described herein.

In some embodiments, -L-R¹ has the structure of:

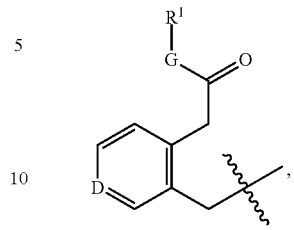

wherein each variable is independently as defined above and described herein.

In some embodiments, -L-R¹ has the structure of:

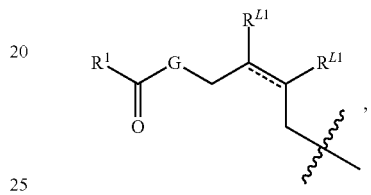

wherein each variable is independently as defined above and described herein.

In some embodiments, -L-R¹ has the structure of:

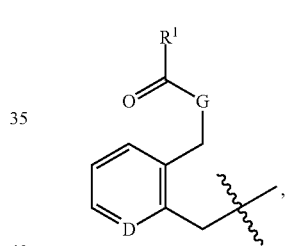

wherein each variable is independently as defined above and described herein.

In some embodiments, -L-R¹ has the structure of:

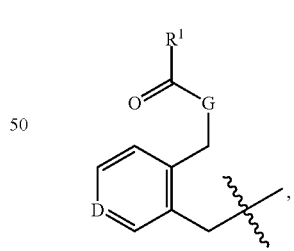

wherein each variable is independently as defined above and described herein.

In some embodiments, -L-R¹ has the structure of:

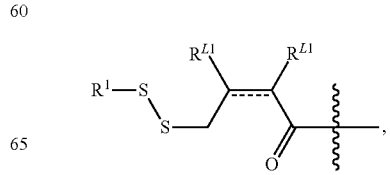

wherein each variable is independently as defined above and described herein.

In some embodiments, L has the structure of:

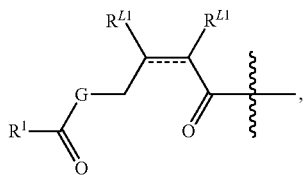

wherein each variable is independently as defined above and described herein.

In some embodiments, —X-L-R¹ has the structure of:

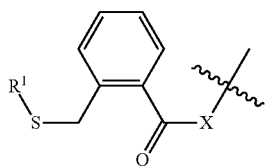

wherein:
the phenyl ring is optionally substituted, and
each of R¹ and X is independently as defined above and described herein.

In some embodiments, -L-R¹ is

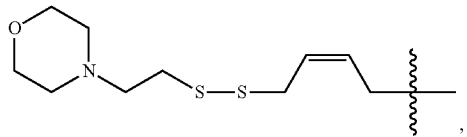,

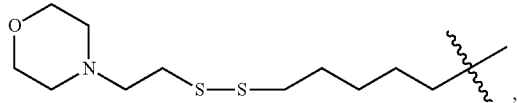,

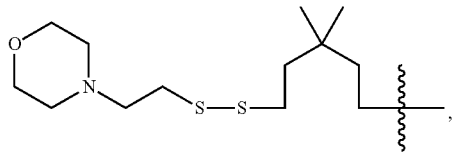,

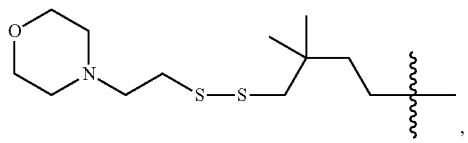,

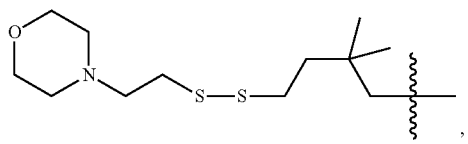,

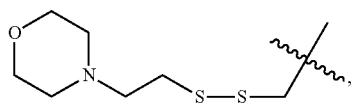,

-continued

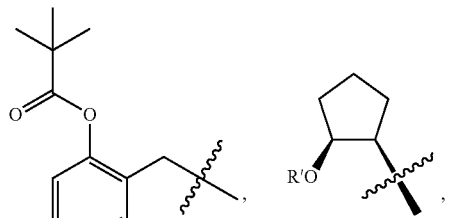,

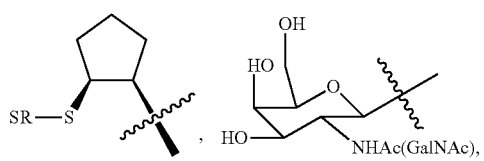,

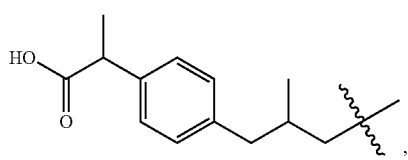,

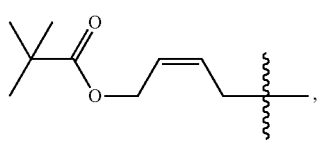,

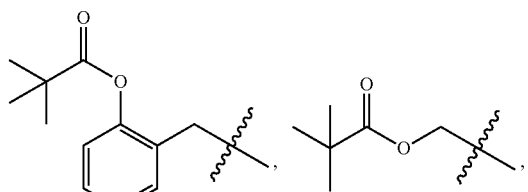,

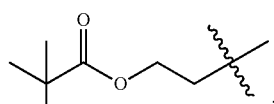,

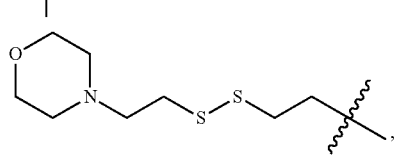,

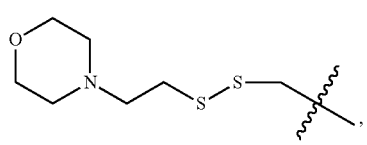,

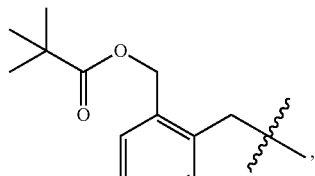,

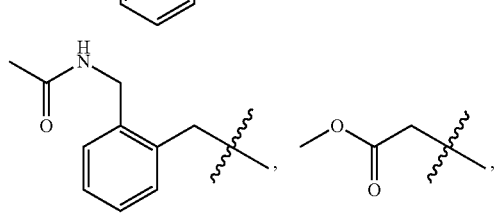,

257
-continued
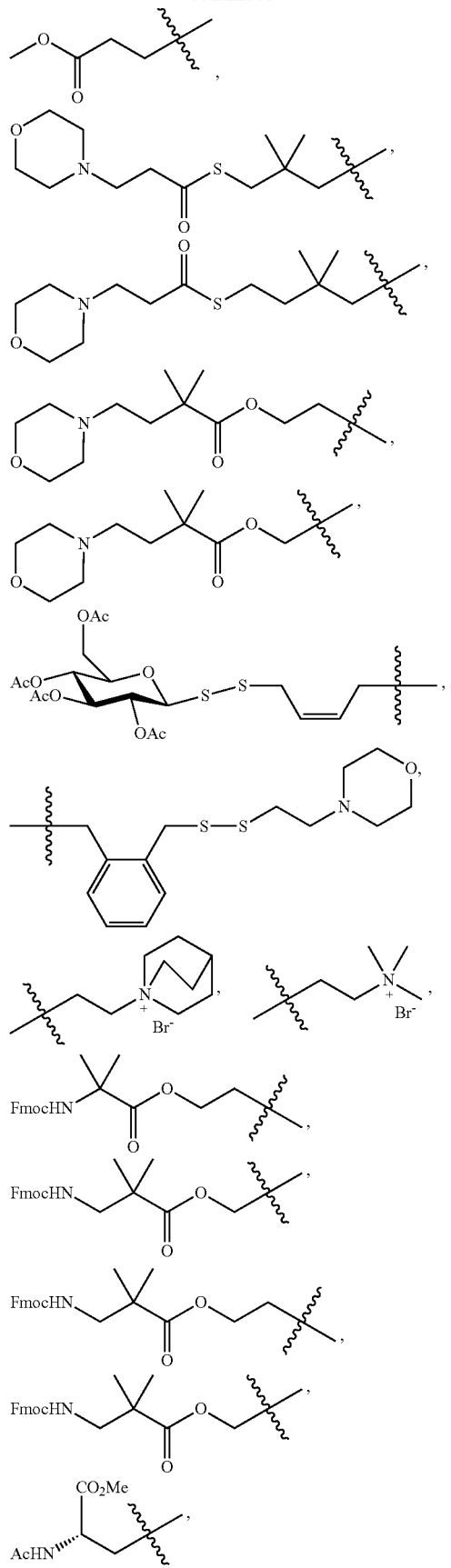
258
-continued
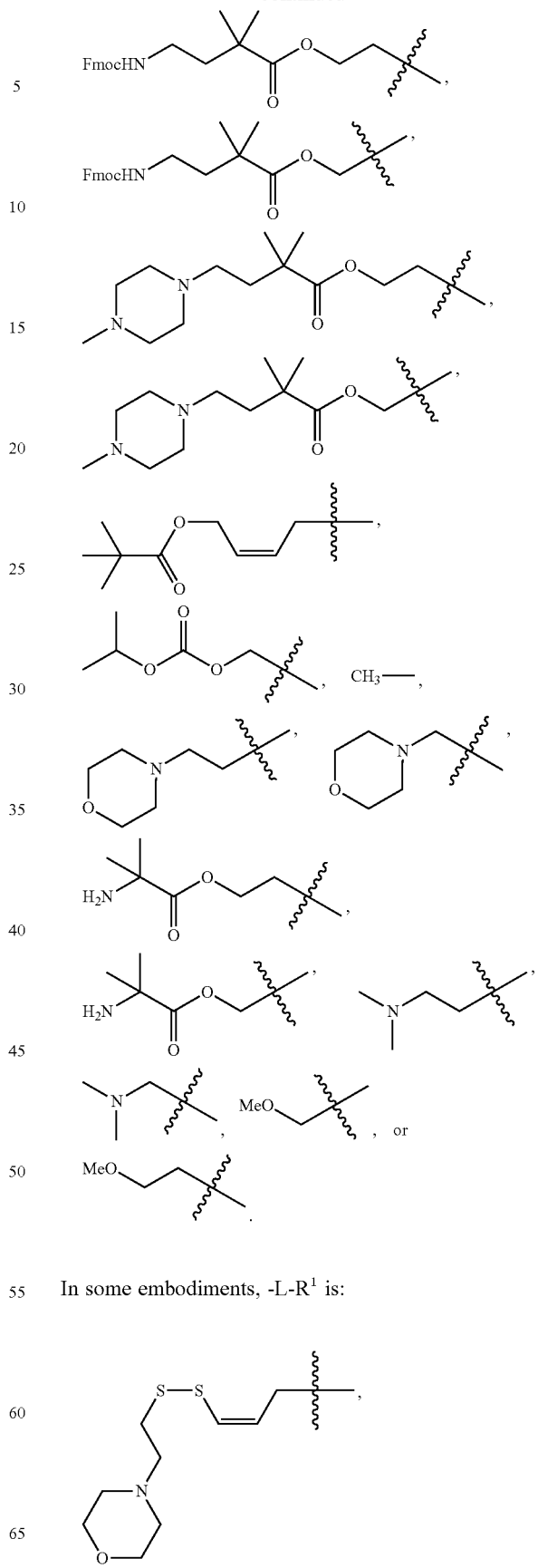
In some embodiments, -L-R¹ is:
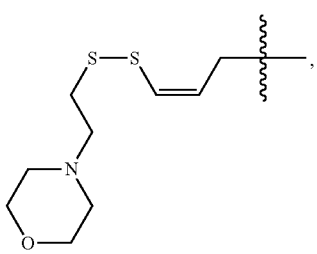

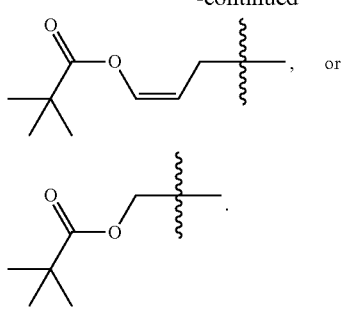

In some embodiments, -L-R¹ is CH₃—,

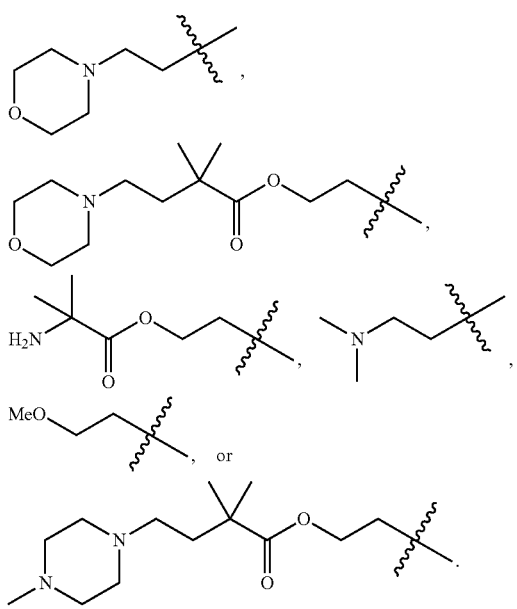

In some embodiments, -L-R¹ is

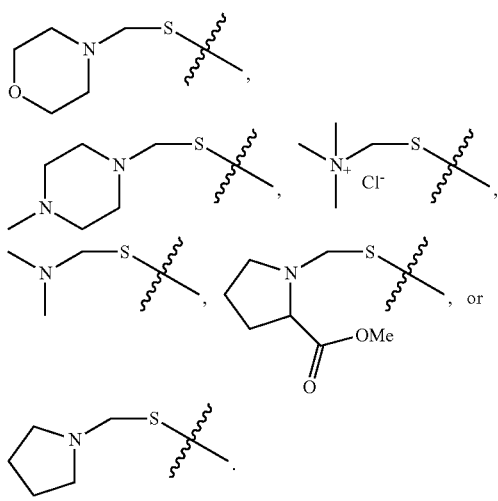

In some embodiments, -L-R¹ comprises a terminal optionally substituted —(CH₂)₂— moiety which is connected to X.

In some embodiments, -L-R¹ comprises a terminal —(CH₂)₂— moiety which is connected to X. Example such -L-R¹ moieties are depicted below:

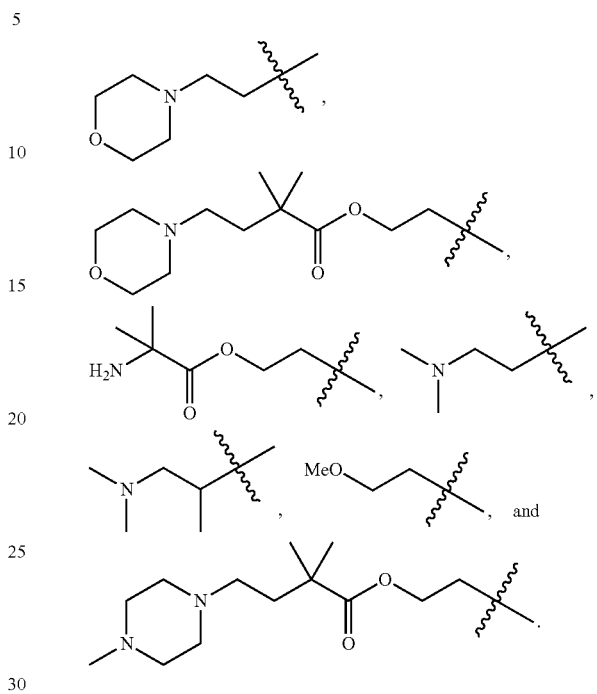

In some embodiments, -L-R¹ comprises a terminal optionally substituted —(CH₂)— moiety which is connected to X. In some embodiments, -L-R¹ comprises a terminal —(CH₂)— moiety which is connected to X. Example such -L-R¹ moieties are depicted below:

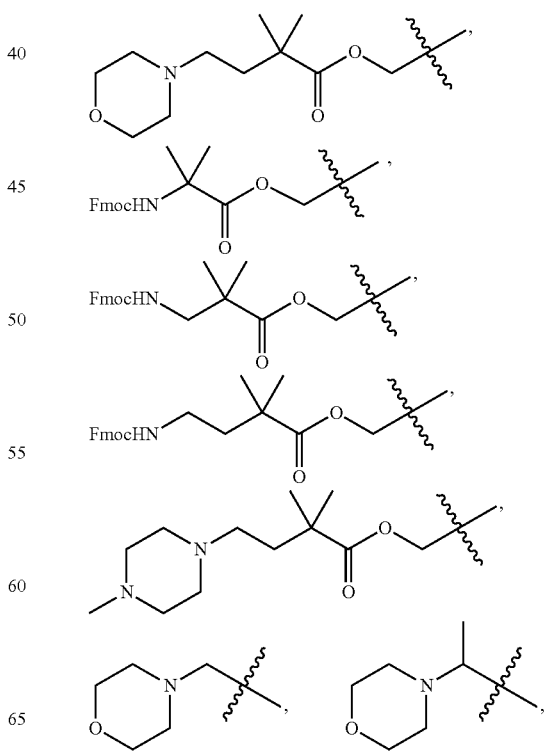

261
-continued
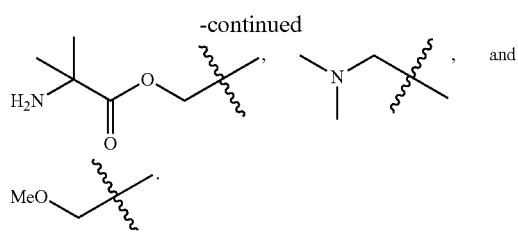
and
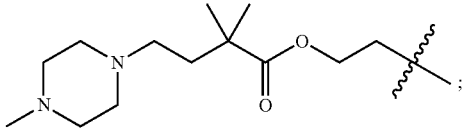
In some embodiments, -L-R¹ is
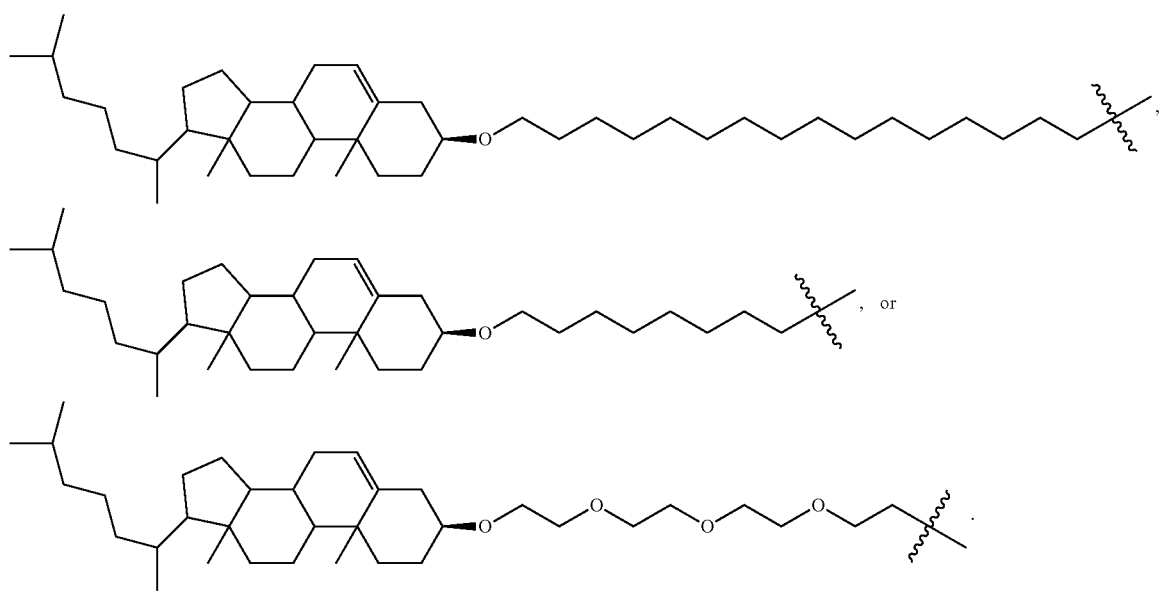
In some embodiments, -L-R¹ is CH₃—,
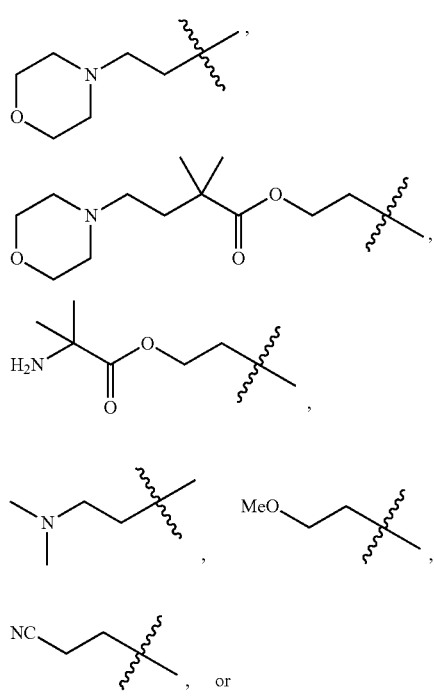
or
262
-continued
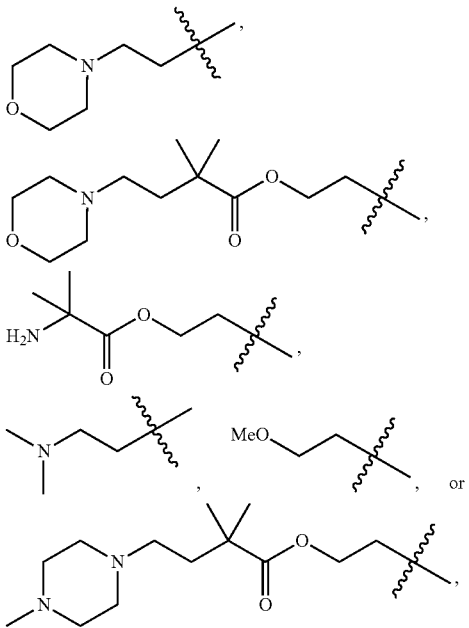
and X is —S—.
In some embodiments, -L-R¹ is CH₃—,
X is —S—, W is O, Y is —O—, and Z is —O—.
In some embodiments, R¹ is

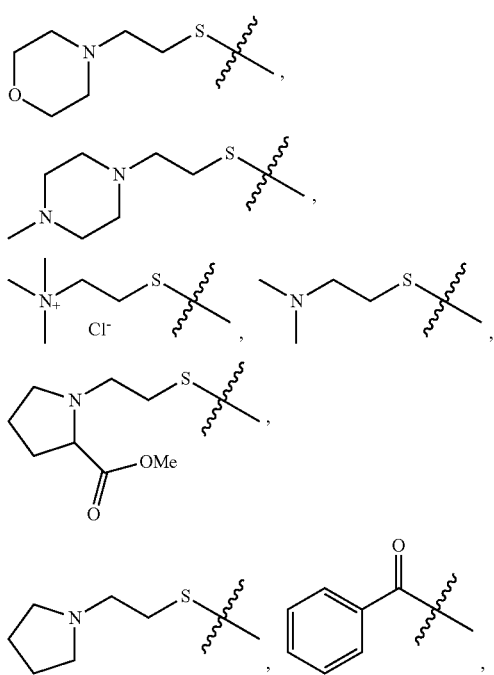
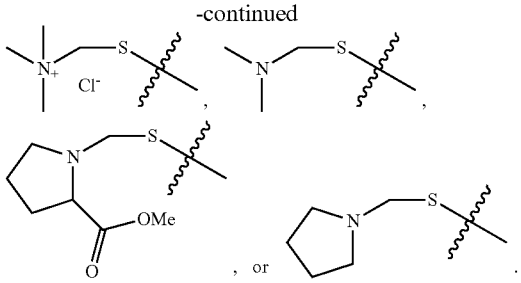
or —S—(C$_1$-C$_{10}$ aliphatic).
In some embodiments, R$^1$ is
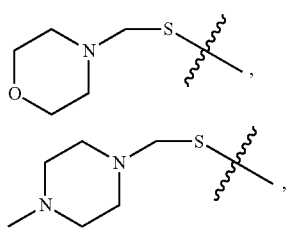
In some embodiments, X is —O— or —S—, and R$^1$ is
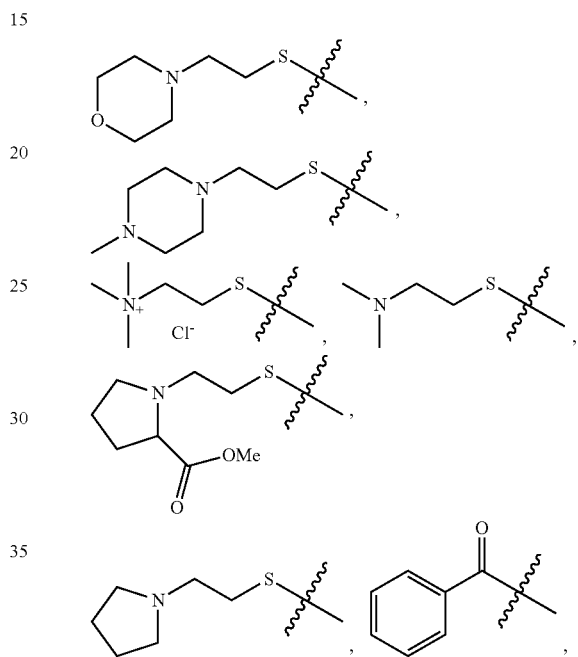
or —S—(C$_1$-C$_{10}$ aliphatic).
In some embodiments, X is —O— or —S—, and R$^1$ is
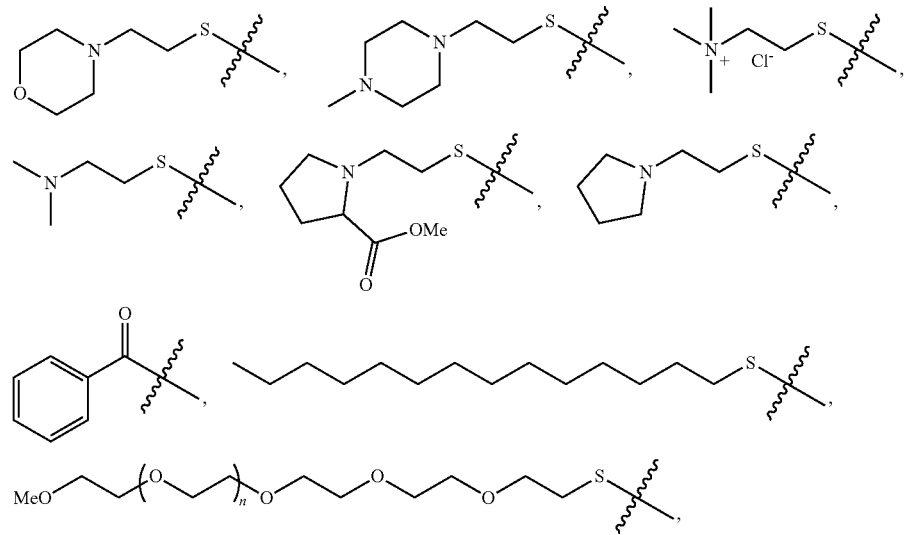

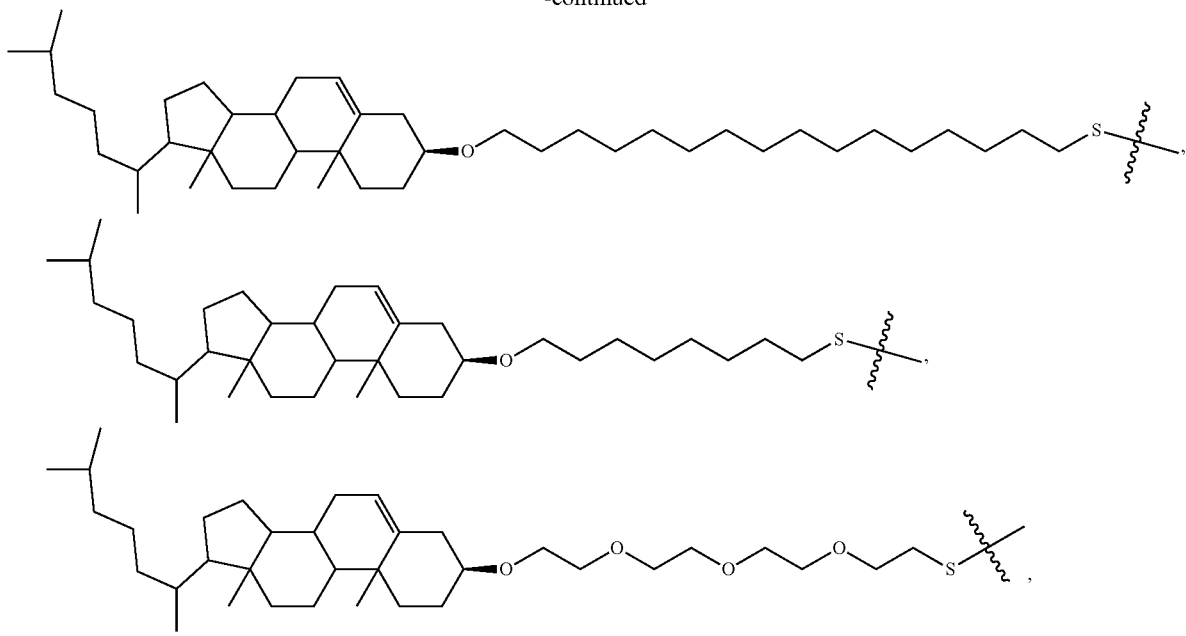
—S—($C_1$-$C_{10}$ aliphatic) or —S—($C_1$-$C_{50}$ aliphatic).
In some embodiments, L is a covalent bond and -L-$R^1$ is $R^1$.
In some embodiments, -L-$R^1$ is not hydrogen.
In some embodiments, —X-L-$R^1$ is $R^1$ is
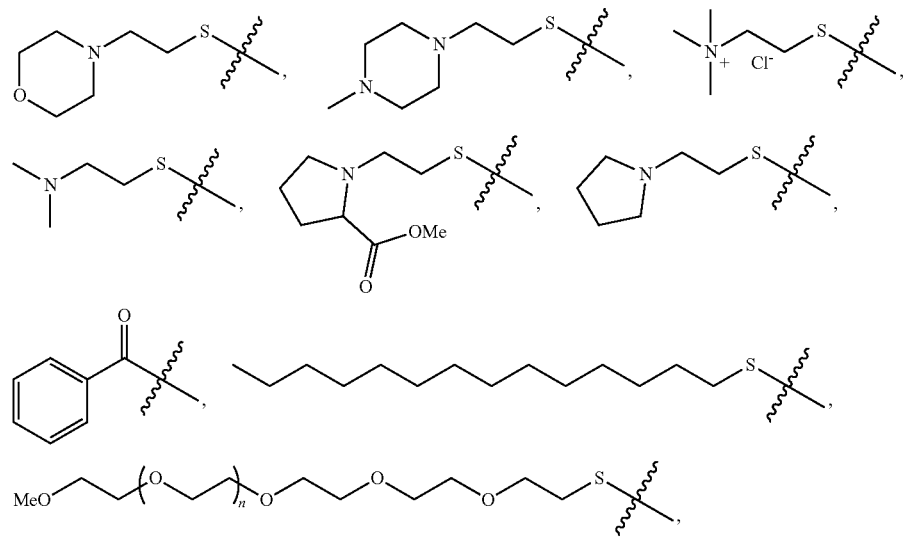
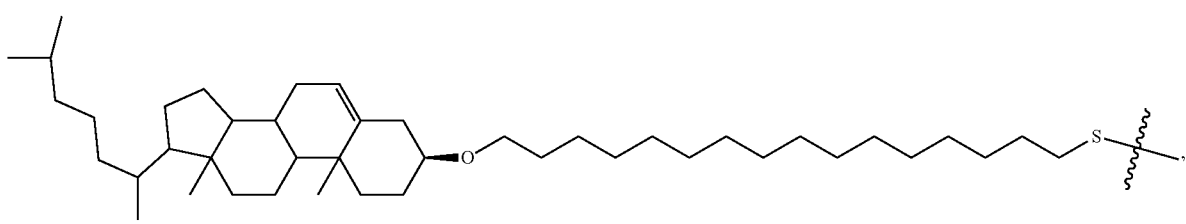

-continued

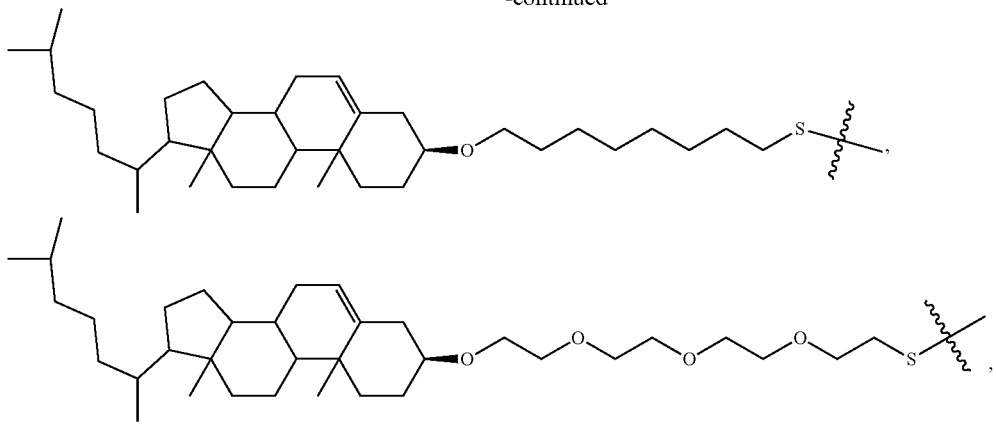

—S—($C_1$-$C_{10}$ aliphatic) or —S—($C_1$-$C_{50}$ aliphatic).

In some embodiments, —X-L-R has the structure of

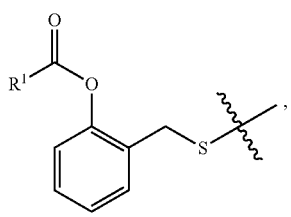

wherein the

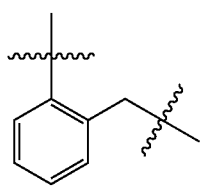 [SMILES: *Cc1ccccc1*]

moiety is optionally substituted. In some embodiments, —X-L-$R^1$ is

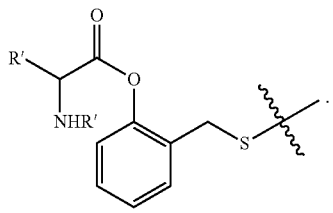

In some embodiments, —X-L-$R^1$ is

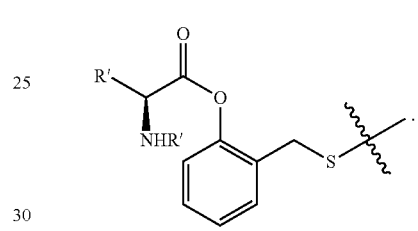

In some embodiments, —X-L-$R^1$ is

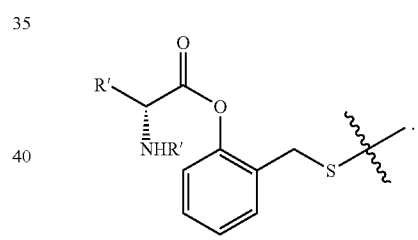

In some embodiments, —X-L-$R^1$ has the structure of

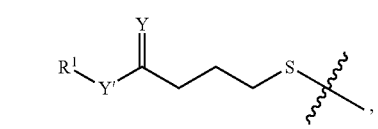

wherein x' is O or S, Y' is —O—, —S— or —NR'—, and the moiety is optionally substituted. In some embodiments, Y' is —O—, —S— or —NH—. In some embodiments,

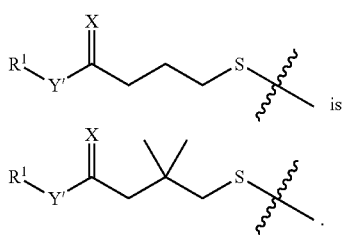

is

In some embodiments,

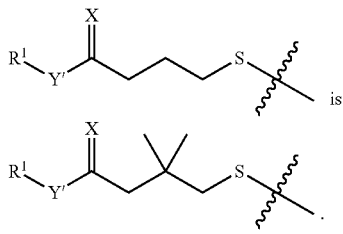

is

In some embodiments,

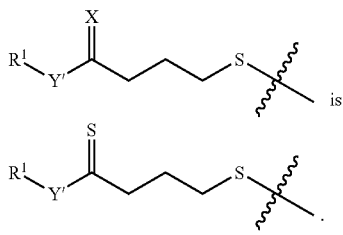

is

In some embodiments, —X-L-R¹ has the structure of

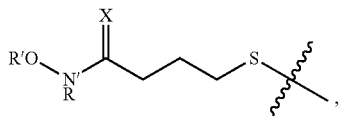

wherein X' is O or S, and the

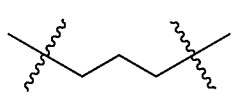 [SMILES: *CCC*]

moiety is optionally substituted. In some embodiments,

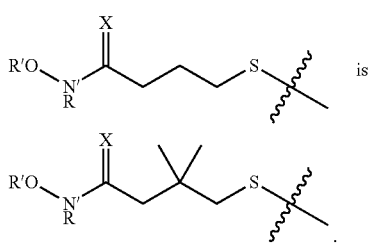

is

In some embodiments, —X-L-R¹ is

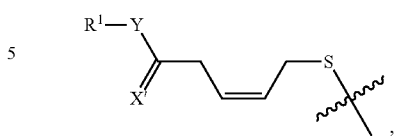

wherein the

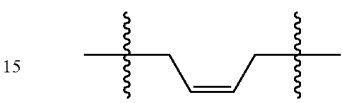

is optionally substituted. In some embodiments, —X-L-R¹ is

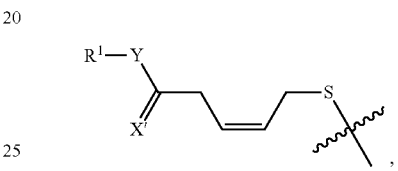

wherein the

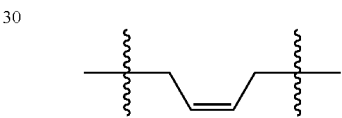

is substituted. In some embodiments, —X-L-R¹ is

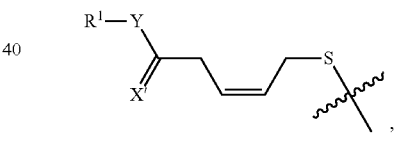

wherein the

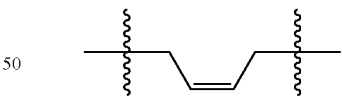

is unsubstituted.

In some embodiments, —X-L-R¹ is R¹—C(O)—S-L$^x$-S—, wherein L$^x$ is an optionally substituted group selected from

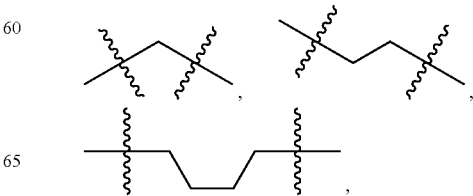

-continued

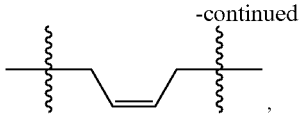

and

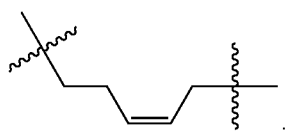 [SMILES: *C/C=C\CC* ; "."]

In some embodiments, $L^x$ is

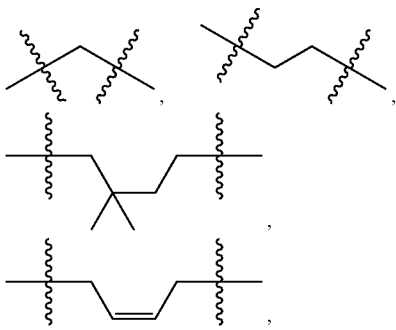

and

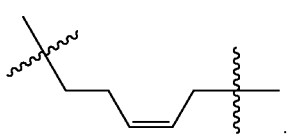 [SMILES: *C/C=C\CC* ; "."]

In some embodiments, —X-L-R$^1$ is (CH$_3$)$_3$C—S—S-L$^x$-S—. In some embodiments, —X-L-R$^1$ is R$^1$—C(=X')—Y'—C(R)$_2$—S-L$^x$-S—. In some embodiments, —X-L-R$^1$ is R—C(=X')—Y'—CH$_2$—S-L$^x$-S—. In some embodiments, —X-L-R$^1$ is

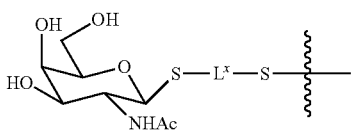

As will be appreciated by a person skilled in the art, many of the —X-L-R$^1$ groups described herein are cleavable and can be converted to —X$^-$ after administration to a subject. In some embodiments, —X-L-R$^1$ is cleavable. In some embodiments, —X-L-R$^1$ is —S-L-R$^1$, and is converted to —S$^-$ after administration to a subject. In some embodiments, the conversion is promoted by an enzyme of a subject. As appreciated by a person skilled in the art, methods of determining whether the —S-L-R$^1$ group is converted to —S$^-$ after administration is widely known and practiced in the art, including those used for studying drug metabolism and pharmacokinetics.

In some embodiments, the internucleotidic linkage having the structure of formula I is

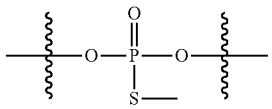

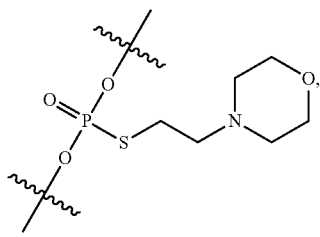

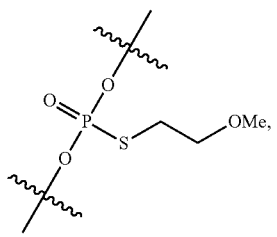

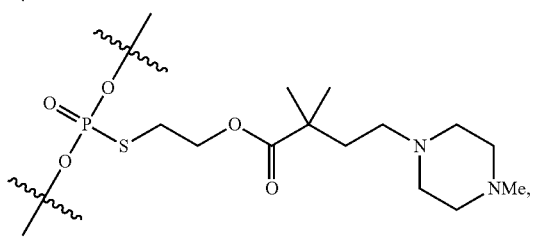

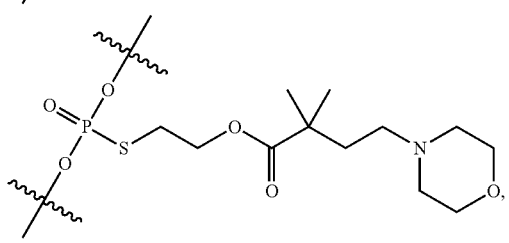

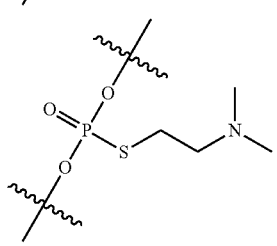

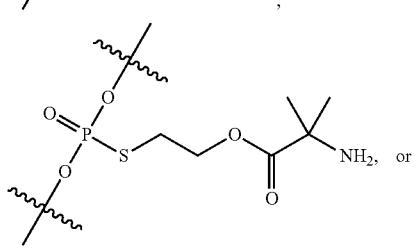

-continued

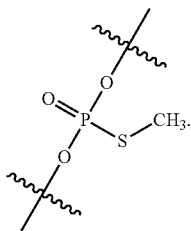

In some embodiments, the internucleotidic linkage of formula I has the structure of formula I-a:

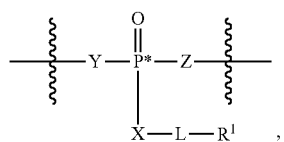
(I-a)

wherein each variable is independently as defined above and described herein.

In some embodiments, the internucleotidic linkage of formula I has the structure of formula I-b:

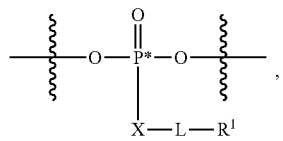
(I-b)

wherein each variable is independently as defined above and described herein.

In some embodiments, the internucleotidic linkage of formula I is an phosphorothioate triester linkage having the structure of formula I-c:

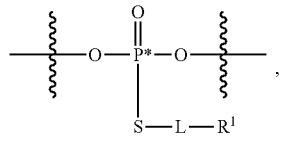
(I-c)

wherein:
P* is an asymmetric phosphorus atom and is either Rp or Sp;
L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
each R' is independently —R, —C(O)R, —CO$_2$R, or —SO$_2$R, or:
  two R' on the same nitrogen are taken together with their intervening atoms to form an optionally substituted heterocyclic or heteroaryl ring, or
  two R' on the same carbon are taken together with their intervening atoms to form an optionally substituted aryl, carbocyclic, heterocyclic, or heteroaryl ring;
-Cy- is an optionally substituted bivalent ring selected from phenylene, carbocyclylene, arylene, heteroarylene, or heterocyclylene;
each R is independently hydrogen, or an optionally substituted group selected from $C_1$-$C_6$ aliphatic, phenyl, carbocyclyl, aryl, heteroaryl, or heterocyclyl;
each

independently represents a connection to a nucleoside; and
$R^1$ is not —H when L is a covalent bond.

In some embodiments, the internucleotidic linkage having the structure of formula I is

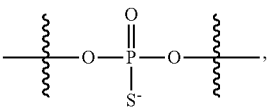

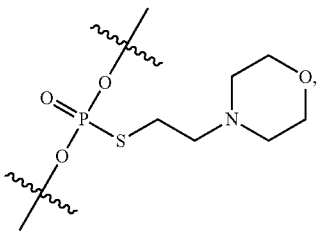

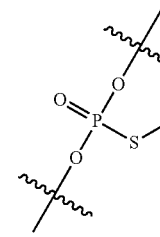

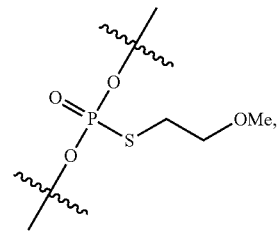

275
-continued
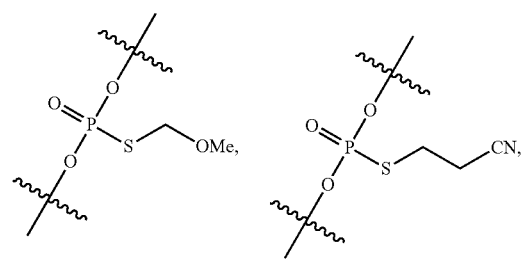
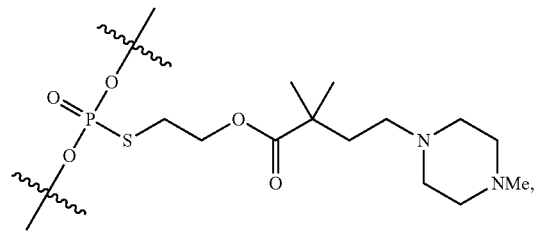
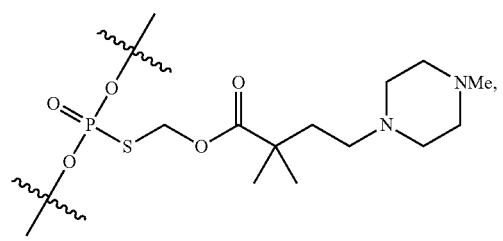
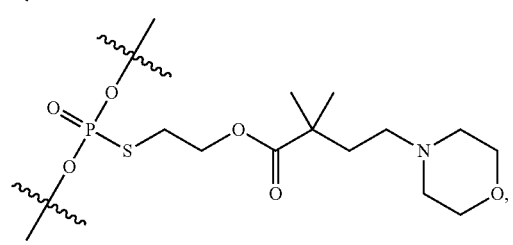
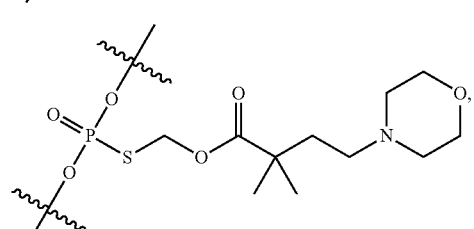
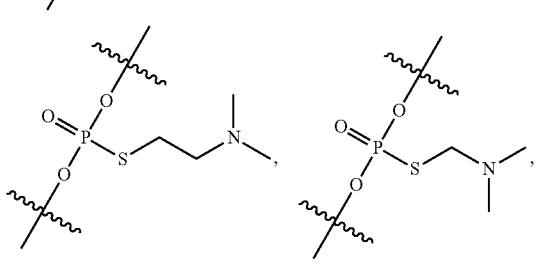
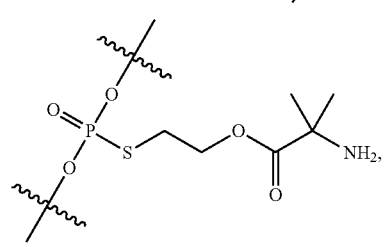
276
-continued
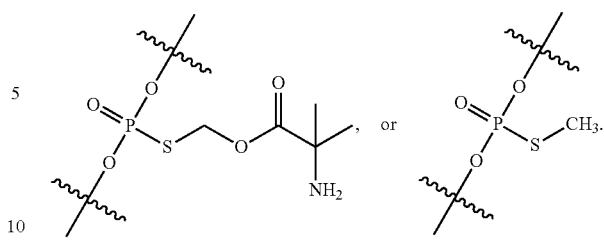
In some embodiments, the internucleotidic linkage having the structure of formula I-c is
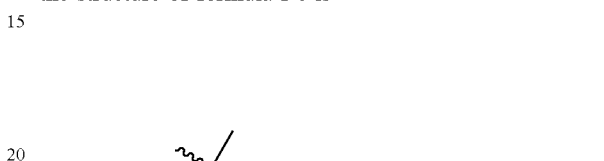
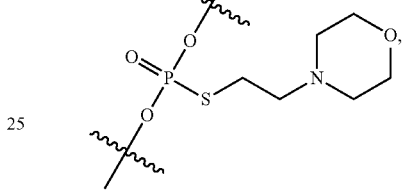
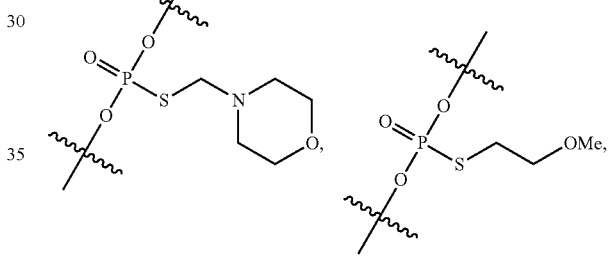
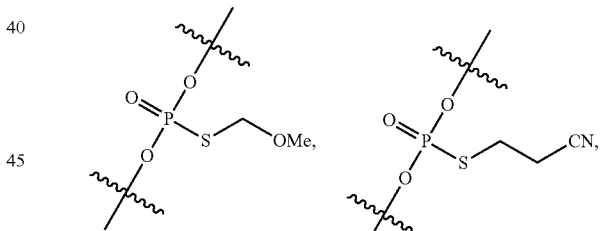
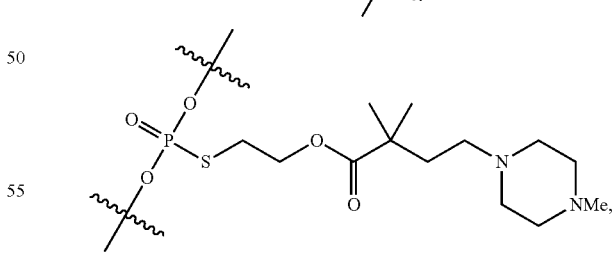
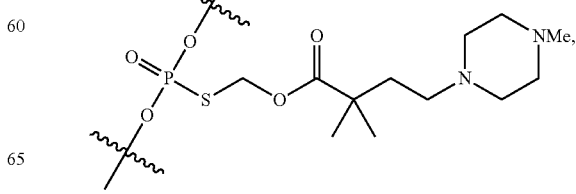

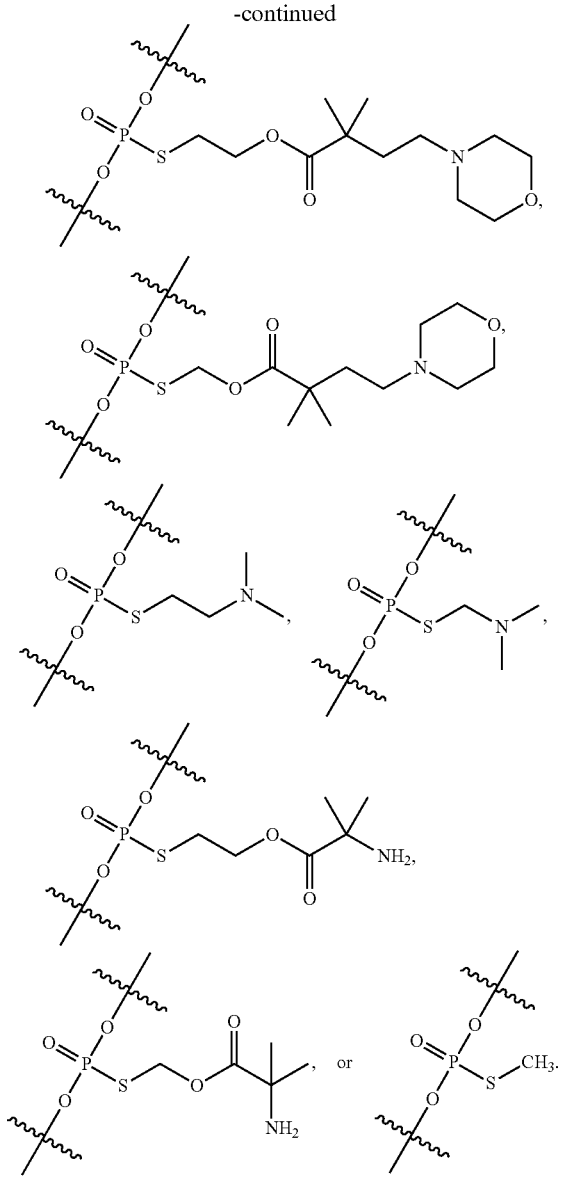

In some embodiments, the present disclosure provides a chirally controlled CpG oligonucleotide comprising one or more phosphate diester linkages, and one or more modified internucleotide linkages having the formula of I-a, I-b, or I-c.

In some embodiments, a modified internucleotidic linkage has the structure of I. In some embodiments, a modified internucleotidic linkage has the structure of I-a. In some embodiments, a modified internucleotidic linkage has the structure of I-b. In some embodiments, a modified internucleotidic linkage has the structure of I-c.

In some embodiments, a modified internucleotidic linkage is phosphorothioate. Examples of internucleotidic linkages having the structure of formula I are widely known in the art, including but not limited to those described in US 20110294124, US 20120316224, US 20140194610, US 20150211006, US 20150197540, WO 2015107425, PCT/US2016/043542, and PCT/US2016/043598, each of which is incorporated herein by reference.

Non-limiting examples of internucleotidic linkages also include those described in the art, including, but not limited to, those described in any of: Gryaznov, S.; Chen, J.-K. J. Am. Chem. Soc. 1994, 116, 3143, Jones et al. J. Org. Chem. 1993, 58, 2983, Koshkin et al. 1998 Tetrahedron 54: 3607-3630, Lauritsen et al. 2002 Chem. Comm. 5: 530-531, Lauritsen et al. 2003 Bioo. Med. Chem. Lett. 13: 253-256, Mesmaeker et al. Angew. Chem., Int. Ed. Engl. 1994, 33, 226, Petersen et al. 2003 TRENDS Biotech. 21: 74-81, Schultz et al. 1996 Nucleic Acids Res. 24: 2966, Ts'o et al. Ann. N. Y. Acad. Sci. 1988, 507, 220, and Vasseur et al. J. Am. Chem. Soc. 1992, 114, 4006.

In some embodiments, provided oligonucleotides in provided compositions, e.g., oligonucleotides of a first plurality, comprise base modifications, sugar modifications, and/or internucleotidic linkage modifications, wherein one or more modifications is enrichment of deuterium. In some embodiments, an oligonucleotide is deuterated at one or more of its sugars, nucleobases, internucleotidic linkages, lipid moieties, linker moieties, targeting components, etc. Such oligonucleotides can be used in any composition or method described herein.

CpG oligonucleotides of the provided technologies can be of various lengths. In some embodiments, provided CpG oligonucleotides comprise 5, 6, 7, 8, 9, 10, 11, 12, 13, 14, 15, 16, 17, 18, 19, 20, 21, 22, 23, 24, 25, 26, 27, 28, 29, 30, 40, 50 or more bases. In some embodiments, provided CpG oligonucleotides comprise 10, 11, 12, 13, 14, 15, 16, 17, 18, 19, 20, 21, 22, 23, 24, 25, 26, 27, 28, 29, 30, 40, 50 or more bases. In some embodiments, provided CpG oligonucleotides comprise 15, 16, 17, 18, 19, 20, 21, 22, 23, 24, 25, 26, 27, 28, 29, 30, 40, 50 or more bases. In some embodiments, provided CpG oligonucleotides comprise 15 or more bases. In some embodiments, provided CpG oligonucleotides comprise 16 or more bases. In some embodiments, provided CpG oligonucleotides comprise 17 or more bases. In some embodiments, provided CpG oligonucleotides comprise 18 or more bases. In some embodiments, provided CpG oligonucleotides comprise 19 or more bases. In some embodiments, provided CpG oligonucleotides comprise 20 or more bases. In some embodiments, provided CpG oligonucleotides comprise 21 or more bases. In some embodiments, provided CpG oligonucleotides comprise 22 or more bases. In some embodiments, provided CpG oligonucleotides comprise 23 or more bases. In some embodiments, provided CpG oligonucleotides comprise 24 or more bases. In some embodiments, provided CpG oligonucleotides comprise 25 or more bases. In some embodiments, provided CpG oligonucleotides comprise 26 or more bases. In some embodiments, provided CpG oligonucleotides comprise 27 or more bases. In some embodiments, provided CpG oligonucleotides comprise 28 or more bases. In some embodiments, provided CpG oligonucleotides comprise 29 or more bases. In some embodiments, provided CpG oligonucleotides comprise 30 or more bases. In some embodiments, provided CpG oligonucleotides comprise 40 or more bases. In some embodiments, provided CpG oligonucleotides comprise 50 or more bases. In some embodiments, provided CpG oligonucleotides are 15mers. In some embodiments, provided CpG oligonucleotides are 16mers. In some embodiments, provided CpG oligonucleotides are 17mers. In some embodiments, provided CpG oligonucleotides are 18mers. In some embodiments, provided CpG oligonucleotides are 19mers. In some embodiments, provided CpG oligonucleotides are 20mers. In some embodiments, provided CpG oligonucleotides are 21mers. In some embodiments, provided CpG oligonucleotides are 22mers. In some embodiments, provided CpG oligonucleotides are 23mers. In some embodiments, provided CpG oligonucleotides are 24mers.

In some embodiments, provided CpG oligonucleotides are 25mers. In some embodiments, provided CpG oligonucleotides are 26mers. In some embodiments, provided CpG oligonucleotides are 27mers. In some embodiments, provided CpG oligonucleotides are 28mers. In some embodiments, provided CpG oligonucleotides are 29mers. In some embodiments, provided CpG oligonucleotides are 30mers.

In some embodiments, the present disclosure provides a chirally controlled CpG oligonucleotide comprising at least one phosphate diester internucleotidic linkage and at least one phosphorothioate triester linkage having the structure of formula I-c. In some embodiments, the present disclosure provides a chirally controlled CpG oligonucleotide comprising at least one phosphate diester internucleotidic linkage and at least two phosphorothioate triester linkages having the structure of formula I-c. In some embodiments, the present disclosure provides a chirally controlled CpG oligonucleotide comprising at least one phosphate diester internucleotidic linkage and at least three phosphorothioate triester linkages having the structure of formula I-c. In some embodiments, the present disclosure provides a chirally controlled CpG oligonucleotide comprising at least one phosphate diester internucleotidic linkage and at least four phosphorothioate triester linkages having the structure of formula I-c. In some embodiments, the present disclosure provides a chirally controlled CpG oligonucleotide comprising at least one phosphate diester internucleotidic linkage and at least five phosphorothioate triester linkages having the structure of formula I-c.

In some embodiments, a chirally controlled CpG oligonucleotide is designed such that one or more nucleotides comprise a phosphorus modification prone to "autorelease" under certain conditions. That is, under certain conditions, a particular phosphorus modification is designed such that it self-cleaves from the CpG oligonucleotide to provide, e.g., a phosphate diester such as those found in naturally occurring DNA and RNA. In some embodiments, such a phosphorus modification has a structure of —O-L-$R^1$, wherein each of L and $R^1$ is independently as defined above and described herein. In some embodiments, an autorelease group comprises a morpholino group. In some embodiments, an autorelease group is characterized by the ability to deliver an agent to the internucleotidic phosphorus linker, which agent facilitates further modification of the phosphorus atom such as, e.g., desulfurization. In some embodiments, the agent is water and the further modification is hydrolysis to form a phosphate diester as is found in naturally occurring DNA and RNA.

In some embodiments, a chirally controlled CpG oligonucleotide is designed such that the resulting pharmaceutical properties are improved through one or more particular modifications at phosphorus. It is well documented in the art that certain oligonucleotides are rapidly degraded by nucleases and exhibit poor cellular uptake through the cytoplasmic cell membrane (Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1): 196-208; Bologna et al., (2002), Antisense & Nucleic Acid Drug Development 12:33-41). For instance, Vives et al., (Nucleic Acids Research (1999), 27(20):4071-76) found that tert-butyl SATE pro-oligonucleotides displayed markedly increased cellular penetration compared to the parent oligonucleotide.

In some embodiments, a modification at phosphorus results in a P-modification moiety characterized in that it acts as a pro-drug, e.g., the P-modification moiety facilitates delivery of a CpG oligonucleotide to a desired location prior to removal. For instance, in some embodiments, a P-modification moiety results from PEGylation at the linkage phosphorus. One of skill in the relevant arts will appreciate that various PEG chain lengths are useful and that the selection of chain length will be determined in part by the result that is sought to be achieved by PEGylation. For instance, in some embodiments, PEGylation is effected in order to reduce RES uptake and extend in vivo circulation lifetime of a CpG oligonucleotide.

In some embodiments, a PEGylation reagent for use in accordance with the present disclosure is of a molecular weight of about 300 g/mol to about 100,000 g/mol. In some embodiments, a PEGylation reagent is of a molecular weight of about 300 g/mol to about 10,000 g/mol. In some embodiments, a PEGylation reagent is of a molecular weight of about 300 g/mol to about 5,000 g/mol. In some embodiments, a PEGylation reagent is of a molecular weight of about 500 g/mol. In some embodiments, a PEGylation reagent of a molecular weight of about 1000 g/mol. In some embodiments, a PEGylation reagent is of a molecular weight of about 3000 g/mol. In some embodiments, a PEGylation reagent is of a molecular weight of about 5000 g/mol.

In certain embodiments, a PEGylation reagent is PEG500. In certain embodiments, a PEGylation reagent is PEG1000. In certain embodiments, a PEGylation reagent is PEG3000. In certain embodiments, a PEGylation reagent is PEG5000.

In some embodiments, a P-modification moiety is characterized in that it acts as a PK enhancer, e.g., lipids, PEGylated lipids, etc.

In some embodiments, a P-modification moiety is characterized in that it acts as an agent which promotes cell entry and/or endosomal escape, such as a membrane-disruptive lipid or peptide.

In some embodiments, a P-modification moiety is characterized in that it acts as a targeting agent. In some embodiments, a P-modification moiety is or comprises a targeting agent. The phrase "targeting agent," as used herein, is an entity that is associates with a payload of interest (e.g., with a CpG oligonucleotide or oligonucleotide composition) and also interacts with a target site of interest so that the payload of interest is targeted to the target site of interest when associated with the targeting agent to a materially greater extent than is observed under otherwise comparable conditions when the payload of interest is not associated with the targeting agent. A targeting agent can be, or comprise, any of a variety of chemical moieties, including, for example, small molecule moieties, nucleic acids, polypeptides, carbohydrates, etc. Targeting agents are described further by Adarsh et al., "Organelle Specific Targeted Drug Delivery—A Review," International Journal of Research in Pharmaceutical and Biomedical Sciences, 2011, p. 895.

Example such targeting agents include, but are not limited to, proteins (e.g. Transferrin), oligopeptides (e.g., cyclic and acylic RGD-containing oligopedptides), antibodies (monoclonal and polyclonal antibodies, e.g. IgG, IgA, IgM, IgD, IgE antibodies), sugars /carbohydrates (e.g., monosaccharides and/or oligosaccharides (mannose, mannose-6-phosphate, galactose, and the like)), vitamins (e.g., folate), or other small biomolecules. In some embodiments, a targeting moiety is a steroid molecule (e.g., bile acids including cholic acid, deoxycholic acid, dehydrocholic acid; cortisone; digoxigenin; testosterone; cholesterol; cationic steroids such as cortisone having a trimethylaminomethyl hydrazide group attached via a double bond at the 3-position of the cortisone ring, etc.). In some embodiments, a targeting moiety is a lipophilic molecule (e.g., alicyclic hydrocarbons, saturated and unsaturated fatty acids, waxes, terpenes, and polyalicyclic hydrocarbons such as adamantine and buckminsterfullerenes). In some embodiments, a lipophilic molecule is a terpenoid such as vitamin A, retinoic acid, retinal, or dehydroretinal. In some embodiments, a targeting moiety is a peptide.

In some embodiments, a P-modification moiety is a targeting agent of formula —X-L-$R^1$ wherein each of X, L, and $R^1$ are as defined in Formula I above.

In some embodiments, a P-modification moiety is characterized in that it facilitates cell specific delivery.

In some embodiments, a P-modification moiety is characterized in that it falls into one or more of the above-described categories. For instance, in some embodiments, a P-modification moiety acts as a PK enhancer and a targeting ligand. In some embodiments, a P-modification moiety acts as a pro-drug and an endosomal escape agent. One of skill in the relevant arts would recognize that numerous other such combinations are possible and are contemplated by the present disclosure.

In some embodiments, a carbocyclyl, aryl, heteroaryl, or heterocyclyl group, or a bivalent or polyvalent group thereof, is a $C_3$-$C_{30}$ carbocyclyl, aryl, heteroaryl, or heterocyclyl group, or a bivalent and/or polyvalent group thereof.

Lipids and Oligonucleotides Comprising Lipid Moieties

Among other things, the present disclosure encompasses the recognition that lipid conjugation can surprisingly improve properties of oligonucleotides. In some embodiments, the present disclosure provides oligonucleotides comprising one or more lipid moieties, and compositions and methods thereof. In some embodiments, lipid conjugation is optionally utilized together with other structural elements, such as base sequence, chemical modifications (e.g., sugar modifications, base modifications, internucleotidic linkage modifications), and/or stereochemistry, to improve oligonucleotide properties. In some embodiments, as demonstrated herein, provided oligonucleotides comprising lipid moieties have unexpected properties, such as immunological properties, activities toward their nucleic acid targets, delivery, pharmacokinetics, etc. In some embodiments, provided oligonucleotides comprising lipid moieties have low TLR9 agonist activities. In some embodiments, provided oligonucleotides comprising lipid moieties have surprisingly enhanced TLR9 antagonist activities, for example, compared to oligonucleotides absent lipid moieties. In some embodiments, provided oligonucleotides comprising lipid moieties possess unexpectedly high hTLR9 antagonist activities, in addition to improved activities, delivery, and/or pharmacokinetic properties (for examples, see FIGS. 23-26).

In some embodiments, in addition to TLR9-related property improvement, provided oligonucleotides comprising lipid moieties provide other improved properties. In some embodiments, provided oligonucleotides comprising lipid moieties provide improved delivery to muscles, e.g., gastrocnemius, triceps, heart, diaphragm, etc., compared to reference oligonucleotides, e.g., having no lipid moieties, having no lipid moieties and different stereochemistry (e.g., chirally controlled v. stereorandom, one pattern of backbone chiral centers v. another pattern of backbone chiral centers, etc.), etc. In some embodiments, provided oligonucleotides comprising lipid moieties provide improved pharmacokinetics compared to reference oligonucleotides. In some embodiments, provided oligonucleotides provides faster clearance from a system than reference oligonucleotides, which, as appreciated by a person having ordinary skill in the art, may provide lower toxicities compared to reference oligonucleotides.

In some embodiments, the present disclosure provides methods for modulating immunoactivities of an oligonucleotide, comprising adding a lipid moiety to the oligonucleotide. In some embodiments, the present disclosure provides methods for modulating immunoactivities of an oligonucleotide, comprising conjugating a lipid with an oligonucleotide. In some embodiments, the present disclosure provides methods for modulating TLR9 agonist activity of an oligonucleotide, comprising adding a lipid moiety to the oligonucleotide. In some embodiments, the present disclosure provides methods for modulating TLR9 agonist activity of an oligonucleotide, comprising conjugating a lipid with an oligonucleotide. In some embodiments, the present disclosure provides methods for decreasing TLR9 agonist activity of an oligonucleotide, comprising adding a lipid moiety to the oligonucleotide. In some embodiments, the present disclosure provides methods for decreasing TLR9 agonist activity of an oligonucleotide, comprising conjugating a lipid with an oligonucleotide. In some embodiments, the present disclosure provides methods for modulating TLR9 antagonist activity of an oligonucleotide, comprising adding a lipid moiety to the oligonucleotide. In some embodiments, the present disclosure provides methods for modulating TLR9 antagonist activity of an oligonucleotide, comprising conjugating a lipid with an oligonucleotide. In some embodiments, the present disclosure provides methods for increasing TLR9 antagonist activity of an oligonucleotide, comprising adding a lipid moiety to the oligonucleotide. In some embodiments, the present disclosure provides methods for increasing TLR9 antagonist activity of an oligonucleotide, comprising conjugating a lipid with an oligonucleotide. In some embodiments, an oligonucleotide without a lipid moiety, for example, those described herein, is converted into an oligonucleotide comprising a lipid moiety, for example, those described herein, for improved properties.

Many lipids can be utilized in provided technologies in accordance with the present disclosure. In some embodiments, a lipid comprises an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein. In some embodiments, a lipid comprises an optionally substituted $C_{10}$-$C_{80}$ saturated or partially unsaturated, aliphatic chain. In some embodiments, a lipid comprises an optionally substituted $C_{10}$-$C_{80}$ linear, saturated or partially unsaturated, aliphatic chain. In some embodiments, a lipid comprises a $C_{10}$-$C_{80}$ linear, saturated or partially unsaturated, aliphatic chain, optionally substituted with one or more $C_{1-4}$ aliphatic group. In some embodiments, a lipid comprises an unsubstituted $C_{10}$-$C_{80}$ linear, saturated or partially unsaturated, aliphatic chain. In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain.

In some embodiments, a lipid comprises an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein. In some embodiments, a lipid comprises an optionally substituted $C_{10}$-$C_{60}$ saturated or partially unsaturated, aliphatic chain. In some embodiments, a lipid comprises an optionally substituted $C_{10}$-$C_{60}$ linear, saturated or partially unsaturated, aliphatic chain. In some embodiments, a lipid comprises a $C_{10}$-$C_{60}$ linear, saturated or partially unsaturated, aliphatic chain, optionally substituted with one or more $C_{1-4}$ aliphatic group. In some embodiments, a lipid comprises an unsubstituted $C_{10}$-$C_{60}$ linear, saturated or partially unsaturated, aliphatic chain. In some embodiments, a lipid comprises no more than one optionally substituted $C_{10}$-$C_{60}$ linear, saturated or partially unsaturated, aliphatic chain. In some embodiments, a lipid comprises two or more optionally substituted $C_{10}$-$C_{60}$ linear, saturated or partially unsaturated, aliphatic chain.

In some embodiments, a lipid comprises an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein. In some embodiments, a lipid comprises an optionally substituted $C_{10}$-$C_{40}$ saturated or partially unsaturated, aliphatic chain. In some embodiments, a lipid comprises an optionally substituted $C_{10}$-$C_{40}$ linear, saturated or partially unsaturated, aliphatic chain. In some embodiments, a lipid comprises an unsubstituted $C_{10}$-$C_{40}$ linear, saturated or partially unsaturated, aliphatic chain. In some embodiments, a lipid comprises two or more optionally substituted $C_{10}$-$C_{40}$ linear, saturated or partially unsaturated, aliphatic chain. In some embodiments, a lipid comprises no more than one optionally substituted $C_{10}$-$C_{40}$ linear, saturated or partially unsaturated, aliphatic chain.

In some embodiments, the present disclosure provides an oligonucleotide comprising a lipid moiety comprising a $C_{10}$-$C_{80}$ linear, saturated or partially unsaturated, aliphatic chain. In some embodiments, the present disclosure provides an oligonucleotide comprising a lipid moiety comprising a $C_{10}$-$C_{80}$ linear, saturated or partially unsaturated, aliphatic chain, optionally substituted with one or more $C_{1-4}$ aliphatic group. In some embodiments, the present disclosure provides an oligonucleotide comprising a lipid moiety comprising a $C_{10}$-$C_{60}$ linear, saturated or partially unsaturated, aliphatic chain. In some embodiments, the present disclosure provides an oligonucleotide comprising a lipid moiety comprising a $C_{10}$-$C_{60}$ linear, saturated or partially unsaturated, aliphatic chain, optionally substituted with one or more $C_{1-4}$ aliphatic group. In some embodiments, the present disclosure provides an oligonucleotide comprising a lipid moiety comprising a $C_{10}$-$C_{40}$ linear, saturated or partially unsaturated, aliphatic chain. In some embodiments, the present disclosure provides an oligonucleotide comprising a lipid moiety comprising a $C_{10}$-$C_{40}$ linear, saturated or partially unsaturated, aliphatic chain, optionally substituted with one or more $C_{1-4}$ aliphatic group.

In some embodiments, the present disclosure provides a chirally controlled oligonucleotide composition comprising a plurality of oligonucleotides, which share:
1) a common base sequence;
2) a common pattern of backbone linkages; and
3) a common pattern of backbone phosphorus modifications;
wherein:
the composition is chirally controlled in that the plurality of oligonucleotides share the same stereochemistry at one or more chiral internucleotidic linkages, and at least 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99% of oligonucleotides in the composition that share the common base sequence, the common pattern of backbone linkages; and the common pattern of backbone phosphorus modifications share the same stereochemistry at the one or more chiral internucleotidic linkages;
one or more oligonucleotides of the plurality are independently conjugated to a lipid; and one or more oligonucleotides of the plurality are optionally and independently conjugated to a target component.

In some embodiments, the percentage is at least 10%. In some embodiments, the plurality of oligonucleotides share the same stereochemistry independently at five or more chiral internucleotidic linkages. In some embodiments, the plurality of oligonucleotides share the same stereochemistry independently at ten or more chiral internucleotidic linkages. In some embodiments, the plurality of oligonucleotides share the same stereochemistry independently at ten or more chiral internucleotidic linkages, and the percentage is at least 10%.

In some embodiments, the present disclosure provides an oligonucleotide composition comprising a plurality of oligonucleotides having the structure of:

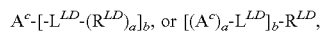

wherein:
$A^c$ is an oligonucleotide chain ($[H]_b$—Ac is an oligonucleotide);
a is 1-1000;
b is 1-1000;
each $L^{LD}$ is independently a linker moiety or a covalent bond; and
each $R^{LD}$ is independently a lipid moiety or a targeting component, wherein at least one $R^{LD}$ is a lipid moiety.

In some embodiments, the present disclosure provides an oligonucleotide composition comprising a plurality of oligonucleotides having the structure of:

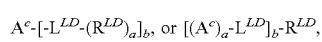

wherein:
$A^c$ is an oligonucleotide chain ($[H]_b$—Ac is an oligonucleotide);
a is 1-1000;
b is 1-1000;
each $L^{LD}$ is independently a linker moiety; and
each $R^{LD}$ is independently a lipid moiety or a targeting component, wherein at least one $R^{LD}$ is a lipid moiety.

In some embodiments, the present disclosure provides an oligonucleotide composition comprising a plurality of oligonucleotides having the structure of:

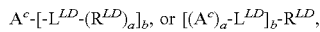

wherein:

$A^c$ is an oligonucleotide chain ($[H]_b$—Ac is an oligonucleotide);

a is 1-1000;

b is 1-1000;

each $L^{LD}$ is independently a covalent bond or an optionally substituted, $C_1$-$C_{80}$ saturated or partially unsaturated aliphatic group, wherein one or more methylene units are optionally and independently replaced by $T^{LD}$ or an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;

each $R^{LD}$ is independently an optionally substituted, $C_1$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;

$T^{LD}$ has the structure of:

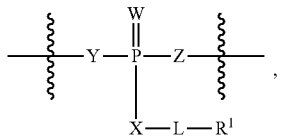

W is O, S or Se;

each of X, Y and Z is independently —O—, —S—, —N(-L-R$^1$)—, or L;

L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;

R$^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O— each R' is independently —R, —C(O)R, —CO$_2$R, or —SO$_2$R, or:

two R' are taken together with their intervening atoms to form an optionally substituted aryl, carbocyclic, heterocyclic, or heteroaryl ring;

-Cy- is an optionally substituted bivalent ring selected from phenylene, carbocylylene, arylene, heteroarylene, and heterocyclylene; and each R is independently hydrogen, or an optionally substituted group selected from $C_1$-$C_6$ aliphatic, carbocyclyl, aryl, heteroaryl, and heterocyclyl.

In some embodiments, [H]a-Ac is an oligonucleotide compound of formula O-I or a salt thereof. In some embodiments, [H]$_b$—Ac is an oligonucleotide compound of formula O-I or a salt thereof. In some embodiments, [H]$_b$—Ac is an oligonucleotide comprising one or more CpG, for example, those examples described herein. In some embodiments, [H]$_b$—Ac is an oligonucleotide of any one of Tables 2-5. In some embodiments, [H]b-Ac is an oligonucleotide of any one of Table 2. In some embodiments, [H]b-Ac is an oligonucleotide of any one of Table 3. In some embodiments, [H]b-Ac is an oligonucleotide of any one of Table 4. In some embodiments, [H]$_b$—Ac is an oligonucleotide of any one of Table 5.

In some embodiments, P in $T^{LD}$ is P*. In some embodiments, a conjugate has the structure of $[(A^c)_a$-$L^{LD}]$b-$R^{LD}$. In some embodiments, a conjugate has the structure of $(A^c)_a$-$L^{LD}$-$R^{LD}$. In some embodiments, a is 1-100. In some embodiments, a is 1-50. In some embodiments, a is 1-40. In some embodiments, a is 1-30. In some embodiments, a is 1-20. In some embodiments, a is 1-15. In some embodiments, a is 1-10. In some embodiments, a is 1-9. In some embodiments, a is 1-8. In some embodiments, a is 1-7. In some embodiments, a is 1-6. In some embodiments, a is 1-5. In some embodiments, a is 1-4. In some embodiments, a is 1-3. In some embodiments, a is 1-2. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10. In some embodiments, a is more than 10. In some embodiments, b is 1-100. In some embodiments, b is 1-50. In some embodiments, b is 1-40. In some embodiments, b is 1-30. In some embodiments, b is 1-20. In some embodiments, b is 1-15. In some embodiments, b is 1-10. In some embodiments, b is 1-9. In some embodiments, b is 1-8. In some embodiments, b is 1-7. In some embodiments, b is 1-6. In some embodiments, b is 1-5. In some embodiments, b is 1-4. In some embodiments, b is 1-3. In some embodiments, b is 1-2. In some embodiments, b is 1. In some embodiments, b is 2. In some embodiments, b is 3. In some embodiments, b is 4. In some embodiments, b is 5. In some embodiments, b is 6. In some embodiments, b is 7. In some embodiments, b is 8. In some embodiments, b is 9. In some embodiments, b is 10. In some embodiments, a is 1 and b is 1. In some embodiments, b is more than 10. In some embodiments, a conjugate has the structure of $A^c$-$L^{LD}$-$R^{LD}$. In some embodiments, $A^c$ is conjugated through one or more of its sugar, base and/or internucleotidic linkage moieties. In some embodiments, $A^c$ is conjugated through its 5'-OH (5'-O—). In some embodiments, $A^c$ is conjugated through its 3'-OH (3'-O—). In some embodiments, before conjugation, $A^c$-(H)b (b is an integer of 1-1000 depending on valency of $A^c$) is an oligonucleotide as described herein, for example, one of those described in any one of the Tables. In some embodiments, $L^{LD}$ is -L-. In some embodiments, $L^{LD}$ comprises a phosphorothioate group. In some embodiments, $L^{LD}$ is —C(O)NH—(CH$_2$)$_6$—OP(=O)(S$^-$)—O—. In some embodiments, the —C(O)NH end is connected to $R^{LD}$, and the —O— end is connected to the oligonucleotide, e.g., through 5'- or 3'-end. In some embodiments, $R^{LD}$ is optionally substituted $C_{10}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ to $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{60}$, $C_{70}$, or $C_{80}$ aliphatic. In some embodiments, $R^{LD}$ is optionally substituted $C_{10-80}$ aliphatic. In some embodiments, $R^{LD}$ is optionally substituted $C_{20-80}$ aliphatic. In some embodiments, $R^{LD}$ is optionally substituted $C_{10-70}$ aliphatic. In some embodiments, $R^{LD}$ is optionally substituted $C_{20-70}$ aliphatic. In some embodiments, $R^{LD}$ is optionally substituted $C_{10-60}$ aliphatic. In some embodiments, $R^{LD}$ is optionally substituted $C_{20-60}$ aliphatic. In some embodiments, $R^{LD}$ is optionally substituted $C_{10-50}$ aliphatic. In some embodiments, $R^{LD}$ is optionally substituted $C_{20-50}$ aliphatic. In some embodiments, $R^{LD}$ is optionally substituted $C_{10-40}$ aliphatic. In some embodiments, $R^{LD}$ is optionally substituted $C_{20-40}$ aliphatic. In some embodiments, $R^{LD}$ is optionally substituted $C_{10-30}$ aliphatic. In some embodiments, $R^{LD}$ is optionally substituted $C_{20-30}$ aliphatic. In some embodiments, $R^{LD}$ is unsubstituted $C_{10}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ to $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{60}$, $C_{70}$, or $C_{80}$ aliphatic. In some embodiments, $R^{LD}$ is unsubstituted $C_{10-80}$ aliphatic. In some embodiments, $R^{LD}$ is unsubstituted $C_{20-80}$ aliphatic. In some embodiments, $R^{LD}$ is unsubstituted $C_{10-70}$ aliphatic. In some embodiments, $R^{LD}$ is unsubstituted $C_{20-70}$ aliphatic. In some embodiments, $R^{LD}$ is unsubstituted $C_{10-60}$ aliphatic. In some embodiments, $R^{LD}$ is unsubstituted $C_{20-60}$ aliphatic. In some embodiments, $R^{LD}$ is unsubstituted $C_{10-50}$ aliphatic. In some embodiments, $R^{LD}$ is unsubstituted $C_{20-50}$ aliphatic. In some embodiments, $R^{LD}$ is unsubstituted $C_{10-40}$ aliphatic. In some embodiments, $R^{LD}$ is unsubstituted $C_{20-40}$ aliphatic. In some embodiments, $R^{LD}$ is unsubstituted $C_{10-30}$ aliphatic. In some embodiments, $R^{LD}$ is unsubstituted $C_{20-30}$ aliphatic.

In some embodiments, a lipid comprises an $R^{LD}$ group. In some embodiments, a lipid is $R^{LD}$—COOH. In some embodiments, a lipid is $R^{LD}$—OH. In some embodiments, provided oligonucleotides comprise a lipid moiety which is $R^{LD}$. In some embodiments, $R^{LD}$ is $R^1$.

In some embodiments, $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein:
each R' is independently —R, —C(O)R, —CO$_2$R, or —SO$_2$R, or:
    two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroarylene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein:
each R' is independently —R, —C(O)R, —CO$_2$R, or —SO$_2$R, or:
    two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroarylene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, $R^{LD}$ is an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein:
each R' is independently —R, —C(O)R, —CO$_2$R, or —SO$_2$R, or:
    two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroaryl ene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

In some embodiments, $R^{LD}$ is an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

The aliphatic group of $R^{LD}$ can be a variety of suitable length. In some embodiments, it is $C_{10}$-$C_{80}$. In some embodiments, it is $C_{10}$-$C_{75}$. In some embodiments, it is $C_{10}$-$C_{70}$. In some embodiments, it is $C_{10}$-$C_{65}$. In some embodiments, it is $C_{10}$-$C_{60}$. In some embodiments, it is $C_{10}$-$C_{50}$. In some embodiments, it is $C_{10}$-$C_{40}$. In some embodiments, it is $C_{10}$-$C_{35}$. In some embodiments, it is $C_{10}$-$C_{30}$. In some embodiments, it is $C_{10}$-$C_{25}$. In some embodiments, it is $C_{10}$-$C_{24}$. In some embodiments, it is $C_{10}$-$C_{23}$. In some embodiments, it is $C_{10}$-$C_{22}$. In some embodiments, it is $C_{10}$-$C_{21}$. In some embodiments, it is $C_{12}$-$C_{22}$. In some embodiments, it is $C_{13}$-$C_{22}$. In some embodiments, it is $C_{14}$-$C_{22}$. In some embodiments, it is $C_{15}$-$C_{22}$. In some embodiments, it is $C_{16}$-$C_{22}$. In some embodiments, it is $C_{17}$-$C_{22}$. In some embodiments, it is $C_{18}$-$C_{22}$. In some embodiments, it is $C_{10}$-$C_{20}$. In some embodiments, the lower end of the range is $C_{10}$, $C_{u}$, $C_{12}$, $C_{13}$, $C_{14}$, $C_{15}$, $C_{16}$, $C_{17}$, or $C_{18}$. In some embodiments, the higher end of the range is $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{55}$, or $C_{60}$. In some embodiments, it is $C_{10}$. In some embodiments, it is Cn. In some embodiments, it is $C_{12}$. In some embodiments, it is $C_{13}$. In some embodiments, it is $C_{14}$. In some embodiments, it is $C_{15}$. In some embodiments, it is $C_{16}$. In some embodiments, it is $C_{17}$. In some embodiments, it is $C_{18}$. In some embodiments, it is $C_{19}$. In some embodiments, it is $C_{20}$. In some embodiments, it is $C_{21}$. In some embodiments, it is $C_{22}$. In some embodiments, it is $C_{23}$. In some embodiments, it is $C_{24}$. In some embodiments, it is $C_{25}$. In some embodiments, it is $C_{30}$. In some embodiments, it is $C_{35}$. In some embodiments, it is $C_{40}$. In some embodiments, it is $C_{45}$. In some embodiments, it is $C_{50}$. In some embodiments, it is $C_{55}$. In some embodiments, it is $C_{60}$.

In some embodiments, a lipid comprises no more than one $R^{LD}$ group. In some embodiments, a lipid comprises two or more $R^{LD}$ groups.

In some embodiments, a lipid is conjugated to a biologically active agent, optionally through a linker, as a moiety comprising an $R^{LD}$ group. In some embodiments, a lipid is conjugated to a biologically active agent, optionally through a linker, as a moiety comprising no more than one $R^{LD}$ group. In some embodiments, a lipid is conjugated to a biologically active agent, optionally through a linker, as an $R^{LD}$ group. In some embodiments, a lipid is conjugated to a biologically active agent, optionally through a linker, as a moiety comprising two or more $R^{LD}$ groups.

In some embodiments, $R^{LD}$ is an optionally substituted, $C_{10}$-$C_{40}$ saturated or partially unsaturated, aliphatic chain. In some embodiments, a lipid comprises an optionally substituted $C_{10}$-$C_{40}$ saturated or partially unsaturated, aliphatic chain.

In some embodiments, $R^{LD}$ is an optionally substituted $C_{10}$-$C_{40}$ linear, saturated or partially unsaturated, aliphatic chain. In some embodiments, a lipid comprises an optionally substituted $C_{10}$-$C_{40}$ linear, saturated or partially unsaturated, aliphatic chain.

In some embodiments, $R^{LD}$ is a $C_{10}$-$C_{40}$ linear, saturated or partially unsaturated, aliphatic chain, optionally substituted with one or more $C_{1-4}$ aliphatic groups. In some embodiments, a lipid comprises a $C_{10}$-$C_{40}$ linear, saturated or partially unsaturated, aliphatic chain, optionally substituted with one or more $C_{1-4}$ aliphatic groups. In some embodiments, $R^{LD}$ is a $C_{10}$-$C_{40}$ linear, saturated or partially unsaturated, aliphatic chain, optionally substituted with one or more $C_{1-2}$ aliphatic groups. In some embodiments, a lipid comprises a $C_{10}$-$C_{40}$ linear, saturated or partially unsaturated, aliphatic chain, optionally substituted with one or more $C_{1-2}$ aliphatic groups. In some embodiments, $R^{LD}$ is a $C_{10}$-$C_{40}$ linear, saturated or partially unsaturated, aliphatic chain, optionally substituted with one or more methyl groups. In some embodiments, a lipid comprises a $C_{10}$-$C_{40}$ linear, saturated or partially unsaturated, aliphatic chain, optionally substituted with one or more methyl groups.

In some embodiments, $R^{LD}$ is an unsubstituted $C_{10}$-$C_{40}$ linear, saturated or partially unsaturated, aliphatic chain. In some embodiments, a lipid comprises an unsubstituted $C_{10}$-$C_{40}$ linear, saturated or partially unsaturated, aliphatic chain.

In some embodiments, a lipid comprises no more than one optionally substituted $C_{10}$-$C_{40}$ linear, saturated or partially unsaturated, aliphatic chain. In some embodiments, a lipid comprises two or more optionally substituted $C_{10}$-$C_{40}$ linear, saturated or partially unsaturated, aliphatic chain.

In some embodiments, $R^{LD}$ is an optionally substituted, $C_{10}$-$C_{60}$ saturated or partially unsaturated, aliphatic chain. In some embodiments, a lipid comprises an optionally substituted $C_{10}$-$C_{60}$ saturated or partially unsaturated, aliphatic chain.

In some embodiments, $R^{LD}$ is an optionally substituted $C_{10}$-$C_{60}$ linear, saturated or partially unsaturated, aliphatic chain. In some embodiments, a lipid comprises an optionally substituted $C_{10}$-$C_{60}$ linear, saturated or partially unsaturated, aliphatic chain.

In some embodiments, $R^{LD}$ is a $C_{10}$-$C_{60}$ linear, saturated or partially unsaturated, aliphatic chain, optionally substituted with one or more $C_{1-4}$ aliphatic groups. In some embodiments, a lipid comprises a $C_{10}$-$C_{60}$ linear, saturated or partially unsaturated, aliphatic chain, optionally substituted with one or more $C_{1-4}$ aliphatic groups. In some embodiments, $R^{LD}$ is a $C_{10}$-$C_{60}$ linear, saturated or partially unsaturated, aliphatic chain, optionally substituted with one or more $C_{1-2}$ aliphatic groups. In some embodiments, a lipid comprises a $C_{10}$-$C_{60}$ linear, saturated or partially unsaturated, aliphatic chain, optionally substituted with one or more $C_{1-2}$ aliphatic groups. In some embodiments, $R^{LD}$ is a $C_{10}$-$C_{60}$ linear, saturated or partially unsaturated, aliphatic chain, optionally substituted with one or more methyl groups. In some embodiments, a lipid comprises a $C_{10}$-$C_{60}$ linear, saturated or partially unsaturated, aliphatic chain, optionally substituted with one or more methyl groups.

In some embodiments, $R^{LD}$ is an unsubstituted $C_{10}$-$C_{60}$ linear, saturated or partially unsaturated, aliphatic chain. In some embodiments, a lipid comprises an unsubstituted $C_{10}$-$C_{60}$ linear, saturated or partially unsaturated, aliphatic chain.

In some embodiments, a lipid comprises no more than one optionally substituted $C_{10}$-$C_{60}$ linear, saturated or partially unsaturated, aliphatic chain. In some embodiments, a lipid comprises two or more optionally substituted $C_{10}$-$C_{60}$ linear, saturated or partially unsaturated, aliphatic chain.

In some embodiments, $R^{LD}$ is an optionally substituted, $C_{10}$-$C_{80}$ saturated or partially unsaturated, aliphatic chain. In some embodiments, a lipid comprises an optionally substituted $C_{10}$-$C_{80}$ saturated or partially unsaturated, aliphatic chain.

In some embodiments, $R^{LD}$ is an optionally substituted $C_{10}$-$C_{80}$ linear, saturated or partially unsaturated, aliphatic chain. In some embodiments, a lipid comprises an optionally substituted $C_{10}$-$C_{80}$ linear, saturated or partially unsaturated, aliphatic chain.

In some embodiments, $R^{LD}$ is a $C_{10}$-$C_{80}$ linear, saturated or partially unsaturated, aliphatic chain, optionally substituted with one or more $C_{1-4}$ aliphatic groups. In some embodiments, a lipid comprises a $C_{10}$-$C_{80}$ linear, saturated or partially unsaturated, aliphatic chain, optionally substituted with one or more $C_{1-4}$ aliphatic groups. In some embodiments, $R^{LD}$ is a $C_{10}$-$C_{80}$ linear, saturated or partially unsaturated, aliphatic chain, optionally substituted with one or more $C_{1-2}$ aliphatic groups. In some embodiments, a lipid comprises a $C_{10}$-$C_{80}$ linear, saturated or partially unsaturated, aliphatic chain, optionally substituted with one or more $C_{1-2}$ aliphatic groups. In some embodiments, $R^{LD}$ is a $C_{10}$-$C_{80}$ linear, saturated or partially unsaturated, aliphatic chain, optionally substituted with one or more methyl groups. In some embodiments, a lipid comprises a $C_{10}$-$C_{80}$ linear, saturated or partially unsaturated, aliphatic chain, optionally substituted with one or more methyl groups.

In some embodiments, $R^{LD}$ is an unsubstituted $C_{10}$-$C_{80}$ linear, saturated or partially unsaturated, aliphatic chain. In some embodiments, a lipid comprises an unsubstituted $C_{10}$-$C_{80}$ linear, saturated or partially unsaturated, aliphatic chain.

In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain.

In some embodiments, $R^{LD}$ is or comprises a $C_{10}$ saturated linear aliphatic chain. In some embodiments, $R^{LD}$ is or comprises a $C_{10}$ partially unsaturated linear aliphatic chain. In some embodiments, $R^{LD}$ is or comprises a Cn saturated linear aliphatic chain. In some embodiments, $R^{LD}$ is or comprises a Cn partially unsaturated linear aliphatic chain. In some embodiments, $R^{LD}$ is or comprises a $C_{12}$ saturated linear aliphatic chain. In some embodiments, $R^{LD}$ is or comprises a $C_{12}$ partially unsaturated linear aliphatic chain. In some embodiments, $R^{LD}$ is or comprises a $C_{13}$ saturated linear aliphatic chain. In some embodiments, $R^{LD}$ is or comprises a $C_{13}$ partially unsaturated linear aliphatic chain. In some embodiments, $R^{LD}$ is or comprises a $C_{14}$ saturated linear aliphatic chain. In some embodiments, $R^{LD}$ is or comprises a $C_{14}$ partially unsaturated linear aliphatic chain. In some embodiments, $R^{LD}$ is or comprises a $C_{15}$ saturated linear aliphatic chain. In some embodiments, $R^{LD}$ is or comprises a $C_{15}$ partially unsaturated linear aliphatic chain. In some embodiments, $R^{LD}$ is or comprises a $C_{16}$ saturated linear aliphatic chain. In some embodiments, $R^{LD}$ is or comprises a $C_{16}$ partially unsaturated linear aliphatic chain. In some embodiments, $R^{LD}$ is or comprises a $C_{17}$ saturated linear aliphatic chain. In some embodiments, $R^{LD}$ is or comprises a $C_{17}$ partially unsaturated linear aliphatic chain. In some embodiments, $R^{LD}$ is or comprises a $C_{18}$ saturated linear aliphatic chain. In some embodiments, $R^{LD}$ is or comprises a $C_{18}$ partially unsaturated linear aliphatic chain. In some embodiments, $R^{LD}$ is or comprises a $C_{19}$ saturated linear aliphatic chain. In some embodiments, $R^{LD}$ is or comprises a $C_{19}$ partially unsaturated linear aliphatic chain. In some embodiments, $R^{LD}$ is or comprises a $C_{20}$ saturated linear aliphatic chain. In some embodiments, $R^{LD}$ is or comprises a $C_{20}$ partially unsaturated linear aliphatic chain. In some embodiments, $R^{LD}$ is or comprises a $C_{21}$ saturated linear aliphatic chain. In some embodiments, $R^{LD}$ is or comprises a $C_{21}$ partially unsaturated linear aliphatic chain. In some embodiments, $R^{LD}$ is or comprises a $C_{22}$ saturated linear aliphatic chain. In some embodiments, $R^{LD}$ is or comprises a $C_{22}$ partially unsaturated linear aliphatic chain. In some embodiments, $R^{LD}$ is or comprises a $C_{23}$ saturated linear aliphatic chain. In some embodiments, $R^{LD}$ is or comprises a $C_{23}$ partially unsaturated linear aliphatic chain. In some embodiments, $R^{LD}$ is or comprises a $C_{24}$ saturated linear aliphatic chain. In some embodiments, $R^{LD}$ is or comprises a $C_{24}$ partially unsaturated linear aliphatic chain. In some embodiments, $R^{LD}$ is or comprises a $C_{25}$ saturated linear aliphatic chain. In some embodiments, $R^{LD}$ is or comprises a $C_{25}$ partially unsaturated linear aliphatic chain. In some embodiments, $R^{LD}$ is or comprises a $C_{26}$ saturated linear aliphatic chain. In some embodiments, $R^{LD}$ is or comprises a $C_{26}$ partially unsaturated linear aliphatic chain. In some embodiments, $R^{LD}$ is or comprises a $C_{27}$ saturated linear aliphatic chain. In some embodiments, $R^{LD}$ is or comprises a $C_{27}$ partially unsaturated linear aliphatic chain. In some embodiments, $R^{LD}$ is or comprises a $C_{28}$ saturated linear aliphatic chain. In some embodiments, $R^{LD}$ is or comprises a $C_{28}$ partially unsaturated linear aliphatic chain. In some embodiments, $R^{LD}$ is or comprises a $C_{29}$ saturated linear aliphatic chain. In some embodiments, $R^{LD}$ is or comprises a $C_{29}$ partially unsaturated linear aliphatic chain. In some embodiments, $R^{LD}$ is or comprises a $C_{30}$ saturated linear aliphatic chain. In some embodiments, $R^{LD}$ is or comprises a $C_{30}$ partially unsaturated linear aliphatic chain.

In some embodiments, a lipid has the structure of $R^{LD}$—OH. In some embodiments, a lipid has the structure of $R^{LD}$—C(O)OH, In some embodiments. $R^{LD}$ is

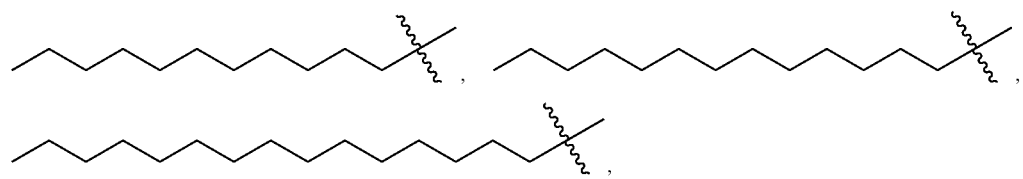

-continued

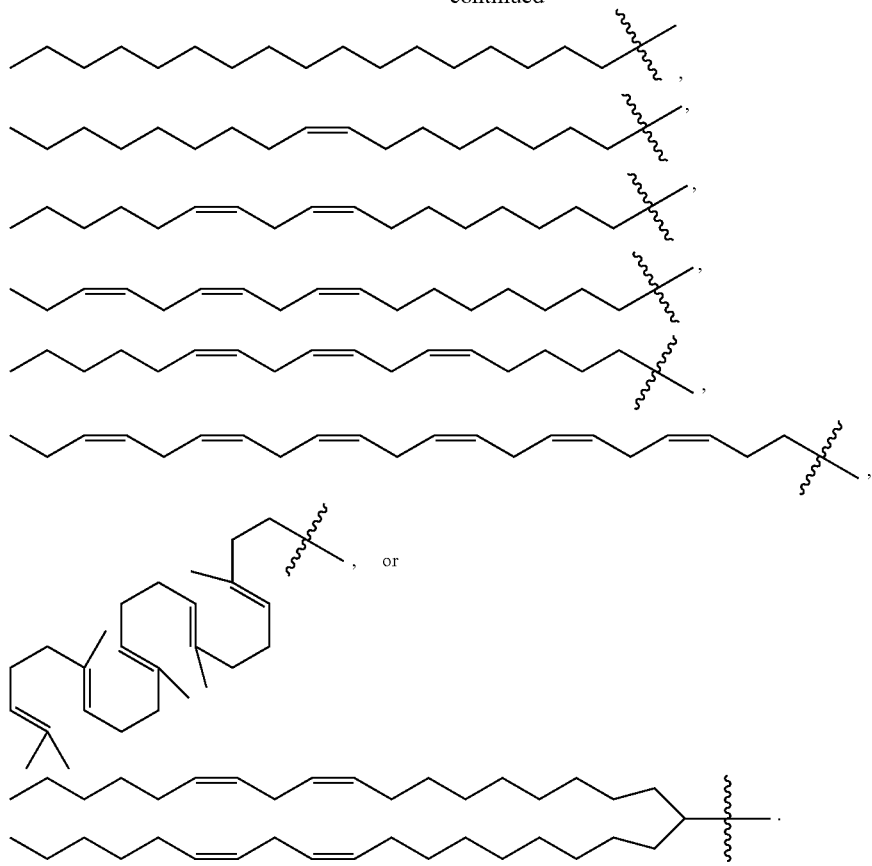

Example oligonucleotides comprising such $R^D$ groups are illustrated, e.g., in Table 2. In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid, arachidonic acid, and dilinoleyl. In some embodiments, a lipid has a structure of:

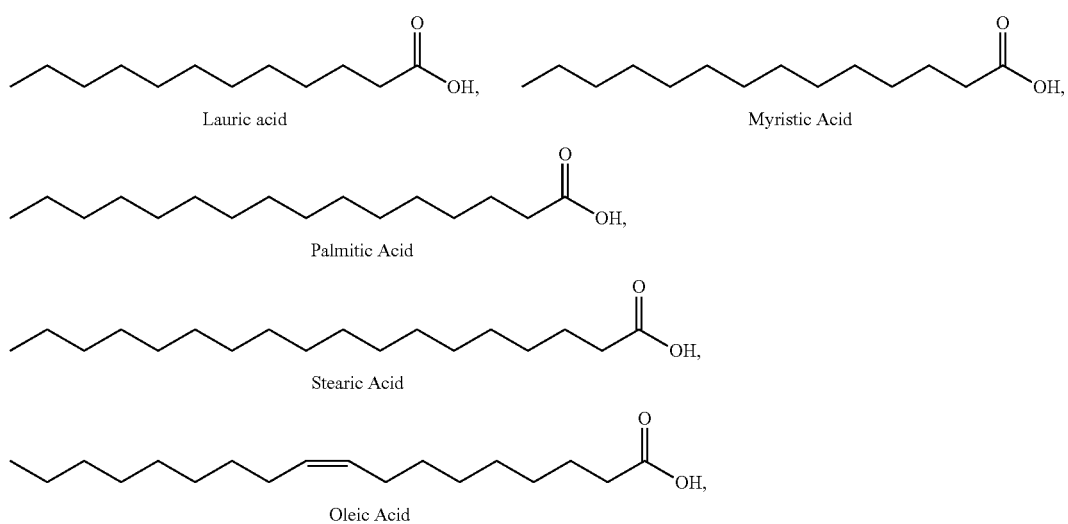

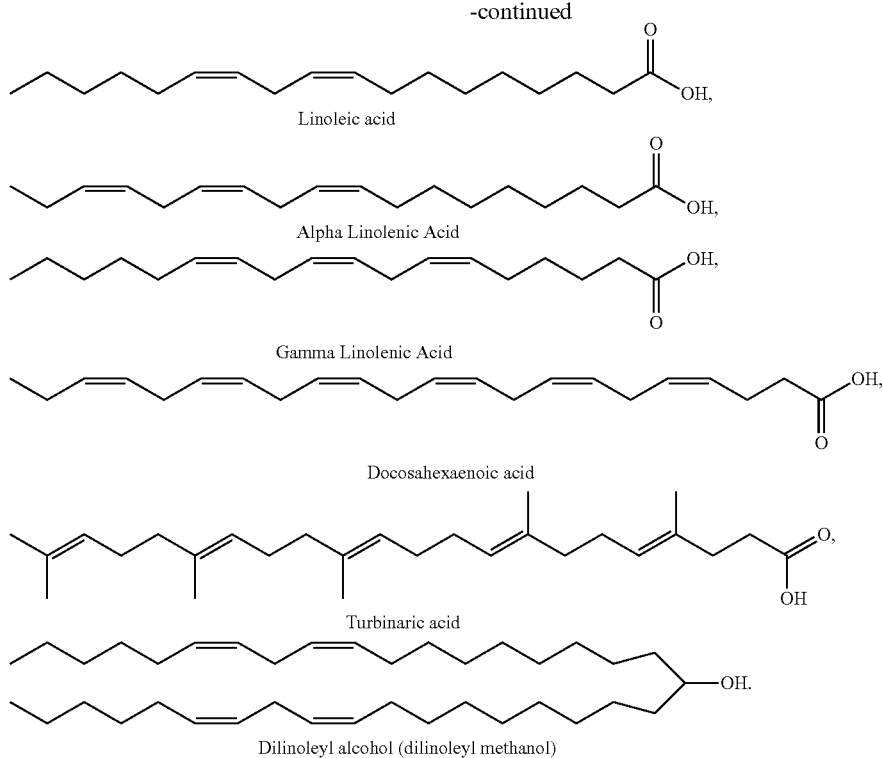

Linoleic acid

Alpha Linolenic Acid

Gamma Linolenic Acid

Docosahexaenoic acid

Turbinaric acid

Dilinoleyl alcohol (dilinoleyl methanol)

Example oligonucleotides comprising conjugation with these lipids are illustrated, e.g., in Table 2.

In some embodiments, a lipid is, comprises or consists of any of: an at least partially hydrophobic or amphiphilic molecule, a phospholipid, a triglyceride, a diglyceride, a monoglyceride, a fat-soluble vitamin, a sterol, a fat and a wax. In some embodiments, a lipid is any of: a fatty acid, glycerolipid, glycerophospholipid, sphingolipid, sterol lipid, prenol lipid, saccharolipid, polyketide, and other molecule.

Figure 25:
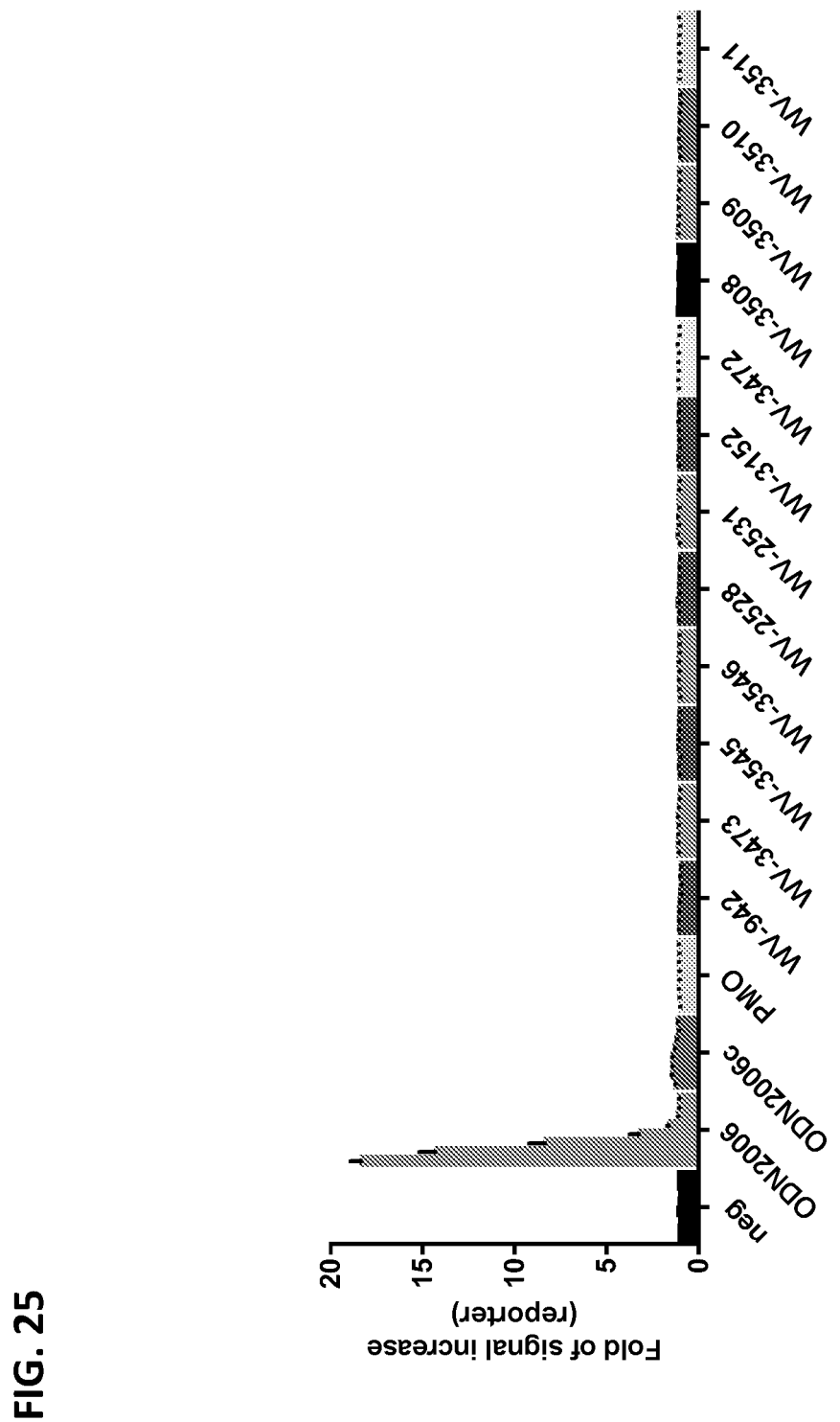
FIG. 25 shows that several example provided oligonucleotides do not have hTLR9 agonist activity under the tested conditions. The experiment was done in triplicate, with average data shown.
Figure 26:
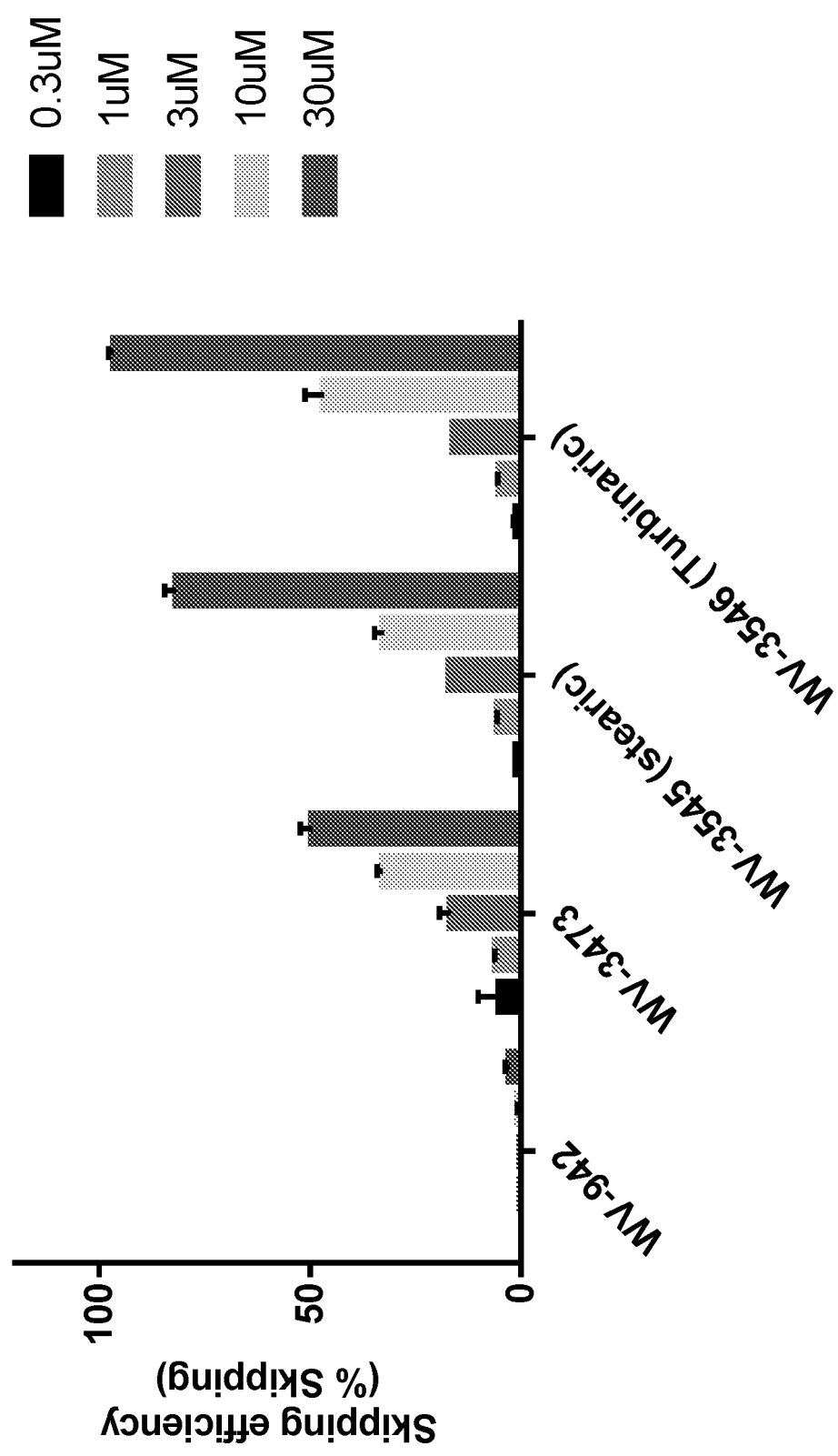
FIG. 26 shows lipid conjugation can improve TLR9-related activities and other properties. Presented are example data of oligonucleotides comprising lipid moieties in skipping exon 51 of human dystrophin. Data for different doses from 0.3 μM to 30 μM, are presented. Skipping efficiency generally increases with increased concentration. WV-3545 (WV-3473 conjugated to stearic acid by PO and C6 amino linker) and WV-3546 (WV-3473 conjugated to turbinaric acid by PO and C6 amino linker), both containing lipid moieties, demonstrated higher efficiency. Treatment was gymnotic (without transfection reagent). The experiment was done in triplicate, with average data shown.

In some embodiments, the present disclosure provides example data demonstrating that many of provided oligonucleotides do not mediate an immune response, as determined by a lack of agonism of hTLR9; for example, see FIG. 25. Among other things, the present disclosure demonstrates that oligonucleotides conjugated to lipids surprisingly counteracted hTLR9 agonism, for example, that mediated by control oligonucleotide ODN2006 (e.g., conjugation of lipids to oligonucleotides antagonizes hTLR9 activity mediated by ODN2006); for examples, see FIGS. 23 and 24, WV-3545 and WV-3546 (which are oligonucleotides to the target Dystrophin). Other oligonucleotides comprising lipid moieties were also tested and were shown to have greatly enhanced ability to antagonize hTLR9 activity. For example, WV-2824 and WV-2830, conjugates of Malat1-targeting WV-2735 with stearic acid (WV-2824) and turbinaric acid (WV-2830), respectively, also demonstrated greatly enhanced ability to antagonize hTLR9 activity mediated by ODN2006. Among other things, these experiments show that conjugation of lipids, such as stearic acid, turbinaric acid, etc., with oligonucleotides can greatly increase hTLR9 antagonist activity.

Linkers

A person having ordinary skill in the art appreciates that various technologies can be utilized to conjugate lipids to biologically active agent in accordance with the present disclosure. For example, for lipids comprising carboxyl groups, such lipids can be conjugated through the carboxyl groups. In some embodiments, a lipid is conjugated to an oligonucleotide optionally through a linker moiety.

In some embodiments, a linker has the structure of -$L^{LD}$-. In some embodiments, $L^{LD}$ is $T^{LD}$ having the structure of

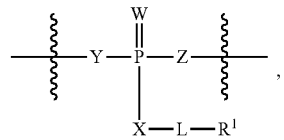

wherein each variable is independently as defined and described. In some embodiments, $T^{LD}$ has the structure of formula I. In some embodiments, $T^{LD}$ with the 5'-O— of an oligonucleotide chain form a phosphorothioate linkage (—OP(O)(S$^-$)O—). In some embodiments, $T^{LD}$ with the 5'-O— of an oligonucleotide chain form an Sp phosphorothioate linkage. In some embodiments, $T^{LD}$ with the 5'-O— of an oligonucleotide chain form an Rp phosphorothioate linkage. In some embodiments, $T^{LD}$ with the 5'-O— of an oligonucleotide chain form a phosphate linkage (—OP(O)(O$^-$)O—). In some embodiments, $T^{LD}$ with the 5'-O— of an oligonucleotide chain form a phosphorodithioate linkage. In some embodiments, $L^{LD}$ is -L-$T^{LD}$-. In some embodiments, Y connects to L and —Z— is a covalent bond, so that P directly connects to a hydroxyl group of the oligonucleotide chain. In some embodiments, P connects to the 5'-end hydroxyl (5'-O—) to form a phosphate group (natural phosphate linkage) or phosphorothioate group (phosphorothioate linkage). In some embodiments, the phosphorothioate linkage is chirally controlled and can be either Rp or Sp. Unless otherwise specified, chiral centers in the linkers (e.g., P in $T^{LD}$) can be either stereorandom or chirally controlled, and they are not considered as part of the backbone chiral centers, e.g., for determining whether a composition is chirally controlled. In some embodiments, $L^{LD}$ is —NH—$(CH_2)_6$-$T^{LD}$-. In some embodiments, $L^{LD}$ is —C(O)—NH—$(CH_2)_6$-$T^{LD}$-.

In some embodiments, a linker has the structure of -L-. In some embodiments, after conjugation to oligonucleotides, a lipid forms a moiety having the structure of -L-$R^{LD}$, wherein each of L and $R^{LD}$ is independently as defined and described herein.

In some embodiments, -L- comprises a bivalent aliphatic chain. In some embodiments, -L- comprises a phosphate group. In some embodiments, -L- comprises a phosphorothioate group. In some embodiments, -L- has the structure of —C(O)NH—$(CH_2)_6$—OP (=O)(S$^-$)—. In some embodiments, -L- has the structure of —C(O)NH—$(CH_2)_6$—OP (=O)(O$^-$)—.

Lipids, optionally through linkers, can be conjugated to oligonucleotides at various suitable locations. In some embodiments, lipids are conjugated through the 5'-OH group. In some embodiments, lipids are conjugated through the 3'-OH group. In some embodiments, lipids are conjugated through one or more sugar moieties. In some embodiments, lipids are conjugated through one or more bases. In some embodiments, lipids are incorporated through one or more internucleotidic linkages. In some embodiments, an oligonucleotide may contain multiple conjugated lipids which are independently conjugated through its 5'-OH, 3'-OH, sugar moieties, base moieties and/or internucleotidic linkages.

In some embodiments, a linker is a moiety that connects two parts of a composition; as a non-limiting example, a linker physically connects a active compound to a lipid. Non-limiting examples of suitable linkers include: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group.

In some embodiments, a linker comprises an uncharged linker or a charged linker.

In some embodiments, a linker comprises an alkyl.

In some embodiments, a linker comprises a phosphate. In various embodiments, a phosphate can also be modified by replacement of a bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. In some embodiments, the bridging oxygen is the 3'-oxygen of a nucleoside, replacement with carbon is done. In some embodiments, the bridging oxygen is the 5'-oxygen of a nucleoside, replacement with nitrogen is done. In various embodiments, the linker comprising a phosphate comprises any one or more of: a phosphorodithioate, phosphoramidate, boranophosphonate, or a compound of formula (I):

where $R^3$ is selected from OH, SH, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

In some embodiments, a linker comprises a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R_1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, a linker is a branched linker. In some embodiments, a branchpoint of the branched linker may be at least bivalent, but may be a tetravalent, pentavalent or hexavalent atom, or a group presenting such multiple valencies. In some embodiments, a branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branchpoint is glycerol or glycerol derivative.

In one embodiment, a linker comprises at least one cleavable linking group.

As a non-limiting example, a cleavable linking group can be sufficiently stable outside the cell, but which upon entry into a target cell is cleaved to release the two parts the linker is holding together. As a non-limiting example, a cleavable linking group is cleaved at least 10 times or more, at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum). Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

As a non-limiting example, a cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a desired pH, thereby releasing the cationic lipid from the ligand inside the cell, or into the desired compartment of the cell.

As a non-limiting example, a linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

As a non-limiting example, a linker can contain a peptide bond, which can be used when targeting cell types rich in peptidases, such as liver cells and synoviocytes.

As a non-limiting example, suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. As a non-limiting example, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In some embodiments, a linker comprises a redox cleavable linking group. As a non-limiting example, one class of cleavable linking groups are redox cleavable linking groups that are cleaved upon reduction or oxidation. A non-limiting example of reductively cleavable linking group is a disulphide linking group (—S—S—). To determine if a candidate cleavable linking group is a suitable "reductively cleavable linking group," or for example is suitable for use with a particular oligonucleotide moiety and particular targeting agent one can look to methods described herein. As a non-limiting example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. As a non-limiting example, candidate compounds are cleaved by at most 10% in the blood. As a non-limiting example, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

In some embodiments, a linker comprises a phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Additional non-limiting examples are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. An additional non-limiting examples is —O—P(O)(OH)—O— In various embodiments, Rk is any of: OH, SH, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

In some embodiments, a linker comprises an acid cleavable linking groups are linking groups that are cleaved under acidic conditions. As a non-limiting example, acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). In an additional non-limiting example, when the carbon attached to the oxygen of the ester (the alkoxy group) is an aryl group, substituted alkyl group, or tertiary alkyl group such as dimethyl pentyl or t-butyl.

In some embodiments, a linker comprises an ester-based linking groups. As a non-limiting example, ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

In some embodiments, a linker comprises a peptide-based cleaving group. Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. As a non-limiting example, peptide-based cleavable groups do not include the amide group (—C(O)NH—). The amide group can be formed between any alkylene, alkenylene or alkynylene. A peptide bond is a special type of amide bond formed between amino acids to yield peptides and proteins. As a non-limiting example, a peptide based cleavage group can be limited to the peptide bond (i.e., the amide bond) formed between amino acids yielding peptides and proteins and does not include the entire amide functional group. As a non-limiting example, a peptide-based cleavable linking groups can have the general formula —NHCHR$^A$C(O)NHCHR$^B$C(O)—, where R$^A$ and R$^B$ are the R groups of the two adjacent amino acids. These candidates can be evaluated using methods analogous to those described above.

Any linker reported in the art can be used, including, as non-limiting examples, those described in: U.S. Pat. App. No. 20150265708.

In some embodiments, a lipid is conjugated through a linker having the structure of -L-, wherein L is as defined and described in formula I. In some embodiments, L comprises a phosphate diester or modified phosphate diester moiety. In some embodiments, a compound formed by lipid conjugation has the structure of (R$^{LD}$-L-)$_x$-(active compound), wherein x is 1 or an integer greater than 1, and each of R$^{LD}$ and L is independently as defined and described herein. In some embodiments, x is 1. In some embodiments, x is greater than 1. In some embodiments, x is 1-50. In some embodiments, an active compound is an oligonucleotide. For example, in some embodiments, a conjugate has the following structures:

cleavage group; a linker comprising at least one acid-cleavage group; a linker comprising at least one ester-based cleavage group; and a linker comprising at least one peptide-based cleavage group. Other non-limiting examples of linkers are described herein, or detailed in FIG. 7. In some embodiments, a linker has the structure of -L$^{LD}$-. In some embodiments, a linker has the structure of L. In some embodiments, a linker comprises a linkage of formula I. In some embodiments, a linker is —C(O)NH—(CH$_2$)$_6$-L$^1$-, wherein L$^1$ has the structure of formula I as described herein. In some embodiments, a linker is —C(O)NH—(CH$_2$)$_6$—O—P(=O)(SR$^1$)—O—. In some embodiments, R$^1$ is —H, and a linker is —C(O)NH—(CH$_2$)$_6$—O—P(=O)(SH)—O—, in some conditions, e.g., certain pH, —C(O)NH—(CH$_2$)$_6$—O—P(=O)(S$^-$)—O—. In some embodiments, a linker is —C(O)NH—(CH$_2$)$_6$—O—P(=S)(SR$^1$)—O—. In some embodiments, R$^1$ is —H, and a linker is —C(O)NH—(CH$_2$)$_6$—O—P(=S)(SH)—O—, in some conditions, e.g., certain pH, —C(O)NH—(CH$_2$)$_6$—O—P(=S)(S$^-$)—O—. In some embodiments, a linker is —C(O)NH—(CH$_2$)$_6$—O—P(=S)(OR$^1$)—O—, wherein R$^1$ is —CH$_2$CH$_2$CN. In some embodiments, a linker is —C(O)NH—(CH$_2$)$_6$—O—P(=S)(SR$^1$)—O—, wherein R$^1$ is —CH$_2$CH$_2$CN. In some embodiments, a provided oligonucleotide is coupled with a linker and forms a structure of H-linker-oligonucleotide. In some embodiments, a provided oligonucleotide is conjugated to a lipid and forms the structure of lipid-linker-oligonucleotide, e.g., R$^{LD}$-L$^{LD}$-oligonucleotide. In some embodiments, the —O— end of a linker is connected to an oligonucleotide. In some embodiments, the —O— end of a linker is connected to the 5'-end oligonucleotide (—O— being the oxygen in the 5'-OH).

In some embodiments, a linker comprises a PO (phosphodiester linkage), a PS (phosphorothioate linkage) or PS2 (phosphorodithioate linkage). A non-limiting example including a PS linker is shown below. In some embodiments, a linker is —O—P(O)(OH)—O-[phosphodiester], —O—P(O)(SH)—O— [phosphorothioate] or —O—P(S)(SH)—O-

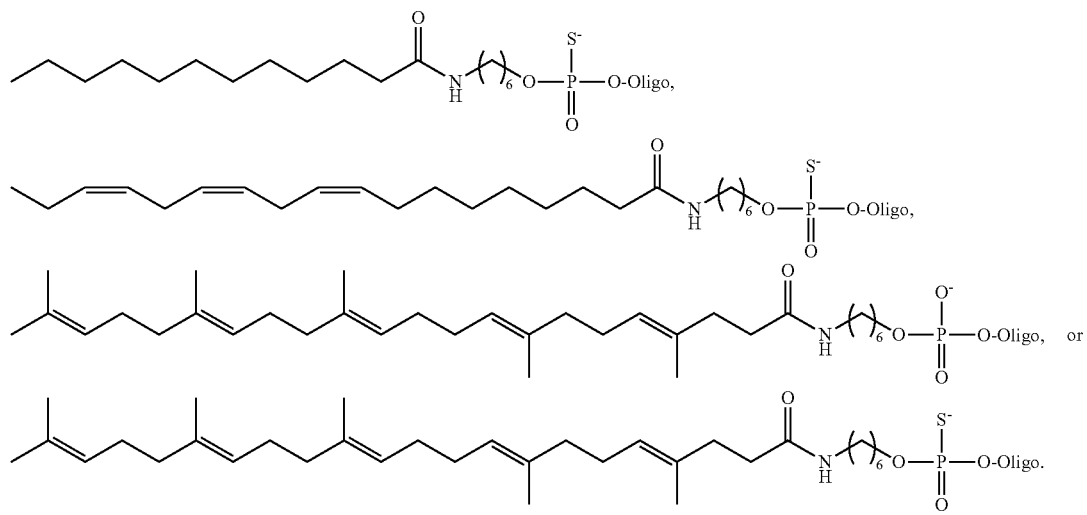

In some embodiments, a linker is selected from: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based [phosphorodithioate]. In some embodiments, a linker comprises a C6 amino moiety (—NH—(CH$_2$)$_6$—), which is illustrated below. In some embodiments, a linker comprises a C6 amino bound to a PO, a PS, or PS2. In some embodiments, a linker is a C6 amino bound to a PO, a PS, or PS2. In some embodiments, a linker, e.g., L$^{LD}$ or L, is —C(O)—

NH—(CH$_2$)$_6$—P(O)(OH)—. In some embodiments, a linker, e.g., L$^{LD}$ or L, is —C(O)—NH—(CH$_2$)$_6$—P(O)(OH)—, wherein —C(O)— is connected to a lipid moiety and —P(O)(OH)— is connected to an oligonucleotide chain. In some embodiments, a linker, e.g., L$^{LD}$ or L, is —C(O)—NH—(CH$_2$)$_6$—P(O)(OH)—, wherein —C(O)— is connected to a lipid moiety and —P(O)(OH)— is connected to the 5'-O— of an oligonucleotide chain. In some embodiments, a linker, e.g., L$^{LD}$ or L, is —C(O)—NH—(CH$_2$)$_6$—P(O)(OH)—, wherein —C(O)— is connected to a lipid moiety and —P(O)(OH)— is connected to the 3'-O— of an oligonucleotide chain. In some embodiments, a linker, e.g., L$^{LD}$ or L, is —C(O)—NH—(CH$_2$)$_6$—P(O)(SH)—. In some embodiments, a linker, e.g., L$^{LD}$ or L, is —C(O)—NH—(CH$_2$)$_6$—P(O)(SH)—, wherein —C(O)— is connected to a lipid moiety and —P(O)(SH)— is connected to an oligonucleotide chain. In some embodiments, a linker, e.g., L$^{LD}$ or L, is —C(O)—NH—(CH$_2$)$_6$—P(O)(SH)—, wherein —C(O)— is connected to a lipid moiety and —P(O)(SH)— is connected to the 5'-O— of an oligonucleotide chain. In some embodiments, a linker, e.g., L$^{LD}$ or L, is —C(O)—NH—(CH$_2$)$_6$—P(O)(SH)—, wherein —C(O)— is connected to a lipid moiety and —P(O)(SH)— is connected to the 3'-O— of an oligonucleotide chain. In some embodiments, a linker, e.g., L$^{LD}$ or L, is —C(O)—NH—(CH$_2$)$_6$—P(S)(SH)—. In some embodiments, a linker, e.g., L$^{LD}$ or L, is —C(O)—NH—(CH$_2$)$_6$—P(S)(SH)—, wherein —C(O)— is connected to a lipid moiety and —P(S)(SH)— is connected to an oligonucleotide chain. In some embodiments, a linker, e.g., L$^{LD}$ or L, is —C(O)—NH—(CH$_2$)$_6$—P(S)(SH)—, wherein —C(O)— is connected to a lipid moiety and —P(S)(SH)— is connected to the 5'-O— of an oligonucleotide chain. In some embodiments, a linker, e.g., L$^{LD}$ or L, is —C(O)—NH—(CH$_2$)$_6$—P(S)(SH)—, wherein —C(O)— is connected to a lipid moiety and —P(S)(SH)— is connected to the 3'-O— of an oligonucleotide chain. As appreciated by a person having ordinary skill in the art, at certain pH —P(O)(OH)—, —P(O)(SH)—, —P(S)(SH)— may exist as —P(O)(O$^-$)—, —P(O)(S$^-$)—, —P(S)(S$^-$)—, respectively. In some embodiments, a lipid moiety is R$^{LD}$.

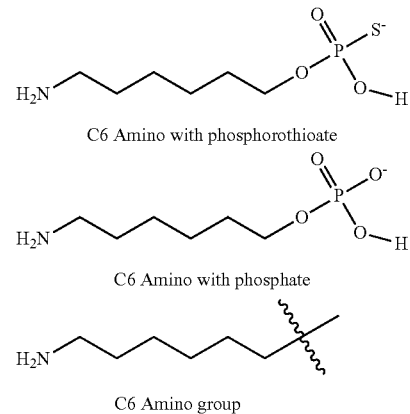

C6 Amino with phosphorothioate

C6 Amino with phosphate

C6 Amino group

Various chemistry and linkers can be used for conjugation in accordance with the present disclosure. For example, lipids, targeting components, etc. can be conjugated to oligonucleotides through linkers using chemistry as described below either on solid phase or insolution phase to prepare certain provided oligonucleotides, for example, those described in Table 4 (WV-2538, WV-2733, WV-2734, WV-2578 to WV-2588, WV-2807, WV-2808, WV-3022 to WV-3027, WV-3029 to WV-3038, WV-3084 to WV-3089, WV-3357 to WV-3366, WV-3517, WV-3520, WV-3543 to WV-3560, WV-3753, WV-3754, WV-3820, WV-3821, WV-3855, WV-3856, WV-3976, WV-3977, WV-3979, WV-3980, WV-4106, WV-4107, etc.):

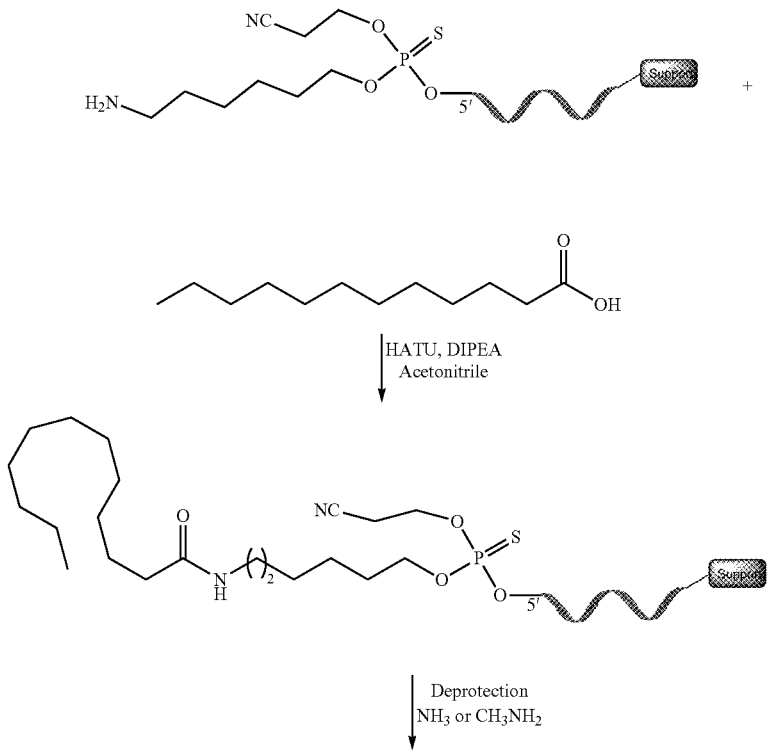

-continued

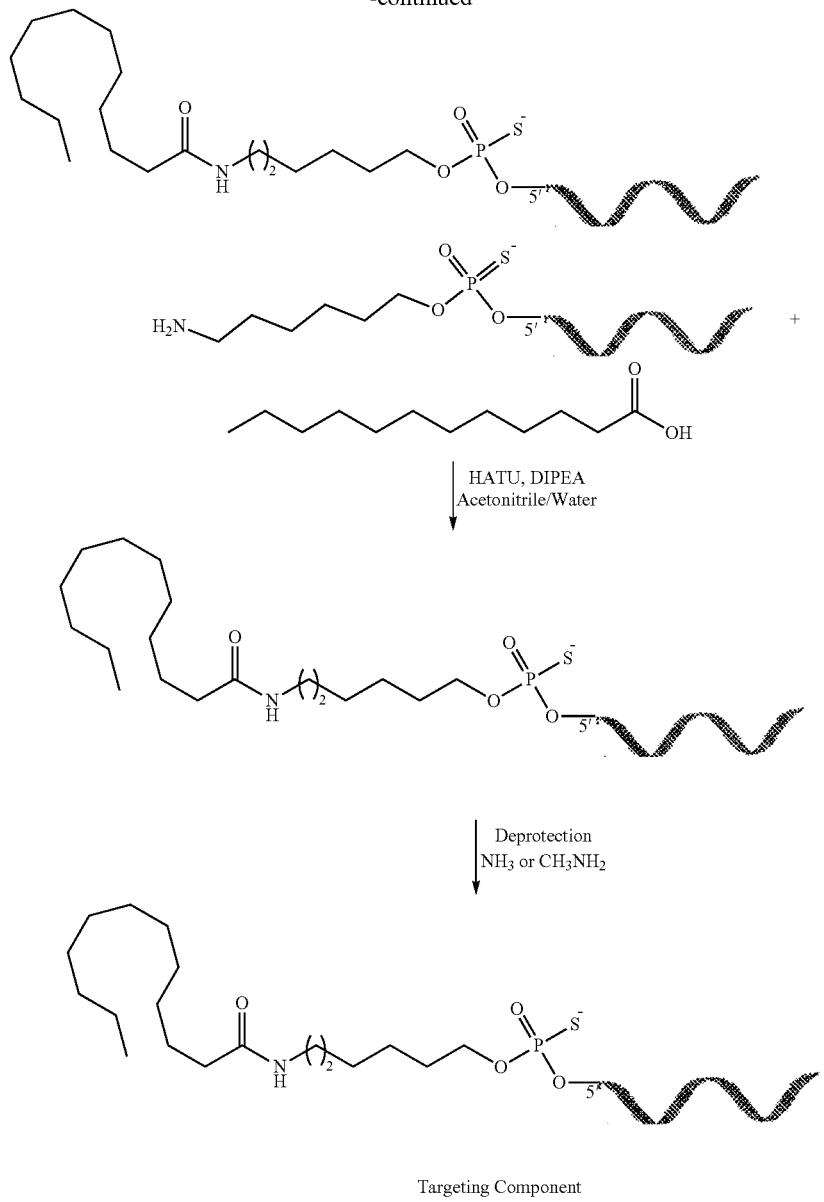

Targeting Component

In some embodiments, a provided composition further comprises a targeting component. A targeting component can be either conjugated or not conjugated to a lipid or a biologically active agent. In some embodiments, a targeting component is conjugated to a biologically active agent. In some embodiments, a biologically active agent is conjugated to both a lipid and a targeting component. As described in here, in some embodiments, a biologically active agent is a provided oligonucleotide. Thus, in some embodiments, a provided oligonucleotide composition further comprises, besides a lipid and oligonucleotides, a target elements. Various targeting components can be used in accordance with the present disclosure, e.g., lipids, antibodies, peptides, carbohydrates, etc. In some embodiments, provided oligonucleotides have the structure of $A^c$-$[-L^{LD}$-$(R^{LD})_a]_b$. In some embodiments, provided oligonucleotides have the structure of $[(A^c)_a$-$L^{LU}]_b$-$R^{LU}$, In some embodiments, $L^{LD}$, $R^{LD}$, combinations of $L^{LD}$ and $R^{LD}$, or -$[-L^{LD}$-$(R^{LD})_a]_b$ comprises one or more targeting components.

In some embodiments, a targeting component interacts with a protein on the surface of targeted cells. In some embodiments, such interaction facilitates internalization into targeted cells. In some embodiments, a targeting component comprises a sugar moiety. In some embodiments, a targeting component comprises a polypeptide moiety. In some embodiments, a targeting component comprises an antibody. In some embodiments, a targeting component is an antibody. In some embodiments, a targeting component comprises an inhibitor. In some embodiments, a targeting component is a moiety from a small molecule inhibitor. In some embodiments, an inhibitor is an inhibitor of a protein on the surface of targeted cells. In some embodiments, an inhibitor is a carbonic anhydrase inhibitor. In some embodiments, an inhibitor is a carbonic anhydrase inhibitor expressed on the surface of target cells. In some embodiments, a carbonic anhydrase is I, II, III, IV, V, VI, VII, VIII, IX, X, XI, XII, XIII, XIV, XV or XVI. In some embodiments, a carbonic anhydrase is membrane bound. In some embodiments, a carbonic anhydrase is IV, IX, XII or XIV. In some embodiments, an inhibitor is for IV, IX, XII and/or XIV. In some embodiments, an inhibitor is a carbonic anhydrase III inhibitor. In some embodiments, an inhibitor is a carbonic anhydrase IV inhibitor. In some embodiments, an inhibitor is a carbonic anhydrase IX inhibitor. In some embodiments, an inhibitor is a carbonic anhydrase XII inhibitor. In some embodiments, an inhibitor is a carbonic anhydrase XIV inhibitor. In some embodiments, an inhibitor comprises or is a sulfonamide (e.g., those described in Supuran, C T. *Nature Rev Drug Discover* 2008, 7, 168-181, which sulfonamides are incorporated herein by reference). In some embodiments, an inhibitor is a sulfonamide. In some embodiments, targeted cells are muscle cells.

In some embodiments, a targeting component is $R^{LD}$ as defined and described in the present disclosure. In some embodiments, the present disclosure provides oligonucleotides comprising $R^{LD}$. In some embodiments, the present disclosure provides oligonucleotide compositions comprising oligonucleotides comprising $R^{LD}$. In some embodiments, the present disclosure provides oligonucleotide compositions comprising a first plurality of oligonucleotides comprising $R^{LD}$. In some embodiments, the present disclosure provides chirally controlled oligonucleotide compositions of oligonucleotides comprising $R^{LD}$. In some embodiments, $R^{LD}$ composes or is

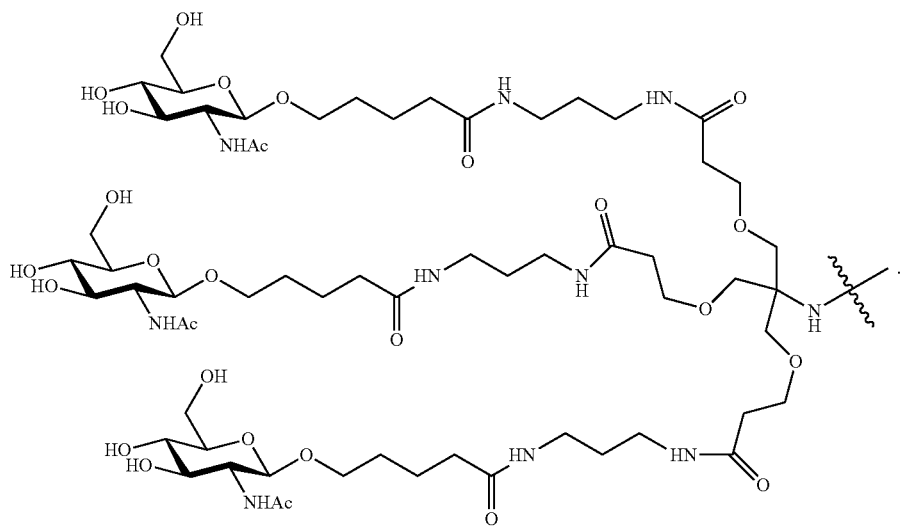

In some embodiments, $R^{LD}$ comprises or is

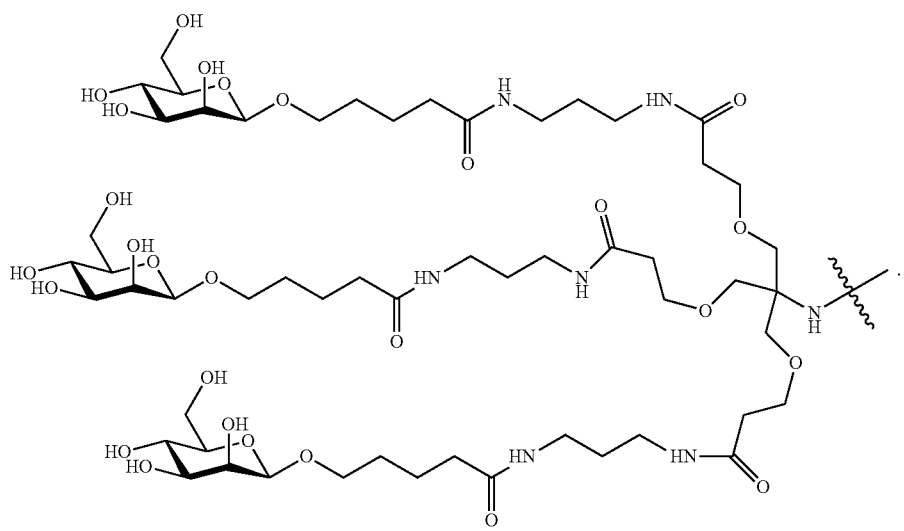

In some embodiments, $R^{LD}$ comprises or is
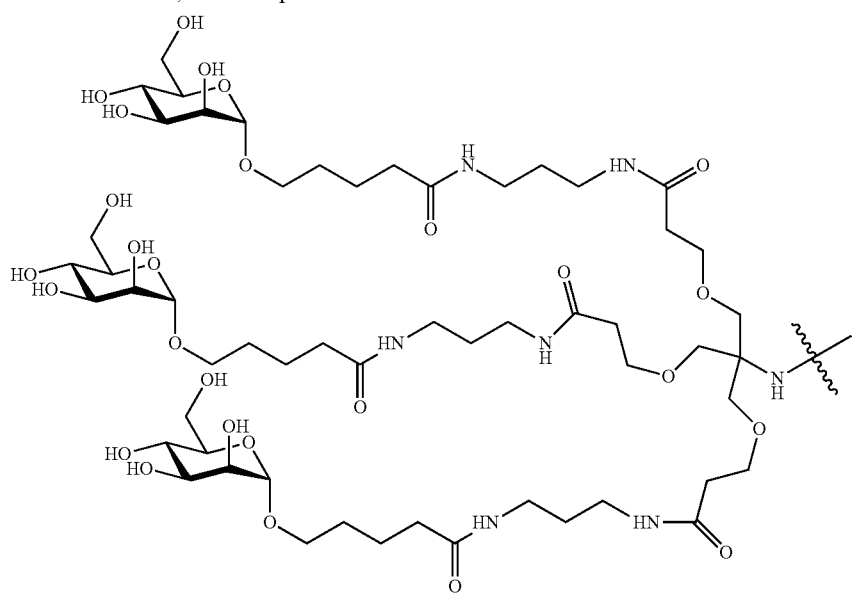
In some embodiments, $R^{LD}$ comprises or is
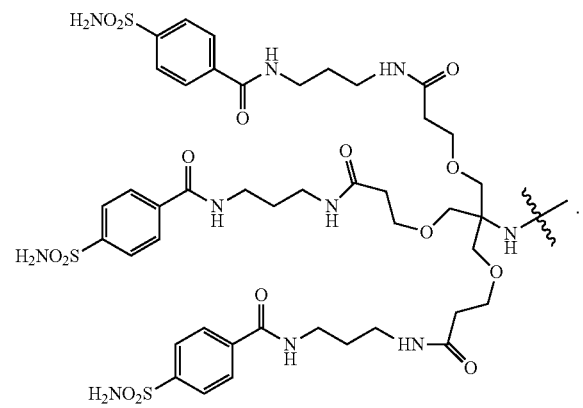 [SMILES: *NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
In some embodiments, $R^{LD}$ comprises or is
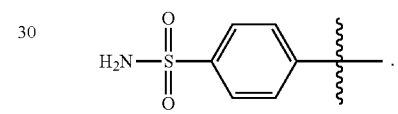
In some embodiments, $R^{LD}$ comprises or is
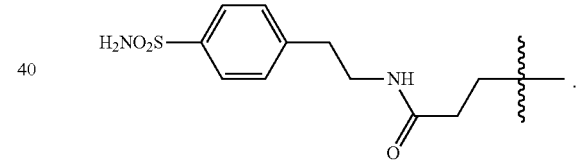
In some embodiments, R comprises or is
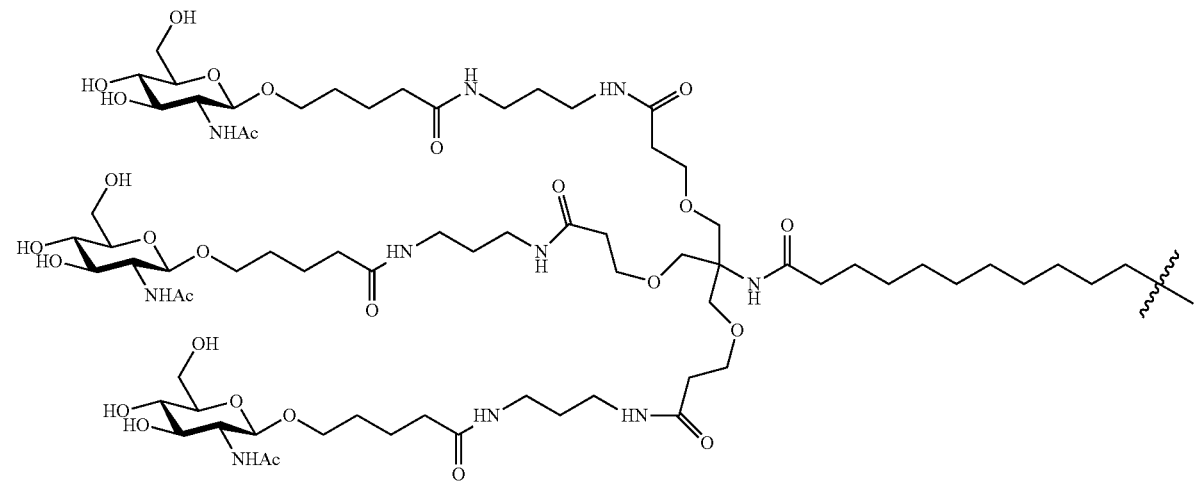

In some embodiments, $R^{LD}$ comprises or is
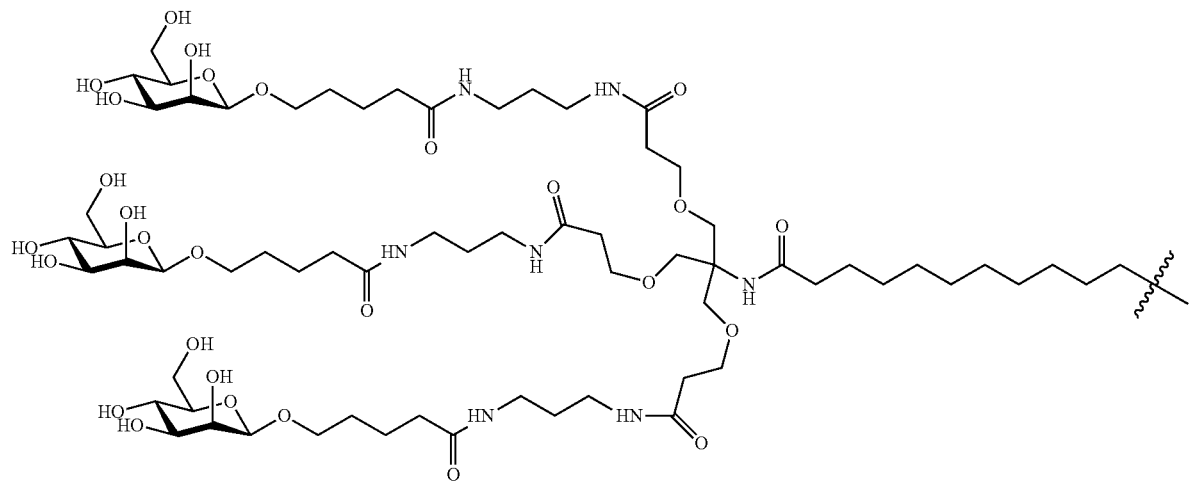
In some embodiments, $R^{LD}$ comprises or is
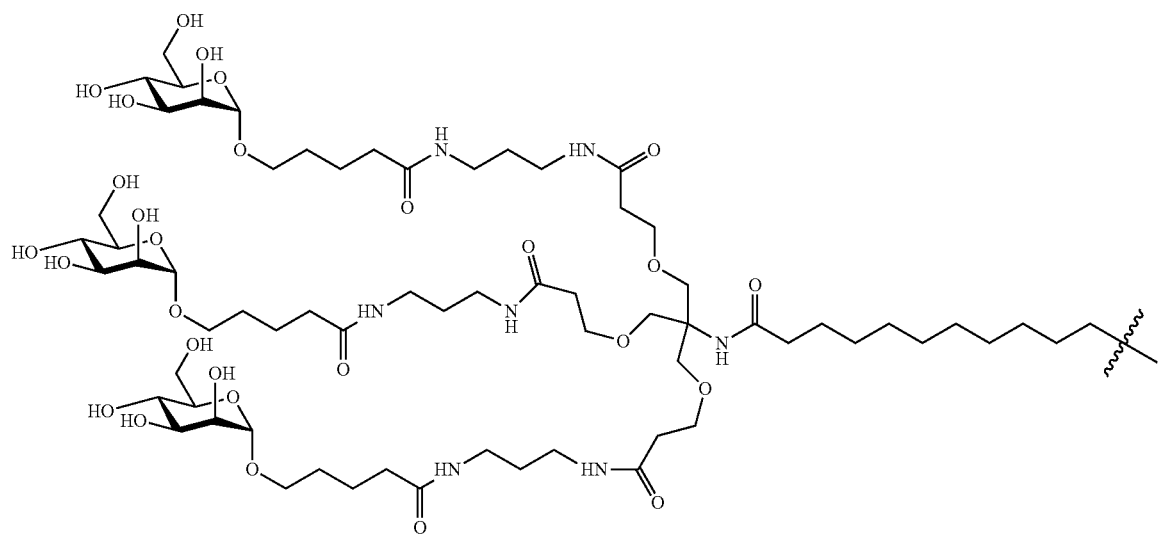

In some embodiments, $R^{LD}$ comprises or is
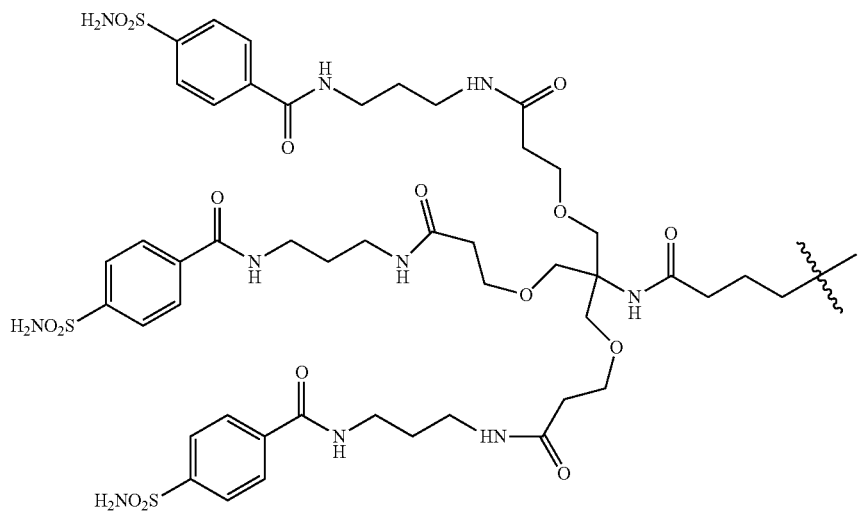 [SMILES: *CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
In some embodiments, $R^{LD}$ comprises or is
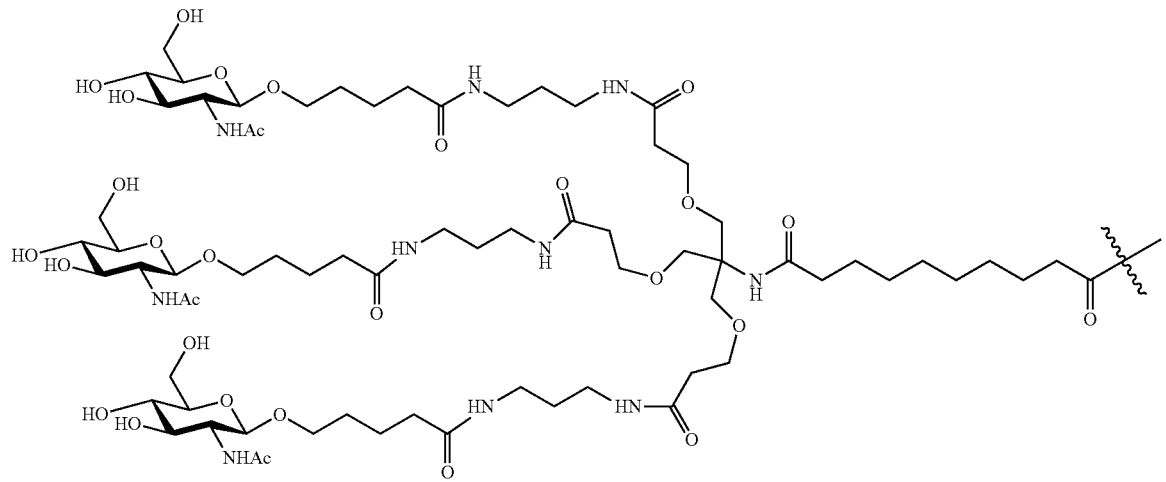
In some embodiments, $R^{LD}$ comprises or is
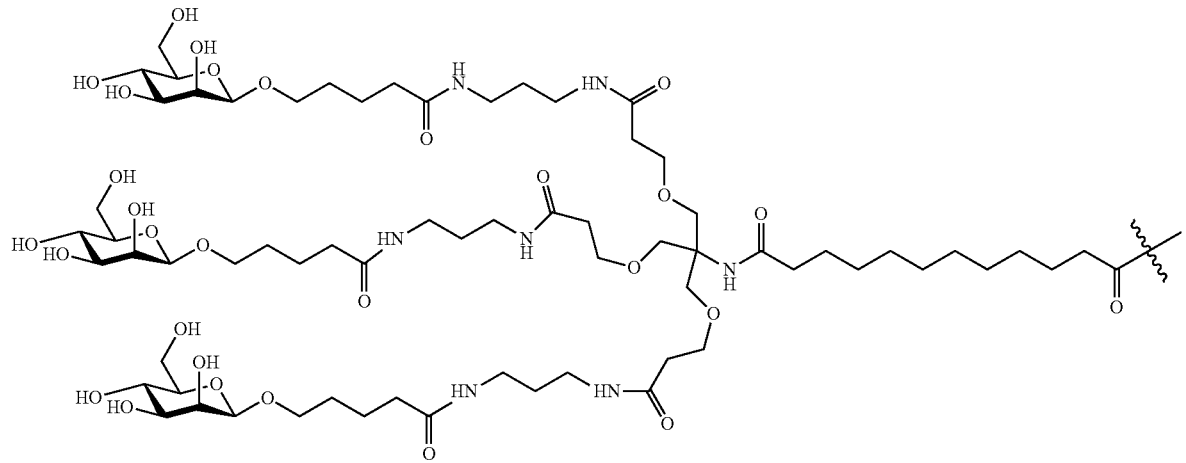

In some embodiments, $R^{LD}$ comprises or is
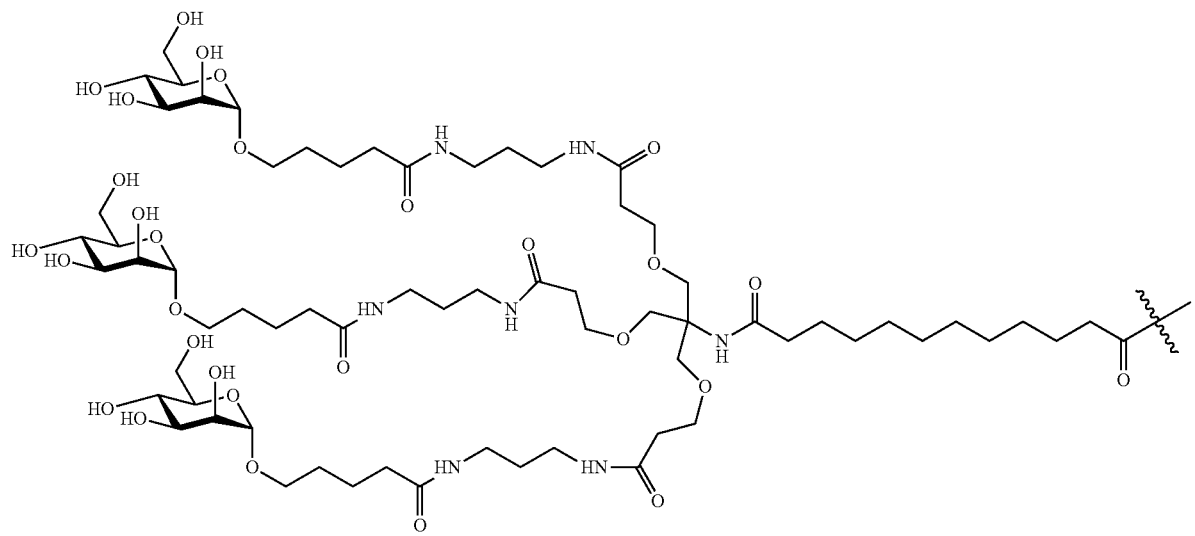
In some embodiments, $R^{LD}$ comprises or is
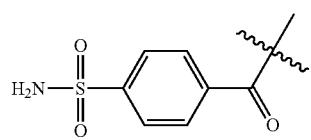
In some embodiments, $R^{LD}$ comprises or is
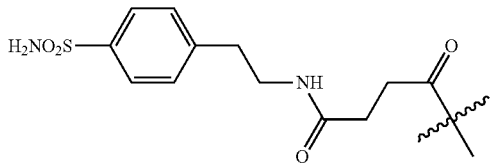
In some embodiments, R comprises or is
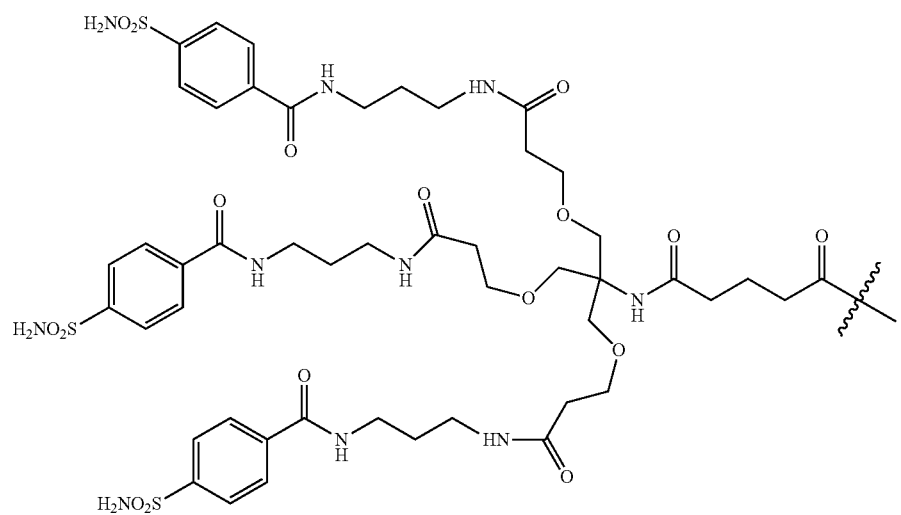 [SMILES: *C(=O)CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]

In some embodiments, R$^{LD}$ comprises
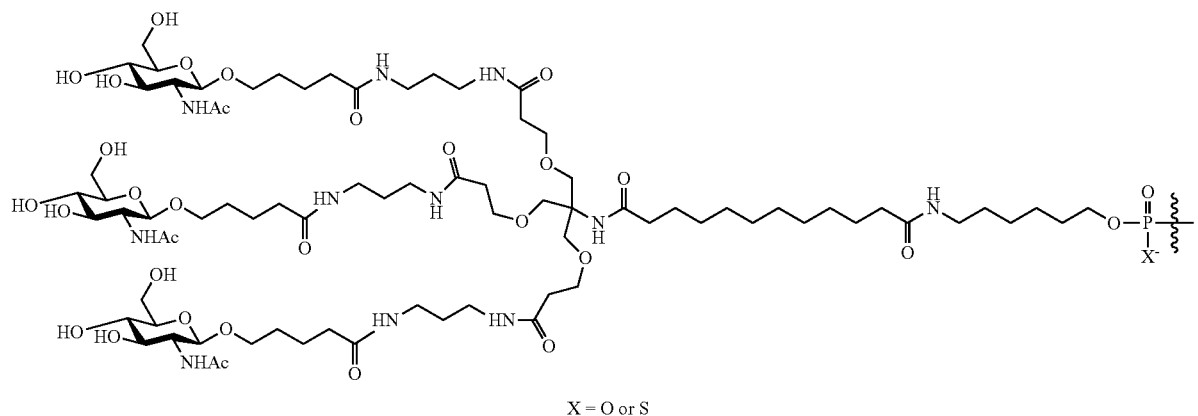
X = O or S
20
In some embodiments, R$^{LD}$ comprises or is
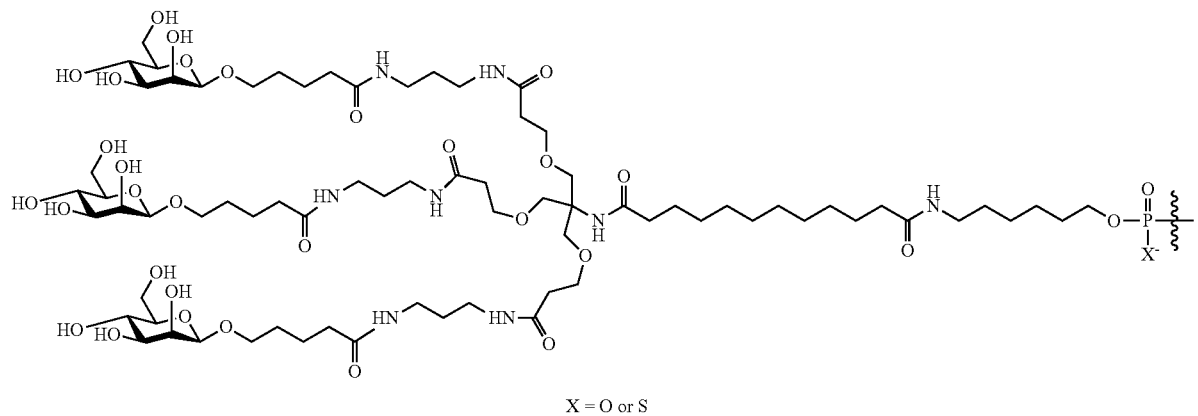
X = O or S
In some embodiments, R$^{LD}$ comprises or is
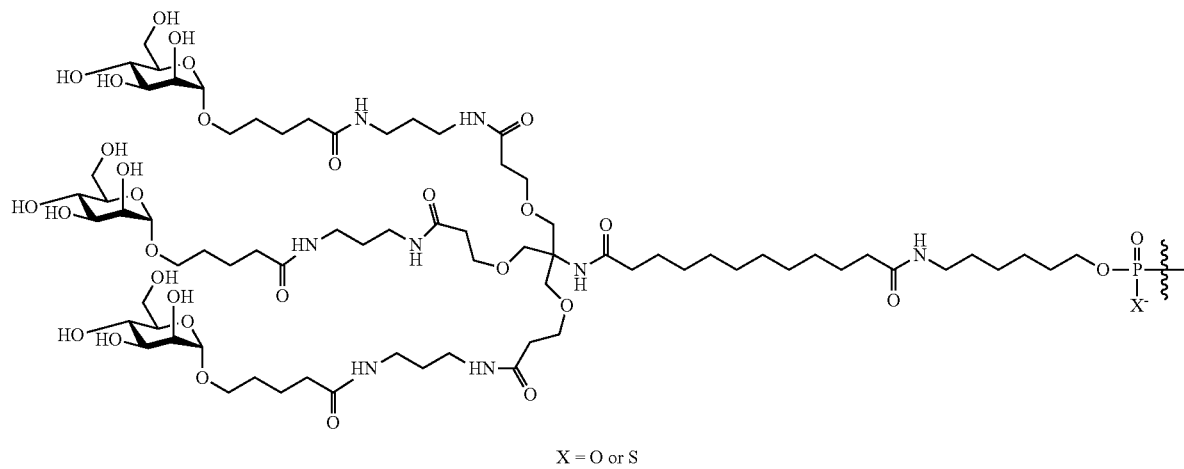
X = O or S In some embodiments, $R^{LD}$ comprises or is

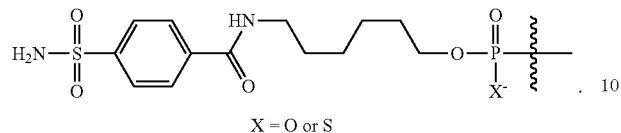

X = O or S

In some embodiments, $R^{LD}$ comprises or is

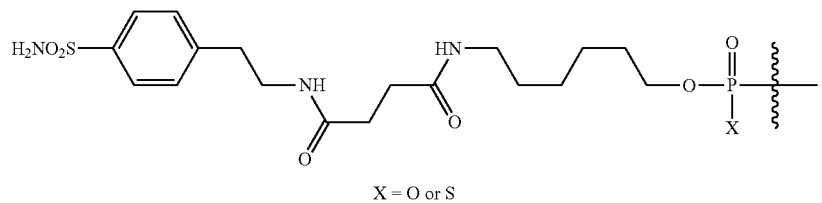

X = O or S

In some embodiments, $R^{LD}$ comprises or is

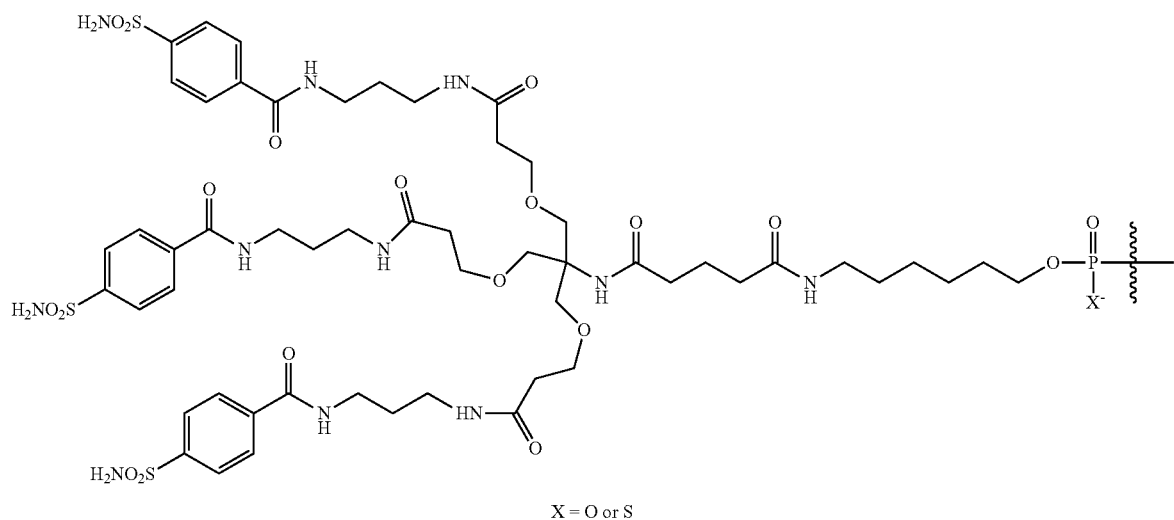

X = O or S

In some embodiments, X is O. In some embodiments, X is S.

In some embodiments, the present disclosure provides technologies (e.g., reagents, methods, etc.) for conjugating various moieties to oligonucleotide chains. In some embodiments, the present disclosure provides technologies for conjugating targeting component to oligonucleotide chains. In some embodiments, the present disclosure provides acids comprising targeting components for conjugation, e.g., $R^{LD}$—COOH. In some embodiments, the present disclosure provides linkers for conjugation, e.g., $L^{LD}$. A person having ordinary skill in the art understands that many known and widely practiced technologies can be utilized for conjugation with oligonucleotide chains in accordance with the present disclosure. In some embodiments, a provided acid is 321
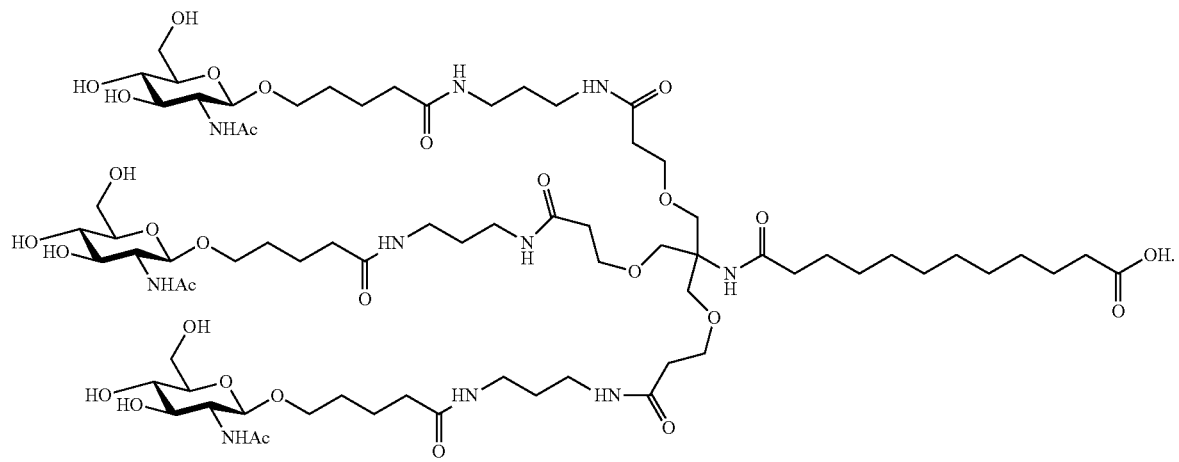
In some embodiments, a provided acid is
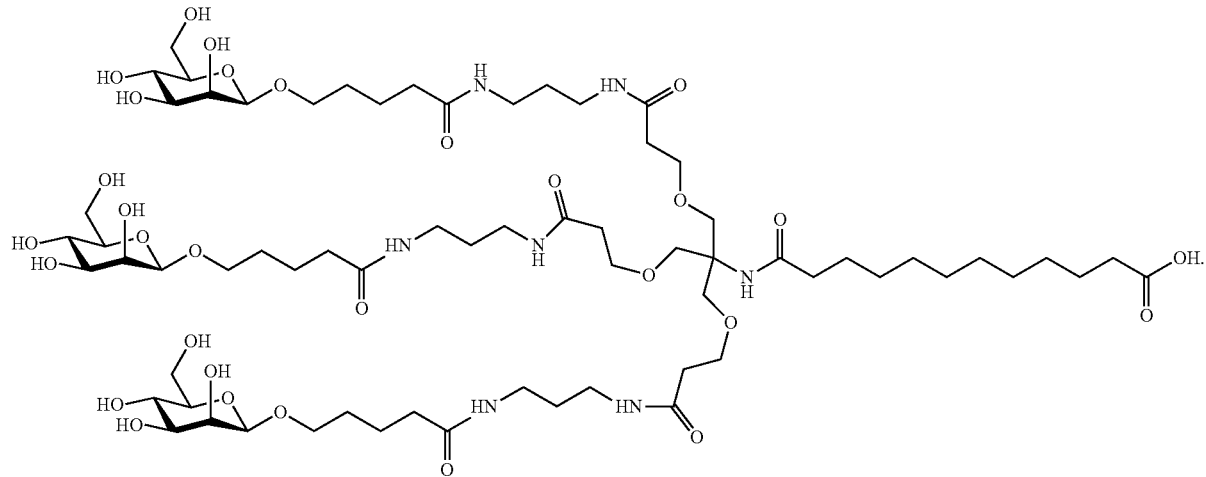
In some embodiments, a provided acid is
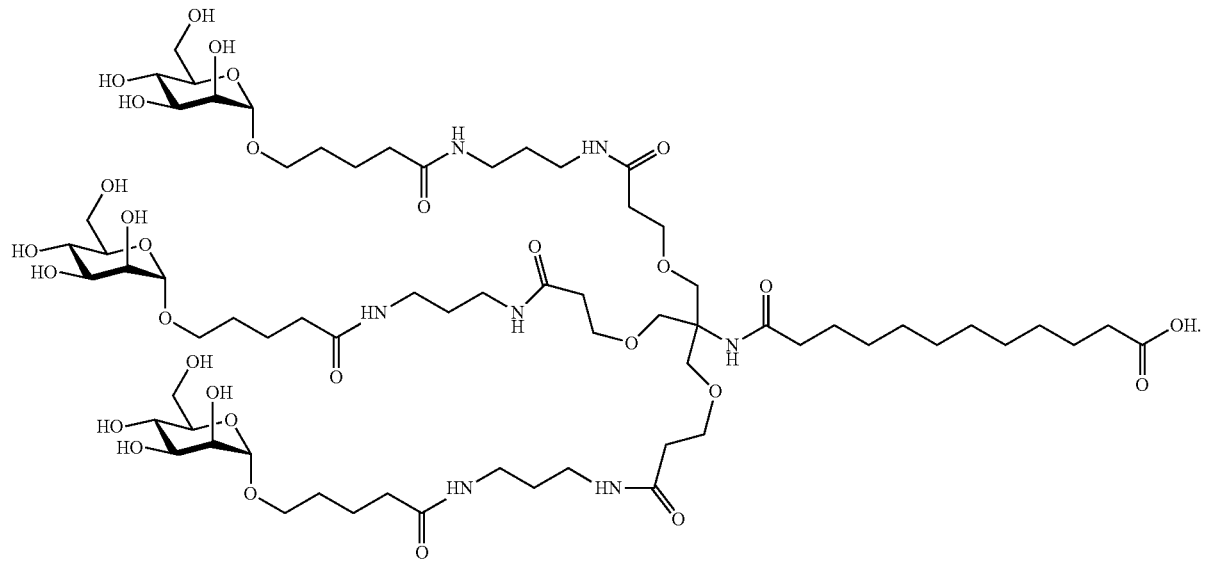

In some embodiments, a provided acid is

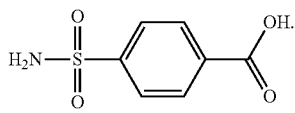

In some embodiments, a provided acid is In some embodiments, a provided acid is

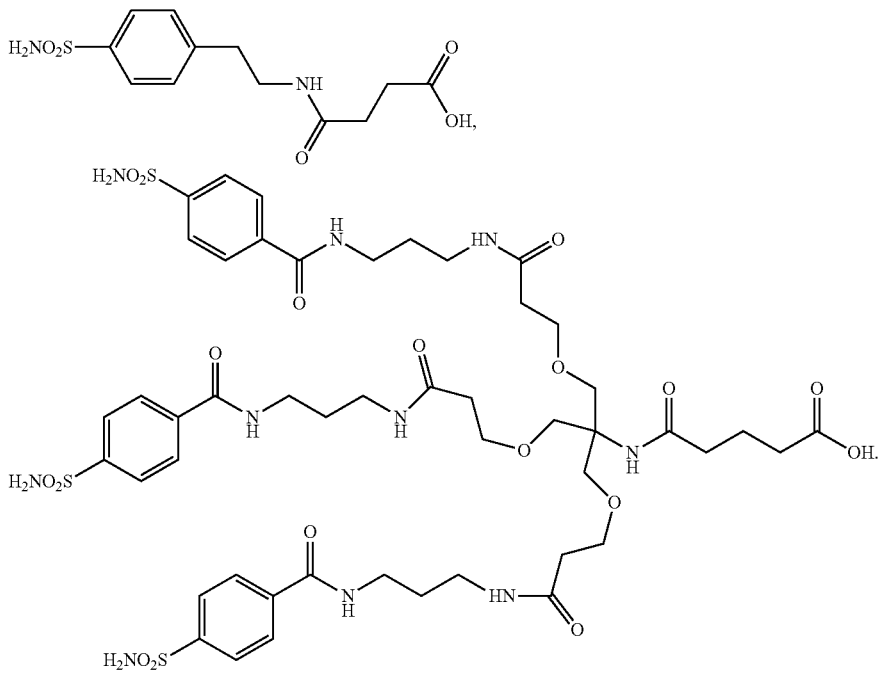

In some embodiments, the present disclosure provides methods and reagents for preparing such acids.

In some embodiments, provided compounds, e.g., reagents, products (e.g., oligonucleotides, amidites, etc.) etc. are at least 10%, 20%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 97% or 99% pure. In some embodiments, the purity is at least 50%. In some embodiments, the purity is at least 75%. In some embodiments, the purity is at least 80%. In some embodiments, the purity is at least 85%. In some embodiments, the purity is at least 90%. In some embodiments, the purity is at least 95%. In some embodiments, the purity is at least 96%. In some embodiments, the purity is at least 97%. In some embodiments, the purity is at least 98%. In some embodiments, the purity is at least 99%.

Target components can be incorporated into provided technologies through many types of methods in accordance with the present disclosure. In some embodiments, target components are physically mixed with provided oligonucleotides to form provided compositions. In some embodiments, target components are chemically conjugated with oligonucleotides. In some embodiments, target components are chemically conjugated with oligonucleotides through a linker, for example, $L^{LD}$.

In some embodiments, provided compositions comprise two or more target components. In some embodiments, provided oligonucleotides comprise two or more conjugated target components. In some embodiments, the two or more conjugated target components are the same. In some embodiments, the two or more conjugated target components are different. In some embodiments, provided oligonucleotides comprise no more than one target component. In some embodiments, oligonucleotides of a provided composition comprise different types of conjugated target components. In some embodiments, oligonucleotides of a provided composition comprise the same type of target components.

Target components can be conjugated to oligonucleotides optionally through linkers. Various types of linkers in the art can be utilized in accordance of the present disclosure. In some embodiments, a linker comprise a phosphate group, which can, for example, be used for conjugating target components through chemistry similar to those employed in oligonucleotide synthesis. In some embodiments, a linker comprises an amide, ester, or ether group. In some embodiments, a linker has the structure of -L-. Target components can be conjugated through either the same or different linkers compared to lipids.

Target components, optionally through linkers, can be conjugated to oligonucleotides at various suitable locations. In some embodiments, target components are conjugated through the 5'-OH group. In some embodiments, target components are conjugated through the 3'-OH group. In some embodiments, target components are conjugated through one or more sugar moieties. In some embodiments, target components are conjugated through one or more bases. In some embodiments, target components are incorporated through one or more internucleotidic linkages. In some embodiments, an oligonucleotide may contain multiple conjugated target components which are independently conjugated through its 5'-OH, 3'-OH, sugar moieties, base moieties and/or internucleotidic linkages. Target components and lipids can be conjugated either at the same, neighboring and/or separated locations. In some embodiments, a target component is conjugated at one end of an oligonucleotide, and a lipid is conjugated at the other end.

Nucleobases

In some embodiments, a nucleobase present in a provided CpG oligonucleotide is a natural nucleobase or a modified nucleobase derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Example modified nucleobases are disclosed in Chiu and Rana, RNA, 2003, 9, 1034-1048, Limbach et al. Nucleic Acids Research, 1994, 22, 2183-2196 and Revankar and Rao, Comprehensive Natural Products Chemistry, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a modified base is optionally substituted adenine, cytosine, guanine, thymine, or uracil. In some embodiments, a modified nucleobase is independently adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

(2) one or more atoms of a nucleobase are independently replaced with a different atom selected from carbon, nitrogen or sulfur;

(3) one or more double bonds in a nucleobase are independently hydrogenated; or (4) one or more aryl or heteroaryl rings are independently inserted into a nucleobase.

Structures represented by the following general formulae are also contemplated as modified nucleobases:

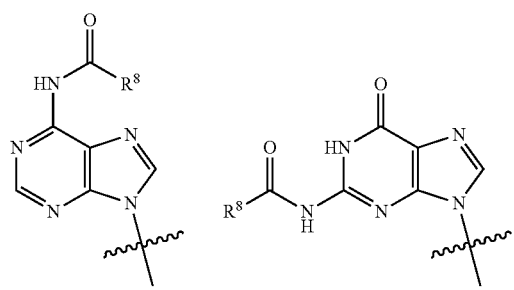

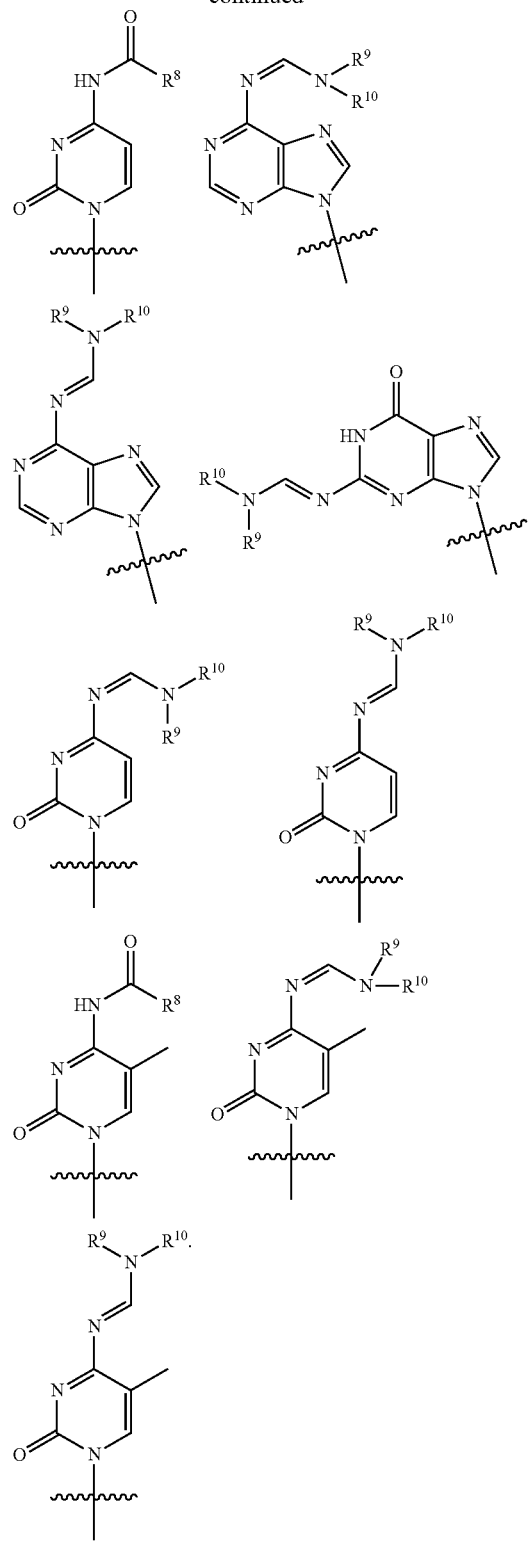

wherein $R^8$ is an optionally substituted, linear or branched group selected from aliphatic, aryl, aralkyl, aryloxylalkyl, carbocyclyl, heterocyclyl or heteroaryl group having 1 to 15 carbon atoms, including, by way of example only, a methyl, isopropyl, phenyl, benzyl, or phenoxymethyl group; and each of $R^9$ and $R^{10}$ is independently an optionally substituted group selected from linear or branched aliphatic, carbocyclyl, aryl, heterocyclyl and heteroaryl.

Modified nucleobases also include expanded-size nucleobases in which one or more aryl rings, such as phenyl rings, have been added. Nucleic base replacements described in the Glen Research catalog (www.glenresearch.com); Krueger A T et al, Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the nucleic acids described herein. Some examples of these expanded-size nucleobases are shown below:

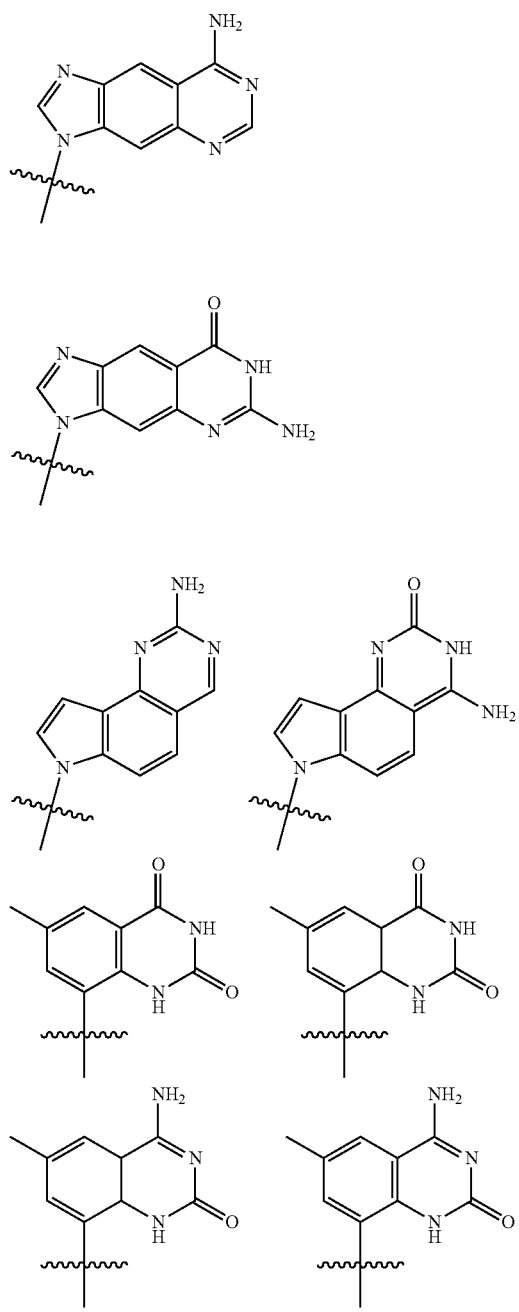
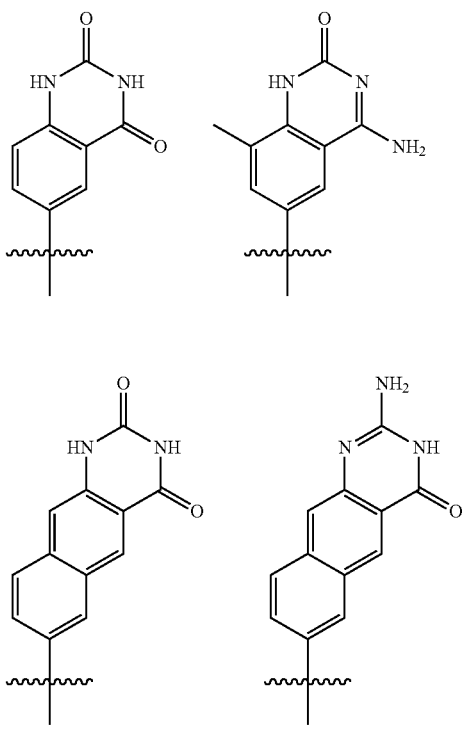

Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, E T, Org. Lett., 2002, 4, 4377-4380. Shown below is an example of a porphyrin-derived ring which can be used as a base replacement:

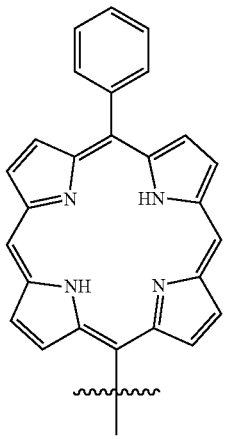

In some embodiments, modified nucleobases are of any one of the following structures, optionally substituted:

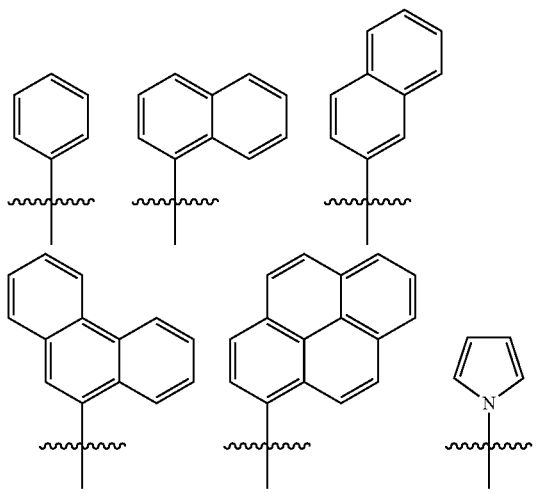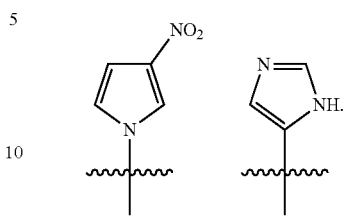
In some embodiments, a modified nucleobase is fluorescent. Example such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:
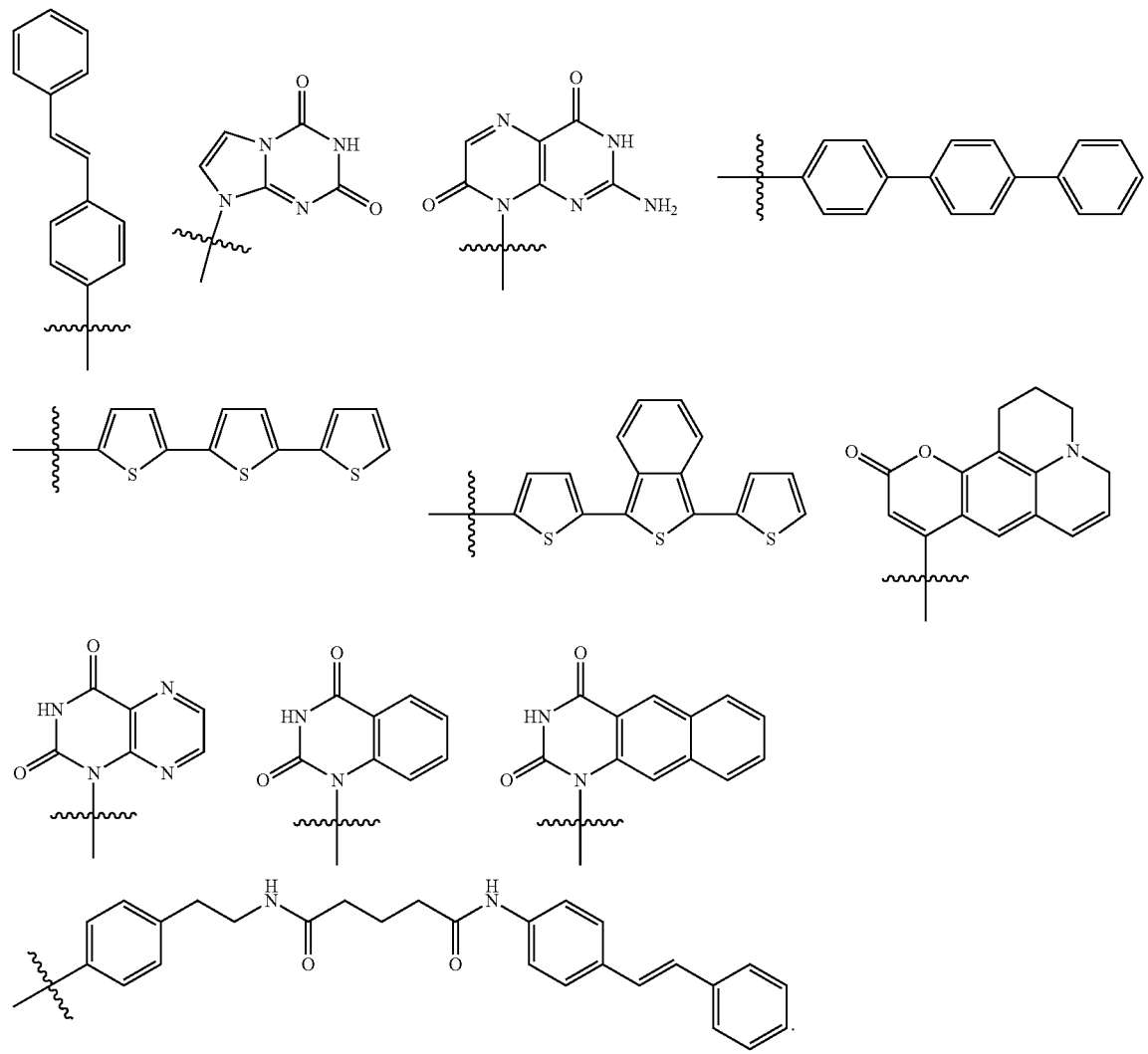

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, other nucleosides can also be used in the process disclosed herein and include nucleosides that incorporate modified nucleobases, or nucleobases covalently bound to modified sugars. Some examples of nucleosides or nucleotides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in US Patent Application Publication No. 20070287831.

In some embodiments, a nucleobase or modified nucleobase comprises one or more biomolecule binding moieties such as e.g., antibodies, antibody fragments, biotin, avidin, streptavidin, receptor ligands, or chelating moieties. In other embodiments, a nucleobase or modified nucleobase is 5-bromouracil, 5-iodouracil, or 2,6-diaminopurine. In some embodiments, a nucleobase or modified nucleobase is modified by substitution with a fluorescent or biomolecule binding moiety. In some embodiments, the substituent on a nucleobase or modified nucleobase is a fluorescent moiety. In some embodiments, the substituent on a nucleobase or modified nucleobase is biotin or avidin.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088.

In some embodiments, a base is optionally substituted A, T, C, G or U, wherein one or more —$NH_2$ are independently and optionally replaced with —C(-L-$R^1$)$_3$, one or more —NH— are independently and optionally replaced with -Q-L-$R^1$)—, one or more =N— are independently and optionally replaced with —C(-L-$R^1$)—, one or more =CH— are independently and optionally replaced with =N—, and one or more =O are independently and optionally replaced with =S, =N(-L-$R^1$), or =C(-L-$R^1$)$_2$, wherein two or more -L-$R^1$ are optionally taken together with their intervening atoms to form a 3-30 membered bicyclic or polycyclic ring having 0-10 heteroatom ring atoms. In some embodiments, a modified base is optionally substituted A, T, C, G or U, wherein one or more —$NH_2$ are independently and optionally replaced with —C(-L-$R^1$)$_3$, one or more —NH— are independently and optionally replaced with —C(-L-$R^1$)$_2$—, one or more =N— are independently and optionally replaced with —C(-L-$R^1$)—, one or more =CH— are independently and optionally replaced with =N, and one or more =O are independently and optionally replaced with =S, =N(-L-$R^1$), or =C(-L-$R^1$)$_2$, wherein two or more -L-$R^1$ are optionally taken together with their intervening atoms to form a 3-30 membered bicyclic or polycyclic ring having 0-10 heteroatom ring atoms, wherein the modified base is different than the natural A, T, C, G and U. In some embodiments, a base is optionally substituted A, T, C, G or U. In some embodiments, a modified base is substituted A, T, C, G or U, wherein the modified base is different than the natural A, T, C, G and U.

In some embodiments, a modified nucleotide or nucleotide analog is any modified nucleotide or nucleotide analog described in any of: Albaek et al. 2006 J. Org. Chem. 71: 7731-7740; Braasch et al., Chem. Biol., 2001, 8, 1-7; Chattopadhyaya et al. 2009 J. Org. Chem. 74: 18-134; Elayadi et al, Curr. Opinion Invens. Drugs, 2001, 2, 5561; Frieden et al. 2003 Nucl. Acids Res. 21: 6365-6372; Freier et al. 1997 Nucl. Acids Res. 25: 4429-4443; Gryaznov et al. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Leumann et al. 2002 Bioorg. Med. Chem. 10: 841-854; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Oram et al, Curr. Opinion Mol. Ther., 2001, 3, 239-243; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Singh et al. 1998 Chem. Commun. 4: 455-456; Sorensen 2003 Chem. Comm. 2130-2131; Srivastava et al. 2007 J. Am. Chem. Soc, 129: 8362-8379; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; Wahlestedt et al. 2000 Proc. Natl. Acad. Sci. U.S.A 97: 5633-5638; U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 6,268,490; 6,525,191; 6,670,461; 6,770,748; 6,794,499; 7,034,133; 7,053,207; 7,399,845; and 7,427,672; U.S. Patent Publication Nos. US2004/0171570; US2005/0130923; US2007/0287831; and US2008/0039618; U.S. patent application Ser. Nos. 12/129,154; 60/989,574; 61/026,995; 61/026,998; 61/056,564; 61/086,231; 61/097,787; and 61/099,844; PCT International Applications Nos. PCT/US2008/064591; PCT/US2008/066154; and PCT/US2008/068922. WO 2004/106356; WO 1994/14226; WO 2005/021570; WO 2007/134181; WO 2007/0900071; WO 2008/154401; WO2008/101157; WO2008/150729; WO2009/006478; or WO 2016/079181.

Example nucleobases are also described in US 20110294124, US 20120316224, US 20140194610, US 20150211006, US 20150197540, WO 2015107425, PCT/US2016/043542, and PCT/US2016/043598, each of which is incorporated herein by reference Sugars In some embodiments, provided CpG oligonucleotides comprise one or more modified sugar moieties.

The most common naturally occurring nucleotides are comprised of ribose sugars linked to the nucleobases adenosine (A), cytosine (C), guanine (G), and thymine (T) or uracil (U). Also contemplated are modified nucleotides wherein a phosphate group or linkage phosphorus in the nucleotides can be linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with methods of the present disclosure.

Other modified sugars can also be incorporated within a provided CpG oligonucleotide. In some embodiments, a modified sugar contains one or more substituents at the 2' position including one of the following: —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-C$_1$-C$_{10}$ alkylene)-O—(C$_1$-C$_{10}$ alkyl), wherein the alkyl, alkylene, alkenyl and alkynyl can be substituted or unsubstituted. Examples of substituents include, and are not limited to, —O(CH$_2$)$_n$OCH$_3$, and —O(CH$_2$)$_n$NH$_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

In some embodiments, a 2'-modification is 2'-OR$^1$. In some embodiments, a T-modification is 2'-R$^1$. In some embodiments, a 2'-modification is 2'-F.

In some embodiments, the 2'-OH of a ribose is replaced with a substituent including one of the following: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alky 1) (C$_1$-C$_{10}$ alkylene)-O—(C$_1$-C$_{10}$ alkyl), wherein the alkyl, alkylene, alkenyl and alkynyl can be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the T-OH is replaced with —OCH$_2$CH$_2$OMe.

Modified sugars also include locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L- as defined herein. In some embodiments, -L- is —O—CH$_2$—, wherein —CH$_2$— is optionally substituted. In some embodiments, -L- is —O—CH$_2$—. In some embodiments, -L- is —O—CH(Et)-. In some embodiments, -L- is between C2 and C4 of a sugar moiety. In some embodiments, a locked nucleic acid has the structure indicated below. A locked nucleic acid of the structure below is indicated, wherein Ba represents a nucleobase or modified nucleobase as described herein, and wherein R$^{2s}$ is —OCH$_2$C4'-.

C2'OCH$_2$C4' = LNA
(Locked Nucleic Acid)

R$^{2s}$ = OCH$_2$C4'

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xeno-nucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar. Representative united States patents that teach the preparation of such modified sugar structures include, but are not limited to, U.S. Pat. Nos. 4,981,957; 5,118,800; 5,319,080; and 5,359,044. Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

Non-limiting examples of modified sugars include glycerol, which form glycerol nucleic acid (GNA) analogues. One example of a GNA analogue is shown below and is described in Zhang, R et al., J. Am. Chem. Soc., 2008, 130, 5846-5847; Zhang L, et al., J. Am. Chem. Soc., 2005, 127, 4174-4175 and Tsai C H et al., PNAS, 2007, 14598-14603 (X=O$^-$):

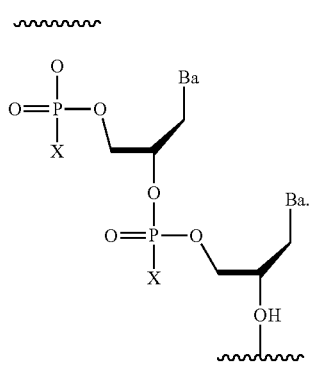

Another example of a GNA derived analogue, flexible nucleic acid (FNA) based on the mixed acetal aminal of formyl glycerol, is described in Joyce G F et al., PNAS, 1987, 84, 4398-4402 and Heuberger B D and Switzer C, J. Am. Chem. Soc., 2008, 130, 412-413, and is shown below:

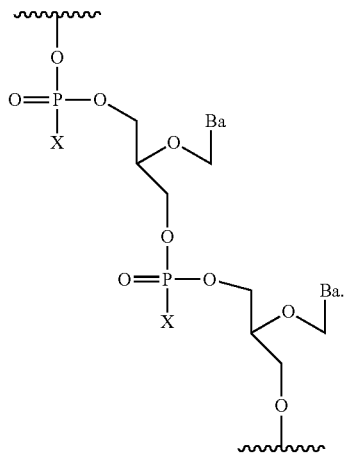

Additional non-limiting examples of modified sugars include hexopyranosyl (6' to 4'), pentopyranosyl (4' to 2'), pentopyranosyl (4' to 3'), or tetrofuranosyl (3' to 2') sugars. In some embodiments, a hexopyranosyl (6' to 4') sugar is of any one in the following formulae:

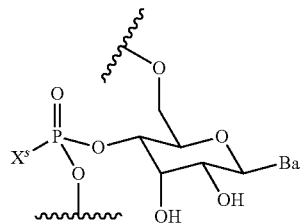

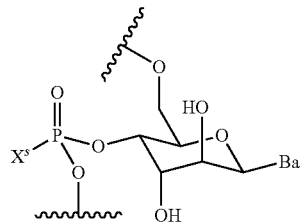

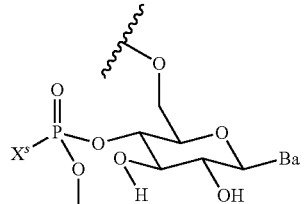

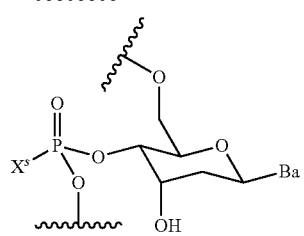

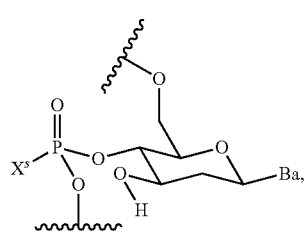

wherein $X^s$ corresponds to the P-modification group "—XLR$^1$" described herein and Ba is as defined herein.

In some embodiments, a pentopyranosyl (4' to 2') sugar is of any one in the following formulae:

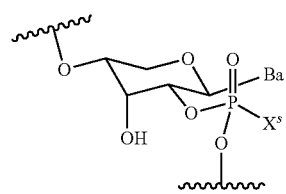

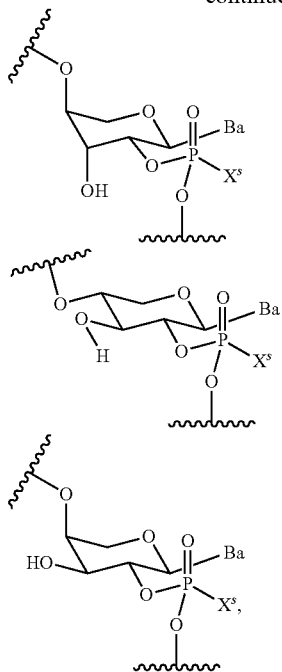

wherein $X^s$ corresponds to the P-modification group "—XLR$^1$" described herein and Ba is as defined herein.

In some embodiments, a pentopyranosyl (4' to 3') sugar is of any one in the following formulae:

wherein $X^s$ corresponds to the P-modification group "—XLR$^1$" described herein and Ba is as defined herein.

In some embodiments, a tetrofuranosyl (3' to 2') sugar is of either in the following formulae:

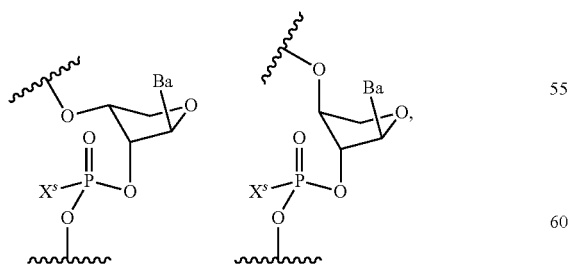

wherein $X^s$ corresponds to the P-modification group "—XLR$^1$" described herein and Ba is as defined herein.

In some embodiments, a modified sugar is of any one in the following formulae:

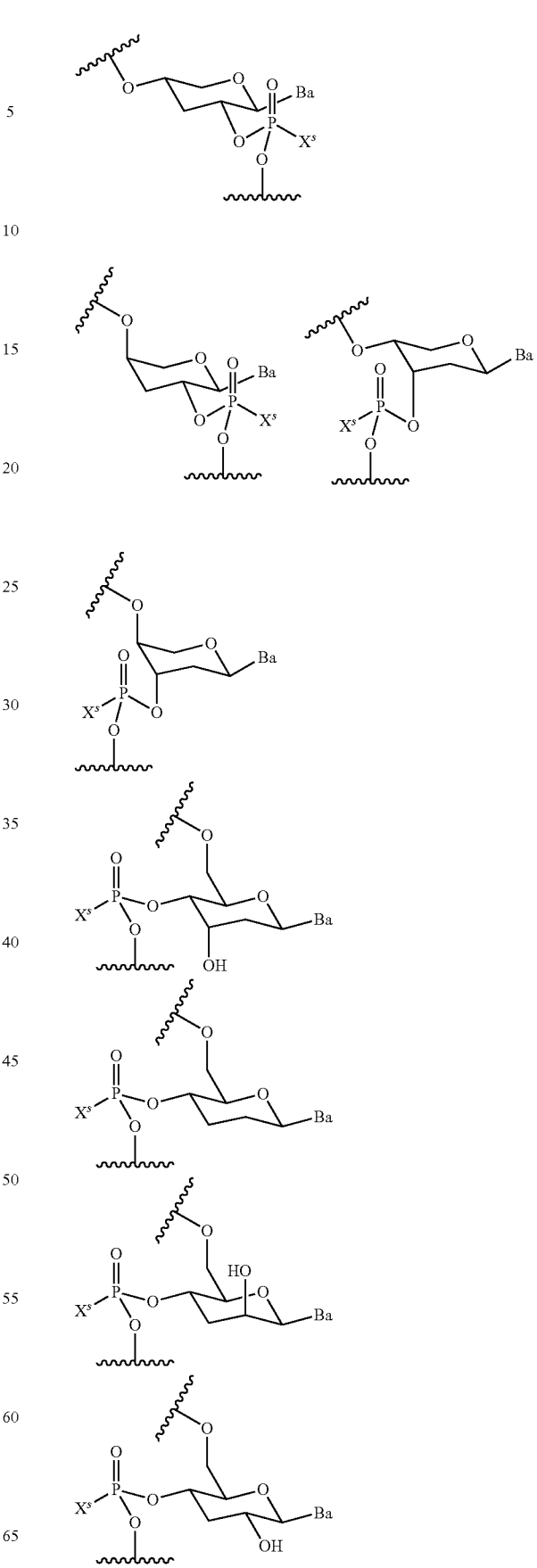

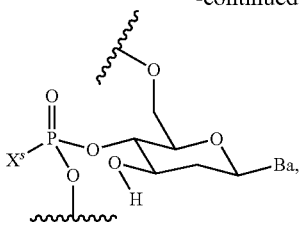

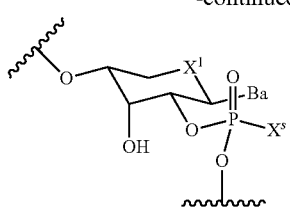

wherein $X^s$ corresponds to the P-modification group "—XLR$^1$" described herein and Ba is as defined herein.

In some embodiments, one or more hydroxyl group in a sugar moiety is optionally and independently replaced with halogen, R'—N(R')$_2$, —OR', or —SR', wherein each R' is independently as defined above and described herein.

In some embodiments, a sugar mimetic is as illustrated below, wherein $X^s$ corresponds to the P-modification group "—XLR$^1$" described herein, Ba is as defined herein, and $X^1$ is selected from —S—, —Se—, —CH$_2$—, —NMe-, -NEt- or —NiPr—.

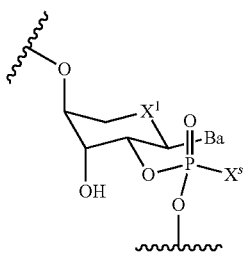

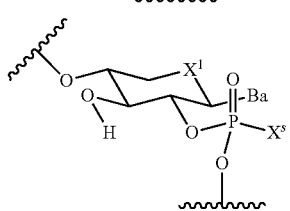

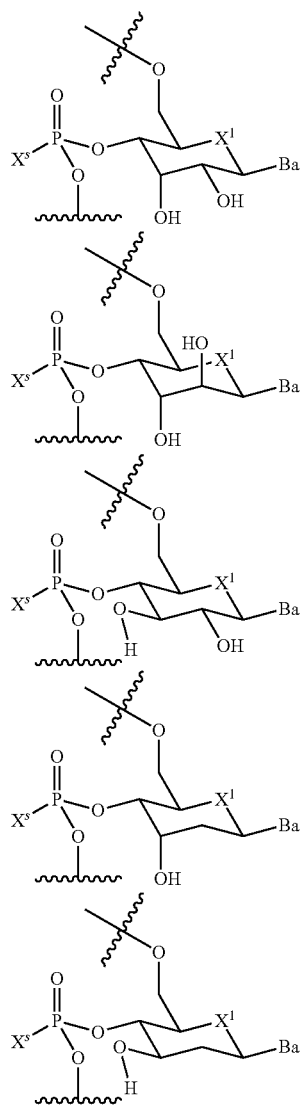

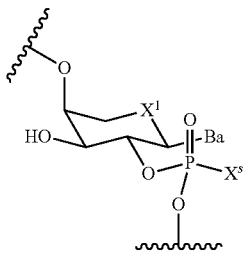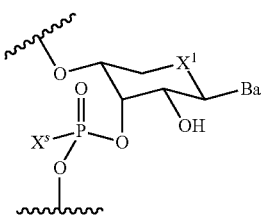

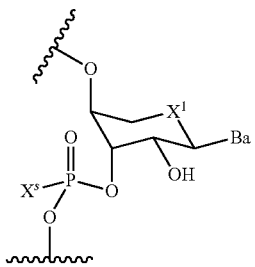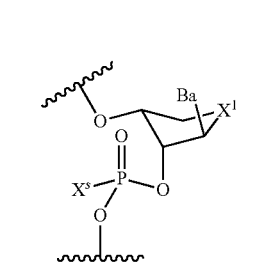

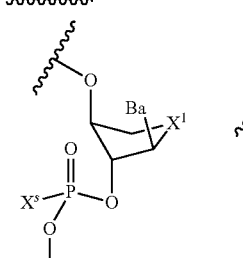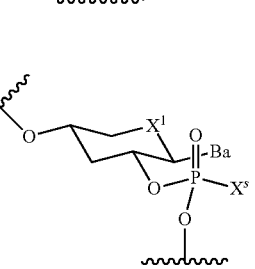

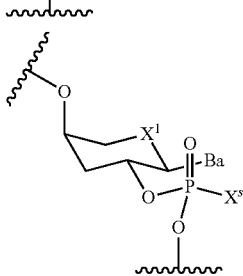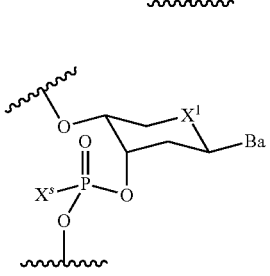

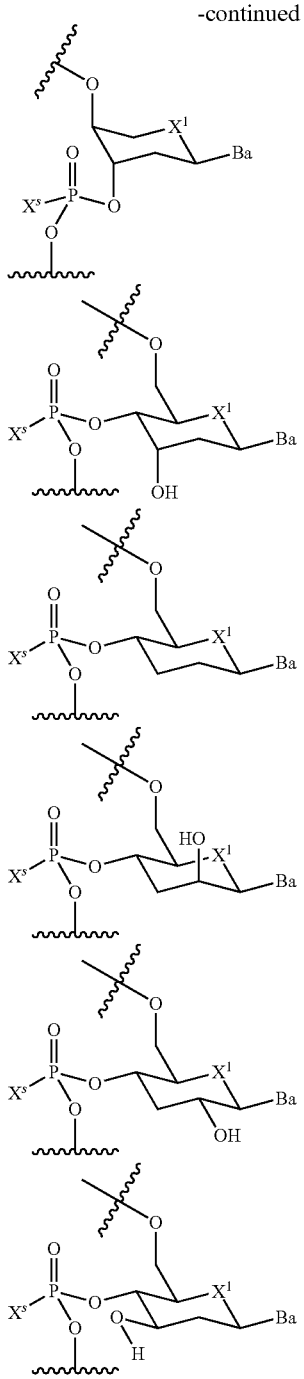

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a chirally controlled CpG oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33): 10847-56; A. Eschenmoser in Chemical Synthesis: Gnosis to Prognosis, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310). In some embodiments, a modified sugar is any of those described in PCT Publication No. WO2012/030683, incorporated herein by reference, and/or depicted herein. In some embodiments, a modified sugar is any modified sugar described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, PunitP; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm.

2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, an example modified internucleotidic linkage and/or sugar is selected from those of:

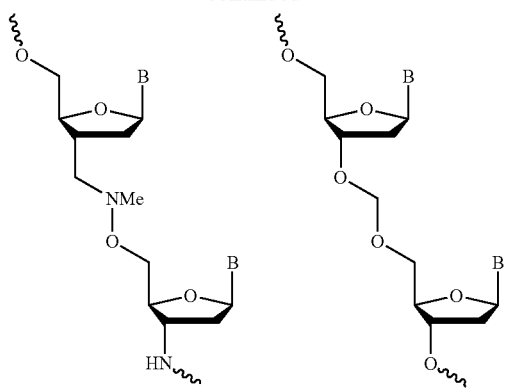

-continued

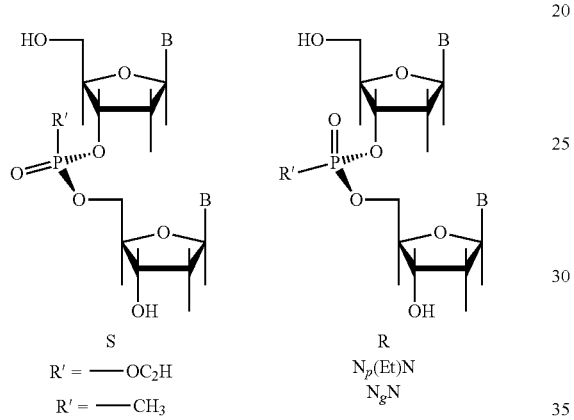

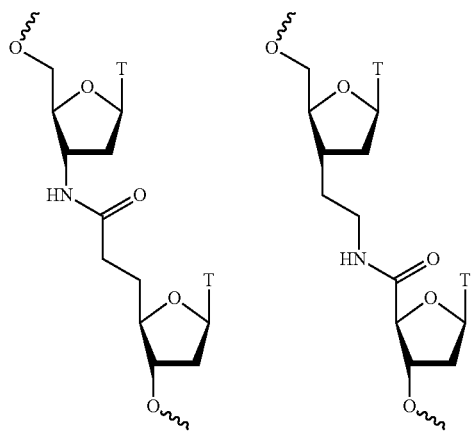

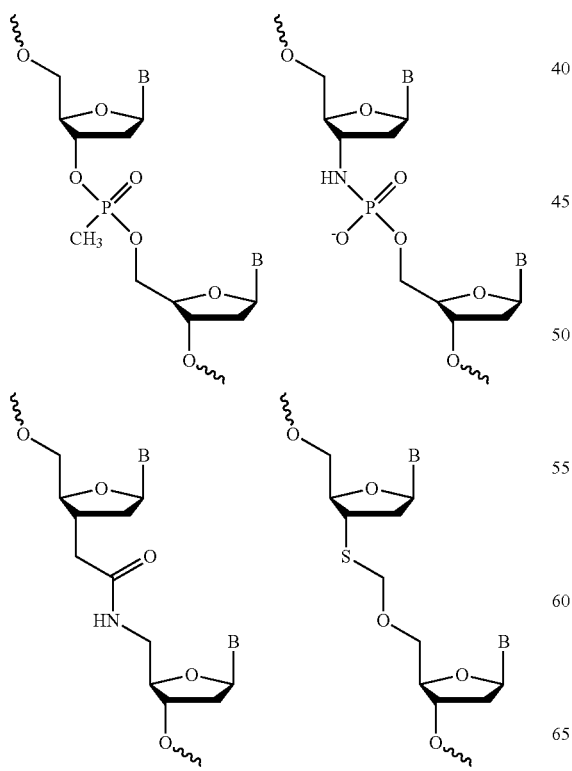

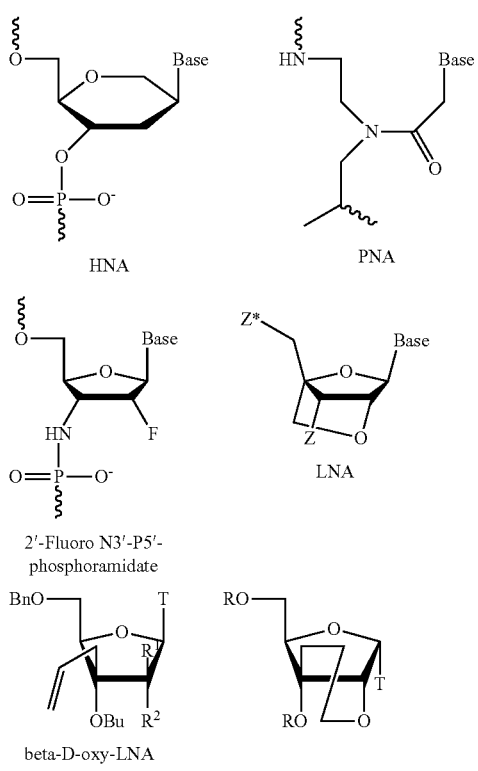

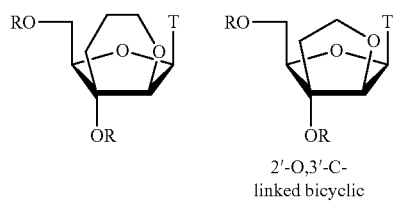
2'-O,3'-C-linked bicyclic
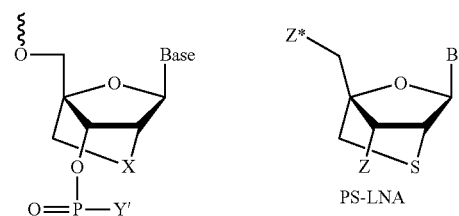
LNA: X = O, Y = O
2'-Thio-LNA: X = S, Y = O
2'-Phosphorothioate-LNA: X = O, Y = S
PS-LNA
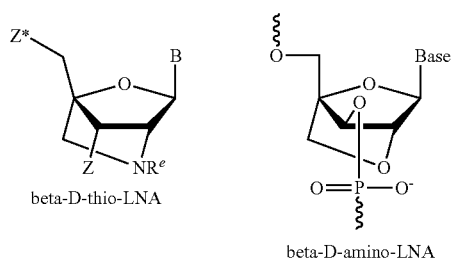
beta-D-thio-LNA
beta-D-amino-LNA
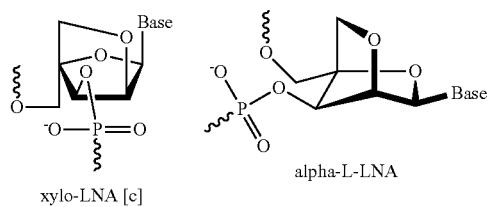
xylo-LNA [c]
alpha-L-LNA
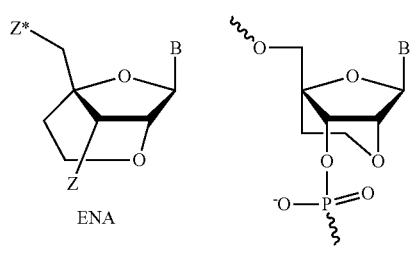
ENA
beta-D-ENA
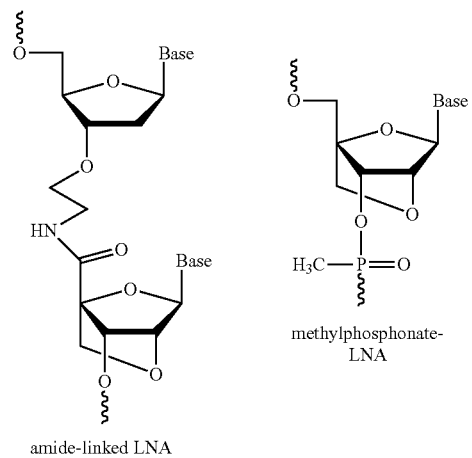
amide-linked LNA
methylphosphonate-LNA
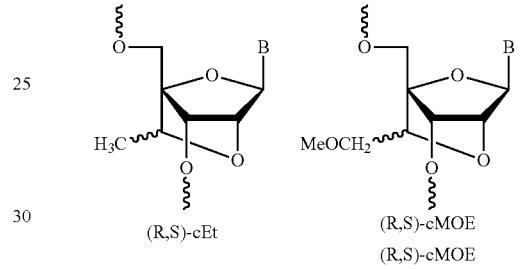
(R,S)-cEt
(R,S)-cMOE
(R,S)-cMOE
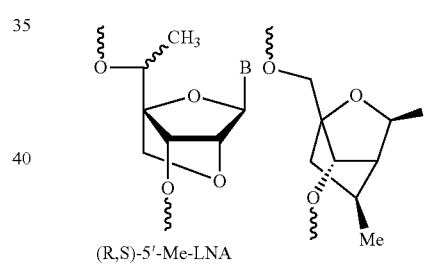
(R,S)-5'-Me-LNA
S-Me cLNA
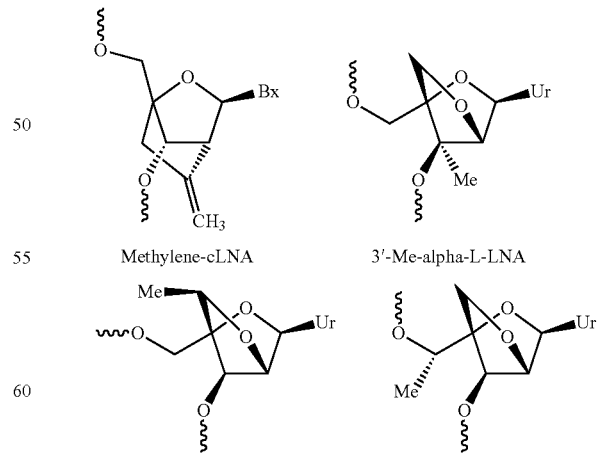
Methylene-cLNA
3'-Me-alpha-L-LNA
R-6'-Me-alpha-L-LNA
S-5'-Me-alpha-L-LNA

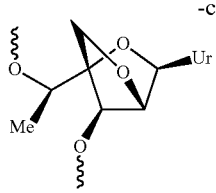

R-5'-Me-alpha-L-LNA

In some embodiments, $R^1$ is R as defined and described. In some embodiments, $R^2$ is R. In some embodiments, $R^e$ is R. In some embodiments, $R^e$ is H, $CH_3$, Bn, $COCF_3$, benzoyl, benzyl, pyren-1-ylcarbonyl, pyren-1-ylmethyl, 2-aminoethyl. In some embodiments, an example modified internucleotidic linkage and/or sugar is selected from those described in Ts'o et al. Ann. N. Y. Acad. Sci. 1988. 507, 220; Gryaznov, S.; Chen, J.-K. J. Am. Chem. Soc. 1994. 116, 3143; Mesmaeker et al. Angew. Chem., Int. Ed. Engl. 1994. 33, 226; Jones et al. J. Org. Chem. 1993. 58, 2983; Vasseur et al. J. Am. Chem. Soc. 1992. 114, 4006; Van Aerschot et al. 1995 Angew. Chem. Int. Ed. Engl. 34: 1338; Hendrix et al. 1997 Chem. Eur. J. 3: 110; Koshkin et al. 1998 Tetrahedron 54: 3607-3630; Hyrup et al. 1996 Bioorg. Med. Chem. 4: 5; Nielsen et al. 1997 Chem. Soc. Rev. 73; Schultz et al. 1996 Nucleic Acids Res. 24: 2966; Obika et al. 1997 Tetrahedron Lett. 38 (50): 8735-8; Obika et al. 1998 Tetrahedron Lett. 39: 5401-5404; Singh et al. 1998 Chem. Comm. 1247-1248; Kumar et al. 1998 Bioo. Med. Chem. Let. 8: 2219-2222; Nielsen et al. 1997 J. Chem. Soc. Perkins Transl. 1: 3423-3433; Singh et al. 1998 J. Org. Chem. 63: 6078-6079; Seth et al. 2010 J. Org. Chem. 75: 1569-1581; Singh et al. 1998 J. Org. Chem. 63: 10035-39; Sorensen 2003 Chem. Comm. 2130-2131; Petersen et al. 2003 TRENDS Biotech. 21: 74-81; Rajwanshi et al. 1999 Chem. Commun. 1395-1396; Jepsen et al. 2004 Oligo. 14: 130-146; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Koizumi et al. 2003 Nuc. Acids Res. 12: 3267-3273; Lauritsen et al. 2002 Chem. Comm. 5: 530-531; Lauritsen et al. 2003 Bioo. Med. Chem. Lett. 13: 253-256; WO 20070900071; Seth et al., Nucleic Acids Symposium Series (2008), 52(1), 553-554; Seth et al. 2009 J. Med. Chem. 52: 10-13; Seth et al. 2012 Mol. Ther-Nuc. Acids. 1, e47; Pallan et al. 2012 Chem. Comm. 48: 8195-8197; Seth et al. 2010 J. Med. Chem. 53: 8309-8318; Seth et al. 2012 Bioo. Med. Chem. Lett. 22: 296-299; WO 2016/079181; U.S. Pat. Nos. 6,326,199; 6,066,500; and 6,440,739, the base and sugar modifications of each of which is herein incorporated by reference.

Certain Example Oligonucleotides and Compositions

In some embodiments, the present disclosure provides oligonucleotides and compositions thereof. In some embodiments, a provided composition is a chirally controlled oligonucleotide composition. In some embodiments, a provided composition is a completely chirally controlled oligonucleotide composition, wherein each chiral internucleotidic linkage of the oligonucleotide is independently chirally controlled. Certain example oligonucleotides are provided in Table 2. In some embodiments, a provided oligonucleotide comprises one or more structural elements comprising or consisting of structural elements of any of the oligonucleotides presented in the Tables. In some embodiments, structural elements of an oligonucleotide includes any one or more of: base sequence (including length), pattern of chemical modifications to sugar and base moieties, pattern of backbone linkages (e.g., pattern of natural phosphate linkages, phosphorothioate linkages, phosphorothioate triester linkages, and combinations thereof), pattern of backbone chiral centers (e.g., pattern of stereochemistry (Rp/Sp) of chiral internucleotidic linkages), and pattern of backbone phosphorus modifications (e.g., pattern of modifications on the internucleotidic phosphorus atom, such as —S⁻, and -L-$R^1$ of formula I). In some embodiments, structural elements include lipid moieties and/or targeting components, for example, as moieties connected to sugars, bases, and/or internucleotidic linkages. In some embodiments, a structural element is base sequence. In some embodiments, a structural element is pattern of chemical modifications. In some embodiments, a structural element is pattern of sugar modifications. In some embodiments, a structural element is nucleobase modifications. In some embodiments, a structural element is pattern of lipid moieties. In some embodiments, a structural element is pattern of targeting component. In some embodiments, a structural element is a linker connecting a biologically active agent, e.g., a provided oligonucleotide, and a lipid moiety and/or a targeting component. In some embodiments, a structural element is pattern of backbone linkages. In some embodiments, a structural element is pattern of backbone chiral centers. In some embodiments, a structural element is pattern of backbone phosphorus modifications. In some embodiments, an oligonucleotide or oligonucleotide composition of any structural elements of any oligonucleotide listed herein can be used in combination with any composition and/or method described herein, including, but not limited to, any combination with any lipid described herein, any additional component described herein, or any other composition (or component thereof) or method described herein. In some embodiments, structural elements of provided oligonucleotides comprise or consist of one or more structural elements of any oligonucleotides described herein. In some embodiments, structural elements of provided oligonucleotides comprise or consist of one or more structural elements of listed in Table 1. In some embodiments, structural elements of provided oligonucleotides comprise or consist of one or more structural elements of any oligonucleotides listed in Table 2. In some embodiments, structural elements of provided oligonucleotides comprise or consist of one or more structural elements of any oligonucleotides listed in Table 3. In some embodiments, structural elements of provided oligonucleotides comprise or consist of one or more structural elements of any oligonucleotides listed in Table 4. In some embodiments, structural elements of provided oligonucleotides comprise or consist of one or more structural elements of any oligonucleotides listed in Table 5.

TABLE 2

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| ONT-395 | UCAAGGAAGAUGGCAUUUCU | 10 | mU*SmC*SmA*SmA*SmG*SmG*SmA*SmA*SmG*SmA*SmU*SmG*SmG*SmC*SmA*SmU*SmU*SmU*SmC*SmU | 762 | SSSSSSSSSSSSSSSSSSS | Chiral version of PRO051 (Drisapersen) | DMD |
| WV-942 | UCAAGGAAGAUGGCAUUUCU | 11 | mU*mC*mA*mA*mG*mG*mA*mA*mG*mA*mU*mG*mG*mC*mA*mU*mU*mU*mC*mU | 763 | XXXXXXXXXXXXXXXXXXX | PRO051 (Drisapersen) | DMD |
| WV-943 | GGCCAAACCUCGGCUUACCU | 12 | mG*mG*mC*mC*mA*mA*mA*mC*mC*mU*mC*mG*mG*mC*mU*mU*mA*mC*mC*mU | 764 | XXXXXXXXXXXXXXXXXXX | Exon 23 control | DMD |
| WV-2165 | CUCCAACAUCAAGGAAGAUGGCAUUUCUAG | 13 | mC*mU*mC*mC*mA*mA*mC*mA*mU*mC*mA*mA*mG*mG*mA*mA*mG*mA*mU*mG*mG*mC*mA*mU*mU*mU*mC*mU*mA*mG | 765 | XXXXXXXXXXXXXXXXXXXXXXXXXXXXX | eteplirsen-all-2'-Me 30 mer | DMD |
| WV-2179 | ACCAGAGUAACAGUCUGAGUAGGAG | 14 | mA*mC*mC*mA*mG*mA*mG*mU*mA*mA*mC*mA*mG*mU*mC*mU*mG*mA*mG*mU*mA*mG*mG*mA*mG | 766 | XXXXXXXXXXXXXXXXXXXXXXXX | 25-mer 2'-OMethyl | DMD |
| WV-2180 | CACCAGAGUAACAGUCUGAGUAGGA | 15 | mC*mA*mC*mC*mA*mG*mA*mG*mU*mA*mA*mC*mA*mG*mU*mC*mU*mG*mA*mG*mU*mA*mG*mG*mA | 767 | XXXXXXXXXXXXXXXXXXXXXXXX | 25-mer 2'-OMethyl | DMD |
| WV-2181 | UCACCAGAGUAACAGUCUGAGUAGG | 16 | mU*mC*mA*mC*mC*mA*mG*mA*mG*mU*mA*mA*mC*mA*mG*mU*mC*mU*mG*mA*mG*mU*mA*mG*mG | 768 | XXXXXXXXXXXXXXXXXXXXXXXX | 25-mer 2'-OMethyl | DMD |
| WV-2182 | GUCACCAGAGUAACAGUCUGAGUAG | 17 | mG*mU*mC*mA*mC*mC*mA*mG*mA*mG*mU*mA*mA*mC*mA*mG*mU*mC*mU*mG*mA*mG*mU*mA*mG | 769 | XXXXXXXXXXXXXXXXXXXXXXXX | 25-mer 2'-OMethyl | DMD |
| WV-2183 | GUUGUGUCACCAGAGUAACAGUCUG | 18 | mG*mU*mU*mG*mU*mG*mU*mC*mA*mC*mC*mA*mG*mA*mG*mU*mA*mA*mC*mA*mG*mU*mC*mU*mG | 770 | XXXXXXXXXXXXXXXXXXXXXXXX | 25-mer 2'-OMethyl | DMD |
| WV-2184 | GGUUGUGUCACCAGAGUAACAGUCU | 19 | mG*mG*mU*mU*mG*mU*mG*mU*mC*mA*mC*mC*mA*mG*mA*mG*mU*mA*mA*mC*mA*mG*mU*mC*mU | 771 | XXXXXXXXXXXXXXXXXXXXXXXX | 25-mer 2'-OMethyl | DMD |
| WV-2185 | AGGUUGUGUCACCAGAGUAACAGUC | 20 | mA*mG*mG*mU*mU*mG*mU*mG*mU*mC*mA*mC*mC*mA*mG*mA*mG*mU*mA*mA*mC*mA*mG*mU*mC | 772 | XXXXXXXXXXXXXXXXXXXXXXXX | 25-mer 2'-OMethyl | DMD |
| WV-2186 | CAGGUUGUGUCACCAGAGUAACAGU | 21 | mC*mA*mG*mG*mU*mU*mG*mU*mG*mU*mC*mA*mC*mC*mA*mG*mA*mG*mU*mA*mA*mC*mA*mG*mU | 773 | XXXXXXXXXXXXXXXXXXXXXXXX | 25-mer 2'-OMethyl | DMD |
| WV-2187 | ACAGGUUGUGUCACCAGAGUAACAG | 22 | mA*mC*mA*mG*mG*mU*mU*mG*mU*mG*mU*mC*mA*mC*mC*mA*mG*mA*mG*mU*mA*mA*mC*mA*mG | 774 | XXXXXXXXXXXXXXXXXXXXXXXX | 25-mer 2'-OMethyl | DMD |
| WV-2188 | CCACAGGUUGUGUCACCAGAGUAAC | 23 | mC*mC*mA*mC*mA*mG*mG*mU*mU*mG*mU*mG*mU*mC*mA*mC*mC*mA*mG*mA*mG*mU*mA*mA*mC | 775 | XXXXXXXXXXXXXXXXXXXXXXXX | 25-mer 2'-OMethyl | DMD |
| WV-2189 | ACCACAGGUUGUGUCACCAGAGUAA | 24 | mA*mC*mC*mA*mC*mA*mG*mG*mU*mU*mG*mU*mG*mU*mC*mA*mC*mC*mA*mG*mA*mG*mU*mA*mA | 776 | XXXXXXXXXXXXXXXXXXXXXXXX | 25-mer 2'-OMethyl | DMD |
| WV-2190 | AACCACAGGUUGUGUCACCAGAGUA | 25 | mA*mA*mC*mC*mA*mC*mA*mG*mG*mU*mU*mG*mU*mG*mU*mC*mA*mC*mC*mA*mG*mA*mG*mU*mA | 777 | XXXXXXXXXXXXXXXXXXXXXXXX | 25-mer 2'-OMethyl | DMD |
| WV-2191 | UAACCACAGGUUGUGUCACCAGAGU | 26 | mU*mA*mA*mC*mC*mA*mC*mA*mG*mG*mU*mU*mG*mU*mG*mU*mC*mA*mC*mC*mA*mG*mA*mG*mU | 778 | XXXXXXXXXXXXXXXXXXXXXXXX | 25-mer 2'-OMethyl | DMD |
| WV-2192 | GUAACCACAGGUUGUGUCACCAGAG | 27 | mG*mU*mA*mA*mC*mC*mA*mC*mA*mG*mG*mU*mU*mG*mU*mG*mU*mC*mA*mC*mC*mA*mG*mA*mG | 779 | XXXXXXXXXXXXXXXXXXXXXXXX | 25-mer 2'-OMethyl | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2193 | AGUAACCACA GGUUGUGUCA CCAGA | 28 | mA*mG*mU*mA*mA*mC*mC*mA*mC*mA* mG*mG*mU*mU*mG*mU*mG*mU*mC*mA* mC*mC*mA*mG*mA | 780 | XXXXXXXXXX XXXXXXXXXX XXXX | 25-mer 2'-OMethyl | DMD |
| WV-2194 | UAGUAACCAC AGGUUGUGUC ACCAG | 29 | mU*mA*mG*mU*mA*mA*mC*mC*mA*mC* mA*mG*mG*mU*mU*mG*mU*mG*mU*mC* mA*mC*mC*mA*mG | 781 | XXXXXXXXXX XXXXXXXXXX XXXX | 25-mer 2'-OMethyl | DMD |
| WV-2195 | UUAGUAACCA CAGGUUGUGU CACCA | 30 | mU*mU*mA*mG*mU*mA*mA*mC*mC*mA* mC*mA*mG*mG*mU*mU*mG*mU*mG*mU* mC*mA*mC*mC*mA | 782 | XXXXXXXXXX XXXXXXXXXX XXXX | 25-mer 2'-OMethyl | DMD |
| WV-2196 | CUUAGUAACC ACAGGUUGUG UCACC | 31 | mC*mU*mU*mA*mG*mU*mA*mA*mC*mC* mA*mC*mA*mG*mG*mU*mU*mG*mU*mG* mU*mC*mA*mC*mC | 783 | XXXXXXXXXX XXXXXXXXXX XXXX | 25-mer 2'-OMethyl | DMD |
| WV-2197 | CCUUAGUAACC ACAGGUUGUG UCAC | 32 | mC*mC*mU*mU*mA*mG*mU*mA*mA*mC* mC*mA*mC*mA*mG*mG*mU*mU*mG*mU* mG*mU*mC*mA*mC | 784 | XXXXXXXXXX XXXXXXXXXX XXXX | 25-mer 2'-OMethyl | DMD |
| WV-2198 | UCCUUAGUAA CCACAGGUUG UGUCA | 33 | mU*mC*mC*mU*mU*mA*mG*mU*mA*mA* mC*mC*mA*mC*mA*mG*mG*mU*mU*mG* mU*mG*mU*mC*mA | 785 | XXXXXXXXXX XXXXXXXXXX XXXX | 25-mer 2'-OMethyl | DMD |
| WV-2199 | GUUUCCUUAG UAACCACAGG UUGUG | 34 | mG*mU*mU*mU*mC*mC*mU*mU*mA*mG* mU*mA*mA*mC*mC*mA*mC*mA*mG*mG* mU*mU*mG*mU*mG | 786 | XXXXXXXXXX XXXXXXXXXX XXXX | 25-mer 2'-OMethyl | DMD |
| WV-2200 | AGUUUCCUUA GUAACCACAG GUUGU | 35 | mA*mG*mU*mU*mU*mC*mC*mU*mU*mA* mG*mU*mA*mA*mC*mC*mA*mC*mA*mG* mG*mU*mU*mG*mU | 787 | XXXXXXXXXX XXXXXXXXXX XXXX | 25-mer 2'-OMethyl | DMD |
| WV-2201 | CAGUUUCCUU AGUAACCACA GGUUG | 36 | mC*mA*mG*mU*mU*mU*mC*mC*mU*mU* mA*mG*mU*mA*mA*mC*mC*mA*mC*mA* mG*mG*mU*mU*mG | 788 | XXXXXXXXXX XXXXXXXXXX XXXX | 25-mer 2'-OMethyl | DMD |
| WV-2202 | GCAGUUUCCU UAGUAACCAC AGGUU | 37 | mG*mC*mA*mG*mU*mU*mU*mC*mC*mU* mU*mA*mG*mU*mA*mA*mC*mC*mA*mC* mA*mG*mG*mU*mU | 789 | XXXXXXXXXX XXXXXXXXXX XXXX | 25-mer 2'-OMethyl | DMD |
| WV-2203 | GGCAGUUUCC UUAGUAACCA CAGGU | 38 | mG*mG*mC*mA*mG*mU*mU*mU*mC*mC* mU*mU*mA*mG*mU*mA*mA*mC*mC*mA* mC*mA*mG*mG*mU | 790 | XXXXXXXXXX XXXXXXXXXX XXXX | 25-mer 2'-OMethyl | DMD |
| WV-2204 | UGGCAGUUUC CUUAGUAACC ACAGG | 39 | mU*mG*mG*mC*mA*mG*mU*mU*mU*mC* mC*mU*mU*mA*mG*mU*mA*mA*mC*mC* mA*mC*mA*mG*mG | 791 | XXXXXXXXXX XXXXXXXXXX XXXX | 25-mer 2'-OMethyl | DMD |
| WV-2205 | AUGGCAGUUU CCUUAGUAAC CACAG | 40 | mA*mU*mG*mG*mC*mA*mG*mU*mU*mU* mC*mC*mU*mU*mA*mG*mU*mA*mA*mC* mC*mA*mC*mA*mG | 792 | XXXXXXXXXX XXXXXXXXXX XXXX | 25-mer 2'-OMethyl | DMD |
| WV-2206 | AGAUGGCAGU UUCCUUAGUA ACCAC | 41 | mA*mG*mA*mU*mG*mG*mC*mA*mG*mU* mU*mU*mC*mC*mU*mU*mA*mG*mU*mA* mA*mC*mC*mA*mC | 793 | XXXXXXXXXX XXXXXXXXXX XXXX | 25-mer 2'-OMethyl | DMD |
| WV-2207 | GAGAUGGCAG UUUCCUUAGU AACCA | 42 | mG*mA*mG*mA*mU*mG*mG*mC*mA*mG* mU*mU*mU*mC*mC*mU*mU*mA*mG*mU* mA*mA*mC*mC *mA | 794 | XXXXXXXXXX XXXXXXXXXX XXXX | 25-mer 2'-OMethyl | DMD |
| WV-2208 | GGAGAUGGCA GUUUCCUUAG UAACC | 43 | mG*mG*mA*mG*mA*mU*mG*mG*mC*mA* mG*mU*mU*mU*mC*mC*mU*mU*mA*mG* mU*mA*mA*mC*mC | 795 | XXXXXXXXXX XXXXXXXXXX XXXX | 25-mer 2'-OMethyl | DMD |
| WV-2209 | UGGAGAUGGC AGUUUCCUUA GUAAC | 44 | mU*mG*mG*mA*mG*mA*mU*mG*mG*mC* mA*mG*mU*mU*mU*mC*mC*mU*mU*mA* mG*mU*mA*mA*mC | 796 | XXXXXXXXXX XXXXXXXXXX XXXX | 25-mer 2'-OMethyl | DMD |
| WV-2210 | UUGGAGAUGG CAGUUUCCUU AGUAA | 45 | mU*mU*mG*mG*mA*mG*mA*mU*mG*mG* mC*mA*mG*mU*mU*mU*mC*mC*mU*mU* mA*mG*mU*mA*mA | 797 | XXXXXXXXXX XXXXXXXXXX XXXX | 25-mer 2'-OMethyl | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2211 | UUUGGAGAUGGCAGUUUCCUUAGUA | 46 | mU*mU*mU*mG*mG*mA*mG*mA*mU*mG*mG*mC*mA*mG*mU*mU*mU*mC*mC*mU*mU*mA*mG*mU*mA | 798 | XXXXXXXXXXXXXXXXXXXXXXXXX | 25-mer 2'-OMethyl | DMD |
| WV-2212 | AGUUUGGAGAUGGCAGUUUCCUUAG | 47 | mA*mG*mU*mU*mU*mG*mG*mA*mG*mA*mU*mG*mG*mC*mA*mG*mU*mU*mU*mC*mC*mU*mU*mA*mG | 799 | XXXXXXXXXXXXXXXXXXXXXXXXX | 25-mer 2'-OMethyl | DMD |
| WV-2213 | UAGUUUGGAGAUGGCAGUUUCCUUA | 48 | mU*mA*mG*mU*mU*mU*mG*mG*mA*mG*mA*mU*mG*mG*mC*mA*mG*mU*mU*mU*mC*mC*mU*mU*mA | 800 | XXXXXXXXXXXXXXXXXXXXXXXXX | 25-mer 2'-OMethyl | DMD |
| WV-2214 | CUAGUUUGGAGAUGGCAGUUUCCUU | 49 | mC*mU*mA*mG*mU*mU*mU*mG*mG*mA*mG*mA*mU*mG*mG*mC*mA*mG*mU*mU*mU*mC*mC *mU*mU | 801 | XXXXXXXXXXXXXXXXXXXXXXXXX | 25-mer 2'-OMethyl | DMD |
| WV-2215 | UCUAGUUUGGAGAUGGCAGUUUCCU | 50 | mU*mC*mU*mA*mG*mU*mU*mU*mG*mG*mA*mG*mA*mU*mG*mG*mC*mA*mG*mU*mU*mU*mC*mC *mU | 802 | XXXXXXXXXXXXXXXXXXXXXXXXX | 25-mer 2'-OMethyl | DMD |
| WV-2216 | UUCUAGUUUGGAGAUGGCAGUUUCC | 51 | mU*mU*mC*mU*mA*mG*mU*mU*mU*mG*mG*mA*mG*mA*mU*mG*mG*mC*mA*mG*mU*mU*mU*mC*mC | 803 | XXXXXXXXXXXXXXXXXXXXXXXXX | 25-mer 2'-OMethyl | DMD |
| WV-2217 | CAUUUCUAGUUUGGAGAUGGCAGUU | 52 | mC*mA*mU*mU*mU*mC*mU*mA*mG*mU*mU*mU*mG*mG*mA*mG*mA*mU*mG*mG*mC*mA*mG*mU*mU | 804 | XXXXXXXXXXXXXXXXXXXXXXXXX | 25-mer 2'-OMethyl | DMD |
| WV-2218 | GCAUUUCUAGUUUGGAGAUGGCAGU | 53 | mG*mC*mA*mU*mU*mU*mC*mU*mA*mG*mU*mU*mU*mG*mG*mA*mG*mA*mU*mG*mG*mC*mA*mG*mU | 805 | XXXXXXXXXXXXXXXXXXXXXXXXX | 25-mer 2'-OMethyl | DMD |
| WV-2219 | AUGGCAUUUCUAGUUUGGAGAUGGC | 54 | mA*mU*mG*mG*mC*mA*mU*mU*mU*mC*mU*mA*mG*mU*mU*mU*mG*mG*mA*mG*mA*mU*mG*mG*mC | 806 | XXXXXXXXXXXXXXXXXXXXXXXXX | 25-mer 2'-OMethyl | DMD |
| WV-2220 | GAAGAUGGCAUUUCUAGUUUGGAGA | 55 | mG*mA*mA*mG*mA*mU*mG*mG*mC*mA*mU*mU*mU*mC*mU*mA*mG*mU*mU*mU*mG*mG*mA*mG*mA | 807 | XXXXXXXXXXXXXXXXXXXXXXXXX | 25-mer 2'-OMethyl | DMD |
| WV-2221 | AGGAAGAUGGCAUUUCUAGUUUGGA | 56 | mA*mG*mG*mA*mA*mG*mA*mU*mG*mG*mC*mA*mU*mU*mU*mC*mU*mA*mG*mU*mU*mU*mG*mG*mA | 808 | XXXXXXXXXXXXXXXXXXXXXXXXX | 25-mer 2'-OMethyl | DMD |
| WV-2222 | AAGGAAGAUGGCAUUUCUAGUUUGG | 57 | mA*mA*mG*mG*mA*mA*mG*mA*mU*mG*mG*mC*mA*mU*mU*mU*mC*mU*mA*mG*mU*mU*mU*mG*mG | 809 | XXXXXXXXXXXXXXXXXXXXXXXXX | 25-mer 2'-OMethyl | DMD |
| WV-2223 | CAAGGAAGAUGGCAUUUCUAGUUUG | 58 | mC*mA*mA*mG*mG*mA*mA*mG*mA*mU*mG*mG*mC*mA*mU*mU*mU*mC*mU*mA*mG*mU*mU*mU*mG | 810 | XXXXXXXXXXXXXXXXXXXXXXXXX | 25-mer 2'-OMethyl | DMD |
| WV-2224 | CAUCAAGGAAGAUGGCAUUUCUAGU | 59 | mC*mA*mU*mC*mA*mA*mG*mG*mA*mA*mG*mA*mU*mG*mG*mC*mA*mU*mU*mU*mC*mU*mA*mG*mU | 811 | XXXXXXXXXXXXXXXXXXXXXXXXX | 25-mer 2'-OMethyl | DMD |
| WV-2225 | ACAUCAAGGAAGAUGGCAUUUCUAG | 60 | mA*mC*mA*mU*mC*mA*mA*mG*mG*mA*mA*mG*mA*mU*mG*mG*mC*mA*mU*mU*mU*mC*mU*mA*mG | 812 | XXXXXXXXXXXXXXXXXXXXXXXXX | 25-mer 2'-OMethyl | DMD |
| WV-2226 | AACAUCAAGGAAGAUGGCAUUUCUA | 61 | mA*mA*mC*mA*mU*mC*mA*mA*mG*mG*mA*mA*mG*mA*mU*mG*mG*mC*mA*mU*mU*mU*mC*mU*mA | 813 | XXXXXXXXXXXXXXXXXXXXXXXXX | 25-mer 2'-OMethyl | DMD |
| WV-2227 | CAACAUCAAGGAAGAUGGCAUUUCU | 62 | mC*mA*mA*mC*mA*mU*mC*mA*mA*mG*mG*mA*mA*mG*mA*mU*mG*mG*mC*mA*mU*mU*mU*mC*mU | 814 | XXXXXXXXXXXXXXXXXXXXXXXXX | 25-mer 2'-OMethyl | DMD |
| WV-2228 | CUCCAACAUCAAGGAAGAUGGCAUU | 63 | mC*mU*mC*mC*mA*mA*mC*mA*mU*mC*mA*mA*mG*mG*mA*mA*mG*mA*mU*mG*mG*mC*mA*mU*mU | 815 | XXXXXXXXXXXXXXXXXXXXXXXXX | 25-mer 2'-OMethyl | DMD |
| WV-2229 | ACCUCCAACAUCAAGGAAGAUGGCA | 64 | mA*mC*mC*mU*mC*mC*mA*mA*mC*mA*mU*mC*mA*mA*mG*mG*mA*mA*mG*mA*mU*mG*mG*mC*mA | 816 | XXXXXXXXXXXXXXXXXXXXXXXXX | 25-mer 2'-OMethyl | DMD |
| WV-2230 | GUACCUCCAACAUCAAGGAAGAUGG | 65 | mG*mU*mA*mC*mC*mU*mC*mC*mA*mA*mC*mA*mU*mC*mA*mA*mG*mG*mA*mA*mG*mA*mU*mG*mG | 817 | XXXXXXXXXXXXXXXXXXXXXXXXX | 25-mer 2'-OMethyl | DMD |
| WV-2231 | AGGUACCUCCAACAUCAAGGAAGAU | 66 | mA*mG*mG*mU*mA*mC*mC*mU*mC*mC*mA*mA*mC*mA*mU*mC*mA*mA*mG*mG*mA*mA*mG*mA*mU | 818 | XXXXXXXXXXXXXXXXXXXXXXXXX | 25-mer 2'-OMethyl | DMD |
| WV-2232 | AGAGCAGGUACCUCCAACAUCAAGG | 67 | mA*mG*mA*mG*mC*mA*mG*mG*mU*mA*mC*mC*mU*mC*mC*mA*mA*mC*mA*mU*mC*mA*mA*mG*mG | 819 | XXXXXXXXXXXXXXXXXXXXXXXXX | 25-mer 2'-OMethyl | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2233 | CAGAGCAGGU ACCUCCAACA UCAAG | 68 | mC*mA*mG*mA*mG*mC*mA*mG*mG*mU* mA*mC*mC*mU*mC*mC*mA*mA*mC*mA* mU*mC*mA*mA*mG | 820 | XXXXXXXXXX XXXXXXXXXX XXXX | 25-mer 2'-OMethyl | DMD |
| WV-2234 | CUGCCAGAGCA GGUACCUCCAA CAU | 69 | mC*mU*mG*mC*mC*mA*mG*mA*mG*mC* mA*mG*mG*mU*mA*mC*mC*mU*mC*mC* mA*mA*mC*mA*mU | 821 | XXXXXXXXXX XXXXXXXXXX XXXX | 25-mer 2'-OMethyl | DMD |
| WV-2235 | UCUGCCAGAGC AGGUACCUCCA ACA | 70 | mU*mC*mU*mG*mC*mC*mA*mG*mA*mG* mC*mA*mG*mG*mU*mA*mC*mC*mU*mC* mC*mA*mA*mC*mA | 822 | XXXXXXXXXX XXXXXXXXXX XXXX | 25-mer 2'-OMethyl | DMD |
| WV-2236 | AUCUGCCAGA GCAGGUACCUC CAAC | 71 | mA*mU*mC*mU*mG*mC*mC*mA*mG*mA* mG*mC*mA*mG*mG*mU*mA*mC*mC*mU* mC*mC*mA*mA*mC | 823 | XXXXXXXXXX XXXXXXXXXX XXXX | 25-mer 2'-OMethyl | DMD |
| WV-2237 | AAUCUGCCAG AGCAGGUACC UCCAA | 72 | mA*mA*mU*mC*mU*mG*mC*mC*mA*mG* mA*mG*mC*mA*mG*mG*mU*mA*mC*mC* mU*mC*mC*mA*mA | 824 | XXXXXXXXXX XXXXXXXXXX XXXX | 25-mer 2'-OMethyl | DMD |
| WV-2238 | AAAUCUGCCA GAGCAGGUAC CUCCA | 73 | mA*mA*mA*mU*mC*mU*mG*mC*mC*mA* mG*mA*mG*mC*mA*mG*mG*mU*mA*mC* mC*mU*mC*mC*mA | 825 | XXXXXXXXXX XXXXXXXXXX XXXX | 25-mer 2'-OMethyl | DMD |
| WV-2239 | GAAAUCUGCC AGAGCAGGUA CCUCC | 74 | mG*mA*mA*mA*mU*mC*mU*mG*mC*mC* mA*mG*mA*mG*mC*mA*mG*mG*mU*mA* mC*mC*mU*mC*mC | 826 | XXXXXXXXXX XXXXXXXXXX XXXX | 25-mer 2'-OMethyl | DMD |
| WV-2240 | UGAAAUCUGC CAGAGCAGGU ACCUC | 75 | mU*mG*mA*mA*mA*mU*mC*mU*mG*mC* mC*mA*mG*mA*mG*mC*mA*mG*mG*mU* mA*mC*mC*mU*mC | 827 | XXXXXXXXXX XXXXXXXXXX XXXX | 25-mer 2'-OMethyl | DMD |
| WV-2241 | UUGAAAUCUG CCAGAGCAGG UACCU | 76 | mU*mU*mG*mA*mA*mA*mU*mC*mU*mG* mC*mC*mA*mG*mA*mG*mC*mA*mG*mG* mU*mA*mC*mC*mU | 828 | XXXXXXXXXX XXXXXXXXXX XXXX | 25-mer 2'-OMethyl | DMD |
| WV-2242 | CCCGGUUGAA AUCUGCCAGA GCAGG | 77 | mC*mC*mC*mG*mG*mU*mU*mG*mA*mA* mA*mU*mC*mU*mG*mC*mC*mA*mG*mA* mG*mC*mA*mG*mG | 829 | XXXXXXXXXX XXXXXXXXXX XXXX | 25-mer 2'-OMethyl | DMD |
| WV-2243 | CCAAGCCCGGU UGAAAUCUGC CAGA | 78 | mC*mC*mA*mA*mG*mC*mC*mC*mG*mG* mU*mG*mA*mA*mA*mU*mC*mU*mG* mC*mC*mA*mG*mA | 830 | XXXXXXXXXX XXXXXXXXXX XXXX | 25-mer 2'-OMethyl | DMD |
| WV-2244 | UCCAAGCCCGG UUGAAAUCUG CCAG | 79 | mU*mC*mC*mA*mA*mG*mC*mC*mC*mG* mG*mU*mU*mG*mA*mA*mA*mU*mC*mU* mG*mC*mC*mA*mG | 831 | XXXXXXXXXX XXXXXXXXXX XXXX | 25-mer 2'-OMethyl | DMD |
| WV-2245 | GUCCAAGCCCG GUUGAAAUCU GCCA | 80 | mG*mU*mC*mC*mA*mA*mG*mC*mC*mC* mG*mG*mU*mU*mG*mA*mA*mA*mU*mC* mU*mG*mC*mC*mA | 832 | XXXXXXXXXX XXXXXXXXXX XXXX | 25-mer 2'-OMethyl | DMD |
| WV-2246 | UCUGUCCAAGC CCGGUUGAAA UCUG | 81 | mU*mC*mU*mG*mU*mC*mC*mA*mA*mG* mC*mC*mC*mG*mG*mU*mU*mG*mA*mA* mA*mU*mC*mU*mG | 833 | XXXXXXXXXX XXXXXXXXXX XXXX | 25-mer 2'-OMethyl | DMD |
| WV-2247 | UUCUGUCCAA GCCCGGUUGA AAUCU | 82 | mU*mU*mC*mU*mG*mU*mC*mC*mA*mA* mG*mC*mC*mC*mG*mG*mU*mU*mG*mA* mA*mA*mU*mC*mU | 834 | XXXXXXXXXX XXXXXXXXXX XXXX | 25-mer 2'-OMethyl | DMD |
| WV-2248 | GUUCUGUCCA AGCCCGGUUG AAAUC | 83 | mG*mU*mU*mC*mU*mG*mU*mC*mC*mA* mA*mG*mC*mC*mC*mG*mG*mU*mU*mG* mA*mA*mA*mU*mC | 835 | XXXXXXXXXX XXXXXXXXXX XXXX | 25-mer 2'-OMethyl | DMD |
| WV-2249 | AGUUCUGUCC AAGCCCGGUU GAAAU | 84 | mA*mG*mU*mU*mC*mU*mG*mU*mC*mC* mA*mA*mG*mC*mC*mC*mG*mG*mU*mU* mG*mA*mA*mA*mU | 836 | XXXXXXXXXX XXXXXXXXXX XXXX | 25-mer 2'-OMethyl | DMD |
| WV-2250 | AAGUUCUGUC CAAGCCCGGUU GAAA | 85 | mA*mA*mG*mU*mU*mC*mU*mG*mU*mC* mC*mA*mA*mG*mC*mC*mC*mG*mG*mU* mU*mG*mA*mA*mA | 837 | XXXXXXXXXX XXXXXXXXXX XXXX | 25-mer 2'-OMethyl | DMD |
| WV-2251 | UAAGUUCUGU CCAAGCCCGGU UGAA | 86 | mU*mA*mA*mG*mU*mU*mC*mU*mG*mU* mC*mC*mA*mA*mG*mC*mC*mC*mG*mG* mU*mU*mG*mA*mA | 838 | XXXXXXXXXX XXXXXXXXXX XXXX | 25-mer 2'-OMethyl | DMD |
| WV-2252 | GUAAGUUCUG UCCAAGCCCGG UUGA | 87 | mG*mU*mA*mA*mG*mU*mU*mC*mU*mG* mU*mC*mC*mA*mA*mG*mC*mC*mC*mG* mG*mU*mU*mG*mA | 839 | XXXXXXXXXX XXXXXXXXXX XXXX | 25-mer 2'-OMethyl | DMD |
| WV-2253 | GGUAAGUUCU GUCCAAGCCCG GUUG | 88 | mG*mG*mU*mA*mA*mG*mU*mU*mC*mU* mG*mU*mC*mC*mA*mA*mG*mC*mC*mC* mG*mG*mU*mU*mG | 840 | XXXXXXXXXX XXXXXXXXXX XXXX | 25-mer 2'-OMethyl | DMD |
| WV-2254 | CGGUAAGUUC UGUCCAAGCCC GGUU | 89 | mC*mG*mG*mU*mA*mA*mG*mU*mU*mC* mU*mG*mU*mC*mC*mA*mA*mG*mC*mC* mC*mG*mG*mU*mU | 841 | XXXXXXXXXX XXXXXXXXXX XXXX | 25-mer 2'-OMethyl | DMD |
| WV-2255 | UCGGUAAGUU CUGUCCAAGCC CGGU | 90 | mU*mC*mG*mG*mU*mA*mA*mG*mU*mU* mC*mU*mG*mU*mC*mC*mA*mA*mG*mC* mC*mC*mG*mG*mU | 842 | XXXXXXXXXX XXXXXXXXXX XXXX | 25-mer 2'-OMethyl | DMD |
| WV-2256 | GUCGGUAAGU UCUGUCCAAGC CCGG | 91 | mG*mU*mC*mG*mG*mU*mA*mA*mG*mU* mU*mC*mU*mG*mU*mC*mC*mA*mA*mG* mC*mC*mC*mG*mG | 843 | XXXXXXXXXX XXXXXXXXXX XXXX | 25-mer 2'-OMethyl | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2257 | AGUCGGUAAG UUCUGUCCAA GCCCG | 92 | mA*mG*mU*mC*mG*mG*mU*mA*mA*mG* mU*mU*mC*mU*mG*mU*mC*mC*mA*mA* mG*mC*mC*mC*mG | 844 | XXXXXXXXXX XXXXXXXXXX XXXX | 25-mer 2'-OMethyl | DMD |
| WV-2258 | CAGUCGGUAA GUUCUGUCCA AGCCC | 93 | mC*mA*mG*mU*mC*mG*mG*mU*mA*mA* mG*mU*mU*mC*mU*mG*mU*mC*mC*mA* mA*mG*mC*mC*mC | 845 | XXXXXXXXXX XXXXXXXXXX XXXX | 25-mer 2'-OMethyl | DMD |
| WV-2259 | AAAGCCAGUC GGUAAGUUCU GUCCA | 94 | mA*mA*mA*mG*mC*mC*mA*mG*mU*mC* mG*mG*mU*mA*mA*mG*mU*mU*mC*mU* mG*mU*mC*mC*mA | 846 | XXXXXXXXXX XXXXXXXXXX XXXX | 25-mer 2'-OMethyl | DMD |
| WV-2260 | GAAAGCCAGU CGGUAAGUUC UGUCC | 95 | mG*mA*mA*mA*mG*mC*mC*mA*mG*mU* mC*mG*mG*mU*mA*mA*mG*mU*mU*mC* mU*mG*mU*mC*mC | 847 | XXXXXXXXXX XXXXXXXXXX XXXX | 25-mer 2'-OMethyl | DMD |
| WV-2261 | GUCACCCACCA UCACCCUCUGU GAU | 96 | mG*mU*mC*mA*mC*mC*mC*mA*mC*mC* mA*mU*mC*mA*mC*mC*mC*mU*mC*mU* mG*mU*mG*mA*mU | 848 | XXXXXXXXXX XXXXXXXXXX XXXX | 25-mer 2'-OMethyl | DMD |
| WV-2262 | GGUCACCCACC AUCACCCUCUG UGA | 97 | mG*mG*mU*mC*mA*mC*mC*mC*mA*mC* mC*mA*mU*mC*mA*mC*mC*mC*mU*mC* mU*mG*mU*mG*mA | 849 | XXXXXXXXXX XXXXXXXXXX XXXX | 25-mer 2'-OMethyl | DMD |
| WV-2263 | AAGGUCACCCA CCAUCACCCUC UGU | 98 | mA*mA*mG*mG*mU*mC*mA*mC*mC*mC* mA*mC*mC*mA*mU*mC*mA*mC*mC*mC* mU*mC*mU*mG*mU | 850 | XXXXXXXXXX XXXXXXXXXX XXXX | 25-mer 2'-OMethyl | DMD |
| WV-2264 | CAAGGUCACCC ACCAUCACCCU CUG | 99 | mC*mA*mA*mG*mG*mU*mC*mA*mC*mC* mC*mA*mC*mC*mA*mU*mC*mA*mC*mC* mC*mU*mC*mU*mG | 851 | XXXXXXXXXX XXXXXXXXXX XXXX | 25-mer 2'-OMethyl | DMD |
| WV-2265 | UCAAGGUCACC CACCAUCACCC UCU | 100 | mU*mC*mA*mA*mG*mG*mU*mC*mA*mC* mC*mC*mA*mC*mC*mA*mU*mC*mA*mC* mC*mC*mU*mC*mU | 852 | XXXXXXXXXX XXXXXXXXXX XXXX | 25-mer 2'-OMethyl | DMD |
| WV-2266 | CUCAAGGUCAC CCACCAUCACC CUC | 101 | mC*mU*mC*mA*mA*mG*mG*mU*mC*mA* mC*mC*mC*mA*mC*mC*mA*mU*mC*mA* mC*mC*mC*mU*mC | 853 | XXXXXXXXXX XXXXXXXXXX XXXX | 25-mer 2'-OMethyl | DMD |
| WV-2267 | CUUGAUCAAG CAGAGAAAGC CAGUC | 102 | mC*mU*mU*mG*mA*mU*mC*mA*mA*mG* mC*mA*mG*mA*mG*mA*mA*mA*mG*mC* mC*mA*mG*mU*mC | 854 | XXXXXXXXXX XXXXXXXXXX XXXX | 25-mer 2'-OMethyl | DMD |
| WV-2268 | AUAACUUGAU CAAGCAGAGA AAGCC | 103 | mA*mU*mA*mA*mC*mU*mU*mG*mA*mU* mC*mA*mA*mG*mC*mA*mG*mA*mG*mA* mA*mA*mG*mC*mC | 855 | XXXXXXXXXX XXXXXXXXXX XXXX | 20-mer 2'-OMethyl | DMD |
| WV-2273 | AGUAACAGUC UGAGUAGGAG | 104 | mA*mG*mU*mA*mA*mC*mA*mG*mU*mC* mU*mG*mA*mG*mU*mA*mG*mG*mA*mG | 856 | XXXXXXXXXX XXXXXXXXX | 20-mer 2'-OMethyl | DMD |
| WV-2274 | GAGUAACAGU CUGAGUAGGA | 105 | mG*mA*mG*mU*mA*mA*mC*mA*mG*mU* mC*mU*mG*mA*mG*mU*mA*mG*mG*mA | 857 | XXXXXXXXXX XXXXXXXXX | 20-mer 2'-OMethyl | DMD |
| WV-2275 | AGAGUAACAG UCUGAGUAGG | 106 | mA*mG*mA*mG*mU*mA*mA*mC*mA*mG* mU*mC*mU*mG*mA*mG*mU*mA*mG*mG | 858 | XXXXXXXXXX XXXXXXXXX | 20-mer 2'-OMethyl | DMD |
| WV-2276 | CAGAGUAACA GUCUGAGUAG | 107 | mC*mA*mG*mA*mG*mU*mA*mA*mC*mA* mG*mU*mC*mU*mG*mA*mG*mU*mA*mG | 859 | XXXXXXXXXX XXXXXXXXX | 20-mer 2'-OMethyl | DMD |
| WV-2277 | GUCACCAGAG UAACAGUCUG | 108 | mG*mU*mC*mA*mC*mC*mA*mG*mA*mG* mU*mA*mA*mC*mA*mG*mU*mC*mU*mG | 860 | XXXXXXXXXX XXXXXXXXX | 20-mer 2'-OMethyl | DMD |
| WV-2278 | UGUCACCAGA GUAACAGUCU | 109 | mU*mG*mU*mC*mA*mC*mC*mA*mG*mA* mG*mU*mA*mA*mC*mA*mG*mU*mC*mU | 861 | XXXXXXXXXX XXXXXXXXX | 20-mer 2'-OMethyl | DMD |
| WV-2279 | GUGUCACCAG AGUAACAGUC | 110 | mG*mU*mG*mU*mC*mA*mC*mC*mA*mG* mA*mG*mU*mA*mA*mC*mA*mG*mU*mC | 862 | XXXXXXXXXX XXXXXXXXX | 20-mer 2'-OMethyl | DMD |
| WV-2280 | UGUGUCACCA GAGUAACAGU | 111 | mU*mG*mU*mG*mU*mC*mA*mC*mC*mA* mG*mA*mG*mU*mA*mA*mC*mA*mG*mU | 863 | XXXXXXXXXX XXXXXXXXX | 20-mer 2'-OMethyl | DMD |
| WV-2281 | UUGUGUCACC AGAGUAACAG | 112 | mU*mU*mG*mU*mG*mU*mC*mA*mC*mC* mA*mG*mA*mG*mU*mA*mA*mC*mA*mG | 864 | XXXXXXXXXX XXXXXXXXX | 20-mer 2'-OMethyl | DMD |
| WV-2282 | GGUUGUGUCA CCAGAGUAAC | 113 | mG*mG*mU*mU*mG*mU*mG*mU*mC*mA* mC*mC*mA*mG*mA*mG*mU*mA*mA*mC | 865 | XXXXXXXXXX XXXXXXXXX | 20-mer 2'-OMethyl | DMD |
| WV-2283 | AGGUUGUGUC ACCAGAGUAA | 114 | mA*mG*mG*mU*mU*mG*mU*mG*mU*mC* mA*mC*mC*mA*mG*mA*mG*mU*mA*mA | 866 | XXXXXXXXXX XXXXXXXXX | 20-mer 2'-OMethyl | DMD |
| WV-2284 | CAGGUUGUGU CACCAGAGUA | 115 | mC*mA*mG*mG*mU*mU*mG*mU*mG*mU* mC*mA*mC*mC*mA*mG*mA*mG*mU*mA | 867 | XXXXXXXXXX XXXXXXXXX | 20-mer 2'-OMethyl | DMD |
| WV-2285 | ACAGGUUGUG UCACCAGAGU | 116 | mA*mC*mA*mG*mG*mU*mU*mG*mU*mG* mU*mC*mA*mC*mC*mA*mG*mA*mG*mU | 868 | XXXXXXXXXX XXXXXXXXX | 20-mer 2'-OMethyl | DMD |
| WV-2286 | CACAGGUUGU GUCACCAGAG | 117 | mC*mA*mC*mA*mG*mG*mU*mU*mG*mU* mG*mU*mC*mA*mC*mC*mA*mG*mA*mG | 869 | XXXXXXXXXX XXXXXXXXX | 20-mer 2'-OMethyl | DMD |
| WV-2287 | CCACAGGUUG UGUCACCAGA | 118 | mC*mC*mA*mC*mA*mG*mG*mU*mU*mG* mU*mG*mU*mC*mA*mC*mC*mA*mG*mA | 870 | XXXXXXXXXX XXXXXXXXX | 20-mer 2'-OMethyl | DMD |
| WV-2288 | ACCACAGGUU GUGUCACCAG | 119 | mA*mC*mC*mA*mC*mA*mG*mG*mU*mU* mG*mU*mG*mU*mC*mA*mC*mC*mA*mG | 871 | XXXXXXXXXX XXXXXXXXX | 20-mer 2'-OMethyl | DMD |
| WV-2289 | AACCACAGGU UGUGUCACCA | 120 | mA*mA*mC*mC*mA*mC*mA*mG*mG*mU* mU*mG*mU*mG*mU*mC*mA*mC*mC*mA | 872 | XXXXXXXXXX XXXXXXXXX | 20-mer 2'-OMethyl | DMD |
| WV-2290 | UAACCACAGG UUGUGUCACC | 121 | mU*mA*mA*mC*mC*mA*mC*mA*mG*mG* mU*mU*mG*mU*mG*mU*mC*mA*mC*mC | 873 | XXXXXXXXXX XXXXXXXXX | 20-mer 2'-OMethyl | DMD |
| WV- | GUAACCACAG | 122 | mG*mU*mA*mA*mC*mC*mA*mC*mA*mG* | 874 | XXXXXXXXXX | 20-mer 2'- | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| | GUUGUGUCAC | | mG*mU*mU*mG*mU*mG*mU*mC*mA*mC | | | OMethyl | |
| WV-2292 | AGUAACCACA GGUUGUGUCA | 123 | mA*mG*mU*mA*mA*mC*mC*mA*mC*mA* mG*mU*mU*mG*mU*mG*mU*mU*mC*mA | 875 | XXXXXXXXXX XXXXXXXXXX | 20-mer 2'-OMethyl | DMD |
| WV-2293 | CUUAGUAACC ACAGGUUGUG | 124 | mC*mU*mU*mA*mG*mU*mA*mA*mC*mC* mA*mC*mA*mG*mG*mU*mU*mG*mU*mG | 876 | XXXXXXXXXX XXXXXXXXXX | 20-mer 2'-OMethyl | DMD |
| WV-2294 | CCUUAGUAACC ACAGGUUGU | 125 | mC*mC*mU*mU*mA*mG*mU*mA*mA*mC* mC*mA*mC*mA*mG*mG*mU*mU*mG*mU | 877 | XXXXXXXXXX XXXXXXXXXX | 20-mer 2'-OMethyl | DMD |
| WV-2295 | UCCUUAGUAA CCACAGGUUG | 126 | mU*mC*mC*mU*mU*mA*mG*mU*mA*mA* mC*mC*mA*mC*mA*mG*mG*mU*mU*mG | 878 | XXXXXXXXXX XXXXXXXXXX | 20-mer 2'-OMethyl | DMD |
| WV-2296 | UUCCUUAGUA ACCACAGGUU | 127 | mU*mU*mC*mC*mU*mU*mA*mG*mU*mA* mA*mC*mC*mA*mC*mA*mG*mG*mU*mU | 879 | XXXXXXXXXX XXXXXXXXXX | 20-mer 2'-OMethyl | DMD |
| WV-2297 | UUUCCUUAGU AACCACAGGU | 128 | mU*mU*mU*mC*mC*mU*mU*mA*mG*mU* mA*mA*mC*mC*mA*mC*mA*mG*mG*mU | 880 | XXXXXXXXXX XXXXXXXXXX | 20-mer 2'-OMethyl | DMD |
| WV-2298 | GUUUCCUUAG UAACCACAGG | 129 | mG*mU*mU*mU*mC*mC*mU*mU*mA*mG* mU*mA*mA*mC*mC*mA*mC*mA*mG*mG | 881 | XXXXXXXXXX XXXXXXXXXX | 20-mer 2'-OMethyl | DMD |
| WV-2299 | AGUUUCCUUA GUAACCACAG | 130 | mA*mG*mU*mU*mU*mC*mC*mU*mU*mA* mG*mU*mA*mA*mC*mC*mA*mC*mA*mG | 882 | XXXXXXXXXX XXXXXXXXXX | 20-mer 2'-OMethyl | DMD |
| WV-2300 | GCAGUUUCCU UAGUAACCAC | 131 | mG*mC*mA*mG*mU*mU*mU*mC*mC*mU* mU*mA*mG*mU*mA*mA*mC*mC*mA*mC | 883 | XXXXXXXXXX XXXXXXXXXX | 20-mer 2'-OMethyl | DMD |
| WV-2301 | GGCAGUUUCC UUAGUAACCA | 132 | mG*mG*mC*mA*mG*mU*mU*mU*mC*mC* mU*mU*mA*mG*mU*mA*mA*mC*mC*mA | 884 | XXXXXXXXXX XXXXXXXXXX | 20-mer 2'-OMethyl | DMD |
| WV-2302 | UGGCAGUUUC CUUAGUAACC | 133 | mU*mG*mG*mC*mA*mG*mU*mU*mU*mC* mC*mU*mU*mA*mG*mU*mA*mA*mC*mC | 885 | XXXXXXXXXX XXXXXXXXXX | 20-mer 2'-OMethyl | DMD |
| WV-2303 | AUGGCAGUUU CCUUAGUAAC | 134 | mA*mU*mG*mG*mC*mA*mG*mU*mU*mU* mC*mC*mU*mU*mA*mG*mU*mA*mA*mC | 886 | XXXXXXXXXX XXXXXXXXXX | 20-mer 2'-OMethyl | DMD |
| WV-2304 | GAUGGCAGUU UCCUUAGUAA | 135 | mG*mA*mU*mG*mG*mC*mA*mG*mU*mU* mU*mC*mC*mU*mU*mA*mG*mU*mA*mA | 887 | XXXXXXXXXX XXXXXXXXXX | 20-mer 2'-OMethyl | DMD |
| WV-2305 | AGAUGGCAGU UUCCUUAGUA | 136 | mA*mG*mA*mU*mG*mG*mC*mA*mG*mU* mU*mU*mC*mC*mU*mU*mA*mG*mU*mA | 888 | XXXXXXXXXX XXXXXXXXXX | 20-mer 2'-OMethyl | DMD |
| WV-2306 | GGAGAUGGCA GUUUCCUUAG | 137 | mG*mG*mA*mG*mA*mU*mG*mG*mC*mA* mG*mU*mU*mU*mC*mC*mU*mU*mA*mG | 889 | XXXXXXXXXX XXXXXXXXXX | 20-mer 2'-OMethyl | DMD |
| WV-2307 | UGGAGAUGGC AGUUUCCUUA | 138 | mU*mG*mG*mA*mG*mA*mU*mG*mG*mC* mA*mG*mU*mU*mU*mC*mC*mU*mU*mA | 890 | XXXXXXXXXX XXXXXXXXXX | 20-mer 2'-OMethyl | DMD |
| WV-2308 | UUGGAGAUGG CAGUUUCCUU | 139 | mU*mU*mG*mG*mA*mG*mA*mU*mG*mG* mC*mA*mG*mU*mU*mU*mC*mC*mU*mU | 891 | XXXXXXXXXX XXXXXXXXXX | 20-mer 2'-OMethyl | DMD |
| WV-2309 | UUUGGAGAUG GCAGUUUCCU | 140 | mU*mU*mU*mG*mG*mA*mG*mA*mU*mG* mG*mC*mA*mG*mU*mU*mU*mC*mC*mU | 892 | XXXXXXXXXX XXXXXXXXXX | 20-mer 2'-OMethyl | DMD |
| WV-2310 | GUUUGGAGAU GGCAGUUUCC | 141 | mG*mU*mU*mU*mG*mG*mA*mG*mA*mU* mG*mG*mC*mA*mG*mU*mU*mU*mC*mC | 893 | XXXXXXXXXX XXXXXXXXXX | 20-mer 2'-OMethyl | DMD |
| WV-2311 | CUAGUUUGGA GAUGGCAGUU | 142 | mC*mU*mA*mG*mU*mU*mU*mG*mG*mA* mG*mA*mU*mG*mG*mC*mA*mG*mU*mU | 894 | XXXXXXXXXX XXXXXXXXXX | 20-mer 2'-OMethyl | DMD |
| WV-2312 | UCUAGUUUGG AGAUGGCAGU | 143 | mU*mC*mU*mA*mG*mU*mU*mU*mG*mG* mA*mG*mA*mU*mG*mG*mC*mA*mG*mU | 895 | XXXXXXXXXX XXXXXXXXXX | 20-mer 2'-OMethyl | DMD |
| WV-2313 | AUUUCUAGUU UGGAGAUGGC | 144 | mA*mU*mU*mU*mC*mU*mA*mG*mU*mU* mU*mG*mG*mA*mG*mA*mU*mG*mG*mC | 896 | XXXXXXXXXX XXXXXXXXXX | 20-mer 2'-OMethyl | DMD |
| WV-2314 | UGGCAUUUCU AGUUUGGAGA | 145 | mU*mG*mG*mC*mA*mU*mU*mU*mC*mU* mA*mG*mU*mU*mU*mG*mG*mA*mG*mA | 897 | XXXXXXXXXX XXXXXXXXXX | 20-mer 2'-OMethyl | DMD |
| WV-2315 | GAUGGCAUUU CUAGUUUGGA | 146 | mG*mA*mU*mG*mG*mC*mA*mU*mU*mU* mC*mU*mA*mG*mU*mU*mU*mG*mG*mA | 898 | XXXXXXXXXX XXXXXXXXXX | 20-mer 2'-OMethyl | DMD |
| WV-2316 | AGAUGGCAUU UCUAGUUUGG | 147 | mA*mG*mA*mU*mG*mG*mC*mA*mU*mU* mU*mC*mU*mA*mG*mU*mU*mU*mG*mG | 899 | XXXXXXXXXX XXXXXXXXXX | 20-mer 2'-OMethyl | DMD |
| WV-2317 | AAGAUGGCAU UUCUAGUUUG | 148 | mA*mA*mG*mA*mU*mG*mG*mC*mA*mU* mU*mC*mU*mA*mU*mU*mU*mU*mU*mG | 900 | XXXXXXXXXX XXXXXXXXXX | 20-mer 2'-OMethyl | DMD |
| WV-2318 | AGGAAGAUGG CAUUUCUAGU | 149 | mA*mG*mG*mA*mA*mG*mA*mU*mG*mG* mC*mA*mU*mU*mU*mC*mU*mA*mG*mU | 901 | XXXXXXXXXX XXXXXXXXXX | 20-mer 2'-OMethyl | DMD |
| WV-2319 | AAGGAAGAUG GCAUUUCUAG | 150 | mA*mA*mG*mG*mA*mA*mG*mA*mU*mG* mG*mC*mA*mU*mU*mU*mC*mU*mA*mG | 902 | XXXXXXXXXX XXXXXXXXXX | 20-mer 2'-OMethyl | DMD |
| WV-2320 | CAAGGAAGAU GGCAUUUCUA | 151 | mC*mA*mA*mG*mG*mA*mA*mG*mA*mU* mG*mG*mC*mA*mU*mU*mU*mC *mU*mA | 903 | XXXXXXXXXX XXXXXXXXXX | 20-mer 2'-OMethyl | DMD |
| WV-2321 | UCAAGGAAGA UGGCAUUUCU | 152 | mU*mC*mA*mA*mG*mG*mA*mA*mG*mA* mU*mG*mG*mC*mA*mU*mU*mU*mC*mU | 904 | XXXXXXXXXX XXXXXXXXXX | 20-mer 2'-OMethyl | DMD |
| WV-2322 | ACAUCAAGGA AGAUGGCAUU | 153 | mA*mC*mA*mU*mC*mA*mA*mG*mG*mA* mA*mG*mA*mU*mG*mG*mC*mA*mU*mU | 905 | XXXXXXXXXX XXXXXXXXXX | 20-mer 2'-OMethyl | DMD |
| WV-2323 | CAACAUCAAG GAAGAUGGCA | 154 | mC*mA*mA*mC*mA*mU*mC*mA*mA*mG* mG*mA*mA*mG*mA*mU*mG*mG*mC*mA | 906 | XXXXXXXXXX XXXXXXXXXX | 20-mer 2'-OMethyl | DMD |
| WV-2324 | UCCAACAUCAA GGAAGAUGG | 155 | mU*mC*mC*mA*mA*mC*mA*mU*mC*mA* mA*mG*mG*mA*mA*mG*mA*mU*mG*mG | 907 | XXXXXXXXXX XXXXXXXXXX | 20-mer 2'-OMethyl | DMD |
| WV-2325 | CCUCCAACAUC AAGGAAGAU | 156 | mC*mC*mU*mC*mC*mA*mA*mC*mA*mU* mC*mA*mA*mG*mG*mA*mA*mG*mA*mU | 908 | XXXXXXXXXX XXXXXXXXXX | 20-mer 2'-OMethyl | DMD |
| WV-2326 | AGGUACCUCCA ACAUCAAGG | 157 | mA*mG*mG*mU*mA*mC*mC*mU*mC*mC* mA*mA*mC*mA*mU*mC*mA*mA*mG*mG | 909 | XXXXXXXXXX XXXXXXXXXX | 20-mer 2'-OMethyl | DMD |
| WV-2327 | CAGGUACCUCC AACAUCAAG | 158 | mC*mA*mG*mG*mU*mA*mC*mC*mU*mC* mC*mA*mA*mC*mA*mU*mC*mA*mA*mG | 910 | XXXXXXXXXX XXXXXXXXXX | 20-mer 2'-OMethyl | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2328 | AGAGCAGGUACCUCCAACAU | 159 | mA*mG*mA*mG*mC*mA*mG*mG*mU*mA*mC*mC*mU*mC*mC*mA*mA*mC*mA*mU | 911 | XXXXXXXXXXXXXXXXXXX | 20-mer 2'-OMethyl | DMD |
| WV-2329 | CAGAGCAGGUACCUCCAACA | 160 | mC*mA*mG*mA*mG*mC*mA*mG*mG*mU*mA*mC*mC*mU*mC*mC*mA*mA*mC*mA | 912 | XXXXXXXXXXXXXXXXXXX | 20-mer 2'-OMethyl | DMD |
| WV-2330 | CCAGAGCAGGUACCUCCAAC | 161 | mC*mC*mA*mG*mA*mG*mC*mA*mG*mG*mU*mA*mC*mC*mU*mC*mC*mA*mA*mC | 913 | XXXXXXXXXXXXXXXXXXX | 20-mer 2'-OMethyl | DMD |
| WV-2331 | GCCAGAGCAGGUACCUCCAA | 162 | mG*mC*mC*mA*mG*mA*mG*mC*mA*mG*mG*mU*mA*mC*mC*mU*mC*mC*mA*mA | 914 | XXXXXXXXXXXXXXXXXXX | 20-mer 2'-OMethyl | DMD |
| WV-2332 | UGCCAGAGCAGGUACCUCCA | 163 | mU*mG*mC*mC*mA*mG*mA*mG*mC*mA*mG*mG*mU*mA*mC*mC*mU*mC*mC*mA | 915 | XXXXXXXXXXXXXXXXXXX | 20-mer 2'-OMethyl | DMD |
| WV-2333 | CUGCCAGAGCAGGUACCUCC | 164 | mC*mU*mG*mC*mC*mA*mG*mA*mG*mC*mA*mG*mG*mU*mA*mC*mC*mU*mC*mC | 916 | XXXXXXXXXXXXXXXXXXX | 20-mer 2'-OMethyl | DMD |
| WV-2334 | UCUGCCAGAGCAGGUACCUC | 165 | mU*mC*mU*mG*mC*mC*mA*mG*mA*mG*mC*mA*mG*mG*mU*mA*mC*mC*mU*mC | 917 | XXXXXXXXXXXXXXXXXXX | 20-mer 2'-OMethyl | DMD |
| WV-2335 | AUCUGCCAGAGCAGGUACCU | 166 | mA*mU*mC*mU*mG*mC*mC*mA*mG*mA*mG*mC*mA*mG*mG*mU*mA*mC*mC*mU | 918 | XXXXXXXXXXXXXXXXXXX | 20-mer 2'-OMethyl | DMD |
| WV-2336 | UUGAAAUCUGCCAGAGCAGG | 167 | mU*mU*mG*mA*mA*mA*mU*mC*mU*mG*mC*mC*mA*mG*mA*mG*mC*mA*mG*mG | 919 | XXXXXXXXXXXXXXXXXXX | 20-mer 2'-OMethyl | DMD |
| WV-2337 | CCCGGUUGAAAUCUGCCAGA | 168 | mC*mC*mC*mG*mG*mU*mU*mG*mA*mA*mA*mU*mC*mU*mG*mC*mC*mA*mG*mA | 920 | XXXXXXXXXXXXXXXXXXX | 20-mer 2'-OMethyl | DMD |
| WV-2338 | GCCCGGUUGAAAUCUGCCAG | 169 | mG*mC*mC*mC*mG*mG*mU*mU*mG*mA*mA*mA*mU*mC*mU*mG*mC*mC*mA*mG | 921 | XXXXXXXXXXXXXXXXXXX | 20-mer 2'-OMethyl | DMD |
| WV-2339 | AGCCCGGUUGAAAUCUGCCA | 170 | mA*mG*mC*mC*mC*mG*mG*mU*mU*mG*mA*mA*mA*mU*mC*mU*mG*mC*mC*mA | 922 | XXXXXXXXXXXXXXXXXXX | 20-mer 2'-OMethyl | DMD |
| WV-2340 | CCAAGCCCGGUUGAAAUCUG | 171 | mC*mC*mA*mA*mG*mC*mC*mC*mG*mG*mU*mU*mG*mA*mA*mA*mU*mC*mU*mG | 923 | XXXXXXXXXXXXXXXXXXX | 20-mer 2'-OMethyl | DMD |
| WV-2341 | UCCAAGCCCGGUUGAAAUCU | 172 | mU*mC*mC*mA*mA*mG*mC*mC*mC*mG*mG*mU*mU*mG*mA*mA*mA*mU*mC*mU | 924 | XXXXXXXXXXXXXXXXXXX | 20-mer 2'-OMethyl | DMD |
| WV-2342 | GUCCAAGCCCGGUUGAAAUC | 173 | mG*mU*mC*mC*mA*mA*mG*mC*mC*mC*mG*mG*mU*mU*mG*mA*mA*mA*mU*mC | 925 | XXXXXXXXXXXXXXXXXXX | 20-mer 2'-OMethyl | DMD |
| WV-2343 | UGUCCAAGCCCGGUUGAAAU | 174 | mU*mG*mU*mC*mC*mA*mA*mG*mC*mC*mC*mG*mG*mU*mU*mG*mA*mA*mA*mU | 926 | XXXXXXXXXXXXXXXXXXX | 20-mer 2'-OMethyl | DMD |
| WV-2344 | CUGUCCAAGCCCGGUUGAAA | 175 | mC*mU*mG*mU*mC*mC*mA*mA*mG*mC*mC*mC*mG*mG*mU*mU*mG*mA*mA*mA | 927 | XXXXXXXXXXXXXXXXXXX | 20-mer 2'-OMethyl | DMD |
| WV-2345 | UCUGUCCAAGCCCGGUUGAA | 176 | mU*mC*mU*mG*mU*mC*mC*mA*mA*mG*mC*mC*mC*mG*mG*mU*mU*mG*mA*mA | 928 | XXXXXXXXXXXXXXXXXXX | 20-mer 2'-OMethyl | DMD |
| WV-2346 | UUCUGUCCAAGCCCGGUUGA | 177 | mU*mU*mC*mU*mG*mU*mC*mC*mA*mA*mG*mC*mC*mC*mG*mG*mU*mU*mG*mA | 929 | XXXXXXXXXXXXXXXXXXX | 20-mer 2'-OMethyl | DMD |
| WV-2347 | GUUCUGUCCAAGCCCGGUUG | 178 | mG*mU*mU*mC*mU*mG*mU*mC*mC*mA*mA*mG*mC*mC*mC*mG*mG*mU*mU*mG | 930 | XXXXXXXXXXXXXXXXXXX | 20-mer 2'-OMethyl | DMD |
| WV-2348 | AGUUCUGUCCAAGCCCGGUU | 179 | mA*mG*mU*mU*mC*mU*mG*mU*mC*mC*mA*mA*mG*mC*mC*mC*mG*mG*mU*mU | 931 | XXXXXXXXXXXXXXXXXXX | 20-mer 2'-OMethyl | DMD |
| WV-2349 | AAGUUCUGUCCAAGCCCGGU | 180 | mA*mA*mG*mU*mU*mC*mU*mG*mU*mC*mC*mA*mA*mG*mC*mC*mC*mG*mG*mU | 932 | XXXXXXXXXXXXXXXXXXX | 20-mer 2'-OMethyl | DMD |
| WV-2350 | UAAGUUCUGUCCAAGCCCGG | 181 | mU*mA*mA*mG*mU*mU*mC*mU*mG*mU*mC*mC*mA*mA*mG*mC*mC*mC*mG*mG | 933 | XXXXXXXXXXXXXXXXXXX | 20-mer 2'-OMethyl | DMD |
| WV-2351 | GUAAGUUCUGUCCAAGCCCG | 182 | mG*mU*mA*mA*mG*mU*mU*mC*mU*mG*mU*mC*mC*mA*mA*mG*mC*mC*mC*mG | 934 | XXXXXXXXXXXXXXXXXXX | 20-mer 2'-OMethyl | DMD |
| WV-2352 | GGUAAGUUCUGUCCAAGCCC | 183 | mG*mG*mU*mA*mA*mG*mU*mU*mC*mU*mG*mU*mC*mC*mA*mA*mG*mC*mC*mC | 935 | XXXXXXXXXXXXXXXXXXX | 20-mer 2'-OMethyl | DMD |
| WV-2353 | CAGUCGGUAAGUUCUGUCCA | 184 | mC*mA*mG*mU*mC*mG*mG*mU*mA*mA*mG*mU*mU*mC*mU*mG*mU*mC*mC*mA | 936 | XXXXXXXXXXXXXXXXXXX | 20-mer 2'-OMethyl | DMD |
| WV-2354 | CCAGUCGGUAAGUUCUGUCC | 185 | mC*mC*mA*mG*mU*mC*mG*mG*mU*mA*mA*mG*mU*mU*mC*mU*mG*mU*mC*mC | 937 | XXXXXXXXXXXXXXXXXXX | 20-mer 2'-OMethyl | DMD |
| WV-2355 | CCACCAUCACCCUCUGUGAU | 186 | mC*mC*mA*mC*mC*mA*mU*mC*mA*mC*mC*mC*mU*mC*mU*mG*mU*mG*mA*mU | 938 | XXXXXXXXXXXXXXXXXXX | 20-mer 2'-OMethyl | DMD |
| WV-2356 | CCCACCAUCACCCUCUGUGA | 187 | mC*mC*mC*mA*mC*mC*mA*mU*mC*mA*mC*mC*mC*mU*mC*mU*mG*mU*mG*mA | 939 | XXXXXXXXXXXXXXXXXXX | 20-mer 2'-OMethyl | DMD |
| WV-2357 | CACCCACCAUCACCCUCUGU | 188 | mC*mA*mC*mC*mC*mA*mC*mC*mA*mU*mC*mA*mC*mC*mC*mU*mC*mU*mG*mU | 940 | XXXXXXXXXXXXXXXXXXX | 20-mer 2'-OMethyl | DMD |
| WV-2358 | UCACCCACCAUCACCCUCUG | 189 | mU*mC*mA*mC*mC*mC*mA*mC*mC*mA*mU*mC*mA*mC*mC*mC*mU*mC*mU*mG | 941 | XXXXXXXXXXXXXXXXXXX | 20-mer 2'-OMethyl | DMD |
| WV-2359 | GUCACCCACCAUCACCCUCU | 190 | mG*mU*mC*mA*mC*mC*mC*mA*mC*mC*mA*mU*mC*mA*mC*mC*mC*mU*mC*mU | 942 | XXXXXXXXXXXXXXXXXXX | 20-mer 2'-OMethyl | DMD |
| WV-2360 | GGUCACCCACCAUCACCCUC | 191 | mG*mG*mU*mC*mA*mC*mC*mC*mA*mC*mC*mA*mU*mC*mA*mC*mC*mC*mU*mC | 943 | XXXXXXXXXXXXXXXXXXX | 20-mer 2'-OMethyl | DMD |
| WV-2361 | UCAAGCAGAGAAAGCCAGUC | 192 | mU*mC*mA*mA*mG*mC*mA*mG*mA*mG*mA*mA*mA*mG*mC*mC*mA*mG*mU*mC | 944 | XXXXXXXXXXXXXXXXXXX | 20-mer 2'-OMethyl | DMD |
| WV-2362 | UUGAUCAAGCAGAGAAAGCC | 193 | mU*mU*mG*mA*mU*mC*mA*mA*mG*mC*mA*mG*mA*mG*mA*mA*mA*mG*mC*mC | 945 | XXXXXXXXXXXXXXXXXXX | 20-mer 2'-OMethyl | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2625 | CAAAGAAGAU GGCAUUUCUA GUUUG | 194 | mC*mA*mA*mA*mG*mA*mA*mG*mA*mU* mG*mG*mC*mA*mU*mU*mU*mC*mU*mA* mG*mU*mU*mU*mG | 946 | XXXXXXXXXX XXXXXXXXXX XXXX | based on WV-2223 match mouse target sequence | DMD |
| WV-2627 | GCAAAGAAGA UGGCAUUUCU | 195 | mG*mC*mA*mA*mA*mG*mA*mA*mG*mA* mU*mG*mG*mC*mA*mU*mU*mU*mC*mU | 947 | XXXXXXXXXX XXXXXXXXXX | based on WV-942 match mouse target sequence | DMD |
| WV-2628 | GCAAAGAAGA UGGCAUUUCU | 196 | fG*fC*fA*fA*fA*fG*mA*mA*mG*mA*mU* mG*mG*mC*fA*fU*fU*fU*fC*fU | 948 | XXXXXXXXXX XXXXXXXX | based on WV-1714 match mouse target sequence | DMD |
| WV-2095 | UCAAGGAAGA UGGCAUUUCU | 197 | fU*fC*fA*fA*fG*mG*mA*mA*mG*mA*mU* mG*mG*mC*fA*fU*fU*fU*fC*fU | 949 | XXXXXXXXXX XXXXXXXX | Exon51: 5F-10OMe-5F all-PS | DMD Exon51 |
| WV-2096 | UCAAGGAAGA UGGCAUUUCU | 198 | fU*fC*fA*fA*mG*mG*mA*mA*mG*mA*mU* mG*mG*mC*mA*mU*fU*fU*fC*fU | 950 | XXXXXXXXXX XXXXXXXX | Exon51: 4F-12OMe-4F all-PS | DMD Exon51 |
| WV-2097 | UCAAGGAAGA UGGCAUUUCU | 199 | fU*fC*fA*mA*mG*mG*mA*mA*mG*mA*mU *mG*mG*mC*mA*mU*mU*fU*fC*fU | 951 | XXXXXXXXXX XXXXXXXX | Exon51: 3F-14OMe-3F all-PS | DMD Exon51 |
| WV-2098 | UCAAGGAAGA UGGCAUUUCU | 200 | fU*fC*fA*mA*mG*mG*mA*mA*mG*mA* mU*mG*mG*mC*mA*mU*mU*mU*fC*fU | 952 | XXXXXXXXXX XXXXXXXX | Exon51: 2F-16OMe-2F all-PS | DMD Exon51 |
| WV-2099 | UCAAGGAAGA UGGCAUUUCU | 201 | fU*mC*mA*mA*mG*mG*mA*mA*mG*mA* mU*mG*mG*mC*mA*mU*mU*mU*mC*fU | 953 | XXXXXXXXXX XXXXXXXX | Exon51: 1F - 18OMe-1F all-PS | DMD Exon51 |
| WV-2100 | UCAAGGAAGA UGGCAUUUCU | 202 | fU*fC*fA*fA*fG*fGmA*mA*mG*mA*mU*mG *mG*mCfA*fU*fU*fU*fC*fU | 954 | XXXXXOXXXX XXXOXXXXX | Exon51: 6F-8OMe-6F 5PS-1PO-7PS-1PO-5PS | DMD Exon51 |
| WV-2101 | UCAAGGAAGA UGGCAUUUCU | 203 | fU*fC*fA*fA*fGfGmA*mA*mG*mA*mU*mG* mG*mCfAfU*fU*fU*fC*fU | 955 | XXXXOOXXXX XXXOOXXXX | Exon51: 6F-8OMe-6F 4PS-2PO-7PS-2PO-4PS | DMD Exon51 |
| WV-2102 | UCAAGGAAGA UGGCAUUUCU | 204 | fU*fC*fA*fAfGfGmA*mA*mG*mA*mU*mG* mG*mCfAfUfU*fU*fC*fU | 956 | XXXOOOXXXX XXXOOOXXX | Exon51: 6F-8OMe-6F 3PS-3PO-7PS-3PO-3PS | DMD Exon51 |
| WV-2103 | UCAAGGAAGA UGGCAUUUCU | 205 | fU*fC*fAfAfGfGmA*mA*mG*mA*mU*mG* mG*mCfAfUfUfU*fC*fU | 957 | XXOOOOXXXX XXOOOOXX | Exon51: 6F-8OMe-6F 2PS-4PO-7PS-4PO-2PS | DMD Exon51 |
| WV-2104 | UCAAGGAAGA UGGCAUUUCU | 206 | fU*fCfAfAfGfGmA*mA*mG*mA*mU*mG*mG *mCfAfUfUfUfC*fU | 958 | XOOOOOXXXX XXXOOOOOX | Exon51: 6F-8OMe-6F 1PS-5PO-7PS-5PO-1PS | DMD Exon51 |
| WV-2105 | UCAAGGAAGA UGGCAUUUCU | 207 | fUfCfAfAfGfGmA*mA*mG*mA*mU*mG*mG* mCfAfUfUfUfCfU | 959 | OOOOOOXXXX XXXOOOOOO | Exon51: 6F-8OMe-6F 6PO-7PS-6PO | DMD Exon51 |
| WV-2106 | UCAAGGAAGA UGGCAUUUCU | 208 | fU*fC*fA*fA*fG*fG*fA*fG*fA*mU* mG*mG*mC*mU*mU*mU*mC*mU | 960 | XXXXXXXXXX XXXXXXXX | Exon51: 10F-10OMe all-PS | DMD Exon51 |
| WV-2107 | UCAAGGAAGA UGGCAUUUCU | 209 | mU*mC*mA*mA*mG*mG*mA*mA*mG*mA*f U*fG*fG*fC*fA*fU*fU*fU*fC*fU | 961 | XXXXXXXXXX XXXXXXXX | Exon51: 10OMe-10F all-PS | DMD Exon51 |
| WV-2108 | UCAAGGAAGA UGGCAUUUCU | 210 | fU*fC*fA*fA*fG*fG*mA*mA*mG*mA*mU* mG*mG*mC*mA*mU*mU*mU*mC*mU | 962 | XXXXXXXXXX XXXXXXXX | Exon51: 6F-14OMe all-PS | DMD Exon51 |
| WV-2109 | UCAAGGAAGA UGGCAUUUCU | 211 | mU*mC*mA*mA*mG*mG*mA*mA*mG*mA* mU*mG*mG*mC*fA*fU*fU*fU*fC*fU | 963 | XXXXXXXXXX XXXXXXXX | Exon51: 14OMe-6F all-PS | DMD Exon51 |
| WV-884 | UCAAGGAAGA UGGCAUUUCU | 212 | mU*RmC*RmA*RmA*RmG*RmG*RmA*RmA *RmG*RmA*RmU*RmG*RmG*RmC*RmA*R mU*RmU*RmU*RmC*RmU | 964 | RRRRRRRRRR RRRRRRRR | All-R; 2'-OMe oligo | Dystrophin |
| WV-885 | UCAAGGAAGA UGGCAUUUCU | 213 | mU*SmC*RmA*SmA*RmG*SmG*RmA*SmA* RmG*SmA*RmU*SmG*RmG*SmC*RmA*SmU *RU*SmU*RmC*SmU | 965 | SRSRSRSRSRSR SRSRSRS | (SR)9S; 2'-OMe oligo | Dystrophin |
| WV-886 | UCAAGGAAGA UGGCAUUUCU | 214 | mU*RmC*RmA*RmA*SmG*SmG*SmA*SmA* SmG*SmA*SmU*SmG*SmG*SmC*SmA*SmU *SmU*RmU*RmC*RmU | 966 | RRRSSSSSSSS SSSSRRR | R3S13R3; 2'-OMe oligo | Dystrophin |
| WV-887 | UCAAGGAAGA UGGCAUUUCU | 215 | mU*SmC*SmA*SmA*RmG*RmG*RmA*RmA* RmG*RmA*RmU*RmG*RmG*RmC*RmA*Rm U*RmU*SmU*SmC*SmU | 967 | SSSRRRRRRRRR RRRRSSS | S3R13S3; 2'-OMe oligo | Dystrophin |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-888 | UCAAGGAAGAUGGCAUUUCU | 216 | mU*RmC*RmA*RmA*RmG*RmG*SmA*SmA*RmG*SmA*SmU*RmG*SmG*SmC*RmA*RmU*RmU*RmU*RmC*RmU | 968 | RRRRRSSRSSRSSRRRRRR | R5(SSR)3R5; 2'-OMe oligo | Dystrophin |
| WV-889 | UCAAGGAAGAUGGCAUUUCU | 217 | mU*SmC*SmA*SmA*SmG*SmG*RmA*RmA*SmG*RmA*RmU*SmG*RmG*RmC*SmA*SmU*SmU*SmU*SmC*SmU | 969 | SSSSSRRSRRSSRSSSSSS | S5(RRS)3S5; 2'-OMe oligo | Dystrophin |
| WV-890 | UCAAGGAAGAUGGCAUUUCU | 218 | mU*RmC*RmA*RmA*SmG*SmG*RmA*RmA*SmG*RmA*RmU*RmG*SmG*RmC*RmA*SmU*SmU*RmU*RmC*RmU | 970 | RRRSSRSRRRSSRRRSRRR | R3S2R2R3SR2S2R3; 2'-OMe oligo | Dystrophin |
| WV-891 | UCAAGGAAGAUGGCAUUUCU | 219 | mU*SmC*SmA*SmA*RmG*RmG*SmA*SmA*RmG*SmA*SmU*SmG*RmG*SmC*SmA*RmU*RmU*SmU*SmC*SmU | 971 | SSSSRRSSRSSSRSSRSSS | S3R2S2RS3RS2R2S3; 2'-OMe oligo | Dystrophin |
| WV-892 | UCAAGGAAGAUGGCAUUUCU | 220 | mU*SmC*RmA*RmA*RmG*RmG*RmA*RmA*RmG*RmA*RmU*RmG*RmG*RmC*RmA*RmU*RmU*RmU*RmC*SmU | 972 | SRRRRRRRRRRRRRRRRRS | SR17S; 2'-OMe chimeric oligo | Dystrophin |
| WV-893 | UCAAGGAAGAUGGCAUUUCU | 221 | mU*RmC*SmA*SmA*SmG*SmG*SmA*SmA*SmG*SmA*SmU*SmG*SmG*SmC*SmA*SmU*SmU*SmU*SmC*RmU | 973 | RSSSSSSSSSSSSSSSSSR | RS17R; 2'-OMe chimeric oligo | Dystrophin |
| WV-894 | UCAAGGAAGAUGGCAUUUCU | 222 | mU*SmC*RmA*SmA*SmG*RmG*RmA*SmA*SmG*RmA*SmU*SmG*RmG*RmC*RmA*SmU*SmU*SmU*SmC*RmU | 974 | SRSSRRSSRSSRRRSSSR | GC(R) and AU(S) 2'-OMe oligo | Dystrophin |
| WV-895 | UCAAGGAAGAUGGCAUUUCU | 223 | mU*RmC*SmA*RmA*RmG*RmG*SmA*SmA*RmG*SmA*RmU*RmG*SmG*SmC*SmA*RmU*RmU*RmU*RmC*SmU | 975 | RSRRSSRRSRSSRRRS | GC(S) and AU(R) 2'-OMe oligo | Dystrophin |
| WV-896 | UCAAGGAAGAUGGCAUUUCU | 224 | mU*SmC*SmA*RmA*RmG*RmG*RmA*RmA*RmG*RmA*RmU*SmG*RmG*RmC*SmA*RmU*SmU*SmU*SmC*SmU | 976 | SSRRRRRRRRSRSRSSSS | GA(R) and CU(S) 2'-OMe oligo | Dystrophin |
| WV-897 | UCAAGGAAGAUGGCAUUUCU | 225 | mU*RmC*RmA*SmA*SmG*SmG*SmA*SmA*SmG*SmA*SmU*RmG*SmG*SmC*RmA*SmU*RmU*RmU*RmC*RmU | 977 | RRSSSSSSSSRSSRSRRR | GA(S) and CU(R) 2'-OMe oligo | Dystrophin |
| WV-1678 | GGCCAAACCUCGGCUUACCU | 226 | fG*fG*fC*fC*fA*fA*fA*fC*fC*fU*fC*fG*fG*fC*fU*fU*fA*fC*fC*fU | 978 | XXXXXXXXXXXXXXXXXXXX | All 2'-F modified | Exon 23 |
| WV-1679 | GGCCAAACCUCGGCUUACCU | 227 | mG*mG*fC*fC*mA*mA*mA*fC*fC*fU*fC*mG*mG*fC*fU*fU*mA*fC*fC*fU | 979 | XXXXXXXXXXXXXXXXXXXX | 2'-F pyrimidines; 2'-OMe purines | Exon 23 |
| WV-1680 | GGCCAAACCUCGGCUUACCU | 228 | fG*fG*mC*mC*fA*fA*fA*mC*mC*mU*mC*fG*fG*mC*mU*mU*fA*mC*mC*mU | 980 | XXXXXXXXXXXXXXXXXXXX | 2'-F purines; 2'-OMe pyrimidines | Exon 23 |
| WV-1681 | GGCCAAACCUCGGCUUACCU | 229 | mG*fG*mC*fC*mA*fA*mA*fC*mC*fU*mC*fG*mG*fC*mU*fU*mA*fC*mC*fU | 981 | XXXXXXXXXXXXXXXXXXXX | Alternate 2'-OMe/2'F | Exon 23 |
| WV-1682 | GGCCAAACCUCGGCUUACCU | 230 | mG*mG*mC*mC*mA*mA*fA*fC*fC*fU*fC*fG*fG*fC*mU*mU*mA*mC*mC*mU | 982 | XXXXXXXXXXXXXXXXXXXX | 2'-OMe/2'-F/2'-OMe gapmer | Exon 23 |
| WV-1683 | GGCCAAACCUCGGCUUACCU | 231 | fG*fG*fC*fC*fA*fA*mA*mC*mC*mU*mC*mG*mG*mC*fU*fU*fA*fC*fC*fU | 983 | XXXXXXXXXXXXXXXXXXXX | 2'-F/2'-OMe/2'-F gapmer | Exon 23 |
| WV-1684 | GGCCAAACCUCGGCUUACCU | 232 | fG*fG*fC*fC*mA*mA*mA*fC*fC*mU*fC*fG*fG*fC*mU*mU*mA*fC*fC*mU | 984 | XXXXXXXXXXXXXXXXXXXX | 2'-F (C; G); 2'-OMe (U; A) | Exon 23 |
| WV-1685 | GGCCAAACCUCGGCUUACCU | 233 | mG*mG*mC*mC*fA*fA*fA*mC*mC*fU*mC*mG*mG*mC*fU*fU*fA*mC*mC*mU | 985 | XXXXXXXXXXXXXXXXXXXX | 2'-F (U; A); 2'-OMe (C; G) | Exon 23 |
| WV-1709 | UCAAGGAAGAUGGCAUUUCU | 234 | fU*fC*fA*fA*fG*fG*fA*fA*fG*fA*fU*fG*fG*fC*fA*fU*fU*fU*fC*fU | 986 | XXXXXXXXXXXXXXXXXXXX |  | Exon 51 |
| WV-1710 | UCAAGGAAGAUGGCAUUUCU | 235 | fU*mC*mA*mG*mG*mA*mA*mG*mA*mU*mG*mG*fC*mA*fU*fU*fU*fC*fU | 987 | XXXXXXXXXXXXXXXXXXXX |  | Exon 51 |
| WV-1711 | UCAAGGAAGAUGGCAUUUCU | 236 | mU*mC*fA*fA*fG*fG*fA*fA*fG*fA*mU*fG*fG*mC*fA*mU*mU*mU*mC*mU | 988 | XXXXXXXXXXXXXXXXXXXX |  | Exon 51 |
| WV-1712 | UCAAGGAAGAUGGCAUUUCU | 237 | mU*fC*mA*fA*mG*fG*mA*fA*mG*fA*mU*fG*mG*fC*mA*fU*mU*fU*mC*fU | 989 | XXXXXXXXXXXXXXXXXXXX |  | Exon 51 |
| WV-1713 | UCAAGGAAGAUGGCAUUUCU | 238 | mU*mC*mA*mA*mG*mG*fA*fA*fG*fA*fU*fG*fG*mC*mA*mU*mU*mU*mC*mU | 990 | XXXXXXXXXXXXXXXXXXXX |  | Exon 51 |
| WV-1714 | UCAAGGAAGAUGGCAUUUCU | 239 | fU*fC*fA*fA*fG*fG*mA*mA*mG*mA*mU*mG*mG*fC*fA*fU*fU*fU*fC*fU | 991 | XXXXXXXXXXXXXXXXXXXX |  | Exon 51 |
| WV-1715 | UCAAGGAAGAUGGCAUUUCU | 240 | mU*fC*mA*fA*fG*fG*mA*mA*fG*mA*mU*fG*fG*fC*mA*mU*mU*mU*fC*mU | 992 | XXXXXXXXXXXXXXXXXXXX |  | Exon 51 |
| WV-1716 | UCAAGGAAGAUGGCAUUUCU | 241 | fU*mC*fA*fA*mG*mG*fA*fA*mG*fA*mU*mG*mC*fA*fU*fU*fU*mC*fU | 993 | XXXXXXXXXXXXXXXXXXXX |  | Exon 51 |
| WV-1093 | GGCCAAACCTCGGCTTACCT | 242 | G*G*C*C*A*A*A*C*C*T*C*G*G*C*T*T*A*C*C*T | 994 | XXXXXXXXXXXXXXXXXXXX | Stereorandom DNA version of Exon23 full PS: Analog of WV943 | Exon23 |
| WV-1094 | GGCCAAACCUCGGCUUACCU | 243 | mGmGmCmCmAmAmAmCmCmUmCmGmGmCmUmUmAmCmCmU | 995 | OOOOOOOOOOOOOOOOOOO | Full PO version of WV943 | Exon23 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-1095 | GGCCAAACCTC GGCTTACCT | 244 | G*RG*RC*RC*RA*RA*RA*RC*RC*RT*RC* RG*RG*RC*RT*RT*RA*RC*RC*RT | 996 | RRRRRRRRRRR RRRRRRRR | Full Rp DNA version of Exon23: Analog of WV943 | Exon23 |
| WV-1096 | GGCCAAACCTC GGCTTACCT | 245 | G*SG*SC*SC*SA*SA*SA*SC*SC*ST*SC*SG *SG*SC*ST*ST*SA*SC*SC*ST | 997 | SSSSSSSSSSS SSSSSSS | Full Sp DNA version of Exon23: Analog of WV943 | Exon23 |
| WV-1097 | GGCCAAACCUC GGCTTACCT | 246 | G*SG*SC*SC*SA*SmAmAmCmCmUmCmGm GmCT*ST*SA*SC*SC*ST | 998 | SSSSSOOOOO OOOSSSSS | Stereopure DNA/2'OMe chimeric version of Exon23: Analog of 943 | Exon23 |
| WV-1098 | GGCCAAACCUC GGCTTACCU | 247 | mGmGmCmCA*SA*SA*SmCC*ST*SC*SG*Sm GC*ST*ST*SmAmCmU | 999 | OOOOSSSOSSSS OSSSOOO | Stereopure DNA/2'OMe chimeric version of Exon23: Analog of 943 | Exon23 |
| WV-1099 | GGCCAAACCUC GGCTUACCU | 248 | G*SmGC*SmCA*SmAA*SmCC*SmUC*SmGG *SmCT*SmUA*SmCC*SmU | 1000 | SOSOSOSOSOSO SOSOSOS | Stereopure DNA/2'OMe chimeric version of Exon23: Analog of 943 | Exon23 |
| WV-1100 | GGCCAAACCTC GGCUTACCU | 249 | mGG*SmCC*SmAA*SmAC*SmCT*SmCG*Sm GC*SmUT*SmAC*SmCmU | 1001 | OSOSOSOSOSOS OSOSOSO | Stereopure DNA/2'OMe chimeric version of Exon23: Analog of 943 | Exon23 |
| WV-1101 | GGCCAAACCTC GGCTUACCU | 250 | G*SG*SmCmCA*SA*SmAmCC*ST*SC*SmGm GC*ST*SmUmAC*SC*SmU | 1002 | SSOOSSOOSSSO OSSOOSS | Stereopure DNA/2'OMe chimeric version of Exon23: Analog of 943 | Exon23 |
| WV-1102 | GGCCAAACCUC GGCUUACCU | 251 | G*SG*SC*SmCmAmAA*SC*SmCmUmCG*SG *SmCmUmUA*SC*SC*SmU | 1003 | SSSOOOSSOOOS SOOOSSS | Stereopure DNA/2'OMe chimeric version of Exon23: Analog of 943 | Exon23 |
| WV-1103 | GGCCAAACCUC GGCUTACCU | 252 | G*SG*SC*SC*SmAmAmAmCC*ST*SC*SmGm GmCmUT*SA*SC*SC*SmU | 1004 | SSSSOOOOSSSO OOOSSSS | Stereopure DNA/2'OMe chimeric version of Exon23: Analog of 943 | Exon23 |
| WV-1104 | GGCCAAACCTC GGCTUACCU | 253 | G*SG*SC*SmCA*SA*SA*SmCC*ST*SC*SmG G*SC*ST*SmUA*SC*SC*SmU | 1005 | SSSSOSSSOSSSO SSSOSSS | Stereopure DNA/2'OMe chimeric version of Exon23: Analog of 943 | Exon23 |
| WV-1105 | GGCCAAACCUC GGCTTACCU | 254 | mGmGmCmCA*SA*SA*SC*SC*SmUmCmGm GmCT*ST*SA*SC*SC*SmU | 1006 | OOOOSSSSSOO OOOSSSSS | Stereopure DNA/2'OMe chimeric version of Exon23: Analog of 943 | Exon23 |
| WV-1121 | GGCCAAACCUC GGCTTACCT | 255 | G*G*C*C*A*mAmAmCmCmUmCmGmGmCT *T*A*C*C*T | 1007 | XXXXXOOOO OOOOXXXXX | Stereorandom DNA/2'OMe chimeric version of Exon23: Analog of WV1097 | Exon23 |
| WV-1122 | GGCCAAACCTC GGCTTACCU | 256 | mGmGmCmCA*A*A*mCC*T*C*G*mGC*T*T *mAmCmCmU | 1008 | OOOOXXXOXX XXOXXXOOO | Stereorandom DNA/2'OMe chimeric version | Exon23 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-1123 | GGCCAAACCUC GGCUUACCU | 257 | G*mGC*mCA*mAA*mCC*mUC*mGG*mCT*mUA*mCC*mU | 1009 | XOXOXOXOXOXOXOXOX | of Exon23: Analog of WV1098 Stereorandom DNA/2'OMe chimeric version of Exon23: Analog of WV1099 | Exon23 |
| WV-1124 | GGCCAAACCTC GGCUTACCU | 258 | mGG*mCC*mAA*mAC*mCT*mCG*mGC*mUT*mAC*mCmU | 1010 | OXOXOXOXOXOXOXOXO | Stereorandom DNA/2'OMe chimeric version of Exon23: Analog of WV1100 | Exon23 |
| WV-1125 | GGCCAAACCTC GGCTUACCU | 259 | G*G*mCmCA*A*mAmCmCT*C*mGmGC*T*mUmAC*C*mU | 1011 | XXOOXXOOOXXOOXXOOXX | Stereorandom DNA/2'OMe chimeric version of Exon23: Analog of WV1101 | Exon23 |
| WV-1126 | GGCCAAACCUC GGCUUACCU | 260 | G*G*C*mCmAmAA*C*mCmUmCG*G*mCmUmUA*C*C*mU | 1012 | XXXOOOXXOOOXXOOOXXX | Stereorandom DNA/2'OMe chimeric version of Exon23: Analog of WV1102 | Exon23 |
| WV-1127 | GGCCAAACCTC GGCUTACCU | 261 | G*G*C*C*mAmAmAmCC*T*C*mGmGmCmUT*A*C*C*mU | 1013 | XXXXOOOOXXXOOOOXXXX | Stereorandom DNA/2'OMe chimeric version of Exon23: Analog of WV1103 | Exon23 |
| WV-1128 | GGCCAAACCTC GGCTUACCU | 262 | G*G*C*mCA*A*A*mCC*T*C*mGG*C*T*mUA*C*C*mU | 1014 | XXXOXXXOXXXOXXXOXXX | Stereorandom DNA/2'OMe chimeric version of Exon23: Analog of WV1104 | Exon23 |
| WV-1129 | GGCCAAACCUC GGCTTACCU | 263 | mGmGmCmCA*A*A*C*C*mUmCmGmCT*T*A*C*C*mU | 1015 | OOOOXXXXXOOOOOXXXXX | Stereorandom DNA/2'OMe chimeric version of Exon23: Analog of WV1105 | Exon23 |
| WV-1130 | GGCCAAACCUC GGCUTACCU | 264 | G*G*mCmCmAmAmAmCmCmUC*mGmGC*mUT*A*C*C*mU | 1016 | XXOOOOOOOOXOOXOXXXX | Stereorandom DNA/2'OMe chimeric version of Exon23: Analog of WV1106 | Exon23 |
| WV-1141 | GGCCAAACCUC GGCUUACCU | 265 | mG*mG*mC*mC*mA*mAmAmCmCmUmCmGmCmU*mU*mA*mC*mC*mU | 1017 | XXXXXOOOOOOOOOXXXXX | Stereorandom 2'OMe PO/PS chimeric version of exon23: Analog of WV1097 | Exon23 |
| WV-1142 | GGCCAAACCUC GGCUUACCU | 266 | mGmGmCmCmA*mA*mA*mCmC*mU*mC*mG*mGmC*mU*mU*mAmCmCmU | 1018 | OOOOXXXOXXXOOXXXOOO | Stereorandom 2'OMe PO/PS chimeric version of exon23: Analog of WV1098 | Exon23 |
| WV-1143 | GGCCAAACCUC GGCUUACCU | 267 | mG*mGmC*mCmA*mAmA*mCmC*mUmC*mGmG*mCmU*mUmA*mCmC*mU | 1019 | XOXOXOXOXOXOXOXOXOX | Stereorandom 2'OMe PO/PS | Exon23 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-1144 | GGCCAAACCUC GGCUUACCU | 268 | mGmG*mC*mAmA*mAmC*mCmU*mCmG *mGmC*mUmU*mAmC*mCU | 1020 | OXOXOXOXOX OXOXOXOXO | chimeric version of exon23: Analog of WV1099 Stereorandom 2'OMe PO/PS chimeric version of exon23: Analog of WV1100 | Exon23 |
| WV-1145 | GGCCAAACCUC GGCUUACCU | 269 | mG*mG*mCmCmA*mA*mAmCmCmU*mC*m GmGmC*mU*mUmAmC*mC*mU | 1021 | XXOOXXOOOX XOOXXOOXX | Stereorandom 2'OMe PO/PS chimeric version of exon23: Analog of WV1101 | Exon23 |
| WV-1146 | GGCCAAACCUC GGCUUACCU | 270 | mG*mG*mC*mCmAmAmA*mC*mCmUmCmG *mG*mCmUmUmA*mC*mC*mU | 1022 | XXXOOOXXOO OXXOOOXXX | Stereorandom 2'OMe PO/PS chimeric version of exon23: Analog of WV1102 | Exon23 |
| WV-1147 | GGCCAAACCUC GGCUUACCU | 271 | mG*mG*mC*mC*mAmAmAmCmC*mU*mC* mGmGmCmUmU*mA*mC*mC*mU | 1023 | XXXXOOOOXX XOOOOXXXX | Stereorandom 2'OMe PO/PS chimeric version of exon23: Analog of WV1103 | Exon23 |
| WV-1148 | GGCCAAACCUC GGCUUACCU | 272 | mG*mG*mC*mCmA*mA*mA*mCmC*mU*mC *mGmG*mC*mU*mUmA*mC*mC*mU | 1024 | XXXOXXXOXX XOXXXOXXX | Stereorandom 2'OMe PO/PS chimeric version of exon23: Analog of WV1104 | Exon23 |
| WV-1149 | GGCCAAACCUC GGCUUACCU | 273 | mGmGmCmCmA*mA*mA*mC*mC*mUmCmG mGmCmU*mU*mA*mC*mC*mU | 1025 | OOOOXXXXXO OOOOXXXXX | Stereorandom 2'OMe PO/PS chimeric version of exon23: Analog of WV1105 | Exon23 |
| WV-1150 | GGCCAAACCUC GGCUUACCU | 274 | mG*mG*mCmCmAmAmAmCmCmUmC*mGm GmC*mUmU*mA*mC*mC*mU | 1026 | XXOOOOOOOO XOOXOXXXX | Stereorandom 2'OMe PO/PS chimeric version of exon23: Analog of WV1106 | Exon23 |
| WV-2733 | GGCCAAACCUC GGCUUACCU | 275 | L001*mG*mG*mC*mC*mA*mA*mA*mC*mC *mU*mC*mG*mG*mC*mU*mU*mA*mC*mC* mU | 1027 | XXXXXXXXXX XXXXXXXXXX | All-OMe full-PS | Exon23 |
| WV-2734 | GGCCAAACCUC GGCUUACCUG AAAU | 276 | L001*mG*mG*mC*mC*mA*mA*mA*mC*mC *mU*mC*mG*mG*mC*mU*mU*mA*mC*mC* mU*mG*mA*mA*mA*mU | 1028 | XXXXXXXXXX XXXXXXXXXX XXXXX | All-OMe full-PS | Exon23 |
| WV-1106 | GGCCAAACCUC GGCUACCU | 277 | G*SG*SmCmCmAmAmAmCmCmUC*SmGmG C*SmUT*SA*SC*SC*SmU | 1029 | SSOOOOOOOS OOSOSSSS | Stereopure DNA/2'OMe chimeric version of Exon23: Analog of 943 | Exon51 |
| WV-1107 | TCAAGGAAGAT GGCATTTCT | 278 | T*C*A*A*G*G*A*A*G*A*T*G*G*C*A*T*T* T*C*T | 1030 | XXXXXXXXXX XXXXXXXX | Stereorandom DNA version of Exon51 full PS: Analog of WV942 | Exon51 |
| WV-1108 | UCAAGGAAGA UGGCAUUUCU | 279 | mUmCmAmAmGmGmAmAmGmAmUmGmGm CmAmUmUmCmU | 1031 | OOOOOOOOOO OOOOOOOOO | Full PO version of WV942 | Exon51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-1109 | TCAAGGAAGATGGCATTTCT | 280 | T*RC*RA*RA*RG*RG*RA*RA*RG*RA*RT*RG*RG*RC*RA*RT*RT*RT*RC*RT | 1032 | RRRRRRRRRRRRRRRRRRR | Full Rp DNA version of Exon51: Analog of WV942 | Exon51 |
| WV-1110 | TCAAGGAAGATGGCATTTCT | 281 | T*SC*SA*SA*SG*SG*SA*SA*SG*SA*ST*SG*SG*SC*SA*ST*ST*ST*SC*ST | 1033 | SSSSSSSSSSSSSSSSSSS | Full Rp DNA version of Exon51: Analog of WV942 | Exon51 |
| WV-1111 | TCAAGGAAGAUGGCATTTCT | 282 | T*SC*SA*SA*SG*SmGmAmAmGmAmUmGmGmCA*ST*ST*ST*SC*ST | 1034 | SSSSSOOOOOOOOSSSSS | Stereopure DNA/2'OMe chimeric version of Exon51: Analog of 942 | Exon51 |
| WV-1112 | UCAAGGAAGATGGCATUUCU | 283 | mUmCmAmAG*SG*SA*SmAG*SA*ST*SG*SmGC*SA*ST*SmUmUmCmU | 1035 | OOOOSSSOSSSOSSSOOO | Stereopure DNA/2'OMe chimeric version of Exon51: Analog of 942 | Exon51 |
| WV-1113 | TCAAGGAAGATGGCAUUCU | 284 | T*SmCA*SmAG*SmGA*SmAG*SmAT*SmGG*SmCA*SmUT*SmUC*SmU | 1036 | SOSOSOSOSOSOSOSOSOS | Stereopure DNA/2'OMe chimeric version of Exon51: Analog of 942 | Exon51 |
| WV-1114 | UCAAGGAAGAUGGCATUTCU | 285 | mUC*SmAA*SmGG*SmAA*SmGA*SmUG*SmGC*SmAT*SmUT*SmCmU | 10377 | OSOSOSOSOSOSOSOSO | Stereopure DNA/2'OMe chimeric version of Exon51: Analog of 942 | Exon51 |
| WV-1115 | TCAAGGAAGATGGCAUUTCU | 286 | T*SC*SmAmAG*SG*SmAmAG*SA*ST*SmGmGC*SA*SmUmUT*SC*SmU | 1038 | SSOOSSOOSSSOOSSOOSS | Stereopure DNA/2'OMe chimeric version of Exon51: Analog of 942 | Exon51 |
| WV-1116 | TCAAGGAAGAUGGCAUTTCU | 287 | T*SC*SA*SmAmGmGA*SA*SmGmAmUG*SG*SmCmAmUT*ST*SC*SmU | 1039 | SSSOOOSSOOOSSOOOSSS | Stereopure DNA/2'OMe chimeric version of Exon51: Analog of 942 | Exon51 |
| WV-1117 | TCAAGGAAGATGGCATTTCU | 288 | T*SC*SA*SA*SmGmGmAmAG*SA*ST*SmGmGmCmAT*ST*ST*SC*SmU | 1040 | SSSSOOOOSSSOOOSSSS | Stereopure DNA/2'OMe chimeric version of Exon51: Analog of 942 | Exon51 |
| WV-1118 | TCAAGGAAGATGGCATTTCU | 289 | T*SC*SA*SmAG*SG*SA*SmAG*SA*ST*SmGG*SC*SA*SmUT*ST*SC*SmU | 1041 | SSSOSSSOSSSOSSSOSSS | Stereopure DNA/2'OMe chimeric version of Exon51: Analog of 942 | Exon51 |
| WV-1119 | UCAAGGAAGAUGGCATTTCU | 290 | mUmCmAmAG*SG*SA*SA*SG*SmAmUmGmGmCA*ST*ST*ST*SC*SmU | 1042 | OOOOSSSSSOOOOOSSSSS | Stereopure DNA/2'OMe chimeric version of Exon51: Analog of 942 | Exon51 |
| WV-1120 | TCAAGGAAGATGGCATTTCU | 291 | T*SC*SmAmAmGmGmAmAmGmAT*SmGmGC*SmAT*ST*ST*SC*SmU | 1043 | SSOOOOOOOOOSOSOSSSS | Stereopure DNA/2'OMe chimeric version of Exon51: Analog of 942 | Exon51 |
| WV-1131 | TCAAGGAAGAUGGCATTTCT | 292 | T*C*A*A*G*mGmAmAmGmAmUmGmCA*T*T*T*C*T | 1044 | XXXXXOOOOOOOOXXXXX | Stereorandom DNA/2'OMe chimeric version of Exon51: | Exon51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-1132 | UCAAGGAAGA TGGCATUUCU | 293 | mUmCmAmAG*G*A*mAG*A*T*G*mGC*A*T*mUmUmCmU | 1045 | OOOOXXXOXX XXOXXXOOO | Analog of WV1111 Stereorandom DNA/2'OMe chimeric version of Exon51: Analog of WV1111 | Exon51 |
| WV-1133 | TCAAGGAAGAT GGCAUTUCU | 294 | T*mCA*mAG*mGA*mAG*mAT*mGG*mCA*mUT*mUC*mU | 1046 | XOXOXOXOXO XOXOXOXOX | Stereorandom DNA/2'OMe chimeric version of Exon51: Analog of WV1112 | Exon51 |
| WV-1134 | UCAAGGAAGA UGGCATUTCU | 295 | mUC*mAA*mGG*mAA*mGA*mUG*mGC*mAT*mUT*mCmU | 1047 | OXOXOXOXOX OXOXOXOXO | Stereorandom DNA/2'OMe chimeric version of Exon51: Analog of WV1113 | Exon51 |
| WV-1135 | TCAAGGAAGAT GGCAUUTCU | 296 | T*C*mAmAG*G*mAmAG*A*T*mGmGC*A*mUmUT*C*mU | 1048 | XXOOXXOOXX XOOXXOOXX | Stereorandom DNA/2'OMe chimeric version of Exon51: Analog of WV1114 | Exon51 |
| WV-1136 | TCAAGGAAGA UGGCAUTTCU | 297 | T*C*A*mAmGmGA*A*mGmAmUG*G*mCmAmUT*T*C*mU | 1049 | XXXOOOXXOO OXXOOOXXX | Stereorandom DNA/2'OMe chimeric version of Exon51: Analog of WV1115 | Exon51 |
| WV-1137 | TCAAGGAAGAT GGCATTTCU | 298 | T*C*A*A*mGmGmAmAG*A*T*mGmGmCmAT*T*T*C*mU | 1050 | XXXXOOOOXX XOOOOXXXX | Stereorandom DNA/2'OMe chimeric version of Exon51: Analog of WV1116 | Exon51 |
| WV-1138 | TCAAGGAAGAT GGCAUTTCU | 299 | T*C*A*mAG*G*A*mAG*A*T*mGG*C*A*mUT*T*C*mU | 1051 | XXXOXXXOXX XOXXXOXXX | Stereorandom DNA/2'OMe chimeric version of Exon51: Analog of WV1117 | Exon51 |
| WV-1139 | UCAAGGAAGA UGGCATTTCU | 300 | mUmCmAmAG*G*A*A*G*mAmUmGmCA*T*T*T*C*mU | 1052 | OOOOXXXXXO OOOOXXXXX | Stereorandom DNA/2'OMe chimeric version of Exon51: Analog of WV1118 | Exon51 |
| WV-1140 | TCAAGGAAGAT GGCATTTCU | 301 | T*C*mAmAmGmGmAmAmGmAT*mGmGC*mAT*T*T*C*mU | 1053 | XXOOOOOOOO XOOXOXXXX | Stereorandom DNA/2'OMe chimeric version of Exon51: Analog of WV1119 | Exon51 |
| WV-1151 | UCAAGGAAGA UGGCAUUUCU | 302 | mU*mC*mA*mA*mG*mGmAmAmGmAmUm GmGmCmA*mU*mU*mU*mC*mU | 1054 | XXXXXOOOOO OOOOXXXXX | Stereorandom 2'OMe PO/PS chimeric version of exon51: Analog of WV1111 | Exon51 |
| WV-1152 | UCAAGGAAGA UGGCAUUUCU | 303 | mUmCmAmAmG*mG*mA*mAmG*mA*mU*mG*mGmC*mA*mU*mUmUmCmU | 1055 | OOOOXXXOXX XXOXXXOOO | Stereorandom 2'OMe PO/PS | Exon51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-1153 | UCAAGGAAGAUGGCAUUUCU | 304 | mU*mCmA*mAmG*mGmA*mAmG*mAmU*mGmG*mCmA*mUmU*mUmC*mU | 1056 | XOXOXOXOXOXOXOXOXOX | chimeric version of exon51: Analog of WV1112 Stereorandom 2'OMe PO/PS chimeric version of exon51: Analog of WV1113 | Exon51 |
| WV-1154 | UCAAGGAAGAUGGCAUUUCU | 305 | mUmC*mAmA*mGmG*mAmA*mGmG*mUmG*mGmC*mAmU*mUmU*mCmU | 1057 | OXOXOXOXOXOXOXOXOXO | Stereorandom 2'OMe PO/PS chimeric version of exon51: Analog of WV1114 | Exon51 |
| WV-1155 | UCAAGGAAGAUGGCAUUUCU | 306 | mU*mC*mAmAmG*mG*mAmAmG*mA*mU*mGmGmC*mA*mUmUmU*mC*mU | 1058 | XXOOXXOOXXXOOXXOOXX | Stereorandom 2'OMe PO/PS chimeric version of exon51: Analog of WV1115 | Exon51 |
| WV-1156 | UCAAGGAAGAUGGCAUUUCU | 307 | mU*mC*mA*mAmGmA*mA*mGmAmUmG*mG*mCmAmUmU*mU*mC*mU | 1059 | XXXOOOXXOOOXXOOOXXX | Stereorandom 2'OMe PO/PS chimeric version of exon51: Analog of WV1116 | Exon51 |
| WV-1157 | UCAAGGAAGAUGGCAUUUCU | 308 | mU*mC*mA*mA*mGmGmAmAmG*mA*mU*mGmGmCmAmU*mU*mU*mC*mU | 1060 | XXXXOOOOXXXOOOOXXXX | Stereorandom 2'OMe PO/PS chimeric version of exon51: Analog of WV1117 | Exon51 |
| WV-1158 | UCAAGGAAGAUGGCAUUUCU | 309 | mU*mC*mA*mAmG*mG*mA*mAmG*mA*mU*mGmG*mC*mA*mUmU*mU*mC*mU | 1061 | XXXOXXXOXXXOXXXOXXX | Stereorandom 2'OMe PO/PS chimeric version of exon51: Analog of WV1118 | Exon51 |
| WV-1159 | UCAAGGAAGAUGGCAUUUCU | 310 | mUmCmAmAmG*mG*mA*mA*mG*mAmUmGmGmCmA*mU*mU*mU*mC*mU | 1062 | OOOOXXXXXOOOOOXXXXX | Stereorandom 2'OMe PO/PS chimeric version of exon51: Analog of WV1119 | Exon51 |
| WV-1160 | UCAAGGAAGAUGGCAUUUCU | 311 | mU*mC*mAmAmGmGmAmAmGmAmU*mGmGmC*mAmU*mU*mU*mC*mU | 1063 | XXOOOOOOOXOOXOXXXX | Stereorandom 2'OMe PO/PS chimeric version of exon51: Analog of WV1120 | Exon51 |
| WV-1687 | AGAAAUGCCAUCUUCCUUGA | 312 | rArGrArArArUrGrCrCrArUrCrUrUrCrCrUrUrGrA | 1064 | OOOOOOOOOOOOOOOOOOO | RNA | Exon51 |
| WV-2363 | UCAAGGAAGAUGGCAUUUCU | 313 | mU*SmC*SmA*RmA*RmG*RmG*RmA*RmA*RmG*RmA*RmU*RmG*RmG*RmC*RmA*RmU*RmU*RmU*SmC*SmU | 1065 | SSRRRRRRRRRRRRRRSS | Exon51: 2S-15R-2S | Exon51 |
| WV-2364 | UCAAGGAAGAUGGCAUUUCU | 314 | mU*SmC*SmA*SmA*SmG*RmG*RmA*RmA*RmG*RmA*RmU*RmG*RmG*RmC*RmA*RmU*SmU*SmU*SmC*SmU | 1066 | SSSSRRRRRRRRRRRSSSS | Exon51: 4S-11R-4S | Exon51 |
| WV-2365 | UCAAGGAAGAUGGCAUUUCU | 315 | mU*SmC*SmA*SmA*SmG*SmG*RmA*RmA*RmG*RmA*RmU*RmG*RmG*RmC*RmA*SmU*SmU*SmU*SmC*SmU | 1067 | SSSSSRRRRRRRRRSSSSS | Exon51: 5S-9R-5S | Exon51 |
| WV-2366 | UCAAGGAAGAUGGCAUUUCU | 316 | mU*SmCmAmAmGmGmAmAmGmAmUmGmGmCmAmUmUmUmC*SmU | 1068 | SOOOOOOOOOOOOOOOOOS | Exon51: 1S-17PO-1S | Exon51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2367 | UCAAGGAAGAUGGCAUUUCU | 317 | mU*SmC*SmAmAmGmGmAmAmGmAmUmGmGmCmAmUmU*SmC*SmU | 1069 | SSO00000000000000SS | Exon51: 2S-15PO-2S | Exon51 |
| WV-2368 | UCAAGGAAGAUGGCAUUUCU | 318 | mU*SmC*SmA*SmAmGmGmAmAmGmAmUmGmGmCmAmU*SmU*SmC*SmU | 1070 | SSSO00000000000SSS | Exon51: 3S-13PO-3S | Exon51 |
| WV-2369 | UCAAGGAAGAUGGCAUUUCU | 319 | mU*SmC*SmA*SmA*SmGmGmAmAmGmAmUmGmGmCmAmU*SmU*SmU*SmC*SmU | 1071 | SSSSO0000000SSSS | Exon51: 4S-11PO-4S | Exon51 |
| WV-2370 | UCAAGGAAGAUGGCAUUUCU | 320 | mU*SmC*SmA*SmA*SmG*SmGmAmAmGmAmUmGmGmCmA*SmU*SmU*SmU*SmC*SmU | 1072 | SSSSSO00000000SSSSS | Exon51: 5S-9PO-5S | Exon51 |
| WV-2381 | UCAAGGAAGAUGGCAUUUCU | 321 | mU*mCmAmAmGmGmAmAmGmAmUmGmGmCmAmUmUmC*mU | 1073 | X000000000000000X | Exon51: 1PS-17PO-1PS stereorandom | Exon51 |
| WV-2382 | UCAAGGAAGAUGGCAUUUCU | 322 | mU*mC*mAmAmGmGmAmAmGmAmUmGmGmCmAmUmU*mC*mU | 1074 | XX0000000000000XX | Exon51: 2PS-15PO-2PS stereorandom | Exon51 |
| WV-2383 | UCAAGGAAGAUGGCAUUUCU | 323 | mU*mC*mA*mAmGmGmAmAmGmAmUmGmGmCmAmU*mU*mC*mU | 1075 | XXX0000000000XXX | Exon51: 3PS-13PO-3PS stereorandom | Exon51 |
| WV-2384 | UCAAGGAAGAUGGCAUUUCU | 324 | mU*mC*mA*mA*mGmGmAmAmGmAmUmGmGmCmAmU*mU*mU*mC*mU | 1076 | XXXX0000000XXXX | Exon51: 4PS-11PO-4PS stereorandom | Exon51 |
| WV-2385 | UCAAGGAAGAUGGCAUUUCU | 325 | mU*mC*mA*mA*mG*mGmAmAmGmAmUmGmGmCmA*mU*mU*mU*mC*mU | 1077 | XXXXX00000XXXXX | Exon51: 5PS-9PO-5PS stereorandom | Exon51 |
| WV-2432 | UCAAGGAAGAUGGCAUUUCU | 326 | fU*fC*fA*fA*fG*fG*mAmAmGmAmUmGmGmC*fA*fU*fU*fU*fC*fU | 1078 | XXXXXX0000XXXXXX | 6F-8OMe-6F 6PS-7PO-6PS | Exon51 |
| WV-2433 | UCAAGGAAGAUGGCAUUUCU | 327 | fU*fC*fA*fA*fG*fG*mGmAmAmGmAmUmGmGmCmA*fU*fU*fU*fC*fU | 1079 | XXXXX00000XXXXX | 5F-10OMe-5F 5PS-9PO-5PS | Exon51 |
| WV-2434 | UCAAGGAAGAUGGCAUUUCU | 328 | fU*fC*fA*fA*mGmAmAmGmAmUmGmGmCmAmU*fU*fU*fC*fU | 1080 | XXXX0000000XXXX | 4F-12OMe-4F 4PS-11PO-4PS | Exon51 |
| WV-2435 | UCAAGGAAGAUGGCAUUUCU | 329 | fU*fC*fA*mAmGmGmAmAmGmAmUmGmGmCmAmU*fU*fC*fU | 1081 | XXX0000000000XXX | 3F-14OMe-3F 3PS-13PO-3PS | Exon51 |
| WV-2436 | UCAAGGAAGAUGGCAUUUCU | 330 | fU*fC*mAmAmGmGmAmAmGmAmUmGmGmCmAmUmU*fC*fU | 1082 | XX0000000000000XX | 2F-16OMe-2F 2PS-15PO-2PS | Exon51 |
| WV-2437 | UCAAGGAAGAUGGCAUUUCU | 331 | fU*mCmAmAmGmGmAmAmGmAmUmGmGmCmAmUmUmC*fU | 1083 | X0000000000000000X | 1F-18OMe-1F 1PS-17PO-1PS | Exon51 |
| WV-2438 | UCAAGGAAGAUGGCAUUUCU | 332 | fU*SfC*SfA*SfA*SfG*SfG*SmAmAmGmAmUmGmGmC*SfA*SfU*SfU*SfU*SfC*SfU | 1084 | SSSSSS0000SSSSSS | 6F-8OMe-6F 6Sp-7PO-6Sp | Exon51 |
| WV-2439 | UCAAGGAAGAUGGCAUUUCU | 333 | fU*SfC*SfA*SfA*SfG*SmGmAmAmGmAmUmGmGmCmA*SfU*SfU*SfU*SfC*SfU | 1085 | SSSSS00000SSSSS | SF-10OMe-5F 5Sp-9PO-5Sp | Exon51 |
| WV-2440 | UCAAGGAAGAUGGCAUUUCU | 334 | fU*SfC*SfA*SfA*SmGmGmAmAmGmAmUmGmGmCmAmU*SfU*SfU*SfC*SfU | 1086 | SSSS0000000SSSS | 4F-12OMe-4F - 4Sp11PO-4Sp | Exon51 |
| WV-2441 | UCAAGGAAGAUGGCAUUUCU | 335 | fU*SfC*SfA*SmAmGmGmAmAmGmAmUmGmGmCmAmU*SfU*SfC*SfU | 1087 | SSSO0000000000SSS | 3F-14OMe-3F 3Sp-13PO-3Sp | Exon51 |
| WV-2442 | UCAAGGAAGAUGGCAUUUCU | 336 | fU*SfC*SmAmAmGmGmAmAmGmAmUmGmGmCmAmUmU*SfC*SfU | 1088 | SSO00000000000000SS | 2F-16OMe-2F 2Sp-15PO-2Sp | Exon51 |
| WV-2443 | UCAAGGAAGAUGGCAUUUCU | 337 | fU*SmCmAmAmGmGmAmAmGmAmUmGmGmCmAmUmUmC*SfU | 1089 | S000000000000000S | 1F-18OMe-1F 1Sp-17PO-1Sp | Exon51 |
| WV-2444 | UCAAGGAAGAUGGCAUUUCU | 338 | fU*SfC*SfA*SfA*SfG*SfG*SmA*RmA*RmG*RmA*RmU*RmG*RmG*RmC*SfA*SfU*SfU*SfU*SfC*SfU | 1090 | SSSSSSRRRRRRSSSSSS | 6F-8OMe-6F 6Sp-7Rp-6Sp | Exon51 |
| WV-2445 | UCAAGGAAGAUGGCAUUUCU | 339 | fU*SfC*SfA*SfA*SfG*SmA*RmA*RmG*RmA*RmU*RmG*RmG*RmC*RmA*SfU*SfU*SfU*SfC*SfU | 1091 | SSSSSRRRRRRRRSSSSS | 5F-10OMe-5F 5Sp-9Rp-5Sp | Exon51 |
| WV-2446 | UCAAGGAAGAUGGCAUUUCU | 340 | fU*SfC*SfA*SfA*SmG*RmG*RmA*RmA*RmG*RmA*RmU*RmG*RmG*RmC*RmA*RmU*SfU*SfU*SfC*SfU | 1092 | SSSSRRRRRRRRRRSSSS | 4F-12OMe-4F 4Sp-11Rp-4Sp | Exon51 |
| WV-2447 | UCAAGGAAGAUGGCAUUUCU | 341 | fU*SfC*SfA*SmA*RmG*RmG*RmA*RmA*RmG*RmA*RmU*RmG*RmG*RmC*RmA*RmU*RmU*SfU*SfC*SfU | 1093 | SSSRRRRRRRRRRRRSSS | 3F-14OMe-3F 3Sp-13Rp-3Sp | Exon51 |
| WV-2448 | UCAAGGAAGAUGGCAUUUCU | 342 | fU*SfC*SmA*RmG*RmG*RmA*RmA*RmG*RmA*RmU*RmG*RmG*RmC*RmA*RmU*RmU*RmU*SfC*SfU | 1094 | SSRRRRRRRRRRRRRRSS | 2F-16OMe-2F 2Sp-15Rp-2Sp | Exon51 |
| WV-2449 | UCAAGGAAGAUGGCAUUUCU | 343 | fU*SmC*RmA*RmA*RmG*RmG*RmA*RmA*RmG*RmA*RmU*RmG*RmG*RmC*RmA*RmU*RmU*RmU*RmC*SfU | 1095 | SRRRRRRRRRRRRRRRRS | 1F-18OMe-1F 1Sp-17Rp-1Sp | Exon51 |
| WV-2526 | UCAAGGAAGAUGGCAUUUCU | 344 | fU*SfC*SfA*SfA*SfG*SfG*SfA*SfA*RmG*RmA*RmU*RmG*RmG*SfC*SfA*SfU*SfU*SfU*SfC*SfU | 1096 | SSSSSSSSRRRRRSSSSSSS | 7F-6OMe-7F 7Sp-5Rp-7Sp | Exon51 |
| WV-2527 | UCAAGGAAGAUGGCAUUUCU | 345 | fU*SfC*SfA*SfA*SfG*SfG*SfA*SfA*SmG*RmA*RmU*RmG*SfG*SfC*SfA*SfU*SfU*SfU*SfC*SfU | 1097 | SSSSSSSSRRRSSSSSSSS | 8F-4OMe-8F 8Sp-3Rp-8Sp | Exon51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2528 | UCAAGGAAGAUGGCAUUUCU | 346 | fU*SfC*SfA*SfA*SfG*SfG*SfA*SfA*SfG*SmA*RmU*SfG*SfG*SfC*SfA*SfU*SfU*SfU*SfC*SfU | 1098 | SSSSSSSSSRSSSSSSSS | 9F-2OMe-9F 9Sp-1Rp-9Sp | Exon51 |
| WV-2529 | UCAAGGAAGAUGGCAUUUCU | 347 | fU*SfC*SfA*SfA*SfG*SfG*SfA*SfAmGmAmUmGmG*SfC*SfA*SfU*SfU*SfU*SfC*SfU | 1099 | SSSSSSSOOOOSSSSSSS | 7F-6OMe-7F 7Sp-5PO-7Sp | Exon51 |
| WV-2530 | UCAAGGAAGAUGGCAUUUCU | 348 | fU*SfC*SfA*SfA*SfG*SfG*SfA*SfA*SfG*SmAmUmG*SfG*SfC*SfA*SfU*SfU*SfU*SfC*SfU | 1100 | SSSSSSSSSOOOSSSSSSS | 8F-4OMe-8F 8Sp-3PO-8Sp | Exon51 |
| WV-2531 | UCAAGGAAGAUGGCAUUUCU | 349 | fU*SfC*SfA*SfA*SfG*SfG*SfA*SfA*SfA*SfG*SmAmU*SfG*SfG*SfC*SfA*SfU*SfU*SfU*SfC*SfU | 1101 | SSSSSSSSSOSSSSSSSS | 9F-2OMe-9F 9Sp-1PO-9Sp | Exon51 |
| WV-2532 | UCAAGGAAGAUGGCAUUUCU | 350 | fU*SfC*SfA*SfA*SfG*SfG*SfA*mA*mG*mAmU*mG*mG*fC*SfA*SfU*SfU*SfU*SfC*SfU | 1102 | SSSSSSXXXXXXSSSSSSS | 6F-8OMe-6F 6Sp-7PS-6Sp | Exon51 |
| WV-2533 | UCAAGGAAGAUGGCAUUUCU | 351 | mU*SmC*SmA*SmA*SmG*SmG*SmA*RmA*RmG*RmA*RmU*RmG*RmG*RmC*SmA*SmU*SmU*SmU*SmC*SmU | 1103 | SSSSSSSRRRRRRSSSSSSS | All-OMe 6Sp-7Rp-6Sp | Exon51 |
| WV-2534 | UCAAGGAAGAUGGCAUUUCU | 352 | mU*SmC*SmA*SmA*SmG*SmG*SmA*SmA*RmG*RmA*RmU*RmG*RmG*SmC*SmA*SmU*SmU*SmU*SmC*SmU | 1104 | SSSSSSSSRRRRRSSSSSSS | All-OMe 7Sp-5Rp-7Sp | Exon51 |
| WV-2535 | UCAAGGAAGAUGGCAUUUCU | 353 | mU*SmC*SmA*SmA*SmG*SmG*SmA*SmA*SmG*RmA*RmU*RmG*SmG*SmC*SmA*SmU*SmU*SmU*SmC*SmU | 1105 | SSSSSSSSSRRRSSSSSSS | All-OMe 8Sp-3Rp-8Sp | Exon51 |
| WV-2536 | UCAAGGAAGAUGGCAUUUCU | 354 | mU*SmC*SmA*SmA*SmG*SmG*SmA*SmA*SmG*SmA*RmU*SmG*SmG*SmC*SmA*SmU*SmU*SmU*SmC*SmU | 1106 | SSSSSSSSSRSSSSSSSS | All-OMe 9Sp-1Rp-9Sp | Exon51 |
| WV-2537 | UCAAGGAAGAUGGCAUUUCU | 355 | mU*SmC*SmA*SmA*SmG*SmG*SmA*mA*mG*mA*mU*mG*mG*mC*SmA*SmU*SmU*SmU*SmC*SmU | 1107 | SSSSSSXXXXXXSSSSSSS | All-OMe 6Sp-7PS-6Sp | Exon51 |
| WV-2538 | UCAAGGAAGAUGGCAUUUCU | 356 | L001*mU*mC*mA*mA*mG*mG*mA*mA*mG*mA*mU*mG*mG*mC*mA*mU*mU*mU*mC*mU | 1108 | XXXXXXXXXXXXXXXXXXXX | Drisapersen with C6 amino linker | Exon51 |
| WV-2578 | UCAAGGAAGAUGGCAUUUCU | 357 | Mod013L001*mU*mC*mA*mA*mG*mG*mA*mA*mG*mA*mU*mG*mG*mC*mA*mU*mU*mU*mC*mU | 1109 | OXXXXXXXXXXXXXXXXXXXX | Drisapersen with C6 and Laurie | Exon51 |
| WV-2579 | UCAAGGAAGAUGGCAUUUCU | 358 | Mod014L001*mU*mC*mA*mA*mG*mG*mA*mA*mG*mA*mU*mG*mG*mC*mA*mU*mU*mU*mC*mU | 1110 | OXXXXXXXXXXXXXXXXXXXX | Drisapersen with C6 and Myristic | Exon51 |
| WV-2580 | UCAAGGAAGAUGGCAUUUCU | 359 | Mod005L001*mU*mC*mA*mA*mG*mG*mA*mA*mG*mA*mU*mG*mG*mC*mA*mU*mU*mU*mC*mU | 1111 | OXXXXXXXXXXXXXXXXXXXX | Drisapersen with C6 and Palmitic | Exon51 |
| WV-2581 | UCAAGGAAGAUGGCAUUUCU | 360 | Mod015L001*mU*mC*mA*mA*mG*mG*mA*mA*mG*mA*mU*mG*mG*mC*mA*mU*mU*mU*mC*mU | 1112 | OXXXXXXXXXXXXXXXXXXXX | Drisapersen with C6 and Stearic | Exon51 |
| WV-2582 | UCAAGGAAGAUGGCAUUUCU | 361 | Mod016L001*mU*mC*mA*mA*mG*mG*mA*mA*mG*mA*mU*mG*mG*mC*mA*mU*mU*mU*mC*mU | 1113 | OXXXXXXXXXXXXXXXXXXXX | Drisapersen with C6 and Oleic | Exon51 |
| WV-2583 | UCAAGGAAGAUGGCAUUUCU | 362 | Mod017L001*mU*mC*mA*mA*mG*mG*mA*mA*mG*mA*mU*mG*mG*mC*mA*mU*mU*mU*mC*mU | 1114 | OXXXXXXXXXXXXXXXXXXXX | Drisapersen with C6 and Linoleic | Exon51 |
| WV-2584 | UCAAGGAAGAUGGCAUUUCU | 363 | Mod018L001*mU*mC*mA*mA*mG*mG*mA*mA*mG*mA*mU*mG*mG*mC*mA*mU*mU*mU*mC*mU | 1115 | OXXXXXXXXXXXXXXXXXXXX | Drisapersen with C6 and alpha-Linolenic | Exon51 |
| WV-2585 | UCAAGGAAGAUGGCAUUUCU | 364 | Mod019L001*mU*mC*mA*mA*mG*mG*mA*mA*mG*mA*mU*mG*mG*mC*mA*mU*mU*mU*mC*mU | 1116 | OXXXXXXXXXXXXXXXXXXXX | Drisapersen with C6 and gamma-Linolenic | Exon51 |
| WV-2586 | UCAAGGAAGAUGGCAUUUCU | 365 | Mod006L001*mU*mC*mA*mA*mG*mG*mA*mA*mG*mA*mU*mG*mG*mC*mA*mU*mU*mU*mC*mU | 1117 | OXXXXXXXXXXXXXXXXXXXX | Drisapersen with C6 and DHA | Exon51 |
| WV-2587 | UCAAGGAAGAUGGCAUUUCU | 366 | Mod020L001*mU*mC*mA*mA*mG*mG*mA*mA*mG*mA*mU*mG*mG*mC*mA*mU*mU*mU*mC*mU | 1118 | OXXXXXXXXXXXXXXXXXXXX | Drisapersen with C6 and Turbinaric | Exon51 |
| WV-2588 | UCAAGGAAGAUGGCAUUUCU | 367 | Mod021*mU*mC*mA*mA*mG*mG*mA*mA*mG*mA*mU*mG*mG*mC*mA*mU*mU*mU*mC*mU | 1119 | XXXXXXXXXXXXXXXXXXXX | Drisapersen with C6 and Dilinoleic | Exon51 |
| WV-2660 | UCAAGGAAGAUGGCAUUUCU | 368 | mU*mC*mA*mA*mG*mG*mAmAmGmAmUmGmGmC*mA*mU*mU*mU*mC*mU | 1120 | XXXXXXOOOOOOOXXXXXXX | All-OMe 6PS-7PO-6PS | Exon51 |
| WV-2661 | UCAAGGAAGAUGGCAUUUCU | 369 | mU*mC*mA*mA*mG*mG*mA*mAmGmAmUmGmG*mC*mA*mU*mU*mU*mC*mU | 1121 | XXXXXXXOOOOOXXXXXXX | All-OMe 7PS-5PO-7PS | Exon51 |
| WV-2662 | UCAAGGAAGAUGGCAUUUCU | 370 | mU*mC*mA*mA*mG*mG*mA*mA*mGmAmUmG*mG*mC*mA*mU*mU*mU*mC*mU | 1122 | XXXXXXXXOOOXXXXXXXX | All-OMe 8PS-3PO-8PS | Exon51 |
| WV-2663 | UCAAGGAAGAUGGCAUUUCU | 371 | mU*mC*mA*mA*mG*mG*mA*mA*mG*mAmU*mG*mG*mC*mA*mU*mU*mU*mC*mU | 1123 | XXXXXXXXXOXXXXXXXXX | All-OMe 9PS-1PO-9PS | Exon51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2664 | UCAAGGAAGAUGGCAUUUCU | 372 | mU*SmC*SmA*SmA*SmG*SmG*SmAmAmG mAmUmGmC*SmA*SmU*SmU*SmU*SmC *SmU | 1124 | SSSSSSOOOOO OSSSSSS | All-OMe 6Sp-7PO-6Sp | Exon51 |
| WV-2665 | UCAAGGAAGAUGGCAUUUCU | 373 | mU*SmC*SmA*SmA*SmG*SmG*SmA*SmAm GmAmUmGmG*SmC*SmA*SmU*SmU*SmU* SmC*SmU | 1125 | SSSSSSSOOOOO SSSSSSS | All-OMe 7Sp-5PO-7Sp | Exon51 |
| WV-2666 | UCAAGGAAGAUGGCAUUUCU | 374 | mU*SmC*SmA*SmA*SmG*SmG*SmA*SmA* SmGmAmUmG*SmG*SmC*SmA*SmU*SmU*S mU*SmC*SmU | 1126 | SSSSSSSSOOOS SSSSSSS | All-OMe 8Sp-3PO-8Sp | Exon51 |
| WV-2667 | UCAAGGAAGAUGGCAUUUCU | 375 | mU*SmC*SmA*SmA*SmG*SmG*SmA*SmA* SmG*SmAmU*SmG*SmG*SmC*SmA*SmU*S mU*SmU*SmC*SmU | 1127 | SSSSSSSSSOSS SSSSSSS | All-OMe 9Sp-1PO-9Sp | Exon51 |
| WV-2668 | UCAAGGAAGAUGGCAUUUCU | 376 | fU*fC*fA*fA*fG*fG*fA*mAmGmAmUmG* fC*fA*fU*fU*fU*fC*fU | 1128 | XXXXXXXOOO OOXXXXXXX | 7F-6OMe-7F 7PS-5PO-7PS | Exon51 |
| WV-2669 | UCAAGGAAGAUGGCAUUUCU | 377 | fU*fC*fA*fA*fG*fG*fA*fA*mGmAmUmG*fG *fC*fA*fU*fU*fU*fC*fU | 1129 | XXXXXXXXOO OXXXXXXXX | 8F-4OMe-8F 8PS-3PO-8PS | Exon51 |
| WV-2670 | UCAAGGAAGAUGGCAUUUCU | 378 | fU*fC*fA*fA*fG*fG*fA*fA*fG*mAmU*fG* fG*fC*fA*fU*fU*fU*fC*fU | 1130 | XXXXXXXXXO XXXXXXXXX | 9F-2OMe-9F 9PS-1PO-9PS | Exon51 |
| WV-2737 | UCAAGGAAGAUGGCAUUUCU | 379 | fU*SfC*SfA*SfA*SfG*SfG*SmAmAmGmA*R mUmGmC*SfA*SfU*SfU*SfU*SfC*SfU | 1131 | SSSSSSOOOROO OSSSSSS | | DMD |
| WV-2738 | UCAAGGAAGAUGGCAUUUCU | 380 | fU*SfC*SfA*SfA*SfG*SfG*SmAmAmG*RmA* RmU*RmGmC*SfA*SfU*SfU*SfU*SfC*Sf U | 1132 | SSSSSSOORRRO OSSSSSS | | Exon 51 |
| WV-2739 | UCAAGGAAGAUGGCAUUUCU | 381 | fU*SfC*SfA*SfA*SfG*SfG*SmAmA*RmG*Rm A*RmU*RmG*RmGmC*SfA*SfU*SfU*SfU*Sf C*SfU | 1133 | SSSSSSORRRRR OSSSSSS | | Exon 51 |
| WV-2740 | UCAAGGAAGAUGGCAUUUCU | 382 | fU*SfC*SfA*SfA*SfG*SfG*SfG*SmA*RmA*RmGm AmUmG*RmG*RmC*SfA*SfU*SfU*SfU*SfC* SfU | 1134 | SSSSSSRROOOR RSSSSSS | | Exon 51 |
| WV-2741 | UCAAGGAAGAUGGCAUUUCU | 383 | fU*SfC*SfA*SfA*SfG*SfG*SmA*RmAmGmA mUmGmG*RmC*SfA*SfU*SfU*SfU*SfC*SfU | 1135 | SSSSSSROOOOO RSSSSSS | | Exon 51 |
| WV-2742 | UCAAGGAAGAUGGCAUUUCU | 384 | fU*SfC*SfA*SfA*SfG*SfG*SmA*SmA*SmGm AmUmG*SmG*SmC*SfA*SfU*SfU*SfU*SfC*S fU | 1136 | SSSSSSSSOOOS SSSSSSS | | Exon 51 |
| WV-2743 | UCAAGGAAGAUGGCAUUUCU | 385 | fU*SfC*SfA*SfA*SfG*SfG*SmA*SmAmGmA mUmG*SmC*SfA*SfU*SfU*SfU*SfC*SfU | 1137 | SSSSSSSOOOOO SSSSSSS | | Exon 51 |
| WV-2744 | UCAAGGAAGAUGGCAUUUCU | 386 | fU*SfC*SfA*SfA*SfG*SfG*SmA*SmA*SmG*S mA*SmU*SmG*SmG*SmC*SfA*SfU*SfU*SfU *SfC*SfU | 1138 | SSSSSSSSSSSS SSSSSSS | | Exon 51 |
| WV-2745 | UCAAGGAAGAUGGCAUUUCU | 387 | fU*SfC*SfA*SfA*SfG*SfG*SmAmAmGmAfU* SmGmG*SfC*SfA*SfU*SfU*SfU*SfC*SfU | 1139 | SSSSSSOOOOSO SSSSSSS | | Exon 51 |
| WV-2746 | UCAAGGAAGAUGGCAUUUCU | 388 | fU*SfC*SfA*SfA*SfG*SfG*SmA*RmA*RmG* RmA*RfU*SmG*RmG*SfC*SfA*SfU*SfU*SfU *SfC*SfU | 1140 | SSSSSSRRRRSR SSSSSSS | | Exon 51 |
| WV-2747 | UCAAGGAAGAUGGCAUUUCU | 389 | fU*SfC*SfA*SfA*SmG*SmG*SfAfAmGmAfU* SmGmG*SfC*SfA*SfU*SfU*SfU*SfC*SfU | 1141 | SSSSSSOOOOSO SSSSSSS | | Exon 51 |
| WV-2748 | UCAAGGAAGAUGGCAUUUCU | 390 | fU*SfC*SfA*SfA*SmG*SmG*SfA*RfA*RmG* RmA*RfU*SmG*RmG*SfC*SfA*SfU*SfU*SfU *SfC*SfU | 1142 | SSSSSSRRRRSR SSSSSSS | | Exon 51 |
| WV-2749 | UCAAGGAAGAUGGCAUUUCU | 391 | fU*SfC*SfA*SfA*SfG*SfG*SfA*SmAmGmAm UmG*SfC*SfA*SfU*SfU*SfU*SfC*SfU | 1143 | SSSSSSSOOOOO SSSSSSS | | Exon 51 |
| WV-2750 | UCAAGGAAGAUGGCAUUUCU | 392 | fU*SfC*SfA*SfA*SfG*SfG*SfA*SmA*RmG*R mA*RmU*RmG*RmG*SfC*SfA*SfU*SfU*SfU *SfC*SfU | 1144 | SSSSSSSRRRRR SSSSSSS | | Exon 51 |
| WV-2791 | UCAAGGAAGAUGGCAUUUCU | 393 | mU*SmC*SmA*SfA*SfG*SfG*SmA*RmA*Rm G*RmA*RmU*RmG*RmC*SfA*SfU*SfU*SfU *SmU*SmC*SmU | 1145 | SSSSSSRRRRRR RSSSSSS | | Exon 51 |
| WV-2792 | UCAAGGAAGAUGGCAUUUCU | 394 | mU*SmC*SmA*SfA*SfG*SfG*SfA*SmA*RmG *RmA*RmU*RmG*RmG*SfC*SfA*SfU*SfU*S mU*SmC*SmU | 1146 | SSSSSSSRRRRR SSSSSSS | | Exon 51 |
| WV-2793 | UCAAGGAAGAUGGCAUUUCU | 395 | mU*SmC*SmA*SmA*SfG*SfG*SfA*SfA*SmG* RmA*RmU*RmG*SfG*SfA*SfU*SfU*SfU*Sm U*SmC*SmU | 1147 | SSSSSSSSRRRS SSSSSSS | | Exon 51 |
| WV-2794 | UCAAGGAAGAUGGCAUUUCU | 396 | mU*SmC*SmA*SfA*SfG*SfG*SfA*SfA*SfG*S mA*RmU*SfG*SfG*SfC*SfA*SfU*SfU*SmU* SmC*SmU | 1148 | SSSSSSSSSRSS SSSSSSS | | Exon 51 |
| WV-2795 | UCAAGGAAGAUGGCAUUUCU | 397 | mU*SmC*SmA*SfA*SfG*SfG*SfA*SfA*SmG mAmUmG*SfG*SfC*SfA*SfU*SfU*SmU*SmC *SmU | 1149 | SSSSSSSSOOOS SSSSSSS | | Exon 51 |
| WV-2796 | UCAAGGAAGAUGGCAUUUCU | 398 | mU*SmC*SmA*SfA*SfG*SfG*SfA*SfA*SfG*S mAmU*SfG*SfG*SfC*SfA*SfU*SfU*SmU*Sm C*SmU | 1150 | SSSSSSSSSOSS SSSSSSS | | Exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2797 | UCAAGGAAGAUGGCAUUUCU | 399 | fU*fC*fA*fA*fG*fG*fA*fA*mG*mA*mU*mG*mG*fC*fA*fU*fU*fU*fC*fU | 1151 | XXXXXXXXXXXXXXXXXXX | randomer based on WV-2526 | DMD |
| WV-2798 | UCAAGGAAGAUGGCAUUUCU | 400 | fU*fC*fA*fA*fG*fG*fA*fA*mG*mA*mU*mG*fG*fC*fA*fU*fU*fU*fC*fU | 1152 | XXXXXXXXXXXXXXXXXXX | randomer based on WV-2527 | DMD |
| WV-2799 | UCAAGGAAGAUGGCAUUUCU | 401 | fU*fC*fA*fA*fG*fG*fA*fA*fG*mA*mU*fG*fG*fC*fA*fU*fU*fU*fC*fU | 1153 | XXXXXXXXXXXXXXXXXXX | randomer based on WV-2528 | DMD |
| WV-2800 | UCAAGGAAGAUGGCAUUUCU | 402 | fU*fC*fA*fA*fG*fG*fA*fA*mA*mG*mA*mU*mG*mG*fC*fA*fU*fU*fU*fC*fU | 1154 | XXXXXXXXXXXXXXXXXXX | randomer based on WV-2750 | DMD |
| WV-2801 | UCAAGGAAGAUGGCAUUUCU | 403 | mU*mC*mA*fA*fG*fG*mA*mA*mG*mA*mU*mG*mG*mC*fA*fU*fU*mU*mC*mU | 1155 | XXXXXXXXXXXXXXXXXXX | randomer based on WV-2791 | DMD |
| WV-2802 | UCAAGGAAGAUGGCAUUUCU | 404 | mU*mC*mA*fA*fG*fG*fA*mA*mG*mA*mU*mG*mG*fC*fA*fU*fU*mU*mC*mU | 1156 | XXXXXXXXXXXXXXXXXXX | randomer based on WV-2792 | DMD |
| WV-2803 | UCAAGGAAGAUGGCAUUUCU | 405 | mU*mC*mA*fA*fG*fG*fA*fA*mG*mA*mU*mG*fG*fC*fA*fU*fU*mU*mC*mU | 1157 | XXXXXXXXXXXXXXXXXXX | randomer based on WV-2793 | DMD |
| WV-2804 | UCAAGGAAGAUGGCAUUUCU | 406 | mU*mC*mA*fA*fG*fG*fA*fA*fG*mA*mU*fG*fG*fC*fA*fU*fU*mU*mC*mU | 1158 | XXXXXXXXXXXXXXXXXXX | randomer based on WV-2794 | DMD |
| WV-2805 | UCAAGGAAGAUGGCAUUUCU | 407 | mU*mC*mA*fA*fG*fG*fA*fA*mGmAmUmG*fG*fC*fA*fU*fU*mU*mC*mU | 1159 | XXXXXXXXXXOOOOXXXXX | randomer based on WV-2795 | DMD |
| WV-2806 | UCAAGGAAGAUGGCAUUUCU | 408 | mU*mC*mA*fA*fG*fG*fA*fA*fG*mAmU*fG*fG*fC*fA*fU*fU*mU*mC*mU | 1160 | XXXXXXXXXXOXXXXXXXX | randomer based on WV-2796 | DMD |
| WV-2807 | UCAAGGAAGAUGGCAUUUCU | 409 | Mod024L001*mU*mC*mA*mA*mG*mG*mA*mA*mG*mA*mU*mG*mG*mC*mA*mU*mU*mU*mC*mU | 1161 | OXXXXXXXXXXXXXXXXXXXX | All-OMe full-PS TriGlcNAc conjugated WV942 C6 PS | Exon 51 |
| WV-2808 | UCAAGGAAGAUGGCAUUUCU | 410 | Mod026L001*mU*mC*mA*mA*mG*mG*mA*mA*mG*mA*mU*mG*mG*mC*mA*mU*mU*mU*mC*mU | 1162 | OXXXXXXXXXXXXXXXXXXXX | All-OMe full-PS Exon 51 TrialphaMannose conjugated WV942 C6 PS | |
| WV-2812 | UCAAGGAAGATGGCAUUUCU | 411 | fU*fC*fA*fA*fG*fG*mA*mA*mG*mA*BrdU*mG*mG*mC*fA*fU*fU*fU*fC*fU | 1163 | XXXXXXXXXXXXXXXXXXX | WV-1714 based BrdU in the center | DMD exon 51 |
| WV-2813 | UCAAGGAAGATGGCAUUUCU | 412 | fU*fC*fA*fA*fG*fG*fA*fA*fG*mA*BrdU*fG*fG*fC*fA*fU*fU*fU*fC*fU | 1164 | XXXXXXXXXXXXXXXXXXX | WV-2528 and WV-2799 based randomer BrdU in the center | DMD exon 51 |
| WV-2814 | UCAAGGAAGATGGCAUUUCU | 413 | mU*mC*mA*mA*mG*mG*mA*mA*mG*mA*BrdU*mG*mG*mC*mA*mU*mU*mU*mC*mU | 1165 | XXXXXXXXXXXXXXXXXXX | WV-942 based BrdU in the center | DMD exon 51 |
| WV-3017 | UCAAGGAAGATGGCAUUUCU | 414 | fU*SfC*SfA*SfA*SfG*SfG*SfA*SfA*SmGmABrdUmG*SfG*SfC*SfA*SfU*SfU*SfU*SfC*SfU | 1166 | SSSSSSSSOOOSSSSSSS | WV-2530 based, BrdU in the middle | Exon 51 |
| WV-3018 | UCAAGGAAGATGGCAUUUCU | 415 | fU*fC*fA*fA*fG*fG*fA*fA*mGmABrdUmG*fG*fC*fA*fU*fU*fU*fC*fU | 1167 | XXXXXXXXOOOXXXXXXX | WV-2530 based, randomer, BrdU in the middle | Exon 51 |
| WV-3019 | UCAAGGAAGATGGCAUUUCU | 416 | fU*SfC*SfA*SfA*SfG*SfG*SmAmAmGmABrdUmGmGmC*SfA*SfU*SfU*SfU*SfC*SfU | 1168 | SSSSSSOOOOOOSSSSSS | WV-2438 based, BrdU in the middle | Exon 51 |
| WV-3020 | UCAAGGAAGATGGCAUUUCU | 417 | fU*fC*fA*fA*fG*fG*mAmAmGmABrdUmGmGmC*fA*fU*fU*fU*fC*fU | 1169 | XXXXXXOOOOOOOXXXXXX | WV-2438 based, randomer, BrdU in the middle | Exon 51 |
| WV-3022 | UCAAGGAAGAUGGCAUUUCU | 418 | L001*fU*SfC*SfA*SfA*SfG*SfG*SmAmAmGmAmUmGmGmC*SfA*SfU*SfU*SfU*SfC*SfU | 1170 | XSSSSSSOOOOOOOSSSSSSS | WV-2438 based; C6 PS; on support; used for conjugation | DMD |
| WV-3023 | UCAAGGAAGAUGGCAUUUCU | 419 | Mod015L001*fU*SfC*SfA*SfA*SfG*SfG*SmAmAmGmAmUmGmGmC*SfA*SfU*SfU*SfU*SfC*SfU | 1171 | OXSSSSSSOOOOOOOSSSSSSS | WV-2438 based; conjugate with stearic acid C6 PS | DMD |
| WV-3024 | UCAAGGAAGAUGGCAUUUCU | 420 | Mod006L001*fU*SfC*SfA*SfA*SfG*SfG*SmAmAmGmAmUmGmGmC*SfA*SfU*SfU*SfU*SfC*SfU | 1172 | OXSSSSSSOOOOOOOSSSSSSS | WV-2438 based; conjugate with DHA C6 PS | DMD |
| WV-3025 | UCAAGGAAGAUGGCAUUUCU | 421 | L001*fU*SfC*SfA*SfA*SfG*SfG*SfA*SfA*SmGmAmUmG*SfG*SfC*SfA*SfU*SfU*SfU*SfC*SfU | 1173 | XSSSSSSSSSOOOOSSSSSSS | WV-2530 based; C6 PS; on support; used for conjugation | DMD |
| WV-3026 | UCAAGGAAGAUGGCAUUUCU | 422 | Mod015L001*fU*SfC*SfA*SfA*SfG*SfG*SfA*SfA*SmGmAmUmG*SfG*SfC*SfA*SfU*SfU*SfU*SfC*SfU | 1174 | OXSSSSSSSSSOOOOSSSSSSSS | WV-2530 based; conjugate with stearic acid C6 PS | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3027 | UCAAGGAAGAUGGCAUUUCU | 423 | Mod006L001*fU*SfC*SfA*SfA*SfG*SfG*SfA*SfA*SmGmAmUmG*SfG*SfC*SfA*SfU*SfU*SfU*SfC*SfU | 1175 | OXSSSSSSSSOOOSSSSSSSS | WV-2530 based; conjugate with DHA C6 PS | DMD |
| WV-3028 | UCAAGGAAGAUGGCAUUUCU | 424 | fU*SfC*SfA*SfA*SfG*SfG*SfA*SfA*SmGmAmUmG*SfC*SfA*SfU*SfU*SfU*SfC*SfU | 1176 | SSSSSSSSOOOOSSSSSSS | WV-2529 based, convert PO between 8th and 9th nt to PS | DMD |
| WV-3029 | UCAAGGAAGAUGGCAUUUCU | 425 | L001*fU*fC*fA*fA*fG*fG*mA*mA*mG*mA*mU*mG*mG*mC*fA*fU*fU*fU*fC*fU | 1177 | XXXXXXXXXXXXXXXXXXX | WV-1714 based; DMD stereorandom; C6 PS; on support | DMD |
| WV-3030 | UCAAGGAAGAUGGCAUUUCU | 426 | Mod015L001*fU*fC*fA*fA*fG*fG*mA*mA*mG*mA*mU*mG*mG*mC*fA*fU*fU*fU*fC*fU | 1178 | OXXXXXXXXXXXXXXXXXXX | WV-1714 based; stereorandom; conjugate with stearic acid C6 PS | DMD |
| WV-3031 | UCAAGGAAGAUGGCAUUUCU | 427 | Mod006L001*fU*fC*fA*fA*fG*fG*mA*mA*mG*mA*mU*mG*mG*mC*fA*fU*fU*fU*fC*fU | 1179 | OXXXXXXXXXXXXXXXXXXX | WV-1714 based; stereorandom; conjugate with DHA C6 PS | DMD |
| WV-3032 | UCAAGGAAGAUGGCAUUUCU | 428 | Mod020L001*fU*fC*fA*fA*fG*fG*mA*mA*mG*mA*mU*mG*mG*mC*fA*fU*fU*fU*fC*fU | 1180 | OXXXXXXXXXXXXXXXXXXX | WV-1714 based; stereorandom; conjugate with turbinaric acid C6PS | DMD |
| WV-3033 | UCAAGGAAGAUGGCAUUUCU | 429 | Mod019L001*fU*fC*fA*fA*fG*fG*mA*mA*mG*mA*mU*mG*mG*mC*fA*fU*fU*fU*fC*fU | 1181 | OXXXXXXXXXXXXXXXXXXX | WV-1714 based; stereorandom; conjugate with gamma-Linolenic acid C6 PS | DMD |
| WV-3034 | UCAAGGAAGAUGGCAUUUCU | 430 | L001*fU*fC*fA*fA*fG*fG*fA*fA*mGmAmUmG*fG*fC*fA*fU*fU*fU*fC*fU | 1182 | XXXXXXXXXOOOXXXXXXXX | WV-2530 based; stereorandom; C6 PS; on support | DMD |
| WV-3035 | UCAAGGAAGAUGGCAUUUCU | 431 | Mod015L001*fU*fC*fA*fA*fG*fG*fA*fA*mGmAmUmG*fG*fC*fA*fU*fU*fU*fC*fU | 1183 | OXXXXXXXXXOOOXXXXXXXX | WV-2530 based; stereorandom; conjugate with stearic acid C6 PS | DMD |
| WV-3036 | UCAAGGAAGAUGGCAUUUCU | 432 | Mod006L001*fU*fC*fA*fA*fG*fG*fA*fA*mGmAmUmG*fG*fC*fA*fU*fU*fU*fC*fU | 1184 | OXXXXXXXXXOOOXXXXXXXX | WV-2530 based; stereorandom; conjugate with DHA C6 PS | DMD |
| WV-3037 | UCAAGGAAGAUGGCAUUUCU | 433 | Mod020L001*fiT*fC*fA*fA*fG*fG*fA*fA*mGmAmUmG*fG*fC*fA*fU*fU*fU*fC*fU | 1185 | OXXXXXXXXXOOOXXXXXXXX | WV-2530 based; stereorandom; conjugatwith turbinaric acid C6 PS | DMD |
| WV-3038 | UCAAGGAAGAUGGCAUUUCU | 434 | Mod019L001*fU*fC*fA*fA*fG*fG*fA*fA*mGmAmUmG*fG*fC*fA*fU*fU*fU*fC*fU | 1186 | OXXXXXXXXXOOOXXXXXXXX | WV-2530 based; stereorandom; conjugate with gamma-Linolenic acid C6 PS | DMD |
| WV-3039 | UCAAGGAAGAUGGCAUUUCU | 435 | fU*fC*fA*fA*fG*fG*mAmAmGmA*mUmGmC*fA*fITTU*fU*fC*fU | 1187 | XXXXXXOOOXOOOXXXXXXX | Randomer of WV-2737; based on WV-2438; with Rp/PO in the core | DMD exon 51 |
| WV-3040 | UCAAGGAAGAUGGCAUUUCU | 436 | fU*fC*fA*fA*fG*fG*mAmAmG*mA*mU*mGmGmC*fA*fU*fU*fU*fC*fU | 1188 | XXXXXXOOXXXOOXXXXXXX | Randomer of WV-2738; based on WV-2438; with Rp/PO in the core | DMD exon 51 |
| WV-3041 | UCAAGGAAGAUGGCAUUUCU | 437 | fU*fC*fA*fA*fG*fG*mA*mG*mA*mU*mG*mGmC*fA*fU*fU*fU*fC*fU | 1189 | XXXXXXXOXXXOOXXXXXXX | Randomer of WV-2739; based on WV-2438; with Rp/PO in the core | DMD exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3042 | UCAAGGAAGA UGGCAUUUCU | 438 | fU*fC*fA*fA*fG*fG*mA*mA*mGmAmUmG*mG*mC*fA*fU*fU*fU*fC*fU | 1190 | XXXXXXXOO OXXXXXXXX | Randomer of WV-2740; based on WV-2438; with Rp/PO in the core | DMD exon 51 |
| WV-3043 | UCAAGGAAGA UGGCAUUUCU | 439 | fU*fC*fA*fA*fG*fG*mA*mAmGmAmUmG*mG*mC*fA*fU*fU*fU*fC*fU | 1191 | XXXXXXXOOO OOXXXXXXX | Randomer of WV-2741; based on WV-2438; with Rp/PO in the core | DMD exon 51 |
| WV-3044 | UCAAGGAAGA UGGCAUUUCU | 440 | fU*fC*fA*fA*fG*fG*mA*mA*mGmAmUmG*mG*mC*fA*fITTU*fU*fC*fU | 1192 | XXXXXXXOO OXXXXXXXX | Randomer of WV-2742; based on WV-2438; with Rp/PO in the core | DMD exon 51 |
| WV-3045 | UCAAGGAAGA UGGCAUUUCU | 441 | fU*fC*fA*fA*fG*fG*mA*mAmGmAmUmG*mG*mC*fA*fU*fU*fU*fC*fU | 1193 | XXXXXXXOOO OOXXXXXXX | Randomer of WV-2743; based on WV-2438; with Rp/PO in the core | DMD exon 51 |
| WV-3046 | UCAAGGAAGA UGGCAUUUCU | 442 | fU*fC*fA*fA*fG*fG*mAmAmGmAfU*mGmG*fC*fA*fU*fU*fU*fC*fU | 1194 | XXXXXXOOOO XOXXXXXXX | Randomer of WV-2745; based on WV-2444; Sp/PO in the core; with additional fU fC in the core | DMD exon 51 |
| WV-3047 | UCAAGGAAGA UGGCAUUUCU | 443 | fU*fC*fA*fA*fG*fG*mA*mA*mG*mA*fU*mG*mG*fC*fA*fU*fU*fU*fC*fU | 1195 | XXXXXXXXXX XXXXXXXX | Randomer of WV-2746; based on WV-2444; Sp/Rp in the core; with additional fU fC in the core | DMD exon 51 |
| WV-3048 | UCAAGGAAGA UGGCAUUUCU | 444 | fU*fC*fA*fA*mG*mG*fAfAmGmAfU*mGmG*fC*fA*fU*fU*fU*fC*fU | 1196 | XXXXXXOOOO XOXXXXXXX | Randomer of WV-2747; based on WV-2444; Sp/PO in the core; with mGmG on left wing, with additional fA fA fU fC in the core | DMD exon 51 |
| WV-3049 | UCAAGGAAGA UGGCAUUUCU | 445 | fU*fC*fA*fA*mG*mG*fA*fA*mG*mA*fU*mG*mG*fC*fA*fU*fU*fU*fC*fU | 1197 | XXXXXXXXXX XXXXXXXX | Randomer of WV-2748; based on WV-2444; Sp/PO in the core; with mGmG on left wing, with additional fA fA fU fC in the core | DMD exon 51 |
| WV-3050 | UCAAGGAAGA UGGCAUUUCU | 446 | fU*fC*fA*fA*fG*fG*mA*mA*mG*mA*fU*mG*mG*fC*fA*fU*fU*fU*fC*fU | 1198 | XXXXXXXXXX XXXXXXXX | All PS version of the randomer of WV-2745/2746; based on WV-2444; with additional fU fC in the core | DMD exon 51 |
| WV-3051 | UCAAGGAAGA UGGCAUUUCU | 447 | fU*fC*fA*fA*mG*mG*fA*fA*mG*mA*fU*mG*mG*fC*fA*fU*fU*fU*fC*fU | 1199 | XXXXXXXXXX XXXXXXXX | All PS version of the randomer of WV-2747/2748; based on WV-2444; Sp/PO in thec score; with mGmG on left wing, with additional | DMD exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3052 | UCAAGGAAGA UGGCAUUUCU | 448 | fU*fC*fA*fA*mG*mG*fA*fA*mGmAmUmG* mG*fC*fA*fU*fU*fU*fC*fU | 1200 | XXXXXXXXOO OXXXXXXXX | fA fA fU fC in the core Based on WV-2530; replace all 2'F G with 2'Ome G | DMD exon 51 |
| WV-3053 | UCAAGGAAGA UGGCAUUUCU | 449 | fU*fC*fA*fA*mG*mG*mA*mA*mGmAfUmG* mG*fC*fA*fU*fU*fU*fC*fU | 1201 | XXXXXXXXOO OXXXXXXXX | Based on WV-2107; four 2'-F on the 5'; seven 2'-F on the 3'; 2'F U in the center | DMD exon 51 |
| WV-3054 | UCAAGGAAGA UGGCAUUUCU | 450 | fU*fC*fA*fA*mG*mG*fA*fA*mG*mA*mU*m G*mG*fC*fA*fU*fU*fU*fC*fU | 1202 | XXXXXXXXXX XXXXXXXX | All PS; based on WV-2530/2529; replace all 2'F G with 2'Ome G | DMD exon 51 |
| WV-3055 | UCAAGGAAGA UGGCAUUUCU | 451 | fU*fC*fA*fA*mG*mG*mA*mA*mG*mA*fU* mG*mG*fC*fA*fU*fU*fU*fC*fU | 1203 | XXXXXXXXXX XXXXXXXX | All PS; based on WV-2107; four 2'-F on the 5'; seven 2'-F on the 3'; 2'FU in the center | DMD exon 51 |
| WV-3056 | UCAAGGAAGA UGGCAUUUCU | 452 | fU*fC*fA*fA*mG*mG*fAfAmGmA*fU*mG G*fC*fA*fU*fU*fU*fC*fU | 1204 | XXXXXXOOOX XOXXXXXXX | Based on WV-2747; with additional PS in the center between A and U | DMD exon 51 |
| WV-3057 | UCAAGGAAGA UGGCAUUUCU | 453 | fU*fC*fA*fA*mG*mG*fA*mG*mA*fU*mG *mG*fC*fA*fU*fU*fU*fC*fU | 1205 | XXXXXXXXXX XXXXXXXX | All PS version; based on WV-2747; with additional PS in the center between A and U | DMD exon 51 |
| WV-3058 | UCAAGGAAGA UGGCAUUUCU | 454 | fU*fC*fA*fA*mG*mG*fA*mG*fA*fU*mG *mG*fC*fA*fU*fU*fU*fC*fU | 1206 | XXXXXXXXXX XXXXXXXX | Based on WV-1716; with all mC converted to fC | DMD exon 51 |
| WV-3059 | UCAAGGAAGA UGGCAUUUCU | 455 | fU*fC*fA*fA*mG*mG*fA*fA*mGmAmUmGm G*fC*fA*fU*fU*fU*fC*fU | 1207 | XXXXXXXXOO OOXXXXXXX | Randomers of based on WV-G as mG; with additional PS between A and G | DMD exon 51 |
| WV-3060 | UCAAGGAAGA UGGCAUUUCU | 456 | fU*fC*fA*fA*mG*mG*fA*fA*mGmAfU*mGm G*fC*fA*fU*fU*fU*fC*fU | 1208 | XXXXXXXXOO XOXXXXXXX | Randomer; Sp/PO in the core; with mGmG on left wing, with additional fA fA fU fC in the core | DMD exon 51 |
| WV-3061 | UCAAGGAAGA UGGCAUUUCU | 457 | fU*fC*fA*fA*mG*mG*mA*mA*mGmAfU*mG mG*fC*fA*fU*fU*fU*fC*fU | 1209 | XXXXXXXXOO XOXXXXXXX | Based on WV-2107; four 2'-F on the 5'; seven 2'-F on the 3'; 2'F U in the center | DMD exon 51 |
| WV-3070 | UCAAGGAAGA UGGCAUUUCU | 458 | fU*SfC*SfA*SfA*SfG*SfG*SmAmAmGmAmU:mGmGmC*SfA*SfU*SfU*SfU*SfC*SfU | 1210 | SSSSSSOOODO OSSSSSS | WV-2438 based with PS2 after nucleotide 11 | Exon 51 |
| WV-3071 | UCAAGGAAGA UGGCAUUUCU | 459 | fU*SfC*SfA*SfA*SfG*SfG*SmAmA:mGmA:m UmG:mGmC*SfA*SfU*SfU*SfU*SfC*SfU | 1211 | SSSSSSODODOD OSSSSSS | WV-2438 based, with PS2 after nucleotide 8, 10, 12 | Exon 51 |
| WV-3072 | UCAAGGAAGA UGGCAUUUCU | 460 | fU*SfC*SfA*SfA*SfG*SfG*SmA:mAmGmAm U:mGmG:mC*SfA*SfU*SfU*SfU*SfC*SfU | 1212 | SSSSSSDODODO DSSSSSS | WV-2438 based, with PS2 after nucleotide 7, 9, 11, 13 | Exon 51 |
| WV-3073 | UCAAGGAAGA UGGCAUUUCU | 461 | fU*SfC*SfA*SfA*SfG*SfG*SmA:mAmGmAm U:mGmG:mC*SfA*SfU*SfU*SfU*SfC*SfU | 1213 | SSSSSSDOOODO DSSSSSS | WV-2438 based, with PS2 after | Exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3074 | UCAAGGAAGA UGGCAUUUCU | 462 | fU*SfC*SfA*SfA*MSG:mAmAmGmAmU:mG mGmC*SfA*SfU*SfU*SfU*SfC*SfU | 1214 | SSSXDDOOOOD OOSSSSSS | WV-2438 based, with PS2 after nucleotide 7, 10, 13 nucleotide 11; two SfG * on 5' wing converted to fG-PS2 | Exon 51 |
| WV-3075 | UCAAGGAAGA UGGCAUUUCU | 463 | fU*SfC*SfA*SfA*mG:mG:mAmAmGmAmU:m GmGmC*SfA*SfU*SfU*SfU*SfC*SfU | 1215 | SSSXDDOOOOD OOSSSSSS | WV-2438 based, with PS2 after nucleotide 11; two SfG * on 5' wing converted to mG-PS2 | Exon 51 |
| WV-3076 | UCAAGGAAGA UGGCAUUUCU | 464 | fU*SfC*SfA*SfA*SfG*SfG*SfA*SmAmGmAm U:mGmG*SfC*SfA*SfU*SfU*SfU*SfC*SfU | 1216 | SSSSSSSOOODO SSSSSSS | WV-2749 based, with PS2 after nucleotide 11 | Exon 51 |
| WV-3077 | UCAAGGAAGA UGGCAUUUCU | 465 | fU*SfC*SfA*SfA*fGSG:fA*SmAmGmAmU:m GmG*SfC*SfA*SfU*SfU*SfU*SfC*SfU | 1217 | SSSXDDSOOOD OSSSSSSS | WV-2749 based, with PS2 after nucleotide 11; two SfG * on 5' wing converted to fG-PS2 | Exon 51 |
| WV-3078 | UCAAGGAAGA UGGCAUUUCU | 466 | fU*SfC*SfA*SfA*mG:mGSA*SmAmGmAmU: mGmG*SfC*SfA*SfU*SfU*SfU*SfC*SfU | 1218 | SSSXDDSOOOD OSSSSSSS | WV-2749 based, with PS2 after nucleotide 11; two SfG * on 5' wing converted to mG-PS2 | Exon 51 |
| WV-3079 | UCAAGGAAGA UGGCAUUUCU | 467 | fU*SfC*SfA*SfA*SfG*SfG*SfA*SfA*SmGmA mU:mG*SfG*SfC*SfA*SfU*SfU*SfU*SfC* SfU | 1219 | SSSSSSSOODS SSSSSSS | WV-2530 based, with PS2 after nucleotide 11 | Exon 51 |
| WV-3080 | UCAAGGAAGA UGGCAUUUCU | 468 | U*SfC*SfA*SfA*SfG*SfG*SfA*SfA*SmG: mAf:mU:mG*SfG*SfC*SfA*SfU*SfU*SfU* SfC*SfU | 1220 | SSSSSSSSDDDS SSSSSSS | WV-2530 based, with PS2 after nucleotide 9, 10, 11 | Exon 51 |
| WV-3081 | UCAAGGAAGA UGGCAUUUCU | 469 | fU*SfC*SfA*SfA*SfG*SfG*SfA*SfA*SmG: mAmU:mG*SfG*SfC*SfA*SfU*SfU*SfU*SfC* SfU | 1221 | SSSSSSSSDODS SSSSSSS | WV-2530 based, with PS2 after nucleotide 9, 11 | Exon 51 |
| WV-3082 | UCAAGGAAGA UGGCAUUUCU | 470 | fU*SfC*SfA*SfA*fG:fG:fA*SfA*SmGmAmU: mG*SfG*SfC*SfA*SfU*SfU*SfU*SfC*SfU | 1222 | SSSXDDSSOODS SSSSSSS | WV-2530 based, with PS2 after nucleotide 11; two SfG * on 5' wing converted to fG-PS2 | Exon 51 |
| WV-3083 | UCAAGGAAGA UGGCAUUUCU | 471 | fU*SfC*SfA*SfA*mG:mGSA*SfA*SmGmAmU :mG*SfG*SfC*SfA*SfU*SfU*SfU*SfC*SfU | 1223 | SSSXDDSSOODS SSSSSSS | WV-2530 based, with PS2 after nucleotide 11; two SfG * on 5' wing converted to mG-PS2 | Exon 51 |
| WV-3084 | UCAAGGAAGA UGGCAUUUCU | 472 | Mod015L001mU*mC*mA*mA*mG*mG*mA*m A*mG*mA*mU*mG*mG*mC*mA*mU*mU*m U*mC*mU | 1224 | OOXXXXXXXX XXXXXXXXXX X | WV942 with C6 PO and Stearic | Exon 51 |
| WV-3085 | UCAAGGAAGA UGGCAUUUCU | 473 | Mod019L001mU*mC*mA*mA*mG*mG*mA*m A*mG*mA*mU*mG*mG*mC*mA*mU*mU*m U*mC*mU | 1225 | OOXXXXXXXX XXXXXXXXXX X | WV942 with C6 PO and gamma-Linolenic | Exon 51 |
| WV-3086 | UCAAGGAAGA UGGCAUUUCU | 474 | Mod020L001mU*mC*mA*mA*mG*mG*mA*m A*mG*mA*mU*mG*mG*mC*mA*mU*mU*m U*mC*mU | 1226 | OOXXXXXXXX XXXXXXXXXX X | WV942 with C6 PO and Turbinaric | Exon 51 |
| WV-3087 | UCAAGGAAGA UGGCAUUUCU | 475 | Mod015L001:mU*mC*mA*mA*mG*mG*mA* mA*mG*mA*mU*mG*mG*mC*mA*mU*mU* mU*mC*mU | 1227 | ODXXXXXXXX XXXXXXXXXX X | WV942 with C6 PS2 and Stearic | Exon 51 |

TABLE 2-continued

Example Oligonucleotides.

| WAVE ID | Base Sequence | SEQ ID NO: | Description | SEQ ID NO: | Stereo-chemistry[1] | Notes | Target/Pro-gram |
|---|---|---|---|---|---|---|---|
| WV-3088 | UCAAGGAAGAUGGCAUUUCU | 476 | Mod019L001:mU*mC*mA*mA*mG*mG*mA* mA*mG*mA*mU*mG*mG*mC*mA*mU* mU*mC*mU | 1228 | ODXXXXXXXX XXXXXXXXXX X | WV942 with C6 PS2 and gamma-Linolenic | Exon 51 |
| WV-3089 | UCAAGGAAGAUGGCAUUUCU | 477 | Mod020L001:mU*mC*mA*mA*mG*mG*mA* mA*mG*mA*mU*mG*mG*mC*mA*mU*mU* mC*mU | 1229 | ODXXXXXXXX XXXXXXXXXX X | WV942 with C6 PS2 and Turbinaric | Exon 51 |
| WV-3113 | UCAAGGAAGAUGGCAUUUCU | 478 | fU*SfC*SfA*SfA*SfGSG:mAmAmGmAmU:mG mGmC*SfA*SfU*SfU*SfU*SfC*SfU | 1230 | SSSSDDOOOOD OOSSSSSS | Variant of WV-3074. There was a randomer PS in WV-3074 | Exon 51 |
| WV-3114 | UCAAGGAAGAUGGCAUUUCU | 479 | fU*SfC*SfA*SfA*SmG:mG:mAmAmGmAmU: mGmGmC*SfA*SfU*SfU*SfU*SfC*SfU | 1231 | SSSSDDOOOOD OOSSSSSS | Variant of WV-3075. There was a randomer PS in WV-3075 | Exon 51 |
| WV-3115 | UCAAGGAAGAUGGCAUUUCU | 480 | fU*SfC*SfA*SfA*SfGSGSA*SmAmGmAmU:m GmG*SfC*SfA*SfU*SfU*SfU*SfC*SfU | 1232 | SSSSDDSOOOD OOSSSSSS | Variant of WV-3077. There was a randomer PS in WV-3077 | Exon 51 |
| WV-3116 | UCAAGGAAGAUGGCAUUUCU | 481 | fU*SfC*SfA*SfA*SmG:mGSA*SmAmGmAmU: mGmG*SfC*SfA*SfU*SfU*SfU*SfC*SfU | 12333 | SSSSDDSOOOD OOSSSSSS | Variant of WV-3078. There was a randomer PS in WV-3078 | Exon 51 |
| WV-3117 | UCAAGGAAGAUGGCAUUUCU | 482 | fU*SfC*SfA*SfA*SfGSG:fA*SfA*SmGmAmU: mG*SfG*SfC*SfA*SfU*SfU*SfU*SfC*SfU | 1234 | SSSSDDSSOODS SSSSSSS | Variant of WV-3082. There was a randomer PS in WV-3082 | Exon 51 |
| WV-3118 | UCAAGGAAGAUGGCAUUUCU | 483 | fU*SfC*SfA*SfA*SmG:mGSA*SfA*SmGmAm U:mG*SfG*SfC*SfA*SfU*SfU*SfU*SfC*SfU | 1235 | SSSSDDSSOODS SSSSSSS | Variant of WV-3083. There was a randomer PS in WV-3083 | Exon 51 |
| WV-3120 | UCAAGGAAGAUGGCAUUUCU | 484 | fU*SfC*SfA*SfA*SfG*SfG*SfA*SfA*SfG* SmAmUmG*SfG*SfC*SfA*SfU*SfU*SfU*SfC* SfU | 1236 | SSSSSSSSSOOS SSSSSSS | 9F-3OMe-8F 9Sp-2PO-8Sp | Exon 51 |
| WV-3121 | UCAAGGAAGAUGGCAUUUCU | 485 | fU*fC*fA*fA*fG*fG*fA*fA*fG*mAmUmG*fG *fC*fA*fU*fU*fU*fC*fU | 1237 | XXXXXXXXXO OXXXXXXXX | 9F-3OMe-8F 9P5-2PO-8PS, randomer version of WV-3120 | Exon 51 |
| WV-3152 | UCAAGGAAGAUGGCAUUUCU | 486 | fU*SfC*SfA*SfA*SfG*SfG*SmAfA*SmGfA*S mUfG*SmGfC*SfA*SfU*SfU*SfU*SfC*SfU | 1238 | SSSSSSOSOSOS OSSSSSS | WV-2438 modified | DMD |
| WV-3153 | UCAAGGAAGAUGGCAUUUCU | 487 | fU*SfC*SfA*SfA*SfG*SfG*SfA*SfA*SmG fA*SmUfG*SmG*SfC*SfA*SfU*SfU*SfU* SfC*SfU | 1239 | SSSSSSSSOSOS SSSSSSS | WV-2529 modified | DMD |
| WV-3357 | UCAAGGAAGAUGGCAUUUCU | 488 | L001mU*mC*mA*mA*mG*mG*mA*mA*mG* mA*mU*mG*mG*mC*mA*mU*mU*mU*mC* mU | 1240 | OXXXXXXXXX XXXXXXXXX | WV942 with C6 PO linker | Exon 51 |
| WV-3358 | UCAAGGAAGAUGGCAUUUCU | 489 | L001fU*SfC*SfA*SfA*SfG*SfG*SfA*SfA* SfG*SmAmU*SfG*SfG*SfC*SfA*SfU*SfU* SfU*SfC*SfU | 1241 | OSSSSSSSSOS SSSSSSS | WV2531 with C6 PO linker | Exon 51 |
| WV-3359 | UCAAGGAAGAUGGCAUUUCU | 490 | Mod013L001mU*mC*mA*mA*mG*mG*mA*m A*mG*mA*mU*mG*mG*mC*mA*mU*mU*m U*mC*mU | 1242 | OOXXXXXXXX XXXXXXXXX X | WV942 with C6 amine PO linker, Lauric acid | Exon 51 |
| WV-3360 | UCAAGGAAGAUGGCAUUUCU | 491 | Mod013L001fU*SfC*SfA*SfA*SfG*SfG* SfA*SfA*SfG*SmAmU*SfG*SfG*SfC*SfA* SfU*SfU*SfU*SfC*SfU | 1243 | OOSSSSSSSSO SSSSSSSS | WV2531 with C6 amine PO linker, Lauric acid | Exon 51 |
| WV-3361 | UCAAGGAAGAUGGCAUUUCU | 492 | Mod014L001fU*SfC*SfA*SfA*SfG*SfG*SfA* SfA*SfG*SmAmU*SfG*SfG*SfC*SfA*SfU*SfU *SfU*SfC*SfU | 1244 | OOSSSSSSSSO SSSSSSSS | WV2531 with C6 amine PO linker, Myristic acid | Exon 51 |
| WV-3362 | UCAAGGAAGAUGGCAUUUCU | 493 | Mod005L001fu*SfC*SfA*SfA*SfG*SfG*SfA* SfA*SfG*SmAmU*SfG*SfG*SfC*SfA*SfU*SfU *SfU*SfC*SfU | 1245 | OOSSSSSSSSO SSSSSSSS | WV2531 with C6 amine PO linker, Palmitic acid | Exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3363 | UCAAGGAAGA UGGCAUUUCU | 494 | Mod015L001fU*SfC*SfA*SfA*SfG*SfG*SfA* SfA*SfG*SmAmU*SfG*SfG*SfC*SfA*SfU*SfU *SfU*SfC*SfU | 1246 | OOSSSSSSSSSO SSSSSSSSS | WV2531 with C6 amine PO linker, Stearic acid | Exon 51 |
| WV-3364 | UCAAGGAAGA UGGCAUUUCU | 495 | Mod020L001fU*SfC*SfA*SfA*SfG*SfG*SfA* SfA*SfG*SmAmU*SfG*SfG*SfC*SfA*SfU*SfU *SfU*SfC*SfU | 1247 | OOSSSSSSSSSO SSSSSSSSS | WV2531 with C6 amine PO linker, Turbinaric acid | Exon 51 |
| WV-3365 | UCAAGGAAGA UGGCAUUUCU | 496 | Mod027L001fU*SfC*SfA*SfA*SfG*SfG*SfA* SfA*SfG*SmAmU*SfG*SfG*SfC*SfA*SfU*SfU *SfU*SfC*SfU | 1248 | OOSSSSSSSSSO SSSSSSSSS | WV2531 with C6 amine PO linker, MonoSulfon-amide | Exon 51 |
| WV-3366 | UCAAGGAAGA UGGCAUUUCU | 497 | Mod029L001fU*SfC*SfA*SfA*SfG*SfG*SfA* SfA*SfG*SmAmU*SfG*SfG*SfC*SfA*SfU*SfU *SfU*SfC*SfU | 1249 | OOSSSSSSSSSO SSSSSSSSS | WV2531 with C6 amine PO linker, TriSulfonamide | Exon 51 |
| WV-3463 | UCAAGGAAGA UGGCAUUUCU | 498 | fU*SfC*SfA*SfA*SfG*SfGfA*SmAfG*SmAfU* SmGfGfC*SfA*SfU*SfU*SfU*SfC*SfU | 1250 | SSSSSOSOSOSO OSSSSSS | modifying WV-3152, 2'f-U and Sp in the middle | Exon 51 |
| WV-3464 | UCAAGGAAGA UGGCAUUUCU | 499 | fU*SfC*SfA*SfA*SfG*SfG*SfA*SfAfG*Sm AfU*SmG*SmG*SfC*SfA*SfU*SfU*SfU*SfC* SfU | 1251 | SSSSSSSOSOSS SSSSSSS | modifying WV-3153, 2'f-U and Sp in the middle | Exon 51 |
| WV-3465 | UCAAGGAAGA UGGCAUUUCU | 500 | fU*SfC*SfA*SfA*SfG*SfG*SfA*SfA*SfG*Sm AfU*SmG*SfG*SfC*SfA*SfU*SfU*SfU*SfC*S fU | 1252 | SSSSSSSSSOSS SSSSSSS | modifying WV-2531,2'f-U and Sp in the middle | Exon 51 |
| WV-3466 | UCAAGGAAGA UGGCAUUUCU | 501 | fU*SfC*SfA*SfA*SfG*SfG*SfA*SfA*SmGmAf U*SmGmG*SfC*SfA*SfU*SfU*SfU*SfC*SfU | 1253 | SSSSSSSSOOSO SSSSSSS | modifying WV-3028, 2'f-U and Sp in the middle | Exon 51 |
| WV-3467 | UCAAGGAAGA UGGCAUUUCU | 502 | fU*SfC*SfA*SfA*SfG*SfG*SfA*SfA*SfG*Sm AfU*SmGfG*SfC*SfA*SfU*SfU*SfU*SfC*SfU | 1254 | SSSSSSSSSOSO SSSSSSS | modifying WV-3120, 2'f-U and Sp in the middle | Exon 51 |
| WV-3468 | UCAAGGAAGA UGGCAUUUCU | 503 | fU*SfC*SfA*SfA*SfG*SfG*mAmAmGmAfU*S mGmG*SfC*SfA*SfU*SfU*SfU*SfC*SfU | 1255 | SSSSSXOOOOSO SSSSSSS | modifying WV-3046, 2'f-U and Sp in the middle | Exon 51 |
| WV-3469 | UCAAGGAAGA UGGCAUUUCU | 504 | fU*SfC*SfA*SfA*SfG*SfG*SmA*SmA*SmG*S mA*SfU*SmG*SmG*SfC*SfA*SfU*SfU*SfU*S fC*SfU | 1256 | SSSSSSSSSSSS SSSSSSS | modifying WV-3047, 2'f-U and Sp in the middle | Exon 51 |
| WV-3470 | UCAAGGAAGA UGGCAUUUCU | 505 | fU*SfC*SfA*SfA*SfG*SfG*SmAfA*SmGfA*Sf UfG*SmGfC*SfA*SfU*SfU*SfU*SfC*SfU | 1257 | SSSSSSOSOSOS OSSSSSS | 2'F on the middle U; modified on WV-3152 | DMD |
| WV-3471 | UCAAGGAAGA UGGCAUUUCU | 506 | fU*SfC*SfA*SfA*SfG*SfG*SmAfA*SmGfA*Sf UmGfC*SfA*SfU*SfU*SfU*SfC*SfU | 1258 | SSSSSOSOSOSOO OSSSSSS | 2'F on the middle U; modified on WV-3152 | DMD |
| WV-3472 | UCAAGGAAGA UGGCAUUUCU | 507 | fU*SfC*SfA*SfA*SfG*SfG*SmAfA*SmGfA*Sf U*SmGmGfC*SfA*SfU*SfU*SfU*SfC*SfU | 1259 | SSSSSOSOSSO OSSSSSS | 2'F on the middle U; modified on WV-3152 | DMD |
| WV-3473 | UCAAGGAAGA UGGCAUUUCU | 508 | fU*SfC*SfA*SfA*SfG*SfG*SmAfA*SmGmA*S fU*SmGmGfC*SfA*SfU*SfU*SfU*SfC*SfU | 1260 | SSSSSOSOSSO OSSSSSS | 2'F on the middle U; modified on WV-3152 | DMD |
| WV-3506 | UCAAGGAAGA UGGCAUUUCU | 509 | fU*SfC*SfA*SfA*SfG*SfG*SmAfA*SmGfAfU* SmGmGfC*SfA*SfU*SfU*SfU*SfC*SfU | 1261 | SSSSSOSOOSO OSSSSSS | modified on WV-3472; except for PO linker between fA (10th nt) and fU (11th nt) | Exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3507 | UCAAGGAAGAUGGCAUUUCU | 510 | fU*SfC*SfA*SfA*SfG*SfG*SmAfA*SmGmAfU*SmGmGfC*SfA*SfU*SfU*SfU*SfC*SfU | 1262 | SSSSSSOSOSSOOSSSSSS | modified on WV-3473; except for PO linker between mA (10th nt) and fU (11th nt) | Exon 51 |
| WV-3508 | UCAAGGAAGAUGGCAUUUCU | 511 | fU*SfC*SfA*SfA*SfG*SfG*SmAfA*SmGfA*SfU*SmGmGfC*SfAfU*SfU*SfU*SfC*SfU | 1263 | SSSSSSOSOSSOOSOSSSS | modified on WV-3472; except for PO linker between fA (15th nt) and fU (16th nt) | Exon 51 |
| WV-3509 | UCAAGGAAGAUGGCAUUUCU | 512 | fU*SfC*SfA*SfA*SfG*SfG*SmAfA*SmGmA*SfU*SmGmGfC*SfAfU*SfU*SfU*SfC*SfU | 1264 | SSSSSSOSOSSOOSOSSSS | modified on WV-3473; except for PO linker between fA (15th nt) and fU (16th nt) | Exon 51 |
| WV-3510 | UCAAGGAAGAUGGCAUUUCU | 513 | fU*SfC*SfA*SfA*SfG*SfG*SmAfA*SmGfAfU*SmGmGfC*SmA*SfU*SfU*SfU*SfC*SfU | 1265 | SSSSSSOSOOSOOSSSSSS | modified on WV-3472; except for mA on 15th nt | Exon 51 |
| WV-3511 | UCAAGGAAGAUGGCAUUUCU | 514 | fU*SfC*SfA*SfA*SfG*SfG*SmAfA*SmGmAfU*SmGmGfC*SmA*SfU*SfU*SfU*SfC*SfU | 1266 | SSSSSSOSOSSOOSSSSSS | modified on WV-3473; except for mA on 15th nt | Exon 51 |
| WV-3512 | UCAAGGAAGAUGGCAUUUCU | 515 | fU*SfC*SfA*SfA*SfG*SfG*SmAfA*SmGfAfU*SmGmGfC*SmAfU*SfU*SfU*SfC*SfU | 1267 | SSSSSSOSOOSOOSOSSSS | modified on WV-3472; except for PO linker between fA (10th nt) and fU (11th nt); mA on 15th nt, and PO between mA (15th nt) and fU (16th nt) | Exon 51 |
| WV-3513 | UCAAGGAAGAUGGCAUUUCU | 516 | fU*SfC*SfA*SfA*SfG*SfG*SmAfA*SmGmAfU*SmGmGfC*SmAfU*SfU*SfU*SfC*SfU | 1268 | SSSSSSOSOSSOOSOSSSS | modified on WV-3472; except for PO linker between mA (10th nt) and fU (11th nt); mA on 15th nt, and PO between mA (15th nt) and fU (16th nt) | Exon 51 |
| WV-3514 | UCAAGGAAGAUGGCAUUUCU | 517 | fU*SfC*SfA*SfA*SfG*SfG*SmAfA*SmGfAfU*SmGmGfC*SfAfU*SfU*SfU*SfC*SfU | 1269 | SSSSSSOSOOSOOSOSSSS | modified on WV-3472; except for PO linker between fA (10th nt) and fU (11th nt); PO between fA (15th nt) and fU (16th nt) | Exon 51 |
| WV-3515 | UCAAGGAAGAUGGCAUUUCU | 518 | fU*SfC*SfA*SfA*SfG*SfG*SmAfA*SmGmAfU*SmGmGfC*SfAfU*SfU*SfU*SfC*SfU | 1270 | SSSSSSOSOSSOOSOSSSS | modified on WV-3472; except for PO linker between mA (10th nt) and fU (11th nt); PO between fA (15th nt) and fU (16th nt) | Exon 51 |
| WV-3516 | UCAAGGAAGAUGGCAUUUCU | 519 | fU*fC*fA*fA*fG*fG*mAfA*mGfA*mUfG*mGfC*fA*fU*fU*fU*fC*fU | 1271 | XXXXXXOXOXOXOXXXXXX | randomer version of WV-3152 | Exon 51 |
| WV-3517 | UCAAGGAAGAUGGCAUUUCU | 520 | Mod030fU*fC*fA*fA*fG*fG*mAfA*mGfA*mUfG*mGfC*fA*fU*fU*fU*fC*fU | 1272 | OXXXXXXOXOXOXXXXXXX | with PO linker, Lauric | Exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3518 | UCAAGGAAGAUGGCAUUUCU | 521 | Mod031fU*fC*fA*fA*fG*fG*mAfA*mGfA*mU fG*mGfC*fA*fU*fU*fU*fC*fU | 1273 | OXXXXXXOXO XOXOXXXXXX | with PO linker, Myristic | Exon 51 |
| WV-3519 | UCAAGGAAGAUGGCAUUUCU | 522 | Mod032fU*fC*fA*fA*fG*fG*mAfA*mGfA*mU fG*mGfC*fA*fU*fU*fU*fC*fU | 1274 | OXXXXXXOXO XOXOXXXXXX | with PO linker, Palmitic | Exon 51 |
| WV-3520 | UCAAGGAAGAUGGCAUUUCU | 523 | Mod033fU*fC*fA*fA*fG*fG*mAfA*mGfA*mU fG*mGfC*fA*fU*fU*fU*fC*fU | 1275 | OXXXXXXOXO XOXOXXXXXX | with PO linker, Stearic | Exon 51 |
| WV-3543 | UCAAGGAAGAUGGCAUUUCU | 524 | Mod013L001fU*SfC*SfA*SfA*SfG*SfG* SmAfA*SmGmA*SfU*SmGmGfC*SfA*SfU*SfU* SfU*SfC*SfU | 1276 | OOSSSSSOSOS SOOSSSSSS | WV-3473, Lauric acid, C6 PO linker | Exon 51 |
| WV-3544 | UCAAGGAAGAUGGCAUUUCU | 525 | Mod005L001fU*SfC*SfA*SfA*SfG*SfG*SmAf A*SmGmA*SfU*SmGmGfC*SfA*SfU*SfU*Sf U*SfC*SfU | 1277 | OOSSSSSOSOS SOOSSSSSS | WV-3473, Palmitic acid, C6 PO linker | Exon 51 |
| WV-3545 | UCAAGGAAGAUGGCAUUUCU | 526 | Mod015L001fU*SfC*SfA*SfA*SfG*SfG*SmAf A*SmGmA*SfU*SmGmGfC*SfA*SfU*SfU*Sf U*SfC*SfU | 1278 | OOSSSSSOSOS SOOSSSSSS | WV-3473, Stearic acid, C6 PO linker | Exon 51 |
| WV-3546 | UCAAGGAAGAUGGCAUUUCU | 527 | Mod020L001fU*SfC*SfA*SfA*SfG*SfG*SmAf A*SmGmA*SfU*SmGmGfC*SfA*SfU*SfU*Sf U*SfC*SfU | 1279 | OOSSSSSOSOS SOOSSSSSS | WV-3473, Turbinaric acid, C6 PO linker | Exon 51 |
| WV-3547 | UCAAGGAAGAUGGCAUUUCU | 528 | Mod027L001fU*SfC*SfA*SfA*SfG*SfG*SmAf A*SmGmA*SfU*SmGmGfC*SfA*SfU*SfU*Sf U*SfC*SfU | 1280 | OOSSSSSOSOS SOOSSSSSS | WV-3473, Monosulfona-mide, C6 PO linker | Exon 51 |
| WV-3548 | UCAAGGAAGAUGGCAUUUCU | 529 | Mod029L001fU*SfC*SfA*SfA*SfG*SfG*SmAf A*SmGmA*SfU*SmGmGfC*SfA*SfU*SfU*Sf U*SfC*SfU | 1281 | OOSSSSSOSOS SOOSSSSSS | WV-3473, Trisulfona-mide, C6 PO linker | Exon 51 |
| WV-3549 | UCAAGGAAGAUGGCAUUUCU | 530 | Mod030fU*SfC*SfA*SfA*SfG*SfG*SmAfA*S mGmA*SfU*SmGmGfC*SfA*SfU*SfU*SfU*Sf C*SfU | 1282 | OSSSSSSOSOSS OOSSSSSS | WV-3473, Lauric, PO linker | Exon 51 |
| WV-3550 | UCAAGGAAGAUGGCAUUUCU | 531 | Mod032fU*SfC*SfA*SfA*SfG*SfG*SmAfA*S mGmA*SfU*SmGmGfC*SfA*SfU*SfU*SfU*Sf C*SfU | 1283 | OSSSSSSOSOSS OOSSSSSS | WV-3473, Palmitic, PO linker | Exon 51 |
| WV-3551 | UCAAGGAAGAUGGCAUUUCU | 532 | Mod033fU*SfC*SfA*SfA*SfG*SfG*SmAfA*S mGmA*SfU*SmGmGfC*SfA*SfU*SfU*SfU*Sf C*SfU | 1284 | OSSSSSSOSOSS OOSSSSSS | WV-3473, Stearic, PO linker | Exon 51 |
| WV-3552 | UCAAGGAAGAUGGCAUUUCU | 533 | Mod020L001*fU*SfC*SfA*SfA*SfG*SfG*SmA fA*SmGmA*SfU*SmGmGfC*SfA*SfU*SfU*Sf U*SfC*SfU | 1285 | OXSSSSSOSOS SOOSSSSSS | WV-3473, Turbinaric acid, C6 PS linker | Exon 51 |
| WV-3553 | UCAAGGAAGAUGGCAUUUCU | 534 | Mod005L001*fU*SfC*SfA*SfA*SfG*SfG* SmAfA*SmGmA*SfU*SmGmGfC*SfA*SfU*SfU *SfU*SfC*SfU | 1286 | OXSSSSSOSOS SOOSSSSSS | WV-3473, Palmitic acid, C6 PS linker | Exon 51 |
| WV-3554 | UCAAGGAAGAUGGCAUUUCU | 535 | Mod014L001*fU*SfC*SfA*SfA*SfG*SfG*Sm AfA*SmGmA*SfU*SmGmGfC*SfA*SfU*SfU*Sf U*SfC*SfU | 1287 | OOSSSSSOSOS SOOSSSSSS | WV-3473, Myristic acid, C6 PO linker | Exon 51 |
| WV-3555 | UCAAGGAAGAUGGCAUUUCU | 536 | Mod030*fU*SfC*SfA*SfA*SfG*SfG*SmAfA* SmGmA*SfU*SmGmGfC*SfA*SfU*SfU*SfU*Sf C*SfU | 1288 | XSSSSSSOSOSS OOSSSSSS | WV-3473, Lauric PS linker | Exon 51 |
| WV-3556 | UCAAGGAAGAUGGCAUUUCU | 537 | Mod032*fU*SfC*SfA*SfA*SfG*SfG*SmAfA* SmGmA*SfU*SmGmGfC*SfA*SfU*SfU*SfU*Sf C*SfU | 1289 | XSSSSSSOSOSS OOSSSSSS | WV-3473, Palmitic PS linker | Exon 51 |
| WV-3557 | UCAAGGAAGAUGGCAUUUCU | 538 | Mod033*fU*SfC*SfA*SfA*SfG*SfG*SmAfA* SmGmA*SfU*SmGmGfC*SfA*SfU*SfU*SfU*Sf C*SfU | 1290 | XSSSSSSOSOSS OOSSSSSS | WV-3473, Stearic PS linker | Exon 51 |
| WV-3558 | UCAAGGAAGAUGGCAUUUCU | 539 | Mod033*fU*fC*fA*fA*fG*fG*mAfA*mGfA* mUfG*mGfC*fA*fU*fU*fU*fC*fU | 1291 | XXXXXXXOXO XOXOXXXXXX | with PS linker, Stearic linker | Exon 51 |
| WV-3559 | UCAAGGAAGAUGGCAUUUCU | 540 | Mod020L001f1J*fC*fA*fA*fG*fG*mAfA* mGfA*mUfG*mGfC*fA*fU*fU*fU*fC*fU | 1292 | OOXXXXXOX OXOXOXXXXXX X | with C6 amine PO linker, Turbinaric acid | Exon 51 |
| WV-3560 | UCAAGGAAGAUGGCAUUUCU | 541 | Mod020L001*fU*fC*fA*fA*fG*fG*mAfA* mGfA*mUfG*mGfC*fA*fU*fU*fU*fC*fU | 1293 | OXXXXXXOX OXOXOXXXXXX X | with C6 amine PS linker, Turbinaric acid | Exon 51 |
| WV-3753 | UCAAGGAAGAUGGCAUUUCU | 542 | L001*fU*SfC*SfA*SfA*SfG*SfG*SmAfA* SmGmA*SfU*SmGmGfC*SfA*SfU*SfU*SfU* SfC*SfU | 1294 | XSSSSSSOSOSS OOSSSSSS | WV-3473, C6 PS linker | Exon 51 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3754 | UCAAGGAAGAUGGCAUUUCU | 543 | L001fU*SfC*SfA*SfA*SfG*SfG*SmAfA*SmGmA*SfU*SmGmGfC*SfA*SfU*SfU*SfU*SfC*SfU | 1295 | OSSSSSSOSOSSOOSSSSSS | WV-3473, C6 PO linker | Exon 51 |
| WV-3812 | GCCAACUGGGAGCUGGAGCGCACCAACCAG | 544 | rGrCrCrArArCrUrGrGrGrArGrCrUrGrGrArGrCrGrCrArCrCrArArCrCrArG | 1296 | OOOOOOOOOOOOOOOOOOOOOOOOOOOOO | Complementary RNA | MSTN |
| WV-3820 | UCAAGGAAGAUGGCAUUUCU | 545 | L001*fU*fC*fA*fA*fG*fG*mAfA*mGfA*mUfG*mGfC*fA*fU*fU*fU*fC*fU | 1297 | XXXXXXXOXOXOXOXXXXXX | WV-3516, C6 PS linker | Exon 51 |
| WV-3821 | UCAAGGAAGAUGGCAUUUCU | 546 | L001fU*fC*fA*fA*fG*fG*mAfA*mGfA*mUfG*mGfC*fA*fU*fU*fU*fC*fU | 1298 | OXXXXXXOXOXOXOXXXXXX | WV-3516, C6 PO linker | Exon 51 |
| WV-3855 | UCAAGGAAGAUGGCAUUUCU | 547 | Mod015L001*fU*fC*fA*fA*fG*fG*mAfA*mGfA*mUfG*mGfC*fA*fU*fU*fU*fC*fU | 1299 | OXXXXXXOXOXOXOXXXXXX | WV-3516, C6 PS linker, Stearic acid | Exon 51 |
| WV-3856 | UCAAGGAAGAUGGCAUUUCU | 548 | Mod015L001fU*fC*fA*fA*fG*fG*mAfA*mGfA*mUfG*mGfC*fA*fU*fU*fU*fC*fU | 1300 | OOXXXXXXOXOXOXOXXXXXX | WV-3516, C6 PO linker, Stearic acid | Exon 51 |
| WV-3975 | CCUUCCCUGAAGGUUCCUCC | 549 | fC*fC*fU*fU*fC*fC*mCfU*GmAfA*mGmGfU*fU*fC*fC*fU*fC*fC | 1301 | XXXXXXXOXOOXOXXXXXX | Negative control | NA |
| WV-3976 | CCUUCCCUGAAGGUUCCUCC | 550 | L001fC*fC*fU*fU*fC*fC*mCfU*GmAfA*mGmGfU*fU*fC*fC*fU*fC*fC | 1302 | OXXXXXXOXOOXOXXXXXX | Negative control | NA |
| WV-3977 | CCUUCCCUGAAGGUUCCUCC | 551 | Mod020L001fC*fC*fU*ffI*fC*fC*mCfU*GmAfA*mGmGfU*fU*fC*fC*fU*fC*fC | 1303 | OOXXXXXXOXOOXOXXXXXX | Negative control | NA |
| WV-3978 | CCUUCCCUGAAGGUUCCUCC | 552 | fC*fC*fU*fU*fC*fC*mCfU*mGmAfA*mGmGfU*fU*fC*fC*fU*fC*fC | 1304 | XXXXXXXOXOOXOXXXXXX | Negative control | NA |
| WV-3979 | CCUUCCCUGAAGGUUCCUCC | 553 | L001fC*fC*fU*fU*fC*fC*mCfU*mGmAfA*mGmGfU*fU*fC*fC*fU*fC*fC | 1305 | OXXXXXXOXOOXOXXXXXX | Negative control | NA |
| WV-3980 | CCUUCCCUGAAGGUUCCUCC | 554 | Mod020L001fC*fC*fU*ffI*fC*fC*mCfU*mGmAfA*mGmGfU*fU*fC*fC*fU*fC*fC | 1306 | OOXXXXXXOXOOXOXXXXXX | Negative control | NA |
| WV-4106 | UCAAGGAAGAUGGCAUUUCU | 555 | Mod015L001*fU*SfC*SfA*SfA*SfG*SfG*SmAfA*SmGmA*SfU*SmGmGfC*SfA*SfU*SfU*SfU*SfC*SfU | 1307 | OXSSSSSSOSOSSOOSSSSSS | WV-3473, C6 PS linker, Stearic acid | Exon 51 |
| WV-4107 | UCAAGGAAGAUGGCAUUUCU | 556 | Mod015L001*SfU*SfC*SfA*SfA*SfG*SfG*SmAfA*SmGmA*SfU*SmGmGfC*SfA*SfU*SfU*SfU*SfC*SfU | 1308 | OSSSSSSOSOSSOOSSSSSS | WV-3473, Sp stereopure C6 linker, stearic acid | DMD |
| WV-4191 | UCAAGGAAGAUGGCAUUUCU | 557 | L001 * SfU * SfC * SfA * SfA * SfG * SfG * SmAfA *SmGmA *SfU *SmGmGfC * SfA * SfU *SfU *SfU *SfC *SfU | 1309 | SSSSSSSOSOSSOOSSSSSS | WV-3473, C6 and Sp stereopure linker | DMD |
| WV-4231 | UCAAGGAAGAUGGCAUUUC | 558 | fU*SfC*SfA*SfA*SfG*SfG*SmAfA*SmGmA*SfU*SmGmGfC*SfA*SfU*SfU*SfC | 1310 | SSSSSSOSOSSOOSSSSS | WV-3473 based, n-1 on 3' | DMD |
| WV-4232 | UCAAGGAAGAUGGCAUUU | 559 | fU*SfC*SfA*SfA*SfG*SfG*SmAfA*SmGmA*SfU*SmGmGfC*SfA*SfU*SfU*SfU | 1311 | SSSSSSOSOSSOOSSSSS | WV-3473 based, n-2 on 3' | DMD |
| WV-4233 | CAAGGAAGAUGGCAUUUCU | 560 | fC*SfA*SfA*SfG*SfG*SmAfA*SmGmA*SfU*SmGmGfC*SfA*SfU*SfU*SfU*SfC*SfU | 1312 | SSSSSOSOSSOOSSSSSS | WV-3473 based, n-1 on 5' | DMD |
| WV-4610 | GGCCAAACCUCGGCUUACCU | 561 | Mod020L001mG*mG*mC*mC*mA*mA*mA*mC*mC*mU*mC*mG*mG*mC*mU*mU*mA*mC*mC*mU | 1313 | OOXXXXXXXXXXXXXXXXXXX | WV-943, C6 linker and PO, Turbinaric acid | DMD mouse Exon23 |
| WV-4611 | GGCCAAACCUCGGCUUACCU | 562 | Mod015L001mG*mG*mC*mC*mA*mA*mA*mC*mC*mU*mC*mG*mG*mC*mU*mU*mA*mC*mC*mU | 1314 | OOXXXXXXXXXXXXXXXXXXX | WV-943, C6 linker and PO, Stearic acid | DMD mouse Exon23 |
| WV-4614 | UUCUGUAAGGUUUUUAUGUG | 563 | fU*fU*fC*fU*fG*fU*mA*mA*mG*mG*mU*mU*mU*mU*fU*fA*fU*fG*fU*fG | 1315 | XXXXXXXXXXXXXXXXXXXX | DMD mouse Exon23 | DMD |
| WV-4615 | AUUCUGUAAGGUUUUUAUG | 564 | fA*fU*fU*fC*fU*fC*mG*mU*mA*mA*mG*mG*mU*mU*fU*fU*fU*fA*fU*fG | 1316 | XXXXXXXXXXXXXXXXXXXX | DMD mouse Exon23 | DMD |
| WV-4616 | CCAUUCUGUAAGGUUUUUA | 565 | fC*fC*fA*fU*fU*fC*mU*mG*mU*mA*mA*mG*mG*mU*fU*fU*fU*fU*fU*fA | 1317 | XXXXXXXXXXXXXXXXXXXX | DMD mouse Exon23 | DMD |
| WV-4617 | AUCCAUUCUGUAAGGUUUU | 566 | fA*fU*fC*fC*fA*fU*mU*mC*mU*mG*mU*mA*mA*mG*fG*fU*fU*fU*fU*fU | 1318 | XXXXXXXXXXXXXXXXXXXX | DMD mouse Exon23 | DMD |
| WV-4618 | CAUCCAUUCUGUAAGGUUU | 567 | fC*fA*fU*fC*fC*fA*mU*mU*mC*mU*mG*mU*mA*mA*fG*fG*fU*fU*fU*fU | 1319 | XXXXXXXXXXXXXXXXXXXX | DMD mouse Exon23 | DMD |
| WV-4619 | CCAUCCAUUCUGUAAGGUU | 568 | fC*fC*fA*fU*fC*fC*mA*mU*mU*mU*mC*mU*mG*mU*fA*fA*fG*fG*fU*fU | 1320 | XXXXXXXXXXXXXXXXXXXX | DMD mouse Exon23 | DMD |
| WV-4620 | GCCAUCCAUUCUGUAAGGU | 569 | fG*fC*fC*fA*fU*fC*mC*mA*mU*fU*mC*mU*mG*mU*fA*fA*fG*fG*fU | 1321 | XXXXXXXXXXXXXXXXXXXX | DMD mouse Exon23 | DMD |
| WV-4621 | AGCCAUCCAUUCUGUAAGG | 570 | fA*fG*fC*fC*fA*fU*mC*mC*mA*mU*mU*mC*mU*mG*fU*mA*fA*fG*fG | 1322 | XXXXXXXXXXXXXXXXXXXX | DMD mouse Exon23 | DMD |
| WV-4622 | CAGCCAUCCAUUCUGUAAG | 571 | fC*fA*fG*fC*fC*fA*mU*mC*mC*mA*mU*mU*mC*mU*fG*fU*fA*fA*fG | 1323 | XXXXXXXXXXXXXXXXXXXX | DMD mouse Exon23 | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-4623 | UCAGCCAUCCA UUUCUGUAA | 572 | fU*fC*fA*fG*fC*fC*mA*mU*mC*mC*mA*m U*mU*mU*fC*fU*fG*fU*fA*fA | 1324 | XXXXXXXXXX XXXXXXXX | DMD mouse Exon23 | DMD |
| WV-4624 | UUCAGCCAUCC AUUUCUGUA | 573 | fU*fU*fC*fA*fG*fC*mC*mA*mU*mC*mC*m A*mU*mU*fU*fC*fU*fG*fU*fA | 1325 | XXXXXXXXXX XXXXXXXX | DMD mouse Exon23 | DMD |
| WV-4625 | CUUCAGCCAUC CAUUUCUGU | 574 | fC*fU*fU*fC*fA*fG*mC*mA*mU*mC*mC*m C*mA*mU*fU*fU*fC*fU*fG*fU | 1326 | XXXXXXXXXX XXXXXXXX | DMD mouse Exon23 | DMD |
| WV-4626 | ACUUCAGCCAU CCAUUUCUG | 575 | fA*fC*fU*fU*fC*fA*mG*mC*mC*mA*mU*m C*mC*mA*fU*fU*fU*fC*fU*fG | 1327 | XXXXXXXXXX XXXXXXXX | DMD mouse Exon23 | DMD |
| WV-4627 | AACUUCAGCCA UCCAUUUCU | 576 | fA*fA*fC*fU*fU*fC*mA*mG*mC*mC*mA*m U*mC*mC*fA*fU*fU*fU*fC*fU | 1328 | XXXXXXXXXX XXXXXXXX | DMD mouse Exon23 | DMD |
| WV-4628 | CAACUUCAGCC AUCCAUUUC | 577 | fC*fA*fA*fC*fU*fU*mC*mA*mG*mC*mC*m A*mU*mC*fC*fA*fU*fU*fU*fC | 1329 | XXXXXXXXXX XXXXXXXX | DMD mouse Exon23 | DMD |
| WV-4629 | UCAACUUCAGC CAUCCAUUU | 578 | fU*fC*fA*fA*fC*fU*mU*mC*mA*mG*mC*m C*mA*mU*fC*fC*fA*fU*fU*fU | 1330 | XXXXXXXXXX XXXXXXXX | DMD mouse Exon23 | DMD |
| WV-4630 | AUCAACUUCA GCCAUCCAUU | 579 | fA*fU*fC*fA*fA*fC*mU*mU*mC*mA*mG*m C*mC*mA*fU*fC*fC*fA*fU*fU | 1331 | XXXXXXXXXX XXXXXXXX | DMD mouse Exon23 | DMD |
| WV-4631 | CAUCAACUUCA GCCAUCCAU | 580 | fC*fA*fU*fC*fA*fA*mC*mU*mU*mC*mA*m G*mC*mC*fA*fU*fC*fC*fA*fU | 1332 | XXXXXXXXXX XXXXXXXX | DMD mouse Exon23 | DMD |
| WV-4632 | ACAUCAACUUC AGCCAUCCA | 581 | fA*fC*fA*fU*fC*fA*mA*mC*mU*mU*mC*m A*mG*mC*fC*fA*fU*fC*fC*fA | 1333 | XXXXXXXXXX XXXXXXXX | DMD mouse Exon23 | DMD |
| WV-4633 | AACAUCAACU UCAGCCAUCC | 582 | fA*fA*fC*fA*fU*fC*mA*mA*mC*mU*mU*m C*mA*mG*fC*fC*fA*fU*fC*fC | 1334 | XXXXXXXXXX XXXXXXXX | DMD mouse Exon23 | DMD |
| WV-4634 | GAAAACAUCA ACUUCAGCCA | 583 | fG*fA*fA*fA*fA*fC*mA*mU*mC*mA*mA*m C*mU*mU*fC*fA*fG*fC*fC*fA | 1335 | XXXXXXXXXX XXXXXXXX | DMD mouse Exon23 | DMD |
| WV-4635 | CAGGAAAACA UCAACUUCAG | 584 | fC*fA*fG*fG*fA*fA*mA*mA*mC*mA*mU*m C*mA*mA*fC*fU*fU*fC*fA*fG | 1336 | XXXXXXXXXX XXXXXXXX | DMD mouse Exon23 | DMD |
| WV-4636 | UUUCAGGAAA ACAUCAACUU | 585 | fU*fU*fU*fC*fA*fG*mG*mA*mA*mA*mA*m C*mA*mU*fC*fA*fA*fC*fU*fU | 1337 | XXXXXXXXXX XXXXXXXX | DMD mouse Exon23 | DMD |
| WV-4637 | CUCUUUCAGG AAAACAUCAA | 586 | fC*fU*fC*fU*fU*fU*mC*mA*mG*mG*mA*m A*mA*mA*fC*fA*fU*fC*fA*fA | 1338 | XXXXXXXXXX XXXXXXXX | DMD mouse Exon23 | DMD |
| WV-4638 | UUCCUCUUUCA GGAAAACAU | 587 | fU*fU*fC*fC*fU*fC*mU*mU*mU*mC*mA*m G*mG*mA*fA*fA*fA*fC*fA*fU | 1339 | XXXXXXXXXX XXXXXXXX | DMD mouse Exon23 | DMD |
| WV-4639 | GCCAUUCCUCU UUCAGGAAA | 588 | fG*fC*fC*fA*fU*fU*mC*mC*mU*mC*mU*m U*mU*mC*fA*fG*fG*fA*fA*fA | 1340 | XXXXXXXXXX XXXXXXXX | DMD mouse Exon23 | DMD |
| WV-4640 | GGCCAUUCCUC UUUCAGGAA | 589 | fG*fG*fC*fC*fA*fU*mU*mC*mC*mU*mC*m U*mU*mU*fC*fA*fG*fG*fA*fA | 1341 | XXXXXXXXXX XXXXXXXX | DMD mouse Exon23 | DMD |
| WV-4641 | AGGCCAUUCCU CUUUCAGGA | 590 | fA*fG*fG*fC*fC*fA*mU*mU*mC*mC*mU*m C*mU*mU*fU*fC*fA*fG*fG*fA | 1342 | XXXXXXXXXX XXXXXXXX | DMD mouse Exon23 | DMD |
| WV-4642 | CAGGCCAUUCC UCUUUCAGG | 591 | fC*fA*fG*fG*fC*fC*mA*mU*mU*mC*mC*m U*mC*mU*fU*fU*fC*fA*fG*fG | 1343 | XXXXXXXXXX XXXXXXXX | DMD mouse Exon23 | DMD |
| WV-4643 | GCAGGCCAUUC CUCUUUCAG | 592 | fG*fC*fA*fG*fG*fC*mC*mA*mU*mU*mC*m C*mU*mC*fU*fU*fU*fC*fA*fG | 1344 | XXXXXXXXXX XXXXXXXX | DMD mouse Exon23 | DMD |
| WV-4644 | GGCAGGCCAU UCCUCUUUCA | 593 | fG*fG*fC*fA*fG*fG*mC*mC*mA*mU*mU*m C*mC*mU*fC*fU*fU*fU*fC*fA | 1345 | XXXXXXXXXX XXXXXXXX | DMD mouse Exon23 | DMD |
| WV-4645 | GGGCAGGCCA UUCCUCUUUC | 594 | fG*fG*fG*fC*fA*fG*mG*mC*mC*mA*mU*m U*mC*mC*fU*fC*fU*fU*fU*fC | 1346 | XXXXXXXXXX XXXXXXXX | DMD mouse Exon23 | DMD |
| WV-4646 | AGGGCAGGCC AUUCCUCUUU | 595 | fA*fG*fG*fG*fC*fA*mG*mG*mC*mC*mA*m U*mU*mC*fC*fU*fC*fU*fU*fU | 1347 | XXXXXXXXXX XXXXXXXX | DMD mouse Exon23 | DMD |
| WV-4647 | CAGGGCAGGCC AUUCCUCUU | 596 | fC*fA*fG*fG*fG*fC*mA*mG*mG*mC*mC*m A*mU*mU*fC*fC*fU*fC*fU*fU | 1348 | XXXXXXXXXX XXXXXXXX | DMD mouse Exon23 | DMD |
| WV-4648 | CCAGGGCAGG CCAUUCCUCU | 597 | fC*fC*fA*fG*fG*fG*mC*mA*mG*mG*mC*m C*mA*mU*fU*fC*fC*fU*fC*fU | 1349 | XXXXXXXXXX XXXXXXXX | DMD mouse Exon23 | DMD |
| WV-4649 | CCCAGGGCAGG CCAUUCCUC | 598 | fC*fC*fC*fA*fG*fG*mG*mC*mA*mG*mG*m C*mC*mA*fU*fU*fC*fC*fU*fC | 1350 | XXXXXXXXXX XXXXXXXX | DMD mouse Exon23 | DMD |
| WV-4650 | CCCCAGGGCAG GCCAUUCCU | 599 | fC*fC*fC*fC*fA*fG*mG*mG*mC*mA*mG*m G*mC*mC*fA*fU*fU*fC*fC*fU | 1351 | XXXXXXXXXX XXXXXXXX | DMD mouse Exon23 | DMD |
| WV-4651 | CCCCCAGGGCA GGCCAUUCC | 600 | fC*fC*fC*fC*fC*fA*mG*mG*mG*mC*mA*m G*mG*mC*fC*fA*fU*fU*fC*fC | 1352 | XXXXXXXXXX XXXXXXXX | DMD mouse Exon23 | DMD |
| WV-4652 | UCCCCCAGGGC AGGCCAUUC | 601 | fU*fC*fC*fC*fC*fC*mA*mG*mG*mG*mC*m A*mG*mG*fC*fC*fA*fU*fU*fC | 1353 | XXXXXXXXXX XXXXXXXX | DMD mouse Exon23 | DMD |
| WV-4653 | AUCCCCCAGGG CAGGCCAUU | 602 | fA*fU*fC*fC*fC*fC*mC*mA*mG*mG*mG*m C*mA*mG*fG*fC*fC*fA*fU*fU | 1354 | XXXXXXXXXX XXXXXXXX | DMD mouse Exon23 | DMD |
| WV-4654 | CAUCCCCCAGG GCAGGCCAU | 603 | fC*fA*fU*fC*fC*fC*mC*mC*mA*mG*mG*m G*mC*mA*fG*fG*fC*fC*fA*fU | 1355 | XXXXXXXXXX XXXXXXXX | DMD mouse Exon23 | DMD |
| WV-4655 | GCAUCCCCCAG GGCAGGCCA | 604 | fG*fC*fA*fU*fC*fC*mC*mC*mC*mA*mG*m G*mG*mC*fA*fG*fG*fC*fC*fA | 1356 | XXXXXXXXXX XXXXXXXX | DMD mouse Exon23 | DMD |
| WV-4656 | AGCAUCCCCCA GGGCAGGCC | 605 | fA*fG*fC*fA*fU*fC*mC*mC*mC*mC*mA*m G*mG*mG*fC*fA*fG*fG*fC*fC | 1357 | XXXXXXXXXX XXXXXXXX | DMD mouse Exon23 | DMD |
| WV-4657 | CAGCAUCCCCC AGGGCAGGC | 606 | fC*fA*fG*fC*fA*fU*mC*mC*mC*mC*mC*m A*mG*mG*fG*fC*fA*fG*fG*fC | 1358 | XXXXXXXXXX XXXXXXXX | DMD mouse Exon23 | DMD |
| WV-4658 | UCAGCAUCCCC CAGGGCAGG | 607 | fU*fC*fA*fG*fC*fA*mU*mC*mC*mC*mC*m C*mA*mG*fG*fG*fC*fA*fG*fG | 1359 | XXXXXXXXXX XXXXXXXX | DMD mouse Exon23 | DMD |
| WV- | UUCAGCAUCCC | 608 | fU*fU*fC*fA*fG*fC*mA*mU*mC*mC*mC*m | 1360 | XXXXXXXXXX | DMD mouse | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| | CCAGGGCAG | | C*mC*mA*fG*fG*fG*fC*fA*fG | | XXXXXXXXX XXXXXXXXX | Exon23 | |
| WV-4660 | UUUCAGCAUCC CCCAGGGCA | 609 | fU*fU*fU*fC*fA*fG*mC*mA*mU*mC*mC*m C*mC*mC*fA*fG*fG*fG*fC*fA | 1361 | XXXXXXXXX XXXXXXXXX | DMD mouse Exon23 | DMD |
| WV-4661 | AUUUCAGCAU CCCCCAGGGC | 610 | fA*fU*fU*fU*fC*fA*fG*mC*mA*mU*mC*m C*mC*mC*fC*fA*fG*fG*fG*fC | 1362 | XXXXXXXXX XXXXXXXXX | DMD mouse Exon23 | DMD |
| WV-4662 | GAUUUCAGCA UCCCCCAGGG | 611 | fG*fA*fU*fU*fU*fC*fA*mG*mC*mA*mU*m C*mC*mC*fC*fC*fA*fG*fG*fG | 1363 | XXXXXXXXX XXXXXXXXX | DMD mouse Exon23 | DMD |
| WV-4663 | GGAUUUCAGC AUCCCCCAGG | 612 | fG*fG*fA*fU*fU*fU*fC*mA*mG*mC*mA*m U*mC*mC*fC*fC*fC*fA*fG*fG | 1364 | XXXXXXXXX XXXXXXXXX | DMD mouse Exon23 | DMD |
| WV-4664 | AGGAUUUCAG CAUCCCCCAG | 613 | fA*fG*fG*fA*fU*fU*fU*mC*mA*mG*mC*m A*mU*mC*fC*fC*fC*fC*fA*fG | 1365 | XXXXXXXXX XXXXXXXXX | DMD mouse Exon23 | DMD |
| WV-4665 | CAGGAUUUCA GCAUCCCCCA | 614 | fC*fA*fG*fG*fA*fU*fU*mU*mC*mA*mG*m C*mA*mU*fC*fC*fC*fC*fC*fA | 1366 | XXXXXXXXX XXXXXXXXX | DMD mouse Exon23 | DMD |
| WV-4666 | UCAGGAUUUC AGCAUCCCCC | 615 | fU*fC*fA*fG*fG*fA*fU*mU*mU*mC*mA*m G*mC*mA*fU*fC*fC*fC*fC*fC | 1367 | XXXXXXXXX XXXXXXXXX | DMD mouse Exon23 | DMD |
| WV-4667 | UUCAGGAUUU CAGCAUCCCC | 616 | fU*fU*fC*fA*fG*fG*mA*mU*mU*mU*mC*m A*mG*mC*fA*fU*fC*fC*fC*fC | 1368 | XXXXXXXXX XXXXXXXXX | DMD mouse Exon23 | DMD |
| WV-4668 | UUUCAGGAUU UCAGCAUCCC | 617 | fU*fU*fU*fC*fA*fG*mG*mA*mU*mU*mU*m C*mA*mG*fC*fA*fU*fC*fC*fC | 1369 | XXXXXXXXX XXXXXXXXX | DMD mouse Exon23 | DMD |
| WV-4669 | UUUUCAGGAU UUCAGCAUCC | 618 | fU*fU*fU*fU*fC*fA*mG*mG*mA*mU*mU*m U*mC*mA*fG*fC*fA*fU*fC*fC | 1370 | XXXXXXXXX XXXXXXXXX | DMD mouse Exon23 | DMD |
| WV-4670 | UUUUUCAGGA UUUCAGCAUC | 619 | fU*fU*fU*fU*fU*fC*mA*mG*mG*mA*mU*m U*mU*mC*fA*fG*fC*fA*fU*fC | 1371 | XXXXXXXXX XXXXXXXXX | DMD mouse Exon23 | DMD |
| WV-4671 | UUUUUUCAGG AUUUCAGCAU | 620 | fU*fU*fU*fU*fU*fU*mC*mA*mG*mG*mA*m U*mU*mU*fC*fA*fG*fC*fA*fU | 1372 | XXXXXXXXX XXXXXXXXX | DMD mouse Exon23 | DMD |
| WV-4672 | GUUUUUUCAG GAUUUCAGCA | 621 | fG*fU*fU*fU*fU*fU*mU*mC*mA*mG*mG*m A*mU*mU*fU*fC*fA*fG*fC*fA | 1373 | XXXXXXXXX XXXXXXXXX | DMD mouse Exon23 | DMD |
| WV-4673 | UGUUUUUUCA GGAUUUCAGC | 622 | fU*fG*fU*fU*fU*fU*fU*mU*mC*mA*mG*m G*mA*mU*fU*fU*fC*fA*fG*fC | 1374 | XXXXXXXXX XXXXXXXXX | DMD mouse Exon23 | DMD |
| WV-4674 | CUGUUUUUUC AGGAUUUCAG | 623 | fC*fU*fG*fU*fU*fU*fU*fU*mU*mC*mA*m G*mG*mA*fU*fU*fU*fC*fA*fG | 1375 | XXXXXXXXX XXXXXXXXX | DMD mouse Exon23 | DMD |
| WV-4675 | GCUGUUUUUU CAGGAUUUCA | 624 | fG*fC*fU*fG*fU*fU*fU*fU*fU*mU*mC*m A*mG*mG*fA*fU*fU*fU*fC*fA | 1376 | XXXXXXXXX XXXXXXXXX | DMD mouse Exon23 | DMD |
| WV-4676 | AGCUGUUUUU UCAGGAUUUC | 625 | fA*fG*fC*fU*fG*fU*fU*mU*mU*mU*mU*m C*mA*mG*fG*fA*fU*fU*fU*fC | 1377 | XXXXXXXXX XXXXXXXXX | DMD mouse Exon23 | DMD |
| WV-4677 | GAGCUGUUUU UUCAGGAUUU | 626 | fG*fA*fG*fC*fU*fG*fU*mU*mU*mU*mU*m U*mC*mA*fG*fG*fA*fU*fU*fU | 1378 | XXXXXXXXX XXXXXXXXX | DMD mouse Exon23 | DMD |
| WV-4678 | UGAGCUGUUU UUUCAGGAUU | 627 | fU*fG*fA*fG*fC*fU*fG*mU*mU*mU*mU*m U*mU*mC*fA*fG*fG*fA*fU*fU | 1379 | XXXXXXXXX XXXXXXXXX | DMD mouse Exon23 | DMD |
| WV-4679 | UUGAGCUGUU UUUUCAGGAU | 628 | fU*fU*fG*fA*fG*fC*fU*mG*mU*mU*mU*m U*mU*mU*fC*fA*fG*fG*fA*fU | 1380 | XXXXXXXXX XXXXXXXXX | DMD mouse Exon23 | DMD |
| WV-4680 | UUUGAGCUGU UUUUUCAGGA | 629 | fU*fU*fU*fG*fA*fG*mC*fU*mG*mU*mU*m U*mU*mU*fU*fC*fA*fG*fG*fA | 1381 | XXXXXXXXX XXXXXXXXX | DMD mouse Exon23 | DMD |
| WV-4681 | GUUUGAGCUG UUUUUUCAGG | 630 | fG*fU*fU*fU*fG*fA*mG*mC*mU*fG*mU*m U*mU*mU*fU*fC*fA*fG*fG | 1382 | XXXXXXXXX XXXXXXXXX | DMD mouse Exon23 | DMD |
| WV-4682 | UUGUUUGAGC UGUUUUUUCA | 631 | fU*fU*fG*fU*fU*fU*mG*mA*mG*mC*mU*m G*mU*mU*fU*fU*fU*fU*fC*fA | 1383 | XXXXXXXXX XXXXXXXXX | DMD mouse Exon23 | DMD |
| WV-4683 | CAUUGUUUGA GCUGUUUUUU | 632 | fC*fA*fU*fU*fG*fU*mU*mU*mG*mA*mG*m C*mU*mG*fU*fU*fU*fU*fU*fU | 1384 | XXXXXXXXX XXXXXXXXX | DMD mouse Exon23 | DMD |
| WV-4684 | GCAUUGUUUG AGCUGUUUUU | 633 | fG*fC*fA*fU*fU*fG*mU*mU*mU*mG*mA*m G*mC*mU*fG*fU*fU*fU*fU*fU | 1385 | XXXXXXXXX XXXXXXXXX | DMD mouse Exon23 | DMD |
| WV-4685 | UGCAUUGUUU GAGCUGUUUU | 634 | fU*fG*fC*fA*fU*fU*mG*mU*mU*mU*mG*m A*mG*mC*fU*fG*fU*fU*fU*fU | 1386 | XXXXXXXXX XXXXXXXXX | DMD mouse Exon23 | DMD |
| WV-4686 | CUGCAUUGUU UGAGCUGUUU | 635 | fC*fU*fG*fC*fA*fU*mU*mG*mU*mU*mU*m G*mA*mG*fC*fU*fG*fU*fU*fU | 1387 | XXXXXXXXX XXXXXXXXX | DMD mouse Exon23 | DMD |
| WV-4687 | UCUGCAUUGU UUGAGCUGUU | 636 | fU*fC*fU*fG*fC*fA*mU*mU*mG*mU*mU*m U*mG*mA*fG*fC*fU*fG*fU*fU | 1388 | XXXXXXXXX XXXXXXXXX | DMD mouse Exon23 | DMD |
| WV-4688 | CUCUGCAUUG UUUGAGCUGU | 637 | fC*fU*fC*fU*fG*fC*mA*mU*mU*mG*mU*m U*mU*mG*fA*fG*fC*fU*fG*fU | 1389 | XXXXXXXXX XXXXXXXXX | DMD mouse Exon23 | DMD |
| WV-4689 | ACUCUGCAUU GUUUGAGCUG | 638 | fA*fC*fU*fC*fU*fG*mC*mA*mU*mU*mG*m U*mU*mU*fA*fG*fC*fU*fG | 1390 | XXXXXXXXX XXXXXXXXX | DMD mouse Exon23 | DMD |
| WV-4690 | UACUCUGCAU UGUUUAGCU | 639 | fU*fA*fC*fU*fC*fU*mG*mC*mA*mU*mU*m G*mU*mU*fG*fA*fG*fC*fU | 1391 | XXXXXXXXX XXXXXXXXX | DMD mouse Exon23 | DMD |
| WV-4691 | UUACUCUGCA UUGUUUGAGC | 640 | fU*fU*fA*fC*fU*fC*mU*mG*mC*mA*mU*m U*mG*mU*fU*fG*fA*fG*fC | 1392 | XXXXXXXXX XXXXXXXXX | DMD mouse Exon23 | DMD |
| WV-4692 | CUUACUCUGC AUUGUUUGAG | 641 | fC*fU*fU*fA*fC*fU*mC*mU*mG*mC*mA*m U*mU*mG*fU*fU*fG*fA*fG | 1393 | XXXXXXXXX XXXXXXXXX | DMD mouse Exon23 | DMD |
| WV-4693 | UCUUACUCUG CAUUGUUUGA | 642 | fU*fC*fU*fU*fA*fC*fU*mC*mU*mG*mC*m A*mU*mU*fG*fU*fU*fG*fA | 1394 | XXXXXXXXX XXXXXXXXX | DMD mouse Exon23 | DMD |
| WV-4694 | AUCUUACUCU GCAUUGUUUG | 643 | fA*fU*fC*fU*fU*fA*mC*mU*mC*mU*mG*m *mA*mU*fU*fG*fU*fU*fU*fG | 1395 | XXXXXXXXX XXXXXXXXX | DMD mouse Exon23 | DMD |
| WV-4695 | AAUCUUACUC UGCAUUGUUU | 644 | fA*fA*fU*fC*fU*fU*mA*mC*mU*mC*mU*m G*mC*mA*fU*fU*fG*fU*fU*fU | 1396 | XXXXXXXXX XXXXXXXXX | DMD mouse Exon23 | DMD |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-4696 | CAAAUCUUAC UCUGCAUUGU | 645 | fC*fA*fA*fA*fU*fC*mU*mU*mA*mC*mU*mC*mU*mG*fC*fA*fU*fU*fG*fU | 1397 | XXXXXXXXX XXXXXXXX | DMD mouse Exon23 | DMD |
| WV-4697 | GAUACAAAUC UUACUCUGCA | 646 | fG*fA*fU*fA*fC*fA*mA*mA*mU*mC*mU*mU*mA*mC*fU*fC*fU*fG*fC*fA | 1398 | XXXXXXXXX XXXXXXXX | DMD mouse Exon23 | DMD |
| WV-2559 | GGGUCAGCT GCCAATGCU AG | 647 | mG*mG*mG*mU*mC*A*G*C*T*G*C*C*A*A*T*mG*mC*mU*mA*mG | 1399 | XXXXXXXXX XXXXXXXXX | ASO1 Malat1 2OMe 5-10-5 Full PS version | Malat1 |
| WV-2560 | GGGUCAGCT GCCAATGCU AG | 648 | mG*mGmGmUmC*A*G*C*T*G*C*C*A*A*T*mGmCmUmA*mG | 1400 | XOOOXXXXX XXXXXXOOO X | ASO1 Malat1 2OMe 5-10-5 WV-1497 like version | Malat1 |
| WV-2562 | GGGUCAGCT GCCAATGCU AG | 649 | mG*G*mG*mU*mC*A*G*C*T*G*C*C*A A*T*mG*mC*mU*A*mG | 1401 | XXXXXXXXX XXXXXXXXX | ASO1 Malat1 2OMe 1-1-3-10-3-1-1 Full PS version Frank2 | Malat1 |
| WV-2564 | GGGUCAGCT GCCAATGCU AG | 650 | mG*G*mGmUmC*A*G*C*T*G*C*C*A A*T*mGmCmUA*mG | 1402 | XXOOXXXXX XXXXXXOOO X | ASO1 Malat1 2OMe 1-1-3-10-3-1-1 PO PS Frank2 | Malat1 |
| WV-2566 | GGGUCAGCT GCCAATGCTA G | 651 | mG*mG*G*mU*mC*A*G*C*T*G*C*C*A A*T*mG*mC*T*mA*mG | 1403 | XXXXXXXXX XXXXXXXXX | ASO1 Malat1 2OMe 2-1-2-10-2-1-2 Full PS version Frank3 | Malat1 |
| WV-2568 | GGGUCAGCT GCCAATGCTA G | 652 | mG*mGG*mUmC*A*G*C*T*G*C*C*A A*T*mGmCT*mA*mG | 1404 | XOXOXXXXX XXXXXXOOX X | ASO1 Malat1 2OMe 2-1-2-10-2-1-2 PO PS version Frank3 | Malat1 |
| WV-2570 | GGGTCAGCTG CCAATGCUA G | 653 | mG*mG*mG*T*mC*A*G*C*T*G*C*C*A A*T*mG*C*mU*mA*mG | 1405 | XXXXXXXXX XXXXXXXXX | ASO1 Malat1 2OMe 3-1-1-10-1-1-3 Full PS version Nenad1 | Malat1 |
| WV-2572 | GGGTCAGCTG CCAATGCUA G | 654 | mG*mGmGT*mC*A*G*C*T*G*C*C*A A*T*mGC*mUmA*mG | 1406 | XOOXXXXX XXXXXXOXO X | ASO1 Malat1 2OMe 3-1-1-10-1-1-3 PO PS like version Nenad1 | Malat1 |
| WV-2574 | GGGUCAGCT GCCAATGCU AG | 655 | G*G*mG*mU*mC*A*G*C*T*G*C*C*A*A*T*mG*mC*mU*A*G | 1407 | XXXXXXXXX XXXXXXXXX | ASO1 Malat1 2OMe 2-3-10-3-2 PO PS like version Chandra1 | Malat1 |
| WV-2576 | GGGUCAGCT GCCAATGCU AG | 656 | G*mGmGmUmC*A*G*C*T*G*C*C*A*A*T*mGmCmUmA*G | 1408 | XOOOXXXXX XXXXXXOOO X | ASO1 Malat1 2OMe 1-4-10-4-1 PO PS like version Chandra2 | Malat1 |
| WV-2735 | GGGTCAGCTG CCAATGCTAG | 657 | Geo*Geo*Geo*Teo*m5Ceo*A*G*C*T*G*C*C*A*A*T*Geo*m5Ceo*Teo*Aeo*Geo | 1409 | XXXXXXXXX XXXXXXXXX X | Randomer for WV-2526 | Malat1 |
| WV-2736 | GGGTCAGCTG CCAATGCTAG | 658 | Geo*Geo*Geo*Teo*Ceo*A*G*C*T*G*C*C*A*A*T*Geo*Ceo*Teo*Aeo*Geo | 1410 | XXXXXXXXX XXXXXXXXX X | Randomer for WV-2526 | Malat1 |
| WV-2753 | GGGUCAGCT GCCAATGCU AG | 659 | Mod013L001*mG*mG*mG*mU*mC*A*G*C*T*G*C*C*A*A*T*mG*mC*mU*mA*mG | 1411 | OXXXXXXXX XXXXXXXXX XXX | Lauric acid OMe full-PS | Malat1 |
| WV-2754 | GGGUCAGCT GCCAATGCU AG | 660 | Mod014L001*mG*mG*mG*mU*mC*A*G*C*T*G*C*C*A*A*T*mG*mC*mU*mA*mG | 1412 | OXXXXXXXX XXXXXXXXX XXX | Myristic acid OMe full-PS | Malat1 |
| WV-2755 | GGGUCAGCT GCCAATGCU AG | 661 | Mod005L001*mG*mG*mG*mU*mC*A*G*C*T*G*C*C*A*A*T*mG*mC*mU*mA*mG | 1413 | OXXXXXXXX XXXXXXXXX XXX | Palmitic acid OMe full-PS | Malat1 |
| WV-2756 | GGGUCAGCT GCCAATGCU AG | 662 | Mod015L001*mG*mG*mG*mU*mC*A*G*C*T*G*C*C*A*A*T*mG*mC*mU*mA*mG | 1414 | OXXXXXXXX XXXXXXXXX XXX | Stearic acid OMe full-PS | Malat1 |
| WV- | GGGUCAGCT | 663 | Mod016L001*mG*mG*mG*mU*mC*A*G*C | 1415 | OXXXXXXXX | Oleic acid | Malat1 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| | | | *T*G*C*C*A*A*T*mG*mC*mU*mA*mG | | XXXXXXXX XXX | OMe full-PS | |
| WV-2758 | GGGUCAGCT GCCAATGCU AG | 664 | Mod017L001*mG*mG*mG*mU*mC*A*G*C *T*G*C*C*A*A*T*mG*mC*mU*mA*mG | 1416 | OXXXXXXXX XXXXXXXXX XXX | Linoleic acid OMe full-PS | Malat1 |
| WV-2759 | GGGUCAGCT GCCAATGCU AG | 665 | Mod018L001*mG*mG*mG*mU*mC*A*G*C *T*G*C*C*A*A*T*mG*mC*mU*mA*mG | 1417 | OXXXXXXXX XXXXXXXXX XXX | alpha-Linolenic acid OMe full-PS | Malat1 |
| WV-2760 | GGGUCAGCT GCCAATGCU AG | 666 | Mod019L001*mG*mG*mG*mU*mC*A*G*C *T*G*C*C*A*A*T*mG*mC*mU*mA*mG | 1418 | OXXXXXXXX XXXXXXXXX XXX | gamma-Linolenic acid OMe full-PS | Malat1 |
| WV-2761 | GGGUCAGCT GCCAATGCU AG | 667 | Mod006L001*mG*mG*mG*mU*mC*A*G*C *T*G*C*C*A*A*T*mG*mC*mU*mA*mG | 1419 | OXXXXXXXX XXXXXXXXX XXX | DHA OMe full-PS | Mal at1 |
| WV-2762 | GGGUCAGCT GCCAATGCU AG | 668 | Mod020L001*mG*mG*mG*mU*mC*A*G*C *T*G*C*C*A*A*T*mG*mC*mU*mA*mG | 1420 | OXXXXXXXX XXXXXXXXX XXX | Turbinaric acid OMe full-PS | Malat1 |
| WV-2763 | GGGUCAGCT GCCAATGCU AG | 669 | Mod021*mG*mG*mG*mU*mC*A*G*C*T*G *C*C*A*A*T*mG*mC*mU*mA*mG | 1421 | XXXXXXXXX XXXXXXXXX XX | Dilinol-eyl alcohol OMe full-PS | Mal at1 |
| WV-2764 | GGGUCAGCT GCCAATGCU AG | 670 | Mod024L001*mG*mG*mG*mU*mC*A*G*C *T*G*C*C*A*A*T*mG*mC*mU*mA*mG | 1422 | OXXXXXXXX XXXXXXXXX XXX | Trianten-nary GlcNAc OMe full-PS | Malat1 |
| WV-2765 | GGGUCAGCT GCCAATGCU AG | 671 | Mod025L001*mG*mG*mG*mU*mC *A*G*C *T*G*C*C*A*A*T*mG*mC*mU*mA*mG | 1423 | OXXXXXXXX XXXXXXXXX XXX | Triantennary beta-Mannose OMe full-PS | Malat1 |
| WV-2766 | GGGUCAGCT GCCAATGCU AG | 672 | Mod026L001*mG*mG*mG*mU*mC*A*G*C *T*G*C*C*A*A*T*mG*mC*mU*mA*mG | 1424 | OXXXXXXXX XXXXXXXXX XXX | Triantennary alpha-Mannose OMe full-PS | Malat1 |
| WV-2767 | GGGUCAGCT GCCAATGCU AG | 673 | Mod013L001*mG*mGmGmUmC*A*G*C*T* G*C*C*A*A*T*mGmCmUmA*mG | 1425 | OXXOOOXXX XXXXXXXXO OOX | Lauric acid OMe PSVPO wing | Mal at1 |
| WV-2768 | GGGUCAGCT GCCAATGCU AG | 674 | Mod014L001*mG*mGmGmUmC*A*G*C*T* G*C*C*A*A*T*mGmCmUmA*mG | 1426 | OXXOOOXXX XXXXXXXXO OOX | Myristic acid OMe PSVPO wing | Malat1 |
| WV-2769 | GGGUCAGCT GCCAATGCU AG | 675 | Mod005L001*mG*mGmGmUmC*A*G*C*T* G*C*C*A*A*T*mGmCmUmA*mG | 1427 | OXXOOOXXX XXXXXXXXO OOX | Palmitic acid OMe PSVPO wing | Malat1 |
| WV-2770 | GGGUCAGCT GCCAATGCU AG | 676 | Mod015L001*mG*mGmGmUmC*A*G*C*T* G*C*C*A*A*T*mGmCmUmA*mG | 1428 | OXXOOOXXX XXXXXXXXO OOX | Stearic acid OMe Malat1 PSVPO wing | |
| WV-2771 | GGGUCAGCT GCCAATGCU AG | 677 | Mod016L001*mG*mGmGmUmC*A*G*C*T* G*C*C*A*A*T*mGmCmUmA*mG | 1429 | OXXOOOXXX XXXXXXXXO OOX | Oleic acid PSVPO wing | Malat1 |
| WV-2772 | GGGUCAGCT GCCAATGCU AG | 678 679 | Mod017L001*mG*mGmGmUmC*A*G*C*T* G*C*C*A*A*T*mGmCmUmA*mG | 1430 | OXXOOOXXX XXXXXXXXO OOX | Linoleic acid OMe PSVPO wing | Malat1 |
| WV-2773 | GGGUCAGCT GCCAATGCU AG | | Mod018L001*mG*mGmGmUmC*A*G*C*T* G*C*C*A*A*T*mGmCmUmA*mG | 1431 | OXXOOOXXX XXXXXXXXO OOX | alpha-Linolenic acid OMe PSVPO wing | Malat1 |
| WV-2774 | GGGUCAGCT GCCAATGCU AG | 680 | Mod019L001*mG*mGmGmUmC*A*G*C*T* G*C*C*A*A*T*mGmCmUmA*mG | 1432 | OXXOOOXXX XXXXXXXXO OOX | gamma-Linolenic acid OMe PSVPO wing | Malat1 |
| WV-2775 | GGGUCAGCT GCCAATGCU AG | 681 | Mod006L001*mG*mGmGmUmC*A*G*C*T* G*C*C*A*A*T*mGmCmUmA*mG | 1433 | OXXOOOXXX XXXXXXXXO OOX | DHA OMe PSVPO wing | Malat |
| WV-2776 | GGGUCAGCT GCCAATGCU AG | 682 | Mod020L001*mG*mGmGmUmC*A*G*C*T* G*C*C*A*A*T*mGmCmUmA*mG | 1434 | OXXOOOXXX XXXXXXXXO OOX | Turbinaric acid OMe PSVPO wing | Malat1 |
| WV-2777 | GGGUCAGCT GCCAATGCU AG | 683 | Mod021*mG*mGmGmUmC*A*G*C*T*G*C* C*A*A*T*mGmCmUmA*mG | 1435 | XXOOOXXXX XXXXXXXOO OX | Dilinoleyl alcohol OMe PSVPO wing | Malat1 |
| WV-2778 | GGGUCAGCT GCCAATGCU AG | 684 | Mod024L001*mG*mGmGmUmC*A*G*C*T* G*C*C*A*A*T*mGmCmUmA*mG | 1436 | OXXOOOXXX XXXXXXXXO OOX | Triantennary GlcNAc OMe PSVPO wing | Malat1 |
| WV-2779 | GGGUCAGCT GCCAATGCU AG | 685 | Mod025L001*mG*mGmGmUmC*A*G*C*T* G*C*C*A*A*T*mGmCmUmA*mG | 1437 | OXXOOOXXX XXXXXXXXO OOX | Triantennary beta-Mannose OMe PSVPO wing | Malat1 |
| WV-2780 | GGGUCAGCT GCCAATGCU AG | 686 | Mod026L001*mG*mGmGmUmC*A*G*C*T* G*C*C*A*A*T*mGmCmUmA*mG | 1438 | OXXOOOXXX XXXXXXXXO OOX | Triantennary alpha-Mannose OMe PSVPO wing | Malat1 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-2781 | CUAGCAUUG GCAGCUGAC CC | 687 | rCrUrArGrCrArUrUrGrGrCrArGrCrUrGrAr CrCrC | 1439 | OOOOOOOO OOOOOOOO O | complementary RNA coding Malat1 | Malat1 |
| WV-2809 | GGGTCAGCTG CCAATGCTAG | 688 | L001*Geo*Geo*Geo*Teo*m5Ceo*A*G*C*T* G*C*T*G*C*C*A*A*T*Geo*m5Ceo*Teo*Aeo*Geo | 1440 | XXXXXXXX XXXXXXXX XX | C6amine linker MOE full-PS | Malat1 |
| WV-2810 | GGGUCAGCT GCCAATGCU AG | 689 | L001*mG*mG*mG*mU*mC*A*G*C*T*G*C *C*A*A*T*mG*mC*mU*mA*mG | 1441 | XXXXXXXX XXXXXXXX XX | C6amine linker OMe full-PS | Malat1 |
| WV-2811 | GGGUCAGCT GCCAATGCU AG | 690 | L001*mG*mGmGmUmC*A*G*C*T*G*C*C* A*A*T*mGmCmUmA*mG | 1442 | XOOOXXXX XXXXXXOO OX | C6amine linker OMe PS\/PO wing | Malat1 |
| WV-2821 | GGGTCAGCTG CCAATGCTAG | 691 | Mod013L001*Geo*Geo*Geo*Teo*m5Ceo*A* G*C*T*G*C*C*A*A*T*Geo*m5Ceo*Teo*Ae o*Geo | 1443 | OXXXXXXX XXXXXXXX XXX | Lauric acid MOE full-PS | Malat1 |
| WV-2822 | GGGTCAGCTG CCAATGCTAG | 692 | Mod014L001*Geo*Geo*Geo*Teo*m5Ceo*A* G*C*T*G*C*C*A*A*T*Geo*m5Ceo*Teo*Ae o*Geo | 1444 | OXXXXXXX XXXXXXXX XXX | Myristic acid MOE full-PS | Malat1 |
| WV-2823 | GGGTCAGCTG CCAATGCTAG | 693 | Mod005L001*Geo*Geo*Geo*Teo*m5Ceo*A* G*C*T*G*C*C*A*A*T*Geo*m5Ceo*Teo*Ae o*Geo | 1445 | OXXXXXXX XXXXXXXX XXX | Palmitic acid MOE full-PS | Malat1 |
| WV-2824 | GGGTCAGCTG CCAATGCTAG | 694 | Mod015L001*Geo*Geo*Geo*Teo*m5Ceo*A* G*C*T*G*C*C*A*A*T*Geo*m5Ceo*Teo*Ae o*Geo | 1446 | OXXXXXXX XXXXXXXX XXX | Stearic acid MOE full-PS | Malat1 |
| WV-2825 | GGGTCAGCTG CCAATGCTAG | 695 | Mod016L001*Geo*Geo*Geo*Teo*m5Ceo*A* G*C*T*G*C*C*A*A*T*Geo*m5Ceo*Teo*Ae o*Geo | 1447 | OXXXXXXX XXXXXXXX XXX | Oleic acid MOE full-PS | Malat1 |
| WV-2826 | GGGTCAGCTG CCAATGCTAG | 696 | Mod017L001*Geo*Geo*Geo*Teo*m5C o*A* G*C*T*G*C*C*A*A*T*Geo*m5Ceo*Teo*Ae o*Geo | 1448 | OXXXXXXX XXXXXXXX XXX | Linoleic acid MOE full-PS | Malat1 |
| WV-2827 | GGGTCAGCTG CCAATGCTAG | 697 | Mod018L001*Geo*Geo*Geo*Teo*m5Ceo*A* G*C*T*G*C*C*A*A*T*Geo*m5Ceo*Teo*Ae o*Geo | 1449 | OXXXXXXX XXXXXXXX XXX | alpha-Linolenic acid MOE | Malat1 full-PS |
| WV-2828 | GGGTCAGCTG CCAATGCTAG | 698 | Mod019L001*Geo*Geo*Geo*Teo*m5Ceo*A* G*C*T*G*C*C*A*A*T*Geo*m5Ceo*Teo*Ae o*Geo | 1450 | OXXXXXXX XXXXXXXX XXX | gamma-Linolenic acid MOE full-PS | Malat1 |
| WV-2829 | GGGTCAGCTG CCAATGCTAG | 699 | Mod006L001*Geo*Geo*Geo*Teo*m5Ceo*A* G*C*T*G*C*C*A*A*T*Geo*m5Ceo*Teo*Ae o*Geo | 1451 | OXXXXXXX XXXXXXXX XXX | DHA MOE full-PS | Malat1 |
| WV-2830 | GGGTCAGCTG CCAATGCTAG | 700 | Mod020L001*Geo*Geo*Geo*Teo*m5Ceo*A* G*C*T*G*C*C*A*A*T*Geo*m5Ceo*Teo*Ae o*Geo | 1452 | OXXXXXXX XXXXXXXX XXX | Turbinaric acid MOE full-PS | Malat1 |
| WV-2831 | GGGTCAGCTG CCAATGCTAG | 701 | Mod021*Geo*Geo*Geo*Teo*m5Ceo*A*G*C* T*G*C*C*A*A*T*Geo*m5Ceo*Teo*Aeo*Ge o | 1453 | XXXXXXXX XXXXXXXX XX | Dilinoleyl alcohol MOE full-PS | Malat1 |
| WV-2832 | GGGTCAGCTG CCAATGCTAG | 702 | Mod024L001*Geo*Geo*Geo*Teo*m5Ceo*A* G*C*T*G*C*C*A*A*T*Geo*m5Ceo*Teo*Ae o*Geo | 1454 | OXXXXXXX XXXXXXXX XXX | Triantennary GlcNAc MOE full-PS | Malat1 |
| WV-2833 | GGGTCAGCTG CCAATGCTAG | 703 | Mod025L001*Geo*Geo*Geo*Teo*m5Ceo*A* G*C*T*G*C*C*A*A*T*Geo*m5Ceo*Teo*Ae o*Geo | 1455 | OXXXXXXX XXXXXXXX XXX | Triantennary beta-Mannose MOE full-PS | Malat1 |
| WV-2834 | GGGTCAGCTG CCAATGCTAG | 704 | Mod026L001*Geo*Geo*Geo*Teo*m5Ceo*A* G*C*T*G*C*C*A*A*T*Geo*m5Ceo*Teo*Ae o*Geo | 1456 | OXXXXXXX XXXXXXXX XXX | Triantennary alpha-Mannose MOE full-PS | Malat1 |
| WV-2835 | GGGTCAGCTG CCAATGCTAG | 705 | Mod027L001*Geo*Geo*Geo*Teo*m5Ceo*A* G*C*T*G*C*C*A*A*T*Geo*m5Ceo*Teo*Ae o*Geo | 1457 | OXXXXXXX XXXXXXXX XXX | sulfonamide MOE full-PS | Malat1 |
| WV-2836 | GGGTCAGCTG CCAATGCTAG | 706 | Mod028L001*Geo*Geo*Geo*Teo*m5Ceo*A* G*C*T*G*C*C*A*A*T*Geo*m5Ceo*Teo*Ae o*Geo | 1458 | OXXXXXXX XXXXXXXX XXX | sulfonamide alkylchain MOE full-PS | Malat1 |
| WV-3062 | GGGTCAGCTG CCAATGCTAG | 707 | Mod015L001*Geo*Geo*Geo*Teo*m5Ceo*A* G*C*T*G*C*C*A*A*T*Geo*m5Ceo*Teo*Ae o*Geo*L004Mod024 | 1459 | OXXXXXXX XXXXXXXX XXX | Stearic acid and GlucNAc, MOE, full-PS | Malat1 |
| WV-3063 | GGGTCAGCTG CCAATGCTAG | 708 | Mod019L001*Geo*Geo*Geo*Teo*m5Ceo*A* G*C*T*G*C*C*A*A*T*Geo*m5Ceo*Teo*Ae o*Geo*L004Mod024 | 1460 | OXXXXXXX XXXXXXXX XXX | gamma-Linolenic acid and GlucNAc, MOE, full-PS | Malat1 |
| WV-3064 | GGGTCAGCTG CCAATGCTAG | 709 | Mod020L001*Geo*Geo*Geo*Teo*m5Ceo*A* G*C*T*G*C*C*A*A*T*Geo*m5Ceo*Teo*Ae o*Geo*L004Mod024 | 1461 | OXXXXXXX XXXXXXXX XXX | Turbinaric acid and GlucNAc, MOE, full-PS | Malat1 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3065 | GGGTCAGCTG CCAATGCTAG | 710 | Mod015L001*Geo*Geo*Geo*Teo*m5Ceo*A* G*C*T*G*C*C*A*A*T*Geo*m5Ceo*Teo*Ae o*Geo*L004Mod026 | 1462 | OXXXXXXXX XXXXXXXXX XXX | Stearic acid and Mannose, MOE, full-PS | Malat1 |
| WV-3066 | GGGTCAGCTG CCAATGCTAG | 711 | Mod019L001*Geo*Geo*Geo*Teo*m5Ceo*A* G*C*T*G*C*C*A*A*T*Geo*m5Ceo*Teo*Ae o*Geo*L004Mod026 | 1463 | OXXXXXXXX XXXXXXXXX XXX | gamma-Linolenic acid and Mannose, MOE, full-PS | Malat1 |
| WV-3067 | GGGTCAGCTG CCAATGCTAG | 712 | Mod020L001*Geo*Geo*Geo*Teo*m5Ceo*A* G*C*T*G*C*C*A*A*T*Geo*m5Ceo*Teo*Ae o*Geo*L004Mod026 | 1464 | OXXXXXXXX XXXXXXXXX XXX | Turbinaric acid and Mannose, MOE, full-PS | Malat1 |
| WV-3154 | UAGCGCCCA CCTCACCCCU C | 713 | mU*mA*mG*mC*mG*C*C*C*A*C*C*T*C* A*C*mC*mC*mC*mU*mC | 1465 | XXXXXXXXX XXXXXXXXX X | 20 mers, Full PS, 5-10-5 2'OMe gapmers | Malat1 |
| WV-3155 | UUAGCGCCC ACCTCACCCC U | 714 | mU*mU*mA*mG*mC*G*C*C*C*A*C*C*T* C*A*mC*mC*mC*mC*mU | 1466 | XXXXXXXXX XXXXXXXXX X | 20 mers, Full PS, 5-10-5 2'OMe gapmers | Malat1 |
| WV-3156 | CUUAGCGCC CACCTCACCC C | 715 | mC*mU*mU*mA*mG*C*G*C*C*C*A*C*C* T*C*mA*mC*mC*mC*mC | 1467 | XXXXXXXXX XXXXXXXXX X | 20 mers, Full PS, 5-10-5 2'OMe gapmers | Malat1 |
| WV-3157 | ACCCCGTCCT GGAAACCAG G | 716 | mA*mC*mC*mC*mC*G*T*C*C*T*G*G*A* A*A*mC*mC*mA*mG*mG | 1468 | XXXXXXXXX XXXXXXXXX X | 20 mers, Full PS, 5-10-5 2'OMe gapmers | Malat1 |
| WV-3158 | CCCCGTCCTG GAAACCAGG A | 717 | mC*mC*mC*mC*mG*T*C*C*T*G*G*A*A* A*C*mC*mA*mG*mG*mA | 1469 | XXXXXXXXX XXXXXXXXX X | 20 mers, Full PS, 5-10-5 2'OMe gapmers | Malat1 |
| WV-3159 | GCUUAGCGC CCACCTCACC C | 718 | mG*mC*mU*mU*mA*G*C*G*C*C*C*A*C* C*T*mC*mA*mC*mC*mC | 1470 | XXXXXXXXX XXXXXXXXX X | 20 mers, Full PS, 5-10-5 2'OMe gapmers | Malat1 |
| WV-3160 | GGCUUAGCG CCCACCUCAC C | 719 | mG*mG*mC*mU*mU*A*G*C*G*C*C*C*A *C*C*mU*mC*mA*mC*mC | 1471 | XXXXXXXXX XXXXXXXXX X | 20 mers, Full PS, 5-10-5 2'OMe gapmers | Malat1 |
| WV-3161 | CCCGUCCTGG AAACCAGGA G | 720 | mC*mC*mC*mG*mU*C*C*T*G*G*A*A*A* C*C*mA*mG*mG*mA*mG | 1472 | XXXXXXXXX XXXXXXXXX X | 20 mers, Full PS, 5-10-5 2'OMe gapmers | Malat1 |
| WV-3162 | UGAACCCCGT CCTGGAAACC | 721 | mU*mG*mA*mA*mC*C*C*C*G*T*C*C*T* G*G*mA*mA*mA*mC*mC | 1473 | XXXXXXXXX XXXXXXXXX X | 20 mers, Full PS, 5-10-5 2'OMe gapmers | Malat1 |
| WV-3163 | UUUCCCCTCC CTCATCAACA | 722 | mU*mU*mU*mC*mC*C*C*T*C*C*C*T*C* A*T*mC*mA*mA*mC*mA | 1474 | XXXXXXXXX XXXXXXXXX X | 20 mers, Full PS, 5-10-5 2'OMe gapmers | Malat1 |
| WV-3164 | AGCUCCAGTC CCTGAAGGU G | 723 | mA*mG*mC*mU*mC*C*A*G*T*C*C*C*T* G*A*mA*mG*mG*mU*mG | 1475 | XXXXXXXXX XXXXXXXXX X | 20 mers, Full PS, 5-10-5 2'OMe gapmers | Malat1 |
| WV-3165 | AGGCUTAGC GCCCACCUCA C | 724 | mA*mG*mG*mC*mU*T*A*G*C*G*C*C*C* A*C*mC*mU*mC*mA*mC | 1476 | XXXXXXXXX XXXXXXXXX X | 20 mers, Full PS, 5-10-5 2'OMe gapmers | Malat1 |
| WV-3166 | GUUUCCCCTC CCTCAUCAAC | 725 | mG*mU*mU*mU*mC*C*C*C*T*C*C*C*T* C*A*mU*mC*mA*mA*mC | 1477 | XXXXXXXXX XXXXXXXXX X | 20 mers, Full PS, 5-10-5 2'OMe gapmers | Malat1 |
| WV-3167 | AACCCGUCC TGGAAACCA G | 726 | mA*mA*mC*mC*mC*C*G*T*C*C*T*G*G* A*A*mC*mC*mA*mG | 1478 | XXXXXXXXX XXXXXXXXX X | 20 mers, Full PS, 5-10-5 2'OMe gapmers | Malat1 |
| WV-3168 | GAACCCCGTC CTGGAAACC A | 727 | mG*mA*mA*mC*mC*C*C*G*T*C*C*T*G* G*A*mA*mA*mC*mC*mA | 1479 | XXXXXXXXX XXXXXXXXX X | 20 mers, Full PS, 5-10-5 2'OMe gapmers | Malat1 |
| WV-3169 | GCUCCAGTCC CTGAAGGUG U | 728 | mG*mC*mU*mC*mC*A*G*T*C*C*C*T*G* A*A*mG*mG*mU*mG*mU | 1480 | XXXXXXXXX XXXXXXXXX X | 20 mers, Full PS, 5-10-5 2'OMe gapmers | Malat1 |
| WV-3170 | UUGAACCCC GTCCTGGAAA C | 729 | mU*mU*mG*mA*mA*C*C*C*C*G*T*C*C* T*G*mG*mA*mA*mA*mC | 1481 | XXXXXXXXX XXXXXXXXX X | 20 mers, Full PS, 5-10-5 2'OMe gapmers | Malat1 |
| WV-3171 | UUCCCCTCCC TCATCAACAA | 730 | mU*mU*mC*mC*mC*T*C*C*C*T*C*A* T*C*mA*mA*mC*mA*mA | 1482 | XXXXXXXXX XXXXXXXXX X | 20 mers, Full PS, 5-10-5 2'OMe gapmers | Malat1 |
| WV-3172 | CCGUCCTGGA AACCAGGAG U | 731 | mC*mC*mG*mU*mC*C*T*G*G*A*A*A*C* C*A*mG*mG*mA*mG*mU | 1483 | XXXXXXXXX XXXXXXXXX X | 20 mers, Full PS, 5-10-5 2'OMe gapmers | Malat1 |
| WV-3173 | GCAGCUCCAG TCCCTGAAGG | 732 | mG*mC*mA*mG*mC*T*C*C*A*G*T*C*C* C*T*mG*mA*mA*mG*mG | 1484 | XXXXXXXXX XXXXXXXXX X | 20 mers, Full PS, 5-10-5 2'OMe gapmers | Malat1 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| WV-3174 | UGCCAGGCT GGTTATGACU C | 733 | mU*mG*mC*mC*mA*G*G*C*T*G*G*T*T* A*T*mG*mA*mC*mU*mC | 1485 | XXXXXXXX XXXXXXXX X | 20 mers, Full PS, 5-10-5 2'OMe gapmers | Malat1 |
| WV-3175 | CGUCCTGGA AACCAGGAG UG | 734 | mC*mG*mU*mC*mC*T*G*G*A*A*A*C*C* A*G*mG*mA*mG*mU*mG | 1486 | XXXXXXXX XXXXXXXX X | 20 mers, Full PS, 5-10-5 2'OMe gapmers | Malat1 |
| WV-3176 | CAGCUCCAGT CCCTGAAGG U | 735 | mC*mA*mG*mC*mU*C*C*A*G*T*C*C*C* T*G*mA*mA*mG*mG*mU | 1487 | XXXXXXXX XXXXXXXX X | 20 mers, Full PS, 5-10-5 2'OMe gapmers | Malat1 |
| WV-3177 | CUGCCAGGCT GGTTAUGAC U | 736 | mC*mU*mG*mC*mC*A*G*G*C*T*G*G*T* T*A*mU*mG*mA*mC*mU | 1488 | XXXXXXXX XXXXXXXX X | 20 mers, Full PS, 5-10-5 2'OMe gapmers | Malat1 |
| WV-3178 | UCCUGGAAA CCAGGAGUG CC | 737 | mU*mC*mC*mU*mG*G*A*A*A*C*C*A*G *G*A*mG*mU*mG*mC*mC | 1489 | XXXXXXXX XXXXXXXX X | 20 mers, Full PS, 5-10-5 2'OMe gapmers | Malat1 |
| WV-3179 | AAGGCUUAGC GCCCACCUCA | 738 | mA*mA*mG*mG*mC*T*T*A*G*C*G*C*C* C*A*mC*mC*mU*mC*mA | 1490 | XXXXXXXX XXXXXXXX X | 20 mers, Full PS, 5-10-5 2'OMe gapmers | Malat1 |
| WV-3180 | CCAGGCTGGT TATGACUCAG | 739 | mC*mC*mA*mG*mG*C*T*G*G*T*T*A*T* G*A*mC*mU*mC*mA*mG | 1491 | XXXXXXXX XXXXXXXX X | 20 mers, Full PS, 5-10-5 2'OMe gapmers | Malat1 |
| WV-3181 | CCUGGAAAC CAGGAGUGC CA | 740 | mC*mC*mU*mG*mG*A*A*A*C*C*A*G*G *A*G*mU*mG*mC*mC*mA | 1492 | XXXXXXXX XXXXXXXX X | 20 mers, Full PS, 5-10-5 2'OMe gapmers | Malat1 |
| WV-3182 | GCCAGGCTG GTTATGACUC A | 741 | mG*mC*mC*mA*mG*G*C*T*G*G*T*T*A* T*G*mA*mC*mU*mC*mA | 1493 | XXXXXXXX XXXXXXXX X | 20 mers, Full PS, 5-10-5 2'OMe gapmers | Malat1 |
| WV-3183 | AAAGGCUUA GCGCCCACCU C | 742 | mA*mA*mA*mG*mG*C*T*T*A*G*C*G*C* C*C*mA*mC*mC*mU*mC | 1494 | XXXXXXXX XXXXXXXX X | 20 mers, Full PS, 5-10-5 2'OMe gapmers | Malat1 |
| WV-3184 | GGAUUGGGA GTTACTUGCC A | 743 | mG*mG*mA*mU*mU*G*G*G*A*G*T*T*A *C*T*mU*mG*mC*mC*mA | 1495 | XXXXXXXX XXXXXXXX X | 20 mers, Full PS, 5-10-5 2'OMe gapmers | Malat1 |
| WV-3185 | GUCCUGGAA ACCAGGAGU GC | 744 | mG*mU*mC*mC*mU*G*G*A*A*A*C*C*A *G*G*mA*mG*mU*mG*mC | 1496 | XXXXXXXX XXXXXXXX X | 20 mers, Full PS, 5-10-5 2'OMe gapmers | Malat1 |
| WV-3186 | CAGGCTGGTT ATGACUCAG A | 745 | mC*mA*mG*mG*mC*T*G*G*T*T*A*T*G* A*C*mU*mC*mA*mG*mA | 1497 | XXXXXXXX XXXXXXXX X | 20 mers, Full PS, 5-10-5 2'OMe gapmers | Malat1 |
| WV-3187 | GGGAGTTACT TGCCAACUU G | 746 | mG*mG*mG*mA*mG*T*T*A*C*T*T*G*C* C*A*mA*mC*mU*mU*mG | 1498 | XXXXXXXX XXXXXXXX X | 20 mers, Full PS, 5-10-5 2'OMe gapmers | Malat1 |
| WV-3188 | UGGGAGTTA CTTGCCAACU U | 747 | mU*mG*mG*mG*mA*G*T*T*A*C*T*T*G* C*C*mA*mA*mC*mU*mU | 1499 | XXXXXXXX XXXXXXXX X | 20 mers, Full PS, 5-10-5 2'OMe gapmers | Malat1 |
| WV-3189 | UUGGGAGTT ACTTGCCAAC U | 748 | mU*mU*mG*mG*mG*A*G*T*T*A*C*T*T* G*C*mC*mA*mA*mC*mU | 1500 | XXXXXXXX XXXXXXXX X | 20 mers, Full PS, 5-10-5 2'OMe gapmers | Malat1 |
| WV-3190 | AUUUCCTCA ACACTCAGCC U | 749 | mA*mU*mU*mU*mC*C*T*C*A*A*C*A*C* T*C*mA*mG*mC*mC*mU | 1501 | XXXXXXXX XXXXXXXX X | 20 mers, Full PS, 5-10-5 2'OMe gapmers | Malat1 |
| WV-3191 | CCCCUCCCTC ATCAACAAA A | 750 | mC*mC*mC*mC*mU*C*C*C*T*C*A*T*C* A*A*mC*mA*mA*mA*mA | 1502 | XXXXXXXX XXXXXXXX X | 20 mers, Full PS, 5-10-5 2'OMe gapmers | Malat1 |
| WV-3192 | ACAUUUCCAC TTGCCAGUUA | 751 | mA*mC*mA*mU*mU*T*C*C*A*C*T*T*G* C*C*mA*mG*mU*mU*mA | 1503 | XXXXXXXX XXXXXXXX X | 20 mers, Full PS, 5-10-5 2'OMe gapmers | Malat1 |
| WV-3193 | AAAAGGCUU AGCGCCCACC U | 752 | mA*mA*mA*mA*mG*C*T*T*A*G*C*G*C* C*C*mA*mC*mC*mC*mU | 1504 | XXXXXXXX XXXXXXXX X | 20 mers, Full PS, 5-10-5 2'OMe gapmers | Malat1 |
| WV-3194 | ACCUGTCTGA GGCAAACGA A | 753 | mA*mC*mC*mU*mG*T*C*T*G*A*G*G*C* A*A*mA*mC*mG*mA*mA | 1505 | XXXXXXXX XXXXXXXX X | 20 mers, Full PS, 5-10-5 2'OMe gapmers | Malat1 |
| WV-3195 | AUUGGGAGT TACTTGCCAA C | 754 | mA*mU*mU*mG*mG*G*A*G*T*T*A*C*T* T*G*mC*mC*mA*mA*mC | 1506 | XXXXXXXX XXXXXXXX X | 20 mers, Full PS, 5-10-5 2'OMe gapmers | Malat1 |
| WV-3196 | UCAACAAAA GCCCACCCUC U | 755 | mU*mC*mA*mA*mC*A*A*A*A*G*C*C*C *A*C*mC*mC*mU*mC*mU | 1507 | XXXXXXXX XXXXXXXX X | 20 mers, Full PS, 5-10-5 2'OMe gapmers | Malat1 |
| WV-3197 | CUAAGATGCT AGCTTGGCCA | 756 | mC*mU*mA*mA*mG*A*T*G*C*T*A*G*C* T*T*mG*mG*mC*mC*mA | 1508 | XXXXXXXX XXXXXXXX X | 20 mers, Full PS, 5-10-5 2'OMe gapmers | Malat1 |
| WV- | GGGTCAGCTG | 757 | L001Geo*Geo*Geo*Teo*m5Ceo*A*G*C*T*G | 1509 | OXXXXXXX | C6amine PO | Malat1 |

TABLE 2-continued

Example Oligonucleotides.

| WAVE ID | Base Sequence | SEQ ID NO: | Description | SEQ ID NO: | Stereo-chemistry[1] | Notes | Target/Program |
|---|---|---|---|---|---|---|---|
| 3356 | CCAATGCTAG | | *C*C*A*A*T*Geo*m5Ceo*Teo*Aeo*Geo | | XXXXXXXXX XX | linker, MOE, full-PS | |
| WV-3521 | GGGTCAGCTG CCAATGCTAG | 758 | Mod030Geo*Geo*Geo*Teo*m5Ceo*A*G*C* T*G*C*C*A*A*T*Geo*m5Ceo*Teo*Aeo*Geo | 1510 | OXXXXXXXX XXXXXXXXX XX | WV-2735 based; Malat1 with PO linker, Lauric acid | |
| WV-3522 | GGGTCAGCTG CCAATGCTAG | 759 | Mod031Geo*Geo*Geo*Teo*m5Ceo*A*G*C* T*G*C*C*A*A*T*Geo*m5Ceo*Teo*Aeo*Geo | 1511 | OXXXXXXXX XXXXXXXXX XX | WV-2735 based; Malat1 with PO inker, Myristic acid | |
| WV-3523 | GGGTCAGCTG CCAATGCTAG | 760 | Mod032Geo*Geo*Geo*Teo*m5Ceo*A*G*C* T*G*C*C*A*A*T*Geo*m5Ceo*Teo*Aeo*Geo | 1512 | OXXXXXXXX XXXXXXXXX XX | WV-2735 based; Malat1 with PO linker, Palmitic acid | |
| WV-3524 | GGGTCAGCTG CCAATGCTAG | 761 | Mod033Geo*Geo*Geo*Teo*m5Ceo*A*G*C* T*G*C*C*A*A*T*Geo*m5Ceo*Teo*Aeo*Geo | 1513 | OXXXXXXXX XXXXXXXXX XX | WV-2735 based; Malat1 with PO linker, Stearic acid | |

[1]Including —C(O)— (noted as O) connecting Mod and the amino group of C6 amino linker and phosphate or phosphorothioate linkage connecting C6 amino linker and oligonucleotide chain (noted as X (stereorandom), S (Sp) or R (Sp)).

Abbreviations

2\': 2'
m5Ceo: 5-Methyl 2'-Methoxyethyl C
C6: C6 amino linker (L001, —NH—(CH$_2$)$_6$— wherein —NH— is connected to Mod (through —C(O)—) or —H, and —(CH$_2$)$_6$— is connected to the 5'-end of oligonucleotide chain through, e.g., phosphodiester (illustrated in the Table as O or PO), phosphorothioate (illustrated in the Table as * if the phosphorothioate not chirally controlled; *S, S, or Sp, if chirally controlled and has an Sp configuration, and *R, R, or Rp, if chirally controlled and has an Rp configuration), or phosphorodithioate (illustrated in the Table as PS2 or :). May also be referred to as C6 linker or C6 amine linker)
eo: 2'-MOE
Exon: Exon of Dystrophin
F, f: 2'-F
Laurie (in Mod 013), Myristic (in Mod 014), Palmitic (in Mod 005), Stearic (in Mod 015), Oleic (in Mod 016), Linoleic (in Mod 017), alpha-Linoleinc (in Mod 018), gamma-Linolenic (in Mod 019), DHA (in Mod 006), Turbinaric (in Mod 020), Dilinoleic (in Mod 021), TriGlcNAc (in Mod 024), TrialphaMannose (in Mod 026), MonoSulfonamide (in Mod 027), TriSulfonamide (in Mod 029), Laurie (in Mod 030), Myristic (in Mod 031), Palmitic (in Mod 032), and Stearic (in Mod 033): Laurie acid (for Mod 013), Myristic acid (for Mod 014), Palmitic acid (for Mod 005), Stearic acid (for Mod 015), Oleic acid (for Mod 016), Linoleic acid (for Mod 017), alpha-Linolenic acid (for Mod 018), gamma-Linolenic acid (for Mod 019), docosahexaenoic acid (for Mod 006), Turbinaric acid (for Mod 020), alcohol for Dilinoleyl (for Mod 021), acid for TriGlcNAc (for Mod 024), acid for TrialphaMannose (for Mod 026), acid for MonoSulfonamide (for Mod 027), acid for Tri Sulfonamide (for Mod 029), Lauryl alcohol (for Mod 030), Myristyl alcohol (for Mod 031), Palmityl alcohol (for Mod 032), and Stearyl alcohol (for Mod 033), respectively, conjugated to oligonucleotide chains through amide groups, C6 amino linker, phosphodiester linkage (PO), and/or phosphorothioate linkage (PS): Mod 013 (Laurie acid with C6 amino linker and PO or PS), Mod 014 (Myristic acid with C6 amino linker and PO or PS), Mod 005 (Palmitic acid with C6 amino linker and PO or PS), Mod 015 (Stearic acid with C6 amino linker and PO or PS), Mod 016 (Oleic acid with C6 amino linker and PO or PS), Mod 017 (Linoleic acid with C6 amino linker and PO or PS), Mod 018 (alpha-Linolenic acid with C6 amino linker and PO or PS), Mod 019 (gamma-Linolenic acid with C6 amino linker and PO or PS), Mod 006 (DHA with C6 amino linker and PO or PS), Mod 020 (Turbinaric acid with C6 amino linker and PO or PS), Mod 021 (alcohol (see below) with PO or PS), Mod 024 (acid (see below) with C6 amino linker and PO or PS), Mod 026 (acid (see below) with C6 amino linker and PO or PS), Mod 027 (acid (see below) with C6 amino linker and PO or PS), Mod 029 (acid (see below) with C6 amino linker and PO or PS), Mod 030 (Lauryl alcohol with PO or PS), Mod 031 (Myristyl alcohol with PO or PS), Mod 032 (Palmityl alcohol with PO or PS), and Mod 033 (Stearyl alcohol with PO or PS), with PO or PS for each oligonucleotide indicated in the Table (for example, WV-3473 Laurie acid conjugated to oligonucleotide chain of WV-3473 via amide group, C6, and PO: Mod 013L001fU*SfC *SfA*SfA*SfG*SfG*SmAfA* SmGmA*SfU*SmGmGfC*SfA*SfU*SfU* SfU*SfC*SfU (SEQ ID NO: 1514) (Description), OOSSSSSSOSOSSOOSSSSSS (Stereochemistry), and/or WV-3473, Laurie acid, C6 PO linker (Notes);
WV-3557 Steary alcohol conjugated to oligonucleotide chain of WV-3473 via PS:
Mod 033*fU*SfC *SfA*SfA*SfG*SfG* SmAfA*SmGmA*SfU*SmGmGfC*SfA*SfU*SfU*SfU *SfC*SfU (SEQ ID NO: 1515) (Description), XSSSSSSSOSOSSOOSSSSSS (Stereochemistry), and/or WV-3473, Stearic PS (Notes); and
WV-4106 Stearic acid conjugated to oligonucleotide chain of WV-3473 via amide group, C6, and PS:
Mod 015L001*fU*SfC *SfA*SfA*SfG*SfG* SmAfA*SmGmA*SfU*SmGmGfC*SfA*SfU*SfU *SfU*SfC*SfU (SEQ ID NO: 1516) (Description), OXSSSSSSOSOSSOOSSSSSS (Stereochemistry), and/or WV-3473, C6 PS linker, Stearic acid (Notes))
Moieties for conjugation, and example reagents (many of which were previously known and are commercially available or can be readily prepared using known technologies in accordance with the present disclosure, e.g., Laurie acid (for Mod 013), Myristic acid (for Mod 014), Palmitic acid (for Mod 005), Stearic acid (for Mod 015), Oleic acid (for Mod 016), Linoleic acid (for Mod 017), alpha-Linolenic acid (for Mod 018), gamma-Linolenic acid (for Mod 019), docosahexaenoic acid (for Mod 006), Turbinaric acid (for Mod 020), alcohol for Dilinoleyl (for Mod 021), Lauryl alcohol (for Mod 030), Myristyl alcohol (for Mod 031), Palmityl alcohol (for Mod 032), Stearyl alcohol (for Mod 033), etc.) are listed below m: 2'-OMe.

NA: Not Applicable; this term is generally used for negative controls

OMe: 2'-OMe

O, PO: phoshodiester (phosphate), or when used with Mod and L001, —C(O)— (connecting Mod and L001, for example, Mod 013L001fU*SfC *SfA*SfA*SfG*SfG*SmAfA* SmGmA*SfU*SmGmGfC*SfA*SfU*SfU* SfU*SfC*SfU (SEQ ID NO: 1514) (Description), OOSSSSSSOSOSSOOSSSSS (Stereochemistry) and/or WV-3473, Laurie acid, C6 PO linker (Notes). Note the second O OOSSSSSSOSOSSOOSSSSS (Stereochemistry) represents phosphodiester linkage connecting L001 and 5'-O— of oligonucleotide chain:

Mod 013 L001fU*SfC*SfA*SfA*SfG*SfG* SmAfA*SmGmA*SfU*SmGmGfC*SfA*SfU*SfU* SfU*SfC*SfU) (SEQ ID NO: 1514)

*, PS: Phosphorothioate

PS2, :, D: phosphorodithioate (e.g., WV-3078, wherein a colon (:) indicates a phosphorodithioate)

*R, R, Rp: Phosphorothioate in Rp conformation

*S, S, Sp: Phosphorothioate in Sp conformation

WV, W V—: WV—

X: Phosphorothioate stereorandom

Example moieties (e.g., lipid moieties, targeting component, etc.) and example preparation reagents (e.g., acids, alcohols, etc.) for conjugation to prepare provided oligonucleotides, e.g., example oligonucleotides in Tables 1-4 comprising such moieties, in accordance with the present disclosure include the below:

Mod005 (with —C(O)— connecting to —NH— of L001) and Palmitic acid

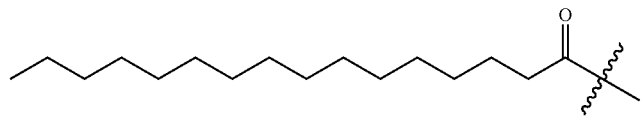

Mod005L001 (with PO or PS connecting to 5' —O— of oligonucleotide chain)

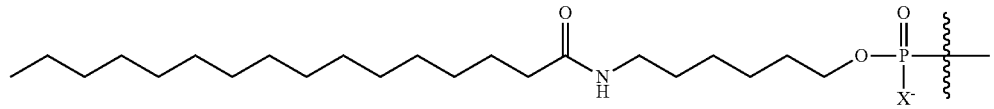

X = O or S

Mod006 (with —C(O)— connecting to —NH— of L001) and DHA

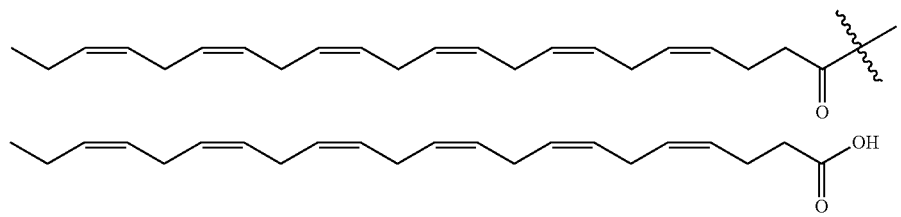

Mod006L001 (with PO or PS connecting to 5' —O— of oligonucleotide chain)

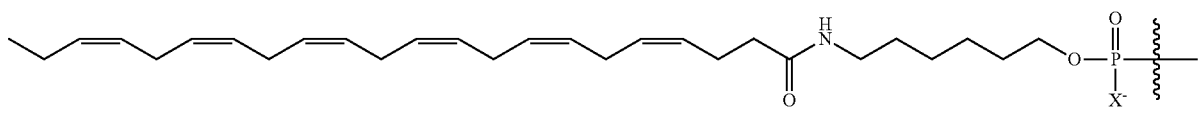

X = O or S

Mod013 (with —C(O)— connecting to —NH— of L001) and Lauric acid

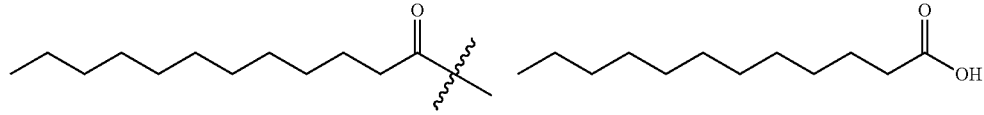

-continued

Mod013L001 (with PO or PS connecting to 5'—O— of oligonucleotide chain)

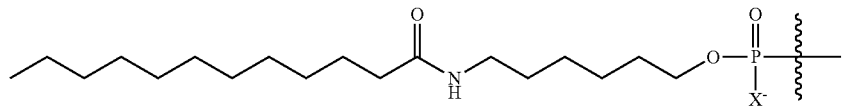

X = O or S

Mod014 (with —C(O)— connecting to —NH— of L001) and Myristic acid

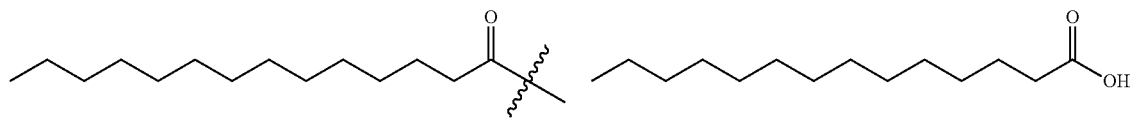

Mod014L001 (with PO or PS connecting to 5'—O— of oligonucleotide chain)

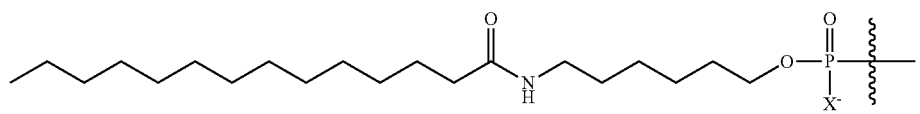

X = O or S

Mod015 (with —C(O)— connecting to —NH— of L001) and Stearic acid

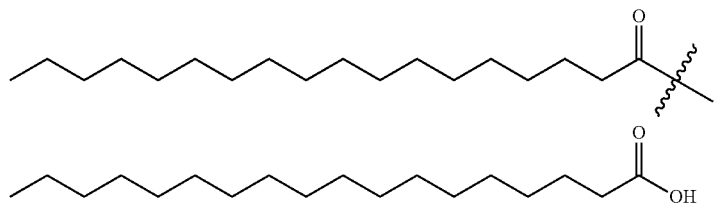

Mod015L001 (with PO or PS connecting to 5'—O— of oligonucleotide chain)

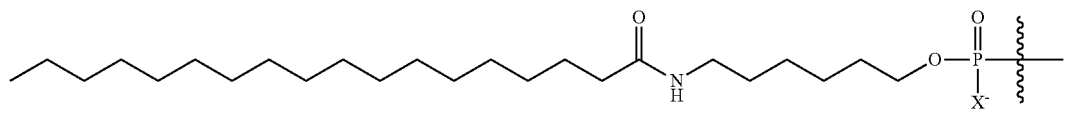

X = O or S

Mod016 (with —C(O)— connecting to —NH— of L001) and Oleic acid

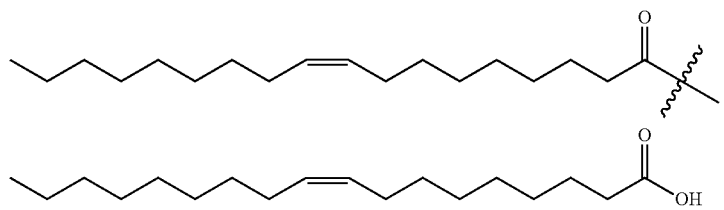

Mod016L001 (with PO or PS connecting to 5'—O— of oligonucleotide chain)

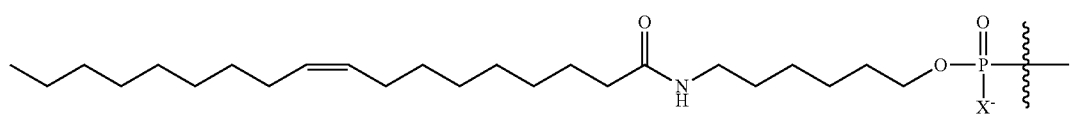

X = O or S

Mod017 (with —C(O)— connecting to —NH— of L001) and Linoleic acid

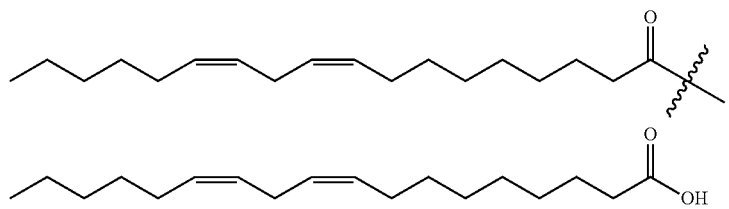

Mod017L001 (with PO or PS connecting to 5'—O— of oligonucleotide chain)

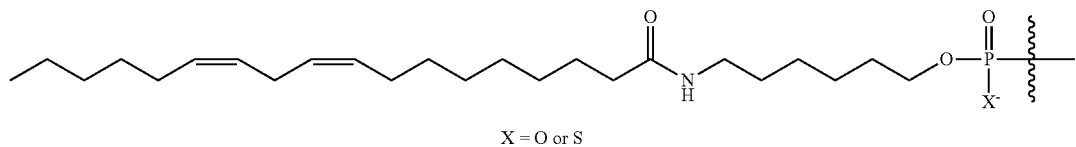

X = O or S

Mod018 (with —C(O)— connecting to —NH— of L001) and alpha-Linoleneic acid

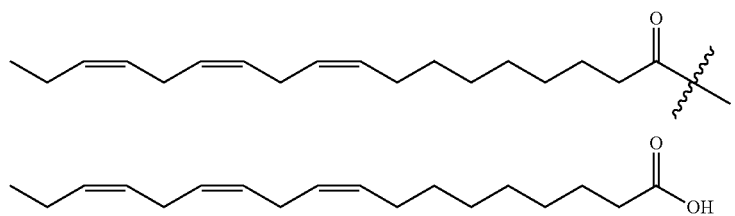

Mod018L001 (with PO or PS connecting to 5'—O— of oligonucleotide chain)

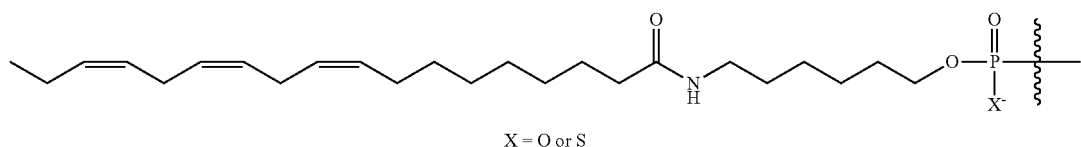

X = O or S

Mod019 (with —C(O)— connecting to —NH— of L001) and gamma-Linoleneic acid

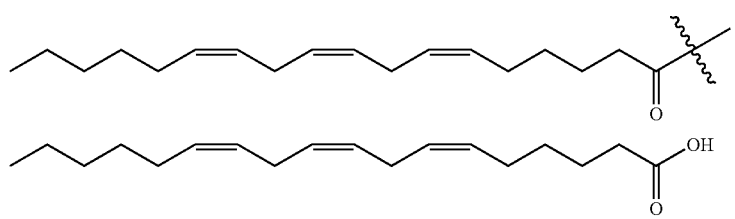

Mod019L001 (with PO or PS connecting to 5'—O— of oligonucleotide chain)

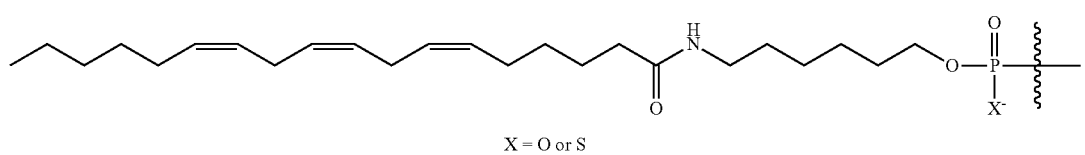

X = O or S

Mod020 (with —C(O)— connecting to —NH— of L001) and Turbinaric acid

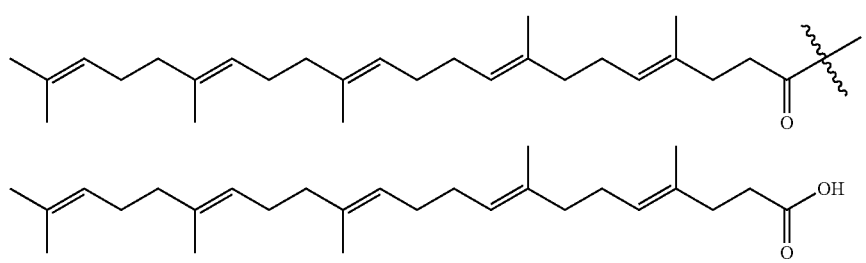

Mod020L001 (with PO or PS connecting to 5'—O— of oligonucleotide chain)

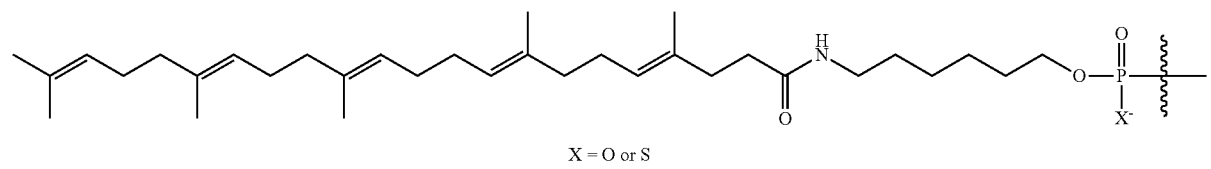

X = O or S

Mod021L001 (with PO or PS connecting to 5'—O— of oligonucleotide chain) and alcohol
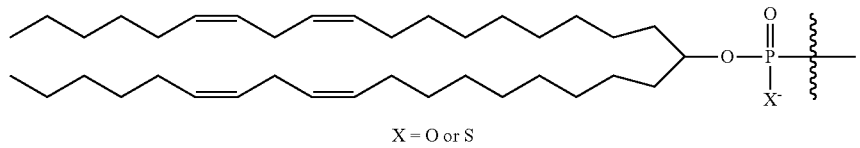
X = O or S
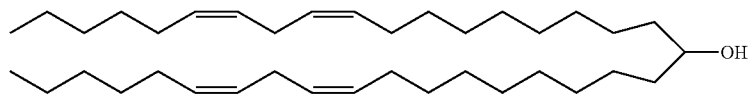
Mod024 (with —C(O)— connecting to —NH— of L001) and acid
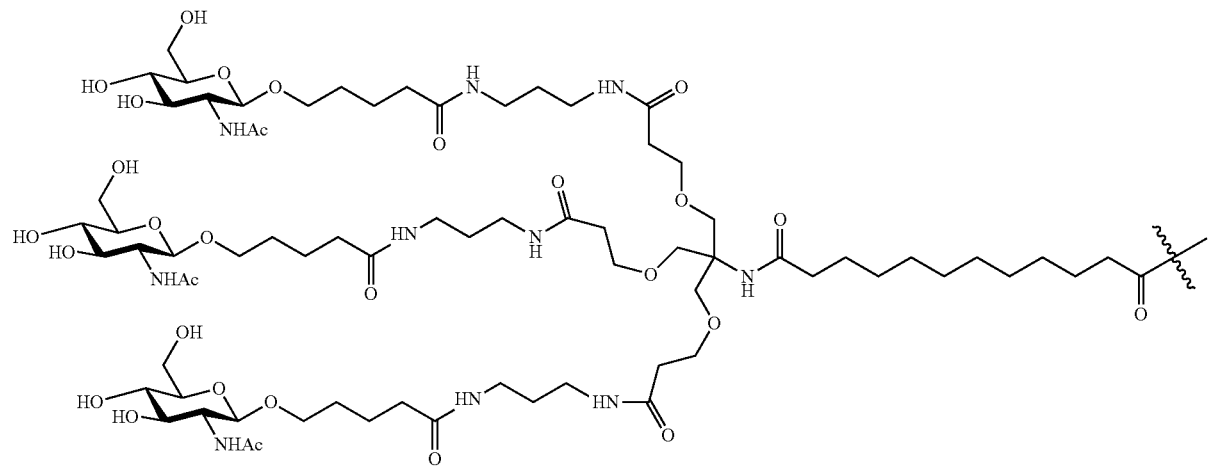
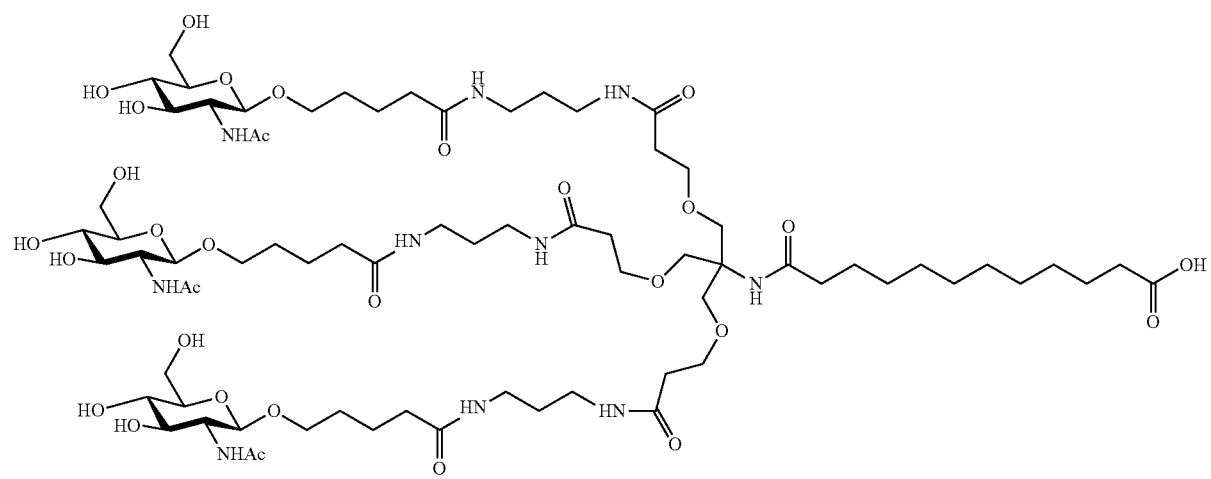

Mod024L001 (with PO or PS connecting to 5'—O— of oligonucleotide chain)
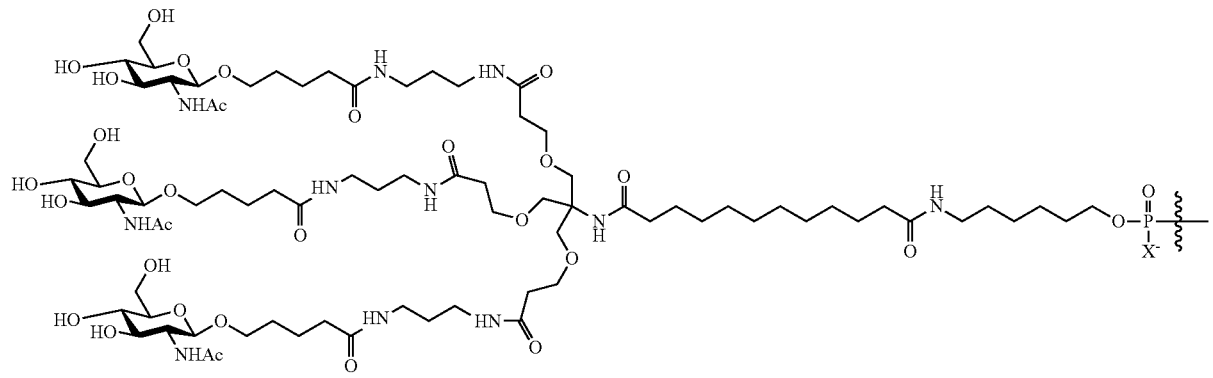
X = O or S
Mod025 (with —C(O)— connecting to —NH— of L001) and acid
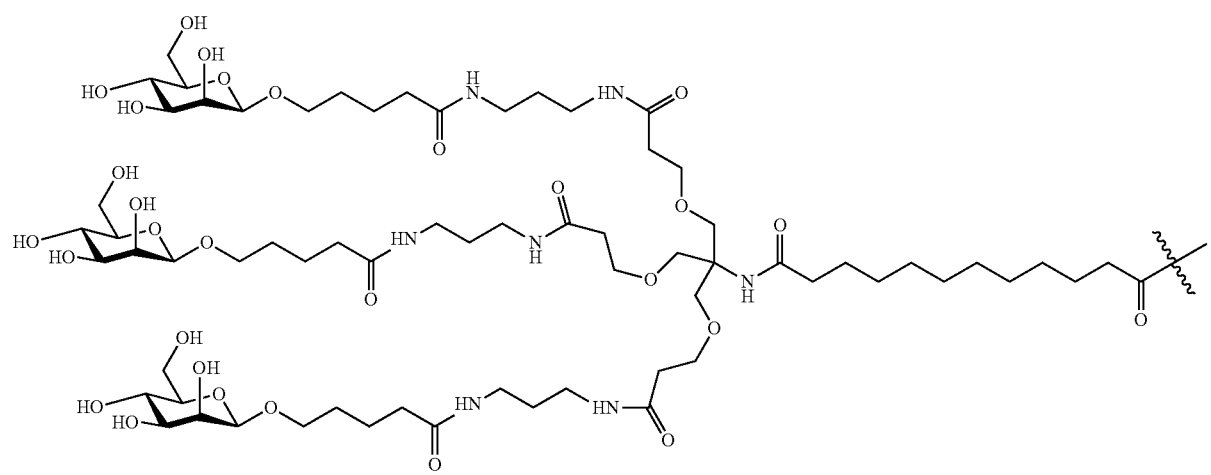
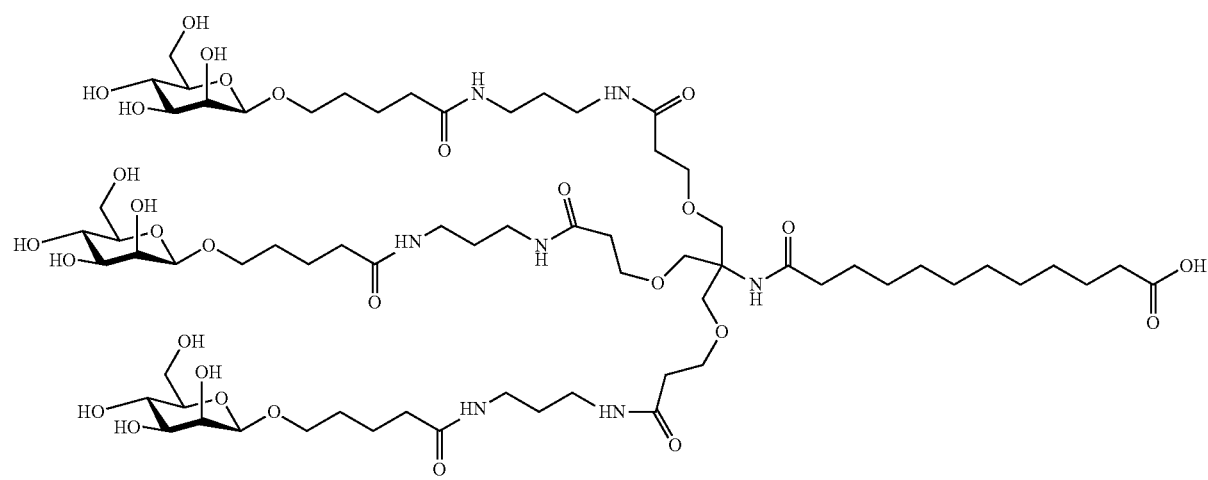

-continued
Mod025L001 (with PO or PS connecting to 5'—O— of oligonucleotide chain)
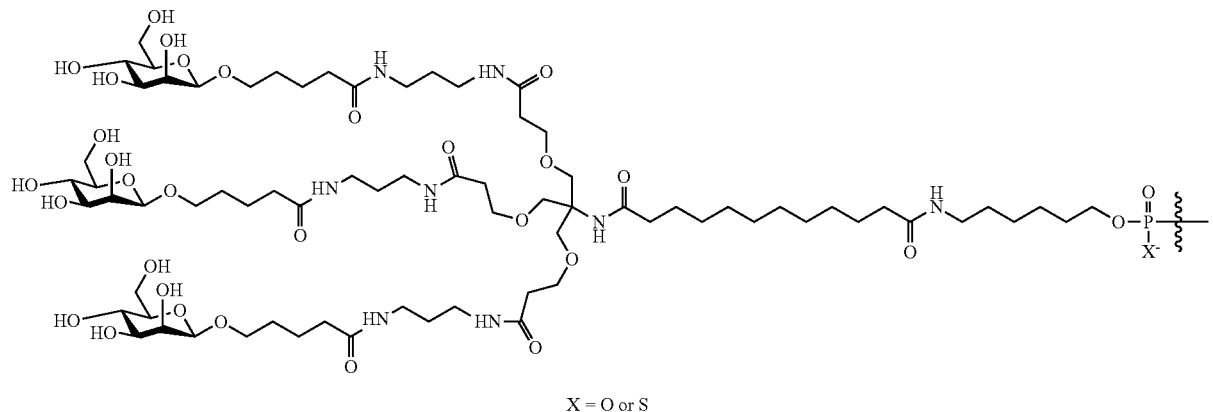
X = O or S
Mod026 (with —C(O)— connecting to —NH— of L001) and acid
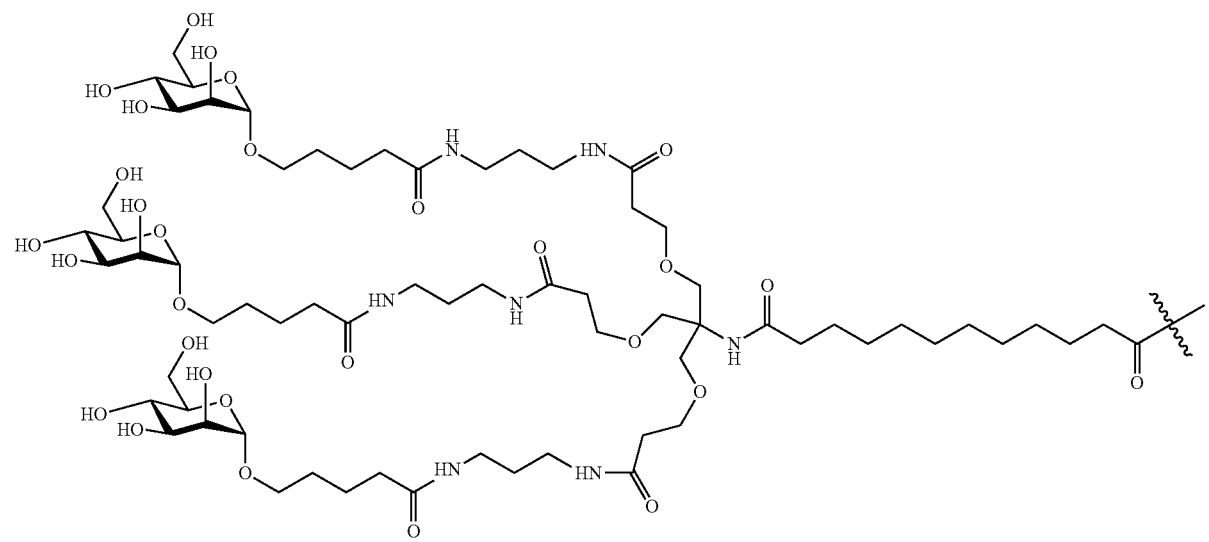
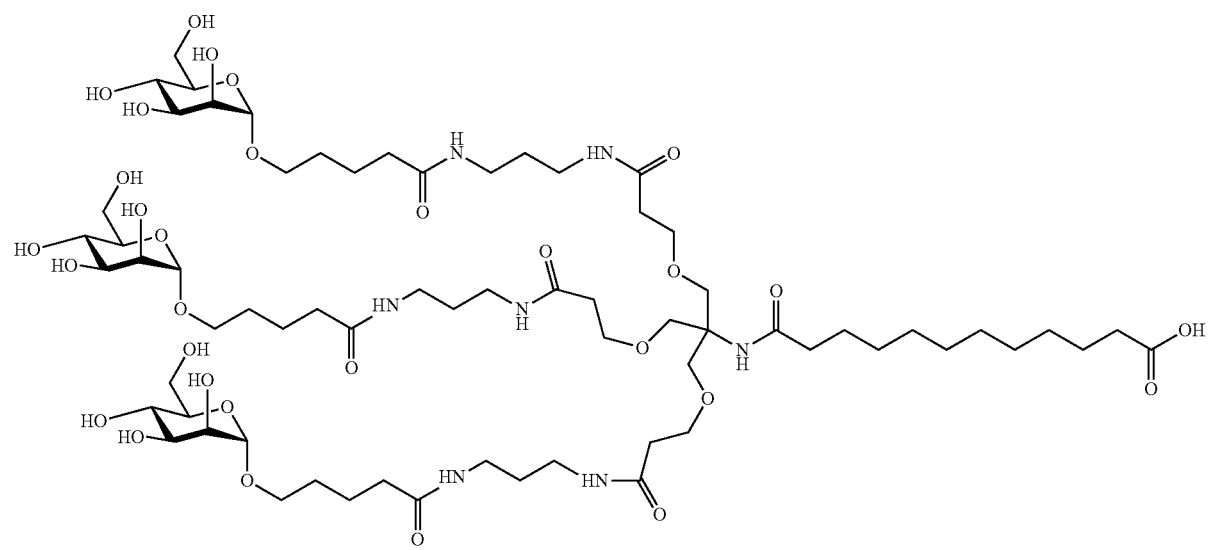

Mod026L001 (with PO or PS connecting to 5'—O— of oligonucleotide chain)
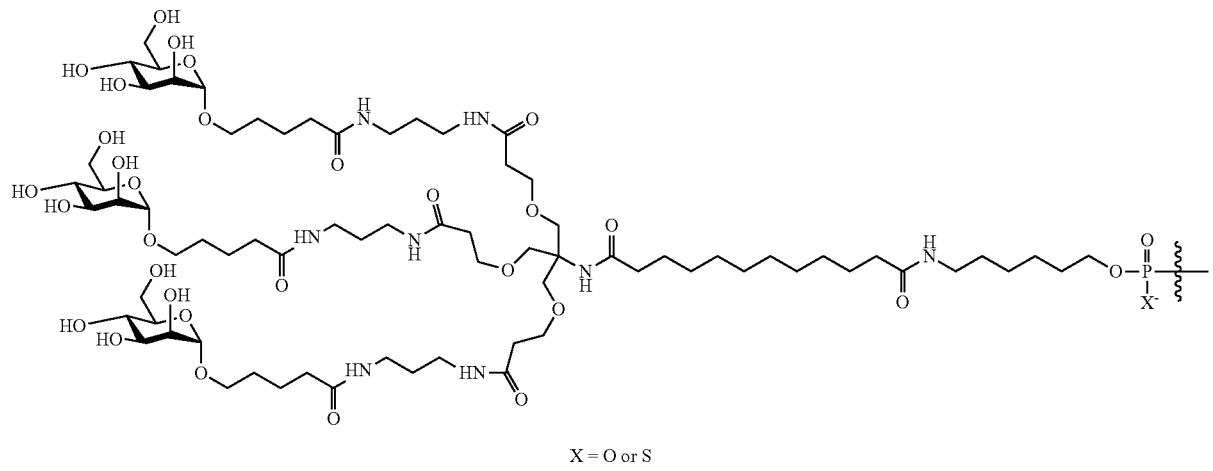
X = O or S
Mod027 (with —C(O)— connecting to —NH— of L001) and acid
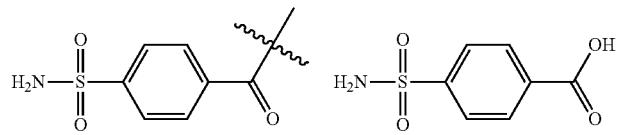
Mod027L001 (with PO or PS connecting to 5'—O— of oligonucleotide chain)
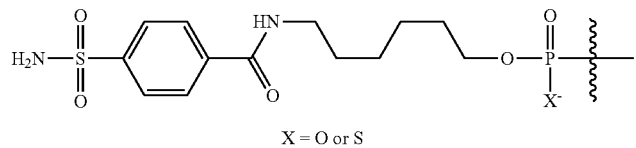
X = O or S
Mod028 (with —C(O)— connecting to —NH— of L001) and acid
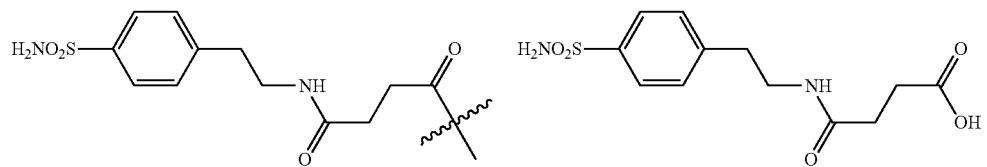
Mod028L001 (with PO or PS connecting to 5'—O— of oligonucleotide chain)
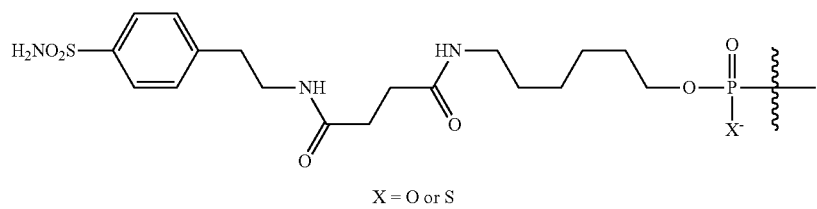
X = O or S Mod029 (with —C(O)— connecting to —NH— of L001) and acid
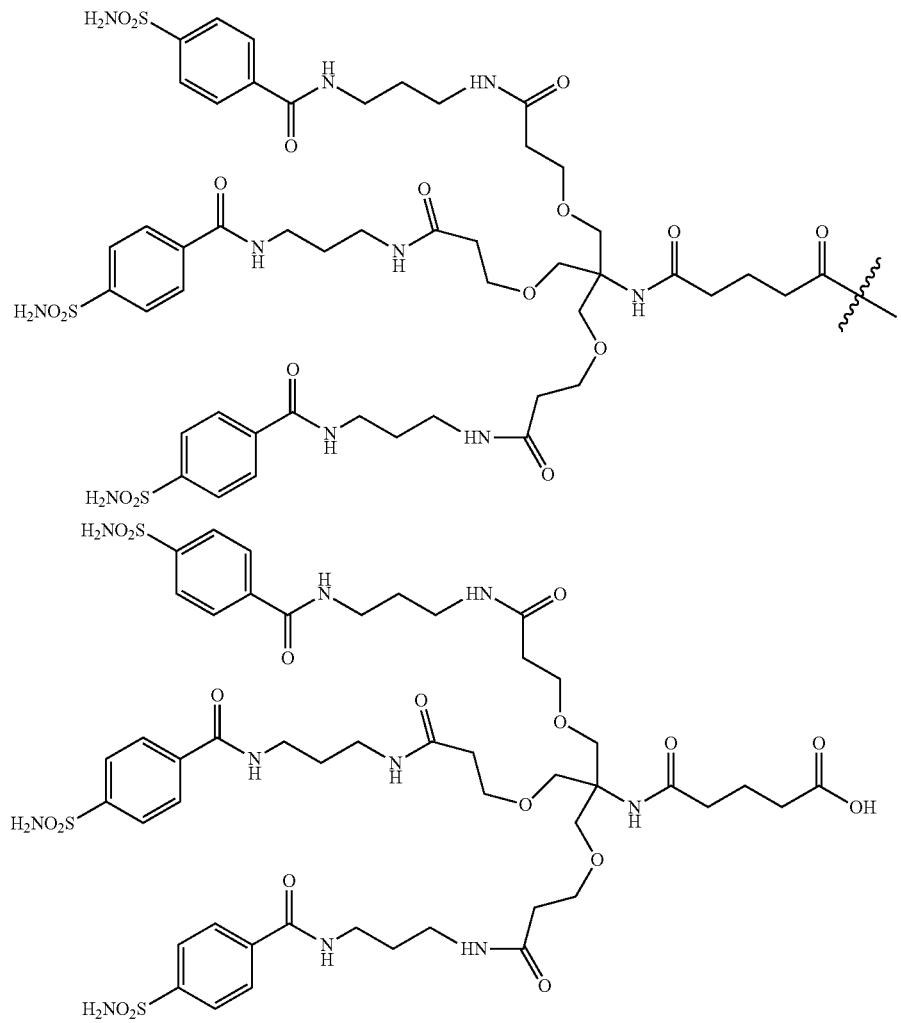
Mod029L001 (with PO or PS connecting to 5'—O— of oligonucleotide chain)
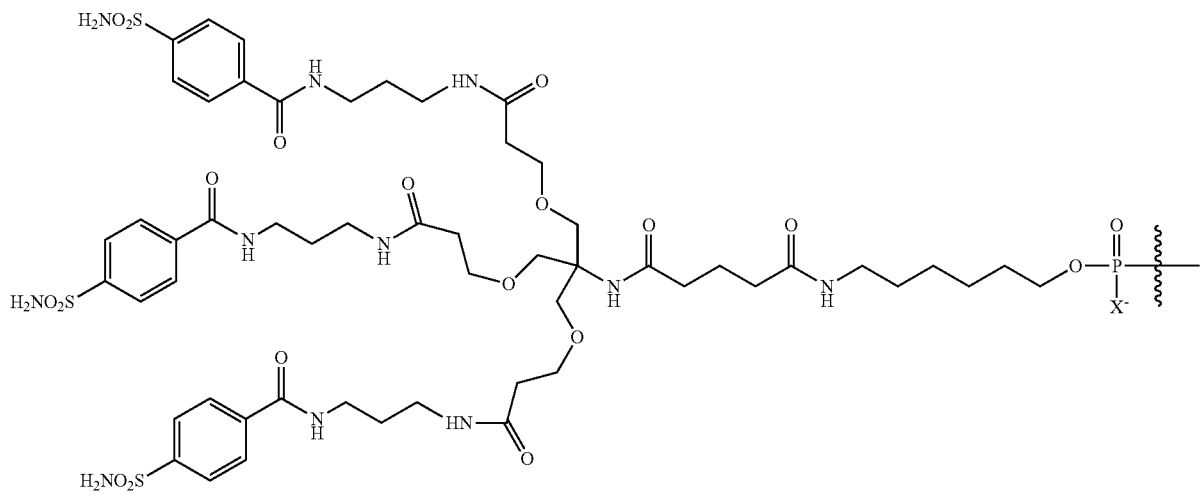
X = O or S -continued Mod030L001 (with PO or PS connecting to 5'—O— of oligonucleotide chain) and Lauryl alcohol

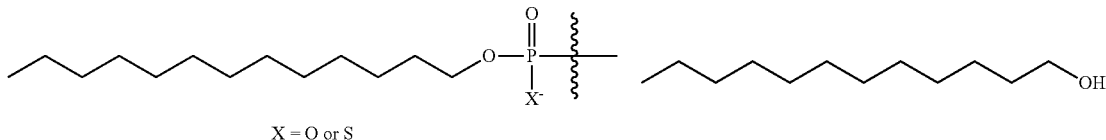

X = O or S

Mod031L001 (with PO or PS connecting to 5'—O— of oligonucleotide chain) and Myristyl alcohol

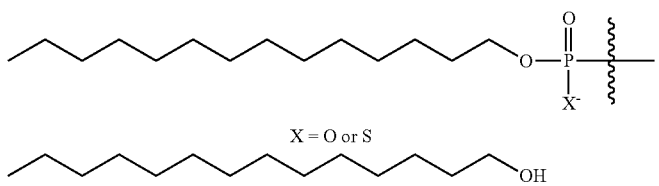

X = O or S

Mod032L001 (with PO or PS connecting to 5'—O— of oligonucleotide chain) and Palmityl alcohol

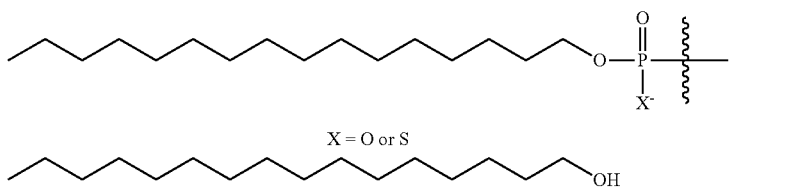

X = O or S

Mod032L001 (with PO or PS connecting to 5'—O— of oligonucleotide chain) and Stearyl alcohol

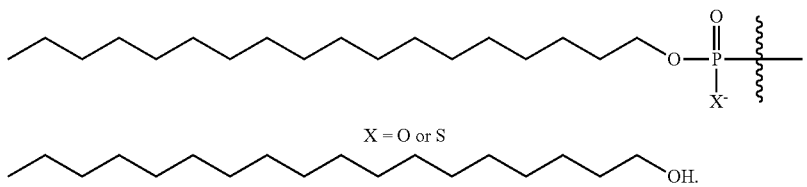

X = O or S

Applicant notes that presented above in the Table are example ways of presenting structures of provided oligonucleotides, for example, WV-3546 (Mod 020L001 fU*SfC *SfA*SfA*SfG*SfG*Sm AfA*SmGmA*SfU*SmGmGfC *SfA*SfU*SfU *SfU*SfC*SfU) (SEQ ID NO: 1517) can be presented as a lipid moiety in many different ways, wherein in each way the combination of the units provides the same oligonucleotide. For example, WV-3546, can be considered to have a structure of $A^c$-[-$L^{LD}$-($R^{LD}$)$_a$]b, wherein a is 1, b is 1, and have a lipid moiety $R^{LD}$ of

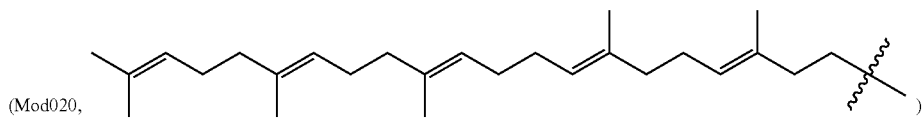 [SMILES: *CC/C(C)=C/CC/C(C)=C/CC/C=C(\C)CC/C=C(\C)CCC=C(C)C]

(Mod020, connected via —C(O)—(OOSSSSSSOSOSSOOSSSSSS) to the —NH— of —NH—(CH$_2$)$_6$— wherein the

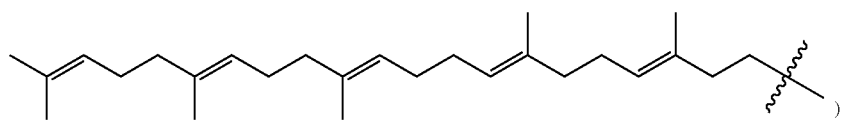 [SMILES: *CC/C(C)=C/CC/C(C)=C/CC/C=C(\C)CC/C=C(\C)CCC=C(C)C]

—(CH$_2$)$_6$— is connected to the 5'-end of the oligonucleotide chain via a phosphodiester linkage (OOSSSSSSOSOS-SOOSSSSSS). One having ordinary skill in the art understands that a provided oligonucleotide can be presented as combinations of lipid, linker and oligonucleotide chain units connected to its oligonucleotide chain ($A^c$) portion through a linker $L^{LD}$ of —C(O)—NH—(CH$_2$)$_6$—OP(=O)(OH)—O—, wherein —C(O)— is connected to $R^{LD}$, and —O— is connected to $A^c$ (as 5'-O— of the oligonucleotide chain); one of the many alternative ways is that $R^{LD}$ is

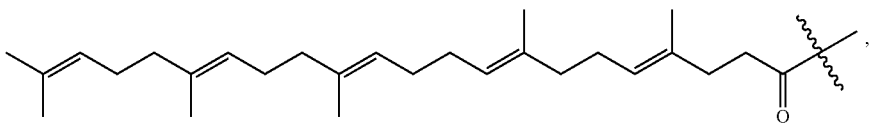 [SMILES: *C(=O)CC/C(C)=C/CC/C(C)=C/CC/C=C(\C)CC/C=C(\C)CCC=C(C)C]

and $L^{LD}$ is —NH—$(CH_2)_6$—OP(=O)(OH)—O—, wherein —NH— is connected to $R^{LD}$, and —O— is connected to $A^c$ (as 5'-O— of the oligonucleotide chain).

Oligonucleotides were prepared and characterized using a variety of methods in accordance of the present disclosure. Example MS data are presented below:

TABLE 6

Example MS data.

| WAVE ID | Calculated Mass | Found Mass |
|---|---|---|
| WV-2531 | 6767.90000 | 6766.3 |
| WV-3152 | 6743.77000 | 6742.8 |
| WV-3472 | 6720.78472 | 6720.8 |
| WV-3473 | 6732.82024 | 6735 |
| WV-3507 | 6716.75464 | 6717.3 |
| WV-3508 | 6704.71912 | 6706 |
| WV-3509 | 6716.75464 | 6718 |
| WV-3510 | 6716.75464 | 6717.6 |
| WV-3511 | 6728.79016 | 6731 |
| WV-3512 | 6700.68904 | 6702 |
| WV-3513 | 6712.72456 | 6713 |
| WV-3514 | 6688.65352 | 6688.9 |
| WV-3515 | 6700.68904 | 6701.2 |
| WV-3545 | 7178.43622 | 7178 |
| WV-3546 | 7294.59604 | 7295 |

*Calculated and found mass data of WV-2531 and WV-3152 are for sodium adducts.

In some embodiments, the present disclosure provides CpG oligonucleotides and oligonucleotide compositions that are chirally controlled. For instance, in some embodiments, a provided composition contains predetermined levels of one or more individual CpG oligonucleotide types, wherein a CpG oligonucleotide type is defined by: 1) base sequence; 2) pattern of backbone linkages; 3) pattern of backbone chiral centers; and 4) pattern of backbone P-modifications. In some embodiments, a particular CpG oligonucleotide type can be defined by 1A) base identity; 1B) pattern of base modification; 1C) pattern of sugar modification; 2) pattern of backbone linkages; 3) pattern of backbone chiral centers; and 4) pattern of backbone P-modifications. In some embodiments, CpG oligonucleotides of the same CpG oligonucleotide type are identical.

In some embodiments, a provided CpG oligonucleotide is a hemimer. In some embodiments, a hemimer is a CpG oligonucleotide wherein the 5'-end or the 3'-end has a sequence that possesses a structure feature that the rest of the CpG oligonucleotide does not have. In some embodiments, the 5'-end or the 3'-end has or comprises 2 to 20 nucleotides. In some embodiments, a structural feature is a base modification. In some embodiments, a structural feature is a sugar modification. In some embodiments, a structural feature is a P-modification. In some embodiments, a structural feature is stereochemistry of the chiral internucleotidic linkage. In some embodiments, a structural feature is or comprises a base modification, a sugar modification, a P-modification, or stereochemistry of the chiral internucleotidic linkage, or combinations thereof. In some embodiments, a hemimer is a CpG oligonucleotide in which each sugar moiety of the 5'-end sequence shares a common modification. In some embodiments, a hemimer is a CpG oligonucleotide in which each sugar moiety of the 3'-end sequence shares a common modification. In some embodiments, a common sugar modification of the 5' or 3' end sequence is not shared by any other sugar moieties in the CpG oligonucleotide. In some embodiments, an example hemimer is a CpG oligonucleotide comprising a sequence of substituted or unsubstituted 2'-O-alkyl sugar modified nucleosides, bicyclic sugar modified nucleosides, β-D-ribonucleosides or β-D-deoxyribonucleosides (for example 2'-MOE modified nucleosides, and LNA™ or ENA™ bicyclic sugar modified nucleosides) at one terminus and a sequence of nucleosides with a different sugar moiety (such as a substituted or unsubstituted 2'-O-alkyl sugar modified nucleosides, bicyclic sugar modified nucleosides or natural ones) at the other terminus. In some embodiments, a provided CpG oligonucleotide is a combination of one or more of unimer, altmer, blockmer, gapmer, hemimer and skipmer. In some embodiments, a provided CpG oligonucleotide is a combination of one or more of unimer, altmer, blockmer, gapmer, and skipmer. For instance, in some embodiments, a provided CpG oligonucleotide is both an altmer and a gapmer. In some embodiments, a provided nucleotide is both a gapmer and a skipmer. One of skill in the chemical and synthetic arts will recognize that numerous other combinations of patterns are available and are limited only by the commercial availability and/or synthetic accessibility of constituent parts required to synthesize a provided CpG oligonucleotide in accordance with methods of the present disclosure. In some embodiments, a hemimer structure provides advantageous benefits. In some embodiments, provided CpG oligonucleotides are 5'-hemimers that comprises modified sugar moieties in a 5'-end sequence. In some embodiments, provided CpG oligonucleotides are 5'-hemimers that comprises modified T-sugar moieties in a 5'-end sequence.

In some embodiments, a provided CpG oligonucleotide comprises one or more optionally substituted nucleotides. In some embodiments, a provided CpG oligonucleotide comprises one or more modified nucleotides. In some embodiments, a provided CpG oligonucleotide comprises one or more optionally substituted nucleosides. In some embodiments, a provided CpG oligonucleotide comprises one or more modified nucleosides. In some embodiments, a provided CpG oligonucleotide comprises one or more optionally substituted LNAs.

In some embodiments, a provided CpG oligonucleotide comprises one or more optionally substituted nucleobases. In some embodiments, a provided CpG oligonucleotide comprises one or more optionally substituted natural nucleobases. In some embodiments, a provided CpG oligonucleotide comprises one or more optionally substituted modified nucleobases. In some embodiments, a provided CpG oligonucleotide comprises one or more 5-methylcytidine; 5-hydroxymethylcytidine, 5-formylcytosine, or 5-carboxylcytosine. In some embodiments, a provided CpG oligonucleotide comprises one or more 5-methylcytidine.

In some embodiments, a provided CpG oligonucleotide comprises one or more optionally substituted sugars. In some embodiments, a provided CpG oligonucleotide comprises one or more optionally substituted sugars found in naturally occurring DNA and RNA. In some embodiments, a provided CpG oligonucleotide comprises one or more optionally substituted ribose or deoxyribose. In some embodiments, a provided CpG oligonucleotide comprises one or more optionally substituted ribose or deoxyribose, wherein one or more hydroxyl groups of the ribose or deoxyribose moiety is optionally and independently replaced by halogen, R', —N(R')$_2$, —OR', or —SR', wherein each R' is independently as defined above and described herein. In some embodiments, a provided CpG oligonucleotide comprises one or more optionally substituted deoxyribose, wherein the T position of the deoxyribose is optionally and independently substituted with halogen, R', —N(R')$_2$, —OR', or —SR', wherein each R' is independently as defined above and described herein. In some embodiments, a provided CpG oligonucleotide comprises one or more optionally substituted deoxyribose, wherein the T position of the deoxyribose is optionally and independently substituted with halogen. In some embodiments, a provided CpG oligonucleotide comprises one or more optionally substituted deoxyribose, wherein the T position of the deoxyribose is optionally and independently substituted with one or more —F. halogen. In some embodiments, a provided CpG oligonucleotide comprises one or more optionally substituted deoxyribose, wherein the T position of the deoxyribose is optionally and independently substituted with —OR', wherein each R' is independently as defined above and described herein. In some embodiments, a provided CpG oligonucleotide comprises one or more optionally substituted deoxyribose, wherein the T position of the deoxyribose is optionally and independently substituted with —OR', wherein each R' is independently an optionally substituted $C_1$-$C_6$ aliphatic. In some embodiments, a provided CpG oligonucleotide comprises one or more optionally substituted deoxyribose, wherein the T position of the deoxyribose is optionally and independently substituted with —OR', wherein each R' is independently an optionally substituted $C_1$-$C_6$ alkyl. In some embodiments, a provided CpG oligonucleotide comprises one or more optionally substituted deoxyribose, wherein the T position of the deoxyribose is optionally and independently substituted with —OMe. In some embodiments, a provided CpG oligonucleotide comprises one or more optionally substituted deoxyribose, wherein the T position of the deoxyribose is optionally and independently substituted with —O-methoxyethyl.

In some embodiments, a provided CpG oligonucleotide is single-stranded CpG oligonucleotide.

In some embodiments, a provided CpG oligonucleotide is a hybridized oligonucleotide strand. In certain embodiments, a provided CpG oligonucleotide is a partially hybridized CpG oligonucleotide strand. In certain embodiments, a provided CpG oligonucleotide is a completely hybridized CpG oligonucleotide strand. In certain embodiments, a provided CpG oligonucleotide is a double-stranded CpG oligonucleotide. In certain embodiments, a provided CpG oligonucleotide is a triple-stranded CpG oligonucleotide (e.g., a triplex).

In some embodiments, a provided CpG oligonucleotide is chimeric. For example, in some embodiments, a provided CpG oligonucleotide is DNA-RNA chimera, DNA-LNA chimera, etc. In some embodiments, one or both wings can comprise LNA, and the core can comprise phosphorothioate. In some embodiments, the CpG oligonucleotide can comprise a format (e.g., architecture) of wing-core-wing which is LNA-phosphorothioate-LNA.

In some embodiments, any one of the structures comprising a CpG oligonucleotide depicted in WO2012/030683 can be modified in accordance with methods of the present disclosure to provide chirally controlled variants thereof. For example, in some embodiments the chirally controlled variants comprise a stereochemical modification at any one or more of the linkage phosphorus and/or a P-modification at any one or more of the linkage phosphorus. For example, in some embodiments, a particular nucleotide unit of a CpG oligonucleotide of WO2012/030683 is preselected to be stereochemically modified at the linkage phosphorus of that nucleotide unit and/or P-modified at the linkage phosphorus of that nucleotide unit.

In some embodiments, a provided CpG oligonucleotide is a therapeutic agent.

In some embodiments, a provided CpG oligonucleotide is an antisense oligonucleotide.

In some embodiments, a provided CpG oligonucleotide is an antigene oligonucleotide.

In some embodiments, a provided CpG oligonucleotide is a decoy oligonucleotide.

In some embodiments, a provided CpG oligonucleotide is part of a DNA vaccine.

In some embodiments, a provided CpG oligonucleotide is an immunomodulatory oligonucleotide, e.g., immunostimulatory oligonucleotide and immunoinhibitory oligonucleotide.

In some embodiments, a provided CpG oligonucleotide is an adjuvant.

In some embodiments, a provided CpG oligonucleotide is an aptamer.

In some embodiments, a provided CpG oligonucleotide is a ribozyme.

In some embodiments, a provided CpG oligonucleotide is a deoxyribozyme (DNAzymes or DNA enzymes).

In some embodiments, a provided CpG oligonucleotide is an siRNA.

In some embodiments, a provided CpG oligonucleotide is a microRNA, or miRNA.

In some embodiments, a provided CpG oligonucleotide is a ncRNA (non-coding RNAs), including a long non-coding RNA (lncRNA) and a small non-coding RNA, such as piwi-interacting RNA (piRNA).

In some embodiments, a provided CpG oligonucleotide is complementary to a structural RNA, e.g., tRNA.

In some embodiments, a provided CpG oligonucleotide is a nucleic acid analog, e.g., GNA, LNA, PNA, TNA and Morpholino.

In some embodiments, a provided CpG oligonucleotide is a P-modified prodrug.

In some embodiments, a provided CpG oligonucleotide is a primer. In some embodiments, a primers is for use in polymerase-based chain reactions (i.e., PCR) to amplify nucleic acids. In some embodiments, a primer is for use in any known variations of PCR, such as reverse transcription PCR (RT-PCR) and real-time PCR.

In some embodiments, a provided CpG oligonucleotide is characterized as having the ability to modulate RNase H activation. For example, in some embodiments, RNase H activation is modulated by the presence of stereocontrolled phosphorothioate nucleic acid analogs, with natural DNA/RNA being more or equally susceptible than the Rp stereoisomer, which in turn is more susceptible than the corresponding Sp stereoisomer.

In some embodiments, a provided CpG oligonucleotide is characterized as having the ability to indirectly or directly increase or decrease activity of a protein or inhibition or promotion of the expression of a protein. In some embodiments, a provided CpG oligonucleotide is characterized in that it is useful in the control of cell proliferation, viral replication, and/or any other cell signaling process.

In some embodiments, a provided CpG oligonucleotide is from about 2 to about 200 nucleotide units in length. In some embodiments, a provided CpG oligonucleotide is from about 2 to about 180 nucleotide units in length. In some embodiments, a provided CpG oligonucleotide is from about 2 to about 160 nucleotide units in length. In some embodiments, a provided CpG oligonucleotide is from about 2 to about 140 nucleotide units in length. In some embodiments, a provided CpG oligonucleotide is from about 2 to about 120 nucleotide units in length. In some embodiments, a provided CpG oligonucleotide is from about 2 to about 100 nucleotide units in length. In some embodiments, a provided CpG oligonucleotide is from about 2 to about 90 nucleotide units in length. In some embodiments, a provided CpG oligonucleotide is from about 2 to about 80 nucleotide units in length. In some embodiments, a provided CpG oligonucleotide is from about 2 to about 70 nucleotide units in length. In some embodiments, a provided CpG oligonucleotide is from about 2 to about 60 nucleotide units in length. In some embodiments, a provided CpG oligonucleotide is from about 2 to about 50 nucleotide units in length. In some embodiments, a provided CpG oligonucleotide is from about 2 to about 40 nucleotide units in length. In some embodiments, a provided CpG oligonucleotide is from about 2 to about 30 nucleotide units in length. In some embodiments, a provided CpG oligonucleotide is from about 2 to about 29 nucleotide units in length. In some embodiments, a provided CpG oligonucleotide is from about 2 to about 28 nucleotide units in length. In some embodiments, a provided CpG oligonucleotide is from about 2 to about 27 nucleotide units in length. In some embodiments, a provided CpG oligonucleotide is from about 2 to about 26 nucleotide units in length. In some embodiments, a provided CpG oligonucleotide is from about 2 to about 25 nucleotide units in length. In some embodiments, a provided CpG oligonucleotide is from about 2 to about 24 nucleotide units in length. In some embodiments, a provided CpG oligonucleotide is from about 2 to about 23 nucleotide units in length. In some embodiments, a provided CpG oligonucleotide is from about 2 to about 22 nucleotide units in length. In some embodiments, a provided CpG oligonucleotide is from about 2 to about 21 nucleotide units in length. In some embodiments, a provided CpG oligonucleotide is from about 2 to about 20 nucleotide units in length.

In some embodiments, a provided CpG oligonucleotide is from about 4 to about 200 nucleotide units in length. In some embodiments, a provided CpG oligonucleotide is from about 4 to about 180 nucleotide units in length. In some embodiments, a provided CpG oligonucleotide is from about 4 to about 160 nucleotide units in length. In some embodiments, a provided CpG oligonucleotide is from about 4 to about 140 nucleotide units in length. In some embodiments, a provided CpG oligonucleotide is from about 4 to about 120 nucleotide units in length. In some embodiments, a provided CpG oligonucleotide is from about 4 to about 100 nucleotide units in length. In some embodiments, a provided CpG oligonucleotide is from about 4 to about 90 nucleotide units in length. In some embodiments, a provided CpG oligonucleotide is from about 4 to about 80 nucleotide units in length. In some embodiments, a provided CpG oligonucleotide is from about 4 to about 70 nucleotide units in length. In some embodiments, a provided CpG oligonucleotide is from about 4 to about 60 nucleotide units in length. In some embodiments, a provided CpG oligonucleotide is from about 4 to about 50 nucleotide units in length. In some embodiments, a provided CpG oligonucleotide is from about 4 to about 40 nucleotide units in length. In some embodiments, a provided CpG oligonucleotide is from about 4 to about 30 nucleotide units in length. In some embodiments, a provided CpG oligonucleotide is from about 4 to about 29 nucleotide units in length. In some embodiments, a provided CpG oligonucleotide is from about 4 to about 28 nucleotide units in length. In some embodiments, a provided CpG oligonucleotide is from about 4 to about 27 nucleotide units in length. In some embodiments, a provided CpG oligonucleotide is from about 4 to about 26 nucleotide units in length. In some embodiments, a provided CpG oligonucleotide is from about 4 to about 25 nucleotide units in length. In some embodiments, a provided CpG oligonucleotide is from about 4 to about 24 nucleotide units in length. In some embodiments, a provided CpG oligonucleotide is from about 4 to about 23 nucleotide units in length. In some embodiments, a provided CpG oligonucleotide is from about 4 to about 22 nucleotide units in length. In some embodiments, a provided CpG oligonucleotide is from about 4 to about 21 nucleotide units in length. In some embodiments, a provided CpG oligonucleotide is from about 4 to about 20 nucleotide units in length.

In some embodiments, a provided CpG oligonucleotide is from about 5 to about 10 nucleotide units in length. In some embodiments, a provided CpG oligonucleotide is from about 10 to about 30 nucleotide units in length. In some embodiments, a provided CpG oligonucleotide is from about 15 to about 25 nucleotide units in length. In some embodiments, a provided CpG oligonucleotide is from about 5, 6, 7, 8, 9, 10, 11, 12, 13, 14, 15, 16, 17, 18, 19, 20, 21, 22, 23, 24, or 25 nucleotide units in length.

In some embodiments, a CpG oligonucleotide is at least 2 nucleotide units in length. In some embodiments, a CpG oligonucleotide is at least 3 nucleotide units in length. In some embodiments, a CpG oligonucleotide is at least 4 nucleotide units in length. In some embodiments, a CpG oligonucleotide is at least 5 nucleotide units in length. In some embodiments, a CpG oligonucleotide is at least 6 nucleotide units in length. In some embodiments, a CpG oligonucleotide is at least 7 nucleotide units in length. In some embodiments, a CpG oligonucleotide is at least 8 nucleotide units in length. In some embodiments, a CpG oligonucleotide is at least 9 nucleotide units in length. In some embodiments, a CpG oligonucleotide is at least 10 nucleotide units in length. In some embodiments, a CpG oligonucleotide is at least 11 nucleotide units in length. In some embodiments, a CpG oligonucleotide is at least 12 nucleotide units in length. In some embodiments, a CpG oligonucleotide is at least 13 nucleotide units in length. In some embodiments, a CpG oligonucleotide is at least 14 nucleotide units in length. In some embodiments, a CpG oligonucleotide is at least 15 nucleotide units in length. In some embodiments, a CpG oligonucleotide is at least 16 nucleotide units in length. In some embodiments, a CpG oligonucleotide is at least 17 nucleotide units in length. In some embodiments, a CpG oligonucleotide is at least 18 nucleotide units in length. In some embodiments, a CpG oligonucleotide is at least 19 nucleotide units in length. In some embodiments, a CpG oligonucleotide is at least 20 nucleotide units in length. In some embodiments, a CpG oligonucleotide is at least 21 nucleotide units in length. In some embodiments, a CpG oligonucleotide is at least 22 nucleotide units in length. In some embodiments, a CpG oligonucleotide is at least 23 nucleotide units in length. In some embodiments, a CpG oligonucleotide is at least 24 nucleotide units in length. In some embodiments, a CpG oligonucleotide is at least 25 nucleotide units in length. In some other embodiments, a CpG oligonucleotide is at least 30 nucleotide units in length. In some other embodiments, a CpG oligonucleotide is a duplex of complementary strands of at least 18 nucleotide units in length. In some other embodiments, a CpG oligonucleotide is a duplex of complementary strands of at least 21 nucleotide units in length.

In some embodiments, the 5'-end and/or the 3'-end of a provided CpG oligonucleotide is modified. In some embodiments, the 5'-end and/or the 3'-end of a provided CpG oligonucleotide is modified with a terminal cap moiety. Example such modifications, including terminal cap moieties are extensively described herein and in the art, for example but not limited to those described in US Patent Application Publication US 2009/0023675A1.

In some embodiments, CpG oligonucleotides of a CpG oligonucleotide type characterized by 1) a common base sequence and length, 2) a common pattern of backbone linkages, and 3) a common pattern of backbone chiral centers, have the same chemical structure. For example, they have the same base sequence, the same pattern of nucleoside modifications, the same pattern of backbone linkages (i.e., pattern of internucleotidic linkage types, for example, phosphate, phosphorothioate, etc.), the same pattern of backbone chiral centers (i.e. pattern of linkage phosphorus stereochemistry (Rp/Sp)), and the same pattern of backbone phosphorus modifications (e.g., pattern of "—XLR$^1$" groups in formula I).

The present disclosure provides compositions comprising or consisting of a plurality of provided CpG oligonucleotides (e.g., chirally controlled CpG oligonucleotide compositions). In some embodiments, all such provided CpG oligonucleotides are of the same type, i.e., all have the same base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "—XLR$^1$" groups in formula I). In some embodiments, all CpG oligonucleotides of the same type are identical. In many embodiments, however, provided compositions comprise a plurality of CpG oligonucleotides types, typically in pre-determined relative amounts.

In some embodiments, a provided chirally controlled CpG oligonucleotide composition comprises a combination of one or more provided CpG oligonucleotide types. One of skill in the chemical and medicinal arts will recognize that the selection and amount of each of the one or more types of provided CpG oligonucleotides in a provided composition will depend on the intended use of that composition. That is to say, one of skill in the relevant arts would design a provided chirally controlled CpG oligonucleotide composition such that the amounts and types of provided CpG oligonucleotides contained therein cause the composition as a whole to have certain desirable characteristics (e.g., biologically desirable, therapeutically desirable, etc.).

In some embodiments, a provided chirally controlled CpG oligonucleotide composition comprises a combination of two or more provided CpG oligonucleotide types. In some embodiments, a provided chirally controlled CpG oligonucleotide composition comprises a combination of three or more provided CpG oligonucleotide types. In some embodiments, a provided chirally controlled CpG oligonucleotide composition comprises a combination of four or more provided CpG oligonucleotide types. In some embodiments, a provided chirally controlled CpG oligonucleotide composition comprises a combination of five or more provided CpG oligonucleotide types. In some embodiments, a provided chirally controlled CpG oligonucleotide composition comprises a combination of six or more provided CpG oligonucleotide types. In some embodiments, a provided chirally controlled CpG oligonucleotide composition comprises a combination of seven or more provided CpG oligonucleotide types. In some embodiments, a provided chirally controlled CpG oligonucleotide composition comprises a combination of eight or more provided CpG oligonucleotide types. In some embodiments, a provided chirally controlled CpG oligonucleotide composition comprises a combination of nine or more provided CpG oligonucleotide types. In some embodiments, a provided chirally controlled CpG oligonucleotide composition comprises a combination of ten or more provided CpG oligonucleotide types. In some embodiments, a provided chirally controlled CpG oligonucleotide composition comprises a combination of fifteen or more provided CpG oligonucleotide types.

In some embodiments, a provided chirally controlled CpG oligonucleotide composition is a combination of an amount of chirally uniform mipomersen of the Rp configuration and an amount of chirally uniform mipomersen of the Sp configuration.

In some embodiments, a provided chirally controlled CpG oligonucleotide composition is a combination of an amount of chirally uniform mipomersen of the Rp configuration, an amount of chirally uniform mipomersen of the Sp configuration, and an amount of one or more chirally pure mipomersen of a desired diastereomeric form.

In some embodiments, a provided CpG oligonucleotide type is selected from those produced by a method described in WO/2014/012081 and WO/2015/107425, the CpG oligonucleotides, CpG oligonucleotide types, CpG oligonucleotide compositions, and methods thereof of each of which are incorporated herein by reference. In some embodiments, a provided chirally controlled CpG oligonucleotide composition comprises CpG oligonucleotides of a CpG oligonucleotide type selected from those produced by a method described in WO/2014/012081 and WO/2015/107425.

In some embodiments, oligonucleotides, e.g., oligonucleotides of a plurality, oligonucleotides of a type, etc., or provided compounds, are of predetermined levels in compositions. In some embodiments, a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition. In some embodiments, a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that are of or comprise a common base sequence. In some embodiments, all oligonucleotides in a provided composition that are of or comprise a common base sequence are at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition. In some embodiments, a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that are of or comprise a common base sequence, base modification, sugar modification and/or modified internucleotidic linkage. In some embodiments, all oligonucleotides in a provided composition that are of or comprise a common base sequence, base modification, sugar modification and/or modified internucleotidic linkage are at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition. In some embodiments, a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that are of or comprise a common base sequence, pattern of base modification, pattern of sugar modification, and/or pattern of modified internucleotidic linkage. In some embodiments, all oligonucleotides in a provided composition that are of or comprise a common base sequence, pattern of base modification, pattern of sugar modification, and/or pattern of modified internucleotidic linkage are at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition. In some embodiments, a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that share a common base sequence, a common pattern of base modification, a common pattern of sugar modification, and/or a common pattern of modified internucleotidic linkages. In some embodiments, all oligonucleotides in a provided composition that share a common base sequence, a common pattern of base modification, a common pattern of sugar modification, and/or a common pattern of modified internucleotidic linkages are at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition. In some embodiments, a predetermined level is 1-100%. In some embodiments, a predetermined level is at least 1%. In some embodiments, a predetermined level is at least 5%. In some embodiments, a predetermined level is at least 10%. In some embodiments, a predetermined level is at least 20%. In some embodiments, a predetermined level is at least 30%. In some embodiments, a predetermined level is at least 40%. In some embodiments, a predetermined level is at least 50%. In some embodiments, a predetermined level is at least 60%. In some embodiments, a predetermined level is at least 10%. In some embodiments, a predetermined level is at least 70%. In some embodiments, a predetermined level is at least 80%. In some embodiments, a predetermined level is at least 90%. In some embodiments, a predetermined level is at least $5*(\frac{1}{2}^g)$, wherein g is the number of chirally controlled internucleotidic linkages. In some embodiments, a predetermined level is at least $10*(\frac{1}{2}^g)$, wherein g is the number of chirally controlled internucleotidic linkages. In some embodiments, a predetermined level is at least $100*(\frac{1}{2}^g)$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.85)^g$, wherein g is the number of chirally controlled internucleotidic linkages. In some embodiments, a predetermined level is at least $(0.90)^g$, wherein g is the number of chirally controlled internucleotidic linkages. In some embodiments, a predetermined level is at least $(0.95)^g$, wherein g is the number of chirally controlled internucleotidic linkages. In some embodiments, a predetermined level is at least $(0.96)^g$, wherein g is the number of chirally controlled internucleotidic linkages. In some embodiments, a predetermined level is at least $(0.97)^g$, wherein g is the number of chirally controlled internucleotidic linkages. In some embodiments, a predetermined level is at least $(0.98)^g$, wherein g is the number of chirally controlled internucleotidic linkages. In some embodiments, a predetermined level is at least $(0.99)^g$, wherein g is the number of chirally controlled internucleotidic linkages. In some embodiments, to determine level of oligonucleotides having g chirally controlled internucleotidic linkages in a composition, product of diastereopurity of each of the g chirally controlled internucleotidic linkages: (diastereopurity of chirally controlled internucleotidic linkage 1)*(diastereopurity of chirally controlled internucleotidic linkage 2)* . . . *(diastereopurity of chirally controlled internucleotidic linkage g) is utilized as the level, wherein diastereopurity of each chirally controlled internucleotidic linkage is independently represented by diastereopurity of a dimer comprising the same internucleotidic linkage and nucleosides flanking the internucleotidic linkage and prepared under comparable methods as the oligonucleotides (e.g., comparable or preferably identical oligonucleotide preparation cycles, including comparable or preferably identical reagents and reaction conditions). In some embodiments, levels of oligonucleotides and/or diastereopurity can be determined by analytical methods, e.g., chromatographic, spectrometric, spectroscopic methods or any combinations thereof.

In some embodiments, provided oligonucleotides may exist as salts, for example, provided oligonucleotides may exist as metal and/or ammonium ($-N(R)_3^+$) salts in weakly acidic, neutral or basic aqueous solutions, etc. In some embodiments, a salt is a pharmaceutically acceptable salt. In some embodiments, a provided salt may be formulated as a solid as tablet, powder, etc. In some embodiments, a salt, e.g., a pharmaceutically acceptable salt, of a provided oligonucleotide comprises two or more cations, which can be the same or different. In some embodiments, in a salt e.g., a pharmaceutically acceptable salt, all ionizable hydrogen in the acidic groups are replaced with cations. In some embodiments, each hydrogen ion that may be donated to a base (e.g., under conditions of an aqueous solution, a pharmaceutical composition, etc.) is replaced by a non-H$^+$ cation. For example, in some embodiments, a pharmaceutically acceptable salt of an oligonucleotide is an all-metal ion salt, wherein each hydrogen ion (for example, of —OH, —SH, etc.) of each linkage (e.g., a natural phosphate linkage, a phosphorothioate diester linkage, etc.) is replaced by a metal ion. In some embodiments, a provided salt is an all-sodium salt. In some embodiments, a provided pharmaceutically acceptable salt is an all-sodium salt. For example, a sodium salt of WV-3473 containing 19 Na$^+$; a sodium salt of WV-3545 containing 20 Na$^+$; etc. In some embodiments, a provided salt is an all-sodium salt, wherein each linkage which is a natural phosphate linkage (acid form —O—P(O)(OH)—O—), if any, exists as its sodium salt form (—O—P(O)(ONa)—O—), and each linkage which is a phosphorothioate diester linkage (acid form —O—P(O)(SH)—O—), if any, exists as its sodium salt form (—O—P(O)(SNa)—O—).

Certain Biological Applications and Use

As described herein, provided compositions and methods are capable of altering splicing of transcripts. In some embodiments, provided compositions and methods provide improved splicing patterns of transcripts compared to a reference pattern, which is a pattern from a reference condition selected from the group consisting of absence of the composition, presence of a reference composition, and combinations thereof. An improvement can be an improvement of any desired biological functions. In some embodiments, for example, in Duchenne muscular dystrophy (DMD), an improvement is production of an mRNA from which a dystrophin protein with improved biological activities is produced. In some other embodiments, for example, an improvement is down-regulation of STAT3, HNRNPH1 and/or KDR to mitigate tumor progression, malignancy, and angiogenesis through forced splicing-induced nonsense-mediated decay (DSD-NMD).

In some embodiments, the present disclosure provides a method for altering splicing of a target transcript, comprising administering a composition comprising a first plurality of CpG oligonucleotides, wherein the splicing of the target transcript is altered relative to reference conditions selected from the group consisting of absence of the composition, presence of a reference composition, and combinations thereof.

As widely known in the art, many diseases and/or conditions are associated with transcript splicing. For examples, see Garcia-Bianco, et al., Alternative splicing in disease and therapy, Nat. Biotechnol. 2004 May; 22(5):535-46; Wang, et al., Splicing in disease: disruption of the splicing code and the decoding machinery, Nat. Rev. Genet. 2007 October; 8(10):749-61; Havens, et al., Targeting RNA splicing for disease therapy, Wiley Interdiscip. Rev. RNA. 2013 May-June; 4(3):247-66; Perez, et al., Antisense mediated splicing modulation for inherited metabolic diseases: challenges for delivery, Nucleic Acid Ther. 2014 February; 24(1):48-56; etc. Additional example targets and/or disease are described in Xiong, et al., The human splicing code reveals new insights into the genetic determinants of disease, Science. 2015 Jan. 9; 347(6218): 1254806. doi: 10.1126/science.1254806. In some embodiments, the present disclosure provides compositions and methods for treating or preventing diseases, including but not limited to those described in references cited in this disclosure.

In some embodiments, the present disclosure provides a method for treating or preventing a disease, comprising administering to a subject a CpG oligonucleotide composition described herein.

In some embodiments, the present disclosure provides a method for treating or preventing a disease, comprising administering to a subject a CpG oligonucleotide composition comprising a first plurality of CpG oligonucleotides of a particular CpG oligonucleotide type defined by:
1) base sequence;
2) pattern of backbone linkages;
3) pattern of backbone chiral centers; and
4) pattern of backbone phosphorus modifications, which composition is chirally controlled in that it is enriched, relative to a substantially racemic preparation of CpG oligonucleotides having the same base sequence, for CpG oligonucleotides of the particular CpG oligonucleotide type, wherein:

the CpG oligonucleotide composition being characterized in that, when it is contacted with the transcript in a transcript splicing system, splicing of the transcript is altered relative to that observed under reference conditions selected from the group consisting of absence of the composition, presence of a reference composition, and combinations thereof.

In some embodiments, a disease is one in which, after administering a provided composition, one or more spliced transcripts repair, a gene is effectively knockdown by altering splicing of the gene transcript.

In some embodiments, a disease is Duchenne muscular dystrophy. In some embodiments, a disease is spinal muscular atrophy. In some embodiments, a disease is cancer.

In some embodiments, the present disclosure provides a method of treating a disease by administering a composition comprising a first plurality of CpG oligonucleotides sharing a common base sequence comprising a common base sequence, which nucleotide sequence is complementary to a target sequence in the target transcript, the improvement that comprises using as the CpG oligonucleotide composition a stereocontrolled CpG oligonucleotide composition characterized in that when it is contacted with the transcript in a transcript splicing system, splicing of the transcript is altered relative to that observed under reference conditions selected from the group consisting of absence of the composition, presence of a reference composition, and combinations thereof.

In some embodiments, the present disclosure provides a method of treating a disease by administering a composition comprising a first plurality of CpG oligonucleotides sharing a common base sequence comprising a common base sequence, which nucleotide sequence is complementary to a target sequence in the target transcript, the improvement that comprises using as the CpG oligonucleotide composition a stereocontrolled CpG oligonucleotide composition characterized in that when it is contacted with the transcript in a transcript splicing system, splicing of the transcript is altered relative to that observed under reference conditions selected from the group consisting of absence of the composition, presence of a reference composition, and combinations thereof.

In some embodiments, sequence of provide CpG oligonucleotides is or comprises an element that is substantially complementary to a targeted element in a cellular nucleic acid. In some embodiments, a sequence is or comprises a sequence element that is associated with a muscle disease, disorder or condition. In some embodiments, a cellular nucleic acid is or comprises a transcript. In some embodiments, a cellular nucleic acid is or comprises a primary transcript. In some embodiments, a cellular nucleic acid is RNA. In some embodiments, a cellular nucleic acid is pre-mRNA. In some embodiments, a cellular nucleic acid is mRNA. In some embodiments, a cellular nucleic acid is or comprises genomic nucleic acid. In some embodiments, a sequence is or comprises an element that is substantially complementary to a targeted an RNA, and provided CpG oligonucleotides of the sequence provide exon-skipping to form mRNA which are translated into proteins that have improved functions than proteins formed absence of the provided CpG oligonucleotides. In some embodiments, such proteins with improved activities can restore or partially restore one or more muscular functions and can be used for treatment of muscle diseases, disorders and/or conditions. In some embodiments, a provided CpG oligonucleotide composition is administered at a dose and/or frequency lower than that of an otherwise comparable reference CpG oligonucleotide composition with comparable effect in altering the splicing of a target transcript. In some embodiments, a stereocontrolled CpG oligonucleotide composition is administered at a dose and/or frequency lower than that of an otherwise comparable stereorandom reference CpG oligonucleotide composition with comparable effect in altering the splicing of the target transcript. If desired, a provided composition can also be administered at higher dose/frequency due to its lower toxicities.

In some embodiments, the present disclosure recognizes that properties, e.g., activities, toxicities, etc. of CpG oligonucleotides and compositions thereof can be optimized by chemical modifications and/or stereochemistry. In some embodiments, the present disclosure provides methods for optimizing oligonucleotide properties through chemical modifications and stereochemistry. In some embodiments, the present disclosure provides CpG oligonucleotides and compositions and methods thereof with low toxicities. In some embodiments, the present disclosure provides CpG oligonucleotides and compositions and methods thereof with low toxicities and enhanced activities (e.g., target-inhibition efficiency, specificity, cleavage rates, cleavage pattern, etc.). In some embodiments, the present disclosure provides CpG oligonucleotides and compositions and methods thereof with improved protein binding profile. In some embodiments, the present disclosure provides CpG oligonucleotides and compositions and methods thereof with improved protein binding profile and enhanced activities. In some embodiments, the present disclosure provides CpG oligonucleotides and compositions and methods thereof with improved delivery and enhanced activities.

In some embodiments, provided CpG oligonucleotides, compositions and methods have low toxicities, e.g., when compared to a reference composition. As widely known in the art, CpG oligonucleotides can induce toxicities when administered to, e.g., cells, tissues, organism, etc. In some embodiments, CpG oligonucleotides can induce undesired immune response. In some embodiments, CpG oligonucleotide can induce complement activation. In some embodiments, CpG oligonucleotides can induce activation of the alternative pathway of complement. In some embodiments, CpG oligonucleotides can induce inflammation. Among other things, the complement system has strong cytolytic activity that can damages cells and should therefore be modulated to reduce potential injuries. In some embodiments, CpG oligonucleotide-induced vascular injury is a recurrent challenge in the development of CpG oligonucleotides for e.g., pharmaceutical use. In some embodiments, a primary source of inflammation when high doses of CpG oligonucleotides are administered involves activation of the alternative complement cascade. In some embodiments, complement activation is a common challenge associated with phosphorothioate-containing CpG oligonucleotides, and there is also a potential of some sequences of phosphorothioates to induce innate immune cell activation. In some embodiments, cytokine release is associated with administration of CpG oligonucleotides. For example, in some embodiments, increases in interleukin-6 (IL-6) monocyte chemoattractant protein (MCP-1) and/or interleukin-12 (IL-12) is observed. See, e.g., Frazier, Antisense Oligonucleotide Therapies: The Promise and the Challenges from a Toxicologic Pathologist's Perspective. Toxicol Pathol., 43: 78-89, 2015; and Engelhardt, et al., Scientific and Regulatory Policy Committee Points-to-consider Paper: Drug-induced Vascular Injury Associated with Nonsmall Molecule Therapeutics in Preclinical Development: Part 2. Antisense CpG oligonucleotides. Toxicol Pathol. 43: 935-944, 2015.

By controlling of chemical modifications and/or stereochemistry, the present disclosure provides improved CpG oligonucleotide compositions and methods. In some embodiments, provided CpG oligonucleotides comprise chemical modifications. In some embodiments, provided CpG oligonucleotides comprise base modifications, sugar modifications, internucleotidic linkage modifications, or any combinations thereof. In some embodiments, provided CpG oligonucleotides comprise base modifications. In some embodiments, provided CpG oligonucleotides comprise sugar modifications. In some embodiments, provided CpG oligonucleotides comprises 2'-modifications on the sugar moieties. In some embodiments, the present disclosure demonstrates that 2'-modifications can lower toxicity. In some embodiments, provided CpG oligonucleotides comprises one or more modified internucleotidic linkages and one or more natural phosphate linkages. In some embodiments, the present disclosure demonstrates that incorporation of one or more natural phosphate linkages into CpG oligonucleotides comprising one or more modified internucleotidic linkages can lower toxicity. A natural phosphate linkage can be incorporated into various locations of a CpG oligonucleotide. In some embodiments, a natural phosphate linkage is incorporated into a wing region, or a region close to the 5'- or the 3'-end. In some embodiments, a natural phosphate linkage is incorporated into the middle of a CpG oligonucleotide. In some embodiments, a natural phosphate linkage is incorporated into a core region. In some embodiments, the present disclosure demonstrates that stereochemistry, either alone or in combination with chemical modifications, can modulate toxicity. In some embodiments, the present disclosure demonstrates that stereochemistry, either alone or in combination with chemical modifications, can modulate immune response. In some embodiments, the present disclosure demonstrates that stereochemistry, either alone or in combination with chemical modifications, can modulate complement activation. It is surprisingly found that a chirally controlled CpG oligonucleotide composition of an individual stereoisomer can have dramatically different toxicity profile, e.g., complement activation, compared to the corresponding stereorandom composition, and/or a chirally controlled CpG oligonucleotide composition of another individual stereoisomer. For examples, see FIGS. 1-5. In some embodiments, the present disclosure demonstrates that stereochemistry, either alone or in combination with chemical modifications, can modulate complement activation via the alternative pathway. Example chemical modifications, stereochemistry and patterns thereof are extensively described in this disclosure, and they can be used in combinations. Example compositions and methods of are also extensively described in this disclosure. A person having ordinary skill in the art understands that methods and compositions described herein can be used to either increase or decrease immune responses, including complement activation, relative to a reference composition.

In some embodiments, provided CpG oligonucleotides comprise one or more structural elements (e.g., modifications, stereochemistry, patterns, etc.) that CpG oligonucleotides of the reference plurality do not all have. Such structural elements can be any one described in this disclosure.

In some embodiments, CpG oligonucleotides of a provided composition comprise more phosphorothioate linkages than CpG oligonucleotides of the reference composition. In some embodiments, CpG oligonucleotides of a provided composition comprise more phosphorothioate linkages than CpG oligonucleotides of the reference composition at the 5'-end region. In some embodiments, CpG oligonucleotides of a provided composition comprise more phosphorothioate linkages than CpG oligonucleotides of the reference composition at the 3'-end region. In some embodiments, CpG oligonucleotides of a provided composition comprise more phosphorothioate linkages in a wing region than the corresponding region of CpG oligonucleotides of the reference composition. In some embodiments, CpG oligonucleotides of a provided composition comprise more phosphorothioate linkages in each wing region than the corresponding regions in CpG oligonucleotides of the reference composition. In some embodiments, CpG oligonucleotides of a provided composition comprise more Sp chiral internucleotidic linkages than CpG oligonucleotides of the reference composition. In some embodiments, CpG oligonucleotides of a provided composition comprise more Sp phosphorothioate linkages than CpG oligonucleotides of the reference composition. In some embodiments, CpG oligonucleotides of a provided composition comprise more Sp phosphorothioate linkages than CpG oligonucleotides of the reference composition at the 5'-end region. In some embodiments, CpG oligonucleotides of a provided composition comprise more Sp phosphorothioate linkages than CpG oligonucleotides of the reference composition at the 3'-end region. In some embodiments, CpG oligonucleotides of a provided composition comprise more Sp phosphorothioate linkages in a wing region than CpG oligonucleotides of the reference composition. In some embodiments, CpG oligonucleotides of a provided composition comprise more Sp phosphorothioate linkages in each wing region than CpG oligonucleotides of the reference composition. In some embodiments, CpG oligonucleotides of a provided composition comprise more modified bases than CpG oligonucleotides of the reference composition. In some embodiments, CpG oligonucleotides of a provided composition comprise more methylated bases than CpG oligonucleotides of the reference composition. In some embodiments, CpG oligonucleotides of a provided composition comprise more methylated bases than CpG oligonucleotides of the reference composition at the 5'-end region. In some embodiments, CpG oligonucleotides of a provided composition comprise more methylated bases than CpG oligonucleotides of the reference composition at the 3'-end region. In some embodiments, CpG oligonucleotides of a provided composition comprise more methylated bases than in a wing region than CpG oligonucleotides of the reference composition. In some embodiments, CpG oligonucleotides of a provided composition comprise more methylated bases than in each wing region than CpG oligonucleotides of the reference composition.

In some embodiments, CpG oligonucleotides of a provided composition comprise fewer 2'-MOE modifications than CpG oligonucleotides of the reference composition. In some embodiments, CpG oligonucleotides of a provided composition comprise fewer 2'-MOE modifications than CpG oligonucleotides of the reference composition. In some embodiments, CpG oligonucleotides of a provided composition comprise fewer 2'-MOE modifications than CpG oligonucleotides of the reference composition at the 5'-end region. In some embodiments, CpG oligonucleotides of a provided composition comprise fewer 2'-MOE modifications than CpG oligonucleotides of the reference composition at the 3'-end. In some embodiments, CpG oligonucleotides of a provided composition comprise fewer 2'-MOE modifications than in a wing region than CpG oligonucleotides of the reference composition. In some embodiments, CpG oligonucleotides of a provided composition comprise fewer 2'-MOE modifications than in each wing region than CpG oligonucleotides of the reference composition. In some embodiments, individual CpG oligonucleotides within the reference plurality differ from one another in stereochemical structure. In some embodiments, at least some CpG oligonucleotides within the reference plurality have a structure different from a structure represented by the plurality of CpG oligonucleotides of the composition. In some embodiments, at least some CpG oligonucleotides within the reference plurality do not comprise a wing region and a core region. In some embodiments, the reference composition is a substantially racemic preparation of CpG oligonucleotides that share the base sequence. In some embodiments, the reference composition is a chirally controlled CpG oligonucleotide composition of another CpG oligonucleotide type. In some embodiments, CpG oligonucleotides of the reference composition comprise more phosphorothioate linkages. In some embodiments, CpG oligonucleotides of the reference composition comprise only phosphorothioate linkages. In some embodiments, CpG oligonucleotides of the reference composition comprise fewer modified sugar moieties. In some embodiments, CpG oligonucleotides of the reference composition comprise fewer modified sugar moieties, wherein the modification is 2'-OR$^1$. In some embodiments, CpG oligonucleotides of the reference composition comprise more modified sugar moieties. In some embodiments, CpG oligonucleotides of the reference composition comprise more modified sugar moieties, the modification is 2'-OR$^1$. In some embodiments, CpG oligonucleotides of the reference composition comprise fewer phosphorothioate linkages. In some embodiments, CpG oligonucleotides of the reference composition have a wing, and comprise fewer phosphorothioate linkages at the wing. In some embodiments, CpG oligonucleotides of the reference composition comprise fewer Sp phosphorothioate linkages. In some embodiments, CpG oligonucleotides of the reference composition have a wing, and comprise fewer Sp phosphorothioate linkages at the wing. In some embodiments, CpG oligonucleotides of the reference composition comprise more Rp phosphorothioate linkages. In some embodiments, CpG oligonucleotides of the reference composition have a wing, and comprise more Rp phosphorothioate linkages at the wing. In some embodiments, CpG oligonucleotides of the reference composition comprise fewer methylated bases. In some embodiments, CpG oligonucleotides of the reference composition comprise more 2'-MOE modifications. In some embodiments, CpG oligonucleotides of the reference composition comprise fewer natural phosphate linkages. In some embodiments, CpG oligonucleotides of the reference composition comprise fewer natural phosphate linkages at the 5'- and/or 3'-end. In some embodiments, CpG oligonucleotides of the reference composition comprise fewer natural phosphate linkages in a region corresponding to a wing of CpG oligonucleotides of the first plurality. In some embodiments, CpG oligonucleotides of a provided composition comprise natural phosphate linkages in a wing, and CpG oligonucleotides of the reference composition comprise fewer natural phosphate linkages at the corresponding wing region. In some embodiments, CpG oligonucleotides of a provided composition comprises natural phosphate linkages in a wing, and CpG oligonucleotides of the reference composition comprises modified internucleotidic linkages at one or more such natural phosphate linkage locations in a wing. In some embodiments, CpG oligonucleotides of a provided composition comprise natural phosphate linkages in a wing, and CpG oligonucleotides of the reference composition comprises phosphorothioate linkages at one or more such natural phosphate linkage locations in a wing. In some embodiments, CpG oligonucleotides of the reference composition comprise no natural phosphate linkages. In some embodiments, CpG oligonucleotides of the reference composition comprise no wing-core-wing structure. In some embodiments, CpG oligonucleotides of a provided composition comprise a 5'-end wing region comprising a natural phosphate linkage between the two nucleosides at its 3'-end, and CpG oligonucleotides of a reference plurality do not have a natural phosphate linkage at the same position. In some embodiments, CpG oligonucleotides of a provided composition comprise a 3'-end wing region comprising a natural phosphate linkage between the two nucleosides at its 5'-end, and CpG oligonucleotides of a reference plurality do not have a natural phosphate linkage at the same position.

In some embodiments, CpG oligonucleotides of a provided composition contain more 2'-F modifications than CpG oligonucleotides of a reference composition. In some embodiments, CpG oligonucleotides of a provided composition contain more 2'-F modifications in a wing region. In some embodiments, CpG oligonucleotides of a provided composition contain more 2'-F modifications in each wing region.

In some embodiments, provided chirally controlled CpG oligonucleotide compositions comprises CpG oligonucleotides of one CpG oligonucleotide type. In some embodiments, provided chirally controlled CpG oligonucleotide compositions comprises CpG oligonucleotides of only one CpG oligonucleotide type. In some embodiments, provided chirally controlled CpG oligonucleotide compositions has CpG oligonucleotides of only one CpG oligonucleotide type. In some embodiments, provided chirally controlled CpG oligonucleotide compositions comprises CpG oligonucleotides of two or more CpG oligonucleotide types. In some embodiments, using such compositions, provided methods can target more than one target. In some embodiments, a chirally controlled CpG oligonucleotide composition comprising two or more CpG oligonucleotide types targets two or more targets. In some embodiments, a chirally controlled CpG oligonucleotide composition comprising two or more CpG oligonucleotide types targets two or more mismatches. In some embodiments, a single CpG oligonucleotide type targets two or more targets, e.g., mutations. In some embodiments, a target region of CpG oligonucleotides of one CpG oligonucleotide type comprises two or more "target sites" such as two mutations or SNPs.

In some embodiments, CpG oligonucleotides in a provided chirally controlled CpG oligonucleotide composition optionally comprise modified bases or sugars. In some embodiments, a provided chirally controlled CpG oligonucleotide composition does not have any modified bases or sugars. In some embodiments, a provided chirally controlled CpG oligonucleotide composition does not have any modified bases. In some embodiments, CpG oligonucleotides in a provided chirally controlled CpG oligonucleotide composition comprise modified bases and sugars. In some embodiments, CpG oligonucleotides in a provided chirally controlled CpG oligonucleotide composition comprise a modified base. In some embodiments, CpG oligonucleotides in a provided chirally controlled CpG oligonucleotide composition comprise a modified sugar. Modified bases and sugars for CpG oligonucleotides are widely known in the art, including but not limited in those described in the present disclosure. In some embodiments, a modified base is 5-mC. In some embodiments, a modified sugar is a T-modified sugar. Suitable 2'-modification of CpG oligonucleotide sugars are widely known by a person having ordinary skill in the art. In some embodiments, 2'-modifications include but are not limited to 2'-OR$^1$, wherein R$^1$ is not hydrogen. In some embodiments, a 2'-modification is 2'-OR$^1$, wherein R$^1$ is optionally substituted C$_{1-6}$ aliphatic. In some embodiments, a 2'-modification is 2'-MOE. In some embodiments, a modification is 2'-halogen. In some embodiments, a modification is 2'-F. In some embodiments, modified bases or sugars can further enhance activity, stability and/or selectivity of a chirally controlled CpG oligonucleotide composition, whose common pattern of backbone chiral centers provides unexpected activity, stability and/or selectivity.

In some embodiments, a provided chirally controlled CpG oligonucleotide composition does not have any modified sugars. In some embodiments, a provided chirally controlled CpG oligonucleotide composition does not have any 2'-modified sugars. In some embodiments, the present disclosure surprising found that by using chirally controlled CpG oligonucleotide compositions, modified sugars are not needed for stability, activity, and/or control of cleavage patterns. Furthermore, in some embodiments, the present disclosure surprisingly found that chirally controlled CpG oligonucleotide compositions of CpG oligonucleotides without modified sugars deliver better properties in terms of stability, activity, turn-over and/or control of cleavage patterns. For example, in some embodiments, it is surprising found that chirally controlled CpG oligonucleotide compositions of CpG oligonucleotides having no modified sugars dissociates much faster from cleavage products and provide significantly increased turn-over than compositions of CpG oligonucleotides with modified sugars.

As discussed in detail herein, the present disclosure provides, among other things, a chirally controlled CpG oligonucleotide composition, meaning that the composition contains a plurality of CpG oligonucleotides of at least one type. Each oligonucleotide molecule of a particular "type" is comprised of preselected (e.g., predetermined) structural elements with respect to: (1) base sequence; (2) pattern of backbone linkages; (3) pattern of backbone chiral centers; and (4) pattern of backbone P-modification moieties. In some embodiments, provided oligonucleotide compositions contain CpG oligonucleotides that are prepared in a single synthesis process. In some embodiments, provided compositions contain oligonucleotides having more than one chiral configuration within a single CpG oligonucleotide molecule (e.g., where different residues along the CpG oligonucleotide have different stereochemistry); in some such embodiments, such CpG oligonucleotides can be obtained in a single synthesis process, without the need for secondary conjugation steps to generate individual CpG oligonucleotide molecules with more than one chiral configuration.

Oligonucleotide compositions as provided herein can be used as agents for modulating a number of cellular processes and machineries, including but not limited to, transcription, translation, immune responses, epigenetics, etc. In addition, CpG oligonucleotide compositions as provided herein can be used as reagents for research and/or diagnostic purposes. One of ordinary skill in the art will readily recognize that the present disclosure herein is not limited to particular use but is applicable to any situations where the use of synthetic oligonucleotides is desirable. Among other things, provided compositions are useful in a variety of therapeutic, diagnostic, agricultural, and/or research applications.

In some embodiments, provided oligonucleotide compositions comprise CpG oligonucleotides and/or residues thereof that include one or more structural modifications as described in detail herein. In some embodiments, provided CpG oligonucleotide compositions comprise oligonucleoties that contain one or more nucleic acid analogs. In some embodiments, provided CpG oligonucleotide compositions comprise CpG oligonucleotides that contain one or more artificial nucleic acids or residues, including but not limited to: peptide nucleic acids (PNA), Morpholino and locked nucleic acids (LNA), glycon nucleic acids (GNA), threose nucleic acids (TNA), Xeno nucleic acids (ZNA), and any combination thereof.

In any of the embodiments, the disclosure is useful for CpG oligonucleotide-based modulation of gene expression, immune response, etc. Accordingly, stereo-defined, CpG oligonucleotide compositions of the disclosure, which contain CpG oligonucleotides of predetermined type (i.e., which are chirally controlled, and optionally chirally pure), can be used in lieu of conventional stereo-random or chirally impure counterparts. In some embodiments, provided compositions show enhanced intended effects and/or reduced unwanted side effects. Certain embodiments of biological and clinical/therapeutic applications of the disclosure are discussed explicitly below.

A provided CpG oligonucleotide composition as used herein can comprise single stranded and/or multiply stranded CpG oligonucleotides. In some embodiments, single-stranded CpG oligonucleotides contain self-complementary portions that can hybridize under relevant conditions so that, as used, even single-stranded CpG oligonucleotides can have at least partially double-stranded character. In some embodiments, a CpG oligonucleotide included in a provided composition is single-stranded, double-stranded, or triple-stranded. In some embodiments, a CpG oligonucleotide included in a provided composition comprises a single-stranded portion and a multiple-stranded portion within the CpG oligonucleotide. In some embodiments, as noted above, individual single-stranded CpG oligonucleotides can have double-stranded regions and single-stranded regions.

In some embodiments, provided compositions include one or more CpG oligonucleotides fully or partially complementary to strand of: structural genes, genes control and/or termination regions, and/or self-replicating systems such as viral or plasmid DNA. In some embodiments, provided compositions include one or more CpG oligonucleotides that are or act as siRNAs or other RNA interference reagents (RNAi agents or iRNA agents), shRNA, antisense CpG oligonucleotides, self-cleaving RNAs, ribozymes, fragment thereof and/or variants thereof (such as Peptidyl transferase 23 S rRNA, RNase P, Group I and Group II introns, GIR1 branching ribozymes, Leadzyme, Hairpin ribozymes, Hammerhead ribozymes, HDV ribozymes, Mammalian CPEB3 ribozyme, VS ribozymes, glmS ribozymes, CoTC ribozyme, etc.), microRNAs, microRNA mimics, supermirs, aptamers, antimirs, antagomirs, U1 adaptors, triplex-forming CpG oligonucleotides, RNA activators, long non-coding RNAs, short non-coding RNAs (e.g., piRNAs), immunomodulatory CpG oligonucleotides (such as immunostimulatory CpG oligonucleotides, immunoinhibitory CpG oligonucleotides), GNA, LNA, ENA, PNA, TNA, morpholinos, G-quadruplex (RNA and DNA), antiviral CpG oligonucleotides, and decoy CpG oligonucleotides.

In some embodiments, provided compositions include one or more hybrid (e.g., chimeric) CpG oligonucleotides. In the context of the present disclosure, the term "hybrid" broadly refers to mixed structural components of oligonucleotides. Hybrid oligonucleotides can refer to, for example, (1) a CpG oligonucleotide molecule having mixed classes of nucleotides, e.g., part DNA and part RNA within the single molecule (e.g., DNA-RNA); (2) complementary pairs of nucleic acids of different classes, such that DNA:RNA base pairing occurs either intramolecularly or intermolecularly; or both; (3) a CpG oligonucleotide with two or more kinds of the backbone or internucleotide linkages.

In some embodiments, provided compositions include one or more CpG oligonucleotide that comprises more than one classes of nucleic acid residues within a single molecule. For example, in any of the embodiments described herein, a CpG oligonucleotide can comprise a DNA portion and an RNA portion. In some embodiments, a CpG oligonucleotide can comprise a unmodified portion and modified portion.

Provided CpG oligonucleotide compositions can include CpG oligonucleotides containing any of a variety of modifications, for example as described herein. In some embodiments, particular modifications are selected, for example, in light of intended use. In some embodiments, it is desirable to modify one or both strands of a double-stranded CpG oligonucleotide (or a double-stranded portion of a single-stranded oligonucleotide). In some embodiments, the two strands (or portions) include different modifications. In some embodiments, the two strands include the same modifications. One of skill in the art will appreciate that the degree and type of modifications enabled by methods of the present disclosure allow for numerous permutations of modifications to be made. Example such modifications are described herein and are not meant to be limiting.

The phrase "antisense strand", as used herein, in reference to a CpG oligonucleotide, refers to a CpG oligonucleotide that is substantially or 100% complementary to a target sequence of interest. The phrase "antisense strand" includes the antisense region of both CpG oligonucleotides that are formed from two separate strands, as well as unimolecular CpG oligonucleotides that are capable of forming hairpin or dumbbell type structures. The terms "antisense strand" and "guide strand" are used interchangeably herein. The phrase "sense strand", as used herein, in reference to a CpG oligonucleotide, refers to a CpG oligonucleotide that has the same nucleoside sequence, in whole or in part, as a target sequence such as a messenger RNA or a sequence of DNA. The terms "sense strand" and "passenger strand" are used interchangeably herein.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant. In some embodiments, a target sequence is associated with a disease or disorder.

By "specifically hybridizable" and "complementary" is meant that a nucleic acid can form hydrogen bond(s) with another nucleic acid sequence by either traditional Watson-Crick or other non-traditional types. In reference to the nucleic molecules of the present disclosure, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, CSH Symp. Quant. Biol. LII pp. 123-133; Frier et al., 1986, Proc. Nat. Acad. Sci. USA83:9373-9377; Turner et al., 1987, Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 1, 8, 9,10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, e.g., under physiological conditions in the case of in vivo assays or therapeutic treatment, or in the case of in vitro assays, under conditions in which the assays are performed. In some embodiments, non-target sequences differ from corresponding target sequences by at least 5 nucleotides.

Biologically active agent: A CpG oligonucleotide

In some embodiments, the present disclosure pertains to compositions and methods related to a CpG oligonucleotide composition.

In some embodiments, a CpG oligonucleotide is selected from: an antisense oligonucleotide, an RNAi agent, a miRNA, splice switching oligonucleotide (SSO), immunomodulatory nucleic acid, an aptamer, a ribozyme, a Piwi-interacting RNA (piRNA), a small nucleolar RNA (snoRNA), a mRNA, a lncRNA, a ncRNA, an antigomir (e.g., an antagonist to a miRNA, lncRNA, ncRNA or other nucleic acid), a plasmid, a vector, or a portion thereof.

In some embodiments, the present disclosure pertains to: a CpG oligonucleotide composition comprising a plurality of CpG oligonucleotides, which share: 1) a common base sequence; 2) a common pattern of backbone linkages; and 3) a common pattern of backbone phosphorus modifications. In some embodiments, the present disclosure pertains to: a chirally controlled CpG oligonucleotide composition comprising a plurality of CpG oligonucleotides, which share: 1) a common base sequence; 2) a common pattern of backbone linkages; and 3) a common pattern of backbone phosphorus modifications; wherein: the composition is chirally controlled in that the plurality of CpG oligonucleotides share the same stereochemistry at one or more chiral internucleotidic linkages; and one or more CpG oligonucleotides of the plurality are optionally and individually conjugated to a targeting compound or moiety. In some embodiments, a CpG oligonucleotide is a splice-switching oligonucleotide. In some embodiments, a CpG oligonucleotide is capable of skipping or mediating skipping of an exon in a gene related to a muscle-related disease or disorder. In some embodiments, a CpG oligonucleotide is capable of skipping or mediating skipping of an exon in the dystrophin gene. In some embodiments, the sequence of the CpG oligonucleotide comprises or consists of the sequence of any splice-switching oligonucleotide disclosed herein.

In some embodiments, the plurality of CpG oligonucleotides share the same stereochemistry at five or more chiral internucleotidic linkages. In some embodiments, the plurality of CpG oligonucleotides share the same stereochemistry at ten or more chiral internucleotidic linkages. In some embodiments, the plurality of CpG oligonucleotides share the same stereochemistry at each of the chiral internucleotidic linkages so that they share a common pattern of backbone chiral centers. In some embodiments, CpG oligonucleotides of the plurality share the same chemical modification patterns. In some embodiments, CpG oligonucleotides of the plurality share the same chemical modification patterns comprising one or more base modifications. In some embodiments, CpG oligonucleotides of the plurality share the same chemical modification patterns comprising one or more sugar modifications. In some embodiments, the sequence of the CpG oligonucleotide(s) comprises or consists of the sequence of any splice-switching oligonucleotide disclosed herein.

In some embodiments, the plurality of CpG oligonucleotides share a common pattern of sugar modification, which comprises 3 or more 2'-F. In some embodiments, the plurality of CpG oligonucleotides share a common pattern of sugar modification, which comprises 3 or more consecutive 2'-F. In some embodiments, the plurality of CpG oligonucleotides share a common pattern of sugar modification, which comprises 3 or more consecutive 2'-F within the 10 nucleotide at the 5'-end. In some embodiments, the plurality of CpG oligonucleotides share a common pattern of sugar modification, which comprises 3 or more 2'-F within the 10 nucleotide at the 5'-end. In some embodiments, the plurality of CpG oligonucleotides share a common pattern of sugar modification, which comprises 3 or more consecutive 2'-F at the 5'-end. In some embodiments, the plurality of CpG oligonucleotides share a common pattern of sugar modification, which comprises 5 or more consecutive 2'-F within the first 10 nucleotide at the 3'-end. In some embodiments, the plurality of CpG oligonucleotides share a common pattern of sugar modification, which comprises 5 or more 2'-F within the 10 nucleotide at the 3'-end. In some embodiments, the plurality of CpG oligonucleotides share a common pattern of sugar modification, which comprises 7 or more consecutive 2'-F at the 3'-end. In some embodiments, the plurality of CpG oligonucleotides share a common pattern of sugar modification, which comprises 3 or more consecutive 2'-F at the 5'-end, 3 or more consecutive 2'-F at the 3'-end, and 3 or more 2'-OR between the 5'-end 2'-F and the 3'-end 2'-F modifications. In some embodiments, the plurality of CpG oligonucleotides share a common pattern of sugar modification, which comprises 3 or more 2'-F at the 5'-end, 3 or more 2'-F at the 3'-end, and 3 or more 2'-OR between the 5'-end 2'-F and the 3'-end 2'-F modifications. In some embodiments, the plurality of CpG oligonucleotides share a common pattern of sugar modification, which comprises 5 or more 2'-F within the 10 nucleotides at the 5'-end. In some embodiments, the plurality of CpG oligonucleotides share a common pattern of sugar modification, which comprises 3 or more consecutive 2'-F at the 5'-end. In some embodiments, the plurality of CpG oligonucleotides share a common pattern of sugar modification, which comprises 7 or more 2'-F within the 10 nucleotides at the 3'-end. In some embodiments, the plurality of CpG oligonucleotides share a common pattern of sugar modification, which comprises 5 or more consecutive 2'-F within the 10 nucleotides at the 3'-end. In some embodiments, the plurality of CpG oligonucleotides share a common pattern of sugar modification, which comprises 7 or more consecutive 2'-F at the 3'-end. In some embodiments, the plurality of CpG oligonucleotides comprises a 5'-wing-core-wing-3' structure, wherein each wing region independently comprises 3 to 10 nucleosides, and the core region independently comprises 3 to 10 nucleosides. In some embodiments, the sequence of the CpG oligonucleotide(s) comprises or consists of the sequence of any CpG oligonucleotide disclosed herein.

In some embodiments, the present disclosure pertains to: a method of delivering a CpG oligonucleotide to a muscle cell or tissue in a human subject, comprising: (a) providing a composition of any one of the preceding embodiments; and (b) Administering the composition to the human subject such that the CpG oligonucleotide is delivered to a muscle cell or tissue in the subject. In some embodiments, the sequence of the CpG oligonucleotide(s) comprises or consists of the sequence of any CpG oligonucleotide disclosed herein.

In some embodiments, the common base sequence is capable of hybridizing with a transcript in a muscle cell, which transcript contains a mutation that is linked to a muscle disease, or whose level, activity and/or distribution is linked to a muscle disease. In some embodiments, the common base sequence is capable of hybridizing with a transcript in a muscle cell, and the composition is characterized in that when it is contacted with the transcript in a transcript splicing system, splicing of the transcript is altered relative to that observed under reference conditions selected from the group consisting of absence of the composition, presence of a reference composition, and combinations thereof. In some embodiments, the common base sequence is capable of hybridizing with a transcript in a cell. In some embodiments, a common base sequence hybridizes with a transcript of dystrophin, Huntingtin, myostatin, a myostatin receptor, ActRIIA, ActRIIB, DMPK, SMN2, dystrophia myotonica protein kinase (DMPK), Proprotein convertase subtilisin/kexin type 9 (PCSK9), SMAD7, transthyretin (TTR), alpha-1 antitrypsin (AAT), aminolevulinate synthase 1 (ALAS1), antithrombin 3 (ATIII), factor VII (FVII), factor XI (FXI), factor XII (FXII), hepcidin antimicrobial peptide (HAMP), a gene of hepatitis B (HBV), hepatitis C (HCV) or hepatitis D (HDV), programmed death-ligand 1 (PD-L1), complement component 5 (C5), transmembrane protease, serine 6 (TMPRSS6), or KRT14 (Keratin 14). In some embodiments, the common base sequence hybridizes with a transcript of dystrophin. In some embodiments, the common base sequence hybridizes with a transcript of dystrophin, and the composition increases the production of one or more functional or partially functional proteins encoded by dystrophin. In some embodiments, the sequence of the CpG oligonucleotide(s) comprises or consists of the sequence of any CpG oligonucleotide disclosed herein.

In some embodiments, the CpG oligonucleotide or CpG oligonucleotides is or are splice switching oligonucleotide or CpG oligonucleotides. In some embodiments, the sequence of the CpG oligonucleotide(s) comprises or consists of the sequence of any CpG oligonucleotide disclosed herein.

In various embodiments, a composition comprises a nucleic acid comprising a CpG region motif [as non-limiting examples: a CpG oligonucleotide, an antisense oligonucleotide, an RNAi agent, a miRNA, immunomodulatory nucleic acid, an aptamer, a Piwi-interacting RNA (piRNA), a small nucleolar RNA (snoRNA), a ribozyme, a mRNA, a lncRNA, a ncRNA, an antigomir (e.g., an antagonist to a miRNA, lncRNA, ncRNA or other nucleic acid), a plasmid, or a vector, or a portion thereof] which targets any gene listed herein.

In some embodiments, a composition comprises a nucleic acid comprising a CpG region motif which targets any of: AFF2, APOB, APOC3, AR, ATM, ATN1, ATXN1, ATXN10, ATXN2, ATXN3, ATXN7, ATXN80S, BACE1, BBS1, BCL2L1, BRCA1, BRCA2, C9orf72, CACNA1A, CD40, CD40, CDKN1A, CFTR, CLC1, CNBP, COL7A1, CYP11A, DMD, DMPK, DYSF, Dystrophin, ERBB2, F7, F9, FANCC, FGB, FGFR1, FKTN, FLT1, FMR1, FXN, GHR, GRP143, HBB, HNRNPH1, HTT (Huntingtin), IKBKAP, IL5RA, ISCU, JPH3, KDR, LMNA, MAPT, MCL1, MDM2, MLC1, MST1R, MSTN, MUT, MYC, NF1, NPC1, PCCA, PCCB, PHB, PKM, PMM2, PPP2R2B, PTCH1, PTS, PTS, RHO, RHO, RPGR, RPGR, SMN2, SRA1, STAT3, TBP, TERT, TMPRSS2, TNFRSF1B, USH1C, USP5, AAT, ALAS1, ATIII, C5, DMPK, FVII, FXI, FXII, HAMP, a gene of HBV, HCV, or HDV, Keratin 14, PCSK9, PD-L1, TMPRSS6, TTR, and WT1. In some embodiments, the common base sequence is capable of hybridizing with a transcript in a cell. In some embodiments, a common base sequence hybridizes with a transcript of any gene described herein or known in the art.

In some embodiments, a composition comprises a nucleic acid comprising a CpG region motif suitable for treatment of any of: Afibrinogenemia, Alzheimer's disease, Alzheimer's disease/FTDP-17 Taupathies, Ataxia telangiectasia, Autoimmune disease, Bardet-Biedl syndrome, Beta-thalassemia, Cancer, CDG1A, Congenital adrenal insufficiency, Crohn's Disease, Cystic fibrosis, Dementia, Dentatorubral-pallidoluysian atrophy, Duchenne muscular dystrophy, Dystrophic epidermolysis bullosa, Epidermolysis Bullosa Simplex, Factor VII deficiency, Familial dysautonomia, Fanconi anemia, FHBL/atherosclerosis, Fragile X mental retardation, Fragile X syndrome, Friedreich's ataxia, Frontotemporal dementia, Fukuyama congenital muscular dystrophy (FCMD), Growth hormone insensitivity, Hemophilia A, HPABH4A, Huntington's Diease, Huntington's Disease-like 2, Hutchinson-Gilford progeria (HGPS), Immune-response, Infection, Inflammatory disease, Influenza virus, Irritable Bowel Syndrome, Machado-Joseph disease, Mental retardation, Mental retardation, X-linked, associated with FRAXE, Methylmalonic aciduria, Miyoshi myopathy, MLC1, Muscle wasting diseases, Muscular Dystrophy, Myopathy with lactic acidosis, Myotonic muscular dystrophy, Myotonic dystrophy type 1, Neurofibromatosis, Niemann-Pick type C, Ocular albinism type 1, Oculpopharyngeal muscular dystrophy, Propionic acidemia, Retinitis pigmentosa, Spinal muscular atrophy, Spinocerebellar ataxia, Spinocerebellar ataxia type 1, Spinomuscular bulbar atrophy, or Usher syndrome.

In some embodiments, an antisense oligonucleotide is a CpG oligonucleotide which participates in RNaseH-mediated cleavage; for example, an antisense oligonucleotide hybridizes in a sequence-specific manner to a portion of a target mRNA, thus targeting the mRNA for cleavage my RNaseH. In some embodiments, an antisense oligonucleotide is able to differentiate between a wild-type and a mutant allele of a target. In some embodiments, an antisense oligonucleotide significantly participates in RNaseH-mediated cleavage of a mutant allele but participates in RNaseH-mediated cleavage of a wild-type allele to a much less degree (e.g., does not significantly participate in RNaseH-mediated cleavage of the wild-type allele of the target). Various CpG oligonucleotides and CpG region motifs are listed herein.

In some embodiments, the present disclosure pertains to a composition comprising a nucleic acid (including, but not limited to, a CpG oligonucleotide) and a lipid comprising a $C_{10}$-$C_{80}$ linear, saturated or partially unsaturated, aliphatic chain. In some embodiments, the present disclosure pertains to a composition comprising a nucleic acid (including, but not limited to, a CpG oligonucleotide) and a lipid comprising a $C_{10}$-$C_{80}$ linear, saturated or partially unsaturated, aliphatic chain, optionally substituted with one or more $C_{1-4}$ aliphatic group. In some embodiments, the present disclosure pertains to a composition comprising a nucleic acid (including, but not limited to, a CpG oligonucleotide) agent and a lipid comprising a $C_{10}$-$C_{60}$ linear, saturated or partially unsaturated, aliphatic chain. In some embodiments, the present disclosure pertains to a composition comprising a nucleic acid (including, but not limited to, a CpG oligonucleotide) and a lipid comprising a $C_{10}$-$C_{60}$ linear, saturated or partially unsaturated, aliphatic chain, optionally substituted with one or more $Cr_4$ aliphatic group. In some embodiments, the present disclosure pertains to a composition comprising a nucleic acid (including, but not limited to, a CpG oligonucleotide) and a lipid comprising a $C_{10}$-$C_{40}$ linear, saturated or partially unsaturated, aliphatic chain. In some embodiments, the present disclosure pertains to a composition comprising a nucleic acid (including, but not limited to, a CpG oligonucleotide) and a lipid comprising a $C_{10}$-$C_{40}$ linear, saturated or partially unsaturated, aliphatic chain, optionally substituted with one or more $C_{1-4}$ aliphatic group.

In some embodiments, provided oligonucleotides are optionally conjugated with another agent. In some embodiments, provided oligonucleotides are conjugated with lipids. In some embodiments, provided oligonucleotides are conjugated with biotin. Various technologies can be utilized for conjugation of oligonucleotides with another agent, in some embodiments, optionally through a linker.

Certain Example CpG Oligonucleotides and Interactions of CpG Oligonucleotides with TLR9

Certain structural characteristics and classes of CpG oligonucleotides, and the interactions of CpG oligonucleotides, are described below.

The present disclosure, among other things, details the novel and surprising finding that the chirality of the phosphorothioates or other internucleotidic linkages in the CpG region motifs can greatly alter activity of the CpG oligonucleotides. A chirally controlled CpG oligonucleotide composition comprising a CpG oligonucleotide which has a novel CpG region motif described herein [and defined at least in part by the chirality of the phosphorothioates] and is useful in modulating an immune response. Depending on the CpG region motif, different CpG oligonucleotides were found to be either agonistic or antagonistic to the immune response. A chirally controlled CpG oligonucleotide composition comprising an agonistic CpG oligonucleotide can thus be used as an immunostimulatory agent, e.g., vaccine, adjuvant or monotherapy. Antagonistic CpG oligonucleotides can be used to antagonize the immune response. If no alteration of the immune response is desired, one can design a therapeutic oligonucleotide which avoids CpG region motifs which are agonistic or antagonistic.

Certain characteristics and classes of CpG oligonucleotides, and the interactions of CpG oligonucleotides with TLR9 (based on reports using stereorandom CpG oligonucleotide compositions) are described below, followed by additional detailed description of the novel CpG region motifs and methods of making and using chirally controlled CpG oligonucleotide compositions comprising them. In some embodiments, an active or efficacious CpG oligonucleotide is one which exhibits significantly altered immunomodulatory activity (either agonism or antagonism) compared to a negative control (e.g., in the absence of the oligonucleotide) and/or a reference.

Structural Characteristics of Example CpG oligonucleotides

Many reported structural characteristics of CpG oligonucleotides that can elicit a desired immune response can be utilized in provided oligonucleotides in accordance with the present disclosure.

Length of CpG Oligonucleotides

Various lengths can be utilized in accordance with the present disclosure, for example, the following:

Several reportedly active CpG oligonucleotides comprise strands of 46 nt. Pohar et al. 2015 J. Immunol. 194: 3901-3908 and Supplemental Figures.

Pohar et al. also reported an efficacious 40-mer CpG oligonucleotide. Pohar et al. 2015 J. Immunol. 194: 3901-3908.

Several active CpG oligonucleotides reportedly are 38 nt long. Pohar et al. 2015 J. Immunol. 194: 3901-3908 and Supplemental Figures.

A 34-mer variant of ODN2006 (a 24-mer) reportedly still retained over 90% of the potency of ODN2006 to activate human TLR9. Pohar et al. 2015 J. Immunol. 194: 3901-3908.

Several efficacious CpG oligonucleotides reportedly are 32-nt long. WO 2015/108047.

Several active CpG oligonucleotides reportedly are 30 nt long. Pohar et al. 2015 J. Immunol. 194: 3901-3908 and Supplemental Figures.

ODN2006 is a reportedly efficacious 24-mer CpG oligonucleotide. Pohar et al. 2015 J. Immunol. 194: 3901-3908. Class C CpG oligonucleotide 2395 reportedly is 22 nt long. Lahoud et al. 2012 Proc. Natl. Acad. Sci. USA 109: 16270-16275.

High activity CpG oligonucleotides have been designed which reportedly are 21 nt in length. Pohar et al. 2015 J. Immunol. 194: 3901-3908.

Class B CpG oligos 1668 and 1826 reportedly are both 20 nt long. Lahoud et al. 2012 Proc. Natl. Acad. Sci. USA 109: 16270-16275.

A 16-mer shortened variant of ODN2006 (a 24-mer) reportedly still retains significant potency to activate human TLR9. Pohar et al. 2015 J. Immunol. 194: 3901-3908.

An active CpG oligonucleotide reportedly is 16 nt long. Verthelyi et al. 2001 J. Immunol. 166: 2372-2377.

Several active CpG oligonucleotides reportedly are 15 nt long. Krieg et al. 1995 Nature 374:546-549.

An active CpG oligonucleotide reportedly is 14 nt long. PCT/JP2013/069107.

Several immunostimulatory CpG oligonucleotides reportedly are 12 nt long. Verthelyi et al. 2002 J. Immunol. 168: 1659-1663.

An oligonucleotide as short as 8 nt reportedly stimulated IgM production in a study by Krieg et al. 1995 Nature 374: 546-549.

Several reportedly active CpG oligonucleotides are 8 nt long. Krieg et al. 2003 Oligo. 13: 491-499.

Thus, a variety of lengths have been reported for active CpG oligonucleotides.

Base Sequence of CpG Region Motif

Various base sequences, including around the CpG motif (the CpG region motif), can be utilized in accordance with the present disclosure, for example the following:

Several researchers have attempted to define the base sequence parameters for the CpG region motif (also referenced as "Core CpG motif" in the literature). In the sequences listed below, the CpG is indicated as "CG".

The sequence of RRCGYY, where R is a purine (Pu) and Y is a pyrimidine (Py) [Krieg et al. 1995 Nature 374: 546-549], and GACGTT [Yi et al. 1998 J. Immunol. 160: 5898-5906] have been reported as immunostimulatory in mice.

In contrast, the sequence GTCGTT reportedly was proposed as immunostimulatory in the human. Hartmann et al. 2000 J. Immun. 164: 944-953.

The base sequences Pu Py CG Py Py and NNNQ CGWNNN (SEQ ID NO: 1518), where Q=T, G or A, W=A or T, and N=any nucleotide, have been reported for Type K CpG oligonucleotides.

The base sequence RYCGRY, where R=A or G and Y=C or T reportedly has been reported for Type D CpG oligonucleotides.

The base sequence TCGTCG at the 5' end of the oligonucleotide reportedly has been reported for Class C CpG oligonucleotides.

ODN2006 reportedly has a T immediately 5' to each of its four CpG motifs (thus, TCG); changing any T to A reduce immunostimulation, though significant activity was retained. Pohar et al. 2015 J. Immunol. 194: 3901-3908.

Thus, a variety of potentially immunogenic base sequences have been reported for the CpG region.

Number of CpG Motifs

Active CpG oligonucleotides have been reported which have any of a variety of numbers of CpG motifs.

Several reported CpG oligonucleotides include the following:

Several reportedly active CpG oligonucleotides reportedly have only 1 CpG motif. Krieg et al. 1995 Nature 374:546-549.

Several active variants of ODN2006 reportedly have only 1 CpG motif. Pohar et al. 2015 J. Immunol. 194: 3901-3908 and Supplemental Figures.

Several active CpG oligonucleotides reportedly have 1 CpG motif. Krieg et al. 2003 Oligo. 13: 491-499.

An efficacious CpG oligonucleotide reportedly has only 1 CpG motif, 21 nt from the 3' end. Pohar et al. 2015 J. Immunol. 194: 3901-3908 and Supplemental Figures.

Several active CpG oligonucleotides reportedly have only 1 CpG motif. Verthelyi et al. 2001 J. Immunol. 166: 2372-2377.

SMAD7 series CpG oligonucleotide reportedly has 2 CpG motifs. Monteleone et al. 2015 NEJM 372: 12.

Several immunostimulatory CpG oligonucleotides reportedly have 2 CpG motifs. Verthelyi et al. 2002 J. Immunol. 168: 1659-1663.

SOD1 series CpG oligonucleotide reportedly has 3 CpG motifs. Miller et al. 2013 Lancet Neurol. 12: 435.

ODN2006 reportedly has 4 CpG motifs. Pohar et al. 2015 J. Immunol. 194: 3901-3908.

Additional variants of ODN2006 have 2, 3, 6 or 8 CpG motifs reportedly showed significant immunostimulation. Pohar et al. 2015 J. Immunol. 194: 3901-3908.

Efficacious CpG oligonucleotides have thus been reported with a variety of numbers of CpG motifs.

In some embodiments, provided oligonucleotides comprise one or more CpG. In some embodiments, provided oligonucleotides comprise two or more CpG. In some embodiments, provided oligonucleotides comprise three or more CpG. In some embodiments, provided oligonucleotides comprise four or more CpG. In some embodiments, provided oligonucleotides comprise five or more CpG.

Location of CpG Motifs

CpG motifs can be present at or near the 5' or 3' end of an oligonucleotide, and/or in the middle of the oligonucleotide. Certain examples are described herein.

5' End:

The distance between the furthest upstream (most 5') CpG and the 5' end can vary from oligonucleotide to oligonucleotide. Active CpG oligonucleotides can have any of a variety of distances between the most upstream CpG motif and the 5' end. Certain examples are described herein.

Several reported CpG oligonucleotides include the following:

The ODN2006 CpG oligonucleotide reportedly comprises a CpG at a position 1 nt (T) away from the 5' end. Vollmer et al. 2004 Eur. J. Immunol. 34: 251-262.

A SOD1 CpG oligonucleotide reportedly comprises a CpG 1 nt (C) from the 5' end. Miller et al. 2013 Lancet Neurol. 12: 435.

Class C CpG oligonucleotide 2395 has a CpG 1 nt (T) from the 5' end. Lahoud et al. 2012 Proc. Natl. Acad. Sci. USA 109: 16270-16275.

A SMAD7 CpG oligonucleotide reportedly comprises a CpG 2 nt (GT) from the 5' end. Monteleone et al. 2015 NEJM 372: 12.

Several CpG oligonucleotides reportedly comprise a CpG 4 nt from the 5' end. WO 2015/108047.

Class A CpG oligonucleotide 2216 reportedly has an upstream CpG 6 nt (GGGGGA) from the 5' end. Lahoud et al. 2012 Proc. Natl. Acad. Sci. USA 109: 16270-16275.

Class B CpG oligos 1668 and 1826 reportedly both have a CpG 7 nt from the 5' end (in both cases, TCCATGA). Lahoud et al. 2012 Proc. Natl. Acad. Sci. USA 109: 16270-16275.

Efficacious CpG oligonucleotides have thus been reported with the furthest upstream CpG at a variety of distances from the 5' end.

Middle:

The location of CpG motifs, including those in the middle, and the distance between CpG motifs can vary from oligonucleotide to oligonucleotide. Active CpG oligonucleotides have been reported which have any of a variety of locations of CpG motifs and distances between them. Certain examples are described herein.

Several reported CpG oligonucleotides include the following:

Pohar et al. has reportedly shown that from 1 to 6 CpG motifs can be located in the middle of a CpG oligonucleotide, and the distances between them can be varied.

Pohar et al. show several CpG oligonucleotides reportedly comprising CpG motifs which are only 1 nt apart. Pohar et al. 2015 J. Immunol. 194: 3901-3908.

Several CpG oligonucleotides reportedly comprise 4, 6 or 7 nt between various CpG motifs. WO 2015/108047.

An efficacious CpG oligonucleotide reportedly comprising 4 CpG motifs comprised sequences of 11 nt between the second and third, and 11 nt between the third and fourth CpG motifs; both 11-nt sequences were TTTTTTTTTGT (SEQ ID NO: 1519). Pohar et al. 2015 J. Immunol. 194: 3901-3908.

Several active CpG oligonucleotides reportedly comprised 2 CpG motifs 12 nt apart. Pohar et al. 2015 J. Immunol. 194: 3901-3908.

An active CpG oligonucleotide reportedly comprised 2 CpG motifs 16 nt apart. Pohar et al. 2015 J. Immunol. 194: 3901-3908.

An active CpG oligonucleotide reportedly comprised 2 CpG motifs 20 nt apart. Pohar et al. 2015 J. Immunol. 194: 3901-3908.

An active CpG oligonucleotide reportedly comprised 2 CpG motifs 24 nt apart. Pohar et al. 2015 J. Immunol. 194: 3901-3908.

Efficacious CpG oligonucleotides have thus been reported with a variety of distances between the middle CpG motifs, and between the middle CpG motifs and the most upstream or downstream CpG motifs.

3' End:

The distance between the most downstream CpG and the 3' end can vary from oligonucleotide to oligonucleotide. Active CpG oligonucleotides can have any of a variety of distances between the most downstream CpG motif and the 3' end. Certain examples are described herein.

Several reported CpG oligonucleotides include the following:

Class C CpG oligonucleotide 2395 reportedly has a CpG at the 3' end. Lahoud et al. 2012 Proc. Natl. Acad. Sci. USA 109: 16270-16275.

An active CpG oligonucleotide reportedly has a CpG motif 1 nt from the 3' end. Pohar et al. 2015 J. Immunol. 194: 3901-3908 and Supplement Figures.

A SOD1 CpG oligonucleotide reportedly has a CpG motif 2 nt (CA) from the 3' end. Miller et al. 2013 Lancet Neurol. 12: 435.

Class B CpG oligonucleotide 1826 reportedly has a downstream CpG 2 nt from the 3' end (TT). Lahoud et al. 2012 Proc. Natl. Acad. Sci. USA 109: 16270-16275.

ODN2006 reportedly has a CpG motif 2 nt (TT) from the 3' end. Vollmer et al. 2004 Eur. J. Immunol. 34: 251-262.

Several efficacious CpG oligonucleotides reportedly have a CpG 3 nt (GGG) from the 3' end. WO 2015/108047.

A SMAD CpG oligonucleotide reportedly has a CpG motif 4 nt (CAGC) from the 3' end. Monteleone et al. 2015 NEJM 372: 12.

Class A CpG oligonucleotide 2216 reportedly has a downstream CpG 5 nt from the 3' end (GGGGG). Lahoud et al. 2012 Proc. Natl. Acad. Sci. USA 109: 16270-16275.

A reportedly active CpG oligonucleotide has a CpG motif 7 nt from the 3' end. Pohar et al. 2015 J. Immunol. 194: 3901-3908 and Supplement Figures.

Several reportedly efficacious CpG oligonucleotides have a CpG 9 nt (GGG) from the 3' end. WO 2015/108047.

Deletion of the CpG motif at the 3' end of ODN2006 reportedly left 3 remaining CpG motifs; the furthest downstream CpG was 10 nt (TTTTTTTTTT) (SEQ ID NO: 1520) from the 3' end. This CpG oligonucleotide remained highly active. Pohar et al. 2015 J. Immunol. 194: 3901-3908.

Class B CpG oligonucleotide 1668 reportedly has a sole CpG 11 nt from the 3' end (TTCCTGATGCT) (SEQ ID NO: 1521). Lahoud et al. 2012 Proc. Natl. Acad. Sci. USA 109: 16270-16275.

Another variant of ODN2006, reportedly comprising only two CpG motifs was also active; the further downstream CpG was 13 nt (TTTTTTTTTTTTT) (SEQ ID NO: 1522) from the 3' end. Pohar et al. 2015 J. Immunol. 194: 3901-3908.

Another efficacious CpG oligonucleotide reportedly comprised a CpG motif 15 nt from the 3' end. Pohar et al. 2015 J. Immunol. 194: 3901-3908 and Supplemental Figures.

Another efficacious CpG oligonucleotide reportedly comprised a CpG motif 16 nt from the 3' end. Pohar et al. 2015 J. Immunol. 194: 3901-3908 and Supplemental Figures.

Another efficacious CpG oligonucleotide reportedly comprised a CpG motif 17 nt from the 3' end. Pohar et al. 2015 J. Immunol. 194: 3901-3908 and Supplemental Figures.

Another efficacious CpG oligonucleotide reportedly comprised a CpG motif 19 nt from the 3' end. Pohar et al. 2015 J. Immunol. 194: 3901-3908 and Supplemental Figures.

Another CpG oligonucleotide reportedly showing substantial activity comprises a CpG motif 21 nt (all T) from the 3' end. Pohar et al. 2015 J. Immunol. 194: 3901-3908.

Another efficacious CpG oligonucleotide reportedly had only 1 CpG motif, 21 nt from the 3' end. Pohar et al. 2015 J. Immunol. 194: 3901-3908 and Supplemental Figures.

Another CpG oligonucleotide reportedly showing substantial activity comprises a CpG 27 nt (all T) from the 3' end. Pohar et al. 2015 J. Immunol. 194: 3901-3908.

Efficacious CpG oligonucleotides have thus been reported with a variety of distances between the furthest downstream CpG and the 3' end.

Several types of CpG oligonucleotides have been reported in the literature and can be utilized in accordance with the present disclosure. In some embodiments, these have been divided into various classes and types:

| Class or Type | Reported structural details and sequence motifs | Reported biology | References |
| --- | --- | --- | --- |
| Type K (also known as Class B or B type) | One to five CpG motifs, typically in a PS backbone. Sequence motif: Pu Py C p G Py Py or NNNQ-CpG-WNNN (SEQ ID NO: 1523 Q = T, G or A W = A or T N = any nucleotide | Stimulate humoral response Stimulate proliferation of peripheral blood mononuclear cells and increase expression of IL-6 and IL-12 Stimulate B cell proliferation and antibody production, e.g., IgM and IgG. Trigger pDC to differentiate and produce TNF-alpha | Mutwiri et al. 2004 J. Control. Rel. 97: 1-17; Verthelyi et al. 2001 J. Immunol. 166: 2372-2377; Hartmann et al. 2003 Eur. J. Immun. 33: 1633-1641; WO 98/18810A1; U.S. Pat. No. 8,470,342. |
| Type C (also known as Class C) | Like Type K, are composed entirely of PS nucleotides, but resemble D-type in containing palindromic CpG motifs that form a stem-loop. TCGTCG motif at 5' end, linked by a T spacer to GC-rich palindromic sequence. | Stimulates B cells to secrete IL-6 Stimulates plasmacytoid dendritic cells (pDC) to produce IFN-alpha Induce IP-10 production and strong NK activation | Marshall et al. 2003 J. Leukoc. Biol. 73: 781-92; Vollmer et al. 2004 Eur. J. Immun. 34: 251-262; U.S. Pat. No. 8,470,342. |
| Type D (also known as Class A or A type) | Phosphodiester core flanked by PS terminal nucleotides. A single CpG motif flanked by palindromic sequences that enables formation of a stem-loop. PolyG motifs at 3' and 5' ends that facilitate formation of concatemers, intermolecular tetrads, and high molecular weight aggregates. Sequence motif: RY-CpG-RY | Stimulate cellular response Trigger pDC to mature and secrete IFN-alpha but have no effect on B cells | Verthelyi et al. 2001 J. Immunol. 166: 2372-2377; Krug et al. 2001 Eur. J. Immun. 31: 3026-3037; Uhlmann et al. 2003 Curr. Opin. Drug Discov. Dev. 6: 204-217; Ballas 1996 J. Immun. 157: 1840-1845; Krug et al. 2001 Eur. J. Immunol. 31: 2154-2163; Marshall et al. 2003 J. Leukoc. |

-continued

| Class or Type | Reported structural details and sequence motifs | Reported biology | References |
|---|---|---|---|
| | R = A or G<br>Y = C or T | | Biol. 73: 781-792;<br>Vollmer et al. Eur. J. Immunol. 34: 251-262;<br>U.S. Pat. No. 8,470,342. |
| Type P (for "Palindromic") | Contain double palindromes that can form hairpins at their GC-rich 3'-ends as well as concatamerize due to the presence of 5' palindromes | Strong Type I IFN production | Vollmer et al. 2009 Adv. Drug Del. Rev. 61: 195-204;<br>Samulowit et al. 2010 Oligo. 20: 93-101 |

Many developed CpG oligonucleotides belong to class B and activate B cells and other immune cells to release IL-6, IL-10, IL-12 and MIP-lb. Rutz et al. 2004 Eur. J. Immunol. 34: 2541-2550; and Vollmer et al. 2004 Eur. J. Immunol. 34: 251-262.

It is noted, however, that there is some variability and inconsistency in the reporting of the characteristics of various CpG oligonucleotides and classes thereof; without being wishing to be bound by any particular theory, the present disclosure suggests that this can be due to variations in experimental compositions and methods used by different researchers. It is also noted that, as described herein, there is variability between efficacious CpG oligonucleotides in the mouse and human, and equivalent studies have not been performed in both mouse and human in all cases.

TLR9

TLR9 is Toll-Like Receptor 9, also known as CD289; RefSeq (mRNA) NM_017442; RefSeq (protein) NP_059138.

TLR9 is reported to recognize and to be activated by CpG motifs in bacterial DNA. Hemmi et al. 2000 Nature 408: 740-745; Takeshita et al. 2004 J. Immun. 173: 2552-2561. The crystal structures of three forms of TLR9 have been reported: unliganded, bound to agonistic CpG-DNA, and bound to inhibitory DNA. Ohto et al. 2015 Nature 520: 702-705. A single CpG oligonucleotide reportedly acts as a molecular glue bridging two TLR9 molecules.

TLR9 is reported to be a member of a group of genes known as Toll Like Receptors (TLRs). As reported by Shirota et al. 2015, Vaccines 3: 390-407, TLRs are an important component of the mammalian host's pathogen sensing mechanism. Janeway et al. 2002 Ann. Rev. Immun. 20: 197-216; Akira et al. 2004 Nat. Rev. Immun. 4: 499-511. TLRs are reportedly typically divided into two families, based on their subcellular localization: TLRs 1, 2 and 4-6 are reportedly expressed on the cell surface and sense bacterial cell wall components, whereas TLRs 3 and 7-9 are reportedly expressed in endosomes and sense viral or bacterial nucleic acids. Kawasaki et al. 2014 Front. Immun. Doi: 10.2289/fimmu.2014.00461. The molecular structures recognized by TLRs have been reportedly evolutionarily conserved, are expressed by a variety of infectious microorganisms, and are termed pathogen-associated molecular patterns (PAMPs). For example, TLR4 reportedly recognizes bacterial lipopolysaccharides. Janeway et al. 2002 Ann. Rev. Immun. 20: 197-216; Akira et al. 2004 Nat. Rev. Immun. 4: 499-511.

Gene knockdown and gain of function experiments reported TLR9 as the receptor conferring CpG reactivity by directly engaging bacterial DNA or synthetic CpG oligos in a CpG motif-dependent manner. Hemmi et al. 2000 Nature 408: 740-745; Rutz et al. 2004 Eur. J. Immunol. 34: 2541-2550; Bauer et al. 2001 Proc. Natl. Acad. Sci. USA 98: 9237-9242; Latz et al. 2004 Nat. Immunol. 5: 190-198; Cornelie et al. 2004 J. Biol. Chem. 279: 15124-15129. Human immune cells reported to constituitively express TLR9 are reported to include plasmacytoid dendritic cells (pDC) and B cells. Iwasaki et al. 2004 Nat. Immunol. 5: 987-995. TLR9 expression has also been reported on some nonimmune cells, including pulmonary epithelial cells and lung cancers, keratinocytes, and intestinal epithelium. Droemann et al. 2005 Respir. Res. 6: 1; Platz et al. 2004 J. Immunol. 173: 1219-1223; Lebre et al. 2007 J. Invest. Dermatol. 127: 331-341; Pedersen et al. 2005 Clin. Exp. Immunol. 141: 298-306; Zannetti et al. 2014 J. Immunol. 193: 3398-3408.

Binding of CpG oligos to TLR9 dimers reportedly results in allosteric conformational changes in the TLR9 cytoplasmic signaling domains, resulting in the recruitment of signal adaptor molecules. TLR9 reportedly associates with MyD88 to initiate CpG-mediated effects via signal transducing proteins such as member of the IL-1 receptor-associated kinase (IRAK) family, mitogen activated kinases (MAPK) or IFN regulatory factors. These events are reported to lead to the activation of nuclear factor-kB (NFkB) transcription factors, cytokine production or expression of co-stimulatory molecules in human B cells and pDCs. Lebre et al. 2007 J. Invest. Dermatol. 127: 331-341; Latz 2007 Nat. Immunol. 8: 772-779; Barton et al. 2003 Science 300: 1524-1525; Uematsu et al. 2005 J. Exp. Med. 201: 915-923; Xu et al. 2003 J. Biol. Chem. 278: 36334-36340; Tsujimura et al. 2004 J. Immunol. 172: 6820-6827; Yang et al. 2005 Immunity 23: 465-478; Tailor et al. 2006 Cell Res. 16: 134-140; Krieg et al. 2002 Ann. Rev. Immunol. 20: 709-760; Schetter et al. 2004 Curr. Opin. Drug Discov. Dev. 7: 204-210.

The innate immune response elicited by TLR activation is characterized by the production of pro-inflammatory cytokines, chemokines, type 1 interferons and anti-microbial peptides. This innate response promotes and modulates the adaptive immune system.

As shown above, various characteristics of many CpG oligonucleotides have been reported, along with different classes of CpG oligonucleotides, and the interactions of CpG oligonucleotides with TLR9.

Previously published reports generally used stereorandom CpG oligonucleotides (rather than the present disclosure, which shows data involving stereocontrolled CpG oligonucleotide compositions). Only very few studies have attempted to address the role of stereochemistry in CpG oligonucleotides. One study reported a comparison of Rp- or Sp-enriched CpG-containing oligonucleotides [Yu et al. 2000 Bioorg. Med. Chem. 8:275-284]; however, this study used Rp- or Sp-enriched rather than stereopure oligonucleotides. In contrast to Yu et al., the present disclosure presents, among other things, data from high purity stereocontrolled CpG oligonucleotide compositions. In contrast to Yu et al., CpG oligonucleotides described herein is prepared with 98:2 to >99:1 diastereoselectivity at each chiral internucleotidic linkage. Yu et al. and another study examining chirality [Krieg et al. 2003 Oligonucleotides 13: 491-499] also used only mouse cells and not human cells for TLR9-related studies. The present disclosure shows that stereocontrolled CpG oligonucleotides can demonstrate very different effects in mouse and human cells. In addition, in contrast to the present disclosure, various previous studies did not utilize chirally controlled CpG oligonucleotides wherein the CpG region motif comprised at least one phosphorothioate or other internucleotidic linkage in the Rp conformation and at least one phosphorothioate or other internucleotidic linkage in the Sp conformation.

Some but not all the characteristics of stereorandom CpG oligonucleotides are shared with stereocontrolled CpG oligonucleotide compositions, as detailed herein. Some stereorandom CpG oligonucleotides demonstrate very different immunomodulatory activities than stereocontrolled CpG oligonucleotide compositions of the same base sequence. The present disclosure shows the novel finding that the chirality of the phosphorothioate in a CpG region motif greatly alters the immunogenicity of a CpG oligonucleotide.

The present disclosure thus presents novel CpG region motifs, defined by sequences of chirality of each phosphorothioate (the phosphorothioate being in either the Rp or Sp conformation), and, in some cases, also by the sequences of bases immediately 5' and/or 3' to the CpG dinucleotide.

Chirality

In many synthetic CpG oligonucleotides, the phosphodiester in the sugar-phosphate backbone has been replaced by a modified internucleotidic linkage such as a phosphorothioate (PS). In some embodiments, PS increases stability against nucleases. A PS comprises a chiral center at the phosphorus atom which can exist in either of two configurations: Rp or Sp.

The present disclosure demonstrates, among other things, that the chirality (Rp or Sp) of the phosphorothioates and in and around the CpG (in the CpG region motif) are important for activity.

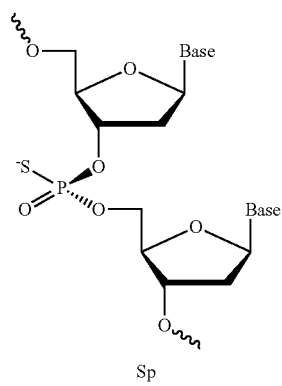

Sp

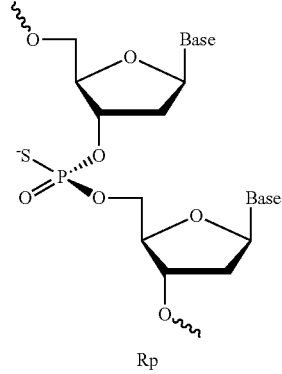

Rp

In the present disclosure, we provide novel data related to the effects of the chirality of the phosphorothioates in and around the CpG motif, leading to new insights into the structural requirements thereof. The present disclosure also shows that the effects of chirality differ in mouse and human. Thus, data generated from mouse studies is not necessarily predictive of the effects in human.

The present disclosure demonstrates in both mouse models and human PBMCs that a stereorandom oligonucleotide and a corresponding chirally controlled oligonucleotide composition can display very different activities against TLR9. The present disclosure demonstrates that for mouse TLR9, some stereopure CpG-oligos with all-Sp backbone are strong agonists, whose activities are further modulated by the chirality of the PS bonds in and adjacent to the CpG motifs (CpG regions). Human TLR9 (hTLR9) activities are affected very differently, in several cases, with agonists preferring Sp chirality on the 3' of CpG motif. Furthermore, the present disclosure demonstrates that, in many oligonucleotides shown herein, 2'-modifications on the ribose ring completely eliminate agonist activity on mouse TLR9, but not on human TLR9, which is more relevant to drug discovery for human diseases. Mouse and human TLR9 respond differently to stereopure CpG oligonucleotide compositions with 2'-modifications and CpG methylations. These data surprisingly define phosphorothioate chirality as an important determinant of TLR9 activity.

The present disclosure presents various CpG region motifs which can be used to design CpG oligonucleotides which capable of eliciting a desired immune response.

A CpG region motif is a particular motif, comprising the CpG dinucleotide, plus one or more of the positions flanking (immediately 5' and/or 3' of) the CpG, which positions are defined by the base sequence, the chemistry of the phosphate or internucleoside linker (e.g., a phosphorothioate), and/or the chirality of the internucleoside linker (e.g., if the phosphorothioate at a particular position is in the Rp or Sp configuration).

While the present disclosure showed that, in at least some chirally controlled CpG oligonucleotide compositions, some CpG region motifs had greater immunomodulatory activity (e.g., greater agonistic or greater antagonistic activity) than others, the present disclosure encompasses any chirally controlled CpG oligonucleotide composition, wherein the CpG region motif comprises a stereodefined phosphorothioate or internucleotidic linkage, wherein the CpG oligonucleotide demonstrates a greater agonistic or antagonistic activity than a negative control (e.g., in the absence of the oligonucleotide composition). The present disclosure thus encompasses a chirally controlled CpG oligonucleotide comprising any CpG region motif disclosed herein.

Example CpG region motifs include, as non-limiting examples, listed below in Table 1, each presented in 5' to 3' direction:

TABLE 1

EXAMPLE CpG REGION MOTIFS

1. $N_1$-p-$N_2$-p-C-p-G-p-$N_3$-p-$N_4$ p
2. $N_1$-(*)-$N_2$-(*)-C-(*)-G-(*)-$N_3$-(*)-$N_4$-(*)
3. $N_1$-(*S)-$N_2$-(*S)-C-(*S)-G-(*S)-$N_3$-(*S)-$N_4$-(*S)
4. $N_1$-(*R)-$N_2$-(*R)-C-(*R)-G-(*R)-$N_3$-(*R)-$N_4$-(*R)
5. $N_1$-(*R/S)-$N_2$-(*R/S)-C-(*R)-G-(*S)-$N_3$-(*R/S)-$N_4$-(*R/S)
6. $N_1$-(*R)-$N_2$-(*S)-C-(*R)-G-(*S)-$N_3$-(*S)-$N_4$-(*S)
7. $N_1$-(*S)-$N_2$-(*R)-C-(*R)-G-(*S)-$N_3$-(*S)-$N_4$-(*S)
8. $N_1$-(*S)-$N_2$-(*S)-C-(*R)-G-(*S)-$N_3$-(*R)-$N_4$-(*S)
9. $N_1$-(*S)-$N_2$-(*S)-C-(*R)-G-(*S)-$N_3$-(*S)-$N_4$-(*R)
10. $N_1$-(*R)-$N_2$-(*S)-C-(*R)-G-(*S)-$N_3$-(*S)-$N_4$-(*R)
11. $N_1$-(*R)-$N_2$-(*S)-C-(*R)-G-(*S)-$N_3$-(*R)-$N_4$-(*S)
12. $N_1$-(*R)-$N_2$-(*R)-C-(*R)-G-(*S)-$N_3$-(*S)-$N_4$-(*S)
13. $N_1$-(*S)-$N_2$-(*S)-C-(*R)-G-(*S)-$N_3$-(*R)-$N_4$-(*R)
14. $N_1$-(*S)-$N_2$-(*R)-C-(*R)-G-(*S)-$N_3$-(*R)-$N_4$-(*S)
15. $N_1$-(*R)-$N_2$-(*R)-C-(*R)-G-(*S)-$N_3$-(*R)-$N_4$-(*S)
16. $N_1$-(*R)-$N_2$-(*R)-C-(*R)-G-(*S)-$N_3$-(*S)-$N_4$-(*R)
17. $N_1$-(*R)-$N_2$-(*S)-C-(*R)-G-(*S)-$N_3$-(*R)-$N_4$-(*R)
18. $N_1$-(*S)-$N_2$-(*R)-C-(*R)-G-(*S)-$N_3$-(*S)-$N_4$-(*S)
19. Pu-(*R/S)-Py-(*R/S)-C-(*R)-G-(*S)-Py-(*R/S)-Py/Pu-(*R/S)
20. Py/Pu-(*R/S)-Py-(*R/S)-C-(*R)-G-(*S)-Py-(*R/S)-Py/Pu-(*R/S)
21. Py-(*R/S)-Py-(*R/S)-C-(*R)-G-(*S)-Py-(*R/S)-Pu-(*R/S)
22. Pu-(*R/S)-Py-(*R/S)-C-(*R)-G-(*S)-Py-(*R/S)-Py/Pu-(*R/S)
23. Py-(*R/S)-Pu-(*R/S)-C-(*R)-G-(*S)-Pu-(*R/S)-Py-(*R/S)
24. $N_1$-(*R)-$N_2$-(*R)-m5C-(*R)-G-(*R)-$N_3$-(*R)-$N_4$-(*R)
25. Pu-(*R)-Py-(*R)-m5C-(*R)-G-(*R)-Py-(*R)-Py/Pu-(*R)
26. $N_1$-(*R/S)-$N_2$-(*R/S)-m5C-(*R)-G-(*S)-$N_3$-(*R/S)-$N_4$-(*R/S)
27. $N_1$-(*R/S)-$N_2$-(*R/S)-C-(*R)-G-(*S)-$N_3$-(*R/S)-$N_4$-(*R/S), wherein the C and G are both 2'H (DNA)
28. $N_1$-(*R/S)-$N_2$-(*R/S)-m5C-(*R)-G-(*S)-$N_3$-(*R/S)-$N_4$-(*R/S)
29. $N_1$-(*R)-$N_2$-(*R)-C-(*R)-G-(*R)-$N_3$-(*R)-$N_4$-(*R)
30. $N_1$-(*R)-Py-(*R)-C-(*R)-G-(*R)-Py-(*R)-$N_2$-(*S)
31. $N_1$-(*S)-Py-(*R)-C-(*R)-G-(*R)-Py-(*S)-$N_2$-(*S)
32. Pu-(*S)-Py-(*S)-C-(*R)-G-(*S)-Py-(*S)-$N_2$-(*S), wherein C and G are 2'-MOE or 2'-OMe, and C is methylated or unmethylated
33. $N_1$-(*S)-$N_2$-(*S)-m5C-(*R)-G-(*S)-$N_3$-(*S)-$N_4$-(*S)
34. $N_1$-(*R/S)-C-(*R/S)-G-(*S)-$N_2$
35. $N_1$-(*S)-C-(*S)-G-(*S)-$N_2$-(*S)
36. $N_1$-(*S)-C-(*S)-G-(*S)-$N_2$-(*S), wherein the C and G are both 2'H (DNA)
37. $N_1$-(*S)-C-(*S)-G-(*S)-$N_2$-(*S), wherein each nucleoside is 2'H (DNA)
38. $N_1$-(*S)-C-(*S)-G-(*S)-$N_2$-(*S), wherein each nucleoside is 2'-modified
39. $N_1$-(*S)-C-(*S)-G-(*S)-$N_2$-(*S), wherein each nucleoside is 2'-MOE
40. T-(*S)-C-(*S)-G-(*S)-T-(*S)-$N_1$
41. T-(*S)-C-(*S)-G-(*S)-T-(*S)-$N_1$, wherein C and G are both 2'H (DNA)
42. T-(*S)-C-(*S)-G-(*S)-T-(*S)-$N_1$, wherein each nucleoside is 2'H (DNA)
43. $N_1$-(*S)-C-(*R)-G-(*S)-$N_2$-(*S)
44. $N_1$-(*S)-C-(*R)-G-(*S)-$N_2$-(*S), wherein the C and G are both 2'H (DNA)
45. $N_1$-(*S)-C-(*R)-G-(*S)-$N_2$-(*S), wherein each nucleoside is 2'H (DNA)
46. Py-(*S)-C-(*R)-G-(*S)-Py-(*S)
47. Py-(*S)-C-(*R)-G-(*S)-Py-(*S), wherein the C and G are both 2'H (DNA)
48. Py-(*S)-C-(*R)-G-(*S)-Py-(*S), wherein each nucleoside is 2'H (DNA)
49. T-(*S)-C-(*R)-G-(*S)-T-(*S)
50. T-(*S)-C-(*R)-G-(*S)-T-(*S), wherein the C and G are both 2'H (DNA)
51. T-(*S)-C-(*R)-G-(*S)-T-(*S), wherein each nucleoside is 2'H (DNA)
52. $N_1$-(*R)-C-(*R)-G-(*S)-N-(*S)
53. $N_1$-(*R)-C-(*R)-G-(*S)-N-(*S), wherein the C and G are both 2'H (DNA)
54. $N_1$-(*R)-C-(*R)-G-(*S)-N-(*S), wherein each nucleoside is 2'H (DNA)
55. $N_1$-(*R)-C-(*R)-G-(*S)-N-(*R)
56. $N_1$-(*R)-C-(*R)-G-(*S)-N-(*R), wherein the C and G are both 2'H (DNA)
57. $N_1$-(*R)-C-(*R)-G-(*S)-N-(*R), wherein each nucleoside is 2'H (DNA)
58. $N_1$-(*R)-C-(*R)-G-(*R)-$N_2$
59. Py-(*R)-C-(*R)-G-(*R)-Py
60. $N_1$-(*R/S)-C-(*S)-G-(*S)-$N_2$
61. $N_1$-(*R/S)-C-(*S)-G-(*S)-$N_2$, wherein the C and G are both 2'H (DNA)
62. $N_1$-(*R/S)-C-(*S)-G-(*S)-$N_2$, wherein each nucleoside is 2'H (DNA)
63. $N_1$-(*R)-C-(*R)-G-(*R)-$N_2$-(*R)-$N_3$, wherein each nucleoside is 2'-modified and C is methylated or unmethylated
64. $N_1$-(*R)-C-(*R)-G-(*R)-$N_2$-(*R)-$N_3$, wherein each nucleoside is 2'-MOE and C is methylated or unmethylated
65. $N_1$-(*R)-m5C-(*R)-G-(*R)-$N_2$-(*R)-$N_3$, wherein each nucleoside is 2'-modified
66. $N_1$-(*R)-m5C-(*R)-G-(*R)-$N_2$-(*R)-$N_3$, wherein each nucleoside is 2'-MOE, 2'-F or 2'-OMe TABLE 1-continued EXAMPLE CpG REGION MOTIFS 67. $N_1$-(*R)-m5C-(*R)-G-(*R)-$N_2$-(*R)-$N_3$, wherein each nucleoside is 2'-MOE
68. $N_1$-(*R/S)-C-(*R)-G-(*R/S)-$N_2$, wherein the two *R/S are not both R or both S
69. $N_1$-(*R/S)-C-(*S)-G-(*R/S)-$N_2$, wherein the two *R/S are not both R or both S
70. $N_1$-(*R/S)-C-(*R/S)-G-(*R/S)-$N_2$
71. $N_1$-(*R/S)-C-(*R/S)-G-(*R/S)-$N_2$, wherein at least one *R/S is *R and at least one *R/S is *S
72. $N_1$-(*R/S)-C-(*R/S)-G-(*R/S)-$N_2$, wherein at least one *R/S is *R and at least one *R/S is *S, and wherein C is unmethylated
73. $N_1$-(*R/S)-C-(*R/S)-G-(*R)-$N_2$
74. $N_1$-(*R/S)-C-(*R/S)-G-(*S)-$N_2$
75. $N_1$-(*R)-C-(*R)-G-(*S)-$N_2$
76. $N_1$-(*R)-C-(*S)-G-(*S)-$N_2$
77. $N_1$-(*R)-C-(*S)-G-(*R)-$N_2$
78. $N_1$-(*S)-C-(*R)-G-(*S)-$N_2$
79. $N_1$-(*S)-C-(*R)-G-(*R)-$N_2$
80. $N_1$-(*S)-C-(*S)-G-(*R)-$N_2$
81. Py-(*R/S)-C-(*R/S)-G-(*R/S)-$N_1$
82. Py-(*R/S)-C-(*R/S)-G-(*R/S)-$N_1$, wherein at least one *R/S is *R and at least one *R/S is *S
83. Py-(*R/S)-C-(*R/S)-G-(*R/S)-$N_1$, wherein at least one *R/S is *R and at least one *R/S is *S, and wherein C is unmethylated
84. Py-(*R)-C-(*R)-G-(*S)-$N_1$
85. Py-(*R)-C-(*S)-G-(*S)-$N_1$
86. Py-(*R)-C-(*S)-G-(*R)-$N_1$
87. Py-(*S)-C-(*R)-G-(*S)-$N_1$
88. Py-(*S)-C-(*R)-G-(*R)-$N_1$
89. Py-(*S)-C-(*S)-G-(*R)-$N_1$
90. $N_1$-(*R/S)-C-(*R/S)-G-(*R/S)-Py
91. $N_1$-(*R/S)-C-(*R/S)-G-(*R/S)-Py, wherein at least one *R/S is *R and at least one *R/S is *S
92. $N_1$-(*R/S)-C-(*R/S)-G-(*R/S)-Py, wherein at least one *R/S is *R and at least one *R/S is *S, and wherein C is unmethylated
93. $N_1$-(*R)-C-(*R)-G-(*S)-Py
94. $N_1$-(*R)-C-(*S)-G-(*S)-Py
95. $N_1$-(*R)-C-(*S)-G-(*R)-Py
96. $N_1$-(*S)-C-(*R)-G-(*S)-Py
97. $N_1$-(*S)-C-(*R)-G-(*R)-Py
98. $N_1$-(*S)-C-(*S)-G-(*R)-Py
99. Py-(*R/S)-C-(*R/S)-G-(*R/S)-Py
100. Py-(*R/S)-C-(*R/S)-G-(*R/S)-Py, wherein at least one *R/S is *R and at least one *R/S is *S
101. Py-(*R/S)-C-(*R/S)-G-(*R/S)-Py, wherein at least one *R/S is *R and at least one *R/S is *S, and wherein C is unmethylated
102. Py-(*R)-C-(*R)-G-(*S)-Py
103. Py-(*R)-C-(*S)-G-(*S)-Py
104. Py-(*R)-C-(*S)-G-(*R)-Py
105. Py-(*S)-C-(*R)-G-(*S)-Py
106. Py-(*S)-C-(*R)-G-(*R)-Py
107. Py-(*S)-C-(*S)-G-(*R)-Py
108. $N_1$-(*S)-C-(*R)-G
109. $N_1$-(*R)-C-(*R)-G
110. $N_1$-(*S)-C-(*S)-G
111. $N_1$-(*R)-C-(*S)-G
112. C-(*R/S)-G-(*R/S)
113. C-(*R)-G-(*R)
114. C-(*R)-G-(*S)
115. C-(*S)-G-(*R)
116. C-(*S)-G-(*S)
117. C-(*R/S)-G
118. C-(*R)-G
119. C-(*S)-G
120. $N_1$-(*R/S)-$N_2$-(*R/S)-C-(*R/S)-G-(*R/S)-$N_3$-(*R/S)-$N_4$
121. m5C-(*R)-m5C-(*R)-G-(*R)-$N_1$, where all the nucleosides are 2'-MOE.
122. m5C-(*R)-m5C-(*R)-G-(*R)-Py, where all the nucleosides are 2'-MOE.
123. m5C-(*R)-m5C-(*R)-G-(*R)-T, where all the nucleosides are 2'-MOE.
124. m5C-(*R)-m5C-(*S)-G-(*R)-T, where all the nucleosides are 2'-MOE.
125. $N_1$-(*R)-m5C-(*R)-G-(*R)-$N_2$, wherein $N_1$ is methylated or not methylated, and all the nucleosides are 2'-MOE.
126. $N_1$-(*R)-m5C-(*R)-G-(*R)-Py, wherein $N_1$ is methylated or not methylated, and all the nucleosides are 2'-MOE.
127. $N_1$-(*R/S)-m5C-(*R/S)-G-(*R/S)-$N_2$, wherein at least 2 of the *R/S are *R, all the nucleosides are 2'-MOE, and $N_1$ and $N_2$ are methylated or not methylated.
128. $N_1$-(*R)-m5C-(*R/S)-G-(*R)-$N_2$, wherein at least 2 of the *R/S are *R, all the nucleosides are 2'-MOE, and $N_1$ and $N_2$ are methylated or not methylated.
129. $N_1$-(*R)-[C]-(*R)-[G]-(*R)-$N_2$, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.

TABLE 1-continued

EXAMPLE CpG REGION MOTIFS

Figure 2:
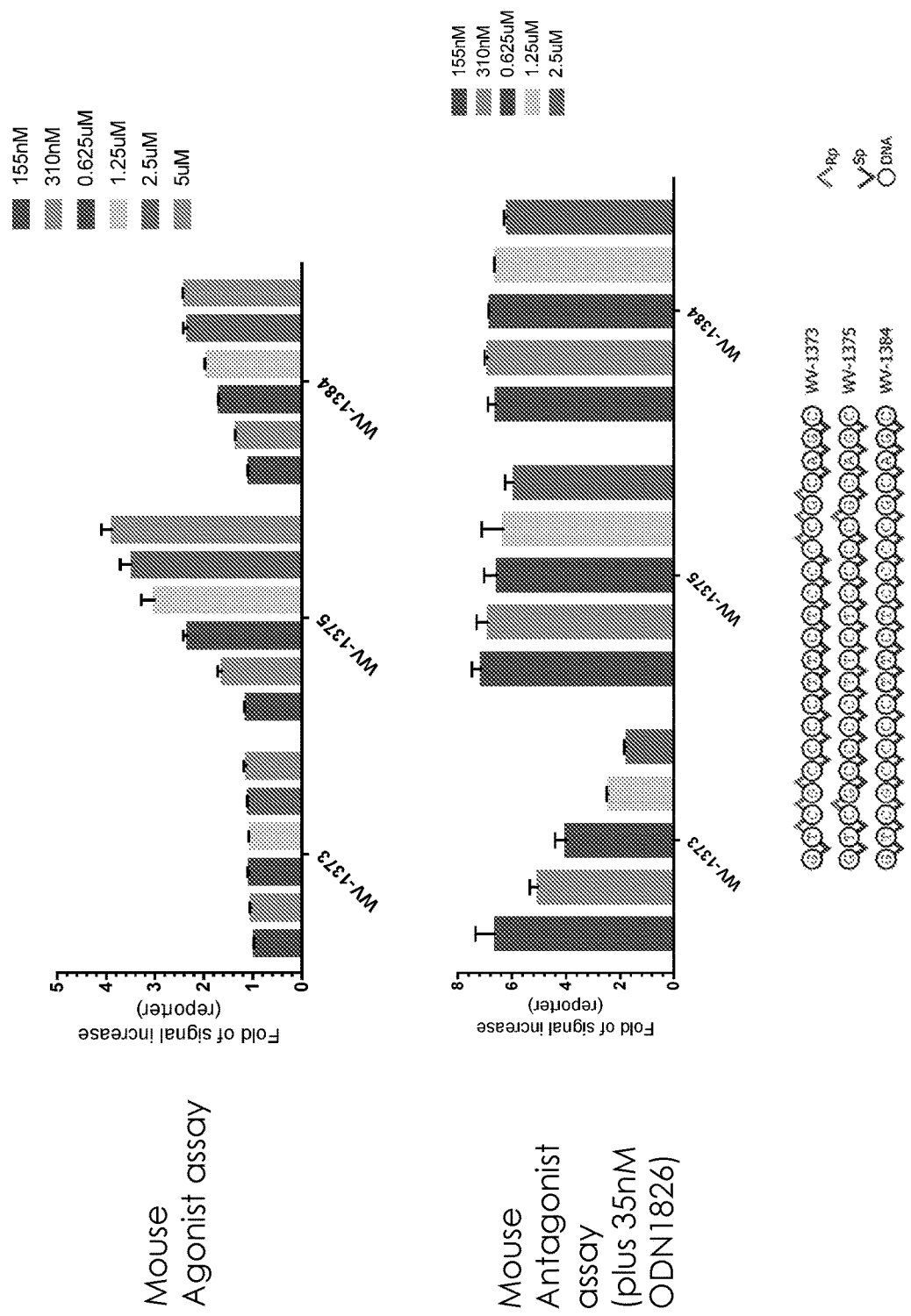
FIG. 2 shows that stereochemistry of CpG and flanking linkages modulate activities of mouse TLR9; data from SMAD7 series.
Figure 3:
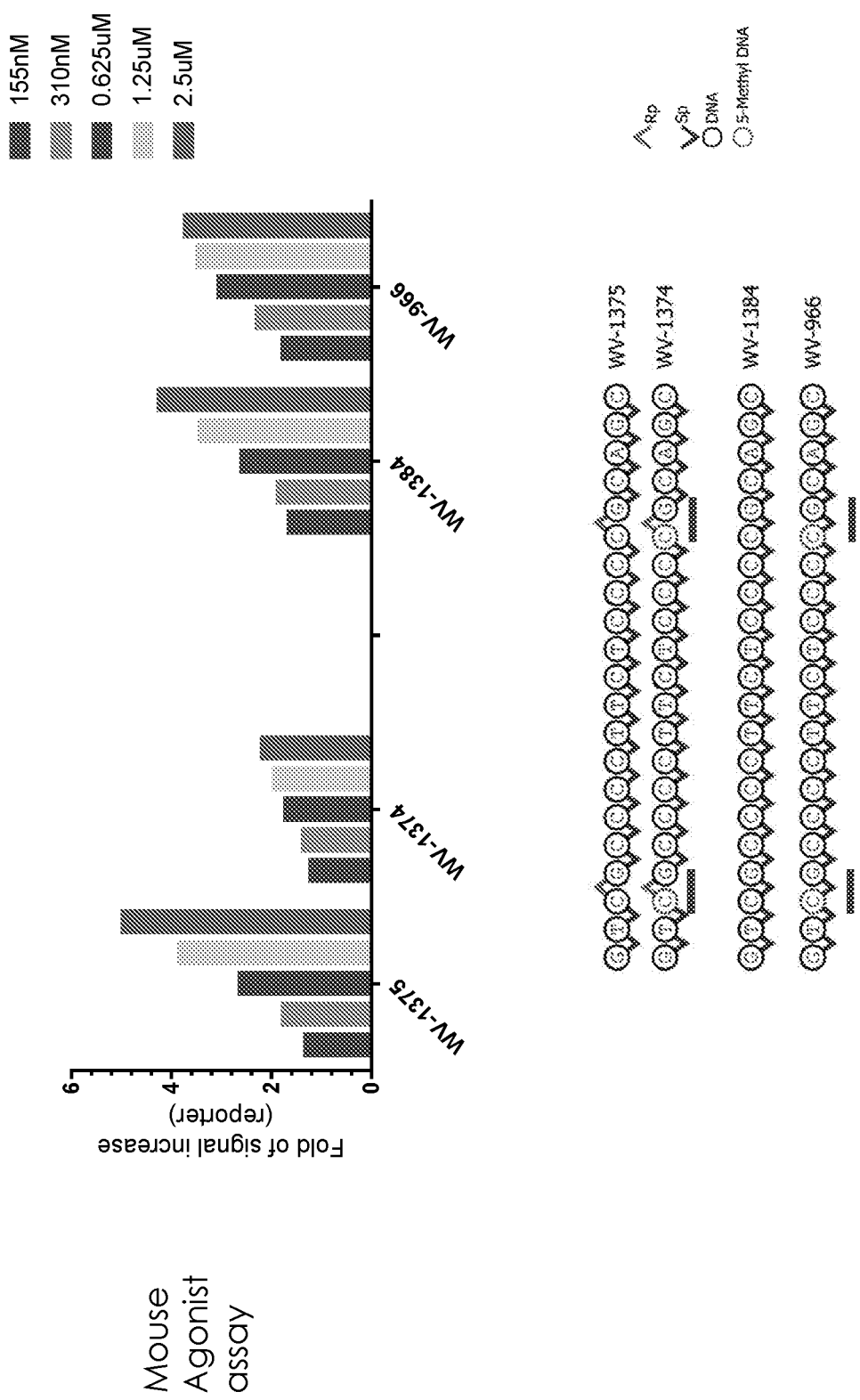
FIG. 3 shows that methylation of CpG does not always significantly reduce mouse TLR9 activity and that the results are also dependent on stereochemistry of internucleotidic linkages; data from SMAD7 series.
Figure 10:
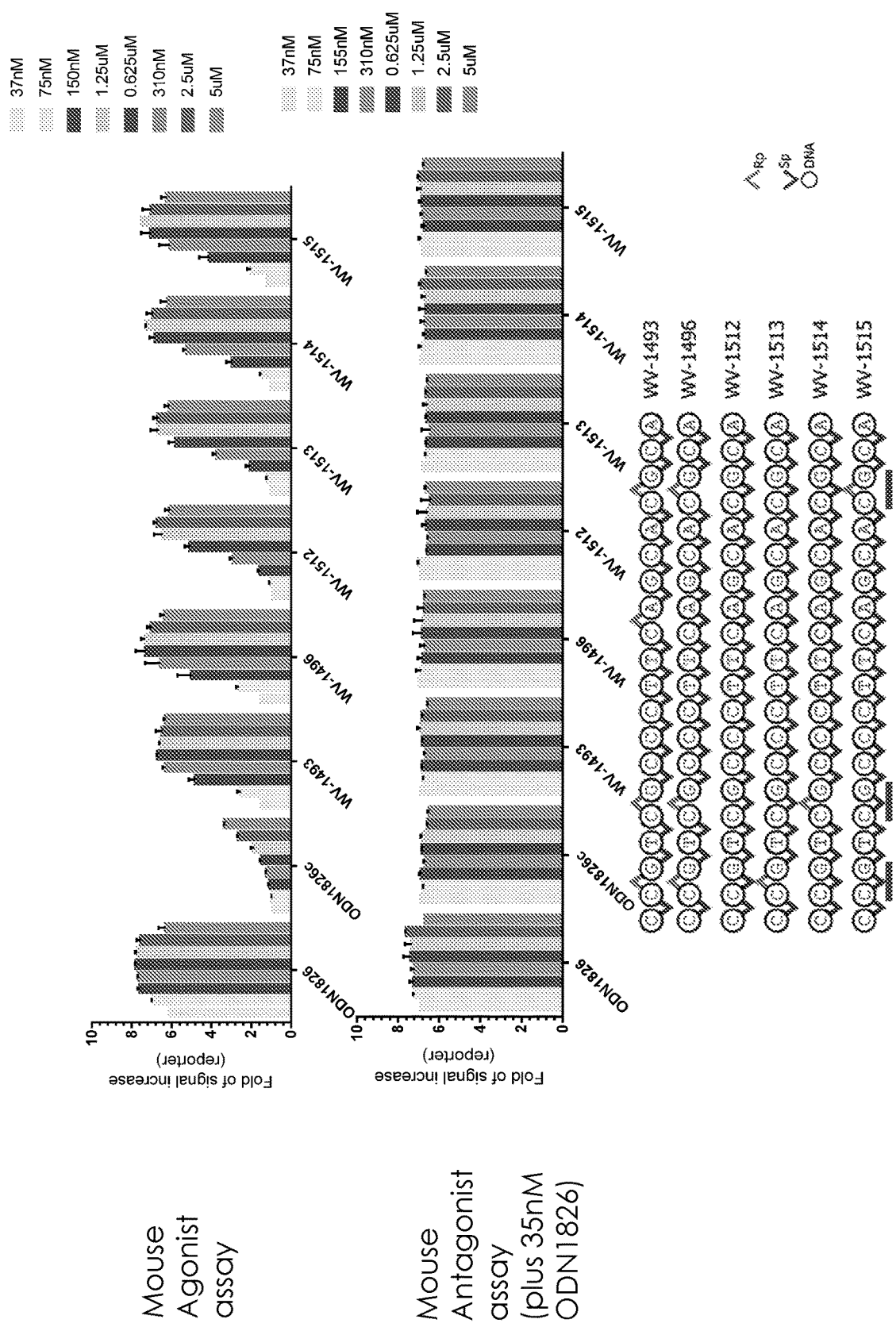
FIG. 10 shows that stereochemistry of the CpG region motif affects activities of mouse TLR9; data from SOD1 series.
Figure 11:
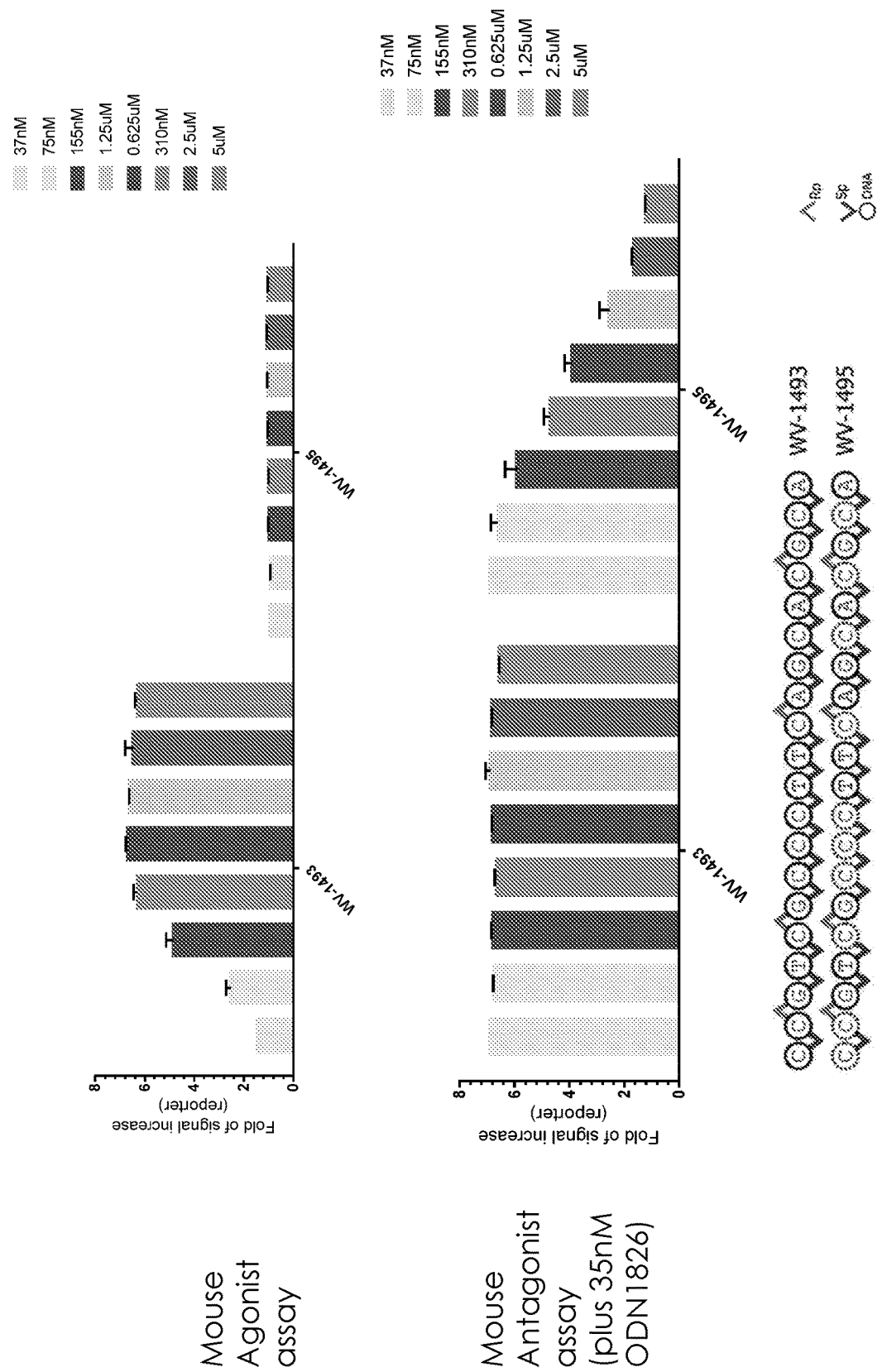
FIG. 11 shows that methylation of CpG may affect activities of mouse TLR9; data from SOD1 series.
Figure 12:
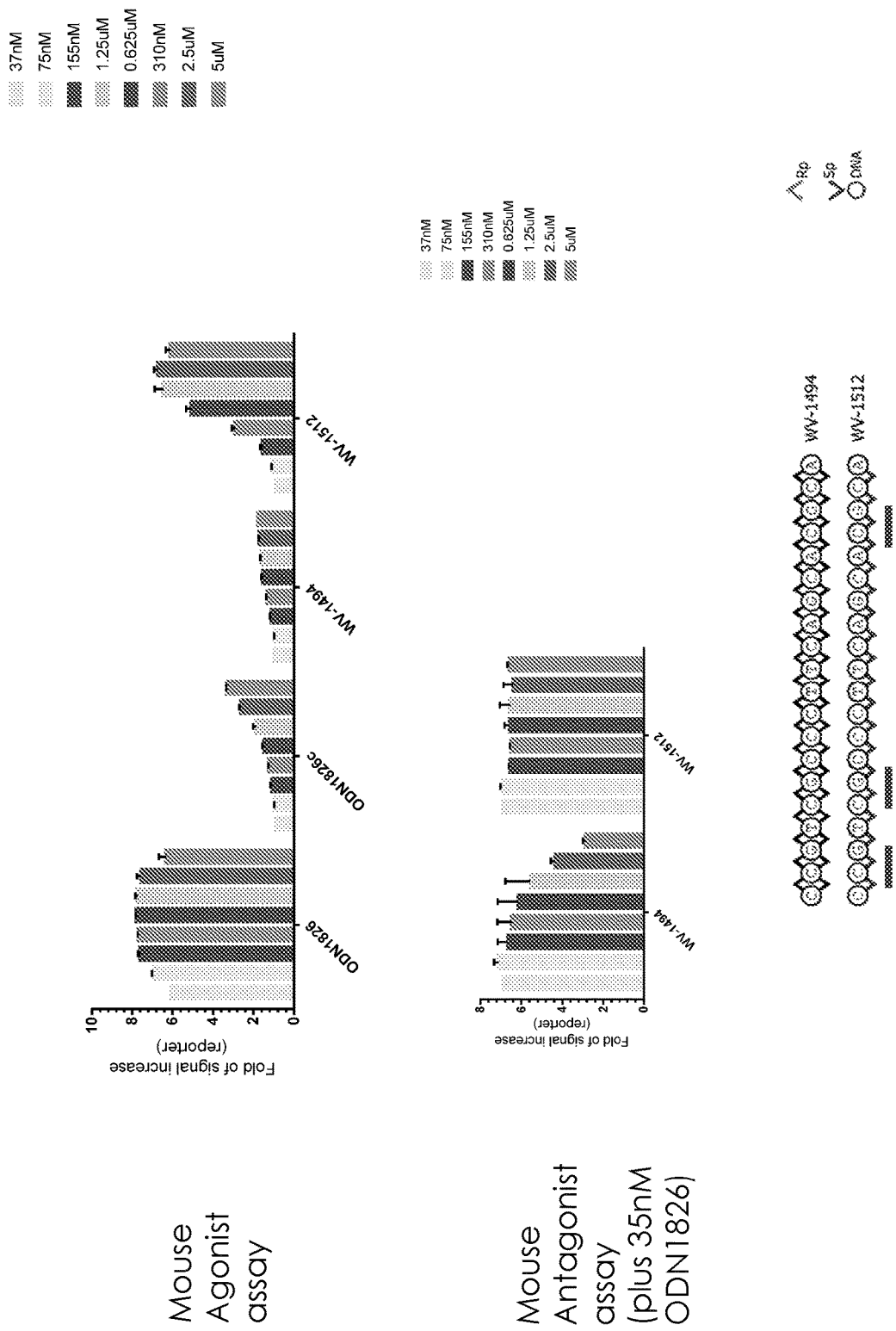
FIG. 12 shows that stereochemistry of oligonucleotide backbone internucleotidic linkages affects activities of mouse TLR9; data from SOD1 series.
Figure 13:
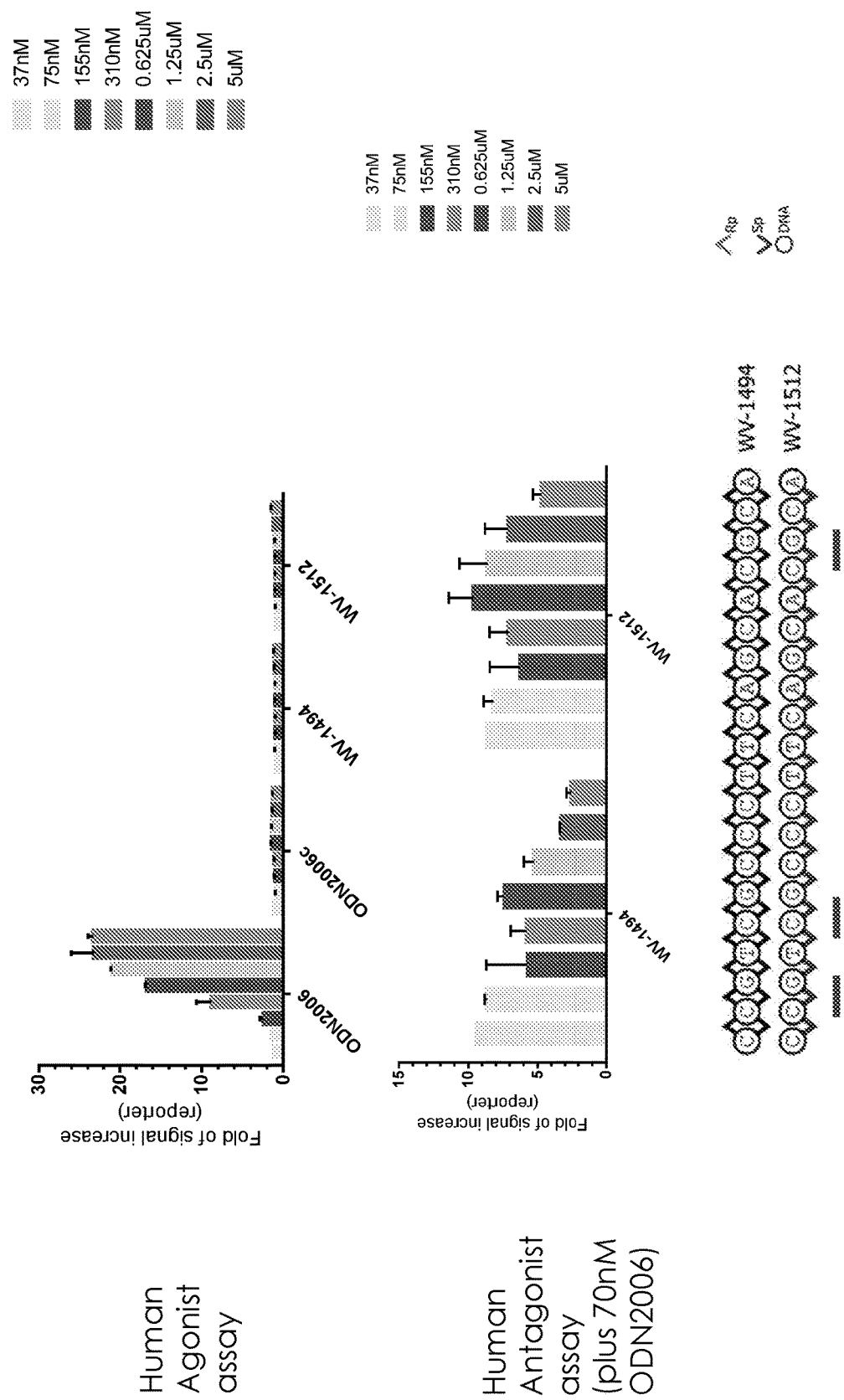
FIG. 13 shows assay results of certain oligonucleotides of the SOD1 series.

130. $N_1$-(*S)-[C]-(*R)-[G]-(*S)-$N_2$, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.
131. $N_1$-(*S)-[C]-(*R)-[G]-(*S)-$N_2$, where $N_1$ is 2'H; [C] is C, m5C, 2'-MOE C, or 2'-MOE m5C; [G] is optionally G, 2'-Ome G, or 2'-MOE G; and $N_2$ is 2'H.
132. $N_1$-(*R)-[C]-(*R)-[G]-(*R)-Pyeo, where $N_1$ and Py are 2'H, 2'-MOE or 2'OMe; and [C] is C or 2'-MOE C; and [G] is G or 2'-MOE G
133. $N_1$-(*R)-[C]-(*R)-[G]-(*R)-Neo, where $N_1$ and $N_2$ are 2'H, 2'-MOE or 2'OMe; and [C] is 2'-MOE m5C
134. Py-(*R)-C-(*R)-G-(*R)-Py
135. Py-(*R)-C-(*R)-G-(*R)-Py
136. Py-(*S)-C-(*R)-G-(*S)-Py
137. Py-(*S)-C-(*S)-G-(*S)-Py
138. Py-(*R)-[C]-(*R)-[G]-(*R)-Py, where [C] is 2'-MOE C; and [G] is 2'-MOE G
139. Py-(*R)-[C]-(*R)-[G]-(*S)-Py, where [C] is 2'-MOE C; and [G] is 2'-MOE G
140. Py-(*R)-[C]-(*R)-G-(*R)-Py
141. Py-(*R)-[C]-(*R)-G-(*R)-Py
142. Py-(*R)-[C]-(*R)-[G]-(*R)-$N_1$, where [C] is 2'-OMe m5C, and [G] is 2'-OMe G, and $N_1$ is 2'-OMe
143. Py-(*R)-[C]-(*R)-[G]-(*R)-Py, where [C] is 2'-OMe m5C, and [G] is 2'-OMe G
144. Py-(*R)-[C]-(*R)-[G]-(*R)-Py, where [C] is 2'-OMe C and [G] is 2'-OMe G
145. Py-(*S)-[C]-(*R)-[G]-(*S)-Py, where [C] is 2'-MOE C and [G] is 2'-MOE G
146. Py-(*S)-[C]-(*R)-G-(*S)-Py
147. Py-(*S)-[C]-(*R)-[G]-(*S)-Py, where [C] is 2'-MOE m5C and [G] is 2'-MOE G
148. Py-(*S)-[C]-(*R)-[G]-(*S)-Py, where [C] is 2'-OMe m5C and [G] is 2'-OMe G
149. Py-(*S)-[C]-(*R)-[G]-(*S)-Py, where [C] is 2'-OMe C and [G] is 2'-OMe G
150. Py-(*R)-[C]-(*R)-[G]-(*R)-Py, where both [C] and [G] are 2'-modified
151. $N_1$-(*R)-[C]-(*R)-[G]-(*R)-$N_2$, where both [C] and [G] are 2'-modified
152. N-(*X)-C-(*R/S)-G*R/SN
153. N-(*R/S)-C-(*X)-G*R/SN
154. N-(*R/S)-C-(*R/S)-G-(*X)-N
155. N-(*X)-C-(*R)-G-(*R)-N
156. N-(*X)-C-(*R)-G-(*S)-N
157. N-(*X)-C-(*S)-G-(*R)-N
158. N-(*X)-C-(*S)-G-(*S)-N
159. N-(*R)-C-(*X)-G-(*R)-N
160. N-(*R)-C-(*X)-G-(*S)-N
161. N-(*S)-C-(*X)-G-(*R)-N
162. N-(*S)-C-(*X)-G-(*S)-N
163. N-(*R)-C-(*R)-G-(*X)-N
164. N-(*R)-C-(*S)-G-(*X)-N
165. N-(*S)-C-(*S)-G-(*X)-N
166. N-(*S)-C-(*R)-G-(*X)-N
167. N-(*X)-C-(*R)--(*X)-N
168. N-(*X)-C-(*S)--(*X)-N
169. N-(*R)-C-(*X)--(*X)-N
170. N-(*S)-C-(*X)--(*X)-N
171. N-(*X)-C-(*X)-G-(*R)-N
172. N-(*X)-C-(*X)-G-(*S)-N
173. N-(*D)-C-(*R/S)-G-(*R/S)-N
174. N-(*R/S)-C-(*D)-G-(*R/S)-N
175. N-(*R/S)-C-(*R/S)-G-(*D)-N
176. N-(*D)-C-(*R)-G-(*R)-N
177. N-(*D)-C-(*R)-G-(*S)-N
178. N-(*D)-C-(*S)-G-(*R)-N
179. N-(*D)-C-(*S)-G-(*S)-N
180. N-(*R)-C-(*D)-G-(*R)-N
181. N-(*R)-C-(*D)-G-(*S)-N
182. N-(*S)-C-(*D)-G-(*R)-N
183. N-(*S)-C-(*D)-G-(*S)-N
184. N-(*R)-C-(*R)-G-(*D)-N
185. N-(*R)-C-(*S)-G-(*D)-N
186. N-(*S)-C-(*S)-G-(*D)-N
187. N-(*S)-C-(*R)-G-(*D)-N
188. N-(*D)-C-(*R)--(*D)-N
189. N-(*D)-C-(*S)--(*D)-N
190. N-(*R)-C-(*D)-G-(*D)-N
191. N-(*S)-C-(*D)-G-(*D)-N
192. N-(*D)-C-(*D)-G-(*R)-N
193. N-(*D)-C-(*D)-G-(*S)-N In these various motifs, and as otherwise used herein:
$N_1$, $N_2$, $N_3$, $N_4$: a nucleobase which is A, G, C, T or U, or a modified variant thereof.
p: a phosphodiester linkage
*a phosphorothioate which can be in the Rp or Sp configuration, in a stereomixture
*R: a phosphorothioate in the Rp configuration
*S: a phosphorothioate in the Sp configuration
*R/S: a phosphorothioate which is defined as Rp or Sp, in any one of several stereopure preparations In the present disclosure, unless otherwise specified, the terms "*" and "*R/S" are distinguished. "*" is used in a stereomixture; "*R/S" and "*S/R" (which are equivalent) represent any of several defined stereopure preparations. For example, the motif (2) $N_1$-(*)-$N_2$-(*)-C-(*)-G-(*)-$N_3$-(*)-$N_4$-(*) represents a stereomixture of molecules; for example, a mixture comprising molecules with motifs (6) and (7) and (8) and (9), etc. In contrast, the motif (5) $N_1$-(*R/S)—$N_2$-(*R/S)—C—(*R)-G-(*S)—$N_3$-(*R/S)—$N_4$-(*R/S) represents any one of several defined molecules; for example, a preparation of molecules only of motif (6) or only (7) or only (8) or only (9), etc. Thus, motif (2) $N_1$-(*)-$N_2$-(*)-C-(*)-G-(*)-$N_3$-(*)-$N_4$-(*) is a mixture of, for example, molecules of motifs (3), (4), (6), (7), (8), (9), (10), (11), (12), (13), (14), (15), (16), (17) and (18). The motif (5) $N_1$-(*R/S)—$N_2$-(*R/S)—C—(*R)-G-(*S)—$N_3$-(*R/S)—$N_4$-(*R/S) represents molecules of motifs (3), (4), (6), (7), (8), (9), (10), (11), (12), (13), (14), (15), (16), (17) or (18). By "stereopure" in this context means that the majority (in various cases, at least 50%, at least 60%, at least 70%, at least 80%, at least 90% or at least 95%) of the CpG oligonucleotides all have the same CpG region motif. Thus, as another non-limiting example, a preparation wherein 80% of the CpG oligonucleotides are of the motif (14) is an example of a preparation of a CpG oligonucleotide of CpG region motif (5) $N_1$-(*R/S)—$N_2$-(*R/S)—C—(*R)-G-(*S)—$N_3$-(*R/S)—$N_4$-(*R/S). A non-limiting example of $N_1$-(*)-$N_2$-(*)-C-(*)-G-(*)-$N_3$-(*)-$N_4$-(*) is WV-1494 (FIGS. 12 and 13). Some non-limiting examples of CpG oligonucleotides of motif $N_1$-(*R/S)—$N_2$-(*R/S)—C—(*R)-G-(*S)—$N_3$-(*R/S)—$N_4$-(*R/S) include WV-1375 (FIGS. 2 and 3), WV-1374 (FIG. 3); WV-1696 (FIGS. 7 and 10), WV-1698 (FIG. 7), WV-1493 (FIGS. 10 and 11). In some embodiments of the present disclosure, the CpG oligonucleotide comprises a strand of 15 to 49 nucleotides, the strand comprising at least two copies of the CpG region motif of $N_1$-(*R/S)—$N_2$-(*R/S)—C—(*R)-G-(*S)—$N_3$-(*R/S)—$N_4$-(*R/S). In some embodiments of the present disclosure, the CpG oligonucleotide comprises a strand of 15 to 49 nucleotides, the strand comprising at least two copies of the CpG region motif of $N_1$-(*R/S)—$N_2$-(*R/S)—C—(*R)-G-(*S)—$N_3$-(*R/S)—$N_4$-(*R/S), wherein the C and G are both 2'H (DNA). Another non-limiting example of a motif is $N_1$-(*R/S)—$N_2$-(*R/S)—C—(*R)-G-(*S)—$N_3$-(*R/S)—$N_4$-(*R/S), where C and G are both neither 2'-MOE or 2'-OMe.

Another non-limiting example of a motif is $N_1$-(*R/S)—$N_2$-(*R/S)—C—(*R)-G-(*S)—$N_3$-(*R/S)—$N_4$-(*R/S), where C and G are both DNA. The present disclosure thus encompasses a composition comprising an oligonucleotide comprising a strand comprising one of any motif described herein.

The present disclosure thus encompasses a composition comprising an oligonucleotide comprising a strand comprising two or more of any motif described herein. *R/S can also be represented as:

Pu: Purine (A or G, or a modified variant thereof)
Py: Pyrimidine (C, U or T, or a modified variant thereof)
Pu/Py or Py/Pu: A position which can be Pu or Py.
m5C: 5-methyl-Cytosine

*D or (*D): a phosphorodithioate, wherein both of the non-bridging phosphorus atoms in a phosphodiester have been replaced by sulfur.
*X or (*X): in a population of oligonucleotides or an oligonucleotide composition, some of the individual oligonucleotides have a phosphorothioate in the Rp conformation and some have a phosphorothioate in the Sp conformation at this position.

It is also noted that in CpG region motifs, a space (" ") is equivalent to a hyphen ("-").

It is also noted that some motifs result in CpG oligonucleotides which are agonists (e.g., motifs 3 to 28) and some which are antagonists (e.g., motifs 29 to 33).

Length of CpG Oligonucleotides

A CpG oligonucleotide or a chirally controlled CpG oligonucleotide composition which comprises a strand comprising any CpG region motif disclosed herein can be of any sequence, either a minimum or a maximum, which allows the CpG oligonucleotide to either agonize an immune response, antagonize an immune response, or neither, as desired.

In some embodiments, a CpG oligonucleotide or a chirally controlled CpG oligonucleotide composition which comprises a strand comprising a CpG region motif disclosed herein can be no more than 2 nt long. In some embodiments, a CpG oligonucleotide or a chirally controlled CpG oligonucleotide composition which comprises a strand comprising a CpG region motif disclosed herein can be no more than 3 nt long. In some embodiments, a CpG oligonucleotide or a chirally controlled CpG oligonucleotide composition which comprises a strand comprising a CpG region motif disclosed herein can be no more than 4 nt long. In some embodiments, a CpG oligonucleotide or a chirally controlled CpG oligonucleotide composition which comprises a strand comprising a CpG region motif disclosed herein can be no more than 5 nt long. In some embodiments, a CpG oligonucleotide or a chirally controlled CpG oligonucleotide composition which comprises a strand comprising a CpG region motif disclosed herein can be no more than 6 nt long. In some embodiments, a CpG oligonucleotide or a chirally controlled CpG oligonucleotide composition which comprises a strand comprising a CpG region motif disclosed herein can be no more than 7 nt long. In some embodiments, a CpG oligonucleotide or a chirally controlled CpG oligonucleotide composition which comprises a strand comprising a CpG region motif disclosed herein can be no more than 8 nt long. In some embodiments, a CpG oligonucleotide or a chirally controlled CpG oligonucleotide composition which comprises a strand comprising a CpG region motif disclosed herein can be no more than 9 nt long. In some embodiments, a CpG oligonucleotide or a chirally controlled CpG oligonucleotide composition which comprises a strand comprising a CpG region motif disclosed herein can be no more than 10 nt long. In some embodiments, a CpG oligonucleotide or a chirally controlled CpG oligonucleotide composition which comprises a strand comprising a CpG region motif disclosed herein can be no more than 11 nt long. In some embodiments, a CpG oligonucleotide or a chirally controlled CpG oligonucleotide composition which comprises a strand comprising a CpG region motif disclosed herein can be no more than 12 nt long. In some embodiments, a CpG oligonucleotide or a chirally controlled CpG oligonucleotide composition which comprises a strand comprising a CpG region motif disclosed herein can be no more than 13 nt long. In some embodiments, a CpG oligonucleotide or a chirally controlled CpG oligonucleotide composition which comprises a strand comprising a CpG region motif disclosed herein can be no more than 14 nt long. In some embodiments, a CpG oligonucleotide or a chirally controlled CpG oligonucleotide composition which comprises a strand comprising a CpG region motif disclosed herein can be no more than 15 nt long. In some embodiments, a CpG oligonucleotide or a chirally controlled CpG oligonucleotide composition which comprises a strand comprising a CpG region motif disclosed herein can be no more than 16 nt long. In some embodiments, a CpG oligonucleotide or a chirally controlled CpG oligonucleotide composition which comprises a strand comprising a CpG region motif disclosed herein can be no more than 17 nt long. In some embodiments, a CpG oligonucleotide or a chirally controlled CpG oligonucleotide composition which comprises a strand comprising a CpG region motif disclosed herein can be no more than 18 nt long. In some embodiments, a CpG oligonucleotide or a chirally controlled CpG oligonucleotide composition which comprises a strand comprising a CpG region motif disclosed herein can be no more than 19 nt long. In some embodiments, a CpG oligonucleotide or a chirally controlled CpG oligonucleotide composition which comprises a strand comprising a CpG region motif disclosed herein can be no more than 20 nt long. In some embodiments, a CpG oligonucleotide or a chirally controlled CpG oligonucleotide composition which comprises a strand comprising a CpG region motif disclosed herein can be no more than 21 nt long. In some embodiments, a CpG oligonucleotide or a chirally controlled CpG oligonucleotide composition which comprises a strand comprising a CpG region motif disclosed herein can be no more than 22 nt long. In some embodiments, a CpG oligonucleotide or a chirally controlled CpG oligonucleotide composition which comprises a strand comprising a CpG region motif disclosed herein can be no more than 23 nt long. In some embodiments, a CpG oligonucleotide or a chirally controlled CpG oligonucleotide composition which comprises a strand comprising a CpG region motif disclosed herein can be no more than 24 nt long. In some embodiments, a CpG oligonucleotide or a chirally controlled CpG oligonucleotide composition which comprises a strand comprising a CpG region motif disclosed herein can be no more than 25 nt long. In some embodiments, a CpG oligonucleotide or a chirally controlled CpG oligonucleotide composition which comprises a strand comprising a CpG region motif disclosed herein can be no more than 26 nt long. In some embodiments, a CpG oligonucleotide or a chirally controlled CpG oligonucleotide composition which comprises a strand comprising a CpG region motif disclosed herein can be no more than 27 nt long. In some embodiments, a CpG oligonucleotide or a chirally controlled CpG oligonucleotide composition which comprises a strand comprising a CpG region motif disclosed herein can be no more than 28 nt long. In some embodiments, a CpG oligonucleotide or a chirally controlled CpG oligonucleotide composition which comprises a strand comprising a CpG region motif disclosed herein can be no more than 29 nt long. In some embodiments, a CpG oligonucleotide or a chirally controlled CpG oligonucleotide composition which comprises a strand comprising a CpG region motif disclosed herein can be no more than 30 nt long. In some embodiments, a CpG oligonucleotide or a chirally controlled CpG oligonucleotide composition which comprises a strand comprising a CpG region motif disclosed herein can be no more than 31 nt long. In some embodiments, a CpG oligonucleotide or a chirally controlled CpG oligonucleotide composition which comprises a strand comprising a CpG region motif disclosed herein can be no more than 32 nt long. In some embodiments, a CpG oligonucleotide or a chirally controlled CpG oligonucleotide composition which comprises a strand comprising a CpG region motif disclosed herein can be no more than 33 nt long. In some embodiments, a CpG oligonucleotide or a chirally controlled CpG oligonucleotide composition which comprises a strand comprising a CpG region motif disclosed herein can be no more than 34 nt long. In some embodiments, a CpG oligonucleotide or a chirally controlled CpG oligonucleotide composition which comprises a strand comprising a CpG region motif disclosed herein can be no more than 35 nt long. In some embodiments, a CpG oligonucleotide or a chirally controlled CpG oligonucleotide composition which comprises a strand comprising a CpG region motif disclosed herein can be no more than 36 nt long. In some embodiments, a CpG oligonucleotide or a chirally controlled CpG oligonucleotide composition which comprises a strand comprising a CpG region motif disclosed herein can be no more than 37 nt long. In some embodiments, a CpG oligonucleotide or a chirally controlled CpG oligonucleotide composition which comprises a strand comprising a CpG region motif disclosed herein can be no more than 38 nt long. In some embodiments, a CpG oligonucleotide or a chirally controlled CpG oligonucleotide composition which comprises a strand comprising a CpG region motif disclosed herein can be no more than 39 nt long. In some embodiments, a CpG oligonucleotide or a chirally controlled CpG oligonucleotide composition which comprises a strand comprising a CpG region motif disclosed herein can be no more than 40 nt long. In some embodiments, a CpG oligonucleotide or a chirally controlled CpG oligonucleotide composition which comprises a strand comprising a CpG region motif disclosed herein can be no more than 41 nt long. In some embodiments, a CpG oligonucleotide or a chirally controlled CpG oligonucleotide composition which comprises a strand comprising a CpG region motif disclosed herein can be no more than 42 nt long. In some embodiments, a CpG oligonucleotide or a chirally controlled CpG oligonucleotide composition which comprises a strand comprising a CpG region motif disclosed herein can be no more than 43 nt long. In some embodiments, a CpG oligonucleotide or a chirally controlled CpG oligonucleotide composition which comprises a strand comprising a CpG region motif disclosed herein can be no more than 44 nt long. In some embodiments, a CpG oligonucleotide or a chirally controlled CpG oligonucleotide composition which comprises a strand comprising a CpG region motif disclosed herein can be no more than 45 nt long. In some embodiments, a CpG oligonucleotide or a chirally controlled CpG oligonucleotide composition which comprises a strand comprising a CpG region motif disclosed herein can be no more than 46 nt long. In some embodiments, a CpG oligonucleotide or a chirally controlled CpG oligonucleotide composition which comprises a strand comprising a CpG region motif disclosed herein can be no more than 47 nt long. In some embodiments, a CpG oligonucleotide or a chirally controlled CpG oligonucleotide composition which comprises a strand comprising a CpG region motif disclosed herein can be no more than 48 nt long. In some embodiments, a CpG oligonucleotide or a chirally controlled CpG oligonucleotide composition which comprises a strand comprising a CpG region motif disclosed herein can be no more than 49 nt long.

In some embodiments, a CpG oligonucleotide or a chirally controlled CpG oligonucleotide composition which comprises a strand comprising a CpG region motif disclosed herein can be 2 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 5 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 10 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 15 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 16 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 17 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 18 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 19 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 20 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 21 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 22 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 23 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 24 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 25 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 30 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 35 to 49 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 5 to 30 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 10 to 30 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 15 to 30 nucleotides (wherein a nucleotide includes nucleotides, modified nucleotides and/or nucleotide analogs). In some embodiments, a CpG oligonucleotide or a chirally controlled CpG oligonucleotide composition which comprises a strand comprising a CpG region motif disclosed herein can be 20 to 30 nucleotides (wherein a nucleotide includes nucleotides, modified nucleotides and/or nucleotide analogs).

In some embodiments, the base sequence of a CpG oligonucleotide or a chirally controlled CpG oligonucleotide composition which comprises a strand comprising a CpG region motif disclosed herein is or comprises the base sequence related to SMAD7, GTCGCCCCTTCTCCCCGCAGC (SEQ ID NO: 1524).

In some embodiments, the base sequence of a CpG oligonucleotide or a chirally controlled CpG oligonucleotide composition which comprises a strand comprising a CpG region motif disclosed herein is or comprises a portion of the base sequence related to SMAD7, GTCGCCCCTTCTCCCCGCAGC (SEQ ID NO: 1524), including but not limited to: GC, CCCGCAG, GTCGCCCCTT (SEQ ID NO: 1525), GTCGC, CCG, CCGCA, CCCGCA, TCGCCCCTTCTCC (SEQ ID NO: 1526), CTCCCCGCAG (SEQ ID NO: 1527), TCGCCCC, CGCCCCTT, CGCAG, CTCCCCGCA, CCTTCTCCCCGCAGC (SEQ ID NO: 1528), CCCCG, TCGCC, TCGCCCCTTCTC (SEQ ID NO: 1529), TTCTCCCCGC (SEQ ID NO: 1530), GTCGCCCCTTCT (SEQ ID NO: 1531), CCCCGCAGC, CCCCGCA, GTCGCCCCT, TCGCCCCT, CCCTTCTCCCCGC (SEQ ID NO: 1532), TCTCCCCGCA (SEQ ID NO: 1533), CTTCTCCCCGCAG (SEQ ID NO: 1534), TCGCCCCTTCTCCCCGCA (SEQ ID NO: 1535), CGCCCCTTCTCCCCG (SEQ ID NO: 1536), CTTCTCCCCG (SEQ ID NO: 1537), TCCCCGC, TCCCCGCAG, CCCTTCTCCCCG (SEQ ID NO: 1538), GTCGCCCCTTC (SEQ ID NO: 1539), GTCGCCC, CCCCGCAG, GTCGCCCCTTCTCCCCGCA (SEQ ID NO: 1540), TCGCCCCTTCTCCCCG (SEQ ID NO: 1541), CGCCCCTTCTCC (SEQ ID NO: 1542), TCGCCCCTTCTCCCCGCAGC (SEQ ID NO: 1543), CGCCCCTTCTCCCCGCAG (SEQ ID NO: 1544), CGCCCCTTC, CGCCCCTTCTCCC (SEQ ID NO: 1545), GCCCCTTCTCCCCG (SEQ ID NO: 1546), TCG, TCTCCCCGCAG (SEQ ID NO: 1547), CTTCTCCCCGCAGC (SEQ ID NO: 1548), CGCCCCTTCTCCCCGCA (SEQ ID NO: 1549), TCGCCCCTT, CCGCAG, CCGC, GCCCCTTCTCCCCGCA (SEQ ID NO: 1550), CTCCCCGC, CGCCCCTTCTC (SEQ ID NO: 1551), GTCGCCCCTTCTCC (SEQ ID NO: 1552), TCCCCG, GCCCCTTCTCCCCGCAGC (SEQ ID NO: 1553), TTCTCCCCGCA (SEQ ID NO: 1554), TCGC, CCCTTCTCCCCGCAGC (SEQ ID NO: 1555), TCGCCCCTTCTCCC (SEQ ID NO: 1556), CGCCCCTTCTCCCCGCAGC (SEQ ID NO: 1557), CCCCTTCTCCCCGC (SEQ ID NO: 1558), CGCAGC, CTTCTCCCCGC (SEQ ID NO: 1559), TTCTCCCCGCAGC (SEQ ID NO: 1560), TTCTCCCCG, GTCGCCCCTTCTC (SEQ ID NO: 1561), TCTCCCCGC, CCTTCTCCCCGCAG (SEQ ID NO: 1562), CCGCAGC, CGC, CTCCCCG, GTCGCCCCTTCTCCC (SEQ ID NO: 1563), GTCGCCCCTTCTCCC (SEQ ID NO: 1564), CCCCGC, CCCGC, GCCCCTTCTCCCCGC (SEQ ID NO: 1565), TCGCCCCTTCTCCCCGC (SEQ ID NO: 1566), GTCGCCCCTTCTCCCCGCAG (SEQ ID NO: 1567), CCTTCTCCCCGCA (SEQ ID NO: 1568), CGCCCCT, TCGCCCCTTCT (SEQ ID NO: 1569), CCCTTCTCCCCGCAG (SEQ ID NO: 1570), GTCGCCCCTTCTCCCCG (SEQ ID NO: 1571), CGCCCCTTCT (SEQ ID NO: 1572), CGCCCCTTCTCCCC (SEQ ID NO: 1573), CCCCTTCTCCCCGCAGC (SEQ ID NO: 1574), GCCCCTTCTCCCCGCAG (SEQ ID NO: 1575), TCGCCCCTTCTCCCCGCAG (SEQ ID NO: 1576), GTCG, CGCCCC, GTCGCC, TCGCCC, TTCTCCCCGCAG (SEQ ID NO: 1577), CTTCTCCCCGCA (SEQ ID NO: 1578), CCCCTTCTCCCCG (SEQ ID NO: 1579), TCGCCCCTTC (SEQ ID NO: 1580), GTCGCCCCTTCTCCCCGCAGC (SEQ ID NO: 1524), TCTCCCCGCAGC (SEQ ID NO: 1581), CGCCC, CCTTCTCCCCG (SEQ ID NO: 1582), TCCCCGCA, CTCCCCGCAGC (SEQ ID NO: 1583), TCTCCCCG, CCCTTCTCCCCGCA (SEQ ID NO: 1584), GTCGCCCC, CCCG, CCCCTTCTCCCCGCA (SEQ ID NO: 1585), TCGCCCCTTCTCCCC (SEQ ID NO: 1586), CCCCTTCTCCCCGCAG (SEQ ID NO: 1587), CCTTCTCCCCGC (SEQ ID NO: 1588), CCCGCAGC, GTCGCCCCTTCTCCCCG (SEQ ID NO: 1589), TCCCCGCAGC (SEQ ID NO: 1590), CGCCCCTTCTCCCCGC (SEQ ID NO: 1591), CGCC, and CGCA.

In some embodiments, the base sequence of a CpG oligonucleotide or a chirally controlled CpG oligonucleotide composition which comprises a strand comprising a CpG region motif disclosed herein is or comprises the base sequence of ODN2006, TCGTCGTTTTGTCGTTTTGTCGTT (SEQ ID NO: 2).

In some embodiments, the base sequence of a CpG oligonucleotide or a chirally controlled CpG oligonucleotide composition which comprises a strand comprising a CpG region motif disclosed herein is or comprises a portion of the base sequence of ODN2006, TCGTCGTTTTGTCGTTTTGTCGTT (SEQ ID NO: 2), including but not limited to: GC, TTGTCGTTT, TTTGTCGTTTTGTCG (SEQ ID NO: 1592), GTCGT, TTGTCGTTTT (SEQ ID NO: 1593), TGTCG, GTCGTTTTGTCGTTTT (SEQ ID NO: 1594), TCGTCGTTTTGTCGTTTTGTCGT (SEQ ID NO: 1595), TCGTCGTTTTGTCGTTTTGTCG (SEQ ID NO: 1596), GTCGTT, CGTCGTTTTGTCGTTTTGT (SEQ ID NO: 1597), GTCGTTTTGTCGTTTTG (SEQ ID NO: 1598), TCGTCGTT, TTTTGTCGTTTT (SEQ ID NO: 1599), TCGTCGTTT, TTGTCG, TTTGTCGTTTTG (SEQ ID NO: 1600), CGTTTT, TGTCGTTTTGTC (SEQ ID NO: 1601), TTTTGTCGTTTTGTC (SEQ ID NO: 1602), TTGTCGTTTTGTCG (SEQ ID NO: 1603), CGTCGTTTTGTCGTTT (SEQ ID NO: 1604), CGTCGTTTTGT (SEQ ID NO: 1605), TTTTGTCGTTT (SEQ ID NO: 1606), TGTCGTTTTGTCGTT (SEQ ID NO: 1607), CGTCGTTTTGTCGTTTG (SEQ ID NO: 1608), GTTTTGTCGTTTT (SEQ ID NO: 1609), GTCGTTT, CGTCGTTTTGTCGT (SEQ ID NO: 1610), TCGTTTTGTCGTT (SEQ ID NO: 1611), CGTCGTTTTGTCGTT (SEQ ID NO: 1612), CGTCGTTTTGTCG (SEQ ID NO: 1613), CGTCGTTTTGTC (SEQ ID NO: 1614), TCGTTTTGTCGTTTTGTC (SEQ ID NO: 1615), TTTGTCGTTTT (SEQ ID NO: 1616), TCGTTTTGTCGTTTTGTCG (SEQ ID NO: 1617), GTTTTGTCGTTTTGTC (SEQ ID NO: 1618), CGTCGTTTTG (SEQ ID NO: 1619), CGTCGTTTTGTCGTTTT (SEQ ID NO: 1620), GTTTTGTCGTT (SEQ ID NO: 1621), TCGTTT, TTTTGTCG, TCGTTTTGTC (SEQ ID NO: 1622), TCGTCG, TTTTGTCGTTTTGTCGT (SEQ ID NO: 1623), CGTTTTGTCGTTTTGTCGT (SEQ ID NO: 1624), TTTTGTCGTTTTGTCGTT (SEQ ID NO: 1625), GTTTTGTCGTTTTGTCGT (SEQ ID NO: 1626), TGTCGT, CGTCGTTTTGTCGTTTTGTCGT (SEQ ID NO: 1627), TCGTCGTTTTGTCGTTTT (SEQ ID NO: 1628), TGTCGTTTTGTCG (SEQ ID NO: 1629), TCGTTTTGTCGTTTTGTCGT (SEQ ID NO: 1630), TTGTCGT, TCG, CGTTTTGTCGTTTTGTCGTT (SEQ ID NO: 1631), TTTGTCGTTTTGT (SEQ ID NO: 1632), GTCGTTTTGTCGT (SEQ ID NO: 1633), CGTTTTGTCGTTTT (SEQ ID NO: 1634), TTGTCGTTTTGTCGT (SEQ ID NO: 1635), TTTTGTCGTT (SEQ ID NO: 1636), CGTTTTGTCGTTTTG (SEQ ID NO: 1637), TGTCGTTT, GTTTTGTCGTTTTGTCGTT (SEQ ID NO: 1638), TCGTTTTGTCGTTT (SEQ ID NO: 1639), TCGTCGTTTTGTCGTTT (SEQ ID NO: 1640), CGTCGTT, CGTCG, TTTGTCGT, TCGTTTTGTCGTTTTGTCGTT (SEQ ID NO: 1641), CGTTTTGTC, TGTCGTTTTGT (SEQ ID NO: 1642), TCGTCGTTTTGTCG (SEQ ID NO: 1643), TCGT, TGTCGTTTTG (SEQ ID NO: 1644), TCGTTTTGTCGTTTTGT (SEQ ID NO: 1645), GTTTTGTCGT (SEQ ID NO: 1646), GTTTTGTCGTTT (SEQ ID NO: 1647), TTGTCGTT, TCGTCGTTTTGTCGTTTG (SEQ ID NO: 1648), CGTTTTGTCGTTTTGTC (SEQ ID NO: 1649), TCGTCGTTTTGTCGTTTTGTCGTT (SEQ ID NO: 2), CGTTTTGTCG (SEQ ID NO: 1650), CGT, TTGTCGTTTTGT (SEQ ID NO: 1651), TCGTC, GTCGTTTTGTCGTTTGTCG (SEQ ID NO: 1652), CGTTTTGTCGTTTTGT (SEQ ID NO: 1653), GTCGTTTTGTCGTTTTGTC (SEQ ID NO: 1654), GTCGTTTTGTCGTTTTGTCGT (SEQ ID NO: 1655), TCGTCGTTTTGT (SEQ ID NO: 1656), GTCGTTTTGTCGTT (SEQ ID NO: 1657), TCGTT, GTTTTGTCGTTTTG (SEQ ID NO: 1658), CGTCGTTTTGTCGTTTTGTCG (SEQ ID NO: 1659), TCGTCGTTTTGTCGTT (SEQ ID NO: 1660), CGTTTGT, TTTGTCGTTTTGT (SEQ ID NO: 1661), TGTCGTTTTGTCGT (SEQ ID NO: 1662), TCGTTTTGTCGTTTT (SEQ ID NO: 1663), TCGTTTTGTCG (SEQ ID NO: 1664), TCGTCGTTTTG (SEQ ID NO: 1665), CGTT, TTTGTCGTTTTGTCGTT (SEQ ID NO: 1666), GTTTTGTCGTTTTGTCG (SEQ ID NO: 1667), GTCGTTTT, TTTTGTCGT, CGTC, GTCG, GTCGTTTTGTCG (SEQ ID NO: 1668), TTTTGTCGTTTTGTCG (SEQ ID NO: 1669), TGTCGTTTT, GTCGTTTTGTC (SEQ ID NO: 1670), TTTTGTCGTTTTG (SEQ ID NO: 1671), CGTTTTGTCGTTT (SEQ ID NO: 1672), CGTCGT, CGTTT, CGTTTTGTCGTTTTGTCG (SEQ ID NO: 1673), TCGTCGTTTTGTC (SEQ ID NO: 1674), TCGTCGTTTTGTCGTTTTGTC (SEQ ID NO: 1675), TTGTCGTTTTG (SEQ ID NO: 1676), TCGTTTTGT, TTTGTCGTTTTGTCGT (SEQ ID NO: 1677), GTCGTTTTGTCGTTTTGT (SEQ ID NO: 1678), TTTGTCGTTT (SEQ ID NO: 1679), TTGTCGTTTTGTC (SEQ ID NO: 1680), TTTGTCGTT, CGTCGTTTT, GTCGTTTTG, TCGTTTT, GTTTTGTCG, CGTCGTTTTGTCGTTTTGTC (SEQ ID NO: 1681), TCGTCGTTTTGTCGTTTTGT (SEQ ID NO: 1682), GTCGTTTTGT (SEQ ID NO: 1683), GTCGTTTTGTCGTTT (SEQ ID NO: 1684), TCGTTTTGTCGTTTTG (SEQ ID NO: 1685), TCGTCGT, CGTTTTGTCGTT (SEQ ID NO: 1686), TCGTCGTTTT (SEQ ID NO: 1687), CGTCGTTTTGTCGTTTTGTCGTT (SEQ ID NO: 1688), TCGTTTTGTCGT (SEQ ID NO: 1689), TCGTTTTG, CGTTTTGTCGT (SEQ ID NO: 1690), CGTTTTG, TTTGTCGTTTTGTC (SEQ ID NO: 1691), CGTCGTTT, TCGTCGTTTTGTCGT (SEQ ID NO: 1692), GTTTTGTCGTTTTGT (SEQ ID NO: 1693), GTCGTTTTGTCGTTTTGTCGTT (SEQ ID NO: 1694), TTTGTCG, and TTGTCGTTTTGTCGTT (SEQ ID NO: 1695).

In some embodiments, the base sequence of a CpG oligonucleotide or a chirally controlled CpG oligonucleotide composition which comprises a strand comprising a CpG region motif disclosed herein is or comprises the base sequence related to SOD1, CCGTCGCCCTTCAGCACGCA (SEQ ID NO: 1696).

In some embodiments, the base sequence of a CpG oligonucleotide or a chirally controlled CpG oligonucleotide composition which comprises a strand comprising a CpG region motif disclosed herein is or comprises a portion of the base sequence related to SOD1, CCGTCGCCCTTCAGCACGCA (SEQ ID NO: 1696), including but not limited to: GC, TCAGCACGC, CGTCGCC, CGCCCTTCAGCA (SEQ ID NO: 1697), GTCGC, CCG, CCGTC, GCACG, GCACGCA, GTCGCCCTT, AC GCA, TCGCCCTTCAGCACG (SEQ ID NO: 1698), TCGCCCTTCAGCACGC (SEQ ID NO: 1699), GTCGCCCTTC (SEQ ID NO: 1700), CAGCACGCA, TCGCCCT, TCGCC, CACGCA, CCGTCGCCCTTCA (SEQ ID NO: 1701), CCGTCGCCC, CCGTCGC, CGTCGCCCTTCAG (SEQ ID NO: 1702), GTCGCCCTTCAGCACGC (SEQ ID NO: 1703), TCGCCCTTCAGCAC (SEQ ID NO: 1704), CTTCAGCACGC (SEQ ID NO: 1705), TCAGCACG, GTCGCCC, ACGC, CCGTCGCC, CGTCGCCCTTCAGCACGC (SEQ ID NO: 1706), CGTCGCCCTTCAGCACGCA (SEQ ID NO: 1707), CGTCGCCCT, TCAGCACGCA (SEQ ID NO: 1708), CGCCCTTCAGCACGC (SEQ ID NO: 1709), GCCCTTCAGCACG (SEQ ID NO: 1710), AGCACGC, TCGCCCTT, TCG, CCCTTCAGCACGCA (SEQ ID NO: 1711), CCCTTCAGCACG (SEQ ID NO: 1712), GCACGC, CGTCGCCCTTCAGCACG (SEQ ID NO: 1713), AGCACG, CAGCACGC, CCGT, GTCGCCCTTCAGCA (SEQ ID NO: 1714), TCGC, CACG, TCGCCCTTCA (SEQ ID NO: 1715), ACG, CCTTCAGCACGC (SEQ ID NO: 1716), CCGTCGCCCTTCAGCA (SEQ ID NO: 1717), GTCGCCCTTCAGC (SEQ ID NO: 1718), CCGTCGCCCTTCAGCACG (SEQ ID NO: 1719), CCGTCGCCCTT (SEQ ID NO: 1720), AGCACGCA, CCGTCGCCCTTCAG (SEQ ID NO: 1721), CTTCAGCACG (SEQ ID NO: 1722), TTCAGCACG, TCGCCCTTCAGCACGCA (SEQ ID NO: 1723), GTCGCCCTTCAG (SEQ ID NO: 1724), CGC, CGTCGCCCTTCAGCAC (SEQ ID NO: 1725), TCGCCCTTCAGC (SEQ ID NO: 1726), TCGCCC, GTCGCCCTTCA (SEQ ID NO: 1727), CGT, CGCCCTTCAGCACG (SEQ ID NO: 1728), CACGC, GTCGCCCTTCAGCACG (SEQ ID NO: 1729), CCGTCGCCCTTCAGCACGC (SEQ ID NO: 1730), CGCCCTTCA, CGTCGCCCTTCAGC (SEQ ID NO: 1731), CCGTCGCCCT (SEQ ID NO: 1732), GTCGCCCTTCAGCACGCA (SEQ ID NO: 1733), GCCCTTCAGCACGCA (SEQ ID NO: 1734), CTTCAGCACGCA (SEQ ID NO: 1735), CGCCCT, GTCGCCCTTCAGCAC (SEQ ID NO: 1736), CAGCACG, CGTCG, CGTC, CCGTCGCCCTTC (SEQ ID NO: 1737), CGTCGC, GTCG, GTCGCC, CCTTC AGCACG (SEQ ID NO: 1738), CGTCGCCC, CGCCCTTC, CGTCGCCCTTCAGCA (SEQ ID NO: 1739), CGCCCTTC AGC AC (SEQ ID NO: 1740), CCGTCG, CCCTTCAGCACGC (SEQ ID NO: 1741), CGTCGCCCTTCA (SEQ ID NO: 1742), TTCAGCACGCA (SEQ ID NO: 1743), CGCCCTT, CGCCC, GCCCTTCAGCACGC (SEQ ID NO: 1744), TCGCCCTTC, CGCCCTTCAGC (SEQ ID NO: 1745), CCGTCGCCCTTCAGC (SEQ ID NO: 1746), CCGTCGCCCTTCAGCACGC A (SEQ ID NO: 1696), CCTTCAGCACGC A (SEQ ID NO: 1747), CGCCCTTCAG (SEQ ID NO: 1748), CCGTCGCCCTTCAGCAC (SEQ ID NO: 1749), CGTCGCCCTT (SEQ ID NO: 1750), GTCGCCCT, CGCCCTTCAGCACGCA (SEQ ID NO: 1751), TCGCCCTTCAGCA (SEQ ID NO: 1752), TTCAGCACGC (SEQ ID NO: 1753), CGTCGCCCTTC (SEQ ID NO: 1754), CGCC, TCGCCCTTCAG (SEQ ID NO: 1755), and CGCA.

A CpG oligonucleotide or a chirally controlled CpG oligonucleotide composition which comprises a strand comprising a CpG region motif disclosed herein can have any length or base sequence suitable for allowing agonism of an immune response, antagonism of an immune response, or neither agonism nor antagonism of an immune response, as desired.

Optional 5' and 3' End Modifications

In various embodiments, the CpG oligonucleotide can optionally comprise a 5' end or 3' end cap (also referenced as a "modification"), which is non-nucleotidic. By describing a 5' end cap or 3' end cap as "non-nucleotidic", it is meant that a nucleotide comprises three components: a phosphate, a sugar (e.g., a ribose or deoxyribose) and a nucleobase, and a 3' end cap does not comprise all three of the components.

The 5' end cap can be selected, as non-limiting examples, from any of: a composition comprising GalNAc; a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT. Any 5' end cap known in the art can be used on a CpG oligonucleotide.

The 3' end cap can be selected, as non-limiting examples, from any of: C3, C6, C8, C10, C12, lithocholic acid, biphenyl, triethylene glycol, cyclohexyl, phenyl, adamantane, C3 amino, C7 amino, X027, X038, X050 to 52, X058 to 69, X097 to 98, X109 to 113, X1009 to 1028, and X1047 to 1049. See, for example, U.S. Pat. Nos. 8,084,600; 8,404,832; 8,404,831; 8,957,041; and WO 2015051366.

Any 3' end cap known in the art can be used on a CpG oligonucleotide.

Any 5' end cap can be used in combination with any 3' end cap.

In various embodiments, the CpG oligonucleotide comprises a 5' end cap; a 3' end cap; a 5' end cap and a 3' end cap; or neither a 5' nor a 3' end cap.

Any CpG oligonucleotide comprising a strand comprising a CpG region motif described herein can optionally be used with any 5' or 3' end cap described herein or known in the art.

In some embodiments, provided CpG oligonucleotides comprise one or more lipid moieties. In some embodiments, lipid conjugation provides unexpectedly improved properties. In some embodiments, the present disclosure encompasses the surprising finding that lipid conjugation can effectively antagonize an immune response, e.g., that mediated by TLR9.

Methods of Making CpG Oligonucleotides

Various methods for making chirally controlled oligonucleotide compositions can be utilized in accordance with the present disclosure. Example methods include those described in WO/2010/064146, WO/2011/005761, WO/2011/108682, WO/2012/03 9448, WO/2012/073 857 WO/2013/01275 8, WO/2014/010250, WO/2014/012081, and WO/2015/107425, the oligonucleotide preparation methods of each of which are incorporated herein by reference.

Mouse Versus Human TLR9 and CpG Immunogenicity

Various researchers have reported some differences in the immune responses involving CpG motifs and TLR9 in mouse and human systems. The TLR9 genes differ between the species, with the human and mouse sequences reportedly differing by 24%. Hemmi et al. 2000 Nature 408: 740-745. There is also reported variation between species in which cell types express TLR9. The TLR9 receptor is reportedly present in rodent but not in primate macrophages and myeloid dendritic cells (DC). In humans, TLR9 is reportedly expressed primarily by plasmacytoid DC and B cells. Homung et al. 2002 J. Immun. 168: 4531-4537; Suzuki et al. 2004 Cancer Res. 64: 8754-8760; Kadowaki et al. 2001 J. Exp. Med. 194: 863-869; Bemasconi et al. 2003 Blood 101: 4500-4504.

For B-class oligonucleotides, the 6-mer motif 5'-GTCGTT-3' reportedly represents the optimal human CpG motif, but 5'-GACGTT-3' is the optimal murine CpG motif. Krieg et al. 1995 Nature 374: 546-549; Hartmann et al. 2000 J. Immunol. 164: 944-953; Hartmann et al. 2000 J. Immunol. 164: 1617-1624.

Pohar et al. also reported the differences between mouse and human B class CpG oligonucleotides. Pohar et al. 2015 J. Immunol. 195: 4396-4405.

Among other things, the present disclosure provides data surprisingly demonstrating that particular CpG region motifs differ in activity in mouse and human, in some embodiments, to a degree and/or extent unexpected prior to the present disclosure.

As shown herein, CpG oligonucleotides comprising the CpG region motif of $N_1$-(*S)—$N_2$-(*S)—C—(*S)-G-(*S)—$N_3$-(*S)—$N_4$-(*S) are agonistic in the mouse, but not the human. See, for example, WV-1384, which is shown to be agonistic in the mouse in FIG. 3, but not agonistic in human in FIG. 9.

Thus, the present disclosure demonstrates that studies in mice do not necessarily predict agonistic or antagonistic properties in human. For example, the different effects of chirality in mouse and human are shown by CpG ODNs WV-1384 and WV-1512. These two CpG ODNs, which are both all Sp, agonize the desired immune response in mouse, but not in human. CpG ODN WV-1384 (all Sp) shows agonist activity in mouse (FIGS. 1A and 2A), but not in human (FIG. 9A). Similarly, CpG ODN WV-1512, which is also all Sp, showed high activity in mouse (FIGS. 10A and 12A) but not in human (FIG. 13A). The present disclosure demonstrates, among other things, that data related to structural determinants of eliciting an immune response in mouse are not necessarily predictive of the immune response in human.

Combination of CpG Oligonucleotide and Another Agent

In various embodiments, the present disclosure pertains to methods and compositions related to the combination of (a) a CpG oligonucleotide and (b) another active agent.

In various embodiments, the active agent (b) can be co-administered with the CpG and/or separately administered. The methods by which the CpG oligonucleotide and active agent (b) are administered can be the same or different, or they can be simultaneous or in any order. In various embodiments, the CpG oligonucleotide and active agent (b) can be combined in a single composition, or can be in separate compositions (which can be co-administered or separately administered).

In various embodiments, the active agent (b) can be a separate treatment for a disease afflicting a human patient.

In various embodiments, the human patient can be afflicted with cancer.

In some embodiments, an active agent is an antibody. In some embodiments, an antibody has therapeutic effect. In some embodiments, an active agent is a vaccine.

As a non-limiting example, ibrutinib is useful for treatment of lymphoma, and can be co-administered with a CpG oligonucleotide. Ibrutinib is an irreversible inhibitor of Bruton's tyrosine kiase, a key enzyme in the singaling pathway downstream of B-cell receptor, and an effective treatment against many types of B-cell lymphomas. The combination of intratumoral injection of CpG oligonucleotides with systemic treatment by ibrutinib resulted in eradication of the tumors not only in the injected site, but also at distant sites. Sagiv-Barfi et al. 2015 Blood 125: 2079-2086.

In various embodiments, the active agent (b) can be an immunologically active component, as the co-administration of a CpG and an immunologically active agent has been shown to increase the immunological response to the agent.

Combination of a CpG and an Immunologically Active Agent

The present disclosure also encompasses a pharmaceutical composition comprising (a) a CpG oligonucleotide and (b) an immunologically active component; and, optionally, (c) an additional component.

The immunologically active component can comprise, for example, an immunogen, an antigen, e.g., a toxin, virus, bacterium, fungus, or other infectious agent, cancer antigen, pathogen, or component thereof.

Infectious Agent: An agent that can infect a subject, including, but not limited to, viruses, bacteria, and fungi.

Non-limiting examples of infectious virus include: Adenoviridae (most adenoviruses); Arena viridae (hemorrhagic fever viruses); Bimaviridae; Bungaviridae (for example, Hantaan viruses, bunga viruses, phleboviruses and Nairo viruses); Calciviridae (such as strains that cause gastroenteritis); Coronaviridae (for example, coronaviruses); enteroviruses, human coxsackie viruses, rhinoviruses, echoviruses); Filoviridae (for example, ebola viruses); Flaviridae (for example, dengue viruses, encephalitis viruses, yellow fever viruses); Hepadnaviridae (Hepatitis B virus); Herpesviridae (herpes simplex virus (HSV) 1 and HSV-2, varicella zoster virus, cytomegalovirus (CMV), herpes viruses); Iridoviridae (such as African swine fever virus); Orthomyxoviridae (for example, influenza viruses); Papovaviridae (papilloma viruses, polyoma viruses); Paramyxoviridae (for example, parainfluenza viruses, mumps virus, measles virus, respiratory syncytial virus); Parvoviridae (parvoviruses); Picornaviridae (for example, polio viruses, hepatitis A virus; Poxviridae (variola viruses, vaccinia viruses, pox viruses); Reoviridae (e.g., reoviruses, orbiviurses and rotaviruses); Retroviridae; Rhabdoviridae (for example, vesicular stomatitis viruses, rabies viruses); Togaviridae (for example, equine encephalitis viruses, rubella viruses); and unclassified viruses (for example, the etiological agents of Spongiform encephalopathies, the agent of delta hepatitis (thought to be a defective satellite of Hepatitis B virus), the agents of non-A, non-B Hepatitis (class 1=internally transmitted; class 2=parenterally transmitted (i.e., Hepatitis C); Norwalk and related viruses, and astroviruses).

Non-limiting examples of infectious bacteria include: *Actinomyces israelii; Bacillus* an tracts; *Bacteroides* sp.; *Borelia burgdorferi; Clostridium perfringers; Clostridium tetani; Corynebacterium diphtheriae; Corynebacterium* sp.; *Enterobacter aerogenes; Enterococcus* sp.; *Erysipelothrix rhusiopathiae; Fusobacterium nucleatum; Haemophilus influenzae; Helicobacter pyloris; Klebsiella pneumoniae; Legionella pneumophilia; Leptospira; Listeria monocytogenes; Mycobacteria* sps (such as, *M. tuberculosis, M. avium, M. intracellulare, M. kansaii, M. gordonae); Neisseria meningitidis; Pasteurella multocida*; pathogenic *Campylobacter* sp.; *Staphylococcus aureus, Neisseria gonorrhoeae; Streptobacillus moniliformis; Streptococcus* (anaerobic sps); *Streptococcus* (*viridans* group); *Streptococcus agalactiae* (Group B *Streptococcus*); *Streptococcus Bovis; Streptococcus faecalis; Streptococcus pneumoniae; Streptococcus pyogenes* (Group A *Streptococcus*); *Treponema pallidum*; and *Treponema pertenue*.

Non-limiting examples of infectious fungi include, but are not limited to, *Cryptococcus neoformans; Histoplasma capsulatum; Coccidioides immitis; Blastomyces dermatitidis; Chlamydia trachomatis*; and *Candida albicans*.

Other infectious organisms (such as protists) include: *Plasmodium falciparum* and *Toxoplasma gondii*.

In various embodiments, the CpG oligonucleotide can be conjugated to the antigen. Various studies have reported that conjugation of a CpG oligonucleotide to an antigen can enhance antigen uptake and reduce the requirement for the quantity of antigen administered. Tighe et al. 2000 Eur. J. Immunol. 30: 1939-1947; Hartmann et al. 2003 Cancer Res. 63: 6478-6487.

The additional agent can comprise any one of more of, as various non-limiting examples: an additional adjuvant, a stabilizer, a preservative, an antibiotic, and a trace component.

The additional adjuvant can comprise any one or more of, as non-limiting examples: aluminium hydroxide, aluminium phosphate, an immunostimulatory agent, saponin-based adjuvant, In various embodiments, the immunostimulatory agent can be an immunostimulatory nucleic acid or protein. In various embodiments, the additional immunostimulatory agent can be selected from Montanide ISA-51, GM-CSF, and IF A. Shirota et al. 2015. Stimulator of IFN Gene (STING) is also reported to act synergistically with CpG oligonucleotides as an adjuvant. Temizoz et al. 2014 Eur. J. Immun. 45: 1159-1169.

The stabilizer can comprise any one of more of, as non-limiting examples: an inorganic magnesium salt, such as magnesium sulfate or magnesium chloride, lactose, sorbitol, gelatin, monosodium glutamate, glycine.

The preservative can comprise any one of more of, as various non-limiting examples: Thiomersal, phenol, phenoxyethanol.

The antibiotic can comprise any one or more of, as various non-limiting examples: gentamicin, neomycin, penicillin, a beta-lactam, A composition or pharmaceutical composition comprising a CpG oligonucleotide, and optionally an active component and/or an additional component, can be formulated and/or delivered using any composition or method known in the art.

For example, the composition can be formed as a microparticle, nanoparticle, lipid emulsion, or other delivery modality known in the art.

Any composition comprising a CpG oligonucleotide comprising a strand comprising a CpG region motif disclosed herein can be used in combination with any immunologically active agent, vaccine, adjuvant or antigen described herein or otherwise known in the art.

Pharmaceutical Compositions Comprising a CpG Oligonucleotide

A pharmaceutical composition can comprise a CpG oligonucleotide comprising a strand comprising any CpG region motif disclosed herein.

In some embodiments, pharmaceutical compositions can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. A pharmaceutical composition comprising a CpG oligonucleotide can be delivered by intravenous infusion, subcutaneous injection, intramuscular injection, intranasal, intrathecal, topical, mucosal delivery, vaginal delivery, oral delivery, intrarectal delivery, conjunctival delivery, intraocular delivery, transcutaneous delivery, or any other modality known in the art.

This pharmaceutical composition can further comprise any component appropriate for delivery of the CpG oligonucleotide. Such components include, as non-limiting examples, a pharmaceutically acceptable salt, a pharmaceutically accept carrier.

Pharmaceutically acceptable salts are reported in the art. For example, S. M. Berge, et al. describes pharmaceutically acceptable salts in detail in J. Pharmaceutical Sciences, 66: 1-19 (1977). Any pharmaceutically acceptable salt described herein or reported in the art can be used in the compositions and methods of the present disclosure.

In some embodiments, in provided compositions provided oligonucleotides may exist as salts, preferably pharmaceutically acceptable salts, e.g., sodium salts, ammonium salts, etc. In some embodiments, a salt of a provided oligonucleotide comprises two or more cations, for example, in some embodiments, up to the number of negatively charged acidic groups (e.g., phosphate, phosphorothioate, etc.) in an oligonucleotide.

Pharmaceutically acceptable carriers are well known in the art. For example, acceptable carriers (e.g., pharmaceutically acceptable carriers), diluents, stabilizers, buffers, preservatives, etc., can be included as described infra.

A pharmaceutically acceptable carrier includes a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Any pharmaceutically acceptable carrier described herein or reported in the art can be used in the compositions and methods of the present disclosure.

Any composition comprising a CpG oligonucleotide comprising a strand comprising a CpG region motif disclosed herein can be used in any pharmaceutical composition described herein or otherwise known in the art.

Methods of Delivery of a Pharmaceutical Composition Comprising a CpG Oligonucleotide A pharmaceutical composition comprising a CpG oligonucleotide can be delivered using any method or device or other modality known in the art, including, but not limited, to any method of administration described herein.

As a non-limiting example: A pharmaceutical composition comprising a CpG oligonucleotide can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, intraperitoneal, or intrathecal injection, or infusion techniques and the like. As another non-limiting example: A pharmaceutical composition comprising a CpG oligonucleotide can be delivered by intravenous infusion, subcutaneous injection, intramuscular injection, intranasal, intrathecal, topical, mucosal delivery, vaginal delivery, oral delivery, intrarectal delivery, conjunctival delivery, intraocular delivery, transcutaneous delivery, or any other modality known in the art.

Various methods of delivering CpG oligonucleotides are reported in the art. See, for example, Moldoveanu et al. 1998 Vaccine 16: 1216-1224; Gallichan et al. 2001 J. Immunol. 166: 3451-3457; McCluskie et al. 1998 J. Immunol. 161: 4463-4466; McCluskie et al. 2000 Vaccine 19: 413-422; Kwant et al. 2004 Vaccine 22: 3098-3104; Eastcott et al. 2001 Vaccine 19: 1636-1642; McCluskie et al. 2001 Vaccine 19: 950-957; Dong et al. 2005 Virology. Nesburn et al. 2005 Vaccine 23: 873-883; Berry et al. 2004 Infect. Immun. 72: 1019-1028; Dumais et al. 2002 J. Infect. Dis. 186: 1098-1105; Gallichan et al. 2001 J. Immunol. 166: 3451-3457; and Qin et al. 2014 Immunopharm. Immunotox. 36: 251-260.

The pharmaceutical composition can comprise an therapeutically effective amount or dosage of a CpG oligonucleotide.

Dosage levels of the order of from about 0.1 mg to about 140 mg per kilogram of body weight per day are useful in the treatment of the various conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Any composition comprising a CpG oligonucleotide comprising a strand comprising a CpG region motif disclosed herein can be used in any pharmaceutical composition described herein or otherwise known in the art, and can be used with any method of delivery described herein or otherwise known in the art.

Treatment of Injection Site Reactions and Adverse Effects Associated with Administration of Nucleic Acids In at least some cases, subcutaneous or intramuscular injection of nucleic acids has resulted in injection site reaction (ISR), e.g., erythema, bruising, induration, inflammation, blistering, burning sensation, itching, discomfort, tenderness, pain, rash, hyperpigmentation, hypopigmentation, alopecia, desquamation, flare-ups, ulceration, necrosis, hematoma, vasculitis, leukocytoclastic vasculitis, infection, eczema, slow distribution of the nucleic acid out of the skin and/or immediate region of injection, etc. ISRs can vary in intensity, e.g., they can be mild, moderate or severe. ISRs can also vary in duration, from being transient to permanent. In many cases, an ISR is not desirable. Thus: In various embodiments, the present disclosure pertains to methods and compositions for administering to a patient in need thereof a therapeutically effective amount of a CpG oligonucleotide comprising a strand comprising a CpG region motif, further comprising the step of administering a method or composition which relieves an injection site reaction asssociated with administration of the CpG oligonucleotide, wherein the methods or compositions can be performed or administered in any order. Various such methods and compositions are known in the art. As non-limiting examples, the inflammatory potential of some nucleic acids is reported to be reduced by conjugation with GalNAc, chelation or formulation with particular nanoparticles, e.g., use of liphophilic molecules, basic peptides, folate, anisamide, polyamines, receptor binding molecules, or dynamic conjugates, or slowing and/or decreasing the amount or rate of administration. See, for example: Seth et al. 2012 Mol. Ther. 1: e47; van der Ree 2015 EASL; Gish et al. 2015 Antivir. Res. 121: 97-108. An method or composition known in the art for treating an injection site reaction can be combined with a method or composition pertaining to a CpG oligonucleotide of the present disclosure.

In at least some cases, ISRs are particularly common with CpG oligonucleotides or 5-methyl-cytosine-substituted nucleic acids, compared to other types of nucleic acids; however, in some cases, as an injection site reaction can be the result of immune stimulation, such a reaction can be tolerable or even preferable, depending on the site of injection.

In at least some cases, administration of nucleic acids is reported to lead to other adverse effects, including flu-like symptoms, fever, chills, myalgia, arthralgia, malaise, fatigue, nephrotoxicity, hepatotoxicity, thrombocytopenia, drug-induced vascular injury, decrease in platelets, glomerulopathy, vascular degeneration, perivascular inflammation, etc. See, for example, Frazier 2015 Tox. Path. 43: 78-89; Engelhardt et al. 2015 Toxicol. 1-10. In some embodiments, adverse effects are not desirable. However, various methods and compositions for treating adverse effects are known in the art. Modification of backbone chemistry, conjugation to various moieties, use of particular delivery compositions and methods, improved tissue penetration, enhanced intracellular target and less frequent dosing, and various other methods and compositions known in the art, can result in reduced adverse effects.

Thus: In various embodiments, the present disclosure pertains to methods and compositions for administering a patient in need thereof a therapeutically effective amount of a CpG oligonucleotide comprising a strand comprising a CpG region motif, further comprising the step of administering a method or composition which treats an adverse effect associated with administration of the CpG oligonucleotide, wherein the methods or compositions can be performed or administered in any order.

In some embodiments, the present disclosure describes various CpG region motifs which are immunostimulatory. If immunostimulation is not desirable for a nucleic acid, these particular motifs can be avoided in the design of the nucleic acid. Furthermore, various methods and compositions for reducing ISRs and adverse effects of nucleic acid administration can be used in combination with methods and compositions for administration of the nucleic acid, if immunostimulation is not desired.

Methods of Use

The present disclosure pertains to, inter alia, compositions comprising a CpG oligonucleotide comprising one or more of any CpG region motif disclosed herein.

Such compositions can be used for any purpose previously described in the literature for CpG oligonucleotides. Agonistic CpG oligonucleotides can be used, as a non-limiting example, as an immunostimulatory agent, such as an adjuvant, vaccine or monotherapy. Antagonistic CpG oligonucleotides can be used to antagonize an immune response.

Use of CpG Oligonucleotides as Adjuvants

An adjuvant enhances an immune response generated against an active component, e.g., a co-administered antigen (Ag).

There are several ways, described in the scientific literature, such as Shirota et al. 2015 Vaccines 3: 390-407, that an adjuvant can promote immunity:

Stabilizing or entrapping the antigen (Ag) to extend release and thus prolong immune stimulation;

Promoting an inflammatory response at the site of Ag deposition, thereby attracting activated macrophages and dendritic cells to improve Ag uptake and presentation; and Presenting co-stimulatory signals to T and B cells to enhance induction of Ag-specific immunity.

As TLR9 agonists, CpG oligos are reportedly useful as vaccine adjuvants, and as mono- or combination therapies for the treatment of cancer and infectious and allergic diseases. Vollmer et al. 2009 Adv. Drug Del. Rev. 61: 195-204. CpG oligonucleotides can reportedly enhance both the humoral and cellular (Th1 cells and CTL) immune response elicited by vaccines against pathogens, allergens and/or tumors. Shirota et al. 2014 Expert Rev. Vaccines 13: 299-312. As reported by Shirota et al., to optimize the efficiency of antigen presentation by DCs requires that they encounter CpG oligonucleotides in the presence of the vaccine antigen. Co-delivery of the oligonucleotide plus antigen to the same APC accelerates the induction, reportedly increases the maximal level and extends the duration of the induced immune response. Klinman et al. 2009 Adv. Drug Del. Rev. 61: 248-255. It also supports modulation of antigen isotype and increases the immuogenicity of weak antigens. Klinman et al. 2004 Nat. Rev. Immun. 4: 249-258. For example, when ovalbumin or hepatitis B surface antigen vaccine were administered to CpG oligonucleotides, co-delivery to the same site reportedly significantly enhanced humoral protective immunity. Mutwiri et al. 2004 J. Control. Rel. 97: 1-17; Cooper et al. 2004 J. Clin. Immun. 24: 693-701; Maurer et al. 2002 Eur. J. Immun. 32: 2356-2364. A CpG oligonucleotide is reported to also accelerate the immune response. Co-administration of a CpG oligonucleotide reportedly reduced the timing of peak titer of antibody to an anthrax vaccine from day 46 to day 22. Rynkiewicz et al. Marked Enhancement of Antibody Response to Anthrax Vaccine Adsorbed with CPG 7909 in Healthy Volunteers, ICAAC, 2005. A CpG oligonucleotide can also reportedly reduce the amount of vaccine required to induce protection, in some cases up to 10-fold or more. The CpG oligonucleotide can thus reduce cost, increase safety, and increase the number of patients that can receive the vaccine if it is in short supply, as has occurred with some influenza vaccines. Weeratna et al. 2003 Immunol. Cell Biol. 81: 59-62. In at least some cases, a CpG oligonucleotide can reportedly alter or reprogram an immune response. The Th1-biased immune response induced by CpG oligos can reportedly facilitate the development of improved allergy vaccines, to reprogram the pathogenic Th2 allergic response. CpG oligos reportedly redirect the allergic Th2 response in allergic mice, preventing inflammatory disease manifestations. Kline et al. 1998 J. Immunol. 160: 2555-2559; Jain et al. 2002 J. Allergy Clin. Immunol. 110: 867-872.

In some embodiments, the CpG oligos can be used for reducing tumor size and/or tumor burden in a subject in need thereof. In some embodiments, the vaccine is designed to prevent or slow tumor growth. Various studies have reported the use of tumor vaccines adjuvanted with CpG oligonucleotides. Krieg et al. 2004 Curr. Oncol. Rep. 6: 88-95; Heckelsmiller et al. 2002 Eur. J. Immun. 32: 3235-3245; Muraoka et al. 2010 J. Immun. 185: 3768-3776; Junqueira et al. 2012 PloS ONE 7: e36245; Sin et al. 2013 Cancer Lett. 330: 190-199; Silva et al. 2015 J. Immun. 194: 2199-2207; Aurisicchio et al. 2009 Clin. Cancer Res. 15: 1575-1584; Jacobs et al. 2011 Int. J. Cancer 128: 897-907. In one report, combining a CpG oligonucleotide with a peptide vaccine targeting HPV16 E7 reportedly resulted in the elimination of tumors up to 250 mm3 in size, and delay in the growth of even larger tumors. Zwaveling et al. 2002 J. Immun. 169: 350-358. Eradication of very large tumors was reportedly observed in 50% of mice using a fusion protein vaccine targeting the E7 epitope in combination with CpG oligonucleotide plus a chemotherapeutic agent. Mansilla et al. 2012 Int. J. cancer 131: 641-651.

Several clinical trials have examined the use of CpG oligonucleotides combined with peptide-based vaccines targeting tumor antigens. Such antigens include Engerix-B HBV vaccine; MART-1 peptide vaccine (for patients with melanoma); multi-epitope peptide vaccine (including MART-1, gp100, and tyrosinase); and NY-ESO-1 peptide or LAGE-1 tumor antigen; Wilms' Tumor-1 antigen (WT-1); cancer-testis Ag peptides LY6K and TTK (for metstatic esophaegeal squamous cell carcinoma). Shirota et al.; Cooper et al. 2004 J. Clin. Immunol.; Speiser et al. 2010 J. Immunother. 33: 848-858; Speiser et al. 2005 J. Clin. Invest. 115: 739-746; Baumgaertner et al. 2012 Int. J. Cancer 130: 2607-2617; Tarhini et al. 2012 J. Immunother. 35: 359-366;

Fourcade et al. 2008 J. Immunother. 31: 781-791; Valmori et al. 2007 Proc. Natl. Acad. Sci. USA 104: 8947-8952; Karbach et al. 2010 Int. J. Cancer 126: 909-918; Ohno et al. 2012 Anticancer Res. 32: 2263-2269; Iwahashi et al. 2010 Cancer Sci. 101: 2510-2517.

In various embodiments, the cancer is selected from cancers of the lung, breast, colon and rectum, skin, head and neck, brain, stomach, prostate, liver, cervix, intestine, and esophagus.

In various embodiments, the CpG oligonucleotide can be administered along with a chemotherapeutic agent. In various embodiments, the chemotherapeutic agent is selected from the group consisting of Anti-estrogens, Anthracyclins, Azacitidine, Azathioprine, Bleomycin, Busulfan, Carboplatin, Capecitabine, Cisplatin, Chlorambucil, Cyclophosphamide, Cytarabine, Dacarbazine, Daunorubicin, Docetaxel, Doxifluridine, Doxorubicin, Epirubicin, Epothilone, Etoposide, 5-Fluorouracil, Gemcitabine, Hydroxyurea, Idarubicin, Imatinib, Interferons, Mechlorethamine, Melphalan, Mercaptopurine, Methotrexate, Mitomycin C, Mitoxantrone, Oxaliplatin, Paclitaxel, Pemetrexed, Retinoic acid, Taxol, Taxotere, Tamoxifen, Teniposide, Thiotepa, Tioguanine, Valrubicin, Vinblastine, Vincristine, Vindesine, and Vinorelbine, and any combination thereof.

CpG oligonucleotides have also been reported to be useful in treatment of trauma, bacterial pneumonia and burns. Wanke-Jellinek et al. 2016 J. Imm. 196: 767-777.

The methods and compositions comprising a CpG oligonucleotide of the present disclosure can thus be used in treatment of any disease known in the art to be amenable to treatment with a CpG oligonucleotide.

Combining CpG Oligonucleotides with Additional Therapies

In various embodiments, the present disclosure pertains to treatment of a disease, the treatment comprising the step of administering a CpG oligonucleotide comprising a strand comprising one or more copies of a CpG region motif described herein, wherein the oligonucleotide is administered as a monotherapy or in combination with an additional therapy.

In various embodiments, the additional therapy can be selected from: a vaccine, an antibody, a cellular therapy, an immunotherapy, and antiangiogenic agent, a radiotherapy, a cryotherapy, and a chemotherapy.

In various embodiments, the vaccine can comprise an active component (e.g., an antigen).

Use of Immunomodulatory CpG Oligonucleotides in Treating Inflammatory, Autoimmune and Other Diseases Immunomodulatory CpG oligonucleotides can be administered as treatments, or co-administered with other treatments, for treatment and/or prevention of inflammatory diseases, autoimmune diseases, cancer, allergic, asthma, and other diseases.

In some embodiments, an immunomodulatory CpG oligonucleotide can be co-administered with an anti-inflammatory agent. In some embodiments, an antagonistic CpG oligonucleotide can be co-administered with an anti-inflammatory agent.

If it is desirable to limit inflammation, e.g., in a disease associated with excessive inflammation, an antagonistic CpG oligonucleotide can be co-administered with an anti-inflammatory agent.

In some embodiments, a disease associated with excessive inflammation is inflammatory bowel disease, hay fever, periodontitis, atherosclerosis, rheumatoid arthritis, or cancer (e.g., gallbladder carcinoma), Acne vulgaris, Asthma, Autoimmune diseases, Autoinflammatory diseases, Celiac disease, Chronic prostatitis, Glomerulonephritis, Hypersensitivities, Inflammatory bowel diseases, Pelvic inflammatory disease, Reperfusion injury, Rheumatoid arthritis, Sarcoidosis, Transplant rejection, Vasculitis, Interstitial cystitis, or Atherosclerosis. In some embodiments, a disease associated with excessive inflammation is inflammatory bowel disease. In some embodiments, an anti-inflammatory agent is a short chain fatty acid (SCFA). SCFAs include, as non-limiting examples, butyrate, propionate and acetate. SCFAs can be administered in several manners. SCFAs can, for example, be administered orally. In some embodiments, SCFAs can be administered as a component in the diet, e.g., via butyrated or acetylated starch. In some embodiments, SCFAs are produced in the digestive system of a subject by the fermentation of dietary fiber by normal, healthy gut flora. Butyrate and other SCFAs are reportedly antiinflammatory, inhibiting IL-12, IFN-gamma signalling, and NFK3. In contrast, TLR9 activation by agonistic CpG oligonucleotides is pro-inflammatory, with pro-inflammatory reactions mediated by Type I interferon and IL-12. Antagonistic CpG oligonucleotides can act synergistically with SCFAs. SCFAs are reportedly important as food for cells lining the mammalian colon (colonocytes); without butyrates for energy, colon cells reportedly undergo autophagy and die. Without wishing to be bound by any particular theory, the present disclosure notes that SCFAs reportedly benefit colonocytes by increasing energy production and cell proliferation, and may help protect against colon cancer; and butyrate reportedly possesses both preventive and therapeutic potential to counteract inflammation-mediated ulcerative colitis and colorectal cancer.

Antagonistic CpG oligonucleotides can be administered as treatments for inflammatory diseases and autoimmune diseases. In many autoimmune diseases, TLR7 and TLR9 have been reported to mediate inflammation induced by immune complexes, leading to maintenance and progression of disease. Reportedly, activation of TLR7, TLR8 and TLR9 in pDC and mDC through the interaction of these receptors with the antimicrobial peptide LL37 complexed with self-RNA or DNA contributes to psoriasis development. In some embodiments, an antagonistic CpG oligonucleotide is used to treat psoriasis and other autoimmune diseases. In some embodiments, an antagonistic CpG oligonucleotide is capable of inhibiting skin inflammation mediated by IL-23; reduces IL-17; and/or increases IL-10.

In some embodiments, an antagonistic CpG oligonucleotide is used, alone or in combination with another agent, as a treatment of an autoimmune disease. In some embodiments, an autoimmune disease is selected from: arthritis, rheumatoid arthritis, and Systemic Lupus Erythematosus (SLE).

In various embodiments, an immunomodulatory CpG oligonucleotide is administered, or co-administered with another agent, in a treatment of cancer.

In some embodiments, an antagonistic CpG oligonucleotide is administered in treatment of cancer. In some embodiments, cancer is associated with inflammation (as non-limiting example, inflammation-mediated ulcerative colitis and colorectal cancer). In some embodiments, an antagonistic CpG oligonucleotide acts to counteract inflammation.

In some embodiments, an agonistic CpG oligonucleotide is administered, or co-administered with another agent, in a treatment of cancer. In some embodiments, an agonistic CpG oligonudleotide increase an immune response against cancer.

In some embodiments, an agonistic CpG oligonucleotide is co-administered with an immune checkpoint inhibitor, a PD-1 (programmed cell death protein 1) inhibitor, CD20 inhibitor (e.g., rituximab), an oncolytic virus, and/or an IDO-1 (indoleamine 2,3-dioxygenase 1) inhibitor, EGFR inhibitor, tyrosine kinase inhibitor, and/or a modulator of TIM3, CEACAM and/or LAG3, or a tumor-specific antibody, cellular therapy, anti angiogenic agent, radiotherapy, and/or chemotherapy, for a treatment of cancer. Some embodiments, , an agonistic CpG oligonucleotide is co-administered with an agent selected from: cetuximab, ipilimumab, and gefitinib. In various embodiments, an inhibitor is an antibody, a RNAi agent, a small molecule, a CRISPR, a TALEN, or other molecule capable of decreasing the activity and/or level of the target. In some embodiments, a cancer is selected from: Non-Hodgkin's Lymphoma (NHL), renal cell carcinoma, melanoma, metastatic melanoma, colorectal cancer, colon cancer, breast cancer, soft tissue cancer, hepatic cancer, lung cancer, or non-small cell lung cancer. In some embodiments, a cancer is selected from: Bladder Cancer, Breast Cancer, Colon and Rectal Cancer, Endometrial Cancer, Kidney Cancer, Leukemia, Lung Cancer, Melanoma, Non-Hodgkin Lymphoma, Pancreatic Cancer, Prostate Cancer, and Thyroid Cancer.

In some embodiments, an agonistic CpG oligonucleotide is co-administered with a checkpoint inhibitor. In some embodiments, an agonistic CpG oligonucleotide is co-administered with ipilimumab, a CTLA4 antibody. In some embodiments, an agonistic CpG oligonucleotide is co-administered with a checkpoint inhibitor for treatment of cancer. In some embodiments, an agonistic CpG oligonucleotide is co-administered with ipilimumab, a CTLA4 antibody for treatment of cancer. In some embodiments, an agonistic CpG oligonucleotide is co-administered with a checkpoint inhibitor for treatment of Non-Hodgkin's Lymphoma, renal cell carcinoma, melanoma, metastatic melanoma, colorectal cancer, colon cancer, breast cancer, soft tissue cancer, hepatic cancer, lung cancer, or non-small cell lung cancer. In some embodiments, an agonistic CpG oligonucleotide is co-administered with ipilimumab, a CTLA4 antibody for treatment of NHL, B-cell lymphoma, Waldenstrom's macroglobulinemia, renal cell carcinoma, melanoma, metastatic melanoma, lung cancer, or non-small cell lung cancer.

In some embodiments, an immunomodulatory CpG oligonucleotide is co-administered with a complement inhibitor. In some embodiments, an agonistic CpG oligonucleotide is co-administered with a complement inhibitor.

Complement is reportedly a major component of innate immunity and plays a crucial role in host defense. Crosstalk between TLR9 (and other Toll-Like Receptors) and complement has been reported. Hajishengallis et al. 2010 Trends Immunol. 31: 154-163; Song 2012 Tox. Pathol. 40: 174-182; andHovland et al. 2015 Atherosclerosis 241: 480-494. Modified LDL-cholesterol reportedly activates complement and TLRs, leading to inflammation. Both complement and TLRs are upread in atherosclerosis. Activated complement regulates TLR signaling through the activities of G protein-coupled anaphylatoxin receptors C5aR and C3aR, intracellular signaling molecules such as MAPKs, and transcriptional factors such as NF-κ3. In some embodiments, an agonistic CpG oligonucleotide is co-administered with a complement inhibitor. In some embodiments, a complement inhibitor inhibits C3 or C5. In some embodiments, a complement inhibitor inhibits cleavage, hydrolysis and/or activation of C3 and/or C5. In some embodiments, a complement inhibitor inhibits C3 or C5. In some embodiments, a complement inhibitor inhibits a C5 convertase. In some embodiments, a complement inhibitor inhibits a C3 convertase.

In some embodiments, a CpG oligonucleotide can be administered alone or co-administered with another agent, and the CpG oligonucleotide can comprise a novel CpG region motif disclosed herein.

Determination of Novel CpG Region Motifs

In the present disclosure, a variety of CpG oligonucleotides were used to explore, inter alia, the effect, if any, on immunogenicity mediated by the conformation of the phosphorothioates.

In various CpG oligonucleotides described in the literature, one or more phosphorothioesters have been replaced by a phosphorothioate. However, a phosphorothioate can exist in either of two conformations, Rp and Sp, as illustrated herein.

In some embodiments, the CpG region motif comprises at least one phosphorothioate in the Rp conformation and at least one phosphorothioate in the Sp conformation. In some embodiments, the present disclosure pertains to a composition comprising a CpG oligonucleotide comprising a strand comprising 14 to 49 nucleotides, wherein the strand comprises at least one copy of the CpG region motif $N_1$-(*R/S)—C—(*R/S)-G-(*R/S)—$N_2$, wherein at least one *R/S is a phosphorothioate in the Rp conformation and at least one *R/S is a phosphorothioate in the Sp conformation, and N i and $N_2$ are any nucleotide.

In most of the previously-described studies of CpG oligonucleotides, the conformation at the various phosphorothioates was not controlled. These previously-described oligos thus are, in fact, mixtures of molecules; as a group, they all have the same base sequence, and sequence of modifications, and sequence of phosphorothioates in their backbones, but they vary molecule by molecule in the stereochemistry of the phosphorothioate backbones.

In contrast, the present disclosure describes various novel CpG oligonucleotides which were created, which have been chirally controlled at the various phosphorothioates. Thus, many of the CpG oligos described herein have been designed to be stereopure, wherein at each position the phosphorothioate is stereodefined as Rp or Sp; many of the CpG oligos described herein thus are stereopure, rather than stereomixtures.

Other studies were performed in which each and every phosphorothioate in a CpG oligonucleotide was in the Rp conformation; or each and every phosphorothioate was in the Sp conformation.

Uniquely, the present disclosure presents data related to chirally controlled CpG oligonucleotides wherein the CpG region motif comprises at least one phosphorothioate in the Rp conformation and at least one phosphorothioate in the Sp conformation. The present disclosure presents data showing that various CpG region motifs with at least one phosphorothioate in the Rp conformation and at least one phosphorothioate in the Sp conformation are capable of, depending on the region motif, either agonizing or antagonizing an immune response.

Effect of Chirality on CpG Region Motifs

Many CpG oligonucleotides were constructed in which the chirality (Rp or Sp) of the CpG motif and/or CpG region motif were chirally controlled; these are listed in Table 4 (including Tables 4A, 4B and 4C).

Certain CpG oligonucleotides were tested for their ability to agonize or antagonize an immune response in the mouse and the human. Certain experimental methods are presented in Examples and certain results shown in the Figures. Certain oligonucleotide sequences used are listed in Table 3, and the specific sequences of the CpG oligonucleotides are listed in Table 4 (Tables 4A to 4C).

The Present Disclosure Demonstrates that Stereochemistry of Chiral Internucleotidic Linkages has Effects on Agonism and Antagonism Mediated by CpG Oligonucleotides Without being bound by any particular theory, the present disclosure notes that several findings arise from the data disclosed herein.

In some embodiments, the present disclosure demonstrates that a pattern of chirality of the phosphorothioates in the CpG region motifs greatly alters the agonism or antagonism of an immune response mediated by a CpG oligonucleotide.

In some embodiments, the chirality of the phosphorothioate in the CpG dinucleotide as well as the flanking phosphorothioates affects the immune response.

In some embodiments, a CpG oligonucleotide which is a stereomixture may be able to mediate a certain level of agonism, but a stereopure version of this oligonucleotide may show different activity. For example, WV-1494 is a stereomixture which show modest agonism, but a stereopure version of this molecule, WV-1512, which has the same sequence but controlled stereochemistry, is very agonistic (see FIG. 12). Similarly, WV-499, a stereomix, shows essentially no agonism, but a stereopure variant with the same sequence and different sequence of stereochemistry, WV-966, is very active (see FIG. 4).

In some embodiments, not all stereopure variants of a particular base sequence are equally active. For example, WV-1373, WV-1375 and WV-1384 all share the same base sequence and are all stereopure. However, they differ in the stereochemistry (the sequence of Rp and Sp in the CpG region motif) and greatly differ in ability to agonize an immune response (see FIG. 2).

In some embodiments, various CpG region motifs, defined at least in part by the sequence of stereochemistry, are either agonistic or antagonistic.

Various CpG region motifs are described herein, e.g., in Table 1.

In some embodiments, some are associated with agonism, while others are associated with antagonism.

As non-limiting examples, some of the CpG region motifs associated with agonism are:

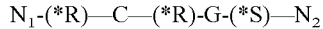
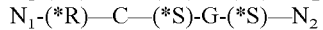
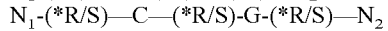
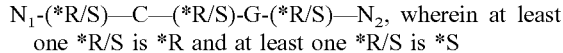, wherein at least one *R/S is *R and at least one *R/S is *S
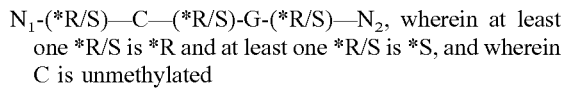, wherein at least one *R/S is *R and at least one *R/S is *S, and wherein C is unmethylated In these CpG region motifs, *R/S indicates a phosphorothioate which can be either *R or *S in a stereopure (e.g., a pure or mostly pure) preparation.

As non-limiting examples, some of the CpG region motifs associated with antagonism are:

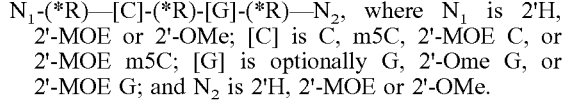, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.

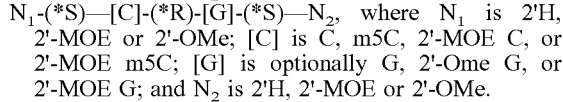, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.

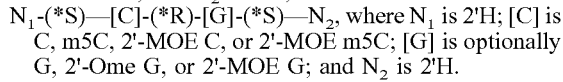, where $N_1$ is 2'H; [C] is C, m5C, 2'-MOE C, or 2'-MOE m5C; [G] is optionally G, 2'-Ome G, or 2'-MOE G; and $N_2$ is 2'H.

Various CpG region motifs associated with agonism or antagonism are described herein.

In some embodiments, CpG region motifs comprising a 5mC agonize an immune response.

Previous work has reported that generally bacterial DNA comprising a CpG motif with an unmethylated C is immunogenic, while mammalian nuclear DNA comprising a CpG motif with a methylated C is not.

The present disclosure reveals that some immunostimulatory CpG oligonucleotides can comprise a CpG with a methylated C.

As non-limiting examples, these include the following CpG region motifs:

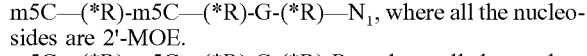, where all the nucleosides are 2'-MOE.

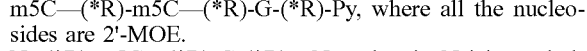, where all the nucleosides are 2'-MOE.

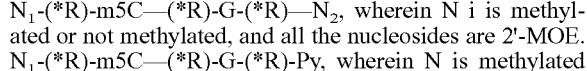, wherein N i is methylated or not methylated, and all the nucleosides are 2'-MOE.

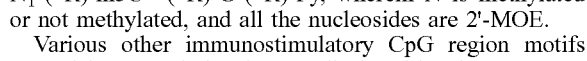, wherein N is methylated or not methylated, and all the nucleosides are 2'-MOE.

Various other immunostimulatory CpG region motifs comprising a methylated C are disclosed herein.

In some embodiments, mouse and human results with CpG oligonucleotides are not necessarily correlated.

The present disclosure reveals that, with stereochemically defined molecules, the same results are not necessarily found in mouse and human.

For example, CpG oligonucleotide WV-1512 is agonistic in mouse, but not in human (see FIGS. 10 and 13). Similarly, CpG oligonucleotide WV-1384 is agonistic in the mouse, but not in the human (see FIGS. 1 and 9). Other CpG oligonucleotides have shown different effects in the mouse and human.

Base Sequences of Some CpG Oligonucleotides Used Herein

In the data shown in this disclosure, chirally controlled variants of known CpG oligonucleotides were constructed and tested for activity. These include those shown below in Table 3.

TABLE 3

CpG OLIGONUCLEOTIDE BASE SEQUENCES

| Series | Reported Sequence (CpG is underlined) | Reference |
|---|---|---|
| SMAD7 series | GTCGCCCTTCTCCCCGCAGC (SEQ ID NO: 1524) | U.S. Pat. No. 9,096,854; Monteleone et al. 2015 NEJM 372: 12. |
| ODN2006 series | TCGTCGTTTTGTCGTTTTGTCGTT (SEQ ID NO: 2) | Vollmer et al. 2004 Eur. J. Immunol. 34: 251-262; Mangsbo et al. 2009 J. |

TABLE 3-continued

CpG OLIGONUCLEOTIDE BASE SEQUENCES

| Series | Reported Sequence (CpG is underlined) | Reference |
|---|---|---|
| | | Immunol. 183: 6724-6732; Pohar et al. 2015 J. Immunol. 194: 3901-3908. |
| SOD1 series | CCGTCGCCCTTCAGCACGCA (SEQ ID NO: 1696) | US Pat. App. No. 20120214865; Miller et al. 2013 Lancet Neurol. 12: 435; Fratta 2013 Lancet Neurol. 12: 416-417. |

CpG oligonucleotides used in the present disclosure are of various classes. They also differ in significant ways. For example, they differ in length (for example, ranging from 20 to 24) and in the number of CpG region motifs (for example, from 2 to 4). Example CpG oligonucleotides also differ in the position of the furthest upstream (most 5') CpG, as some are 1 nt and some are 2 nt from the 5' end. They also differ in the position of the furthest downstream (most 3') CpG, as some are 2 nt and some are 4 nt from the 3' end. The tested CpG oligonucleotides also differ in distances between their CpG motifs; for example, some distances are as short as 1 nt and as long as 11 nt. The tested CpG oligonucleotides also differ in the base sequences flanking the CpG motifs. The tested CpG oligonucleotides thus are of considerable diversity.

The SMAD7 series CpG oligonucleotide used in the present disclosure is also designated Mongersen, formerly GED0301, for the treatment of Crohn's disease (CD). CD-related inflammation is characterized by reduced activity of the immunosuppressive cytokine transforming growth factor β1 (TGF-β1) due to high levels of SMAD7, an inhibitor of TGF-B1 signaling. Mongersen targets ileal and colonic SMAD7. In a phase 2 clinical trial, study participants with CD who received Mongersen had significantly higher rates of remission and clinical response than those who received placebo. U.S. Pat. No. 9,096,854; Monteleone et al. 2015 NEJM 372: 12.

ODN2006 is a Class B CpG oligonucleotide, also known as ODN 2006, ODN 7909 or PF-3512676. It comprises four CpG motifs and has been extensively studied. ODN2006 is commercially available from InvivoGen, San Diego, Calif., as Catalog #tlrl-2006, tlrl-2006-1, tlrl-2006-5. HEK-Blue™ TLR9 cells.

HEK-Blue™ TLR9 cells stably overexpress the TLR9 gene and an NF-κβ inducible secreted embryonic alkaline phosphatase (SEAP) reporter gene. Vollmer et al. 2004 Eur. J. Immunol. 34: 251-262; Mangsbo et al. 2009 J. Immunol. 183: 6724-6732. A systematic study was performed varying the length, number of CpG motifs and other parameters of ODN2006. Pohar et al. 2015 J. Immunol. 194: 3901-3908.

The SOD1 CpG oligonucleotide is also designated ISIS 333611. This is an antisense oligonucleotide targeting SOD1, for use in treatment of familial amyotrophic lateral sclerosis. This oligonucleotide was used in the first clinical study of intrathecal delivery of an antisense oligonucleotide; it was well tolerated, with no dose-limiting toxic effects or any safety or tolerability concerns related to the oligonucleotide. US Pat. App. No. 20120214865; Miller et al. 2013 Lancet Neurol. 12: 435; Fratta 2013 Lancet Neurol. 12: 416-417.

The sequences of various CpG oligonucleotides described in the present disclosure are listed below, in Table 4 (including Tables 4A, 4B and 4C).

Table 4. CpG Oligonucleotide Base Sequences and Chirality

TABLE 4A

SMAD7 CpG OLIGONUCLEOTIDES

| WV-1372 | G*ST*Rm5C*RG*RC*SC*SC*SC*ST*SC*ST*SC*SC*SC*Rm5C*RG*RC*SA*SG*SC | (SEQ ID NO: 1756) |
| WV-1373 | G*ST*RC*RG*RC*SC*SC*SC*ST*ST*SC*ST*SC*SC*SC-RC*RG*RC*SA*SG*SC | (SEQ ID NO: 1757) |
| WV-1374 | G*ST*Sm5C*RG*SC*SC*SC*SC*ST*ST*SC*ST*SC*SC*SC*Sm5C*RG*SC*SA*SG*SC | (SEQ ID NO: 1758) |
| WV-1375 | G*ST*SC*RG*SC*SC*SC*SC*ST*ST*SC*ST*SC*SC*SC*SC*RG*SC*SA*SG*SC | (SEQ ID NO: 1759) |
| WV-1376 | G*ST*Sm5Ceo*RGeo*SC*SC*SC*SC*ST*ST*SC*ST*SC*SC*SC*Sm5Ceo*RGeo*SC*SA*SG*SC | (SEQ ID NO: 1760) |
| WV-1377 | G*ST*SCeo*RGeo*SC*SC*SC*SC*ST*ST*SC*ST*SC*SC*SC*SCeo*RGeo*SC*SA*SG*SC | (SEQ ID NO: 1761) |
| WV-1378 | G*ST*Rm5Ceo*RGeo*RC*SC*SC*SC*ST*ST*SC*ST*SC*SC*SC*Rm5Ceo*RGeo*RC*SA*SG*SC | (SEQ ID NO: 1762) |
| WV-1379 | G*ST*RCeo*RGeo*RC*SC*SC*SC*ST*ST*SC*ST*SC*SC*SC*RCeo*RGeo*RC*SA*SG*SC | (SEQ ID NO: 1763) |
| WV-1380 | G*ST*Sm5mC*RmG*SC*SC*SC*SC*ST*ST*SC*ST*SC*SC*SC*Sm5mC*RmG*SC*SA*SG*SC | (SEQ ID NO: 1764) |
| WV-1381 | G*ST*SmC*RmG*SC*SC*SC*SC*ST*ST*SC*ST*SC*SC*SC*SmC*RmG*SC*SA*SG*SC | (SEQ ID NO: 1765) |
| WV-1382 | G*ST*Rm5mC*RmG*RC*SC*SC*SC*ST*ST*SC*ST*SC*SC*SC*Rm5mC*RmG*RC*SA*SG*SC | (SEQ ID NO: 1766) |
| WV-1383 | G*ST*RmC*RmG*RC*SC*SC*SC*ST*ST*SC*ST*SC*SC*SC*RmC*RmG*RC*SA*SG*SC | (SEQ ID NO: 1767) |
| WV-1384 | G*ST*SC*SG*SC*SC*SC*SC*ST*ST*SC*ST*SC*SC*SC*SC*SG*SC*SA*SG*SC | (SEQ ID NO: 1768) |
| WV-1385 | G*RT*Rm5C*RG*RC*RC*RC*RC*RT*RT*RC*RT*RC*RC*RC*Rm5C*RG*RC*RA*RRG*RC | (SEQ ID NO: 1769) |
| WV-1386 | G*RT*RC*RG*RC*RC*RC*RC*RT*RT*RC*RT*RC*RC*RC*RC*RG*RC*RA*RG*RC | (SEQ ID NO: 1770) |
| WV-1387 | Geo*RTeo*Rm5Ceo*RGeo*RCeo*RC*SC*SC*ST*ST*SC*ST*SC*SC*SC*Rm5Ceo*RGeo*RCeo*RAeo*RGeo*RCeo | (SEQ ID NO: 1771) |
| WV-1388 | Geo*RTeo*RCeo*RGeo*RCeo*RC*SC*SC*ST*ST*SC*ST*SC*SC*SC*RCeo*RGeo*RCeo*RAeo*RGeo*RCeo | (SEQ ID NO: 1772) |
| WV-1389 | mG*RmU*Rm5mC*RmG*RmC*RC*SC*SC*ST*ST*SC*ST*SC*SC*SC*Rm5mC*RmG*RmC*RmA*RmG*RmC | (SEQ ID NO: 1773) |
| WV-1390 | mG*RmU*RmC*RmG*RmC*RC*SC*SC*ST*ST*SC*ST*SC*SC*SC*RmC*RmG*RmC*RmA*RmG*RmC | (SEQ ID NO: 1774) |
| WV-499 | G*T*m5C*G*C*C*C*T*T*C*T*C*C*m5C*G*C*A*G*C | (SEQ ID NO: 1775) |

TABLE 4A-continued

SMAD7 CpG OLIGONUCLEOTIDES

| | | |
|---|---|---|
| WV-901 | G*ST*Sm5C*SG*SC*SC*SC*SC*ST*ST*RC*ST*SC*RC*SC*Sm5C*SG*SC*SA*SG*SC | (SEQ ID NO: 1776) |
| WV-966 | G*ST*Sm5C*SG*SC*SC*SC*SC*ST*ST*SC*ST*SC*SC*SC*Sm5C*SG*SC*SA*SG*SC | (SEQ ID NO: 1777) |
| WV-1517 | G*T*C*G*C*C*C*T*T*C*T*C*C*C*m5C*G*C*A*G*C | (SEQ ID NO: 1778) |
| WV-1518 | G*T*m5C*G*C*C*C*C*T*T*C*T*C*C*C*C*G*C*A*G*C | (SEQ ID NO: 1779) |
| WV-1371 | G*T*C*G*C*C*C*C*T*T*C*T*C*C*C*C*G*C*A*G*C | (SEQ ID NO: 1780) |

TABLE 4B

ODN2006 SERIES CpG OLIGONUCLEOTIDES

| | | |
|---|---|---|
| WV-1694 | T*SC*SG*ST*SC*SG*ST*ST*ST*ST*SG*ST*SC*SG*ST*ST*ST*ST*SG*ST*SC*SG*ST*ST | (SEQ ID NO: 1781) |
| WV-1695 | T*RC*SG*ST*RC*SG*ST*ST*ST*ST*SG*ST*RC*SG*ST*ST*ST*ST*SG*ST*RC*SG*ST*ST | (SEQ ID NO: 1782) |
| WV-1696 | T*SC*RG*ST*SC*RG*ST*ST*ST*ST*SG*ST*SC*RG*ST*ST*ST*ST*SG*ST*SC*RG*ST*ST | (SEQ ID NO: 1783) |
| WV-1697 | T*SC*SG*RT*SC*SG*RT*ST*ST*ST*SG*ST*SC*SG*RT*ST*ST*ST*SG*ST*SC*SG*SG*RT*ST | (SEQ ID NO: 1784) |
| WV-1698 | T*RC*RG*ST*RC*RG*ST*ST*ST*ST*SG*ST*RC*RG*ST*ST*ST*ST*SG*ST*RC*RG*ST*ST | (SEQ ID NO: 1785) |
| WV-1699 | T*SC*RG*RT*SC*RG*RT*ST*ST*ST*SG*ST*SC*RG*RT*ST*ST*ST*SG*ST*SC*RG*RT*ST | (SEQ ID NO: 1786) |
| WV-1700 | T*RC*SG*RT*RC*SG*RT*ST*ST*ST*SG*ST*RC*SG*RT*ST*ST*ST*SG*ST*RC*SG*RT*ST | (SEQ ID NO: 1787) |
| WV-1701 | T*RC*SG*RT*RC*SG*RT*ST*ST*ST*SG*ST*RC*RG*RT*ST*ST*ST*SG*ST*RC*RG*RT*ST | (SEQ ID NO: 1787) |
| WV-1702 | ST*ST*ST*SG*ST*RC*SG*ST*ST*ST*ST*SG*ST | (SEQ ID NO: 1788) |
| WV-1703 | ST*ST*ST*SG*ST*SC*RG*ST*ST*ST*ST*SG*ST | (SEQ ID NO: 1790) |
| WV-1704 | ST*ST*ST*SG*ST*SC*SG*RT*ST*ST*ST*SG*ST | (SEQ ID NO: 1791) |
| WV-1705 | ST*ST*ST*SG*ST*RC*RG*ST*ST*ST*ST*SG*ST | (SEQ ID NO: 1792) |
| WV-1706 | ST*ST*ST*SG*ST*SC*RG*RT*ST*ST*ST*SG*ST | (SEQ ID NO: 1793) |
| WV-1707 | ST*ST*ST*SG*ST*RC*SG*RT*ST*ST*ST*SG*ST | (SEQ ID NO: 1794) |
| WV-1708 | ST*ST*ST*SG*ST*RC*RG*RT*ST*ST*ST*SG*ST | (SEQ ID NO: 1795) |

TABLE 4C

SOD1 SERIES CpG OLIGONUCLEOTIDES

| | | |
|---|---|---|
| WV-458 | m5Ceo*m5Ceo*Geo*Teo*m5Ceo*G*m5C*m5C*m5C*T*T*m5C*A*G*m5C*Aeo*m5Ceo*Geo*m5Ceo*Aeo | (SEQ ID NO: 1796) |
| WV-459 | m5C*m5C*G*T*m5C*G*m5C*m5C*m5C*T*T*m5C*A*G*m5C*A*m5C*G*m5C*A | (SEQ ID NO: 1797) |
| WV-486 | m5Ceo*Sm5Ceo*SGeo*STeo*Sm5Ceo*SG*Sm5C*Sm5C*Sm5C*ST*ST*Sm5C*SA*SG*Sm5C*SAeo*Sm5Ceo*SGeo*Sm5Ceo*SAeo | (SEQ ID NO: 1798) |
| WV-487 | Sm5Ceo*Sm5Ceo*SGeo*STeo*Sm5Ceo*SG*Sm5C*Sm5C*Sm5C*ST*ST*Sm5C*RA*SG*Sm5C*SAeo*Sm5Ceo*Geo*Sm5Ceo*SAeo | (SEQ ID NO: 1799) |
| WV-488 | m5Ceo*Rm5Ceo*RGeo*RTeo*Rm5Ceo*RG*Sm5C*Sm5C*Sm5C*ST*ST*Sm5C*RA*SG*Sm5C*SAeo*Rm5Ceo*RGeo*Rm5Ceo*RAeo | (SEQ ID NO: 1800) |
| WV-1489 | m5Ceo*Rm5Ceo*SGeo*RTeo*Rm5Ceo*RG*Sm5C*Sm5C*Sm5C*ST*ST*Sm5C*RA*SG*Sm5C*SAeo*Rm5Ceo*RGeo*Rm5Ceo*RAeo | (SEQ ID NO: 1801) |
| WV-1490 | m5Ceo*Rm5Ceo*RGeo*RTeo*Rm5Ceo*SG*Sm5C*Sm5C*Sm5C*ST*ST*Sm5C*RA*SG*Sm5C*SAeo*Rm5Ceo*RGeo*Rm5Ceo*RAeo | (SEQ ID NO: 1802) |
| WV-1491 | m5Ceo*Rm5Ceo*RGeo*RTeo*Rm5Ceo*RG*Sm5C*Sm5C*Sm5C*ST*ST*Sm5C*RA*SG*Sm5C*SAeo*Rm5Ceo*SGeo*Rm5Ceo*RAeo | (SEQ ID NO: 1803) |
| WV-1492 | m5Ceo*Sm5Ceo*RGeo*STeo*Sm5Ceo*RG*Sm5C*Sm5C*Sm5C*ST*ST*Sm5C*RA*SG*Sm5C*SAeo*Sm5Ceo*RGeo*Sm5Ceo*SAeo | (SEQ ID NO: 1804) |
| WV1493.02 | C*SC*RG*ST*SC*RG*SC*SC*SC*ST*ST*SC*RA*SG*SC*SA*SC*RG*SC*SA | (SEQ ID NO: 1805) |
| WV1494.01 | C*C*G*T*C*G*C*C*C*T*T*C*A*G*C*A*C*G*C*A | (SEQ ID NO: 1806) |
| WV1495.02 | m5C*Sm5C*RG*ST*Sm5C*RG*Sm5C*Sm5C*Sm5C*ST*ST*Sm5C*RA*SG*Sm5C*SA*Sm5C*RG*Sm5C*SA | (SEQ ID NO: 1807) |
| WV1496.02 | C*SC*RG*ST*SC*RG*SC*SC*SC*ST*ST*SC*SA*SG*SC*SA*SC*RG*SC*SA | (SEQ ID NO: 1808) |
| WV1512.02 | C*SC*SG*ST*SC*SG*SC*SC*SC*ST*ST*SC*SA*SG*SC*SA*SC*SG*SC*SA | (SEQ ID NO: 1809) |
| WV1513.02 | C*SC*RG*ST*SC*SG*SC*SC*SC*ST*ST*SC*SA*SG*SC*SA*SC*SG*SC*SA | (SEQ ID NO: 1810) |
| WV1514.02 | C*SC*SG*ST*SC*RG*SC*SC*SC*ST*ST*SC*SA*SG*SC*SA*SC*SG*SC*SA | (SEQ ID NO: 1811) |
| WV1515.02 | C*SC*SG*ST*SC*SG*SC*SC*SC*ST*ST*SC*SA*SG*SC*SA*SC*RG*SC*SA | (SEQ ID NO: 1812) |
| WV-1669 | m5Ceo*Sm5Ceo*SGeo*STeo*Sm5Ceo*SG*Sm5C*Sm5C*Sm5C*ST*ST*Sm5C*RA*SG*Sm5C*SAeo*Sm5Ceo*SGeo*Sm5Ceo*SAeo-Biotin | (SEQ ID NO: 1813) |
| WV-1670 | m5Ceo*Rm5Ceo*RGeo*RTeo*Rm5Ceo*RG*Sm5C*Sm5C*Sm5C*ST*ST*Sm5C*RA*SG*Sm5C*SAeo*Rm5Ceo*RGeo*Rm5Ceo*RAeo-Biotin | (SEQ ID NO: 1814) |
| WV-1671 | Biotin-m5Ceo*Sm5Ceo*SGeo*STeo*Sm5Ceo*SG*Sm5C*Sm5C*Sm5C*ST*ST*Sm5C*RA*SG*Sm5C*SAeo*Sm5Ceo*SGeo*Sm5Ceo*SAeo | (SEQ ID NO: 1815) |

TABLE 4C-continued

SOD1 SERIES CpG OLIGONUCLEOTIDES

| | | |
|---|---|---|
| WV-1672 | Biotin-m5Ceo*Rm5Ceo*RGeo*RTeo*Rm5Ceo*RG*Sm5C*Sm5C*Sm5C*ST*ST*Sm5C*RA*SG*Sm5C*SAeo*Rm5Ceo*RGeo*Rm5Ceo*RAeo | (SEQ ID NO: 1816) |
| WV-1673 | m5Ceo*RAeo*RGeo*RTeo*Rm5Ceo*RG*Sm5C*Sm5C*Sm5C*ST*ST*Sm5C*RA*SG*Sm5C*SAeo*Rm5Ceo*RGeo*Rm5Ceo*RAeo | (SEQ ID NO: 1817) |
| WV-1674 | m5Ceo*Rm5Ceo*RGeo*RTeo*RAeo*RG*Sm5C*Sm5C*Sm5C*ST*ST*Sm5C*RA*SG*Sm5C*SAeo*Rm5Ceo*RGeo*Rm5Ceo*RAeo | (SEQ ID NO: 1818) |

In some embodiments,
* only represents a stereorandom phosphorothioate linkage;
*S represents an Sp phosphorothioate linkage;
*R represents an Rp phosphorothioate linkage;
all non-labeled linkage is a natural phosphate linkage;
m preceding a base represents 2'-OMe (e.g., mC is 2'-OMe C);
eo following a base represents 2'-MOE (e.g., Geo is 2'-MOE);
m5m preceding a base represents a 2'-OMe and 5'-methylation (e.g., m5mC is 2'-OMe 5-methyl C);
m5Ceo is 2'-MOE m5C.

Other oligonucleotides used herein include reference and control oligonucleotides:

```
ODN 1826 (SMAD7 series)
5'-TCCATGACGTTCCTGACGTT-3'        (SEQ ID NO: 1819)

ODN 1826c (negative control)
5'-TCCATGAGCTTCCTGAGCTT-3'        (SEQ ID NO: 1820)

ODN2006
5'-TCGTCGTTTTGTCGTTTTGTCGTT-3'    (SEQ ID NO: 2)

ODN2006c (negative control)
5'-TGCTGCTTTTGTGCTTTTGTGCTT-3'    (SEQ ID NO: 1821)

SOD1
5'-CCGTCGCCCTTCAGCACGCA-3'        (SEQ ID NO: 1696)
```

Many tested oligonucleotides were stereopure (or mostly stereopure) or chirally controlled CpG oligonucleotide compositions, but reference oligonucleotides ODN 1826, ODN 1826c, ODN2006, ODN2006 and SOD1 are all stereomixtures or stereorandom CpG oligonucleotide compositions. Each of ODN 1826, ODN 1826c, ODN2006, ODN2006 and SOD1 has all phosphorothioates as internucleoside linkages (no phosphodiesters).

ODN2006c is a negative control of ODN2006, wherein the sequences CpG were swapped with GpC (which is generally not immunogenic). Similarly, ODN1826c is a negative control version of ODN1826, in which CpG is again replaced by GpC.

The large number of CpG oligonucleotides tested allows certain general conclusions to be made. The present disclosure notes, however, that it is not bound by any particular theory or point of conjecture.

The present disclosure notes that many different CpG oligonucleotides were found to be effective at agonizing an immune response. These differ in CpG region motif, wherein the CpG region motif is defined at least partially by the chirality of the phosphorothioate linkages.

Various CpG region motifs are listed in Table 1. These include both CpG region motifs of agonistic and antagonistic CpG oligonucleotides.

Agonistic CpG Oligonucleotides Comprising a Strand Comprising a CpG Region Motif In some embodiments, a CpG oligonucleotide can be determined to be agonistic or antagonistic based on a measurement of a change in secretion of a cytokine, e.g., interferon-alpha, interferon-gamma, IL-4, IL-6, IL-8, IL-10, IL-12, TNF-alpha, etc.

As a non-limiting example, in several figures in the present disclosure, agonistic activity of CpG oligonucleotides was measured as an increase in NF-κβ activity. In a non-limiting example, in several figures, agonistic activity of CpG oligonucleotides was measured by secretion of inflammatory cytokines (IL-6 and MIP-1β). As a non-limiting example, in several figures in the present disclosure, antagonistic activity of CpG oligonucleotides was measured as a decrease in NF-κβ activity (in competition with a TLR9 agonist).

In some embodiments, an agonistic CpG oligonucleotide is capable of mediating at least a 10% increase in a cytokine in vitro (relative to the absence of the oligonucleotide). In some embodiments, an agonistic CpG oligonucleotide is capable of mediating at least a 20% increase in a cytokine in vitro in human cells. In some embodiments, an agonistic CpG oligonucleotide is capable of mediating at least a 30% increase in a cytokine in vitro in human cells. In some embodiments, an agonistic CpG oligonucleotide is capable of mediating at least a 40% increase in a cytokine in vitro in human cells. In some embodiments, an agonistic CpG oligonucleotide is capable of mediating at least a 50% increase in a cytokine in vitro in human cells. In some embodiments, an agonistic CpG oligonucleotide is capable of mediating at least a 60% increase in a cytokine in vitro in human cells. In some embodiments, an agonistic CpG oligonucleotide is capable of mediating at least a 70% increase in a cytokine in vitro in human cells. In some embodiments, an agonistic CpG oligonucleotide is capable of mediating at least a 80% increase in a cytokine in vitro in human cells. In some embodiments, an agonistic CpG oligonucleotide is capable of mediating at least a 90% increase in a cytokine in vitro in human cells. In some embodiments, an agonistic CpG oligonucleotide is capable of mediating at least a 100% increase in a cytokine in vitro in human cells. In some embodiments, an agonistic CpG oligonucleotide is capable of mediating at least a 110% increase in a cytokine in vitro (relative to the absence of the oligonucleotide). In some embodiments, an agonistic CpG oligonucleotide is capable of mediating at least a 120% increase in a cytokine in vitro in human cells. In some embodiments, an agonistic CpG oligonucleotide is capable of mediating at least a 130% increase in a cytokine in vitro in human cells. In some embodiments, an agonistic CpG oligonucleotide is capable of mediating at least a 140% increase in a cytokine in vitro in human cells. In some embodiments, an agonistic CpG oligonucleotide is capable of mediating at least a 150% increase in a cytokine in vitro in human cells. In some embodiments, an agonistic CpG oligonucleotide is capable of mediating at least a 160% increase in a cytokine in vitro in human cells. In some embodiments, an agonistic CpG oligonucleotide is capable of mediating at least a 170% increase in a cytokine in vitro in human cells. In some embodiments, an agonistic CpG oligonucleotide is capable of mediating at least a 180% increase in a cytokine in vitro in human cells. In some embodiments, an agonistic CpG oligonucleotide is capable of mediating at least a 190% increase in a cytokine in vitro in human cells. In some embodiments, an agonistic CpG oligonucleotide is capable of mediating at least a 200% increase in a cytokine in vitro in human cells.

In some embodiments, an agonistic CpG oligonucleotide is capable of mediating at least a 10% increase in NF-κP activity in vitro (relative to the absence of the oligonucleotide). In some embodiments, an agonistic CpG oligonucleotide is capable of mediating at least a 20% increase in NF-κP activity in vitro in human cells. In some embodiments, an agonistic CpG oligonucleotide is capable of mediating at least a 30% increase in NF-κP activity in vitro in human cells. In some embodiments, an agonistic CpG oligonucleotide is capable of mediating at least a 40% increase in NF-κP activity in vitro in human cells. In some embodiments, an agonistic CpG oligonucleotide is capable of mediating at least a 50% increase in NF-κP activity in vitro in human cells. In some embodiments, an agonistic CpG oligonucleotide is capable of mediating at least a 60% increase in NF-κP activity in vitro in human cells. In some embodiments, an agonistic CpG oligonucleotide is capable of mediating at least a 70% increase in NF-κP activity in vitro in human cells. In some embodiments, an agonistic CpG oligonucleotide is capable of mediating at least a 80% increase in NF-κP activity in vitro in human cells. In some embodiments, an agonistic CpG oligonucleotide is capable of mediating at least a 90% increase in NF-κP activity in vitro in human cells. In some embodiments, an agonistic CpG oligonucleotide is capable of mediating at least a 100% increase in NF-κP activity in vitro in human cells. In some embodiments, an agonistic CpG oligonucleotide is capable of mediating at least a 110% increase in NF-κP activity in vitro (relative to the absence of the oligonucleotide). In some embodiments, an agonistic CpG oligonucleotide is capable of mediating at least a 120% increase in NF-κP activity in vitro in human cells. In some embodiments, an agonistic CpG oligonucleotide is capable of mediating at least a 130% increase in NF-κP activity in vitro in human cells. In some embodiments, an agonistic CpG oligonucleotide is capable of mediating at least a 140% increase in NF-κP activity in vitro in human cells. In some embodiments, an agonistic CpG oligonucleotide is capable of mediating at least a 150% increase in NF-κP activity in vitro in human cells. In some embodiments, an agonistic CpG oligonucleotide is capable of mediating at least a 160% increase in NF-κP activity in vitro in human cells. In some embodiments, an agonistic CpG oligonucleotide is capable of mediating at least a 170% increase in NF-κP activity in vitro in human cells. In some embodiments, an agonistic CpG oligonucleotide is capable of mediating at least a 180% increase in NF-κP activity in vitro in human cells. In some embodiments, an agonistic CpG oligonucleotide is capable of mediating at least a 190% increase in NF-κP activity in vitro in human cells. In some embodiments, an agonistic CpG oligonucleotide is capable of mediating at least a 200% increase in NF-κP activity in vitro in human cells.

In some embodiments, an antagonistic CpG oligonucleotide is capable of mediating at least a 10% decrease in a cytokine in vitro (relative to the absence of the oligonucleotide). In some embodiments, an antagonistic CpG oligonucleotide is capable of mediating at least a 20% decrease in a cytokine in vitro in human cells. In some embodiments, an antagonistic CpG oligonucleotide is capable of mediating at least a 30% decrease in a cytokine in vitro in human cells. In some embodiments, an antagonistic CpG oligonucleotide is capable of mediating at least a 40% decrease in a cytokine in vitro in human cells. In some embodiments, an antagonistic CpG oligonucleotide is capable of mediating at least a 50% decrease in a cytokine in vitro in human cells. In some embodiments, an antagonistic CpG oligonucleotide is capable of mediating at least a 60% decrease in a cytokine in vitro in human cells. In some embodiments, an antagonistic CpG oligonucleotide is capable of mediating at least a 70% decrease in a cytokine in vitro in human cells. In some embodiments, an antagonistic CpG oligonucleotide is capable of mediating at least a 80% decrease in a cytokine in vitro in human cells. In some embodiments, an antagonistic CpG oligonucleotide is capable of mediating at least a 90% decrease in a cytokine in vitro in human cells. In some embodiments, an antagonistic CpG oligonucleotide is capable of mediating at least a 100% decrease in a cytokine in vitro in human cells.

In some embodiments, an antagonistic CpG oligonucleotide is capable of mediating at least a 10% decrease in NF-κP activity in vitro (relative to the absence of the oligonucleotide). In some embodiments, an antagonistic CpG oligonucleotide is capable of mediating at least a 20% decrease in NF-κP activity in vitro in human cells. In some embodiments, an antagonistic CpG oligonucleotide is capable of mediating at least a 30% decrease in NF-κβ activity in vitro in human cells. In some embodiments, an antagonistic CpG oligonucleotide is capable of mediating at least a 40% decrease in NF-κβ activity in vitro in human cells. In some embodiments, an antagonistic CpG oligonucleotide is capable of mediating at least a 50% decrease in NF-κβ activity in vitro in human cells. In some embodiments, an antagonistic CpG oligonucleotide is capable of mediating at least a 60% decrease in NF-κβ activity in vitro in human cells. In some embodiments, an antagonistic CpG oligonucleotide is capable of mediating at least a 70% decrease in NF-κβ activity in vitro in human cells. In some embodiments, an antagonistic CpG oligonucleotide is capable of mediating at least a 80% decrease in NF-κβ activity in vitro in human cells. In some embodiments, an antagonistic CpG oligonucleotide is capable of mediating at least a 90% decrease in NF-κβ activity in vitro in human cells. In some embodiments, an antagonistic CpG oligonucleotide is capable of mediating at least a 100% decrease in NF-κβ activity in vitro in human cells.

Any method known in the art can be used to determine if a CpG oligonucleotide is agonistic or antagonistic (or neither).

In some embodiments, the present disclosure provides methods for assaying TLR9 agonist or antagonist activities, comprising providing a provided chirally controlled oligonucleotide composition described herein. In some embodiments, the present disclosure provides assay systems for assaying TLR9 agonist or antagonist activities, comprising providing a provided chirally controlled oligonucleotide composition.

CpG Oligonucleotides Comprising a Strand Comprising a CpG Region Motif: All Rp

Figure 7:
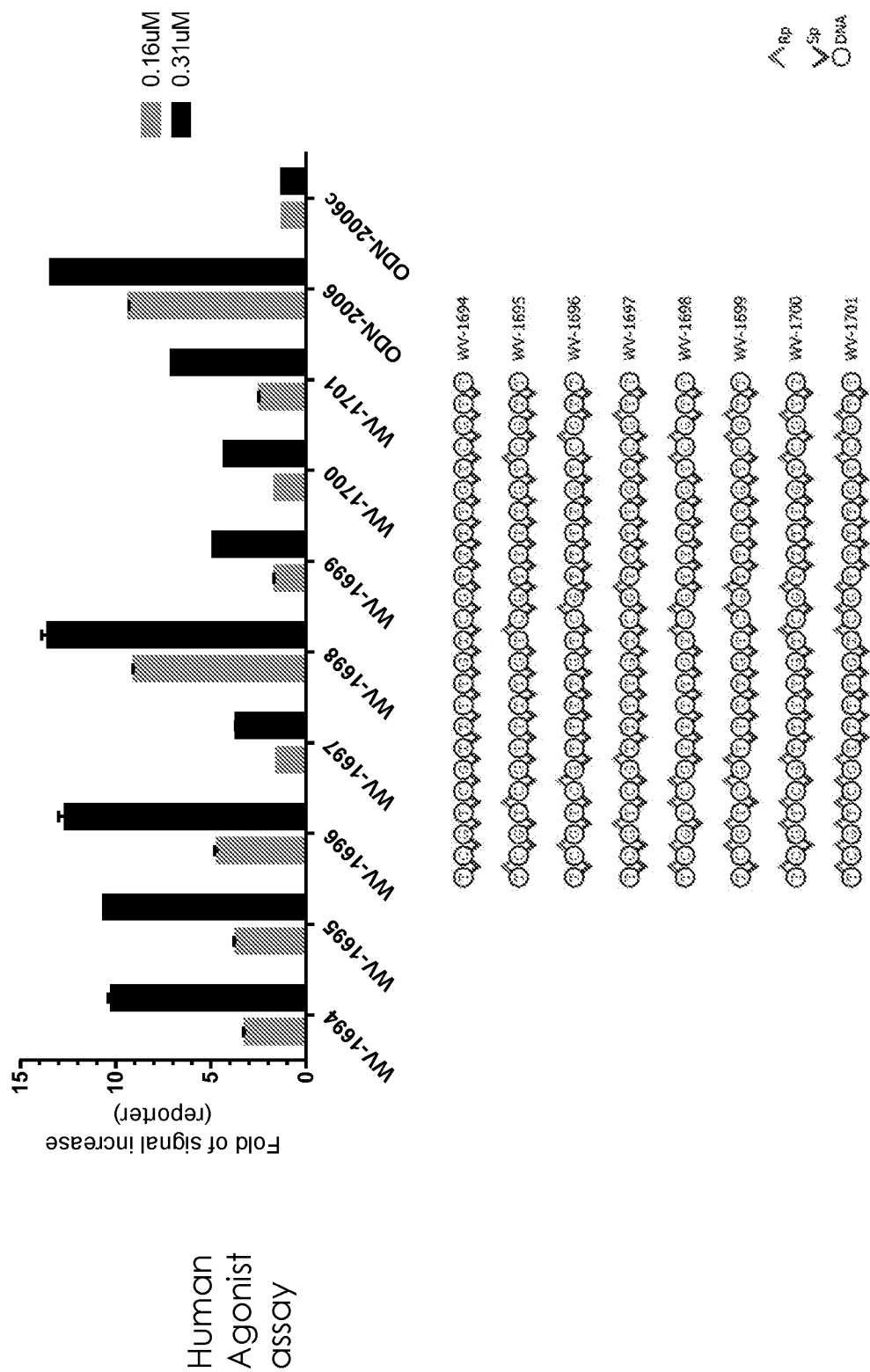
FIG. 7 shows the effects of stereochemistry of CpG region motifs on human TLR9 activities; data from ODN2006 series.
Figure 8:
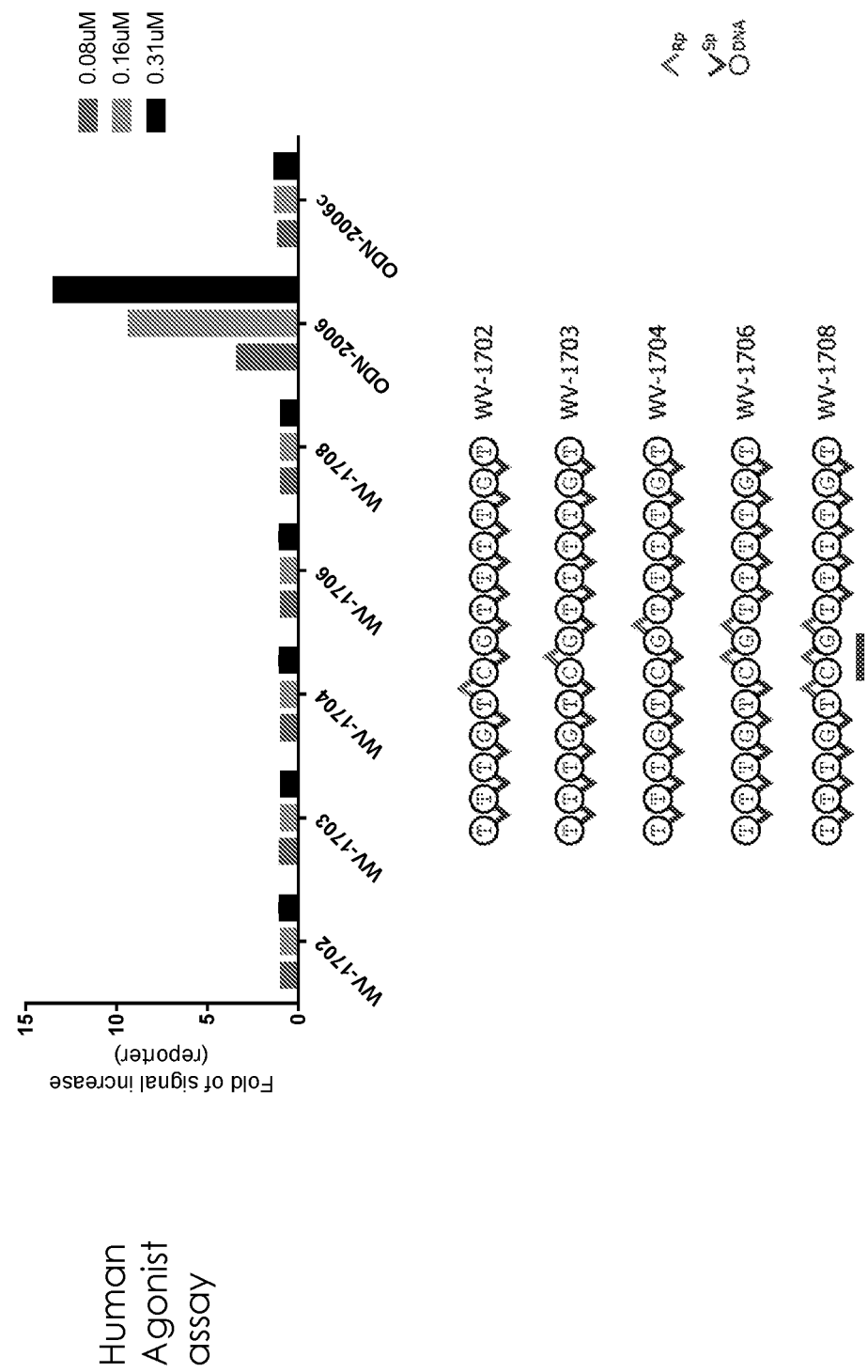
FIG. 8 shows that, in this experiment, some CpG oligonucleotides were not highly active.

One design of PS chirality in a CpG region motif is that all the PS are of the same chirality; thus, they are either all Rp or all Sp. Many CpG oligonucleotides were constructed and tested wherein all the PS in the CpG region motif were either all Rp or Sp. For example, CpG oligonucleotide WV-1701 was effective at agonizing an immune response in human cells (FIG. 7). Without wishing to be bound to any particular theory, the present disclosure notes that the finding that some CpG oligos were effective and some were not if the entire CpG region motif was Rp is consistent with the idea that both the base sequence and the sequence of PS chirality may be relevant for effecting agonism. Efficacious CpG oligonucleotide WV-1701 comprises the agonistic CpG region motif of T-(*R)—C—(*R)-*G-(*R)-T. In some embodiments, CpG oligonucleotides which comprise only 1 copy of a CpG motif are capable of agonizing an immune response In some embodiments, the present disclosure provides: A chirally controlled CpG oligonucleotide composition comprising a CpG oligonucleotide comprising a strand comprising at least one copy of the CpG region motif T-(*R)—C—(*R)-*G-(*R)-T.
A chirally controlled CpG oligonucleotide composition comprising a CpG oligonucleotide comprising a strand comprising at least two copies of the CpG region motif T-(*R)—C—(*R)-*G-(*R)-T.
A chirally controlled CpG oligonucleotide composition comprising a CpG oligonucleotide comprising a strand comprising at least three copies of the CpG region motif T-(*R)—C—(*R)-*G-(*R)-T.
A chirally controlled CpG oligonucleotide composition comprising a CpG oligonucleotide comprising a strand comprising at least four copies of the CpG region motif T-(*R)—C—(*R)-*G-(*R)-T.
The CpG region motif of WV-1701 could also be described as four copies of T-(*R)—C—(*R)-G-(*R)-T-(*R)-Py, wherein Py is a pyrimidine.

In some embodiments, the present disclosure has also shown that many CpG oligonucleotides which comprise only 1 copy of a CpG motif are capable of agonizing an immune response.

In some embodiments, the present disclosure provides:
A chirally controlled CpG oligonucleotide composition comprising a CpG oligonucleotide comprising a strand comprising at least one copy of the CpG region motif T-(*R)—C—(*R)-G-(*R)-T-(*R)-Py.
A chirally controlled CpG oligonucleotide composition comprising a CpG oligonucleotide comprising a strand comprising at least two copies of the CpG region motif T-(*R)—C—(*R)-G-(*R)-T-(*R)-Py.
A chirally controlled CpG oligonucleotide composition comprising a CpG oligonucleotide comprising a strand comprising at least three copies of the CpG region motif T-(*R)—C—(*R)-G-(*R)-T-(*R)-Py.
A chirally controlled CpG oligonucleotide composition comprising a CpG oligonucleotide comprising a strand comprising at least four copies of the CpG region motif T-(*R)—C—(*R)-G-(*R)-T-(*R)-Py.

In various embodiments, the CpG oligonucleotide is capable of agonizing an immune response in human cells. In various embodiments, C is unmethylated C. In various embodiments, at least one nucleoside is 2'H (DNA). In various embodiments, each nucleoside is 2'H (DNA). In various embodiments, the CpG oligonucleotide is between 15 and 49 nt in length. In various embodiments, the CpG oligonucleotide is capable of agonizing an immune response in human cells, and/or C is unmethylated C, and/or at least one nucleoside is 2'H (DNA), and/or each nucleoside is 2'H (DNA), and/or the CpG oligonucleotide is between 15 and 49 nt in length.

WV-1701, which agonizes an immune response in the human (see FIG. 7) also has the format of comprising at least two CpG region motifs of $N_1$-(*R)—C—(*R)-G-(*R)—$N_2$, and comprises at least one phosphorothioate in the Sp conformation between the CpG region motifs.

In some embodiments, the present disclosure provides: A chirally controlled CpG oligonucleotide composition comprising a CpG oligonucleotide comprising a strand comprising at least two non-adjacent copies of the CpG region motif of $N_1$-(*R)—C—(*R)-G-(*R)—$N_2$, wherein at least one phosphorothioate between the CpG region motifs is in the Sp conformation. In various embodiments, at least one nucleoside is 2'H (DNA). In various embodiments, each nucleoside is 2'H (DNA). In various embodiments, the CpG oligonucleotide is between 15 and 49 nt in length. In various embodiments, the CpG oligonucleotide is capable of agonizing an immune response in human cells, and/or C is unmethylated C, and/or at least one nucleoside is 2'H (DNA), and/or each nucleoside is 2'H (DNA), and/or the CpG oligonucleotide is between 15 and 49 nt in length.

CpG oligonucleotides comprising a strand comprising a CpG region motif: All Sp
Many CpG oligonucleotides were constructed and tested wherein all the PS in the CpG region motif were all 5'p. CpG oligonucleotide WV-1694 was effective at agonizing an immune response in human cells (FIG. 7). In some embodiments, the present disclosure provides:
A chirally controlled CpG oligonucleotide composition comprising a CpG oligonucleotide comprising a strand comprising the agonistic CpG region motif T-(*S)—C—(*S)-G-(*S)-T-(*S)-T.
A chirally controlled CpG oligonucleotide composition comprising a CpG oligonucleotide comprising a strand comprising at least one copy of the CpG region motif T-(*S)—C—(*S)-G-(*S)-T-(*S)-T.
A chirally controlled CpG oligonucleotide composition comprising a CpG oligonucleotide comprising a strand comprising at least two copies of the CpG region motif T-(*S)—C—(*S)-G-(*S)-T-(*S)-T.
A chirally controlled CpG oligonucleotide composition comprising a CpG oligonucleotide comprising a strand comprising at least three copies of the CpG region motif T-(*S)—C—(*S)-G-(*S)-T-(*S)-T.
A chirally controlled CpG oligonucleotide composition comprising a CpG oligonucleotide comprising a strand comprising at least four copies of the CpG region motif T-(*S)—C—(*S)-G-(*S)-T-(*S)-T.

In various embodiments, a chirally controlled CpG oligonucleotide composition comprising a CpG oligonucleotide is capable of agonizing an immune response in human cells. In various embodiments, C is unmethylated C. In various embodiments, at least one nucleoside is 2'H (DNA). In various embodiments, each nucleoside is 2'H (DNA). In various embodiments, the CpG oligonucleotide is between 15 and 49 nt in length. In various embodiments, the CpG oligonucleotide is capable of agonizing an immune response in human cells, and/or C is unmethylated C, and/or at least one nucleoside is 2'H (DNA), and/or each nucleoside is 2'H (DNA), and/or the CpG oligonucleotide is between 15 and 49 nt in length.

Agonistic CpG Region Motifs Comprising a Mixture of Rp and Sp
Many CpG oligonucleotides were constructed and tested wherein the PS in the CpG region motif were a mixture of Rp and Sp. Several CpG oligonucleotides are shown herein to be capable of mediating agonism in human cells, including: WV-1698, WV-1696, WV-1695, WV-1699, WV-1700, WV-1697 all mediated agonism in the human (see FIG. 7).

In some embodiments, various CpG oligonucleotides comprise a CpG region motif of:

$N_1$-(*R/S)—C—(*R/S)-G-(*R/S)—$N_2$ $N_1$-(*R/S)—C—(*R/S)-G-(*R/S)—$N_2$, wherein at least one *R/S is *R and at least one *R/S is *S $N_1$-(*R/S)—C—(*R/S)-G-(*R/S)—$N_2$, wherein at least one *R/S is *R and at least one *R/S is *S, and wherein C is unmethylated $N_1$-(*R)—C—(*R)-G-(*S)—$N_2$ $N_1$-(*R)—C—(*S)-G-(*S)—$N_2$ $N_1$-(*R)—C—(*S)-G-(*R)—$N_2$ $N_1$-(*S)—C—(*R)-G-(*S)—$N_2$ $N_1$-(*S)—C—(*R)-G-(*R)—$N_2$ $N_1$-(*S)—C—(*S)-G-(*R)—$N_2$ Py-(*R/S)—C—(*R/S)-G-(*R/S)-Py, wherein at least one *R/S is *R and at least one *R/S is *S, and wherein C is unmethylated $N_1$-(*R/S)—C—(*R/S)-G-(*R)—$N_2$ $N_1$-(*R/S)—C—(*R/S)-G-(*S)—$N_2$ In some embodiments, the present disclosure provides:

A chirally controlled CpG oligonucleotide composition comprising a CpG oligonucleotide comprising a strand comprising at least one copy of the CpG region motif $N_1$-(*R/S)—C—(*R/S)-G-(*R/S)—$N_2$.

A chirally controlled CpG oligonucleotide composition comprising a CpG oligonucleotide comprising a strand comprising at least two copies of the CpG region motif $N_1$-(*R/S)—C—(*R/S)-G-(*R/S)—$N_2$.

A chirally controlled CpG oligonucleotide composition comprising a CpG oligonucleotide comprising a strand comprising at least three copies of the CpG region motif $N_1$-(*R/S)—C—(*R/S)-G-(*R/S)—$N_2$.

A chirally controlled CpG oligonucleotide composition comprising a CpG oligonucleotide comprising a strand comprising at least four copies of the CpG region motif $N_1$-(*R/S)—C—(*R/S)-G-(*R/S)—$N_2$.

A chirally controlled CpG oligonucleotide composition comprising a CpG oligonucleotide comprising a strand comprising at least one copy of the CpG region motif $N_1$-(*R/S)—C—(*R/S)-G-(*R/S)—$N_2$, wherein at least one *R/S is *R and at least one *R/S is *S.

A chirally controlled CpG oligonucleotide composition comprising a CpG oligonucleotide comprising a strand comprising at least two copies of the CpG region motif $N_1$-(*R/S)—C—(*R/S)-G-(*R/S)—$N_2$, wherein at least one *R/S is *R and at least one *R/S is *S.

A chirally controlled CpG oligonucleotide composition comprising a CpG oligonucleotide comprising a strand comprising at least three copies of the CpG region motif $N_1$-(*R/S)—C—(*R/S)-G-(*R/S)—$N_2$, wherein at least one *R/S is *R and at least one *R/S is *S.

A chirally controlled CpG oligonucleotide composition comprising a CpG oligonucleotide comprising a strand comprising at least four copies of the CpG region motif $N_1$-(*R/S)—C—(*R/S)-G-(*R/S)—$N_2$, wherein at least one *R/S is *R and at least one *R/S is *S.

A chirally controlled CpG oligonucleotide composition comprising a CpG oligonucleotide comprising a strand comprising at least one copy of the CpG region motif $N_1$-(*R/S)—C—(*R/S)-G-(*R/S)—$N_2$, wherein at least one *R/S is *R and at least one *R/S is *S, and wherein C is unmethylated.

A chirally controlled CpG oligonucleotide composition comprising a CpG oligonucleotide comprising a strand comprising at least two copies of the CpG region motif $N_1$-(*R/S)—C—(*R/S)-G-(*R/S)—$N_2$, wherein at least one *R/S is *R and at least one *R/S is *S, and wherein C is unmethylated.

A chirally controlled CpG oligonucleotide composition comprising a CpG oligonucleotide comprising a strand comprising at least three copies of the CpG region motif $N_1$-(*R/S)—C—(*R/S)-G-(*R/S)—$N_2$, wherein at least one *R/S is *R and at least one *R/S is *S, and wherein C is unmethylated.

A chirally controlled CpG oligonucleotide composition comprising a CpG oligonucleotide comprising a strand comprising at least four copies of the CpG region motif $N_1$-(*R/S)—C—(*R/S)-G-(*R/S)—$N_2$, wherein at least one *R/S is *R and at least one *R/S is *S, and wherein C is unmethylated.

A chirally controlled CpG oligonucleotide composition comprising a CpG oligonucleotide comprising a strand comprising at least one copy of the CpG region motif $N_1$-(*R)—C—(*R)-G-(*S)—$N_2$.

A chirally controlled CpG oligonucleotide composition comprising a CpG oligonucleotide comprising a strand comprising at least two copies of the CpG region motif $N_1$-(*R)—C—(*R)-G-(*S)—$N_2$.

A chirally controlled CpG oligonucleotide composition comprising a CpG oligonucleotide comprising a strand comprising at least three copies of the CpG region motif $N_1$-(*R)—C—(*R)-G-(*S)—$N_2$.

A chirally controlled CpG oligonucleotide composition comprising a CpG oligonucleotide comprising a strand comprising at least four copies of the CpG region motif $N_1$-(*R)—C—(*R)-G-(*S)—$N_2$.

A chirally controlled CpG oligonucleotide composition comprising a CpG oligonucleotide comprising a strand comprising at least one copy of the CpG region motif $N_1$-(*R)—C—(*S)-G-(*S)—$N_2$.

A chirally controlled CpG oligonucleotide composition comprising a CpG oligonucleotide comprising a strand comprising at least two copies of the CpG region motif $N_1$-(*R)—C—(*S)-G-(*S)—$N_2$.

A chirally controlled CpG oligonucleotide composition comprising a CpG oligonucleotide comprising a strand comprising at least three copies of the CpG region motif $N_1$-(*R)—C—(*S)-G-(*S)—$N_2$.

A chirally controlled CpG oligonucleotide composition comprising a CpG oligonucleotide comprising a strand comprising at least four copies of the CpG region motif $N_1$-(*R)—C—(*S)-G-(*S)—$N_2$.

A chirally controlled CpG oligonucleotide composition comprising a CpG oligonucleotide comprising a strand comprising at least one copy of the CpG region motif $N_1$-(*R)—C—(*S)-G-(*R)—$N_2$.

A chirally controlled CpG oligonucleotide composition comprising a CpG oligonucleotide comprising a strand comprising at least two copies of the CpG region motif $N_1$-(*R)—C—(*S)-G-(*R)—$N_2$.

A chirally controlled CpG oligonucleotide composition comprising a CpG oligonucleotide comprising a strand comprising at least three copies of the CpG region motif $N_1$-(*R)—C—(*S)-G-(*R)—$N_2$.

A chirally controlled CpG oligonucleotide composition comprising a CpG oligonucleotide comprising a strand comprising at least four copies of the CpG region motif $N_1$-(*R)—C—(*S)-G-(*R)—$N_2$.

A chirally controlled CpG oligonucleotide composition comprising a CpG oligonucleotide comprising a strand comprising at least one copy of the CpG region motif $N_1$-(*S)—C—(*R)-G-(*S)—$N_2$.

A chirally controlled CpG oligonucleotide composition comprising a CpG oligonucleotide comprising a strand comprising at least two copies of the CpG region motif $N_1$-(*S)—C—(*R)-G-(*S)—$N_2$.

A chirally controlled CpG oligonucleotide composition comprising a CpG oligonucleotide comprising a strand comprising at least three copies of the CpG region motif $N_1$-(*S)—C—(*R)-G-(*S)—$N_2$.

A chirally controlled CpG oligonucleotide composition comprising a CpG oligonucleotide comprising a strand comprising at least four copies of the CpG region motif $N_1$-(*S)—C—(*R)-G-(*S)—$N_2$.

A chirally controlled CpG oligonucleotide composition comprising a CpG oligonucleotide comprising a strand comprising at least one copy of the CpG region motif $N_1$-(*S)—C—(*R)-G-(*R)—$N_2$.

A chirally controlled CpG oligonucleotide composition comprising a CpG oligonucleotide comprising a strand comprising at least two copies of the CpG region motif $N_1$-(*S)—C—(*R)-G-(*R)—$N_2$.

A chirally controlled CpG oligonucleotide composition comprising a CpG oligonucleotide comprising a strand comprising at least three copies of the CpG region motif $N_1$-(*S)—C—(*R)-G-(*R)—$N_2$.

A chirally controlled CpG oligonucleotide composition comprising a CpG oligonucleotide comprising a strand comprising at least four copies of the CpG region motif $N_1$-(*S)—C—(*R)-G-(*R)—$N_2$.

A chirally controlled CpG oligonucleotide composition comprising a CpG oligonucleotide comprising a strand comprising at least one copy of the CpG region motif $N_1$-(*S)—C—(*S)-G-(*R)—$N_2$.

A chirally controlled CpG oligonucleotide composition comprising a CpG oligonucleotide comprising a strand comprising at least two copies of the CpG region motif $N_1$-(*S)—C—(*S)-G-(*R)—$N_2$.

A chirally controlled CpG oligonucleotide composition comprising a CpG oligonucleotide comprising a strand comprising at least three copies of the CpG region motif $N_1$-(*S)—C—(*S)-G-(*R)—$N_2$.

A chirally controlled CpG oligonucleotide composition comprising a CpG oligonucleotide comprising a strand comprising at least four copies of the CpG region motif $N_1$-(*S)—C—(*S)-G-(*R)—$N_2$.

A chirally controlled CpG oligonucleotide composition comprising a CpG oligonucleotide comprising a strand comprising at least one copy of the CpG region motif Py-(*R/S)—C—(*R/S)-G-(*R/S)-Py, wherein at least one *R/S is *R and at least one *R/S is *S, and wherein C is unmethylated.

A chirally controlled CpG oligonucleotide composition comprising a CpG oligonucleotide comprising a strand comprising at least two copies of the CpG region motif Py-(*R/S)—C—(*R/S)-G-(*R/S)-Py, wherein at least one *R/S is *R and at least one *R/S is *S, and wherein C is unmethylated.

A chirally controlled CpG oligonucleotide composition comprising a CpG oligonucleotide comprising a strand comprising at least three copies of the CpG region motif Py-(*R/S)—C—(*R/S)-G-(*R/S)-Py, wherein at least one *R/S is *R and at least one *R/S is *S, and wherein C is unmethylated.

A chirally controlled CpG oligonucleotide composition comprising a CpG oligonucleotide comprising a strand comprising at least four copies of the CpG region motif Py-(*R/S)—C—(*R/S)-G-(*R/S)-Py, wherein at least one *R/S is *R and at least one *R/S is *S, and wherein C is unmethylated.

A chirally controlled CpG oligonucleotide composition comprising a CpG oligonucleotide comprising a strand comprising at least one copy of the CpG region motif $N_1$-(*R/S)—C—(*R/S)-G-(*R)—$N_2$.

A chirally controlled CpG oligonucleotide composition comprising a CpG oligonucleotide comprising a strand comprising at least two copies of the CpG region motif $N_1$-(*R/S)—C—(*R/S)-G-(*R)—$N_2$.

A chirally controlled CpG oligonucleotide composition comprising a CpG oligonucleotide comprising a strand comprising at least three copies of the CpG region motif $N_1$-(*R/S)—C—(*R/S)-G-(*R)—$N_2$.

A chirally controlled CpG oligonucleotide composition comprising a CpG oligonucleotide comprising a strand comprising at least four copies of the CpG region motif $N_1$-(*R/S)—C—(*R/S)-G-(*R)—$N_2$.

A chirally controlled CpG oligonucleotide composition comprising a CpG oligonucleotide comprising a strand comprising at least one copy of the CpG region motif $N_1$-(*R/S)—C—(*R/S)-G-(*S)—$N_2$.

A chirally controlled CpG oligonucleotide composition comprising a CpG oligonucleotide comprising a strand comprising at least two copies of the CpG region motif $N_1$-(*R/S)—C—(*R/S)-G-(*S)—$N_2$.

A chirally controlled CpG oligonucleotide composition comprising a CpG oligonucleotide comprising a strand comprising at least three copies of the CpG region motif $N_1$-(*R/S)—C—(*R/S)-G-(*S)—$N_2$.

A chirally controlled CpG oligonucleotide composition comprising a CpG oligonucleotide comprising a strand comprising at least four copies of the CpG region motif $N_1$-(*R/S)—C—(*R/S)-G-(*S)—$N_2$.

In various embodiments, a chirally controlled CpG oligonucleotide composition comprising a CpG oligonucleotide is capable of agonizing an immune response in human cells. In various embodiments, C is unmethylated C. In various embodiments, at least one nucleoside is 2'H (DNA). In various embodiments, each nucleoside is 2'H (DNA). In various embodiments, the CpG oligonucleotide is between 15 and 49 nt in length. In various embodiments, the CpG oligonucleotide is capable of agonizing an immune response in human cells, and/or C is unmethylated C, and/or at least one nucleoside is 2'H (DNA), and/or each nucleoside is 2'H (DNA), and/or the CpG oligonucleotide is between 15 and 49 nt in length.

Agonistic CpG Region Motifs Comprising m5C (5-Methyl C)

As noted above, DNA comprising unmethylated CpG motifs (e.g., bacterial, viral and mitochondrial DNA) generally mediated immune responses, while DNA comprising methylated CpG motifs (e.g., mammalian nuclear DNA) generally do not. For example, in B-type CpG oligonucleotides, in principle, modification of cytosine is usually not well tolerated. Vollmer et al. 2009 Adv. Drug Del. Rev. 61: 195-204.

The present disclosure showed that, surprisingly, some CpG oligonucleotides were agonistic, which comprise a CpG region motif comprising a methylated C (m5C or 5-Methyl C) and various chirally controlled phosphorothioates.

Figure 14:
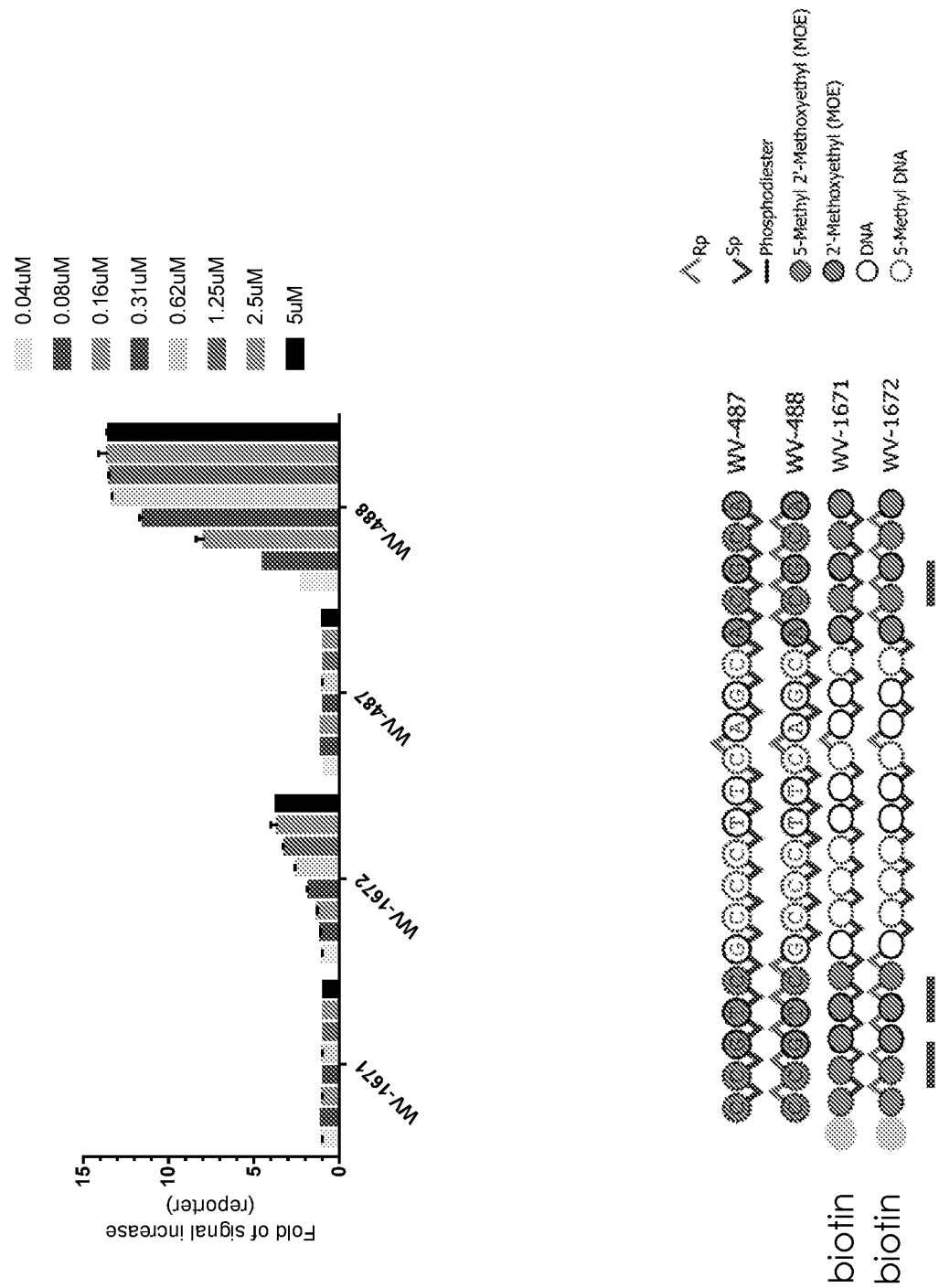
FIG. 14 shows that sugar modifications and/or methylation of C did not always significantly reduce or eliminate human TLR9 agonist activity; data from SOD1 series.

Several CpG oligonucleotides comprising a CpG region motif comprising a m5C are shown herein to be capable of mediating agonism in human cells, including: WV-1490, WV-488, WV-1672, WV-1491, and WV-1489 (See FIGS. 14 and 15).

In some embodiments, various CpG oligonucleotides comprise a CpG region motif of:

m5C—(*R)-m5C—(*R)-G-(*R)—$N_1$, where all the nucleosides are 2'-MOE.

m5C—(*R)-m5C—(*R)-G-(*R)-Py, where all the nucleosides are 2'-MOE.

$N_1$-(*R)-m5C—(*R)-G-(*R)—$N_2$, wherein N i is methylated or not methylated, and all the nucleosides are 2'-MOE.

$N_1$-(*R)-m5C—(*R)-G-(*R)-Py, wherein N i is methylated or not methylated, and all the nucleosides are 2'-MOE.

$N_1$-(*R/S)-m5C—(*R/S)-G-(*R/S)—$N_2$, wherein at least 2 of the *R/S are *R, all the nucleosides are 2'-MOE, and $N_1$ and $N_2$ are methylated or not methylated.

$N_1$-(*R)-m5C—(*R/S)-G-(*R)—$N_2$, wherein at least 2 of the *R/S are *R, all the nucleosides are 2'-MOE, and $N_1$ and $N_2$ are methylated or not methylated.

In some embodiments, the present disclosure provides:

A chirally controlled CpG oligonucleotide composition comprising a CpG oligonucleotide comprising a strand comprising at least one copy of the CpG region motif m5C—(*R)-m5C—(*R)-G-(*R)—$N_1$, where all the nucleosides are 2'-MOE.

A chirally controlled CpG oligonucleotide composition comprising a CpG oligonucleotide comprising a strand comprising at least two copies of the CpG region motif m5C—(*R)-m5C—(*R)-G-(*R)—$N_1$, where all the nucleosides are 2'-MOE.

A chirally controlled CpG oligonucleotide composition comprising a CpG oligonucleotide comprising a strand comprising at least three copies of the CpG region motif m5C—(*R)-m5C—(*R)-G-(*R)—$N_1$, where all the nucleosides are 2'-MOE.

A chirally controlled CpG oligonucleotide composition comprising a CpG oligonucleotide comprising a strand comprising at least four copies of the CpG region motif m5C—(*R)-m5C—(*R)-G-(*R)—$N_1$, where all the nucleosides are 2'-MOE.

A chirally controlled CpG oligonucleotide composition comprising a CpG oligonucleotide comprising a strand comprising at least one copy of the CpG region motif m5C—(*R)-m5C—(*R)-G-(*R)-Py, where all the nucleosides are 2'-MOE.

A chirally controlled CpG oligonucleotide composition comprising a CpG oligonucleotide comprising a strand comprising at least two copies of the CpG region motif m5C—(*R)-m5C—(*R)-G-(*R)-Py, where all the nucleosides are 2'-MOE.

A chirally controlled CpG oligonucleotide composition comprising a CpG oligonucleotide comprising a strand comprising at least three copies of the CpG region motif m5C—(*R)-m5C—(*R)-G-(*R)-Py, where all the nucleosides are 2'-MOE.

A chirally controlled CpG oligonucleotide composition comprising a CpG oligonucleotide comprising a strand comprising at least four copies of the CpG region motif m5C—(*R)-m5C—(*R)-G-(*R)-Py, where all the nucleosides are 2'-MOE.

A chirally controlled CpG oligonucleotide composition comprising a CpG oligonucleotide comprising a strand comprising at least one copy of the CpG region motif $N_1$-(*R)-m5C—(*R)-G-(*R)—$N_2$, wherein N i is methylated or not methylated, and all the nucleosides are 2'-MOE.

A chirally controlled CpG oligonucleotide composition comprising a CpG oligonucleotide comprising a strand comprising at least two copies of the CpG region motif $N_1$-(*R)-m5C—(*R)-G-(*R)—$N_2$, wherein N i is methylated or not methylated, and all the nucleosides are 2'-MOE.

A chirally controlled CpG oligonucleotide composition comprising a CpG oligonucleotide comprising a strand comprising at least three copies of the CpG region motif $N_1$-(*R)-m5C—(*R)-G-(*R)—$N_2$, wherein N i is methylated or not methylated, and all the nucleosides are 2'-MOE.

A chirally controlled CpG oligonucleotide composition comprising a CpG oligonucleotide comprising a strand comprising at least four copies of the CpG region motif $N_1$-(*R)-m5C—(*R)-G-(*R)—$N_2$, wherein N i is methylated or not methylated, and all the nucleosides are 2'-MOE.

A chirally controlled CpG oligonucleotide composition comprising a CpG oligonucleotide comprising a strand comprising at least one copy of the CpG region motif $N_1$-(*R)-m5C—(*R)-G-(*R)-Py, wherein N i is methylated or not methylated, and all the nucleosides are 2'-MOE.

A chirally controlled CpG oligonucleotide composition comprising a CpG oligonucleotide comprising a strand comprising at least two copies of the CpG region motif $N_1$-(*R)-m5C—(*R)-G-(*R)-Py, wherein N i is methylated or not methylated, and all the nucleosides are 2'-MOE.

A chirally controlled CpG oligonucleotide composition comprising a CpG oligonucleotide comprising a strand comprising at least three copies of the CpG region motif $N_1$-(*R)-m5C—(*R)-G-(*R)-Py, wherein N i is methylated or not methylated, and all the nucleosides are 2'-MOE.

A chirally controlled CpG oligonucleotide composition comprising a CpG oligonucleotide comprising a strand comprising at least four copies of the CpG region motif $N_1$-(*R)-m5C—(*R)-G-(*R)-Py, wherein N i is methylated or not methylated, and all the nucleosides are 2'-MOE.

A chirally controlled CpG oligonucleotide composition comprising a CpG oligonucleotide comprising a strand comprising at least one copy of the CpG region motif $N_1$-(*R/S)-m5C—(*R/S)-G-(*R/S)—$N_2$, wherein at least 2 of the *R/S are *R, all the nucleosides are 2'-MOE, and $N_1$ and $N_2$ are methylated or not methylated.

A chirally controlled CpG oligonucleotide composition comprising a CpG oligonucleotide comprising a strand comprising at least two copies of the CpG region motif $N_1$-(*R/S)-m5C—(*R/S)-G-(*R/S)—$N_2$, wherein at least 2 of the *R/S are *R, all the nucleosides are 2'-MOE, and $N_1$ and $N_2$ are methylated or not methylated.

A chirally controlled CpG oligonucleotide composition comprising a CpG oligonucleotide comprising a strand comprising at least three copies of the CpG region motif $N_1$-(*R/S)-m5C—(*R/S)-G-(*R/S)—$N_2$, wherein at least 2 of the *R/S are *R, all the nucleosides are 2'-MOE, and $N_1$ and $N_2$ are methylated or not methylated.

A chirally controlled CpG oligonucleotide composition comprising a CpG oligonucleotide comprising a strand comprising at least four copies of the CpG region motif $N_1$-(*R/S)-m5C—(*R/S)-G-(*R/S)—$N_2$, wherein at least 2 of the *R/S are *R, all the nucleosides are 2'-MOE, and $N_1$ and $N_2$ are methylated or not methylated.

A chirally controlled CpG oligonucleotide composition comprising a CpG oligonucleotide comprising a strand comprising at least one copy of the CpG region motif $N_1$-(*R)-m5C—(*R/S)-G-(*R)—$N_2$, wherein at least 2 of the *R/S are *R, all the nucleosides are 2'-MOE, and $N_1$ and $N_2$ are methylated or not methylated.

A chirally controlled CpG oligonucleotide composition comprising a CpG oligonucleotide comprising a strand comprising at least two copies of the CpG region motif $N_1$-(*R)-m5C—(*R/S)-G-(*R)—$N_2$, wherein at least 2 of the *R/S are *R, all the nucleosides are 2'-MOE, and N₁ and N₂ are methylated or not methylated.

A chirally controlled CpG oligonucleotide composition comprising a CpG oligonucleotide comprising a strand comprising at least three copies of the CpG region motif N₁-(*R)-m5C—(*R/S)-G-(*R)—N₂, wherein at least 2 of the *R/S are *R, all the nucleosides are 2'-MOE, and N₁ and N₂ are methylated or not methylated.

A chirally controlled CpG oligonucleotide composition comprising a CpG oligonucleotide comprising a strand comprising at least four copies of the CpG region motif N₁-(*R)-m5C—(*R/S)-G-(*R)—N₂, wherein at least 2 of the *R/S are *R, all the nucleosides are 2'-MOE, and N₁ and N₂ are methylated or not methylated.

In various embodiments, provided chirally controlled CpG oligonucleotide composition comprising a CpG oligonucleotide is capable of agonizing an immune response in human cells. In various embodiments, at least one nucleoside is 2'H (DNA). In various embodiments, the CpG oligonucleotide is between 15 and 49 nt in length. In various embodiments, the CpG oligonucleotide is capable of agonizing an immune response in human cells, and/or C is unmethylated C, and/or at least one nucleoside is 2'H (DNA), and/or the CpG oligonucleotide is between 15 and 49 nt in length.

Figure 9:
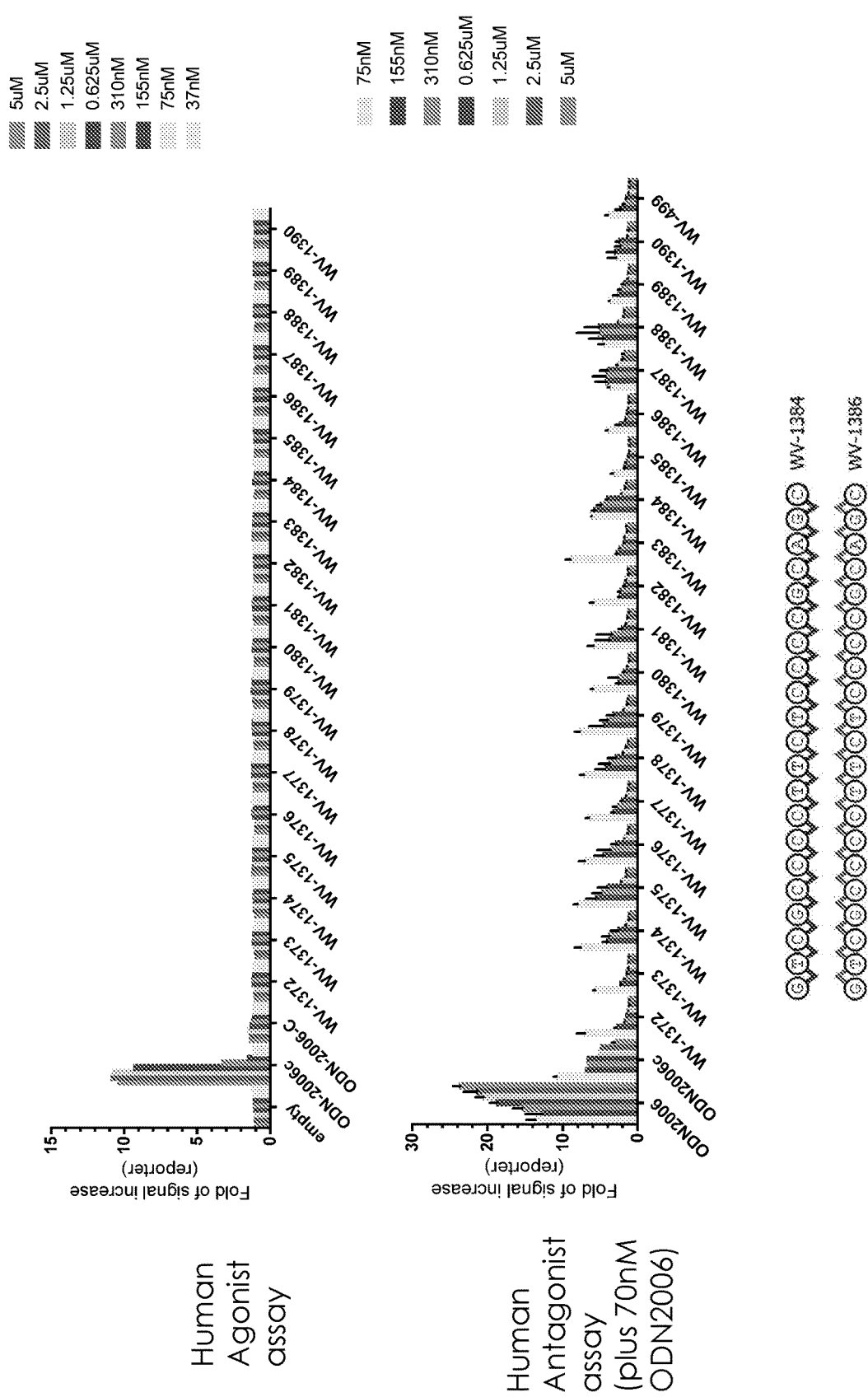
FIG. 9 shows that certain activities of the SMAD7 series oligonucleotides. WV-1384 is a mouse TLR9 agonist, but not human TLR9 agonist. Data from SMAD7 series.

Several additional CpG oligonucleotides were tested for agonism, but none activated hTLR9, These CpG oligonucleotides were:

WV-1386, WV-1387, WV-1388, WV-1389, WV-1390, WV-1494, WV-1512 (See FIGS. 9 and 13).

In some embodiments, various CpG oligonucleotides comprise a CpG region motif of:

N₁-(*R)—[C]-(*R)-[G]-(*R)—N₂, where N₁ is 2'H, 2'-MOE or 2'-OMe; [C] is C, m5C, 2'-MOE C, or 2'-MOE m5C; [G] is optionally G, 2'-Ome G, or 2'-MOE G; and N₂ is 2'H, 2'-MOE or 2'-OMe.

N₁-(*S)—[C]-(*R)-[G]-(*S)—N₂, where N₁ is 2'H, 2'-MOE or 2'-OMe; [C] is C, m5C, 2'-MOE C, or 2'-MOE m5C; [G] is optionally G, 2'-Ome G, or 2'-MOE G; and N₂ is 2'H, 2'-MOE or 2'-OMe.

N₁-(*S)—[C]-(*R)-[G]-(*S)—N₂, where N₁ is 2'H; [C] is C, m5C, 2'-MOE C, or 2'-MOE m5C; [G] is optionally G, 2'-Ome G, or 2'-MOE G; and N₂ is 2'H.

N₁-(*R)—[C]-(*R)-[G]-(*R)-Pyeo, where N₁ and Py are 2'H, 2'-MOE or 2'OMe; and [C] is C or 2'-MOE C; and [G] is G or 2'-MOE G N₁-(*R)—[C]-(*R)-[G]-(*R)-Neo, where N₁ and N₂ are 2'H, 2'-MOE or 2'OMe; and [C] is 2'-MOE m5C Py-(*R)—C—(*R)-G-(*R)-Py
Py-(*R)—C—(*R)-G-(*R)-Py
Py-(*S)—C—(*R)-G-(*S)-Py
Py-(*S)—C—(*S)-G-(*S)-Py
Py-(*R)—[C]-(*R)-[G]-(*R)-Py, where [C] is 2'-MOE C; and [G] is 2'-MOE G
Py-(*R)—[C]-(*R)-[G]-(*S)-Py, where [C] is 2'-MOE C; and [G] is 2'-MOE G

| | | |
|---|---|---|
| ONT-41 | 5'-Geo*m5Ceo*m5Ceo*Teo*m5Ceo*A*G*T*m5C*T*G*m5C*T*T*m5C*Geo*m5Ceo*Aeo*m5Ceo*m5Ceo-3' | (SEQ ID NO: 1822) |
| ONT-75 | 5'-Geo*Rm5Ceo*Rm5Ceo*RTeo*Rm5Ceo*RA*RG*RT*Rm5C*RT*RG*Rm5C*RT*RT*Rm5C*RGeo*Rm5Ceo*RAeo*Rm5Ceo*Rm5Ceo-3' | (SEQ ID NO: 1823) |
| ONT-80 | 5'-Geo*Sm5Ceo*Sm5Ceo*STeo*Sm5Ceo*SA*SG*ST*Sm5C*ST*SG*Sm5C*ST*ST*Sm5C*SGeo*Sm5Ceo*SAeo*Sm5Ceo*Sm5Ceo-3' | (SEQ ID NO: 1824) |
| ONT-82 | 5'-Geo*RTeo*Rm5Ceo*Rm5Ceo*Rm5Ceo*RT*RG*RA*RA*RG*RA*RT*RG*RT*Rm5C*RAeo*RAeo*RTeo*RGeo*Rm5Ceo-3' | (SEQ ID NO: 1825) |
| ONT-83 | 5'-Geo*Teo*m5Ceo*m5Ceo*m5Ceo*T*G*A*A*G*A*T*G*T*m5C*Aeo*Aeo*Teo*Geo*m5Ceo-3' | (SEQ ID NO: 1826) |
| ONT-84 | 5'-Geo*STeo*Sm5Ceo*Sm5Ceo*Sm5Ceo*ST*SG*SA*SA*SG*SA*ST*SG*ST*Sm5C*SAeo*SAeo*STeo*SGeo*Sm5Ceo-3' | (SEQ ID NO: 1827) |
| ONT-85 | 5'-Geo*RTeo*Rm5Ceo*Rm5Ceo*Rm5Ceo*RT*SG*SA*SA*SG*SA*ST*SG*ST*Sm5C*SAeo*RAeo*RTeo*RGeo*Rm5Ceo-3' | (SEQ ID NO: 1828) |
| ONT-86 | 5'-Geo*STeo*Sm5Ceo*Sm5Ceo*Sm5Ceo*ST*RG*RA*RA*RG*RA*RT*RG*RT*Rm5C*RAeo*SAeo*STeo*SGeo*Sm5Ceo-3' | (SEQ ID NO: 1829) |
| ONT-87 | 5'-Geo*Rm5Ceo*Rm5Ceo*RTeo*Rm5Ceo*RA*SG*ST*Rm5C*ST*SG*Rm5C*ST*ST*Rm5C*RGeo*Rm5Ceo*RAeo*Rm5Ceo*Rm5Ceo-3' | (SEQ ID NO: 1830) |
| ONT-88 | 5'-Geo*Sm5Ceo*Sm5Ceo*STeo*Sm5Ceo*SA*RG*RT*Sm5C*RT*RG*Sm5C*RT*RT*Sm5C*SGeo*Sm5Ceo*SAeo*Sm5Ceo*Sm5Ceo-3' | (SEQ ID NO: 1831) |

Antagonistic CpG Oligonucleotides Comprising a CpG Region Motif

While the present disclosure shows that various CpG region motifs are agonistic, the data also indicate that various other CpG region motifs are antagonistic. Several CpG oligonucleotides are shown herein to be capable of mediating antagonism in human cells, including:

WV-499, WV-1372, WV-1373, WV-1374, WV-1375, WV-1376, WV-1377, WV-1378, WV-1379, WV-1380, WV-1381, WV-1382, WV-1383, WV-1384, WV-1385,

Py-(*R)-m5C—(*R)-G-(*R)-Py
Py-(*R)-m5C—(*R)-G-(*R)-Py
Py-(*R)—[C]-(*R)-[G]-(*R)—N₁, where [C] is 2'-OMe m5C, and [G] is 2'-OMe G, and N₁ is 2'-OMe
Py-(*R)—[C]-(*R)-[G]-(*R)-Py, where [C] is 2'-OMe m5C, and [G] is 2'-OMe G
Py-(*R)—[C]-(*R)-[G]-(*R)-Py, where [C] is 2'-OMe C and [G] is 2'-OMe G
Py-(*S)—[C]-(*R)-[G]-(*S)-Py, where [C] is 2'-MOE C and [G] is 2'-MOE G
Py-(*S)—[C]-(*R)-G-(*S)-Py Py-(*S)—[C]-(*R)-[G]-(*S)-Py, where [C] is 2'-MOE m5C and [G] is 2'-MOE G Py-(*S)—[C]-(*R)-[G]-(*S)-Py, where [C] is 2'-OMe m5C and [G] is 2'-OMe G Py-(*S)—[C]-(*R)-[G]-(*S)-Py, where [C] is 2'-OMe C and [G] is 2'-OMe G Py-(*S)—[C]-(*R)-[G]-(*R)-Py, where both [C] and [G] are 2'-modified or $N_1$-(*R)—[C]-(*R)-[G]-(*R)—$N_2$, where both [C] and [G] are 2'-modified.

In some embodiments, the present disclosure pertains to:

A chirally controlled CpG oligonucleotide composition comprising a CpG oligonucleotide comprising a strand comprising at least one copy of the CpG region motif $N_1$-(*S)—[C]-(*R)-[G]-(*S)—$N_2$, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.

A chirally controlled CpG oligonucleotide composition comprising a CpG oligonucleotide comprising a strand comprising at least two copies of the CpG region motif $N_1$-(*S)—[C]-(*R)-[G]-(*S)—$N_2$, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.

A chirally controlled CpG oligonucleotide composition comprising a CpG oligonucleotide comprising a strand comprising at least three copies of the CpG region motif $N_1$-(*S)—[C]-(*R)-[G]-(*S)—$N_2$, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.

A chirally controlled CpG oligonucleotide composition comprising a CpG oligonucleotide comprising a strand comprising at least four copies of the CpG region motif $N_1$-(*S)—[C]-(*R)-[G]-(*S)—$N_2$, where $N_1$ is 2'H, 2'-MOE or 2'-OMe; [C] is C, m5C, 2'-MOE C, or 2'-MOE m5C; [G] is optionally G, 2'-Ome G, or 2'-MOE G; and $N_2$ is 2'H, 2'-MOE or 2'-OMe.

A chirally controlled CpG oligonucleotide composition comprising a CpG oligonucleotide comprising a strand comprising at least one copy of the CpG region motif $N_1$-(*S)—[C]-(*R)-[G]-(*S)—$N_2$, where $N_1$ is 2'H; [C] is C, m5C, 2'-MOE C, or 2'-MOE m5C; [G] is optionally G, 2'-Ome G, or 2'-MOE G; and $N_2$ is 2'H.

A chirally controlled CpG oligonucleotide composition comprising a CpG oligonucleotide comprising a strand comprising at least two copies of the CpG region motif $N_1$-(*S)—[C]-(*R)-[G]-(*S)—$N_2$, where $N_1$ is 2'H; [C] is C, m5C, 2'-MOE C, or 2'-MOE m5C; [G] is optionally G, 2'-Ome G, or 2'-MOE G; and $N_2$ is 2'H.

A chirally controlled CpG oligonucleotide composition comprising a CpG oligonucleotide comprising a strand comprising at least three copies of the CpG region motif $N_1$-(*S)—[C]-(*R)-[G]-(*S)—$N_2$, where $N_1$ is 2'H; [C] is C, m5C, 2'-MOE C, or 2'-MOE m5C; [G] is optionally G, 2'-Ome G, or 2'-MOE G; and $N_2$ is 2'H.

A chirally controlled CpG oligonucleotide composition comprising a CpG oligonucleotide comprising a strand comprising at least four copies of the CpG region motif $N_1$-(*S)—[C]-(*R)-[G]-(*S)—$N_2$, where $N_1$ is 2'H; [C] is C, m5C, 2'-MOE C, or 2'-MOE m5C; [G] is optionally G, 2'-Ome G, or 2'-MOE G; and $N_2$ is 2'H.

A chirally controlled CpG oligonucleotide composition comprising a CpG oligonucleotide comprising a strand comprising at least one copy of the CpG region motif $N_1$-(*R)—[C]-(*R)-[G]-(*R)-Py, where $N_1$ and Py are 2'H, 2'-MOE or 2'OMe; and [C] is C or 2'-MOE C; and [G] is G or 2'-MOE G, and Py is 2'-H or 2'-MOE.

A chirally controlled CpG oligonucleotide composition comprising a CpG oligonucleotide comprising a strand comprising at least two copies of the CpG region motif $N_1$-(*R)—[C]-(*R)-[G]-(*R)-Py, where $N_1$ and Py are 2'H, 2'-MOE or 2'OMe; and [C] is C or 2'-MOE C; and [G] is G or 2'-MOE G, and Py is 2'-H or 2'-MOE.

A chirally controlled CpG oligonucleotide composition comprising a CpG oligonucleotide comprising a strand comprising at least three copies of the CpG region motif $N_1$-(*R)—[C]-(*R)-[G]-(*R)-Py, where $N_1$ and Py are 2'H, 2'-MOE or 2'OMe; and [C] is C or 2'-MOE C; and [G] is G or 2'-MOE G, and Py is 2'-H or 2'-MOE.

A chirally controlled CpG oligonucleotide composition comprising a CpG oligonucleotide comprising a strand comprising at least four copies of the CpG region motif $N_1$-(*R)—[C]-(*R)-[G]-(*R)-Py, where $N_1$ and Py are 2'H, 2'-MOE or 2'OMe; and [C] is C or 2'-MOE C; and [G] is G or 2'-MOE G, and Py is 2'-H or 2'-MOE.

A chirally controlled CpG oligonucleotide composition comprising a CpG oligonucleotide comprising a strand comprising at least one copy of the CpG region motif $N_1$-(*R)—[C]-(*R)-[G]-(*R)—$N_2$, where $N_1$ and $N_2$ are 2'H, 2'-MOE or 2'OMe; and [C] is 2'-MOE m5C; $N_2$ is 2'-H or 2'-MOE.

A chirally controlled CpG oligonucleotide composition comprising a CpG oligonucleotide comprising a strand comprising at least two copies of the CpG region motif $N_1$-(*R)—[C]-(*R)-[G]-(*R)—$N_2$, where $N_1$ and $N_2$ are 2'H, 2'-MOE or 2'OMe; and [C] is 2'-MOE m5C; $N_2$ is 2'-H or 2'-MOE.

A chirally controlled CpG oligonucleotide composition comprising a CpG oligonucleotide comprising a strand comprising at least three copies of the CpG region motif $N_1$-(*R)—[C]-(*R)-[G]-(*R)—$N_2$, where $N_1$ and $N_2$ are 2'H, 2'-MOE or 2'OMe; and [C] is 2'-MOE m5C; $N_2$ is 2'-H or 2'-MOE.

A chirally controlled CpG oligonucleotide composition comprising a CpG oligonucleotide comprising a strand comprising at least four copies of the CpG region motif $N_1$-(*R)—[C]-(*R)-[G]-(*R)—$N_2$, where $N_1$ and $N_2$ are 2'H, 2'-MOE or 2'OMe; and [C] is 2'-MOE m5C; $N_2$ is 2'-H or 2'-MOE.

A chirally controlled CpG oligonucleotide composition comprising a CpG oligonucleotide comprising a strand comprising at least one copy of the CpG region motif Py-(*R)—C—(*R)-G-(*R)-Py.

A chirally controlled CpG oligonucleotide composition comprising a CpG oligonucleotide comprising a strand comprising at least two copies of the CpG region motif Py-(*R)—C—(*R)-G-(*R)-Py.

A chirally controlled CpG oligonucleotide composition comprising a CpG oligonucleotide comprising a strand comprising at least three copies of the CpG region motif Py-(*R)—C—(*R)-G-(*R)-Py.

A chirally controlled CpG oligonucleotide composition comprising a CpG oligonucleotide comprising a strand comprising at least four copies of the CpG region motif Py-(*R)—C—(*R)-G-(*R)-Py.

A chirally controlled CpG oligonucleotide composition comprising a CpG oligonucleotide comprising a strand comprising at least one copy of the CpG region motif Py-(*R)—C—(*R)-G-(*R)-Py.

A chirally controlled CpG oligonucleotide composition comprising a CpG oligonucleotide comprising a strand comprising at least two copies of the CpG region motif Py-(*R)—C—(*R)-G-(*R)-Py.

A chirally controlled CpG oligonucleotide composition comprising a CpG oligonucleotide comprising a strand comprising at least three copies of the CpG region motif Py-(*R)—C—(*R)-G-(*R)-Py.

A chirally controlled CpG oligonucleotide composition comprising a CpG oligonucleotide comprising a strand comprising at least four copies of the CpG region motif Py-(*R)—C—(*R)-G-(*R)-Py.

A chirally controlled CpG oligonucleotide composition comprising a CpG oligonucleotide comprising a strand comprising at least one copy of the CpG region motif Py-(*S)—C—(*R)-G-(*S)-Py.

A chirally controlled CpG oligonucleotide composition comprising a CpG oligonucleotide comprising a strand comprising at least two copies of the CpG region motif Py-(*S)—C—(*R)-G-(*S)-Py.

A chirally controlled CpG oligonucleotide composition comprising a CpG oligonucleotide comprising a strand comprising at least three copies of the CpG region motif Py-(*S)—C—(*R)-G-(*S)-Py.

A chirally controlled CpG oligonucleotide composition comprising a CpG oligonucleotide comprising a strand comprising at least four copies of the CpG region motif Py-(*S)—C—(*R)-G-(*S)-Py.

A chirally controlled CpG oligonucleotide composition comprising a CpG oligonucleotide comprising a strand comprising at least one copy of the CpG region motif Py-(*S)—C—(*S)-G-(*S)-Py.

A chirally controlled CpG oligonucleotide composition comprising a CpG oligonucleotide comprising a strand comprising at least two copies of the CpG region motif Py-(*S)—C—(*S)-G-(*S)-Py.

A chirally controlled CpG oligonucleotide composition comprising a CpG oligonucleotide comprising a strand comprising at least three copies of the CpG region motif Py-(*S)—C—(*S)-G-(*S)-Py.

A chirally controlled CpG oligonucleotide composition comprising a CpG oligonucleotide comprising a strand comprising at least four copies of the CpG region motif Py-(*S)—C—(*S)-G-(*S)-Py.

A chirally controlled CpG oligonucleotide composition comprising a CpG oligonucleotide comprising a strand comprising at least one copy of the CpG region motif Py-(*R)—[C]-(*R)-[G]-(*R)-Py, where [C] is 2'-MOE C; and [G] is 2'-MOE G.

A chirally controlled CpG oligonucleotide composition comprising a CpG oligonucleotide comprising a strand comprising at least two copies of the CpG region motif Py-(*R)—[C]-(*R)-[G]-(*R)-Py, where [C] is 2'-MOE C; and [G] is 2'-MOE G.

A chirally controlled CpG oligonucleotide composition comprising a CpG oligonucleotide comprising a strand comprising at least three copies of the CpG region motif Py-(*R)—[C]-(*R)-[G]-(*R)-Py, where [C] is 2'-MOE C; and [G] is 2'-MOE G.

A chirally controlled CpG oligonucleotide composition comprising a CpG oligonucleotide comprising a strand comprising at least four copies of the CpG region motif Py-(*R)—[C]-(*R)-[G]-(*R)-Py, where [C] is 2'-MOE C; and [G] is 2'-MOE G.

A chirally controlled CpG oligonucleotide composition comprising a CpG oligonucleotide comprising a strand comprising at least one copy of the CpG region motif Py-(*R)—[C]-(*R)-[G]-(*S)-Py, where [C] is 2'-MOE C; and [G] is 2'-MOE G.

A chirally controlled CpG oligonucleotide composition comprising a CpG oligonucleotide comprising a strand comprising at least two copies of the CpG region motif Py-(*R)—[C]-(*R)-[G]-(*S)-Py, where [C] is 2'-MOE C; and [G] is 2'-MOE G.

A chirally controlled CpG oligonucleotide composition comprising a CpG oligonucleotide comprising a strand comprising at least three copies of the CpG region motif Py-(*R)—[C]-(*R)-[G]-(*S)-Py, where [C] is 2'-MOE C; and [G] is 2'-MOE G.

A chirally controlled CpG oligonucleotide composition comprising a CpG oligonucleotide comprising a strand comprising at least four copies of the CpG region motif Py-(*R)—[C]-(*R)-[G]-(*S)-Py, where [C] is 2'-MOE C; and [G] is 2'-MOE G.

A chirally controlled CpG oligonucleotide composition comprising a CpG oligonucleotide comprising a strand comprising at least one copy of the CpG region motif Py-(*R)—[C]-(*R)-G-(*R)-Py, where [C] is C, 2'-OMe m5C, or 2'-MOE C.

A chirally controlled CpG oligonucleotide composition comprising a CpG oligonucleotide comprising a strand comprising at least two copies of the CpG region motif Py-(*R)—[C]-(*R)-G-(*R)-Py, where [C] is C, 2'-OMe m5C, or 2'-MOE C.

A chirally controlled CpG oligonucleotide composition comprising a CpG oligonucleotide comprising a strand comprising at least three copies of the CpG region motif Py-(*R)—[C]-(*R)-G-(*R)-Py, where [C] is C, 2'-OMe m5C, or 2'-MOE C.

A chirally controlled CpG oligonucleotide composition comprising a CpG oligonucleotide comprising a strand comprising at least four copies of the CpG region motif Py-(*R)—[C]-(*R)-G-(*R)-Py, where [C] is C, 2'-OMe m5C, or 2'-MOE C.

A chirally controlled CpG oligonucleotide composition comprising a CpG oligonucleotide comprising a strand comprising at least one copy of the CpG region motif Py-(*R)—[C]-(*R)-[G]-(*R)—$N_1$, where [C] is 2'-OMe m5C, and [G] is 2'-OMe G, and $N_1$ is 2'-OMe.

A chirally controlled CpG oligonucleotide composition comprising a CpG oligonucleotide comprising a strand comprising at least two copies of the CpG region motif Py-(*R)—[C]-(*R)-[G]-(*R)—$N_1$, where [C] is 2'-OMe m5C, and [G] is 2'-OMe G, and $N_1$ is 2'-OMe.

A chirally controlled CpG oligonucleotide composition comprising a CpG oligonucleotide comprising a strand comprising at least three copies of the CpG region motif Py-(*R)—[C]-(*R)-[G]-(*R)—$N_1$, where [C] is 2'-OMe m5C, and [G] is 2'-OMe G, and $N_1$ is 2'-OMe.

A chirally controlled CpG oligonucleotide composition comprising a CpG oligonucleotide comprising a strand comprising at least four copies of the CpG region motif Py-(*R)—[C]-(*R)-[G]-(*R)—$N_1$, where [C] is 2'-OMe m5C, and [G] is 2'-OMe G, and $N_1$ is 2'-OMe.

A chirally controlled CpG oligonucleotide composition comprising a CpG oligonucleotide comprising a strand comprising at least one copy of the CpG region motif Py-(*R)—[C]-(*R)-[G]-(*R)-Py, where [C] is 2'-OMe m5C, and [G] is 2'-OMe G.

A chirally controlled CpG oligonucleotide composition comprising a CpG oligonucleotide comprising a strand comprising at least two copies of the CpG region motif Py-(*R)—[C]-(*R)-[G]-(*R)-Py, where [C] is 2'-OMe m5C, and [G] is 2'-OMe G.

A chirally controlled CpG oligonucleotide composition comprising a CpG oligonucleotide comprising a strand comprising at least three copies of the CpG region motif Py-(*R)—[C]-(*R)-[G]-(*R)-Py, where [C] is 2'-OMe m5C, and [G] is 2'-OMe G.

A chirally controlled CpG oligonucleotide composition comprising a CpG oligonucleotide comprising a strand comprising at least four copies of the CpG region motif Py-(*R)—[C]-(*R)-[G]-(*R)-Py, where [C] is 2'-OMe m5C, and [G] is 2'-OMe G.

A chirally controlled CpG oligonucleotide composition comprising a CpG oligonucleotide comprising a strand comprising at least one copy of the CpG region motif Py-(*R)—[C]-(*R)-[G]-(*R)-Py, where [C] is 2'-OMe C and [G] is 2'-OMe G.

A chirally controlled CpG oligonucleotide composition comprising a CpG oligonucleotide comprising a strand comprising at least two copies of the CpG region motif Py-(*R)—[C]-(*R)-[G]-(*R)-Py, where [C] is 2'-OMe C and [G] is 2'-OMe G.

A chirally controlled CpG oligonucleotide composition comprising a CpG oligonucleotide comprising a strand comprising at least three copies of the CpG region motif Py-(*R)—[C]-(*R)-[G]-(*R)-Py, where [C] is 2'-OMe C and [G] is 2'-OMe G.

A chirally controlled CpG oligonucleotide composition comprising a CpG oligonucleotide comprising a strand comprising at least four copies of the CpG region motif Py-(*R)—[C]-(*R)-[G]-(*R)-Py, where [C] is 2'-OMe C and [G] is 2'-OMe G.

A chirally controlled CpG oligonucleotide composition comprising a CpG oligonucleotide comprising a strand comprising at least one copy of the CpG region motif Py-(*S)—[C]-(*R)-[G]-(*S)-Py, where [C] is 2'-MOE C and [G] is 2'-MOE G.

A chirally controlled CpG oligonucleotide composition comprising a CpG oligonucleotide comprising a strand comprising at least two copies of the CpG region motif Py-(*S)—[C]-(*R)-[G]-(*S)-Py, where [C] is 2'-MOE C and [G] is 2'-MOE G.

A chirally controlled CpG oligonucleotide composition comprising a CpG oligonucleotide comprising a strand comprising at least three copies of the CpG region motif Py-(*S)—[C]-(*R)-[G]-(*S)-Py, where [C] is 2'-MOE C and [G] is 2'-MOE G.

A chirally controlled CpG oligonucleotide composition comprising a CpG oligonucleotide comprising a strand comprising at least four copies of the CpG region motif Py-(*S)—[C]-(*R)-[G]-(*S)-Py, where [C] is 2'-MOE C and [G] is 2'-MOE G.

A chirally controlled CpG oligonucleotide composition comprising a CpG oligonucleotide comprising a strand comprising at least one copy of the CpG region motif Py-(*R)-m5C—(*R)-G-(*R)-Py.

A chirally controlled CpG oligonucleotide composition comprising a CpG oligonucleotide comprising a strand comprising at least two copies of the CpG region motif Py-(*R)-m5C—(*R)-G-(*R)-Py.

A chirally controlled CpG oligonucleotide composition comprising a CpG oligonucleotide comprising a strand comprising at least three copies of the CpG region motif Py-(*R)-m5C—(*R)-G-(*R)-Py.

A chirally controlled CpG oligonucleotide composition comprising a CpG oligonucleotide comprising a strand comprising at least four copies of the CpG region motif Py-(*R)-m5C—(*R)-G-(*R)-Py.

A chirally controlled CpG oligonucleotide composition comprising a CpG oligonucleotide comprising a strand comprising at least one copy of the CpG region motif Py-(*R)-m5C—(*R)-G-(*R)-Py.

A chirally controlled CpG oligonucleotide composition comprising a CpG oligonucleotide comprising a strand comprising at least two copies of the CpG region motif Py-(*R)-m5C—(*R)-G-(*R)-Py.

A chirally controlled CpG oligonucleotide composition comprising a CpG oligonucleotide comprising a strand comprising at least three copies of the CpG region motif Py-(*R)-m5C—(*R)-G-(*R)-Py.

A chirally controlled CpG oligonucleotide composition comprising a CpG oligonucleotide comprising a strand comprising at least four copies of the CpG region motif Py-(*R)-m5C—(*R)-G-(*R)-Py.

A chirally controlled CpG oligonucleotide composition comprising a CpG oligonucleotide comprising a strand comprising at least one copy of the CpG region motif Py-(*S)-m5C—(*R)-G-(*S)-Py.

A chirally controlled CpG oligonucleotide composition comprising a CpG oligonucleotide comprising a strand comprising at least two copies of the CpG region motif Py-(*S)-m5C—(*R)-G-(*S)-Py.

A chirally controlled CpG oligonucleotide composition comprising a CpG oligonucleotide comprising a strand comprising at least three copies of the CpG region motif Py-(*S)-m5C—(*R)-G-(*S)-Py.

A chirally controlled CpG oligonucleotide composition comprising a CpG oligonucleotide comprising a strand comprising at least four copies of the CpG region motif Py-(*S)-m5C—(*R)-G-(*S)-Py.

A chirally controlled CpG oligonucleotide composition comprising a CpG oligonucleotide comprising a strand comprising at least one copy of the CpG region motif Py-(*S)—[C]-(*R)-[G]-(*S)-Py, where [C] is 2'-MOE m5C and [G] is 2'-MOE G.

A chirally controlled CpG oligonucleotide composition comprising a CpG oligonucleotide comprising a strand comprising at least two copies of the CpG region motif Py-(*S)—[C]-(*R)-[G]-(*S)-Py, where [C] is 2'-MOE m5C and [G] is 2'-MOE G.

A chirally controlled CpG oligonucleotide composition comprising a CpG oligonucleotide comprising a strand comprising at least three copies of the CpG region motif Py-(*S)—[C]-(*R)-[G]-(*S)-Py, where [C] is 2'-MOE m5C and [G] is 2'-MOE G.

A chirally controlled CpG oligonucleotide composition comprising a CpG oligonucleotide comprising a strand comprising at least four copies of the CpG region motif Py-(*S)—[C]-(*R)-[G]-(*S)-Py, where [C] is 2'-MOE m5C and [G] is 2'-MOE G.

A chirally controlled CpG oligonucleotide composition comprising a CpG oligonucleotide comprising a strand comprising at least one copy of the CpG region motif Py-(*S)—[C]-(*R)-[G]-(*S)-Py, where [C] is 2'-OMe m5C and [G] is 2'-OMe G.

A chirally controlled CpG oligonucleotide composition comprising a CpG oligonucleotide comprising a strand comprising at least two copies of the CpG region motif Py-(*S)—[C]-(*R)-[G]-(*S)-Py, where [C] is 2'-OMe m5C and [G] is 2'-OMe G.

A chirally controlled CpG oligonucleotide composition comprising a CpG oligonucleotide comprising a strand comprising at least three copies of the CpG region motif Py-(*S)—[C]-(*R)-[G]-(*S)-Py, where [C] is 2'-OMe m5C and [G] is 2'-OMe G.

A chirally controlled CpG oligonucleotide composition comprising a CpG oligonucleotide comprising a strand comprising at least four copies of the CpG region motif Py-(*S)—[C]-(*R)-[G]-(*S)-Py, where [C] is 2'-OMe m5C and [G] is 2'-OMe G.

A chirally controlled CpG oligonucleotide composition comprising a CpG oligonucleotide comprising a strand comprising at least one copy of the CpG region motif Py-(*S)—[C]-(*R)-[G]-(*S)-Py, where [C] is 2'-OMe C and [G] is 2'-OMe G.

A chirally controlled CpG oligonucleotide composition comprising a CpG oligonucleotide comprising a strand comprising at least two copies of the CpG region motif Py-(*S)—[C]-(*R)-[G]-(*S)-Py, where [C] is 2'-OMe C and [G] is 2'-OMe G.

A chirally controlled CpG oligonucleotide composition comprising a CpG oligonucleotide comprising a strand comprising at least three copies of the CpG region motif Py-(*S)—[C]-(*R)-[G]-(*S)-Py, where [C] is 2'-OMe C and [G] is 2'-OMe G.

A chirally controlled CpG oligonucleotide composition comprising a CpG oligonucleotide comprising a strand comprising at least four copies of the CpG region motif Py-(*S)—[C]-(*R)-[G]-(*S)-Py, where [C] is 2'-OMe C and [G] is 2'-OMe G.

A chirally controlled CpG oligonucleotide composition comprising a CpG oligonucleotide comprising a strand comprising at least one copy of the CpG region motif Py-(*R)—[C]-(*R)-[G]-(*R)-Py, where both [C] and [G] are 2'-modified.

A chirally controlled CpG oligonucleotide composition comprising a CpG oligonucleotide comprising a strand comprising at least two copies of the CpG region motif Py-(*R)—[C]-(*R)-[G]-(*R)-Py, where both [C] and [G] are 2'-modified.

A chirally controlled CpG oligonucleotide composition comprising a CpG oligonucleotide comprising a strand comprising at least three copies of the CpG region motif Py-(*R)—[C]-(*R)-[G]-(*R)-Py, where both [C] and [G] are 2'-modified.

A chirally controlled CpG oligonucleotide composition comprising a CpG oligonucleotide comprising a strand comprising at least four copies of the CpG region motif Py-(*R)—[C]-(*R)-[G]-(*R)-Py, where both [C] and [G] are 2'-modified.

A chirally controlled CpG oligonucleotide composition comprising a CpG oligonucleotide comprising a strand comprising at least one copy of the CpG region motif $N_1$-(*R)—[C]-(*R)-[G]-(*R)—$N_2$, where both [C] and [G] are 2'-modified.

A chirally controlled CpG oligonucleotide composition comprising a CpG oligonucleotide comprising a strand comprising at least two copies of the CpG region motif $N_1$-(*R)—[C]-(*R)-[G]-(*R)—$N_2$, where both [C] and [G] are 2'-modified.

A chirally controlled CpG oligonucleotide composition comprising a CpG oligonucleotide comprising a strand comprising at least three copies of the CpG region motif $N_1$-(*R)—[C]-(*R)-[G]-(*R)—$N_2$, where both [C] and [G] are 2'-modified.

A chirally controlled CpG oligonucleotide composition comprising a CpG oligonucleotide comprising a strand comprising at least four copies of the CpG region motif $N_1$-(*R)—[C]-(*R)-[G]-(*R)—$N_2$, where both [C] and [G] are 2'-modified.

In various embodiments, the CpG oligonucleotide is capable of antagonizing an immune response in human cells. In various embodiments, at least one nucleoside is 2'H (DNA). In various embodiments, the CpG oligonucleotide is between 15 and 49 nt in length. In various embodiments, the CpG oligonucleotide is capable of antagonizing an immune response in human cells, and/or C is unmethylated C, and/or at least one nucleoside is 2'H (DNA), and/or the CpG oligonucleotide is between 15 and 49 nt in length.

In some embodiments, the present disclosure provides various CpG oligonucleotides comprising any of various CpG region motifs which either agonize or antagonize an immune response.

Methods of Identifying Oligonucleotides with Decreased Immune Response

The present disclosure notes that it may be desirable to produce a variant of an oligonucleotide with decreased agonism of an immune response. In some embodiments, such a variant can be, for example, modified and/or be stereopure or chirally controlled oligonucleotide composition. In some embodiments, such a variant can also, for example, have higher stability, a shorter length, improved biological activity (e.g., if the oligonucleotide of which the variant is made has a desirable biological activity), etc. For example, if an oligonucleotide has a desirable biological activity but is immunogenic, a variant can be generated which has a higher biological activity, thus allowing a lower amount of nucleic acid to be administered to a patient, which can act to reduce the immunogenicity.

The oligonucleotide can be, as a non-limiting example, an oligonucleotide intended for therapeutic use. The oligonucleotide can be an antisense oligonucleotide (ASO), RNAi agent (e.g., single or double stranded siRNA), miRNA, miRNA inhibitor, CRISPR, mRNA, etc. As a non-limiting example, the oligonucleotide may be designed to perform a function such as reducing or increasing the expression of a target gene or level of a target protein, which is completely independent of any immune reaction.

As a non-limiting example, the oligonucleotide intended for therapeutic use can be a stereomixture. Various stereopure (or mostly stereopure) variants can be produced, including variants which may avoid CpG region motifs which agonize an immune response. The variants can be tested for immune stimulation (using any method known in the art to test the immune stimulation mediated by a CpG oligonucleotide). A variant which has decreased agonism of an immune response can then be selected.

Alternatively, if the oligonucleotide is already stereopure (or mostly stereopure), then one or more variants can be provided and tested, and one or more variant oligonucleotides with the desired immune response can be selected.

In some cases, it can be desirable that a variant oligonucleotide be produced which neither agonizes nor antagonizes an immune response. Thus, variants can be designed and provided which can avoid CpG region motifs that agonize or antagonize an immune response.

In some cases, it may not be possible to design an oligonucleotide which completely eliminates agonism of an immune response, but it can be possible to provide variants with different stereochemistry, at least one of which has a reduced ability to agonize an immune response. Thus, CpG region motifs can be selected for use in the variant oligonucleotides which mediate a reduced immune response. For example, the CpG region motif $N_1$-(*R/S)—C—(*R/S)-G-(*R)—$N_2$ is generally less agonistic than CpG oligonucleotides comprising the CpG region motif $N_1$-(*R/S)—C—(*R/S)-G-(*S)—$N_2$ (see FIG. 7, for example), selection of an oligonucleotide which mediates a decreased immune response can involve the step of selecting a CpG region motif which mediates a decreased immune response.

Thus, the present disclosure provides the method of designing and/or producing an oligonucleotide, wherein the oligonucleotide neither agonizes nor antagonizes an immune response, the method comprising the step of designing and/or producing the oligonucleotide to not include a novel CpG region motif associated with agonism or antagonism of an immune response, as described herein.

Methods of Identifying Oligonucleotides with Greater Antagonism of an Immune Response The present disclosure notes that it may be desirable to produce a variant of an oligonucleotide with greater, increased or higher antagonism of an immune response. In some embodiments, such a variant can be, for example, modified and/or be stereopure or chirally controlled oligonucleotide composition. In some embodiments, such a variant can also, for example, have higher stability, a shorter length, improved biological activity (e.g., if the oligonucleotide of which the variant is made has a desirable biological activity), etc.

The oligonucleotide can be, as a non-limiting example, an oligonucleotide intended for therapeutic use. The oligonucleotide can be an antisense oligonucleotide (ASO), RNAi agent (e.g., single or double stranded siRNA), miRNA, miRNA inhibitor, CRISPR, mRNA, etc. As a non-limiting example, the oligonucleotide may be designed to perform a function such as reducing or increasing the expression of a target gene or level of a target protein, which is completely independent of any immune reaction.

As a non-limiting example, the oligonucleotide intended for therapeutic use can be a stereomixture. Various stereopure (or mostly stereopure) variants can be produced, including variants which may avoid CpG region motifs which agonize an immune response or variants which incorporate CpG region motifs identified herein which antagonise an immune response. The variants can be tested for immune stimulation (using any method known in the art to test the immune stimulation mediated by a CpG oligonucleotide). A variant which has greater antagonism of an immune response can then be selected.

Alternatively, if the oligonucleotide is already stereopure (or mostly stereopure), then one or more variants can be provided and tested, and one or more variant oligonucleotides with the desired immune response can be selected.

Thus, the present disclosure provides the method of designing and/or producing an oligonucleotide, wherein the oligonucleotide has greater or increased antagonism of an immune response, the method comprising the step of designing and/or producing the oligonucleotide to not include a novel CpG region motif associated with agonism and/or to include a novel CpG region motif associated with antagonism of an immune response, as described herein.

In some embodiments, the present disclosure pertains to:

A method of identifying a second oligonucleotide mediating decreased immune stimulation in a human cell relative to the immune stimulation mediated by a first oligonucleotide, the method comprising the steps of:

(a) measuring the immune stimulation mediated by a first oligonucleotide, wherein the first oligonucleotide has a defined base sequence comprising at least one CpG region;

(b) measuring the immune stimulation mediated by one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides, wherein steps (a) and (b) can be performed in any order;

(c) selecting a second oligonucleotide which mediates less immune stimulation than the first oligonucleotide.

The method of any preceding embodiment, wherein the first oligonucleotide is immunostimulatory in a human cell.

The method of any preceding embodiments, wherein the second oligonucleotide comprises at least one phosphorothioate in the Sp conformation and at least one phosphorothioate in the Rp conformation in the CpG region motif.

The method of any preceding embodiment, wherein the second oligonucleotide does not comprise an agonistic CpG region motif described herein.

The method of any preceding embodiment, wherein the second oligonucleotide does not comprise an antagonistic CpG region motif described herein.

The method of any preceding embodiment, wherein the second oligonucleotide does not comprise an agonistic or antagonistic CpG region motif described herein.

A method of designing a second oligonucleotide mediating decreased immune stimulation in a human cell relative to the immune stimulation mediated by a first oligonucleotide, the method comprising the steps of:

(a) measuring the immune stimulation mediated by a first oligonucleotide, wherein the first oligonucleotide has a defined base sequence comprising at least one CpG region;

(b) measuring the immune stimulation mediated by one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides, wherein steps (a) and (b) can be performed in any order;

(c) selecting a second oligonucleotide which mediates less immune stimulation than the first oligonucleotide.

The method of any preceding embodiment, wherein the first oligonucleotide is immunostimulatory in a human cell.

The method of any preceding embodiments, wherein the second oligonucleotide comprises at least one phosphorothioate in the Sp conformation and at least one phosphorothioate in the Rp conformation in the CpG region motif.

The method of any preceding embodiment, wherein the second oligonucleotide does not comprise an agonistic CpG region motif described herein.

The method of any preceding embodiment, wherein the second oligonucleotide does not comprise an antagonistic CpG region motif described herein.

The method of any preceding embodiment, wherein the second oligonucleotide does not comprise an agonistic or antagonistic CpG region motif described herein.

A method of decreasing the immune stimulation in a human cell mediated by a first oligonucleotide, the method comprising the steps of:

(a) providing the first oligonucleotide, wherein the first oligonucleotide has a defined base sequence comprising at least one CpG region; and measuring the immune stimulation in a human cell mediated by the first oligonucleotide;

(b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order;

(c) selecting a second oligonucleotide which mediates less immune stimulation than the first oligonucleotide; and (d) contacting the cell with the second oligonucleotide.

The method of any preceding embodiment, wherein the first oligonucleotide is immunostimulatory in a human cell.

The method of any preceding embodiments, wherein the second oligonucleotide comprises at least one phosphorothioate in the Sp conformation and at least one phosphorothioate in the Rp conformation in the CpG region motif.

The method of any preceding embodiment, wherein the second oligonucleotide does not comprise an agonistic CpG region motif described herein.

The method of any preceding embodiment, wherein the second oligonucleotide does not comprise an antagonistic CpG region motif described herein.

The method of any preceding embodiment, wherein the second oligonucleotide does not comprise an agonistic or antagonistic CpG region motif described herein.

A composition comprising an oligonucleotide, wherein the oligonucleotide mediates less immune stimulation than a reference oligonucleotide, wherein the second oligonucleotide is selected using a method comprising the steps of:

(a) providing the reference oligonucleotide, wherein the reference oligonucleotide has a defined base sequence comprising at least one CpG region; and measuring the immune stimulation in a human cell mediated by the reference oligonucleotide;

(b) providing one or more second oligonucleotides, wherein the second oligonucleotides have the same base sequence as the reference oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the reference oligonucleotides; and measuring the immune stimulation in a human cell of the second oligonucleotides, wherein steps (a) and (b) can be performed in any order;

(c) selecting a second oligonucleotide which mediates less immune stimulation than the reference oligonucleotide.

The method or composition of any preceding embodiment, wherein the reference oligonucleotide is immunostimulatory in a human cell.

The method or composition of any preceding embodiments, wherein the second oligonucleotide comprises at least one phosphorothioate in the Sp conformation and at least one phosphorothioate in the Rp conformation in the CpG region motif.

The method or composition of any preceding embodiment, wherein the second oligonucleotide does not comprise an agonistic CpG region motif described herein.

The method or composition of any preceding embodiment, wherein the second oligonucleotide does not comprise an antagonistic CpG region motif described herein.

The method or composition of any preceding embodiment, wherein the second oligonucleotide does not comprise an agonistic or antagonistic CpG region motif described herein.

A method of administering a therapeutic oligonucleotide to a patient, wherein the therapeutic oligonucleotide mediates less immune stimulation than a first oligonucleotide, wherein the therapeutic oligonucleotide is selected using a method comprising the steps of:

(a) providing the first oligonucleotide, wherein the first oligonucleotide has a defined base sequence comprising at least one CpG region; and measuring the immune stimulation in a human cell mediated by the first oligonucleotide;

(b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order;

(c) selecting a second oligonucleotide which mediates less immune stimulation than the first oligonucleotide as the therapeutic oligonucleotide.

The method of any preceding embodiment, wherein the first oligonucleotide is immunostimulatory in a human cell.

The method of any preceding embodiment, wherein the second oligonucleotide comprises at least one phosphorothioate in the Sp conformation and at least one phosphorothioate in the Rp conformation in the CpG region motif.

The method of any preceding embodiment, wherein the second oligonucleotide does not comprise an agonistic CpG region motif described herein.

The method of any preceding embodiment, wherein the second oligonucleotide does not comprise an antagonistic CpG region motif described herein.

The method of any preceding embodiment, wherein the second oligonucleotide does not comprise an agonistic or antagonistic CpG region motif described herein.

The present disclosure thus presents various methods for identifying variants of oligonucleotides comprising a CpG region which are capable of mediating less agonism of an immune response.

Methods of Identifying Oligonucleotides with Increased Agonism of an Immune Response The present disclosure also provides methods of increasing the immune response agonized by an oligonucleotide intended for therapeutic use and comprising a CpG, if an agonized immune response is desired. The present disclosure notes that it may be desirable to produce a variant of an oligonucleotide with increased agonism of an immune response. In some embodiments, such a variant can be, for example, modified and/or be stereopure or chirally controlled oligonucleotide composition. In some embodiments, such a variant can also, for example, have higher stability, a shorter length, improved biological activity (e.g., if the oligonucleotide of which the variant is made has a desirable biological activity), etc.

The oligonucleotide can be, as non-limiting examples, an antisense oligonucleotide (ASO), RNAi agent (e.g., single or double stranded siRNA), miRNA, miRNA inhibitor, CRISPR, mRNA, etc. Such oligonucleotides may be designed to perform a function such as reducing or increasing the expression of a target gene or level of a target protein, which is completely independent of any immune reaction.

Many CpG oligonucleotides, as disclosed herein and including some designed for therapeutic use, are capable of agonizing an immune response, making them useful as vaccine adjuvants and mono- and combination therapies. It may be desirable to increase the immune response mediated by a CpG oligonucleotide.

As a non-limiting example, the oligonucleotide intended for therapeutic use can be a stereomixture. Various stereopure (or mostly stereopure) variants can be produced, including variants which may include CpG region motifs which agonize an immune response. The variants can be tested for immune stimulation (using any method known in the art to test the immune stimulation mediated by a CpG oligonucleotide). A variant which has increased agonism of an immune response can then be selected.

Alternatively, if the oligonucleotide is already stereopure (or mostly stereopure), then one or more variants can be provided and tested, and one or more variant oligonucleotides with the desired immune response can be selected.

The present disclosure notes that some CpG region motifs appear, in at least some experiments, to elicit a greater immune response than others. For example, the CpG region motif $N_1$-(*R/S)—C—(*R/S)-G-(*R)—$N_2$ is generally less agonistic than CpG oligonucleotides comprising the CpG region motif $N_1$-(*R/S)—C—(*R/S)-G-(*S)—$N_2$ (see FIG. 7, for example). Thus, selection of an oligonucleotide which mediates an increased immune response can involve the step of selecting a CpG region motif which mediates an increased immune response.

In some embodiments, the present disclosure pertains to:

A method of identifying a second oligonucleotide mediating increased immune stimulation in a human cell relative to the immune stimulation mediated by a first oligonucleotide, the method comprising the steps of:

(a) measuring the immune stimulation mediated by a first oligonucleotide, wherein the first oligonucleotide has a defined base sequence comprising at least one CpG region;

(b) measuring the immune stimulation mediated by one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides, wherein steps (a) and (b) can be performed in any order;

(c) selecting a second oligonucleotide which mediates more immune stimulation than the first oligonucleotide.

The method of any preceding embodiment, wherein the first oligonucleotide is immunostimulatory in a human cell.

The method of any preceding embodiments, wherein the second oligonucleotide comprises at least one phosphorothioate in the Sp conformation and at least one phosphorothioate in the Rp conformation in the CpG region motif.

The method of any preceding embodiment, wherein the second oligonucleotides comprises an agonistic CpG region motif described herein.

The method of any preceding embodiment, wherein the second oligonucleotide does not comprise an antagonistic CpG region motif described herein.

A method of designing a second oligonucleotide mediating increased immune stimulation in a human cell relative to the immune stimulation mediated by a first oligonucleotide, the method comprising the steps of:

(a) measuring the immune stimulation mediated by a first oligonucleotide, wherein the first oligonucleotide has a defined base sequence comprising at least one CpG region;

(b) measuring the immune stimulation mediated by one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides, wherein steps (a) and (b) can be performed in any order;

(c) selecting a second oligonucleotide which mediates more immune stimulation than the first oligonucleotide.

The method of any preceding embodiment, wherein the first oligonucleotide is immunostimulatory in a human cell.

The method of any preceding embodiments, wherein the second oligonucleotide comprises at least one phosphorothioate in the Sp conformation and at least one phosphorothioate in the Rp conformation in the CpG region motif.

The method of any preceding embodiment, wherein the second oligonucleotides comprises an agonistic CpG region motif described herein.

The method of any preceding embodiment, wherein the second oligonucleotide does not comprise an antagonistic CpG region motif described herein.

A method of decreasing the immune stimulation in a human cell mediated by a first oligonucleotide, the method comprising the steps of:

(a) providing the first oligonucleotide, wherein the first oligonucleotide has a defined base sequence comprising at least one CpG region; and measuring the immune stimulation in a human cell mediated by the first oligonucleotide;

(b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order;

(c) selecting a second oligonucleotide which mediates more immune stimulation than the first oligonucleotide; and (d) contacting the cell with the second oligonucleotide.

The method of any preceding embodiment, wherein the first oligonucleotide is immunostimulatory in a human cell.

The method of any preceding embodiments, wherein the second oligonucleotide comprises at least one phosphorothioate in the Sp conformation and at least one phosphorothioate in the Rp conformation in the CpG region motif.

The method of any preceding embodiment, wherein the second oligonucleotides comprises an agonistic CpG region motif described herein.

The method of any preceding embodiment, wherein the second oligonucleotide does not comprise an antagonistic CpG region motif described herein.

A composition comprising an oligonucleotide, wherein the oligonucleotide mediates more immune stimulation than a reference oligonucleotide, wherein the second oligonucleotide is selected using a method comprising the steps of:

(a) providing the reference oligonucleotide, wherein the reference oligonucleotide has a defined base sequence comprising at least one CpG region; and measuring the immune stimulation in a human cell mediated by the reference oligonucleotide;

(b) providing one or more second oligonucleotides, wherein the second oligonucleotides have the same base sequence as the reference oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the reference oligonucleotides; and measuring the immune stimulation in a human cell of the second oligonucleotides, wherein steps (a) and (b) can be performed in any order;

(c) selecting a second oligonucleotide which mediates more immune stimulation than the reference oligonucleotide.

The method or composition of any preceding embodiment, wherein the reference oligonucleotide is immunostimulatory in a human cell.

The method or composition of any preceding embodiments, wherein the second oligonucleotide comprises at least one phosphorothioate in the Sp conformation and at least one phosphorothioate in the Rp conformation in the CpG region motif.

The method or composition of any preceding embodiment, wherein the second oligonucleotides comprises an agonistic CpG region motif described herein.

The method or composition of any preceding embodiment, wherein the second oligonucleotide does not comprise an antagonistic CpG region motif described herein.

A method of administering a therapeutic oligonucleotide to a patient, wherein the therapeutic oligonucleotide mediates more immune stimulation than a first oligonucleotide, wherein the therapeutic oligonucleotide is selected using a method comprising the steps of:

(a) providing the first oligonucleotide, wherein the first oligonucleotide has a defined base sequence comprising at least one CpG region; and measuring the immune stimulation in a human cell mediated by the first oligonucleotide;

(b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order;

(c) selecting a second oligonucleotide which mediates more immune stimulation than the first oligonucleotide as the therapeutic oligonucleotide.

The method of any preceding embodiment, wherein the first oligonucleotide is immunostimulatory in a human cell.

The method of any preceding embodiment, wherein the second oligonucleotide comprises at least one phosphorothioate in the Sp conformation and at least one phosphorothioate in the Rp conformation in the CpG region motif.

The method of any preceding embodiment, wherein the second oligonucleotides comprises an agonistic CpG region motif described herein.

The method of any preceding embodiment, wherein the second oligonucleotide does not comprise an antagonistic CpG region motif described herein.

The present disclosure pertains to the recognition that the immune response mediated by a CpG oligonucleotide can be affected by the stereochemistry of the phosphorothioates in a CpG region motif in the oligonucleotide.

The present disclosure thus pertains to compositions and methods related to CpG oligonucleotides comprising one or more copies of a CpG region motif. Various motifs, which are defined at least in part by the stereochemistry of the phosphorothioates in the CpG region, can either agonize or antagonize an immunostimulatory effect. CpG oligonucleotides comprising an immunostimulatory CpG region motif can be used, for example, as a vaccine adjuvant or mono- or combination therapy. If no immune modulation is desired, the present disclosure also provides methods of identifying oligonucleotides which have decreased immune modulation, e.g., those lacking CpG region motifs which agonize or antagonize an immune response. Oligos intended for therapeutic use can thus be screened for immune modulation mediated by CpG region motifs, and modified variants of these oligonucleotides can be prepared which have less immune modulation. In some embodiments, if more immune response is desired, the present disclosure provides methods of identifying a modified variant of an oligonucleotide with a CpG region motif capable of mediating an increased immune response.

In some embodiments, the present disclosure provides the following example embodiments:

1. A chirally controlled oligonucleotide composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a modified internucleotidic linkage in the Rp conformation and at least one (*R/S) is a modified internucleotidic linkage in the Sp conformation, and each of N and $N_2$ is independently any nucleoside.

2. A chirally controlled oligonucleotide composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and each of N i and $N_2$ is independently any nucleoside.

3. A composition comprising a CpG oligonucleotide comprising a strand comprising about 14 to about 49 nucleotides, wherein the strand comprises at least one copy of CpG region motif $N_1$-(*R/S)—C—(*R/S)-G-(*R/S)—$N_2$, wherein at least one (*R/S) is a phosphorothioate in the Rp conformation and at least one (*R/S) is a phosphorothioate in the Sp conformation, and each of $N_1$ and $N_2$ is independently any nucleoside.

4. A composition comprising a plurality of oligonucleotides, each of which:

(a) hybridizes with a particular target sequence; and (b) comprises a sequence that includes at least one CpG region motif present in all oligonucleotides of the plurality (a "common CpG region motif"), which CpG region motif has a structure:

$N_1$-(*R/S)—C—(*R/S)-G-(*R/S)—$N_2$;

wherein each (*R/S) is independently a chiral internucleotidic linkage, and each of $N_1$ and $N_2$ is independently any nucleoside.

5. A composition comprising a plurality of oligonucleotides, each of which:

(a) consists of a particular base sequence; and (b) comprises a sequence that includes at least one CpG region motif present in all oligonucleotides of the plurality (a "common CpG region motif"), which CpG region motif has a structure:

$N_1$-(*R/S)—C—(*R/S)-G-(*R/S)—$N_2$;

wherein at least one (*R/S) is a phosphorothioate in the Rp conformation and at least one (*R/S) is a phosphorothioate in the Sp conformation, and each of $N_1$ and $N_2$ is independently any nucleoside.

4. A composition comprising a plurality of oligonucleotides, each of which:

(a) hybridizes with a particular target sequence; and (b) has a sequence that includes at least one CpG region motif present in all oligonucleotides of the plurality (a "common CpG region motif"), which CpG region motif has a structure:

$N_1$-(*R/S)—C—(*R/S)-G-(*R/S)—$N_2$;

wherein each (*R/S) is independently a chiral internucleotidic linkage, wherein the composition is chirally controlled in that it contains a predetermined level of each of stereoisomers 1-8 (S1-S8) for each common CpG region motif:
S1: $N_1$-(*R)—C—(*R)-G-(*R)—$N_2$;
S2: $N_1$-(*R)—C—(*R)-G-(*S)—$N_2$;
S3: $N_1$-(*R)—C—(*S)-G-(*R)—$N_2$;
S4: $N_1$-(*R)—C—(*S)-G-(*S)—$N_2$;
S5: $N_1$-(*S)—C—(*R)-G-(*R)—$N_2$;
S6: $N_1$-(*S)—C—(*R)-G-(*S)—$N_2$;
S7: $N_1$-(*S)—C—(*S)-G-(*R)—$N_2$;
S8: $N_1$-(*S)—C—(*S)-G-(*S)—$N_2$.

5. An oligonucleotide composition that is chirally controlled in that the composition comprises a predetermined level of oligonucleotides of an individual oligonucleotide type, wherein an oligonucleotide type is defined by:
   1) base sequence;
   2) pattern of backbone linkages;
   3) pattern of backbone chiral centers; and
   4) pattern of backbone phosphorus modifications;
wherein each oligonucleotide of the individual oligonucleotide type independently comprises at least one common CpG region motif:
$N_1$-(*R/S)—C—(*R/S)-G-(*R/S)—$N_2$;
wherein each (*R/S) is independently a chiral internucleotidic linkage, and each of N i and $N_2$ is independently any nucleoside.

5a. An oligonucleotide composition that is chirally controlled in that the composition comprises a predetermined level of oligonucleotides of an individual oligonucleotide type, wherein an oligonucleotide type is defined by:
   1) base sequence;
   2) pattern of backbone linkages;
   3) pattern of backbone chiral centers; and
   4) pattern of backbone phosphorus modifications;
wherein each oligonucleotide of the individual oligonucleotide type independently comprises at least one common CpG.

5b. An oligonucleotide composition that is chirally controlled in that the composition comprises a predetermined level of a plurality of oligonucleotides, which plurality of oligonucleotides share common:
   1) base sequence;
   2) pattern of backbone linkages;
   3) pattern of backbone phosphorus modifications;
wherein each oligonucleotide of the plurality independently comprises at least one common CpG region motif:
$N_1$-(*R/S)—C—(*R/S)-G-(*R/S)—$N_2$;
wherein each (*R/S) is independently a chiral internucleotidic linkage, and each of N i and $N_2$ is independently any nucleoside; and
where the plurality of oligonucleotides share the same stereochemistry at at least 1, 2, 3, 4, 5, 6, 7, 8, 9, 10, 11, 12, 13, 14, 15, 16, 17, 18, 19, or 20 chiral linkage phosphorus atoms of chiral internucleotidic linkages.

5c. The oligonucleotide composition of embodiment 5b, wherein the plurality of oligonucleotides share the same stereochemistry at at least 5, 6, 7, 8, 9, 10, 11, 12, 13, 14, 15, 16, 17, 18, 19, or 20 chiral linkage phosphorus atoms of chiral internucleotidic linkages.

5d. The oligonucleotide composition of embodiment 5b, wherein the plurality of oligonucleotides share the same stereochemistry at at least 10, 11, 12, 13, 14, 15, 16, 17, 18, 19, or 20 chiral linkage phosphorus atoms of chiral internucleotidic linkages.

6. A composition comprising a plurality of oligonucleotides, each of which:
   (a) hybridizes with a particular target sequence;
   (b) has a base sequence that includes at least one C residue in a CpG region motif that is present in all oligonucleotides of the plurality (a "common C residue") and that has a modified base moiety, a modified sugar moiety, or both; and
   (c) includes one or more chiral internucleotidic linkages, so that each oligonucleotide is a particular stereoform, characterized by its stereoidentity at each of the one or more chiral internucleotidic linkages, wherein stereoidentity identifies which stereoisomer is present at a particular chiral internucleotidic linkage, wherein the composition is chirally controlled in that it contains a predetermined level of each stereoform.

6a. A composition comprising a plurality of oligonucleotides, each of which:
   (a) hybridizes with a particular target sequence;
   (b) has a base sequence that includes at least one C residue in a CpG region motif that is present in all oligonucleotides of the plurality (a "common C residue") and that has a 5-methyl group, a modified sugar moiety, or both; and
   (c) includes one or more chiral internucleotidic linkages, so that each oligonucleotide is a particular stereoform, characterized by its stereoidentity at each of the one or more chiral internucleotidic linkages, wherein stereoidentity identifies which stereoisomer is present at a particular chiral internucleotidic linkage, wherein the composition is chirally controlled in that it contains a predetermined level of each stereoform.

6b. The composition of any one of the preceding embodiments, wherein oligonucleotides of the composition are TLR9 agonists.

6c. The composition of any one of the preceding embodiments, wherein the composition has an enhanced ability to activate a TLR9-mediated and/or TLR9-associated immune response relative to the ability of a composition that is not chirally controlled in that the composition comprises a random level of oligonucleotides of an individual oligonucleotide type.

7. An oligonucleotide composition that is chirally controlled in that the composition comprises a predetermined level of oligonucleotides of an individual oligonucleotide type, wherein an oligonucleotide type is defined by:
   1) base sequence;
   2) pattern of backbone linkages;
   3) pattern of backbone chiral centers; and
   4) pattern of backbone phosphorus modifications;
wherein the base sequence includes at least one C residue in a CpG region motif that has a modified base, a modified sugar moiety, or both; and
the composition has a reduced ability to activate a TLR9-mediated and/or TLR9-associated immune response relative to the ability of a composition that is not chirally controlled in that the composition comprises a random level of oligonucleotides of an individual oligonucleotide type.

7a. An oligonucleotide composition that is chirally controlled in that the composition comprises a predetermined level of oligonucleotides of an individual oligonucleotide type, wherein an oligonucleotide type is defined by:
   1) base sequence;
   2) pattern of backbone linkages;
   3) pattern of backbone chiral centers; and
   4) pattern of backbone phosphorus modifications;
wherein the base sequence includes at least one C residue in a CpG region motif that has a 5-methyl group, a modified sugar moiety, or both; and
the composition has a reduced ability to activate a TLR9-mediated and/or TLR9-associated immune response relative to the ability of a composition that is not chirally controlled in that the composition comprises a random level of oligonucleotides of an individual oligonucleotide type.

8. The composition of any one of the preceding embodiments, wherein oligonucleotides of the composition comprise two or more CpG.

8a. The composition of any one of the preceding embodiments, wherein oligonucleotides of the composition comprise three or more CpG.

8b. The composition of any one of the preceding embodiments, wherein oligonucleotides of the composition comprise four or more CpG.

8c. The composition of any one of the preceding embodiments, wherein oligonucleotides of the composition comprise five or more CpG.

8d. A chirally controlled oligonucleotide composition comprising a CpG oligonucleotide comprising a strand comprising about 14 to about 49 nucleotides, wherein the strand comprises at least one copy of any CpG region motif disclosed herein.

9. A chirally controlled oligonucleotide composition comprising a CpG oligonucleotide comprising a strand comprising about 14 to about 49 nucleotides, wherein the strand comprises at least one copy of any CpG region motif of any CpG oligonucleotide disclosed herein.

10. A chirally controlled oligonucleotide composition comprising a CpG oligonucleotide comprising a strand comprising about 14 to about 49 nucleotides, wherein the strand comprises or consists of the sequence of any oligonucleotide disclosed herein.

11. A chirally controlled oligonucleotide composition comprising a CpG oligonucleotide comprising a strand comprising 14 to 49 nucleotides, wherein the strand comprises at least one copy of any CpG region motif disclosed herein.

12. A chirally controlled oligonucleotide composition comprising a CpG oligonucleotide comprising a strand comprising 14 to 49 nucleotides, wherein the strand comprises at least one copy of any CpG region motif of any CpG oligonucleotide disclosed herein.

13. A chirally controlled oligonucleotide composition comprising a CpG oligonucleotide comprising a strand comprising at least one copy of the CpG region motif T-(*R)—C—(*R)-G-(*R)-T, wherein the CpG oligonucleotide is capable of agonizing an immune response in the human.

14. A chirally controlled oligonucleotide composition comprising a CpG oligonucleotide comprising a strand comprising at least one copy of the CpG region motif T-(*R)—C—(*R)-G-(*R)-T-(*R)-Py, wherein the CpG oligonucleotide is capable of agonizing an immune response in the human.

15. A chirally controlled oligonucleotide composition comprising a CpG oligonucleotide comprising a strand comprising at least two non-adjacent copies of the CpG region motif of $N_1$-(*R)—C—(*R)-G-(*R)—$N_2$, wherein at least one phosphorothioate between the CpG region motifs is in the Sp conformation, and wherein the CpG oligonucleotide is capable of agonizing an immune response in the human.

16. A chirally controlled oligonucleotide composition comprising a CpG oligonucleotide comprising a strand comprising at least one copy of the CpG region motif T-(*S)—C—(*S)-G-(*S)-T-(*S)-T, wherein the CpG oligonucleotide is capable of agonizing an immune response in the human.

17. A chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein the CpG oligonucleotide is capable of agonizing an immune response in the human.

18. A chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein at least one (*R/S) is (*R) and at least one (*R/S) is (*S), wherein the CpG oligonucleotide is capable of agonizing an immune response in the human.

19. A chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein at least one (*R/S) is (*R) and at least one (*R/S) is (*S), and wherein C is unmethylated, wherein the CpG oligonucleotide is capable of agonizing an immune response in the human.

20. A chirally controlled oligonucleotide composition comprising a CpG oligonucleotide comprising a strand comprising at least one copy of the CpG region motif $N_1$-(*R)—C—(*R)-G-(*S)—$N_2$, wherein the CpG oligonucleotide is capable of agonizing an immune response in the human.

21. A chirally controlled oligonucleotide composition comprising a CpG oligonucleotide comprising a strand comprising at least one copy of the CpG region motif $N_1$-(*R)—C—(*S)-G-(*S)—$N_2$, wherein the CpG oligonucleotide is capable of agonizing an immune response in the human.

22. A chirally controlled oligonucleotide composition comprising a CpG oligonucleotide comprising a strand comprising at least one copy of the CpG region motif $N_1$-(*R)—C—(*S)-G-(*R)—$N_2$, wherein the CpG oligonucleotide is capable of agonizing an immune response in the human.

23. A chirally controlled oligonucleotide composition comprising a CpG oligonucleotide comprising a strand comprising at least one copy of the CpG region motif $N_1$-(*S)—C—(*R)-G-(*S)—$N_2$, wherein the CpG oligonucleotide is capable of agonizing an immune response in the human.

24. A chirally controlled oligonucleotide composition comprising a CpG oligonucleotide comprising a strand comprising at least one copy of the CpG region motif $N_1$-(*S)—C—(*R)-G-(*R)—$N_2$, wherein the CpG oligonucleotide is capable of agonizing an immune response in the human.

25. A chirally controlled oligonucleotide composition comprising a CpG oligonucleotide comprising a strand comprising at least one copy of the CpG region motif $N_1$-(*S)—C—(*S)-G-(*R)—$N_2$, wherein the CpG oligonucleotide is capable of agonizing an immune response in the human.

26. A chirally controlled oligonucleotide composition comprising a CpG oligonucleotide comprising a strand comprising at least one copy of the CpG region motif Py-(*R/S)—C—(*R/S)-G-(*R/S)-Py, wherein at least one (*R/S) is (*R) and at least one (*R/S) is (*S), and wherein C is unmethylated, wherein the CpG oligonucleotide is capable of agonizing an immune response in the human.

27. A chirally controlled oligonucleotide composition comprising a CpG oligonucleotide comprising a strand comprising at least one copy of the CpG region motif m5C—(*R)-m5C—(*R)-G-(*R)—$N_1$, where all the nucleosides are 2-MOE, wherein the CpG oligonucleotide is capable of agonizing an immune response in the human.

28. A chirally controlled oligonucleotide composition comprising a CpG oligonucleotide comprising a strand comprising at least one copy of the CpG region motif m5C—(*R)-m5C—(*R)-G-(*R)-Py, where all the nucleosides are 2'-MOE, wherein the CpG oligonucleotide is capable of agonizing an immune response in the human.

29. A chirally controlled oligonucleotide composition comprising a CpG oligonucleotide comprising a strand comprising at least one copy of the CpG region motif $N_1$-(*R)-m5C—(*R)-G-(*R)—$N_2$, wherein $N_1$ is methylated or not methylated, and all the nucleosides are 2'-MOE, wherein the CpG oligonucleotide is capable of agonizing an immune response in the human.

30. A chirally controlled oligonucleotide composition comprising a CpG oligonucleotide comprising a strand comprising at least one copy of the CpG region motif $N_1$-(*R)-m5C—(*R)-G-(*R)-Py, wherein $N_1$ is methylated or not methylated, and all the nucleosides are 2'-MOE, wherein the CpG oligonucleotide is capable of agonizing an immune response in the human.

31. A chirally controlled oligonucleotide composition comprising a CpG oligonucleotide comprising a strand comprising at least one copy of the CpG region motif $N_1$-(*R/S)-m5C—(*R/S)-G-(*R/S)—$N_2$, wherein at least 2 of the (*R/S) are (*R), all the nucleosides are 2'-MOE, and $N_1$ and $N_2$ are methylated or not methylated, wherein the CpG oligonucleotide is capable of agonizing an immune response in the human.

32. A chirally controlled oligonucleotide composition comprising a CpG oligonucleotide comprising a strand comprising at least one copy of the CpG region motif $N_1$-(*R/S)-m5C—(*R/S)-G-(*R/S)—$N_2$, wherein at least 2 of the (*R/S) are (*R), all the nucleosides are 2'-MOE; and $N_1$ and $N_2$ are methylated or not methylated, wherein the CpG oligonucleotide is capable of agonizing an immune response in the human.

33. A chirally controlled oligonucleotide composition comprising a CpG oligonucleotide comprising a strand comprising at least one copy of the CpG region motif $N_1$-(*S)—[C]-(*R)-[G]-(*S)—$N_2$, where $N_1$ is 2'H, 2'-MOE or 2'-OMe; [C] is C, m5C, 2'-MOE C, or 2'-MOE m5C; [G] is G, 2'-Ome G, or 2'-MOE G; and $N_2$ is 2'H, 2'-MOE or 2'-OMe, wherein the CpG oligonucleotide is capable of antagonizing an immune response in the human.

34. A chirally controlled oligonucleotide composition comprising a CpG oligonucleotide comprising a strand comprising at least one copy of the CpG region motif $N_1$-(*S)—[C]-(*R)-[G]-(*S)—$N_2$, where $N_1$ is 2'H; [C] is C, m5C, 2'-MOE C, or 2'-MOE m5C; [G] is G, 2'-Ome G, or 2'-MOE G; and $N_2$ is 2'H, wherein the CpG oligonucleotide is capable of antagonizing an immune response in the human.

35. A chirally controlled oligonucleotide composition comprising a CpG oligonucleotide comprising a strand comprising at least one copy of the CpG region motif $N_1$-(*R)—[C]-(*R)-[G]-(*R)-Py, where $N_1$ and Py are 2'H, 2'-MOE or 2'OMe; and [C] is C or 2'-MOE C; and [G] is G or 2'-MOE G; and Py is 2'-H or 2'-MOE, wherein the CpG oligonucleotide is capable of antagonizing an immune response in the human.

36. A chirally controlled oligonucleotide composition comprising a CpG oligonucleotide comprising a strand comprising at least one copy of the CpG region motif $N_1$-(*R)—[C]-(*R)-[G]-(*R)—$N_2$, where $N_1$ and $N_2$ are 2'H, 2'-MOE or 2'OMe; and [C] is 2'-MOE m5C; $N_2$ is 2'-H or 2'-MOE, wherein the CpG oligonucleotide is capable of antagonizing an immune response in the human.

37. A chirally controlled oligonucleotide composition comprising a CpG oligonucleotide comprising a strand comprising at least one copy of the CpG region motif Py-(*R)—C—(*R)-G-(*R)-Py, wherein the CpG oligonucleotide is capable of antagonizing an immune response in the human.

38. A chirally controlled oligonucleotide composition comprising a CpG oligonucleotide comprising a strand comprising at least one copy of the CpG region motif Py-(*R)—C—(*R)-G-(*R)-Py, wherein the CpG oligonucleotide is capable of antagonizing an immune response in the human.

39. A chirally controlled oligonucleotide composition comprising a CpG oligonucleotide comprising a strand comprising at least one copy of the CpG region motif Py-(*S)—C—(*R)-G-(*S)-Py.

40. A chirally controlled oligonucleotide composition comprising a CpG oligonucleotide comprising a strand comprising at least one copy of the CpG region motif Py-(*S)—C—(*S)-G-(*S)-Py, wherein the CpG oligonucleotide is capable of antagonizing an immune response in the human.

41. A chirally controlled oligonucleotide composition comprising a CpG oligonucleotide comprising a strand comprising at least one copy of the CpG region motif Py-(*R)—[C]-(*R)-[G]-(*R)-Py, where [C] is 2'-MOE C; and [G] is 2'-MOE G, wherein the CpG oligonucleotide is capable of antagonizing an immune response in the human.

42. A chirally controlled oligonucleotide composition comprising a CpG oligonucleotide comprising a strand comprising at least one copy of the CpG region motif Py-(*R)—[C]-(*R)-[G]-(*S)-Py, where [C] is 2'-MOE C; and [G] is 2'-MOE G, wherein the CpG oligonucleotide is capable of antagonizing an immune response in the human.

43. A chirally controlled oligonucleotide composition comprising a CpG oligonucleotide comprising a strand comprising at least one copy of the CpG region motif Py-(*R)—[C]-(*R)-G-(*R)-Py, where [C] is C, 2'-OMe m5C, or 2'-MOE C, wherein the CpG oligonucleotide is capable of antagonizing an immune response in the human.

44. A chirally controlled oligonucleotide composition comprising a CpG oligonucleotide comprising a strand comprising at least one copy of the CpG region motif Py-(*R)—[C]-(*R)-[G]-(*R)—$N_1$, where [C] is 2'-OMe m5C, and [G] is 2'-OMe G, and $N_1$ is 2'-OMe, wherein the CpG oligonucleotide is capable of antagonizing an immune response in the human.

45. A chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe m5C, and [G] is 2'-OMe G, wherein the CpG oligonucleotide is capable of antagonizing an immune response in the human.

46. A chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe C and [G] is 2'-OMe G, wherein the CpG oligonucleotide is capable of antagonizing an immune response in the human.

47. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE C and [G] is 2'-MOE G, wherein the CpG oligonucleotide is capable of antagonizing an immune response in the human.

48. A chirally controlled oligonucleotide composition comprising a CpG oligonucleotide comprising a strand comprising at least one copy of the CpG region motif Py-(*R)-m5C—(*R)-G-(*R)-Py, wherein the CpG oligonucleotide is capable of antagonizing an immune response in the human.

49. A chirally controlled oligonucleotide composition comprising a CpG oligonucleotide comprising a strand comprising at least one copy of the CpG region motif Py-(*R)-m5C—(*R)-G-(*R)-Py, wherein the CpG oligonucleotide is capable of antagonizing an immune response in the human.

50. A chirally controlled oligonucleotide composition comprising a CpG oligonucleotide comprising a strand comprising at least one copy of the CpG region motif Py-(*S)-m5C—(*R)-G-(*S)-Py, wherein the CpG oligonucleotide is capable of antagonizing an immune response in the human.

51. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE m5C and [G] is 2'-MOE G, wherein the CpG oligonucleotide is capable of antagonizing an immune response in the human.

52. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe m5C and [G] is 2'-OMe G, wherein the CpG oligonucleotide is capable of antagonizing an immune response in the human.

53. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe C and [G] is 2'-OMe G, wherein the CpG oligonucleotide is capable of antagonizing an immune response in the human.

54. A chirally controlled oligonucleotide composition comprising a CpG oligonucleotide comprising a strand comprising at least one copy of the CpG region motif Py-(*R)—[C]-(*R)-[G]-(*R)-Py, where both [C] and [G] are 2'-modified, wherein the CpG oligonucleotide is capable of antagonizing an immune response in the human.

55. A chirally controlled oligonucleotide composition comprising a CpG oligonucleotide comprising a strand comprising at least one copy of the CpG region motif $N_1$-(*R)—[C]-(*R)-[G]-(*R)—$N_2$, where both [C] and [G] are 2'-modified, wherein the CpG oligonucleotide is capable of antagonizing an immune response in the human.

56. A chirally controlled oligonucleotide composition comprising a CpG oligonucleotide comprising a strand comprising at least one copy of the CpG region motif T-(*R)—C—(*R)-G-(*R)-T.

57. A chirally controlled oligonucleotide composition comprising a CpG oligonucleotide comprising a strand comprising at least one copy of the CpG region motif T-(*R)—C—(*R)-G-(*R)-T-(*R)-Py.

58. A chirally controlled oligonucleotide composition comprising a CpG oligonucleotide comprising a strand comprising at least two non-adjacent copies of the CpG region motif of $N_1$-(*R)—C—(*R)-G-(*R)—$N_2$, wherein at least one phosphorothioate between the CpG region motifs is in the Sp conformation.

59. A chirally controlled oligonucleotide composition comprising a CpG oligonucleotide comprising a strand comprising at least one copy of the CpG region motif T-(*S)—C—(*S)-G-(*S)-T-(*S)-T.

60. A chirally controlled oligonucleotide composition comprising a CpG oligonucleotide comprising a strand comprising at least one copy of the CpG region motif $N_1$-(*R/S)—C—(*R/S)-G-(*R/S)—$N_2$.

61. A chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein at least one (*R/S) is (*R) and at least one (*R/S) is (*S).

62. A chirally controlled oligonucleotide composition comprising a CpG oligonucleotide comprising a strand comprising at least one copy of the CpG region motif $N_1$-(*R/S)—C—(*R/S)-G-(*R/S)—$N_2$, wherein at least one (*R/S) is (*R) and at least one (*R/S) is (*S), and wherein C is unmethylated.

63. A chirally controlled oligonucleotide composition comprising a CpG oligonucleotide comprising a strand comprising at least one copy of the CpG region motif $N_1$-(*R)—C—(*R)-G-(*S)—$N_2$.

64. A chirally controlled oligonucleotide composition comprising a CpG oligonucleotide comprising a strand comprising at least one copy of the CpG region motif $N_1$-(*R)—C—(*S)-G-(*S)—$N_2$.

65. A chirally controlled oligonucleotide composition comprising a CpG oligonucleotide comprising a strand comprising at least one copy of the CpG region motif $N_1$-(*R)—C—(*S)-G-(*R)—$N_2$.

66. A chirally controlled oligonucleotide composition comprising a CpG oligonucleotide comprising a strand comprising at least one copy of the CpG region motif $N_1$-(*S)—C—(*R)-G-(*S)—$N_2$.

67. A chirally controlled oligonucleotide composition comprising a CpG oligonucleotide comprising a strand comprising at least one copy of the CpG region motif $N_1$-(*S)—C—(*R)-G-(*R)—$N_2$.

68. A chirally controlled oligonucleotide composition comprising a CpG oligonucleotide comprising a strand comprising at least one copy of the CpG region motif $N_1$-(*S)—C—(*S)-G-(*R)-$N_2$.

69. A chirally controlled oligonucleotide composition comprising a CpG oligonucleotide comprising a strand comprising at least one copy of the CpG region motif Py-(*R/S)—C—(*R/S)-G-(*R/S)-Py, wherein at least one (*R/S) is (*R) and at least one (*R/S) is (*S), and wherein C is unmethylated.

70. A chirally controlled oligonucleotide composition comprising a CpG oligonucleotide comprising a strand comprising at least one copy of the CpG region motif m5C—(*R)-m5C—(*R)-G-(*R)—$N_1$, where all the nucleosides are 2'-MOE.

71. A chirally controlled oligonucleotide composition comprising a CpG oligonucleotide comprising a strand comprising at least one copy of the CpG region motif m5C—(*R)-m5C—(*R)-G-(*R)-Py, where all the nucleosides are 2'-MOE.

72. A chirally controlled oligonucleotide composition comprising a CpG oligonucleotide comprising a strand comprising at least one copy of the CpG region motif $N_1$-(*R)-m5C—(*R)-G-(*R)—$N_2$, wherein $N_1$ is methylated or not methylated, and all the nucleosides are 2'-MOE.

73. A chirally controlled oligonucleotide composition comprising a CpG oligonucleotide comprising a strand comprising at least one copy of the CpG region motif $N_1$-(*R)-m5C—(*R)-G-(*R)-Py, wherein $N_1$ is methylated or not methylated, and all the nucleosides are 2'-MOE.

74. A chirally controlled oligonucleotide composition comprising a CpG oligonucleotide comprising a strand comprising at least one copy of the CpG region motif $N_1$-(*R/S)-m5C—(*R/S)-G-(*R/S)—$N_2$, wherein at least 2 of the (*R/S) are (*R), all the nucleosides are 2'-MOE, and $N_1$ and $N_2$ are methylated or not methylated.

75. A chirally controlled oligonucleotide composition comprising a CpG oligonucleotide comprising a strand comprising at least one copy of the CpG region motif $N_1$-(*R/S)-m5C—(*R/S)-G-(*R/S)—$N_2$, wherein at least 2 of the (*R/S) are (*R), all the nucleosides are 2'-MOE; and $N_1$ and $N_2$ are methylated or not methylated.

76. A chirally controlled oligonucleotide composition comprising a CpG oligonucleotide comprising a strand comprising at least one copy of the CpG region motif $N_1$-(*S)—[C]-(*R)-[G]-(*S)—$N_2$, where $N_1$ is 2'H, 2'-MOE or 2'-OMe; [C] is C, m5C, 2'-MOE C, or 2'-MOE m5C; [G] is G, 2'-Ome G, or 2'-MOE G; and $N_2$ is 2'H, 2'-MOE or 2'-OMe.

77. A chirally controlled oligonucleotide composition comprising a CpG oligonucleotide comprising a strand comprising at least one copy of the CpG region motif $N_1$-(*S)—[C]-(*R)-[G]-(*S)—$N_2$, where $N_1$ is 2'H; [C] is C, m5C, 2'-MOE C, or 2'-MOE m5C; [G] is G, 2'-Ome G, or 2'-MOE G; and $N_2$ is 2'H.

78. A chirally controlled oligonucleotide composition comprising a CpG oligonucleotide comprising a strand comprising at least one copy of the CpG region motif $N_1$-(*R)—[C]-(*R)-[G]-(*R)-Py, where $N_1$ and Py are 2'H, 2'-MOE or 2'OMe; and [C] is C or
2'-MOE C; and [G] is G or 2'-MOE G; and Py is 2'-H or 2'-MOE.

79. A chirally controlled oligonucleotide composition comprising a CpG oligonucleotide comprising a strand comprising at least one copy of the CpG region motif $N_1$-(*R)—[C]-(*R)-[G]-(*R)—$N_2$, where $N_1$ and $N_2$ are 2'H, 2'-MOE or 2'OMe; and [C] is 2'-MOE m5C; $N_2$ is 2'-H or 2'-MOE.

80. A chirally controlled oligonucleotide composition comprising a CpG oligonucleotide comprising a strand comprising at least one copy of the CpG region motif Py-(*R)—C—(*R)-G-(*R)-Py.

81. A chirally controlled oligonucleotide composition comprising a CpG oligonucleotide comprising a strand comprising at least one copy of the CpG region motif Py-(*R)—C—(*R)-G-(*R)-Py.

82. A chirally controlled oligonucleotide composition comprising a CpG oligonucleotide comprising a strand comprising at least one copy of the CpG region motif Py-(*S)—C—(*R)-G-(*S)-Py.

83. A chirally controlled oligonucleotide composition comprising a CpG oligonucleotide comprising a strand comprising at least one copy of the CpG region motif Py-(*S)—C—(*S)-G-(*S)-Py.

84. A chirally controlled oligonucleotide composition comprising a CpG oligonucleotide comprising a strand comprising at least one copy of the CpG region motif Py-(*R)—[C]-(*R)-[G]-(*R)-Py, where [C] is 2'-MOE C; and [G] is 2'-MOE G.

85. A chirally controlled oligonucleotide composition comprising a CpG oligonucleotide comprising a strand comprising at least one copy of the CpG region motif Py-(*R)—[C]-(*R)-[G]-(*S)-Py, where [C] is 2'-MOE C; and [G] is 2'-MOE G.

86. A chirally controlled oligonucleotide composition comprising a CpG oligonucleotide comprising a strand comprising at least one copy of the CpG region motif Py-(*R)—[C]-(*R)-G-(*R)-Py, where [C] is C, 2'-OMe m5C, or 2'-MOE C.

87. A chirally controlled oligonucleotide composition comprising a CpG oligonucleotide comprising a strand comprising at least one copy of the CpG region motif Py-(*R)—[C]-(*R)-[G]-(*R)—$N_1$, where [C] is 2'-OMe m5C, and [G] is 2'-OMe G, and $N_1$ is 2'-OMe.

88. A chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe m5C, and [G] is 2'-OMe G.

89. A chirally controlled oligonucleotide composition comprising a CpG oligonucleotide comprising a strand comprising at least one copy of the CpG region motif Py-(*R)—[C]-(*R)-[G]-(*R)-Py, where [C] is 2'-OMe C and [G] is 2'-OMe G.

90. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE C and [G] is 2'-MOE G.

91. A chirally controlled oligonucleotide composition comprising a CpG oligonucleotide comprising a strand comprising at least one copy of the CpG region motif Py-(*R)-m5C—(*R)-G-(*R)-Py.

92. A chirally controlled oligonucleotide composition comprising a CpG oligonucleotide comprising a strand comprising at least one copy of the CpG region motif Py-(*R)-m5C—(*R)-G-(*R)-Py.

93. A chirally controlled oligonucleotide composition comprising a CpG oligonucleotide comprising a strand comprising at least one copy of the CpG region motif Py-(*S)-m5C—(*R)-G-(*S)-Py.

94. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-MOE m5C and [G] is 2'-MOE G.

95. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe m5C and [G] is 2'-OMe G.

96. A chirally controlled oligonucleotide composition comprising a CpG oligonucleotide comprising a strand comprising at least one copy of the CpG region motif Py-(*S)—[C]-(*R)-[G]-(*S)-Py, where [C] is 2'-OMe C and [G] is 2'-OMe G.

97. A chirally controlled oligonucleotide composition comprising a CpG oligonucleotide comprising a strand comprising at least one copy of the CpG region motif Py-(*R)—[C]-(*R)-[G]-(*R)-Py, where both [C] and [G] are 2'-modified.

98. A chirally controlled oligonucleotide composition comprising a CpG oligonucleotide comprising a strand comprising at least one copy of the CpG region motif $N_1$-(*R)—[C]-(*R)-[G]-(*R)—$N_2$, where both [C] and [G] are 2'-modified.

98a. The composition of any one of the preceding embodiments, wherein more than above
50%, 55%, 60%, 65%, 70%, 75%, 80%, 85%, 90%, or 95% of chiral internucleotidic linkages of the oligonucleotides are Sp.

98b. The composition of any one of embodiments 1-98a, wherein more than above 50%, 55%,
60%, 65%, 70%, 75%, 80%, 85%, 90%, or 95% of chiral internucleotidic linkages of the oligonucleotides are Rp.

98c. The composition of any one of the preceding embodiments, wherein oligonucleotides of the composition comprise a CpG of —C-Rp-G-.

98d. The composition of any one of the preceding embodiments, wherein oligonucleotides of the composition comprise a CpG of Sp-C-Rp-G-Sp.

98e. The composition of any one of the preceding embodiments, wherein oligonucleotides of the composition comprise a CpG of Rp-CpG-Rp.

98f. The composition of any one of the preceding embodiments, wherein oligonucleotides of the composition comprise a CpG of Rp-C-Rp-G-Rp.

98g. The composition of any one of the preceding embodiments, wherein oligonucleotides of the composition comprise a CpG of -CpG-Sp.

98h. The composition of any one of the preceding embodiments, wherein oligonucleotides of the composition comprise a CpG of Rp-CpG-.

98i. The composition of any one of the preceding embodiments, wherein oligonucleotides of the composition comprise a CpG of Rp-CpG-Sp.

98j. The composition of any one of the preceding embodiments, wherein oligonucleotides of the composition comprise a CpG of Rp-C-Rp-G-Sp.
98k. The composition of any one of the preceding embodiments, wherein oligonucleotides of the composition comprise a CpG of Rp-C-Sp-G-Sp.
98l. The composition of any one of the preceding embodiments, wherein oligonucleotides of the composition comprise a CpG of -CpG-Rp.
98m. The composition of any one of the preceding embodiments, wherein oligonucleotides of the composition comprise a CpG of Rp-CpG-.
98n. The composition of any one of the preceding embodiments, wherein oligonucleotides of the composition comprise a CpG of Rp-CpG-Rp.
98o. The composition of any one of the preceding embodiments, wherein oligonucleotides of the composition comprise a CpG of Rp-C-Rp-G-Rp.
98p. The composition of any one of the preceding embodiments, wherein oligonucleotides of the composition comprise a CpG of Rp-C-Sp-G-Rp.
98q. The composition of any one of the preceding embodiments, wherein oligonucleotides of the composition comprise one or more modified sugars.
98r. The composition of any one of the preceding embodiments, wherein the CpG and/or its two neighboring nucleosides contain one or more modified sugars.
98s. The composition of any one of the preceding embodiments, wherein the CpG contain one or more modified sugars.
98t. The composition of any one of the preceding embodiments, wherein the C of the CpG contains a modified sugar.
98u. The composition of any one of the preceding embodiments, wherein the CpG and/or its two neighboring nucleosides do not all contain a modified sugar.
98v. The composition of any one of the preceding embodiments, wherein the CpG and/or its two neighboring nucleosides do not contain a modified sugar.
98w. The composition of any one of the preceding embodiments, wherein the CpG does not contain a modified sugar.
98x. The composition of any one of the preceding embodiments, wherein the C of the CpG does not contain a modified sugar.
98y. The composition of any one of the preceding embodiments, wherein a modified sugar is 2'-modified.
98ya. The composition of any one of the preceding embodiments, wherein the 2'-modification is T-OR wherein R is optionally substituted $C_{1-6}$ aliphatic.
98z. The composition of any one of the preceding embodiments, wherein the 2'-modification is 2'-MOE.
98aa. The composition of any one of the preceding embodiments, wherein oligonucleotides of the composition comprise one or more modified bases.
98ab. The composition of any one of the preceding embodiments, wherein the CpG and/or its two neighboring nucleosides contain one or more modified bases.
98ac. The composition of any one of the preceding embodiments, wherein the CpG contain one or more modified bases.
98ad. The composition of any one of the preceding embodiments, wherein the C of the CpG contains a modified base.
98ae. The composition of any one of the preceding embodiments, wherein the CpG and/or its two neighboring nucleosides do not all contain a modified base.
98af. The composition of any one of the preceding embodiments, wherein the CpG and/or its two neighboring nucleosides do not contain a modified base.
98ag. The composition of any one of the preceding embodiments, wherein the CpG does not contain a modified base.
98ah. The composition of any one of the preceding embodiments, wherein the C does not contain a modified base.
98ai. The composition of any one of the preceding embodiments, wherein the modified base is 5mC.
99. The composition of any one of the preceding embodiments, wherein at least one internucleotidic linkage has the structure of formula I.
99a. The composition of any one of the preceding embodiments, wherein at least one internucleotidic linkage is a phosphorodithioate.
100. The composition of any one of the preceding embodiments, wherein at least one internucleotidic linkage is selected from: phosphorodithioate, phosphoramidate, boranophosphonoate, an amide linker, or a compound of formula (I):

where $R^3$ is selected from OH, SH, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$, and applicable salts thereof; and $R^4$ is selected from O, S, NH, or $CH_2$.

101. The composition of any one of the preceding embodiments, wherein at least one internucleotidic linkage is selected from:

| Symbol | Modified Internucleotide Linkage |
|---|---|
| s | phosphorothioate ( 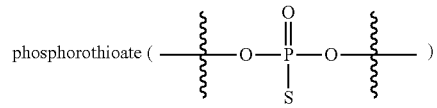 [SMILES: *OP(=O)(S)O*] ) |
| s1 | 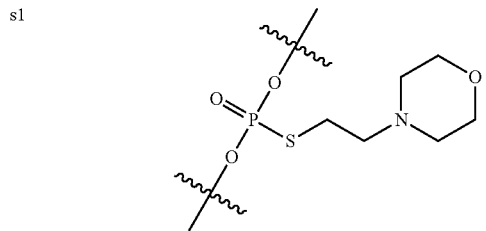 |

549
-continued
| Symbol | Modified Internucleotide Linkage |
|---|---|
| s2 | 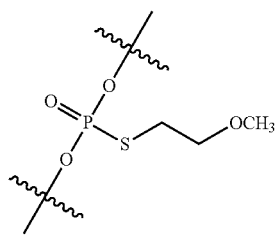 [SMILES: *OP(=O)(O*)SCCOC] |
| s3 | 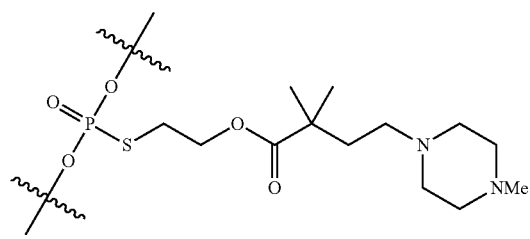 [SMILES: *OP(=O)(O*)SCCOC(=O)C(C)(C)CCN1CCN(C)CC1] |
| s4 | 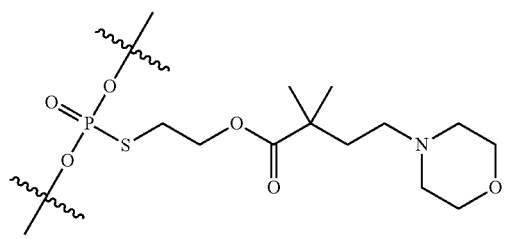 |
| s5 | 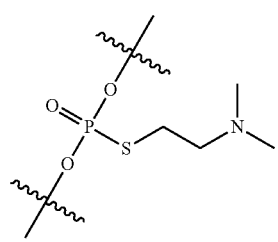 [SMILES: *OP(=O)(O*)SCCN(C)C] |
| s6 | 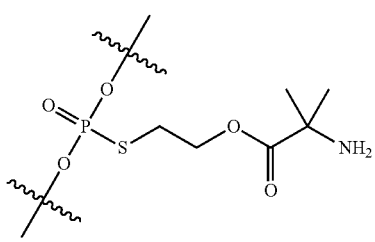 [SMILES: *OP(=O)(O*)SCCOC(=O)C(C)(C)N] |
| s7 | 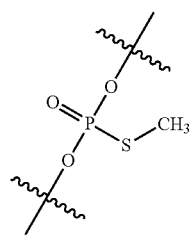 [SMILES: *OP(=O)(O*)SC] |
550
-continued
| Symbol | Modified Internucleotide Linkage |
|---|---|
| s8 | 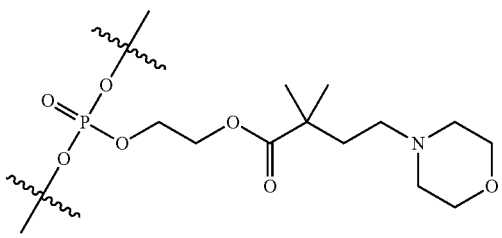 [SMILES: *OP(=O)(O*)OCCOC(=O)C(C)(C)CCN1CCOCC1] |
| s9 | 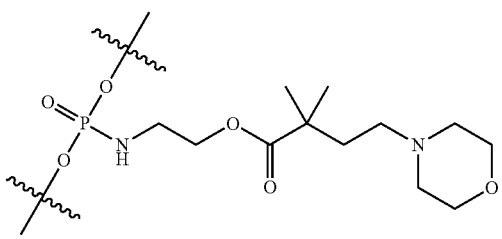 |
| s10 | 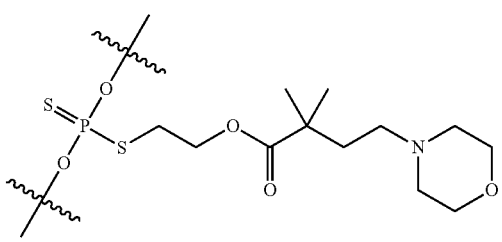 |
| s11 | 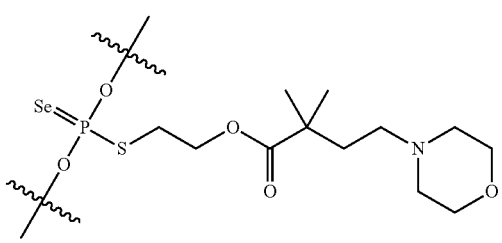 [SMILES: *OP(=S)(O*)SCCOC(=O)C(C)(C)CCN1CCOCC1] |
| s12 | 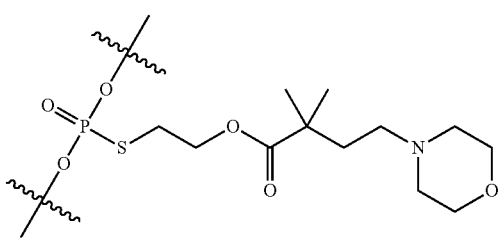 |
| s13 | 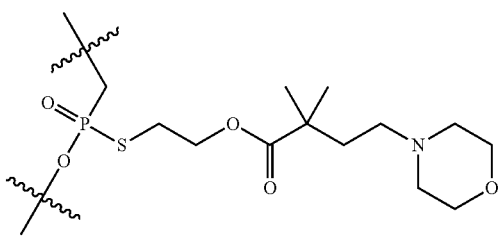 [SMILES: *CP(=O)(O*)SCCOC(=O)C(C)(C)CCN1CCOCC1] |

-continued

| Symbol | Modified Internucleotide Linkage |
|---|---|
| s14 | 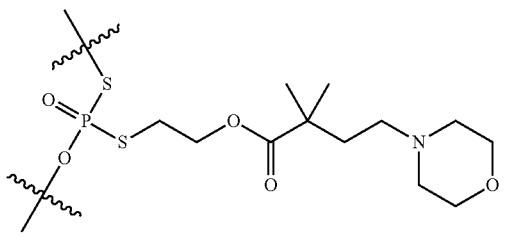 [SMILES: *OP(=O)(S*)SCCOC(=O)C(C)(C)CCN1CCOCC1] |
| s15 | 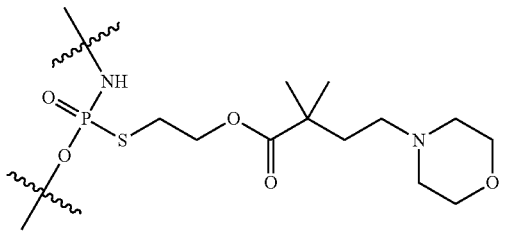 [SMILES: *NP(=O)(O*)SCCOC(=O)C(C)(C)CCN1CCOCC1] |
| s16 | 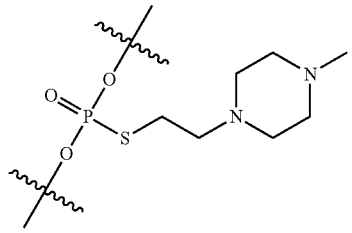 [SMILES: *OP(=O)(O*)SCCN1CCN(C)CC1] |
| s17 | 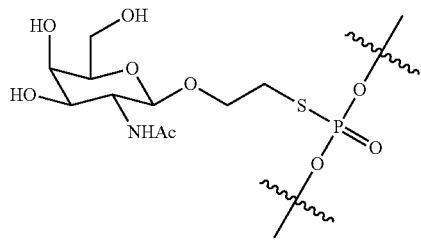 [SMILES: *OP(=O)(O*)SCCOC1OC(CO)C(O)C(O)C1NC(C)=O] |
| s18 | 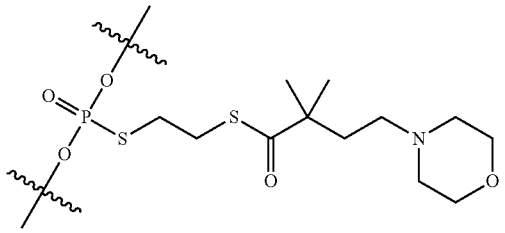 |

102. The composition or method of any one of the preceding embodiments, wherein the oligonucleotide is conjugated to a lipid via a linker.

103. The composition or method of any one of the preceding embodiments, wherein the linker is -$L^{LD}$-.

104. The composition or method of any one of the preceding embodiments, wherein the linker is -L-.

105. The composition or method of any one of the preceding embodiments, wherein the linker is —NH—(CH2)6-.

106. The composition or method of any one of the preceding embodiments, wherein the linker is —C(O)—NH—(CH2)6-P(O)(O—)-.

107. The composition or method of any one of the preceding embodiments, wherein the linker is —C(O)—NH—(CH2)6-P(O)(S—)-.

108. The composition of embodiment 106 or 107, wherein the lipid is a fatty acid which is connected to the linker through formation of the amide group —C(O)—NH—, and the oligonucleotide is connected to the linker through formation of a phosphate or phosphorothioate linkage between its 5'-OH or 3'-OH with —P(O)(O—)- or —P(O)(S—)- of the linker.

109. The composition of embodiment 106 or 107, wherein the lipid is a fatty acid which is connected to the linker through formation of the amide group —C(O)—NH—, and the oligonucleotide is connected to the linker through formation of a phosphate or phosphorothioate linkage between its 5'-OH with —P(O)(O—)- or —P(O)(S—)- of the linker.

110. The composition of embodiment 106 or 107, wherein the lipid is a fatty acid which is connected to the linker through formation of the amide group —C(O)—NH—, and the oligonucleotide is connected to the linker through formation of a phosphate or phosphorothioate linkage between its 3'-OH with —P(O)(O—)- or —P(O)(S—)- of the linker.

111. The composition of any one of the preceding embodiments, further comprising one or more targeting components.

112. A composition comprising a plurality of compounds having the structure of:
$A^c$-[-$L^{LD}$-($R^{LD}$)$_a$]$_b$ or [($A^c$)$_a$-$L^{LD}$]$_b$-$R^{LD}$, or a salt thereof, wherein:
$A^c$ is an oligonucleotide chain ([H]$_b$—Ac is an oligonucleotide);
a is 1-1000;
b is 1-1000;
each $L^{LD}$ is independently a linker moiety; and
each $R^{LD}$ is independently a lipid moiety or a targeting component, wherein at least one $R^{LD}$ is a lipid moiety.

113. A composition comprising a plurality of compounds having the structure of:
$A^c$-[-$L^{LD}$-($R^{LD}$)$_a$]$_b$ or [($A^c$)$_a$-$L^{LD}$]$_b$-$R^{LD}$, or a salt thereof, wherein:
$A^c$ is an oligonucleotide chain ([H]$_b$—Ac is an oligonucleotide);
a is 1-1000;
b is 1-1000;
each $L^{LD}$ is independently a covalent bond or an optionally substituted, $C_1$-$C_{80}$ saturated or partially unsaturated aliphatic group, wherein one or more methylene units are optionally and independently replaced by $T^{LD}$ or an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;

each $R^{LD}$ is independently an optionally substituted, $C_1$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;

$T^{LD}$ has the structure of:

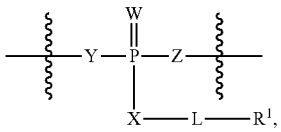

W is O, S or Se;

each of X, Y and Z is independently —O—, —S—, —N(-L-R$^1$)—, or L;

L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—;

R$^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O— each R' is independently —R, —C(O)R, —CO$_2$R, or —SO$_2$R, or:

two R' are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, and heterocyclylene; and each R is independently hydrogen, or an optionally substituted group selected from $C_1$-$C_6$ aliphatic, carbocyclyl, aryl, heteroaryl, and heterocyclyl.

114. The composition of any one of embodiments 112-113, wherein $A^c$ is an oligonucleotide chain of any oligonucleotide of any of the Tables ([H]$_b$—Ac is an oligonucleotide of any of the Tables).

115. The composition or method of any one of embodiments 1-111, wherein the composition is a composition of any one of embodiments 112-114.

116. The composition or method of any one of embodiments 112-115, wherein the oligonucleotides or oligonucleotides have the structure of $A^c$-[-L$^{LD}$-(R$^{LD}$)$_a$]$_b$.

117. The composition or method of any one of embodiments 112-115, wherein the oligonucleotides or oligonucleotides have the structure of [(A$^c$)$_a$-L$^{LD}$]b-R$^{LD}$.

118. The composition or method of any one of embodiments 112-117, wherein L$^{LD}$, R$^{LD}$, combinations of L$^{LD}$ and R$^{LD}$, or -[-L$^{LD}$-(R$^{LD}$)$_a$]$_b$ comprises one or more lipid moieties.

119. The composition or method of any one of embodiments 112-117, wherein -[-L$^{LD}$-(R$^{LD}$)$_a$]$_b$ comprises one or more lipid moieties.

120. The composition or method of any one of embodiments 112-118, wherein R$^{LD}$ comprises one or more lipid moieties.

121. The composition or method of any one of embodiments 112-117, wherein L$^{LD}$, R$^{LD}$, combinations of L$^{LD}$ and R$^{LD}$, or -[-L$^{LD}$-(R$^{LD}$)$_a$]$_b$ comprises one or more targeting components.

122. The composition or method of any one of embodiments 112-117, wherein -[-L$^{LU}$-(R$^{LU}$)$_a$]$_b$ comprises one or more targeting components.

123. The composition or method of any one of embodiments 112-118, wherein R$^{LD}$ comprises one or more targeting components.

124. The composition or method of any one of embodiments 112-123, wherein b is 1. 125. The composition or method of any one of embodiments 112-124, wherein a is 1. 126. The composition or method of any one of embodiments 112-125, wherein $A^c$ comprises one or more modified base, sugar, or internucleotidic linkage moieties.

127. The composition or method of any one of embodiments 112-126, wherein $A^c$ comprises one or more chiral internucleotidic linkages.

128. The composition or method of any one of embodiments 112-127, wherein $A^c$ comprises one or more chiral internucleotidic linkages, and each chiral internucleotidic linkage of $A^c$ is chirally controlled.

129. The composition or method of any one of embodiments 112-128, wherein oligonucleotides having the structure of $A^c$-[-L$^{LD}$-(R$^{LD}$)$_a$]b, or [(A$^c$)$_a$-L$^{LD}$]b-R$^{LD}$, are of a particular type defined by the 1) base sequence; 2) pattern of backbone linkages; 3) pattern of backbone chiral centers; and 4) pattern of backbone phosphorus modifications of $A^c$.

130. The composition or method of any one of embodiments 112-125, wherein $A^c$ is the oligonucleotide chain of any one of the preceding embodiments.

131. The composition or method of any one of embodiments 112-130, wherein $A^c$ is an oligonucleotide of any one of the preceding embodiments, connecting to L$^{LD}$ through a hydroxyl group of a sugar moiety (—O—).

132. The composition or method of any one of embodiments 112-131, wherein $A^c$ is an oligonucleotide of any one of the preceding embodiments, connecting to L$^{LD}$ through its 5'-O—.

133. The composition or method of any one of embodiments 112-130, wherein $A^c$ is an oligonucleotide of any one of the preceding embodiments, connecting to L$^{LD}$ through a nucleobase.

134. The composition or method of any one of embodiments 112-130, wherein $A^c$ is an oligonucleotide of any one of the preceding embodiments, connecting to L$^{LD}$ through an internucleotidic linkage.

135. The composition or method of any one of embodiments 112-132, wherein $A^c$ is an oligonucleotide selected from any of the Tables and connected to L$^{LD}$ and R$^{LD}$ ([H]$_b$—Ac is an oligonucleotide selected from any of the Tables).

136. The composition or method of any one of embodiments 112-132, wherein $A^c$ is WV-887 connected to L$^{LD}$ and R$^{LD}$ ([H]$_b$—Ac is WV-887).

137. The composition or method of any one of embodiments 112-132, wherein $A^c$ is WV-892 connected to L$^{LD}$ and R$^{LD}$.

138. The composition or method of any one of embodiments 112-132, wherein $A^c$ is WV-896 connected to L$^{LD}$ and R$^{LD}$.

139. The composition or method of any one of embodiments 112-132, wherein $A^c$ is WV-1714 connected to L$^{LD}$ and R$^{LD}$.

140. The composition or method of any one of embodiments 112-132, wherein $A^c$ is WV-2444 connected to L$^{LD}$ and R$^{LD}$.

141. The composition or method of any one of embodiments 112-132, wherein $A^c$ is WV-2445 connected to L$^{LD}$ and R$^{LD}$.

142. The composition or method of any one of embodiments 112-132, wherein $A^c$ is WV-2526 connected to L$^{LD}$ and R$^{LD}$.

143. The composition or method of any one of embodiments 112-132, wherein $A^c$ is WV-2527 connected to $L^{LD}$ and $R^{LD}$.
144. The composition or method of any one of embodiments 112-132, wherein $A^c$ is WV-2528 connected to $L^{LD}$ and $R^{LD}$.
145. The composition or method of any one of embodiments 112-132, wherein $A^c$ is WV-2530 connected to $L^{LD}$ and $R^{LD}$.
146. The composition or method of any one of embodiments 112-132, wherein $A^c$ is WV-2531 connected to $L^{LD}$ and $R^{LD}$.
147. The composition or method of any one of embodiments 112-132, wherein $A^c$ is WV-2578 connected to $L^{LD}$ and $R^{LD}$.
148. The composition or method of any one of embodiments 112-132, wherein $A^c$ is WV-2580 connected to $L^{LD}$ and $R^{LD}$.
149. The composition or method of any one of embodiments 112-132, wherein $A^c$ is WV-2587 connected to $L^{LD}$ and $R^{LD}$.
150. The composition or method of any one of embodiments 112-132, wherein $A^c$ is WV-3047 connected to $L^{LD}$ and $R^{LD}$.
151. The composition or method of any one of embodiments 112-132, wherein $A^c$ is WV-3152 connected to $L^{LD}$ and $R^{LD}$.
152. The composition or method of any one of embodiments 112-132, wherein $A^c$ is WV-3472 connected to $L^{LD}$ and $R^{LD}$.
153. The composition or method of any one of embodiments 112-132, wherein $A^c$ is WV-3473 connected to $L^{LD}$ and $R^{LD}$.
154. The composition or method of any one of embodiments 112-132, wherein $A^c$ is WV-3507 connected to $L^{LD}$ and $R^{LD}$.
155. The composition or method of any one of embodiments 112-132, wherein $A^c$ is WV-3508 connected to $L^{LD}$ and $R^{LD}$.
156. The composition or method of any one of embodiments 112-132, wherein $A^c$ is WV-3509 connected to $L^{LD}$ and $R^{LD}$.
157. The composition or method of any one of embodiments 112-132, wherein $A^c$ is WV-3510 connected to $L^{LD}$ and $R^{LD}$.
158. The composition or method of any one of embodiments 112-132, wherein $A^c$ is WV-3511 connected to $L^{LD}$ and $R^{LD}$.
159. The composition or method of any one of embodiments 112-132, wherein $A^c$ is WV-3512 connected to $L^{LD}$ and $R^{LD}$.
160. The composition or method of any one of embodiments 112-132, wherein $A^c$ is WV-3513 connected to $L^{LD}$ and $R^{LD}$.
161. The composition or method of any one of embodiments 112-132, wherein $A^c$ is WV-3514 connected to $L^{LD}$ and $R^{LD}$.
162. The composition or method of any one of embodiments 112-132, wherein $A^c$ is WV-3515 connected to $L^{LD}$ and $R^{LD}$.
163. The composition or method of any one of embodiments 112-162, wherein $L^{LD}$ is an optionally substituted, $C_1$-$C_{10}$ saturated or partially unsaturated aliphatic group, wherein one or more methylene units are optionally and independently replaced by $T^{LD}$ or an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—.
164. The composition or method of any one of embodiments 112-162, wherein $L^{LD}$ is an optionally substituted, $C_1$-$C_{10}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, -Cy-, —O—, —S—, —N(R')—, —C(O)—, —C(O)N(R')—, —N(R')C(O)N(R')—, —OC(O)N(R')—, —S(O)—, —S(O)$_2$—, —S(O)$_2$N(R')—, and —C(O)O—, or $T^{LD}$ wherein W is O or S, each of Y and Z is independently —O—, S, or L.
165. The composition or method of any one of embodiments 112-162, wherein $L^{LD}$ is an optionally substituted, $C_1$-$C_{10}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, -Cy-, —O—, —S—, —N(R')—, —C(O)—, —C(O)N(R')—, —N(R')C(O)N(R')—, —OC(O)N(R')—, —S(O)—, —S(O)$_2$—, —S(O)$_2$N(R')—, and —C(O)O—, or $T^{LD}$ wherein W is O or S, each of X and Y is independently —O—, S, or -L-, and Z is a covalent bond.
166. The composition or method of any one of embodiments 112-164, wherein $L^{LD}$ connects to a hydroxyl group of $A^c$.
167. The composition or method of any one of embodiments 112-164, wherein $L^{LD}$ connects to 5'-OH of $A^c$.
168. The composition or method of any one of embodiments 112-164, wherein $L^{LD}$ connects to 3'-OH of $A^c$.
169. The composition or method of any one of the preceding embodiments, wherein each R' is independently —R, —C(O)R, —CO$_2$R, or —SO$_2$R, or:
two R' are taken together with their intervening atoms to form an optionally substituted $C_3$-$C_{14}$ monocyclic, bicyclic or polycyclic aryl, carbocyclic, heterocyclic, or heteroaryl ring having 0-10 heteroatoms.
170. The composition or method of any one of the preceding embodiments, wherein -Cy- is an optionally substituted bivalent ring selected from $C_3$-$C_{14}$ monocyclic, bicyclic or polycyclic carbocyclylene, arylene, heteroarylene, and heterocyclylene having 0-10 heteroatoms.
171. The composition or method of any one of the preceding embodiments, wherein each R is independently hydrogen, or an optionally substituted group selected from $C_1$-$C_6$ aliphatic, and $C_3$-$C_{14}$ monocyclic, bicyclic or polycyclic aryl, carbocyclic, heterocyclic, or heteroaryl ring having 0-10 heteroatoms.
172. The composition or method of any one of embodiments 112-164, wherein $L^{LD}$ is $T^{LD}$.
173. The composition or method of any one of embodiments 112-164, wherein $L^{LD}$ is —NH—(CH$_2$)$_6$-$T^{LD}$-.
174. The composition or method of any one of embodiments 112-164, wherein $L^{LD}$ is —C(O)—NH—(CH$_2$)$_6$-$T^{LD}$-.
175. The composition or method of embodiment 174, wherein —C(O)— is connected to —$R^{LD}$.
176. The composition or method of any one of embodiments 112-175, wherein $T^{LD}$ is connected to 5'-O— or 3'-O— of $A^c$.
177. The composition or method of any one of embodiments 112-176, wherein $T^{LD}$ is connected to 5'-O— of $A^c$.
178. The composition or method of any one of embodiments 112-176, wherein $T^{LD}$ is connected to 3'-O— of $A^c$.
179. The composition or method of any one of embodiments 112-178, wherein $T^{LD}$ forms a phosphorothioate linkage with 5'-O— or 3'-O— of $A^c$.
180. The composition or method of embodiment 179, wherein a phosphorothioate linkage is chirally controlled and is Sp.
181. The composition or method of embodiment 179, wherein a phosphorothioate linkage is chirally controlled and is Rp.
182. The composition or method of any one of embodiments 112-178, wherein $T^{LD}$ forms a phosphate linkage with 5'-O— or 3'-O— of $A^c$.
183. The composition or method of any one of embodiments 112-162, wherein $L^{LD}$ is a covalent bond.
184. The composition or method of any one of the preceding embodiments, $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—.

185. The composition or method of any one of the preceding embodiments, wherein R$^{LD}$ is an optionally substituted, C$_{10}$-C$_{80}$ saturated or partially unsaturated aliphatic group, wherein one or more methylene units are optionally and independently replaced by —C(O)—.

186. The composition or method of any one of the preceding embodiments, wherein R$^{LD}$ is an optionally substituted, C$_{10}$-C$_{60}$ saturated or partially unsaturated aliphatic group, wherein one or more methylene units are optionally and independently replaced by —C(O)—.

187. The composition or method of any one of the preceding embodiments, wherein R$^{LD}$ is an optionally substituted, C$_{10}$-C$_{40}$ saturated or partially unsaturated aliphatic group, wherein one or more methylene units are optionally and independently replaced by —C(O)—.

188. The composition or method of any one of the preceding embodiments, wherein R$^{LD}$ comprises 10, 11, 12, 13, 14, 15, 16, 17, 18, 19, 20, 21, 22, 23, 24, 25, 26, 27, 28, 29, 30 or more carbon atoms.

189. The composition or method of any one of the preceding embodiments, wherein at least one R$^{LD}$ comprises or is a targeting component.

190. The composition or method of any one of the preceding embodiments, wherein at least one R$^{LD}$ is a targeting component.

191. The composition or method of any one of the preceding embodiments, wherein at least one R$^{LD}$ comprises a lipid moiety.

192. The composition or method of any one of the preceding embodiments, wherein at least one R$^{LD}$ is a lipid moiety.

193. The composition or method of any one of the preceding embodiments, wherein R$^{LD}$ is an optionally substituted, C$_{10}$-C$_{80}$ saturated or partially unsaturated aliphatic group.

194. The composition or method of any one of the preceding embodiments, wherein R$^{LD}$ is an optionally substituted, C$_{10}$-C$_{60}$ saturated or partially unsaturated aliphatic group.

195. The composition or method of any one of the preceding embodiments, wherein R$^{LD}$ is an optionally substituted, C$_{10}$-C$_{40}$ saturated or partially unsaturated aliphatic group.

196. The composition or method of any one of the preceding embodiments, wherein R$^{LD}$ is unsubstituted linear or branched C$_{10}$-C$_{80}$ aliphatic group.

197. The composition or method of any one of the preceding embodiments, wherein R$^{LD}$ is unsubstituted linear or branched C$_{10}$-C$_{60}$ aliphatic group.

198. The composition or method of any one of the preceding embodiments, wherein R$^{LD}$ is unsubstituted linear or branched C$_{10}$-C$_{40}$ aliphatic group.

199. The composition or method of any one of embodiments 112-198, wherein R$^{LD}$ is palmityl.

200. The composition or method of any one of the preceding embodiments 112-198, wherein R$^{LD}$ is 201. The composition or method of any one of embodiments 112-198, wherein R$^{LD}$ is lauryl.

202. The composition or method of any one of embodiments 112-198, wherein R$^{LD}$ is myristyl.

203. The composition or method of any one of embodiments 112-198, wherein R$^{LD}$ is stearyl.

204. The composition or method of any one of embodiments 112-198, wherein R$^{LD}$ is

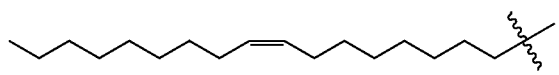

205. The composition or method of any one of embodiments 112-198, wherein R$^{LD}$ is

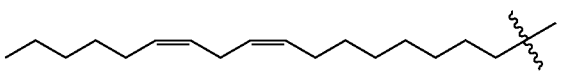

206. The composition or method of any one of embodiments 112-198, wherein R$^{LD}$ is

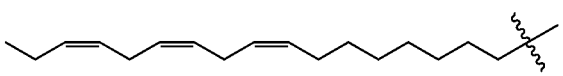

207. The composition or method of any one of embodiments 112-198, wherein R$^{LD}$ is

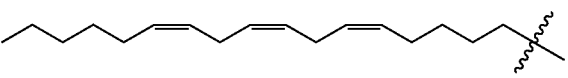

208. The composition or method of any one of embodiments 112-198, wherein R$^{LD}$ is

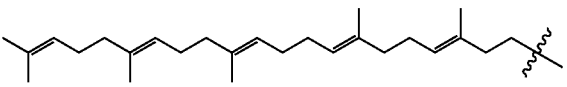

209. The composition or method of any one of embodiments 112-198, wherein R$^{LD}$ is

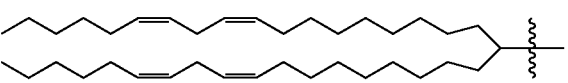

210. The composition or method of any one of embodiments 112-192, wherein R$^{LD}$ is

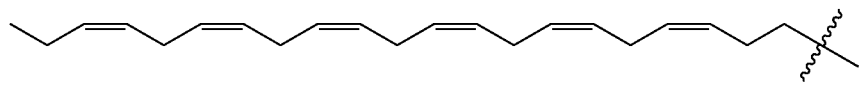

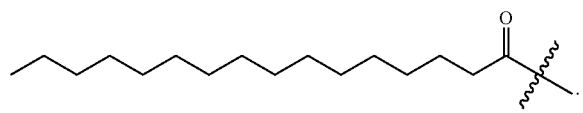 [SMILES: *C(=O)CCCCCCCCCCCCCCC]

211. The composition or method of any one of embodiments 112-192, wherein $R^{LD}$ is

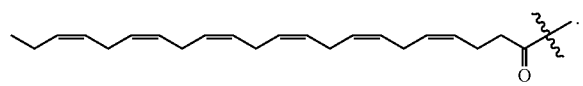

212. The composition or method of any one of embodiments 112-192, wherein $R^{LD}$ is

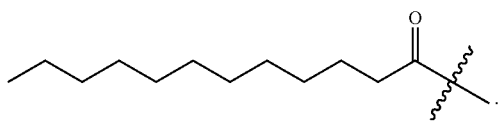 [SMILES: *C(=O)CCCCCCCCCCC]

213. The composition or method of any one of embodiments 112-192, wherein $R^{LD}$ is

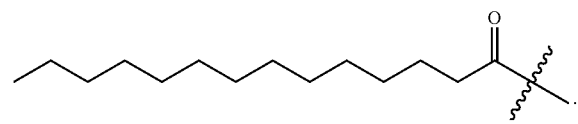 [SMILES: *C(=O)CCCCCCCCCCCCC]

214. The composition or method of any one of embodiments 112-192, wherein $R^{LD}$ is

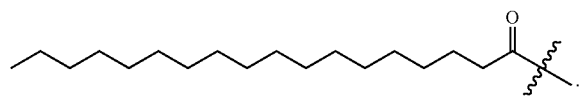 [SMILES: *C(=O)CCCCCCCCCCCCCCCCC]

215. The composition or method of any one of embodiments 112-192, wherein $R^{LD}$ is

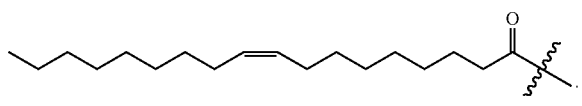 [SMILES: *C(=O)CCCCCCC/C=C\CCCCCCCC]

216. The composition or method of any one of embodiments 112-192, wherein $R^{LD}$ is

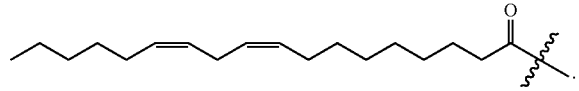 [SMILES: *C(=O)CCCCCCC/C=C\C/C=C\CCCCC]

217. The composition or method of any one of embodiments 112-192, wherein $R^{LD}$ is

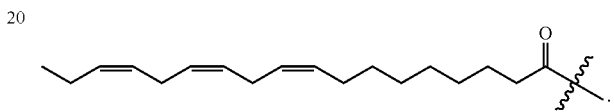

218. The composition or method of any one of embodiments 112-192, wherein $R^{LD}$ is

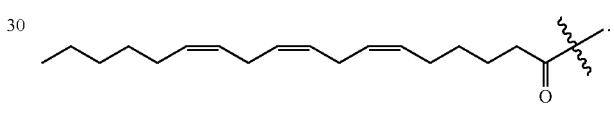

219. The composition or method of any one of embodiments 112-192, wherein $R^{LD}$ is

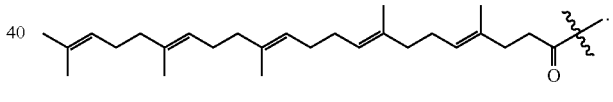

220. The composition or method of any one of embodiments 112-192, wherein $R^{LD}$ is

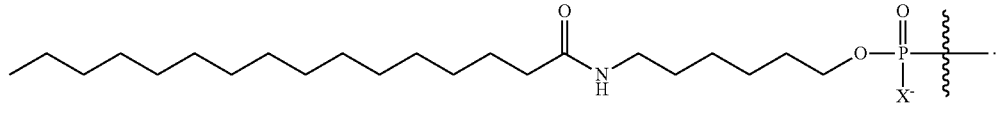

X = O or S

221. The composition or method of any one of embodiments 112-192, wherein $R^{LD}$ is

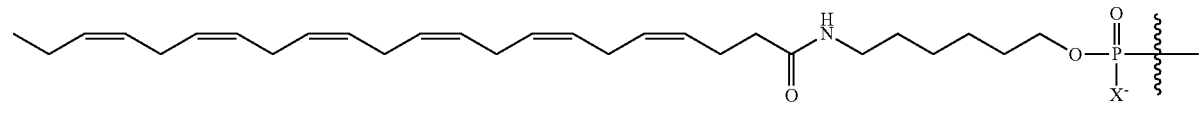

X = O or S

222. The composition or method of any one of embodiments 112-192, wherein $R^{LD}$ is

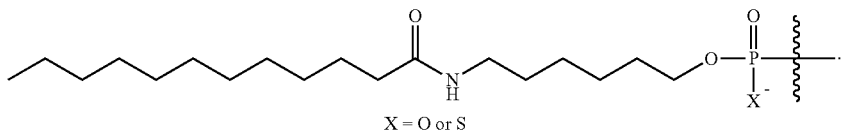

223. The composition or method of any one of embodiments 112-192, wherein $R^{LD}$ is

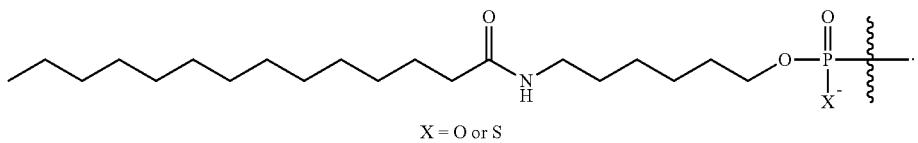

224. The composition or method of any one of embodiments 112-192, wherein $R^{LD}$ is

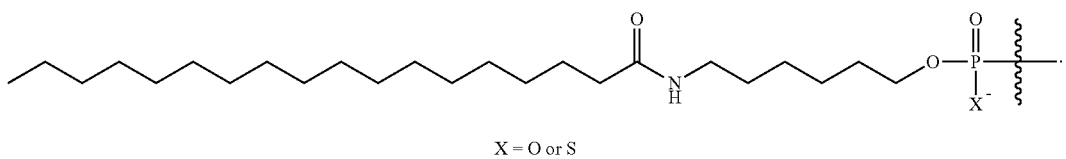

225. The composition or method of any one of embodiments 112-192, wherein $R^{LD}$ is

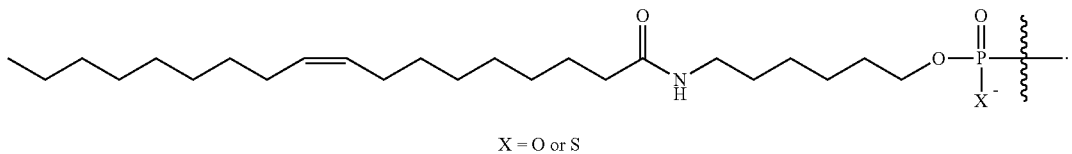

226. The composition or method of any one of embodiments 112-192, wherein $R^{LD}$ is

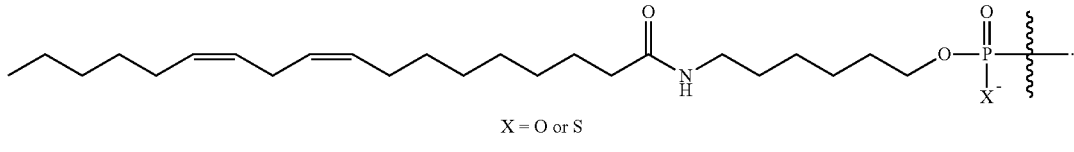

227. The composition or method of any one of embodiments 112-192, wherein $R^{LD}$ is

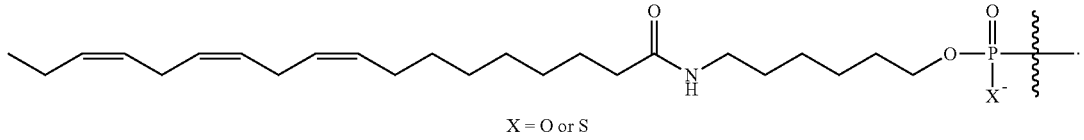

228. The composition or method of any one of embodiments 112-192, wherein $R^{LD}$ is

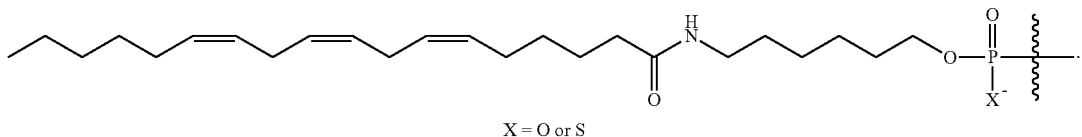

X = O or S

229. The composition or method of any one of embodiments 112-192, wherein $R^{LD}$ is

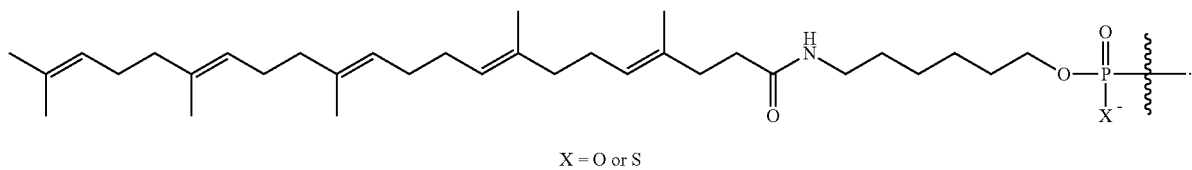

X = O or S

230. The composition or method of any one of embodiments 112-192, wherein $R^{LD}$ is

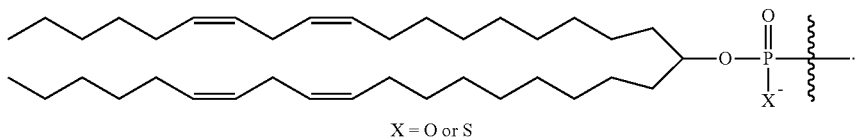

X = O or S

231. The composition or method of any one of embodiments 112-192, wherein $R^{LD}$ is

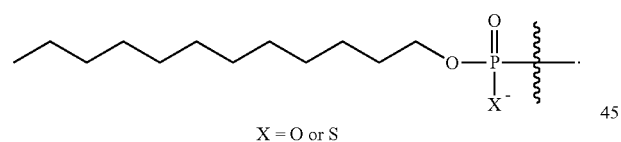

X = O or S

232. The composition or method of any one of embodiments 112-192, wherein $R^{LD}$ is

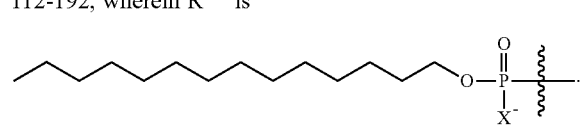

X = O or S

233. The composition or method of any one of embodiments 112-192, wherein $R^{LD}$ is

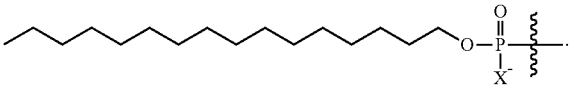

X = O or S

234. The composition or method of any one of embodiments 112-192, wherein $R^{LD}$ is

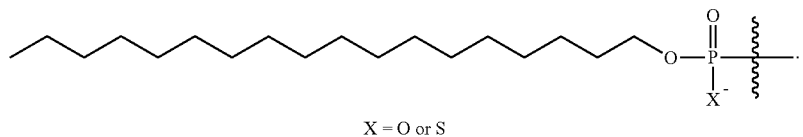

X = O or S

235. The composition or method of any one of embodiments 112-192, wherein -[-L$^{LD}$-(R$^{LD}$)$_a$]$_b$ is

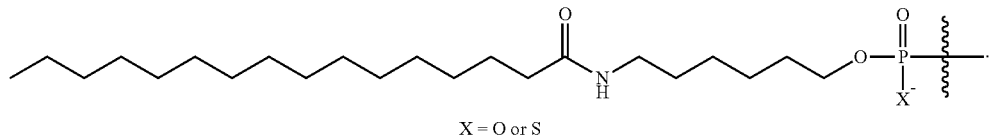

X = O or S

236. The composition or method of any one of embodiments 112-192, wherein -[-L$^{LD}$(R$^{LD}$)$_a$]$_b$ is

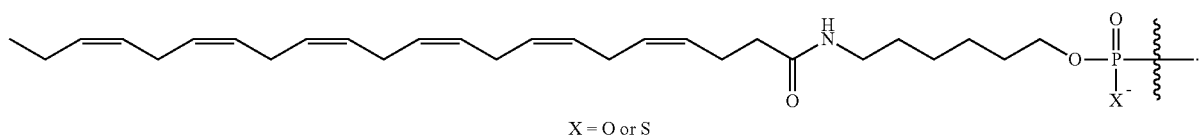

X = O or S

237. The composition or method of any one of embodiments 112-192, wherein -[-L$^{LD}$-(R$^{LD}$)$_a$]$_b$ is

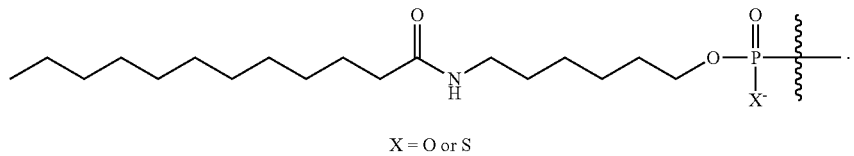

X = O or S

238. The composition or method of any one of embodiments 112-192, wherein -[-L$^{LD}$-(R$^{LD}$)$_a$]$_b$ is

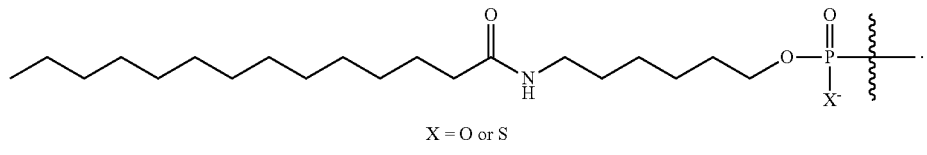

X = O or S

239. The composition or method of any one of embodiments 112-192, wherein -[-L$^{LD}$-(R$^{LD}$)$_a$]$_b$ is

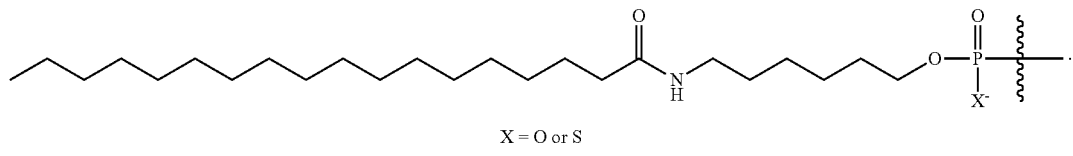

X = O or S

240. The composition or method of any one of embodiments 112-192, wherein -[-L$^{LD}$-(R$^{LD}$)$_a$]$_b$ is

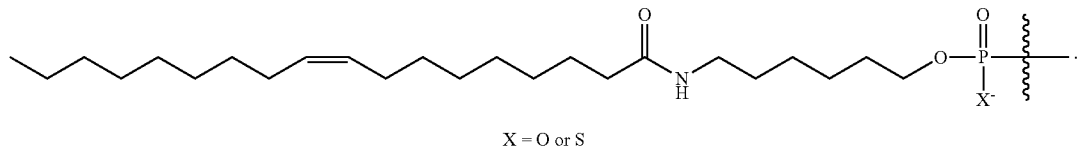

X = O or S

241. The composition or method of any one of embodiments 112-192, wherein -[-L$^{LD}$-(R$^{LD}$)$_a$]$_b$ is

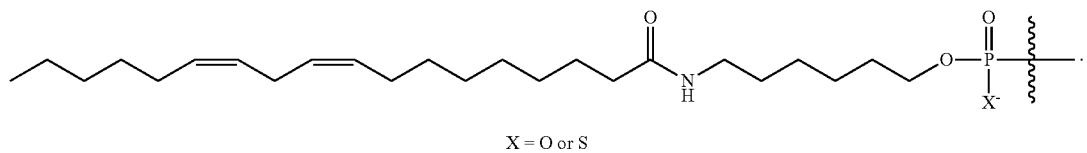

X = O or S

242. The composition or method of any one of embodiments 112-192, wherein -[-L$^{LD}$-(R$^{LD}$)$_a$]$_b$ is

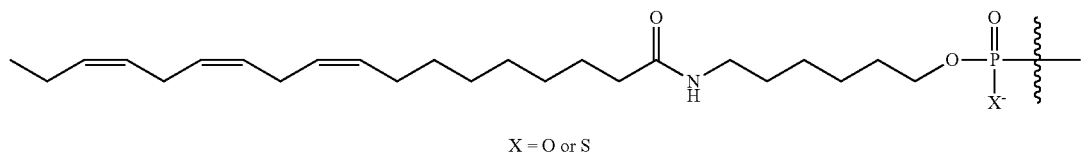

X = O or S

243. The composition or method of any one of embodiments 112-192, wherein -[-L$^{LD}$-(R$^{LD}$)$_a$]$_b$ is

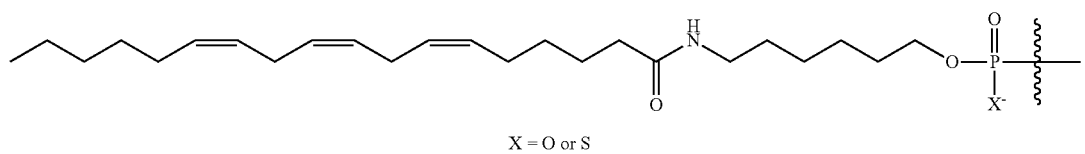

X = O or S

244. The composition or method of any one of embodiments 112-192, wherein -[-L$^{LD}$-(R$^{LD}$)$_a$]$_b$ is

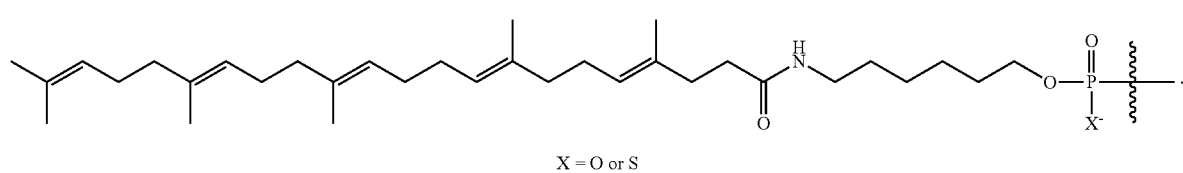

X = O or S

245. The composition or method of any one of embodiments 112-192, wherein -[-L$^{LD}$-(R$^{LD}$)$_a$]$_b$ is

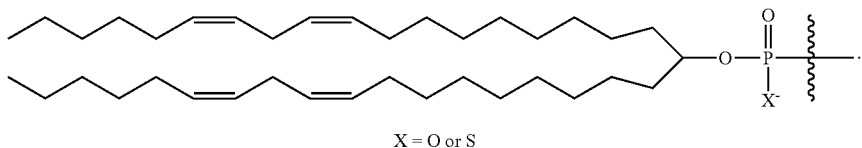

X = O or S

246. The composition or method of any one of embodiments 112-192, wherein -[-L$^{LD}$-(R$^{LD}$)$_a$]$_b$ is

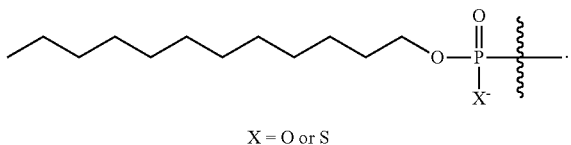

X = O or S

247. The composition or method of any one of embodiments 112-192, wherein -[-L$^{LD}$-(R$^{LD}$)$_a$]$_b$ is

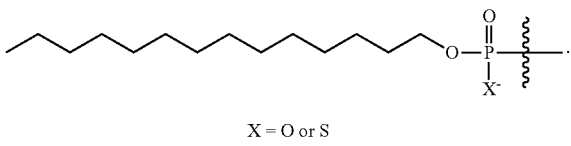

X = O or S

248. The composition or method of any one of embodiments 112-192, wherein -[-L$^{LD}$-(R$^{LD}$)$_a$]$_b$ is

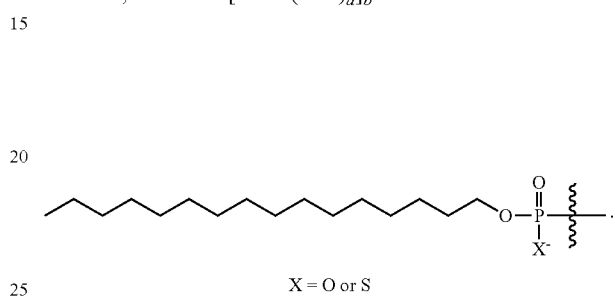

X = O or S

249. The composition or method of any one of embodiments 112-192, wherein -[-L$^{LD}$-(R$^{LD}$)$_a$]$_b$ is

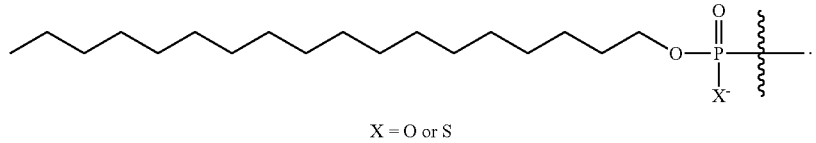

X = O or S

250. The composition of any one of embodiments 112-190, wherein R$^{LD}$ is

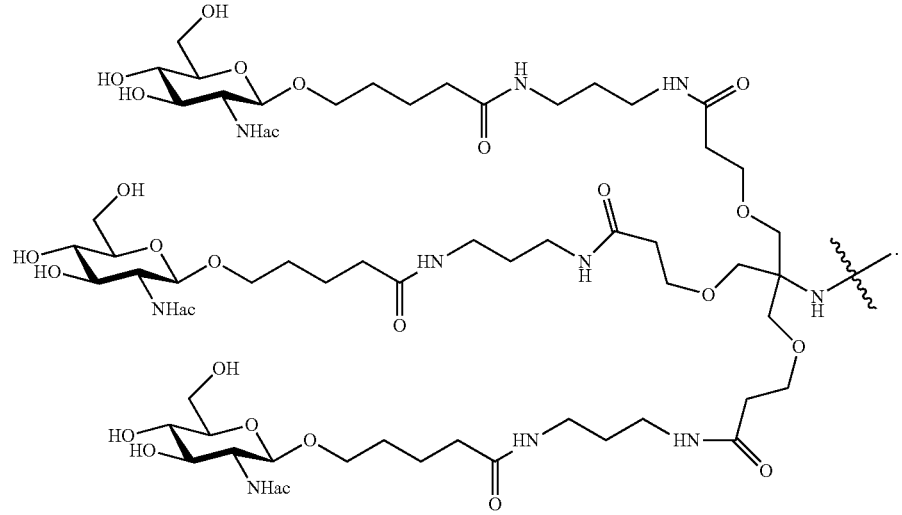

251. The composition of any one of embodiments 112-190, wherein $R^{LD}$ is
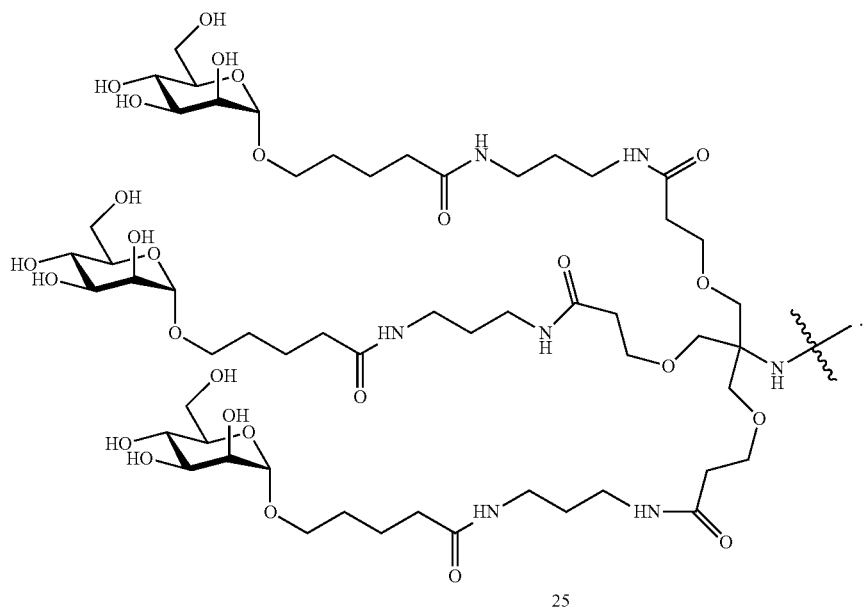
252. The composition of any one of embodiments 112-190, wherein $R^{LD}$ is
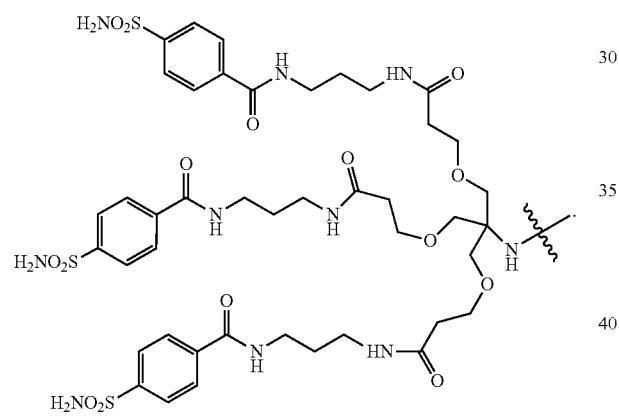
253. The composition of any one of embodiments 112-190, wherein $R^{LD}$ is
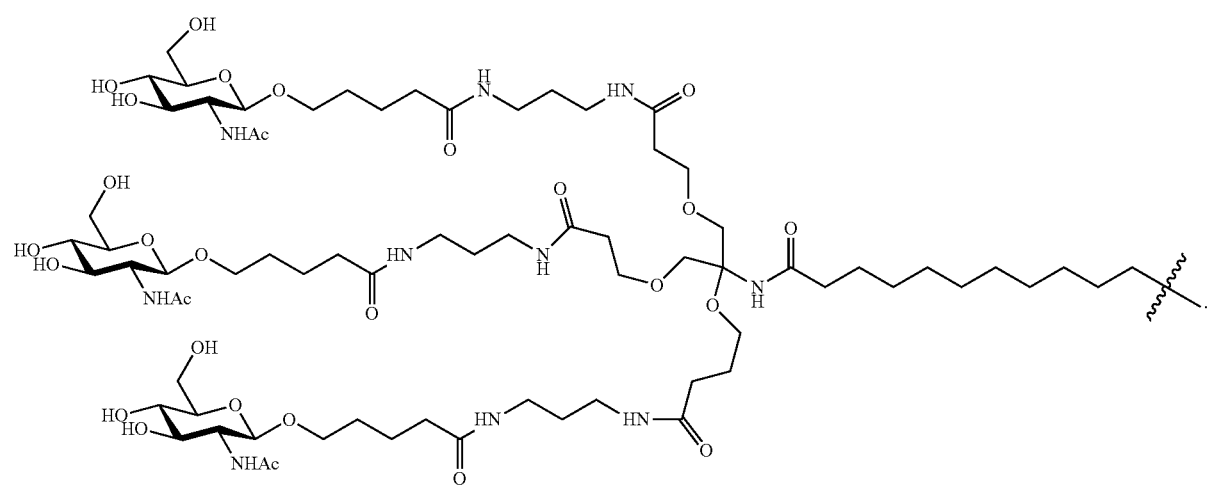

254. The composition of any one of embodiments 112-190, wherein $R^{LD}$ is
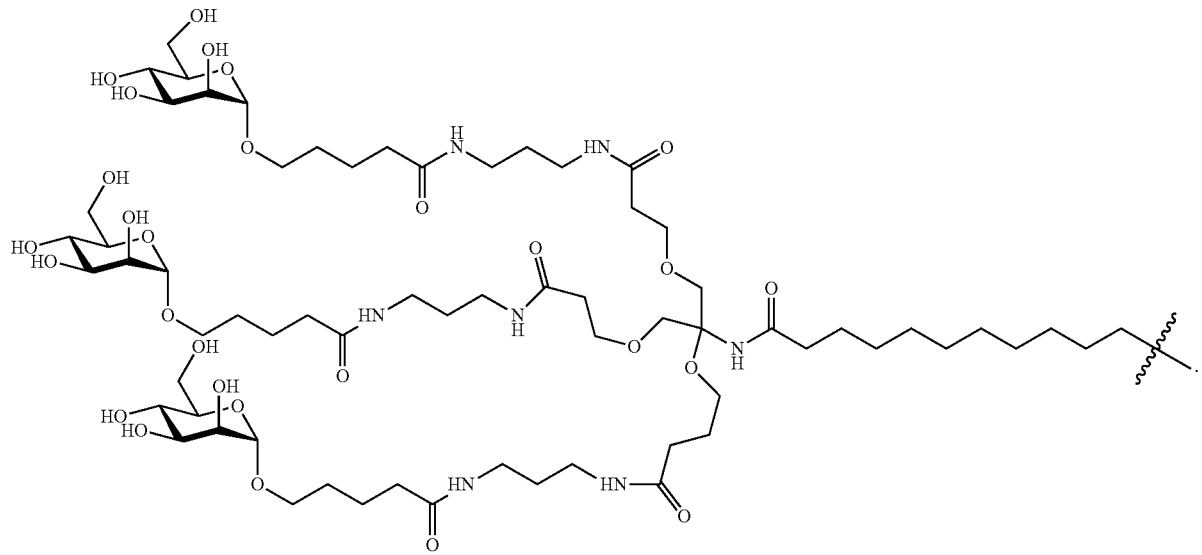
255. The composition of any one of embodiments 112-190, wherein $R^{LD}$ is
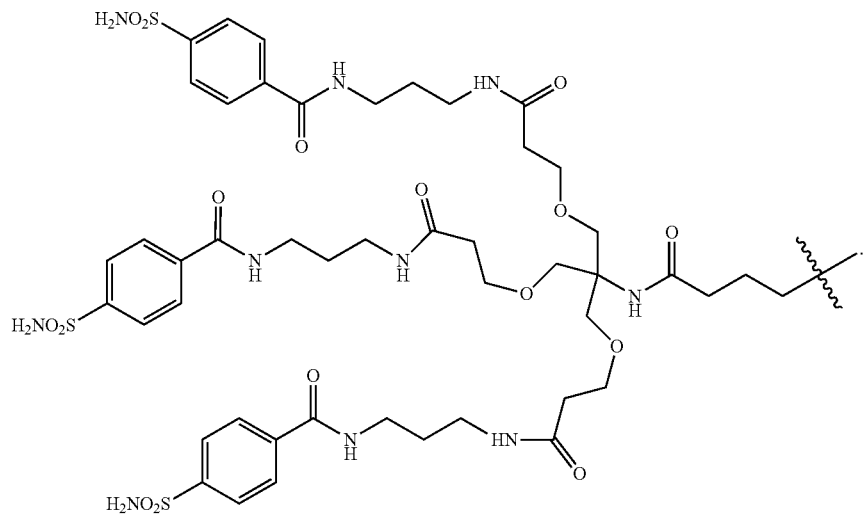 [SMILES: *CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
256. The composition of any one of embodiments 112-184 and 189-190, wherein $R^{LD}$ is
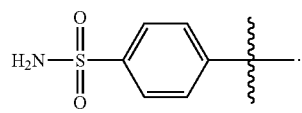
257. The composition of any one of embodiments 112-190, wherein $R^{LD}$ is

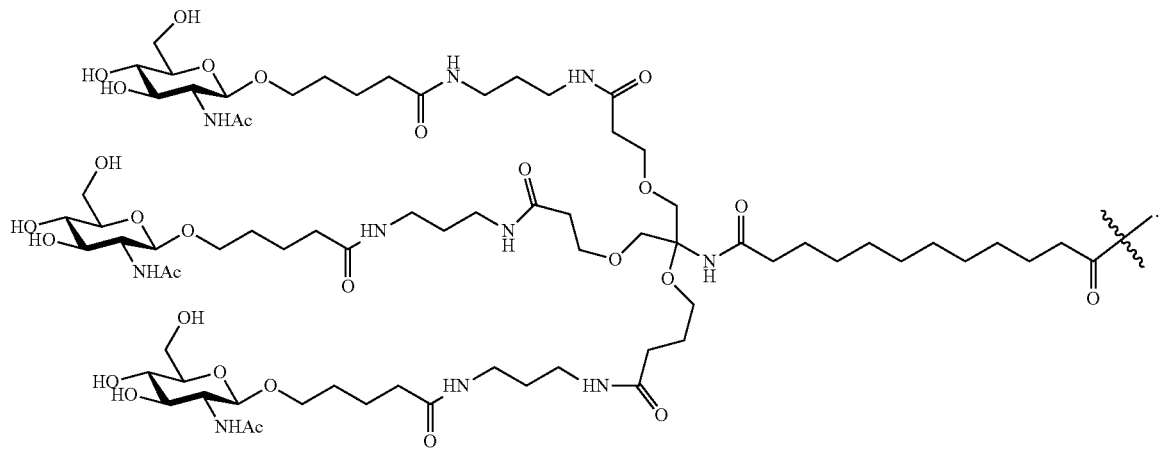
258. The composition of any one of embodiments 112-190, wherein $R^{LD}$ is
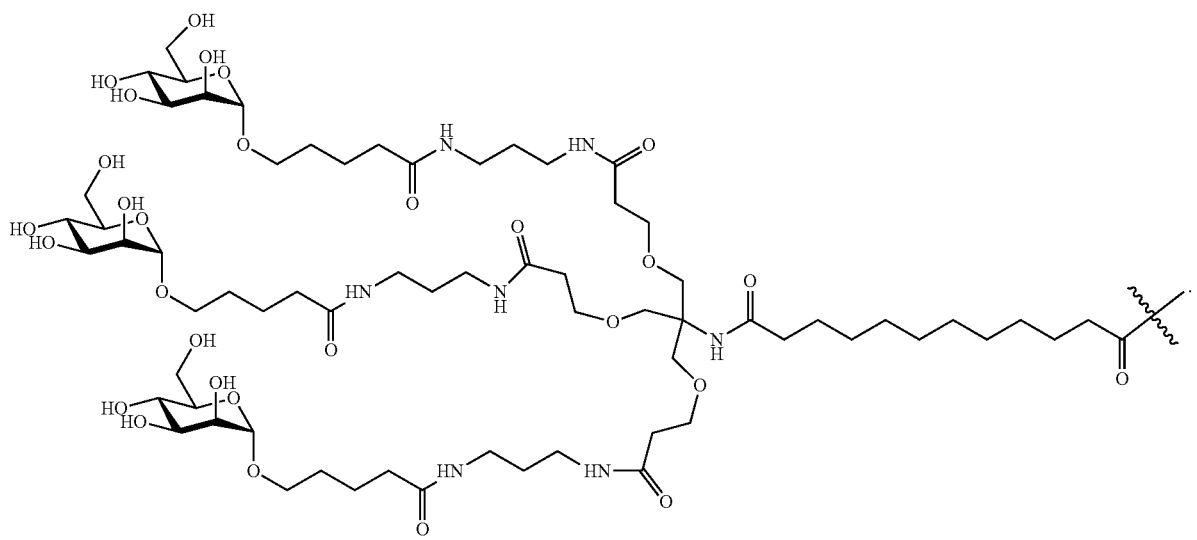
259. The composition of any one of embodiments 112-184 and 189-190, wherein $R^{LD}$ is
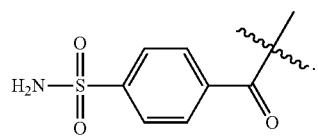 [SMILES: *C(=O)c1ccc(S(N)(=O)=O)cc1]
260. The composition of any one of embodiments 112-190, wherein $R^{LD}$ is

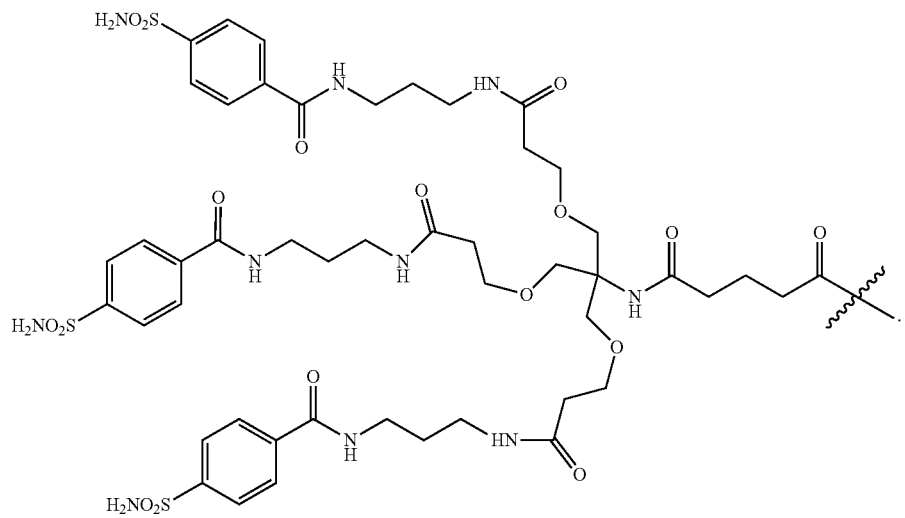 [SMILES: *C(=O)CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
261. The composition of any one of embodiments 112-190, wherein $R^{LD}$ is
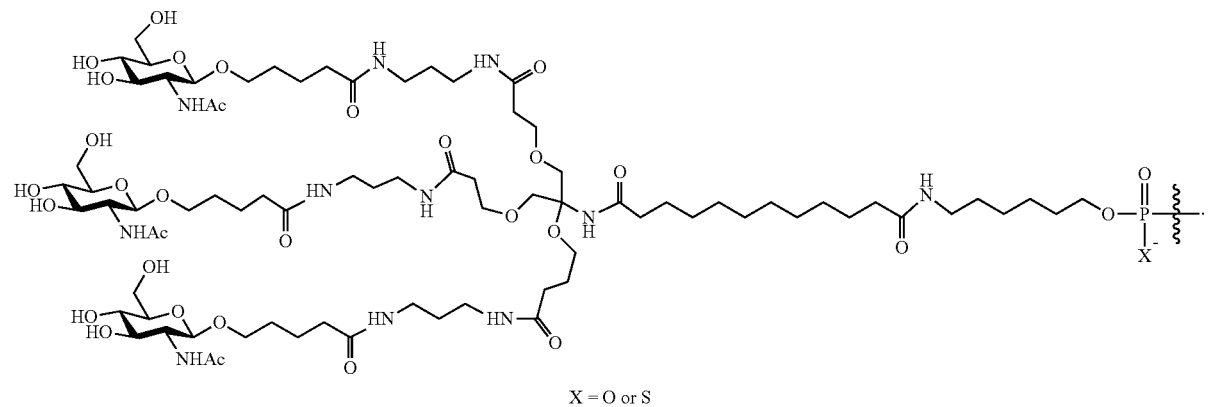
X = O or S
262. The composition of any one of embodiments 112-190, wherein $R^{LD}$ is
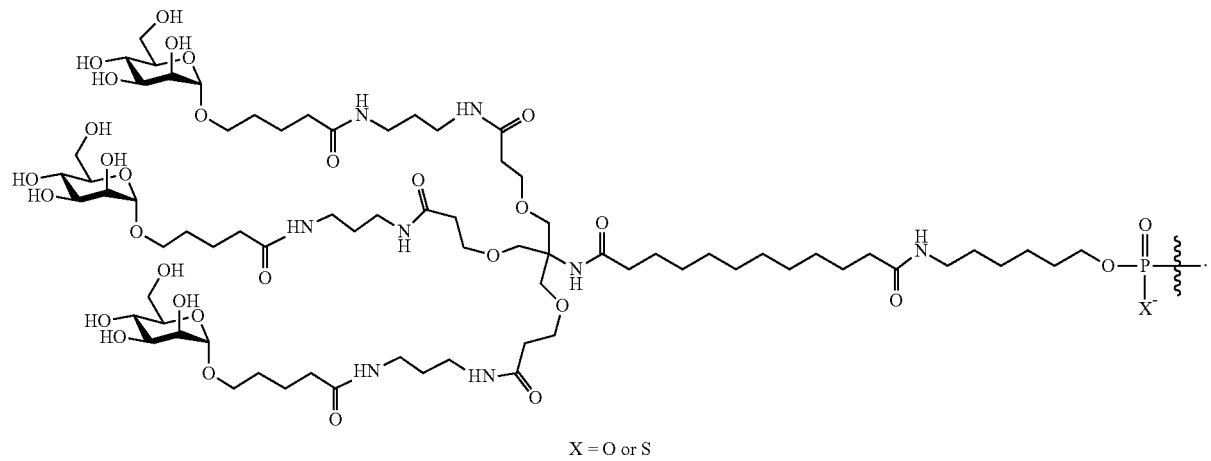
X = O or S 263. The composition of any one of embodiments 112-190, wherein $R^{LD}$ is
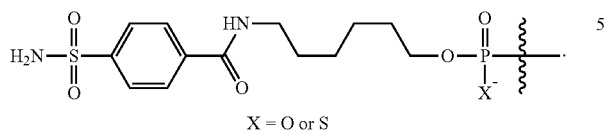
264. The composition of any one of embodiments 112-190, wherein $R^{LD}$ is
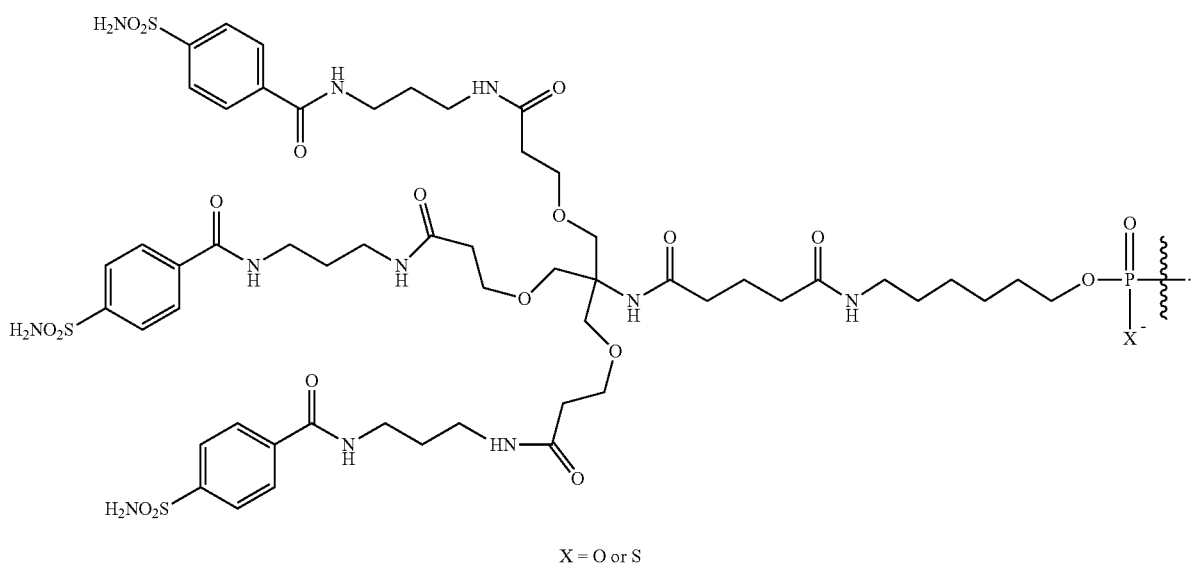
265. The composition of any one of embodiments 112-190, wherein $-[-L^{LD}-(R^{LD})_a]_b$ is
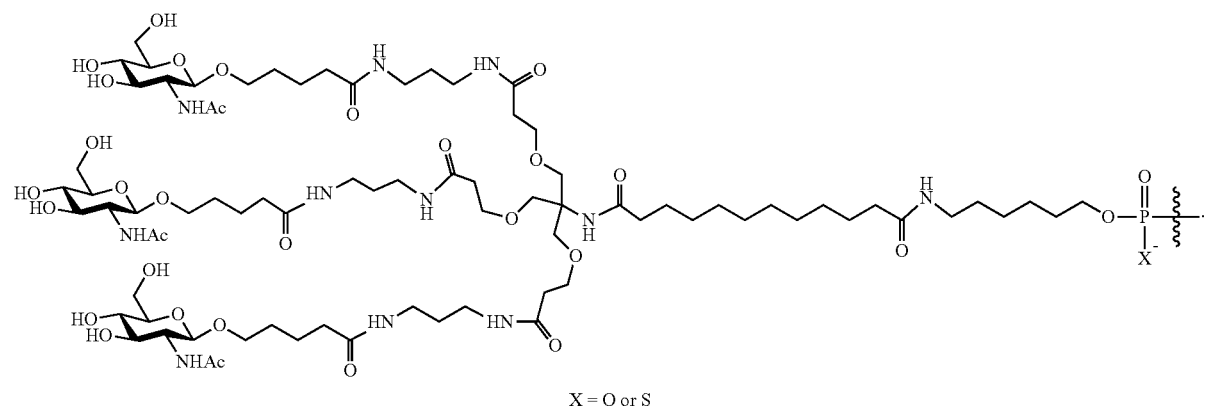
266. The composition of any one of embodiments 112-190, wherein $-[-L^{LD}-(R^{LD})_a]_b$ is

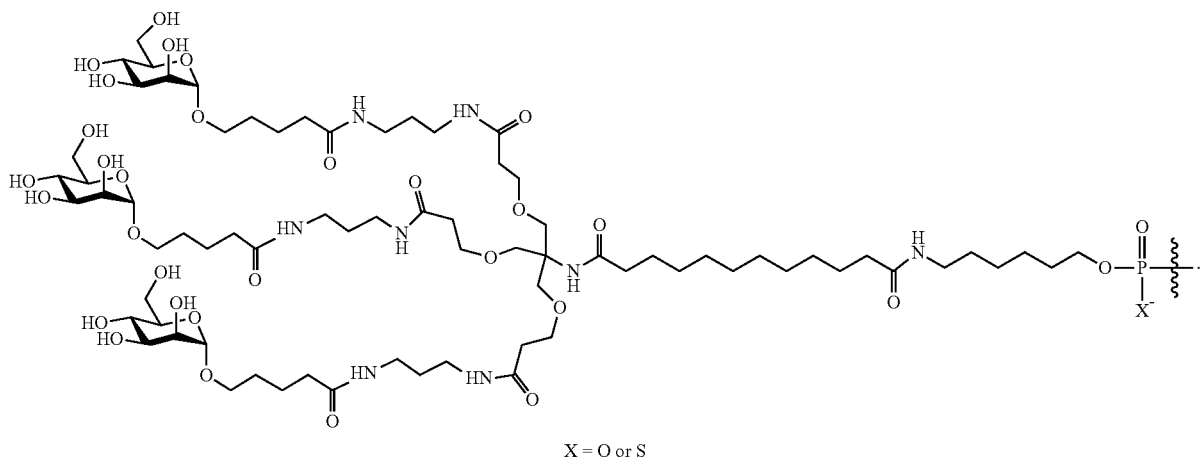

X = O or S

267. The composition of any one of embodiments 112-190, wherein -[-L$^{LD}$-(R$^{LD}$)$_a$]$_b$ is

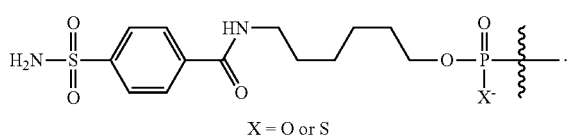

X = O or S

268. The composition of any one of embodiments 112-190, wherein -[-L$^{LD}$-(R$^{LD}$)$_a$]$_b$ is

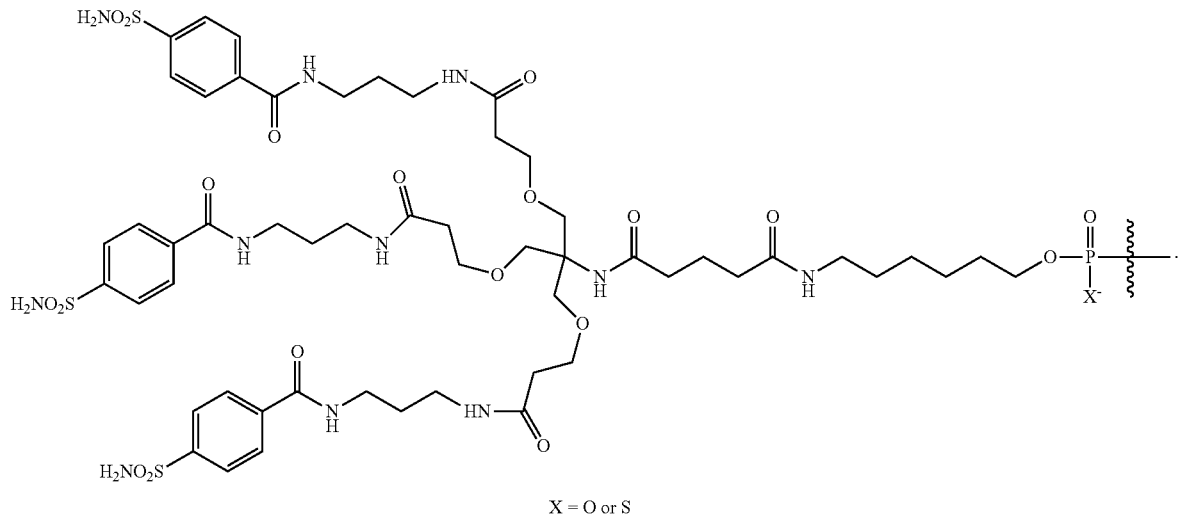

X = O or S

269. The composition of any one of embodiments 220-249 and 261-268, wherein X is O.

270. The composition of any one of embodiments 220-249 and 261-268, wherein X is S.

271. The composition of embodiment 269, wherein —O—P(O)(X$^-$)— connects to 5'-O— of A$^c$ to form a phosphate linkage.

272. The composition of embodiment 269, wherein —O—P(O)(X$^-$)— connects to 3'-O— of A$^c$ to form a phosphate linkage.

273. The composition of embodiment 270, wherein —O—P(O)(X$^-$)— connects to 5'-O— of A$^c$ to form a phosphorothioate linkage.

274. The composition of embodiment 270, wherein —O—P(O)(X$^-$)— connects to 3'-O— of A$^c$ to form a phosphorothioate linkage.

275. The composition of embodiment 273 or 274, wherein the phosphorothioate linkage is chirally controlled.

276. The composition of embodiment 273 or 274, wherein the phosphorothioate linkage is chirally controlled and is Sp.

277. The composition of embodiment 273 or 274, wherein the phosphorothioate linkage is chirally controlled and is Rp.

278. The composition or method of any one of the preceding embodiments, wherein at least 0.5%, 1%, 2%, 3%, 4%, 5%, 6%, 7%, 8%, 9%, 10%, 20%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 97% or 99% of the oligonucleotides that have the base sequence of the particular oligonucleotide type, defined by 1) base sequence; 2) pattern of backbone linkages; 3) pattern of backbone chiral centers; and 4) pattern of backbone phosphorus modifications, are oligonucleotides of the particular oligonucleotide type.

279. The composition or method of any one of the preceding embodiments, wherein at least 10% of the oligonucleotides that have the base sequence of the particular oligonucleotide type, defined by 1) base sequence; 2) pattern of backbone linkages; 3) pattern of backbone chiral centers; and 4) pattern of backbone phosphorus modifications, are oligonucleotides of the particular oligonucleotide type.

280. The composition or method of any one of the preceding embodiments, wherein at least 0.5%, 1%, 2%, 3%, 4%, 5%, 6%, 7%, 8%, 9%, 10%, 20%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 97% or 99% of the oligonucleotides that have the base sequence, pattern of backbone linkages, and pattern of backbone phosphorus modifications of the particular oligonucleotide type, defined by 1) base sequence; 2) pattern of backbone linkages; 3) pattern of backbone chiral centers; and 4) pattern of backbone phosphorus modifications, are oligonucleotides of the particular oligonucleotide type.

281. The composition or method of any one of the preceding embodiments, wherein at least 10% of the oligonucleotides that have the base sequence, pattern of backbone linkages, and pattern of backbone phosphorus modifications of the particular oligonucleotide type, defined by 1) base sequence; 2) pattern of backbone linkages; 3) pattern of backbone chiral centers; and 4) pattern of backbone phosphorus modifications, are oligonucleotides of the particular oligonucleotide type.

282. The composition of any one of embodiments 1-277, wherein the oligonucleotides have a predetermined level of a percentage of 1%-100% of all oligonucleotides in the composition.

283. The composition of any one of embodiments 1-277, wherein the oligonucleotides have a predetermined level of a percentage of 1%-100% of all oligonucleotides in the composition that share the common base sequence.

284. The composition of any one of embodiments 1-277, wherein the oligonucleotides have a predetermined level of a percentage of 1%-100% of all oligonucleotides in the composition that share the common base sequence, the common pattern of base modification, the common pattern of sugar modification, and the common pattern of modified internucleotidic linkages.

285. The composition of any one of embodiments 282-284, wherein the percentage is at least 1%.

286. The composition of any one of embodiments 282-284, wherein the percentage is at least 5%.

287. The composition of any one of embodiments 282-284, wherein the percentage is at least 10%.

288. The composition of any one of embodiments 282-284, wherein the percentage is $(90\%)^n$-100%, wherein n is the number of chirally controlled internucleotidic linkages.

289. The composition of any one of embodiments 282-288, wherein the percentage is at least $(91\%)^n$, $(92\%)^n$, $(93\%)^n$, $(94\%)^n$, $(95\%)^n$, $(96\%)^n$, $(97\%)^n$, $(98\%)^n$, or $(99\%)^n$.

290. The composition of any one of embodiments 282-288, wherein the percentage is at least $(92\%)^n$.

291. The composition of any one of embodiments 282-288, wherein the percentage is at least $(95\%)^n$.

292. The composition of any one of embodiments 282-288, wherein the percentage is at least $(97\%)^n$.

293. The composition of any one of embodiments 282-288, wherein the percentage is at least $(98\%)^n$.

294. The composition of any one of embodiments 289-293, wherein product of diastereopurity of each of the chirally controlled internucleotidic linkages is utilized as the level, wherein diastereopurity of each chirally controlled internucleotidic linkage is represented by diastereopurity of a dimer comprising the same internucleotidic linkage and 5'- and 3'-nucleosides flanking the internucleotidic linkage and prepared under comparable methods as the oligonucleotides, which comparable methods comprise the same oligonucleotide preparation cycles that include identical reagents and reaction conditions for the dimer as for the chirally controlled internucleotidic linkage in the oligonucleotides.

295. The composition of any one of embodiments 282-294, all oligonucleotides in the composition that share a common base sequence, a common pattern of base modification, a common pattern of sugar modification, and/or a common pattern of modified internucleotidic linkages are at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition.

296. The composition of any one of embodiments 282-295, all oligonucleotides in the composition that share a common base sequence, a common pattern of base modification, a common pattern of sugar modification, and/or a common pattern of modified internucleotidic linkages are at least 90% of all oligonucleotides in the composition.

297. The composition of any one of embodiments 282-295, all oligonucleotides in the composition that share a common base sequence, a common pattern of base modification, a common pattern of sugar modification, and/or a common pattern of modified internucleotidic linkages are at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition.

298. The composition of any one of embodiments 282-297, all oligonucleotides in the composition that share a common base sequence, a common pattern of base modification, a common pattern of sugar modification, and/or a common pattern of modified internucleotidic linkages are at least 90% of all oligonucleotides in the composition.

299. The composition or method of any one of the preceding embodiments, wherein the composition is a pharmaceutical composition comprising one or more pharmaceutically acceptable salts of the oligonucleotides.

300. The composition or method of any one of the preceding embodiments, wherein the composition is a pharmaceutical composition comprising one or more pharmaceutically acceptable sodium salts of the oligonucleotides.

301. The composition or method of any one of the proceeding embodiments, wherein the composition further comprises one or more other therapeutic agents.

302. A method for modulating hTLR9 agonist activity, comprising administering an oligonucleotide composition comprising oligonucleotide comprising a lipid moiety.

303. A method for modulating hTLR9 agonist activity, comprising administering an oligonucleotide comprising a lipid moiety, wherein hTLR9 agonist activity is reduced compared to an oligonucleotide absent the lipid moiety but is otherwise identical to the oligonucleotide.

304. A method for modulating hTLR9 antagonist activity, comprising administering an oligonucleotide composition comprising oligonucleotide comprising a lipid moiety.

305. A method for modulating hTLR9 antagonist activity, comprising administering an oligonucleotide comprising a lipid moiety, wherein hTLR9 antagonist activity is increased compared to an oligonucleotide absent the lipid moiety but is otherwise identical to the oligonucleotide.

306. A method for modulating hTLR9 activity of an oligonucleotide, comprising incorporating a lipid moiety to the oligonucleotide.

307. A method for decreasing hTLR9 agonist activity of an oligonucleotide, comprising incorporating a lipid moiety to the oligonucleotide.

308. A method for increasing hTLR9 antagonist activity of an oligonucleotide, comprising incorporating a lipid moiety to the oligonucleotide.

309. The method of any one of the preceding embodiments, wherein the oligonucleotide comprising a lipid moiety is an oligonucleotide comprising a lipid moiety of any one of the preceding embodiments.

310. A method of agonizing an immune response in a human cell, the method comprising the step of contacting the human cell with a CpG oligonucleotide composition of any one of the preceding embodiments, wherein the CpG oligonucleotide is capable of agonizing a TLR9-mediated or TLR9-associated immune response.

311. A method of antagonizing an immune response in a human cell, the method comprising the step of contacting the human cell with a CpG oligonucleotide composition of any one of the preceding embodiments, wherein the CpG oligonucleotide is capable of antagonizing a TLR9-mediated or TLR9-associated immune response.

312. A method of modulating an immune response in a subject, the method comprising the step of administering a composition of any one of preceding embodiments, wherein the CpG oligonucleotide is capable of modulating a TLR9-mediated or TLR9-associated immune response.

313. A method of agonizing an immune response in a human being in need thereof, the method comprising the step of contacting the human with an immunologically effective amount of CpG oligonucleotide composition of any one of the preceding embodiments.

314. The method of any one of the preceding embodiments, wherein the human has a disease.

315. The method of any one of the preceding embodiments, wherein the human has a disease amenable to treatment with an agonized immune response.

316. The method of any one of the preceding embodiments, wherein the human has a disease selected from an infectious disease, a genetic disease, and cancer.

317. A method of increasing an immune response to an immunologically active component in a subject, comprising administering an immunologically effective amount of (a) a composition of any one of the preceding embodiments and (b) the immunologically active component.

318. The composition of any one of the preceding embodiments, wherein the immunologically active component is selected from: an immunogen, an antigen, a toxin, a virus, a bacterium, a fungus, an infectious agent, a cancer antigen, a pathogen, and a component thereof.

319. A method of identifying a second oligonucleotide composition with decreased immune stimulation in a subject compared to a first oligonucleotide composition, the method comprising steps of:
(a) measuring the immune stimulation mediated by the first oligonucleotide composition, wherein the first oligonucleotide composition comprising oligonucleotides that have a common base sequence comprising at least one CpG region;
(b) measuring the immune stimulation mediated by a second oligonucleotide composition, wherein the second oligonucleotide composition has the same common base sequence as the first oligonucleotide composition, and wherein the CpG region of oligonucleotides of the second composition differs in its pattern of chiral centers from the corresponding region of oligonucleotides of the first oligonucleotide composition;
(c) optionally repeating step (b), each repeat with a different second oligonucleotide composition, and selecting a second oligonucleotide composition which mediates less immune stimulation than the first oligonucleotide composition.

320. The method of any one of the preceding embodiments, wherein the first oligonucleotide is immunostimulatory in a human cell.

321. The method of any one of the preceding embodiments, wherein the second oligonucleotide comprises at least one phosphorothioate in the Sp conformation and at least one phosphorothioate in the Rp conformation in the CpG region motif.

322. The method of any one of the preceding embodiments, wherein the second oligonucleotide does not comprise an agonistic CpG region motif described herein.

323. The method of any one of the preceding embodiments, wherein the second oligonucleotide does not comprise an antagonistic CpG region motif described herein.

324. The method of any one of the preceding embodiments, wherein the second oligonucleotide does not comprise an agonistic or antagonistic CpG region motif described herein.

325. A method of improving a characteristic of a CpG oligonucleotide composition comprising at least two CpG oligonucleotides, wherein the method comprises a step of:
(a) decreasing the amount in the composition of at least one of the at least two CpG oligonucleotides, wherein each of the at least two CpG oligonucleotides is defined by the stereochemistry of a CpG region motif, and wherein the at least one of the at least two CpG oligonucleotides is determined to have an inferior characteristic relative to the CpG oligonucleotide composition.

326. A method of improving a characteristic of a stereorandom CpG oligonucleotide composition, wherein the method comprises a step of:
(a) decreasing the amount in the composition of at least one of the at least two CpG oligonucleotides, wherein each of the at least two CpG oligonucleotides is defined by the stereochemistry of a CpG region motif, and wherein the at least one of the at least two CpG oligonucleotides is determined to have an inferior characteristic relative to the CpG oligonucleotide composition, wherein the characteristic is increased activity, improved efficacy, reduced toxicity, increased stability, increased delivery, or increased biological half-life.

327. A method of designing a second oligonucleotide mediating decreased immune stimulation in a human cell relative to the immune stimulation mediated by a first oligonucleotide, the method comprising the steps of:
(a) measuring the immune stimulation mediated by a first oligonucleotide, wherein the first oligonucleotide has a defined base sequence comprising at least one CpG region;
(b) measuring the immune stimulation mediated by one or more second oligonucleotides, wherein the second oligonucleotides have the same base sequence as the first oligonucleotide and further comprise one or more phosphorothioates in the CpG region motif, wherein the stereochemistry of the phosphorothioates in the CpG region motif of the second oligonucleotides differs from the stereochemistry of any phosphorothioates in the CpG region motif of the first oligonucleotides, wherein steps (a) and (b) can be performed in any order;
(c) selecting a second oligonucleotide which mediates less immune stimulation than the first oligonucleotide.

328. The method of any one of the preceding embodiments, wherein the first oligonucleotide is immunostimulatory in a human cell.

329. The method of any one of the preceding embodiments, wherein the second oligonucleotide comprises at least one phosphorothioate in the rip conformation and at least one phosphorothioate in the Rp conformation in the CpG region motif.

330. The method of any one of the preceding embodiments, wherein the second oligonucleotide does not comprise an agonistic CpG region motif described herein.

331. The method of any one of the preceding embodiments, wherein the second oligonucleotide does not comprise an antagonistic CpG region motif described herein.

332. The method of any one of the preceding embodiments, wherein the second oligonucleotide does not comprise an agonistic or antagonistic CpG region motif described herein.

333. A method of decreasing the immune stimulation in a human cell mediated by a first oligonucleotide, the method comprising the steps of:
(a) providing the first oligonucleotide, wherein the first oligonucleotide has a defined base sequence comprising at least one CpG region; and measuring the immune stimulation in a human cell mediated by the first oligonucleotide;
(b) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order;
(c) selecting a second oligonucleotide which mediates less immune stimulation than the first oligonucleotide; and
(d) contacting the cell with the second oligonucleotide.

334. The method of any one of the preceding embodiments, wherein the first oligonucleotide is immunostimulatory in a human cell.

335. The method of any one of the preceding embodiments, wherein the second oligonucleotide comprises at least one phosphorothioate in the Sp conformation and at least one phosphorothioate in the Rp conformation in the CpG region motif.

336. The method of any one of the preceding embodiments, wherein the second oligonucleotide does not comprise an agonistic CpG region motif described herein.

337. The method of any one of the preceding embodiments, wherein the second oligonucleotide does not comprise an antagonistic CpG region motif described herein.

338. The method of any one of the preceding embodiments, wherein the second oligonucleotide does not comprise an agonistic or antagonistic CpG region motif described herein.

339. A composition comprising an oligonucleotide, wherein the oligonucleotide mediates less immune stimulation than a reference oligonucleotide, wherein the second oligonucleotide is selected using a method comprising the steps of:
(a) providing the reference oligonucleotide, wherein the reference oligonucleotide has a defined base sequence comprising at least one CpG region; and measuring the immune stimulation in a human cell mediated by the reference oligonucleotide;
(b) providing one or more second oligonucleotides, wherein the second oligonucleotides have the same base sequence as the reference oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the reference oligonucleotides; and measuring the immune stimulation in a human cell of the second oligonucleotides, wherein steps (a) and (b) can be performed in any order;
(c) selecting a second oligonucleotide which mediates less immune stimulation than the reference oligonucleotide.

340. The method of any one of the preceding embodiments, wherein the reference oligonucleotide is immunostimulatory in a human cell.

341. The method of any one of the preceding embodiments, wherein the second oligonucleotide comprises at least one phosphorothioate in the Sp conformation and at least one phosphorothioate in the Rp conformation in the CpG region motif.

342. The method of any one of the preceding embodiments, wherein the second oligonucleotide does not comprise an agonistic CpG region motif described herein.

343. The method of any one of the preceding embodiments, wherein the second oligonucleotide does not comprise an antagonistic CpG region motif described herein.

344. The method of any one of the preceding embodiments, wherein the second oligonucleotide does not comprise an agonistic or antagonistic CpG region motif described herein.

345. A method of administering a therapeutic oligonucleotide to a patient, wherein the therapeutic oligonucleotide mediates less immune stimulation than a first oligonucleotide, wherein the therapeutic oligonucleotide is selected using a method comprising the steps of:
(e) providing the first oligonucleotide, wherein the first oligonucleotide has a defined base sequence comprising at least one CpG region; and measuring the immune stimulation in a human cell mediated by the first oligonucleotide;
(f) providing one or more second oligonucleotides, wherein the second oligonucleotides have the same base sequence as the first oligonucleotide and further comprise one or more phosphorothioates in the CpG region, wherein the stereochemistry of the phosphorothioates in the CpG region of the second oligonucleotides differs from the stereochemistry of any phosphorothioates in the CpG region of the first oligonucleotides; and measuring the immune stimulation in a human cell of the second oligonucleotides, wherein steps (a) and (b) can be performed in any order;
(g) selecting a second oligonucleotide which mediates less immune stimulation than the first oligonucleotide as the therapeutic oligonucleotide.

346. The method of any one of the preceding embodiments, wherein the first oligonucleotide is immunostimulatory in a human cell.

347. The method of any one of the preceding embodiments, wherein the second oligonucleotide comprises at least one phosphorothioate in the Sp conformation and at least one phosphorothioate in the Rp conformation in the CpG region motif.

348. The method of any one of the preceding embodiments, wherein the second oligonucleotide does not comprise an agonistic CpG region motif described herein.

349. The method of any one of the preceding embodiments, wherein the second oligonucleotide does not comprise an antagonistic CpG region motif described herein.

350. The method of any one of the preceding embodiments, wherein the second oligonucleotide does not comprise an agonistic or antagonistic CpG region motif described herein.

351. A method, comprising administering a composition comprising a first plurality of oligonucleotides, each of which:

(a) hybridizes with a particular target sequence; and
(b) has base sequence that includes at least one CpG region motif present in all oligonucleotides of the plurality (a "common CpG region motif"), which CpG region motif has a structure:

$N_1$-(*R/S)—C—(*R/S)-G-(*R/S)—$N_2$;

wherein each (*R/S) is independently a chiral internucleotidic linkage, wherein the composition is chirally controlled in that it contains a predetermined level of each of stereoisomers 1-8 (S1-S8) for each common CpG region motif:

S1: $N_1$-(*R)—C—(*R)-G-(*R)—$N_2$;
S2: $N_1$-(*R)—C—(*R)-G-(*S)—$N_2$;
S3: $N_1$-(*R)—C—(*S)-G-(*R)—$N_2$;
S4: $N_1$-(*R)—C—(*S)-G-(*S)—$N_2$;
S5: $N_1$-(*S)—C—(*R)-G-(*R)—$N_2$;
S6: $N_1$-(*S)—C—(*R)-G-(*S)—$N_2$;
S7: $N_1$-(*S)—C—(*S)-G-(*R)—$N_2$;
S8: $N_1$-(*S)—C—(*S)-G-(*S)—$N_2$;

wherein the composition is characterized by reduced immune stimulation relative to a reference composition, which differs from the composition in that it is stereorandom with respect to internucleotidic linkages of at least one CpG region motif.

352. In a method of administering an oligonucleotide composition comprising a plurality of oligonucleotides having a common base sequence, the improvement that comprises: administering a composition comprising a first plurality of oligonucleotides, each of which:
(a) hybridizes with a particular target sequence; and
(b) has base sequence that includes at least one CpG region motif present in all oligonucleotides of the plurality (a "common CpG region motif"), which CpG region motif has a structure:

$N_1$-(*R/S)—C—(*R/S)-G-(*R/S)—$N_2$;

wherein each (*R/S) is independently a chiral internucleotidic linkage, wherein the composition is chirally controlled in that it contains a predetermined level of each of stereoisomers 1-8 (S1-S8) for each common CpG region motif:

S1: $N_1$-(*R)—C—(*R)-G-(*R)—$N_2$;
S2: $N_1$-(*R)—C—(*R)-G-(*S)—$N_2$;
S3: $N_1$-(*R)—C—(*S)-G-(*R)—$N_2$;
S4: $N_1$-(*R)—C—(*S)-G-(*S)—$N_2$;
S5: $N_1$-(*S)—C—(*R)-G-(*R)—$N_2$;
S6: $N_1$-(*S)—C—(*R)-G-(*S)—$N_2$;
S7: $N_1$-(*S)—C—(*S)-G-(*R)—$N_2$;
S8: $N_1$-(*S)—C—(*S)-G-(*S)—$N_2$;

wherein the composition is characterized by reduced immune stimulation relative to a reference composition, which differs from the composition in that it is stereorandom with respect to internucleotidic linkages of at least one CpG region motif.

353. A method, comprising administering a chirally controlled oligonucleotide composition that is chirally controlled in that the composition comprises a predetermined level of oligonucleotides of an individual oligonucleotide type, wherein an oligonucleotide type is defined by:
  1) base sequence;
  2) pattern of backbone linkages;
  3) pattern of backbone chiral centers; and
  4) pattern of backbone phosphorus modifications;
wherein each oligonucleotide of the individual oligonucleotide type independently comprises at least one copy of a CpG region motif:

$N_1$-(*R/S)—C—(*R/S)-G-(*R/S)—$N_2$;

wherein:
each (*R/S) is independently a chiral internucleotidic linkage;
oligonucleotides of the individual oligonucleotide have the common base sequence; and
the chirally controlled oligonucleotide composition displays reduced immune stimulation relative to a reference oligonucleotide composition, which reference oligonucleotide composition is a stereorandom oligonucleotide composition comprising oligonucleotides having the same common base sequence, or a chirally controlled oligonucleotide composition of oligonucleotides having the same common base sequence but of a different oligonucleotide type.

354. In a method of administering an oligonucleotide composition comprising a plurality of oligonucleotides having a common base sequence, the improvement that comprises: administering a chirally controlled oligonucleotide composition that is chirally controlled in that the composition comprises a predetermined level of oligonucleotides of an individual oligonucleotide type, wherein an oligonucleotide type is defined by:
  1) base sequence;
  2) pattern of backbone linkages;
  3) pattern of backbone chiral centers; and
  4) pattern of backbone phosphorus modifications;
wherein each oligonucleotide of the individual oligonucleotide type independently comprises at least one copy of a CpG region motif:

$N_1$-(*R/S)—C—(*R/S)-G-(*R/S)—$N_2$;

wherein:
each (*R/S) is independently a chiral internucleotidic linkage;
oligonucleotides of the individual oligonucleotide type have the common base sequence; and
the chirally controlled oligonucleotide composition displays reduced immune stimulation relative to a reference oligonucleotide composition, which reference oligonucleotide composition is a stereorandom oligonucleotide composition comprising oligonucleotides having the same common base sequence, or a chirally controlled oligonucleotide composition of oligonucleotides having the same common base sequence but of a different oligonucleotide type.

355. The method of any one of the preceding embodiments, wherein the reference oligonucleotide composition is a chirally controlled oligonucleotide composition of oligonucleotides having the same common base sequence but a different pattern of backbone chiral centers.

356. The method of any one of the preceding embodiments, wherein the reference oligonucleotide composition is a chirally controlled oligonucleotide composition of oligonucleotides having the same common base sequence but a different pattern of backbone chiral centers.

357. A method, comprising administering a chirally controlled oligonucleotide composition, wherein the composition comprises a plurality of oligonucleotides, each of which:
(a) hybridizes with a particular target sequence;
(b) has base sequence that includes at least one C residue in a CpG that is present in all oligonucleotides of the plurality (a "common C residue") and that has a 5-methyl group, a 2'-OMe group in its sugar moiety, or both; and
(c) includes one or more chiral internucleotidic linkages, so that each oligonucleotide is a particular stereoform, characterized by its stereoidentity [stereoidentity=which stereoisomer is present at a particular chiral linkage] at each of the one or more chiral internucleotidic linkages, wherein
the composition is chirally controlled in that it contains a predetermined level of each stereoform, and the composition is substantially free of those stereoforms that individually, and in the absence of other stereoforms, activate TLR9.

358. In a method comprising administering a chirally controlled oligonucleotide composition, wherein the composition comprises a plurality of oligonucleotides, each of which:
(a) hybridizes with a particular target sequence;
(b) has base sequence that includes at least one C residue in a CpG region motif that is present in all oligonucleotides of the plurality (a "common C residue") and that has a 5-methyl group, a 2'-OMe group in its sugar moiety, or both; and
(c) includes one or more chiral internucleotidic linkages; the improvement that comprises administering a composition comprising a plurality of oligonucleotides, each of which:
(a) hybridizes with the same target sequence;
(b) has base sequence that includes the same common C residue in a CpG region motif that has a 5-methyl group, a T-OMe group in its sugar moiety, or both; and
(c) includes one or more chiral internucleotidic linkages, so that each oligonucleotide is a particular stereoform, characterized by its stereoidentity [stereoidentity=which stereoisomer is present at a particular chiral linkage] at each of the one or more chiral internucleotidic linkages, wherein the composition is chirally controlled in that it contains a predetermined level of each stereoform, and the composition is substantially free of those stereoforms that individually, and in the absence of other stereoforms, activate TLR9.

359. A method, comprising administering a composition that is chirally controlled in that the composition comprises a predetermined level of oligonucleotides of an individual oligonucleotide type, wherein an oligonucleotide type is defined by:
  1) base sequence;
  2) pattern of backbone linkages;
  3) pattern of backbone chiral centers; and
  4) pattern of backbone phosphorus modifications;
wherein the base sequence includes at least one C residue in a CpG region motif that has a 5-methyl group, a 2'-OMe group in its sugar moiety, or both; and
the composition is substantially free of oligonucleotides of a different oligonucleotide type having the same sequence that individually, and in the absence of other stereoforms, activate TLR9.

360. In a method comprising administering a composition of oligonucleotides of a common base sequence, wherein the common base sequence includes at least one C residue in a CpG region motif that has a 5-methyl group, a 2'-OMe group in its sugar moiety, or both;
the improvement comprises administering a composition that is chirally controlled in that the composition comprises a predetermined level of oligonucleotides of an individual oligonucleotide type, wherein an oligonucleotide type is defined by:
  1) base sequence;
  2) pattern of backbone linkages;
  3) pattern of backbone chiral centers; and
  4) pattern of backbone phosphorus modifications;
wherein oligonucleotides of the individual oligonucleotide type has the same common sequence, the base sequence includes the same at least one C residue in a CpG region motif that has a 5-methyl group, a 2'-OMe group in its sugar moiety, or both; and
the composition is substantially free of oligonucleotides of a different oligonucleotide type having the same sequence that individually, and in the absence of other stereoforms, activate TLR9.

361. A method comprising a step of administering to a subject a composition of any one of preceding embodiments.

362. In a method of agonizing an immune response in a subject, the improvement comprises: administering to the subject a composition of any one of the preceding embodiments.

363. In a method of agonizing an immune response in a human subject, the improvement comprises: administering to the subject a composition of any one of the preceding embodiments.

364. The composition or method of any of the preceding embodiments, wherein the oligonucleotides are structurally identical.

365. The composition or method of any of the preceding embodiments, wherein each (*R/S) is independently a phosphorothioate linkage.

366. The composition or method of any of the preceding embodiments, wherein the oligonucleotides comprises an Rp phosphorothioate linkage within a CpG region motif, and an Sp phosphorothioate linkage within a CpG region motif.

367. The composition or method of any of the preceding embodiments, wherein the at least one CpG region motif comprises at least comprises an Rp phosphorothioate linkage and at least one Sp phosphorothioate linkage within a CpG region motif.

368. The composition or method of any of the preceding embodiments, wherein the oligonucleotides comprise at least X nucleotides.

369. The composition or method of any of the preceding embodiments, wherein the oligonucleotides comprise no more than X nucleotides.

370. The composition or method of any of the preceding embodiments, wherein the oligonucleotides comprise 5 or more chiral internucleotidic linkages;

371. The composition or method of any of the preceding embodiments, wherein the oligonucleotides comprise 10 or more chiral internucleotidic linkages;

372. The composition or method of any of the preceding embodiments, wherein the oligonucleotides comprise 15 or more chiral internucleotidic linkages.

373. The composition or method of any one of the preceding embodiments, wherein one or more nucleotides in the CpG region is an RNA or DNA nucleotide.

374. The composition or method of any one of the preceding embodiments, wherein at least one sugar is not modified.

375. The composition or method of any one of the preceding embodiments, wherein at least one sugar is modified.

376. The composition or method of any one of the preceding embodiments, wherein at least one sugar is modified, wherein the modification is 2'-OMe, 2'-MOE, 2'-F, or 2'-OR, wherein R is optionally substituted C1-6 alkyl.

377. The composition or method of any of the preceding embodiments, wherein the modification is 2'-OR, wherein R is optionally substituted C1-6 alkyl.

378. The composition or method of any one of the preceding embodiments, wherein at least five sugars are modified.

379. The composition or method of any one of the preceding embodiments, wherein at least five sugars are modified, wherein the modification is 2'-OMe, 2'-MOE, 2'-F, or 2'-OR, wherein R is optionally substituted C1-6 alkyl.

380. The composition or method of any one of the preceding embodiments, wherein at least ten sugars are modified.

381. The composition or method of any one of the preceding embodiments, wherein at least ten sugars are modified, wherein the modification is 2'-OMe, 2'-MOE, 2'-F, or 2'-OR, wherein R is optionally substituted C1-6 alkyl.

382. The composition or method of any one of the preceding embodiments, wherein the strand further comprises a nucleotide substitute.

383. The composition or method of any one of the preceding embodiments, wherein the strand further comprises a Morpholino, PNA, LNA, BNA, TNA, GNA, ANA, FANA, CeNa, HNA or UNA.

384. The composition or method of any one of the preceding embodiments, wherein at least one internucleotidic linkage is modified.

385. The composition or method of any one of the preceding embodiments, wherein at least one internucleotidic linkage is selected from: phosphorodithioate, phosphoramidate, boranophosphonoate, an amide linker, or a compound of formula (I): (I), where R3 is selected from O", S", NH2, BH3, CH3, C1-6 alkyl, C6-10 aryl, C1-6 alkoxy and C6-10 aryl-oxy, wherein C1-6 alkyl and C6-10 aryl are unsubstituted or optionally independently substituted with 1 to 3 groups independently selected from halo, hydroxyl and NH2; and R4 is selected from O, S, NH, or CH2.

386. The composition or method of any one of the preceding embodiments, wherein at least one internucleotidic linkage is phosphorodithioate.

387. The composition or method of any one of the preceding embodiments, wherein the CpG oligonucleotide further comprises a second strand.

388. The composition or method of any one of the preceding embodiments, wherein the CpG oligonucleotide is capable of agonizing an immune response.

389. The composition or method of any one of the preceding embodiments, wherein the CpG oligonucleotide is capable of agonizing an immune response in human cells.

390. The composition or method of any one of the preceding embodiments, wherein the immune response is agonized in a human cell or human.

391. The composition or method of any one of the preceding embodiments, wherein the CpG oligonucleotide further comprises a second strand.

392. The composition or method of any one of the preceding embodiments, wherein each oligonucleotide in the plurality/composition has the same base sequence 393. The composition or method of any one of the preceding embodiments, wherein, for at least one common CpG region motif, the composition is substantially free of at least stereoisomer S8, so that the predetermined level is considered to be substantially zero.

394. The composition or method of any one of the preceding embodiments, wherein, for at least one common CpG region motif, the composition is substantially free of at least seven of the stereoisomers, so that the predetermined level is considered to be substantially zero for seven of the stereoisomers.

395. The composition or method of any one of the preceding embodiments, wherein each oligonucleotide in the composition includes at least one non-chiral internucleosidic linkage outside of the CpG region motif.

396. The composition or method of any one of the preceding embodiments, wherein the composition is substantially racemic for at least one chiral internucleosidic linkage outside of the CpG region motif.

397. The composition or method of any one of the preceding embodiments, wherein the CpG region motifs "C" residue is methylated and the composition is substantially free of at least stereoisomers.

398. Wherein the composition is capable of activating an TLR9-associated or TLR9-mediated immune response less than a stereorandom composition of oligonucleotides having the same sequence.

399. The composition or method of any one of the preceding embodiments, wherein the C residue in the CpG region motif comprises a 2'-OMe group in its sugar moiety . . . .

400. The composition or method of any one of the preceding embodiments, wherein the C residue in the CpG region motif is a 5-methyl-2'-OMe C residue 401. The composition or method of any one of the preceding embodiments, wherein one or more nucleotides in the CpG region is RNA or DNA.

402. The composition or method of any one of the preceding embodiments, wherein at least one sugar is not modified.

403. The composition or method of any one of the preceding embodiments, wherein at least one sugar is modified.

404. The composition or method of any one of the preceding embodiments, wherein at least one sugar is modified, wherein the modification is 2'-OMe, 2'-MOE, 2'-F, or 2'-OR, wherein R is optionally substituted C1-6 alkyl.

405. The composition or method of any one of the preceding embodiments, wherein at least five sugars are modified.

406. The composition or method of any one of the preceding embodiments, wherein at least five sugars are modified, wherein the modification is 2'-OMe, 2'-MOE, 2'-F, or 2'-OR, wherein R is optionally substituted C1-6 alkyl.

407. The composition or method of any one of the preceding embodiments, wherein at least ten sugars are modified.

408. The composition or method of any one of the preceding embodiments, wherein at least ten sugars are modified, wherein the modification is 2'-OMe, 2'-MOE, 2'-F, or 2'-OR, wherein R is optionally substituted C1-6 alkyl.

409. The composition or method of any one of the preceding embodiments, wherein the strand comprises a nucleotide substitute.

410. The composition or method of any one of the preceding embodiments, wherein the strand further comprises a Morpholino, PNA, LNA, BNA, TNA, GNA, ANA, FANA, CeNa, HNA or UNA.

411. The composition or method of any one of the preceding embodiments, wherein at least one internucleotidic linkage is modified.

412. The composition or method of any one of the preceding embodiments, wherein at least one internucleotidic linkage is selected from: phosphorodithioate, phosphoramidate, boranophosphonoate, an amide linker, or a compound of formula (I): (I), where R3 is selected from O", S", NH2, BH3, CH3, C1-6 alkyl, C6-10 aryl, C1-6 alkoxy and C6-10 aryl-oxy, wherein C1-6 alkyl and C6-10 aryl are unsubstituted or optionally independently substituted with 1 to 3 groups independently selected from halo, hydroxyl and NH2; and R4 is selected from O, S, NH, or CH2.

413. The composition or method of any one of the preceding embodiments, further comprising a immunologically active component.

414. The composition or method of any one of the preceding embodiments, further comprising a immunologically active component selected from: an immunogen, an antigen, a toxin, a virus, a bacterium, a fungus, an infectious agent, a cancer antigen, a pathogen, and a component thereof.

415. The composition or method of any one of the preceding embodiments, further comprising a immunologically active component, wherein the CpG oligonucleotide is conjugated to the immunologically active component.

416. The composition or method of any one of the preceding embodiments, further comprising a immunologically active component selected from: an immunogen, an antigen, a toxin, a virus, a bacterium, a fungus, an infectious agent, a cancer antigen, a pathogen, and a component thereof, wherein the CpG oligonucleotide is conjugated to the immunologically active component.

417. The composition or method of any one of the preceding embodiments, further comprising an additional adjuvant, a stabilizer, a preservative, or an antibiotic.

418. The composition or method of any one of the preceding embodiments, wherein *R is a modified internucleotidic linkage in the Rp conformation, *S is a modified internucleotidic linkage in the Sp conformation, and *R/S is a modified internucleotidic linkage in the Rp or Sp conformation.

419. The composition or method of any one of the preceding embodiments, wherein *R is a phosphorothioate in the Rp conformation, *S is a phosphorothioate in the Sp conformation, and *R/S is phosphorothioate in the Rp or Sp conformation.

420. A chirally controlled oligonucleotide composition comprising a CpG oligonucleotide comprising a strand comprising about 14 to about 49 nucleotides, wherein the strand comprises at least two copies of CpG region motif N1-(*R/S)—C—(*R/S)-G-(*R/S)—N2, wherein at least one (*R/S) is a modified internucleotidic linkage in the Rp conformation and at least one (*R/S) is a modified internucleotidic linkage in the Sp conformation, and each of N1 and N2 is independently any nucleoside.

421. A chirally controlled oligonucleotide composition comprising a CpG oligonucleotide comprising a strand comprising about 14 to about 49 nucleotides, wherein the strand comprises at least two copies of CpG region motif N1-(*R/S)—C—(*R/S)-G-(*R/S)—N2, wherein at least one (*R/S) is a phosphorothioate in the Rp conformation and at least one (*R/S) is a phosphorothioate in the Sp conformation, and each of N1 and N2 is independently any nucleoside.

422. A composition comprising a CpG oligonucleotide comprising a strand comprising about 14 to about 49 nucleotides, wherein the strand comprises at least two copies of CpG region motif N1-(*R/S)—C—(*R/S)-G-(*R/S)—N2, wherein at least one (*R/S) is a phosphorothioate in the Rp conformation and at least one (*R/S) is a phosphorothioate in the Sp conformation, and each of N1 and N2 is independently any nucleoside.

423. The method or composition of any of the preceding embodiments, wherein the CpG oligonucleotide comprises two or more copies of a CpG region motif.

424. The method or composition of any of the preceding embodiments, wherein the CpG oligonucleotide comprises two or more copies of a CpG region motif disclosed herein.

425. The method or composition of any of the preceding embodiments, wherein the CpG oligonucleotide comprises two or more CpG region motifs disclosed herein.

426. The method or composition of any of the preceding embodiments, wherein the CpG oligonucleotide comprises two or more CpG region motifs disclosed herein, wherein the motifs are different from each other.

427. The method or composition of any of the preceding embodiments, wherein the CpG oligonucleotide comprises two or more CpG region motifs disclosed herein, wherein the motifs are the same as each other.

428. The method or composition of any of the preceding embodiments, wherein the CpG oligonucleotide is agonistic.

429. The method or composition of any of the preceding embodiments, wherein the CpG oligonucleotide is agonistic in human cells.

430. The method or composition of any of the preceding embodiments, wherein the CpG oligonucleotide is agonistic, as measured by an increase in secretion of a cytokine, interferon-alpha, interferon-gamma, IL-4, IL-6, IL-8, IL-10, IL-12, and/or TNF-alpha, and/or an increase in NF-κP activity.

431. The method or composition of any of the preceding embodiments, wherein the CpG oligonucleotide is antagonistic.

432. The method or composition of any of the preceding embodiments, wherein the CpG oligonucleotide is antagonistic in human cells.

433. The method or composition of any of the preceding embodiments, wherein the CpG oligonucleotide is antagonistic, as measured by a decrease in secretion of a cytokine, interferon-alpha, interferon-gamma, IL-4, IL-6, IL-8, IL-10, IL-12, and/or TNF-alpha, and/or an increase in NF-κP activity.

434. An assay for assessing TLR9 agonist activity, comprising an oligonucleotide composition of any one of the preceding embodiments.

435. An assay for assessing TLR9 antagonist activity, comprising an oligonucleotide composition of any one of the preceding embodiments.

436. A method for assessing TLR9 agonist activity, comprising providing an oligonucleotide composition of any one of the preceding embodiments.

437. A method for assessing TLR9 antagonist activity, comprising providing an oligonucleotide composition of any one of the preceding embodiments.

438. A method for inducing a cytokine, comprising providing an oligonucleotide composition of any one of the preceding embodiments.

439. A method for reducing production of a cytokine, comprising providing an oligonucleotide composition of any one of the preceding embodiments.

440. A method for modulating production and/or activities of a cytokine, interferon-alpha, interferon-gamma, IL-4, IL-6, IL-8, IL-10, IL-12, TNF-alpha and NF-κ3, comprising providing a composition of any one of the preceding embodiments.

441. A method of any one of the preceding embodiments, comprising incorporating a lipid moiety into an oligonucleotide.

442. A method, comprising administering to a subject an oligonucleotide composition of any one of the preceding embodiments and a second therapeutic agent.

443. A pharmaceutical composition, comprising an oligonucleotide composition of any one of the preceding embodiments and a second therapeutic agent.

444. The method or composition of any one of the preceding embodiments, wherein a second therapeutic agent is an antibody.

445. The method or composition of embodiment 442 or 443, wherein a second therapeutic agent is or comprises an antigen.

446. The method or composition of embodiment 442 or 443, wherein a second therapeutic agent is a vaccine.

447. A compound having the structure of formula O-I:

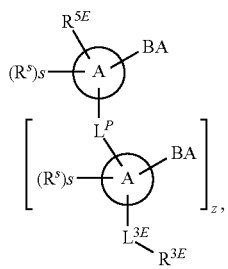

O-I or a salt thereof, wherein:

each BA is independently an optionally substituted group selected from $C_{1-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{5E}$ and $R^s$ is independently —H, —F, —Cl, —Br, —I, —CN, —$N_3$, —NO, —$NO_2$, -L-R', -L-OR', -L-SR', -L-N(R')$_2$, —O-L-OR', —O-L-SR', or —O-L-N(R')$_2$; s is 0-20;

each L is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Ring A is independently an optionally substituted 3-20 membered monocyclic, bicyclic or polycyclic ring having 0-10 heteroatoms;

each $L^P$ is independently an internucleotidic linkage; z is 1-1000;

$L^{3E}$ is -L- or -L-L-;

$R^{3E}$ is —R', -L-R', —OR', or a solid support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

448. A compound having the structure of formula O-I:

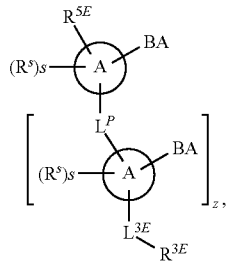

O-I or a salt thereof, wherein:

each BA is independently an optionally substituted group selected from $C_{1-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{5E}$ and $R^s$ is independently —H, —F, —Cl, —Br, —I, —CN, —$N_3$, —NO, —$NO_2$, -L-R', -L-OR', -L-SR', -L-N(R')$_2$, —O-L-OR', —O-L-SR', or —O-L-N(R')$_2$;

s is 0-20;

each L is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Ring A is independently an optionally substituted 3-20 membered monocyclic, bicyclic or polycyclic ring having 0-10 heteroatoms;

each $L^P$ independently has the structure of formula L-I:

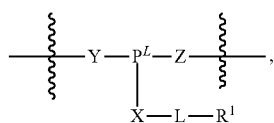

L-I or a salt form thereof, wherein:
$P^L$ is P(=W), P, or P→B(R')$_3$;
W is O, S or Se;
$R^1$ is -L-R, halogen, —CN, —NO$_2$, —Si(R)$_3$, —OR, —SR, or —N(R)$_2$;
each of X, Y and Z is independently —O—, —S—, —N(-L-R$^1$)—, or L;
z is 1-1000;
$L^{3E}$ is -L- or -L-L-;
$R^{3E}$ is —R', -L-R', —OR', or a solid support;
each R' is independently —R, —C(O)R, —C(O)OR, or —S(O)$_2$R;
each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

449. The compound of any one of embodiments 447-448, wherein z is at least 10.

450. The compound of any one of embodiments 447-448, wherein z is at least 15.

451. The compound of any one of embodiments 447-450, wherein each Ring A is independently

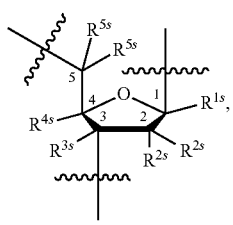

wherein:
BA is connected at C1;
each of $R^{1s}$, $R^{2s}$, $R^{3s}$, $R^{4s}$ and $R^{5s}$ is independently $R^s$.

452. The compound of embodiment 451, wherein each Ring A is independently

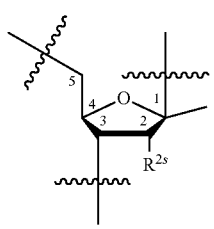

453. The compound of embodiment 451, wherein each Ring A is independently R

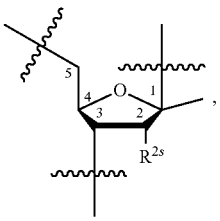

wherein $R^{2s}$ is not —OH.

454. The compound of any one of embodiments 451-453, wherein $R^{2s}$ is —H, halogen, or —OR.

455. The compound of any one of embodiments 451-453, wherein $R^{2s}$ is —H, halogen, or —OR, wherein R is optionally substituted C$_{1-6}$ alkyl.

456. The compound of embodiment 451, wherein each Ring A is independently

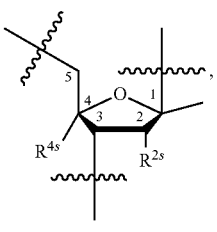

wherein $R^{2s}$ and $R^{4s}$ are R, and the two R groups are taken together with their intervening atoms to form a ring.

457. The compound of embodiment 456, wherein Ring A is optionally substituted

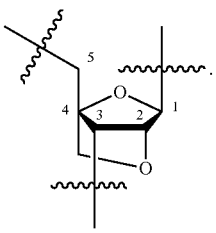 [SMILES: *C[C@]12CO[C@@H](C1*)[C@H](*)O2]

458. The compound of embodiment 456, wherein Ring A is

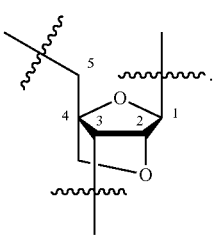 [SMILES: *C[C@]12CO[C@@H](C1*)[C@H](*)O2]

459. The compound of embodiment 456, wherein Ring A is

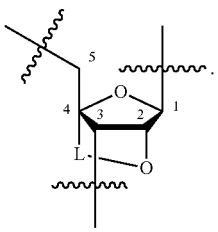

460. The compound of any one of embodiments 447-456, wherein each BA is independently an optionally substituted group selected from $C_{1-30}$ cycloaliphatic, $C_{6-30}$ aryl, $C_{5-30}$ heteroaryl having 1-10 heteroatoms, and $C_{3-30}$ heterocyclyl having 1-10 heteroatoms.
461. The compound of any one of embodiments 447-456, wherein each BA is independently an optionally substituted group selected from $C_{6-30}$ aryl, $C_{5-30}$ heteroaryl having 1-10 heteroatoms, and $C_{3-30}$ heterocyclyl having 1-10 heteroatoms.
462. The compound of any one of embodiments 447-456, wherein each BA is independently an optionally substituted group selected from heteroaryl having 1-10 heteroatoms, and $C_{3-30}$ heterocyclyl having 1-10 heteroatoms.
463. The compound of any one of embodiments 447-456, wherein each BA is independently an optionally substituted $C_{5-30}$ heteroaryl group having 1-10 heteroatoms.
464. The compound of any one of embodiments 447-463, wherein each BA is independently optionally substituted or protected adenine, cytosine, guanosine, thymine, or uracil.
465. The compound of any one of embodiments 447-463, wherein each BA is independently optionally substituted adenine, cytosine, guanosine, thymine, or uracil.
466. The compound of any one of embodiments 447-465, wherein $R^{3E}$ is —H.
467. The compound of any one of embodiments 447-465, wherein $R^{3E}$ is —OH.
468. The compound of any one of embodiments 447-465, wherein $R^{3E}$ is a solid support for oligonucleotide synthesis.
469. The compound of any one of embodiments 447-468, wherein $L^{3E}$ is L.
470. The compound of any one of embodiments 447-468, wherein $L^{3E}$ is a covalent bond.
471. The compound of any one of embodiments 447-468, wherein $L^{3E}$ is —O—.
472. The compound of any one of embodiments 447-471, wherein z is no more than 200.
473. The compound of any one of embodiments 447-472, wherein z is no more than 100.
474. The compound of any one of embodiments 447-473, wherein z is no more than 50.
475. The compound of any one of embodiments 447-474, wherein $R^E$ is —$CH_2OR$.
476. The compound of any one of embodiments 447-474, wherein $R^E$ is —$CH_2OH$.
477. The compound of any one of embodiments 447-474, wherein a heteroatom is independently selected from oxygen, nitrogen, sulfur, phosphorus, boron and silicon.
478. The compound of any one of embodiments 447-474, wherein a heteroatom is independently selected from oxygen, nitrogen, sulfur, and phosphorus.
479. The compound of any one of embodiments 447-474, wherein a heteroatom is independently selected from oxygen, nitrogen, and sulfur.
480. The compound of any one of embodiments 447-479, wherein the compound is a salt.
481. The compound of any one of embodiments 447-480, wherein the compound is an all-sodium salt.
482. The composition or method of any one of the preceding embodiments, wherein the oligonucleotides are each a compound of any one of embodiments 447-481.
483. The composition or method of any one of the preceding embodiments, wherein Ac—[H]a or Ac—[H]b is a compound of any one of embodiments 447-481.

EXEMPLIFICATION

The foregoing has been a description of certain non-limiting embodiments of the disclosure. Accordingly, it is to be understood that the embodiments of the disclosure herein described are merely illustrative of the application of the principles of the disclosure. Reference herein to details of the illustrated embodiments is not intended to limit the scope of the claims.

Non-limiting examples are provided below. A person of ordinary skill in the art would appreciate that multiple methods for testing for agonism or antagonism of an immune response in mouse, human and other cells are known in the art.

Example 1. Example Assessment of TLR9 Agonist and Antagonist Activities

In this example, we have utilized efficient chemical approaches that allowed us to synthesize a series of chirally controlled oligonucleotide compositions. We systemically evaluated how PS chirality influences the immune activities of TLR9. We demonstrate that PS chirality plays critical role in modulating TLR9 activity of synthetic oligos in a species-specific manner. In both mouse model and human PBMCs, we demonstrate that stereopure oligonucleotide and stereorandom mixtures could have very different TLR9 activities. More importantly, we provide evidence that mouse and human TLR9 respond differently to stereopure oligos with 2'-modifications and CpG methylations. These findings demonstrated the advantage of chirally controlled oligonucleotide compositions, for example, avoiding the daunting task of characterizing potential hazardous stereoisomers present in a stereorandom oligonucleotide mixture. A person having ordinary skill in the art appreciates that using technologies described in this disclosure, other chirally controlled oligonucleotide compositions can be prepared with desired agonist, antagonist, or neutral (neither agonist or antagonist) activities for various systems and species.

We evaluated four stereopure oligos that shared a common CpG-containing sequence targeting SMAD7 (FIG. 1a). A reporter cell line specific for mTLR9 was employed to investigate the agonist activities of these oligos. Reporter cells were incubated with serial dilutions of oligos for 16 hrs in the absence of transfection reagent (see methods). Reporter activities were indicated as fold of signal increase. The all-Sp oligonucleotide, WV-1384, was found to be an mTLR9 agonist, while the all-Rp oligonucleotide, WV-1386, was not (FIG. 3). Agonist activity of WV-1384 was mouse-specific, since it did not show any agonist activity toward hTLR9 (FIG. 9).

Antagonist activities of these two stereopure oligos on mTLR9 were examined using the same reporter cell line, but in the presence of ODN1826, a known mTLR9 agonist. The all-Rp oligonucleotide, WV-1386, was a strong antagonist inhibiting the TLR9 activating properties of ODN1826, while the all-Sp oligonucleotide, WV-1384, was not (FIG. 1). The opposite effects of all-Sp and all-Rp oligos on mTLR9 were supported with oligos with different sequences. For example, WV-1512, an all-Sp CpG-oligonucleotide targeting SOD1, similarly showed strong agonist activity on mTLR9 (FIG. 10), and not on hTLR9 (FIG. 13).

We next asked whether the PS chirality in or surrounding the CpG motif was important to mTLR9 activities. In WV-1384, there were two CpG motifs (underlined), both of which had Sp configurations. When these were converted to Rp, we generated WV-1375, which had Rp chirality in the two CpG motifs, and Sp chiralities in all other PS bonds (FIG. 2). WV-1375 showed enhanced agonist activities compared to WV-1384, indicating that Rp chirality in the CpG motif was beneficial to mTLR9 agonist activities. We then went further and converted the chirality of the four PS bonds adjacent to the two CpG motifs from Sp to Rp. Unexpectedly, this oligonucleotide, WV-1373, completely lost the mTLR9 agonist activity and was a strong mTLR9 antagonist. Without the intention to be bound by theory, these results may indicate that in this case Rp chirality adjacent to CpG motifs (e.g., in the CpG region) may not be tolerated for mTLR9 agonists.

Figure 4:
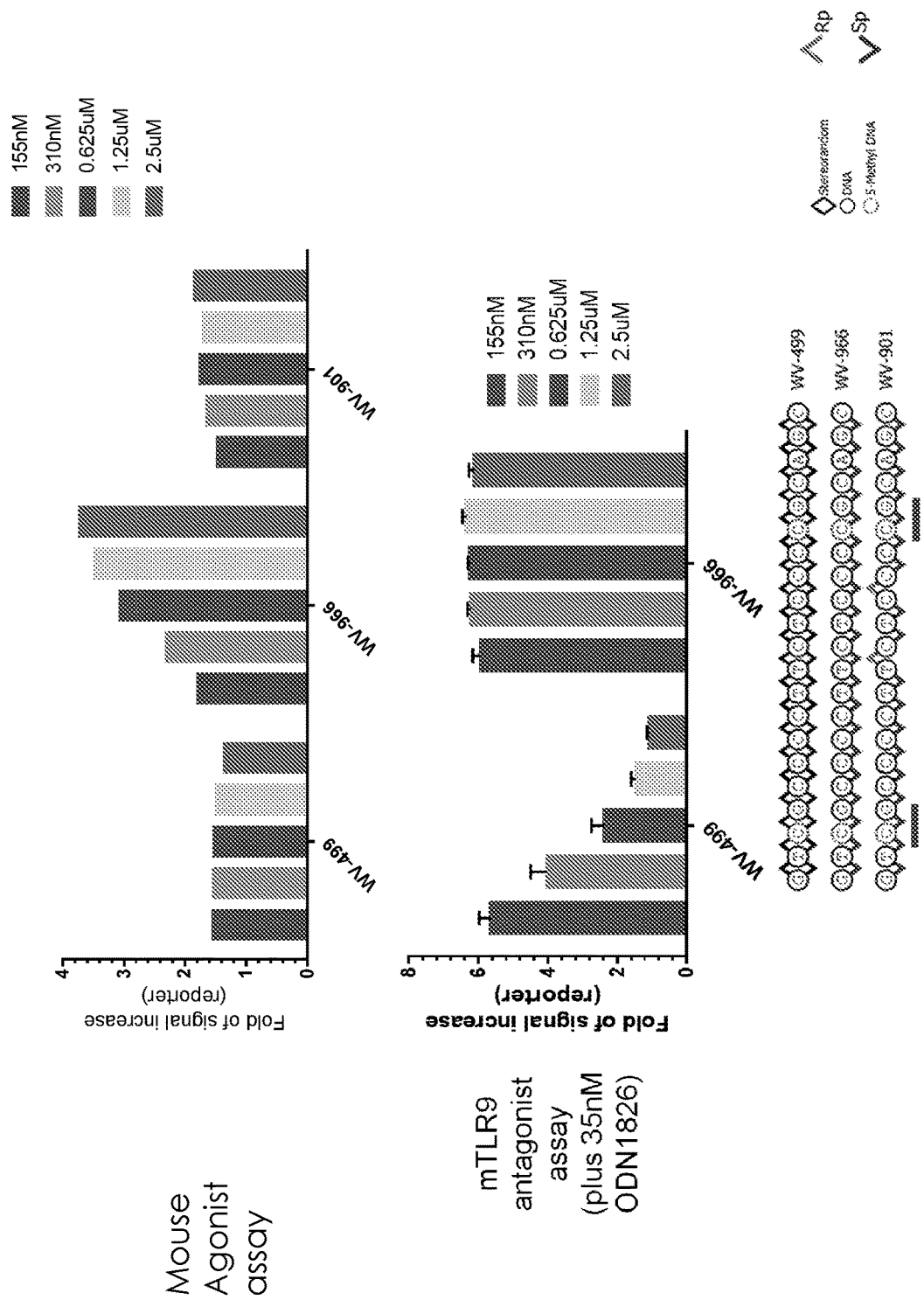
FIG. 4 shows the correlation of mouse TLR9 activities in vitro and in vivo, with in vitro data shown; data from SMAD7 series.
Figure 5:
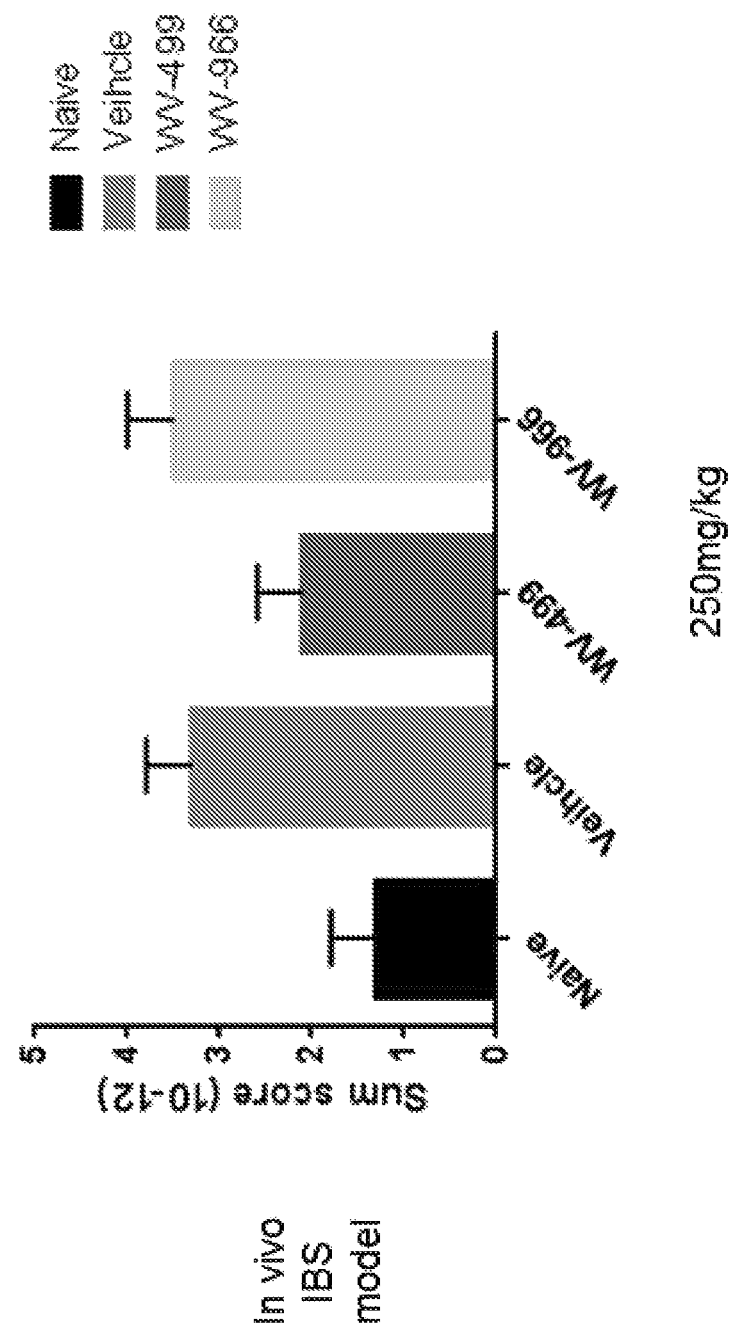
FIG. 5 shows that in an in vivo TNBS induced IBD mouse model, oral administration of WV-499 at 250 mg/kg significantly reduced the inflammation in the gut as measured by colitis score of inflammation, edema and mucosal necrosis of colon sections; the stereopure isomer, WV-966, had little effect.

It is well-known that methylation of CpG often abolishes or significantly reduces the TLR9 agonist activities of an oligonucleotide with normal phosphate (PO) bonds. We asked whether this applies to CpG-oligonucleotide with PS linkages. Two pairs of stereopure oligos were generated (FIGS. 2 to 4). In the first pair WV-966 and WV-1384 had common all-Sp backbones; but they had different methylation statuses on CpG, with WV-966 being the methylated version of WV-1384 (FIG. 3). The second pair of CpG-oligos, WV-1374 and WV-1375, similarly had either methylated (WV-1374) or unmethylated CpG (WV-1375), but with a Rp in the CpG motif (FIG. 3). Agonist activities of these four oligos were tested on mouse TLR9 reporter cells. In the context of an all-Sp backbone, methylation moderately reduced the agonist activity of CpG oligonucleotide by only 2-fold. However, in the context of Rp-substituted CpG motifs, methylation had a very strong effect, with a reduction of activity by about 10-fold (FIG. 3). This PS chirality-dependent effect of methylation on CpG was confirmed with oligos targeting different sequences (FIG. 11).

We next examined the differences in TLR9 activation between stereorandom and stereopure isomers. WV-499, the stereorandom counterpart of the stereopure oligonucleotide WV-966, is completely devoid of mTLR9 agonist activity in vitro (FIG. 4), and was an antagonist on mTLR9. In an in vivo TNBS induced IBD mouse model, oral administration of WV-499 at 250 mg/kg significantly reduced the inflammation in the gut as measured by colitis score of inflammation, edema and mucosal necrosis of colon sections; while its stereopure isomer, WV-966, had little effect. This result demonstrated that a stereorandomer could have activity very different from its stereopure counterparts on mouse TLR9 protein.

To explore the effects of PS chiralities on TLR9 of human origin, we systemically modified the PS linkages in ODN2006, a well-known hTLR9 agonistic oligonucleotide widely used in the field. Modifications were introduced simultaneously to all of the four CpG motifs present in ODN2006. For each of the CpG motif, three relevant PS linkages, one in CpG motif and two adjacent to it, were the focus of PS chirality investigation. These three relevant PS bonds had a total of eight combinations of PS chiralities, which from 5' to 3' were RRR, SRR, RSR, RRS, SSR, SRS, RSS and SSS (FIG. 2a). PS in the rest of the oligos were maintained as Sp configurations. In total, eight stereopure oligos were generated, from WV-1694 to WV-1701 (FIG. 7).

Agonist activity of the eight stereopure oligos was tested in a human TLR9 specific reporter cell line. As shown in FIG. 7, chirality of the PS linkage either within the CpG motif, or on the 5'side of CpG motif, could be either Sp or Rp configuration. A 2 to 5 fold reduction on agonist activity was observed in all four oligos that had an Rp configuration 3' of CpG motif. For example, at concentrations of 0.31 nM or 0.16 nM, WV-1699 (SRR) showed a 2.5-fold weaker agonist activity compared to WV-1696 (SRS). Similarly, WV-1697 (SSR) with Rp on the 3' of CpG motif was 3-fold less potent than WV-1694 (SSS); WV-1700 (RSR) 2-fold less potent than WV-1695 (RSS); WV-1701 (RRR) than WV-1698 (RRS).

In addition to PS linkages, substitutions at the T carbon position with F, OMe or MOE on nucleotide ribose rings may also contribute significantly to improved physical and biological profiles of synthetic oligonucleotides. It was reported that 2'-modifications on CpG motif significantly reduced or eliminated the TLR9 agonist activities of oligonucleotides tested. Haas et al. 2008 Immunity 28: 315-323; and Agrawal et al. 2001 Curr. Cancer Drug Target 1: 197-209.

Figure 6:
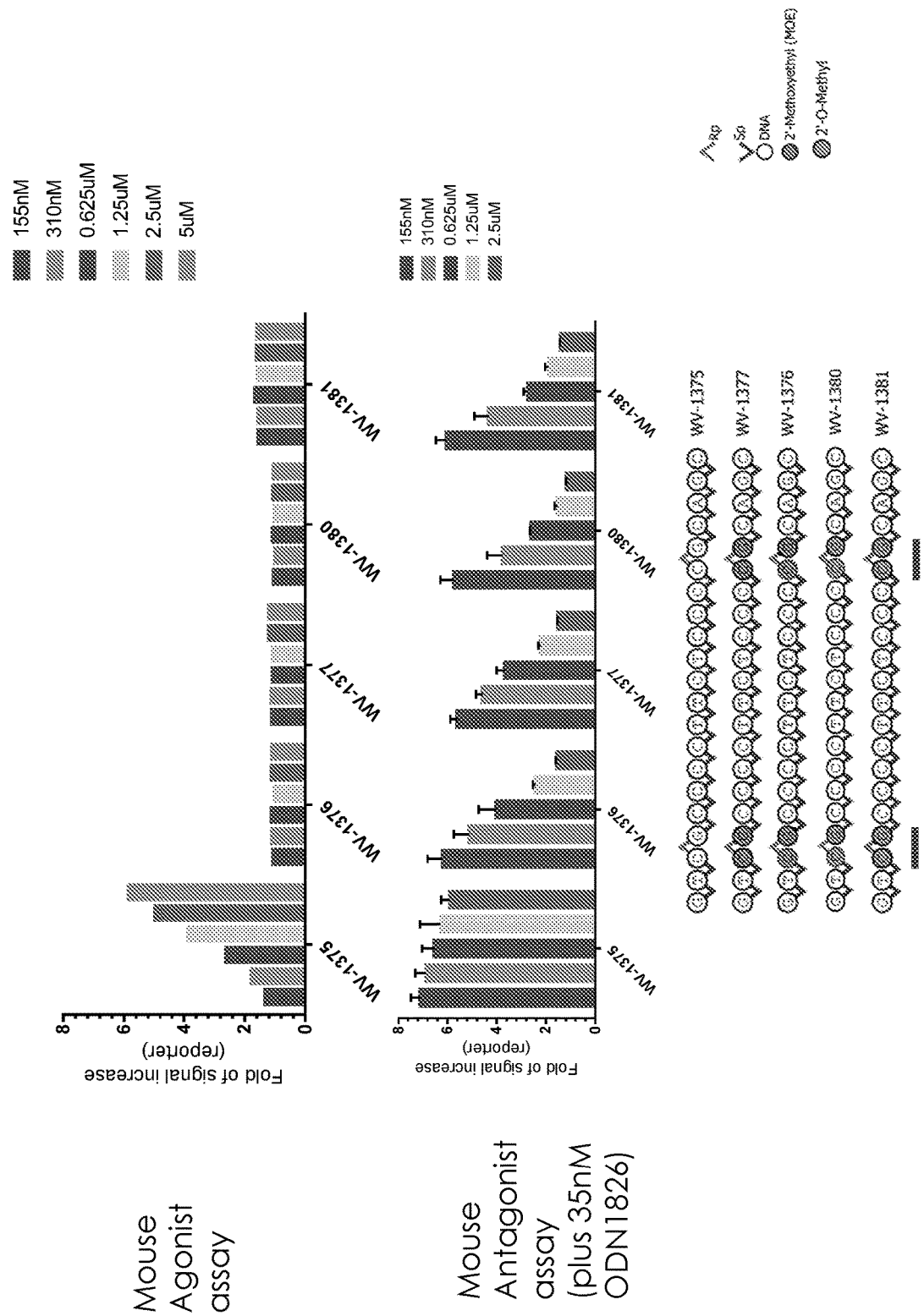
FIG. 6 shows that T modification on CpG in some embodiments eliminates TLR9 agonist activity for mouse TLR9; data from SMAD7 series.

We evaluated the effect of 2'-modifications on a mouse TLR9 agonist. WV-1375 is a stereopure DNA oligonucleotide and a strong mTLR9 agonist (FIGS. 3 and 6). WV-1375 has two CpG motifs composed of DNA monomers, i.e. with hydrogen at the T position. We generated two 2'-modified versions of WV-1375, with Omethyl groups in WV-1381, and MOE groups in WV-1377 (FIG. 6). These substitutions led to complete loss of agonist activities on mouse TLR9, and converted both WV-1381 and WV-1377 into mTLR9 antagonists (FIG. 6). We also examined the effect of CpG methylation. WV-1376 was the CpG methylated counterpart of WV-1377; and WV-1380 the CpG methylated counterpart of WV-1381. CpG methylation had no additional effects on the mTLR9 antagonist activities, indicating that 2'-modifications already strongly suppressed the immune activation activities of the CpG-oligos on mTLR9.

Figure 18:
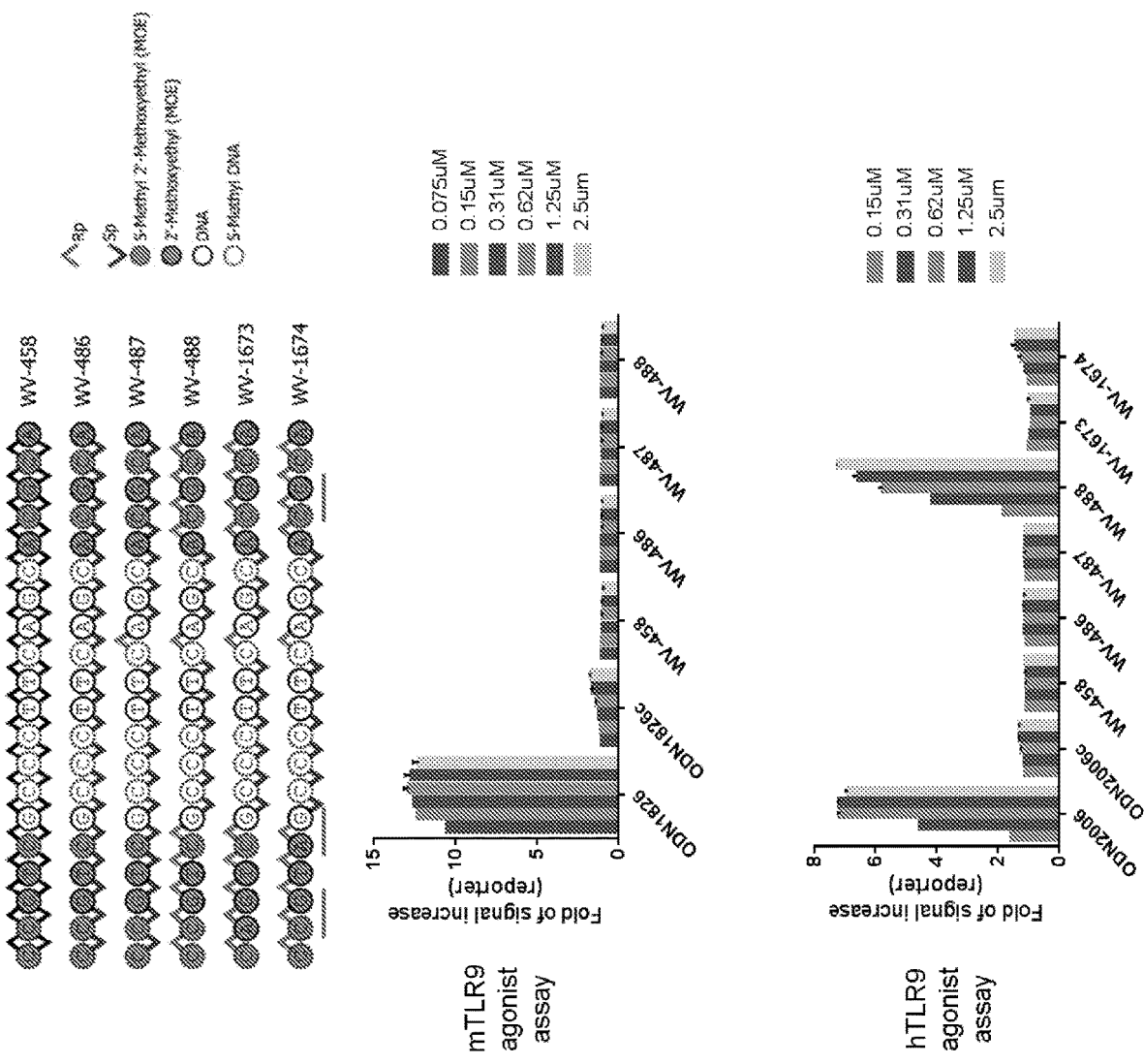
FIG. 18 shows mouse and human TLR9 responses against various CpG oligonucleotides.

We next examined whether 2'-modifications similarly affect human TLR9. WV-458, a stereorandomer, is an antisense oligonucleotide targeting SOD1 (FIG. 18). It was designed as a 5-10-5 type of antisense oligonucleotide (ASO) with a core of ten DNA nucleotides, and five 2'-MOE modified RNA nucleotides on each of the two termini (also called wings). The DNA core binds to target RNAs and induces RNA cleavage through an RNaseH-mediated mechanism. There are a total of three CpG motifs in WV-458, with two CpG on the 5' wing and one CpG on the 3' wing. Since all of the three CpG motifs had methyl-C and were 2'-modified by MOE, it was believed that the modified oligonucleotide would have little or no agonistic activities on TLR9. As shown in FIG. 3b, WV-458 did show no agonist activity on either human or mouse TLR9.

Figure 19:
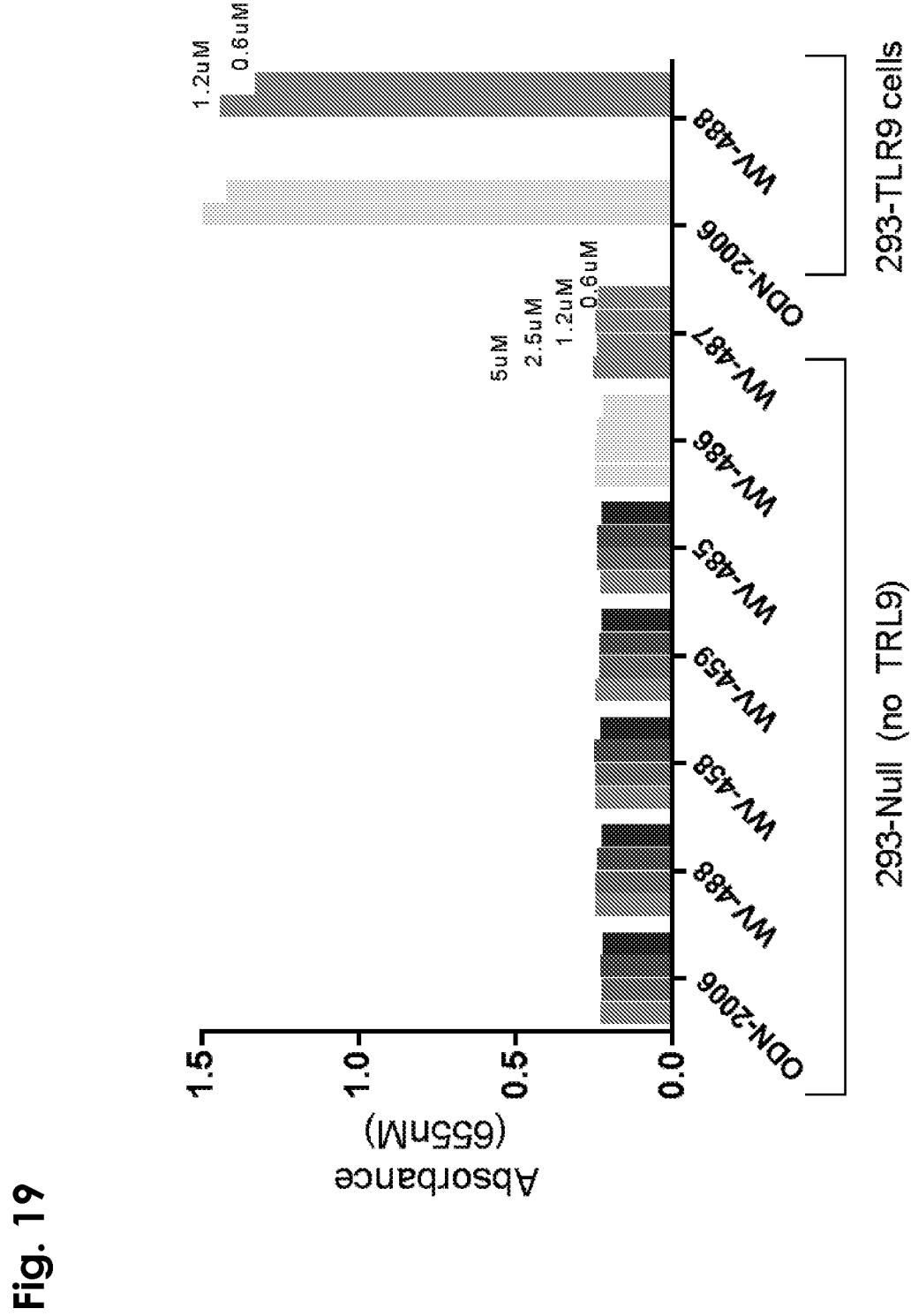
FIG. 19 shows that various CpG oligonucleotides have no immunomodulatory activity on cells lacking TLR9.

We then investigated a series of stereopure oligos that had the same T-modifications and CpG methylation status, but with defined stereochemistry (FIG. 18). In WV-486 and WV-487, we introduced all-Sp configuration to nucleotides on the wings. WV-487 differed from WV-486 by a single Rp at position 12, designed to enhance the RNaseH activities of the antisense oligonucleotide (FIG. 3b). In WV-488, the wings were designed to have an all-Rp configuration. Agonist activities on hTLR9 were then evaluated. Results showed that WV-486 and WV-487 had no agonist activity; however, WV-488 was a surprisingly strong hTLR9 agonist, with activities comparable to that of ODN2006. The agonist activity of WV-488 was specific to human TLR9, as it showed no activity on mouse TLR9 or on cells without TLR9 (FIGS. 18 and 19). These results demonstrated that in some embodiments Rp PS linkages on the CpG may significantly improve the hTLR9 agonist activity of oligonucleotides with 2'-MOE modifications and C methylations.

We next tested whether the activity observed on WV-488 was CpG motif-dependent. Alteration of either CpG motif on the 5' wing to ApG significantly reduced the agonists activity of WV-488 (FIG. 18), suggesting the indispensability of these CpG motifs to these oligonucleotides for TLR9 agonist.

Figure 15:
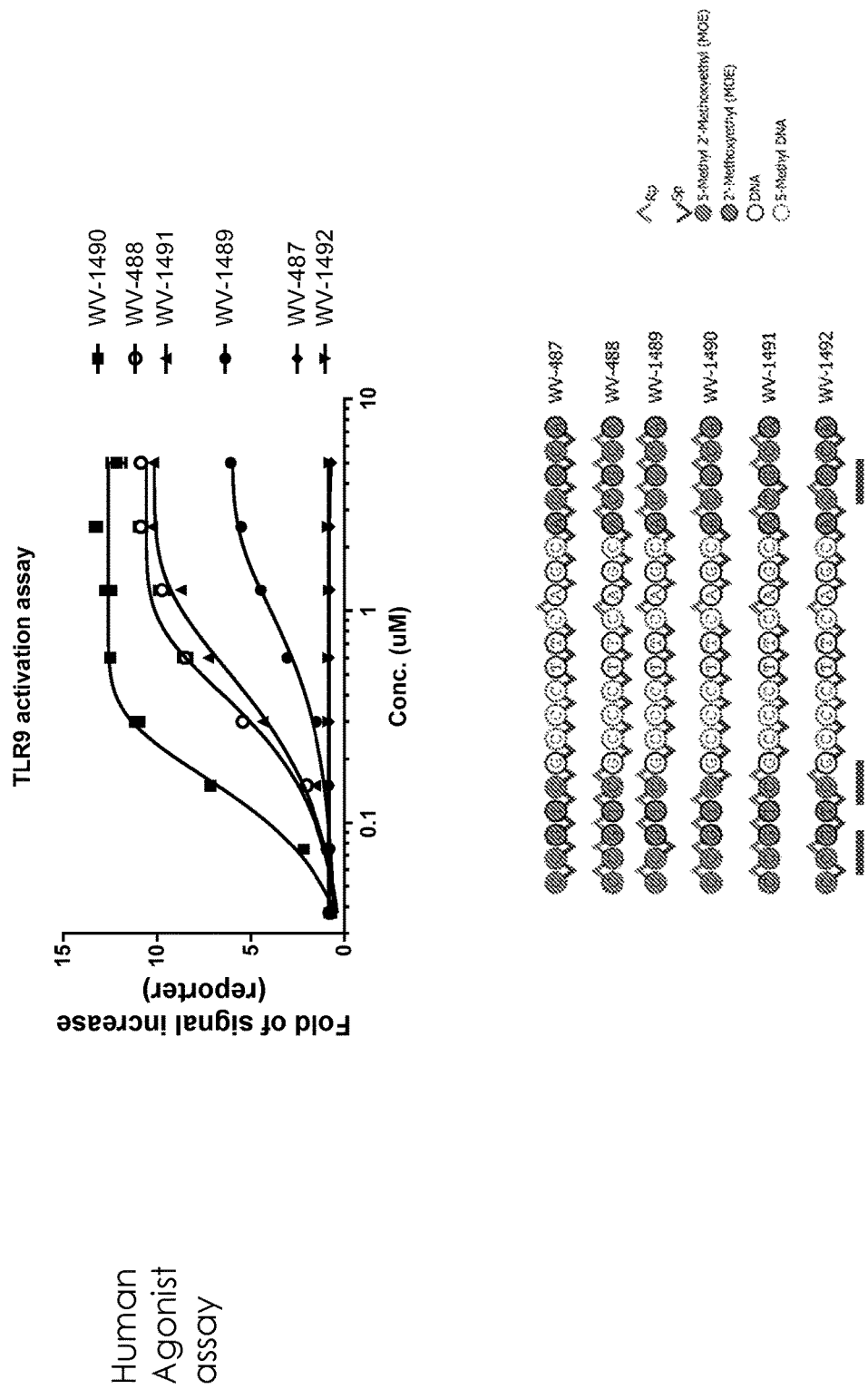
FIG. 15 shows that stereochemistry affects human TLR9 activity even in the presence of base and sugar modifications; data from SOD1 series.
Figure 16:
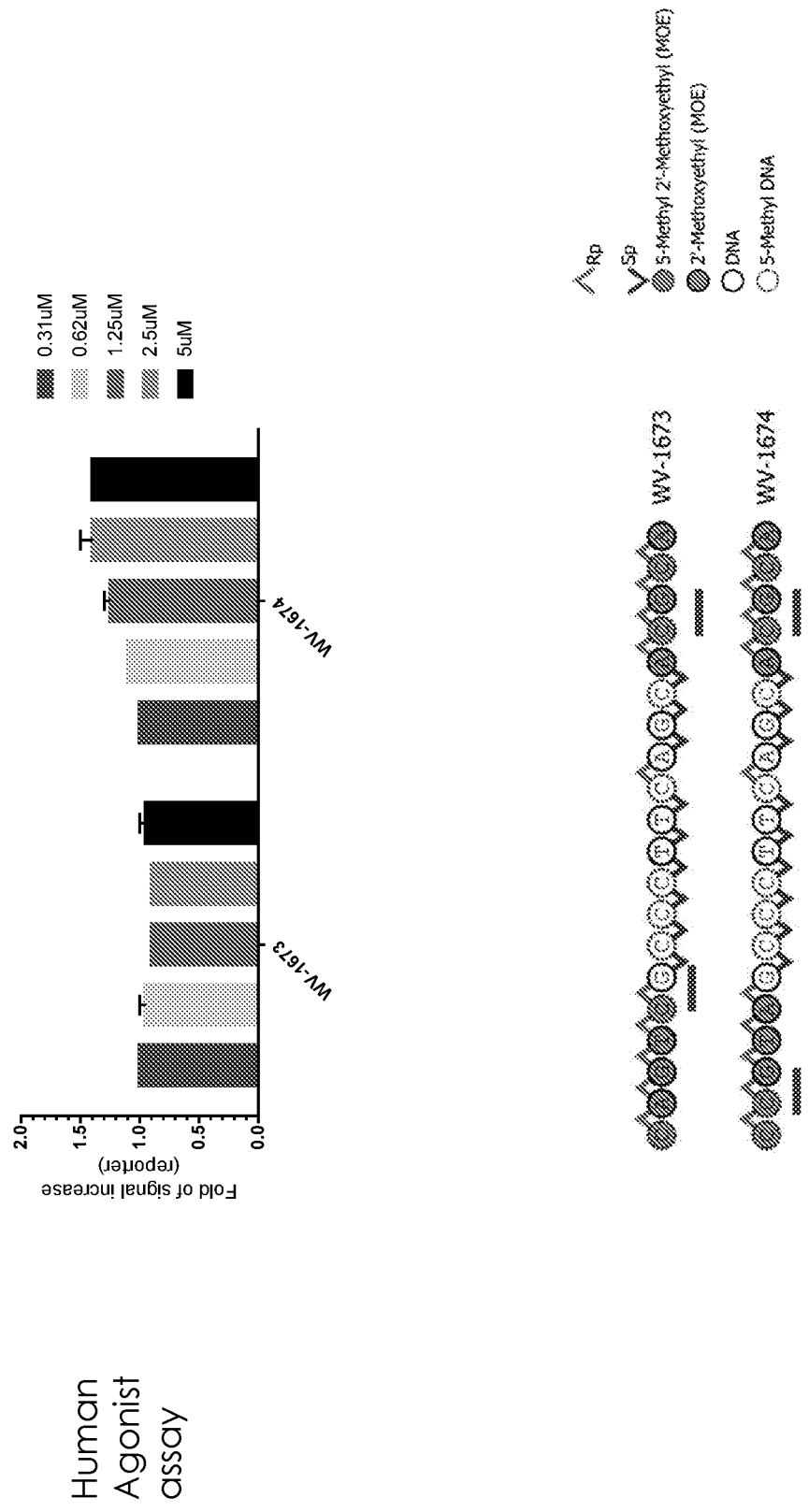
FIG. 16 shows that replacement of CpG with ApG reduces human TLR9 activity of the parental sequence; data from SOD1 series.

We further investigated how each of the three CpG motifs contributed to the overall hTLR9 agonist activities of WV-488. We first generated three stereopure oligos where the chirality of the PS linkage in each of the three CpG motifs was converted one-by-one from Rp to Sp chirality, as shown in WV-1489, WV-1490 and WV-1491 (FIG. 15). For example, in WV-1489, the first CpG from the 5' end of the oligonucleotide was converted from Rp to Sp; in WV-1490, the Rp linkage in the second CpG motif was converted to Sp; and WV-1491, third CpG was converted. Results showed that Rp-to-Sp conversion at each CpG motif had different effects on the overall hTLR9 agonist activities. For example, WV-1489 showed an approximately 2-fold decrease in hTLR9 agonist activity, compared to WV-488, suggesting that an Rp PS linkage in configuration of the first CpG motif on the 5' of the oligonucleotide is beneficial to hTLR9 agonist activity. WV-1490 had about 5-fold increase in TLR9 activation after Rp-to-Sp conversion, indicating a preference for Sp chirality at the second CpG motif. WV-1491 showed no difference in activity from WV-488, indicating that chirality of the CpG on the 3' of WV-488 does not influence hTLR9 activation as much. We next tested if the chiralities of the PS bonds adjacent to the CpG motif were critical to hTLR9 agonist activity. In WV-1492, all the adjacent PS linkages were converted from Rp to Sp, while those of the CpG motif themselves remained as Rp. This conversion showed complete loss of any hTLR9 agonist activity. These results demonstrated that PS chirality in both the CpG motifs themselves and the adjacent PS bonds contributes to the overall TLR9 agonist activities in position- and context-dependent manners.

Figure 17:
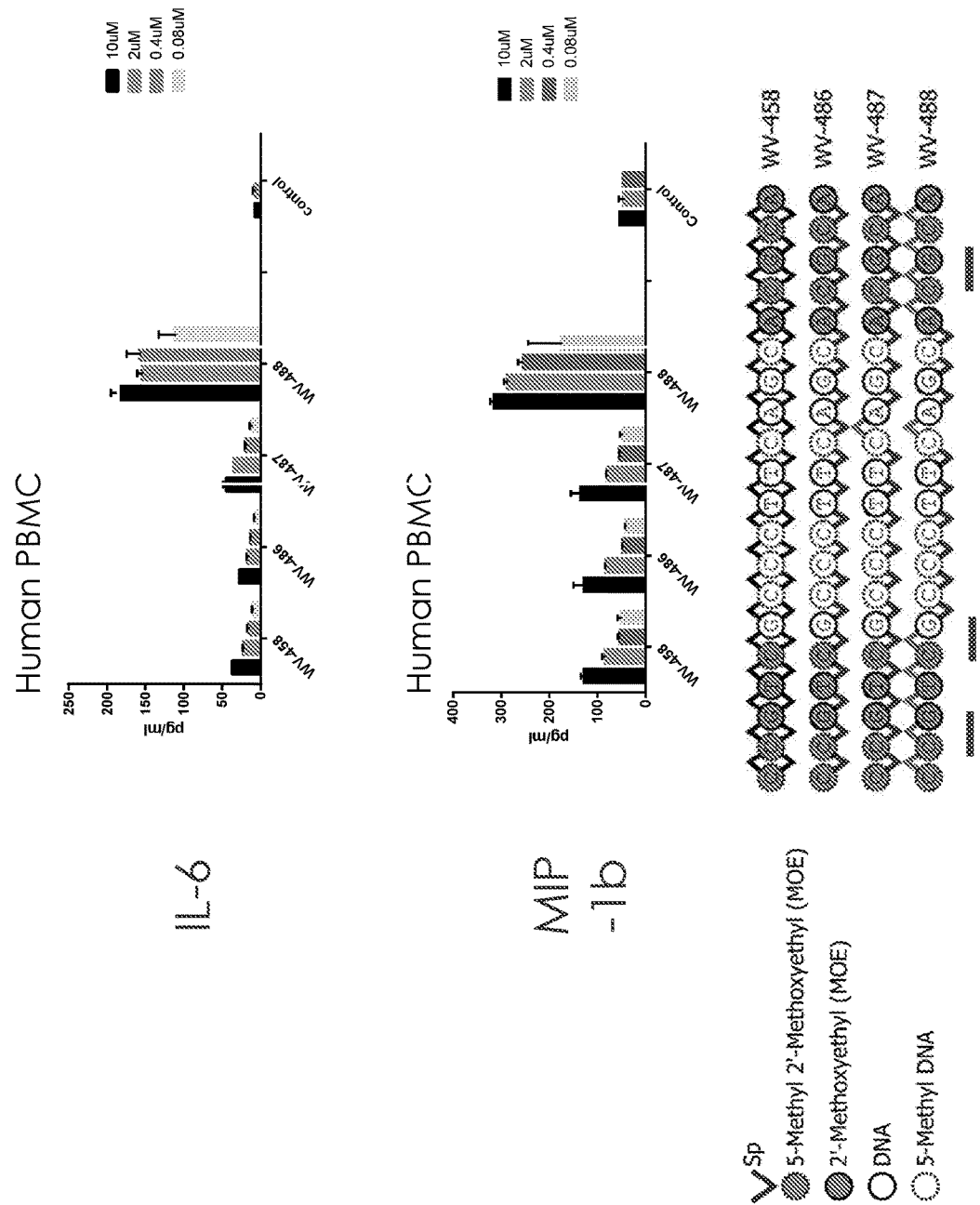
FIG. 17 shows the correlation of reporter assay with cytokine releases from human PBMC; data from SOD1 series. In this figure, agonistic activity of CpG oligonucleotides was measured by secretion of inflammatory cytokines (IL-6 and MIP-1β).
Figure 20:
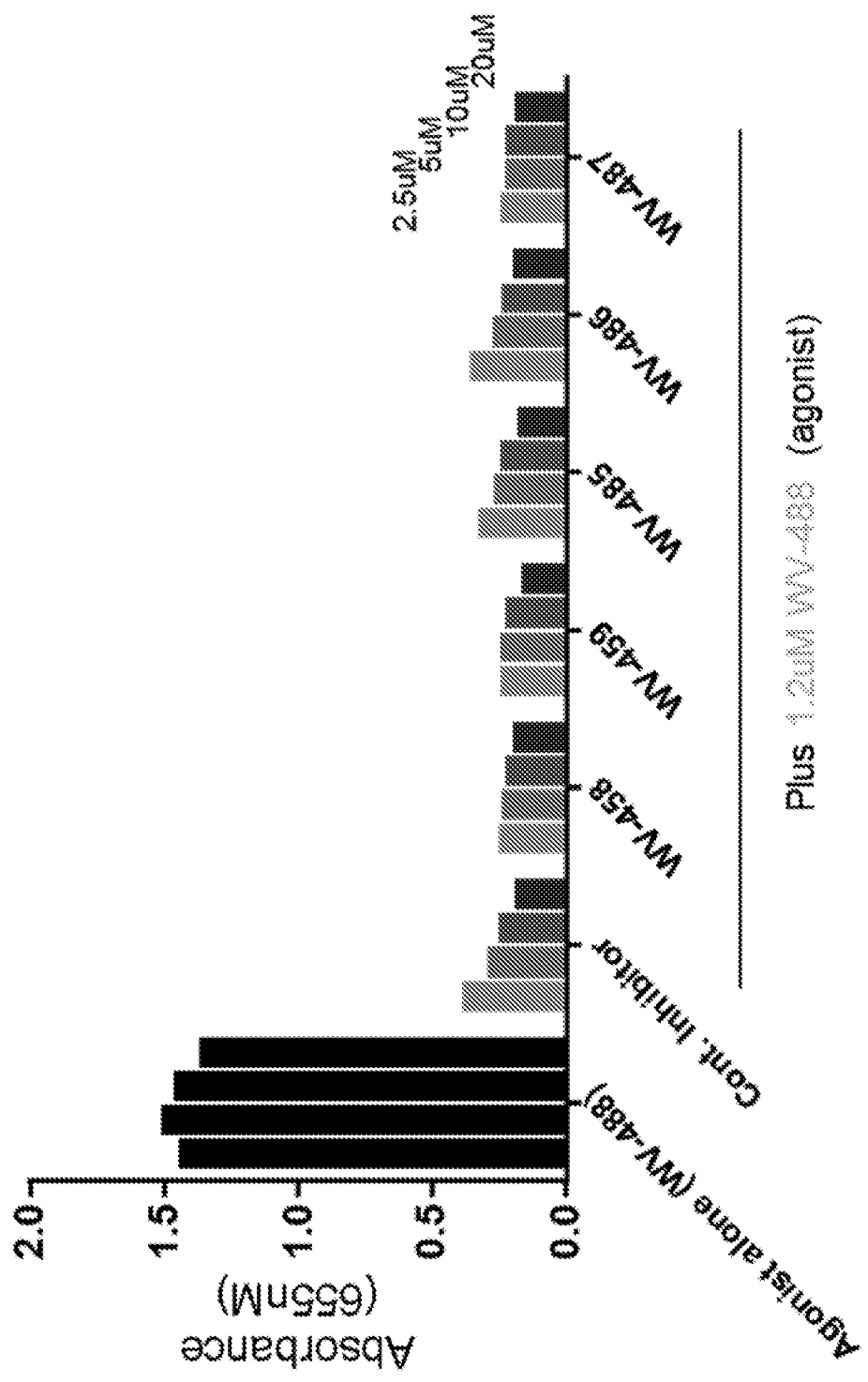
FIG. 20 shows the agonist activity of WV-488 can be sequestered by antagonistic CpG oligonucleotides.
Figure 21:
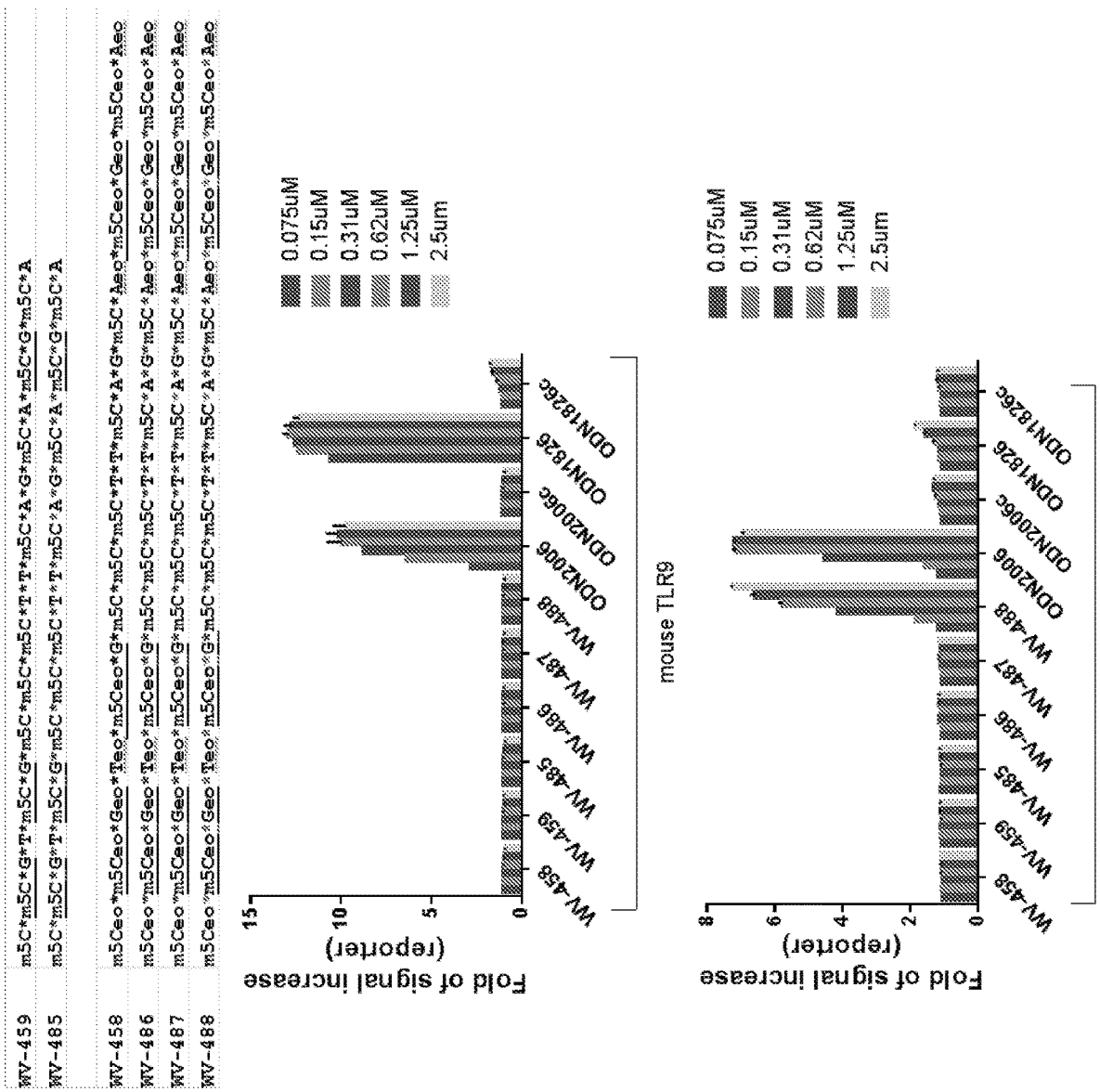
FIG. 21 shows mouse and human TLR9 responses against various CpG oligonucleotides.
Figure 22:
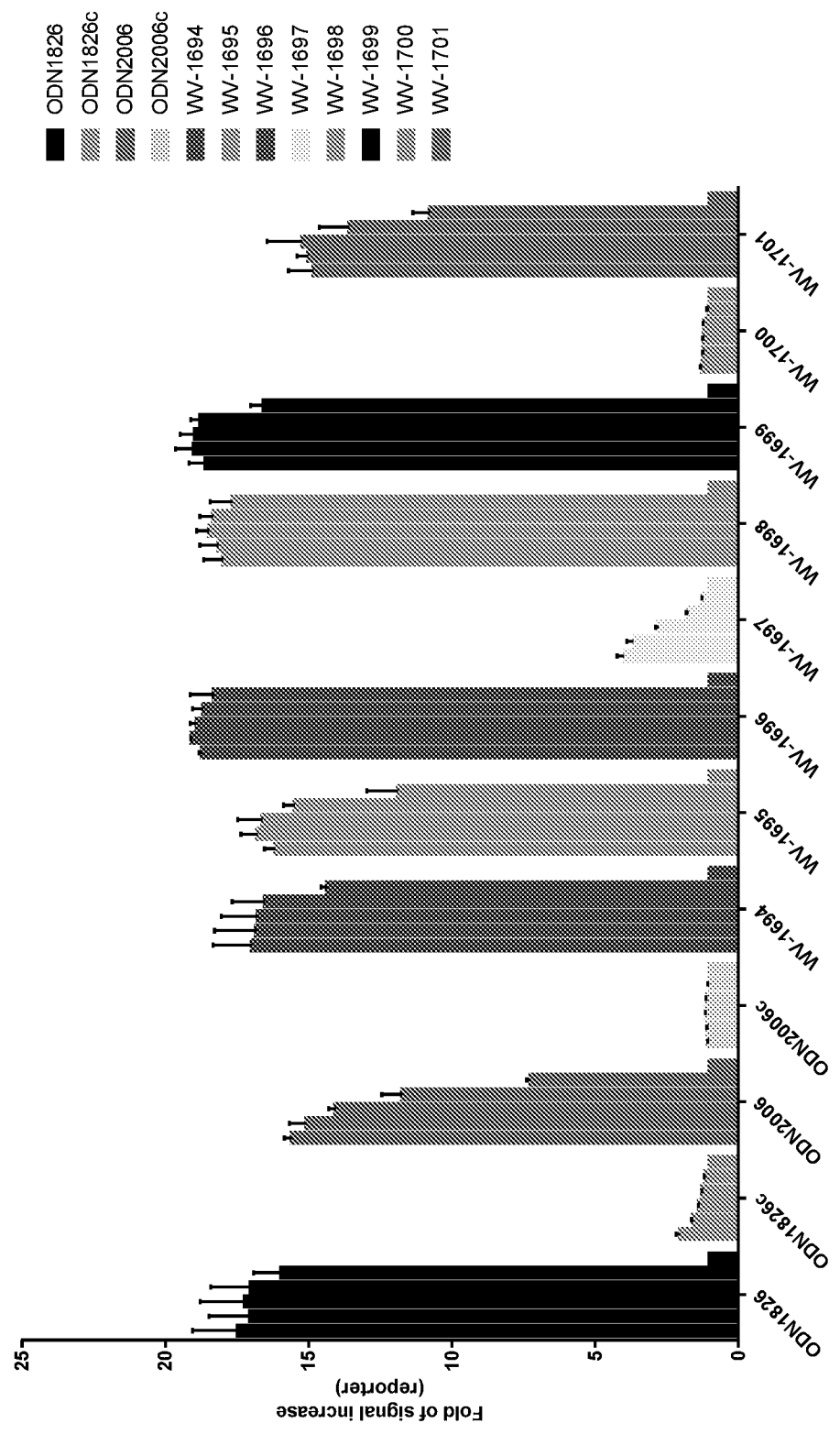
FIG. 22 shows activities of OND2006 series on mouse TLR9.
Figure 23:
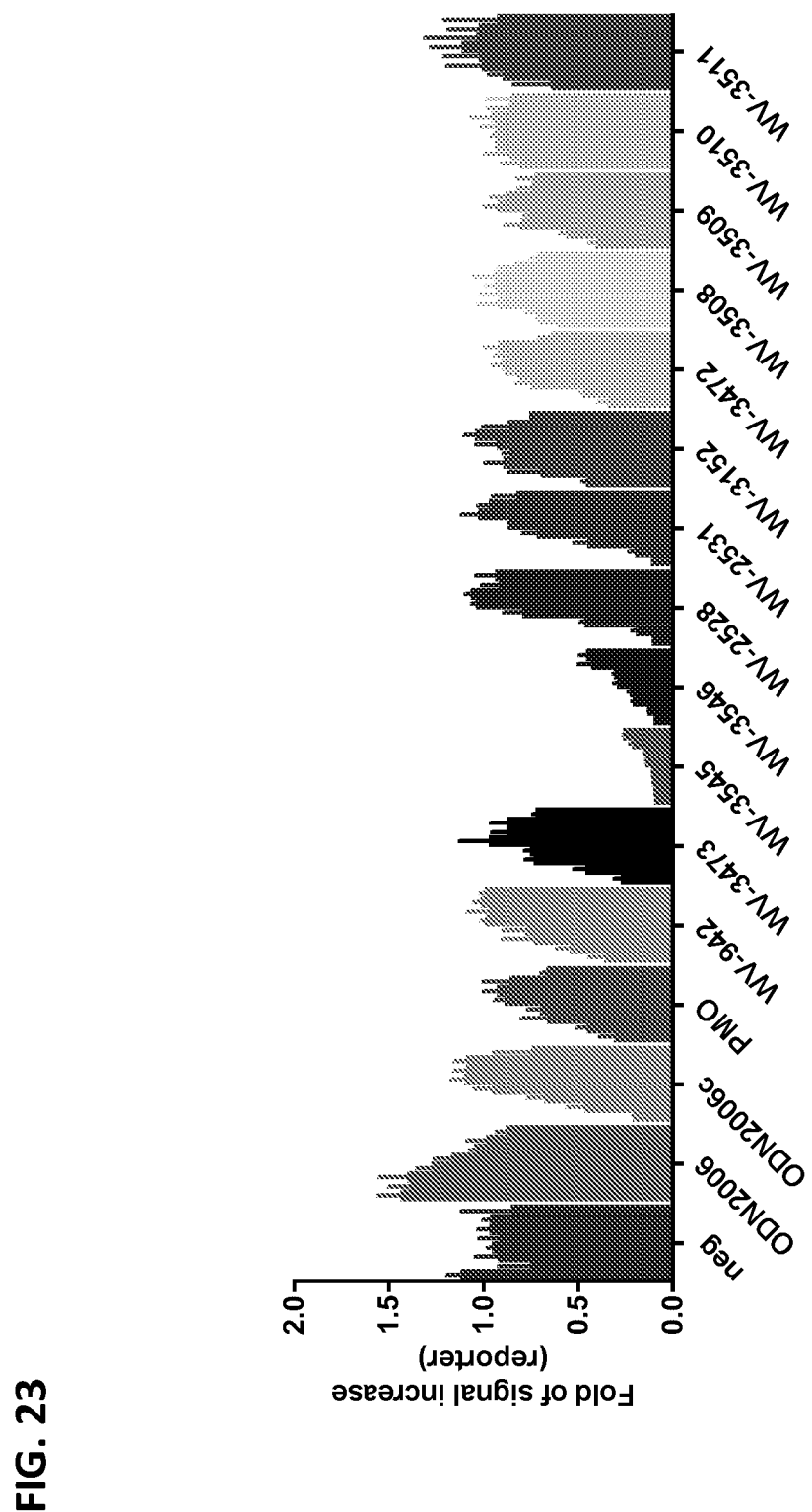
FIG. 23 shows that example provided oligonucleotides comprising lipid moieties can effectively counteract hTLR9 agonistic activity (and to antagonize hTLR9). As demonstrated, conjugates of lipids (e.g., stearic acid (WV-3545) or turbinaric acid (WV-3546)) and oligonucleotides (e.g., WV-3473 (WV-3545 and WV-3546)) have significantly increased hTLR9 antagonistic activities. The concentration of agonistic oligonucleotide ODN2006 was held constant at 0.3 μM. Each oligonucleotide was tested at decreasing concentrations of: 5, 2.5, 1.25, 0.6, 0.3, 0.15 and 0.075 μM (from left to right). Treatment was gymnotic (without transfection reagent). The experiment was done in triplicate, with average data shown.
Figure 24:
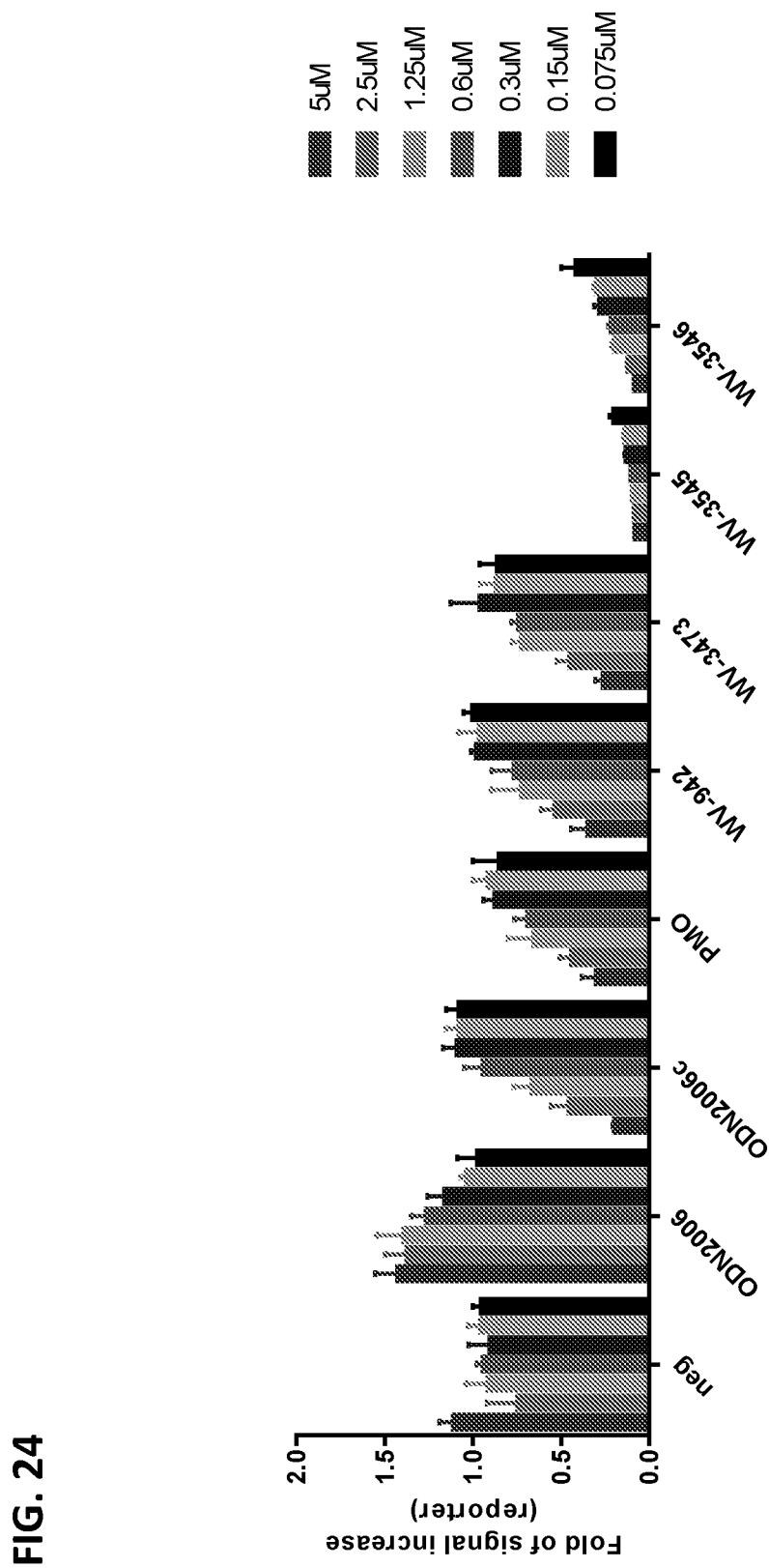
FIG. 24 shows that example provided oligonucleotides comprising lipid moieties can effectively counteract hTLR9 agonistic activity (and to antagonize hTLR9). As demonstrated, conjugates of lipids (e.g., stearic acid (WV-3545) or turbinaric acid (WV-3546)) and oligonucleotides (e.g., WV-3473 (WV-3545 and WV-3546)) have significantly increased hTLR9 antagonistic activities, neg: negative control (buffer only). ODN2006c: an agonistic control in which the CpG sequence is replaced by GpC. PMO: Eteplirsen. The concentration of agonistic oligonucleotide ODN2006 was held constant at 0.3 μM. Each oligonucleotide was tested at decreasing concentrations of: 5, 2.5, 1.25, 0.6, 0.3, 0.15 and 0.075 μM (from left to right). Treatment was gymnotic (without transfection reagent). The experiment was done in triplicate, with average data shown.

We confirmed activities of provided stereopure oligos using human peripheral blood mononuclear cells (PBMCs), and profiled cytokines secreted using a multiplexed luminex assay that could detect and quantify a total of 38 different cytokines (FIG. 17). Consistent with the results generated in reporter cell lines, WV-485, WV-486 and WV-487 showed modest effect on cytokine induction from human PBMCs. Stereopure oligonucleotide WV-488 strongly induced the secretions of IL-6 and MIP-1b. These results generated from both TLR9 reporter cells and PBMCs suggest that stereorandom WV-458 was composed of stereoisomers that could be very potent hTLR9 agonists. In vitro, the agonist activity of WV-488 and other agonistic stereoisomers could be sequestered by other antagonistic stereoisomers (FIG. 20). Thus, the overall TLR9 activities of WV-458 appeared to be an hTLR9 antagonist (FIG. 15). In vivo, however, the immune response of a stereo-random oligos will depend on the half-life and distributions of various stereopure isomers.

FIGS. 1 to 4 show that PS chirality in CpG-oligos affects mouse TLR9 activity. These figures show mouse TLR9 responses against agonistic and inhibitory oligos. The activities were analyzed with an NFκβ-dependent reporter assay. Data represent the mean fold of signal increase with standard deviations of three independent experiments. CpG motifs were underlined. PS chirality was indicated in color, with blue as Sp, red as Rp, black as random.

FIG. 7 shows that PS chirality in CpG-oligos affects human TLR9 activity. Shown are human TLR9 responses against agonistic oligonucleotides. The activities were analyzed with an NF-κ3-dependent reporter assay. Data represent the mean fold of signal increase with standard deviations of three independent experiments. CpG motifs were underlined. PS chirality was indicated in color, with blue as Sp, red as Rp, black as random. Methylated C was indicated with dotted circles.

FIGS. 6, 15, 17 and 18 show that 2'-modifications modulate TLR9 activity in species- and PS chirality-dependent manner. The data show that mouse or human TLR9 responses against agonistic and antagonistic oligonucleotides. The activities were analyzed with an NF-kb-dependent reporter assay. Data represent the mean fold of signal increase with standard deviations of three independent experiments. CpG motifs were underlined. PS chirality was indicated in color, with blue as Sp, red as Rp, black as random. Methylated C was indicated with dotted circles. 2'-Omethyl modification was indicated in gray-shaded circles. 2'-MOE modification was indicated in red-shaded circles. FIG. 17 shows Luminex assay to evaluate cytokines secreted from human PBMCs after treatments with indicated concentrations of oligos.

Materials and Methods

Oligonucleotides: Sequence, chemical modifications, and stereochemistry for each oligos could be found in Table 4, including Table 4A (SMAD7 series), Table 4B (ODN2006 series) and Table 4C (SOD1 series).

Human or mouse TLR9 reporter assays.

HEK-Blue™ TLR9 cells stably overexpress the human or mTLR9 gene and an NF-kB inducible secreted embryonic alkaline phosphatase (SEAP) were obtained from Invivogen (San Diego, Calif., EISA). Oligonucleotides at indicated concentrations were plated into 96-well-plates in the final volume of 20 ul in water. $4 \times 10^4$ HEK-Blue TLR9 cells were added to each well in a volume of 180 ul in SEAP detection medium. In certain conditions, oligos were added in the presence or absence of various concentrations of TLR9 agonists, and the cultures were continued for 16 h. At the end of the treatment, OD was measured at 655 nM. The results are expressed as fold change in NF-κB activation over phosphate buffered saline (PBS)-treated cells.

Human PBMC assays. Peripheral blood mononuclear cells (PBMCs) were freshly drawn from healthy human volunteer blood (Hemacare, MA, USA). Human PBMCs ($5 \times 10^6$/ml) were plated into 96-well plates in RPMI medium Supplemented with 10% heat-inactivated defined FBS, 1.5 mM glutamine, 1 mM sodium pyruvate, 0.1 mM nonessential amino acids, 50 μM 2-mercaptoethanol and 100 IU/ml penicillin-streptomycin mix. Oligos dissolved in water were added to the cells at concentrations indicated. The cells were then incubated at 37° C. for 24 h. The levels of cytokines and chemokines in the culture supernatants were measured by using ELISA (ELISA kits purchased from BD) or human 38-plex luminex kit according to the manufacturer's instructions and analyzed with a Luminex 100 or 200 instruments.

Example data were presented in the Figures.

Example 2. Example In Vivo Delivery of Provided Oligonucleotides and Compositions Example in vivo oligonucleotide treatment: Five-week-old mdx mice were dosed i.v. or subcutaneously at 5 mL/kg at concentration of 10 mg/mL on Day 1. On Day 4 (or other days as desired), all animals were subjected to both terminal blood and tissue collection. Plasma was aliquoted into polupropylene tubes and stored at -70° C. For tissue collections, all animals were euthanized via $CO_2$ asphyxiation, and perfused using PBS. The following tissues were also collected: liver, kidney, spleen, heart, thoracic diaphragm, gastrocnemius, quadriceps and triceps. Tissues were snap-frozen (in liquid nitrogen) and stored at -70° C.

Example procedure: In vivo biodistribution of the control oligonucleotide WV-942 and oligonucleotides to be tested (e.g., WV-2588, WV-2581, WV-2582, WV-2584, WV-2585, WV-2586, WV-2587, etc.) was tested following a single subcutaneous administration to C57BL/10ScSn-Dmd$^{mdx}$/J male mice 5 weeks of age (Jackson Laboratory, Stock #001801), Animals were housed at 18° C. to 26° C. and 30% to 70% humidity two per cage in polycarbonate cages during acclimation and throughout the study. Housing included Beta Chip® and Enviro-Dri contact bedding. Standard chow and water were supplied ad libitum. The study complied with all applicable sections of the Final Rules of the Animal Welfare Act regulations (Code of Federal Regulations, Title 9), the Public Health Service Policy on Humane Care and Use of Laboratory Animals from the Office of Laboratory Animal Welfare, and the Guide for the Care and Use of Laboratory Animals from the National Research Council. The protocol and any amendments or procedures involving the care or use of animals in this study were reviewed and approved by the Testing Facility Institutional Animal Care and Use Committee before the initiation of such procedures. Below was an example study design (Number of animals (males): 3):

overnight). After wash with PBST (1×PBS+0.1% Tween-20), block in 5% fat-free milk/PBST at 37° C. for >1 hour.

Tissue sample preparation: Weigh tissue pieces, add 4 volumes of lysis buffer to tissue to achieve 0.2 g tissue/mL, in tissue lysis buffer (IGEPAL 0.5%, 100 mM NaCl, 5 mM EDTA, 10 mM Tris pH8, protease K 300 µg/mL). The homogenate was generated by Bullet Blender (NextAdvance).

Standard Curve: Dilute Test Article into non-treated blank tissue homogenates (matrix) at 10-50 µg/mL (50-250 µg/g tissue). The standard was further serial diluted 1:1 with matrix for 8 points to form standard curve series.

Hybrid-ELISA: Dilute Standard Curve samples, treated tissue homogenates 100-500 times with hybridization buffer (4 M Guanidine; 0.33% N-Lauryl Sarcosine; 25 mM Sodium Citrate; 10 mM DTT). 20 µL of diluted tissue samples were mixed with 180 µL of detection probe diluted in PBST at 333 nM. Samples were denatured using following condition: 65° C., 10 min; 95° C., 15 min; 4° C., ∞. Add 50 µL/well denatured samples into coated 96 wells. Incubate at 4° C. for overnight. Wash plate 3 times with PBST. Add 1:2000 dilution of streptavidin-AP in PBST. Incubate at room temperature for 1 hour. Wash plate 5 times x 2 cycles with PBST on Molecular Device plate wash machine. Add 100 µL/well AttoPhos substrates. Incubate for 10 min, read plate at Molecular Device M5 in fluorescence channel: Ex435 nm, Em555 nm. Take another read at 20 min. Oligonucleotide concentration is calculated against Standard Curve by using either linear curve fit or 4-parameter curve fit.

| Group | Test Article | Dose, mg/kg | Dosing Route/Dosing Day | Test Article Concentration, mg/ml | Dose Volume, ml/kg | Termination Day |
|---|---|---|---|---|---|---|
| 1 | PBS | — | SC, Day 1 | 0 | 5 | Day 3 |
| 2 | WV-942 | 50 | SC, Day 1 | 10 | 5 | Day 3 |
| 3 | WV-2588 | 50 | SC, Day 1 | 10 | 5 | Day 3 |
| 4 | WV-2581 | 50 | SC, Day 1 | 10 | 5 | Day 3 |
| 5 | WV-2582 | 50 | SC, Day 1 | 10 | 5 | Day 3 |
| 6 | WV-2584 | 50 | SC, Day 1 | 10 | 5 | Day 3 |
| 7 | WV-2585 | 50 | SC, Day 1 | 10 | 5 | Day 3 |
| 8 | WV-2586 | 50 | SC, Day 1 | 10 | 5 | Day 3 |
| 9 | WV-2587 | 50 | SC, Day 1 | 10 | 5 | Day 3 |

Animals were euthanized via $CO_2$ asphyxiation 48 hours (+1 hour) after subcutaneous injection on Day 1. All animals were perfused using PBS. The following collected tissues (liver, kidney 2x, spleen, heart, thoracic diaphragm, gastrocnemius, quadriceps, and triceps) were rinsed briefly with PBS, gently blotted dry, snap frozen (liquid $N_2$) in polypropylene tubes and stored at -70° C. until processing for further analysis.

Oligonucleotide quantification: Briefly, each mouse tissue was weighted and lysed in tissue lysis buffer.

Hybridization assay to detect ASO: Sandwich Methods:

Probe: Capture probe: /5AmMC12/A+GA+AA+TG+CC+A (SEQ ID NO: 1832); Detection probe: T+CT+TC+CT+TG+A/3Bio/(SEQ ID NO: 1833)

Plate: Coat Pierce® Amine-binding, Maleic Anhydride 96-Well Plates, with diluted Capture probe at 500 nM in 2.5% $NaHCO_3$, at 37° C. for at least 1 hour (or 4° C.

Example test results were presented in the Figures, demonstrating that provided oligonucleotides have improved properties (e.g., distribution, metabolism, etc.).

Example 3. Example Synthesis of Turbinaric Acid

Many types of acids, e.g., fatty acids, are widely known in the art and can be utilized in accordance with the present disclosure to incorporate various types of modifications. A person of ordinary skill in the art appreciates that various lipids, .e.g., fatty acids, are commercially available, and/or can be prepared using widely known and practiced technologies (e.g., reagents, methods, etc.), including those illustrated in the present disclosure. The present example describes preparation of turbinaric acid.

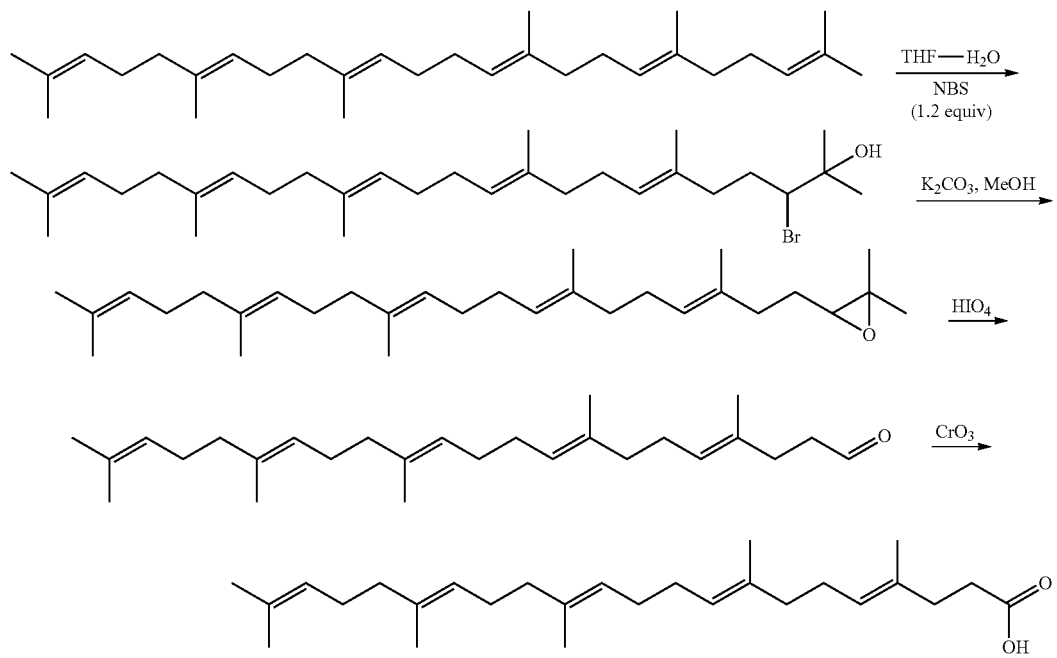

Synthesis of Turbinaric Acid: (4E,8E,12E,16E)-4,8,13,17,21-pentamethyldocosa-4,8,12,16,20-pentaenoic acid. Turbinaric acid has been previously described in, for example, Asari et al. 1989 J. Nat. Prod. 52: 1167-1169.

2-Hydroxy-3-bromosqualene. To a solution of squalene (30.03 g, 73.1 mmol) in THF (210 mL), water (35 mL) was added and then a small amount of THF was added dropwise to obtain a clear solution under Argon. N-bromosuccinimide (15.62 g, 88 mmol) was added portion-wise at 0° C. and the reaction mixture was stirred at 0° C. for 30 minutes and at room temperature for 3 hrs. The solvent was removed under reduced pressure, and brine (500 mL) was added and extracted with EtOA (100 mL×5). The organic layer was dried over anhydrous sodium sulfate and concentrated to give a residue, which was purified by ISCO (220 g gold silica gel cartridge) eluting with hexane to 50% EtOAc in hexane (product was come out at 10-20% EtOAc in hexane) to give 2-hydroxy-3-bromosqualene (9.92 g, 19.54 mmol, 26.7% yield) as a pale yellowish oil. $^1$H NMR (400 MHz, Chloroform-d) δ 5.24-5.05 (m, 5H), 3.98 (dd, J=11.3, 1.9 Hz, 1H), 2.35-2.32 (m, 1H), 2.16-1.90 (m, 18H), 1.85-1.70 (m, 1H), 1.67 (d, J=1.4 Hz, 3H), 1.60 (bs, 15H), 1.34 (s, 3H), 1.32 (s, 3H). MS (ESI), 551.1 and 553.3 (M+HCOO)$^-$.

2,2-Dimethyl-3-((3E,7E,11E,15E)-3,7,12A 6,20-pentamethylhenicosa-3,7,11,15,19-pentaen-1-yl)oxirane. To a solution of 2-hydroxy-3-bromosqualene (9.72 g, 19.15 mmol) in MeOH (360 mL), K$_2$CO$_3$ (5.29 g, 38.3 mmol) was added and the reaction mixture was stirred at room temperature for 2 hrs, filtered and then concentrated under reduced pressure. Then 300 mL EtOAc was added, and filtered, concentrated to give 2,3-oxidosqualene (8.38 g, 19.64 mmol, 100% yield) a colorless oil. $^1$H NMR (400 MHz, Chloroform-d) δ 5.20-5.04 (m, 5H), 2.70 (t, J=7.0 Hz, 1H), 2.20-1.95 (m, 20H), 1.67 (s, 3H), 1.61 (s, 3H), 1.59 (bs, 15H), 1.29 (s, 3H), 1.25 (s, 3H).

(4E,8E,12E,16E)-4,8,13,17,21-pentamethyldocosa-4,8,12A 6,20-pentaenal. To a solution of periodic acid (7.79 g, 34.2 mmol) in water (28 mL) at 0° C., a solution of 2,3-oxidosqualene (8.10 g, 18.98 mmol) in dioxane (65 mL) was added. The reaction mixture was stirred at room temperature for 2 hrs. Water (150 mL) was added and extracted with EtOAc (3×100 mL). The organic layer are dried over anhydrous sodium sulfate and concentrated under reduced pressure to give a residue, which was purified by ISCO (120 g gold silica gel cartridge) eluting with hexane to 10% EtOAc in hexane (product come out at 5-7% EtOAc in hexane to give (4E,8E,12E,16E)-4,8,13,17,21-pentamethyldocosa-4,8,12,16,20-pentaenal (5.80 g, 15.08 mmol, 79% yield) as a colorless oil. $^1$H NMR (400 MHz, Chloroform-d) δ 9.74 (t, J=2.0 Hz, 1H), 5.18-5.04 (m, 5H), 2.50 (td, J=7.5, 2.0 Hz, 2H), 2.31 (t, J=7.5 Hz, 2H), 2.13-1.92 (m, 16H), 1.67 (s, 3H), 1.61 (s, 3H), 1.59 (bs, 12H).

Turbinaric Acid. Sulfuric acid (8.2 mL) followed by sodium dichromate dihydrate (4.42 g, 14.82 mmol) was added to HPLC water (80 mL) at 0° C. The above chromic acid solution was added dropwise to a solution of (4Z,8Z,12E,16E)-4,8,13,17,21-pentamethyldocosa-4,8,12,16,20-pentaenal (5.70 g, 14.82 mmol) in ethyl ether (115 mL) at 0° C. The reaction mixture was stirred at 0° C. for 2 hrs. After 2 hrs, TLC showed the reaction was complete (3:1 hexane/EtOAc). The reaction mixture was diluted with EtOAc (300 mL), washed with brine (100 mL×4), dried over anhydrous, concentrated to give a residue, which was purified by ISCO (80 g silica gel cartridge) eluting with DCM to 5% MeOH in DCM to give turbinaric acid as a colorless oil (5.00 g, 84% yield). $^1$H NMR (400 MHz, Chloroform-d) δ 5.18-5.07 (m, 5H), 2.44 (t, J=6.5 Hz, 2H), 2.30 (t, J=7.7 Hz, 2H), 2.13-1.93 (m, 16H), 1.67 (s, 3H), 1.59 (bs, 15H); MS (ESI), 399.3 (M–H)$^-$.

Example 4. Example Synthesis of 1,7,14-trioxo-12,12-bis((3-oxo-3-((3-(4-sulfamoylbenzamido)propyl)amino)propoxy)methyl)-1-(4-sulfamoylphenyl)-10-oxa-2,6,13-triazaoctadecan-18-oic acid
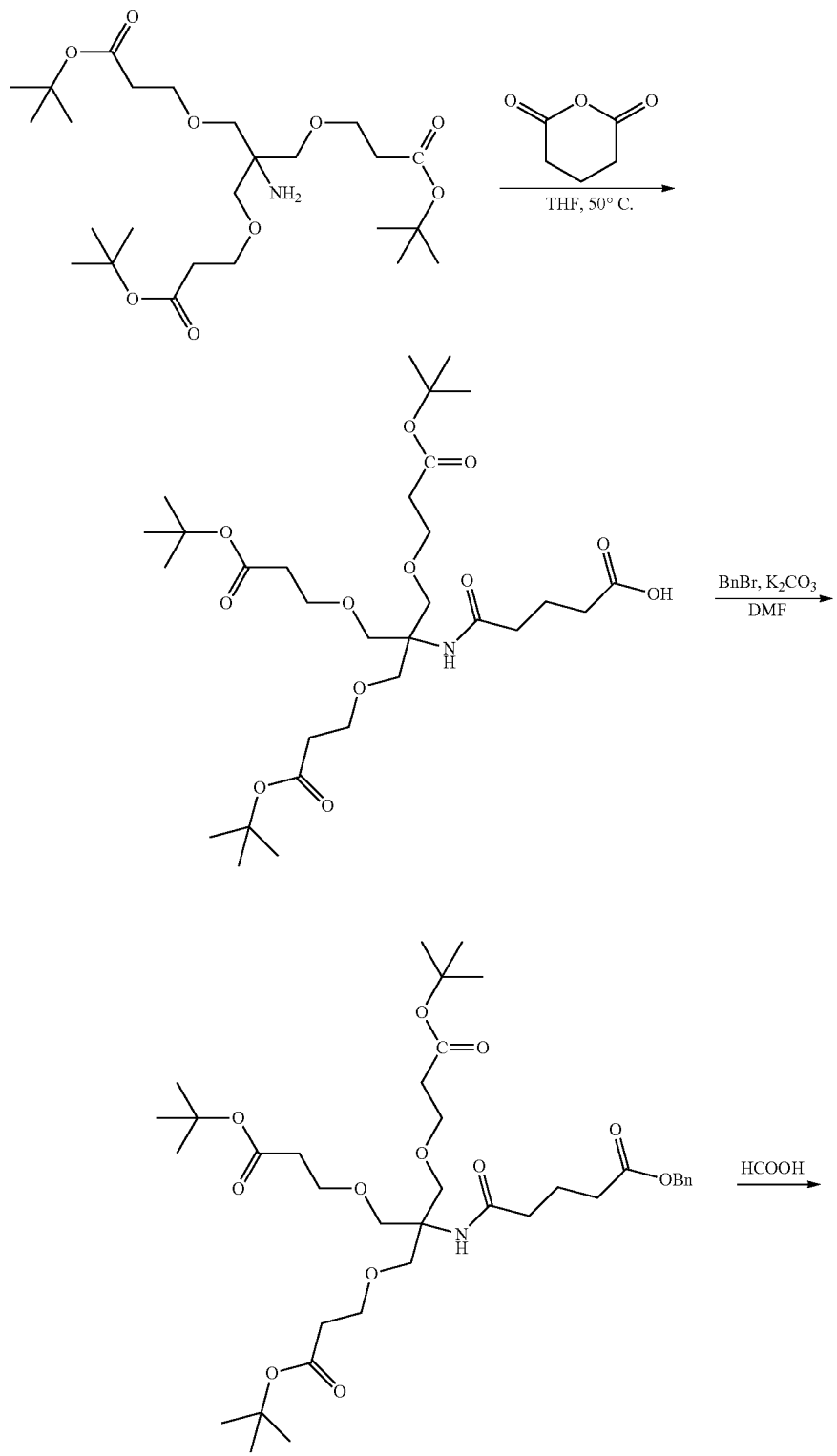

-continued
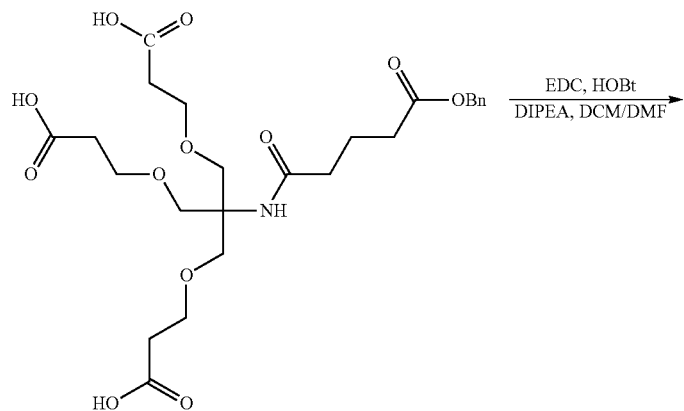
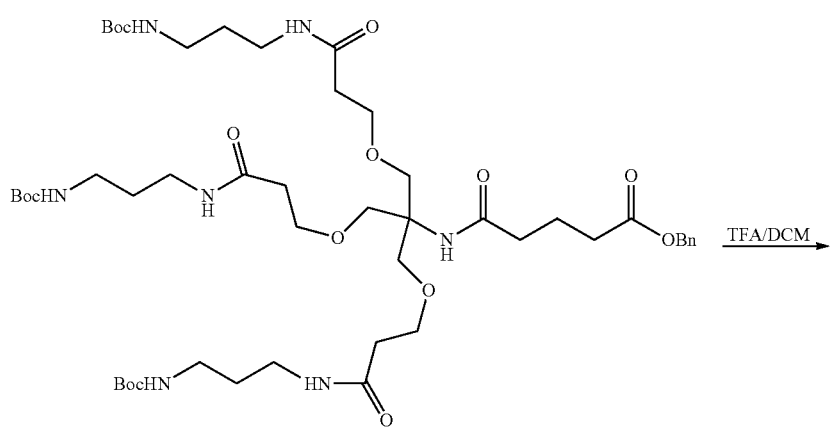
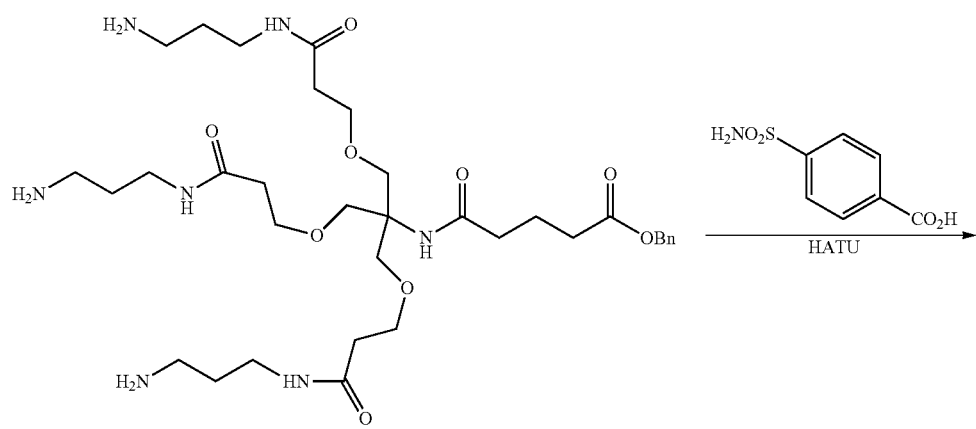

-continued

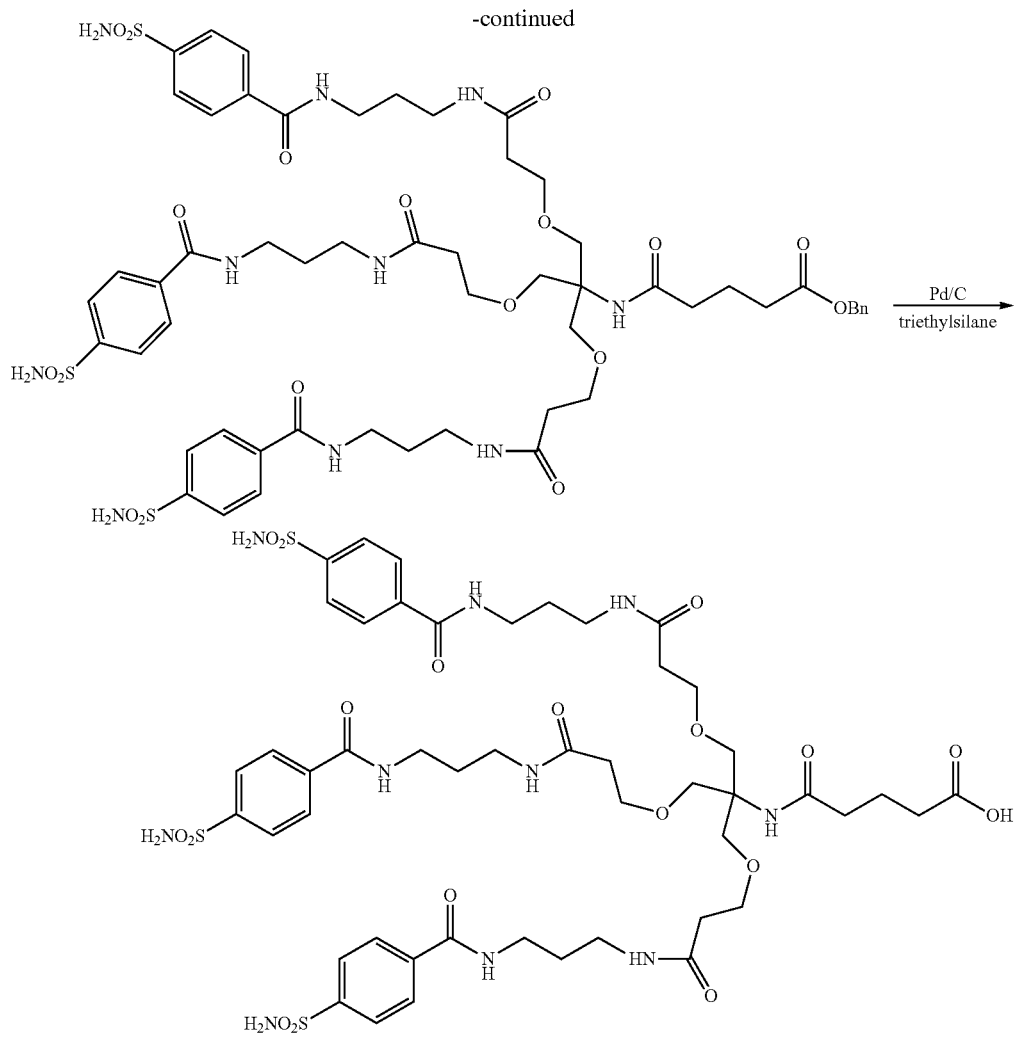

Step 1: A solution of di-tert-butyl 3,3'-((2-amino-2-((3-(tert-butoxy)-3-oxopropoxy)methyl)propane-1,3-diyl)bis(oxy))dipropanoate (4.0 g, 7.91 mmol) and dihydro-2H-pyran-2,6(3H)-dione (0.903 g, 7.91 mmol) in THF (40 mL) was stirred at 50° C. for 3 hrs and at rt for 3 hrs. LC-MS showed desired product. Solvent was evaporated to give 5-((9-((3-(tert-butoxy)-3-oxopropoxy)methyl)-2,2,16,16-tetramethyl-4,14-dioxo-3,7,11,15-tetraoxaheptadecan-9-yl)amino)-5-oxopentanoic acid, which was directly used for next step without purification.

Step 2: To a solution of 5-((9-((3-(tert-butoxy)-3-oxopropoxy)methyl)-2,2,16,16-tetramethyl-4,14-dioxo-3,7,11,15-tetraoxaheptadecan-9-yl)amino)-5-oxopentanoic acid (4.90 g, 7.91 mmol) and (bromomethyl)benzene (1.623 g, 9.49 mmol) in DMF was added anhydrous $K_2CO_3$ (3.27 g, 23.73 mmol). The mixture was stirred at 40° C. for 4 hrs and at room temperature for overnight. Solvent was evaporated under reduced pressure. The reaction mixture was diluted with EtOAc, washed with water, dried over anhydrous sodium sulfate, and concentrated under reduced pressure to give a residue, which was purified by ISCO eluting with 10% EtOAc in hexane to 50% EtOAc in hexane to give di-tert-butyl 3,3'-((2-(5-(benzyloxy)-5-oxopentanamido)-2-((3-(tert-butoxy)-3-oxopropoxy)methyl)propane-1,3-diyl)bis(oxy))dipropanoate (5.43 g, 7.65 mmol, 97% yield) as a colorless oil. $^1$H NMR (400 MHz, Chloroform-d) δ 7.41-7.28 (m, 5H), 6.10 (s, 1H), 5.12 (s, 2H), 3.72-3.60 (m, 12H), 2.50-2.38 (m, 8H), 2.22 (t, J=13 Hz, 2H), 1.95 (p, J=7.4 Hz, 2H), 1.45 (s, 27H); MS (ESI), 710.5 (M+H)$^+$.

Step 3: A solution of di-tert-butyl 3,3'-((2-(5-(benzyloxy)-5-oxopentanamido)-2-((3-(tert-butoxy)-3-oxopropoxy)methyl)propane-1,3-diyl)bis(oxy))dipropanoate (5.43 g, 7.65 mmol) in formic acid (50 mL) was stirred at room temperature for 48 hrs. LC-MS showed the reaction was not complete. Solvent was evaporated under reduced pressure. The crude product was re-dissolved in formic acid (50 mL) and was stirred at room temperature for 6 hrs. LC-MS showed the reaction was complete. Solvent was evaporated under reduced pressure, co-evaporated with toluene (3×) under reduced pressure, and dried under vacuum to give 3,3'-((2-(5-(benzyloxy)-5-oxopentanamido)-2-((2-carboxyethoxy)methyl)propane-1,3-diyl)bis(oxy))dipropanoic acid (4.22 g, 7.79 mmol, 100% yield) as a white solid. $^1$H NMR (500 MHz, DMSO-d$_6$) δ 12.11 (s, 3H), 7.41-7.27 (m, 5H), 6.97 (s, 1H), 5.07 (s, 2H), 3.55 (d, J=6.4 Hz, 6H), 2.40 (t, J=6.3 Hz, 6H), 2.37-2.26 (m, 2H), 2.08 (t, J=13 Hz, 2H), 1.70 (p, J=7.4 Hz, 2H); MS (ESI), 542.3 (M+H)$^+$.

Step 4: To a solution of 3,3'-((2-(5-(benzyloxy)-5-oxopentanamido)-2-((2-carboxyethoxy)methyl)propane-1,3-diyl)bis(oxy))dipropanoic acid (4.10 g, 7.57 mmol) and HOBt (4.60 g, 34.1 mmol) in DCM (60 mL) and DMF (15 mL) at 0° C. was added tert-butyl (3-aminopropyl)carbamate (5.94 g, 34.1 mmol), ED AC HCl salt (6.53 g, 34.1 mmol) and DIPEA (10.55 mL, 60.6 mmol). The reaction mixture was stirred at 0° C. for 15 minutes and at room temperature for 20 hrs. LC-MS showed the reaction was not complete. EDAC HCl salt (2.0 g) and tert-butyl (3-aminopropyl)carbamate (1.0 g) was added into the reaction mixture. The reaction mixture was stirred at room temperature for 4 hrs. Solvent was evaporated to give a residue, which was dissolved in EtOAc (300 mL), washed with water (IX), saturated sodium bicarbonate (2×), 10% citric acid (2×) and water, dried over sodium sulfate, and concentrated to give a residue which was purified by ISCO (80 g gold catridge) eluting with DCM to 30% MeOH in DCM to give benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate 5 (6.99 g, 6.92 mmol, 91% yield) as a white solid. $^1$H NMR (500 MHz, Chloroform-d) δ 7.35 (t, J=4.7 Hz, 5H), 6.89 (s, 3H), 6.44 (s, 1H), 5.22 (d, J=6.6 Hz, 3H), 5.12 (s, 2H), 3.71-3.62 (m, 12H), 3.29 (q, J=6.2 Hz, 6H), 3.14 (q, J=6.5 Hz, 6H), 2.43 (dt, J=27.0, 6.7 Hz, 8H), 2.24 (t, J=7.2 Hz, 2H), 1.96 (p, J=7.5 Hz, 2H), 1.69-1.59 (m, 6H), 1.43 (d, J=5.8 Hz, 27H); MS (ESI): 1011.5 (M+H)+.

Step 5: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate (1.84 g, 1.821 mmol) in DCM (40 mL) was added 2,2,2-trifluoroacetic acid (7.02 mL, 91 mmol). The reaction mixture was stirred at room temperature for overnight. Solvent was evaporated to give benzyl 5-((1,19-di amino-10-((3-((3-aminopropyl)amino)-3-oxopropoxy)methyl)-5,15-dioxo-8,12-dioxa-4,16-diazanonadecan-10-yl)amino)-5-oxopentanoate as a colorless oil. MS (ESI), 710.6 (M+H)+.

Step 6: To a solution of 4-sulfamoylbenzoic acid (1.466 g, 7.28 mmol) in DCM (40 mL) was added HATU (2.77 g, 7.28 mmol) followed by benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate (1.293 g, 1.821 mmol) in DMF (4.0 mL). The mixture was stirred at room temperature for 5 hrs. Solvent was evaporated under reduced pressure to give a residue, which was purified by ISCO (40 g gold column) eluting with DCM to 50% MeOH in DCM to give benzyl 1,7,14-trioxo-12,12-bis((3-oxo-3-((3-(4-sulfamoylbenzamido)propyl)amino)-propoxy)methyl)-1-(4-sulfamoylphenyl)-10-oxa-2,6,13-triazaoctadecan-18-oate (0.36 g, 0.286 mmol, 16% yield). $^1$H NMR (400 MHz, DMSO-d$_6$) δ 8.60 (t, J=5.6 Hz, 3H), 7.96-7.81 (m, 15H), 7.44 (s, 6H), 7.35-7.23 (m, 5H), 7.04 (s, 1H), 5.02 (s, 2H), 3.50 (t, J=6.9 Hz, 6H), 3.48 (s, 6H), 3.23 (q, J=6.6 Hz, 6H), 3.06 (q, J=6.6 Hz, 6H), 2.29 (t, J=7.4 Hz, 2H), 2.24 (t, J=6.5 Hz, 6H), 2.06 (t, J=7.4 Hz, 2H), 1.69-1.57 (m, 8H).

Step 7: To a round bottom flask flushed with Ar was added 10% Pd/C (80 mg, 0.286 mmol) and EtOAc (15 mL). A solution of benzyl 1,7,14-trioxo-12,12-bis((3-oxo-3-((3-(4-sulfamoylbenzamido)propyl)amino)propoxy)methyl)-1-(4-sulfamoylphenyl)-10-oxa-2,6,13-triazaoctadecan-18-oate (360 mg) in methanol (15 mL) was added followed by diethyl(methyl)silane (0.585 g, 5.72 mmol) dropwise. The mixture was stirred at room temperature for 3 hrs. LC-MS showed the reaction was complete. The reaction was diluted with EtOAc, and filtered through celite, washed with 20% MeOH in EtOAc, and concentrated under reduced pressure to give 1,7,14-trioxo-12,12-bis((3-oxo-3-((3-(4-sulfamoylbenzamido)propyl)-amino)propoxy)methyl)-1-(4-sulfamoylphenyl)-10-oxa-2,6,13-triazaoctadecan-18-oic acid (360 mg, 100% yield) as a white solid. $^1$H NMR (400 MHz, DMSO-d$_6$) δ 8.60 (t, J=5.6 Hz, 3H), 7.94-7.81 (m, 15H), 7.44 (s, 6H), 7.04 (s, 1H), 3.50 (t, J=6.9 Hz, 6H), 3.48 (s, 6H), 3.23 (q, J=6.6 Hz, 6H), 3.06 (q, J=6.6 Hz, 6H), 2.24 (t, J=6.4 Hz, 6H), 2.14 (t, J=7.5 Hz, 2H), 2.05 (t, J=7.4 Hz, 2H), 1.66-1.57 (m, 8H); MS (ESI), 1170.4 (M+H)+.

Example 5. Example Synthesis of 2-cyanoethyl ((6Z,9Z,28Z,31Z)-heptatriaconta-6,9,28,31-tetraen-19-yl) diisopropylphosphoramidite and Synthesis of Amidite from Lauryl Alcohol As appreciated by a person having ordinary skill in the art, various alcohols can be converted into phosphoramidites and conjugated to oligonucleotide chains using known technologies in the art in accordance with the present disclosure. The present example illustrates preparation of 2-cyanoethyl ((6Z,9Z,28Z,31Z)-heptatriaconta-6,9,28,31-tetraen-19-yl) diisopropylphosphoramidite, which can be used to, e.g., prepare oligonucleotides comprising Mod 021.

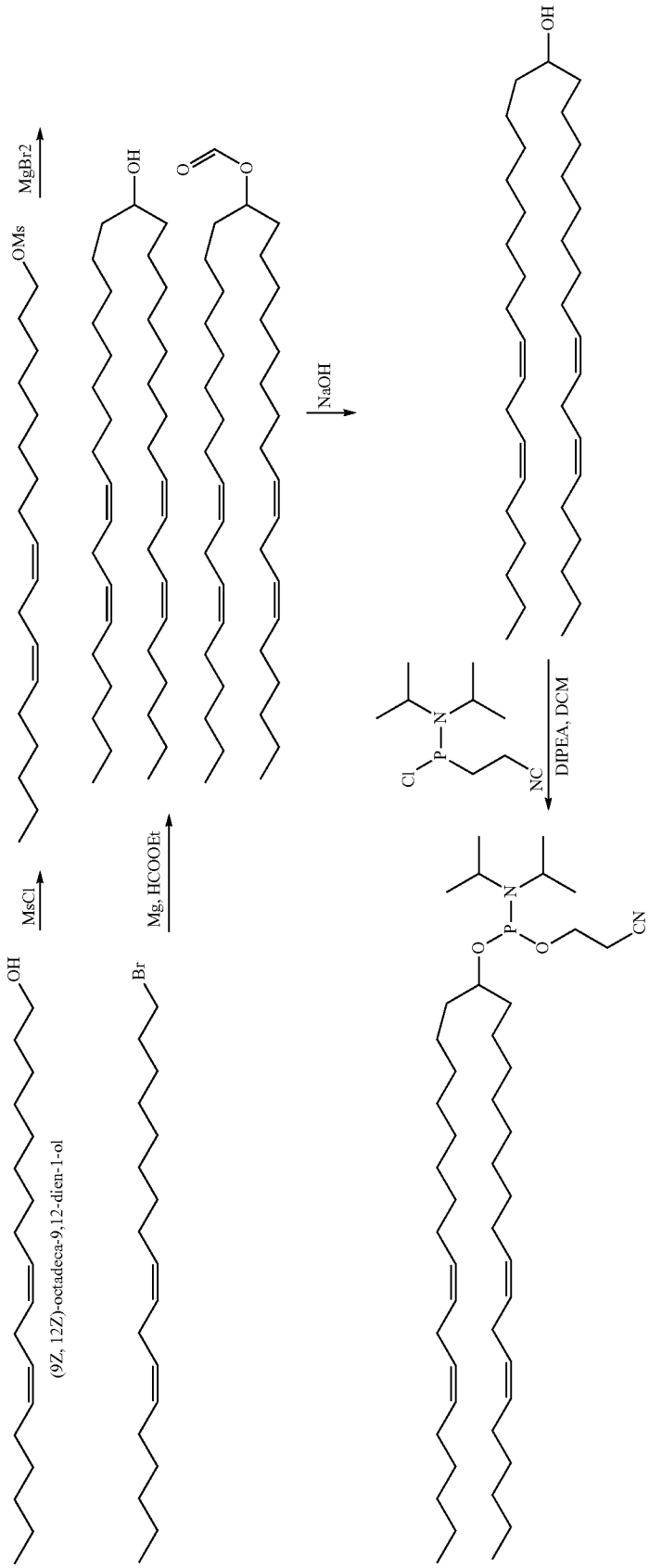

Synthesis of (9Z,12Z)-octadeca-9,12-dien-1-yl methanesulfonate (or linoleyl methanesulfonate). To a solution of linoleyl alcohol (23.31 mL, 75 mmol) and triethylamine (13.60 mL, 98 mmol) in DCM (150 mL) at 0° C. was added methanesulfonyl chloride (6.39 mL, 83 mmol) dropwise. The reaction mixture was stirred at 0° C. for 30 minutes and at room temperature for 3 hrs. The reaction mixture was diluted with DCM (200 mL), washed with water, sat sodium bicarbonate and brine and dried over anhydrous sodium sulfate. Solvent was concentrated to give linoleyl methanesulfonate (26.17 g, 100% yield) as an yellowish oil. Without further purification, the product was directly used for next step. $^1$H NMR (500 MHz, Chloroform-d) δ 5.30-5.41 (m, 4H), 4.22 (t, J=6.6 Hz, 2H), 2.99 (s, 3H), 2.77 (t, J=6.7 Hz, 2H), 2.05 (q, J=6.9 Hz, 4H), 1.74 (p, J=6.7 Hz, 2H), 1.43-1.25 (m, 16H), 0.89 (t, J=6.7 Hz, 3H).

Synthesis of linoleyl bromide. To a solution of linoleyl methanesulfonate (26 g, 75 mmol) in ether (800 mL) was added magnesium bromide ethyl etherate (58.5 g, 226 mmol) under Argon. The reaction mixture was stirred at room temperature for 2 hrs. TLC was used to monitor reaction progress. If not completed, additional magnesium bromide ethyl etherate (14.5 g) was added the reaction mixture and the reaction mixture was stirred at room temperature for 22 hrs. TLC showed the reaction complete (9/1 hexane/EtOAc). The reaction mixture was filtered, washed with ether (200 mL), hexane (100 mL), and concentrated under reduced pressure to give a residue, which was purified by ISCO (200 g gold silica gel cartridge) eluted with hexane to 10% EtOAc in hexane to give linoleyl bromide (22.8 g, 69.2 mmol, 92% yield) as a colorless oil. $^1$H NMR (500 MHz, Chloroform-d) δ 5.42-5.31 (m, 4H), 3.41 (t, J=6.9 Hz, 2H), 2.77 (t, J=6.6 Hz, 2H), 2.05 (q, J=6.9 Hz, 4H), 1.85 (p, J=6.9 Hz, 2H), 1.43-1.25 (m, 16H), 0.89 (t, J=6.8 Hz, 3H).

Synthesis of dilinoleyl methanol. To a suspension of Mg (0.897 g, 36.9 mmol) and ether (20 mL) in RB flask was added linoleyl bromide (10.0 g, 30.4 mmol) in ether (25 mL) dropwise while keeping the reaction under gentle reflux by cooling the RB flask in water. The reaction mixture was stirred at 35° C. for 1 hour. To the above reaction mixture at 0° C. was added ethyl formate (1.013 g, 13.68 mmol) in ether (30 mL) dropwise for 10 minutes and the reaction mixture was stirred at room temperature for 1.5 hrs. The reaction mixture was cooled in ice bath, quenched with water (30 mL), treated with 10% $H_2SO_4$ (150 mL) until the solution became homogeneous and the layer was separated. The aqueous layer was extracted with ether (200 mL×2). The solvent was evaporated under reduced pressure to give a residue, which was re-dissolved in THF (50 mL) and 1 N NaOH (30 mL). The reaction mixture was stirred at 40° C. for 5 hrs. TLC was used to monitor the reaction progress. If not complete, 1.5 g NaOH was added to the reaction mixture and the reaction mixture was continually stirred at 40° C. for overnight. The reaction mixture was extracted with ether (2 x), dried over anhydrous sodium sulfate, and concentrated to give a residue, which was purified by ISCO (120 g gold silica gel cartridge) eluting with hexane to 10% EtOAc in hexane to give dilinoleyl methanol (5.16 g, 9.76 mmol, 71.3% yield) as a colorless oil. $^1$H NMR (500 MHz, Chloroform-d) δ 5.41-5.30 (m, 8H), 3.58 (s, 1H), 2.77 (t, J=6.7 Hz, 4H), 2.05 (q, J=6.9 Hz, 8H), 1.49-1.25 (m, 40H), 0.89 (t, J=6.8 Hz, 6H).

Synthesis of 2-cyanoethyl ((6Z,9Z,28Z,31Z)-heptatriaconta-6,9,28,31-tetraen-19-yl) diisopropylphosphoramidite. To a solution of dilinoleyl methanol (2.5 g, 4.73 mmol) in anhydrous dichloromethane (30 mL) at room temperature was added DIPEA (4.12 mL, 23.63 mmol) and 3-(chloro(diisopropylamino)phosphino)propanenitrile (1.180 mL, 5.67 mmol). The reaction mixture was stirred at room temperature for 2 hours. The reaction mixture was added EtOAc (300 mL), washed with sat sodium bicarbonate, dried over anhydrous sodium sulfate, and concentrated under reduced pressure to give a residue, which was purified by ISCO (40 g gold silica gel cartridge) eluting with hexane to 5% EtOAc in hexane containing 5% TEA to give 2-cyanoethyl (6Z,9Z,28Z,31Z)-heptatriaconta-6,9,28,31-tetraen-19-yl diisopropylphosphoramidite (2.97 g, 4.07 mmol, 86% yield) as a colorless oil. $^1$H NMR (500 MHz, Chloroform-d) δ 5.30-5.41 (m, 8H), 3.85-3.72 (m, 3H), 3.59 (dp, J=10.2, 6.8 Hz, 2H), 2.77 (t, J=6.8 Hz, 4H), 2.61 (t, J=6.6 Hz, 2H), 2.05 (q, J=7.1 Hz, 8H), 1.60-1.46 (m, 4H), 1.42-1.27 (m, 36H), 1.18 (dd, J=6.8, 3.0 Hz, 12H), 0.89 (t, J=6.8 Hz, 6H). $^{31}$P NMR (202 MHz, Chloroform-d) δ 147.68.

Synthesis of amidite from lauryl alcohol. To a solution of lauryl alcohol (5.2 g, 28 mmol) in 60 mL dry DCM, under an atmosphere of argon, at room temperature was added DIPEA (18 g, 140 mmol) and stirred for 5 minutes. To this solution was added 2-cyanoethyl N,N-diisopropylchlorophosphoramidite (7.9 g, 33.5 mmol) dropwise and stirred for 4 hours. Solvent from the reaction mixture was evaporated under reduced pressure, diluted with 300 mL ethyl acetate, washed with sat. $NaHCO_3$ and dried over anhydrous sodium sulfate. Removal of solvent and column chromatography over silica gel (80 g regular silica, 0-30% ethyl acetate in hexane containing 5% triethyl amine) using ISCO provided the product. Weight of product obtained: 3.8 g (35%). $^3$H NMR (500 MHz; $CDCl_3$): δ 3.88-3.76 (m, 2H), 3.68-3.55 (m, 4H), 2.62 (t, 2H), 1.62-1.35 (m, 2H), 1.32-1.28 (m, 18H), 1.19-1.17 (m, 12H), 0.87 (t, 3H). $^{31}$P NMR (202.4 MHz; $CDCl_3$): δ 147.2 (s). The product was utilized to incorporate Mod 030 using oligonucleotide synthesis chemistry by reacting with 5'-OH of oligonucleotide chain. Similar procedures were employed for Mod 031, Mod 032, and Mod 033.

Example 6. Example Synthesis of Amidites for Mod 030-Mod 033

To a solution of lauryl alcohol (5.2 g, 28 mmol) in 60 mL dry DCM, under an atmosphere of argon, at room temperature was added DIPEA (18 g, 140 mmol) and stirred for 5 minutes. To this solution was added 2-cyanoethyl N,N-diisopropylchlorophosphoramidite (7.9 g, 33.5 mmol) dropwise and stirred for 4 hours. Solvent from the reaction mixture was evaporated under reduced pressure, diluted with 300 mL ethyl acetate, washed with sat. $NaHCO_3$ and dried over anhydrous sodium sulfate. Removal of solvent and column chromatography over silica gel (80 g regular silica, 0-30% ethyl acetate in hexane containing 5% triethyl amine) using ISCO afforded the product. Weight of product obtained: 3.8 g (35%). $^3$H NMR (500 MHz; $CDCl_3$): δ 3.88-3.76 (m, 2H), 3.68-3.55 (m, 4H), 2.62 (t, 2H), 1.62-1.35 (m, 2H), 1.32-1.28 (m, 18H), 1.19-1.17 (m, 12H), 0.87 (t, 3H). $^{31}$P NMR (202.4 MHz; $CDCl_3$): δ 147.2 (s). Amidites for Mod 031, Mod 032 and Mod 033 were prepared using the same procedure. These amidites were used as the last amidite in the synthesis cycle to prepare oligonucleotides comprising Mod 030-Mod 033.

Example 7. Example Preparation of Acid for Mod 024

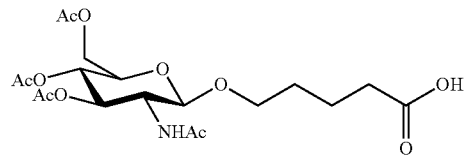

1

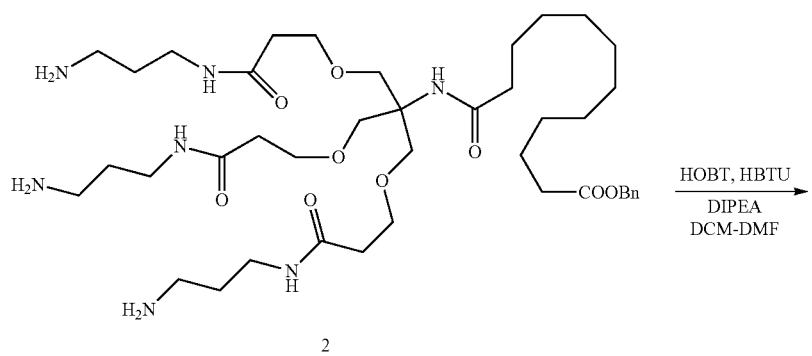

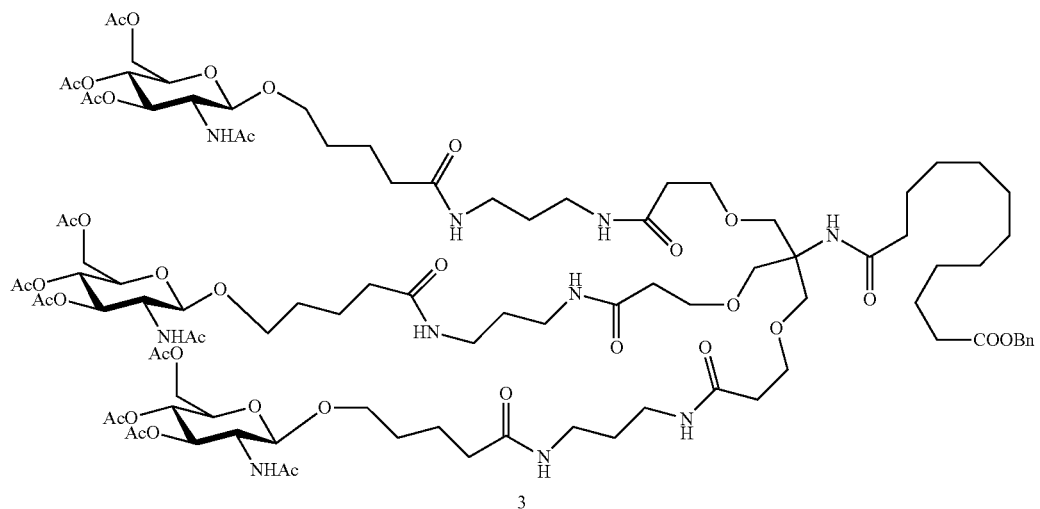

GlucNAc acid 1 (WO 2014/025805 A1) (1.88 g, 4.2 mmol) and HOBT (0.73 g, 5.4 mmol) was stirred in anhydrous DMF-DCM mixture (11+15 mL) under nitrogen at room temperature for 10 minutes. HBTU (2.05 g, 5.4 mmol) was added followed by DIPEA (2.17 g, 16.8 mmol) at 10° C. To this solution was added tri-amine salt 2 (WO 2014/025805 A1) (1.38 g, 1.2 mmol) and stirred overnight. Solvent was removed under vacuum and the residue was dissolved in ethyl acetate (200 mL). To this solution was added 100 ml of a mixture of sat. ammonium chloride, sat. sodium chloride, sat. sodium bicarbonate and water (1:1:1: 1). The ethyl acetate layer was turbid initially. After thoroughly shaking the layers got separated. Aqueous layer was extracted with ethyl acetate (×2). Combined organic fractions were washed with brine and dried over anhydrous sodium sulfate. Solvent removal under reduced pressure afforded 490 mg of crude product. This product was purified by CC on an ISCO machine. The eluent was DCM-Methanol (0-20% methanol in DCM). Amount of product obtained was 1.26 g (50%). LC-MS (+ mode): 1768 (M−1GlucNAc), 1438 (M−2 GlucNAc), 1108 (M−3 GlucNAc), 1049 (M/2+ 1).

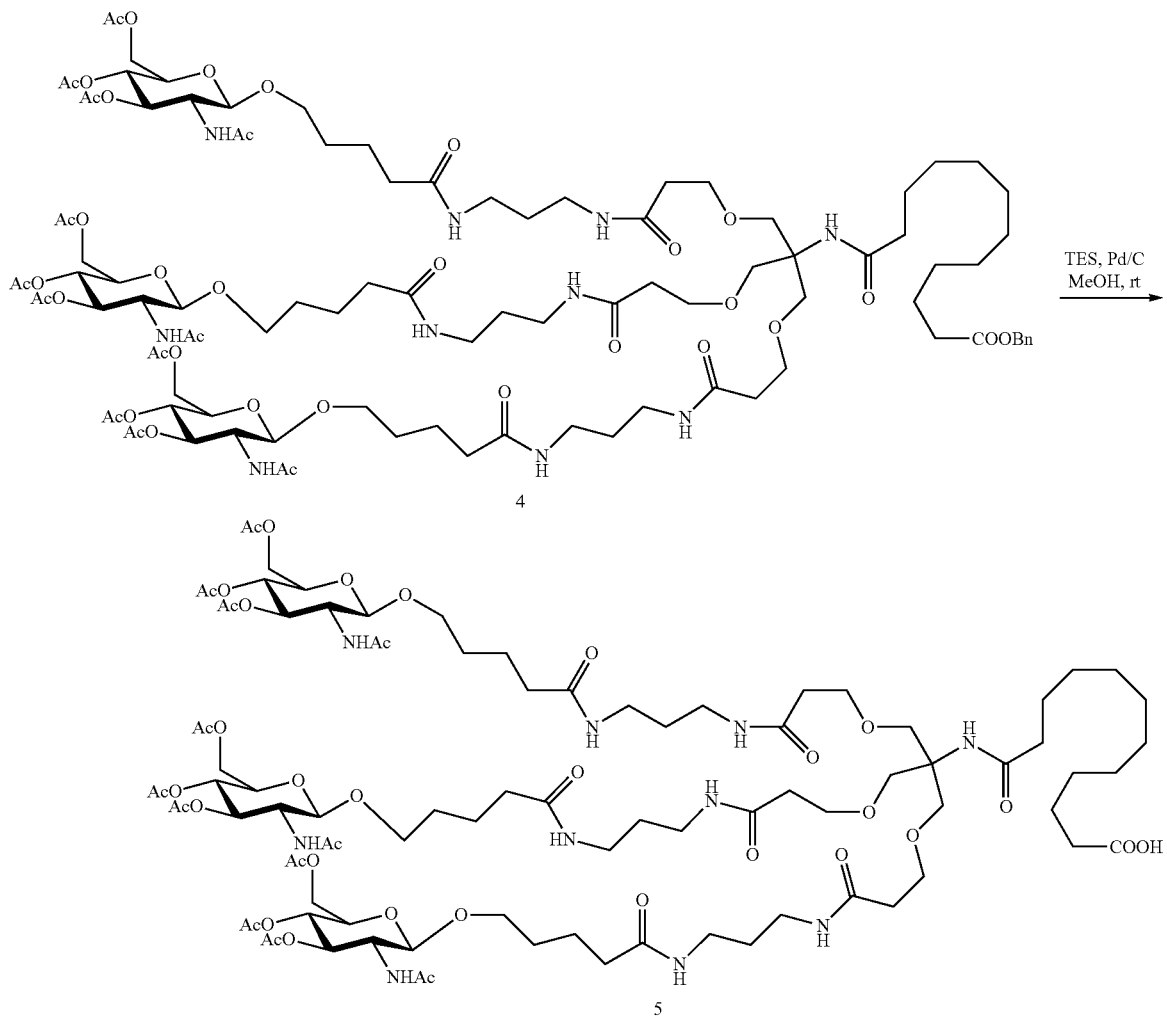

To a solution of benzyl ester 4 (0.25 g, 0.119 mmol) in 7 mL dry methanol, under an atmosphere of argon, 10% Pd/C (50 mg) was added followed by 1.5 mL (9.4 mmol) triethylsilane (TES) drop wise. A vigorous reaction set in and the RM was stirred for 3 hours. LC-MS analysis of the product indicates completion of reaction. The RM was filtered over celite and solvent was removed under vacuum. The crude product was triturated (X3) with ether-methanol (3:1) mixture and dried under vacuum. This product 5 was used for conjugation with oligonucleotide chains without further purification, and after conjugation the hydroxyl groups were deprotected, for example, during cleavage and/or deprotection of oligonucleotides to incorporate Mod 024. If desired, a number of protocols can be utilized to deprotect the hydroxyl groups in 5 to provide the acid with deprotected hydroxyl groups. $^1$H NMR (500 MHz, DMSO-D6): δ 7.90 (3H, d, J=10 Hz), 7.80 (t, 3H), 7.70 (t, 3H), 5.03 (t, 3H), 4.77 (t, 3H), 4.54 (3H, d, J=10 Hz), 4.14 (3H, dd, $J_2$=9 Hz, $J_2$=5 Hz), 3.97-3.93 (m, 3H), 3.79-3.74 (m, 3H), 3.69-3.61 (m, 6H), 3.51-3.47 (m, 3H), 3.40-3.35 (m, 3H), 3.31 (d, 3H, J=9 Hz), 2.98 (m, 12H), 2.23 (t, 3H), 2.13 (t, 3H), 2.01-1.99 (m, 3H), 1.97 (s, 9H), 1.92 (s, 9H), 1.86 (s, 9H), 1.71 (s, 9H), 1.49-1.32 (m, 22H), 1.18 (br s, 12H). Mod 026 were incorporated using similar strategies.

Example 8. Example Procedure for Conjugation—Preparing Oligonucleotide Chains with Amino Groups As appreciated by a person having ordinary skill in the art, various technologies, e.g., linkers, methods, functional groups, etc. can be utilized to prepare provided oligonucleotides in accordance with the present disclosure, including those comprising lipid moieties and/or targeting components. Below are example procedures for preparing oligonucleotides with amino groups for incorporating various moieties, e.g., lipid moieties, targeting components, etc.

"On Support" Conjugation Strategy

Preparation of 5'-amino-modified oligonucleotides for "on support" conjugation was carried out using MMT-amino C6 CE phosphoramidite (ChemGenes Corporation catalog No. CLP-1563 or Glen Research catalog No. 10-1906), which was added as the last phosphoramidite and coupled to 5'-OH of the oligonucleotide chain on solid support using oligonucleotide synthesis chemistry. After coupling, the newly formed linkage was optionally oxidized to provide a phosphodiester linkage if desired using, for example, tert-butyl hydroperoxide (e.g., 1.1 M in 20:80 decane/dichloromethane), $I_2$ (c-g, in pyridine/water, THF/pyridine/water, etc.), etc., depending on the oligonucleotide synthesis chemistry. When a phosphorothioate linkage was desired, PolyOrg Sulfa (e.g., 0.1 M in acetonitrile) or DDTT (e.g., 0.1 M in pyridine) was used for sulfurization. The MMT protecting group was then removed while the oligonucleotide was on support with deblocking reagent (e.g., 3% trichloroacetic acid in dichloromethane, 3% dichloroacetic acid in toluene, etc.) until the yellow color was no longer observed. Various compounds, e.g., fatty acids, sugar acids, etc. were then coupled, and optionally followed by cleavage from the support, deprotection and/or purification.

"In Solution" Conjugation Strategy

Preparation of 5'-amino-modified oligonucleotides for "in solution" conjugation strategy was carried out using TFA-amino C6 CED phosphoramidite (ChemGenes Corporation catalog No. CLP-1553 or Glen Research catalog No. 10-1916), which was added as the last phosphoramidite and coupled to 5'-OH of the oligonucleotide chain on solid support using oligonucleotide synthesis chemistry. After coupling, the newly formed linkage was optionally oxidized to provide a phosphodiester linkage if desired using, for example, tert-butyl hydroperoxide (e.g., 1.1 M in 20:80 decane/dichloromethane), $I_2$ (c-g, in pyridine/water, THF/pyridine/water, etc.), etc., depending on the oligonucleotide synthesis chemistry. When a phosphorothioate linkage was desired, PolyOrg Sulfa (e.g., 0.1 M in acetonitrile) or DDTT (e.g., 0.1 M in pyridine) was used for sulfurization. The amine-modified oligonucleotides were then cleaved from the support, deprotected and purified to provide products with free amino groups for conjugation. Usually the TFA group was removed during cleavage and deprotection of the oligonucleotides. The oligonucleotides were then utilized for conjugation Example 9. Example Procedure for Conjugation on Solid Support As appreciated by a person having ordinary skill in the art, a number of widely known and practiced technologies, e.g., reagents, methods, etc., can be utilized to prepare provided oligonucleotide compositions, including those comprising lipid moieties, in accordance with the present disclosure. Two example schemes are provided in the present and following examples for illustration of conjugation of lipids, targeting components, etc. to oligonucleotides. In some embodiments, $R^{LD}$—COOH is a fatty acid as described herein (prepared and/or commercially available) to provide $R^{LD}$ as illustrated in provided oligonucleotides, e.g., certain example oligonucleotides in Table 4. In some embodiments, $R^{LD}$—COOH is an acid comprising targeting component (prepared and/or commercially available) as described herein to provide $R^{LD}$ as illustrated in provided oligonucleotides, e.g., certain example oligonucleotides in Table 4.

Example procedure for conjugation on solid support:

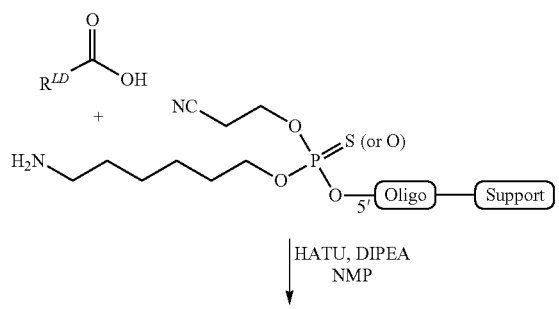

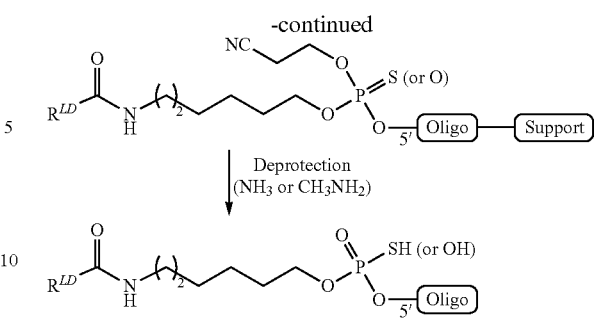

In an example procedure, a mixture of a lipid acid (1 µmol, 1 eq.), HATU (0.9 eq), diisopropylethylamine (10 eq) and NMP (500 µl) was shaken well at room temperature for 10 minutes, in a 3 mL plastic vial. This activated acid was pipetted into a plastic vial containing oligonucleotides (e.g., see example above) on solid support (0.09 µmol, 0.9 eq). The contents of the vial was thoroughly mixed and shaken well for 12 hours. After this time the supernatant NMP was removed carefully. The solid support was washed with acetonitrile (1 mL×3) and dried in a speed vac. A 1:1 mixture (1 mL) of ammonium hydroxide and methyl amine (AMA) was added and heated at 35° C. for 1 hour with intermittent shaking. After 1 hour, the CPG was transferred into a small filtration cartridge, filtered, washed with DMSO (500 µl x 2) and washed with water (1 mL×3). Filtrate and washings were combined and diluted to 10 mL using water. This solution was cooled to 0° C. and neutralized with glacial acetic acid until pH of the solution reached 7.5. (Alternatively the dried solid support can be treated with 35% $NH_4OH$ at 60° C. for 12 hours, cooled, filtered and neutralized with glacial acetic acid. For oligos containing fluoro group at T position, a mixture of 35% ammonium hydroxide and ethanol (3:1) was used with temperature not exceeding 40° C.). Crude product was analyzed by UV spectrometer, reverse phase HPLC and LC-MS. Purification of the crude product was done by RP-HPLC. After HPLC purification each fraction was analyzed by RP-HPLC and LC-MS. Pure fractions were combined and solvent was removed under vacuum (speed vac). Residue was dissolved in water and desalted (Triethyl ammonium ion was replaced with sodium ion) on a C-18 cartridge. Solvent was removed on a speed vaac and the residue was filtered through a centrifugal filter (Amicon Ultra-15 by Millipore), lyophilized and analyzed.

For example, for synthesis of WV-2578, a mixture of lauric acid (11.01 mg, 0.0549 mmol), HATU (19 mg, 0.050 mmol) and diisopropylethyl amine (18 µL, 0.1 mmol) was dissolved in 500 µL of dry NMP and shaken well for five minutes. This activated acid was pipetted into a plastic vial containing oligonucleotides on solid support (70.5 mg, 0.005 mmol). The contents of the vial was thoroughly mixed and shaken well for 12 hours. After this time supernatant NMP was removed carefully. The solid support was washed with acetonitrile (1 mL×3) and dried in a speed vac. A 1:1 mixture (1 mL) of ammonium hydroxide and methyl amine (AMA) was added and heated at 35° C. for 1 hour with intermittent shaking. After 1 hour, the CPG was transferred into a small filtration cartridge, filtered, washed with DMSO (500 µL x 2) and washed with water (1 mL×3). Filtrate and washings were combined and diluted to 10 mL using water. This solution was cooled to 0° C. and neutralized with glacial acetic acid until pH of the solution reached 7.5. Purification of the crude product was done by RP-HPLC. After HPLC purification each fraction was analyzed by RP-HPLC and LC-MS. Pure fractions were combined and solvent was removed under vacuum (speed vac). Residue was dissolved in water and desalted (triethyl ammonium ion was replaced with sodium ion) on a C-18 cartridge. Solvent was removed on a speed vac and the residue was filtered through a centrifugal filter (Amicon Ultra-15 by Millipore), lyophilized and analyzed. Average mass of WV2578 calculated: 7355, found (deconvoluted mass):7358. Additional examples include:

| EXP* | CPG (5 μmol) | Acid (55 μmol) |
|---|---|---|
| 1 | 70.5 | Lauric acid (MW = 200.32) 11.01 mg |
| 2 | 70.5 | Myristic Acid (MW = 228.38) 12.56 mg |
| 3 | 70.5 | Palmitic acid (MW = 256.26) 14.1 mg |
| 4 | 70.5 | Stearic acid (MW = 284.27) 15.63 mg |
| 5 | 70.5 | Oleic acid (MW = 282.47) 15.53 g |
| 6 | 70.5 | Linolenic acid (MW = 280.45) 15.4 mg |
| 7 | 70.5 | α-Linolenic acid (MW = 278.44) 15.3 mg |
| 8 | 70.5 | γ-Linolenic acid (MW = 278.44) 15.3 mg |
| 9 | 70.5 | cis-DHA (MW = 328.24) 18.05 mg |
| 10 | 70.5 | Turbinaric acid(MW = 400.36) 22 mg |

*HATU (50 μmol, MW = 379.24, 19 mg), DIPEA (MW = 129, d = 0.726, 100 μmol, 18 μL), NMP (500 μL). Example products include (Total ODs and Amount of lipid conjugates after purification):

| Oligonucleotide | Conjugated Acid | Total ODs | Amount (μmol) | Amount (mg) |
|---|---|---|---|---|
| WV2578 | Lauric Acid | 287 | 1.40 | 9.79 |
| WV2579 | Myristic Acid | 331 | 1.62 | 11.29 |
| WV2580 | Palmitic Acid | 268 | 1.31 | 9.14 |
| WV2581 | Stearic Acid | 265 | 1.30 | 9.04 |
| WV2582 | Oleic Acid | 262 | 1.28 | 8.94 |
| WV2583 | Linoleic Acid | 120 | 0.59 | 4.09 |
| WV2584 | α-Linolenic Acid | 285 | 1.39 | 9.72 |
| WV2585 | γ-Linolenic Acid | 297 | 1.45 | 10.13 |
| WV2586 | cis-DHA | 274 | 1.34 | 9.35 |
| WV2587 | Turbinaric acid | 186 | 0.91 | 6.35 |
| WV2588 | Dilinoleyl* | 345 | 1.69 | 11.77 |

*Synthesized on a solid support; last cycle using 2-cyanoethyl (((6Z,9Z,28Z,31Z)-hepta-triaconta-6,9,28,31-tetraen-19-yl) diisopropylphosphoramidite.

Example 10. Example Procedure for Conjugation in Solution

In some embodiments, provided oligonucleotides were prepared in solution phase.

Example procedure for conjugation in liquid phase:

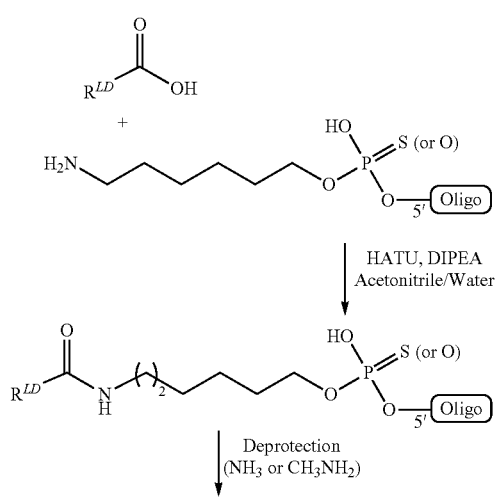

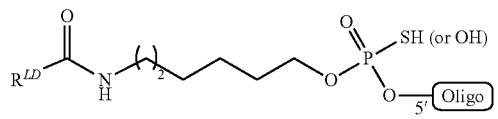

In an example procedure, a mixture of the lipid acid (1 eq.), HATU (1 eq.) and DIPEA (10 eq.) was mixed well in dry AcCN (10 mL) and kept for 10 minutes. This activated acid was added to the oligonucleotide (5 μmol) in water (5 mL) and mixed well on a vortex. This reaction was shaken for 1 hour. After 1 hour completion of the reaction was checked by LC-MS (usually the reaction is complete in 1 hour; if not, more acid-HATU complex can be added to drive the reaction to completion). Acetonitrile and water was removed under vacuum on a speed vac. The solid obtained was treated with 35% ammonium hydroxide (15 mL) and shaken at 60° C. for 12 hours; for T fluro oligonucleotides a 3:1 mixture of 35% ammonium hydroxide and ethanol was used for deprotection). After 12 hours solvent was removed under vacuum and diluted with water (15 mL), analyzed by LC-MS and RP-HPLC. Crude product was then purified by RP-HPLC and desalted.

For example, for synthesis of WV-3546, turbinaric acid (7 mg, 0.0174 mmol), HATU (6.27 mg, 0.0165 mmol) and DIPEA (22.2 mg, 0.172 mmol) was mixed well in dry AcCN (10 mL) and kept for 5 minutes in a 40 mL plastic vial. This activated acid was added to oligonucleotides in 3.77 mL water (80 mg, 0.0117 mmol) and mixed well on a vortex. This reaction was shaken for 2 hours. After 2 hours completion of the reaction was checked by LC-MS (reaction was complete). Acetonitrile and water was removed under vacuum on a speed vac. The solid obtained was treated with ammonia: ethanol mixture (3:1, 15 mL) and shaken at 40° C. for 12 hours. After 12 hours solvent was removed under vacuum and diluted with water (15 mL) and analyzed by LC-MS. Crude product was purified by RP-HPLC (50 mM triethyl ammonium acetate in water-acetonitrile system (0-70% acetonitrile in 45 minutes), X Bridge preparative C8 (19×250 mm column))_. Average mass of WV3546 calculated: 7295. Mass found (deconvoluted mass): 7295.

Example 11. Example Synthesis of MMT-C6-Amino DPSE-L Amidite

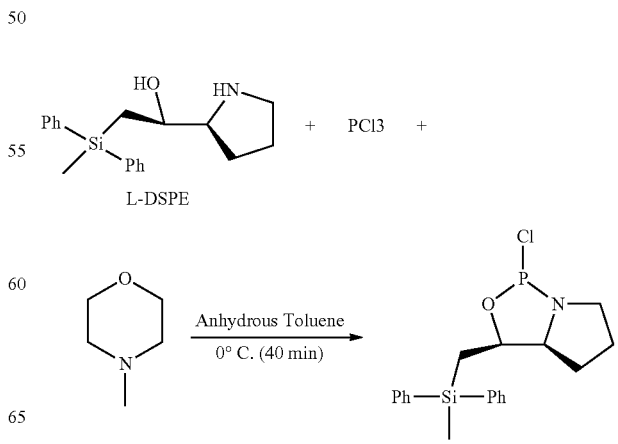

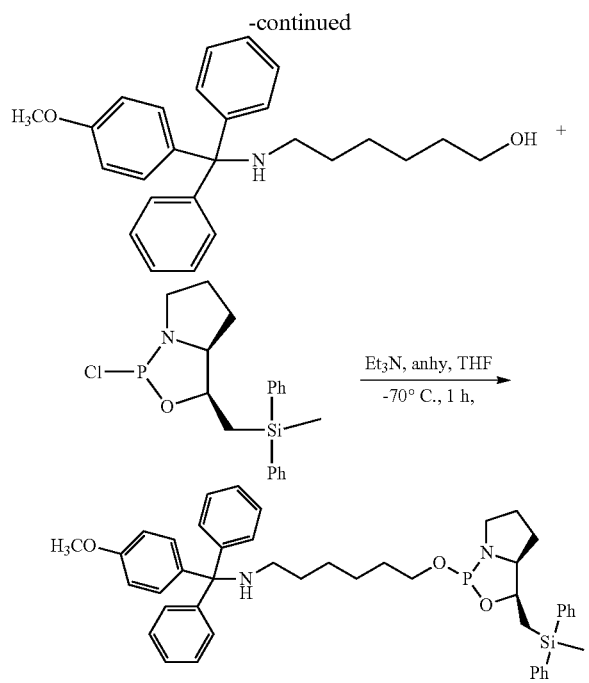

Preparation of chlorooxazaphospholidine: L-DPSE (37.1 g, 119 mmol) was dried by azeotropic evaporation with anhydrous toluene (150 mL) at 35° C. in a rotaevaporator and left in high vacuum for overnight. Then a solution of this dried L-DPSE (37.1 g) and 4-methylmorpholine (26.4 mL, 24.31 g, 240 mmol) dissolved in anhydrous toluene (150 mL) was added to an ice-cold solution of trichlorophosphine (16.51 g, 10.49 mL, 120 mmol) in anhydrous toluene (110 mL) placed in three neck round bottomed flask through cannula under Argon (start Temp: 0.6° C., Max: temp 14° C., 25 min addition) and the reaction mixture was stirred at 0° C. for 40 min. After that the precipitated white solid was filtered by vacuum under argon using spatial filter tube (Chemglass: Filter Tube, 24/40 Inner Joints, 80 mm OD Medium Frit, Airfree, Schlenk). The solvent was removed by rotaevaporator under argon at low temperature (25° C.) followed by dried under vacuum overnight (15 h) and the oily chlorooxazaphospholidine obtained was used for the next step.

MMT-C6-amino DPSE-L amidite. 6-(monomethoxytritylamino)hexan-1-ol (7.0 g, 17.97 mmol) was first dried by azeotropic evaporation by anhydrous toluene (50 ml) and dried under vacuum for overnight. Then the dried 6-(monomethoxytritylamino)hexan-1-ol was dissolved in anhydrous THF (80 mL) and added triethylamine (9.0 g, 90 mmol) and then the reaction solution was cooled to −70° C. To this cooled solution was added chlorooxazaphospholidine (6.76 g, 17.97 mmol) dissolved in anhydrous THF (50 mL) over 10 min. After the reaction mixture slowly warmed to room temperature (~1 h), TLC indicated complete conversion of starting material. Then the reaction mixture was filtered carefully under vacuum/argon using the fitted filtration tube to remove precipitated solid, and washed with THF (80 mL). The solution was evaporated at 25° C. and the resulting oily residue was dissolved in Hexane-$CH_2Cl_2$ mixture with 5% TEA and purified using ISCO Combi-Flash system 220 g silica column (which was pre-de-activated with 3 CV MeOH, then equilibrated with ethyl acetate (5% TEA) 3 CV), with Hexane-EtOAc mixture (5% TEA). Pure fractions were collected and concentrated, dried overnight to afford MMT-C6-amino DPSE-L amidite as a colorless oily liquid. Yield: 8.0 g (62%). MS: calculated: 728.38; found by LCMS analysis at +Ve ion mode m/z: 729.54 ($M^+$ ion), 747.50 ($M^+$+18, H2O). $^1$H-NMR (500 MHz, $CDCl_3$): δ 7.58-7.43 (m, 8H), 7.41-7.31 (m, 6H), 7.31-7.23 (m, 6H), 7.17 (t, J=7.2 Hz, 2H), 6.81 (d, J=8.7 Hz, 2H), 4.82 (dt, J=8.7, 5.7 Hz, 1H), 3.78 (s, 3H), 3.77-3.73 (m, 1H), 3.54 (qt, J=11.0, 5.2 Hz, 2H), 2.54 (q, J=7.2 Hz, 3H), 2.11 (t, 7=7.0 Hz, 2H), 1.64-1.57 (m, 4H), 1.51-1.35 (m, 6H), 1.26 (q, J=9.9, 8.0 Hz, 2H), 1.04 (t, J=7.1 Hz, 2H), 0.67 (s, 3H). $^{13}$C NMR (500 MHz, $CDCl_3$) δ 157.87, 146.73, 146.67, 138.63, 136.89, 136.43, 134.71, 134.57, 134.48, 129.88, 129.46, 129.42, 128.66, 128.05, 127.96, 127.87, 127.81, 126.17, 113.13, 78.14, 78.07, 77.48, 77.43, 77.22, 76.97, 70.45, 68.03, 68.01, 63.50, 63.40, 55.22, 47.46, 47.17, 46.40, 43.69, 34.79, 31.34, 31.07, 27.19, 27.09, 26.04, 25.98, 17.60, 11.78, −3.17. $^{31}$P-NMR (500 MHz, $CDCl_3$): δ 154.27 (92.18%), 157.68 (3.56%), 146.35 (4.26%).

Example 12. Example Preparation of WV-4107

Oligonucleotides were prepared using conditions for WV-3473 with all protecting groups and auxiliaries on and remained on solid support (if cleaved and deprotected, would provide WV-3473) using provided oligonucleotide technologies. In an example procedure, DPSE chemistry and GE Primer Support 5G (2,1 g), and the following cycles were used:

| step | operation | reagents and solvent | volume per cycle | waiting time |
| --- | --- | --- | --- | --- |
| 1 | detritylation | 3% DCA in toluene | ~150 mL | ~6 min |
| 2 | coupling | 0.175M monomer in MeCN or 20% isobutyronitrile in MeCN + 0.6M CMIMT in MeCN | 21 mL | 8 min |
| 3 | capping | 20% $Ac_2O$, 30% 2,6-lutidine in MeCN + 20% MeIm in MeCN | 23 mL | 1.5 min |
| 4 | oxidation or sulfurization | 1.1M TBHP in DCM-decane or 0.1M POS in MeCN | 44 mL or 39 mL | 2 min or 6 min |

After the last cycle, a portion of the oligonucleotides can be cleaved and deprotected for QC or other purposes. In an example procedure the oligonucleotides on support were washed with 6 column volumes of 20% diethylamine in acetonitrile for 15 min followed by an acetonitrile wash. The support was dried and then incubated in 1 M triethylamine hydrofluoride in 3:1 dimethylformamide/water for 1-1.5 h at 50° C. The sample was filtered and washed with acetonitrile and dried. The support was then incubated overnight at 40° C. in 3:1 ammonium hydroxide/ethanol.

For preparation of WV-4107, after the last cycle the DMT protecting group was removed using 3% dichloroacetic acid in toluene. During the coupling step, MMT-C6-amino DPSE-L amidite (0.175 M in isobutyronitrile) and CMIMT activator (0.6 M in acetonitrile) were added with a contact time of 8 min. The percent volume of activator was 55%. Capping was performed with 20% 1-methylimidazole in acetonitrile and 20/30/50 acetic anhydride/2,6-lutidine/acetonitrile. Sulfurization was performed using 0.1 M PolyOrg Sulfa in acetonitrile.

The MMT protecting group was then removed while the oligonucleotide was on support with deblocking reagent (3% dichloroacetic acid in toluene) until the yellow color was no longer observed, providing WV-4191. Stearic acid was then coupled to the amine using described procedure above. The oligonucleotides on support were washed with 20% diethylamine in acetonitrile for 30 min at room temperature followed by an acetonitrile wash. The support was dried and then incubated in 1 M triethylamine hydrofluoride in 3:1 dimethylformamide/water for 1-1.5 h at 50° C. The sample was filtered and washed with acetonitrile and dried. The support was then incubated overnight at 40° C. in 3:1 ammonium hydroxide/ethanol. The crude product was further purified using RP-HPLC to provide WV-4107.

Example 13. Example Preparation of Oligonucleotides with Mod 021

Oligonucleotide was synthesized at a scale of 10 μmol using standard cyanoethyl phosphoramidite chemistry and was left on support with protecting groups using cycle conditions for WV-942 (if cleaved and deprotected, would provide WV-942). The DMT protecting group was removed using 3% trichloroacetic acid in dichloromethane. The lipid amidite was then added to the 5' end of the oligonucleotide on the synthesizer. During the coupling step, equal volumes of lipid amidite (e.g., 0.1 M in isobutyronitrile) and 5-ethylthio tetrazole (e.g., 0.5 M in acetonitrile) were added with a contact time of, e.g., 5 min. The coupling step was optionally repeated a second time. Sulfurization was performed using 0.1 M DDTT in pyridine. The oligonucleotide was cleaved and deprotected using AMA condition (ammonium hydroxide/40% aqueous methylamine 1:1 v/v) to provide WV-2588.

Example 14. Example Preparation of Oligonucleotides with Mod 030, Mod 031, Mod 032 and Mod 033

Oligonucleotides were synthesized using cyanoethyl phosphoramidite chemistry as for WV-2735 and were left on support with the protecting group on (if cleaved and deprotected, would provide WV-2735). The 5'-DMT protecting group was removed using 3% trichloroacetic acid in dichloromethane. The lipid amidites were then added to the 5' end of the oligonucleotide on the synthesizer. During the coupling step, equal volumes of lipid amidite (0.1M in isobutyronitrile or dichloromethane) and 5-ethylthio tetrazole (0.5M in acetonitrile) were added with a contact time of 10 min. The coupling step was repeated again. Oxidation was performed using 0.02 M $I_2$ in THF/pyridine/water. The oligonucleotides were de-protected with 20% diethylamine in acetonitrile wash followed by an acetonitrile wash. The oligonucleotides were cleaved from the support and further de-protected in ammonium hydroxide at 50° C. overnight.

Product oligonucleotides were characterized in various chemical analyses, e.g., UV, HPLC-MS, etc., (for example MS data, see Table 6) and biological assays, e.g., those described herein. Following similar procedures and/or using widely known and practiced technologies in the art, other example provided oligonucleotides were or can be readily prepared and characterized in accordance with the present disclosure.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be examples and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The invention claimed is:

1. A method, comprising:
(i) assessing TLR9 activation by one or more chirally controlled oligonucleotide compositions, comprising: for each chirally controlled oligonucleotide composition, independently administering the oligonucleotide composition to a system and assessing TLR9 activation in the system, wherein each chirally controlled oligonucleotide composition is independently chirally controlled in that the composition comprises a predetermined level of oligonucleotides of an individual oligonucleotide type, wherein an oligonucleotide type is defined by:
   1) base sequence;
   2) pattern of backbone linkages;
   3) pattern of backbone chiral centers; and
   4) pattern of backbone phosphorus modifications:
wherein each oligonucleotide of the individual oligonucleotide type independently comprises at least one common CpG region motif:
5'-$N_1$-(*R/S)-C-(*R/S)-G-(*R/S)-$N_2$-3';
wherein each (*R/S) is independently a chiral internucleotidic linkage, and each of $N_1$ and $N_2$ is independently any nucleoside; and
(ii) administering a reference oligonucleotide composition to a system and assessing TLR9 activation in the system; and
(iii) determining that a chirally controlled oligonucleotide composition displays reduced TLR9 activation compared to the reference oligonucleotide composition.

2. The method of claim 1, wherein at least one (*R/S) in the chirally controlled oligonucleotide composition is a modified internucleotidic linkage in the Rp conformation and at least one (*R/S) is a modified internucleotidic linkage in the Sp conformation.

3. The method of claim 1, wherein at least one (*R/S) in the chirally controlled oligonucleotide composition is a phosphorothioate in the Rp conformation and at least one (*R/S) is a phosphorothioate in the Sp conformation.

4. The method of claim 1, wherein each oligonucleotide of the individual oligonucleotide type in the chirally controlled oligonucleotide composition independently comprises about 14 to about 49 nucleotides.

5. The method of claim 4, wherein each oligonucleotide of the individual oligonucleotide type in the chirally controlled oligonucleotide composition hybridizes with a particular target sequence.

6. The method of claim 1, wherein the chirally controlled oligonucleotide composition comprises oligonucleotides that have a predetermined level of a percentage of 1%-100% of all oligonucleotides in the composition.

7. The method of claim 1, wherein each oligonucleotide of the individual oligonucleotide type in the chirally controlled oligonucleotide composition comprises one or more sugar modifications.

8. The method of claim 7, wherein each oligonucleotide of the individual oligonucleotide type in the chirally controlled oligonucleotide composition comprises one or more 2'-F, 2'-OMe, and/or 2'-MOE sugar modifications.

9. The method of claim 1, wherein the reference oligonucleotide composition is a stereorandom oligonucleotide composition comprising oligonucleotides having the same common base sequence as the chirally controlled oligonucleotide composition.

10. The method of claim 1, wherein the reference oligonucleotide composition is a second chirally controlled oligonucleotide composition comprising oligonucleotides having the same common base sequence as the first chirally controlled oligonucleotide composition, but a different pattern of backbone chiral centers.

11. The method of claim 1, wherein the reference oligonucleotide composition is a second chirally controlled oligonucleotide composition comprising oligonucleotides having the same common base sequence as the first chirally controlled oligonucleotide composition, but of a different oligonucleotide type.

12. The method of claim 1, wherein the method of assessing TLR9 activation comprises measuring changes in secretion of a cytokine, interferon-alpha, interferon-gamma, IL-4, IL-6, IL-8, IL-10, IL-12, and/or TNF-alpha.

13. The method of claim 1, wherein the method of assessing TLR9 activation comprises measuring changes in NF-κP activity.

14. The method of claim 1, wherein the system is a cell or sample.

15. The method of claim 1, further comprising administering to a subject an oligonucleotide composition which is determined to have reduced TLR9 activation.

16. The method of claim 15, wherein the subject is an animal or human.

17. The method of claim 15, wherein the oligonucleotide composition is determined to be a TLR9 antagonist.

18. A method, comprising:
(i) administering an oligonucleotide composition that is chirally controlled in that the composition comprises a predetermined level of oligonucleotides of an individual oligonucleotide type, wherein an oligonucleotide type is defined by:
1) base sequence;
2) pattern of backbone linkages;
3) pattern of backbone chiral centers; and
4) pattern of backbone phosphorus modifications;
wherein each oligonucleotide of the individual oligonucleotide type independently comprises at least one common CpG region motif:
5'-$N_1$-(*R/S)—C—(*R/S)-G-(*R/S)—$N_2$-3';
wherein each (*R/S) is independently a chiral internucleotidic linkage, and each of N i and $N_2$ is independently any nucleoside;
(ii) measuring TLR9 response.

19. The method of claim 18, wherein the chirally controlled oligonucleotide composition comprises oligonucleotides that have a predetermined level of a percentage of 1%-100% of all oligonucleotides in the composition.

20. The method of claim 18, wherein the chirally controlled oligonucleotide composition comprises oligonucleotides that are between about 14 to about 49 nucleotides in length.

* * * * *

```
SEQUENCE LISTING

<160> NUMBER OF SEQ ID NOS: 1834

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgtcgtttt gtcgttttgt cgtt                                           24

<210> SEQ ID NO 2
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcgtcgtttt gtcgttttgt cgtt                                              24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcgtttt gtcgttttgt cgtt                                              24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcctcagtct gcttcgcacc                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gcctcagtct gcttcgcacc                                                   20

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aatcgatcga tcg                                                          13

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcctcagtct gcttcgcacc                                                   20

<210> SEQ ID NO 8
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcctcagtct gcttcgcacc                                                    20

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Arg Lys Lys Arg Arg Gln Arg Arg Arg Pro Pro Gln
1               5                   10

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucaaggaaga uggcauuucu                                                    20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ucaaggaaga uggcauuucu                                                    20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggccaaaccu cggcuuaccu                                                    20

<210> SEQ ID NO 13
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cuccaacauc aaggaagaug gcauuucuag                                         30

<210> SEQ ID NO 14
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
accagaguaa cagucugagu aggag                                          25

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
caccagagua acagucugag uagga                                          25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ucaccagagu aacagucuga guagg                                          25

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gucaccagag uaacagucug aguag                                          25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
guugugucac cagaguaaca gucug                                          25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gguuguguca ccagaguaac agucu                                          25

<210> SEQ ID NO 20
<211> LENGTH: 25
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 20
agguuguguc accagaguaa caguc                                         25

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cagguugugu caccagagua acagu                                         25

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
acagguugug ucaccagagu aacag                                         25

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccacagguug ugucaccaga guaac                                         25

<210> SEQ ID NO 24
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
accacagguu gugucaccag aguaa                                         25

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aaccacaggu ugugucacca gagua                                         25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uaaccacagg uugugucacc agagu                                              25

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
guaaccacag guugugucac cagag                                              25

<210> SEQ ID NO 28
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aguaaccaca gguuguguca ccaga                                              25

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uaguaaccac agguuguguc accag                                              25

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uuaguaacca cagguugugu cacca                                              25

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
cuuaguaacc acagguugug ucacc                                              25

<210> SEQ ID NO 32
<211> LENGTH: 25
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 32
ccuuaguaac cacagguugu gucac                                              25

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uccuuaguaa ccacagguug uguca                                              25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
guuuccuuag uaaccacagg uugug                                              25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aguuuccuua guaaccacag guugu                                              25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
caguuuccuu aguaaccaca gguug                                              25

<210> SEQ ID NO 37
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gcaguuuccu uaguaaccac agguu                                              25

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 38
ggcaguuucc uuaguaacca caggu                                              25

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uggcaguuuc cuuaguaacc acagg                                              25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
auggcaguuu ccuuaguaac cacag                                              25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
agauggcagu uccuuagua accac                                               25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gagauggcag uuccuuagu aacca                                               25

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ggagauggca guuccuuag uaacc                                               25

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 44
uggagauggc aguuccuua guaac                                          25

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uuggagaugg caguuccuu aguaa                                          25

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uuuggagaug gcaguuccu uagua                                          25

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aguuuggaga uggcaguuuc cuuag                                         25

<210> SEQ ID NO 48
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uaguuuggag auggcaguuu ccuua                                         25

<210> SEQ ID NO 49
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cuaguuugga gauggcaguu uccuu                                         25

<210> SEQ ID NO 50
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 50
ucuaguuugg agauggcagu uuccu                                          25

<210> SEQ ID NO 51
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uucuaguuug gagauggcag uuucc                                          25

<210> SEQ ID NO 52
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cauuucuagu uggagaugg caguu                                           25

<210> SEQ ID NO 53
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gcauuucuag uuuggagaug gcagu                                          25

<210> SEQ ID NO 54
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
auggcauuuc uaguuggag auggc                                           25

<210> SEQ ID NO 55
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gaagauggca uuucuaguuu ggaga                                          25

<210> SEQ ID NO 56
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
```

```
aggaagaugg cauuucuagu uugga                                        25

<210> SEQ ID NO 57
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aaggaagaug gcauuucuag uuugg                                        25

<210> SEQ ID NO 58
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
caaggaagau ggcauuucua guuug                                        25

<210> SEQ ID NO 59
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
caucaaggaa gauggcauuu cuagu                                        25

<210> SEQ ID NO 60
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
acaucaagga agauggcauu ucuag                                        25

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aacaucaagg aagauggcau uucua                                        25

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
```
caacaucaag gaagauggca uuucu                                          25

<210> SEQ ID NO 63
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cuccaacauc aaggaagaug gcauu                                          25

<210> SEQ ID NO 64
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
accuccaaca ucaaggaaga uggca                                          25

<210> SEQ ID NO 65
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
guaccuccaa caucaaggaa gaugg                                          25

<210> SEQ ID NO 66
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
agguaccucc aacaucaagg aagau                                          25

<210> SEQ ID NO 67
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
agagcaggua ccuccaacau caagg                                          25

<210> SEQ ID NO 68
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
cagagcaggu accuccaaca ucaag                                          25

```
<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cugccagagc agguaccucc aacau                                            25

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ucugccagag cagguaccuc caaca                                            25

<210> SEQ ID NO 71
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aucugccaga gcagguaccu ccaac                                            25

<210> SEQ ID NO 72
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
aaucugccag agcagguacc uccaa                                            25

<210> SEQ ID NO 73
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aaaucugcca gagcagguac cucca                                            25

<210> SEQ ID NO 74
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gaaaucugcc agagcaggua ccucc                                            25
```

<210> SEQ ID NO 75
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugaaaucugc cagagcaggu accuc                                         25

<210> SEQ ID NO 76
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uugaaaucug ccagagcagg uaccu                                         25

<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
cccgguugaa aucugccaga gcagg                                         25

<210> SEQ ID NO 78
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ccaagcccgg uugaaaucug ccaga                                         25

<210> SEQ ID NO 79
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uccaagcccg guugaaaucu gccag                                         25

<210> SEQ ID NO 80
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
guccaagccc gguugaaauc ugcca                                         25

```
<210> SEQ ID NO 81
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81 ucguccaag cccgguugaa aucug                                              25

<210> SEQ ID NO 82
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uucuguccaa gcccgguuga aaucu                                             25

<210> SEQ ID NO 83
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
guucugucca agcccgguug aaauc                                             25

<210> SEQ ID NO 84
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
aguucugucc aagcccgguu gaaau                                             25

<210> SEQ ID NO 85
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
aaguucuguc caagcccggu ugaaa                                             25

<210> SEQ ID NO 86
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uaaguucugu ccaagcccgg uugaa                                             25

<210> SEQ ID NO 87
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
guaaguucug uccaagcccg guuga                                              25

<210> SEQ ID NO 88
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gguaaguucu guccaagccc gguug                                              25

<210> SEQ ID NO 89
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cgguaaguuc uguccaagcc cgguu                                              25

<210> SEQ ID NO 90
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ucgguaaguu cuguccaagc ccggu                                              25

<210> SEQ ID NO 91
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gucgguaagu ucuguccaag cccgg                                              25

<210> SEQ ID NO 92
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
agucgguaag uucuguccaa gcccg                                              25

<210> SEQ ID NO 93
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cagucgguaa guucugucca agccc                                              25

<210> SEQ ID NO 94
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
aaagccaguc gguaaguucu gucca                                              25

<210> SEQ ID NO 95
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gaaagccagu cgguaaguuc ugucc                                              25

<210> SEQ ID NO 96
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gucacccacc aucacccucu gugau                                              25

<210> SEQ ID NO 97
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ggucacccac caucacccuc uguga                                              25

<210> SEQ ID NO 98
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aaggucaccc accaucaccc ucugu                                              25

<210> SEQ ID NO 99
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 99
caaggucacc caccaucacc cucug                                          25

<210> SEQ ID NO 100
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucaaggucac ccaccaucac ccucu                                          25

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cucaagguca cccaccauca cccuc                                          25

<210> SEQ ID NO 102
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
cuugaucaag cagagaaagc caguc                                          25

<210> SEQ ID NO 103
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
auaacuugau caagcagaga aagcc                                          25

<210> SEQ ID NO 104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
aguaacaguc ugaguaggag                                                20

<210> SEQ ID NO 105
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 105
gaguaacagu cugaguagga                                                    20

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
agaguaacag ucugaguagg                                                    20

<210> SEQ ID NO 107
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
cagaguaaca gucugaguag                                                    20

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gucaccagag uaacagucug                                                    20

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
ugucaccaga guaacagucu                                                    20

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gugucaccag aguaacaguc                                                    20

<210> SEQ ID NO 111
<211> LENGTH: 20
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 111
ugugucacca gaguaacagu                                                20

<210> SEQ ID NO 112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uugugucacc agaguaacag                                                20

<210> SEQ ID NO 113
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gguuguguca ccagaguaac                                                20

<210> SEQ ID NO 114
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
agguuguguc accagaguaa                                                20

<210> SEQ ID NO 115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
cagguugugu caccagagua                                                20

<210> SEQ ID NO 116
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
acagguugug ucaccagagu                                                20

<210> SEQ ID NO 117
<211> LENGTH: 20
<212> TYPE: RNA
<213> ORGANISM: Artificial Sequence
<220> FEATURE:
<223> OTHER INFORMATION: Description of Artificial Sequence: Synthetic

```
                         oligonucleotide

<400> SEQUENCE: 117
cacagguugu gucaccagag                                              20

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ccacagguug ugucaccaga                                              20

<210> SEQ ID NO 119
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
accacagguu gugucaccag                                              20

<210> SEQ ID NO 120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
aaccacaggu ugugucacca                                              20

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uaaccacagg uugugucacc                                              20

<210> SEQ ID NO 122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
guaaccacag guugugucac                                              20

<210> SEQ ID NO 123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 123
aguaaccaca gguuguguca                                           20

<210> SEQ ID NO 124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
cuuaguaacc acagguugug                                           20

<210> SEQ ID NO 125
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ccuuaguaac cacagguugu                                           20

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uccuuaguaa ccacagguug                                           20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uuccuuagua accacagguu                                           20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uuuccuuagu aaccacaggu                                           20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 129
guuuccuuag uaaccacagg                                           20

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
aguuuccuua guaaccacag                                           20

<210> SEQ ID NO 131
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gcaguuuccu uaguaaccac                                           20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ggcaguuucc uuaguaacca                                           20

<210> SEQ ID NO 133
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uggcaguuuc cuuaguaacc                                           20

<210> SEQ ID NO 134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
auggcaguuu ccuuaguaac                                           20

<210> SEQ ID NO 135
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
```

```
gauggcaguu uccuuaguaa                                           20

<210> SEQ ID NO 136
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
agauggcagu uccuuagua                                            20

<210> SEQ ID NO 137
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
ggagauggca guuccuuag                                            20

<210> SEQ ID NO 138
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
uggagauggc aguuccuua                                            20

<210> SEQ ID NO 139
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uuggagaugg caguuccuu                                            20

<210> SEQ ID NO 140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uuuggagaug gcaguuccu                                            20

<210> SEQ ID NO 141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
```
guuuggagau ggcaguuucc                                              20

<210> SEQ ID NO 142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
cuaguuugga gauggcaguu                                              20

<210> SEQ ID NO 143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ucuaguuugg agauggcagu                                              20

<210> SEQ ID NO 144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
auuucuaguu uggagauggc                                              20

<210> SEQ ID NO 145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uggcauuucu aguuuggaga                                              20

<210> SEQ ID NO 146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gauggcauuu cuaguuugga                                              20

<210> SEQ ID NO 147
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
agauggcauu ucuaguuugg                                              20

<210> SEQ ID NO 148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
aagauggcau uucuaguuug                                              20

<210> SEQ ID NO 149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
aggaagaugg cauuucuagu                                              20

<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
aaggaagaug gcauuucuag                                              20

<210> SEQ ID NO 151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
caaggaagau ggcauuucua                                              20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ucaaggaaga uggcauuucu                                              20

<210> SEQ ID NO 153
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
acaucaagga agauggcauu                                              20

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
caacaucaag gaagauggca                                           20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uccaacauca aggaagaugg                                           20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ccuccaacau caaggaagau                                           20

<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
agguaccucc aacaucaagg                                           20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
cagguaccuc caacaucaag                                           20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
agagcaggua ccuccaacau                                           20

```
<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
cagagcaggu accuccaaca                                                   20

<210> SEQ ID NO 161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ccagagcagg uaccuccaac                                                   20

<210> SEQ ID NO 162
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
gccagagcag guaccuccaa                                                   20

<210> SEQ ID NO 163
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ugccagagca gguaccucca                                                   20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cugccagagc agguaccucc                                                   20

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
ucugccagag cagguaccuc                                                   20

<210> SEQ ID NO 166
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
aucugccaga gcagguaccu                                                   20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uugaaaucug ccagagcagg                                                   20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
cccgguugaa aucugccaga                                                   20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gcccgguuga aaucugccag                                                   20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
agcccgguug aaaucugcca                                                   20

<210> SEQ ID NO 171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ccaagcccgg uugaaaucug                                                   20

<210> SEQ ID NO 172
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uccaagcccg guugaaaucu                                                     20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
guccaagccc gguugaaauc                                                     20

<210> SEQ ID NO 174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uguccaagcc cgguugaaau                                                     20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
cuguccaagc ccgguugaaa                                                     20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
ucuguccaag cccgguugaa                                                     20

<210> SEQ ID NO 177
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uucuguccaa gcccgguuga                                                     20

<210> SEQ ID NO 178
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 178
guucugucca agcccgguug                                                20

<210> SEQ ID NO 179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179 aguucuguccc aagcccgguu                                               20

<210> SEQ ID NO 180
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
aaguucuguc caagcccggu                                                20

<210> SEQ ID NO 181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uaaguucugu ccaagcccgg                                                20

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
guaaguucug uccaagcccg                                                20

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gguaaguucu guccaagccc                                                20

<210> SEQ ID NO 184
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 184
cagucgguaa guucugucca                                                    20

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
ccagucggua aguucugucc                                                    20

<210> SEQ ID NO 186
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
ccaccaucac ccucugugau                                                    20

<210> SEQ ID NO 187
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
cccaccauca cccucuguga                                                    20

<210> SEQ ID NO 188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
cacccaccau cacccucugu                                                    20

<210> SEQ ID NO 189
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
ucacccacca ucacccucug                                                    20

<210> SEQ ID NO 190
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 190
gucacccacc aucacccucu                                                    20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ggucacccac caucacccuc                                                    20

<210> SEQ ID NO 192
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
ucaagcagag aaagccaguc                                                    20

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uugaucaagc agagaaagcc                                                    20

<210> SEQ ID NO 194
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
caaagaagau ggcauuucua guuug                                              25

<210> SEQ ID NO 195
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gcaaagaaga uggcauuucu                                                    20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 196
gcaaagaaga uggcauuucu                                               20

<210> SEQ ID NO 197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ucaaggaaga uggcauuucu                                               20

<210> SEQ ID NO 198
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ucaaggaaga uggcauuucu                                               20

<210> SEQ ID NO 199
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
ucaaggaaga uggcauuucu                                               20

<210> SEQ ID NO 200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
ucaaggaaga uggcauuucu                                               20

<210> SEQ ID NO 201
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ucaaggaaga uggcauuucu                                               20

<210> SEQ ID NO 202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ucaaggaaga uggcauuucu                                              20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
ucaaggaaga uggcauuucu                                              20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ucaaggaaga uggcauuucu                                              20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
ucaaggaaga uggcauuucu                                              20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ucaaggaaga uggcauuucu                                              20

<210> SEQ ID NO 207
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
ucaaggaaga uggcauuucu                                              20

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 208
ucaaggaaga uggcauuucu                                                  20

<210> SEQ ID NO 209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
ucaaggaaga uggcauuucu                                                  20

<210> SEQ ID NO 210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ucaaggaaga uggcauuucu                                                  20

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
ucaaggaaga uggcauuucu                                                  20

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
ucaaggaaga uggcauuucu                                                  20

<210> SEQ ID NO 213
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ucaaggaaga uggcauuucu                                                  20

<210> SEQ ID NO 214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
```
ucaaggaaga uggcauuucu                                              20

<210> SEQ ID NO 215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
ucaaggaaga uggcauuucu                                              20

<210> SEQ ID NO 216
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
ucaaggaaga uggcauuucu                                              20

<210> SEQ ID NO 217
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ucaaggaaga uggcauuucu                                              20

<210> SEQ ID NO 218
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ucaaggaaga uggcauuucu                                              20

<210> SEQ ID NO 219
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
ucaaggaaga uggcauuucu                                              20

<210> SEQ ID NO 220
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
ucaaggaaga uggcauuucu    20

<210> SEQ ID NO 221
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
ucaaggaaga uggcauuucu    20

<210> SEQ ID NO 222
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ucaaggaaga uggcauuucu    20

<210> SEQ ID NO 223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ucaaggaaga uggcauuucu    20

<210> SEQ ID NO 224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ucaaggaaga uggcauuucu    20

<210> SEQ ID NO 225
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ucaaggaaga uggcauuucu    20

<210> SEQ ID NO 226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ggccaaaccu cggcuuaccu    20

<210> SEQ ID NO 227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
ggccaaaccu cggcuuaccu                                                   20

<210> SEQ ID NO 228
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
ggccaaaccu cggcuuaccu                                                   20

<210> SEQ ID NO 229
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
ggccaaaccu cggcuuaccu                                                   20

<210> SEQ ID NO 230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
ggccaaaccu cggcuuaccu                                                   20

<210> SEQ ID NO 231
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
ggccaaaccu cggcuuaccu                                                   20

<210> SEQ ID NO 232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
ggccaaaccu cggcuuaccu                                                   20

<210> SEQ ID NO 233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ggccaaaccu cggcuuaccu                                              20

<210> SEQ ID NO 234
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ucaaggaaga uggcauuucu                                              20

<210> SEQ ID NO 235
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
ucaaggaaga uggcauuucu                                              20

<210> SEQ ID NO 236
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ucaaggaaga uggcauuucu                                              20

<210> SEQ ID NO 237
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
ucaaggaaga uggcauuucu                                              20

<210> SEQ ID NO 238
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
ucaaggaaga uggcauuucu                                              20

<210> SEQ ID NO 239
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
ucaaggaaga uggcauuucu                                              20

<210> SEQ ID NO 240
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ucaaggaaga uggcauuucu                                              20

<210> SEQ ID NO 241
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ucaaggaaga uggcauuucu                                              20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ggccaaacct cggcttacct                                              20

<210> SEQ ID NO 243
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ggccaaaccu cggcuuaccu                                              20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggccaaacct cggcttacct                                              20

<210> SEQ ID NO 245

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ggccaaacct cggcttacct                                              20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
ggccaaaccu cggcttacct                                              20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
ggccaaacct cggcttaccu                                              20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
ggccaaaccu cggctuaccu                                              20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
ggccaaacct cggcutaccu                                              20

<210> SEQ ID NO 250
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
ggccaaacct cggctuaccu                                                    20

<210> SEQ ID NO 251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ggccaaaccu cggcuuaccu                                                    20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
ggccaaacct cggcutaccu                                                    20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 253
ggccaaacct cggctuaccu                                                    20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
ggccaaaccu cggcttaccu                                                    20

<210> SEQ ID NO 255
<211> LENGTH: 20
<212> TYPE: DNA
<213> ORGANISM: Artificial Sequence
<220> FEATURE:
```

<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 255
ggccaaaccu cggcttacct                                              20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 256
ggccaaacct cggcttaccu                                              20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 257
ggccaaaccu cggctuaccu                                              20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 258
ggccaaacct cggcutaccu                                              20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 259
ggccaaacct cggctuaccu                                              20

<210> SEQ ID NO 260
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 260
ggccaaaccu cggcuuaccu                                               20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
ggccaaacct cggcutaccu                                               20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
ggccaaacct cggctuaccu                                               20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
ggccaaaccu cggcttaccu                                               20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
ggccaaaccu cggcutaccu                                               20

<210> SEQ ID NO 265
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 265
ggccaaaccu cggcuuaccu                                          20

<210> SEQ ID NO 266
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ggccaaaccu cggcuuaccu                                          20

<210> SEQ ID NO 267
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
ggccaaaccu cggcuuaccu                                          20

<210> SEQ ID NO 268
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
ggccaaaccu cggcuuaccu                                          20

<210> SEQ ID NO 269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
ggccaaaccu cggcuuaccu                                          20

<210> SEQ ID NO 270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ggccaaaccu cggcuuaccu                                          20

<210> SEQ ID NO 271
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 271
ggccaaaccu cggcuuaccu                                                    20

<210> SEQ ID NO 272
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ggccaaaccu cggcuuaccu                                                    20

<210> SEQ ID NO 273
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
ggccaaaccu cggcuuaccu                                                    20

<210> SEQ ID NO 274
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ggccaaaccu cggcuuaccu                                                    20

<210> SEQ ID NO 275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ggccaaaccu cggcuuaccu                                                    20

<210> SEQ ID NO 276
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ggccaaaccu cggcuuaccu gaaau                                              25

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 277
ggccaaaccu cggcutaccu                                                   20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tcaaggaaga tggcatttct                                                   20

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
ucaaggaaga uggcauuucu                                                   20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tcaaggaaga tggcatttct                                                   20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tcaaggaaga tggcatttct                                                   20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
tcaaggaaga uggcatttct                                                   20

<210> SEQ ID NO 283
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
ucaaggaaga tggcatuucu                                                     20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
tcaaggaaga tggcautucu                                                     20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
ucaaggaaga uggcatutcu                                                     20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
tcaaggaaga tggcauutcu                                                     20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
tcaaggaaga uggcauttcu                                                     20

<210> SEQ ID NO 288
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
tcaaggaaga tggcatttcu                                                  20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
tcaaggaaga tggcauttcu                                                  20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
ucaaggaaga uggcatttcu                                                  20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
tcaaggaaga tggcatttcu                                                  20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
tcaaggaaga uggcatttct                                                  20

<210> SEQ ID NO 293
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
ucaaggaaga tggcatuucu                                                    20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
tcaaggaaga tggcautucu                                                    20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
ucaaggaaga uggcatutcu                                                    20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
tcaaggaaga tggcauutcu                                                    20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
tcaaggaaga uggcauttcu                                                    20
```

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
tcaaggaaga tggcatttcu                                              20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
tcaaggaaga tggcauttcu                                              20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
ucaaggaaga uggcatttcu                                              20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
tcaaggaaga tggcatttcu                                              20

<210> SEQ ID NO 302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ucaaggaaga uggcauuucu                                              20

<210> SEQ ID NO 303
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ucaaggaaga uggcauuucu                                                 20

<210> SEQ ID NO 304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ucaaggaaga uggcauuucu                                                 20

<210> SEQ ID NO 305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
ucaaggaaga uggcauuucu                                                 20

<210> SEQ ID NO 306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ucaaggaaga uggcauuucu                                                 20

<210> SEQ ID NO 307
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
ucaaggaaga uggcauuucu                                                 20

<210> SEQ ID NO 308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
ucaaggaaga uggcauuucu                                                 20

<210> SEQ ID NO 309
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 309
ucaaggaaga uggcauuucu                                                   20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
ucaaggaaga uggcauuucu                                                   20

<210> SEQ ID NO 311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
ucaaggaaga uggcauuucu                                                   20

<210> SEQ ID NO 312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
agaaaugcca ucuuccuuga                                                   20

<210> SEQ ID NO 313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
ucaaggaaga uggcauuucu                                                   20

<210> SEQ ID NO 314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ucaaggaaga uggcauuucu                                                   20

<210> SEQ ID NO 315
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 315
ucaaggaaga uggcauuucu                                                     20

<210> SEQ ID NO 316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
ucaaggaaga uggcauuucu                                                     20

<210> SEQ ID NO 317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
ucaaggaaga uggcauuucu                                                     20

<210> SEQ ID NO 318
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
ucaaggaaga uggcauuucu                                                     20

<210> SEQ ID NO 319
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
ucaaggaaga uggcauuucu                                                     20

<210> SEQ ID NO 320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ucaaggaaga uggcauuucu                                                     20

<210> SEQ ID NO 321
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 321
ucaaggaaga uggcauuucu                                                   20

<210> SEQ ID NO 322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
ucaaggaaga uggcauuucu                                                   20

<210> SEQ ID NO 323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
ucaaggaaga uggcauuucu                                                   20

<210> SEQ ID NO 324
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
ucaaggaaga uggcauuucu                                                   20

<210> SEQ ID NO 325
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
ucaaggaaga uggcauuucu                                                   20

<210> SEQ ID NO 326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
ucaaggaaga uggcauuucu                                                   20

<210> SEQ ID NO 327
<211> LENGTH: 20
<212> TYPE: RNA
<213> ORGANISM: Artificial Sequence
<220> FEATURE:
<223> OTHER INFORMATION: Description of Artificial Sequence: Synthetic
```

<400> SEQUENCE: 327
ucaaggaaga uggcauuucu          20

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
ucaaggaaga uggcauuucu          20

<210> SEQ ID NO 329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
ucaaggaaga uggcauuucu          20

<210> SEQ ID NO 330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
ucaaggaaga uggcauuucu          20

<210> SEQ ID NO 331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
ucaaggaaga uggcauuucu          20

<210> SEQ ID NO 332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
ucaaggaaga uggcauuucu          20

<210> SEQ ID NO 333
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
ucaaggaaga uggcauuucu                                                    20

<210> SEQ ID NO 334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
ucaaggaaga uggcauuucu                                                    20

<210> SEQ ID NO 335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
ucaaggaaga uggcauuucu                                                    20

<210> SEQ ID NO 336
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ucaaggaaga uggcauuucu                                                    20

<210> SEQ ID NO 337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
ucaaggaaga uggcauuucu                                                    20

<210> SEQ ID NO 338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
ucaaggaaga uggcauuucu                                                    20

<210> SEQ ID NO 339
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 339
ucaaggaaga uggcauuucu                                               20

<210> SEQ ID NO 340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
ucaaggaaga uggcauuucu                                               20

<210> SEQ ID NO 341
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
ucaaggaaga uggcauuucu                                               20

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
ucaaggaaga uggcauuucu                                               20

<210> SEQ ID NO 343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
ucaaggaaga uggcauuucu                                               20

<210> SEQ ID NO 344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
ucaaggaaga uggcauuucu                                               20

<210> SEQ ID NO 345
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
```
ucaaggaaga uggcauuucu                                              20

<210> SEQ ID NO 346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
ucaaggaaga uggcauuucu                                              20

<210> SEQ ID NO 347
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
ucaaggaaga uggcauuucu                                              20

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
ucaaggaaga uggcauuucu                                              20

<210> SEQ ID NO 349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ucaaggaaga uggcauuucu                                              20

<210> SEQ ID NO 350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
ucaaggaaga uggcauuucu                                              20

<210> SEQ ID NO 351
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ucaaggaaga uggcauuucu                                                    20

<210> SEQ ID NO 352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
ucaaggaaga uggcauuucu                                                    20

<210> SEQ ID NO 353
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
ucaaggaaga uggcauuucu                                                    20

<210> SEQ ID NO 354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
ucaaggaaga uggcauuucu                                                    20

<210> SEQ ID NO 355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
ucaaggaaga uggcauuucu                                                    20

<210> SEQ ID NO 356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
ucaaggaaga uggcauuucu                                                    20

<210> SEQ ID NO 357
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
ucaaggaaga uggcauuucu                                                    20

```
<210> SEQ ID NO 358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ucaaggaaga uggcauuucu                                                   20

<210> SEQ ID NO 359
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
ucaaggaaga uggcauuucu                                                   20

<210> SEQ ID NO 360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
ucaaggaaga uggcauuucu                                                   20

<210> SEQ ID NO 361
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
ucaaggaaga uggcauuucu                                                   20

<210> SEQ ID NO 362
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
ucaaggaaga uggcauuucu                                                   20

<210> SEQ ID NO 363
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
ucaaggaaga uggcauuucu                                                   20
```

<210> SEQ ID NO 364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
ucaaggaaga uggcauuucu                                                    20

<210> SEQ ID NO 365
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
ucaaggaaga uggcauuucu                                                    20

<210> SEQ ID NO 366
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
ucaaggaaga uggcauuucu                                                    20

<210> SEQ ID NO 367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ucaaggaaga uggcauuucu                                                    20

<210> SEQ ID NO 368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
ucaaggaaga uggcauuucu                                                    20

<210> SEQ ID NO 369
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
ucaaggaaga uggcauuucu                                                    20

```
<210> SEQ ID NO 370
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
ucaaggaaga uggcauuucu                                                     20

<210> SEQ ID NO 371
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
ucaaggaaga uggcauuucu                                                     20

<210> SEQ ID NO 372
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
ucaaggaaga uggcauuucu                                                     20

<210> SEQ ID NO 373
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
ucaaggaaga uggcauuucu                                                     20

<210> SEQ ID NO 374
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ucaaggaaga uggcauuucu                                                     20

<210> SEQ ID NO 375
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
ucaaggaaga uggcauuucu                                                     20

<210> SEQ ID NO 376
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
ucaaggaaga uggcauuucu                                                     20

<210> SEQ ID NO 377
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
ucaaggaaga uggcauuucu                                                     20

<210> SEQ ID NO 378
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
ucaaggaaga uggcauuucu                                                     20

<210> SEQ ID NO 379
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ucaaggaaga uggcauuucu                                                     20

<210> SEQ ID NO 380
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
ucaaggaaga uggcauuucu                                                     20

<210> SEQ ID NO 381
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
ucaaggaaga uggcauuucu                                                     20

<210> SEQ ID NO 382
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
ucaaggaaga uggcauuucu                                                      20

<210> SEQ ID NO 383
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ucaaggaaga uggcauuucu                                                      20

<210> SEQ ID NO 384
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
ucaaggaaga uggcauuucu                                                      20

<210> SEQ ID NO 385
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
ucaaggaaga uggcauuucu                                                      20

<210> SEQ ID NO 386
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
ucaaggaaga uggcauuucu                                                      20

<210> SEQ ID NO 387
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
ucaaggaaga uggcauuucu                                                      20

<210> SEQ ID NO 388
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 388
ucaaggaaga uggcauuucu                                                    20

<210> SEQ ID NO 389
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
ucaaggaaga uggcauuucu                                                    20

<210> SEQ ID NO 390
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
ucaaggaaga uggcauuucu                                                    20

<210> SEQ ID NO 391
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
ucaaggaaga uggcauuucu                                                    20

<210> SEQ ID NO 392
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ucaaggaaga uggcauuucu                                                    20

<210> SEQ ID NO 393
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
ucaaggaaga uggcauuucu                                                    20

<210> SEQ ID NO 394
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 394
ucaaggaaga uggcauuucu                                                   20

<210> SEQ ID NO 395
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
ucaaggaaga uggcauuucu                                                   20

<210> SEQ ID NO 396
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
ucaaggaaga uggcauuucu                                                   20

<210> SEQ ID NO 397
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
ucaaggaaga uggcauuucu                                                   20

<210> SEQ ID NO 398
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
ucaaggaaga uggcauuucu                                                   20

<210> SEQ ID NO 399
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
ucaaggaaga uggcauuucu                                                   20

<210> SEQ ID NO 400
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 400
ucaaggaaga uggcauuucu                                              20

<210> SEQ ID NO 401
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
ucaaggaaga uggcauuucu                                              20

<210> SEQ ID NO 402
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
ucaaggaaga uggcauuucu                                              20

<210> SEQ ID NO 403
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
ucaaggaaga uggcauuucu                                              20

<210> SEQ ID NO 404
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
ucaaggaaga uggcauuucu                                              20

<210> SEQ ID NO 405
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
ucaaggaaga uggcauuucu                                              20

<210> SEQ ID NO 406
<211> LENGTH: 20
<212> TYPE: RNA
<213> ORGANISM: Artificial Sequence
<220> FEATURE:
<223> OTHER INFORMATION: Description of Artificial Sequence: Synthetic

```
    oligonucleotide

<400> SEQUENCE: 406
ucaaggaaga uggcauuucu                                           20

<210> SEQ ID NO 407
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
ucaaggaaga uggcauuucu                                           20

<210> SEQ ID NO 408
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
ucaaggaaga uggcauuucu                                           20

<210> SEQ ID NO 409
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
ucaaggaaga uggcauuucu                                           20

<210> SEQ ID NO 410
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
ucaaggaaga uggcauuucu                                           20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 411
ucaaggaaga tggcauuucu                                           20

<210> SEQ ID NO 412
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 412
ucaaggaaga tggcauuucu                                                     20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 413
ucaaggaaga tggcauuucu                                                     20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 414
ucaaggaaga tggcauuucu                                                     20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 415
ucaaggaaga tggcauuucu                                                     20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 416
ucaaggaaga tggcauuucu                                                     20

<210> SEQ ID NO 417
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 417
ucaaggaaga tggcauuucu                                                    20

<210> SEQ ID NO 418
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
ucaaggaaga uggcauuucu                                                    20

<210> SEQ ID NO 419
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
ucaaggaaga uggcauuucu                                                    20

<210> SEQ ID NO 420
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
ucaaggaaga uggcauuucu                                                    20

<210> SEQ ID NO 421
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
ucaaggaaga uggcauuucu                                                    20

<210> SEQ ID NO 422
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
ucaaggaaga uggcauuucu                                                    20

<210> SEQ ID NO 423

<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
ucaaggaaga uggcauuucu                                              20

<210> SEQ ID NO 424
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
ucaaggaaga uggcauuucu                                              20

<210> SEQ ID NO 425
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
ucaaggaaga uggcauuucu                                              20

<210> SEQ ID NO 426
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
ucaaggaaga uggcauuucu                                              20

<210> SEQ ID NO 427
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
ucaaggaaga uggcauuucu                                              20

<210> SEQ ID NO 428
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
ucaaggaaga uggcauuucu                                              20

<210> SEQ ID NO 429
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
ucaaggaaga uggcauuucu                                                   20

<210> SEQ ID NO 430
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
ucaaggaaga uggcauuucu                                                   20

<210> SEQ ID NO 431
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
ucaaggaaga uggcauuucu                                                   20

<210> SEQ ID NO 432
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
ucaaggaaga uggcauuucu                                                   20

<210> SEQ ID NO 433
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
ucaaggaaga uggcauuucu                                                   20

<210> SEQ ID NO 434
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ucaaggaaga uggcauuucu                                                   20

<210> SEQ ID NO 435
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 435
ucaaggaaga uggcauuucu                                                    20

<210> SEQ ID NO 436
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
ucaaggaaga uggcauuucu                                                    20

<210> SEQ ID NO 437
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
ucaaggaaga uggcauuucu                                                    20

<210> SEQ ID NO 438
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
ucaaggaaga uggcauuucu                                                    20

<210> SEQ ID NO 439
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
ucaaggaaga uggcauuucu                                                    20

<210> SEQ ID NO 440
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
ucaaggaaga uggcauuucu                                                    20

<210> SEQ ID NO 441
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 441
ucaaggaaga uggcauuucu                                               20

<210> SEQ ID NO 442
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
ucaaggaaga uggcauuucu                                               20

<210> SEQ ID NO 443
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
ucaaggaaga uggcauuucu                                               20

<210> SEQ ID NO 444
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
ucaaggaaga uggcauuucu                                               20

<210> SEQ ID NO 445
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ucaaggaaga uggcauuucu                                               20

<210> SEQ ID NO 446
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
ucaaggaaga uggcauuucu                                               20

<210> SEQ ID NO 447
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 447
ucaaggaaga uggcauuucu                                                    20

<210> SEQ ID NO 448
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
ucaaggaaga uggcauuucu                                                    20

<210> SEQ ID NO 449
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ucaaggaaga uggcauuucu                                                    20

<210> SEQ ID NO 450
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
ucaaggaaga uggcauuucu                                                    20

<210> SEQ ID NO 451
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
ucaaggaaga uggcauuucu                                                    20

<210> SEQ ID NO 452
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
ucaaggaaga uggcauuucu                                                    20

<210> SEQ ID NO 453
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 453
ucaaggaaga uggcauuucu                                                20

<210> SEQ ID NO 454
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
ucaaggaaga uggcauuucu                                                20

<210> SEQ ID NO 455
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
ucaaggaaga uggcauuucu                                                20

<210> SEQ ID NO 456
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
ucaaggaaga uggcauuucu                                                20

<210> SEQ ID NO 457
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
ucaaggaaga uggcauuucu                                                20

<210> SEQ ID NO 458
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
ucaaggaaga uggcauuucu                                                20

<210> SEQ ID NO 459
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 459
ucaaggaaga uggcauuucu                                               20

<210> SEQ ID NO 460
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
ucaaggaaga uggcauuucu                                               20

<210> SEQ ID NO 461
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
ucaaggaaga uggcauuucu                                               20

<210> SEQ ID NO 462
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
ucaaggaaga uggcauuucu                                               20

<210> SEQ ID NO 463
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ucaaggaaga uggcauuucu                                               20

<210> SEQ ID NO 464
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
ucaaggaaga uggcauuucu                                               20

<210> SEQ ID NO 465
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 465
ucaaggaaga uggcauuucu                                               20

<210> SEQ ID NO 466
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
ucaaggaaga uggcauuucu                                               20

<210> SEQ ID NO 467
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
ucaaggaaga uggcauuucu                                               20

<210> SEQ ID NO 468
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
ucaaggaaga uggcauuucu                                               20

<210> SEQ ID NO 469
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
ucaaggaaga uggcauuucu                                               20

<210> SEQ ID NO 470
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
ucaaggaaga uggcauuucu                                               20

<210> SEQ ID NO 471
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
```
ucaaggaaga uggcauuucu                                         20

<210> SEQ ID NO 472
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ucaaggaaga uggcauuucu                                         20

<210> SEQ ID NO 473
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
ucaaggaaga uggcauuucu                                         20

<210> SEQ ID NO 474
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
ucaaggaaga uggcauuucu                                         20

<210> SEQ ID NO 475
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
ucaaggaaga uggcauuucu                                         20

<210> SEQ ID NO 476
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ucaaggaaga uggcauuucu                                         20

<210> SEQ ID NO 477
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
ucaaggaaga uggcauuucu                                          20

<210> SEQ ID NO 478
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ucaaggaaga uggcauuucu                                          20

<210> SEQ ID NO 479
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
ucaaggaaga uggcauuucu                                          20

<210> SEQ ID NO 480
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
ucaaggaaga uggcauuucu                                          20

<210> SEQ ID NO 481
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
ucaaggaaga uggcauuucu                                          20

<210> SEQ ID NO 482
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
ucaaggaaga uggcauuucu                                          20

<210> SEQ ID NO 483
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
ucaaggaaga uggcauuucu                                          20

```
<210> SEQ ID NO 484
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
ucaaggaaga uggcauuucu                                                   20

<210> SEQ ID NO 485
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
ucaaggaaga uggcauuucu                                                   20

<210> SEQ ID NO 486
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
ucaaggaaga uggcauuucu                                                   20

<210> SEQ ID NO 487
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
ucaaggaaga uggcauuucu                                                   20

<210> SEQ ID NO 488
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
ucaaggaaga uggcauuucu                                                   20

<210> SEQ ID NO 489
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
ucaaggaaga uggcauuucu                                                   20
```

<210> SEQ ID NO 490
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
ucaaggaaga uggcauuucu                                                   20

<210> SEQ ID NO 491
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
ucaaggaaga uggcauuucu                                                   20

<210> SEQ ID NO 492
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
ucaaggaaga uggcauuucu                                                   20

<210> SEQ ID NO 493
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
ucaaggaaga uggcauuucu                                                   20

<210> SEQ ID NO 494
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
ucaaggaaga uggcauuucu                                                   20

<210> SEQ ID NO 495
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
ucaaggaaga uggcauuucu                                                   20

-continued

<210> SEQ ID NO 496
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
ucaaggaaga uggcauuucu                                              20

<210> SEQ ID NO 497
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
ucaaggaaga uggcauuucu                                              20

<210> SEQ ID NO 498
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
ucaaggaaga uggcauuucu                                              20

<210> SEQ ID NO 499
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
ucaaggaaga uggcauuucu                                              20

<210> SEQ ID NO 500
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
ucaaggaaga uggcauuucu                                              20

<210> SEQ ID NO 501
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
ucaaggaaga uggcauuucu                                              20

<210> SEQ ID NO 502

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
ucaaggaaga uggcauuucu                                               20

<210> SEQ ID NO 503
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
ucaaggaaga uggcauuucu                                               20

<210> SEQ ID NO 504
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
ucaaggaaga uggcauuucu                                               20

<210> SEQ ID NO 505
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
ucaaggaaga uggcauuucu                                               20

<210> SEQ ID NO 506
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
ucaaggaaga uggcauuucu                                               20

<210> SEQ ID NO 507
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
ucaaggaaga uggcauuucu                                               20

<210> SEQ ID NO 508
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
ucaaggaaga uggcauuucu                                              20

<210> SEQ ID NO 509
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
ucaaggaaga uggcauuucu                                              20

<210> SEQ ID NO 510
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
ucaaggaaga uggcauuucu                                              20

<210> SEQ ID NO 511
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
ucaaggaaga uggcauuucu                                              20

<210> SEQ ID NO 512
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
ucaaggaaga uggcauuucu                                              20

<210> SEQ ID NO 513
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
ucaaggaaga uggcauuucu                                              20

<210> SEQ ID NO 514
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 514
ucaaggaaga uggcauuucu                                                     20

<210> SEQ ID NO 515
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
ucaaggaaga uggcauuucu                                                     20

<210> SEQ ID NO 516
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
ucaaggaaga uggcauuucu                                                     20

<210> SEQ ID NO 517
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
ucaaggaaga uggcauuucu                                                     20

<210> SEQ ID NO 518
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
ucaaggaaga uggcauuucu                                                     20

<210> SEQ ID NO 519
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
ucaaggaaga uggcauuucu                                                     20

<210> SEQ ID NO 520
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 520
ucaaggaaga uggcauuucu                                                      20

<210> SEQ ID NO 521
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
ucaaggaaga uggcauuucu                                                      20

<210> SEQ ID NO 522
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
ucaaggaaga uggcauuucu                                                      20

<210> SEQ ID NO 523
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
ucaaggaaga uggcauuucu                                                      20

<210> SEQ ID NO 524
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
ucaaggaaga uggcauuucu                                                      20

<210> SEQ ID NO 525
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
ucaaggaaga uggcauuucu                                                      20

<210> SEQ ID NO 526
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 526
ucaaggaaga uggcauuucu                                                    20

<210> SEQ ID NO 527
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
ucaaggaaga uggcauuucu                                                    20

<210> SEQ ID NO 528
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
ucaaggaaga uggcauuucu                                                    20

<210> SEQ ID NO 529
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
ucaaggaaga uggcauuucu                                                    20

<210> SEQ ID NO 530
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
ucaaggaaga uggcauuucu                                                    20

<210> SEQ ID NO 531
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
ucaaggaaga uggcauuucu                                                    20

<210> SEQ ID NO 532
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 532
ucaaggaaga uggcauuucu                                               20

<210> SEQ ID NO 533
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
ucaaggaaga uggcauuucu                                               20

<210> SEQ ID NO 534
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
ucaaggaaga uggcauuucu                                               20

<210> SEQ ID NO 535
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
ucaaggaaga uggcauuucu                                               20

<210> SEQ ID NO 536
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
ucaaggaaga uggcauuucu                                               20

<210> SEQ ID NO 537
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
ucaaggaaga uggcauuucu                                               20

<210> SEQ ID NO 538
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued <210> SEQ ID NO 539
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
ucaaggaaga uggcauuucu                                                    20

<210> SEQ ID NO 540
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
ucaaggaaga uggcauuucu                                                    20

<210> SEQ ID NO 541
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
ucaaggaaga uggcauuucu                                                    20

<210> SEQ ID NO 542
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
ucaaggaaga uggcauuucu                                                    20

<210> SEQ ID NO 543
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
ucaaggaaga uggcauuucu                                                    20

<210> SEQ ID NO 544
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 544
gccaacuggg agcuggagcg caccaaccag                                        30

<210> SEQ ID NO 545
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
ucaaggaaga uggcauuucu                                                   20

<210> SEQ ID NO 546
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
ucaaggaaga uggcauuucu                                                   20

<210> SEQ ID NO 547
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
ucaaggaaga uggcauuucu                                                   20

<210> SEQ ID NO 548
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
ucaaggaaga uggcauuucu                                                   20

<210> SEQ ID NO 549
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
ccuucccuga agguuccucc                                                   20

<210> SEQ ID NO 550
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
```
ccuucccuga agguuccucc                                            20

<210> SEQ ID NO 551
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
ccuucccuga agguuccucc                                            20

<210> SEQ ID NO 552
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
ccuucccuga agguuccucc                                            20

<210> SEQ ID NO 553
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
ccuucccuga agguuccucc                                            20

<210> SEQ ID NO 554
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
ccuucccuga agguuccucc                                            20

<210> SEQ ID NO 555
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
ucaaggaaga uggcauuucu                                            20

<210> SEQ ID NO 556
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556

```
ucaaggaaga uggcauuucu                                               20

<210> SEQ ID NO 557
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
ucaaggaaga uggcauuucu                                               20

<210> SEQ ID NO 558
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
ucaaggaaga uggcauuuc                                                19

<210> SEQ ID NO 559
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
ucaaggaaga uggcauuu                                                 18

<210> SEQ ID NO 560
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
caaggaagau ggcauuucu                                                19

<210> SEQ ID NO 561
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
ggccaaaccu cggcuuaccu                                               20

<210> SEQ ID NO 562
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
ggccaaaccu cggcuuaccu                                               20
```

<210> SEQ ID NO 563
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
uucuguaagg uuuuuaugug                                                  20

<210> SEQ ID NO 564
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
auuucuguaa gguuuuuaug                                                  20

<210> SEQ ID NO 565
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
ccauuucugu aagguuuuua                                                  20

<210> SEQ ID NO 566
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
auccauuucu guaagguuuu                                                  20

<210> SEQ ID NO 567
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
cauccauuuc uguaagguuu                                                  20

<210> SEQ ID NO 568
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
ccauccauuu cuguaagguu                                                  20

<210> SEQ ID NO 569
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 569
gccauccauu ucuguaaggu                                               20

<210> SEQ ID NO 570
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 570
agccauccau uucuguaagg                                               20

<210> SEQ ID NO 571
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 571
cagccaucca uuucuguaag                                               20

<210> SEQ ID NO 572
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 572
ucagccaucc auuucuguaa                                               20

<210> SEQ ID NO 573
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 573
uucagccauc cauuucugua                                               20

<210> SEQ ID NO 574
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 574
cuucagccau ccauuucugu                                               20

```
<210> SEQ ID NO 575
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
acuucagcca uccauuucug                                                      20

<210> SEQ ID NO 576
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
aacuucagcc auccauuucu                                                      20

<210> SEQ ID NO 577
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
caacuucagc cauccauuuc                                                      20

<210> SEQ ID NO 578
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
ucaacuucag ccauccauuu                                                      20

<210> SEQ ID NO 579
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
aucaacuuca gccauccauu                                                      20

<210> SEQ ID NO 580
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
caucaacuuc agccauccau                                                      20

<210> SEQ ID NO 581
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
acaucaacuu cagccaucca                                                     20

<210> SEQ ID NO 582
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
aacaucaacu ucagccaucc                                                     20

<210> SEQ ID NO 583
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
gaaaacauca acuucagcca                                                     20

<210> SEQ ID NO 584
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
caggaaaaca ucaacuucag                                                     20

<210> SEQ ID NO 585
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
uuucaggaaa acaucaacuu                                                     20

<210> SEQ ID NO 586
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
cucuuucagg aaaacaucaa                                                     20

<210> SEQ ID NO 587
<211> LENGTH: 20
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
uuccucuuuc aggaaaacau                                               20

<210> SEQ ID NO 588
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
gccauuccuc uuucaggaaa                                               20

<210> SEQ ID NO 589
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
ggccauuccu cuuucaggaa                                               20

<210> SEQ ID NO 590
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
aggccauucc ucuuucagga                                               20

<210> SEQ ID NO 591
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
caggccauuc cucuuucagg                                               20

<210> SEQ ID NO 592
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
gcaggccauu ccucuuucag                                               20

<210> SEQ ID NO 593
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 593
ggcaggccau uccucuuuca                                                    20

<210> SEQ ID NO 594
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
gggcaggcca uuccucuuuc                                                    20

<210> SEQ ID NO 595
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
agggcaggcc auuccucuuu                                                    20

<210> SEQ ID NO 596
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
cagggcaggc cauuccucuu                                                    20

<210> SEQ ID NO 597
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
ccagggcagg ccauuccucu                                                    20

<210> SEQ ID NO 598
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
cccagggcag gccauuccuc                                                    20

<210> SEQ ID NO 599
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 599
ccccagggca ggccauuccu                                                     20

<210> SEQ ID NO 600
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
cccccagggc aggccauucc                                                     20

<210> SEQ ID NO 601
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
uccccagggg caggccauuc                                                     20

<210> SEQ ID NO 602
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602 auccccagg gcaggccauu                                                      20

<210> SEQ ID NO 603
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603 cauccccag ggcaggccau                                                      20

<210> SEQ ID NO 604
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
gcauccccca gggcaggcca                                                     20

<210> SEQ ID NO 605
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 605 agcaucccccc agggcaggcc                                                    20

<210> SEQ ID NO 606
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
cagcaucccc cagggcaggc                                                     20

<210> SEQ ID NO 607
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
ucagcauccc ccagggcagg                                                     20

<210> SEQ ID NO 608
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
uucagcaucc cccagggcag                                                     20

<210> SEQ ID NO 609
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
uuucagcauc ccccagggca                                                     20

<210> SEQ ID NO 610
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
auuucagcau cccccagggc                                                     20

<210> SEQ ID NO 611
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 611
gauuucagca uccccccaggg         20

<210> SEQ ID NO 612
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
ggauuucagc auccccccagg         20

<210> SEQ ID NO 613
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
aggauuucag cauccccccag         20

<210> SEQ ID NO 614
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
caggauuuca gcauccccca         20

<210> SEQ ID NO 615
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
ucaggauuuc agcaucccccc         20

<210> SEQ ID NO 616
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
uucaggauuu cagcauccccc         20

<210> SEQ ID NO 617
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 617
uuucaggauu ucagcauccc                                                  20

<210> SEQ ID NO 618
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
uuuucaggau uucagcaucc                                                  20

<210> SEQ ID NO 619
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
uuuuucagga uuucagcauc                                                  20

<210> SEQ ID NO 620
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
uuuuuucagg auuucagcau                                                  20

<210> SEQ ID NO 621
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
guuuuuucag gauuucagca                                                  20

<210> SEQ ID NO 622
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
uguuuuuuca ggauuucagc                                                  20

<210> SEQ ID NO 623
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 623 cuguuuuuc aggauuucag                                          20

<210> SEQ ID NO 624
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624 gcuguuuuu caggauuuca                                          20

<210> SEQ ID NO 625
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
agcuguuuuu ucaggauuuc                                         20

<210> SEQ ID NO 626
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
gagcuguuuu uucaggauuu                                         20

<210> SEQ ID NO 627
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
ugagcuguuu uuucaggauu                                         20

<210> SEQ ID NO 628
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
uugagcuguu uuuucaggau                                         20

<210> SEQ ID NO 629
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
```
uuugagcugu uuuuucagga 20

<210> SEQ ID NO 630
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
guuugagcug uuuuuucagg 20

<210> SEQ ID NO 631
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
uuguuugagc uguuuuuuca 20

<210> SEQ ID NO 632
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
cauuguuuga gcuguuuuuu 20

<210> SEQ ID NO 633
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
gcauuguuug agcuguuuuu 20

<210> SEQ ID NO 634
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
ugcauuguuu gagcuguuuu 20

<210> SEQ ID NO 635
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
cugcauuguu ugagcuguuu					20

<210> SEQ ID NO 636
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
ucugcauugu uugagcuguu					20

<210> SEQ ID NO 637
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
cucugcauug uuugagcugu					20

<210> SEQ ID NO 638
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
acucugcauu guuugagcug					20

<210> SEQ ID NO 639
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
uacucugcau uguuugagcu					20

<210> SEQ ID NO 640
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
uuacucugca uuguuugagc					20

<210> SEQ ID NO 641
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
cuuacucugc auuguuugag					20

<210> SEQ ID NO 642
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
ucuuacucug cauuguuuga                                                  20

<210> SEQ ID NO 643
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
aucuuacucu gcauuguuug                                                  20

<210> SEQ ID NO 644
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
aaucuuacuc ugcauuguuu                                                  20

<210> SEQ ID NO 645
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
caaaucuuac ucugcauugu                                                  20

<210> SEQ ID NO 646
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
gauacaaauc uuacucugca                                                  20

<210> SEQ ID NO 647
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 647

```
gggucagctg ccaatgcuag                                               20

<210> SEQ ID NO 648
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 648
gggucagctg ccaatgcuag                                               20

<210> SEQ ID NO 649
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 649
gggucagctg ccaatgcuag                                               20

<210> SEQ ID NO 650
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 650
gggucagctg ccaatgcuag                                               20

<210> SEQ ID NO 651
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 651
gggucagctg ccaatgctag                                               20

<210> SEQ ID NO 652
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 652
gggucagctg ccaatgctag                                               20

<210> SEQ ID NO 653
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 653
gggtcagctg ccaatgcuag                                               20

<210> SEQ ID NO 654
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
gggtcagctg ccaatgcuag                                               20

<210> SEQ ID NO 655
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655
gggucagctg ccaatgcuag                                               20

<210> SEQ ID NO 656
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656
gggucagctg ccaatgcuag                                               20

<210> SEQ ID NO 657
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
gggtcagctg ccaatgctag                                                20

<210> SEQ ID NO 658
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
gggtcagctg ccaatgctag                                                20

<210> SEQ ID NO 659
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659
gggucagctg ccaatgcuag                                                20

<210> SEQ ID NO 660
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660
gggucagctg ccaatgcuag                                                20

<210> SEQ ID NO 661
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
gggucagctg ccaatgcuag                                                20

<210> SEQ ID NO 662
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662
gggucagctg ccaatgcuag                                                20

<210> SEQ ID NO 663
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 663
gggucagctg ccaatgcuag                                              20

<210> SEQ ID NO 664
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664
gggucagctg ccaatgcuag                                              20

<210> SEQ ID NO 665
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
gggucagctg ccaatgcuag                                              20

<210> SEQ ID NO 666
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 666
gggucagctg ccaatgcuag                                              20

<210> SEQ ID NO 667
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 667
gggucagctg ccaatgcuag                                              20

<210> SEQ ID NO 668
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 668
gggucagctg ccaatgcuag                                              20

<210> SEQ ID NO 669
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
gggucagctg ccaatgcuag                                              20

<210> SEQ ID NO 670
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 670
gggucagctg ccaatgcuag                                              20

<210> SEQ ID NO 671
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
gggucagctg ccaatgcuag                                              20

<210> SEQ ID NO 672
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 672
gggucagctg ccaatgcuag                                                 20

<210> SEQ ID NO 673
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
gggucagctg ccaatgcuag                                                 20

<210> SEQ ID NO 674
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
gggucagctg ccaatgcuag                                                 20

<210> SEQ ID NO 675
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 675
gggucagctg ccaatgcuag                                                 20

<210> SEQ ID NO 676
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 676
gggucagctg ccaatgcuag                                                 20

<210> SEQ ID NO 677
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 677
gggucagctg ccaatgcuag                                              20

<210> SEQ ID NO 678
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 678
gggucagctg ccaatgcuag                                              20

<210> SEQ ID NO 679
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 679
gggucagctg ccaatgcuag                                              20

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680
gggucagctg ccaatgcuag                                              20

<210> SEQ ID NO 681
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
gggucagctg ccaatgcuag                                              20

<210> SEQ ID NO 682
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 682
gggucagctg ccaatgcuag                                           20

<210> SEQ ID NO 683
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
gggucagctg ccaatgcuag                                           20

<210> SEQ ID NO 684
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 684
gggucagctg ccaatgcuag                                           20

<210> SEQ ID NO 685
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 685
gggucagctg ccaatgcuag                                           20

<210> SEQ ID NO 686
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 686
gggucagctg ccaatgcuag                                           20

<210> SEQ ID NO 687
<211> LENGTH: 20
<212> TYPE: RNA
<213> ORGANISM: Artificial Sequence
<220> FEATURE:
<223> OTHER INFORMATION: Description of Artificial Sequence:
      Synthetic oligonucleotide

<400> SEQUENCE: 687

-continued cuagcauugg cagcugaccc                                        20

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
gggtcagctg ccaatgctag                                        20

<210> SEQ ID NO 689
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 689
gggucagctg ccaatgcuag                                        20

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 690
gggucagctg ccaatgcuag                                        20

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
gggtcagctg ccaatgctag                                        20

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
gggtcagctg ccaatgctag                                        20

<210> SEQ ID NO 693
<211> LENGTH: 20
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 693
gggtcagctg ccaatgctag                                              20

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
gggtcagctg ccaatgctag                                              20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
gggtcagctg ccaatgctag                                              20

<210> SEQ ID NO 696
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
gggtcagctg ccaatgctag                                              20

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
gggtcagctg ccaatgctag                                              20

<210> SEQ ID NO 698
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
gggtcagctg ccaatgctag                                              20

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 699
gggtcagctg ccaatgctag						20

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
gggtcagctg ccaatgctag						20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
gggtcagctg ccaatgctag						20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
gggtcagctg ccaatgctag						20

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
gggtcagctg ccaatgctag						20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
gggtcagctg ccaatgctag						20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
gggtcagctg ccaatgctag    20

<210> SEQ ID NO 706
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
gggtcagctg ccaatgctag    20

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
gggtcagctg ccaatgctag    20

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
gggtcagctg ccaatgctag    20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
gggtcagctg ccaatgctag    20

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
gggtcagctg ccaatgctag    20

<210> SEQ ID NO 711
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 711
gggtcagctg ccaatgctag                                               20

<210> SEQ ID NO 712
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
gggtcagctg ccaatgctag                                               20

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 713
uagcgcccac ctcaccccuc                                               20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 714
uuagcgccca cctcaccccu                                               20

<210> SEQ ID NO 715
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 715
cuuagcgccc acctcaccccc                                              20

<210> SEQ ID NO 716
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716 acccccgtcct ggaaaccagg                                              20
```

```
<210> SEQ ID NO 717
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
ccccgtcctg gaaaccagga                                                   20

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 718
gcuuagcgcc cacctcaccc                                                   20

<210> SEQ ID NO 719
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
ggcuuagcgc ccaccucacc                                                   20

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 720
cccgucctgg aaaccaggag                                                   20

<210> SEQ ID NO 721
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 721
ugaaccccgt cctggaaacc                                                   20

<210> SEQ ID NO 722
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 722
uuuccccucc ctcatcaaca                                               20

<210> SEQ ID NO 723
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 723
agcuccagtc cctgaagguq                                               20

<210> SEQ ID NO 724
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 724
aggcutagcg cccaccucac                                               20

<210> SEQ ID NO 725
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 725
guuuccccuc cctcaucaac                                               20

<210> SEQ ID NO 726
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
aaccccgtcc tggaaaccag                                               20

<210> SEQ ID NO 727
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 727 gaacccgtc ctggaaacca                                                  20

<210> SEQ ID NO 728
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 728
gcuccagtcc ctgaaggugu                                                 20

<210> SEQ ID NO 729
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 729
uugaaccccg tcctggaaac                                                 20

<210> SEQ ID NO 730
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 730
uucccctccc tcatcaacaa                                                 20

<210> SEQ ID NO 731
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 731
ccguccugga aaccaggagu                                                 20

<210> SEQ ID NO 732
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
```

-continued gcagctccag tccctgaagg                                               20

<210> SEQ ID NO 733
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733
ugccaggctg gttatgacuc                                               20

<210> SEQ ID NO 734
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
cgucctggaa accaggagug                                               20

<210> SEQ ID NO 735
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 735
cagcuccagt ccctgaaggu                                               20

<210> SEQ ID NO 736
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 736
cugccaggct ggttaugacu                                               20

<210> SEQ ID NO 737
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 737
uccuggaaac caggagugcc                                               20

<210> SEQ ID NO 738
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 738
aaggcttagc gcccaccuca         20

<210> SEQ ID NO 739
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 739
ccaggctggt tatgacucag         20

<210> SEQ ID NO 740
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 740
ccuggaaacc aggagugcca         20

<210> SEQ ID NO 741
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 741
gccaggctgg ttatgacuca         20

<210> SEQ ID NO 742
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 742
aaaggcttag cgcccaccuc         20

```
<210> SEQ ID NO 743
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 743
ggauugggag ttactugcca                                               20

<210> SEQ ID NO 744
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
guccuggaaa ccaggagugc                                               20

<210> SEQ ID NO 745
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 745
caggctggtt atgacucaga                                               20

<210> SEQ ID NO 746
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 746
gggagttact tgccaacuug                                               20

<210> SEQ ID NO 747
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 747
ugggagttac ttgccaacuu                                               20

<210> SEQ ID NO 748
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 748 uugggagutta cttgccaacu                                              20

<210> SEQ ID NO 749
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 749
auuuccucaa cactcagccu                                               20

<210> SEQ ID NO 750
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 750
ccccuccctc atcaacaaaa                                               20

<210> SEQ ID NO 751
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 751
acauutccac ttgccaguua                                               20

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 752
aaaaggctta gcgcccaccu                                               20

<210> SEQ ID NO 753
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 753
accugtctga ggcaaacgaa                                                     20

<210> SEQ ID NO 754
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 754
auugggagtt acttgccaac                                                     20

<210> SEQ ID NO 755
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 755
ucaacaaaag cccacccucu                                                     20

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 756
cuaagatgct agcttggcca                                                     20

<210> SEQ ID NO 757
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
gggtcagctg ccaatgctag                                                     20

<210> SEQ ID NO 758
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 758
gggtcagctg ccaatgctag                                               20

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
gggtcagctg ccaatgctag                                               20

<210> SEQ ID NO 760
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
gggtcagctg ccaatgctag                                               20

<210> SEQ ID NO 761
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
gggtcagctg ccaatgctag                                               20

<210> SEQ ID NO 762
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 762
ucaaggaaga uggcauuucu                                               20

<210> SEQ ID NO 763
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 763
ucaaggaaga uggcauuucu                                               20

<210> SEQ ID NO 764
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 764
ggccaaaccu cggcuuaccu                                                   20

<210> SEQ ID NO 765
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765
cuccaacauc aaggaagaug gcauuucuag                                        30

<210> SEQ ID NO 766
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 766
accagaguaa cagucugagu aggag                                             25

<210> SEQ ID NO 767
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767
caccagagua acagucugag uagga                                             25

<210> SEQ ID NO 768
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768
ucaccagagu aacagucuga guagg                                             25

<210> SEQ ID NO 769
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 769
gucaccagag uaacagucug aguag                                             25

<210> SEQ ID NO 770
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 770
guugugucac cagaguaaca gucug                                          25

<210> SEQ ID NO 771
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
gguuguguca ccagaguaac agucu                                          25

<210> SEQ ID NO 772
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
agguuguguc accagaguaa caguc                                          25

<210> SEQ ID NO 773
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 773
cagguugugu caccagagua acagu                                          25

<210> SEQ ID NO 774
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 774
acagguugug ucaccagagu aacag                                          25

<210> SEQ ID NO 775
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 775
ccacagguug ugucaccaga guaac                                          25

<210> SEQ ID NO 776
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 776
```
accacagguu gugucaccag aguaa                                              25

<210> SEQ ID NO 777
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 777
aaccacaggu ugugucacca gagua                                              25

<210> SEQ ID NO 778
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 778
uaaccacagg uugugucacc agagu                                              25

<210> SEQ ID NO 779
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
guaaccacag guugugucac cagag                                              25

<210> SEQ ID NO 780
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
aguaaccaca gguuguguca ccaga                                              25

<210> SEQ ID NO 781
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781
uaguaaccac agguuguguc accag                                              25

<210> SEQ ID NO 782
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782

-continued uuaguaacca cagguugugu cacca                          25

<210> SEQ ID NO 783
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
cuuaguaacc acagguugug ucacc                          25

<210> SEQ ID NO 784
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
ccuuaguaac cacagguugu gucac                          25

<210> SEQ ID NO 785
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785
uccuuaguaa ccacagguug uguca                          25

<210> SEQ ID NO 786
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786
guuuccuuag uaaccacagg uugug                          25

<210> SEQ ID NO 787
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787 aguuccuua guaaccacag guugu                           25

<210> SEQ ID NO 788
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788 caguuccuu aguaaccaca gguug                           25

<210> SEQ ID NO 789
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789
gcaguuuccu uaguaaccac agguu                                         25

<210> SEQ ID NO 790
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
ggcaguuucc uuaguaacca caggu                                         25

<210> SEQ ID NO 791
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
uggcaguuuc cuuaguaacc acagg                                         25

<210> SEQ ID NO 792
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
auggcaguuu ccuuaguaac cacag                                         25

<210> SEQ ID NO 793
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793
agauggcagu uuccuuagua accac                                         25

<210> SEQ ID NO 794
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
gagauggcag uuccuuagu aacca                                          25

```
<210> SEQ ID NO 795
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
ggagauggca guuccuuag uaacc                                             25

<210> SEQ ID NO 796
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
uggagauggc aguuccuua guaac                                             25

<210> SEQ ID NO 797
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
uuggagaugg caguuccuu aguaa                                             25

<210> SEQ ID NO 798
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
uuuggagaug gcaguuccu uagua                                             25

<210> SEQ ID NO 799
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
aguuuggaga uggcaguuc cuuag                                             25

<210> SEQ ID NO 800
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
uaguuuggag auggcaguuu ccuua                                            25
```

```
<210> SEQ ID NO 801
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 801
cuaguuugga gauggcaguu uccuu                                              25

<210> SEQ ID NO 802
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
ucuaguuugg agauggcagu uuccu                                              25

<210> SEQ ID NO 803
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
uucuaguuug gagauggcag uuucc                                              25

<210> SEQ ID NO 804
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
cauuucuagu uggagaugg caguu                                               25

<210> SEQ ID NO 805
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
gcauuucuag uuuggagaug gcagu                                              25

<210> SEQ ID NO 806
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806
auggcauuuc uaguuggag auggc                                               25

<210> SEQ ID NO 807
```

<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
gaagauggca uuucuaguuu ggaga                                           25

<210> SEQ ID NO 808
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 808
aggaagaugg cauuucuagu uugga                                           25

<210> SEQ ID NO 809
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 809
aaggaagaug gcauuucuag uuugg                                           25

<210> SEQ ID NO 810
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 810
caaggaagau ggcauuucua guuug                                           25

<210> SEQ ID NO 811
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 811
caucaaggaa gauggcauuu cuagu                                           25

<210> SEQ ID NO 812
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 812
acaucaagga gauggcauu ucuag                                            25

<210> SEQ ID NO 813
<211> LENGTH: 25

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 813
aacaucaagg aagauggcau uucua                                               25

<210> SEQ ID NO 814
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 814
caacaucaag gaagauggca uuucu                                               25

<210> SEQ ID NO 815
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 815
cuccaacauc aaggaagaug gcauu                                               25

<210> SEQ ID NO 816
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 816
accuccaaca ucaaggaaga uggca                                               25

<210> SEQ ID NO 817
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 817
guaccuccaa caucaaggaa gaugg                                               25

<210> SEQ ID NO 818
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 818
agguaccucc aacaucaagg aagau                                               25

<210> SEQ ID NO 819
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 819
agagcaggua ccuccaacau caagg                                               25

<210> SEQ ID NO 820
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 820
cagagcaggu accuccaaca ucaag                                               25

<210> SEQ ID NO 821
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
cugccagagc agguaccucc aacau                                               25

<210> SEQ ID NO 822
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
ucugccagag cagguaccuc caaca                                               25

<210> SEQ ID NO 823
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 823
aucugccaga gcagguaccu ccaac                                               25

<210> SEQ ID NO 824
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 824
aaucugccag agcagguacc uccaa                                               25

<210> SEQ ID NO 825
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 825
aaaucugcca gagcagguac cucca                                          25

<210> SEQ ID NO 826
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 826
gaaaucugcc agagcaggua ccucc                                          25

<210> SEQ ID NO 827
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
ugaaaucugc cagagcaggu accuc                                          25

<210> SEQ ID NO 828
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 828
uugaaaucug ccagagcagg uaccu                                          25

<210> SEQ ID NO 829
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
cccgguugaa aucugccaga gcagg                                          25

<210> SEQ ID NO 830
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 830
ccaagcccgg uugaaaucug ccaga                                          25

<210> SEQ ID NO 831
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 831
uccaagcccg guugaaaucu gccag                                              25

<210> SEQ ID NO 832
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
guccaagccc gguugaaauc ugcca                                              25

<210> SEQ ID NO 833
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 833
ucuguccaag cccgguugaa aucug                                              25

<210> SEQ ID NO 834
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
uucuguccaa gcccgguuga aaucu                                              25

<210> SEQ ID NO 835
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 835
guucugucca agcccgguug aaauc                                              25

<210> SEQ ID NO 836
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 836
aguucugucc aagcccgguu gaaau                                              25

<210> SEQ ID NO 837
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 837
aaguucuguc caagcccggu ugaaa                                          25

<210> SEQ ID NO 838
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
uaaguucugu ccaagcccgg uugaa                                          25

<210> SEQ ID NO 839
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 839
guaaguucug uccaagcccg guuga                                          25

<210> SEQ ID NO 840
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 840
gguaaguucu guccaagccc gguug                                          25

<210> SEQ ID NO 841
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 841
cgguaaguuc uguccaagcc cgguu                                          25

<210> SEQ ID NO 842
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 842
ucgguaaguu cuguccaagc ccggu                                          25

<210> SEQ ID NO 843
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 843
gucgguaagu ucuguccaag cccgg                                              25

<210> SEQ ID NO 844
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 844
agucgguaag uucuguccaa gcccg                                              25

<210> SEQ ID NO 845
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 845
cagucgguaa guucugucca agccc                                              25

<210> SEQ ID NO 846
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 846
aaagccaguc gguaaguucu gucca                                              25

<210> SEQ ID NO 847
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 847
gaaagccagu cgguaaguuc ugucc                                              25

<210> SEQ ID NO 848
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 848
gucacccacc aucacccucu gugau                                              25

<210> SEQ ID NO 849
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 849
ggucacccac caucacccuc uguga                                       25

<210> SEQ ID NO 850
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
aaggucaccc accaucaccc ucugu                                       25

<210> SEQ ID NO 851
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
caaggucacc caccaucacc cucug                                       25

<210> SEQ ID NO 852
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
ucaaggucac ccaccaucac ccucu                                       25

<210> SEQ ID NO 853
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 853
cucaagguca cccaccauca cccuc                                       25

<210> SEQ ID NO 854
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 854
cuugaucaag cagagaaagc caguc                                       25

<210> SEQ ID NO 855
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
```
auaacuugau caagcagaga aagcc 25

<210> SEQ ID NO 856
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 856
aguaacaguc ugaguaggag 20

<210> SEQ ID NO 857
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 857
gaguaacagu cugaguagga 20

<210> SEQ ID NO 858
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 858
agaguaacag ucugaguagg 20

<210> SEQ ID NO 859
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 859
cagaguaaca gucugaguag 20

<210> SEQ ID NO 860
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 860
gucaccagag uaacagucug 20

<210> SEQ ID NO 861
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 861
ugucaccaga guaacagucu                                           20

<210> SEQ ID NO 862
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 862
gugucaccag aguaacaguc                                           20

<210> SEQ ID NO 863
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 863
ugugucacca gaguaacagu                                           20

<210> SEQ ID NO 864
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 864
uugugucacc agaguaacag                                           20

<210> SEQ ID NO 865
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 865
gguuguguca ccagaguaac                                           20

<210> SEQ ID NO 866
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 866
agguuguguc accagaguaa                                           20

<210> SEQ ID NO 867
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 867
cagguugugu caccagagua                                           20

```
<210> SEQ ID NO 868
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 868
acagguugug ucaccagagu                                                  20

<210> SEQ ID NO 869
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 869
cacagguugu gucaccagag                                                  20

<210> SEQ ID NO 870
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 870
ccacagguug ugucaccaga                                                  20

<210> SEQ ID NO 871
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
accacagguu gugucaccag                                                  20

<210> SEQ ID NO 872
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 872
aaccacaggu ugugucacca                                                  20

<210> SEQ ID NO 873
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 873
uaaccacagg uugugucacc                                                  20
```

```
<210> SEQ ID NO 874
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 874
guaaccacag guugugucac                                                   20

<210> SEQ ID NO 875
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 875
aguaaccaca gguuguguca                                                   20

<210> SEQ ID NO 876
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 876
cuuaguaacc acagguugug                                                   20

<210> SEQ ID NO 877
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877
ccuuaguaac cacagguugu                                                   20

<210> SEQ ID NO 878
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 878
uccuuaguaa ccacagguug                                                   20

<210> SEQ ID NO 879
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 879
uuccuuagua accacagguu                                                   20
```

```
<210> SEQ ID NO 880
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 880
uuuccuuagu aaccacaggu                                              20

<210> SEQ ID NO 881
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 881
guuuccuuag uaaccacagg                                              20

<210> SEQ ID NO 882
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 882 aguuccuua guaaccacag                                               20

<210> SEQ ID NO 883
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 883
gcaguuuccu uaguaaccac                                              20

<210> SEQ ID NO 884
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 884
ggcaguuucc uuaguaacca                                              20

<210> SEQ ID NO 885
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 885
uggcaguuuc cuuaguaacc                                              20

<210> SEQ ID NO 886
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 886
auggcaguuu ccuuaguaac                                              20

<210> SEQ ID NO 887
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 887
gauggcaguu uccuuaguaa                                              20

<210> SEQ ID NO 888
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 888
agauggcagu uuccuuagua                                              20

<210> SEQ ID NO 889
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 889
ggagauggca guuccuuag                                               20

<210> SEQ ID NO 890
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 890
uggagauggc aguuccuua                                               20

<210> SEQ ID NO 891
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 891
uuggagaugg caguuuccuu                                              20

<210> SEQ ID NO 892
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 892
uuuggagaug gcaguuuccu                                                   20

<210> SEQ ID NO 893
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 893
guuuggagau ggcaguuucc                                                   20

<210> SEQ ID NO 894
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 894
cuaguuugga gauggcaguu                                                   20

<210> SEQ ID NO 895
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 895
ucuaguuugg agauggcagu                                                   20

<210> SEQ ID NO 896
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 896
auuucuaguu uggagauggc                                                   20

<210> SEQ ID NO 897
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 897
uggcauuucu aguuuggaga                                                   20

<210> SEQ ID NO 898
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 898
gauggcauuu cuaguuugga                                              20

<210> SEQ ID NO 899
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 899
agauggcauu ucuaguuugg                                              20

<210> SEQ ID NO 900
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 900
aagauggcau uucuaguuug                                              20

<210> SEQ ID NO 901
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 901
aggaagaugg cauuucuagu                                              20

<210> SEQ ID NO 902
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 902
aaggaagaug gcauuucuag                                              20

<210> SEQ ID NO 903
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 903
caaggaagau ggcauuucua                                              20

<210> SEQ ID NO 904
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 904
ucaaggaaga uggcauuucu                                            20

<210> SEQ ID NO 905
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 905
acaucaagga agauggcauu                                            20

<210> SEQ ID NO 906
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 906
caacaucaag gaagauggca                                            20

<210> SEQ ID NO 907
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 907
uccaacauca aggaagaugg                                            20

<210> SEQ ID NO 908
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 908
ccuccaacau caaggaagau                                            20

<210> SEQ ID NO 909
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 909
agguaccucc aacaucaagg                                            20

<210> SEQ ID NO 910
<211> LENGTH: 20
<212> TYPE: RNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 910
cagguaccuc caacaucaag                                              20

<210> SEQ ID NO 911
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 911
agagcaggua ccuccaacau                                              20

<210> SEQ ID NO 912
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 912
cagagcaggu accuccaaca                                              20

<210> SEQ ID NO 913
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 913
ccagagcagg uaccuccaac                                              20

<210> SEQ ID NO 914
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 914
gccagagcag guaccuccaa                                              20

<210> SEQ ID NO 915
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 915
ugccagagca gguaccucca                                              20

<210> SEQ ID NO 916
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 916
cugccagagc agguaccucc                                               20

<210> SEQ ID NO 917
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 917
ucugccagag cagguaccuc                                               20

<210> SEQ ID NO 918
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 918
aucugccaga gcagguaccu                                               20

<210> SEQ ID NO 919
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 919
uugaaaucug ccagagcagg                                               20

<210> SEQ ID NO 920
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 920
cccgguugaa aucugccaga                                               20

<210> SEQ ID NO 921
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 921
gcccgguuga aaucugccag                                               20

<210> SEQ ID NO 922
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 922
agcccgguug aaaucugcca    20

<210> SEQ ID NO 923
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 923
ccaagcccgg uugaaaucug    20

<210> SEQ ID NO 924
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 924
uccaagcccg guugaaaucu    20

<210> SEQ ID NO 925
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 925
guccaagccc gguugaaauc    20

<210> SEQ ID NO 926
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 926
uguccaagcc cgguugaaau    20

<210> SEQ ID NO 927
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 927
cuguccaagc ccgguugaaa    20

<210> SEQ ID NO 928
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 928
ucuguccaag cccgguugaa                                               20

<210> SEQ ID NO 929
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 929
uucuguccaa gcccgguuga                                               20

<210> SEQ ID NO 930
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 930
guucugucca agcccgguug                                               20

<210> SEQ ID NO 931
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 931
aguucugucc aagcccgguu                                               20

<210> SEQ ID NO 932
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 932
aaguucuguc caagcccggu                                               20

<210> SEQ ID NO 933
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 933
uaaguucugu ccaagcccgg                                               20

<210> SEQ ID NO 934
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 934
```
guaaguucug uccaagcccg                                           20

<210> SEQ ID NO 935
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 935
gguaaguucu guccaagccc                                           20

<210> SEQ ID NO 936
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 936
cagucgguaa guucugucca                                           20

<210> SEQ ID NO 937
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 937
ccagucggua aguucugucc                                           20

<210> SEQ ID NO 938
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 938
ccaccaucac ccucugugau                                           20

<210> SEQ ID NO 939
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 939
cccaccauca cccucuguga                                           20

<210> SEQ ID NO 940
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 940
cacccaccau cacccucugu                                              20

<210> SEQ ID NO 941
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 941
ucacccacca ucacccucug                                              20

<210> SEQ ID NO 942
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 942
gucacccacc aucacccucu                                              20

<210> SEQ ID NO 943
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 943
ggucacccac caucacccuc                                              20

<210> SEQ ID NO 944
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 944
ucaagcagag aaagccaguc                                              20

<210> SEQ ID NO 945
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 945
uugaucaagc agagaaagcc                                              20

<210> SEQ ID NO 946
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 946
caaagaagau ggcauuucua guuug                                        25

<210> SEQ ID NO 947
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 947
gcaaagaaga uggcauuucu                                               20

<210> SEQ ID NO 948
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 948
gcaaagaaga uggcauuucu                                               20

<210> SEQ ID NO 949
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949
ucaaggaaga uggcauuucu                                               20

<210> SEQ ID NO 950
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
ucaaggaaga uggcauuucu                                               20

<210> SEQ ID NO 951
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 951
ucaaggaaga uggcauuucu                                               20

<210> SEQ ID NO 952
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 952
ucaaggaaga uggcauuucu                                               20

<210> SEQ ID NO 953
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 953
ucaaggaaga uggcauuucu                                              20

<210> SEQ ID NO 954
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 954
ucaaggaaga uggcauuucu                                              20

<210> SEQ ID NO 955
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
ucaaggaaga uggcauuucu                                              20

<210> SEQ ID NO 956
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
ucaaggaaga uggcauuucu                                              20

<210> SEQ ID NO 957
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 957
ucaaggaaga uggcauuucu                                              20

<210> SEQ ID NO 958
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 958
ucaaggaaga uggcauuucu                                              20

```
<210> SEQ ID NO 959
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 959
ucaaggaaga uggcauuucu                                                     20

<210> SEQ ID NO 960
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
ucaaggaaga uggcauuucu                                                     20

<210> SEQ ID NO 961
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 961
ucaaggaaga uggcauuucu                                                     20

<210> SEQ ID NO 962
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 962
ucaaggaaga uggcauuucu                                                     20

<210> SEQ ID NO 963
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 963
ucaaggaaga uggcauuucu                                                     20

<210> SEQ ID NO 964
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 964
ucaaggaaga uggcauuucu                                                     20

<210> SEQ ID NO 965
```

-continued

<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 965
ucaaggaaga uggcauuucu                                              20

<210> SEQ ID NO 966
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
ucaaggaaga uggcauuucu                                              20

<210> SEQ ID NO 967
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 967
ucaaggaaga uggcauuucu                                              20

<210> SEQ ID NO 968
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
ucaaggaaga uggcauuucu                                              20

<210> SEQ ID NO 969
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
ucaaggaaga uggcauuucu                                              20

<210> SEQ ID NO 970
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
ucaaggaaga uggcauuucu                                              20

<210> SEQ ID NO 971
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 971
ucaaggaaga uggcauuucu                                                     20

<210> SEQ ID NO 972
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
ucaaggaaga uggcauuucu                                                     20

<210> SEQ ID NO 973
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 973
ucaaggaaga uggcauuucu                                                     20

<210> SEQ ID NO 974
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 974
ucaaggaaga uggcauuucu                                                     20

<210> SEQ ID NO 975
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
ucaaggaaga uggcauuucu                                                     20

<210> SEQ ID NO 976
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
ucaaggaaga uggcauuucu                                                     20

<210> SEQ ID NO 977
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 977
ucaaggaaga uggcauuucu                                                   20

<210> SEQ ID NO 978
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
ggccaaaccu cggcuuaccu                                                   20

<210> SEQ ID NO 979
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 979
ggccaaaccu cggcuuaccu                                                   20

<210> SEQ ID NO 980
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 980
ggccaaaccu cggcuuaccu                                                   20

<210> SEQ ID NO 981
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 981
ggccaaaccu cggcuuaccu                                                   20

<210> SEQ ID NO 982
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 982
ggccaaaccu cggcuuaccu                                                   20

<210> SEQ ID NO 983
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 983
ggccaaaccu cggcuuaccu                                                    20

<210> SEQ ID NO 984
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 984
ggccaaaccu cggcuuaccu                                                    20

<210> SEQ ID NO 985
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 985
ggccaaaccu cggcuuaccu                                                    20

<210> SEQ ID NO 986
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 986
ucaaggaaga uggcauuucu                                                    20

<210> SEQ ID NO 987
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 987
ucaaggaaga uggcauuucu                                                    20

<210> SEQ ID NO 988
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 988
ucaaggaaga uggcauuucu                                                    20

<210> SEQ ID NO 989
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 989
ucaaggaaga uggcauuucu                                                   20

<210> SEQ ID NO 990
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 990
ucaaggaaga uggcauuucu                                                   20

<210> SEQ ID NO 991
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 991
ucaaggaaga uggcauuucu                                                   20

<210> SEQ ID NO 992
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 992
ucaaggaaga uggcauuucu                                                   20

<210> SEQ ID NO 993
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 993
ucaaggaaga uggcauuucu                                                   20

<210> SEQ ID NO 994
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 994
ggccaaacct cggcttacct                                                   20

<210> SEQ ID NO 995
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 995
ggccaaaccu cggcuuaccu                                        20

<210> SEQ ID NO 996
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
ggccaaacct cggcttacct                                        20

<210> SEQ ID NO 997
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
ggccaaacct cggcttacct                                        20

<210> SEQ ID NO 998
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 998
ggccaaaccu cggcttacct                                        20

<210> SEQ ID NO 999
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 999
ggccaaacct cggcttaccu                                        20

<210> SEQ ID NO 1000
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1000
ggccaaaccu cggctuaccu                                        20

<210> SEQ ID NO 1001
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1001
ggccaaacct cggcutaccu                                                    20

<210> SEQ ID NO 1002
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1002
ggccaaacct cggctuaccu                                                    20

<210> SEQ ID NO 1003
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1003
ggccaaaccu cggcuuaccu                                                    20

<210> SEQ ID NO 1004
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1004
ggccaaacct cggcutaccu                                                    20

<210> SEQ ID NO 1005
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1005
ggccaaacct cggctuaccu                                                    20

```
<210> SEQ ID NO 1006
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1006
ggccaaaccu cggcttaccu                                             20

<210> SEQ ID NO 1007
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1007
ggccaaaccu cggcttacct                                             20

<210> SEQ ID NO 1008
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1008
ggccaaacct cggcttaccu                                             20

<210> SEQ ID NO 1009
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1009
ggccaaaccu cggctuaccu                                             20

<210> SEQ ID NO 1010
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1010
ggccaaacct cggcutaccu                                             20
```

<210> SEQ ID NO 1011
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1011
ggccaaacct cggctuaccu                                                    20

<210> SEQ ID NO 1012
<211> LENGTH: 20
<212> TYPE: RNA
<213> ORGANISM: Artificial Sequence
<220> FEATURE:
<223> OTHER INFORMATION: Description of Artificial Sequence:
      Synthetic oligonucleotide

<400> SEQUENCE: 1012
ggccaaaccu cggcuuaccu                                                    20

<210> SEQ ID NO 1013
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1013
ggccaaacct cggcutaccu                                                    20

<210> SEQ ID NO 1014
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1014
ggccaaacct cggctuaccu                                                    20

<210> SEQ ID NO 1015
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1015
ggccaaaccu cggcttaccu                                                    20

<210> SEQ ID NO 1016

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1016
ggccaaaccu cggcutaccu                                                    20

<210> SEQ ID NO 1017
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1017
ggccaaaccu cggcuuaccu                                                    20

<210> SEQ ID NO 1018
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1018
ggccaaaccu cggcuuaccu                                                    20

<210> SEQ ID NO 1019
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1019
ggccaaaccu cggcuuaccu                                                    20

<210> SEQ ID NO 1020
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1020
ggccaaaccu cggcuuaccu                                                    20

<210> SEQ ID NO 1021
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1021
ggccaaaccu cggcuuaccu                                                    20
```

<210> SEQ ID NO 1022
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1022
ggccaaaccu cggcuuaccu                                               20

<210> SEQ ID NO 1023
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1023
ggccaaaccu cggcuuaccu                                               20

<210> SEQ ID NO 1024
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1024
ggccaaaccu cggcuuaccu                                               20

<210> SEQ ID NO 1025
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1025
ggccaaaccu cggcuuaccu                                               20

<210> SEQ ID NO 1026
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1026
ggccaaaccu cggcuuaccu                                               20

<210> SEQ ID NO 1027
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1027
ggccaaaccu cggcuuaccu                                               20

```
<210> SEQ ID NO 1028
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1028
ggccaaaccu cggcuuaccu gaaau                                           25

<210> SEQ ID NO 1029
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1029
ggccaaaccu cggcutaccu                                                 20

<210> SEQ ID NO 1030
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1030
tcaaggaaga tggcatttct                                                 20

<210> SEQ ID NO 1031
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1031
ucaaggaaga uggcauuucu                                                 20

<210> SEQ ID NO 1032
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1032
tcaaggaaga tggcatttct                                                 20

<210> SEQ ID NO 1033
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1033
tcaaggaaga tggcatttct                                                 20
```

<210> SEQ ID NO 1034
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1034
tcaaggaaga uggcatttct                                                20

<210> SEQ ID NO 1035
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1035
ucaaggaaga tggcatuucu                                                20

<210> SEQ ID NO 1036
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1036
tcaaggaaga tggcautucu                                                20

<210> SEQ ID NO 1037
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1037
ucaaggaaga uggcatutcu                                                20

<210> SEQ ID NO 1038
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1038
tcaaggaaga tggcauutcu                                                   20

<210> SEQ ID NO 1039
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1039
tcaaggaaga uggcauttcu                                                   20

<210> SEQ ID NO 1040
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1040
tcaaggaaga tggcatttcu                                                   20

<210> SEQ ID NO 1041
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1041
tcaaggaaga tggcauttcu                                                   20

<210> SEQ ID NO 1042
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1042
ucaaggaaga uggcatttcu                                                   20

<210> SEQ ID NO 1043
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1043
tcaaggaaga tggcatttcu                                              20

<210> SEQ ID NO 1044
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1044
tcaaggaaga uggcatttct                                              20

<210> SEQ ID NO 1045
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1045
ucaaggaaga tggcatuucu                                              20

<210> SEQ ID NO 1046
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1046
tcaaggaaga tggcautucu                                              20

<210> SEQ ID NO 1047
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1047
ucaaggaaga uggcatutcu                                              20

<210> SEQ ID NO 1048
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1048
tcaaggaaga tggcauutcu					20

<210> SEQ ID NO 1049
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1049
tcaaggaaga uggcauttcu					20

<210> SEQ ID NO 1050
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1050
tcaaggaaga tggcatttcu					20

<210> SEQ ID NO 1051
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1051
tcaaggaaga tggcauttcu					20

<210> SEQ ID NO 1052
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1052
ucaaggaaga uggcatttcu					20

<210> SEQ ID NO 1053
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1053
tcaaggaaga tggcatttcu                                               20

<210> SEQ ID NO 1054
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1054
ucaaggaaga uggcauuucu                                               20

<210> SEQ ID NO 1055
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1055
ucaaggaaga uggcauuucu                                               20

<210> SEQ ID NO 1056
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1056
ucaaggaaga uggcauuucu                                               20

<210> SEQ ID NO 1057
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1057
ucaaggaaga uggcauuucu                                               20

<210> SEQ ID NO 1058
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1058
ucaaggaaga uggcauuucu                                               20

<210> SEQ ID NO 1059
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1059
ucaaggaaga uggcauuucu                                                    20

<210> SEQ ID NO 1060
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1060
ucaaggaaga uggcauuucu                                                    20

<210> SEQ ID NO 1061
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1061
ucaaggaaga uggcauuucu                                                    20

<210> SEQ ID NO 1062
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1062
ucaaggaaga uggcauuucu                                                    20

<210> SEQ ID NO 1063
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1063
ucaaggaaga uggcauuucu                                                    20

<210> SEQ ID NO 1064
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1064
agaaaugcca ucuuccuuga                                                    20

<210> SEQ ID NO 1065
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1065
```
ucaaggaaga uggcauuucu                                         20

<210> SEQ ID NO 1066
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1066
ucaaggaaga uggcauuucu                                         20

<210> SEQ ID NO 1067
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1067
ucaaggaaga uggcauuucu                                         20

<210> SEQ ID NO 1068
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1068
ucaaggaaga uggcauuucu                                         20

<210> SEQ ID NO 1069
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1069
ucaaggaaga uggcauuucu                                         20

<210> SEQ ID NO 1070
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1070
ucaaggaaga uggcauuucu                                         20

<210> SEQ ID NO 1071
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1071
ucaaggaaga uggcauuucu                                          20

```
<210> SEQ ID NO 1072
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1072
```
ucaaggaaga uggcauuucu                                          20

```
<210> SEQ ID NO 1073
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1073
```
ucaaggaaga uggcauuucu                                          20

```
<210> SEQ ID NO 1074
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1074
```
ucaaggaaga uggcauuucu                                          20

```
<210> SEQ ID NO 1075
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1075
```
ucaaggaaga uggcauuucu                                          20

```
<210> SEQ ID NO 1076
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1076
```
ucaaggaaga uggcauuucu                                          20

```
<210> SEQ ID NO 1077
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1077
```
ucaaggaaga uggcauuucu                                          20

```
<210> SEQ ID NO 1078
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1078
ucaaggaaga uggcauuucu                                                    20

<210> SEQ ID NO 1079
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1079
ucaaggaaga uggcauuucu                                                    20

<210> SEQ ID NO 1080
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1080
ucaaggaaga uggcauuucu                                                    20

<210> SEQ ID NO 1081
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1081
ucaaggaaga uggcauuucu                                                    20

<210> SEQ ID NO 1082
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1082
ucaaggaaga uggcauuucu                                                    20

<210> SEQ ID NO 1083
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1083
ucaaggaaga uggcauuucu                                                    20
```

```
<210> SEQ ID NO 1084
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1084
ucaaggaaga uggcauuucu                                                     20

<210> SEQ ID NO 1085
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1085
ucaaggaaga uggcauuucu                                                     20

<210> SEQ ID NO 1086
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1086
ucaaggaaga uggcauuucu                                                     20

<210> SEQ ID NO 1087
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1087
ucaaggaaga uggcauuucu                                                     20

<210> SEQ ID NO 1088
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1088
ucaaggaaga uggcauuucu                                                     20

<210> SEQ ID NO 1089
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1089
ucaaggaaga uggcauuucu                                                     20
```

-continued

```
<210> SEQ ID NO 1090
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1090
ucaaggaaga uggcauuucu                                                      20

<210> SEQ ID NO 1091
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1091
ucaaggaaga uggcauuucu                                                      20

<210> SEQ ID NO 1092
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1092
ucaaggaaga uggcauuucu                                                      20

<210> SEQ ID NO 1093
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1093
ucaaggaaga uggcauuucu                                                      20

<210> SEQ ID NO 1094
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1094
ucaaggaaga uggcauuucu                                                      20

<210> SEQ ID NO 1095
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1095
ucaaggaaga uggcauuucu                                                      20

<210> SEQ ID NO 1096
```

-continued

<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1096
ucaaggaaga uggcauuucu                                                    20

<210> SEQ ID NO 1097
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1097
ucaaggaaga uggcauuucu                                                    20

<210> SEQ ID NO 1098
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1098
ucaaggaaga uggcauuucu                                                    20

<210> SEQ ID NO 1099
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1099
ucaaggaaga uggcauuucu                                                    20

<210> SEQ ID NO 1100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1100
ucaaggaaga uggcauuucu                                                    20

<210> SEQ ID NO 1101
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1101
ucaaggaaga uggcauuucu                                                    20

<210> SEQ ID NO 1102
<211> LENGTH: 20

```
-continued

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1102
ucaaggaaga uggcauuucu                                              20

<210> SEQ ID NO 1103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1103
ucaaggaaga uggcauuucu                                              20

<210> SEQ ID NO 1104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1104
ucaaggaaga uggcauuucu                                              20

<210> SEQ ID NO 1105
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1105
ucaaggaaga uggcauuucu                                              20

<210> SEQ ID NO 1106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1106
ucaaggaaga uggcauuucu                                              20

<210> SEQ ID NO 1107
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1107
ucaaggaaga uggcauuucu                                              20

<210> SEQ ID NO 1108
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1108
ucaaggaaga uggcauuucu                                                  20

<210> SEQ ID NO 1109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1109
ucaaggaaga uggcauuucu                                                  20

<210> SEQ ID NO 1110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1110
ucaaggaaga uggcauuucu                                                  20

<210> SEQ ID NO 1111
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1111
ucaaggaaga uggcauuucu                                                  20

<210> SEQ ID NO 1112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1112
ucaaggaaga uggcauuucu                                                  20

<210> SEQ ID NO 1113
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1113
ucaaggaaga uggcauuucu                                                  20

<210> SEQ ID NO 1114
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1114
ucaaggaaga uggcauuucu                                                  20

<210> SEQ ID NO 1115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1115
ucaaggaaga uggcauuucu                                                  20

<210> SEQ ID NO 1116
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1116
ucaaggaaga uggcauuucu                                                  20

<210> SEQ ID NO 1117
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1117
ucaaggaaga uggcauuucu                                                  20

<210> SEQ ID NO 1118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1118
ucaaggaaga uggcauuucu                                                  20

<210> SEQ ID NO 1119
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1119
ucaaggaaga uggcauuucu                                                  20

<210> SEQ ID NO 1120
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1120
ucaaggaaga uggcauuucu                                                    20

<210> SEQ ID NO 1121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1121
ucaaggaaga uggcauuucu                                                    20

<210> SEQ ID NO 1122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1122
ucaaggaaga uggcauuucu                                                    20

<210> SEQ ID NO 1123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1123
ucaaggaaga uggcauuucu                                                    20

<210> SEQ ID NO 1124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1124
ucaaggaaga uggcauuucu                                                    20

<210> SEQ ID NO 1125
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1125
ucaaggaaga uggcauuucu                                                    20

<210> SEQ ID NO 1126
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1126
ucaaggaaga uggcauuucu                                          20

<210> SEQ ID NO 1127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1127
ucaaggaaga uggcauuucu                                          20

<210> SEQ ID NO 1128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1128
ucaaggaaga uggcauuucu                                          20

<210> SEQ ID NO 1129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1129
ucaaggaaga uggcauuucu                                          20

<210> SEQ ID NO 1130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1130
ucaaggaaga uggcauuucu                                          20

<210> SEQ ID NO 1131
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1131
ucaaggaaga uggcauuucu                                          20

<210> SEQ ID NO 1132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1132
ucaaggaaga uggcauuucu                                                    20

<210> SEQ ID NO 1133
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1133
ucaaggaaga uggcauuucu                                                    20

<210> SEQ ID NO 1134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1134
ucaaggaaga uggcauuucu                                                    20

<210> SEQ ID NO 1135
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1135
ucaaggaaga uggcauuucu                                                    20

<210> SEQ ID NO 1136
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1136
ucaaggaaga uggcauuucu                                                    20

<210> SEQ ID NO 1137
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1137
ucaaggaaga uggcauuucu                                                    20

<210> SEQ ID NO 1138
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1138
ucaaggaaga uggcauuucu                                               20

<210> SEQ ID NO 1139
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1139
ucaaggaaga uggcauuucu                                               20

<210> SEQ ID NO 1140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1140
ucaaggaaga uggcauuucu                                               20

<210> SEQ ID NO 1141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1141
ucaaggaaga uggcauuucu                                               20

<210> SEQ ID NO 1142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1142
ucaaggaaga uggcauuucu                                               20

<210> SEQ ID NO 1143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1143
ucaaggaaga uggcauuucu                                               20

<210> SEQ ID NO 1144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1144
```
ucaaggaaga uggcauuucu                                              20

<210> SEQ ID NO 1145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1145
ucaaggaaga uggcauuucu                                              20

<210> SEQ ID NO 1146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1146
ucaaggaaga uggcauuucu                                              20

<210> SEQ ID NO 1147
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1147
ucaaggaaga uggcauuucu                                              20

<210> SEQ ID NO 1148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1148
ucaaggaaga uggcauuucu                                              20

<210> SEQ ID NO 1149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1149
ucaaggaaga uggcauuucu                                              20

<210> SEQ ID NO 1150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1150
ucaaggaaga uggcauuucu                                              20

<210> SEQ ID NO 1151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1151
ucaaggaaga uggcauuucu                                              20

<210> SEQ ID NO 1152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1152
ucaaggaaga uggcauuucu                                              20

<210> SEQ ID NO 1153
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1153
ucaaggaaga uggcauuucu                                              20

<210> SEQ ID NO 1154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1154
ucaaggaaga uggcauuucu                                              20

<210> SEQ ID NO 1155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1155
ucaaggaaga uggcauuucu                                              20

<210> SEQ ID NO 1156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1156
ucaaggaaga uggcauuucu                                              20

<210> SEQ ID NO 1157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1157
ucaaggaaga uggcauuucu                                                   20

<210> SEQ ID NO 1158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1158
ucaaggaaga uggcauuucu                                                   20

<210> SEQ ID NO 1159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1159
ucaaggaaga uggcauuucu                                                   20

<210> SEQ ID NO 1160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1160
ucaaggaaga uggcauuucu                                                   20

<210> SEQ ID NO 1161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1161
ucaaggaaga uggcauuucu                                                   20

<210> SEQ ID NO 1162
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1162
ucaaggaaga uggcauuucu                                                   20

```
<210> SEQ ID NO 1163
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1163
ucaaggaaga uggcauuucu                                                      20

<210> SEQ ID NO 1164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1164
ucaaggaaga uggcauuucu                                                      20

<210> SEQ ID NO 1165
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1165
ucaaggaaga uggcauuucu                                                      20

<210> SEQ ID NO 1166
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1166
ucaaggaaga uggcauuucu                                                      20

<210> SEQ ID NO 1167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1167
ucaaggaaga uggcauuucu                                                      20

<210> SEQ ID NO 1168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1168
ucaaggaaga uggcauuucu                                                      20
```

```
<210> SEQ ID NO 1169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1169
ucaaggaaga uggcauuucu                                                   20

<210> SEQ ID NO 1170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1170
ucaaggaaga uggcauuucu                                                   20

<210> SEQ ID NO 1171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1171
ucaaggaaga uggcauuucu                                                   20

<210> SEQ ID NO 1172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1172
ucaaggaaga uggcauuucu                                                   20

<210> SEQ ID NO 1173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173
ucaaggaaga uggcauuucu                                                   20

<210> SEQ ID NO 1174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1174
ucaaggaaga uggcauuucu                                                   20

<210> SEQ ID NO 1175
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1175
ucaaggaaga uggcauuucu                                              20

<210> SEQ ID NO 1176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1176
ucaaggaaga uggcauuucu                                              20

<210> SEQ ID NO 1177
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1177
ucaaggaaga uggcauuucu                                              20

<210> SEQ ID NO 1178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1178
ucaaggaaga uggcauuucu                                              20

<210> SEQ ID NO 1179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1179
ucaaggaaga uggcauuucu                                              20

<210> SEQ ID NO 1180
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1180
ucaaggaaga uggcauuucu                                              20

<210> SEQ ID NO 1181
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1181
ucaaggaaga uggcauuucu                                              20

<210> SEQ ID NO 1182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1182
ucaaggaaga uggcauuucu                                              20

<210> SEQ ID NO 1183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1183
ucaaggaaga uggcauuucu                                              20

<210> SEQ ID NO 1184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1184
ucaaggaaga uggcauuucu                                              20

<210> SEQ ID NO 1185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1185
ucaaggaaga uggcauuucu                                              20

<210> SEQ ID NO 1186
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1186
ucaaggaaga uggcauuucu                                              20

<210> SEQ ID NO 1187
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1187
ucaaggaaga uggcauuucu                                                  20

<210> SEQ ID NO 1188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1188
ucaaggaaga uggcauuucu                                                  20

<210> SEQ ID NO 1189
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1189
ucaaggaaga uggcauuucu                                                  20

<210> SEQ ID NO 1190
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1190
ucaaggaaga uggcauuucu                                                  20

<210> SEQ ID NO 1191
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1191
ucaaggaaga uggcauuucu                                                  20

<210> SEQ ID NO 1192
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1192
ucaaggaaga uggcauuucu                                                  20

<210> SEQ ID NO 1193
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1193
ucaaggaaga uggcauuucu                                                20

<210> SEQ ID NO 1194
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1194
ucaaggaaga uggcauuucu                                                20

<210> SEQ ID NO 1195
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1195
ucaaggaaga uggcauuucu                                                20

<210> SEQ ID NO 1196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1196
ucaaggaaga uggcauuucu                                                20

<210> SEQ ID NO 1197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1197
ucaaggaaga uggcauuucu                                                20

<210> SEQ ID NO 1198
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1198
ucaaggaaga uggcauuucu                                                20

<210> SEQ ID NO 1199
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1199
ucaaggaaga uggcauuucu                                                    20

<210> SEQ ID NO 1200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1200
ucaaggaaga uggcauuucu                                                    20

<210> SEQ ID NO 1201
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1201
ucaaggaaga uggcauuucu                                                    20

<210> SEQ ID NO 1202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1202
ucaaggaaga uggcauuucu                                                    20

<210> SEQ ID NO 1203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
ucaaggaaga uggcauuucu                                                    20

<210> SEQ ID NO 1204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1204
ucaaggaaga uggcauuucu                                                    20

<210> SEQ ID NO 1205
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1205
ucaaggaaga uggcauuucu                                                         20

<210> SEQ ID NO 1206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1206
ucaaggaaga uggcauuucu                                                         20

<210> SEQ ID NO 1207
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1207
ucaaggaaga uggcauuucu                                                         20

<210> SEQ ID NO 1208
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1208
ucaaggaaga uggcauuucu                                                         20

<210> SEQ ID NO 1209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1209
ucaaggaaga uggcauuucu                                                         20

<210> SEQ ID NO 1210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1210
ucaaggaaga uggcauuucu                                                         20

<210> SEQ ID NO 1211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1211
ucaaggaaga uggcauuucu					20

<210> SEQ ID NO 1212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1212
ucaaggaaga uggcauuucu					20

<210> SEQ ID NO 1213
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1213
ucaaggaaga uggcauuucu					20

<210> SEQ ID NO 1214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1214
ucaaggaaga uggcauuucu					20

<210> SEQ ID NO 1215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1215
ucaaggaaga uggcauuucu					20

<210> SEQ ID NO 1216
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1216
ucaaggaaga uggcauuucu					20

<210> SEQ ID NO 1217
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1217
ucaaggaaga uggcauuucu                                               20

<210> SEQ ID NO 1218
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1218
ucaaggaaga uggcauuucu                                               20

<210> SEQ ID NO 1219
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1219
ucaaggaaga uggcauuucu                                               20

<210> SEQ ID NO 1220
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1220
ucaaggaaga uggcauuucu                                               20

<210> SEQ ID NO 1221
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1221
ucaaggaaga uggcauuucu                                               20

<210> SEQ ID NO 1222
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1222
ucaaggaaga uggcauuucu                                               20

<210> SEQ ID NO 1223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1223
ucaaggaaga uggcauuucu                                              20

<210> SEQ ID NO 1224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1224
ucaaggaaga uggcauuucu                                              20

<210> SEQ ID NO 1225
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1225
ucaaggaaga uggcauuucu                                              20

<210> SEQ ID NO 1226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1226
ucaaggaaga uggcauuucu                                              20

<210> SEQ ID NO 1227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1227
ucaaggaaga uggcauuucu                                              20

<210> SEQ ID NO 1228
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1228
ucaaggaaga uggcauuucu                                              20

<210> SEQ ID NO 1229
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1229
ucaaggaaga uggcauuucu                                              20

<210> SEQ ID NO 1230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1230
ucaaggaaga uggcauuucu                                              20

<210> SEQ ID NO 1231
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1231
ucaaggaaga uggcauuucu                                              20

<210> SEQ ID NO 1232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1232
ucaaggaaga uggcauuucu                                              20

<210> SEQ ID NO 1233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1233
ucaaggaaga uggcauuucu                                              20

<210> SEQ ID NO 1234
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1234
ucaaggaaga uggcauuucu                                              20

<210> SEQ ID NO 1235
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1235
ucaaggaaga uggcauuucu                                              20

<210> SEQ ID NO 1236
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1236
ucaaggaaga uggcauuucu                                                   20

<210> SEQ ID NO 1237
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1237
ucaaggaaga uggcauuucu                                                   20

<210> SEQ ID NO 1238
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
ucaaggaaga uggcauuucu                                                   20

<210> SEQ ID NO 1239
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1239
ucaaggaaga uggcauuucu                                                   20

<210> SEQ ID NO 1240
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1240
ucaaggaaga uggcauuucu                                                   20

<210> SEQ ID NO 1241
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1241
ucaaggaaga uggcauuucu                                                   20

```
<210> SEQ ID NO 1242
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1242
ucaaggaaga uggcauuucu                                               20

<210> SEQ ID NO 1243
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1243
ucaaggaaga uggcauuucu                                               20

<210> SEQ ID NO 1244
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1244
ucaaggaaga uggcauuucu                                               20

<210> SEQ ID NO 1245
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1245
ucaaggaaga uggcauuucu                                               20

<210> SEQ ID NO 1246
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1246
ucaaggaaga uggcauuucu                                               20

<210> SEQ ID NO 1247
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1247
ucaaggaaga uggcauuucu                                               20
```

```
<210> SEQ ID NO 1248
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1248
ucaaggaaga uggcauuucu                                                     20

<210> SEQ ID NO 1249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1249
ucaaggaaga uggcauuucu                                                     20

<210> SEQ ID NO 1250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1250
ucaaggaaga uggcauuucu                                                     20

<210> SEQ ID NO 1251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1251
ucaaggaaga uggcauuucu                                                     20

<210> SEQ ID NO 1252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1252
ucaaggaaga uggcauuucu                                                     20

<210> SEQ ID NO 1253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1253
ucaaggaaga uggcauuucu                                                     20

<210> SEQ ID NO 1254
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1254
ucaaggaaga uggcauuucu                                                    20

<210> SEQ ID NO 1255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1255
ucaaggaaga uggcauuucu                                                    20

<210> SEQ ID NO 1256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1256
ucaaggaaga uggcauuucu                                                    20

<210> SEQ ID NO 1257
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1257
ucaaggaaga uggcauuucu                                                    20

<210> SEQ ID NO 1258
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1258
ucaaggaaga uggcauuucu                                                    20

<210> SEQ ID NO 1259
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1259
ucaaggaaga uggcauuucu                                                    20

<210> SEQ ID NO 1260
<211> LENGTH: 20
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1260
ucaaggaaga uggcauuucu                                              20

<210> SEQ ID NO 1261
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1261
ucaaggaaga uggcauuucu                                              20

<210> SEQ ID NO 1262
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1262
ucaaggaaga uggcauuucu                                              20

<210> SEQ ID NO 1263
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1263
ucaaggaaga uggcauuucu                                              20

<210> SEQ ID NO 1264
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1264
ucaaggaaga uggcauuucu                                              20

<210> SEQ ID NO 1265
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1265
ucaaggaaga uggcauuucu                                              20

<210> SEQ ID NO 1266
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1266
ucaaggaaga uggcauuucu                                                     20

<210> SEQ ID NO 1267
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1267
ucaaggaaga uggcauuucu                                                     20

<210> SEQ ID NO 1268
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1268
ucaaggaaga uggcauuucu                                                     20

<210> SEQ ID NO 1269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1269
ucaaggaaga uggcauuucu                                                     20

<210> SEQ ID NO 1270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1270
ucaaggaaga uggcauuucu                                                     20

<210> SEQ ID NO 1271
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1271
ucaaggaaga uggcauuucu                                                     20

<210> SEQ ID NO 1272
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1272
ucaaggaaga uggcauuucu                                                     20

<210> SEQ ID NO 1273
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1273
ucaaggaaga uggcauuucu                                                     20

<210> SEQ ID NO 1274
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1274
ucaaggaaga uggcauuucu                                                     20

<210> SEQ ID NO 1275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1275
ucaaggaaga uggcauuucu                                                     20

<210> SEQ ID NO 1276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1276
ucaaggaaga uggcauuucu                                                     20

<210> SEQ ID NO 1277
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1277
ucaaggaaga uggcauuucu                                                     20

<210> SEQ ID NO 1278
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1278
ucaaggaaga uggcauuucu                                                     20

<210> SEQ ID NO 1279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1279
ucaaggaaga uggcauuucu                                                     20

<210> SEQ ID NO 1280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
ucaaggaaga uggcauuucu                                                     20

<210> SEQ ID NO 1281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
ucaaggaaga uggcauuucu                                                     20

<210> SEQ ID NO 1282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
ucaaggaaga uggcauuucu                                                     20

<210> SEQ ID NO 1283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1283
ucaaggaaga uggcauuucu                                                     20

<210> SEQ ID NO 1284
<211> LENGTH: 20
<212> TYPE: RNA
<213> ORGANISM: Artificial Sequence
<220> FEATURE:
<223> OTHER INFORMATION: Description of Artificial Sequence: Synthetic

```
              oligonucleotide

<400> SEQUENCE: 1284
ucaaggaaga uggcauuucu                                                  20

<210> SEQ ID NO 1285
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1285
ucaaggaaga uggcauuucu                                                  20

<210> SEQ ID NO 1286
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1286
ucaaggaaga uggcauuucu                                                  20

<210> SEQ ID NO 1287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1287
ucaaggaaga uggcauuucu                                                  20

<210> SEQ ID NO 1288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1288
ucaaggaaga uggcauuucu                                                  20

<210> SEQ ID NO 1289
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1289
ucaaggaaga uggcauuucu                                                  20

<210> SEQ ID NO 1290
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 1290
ucaaggaaga uggcauuucu                                                20

<210> SEQ ID NO 1291
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1291
ucaaggaaga uggcauuucu                                                20

<210> SEQ ID NO 1292
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1292
ucaaggaaga uggcauuucu                                                20

<210> SEQ ID NO 1293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1293
ucaaggaaga uggcauuucu                                                20

<210> SEQ ID NO 1294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1294
ucaaggaaga uggcauuucu                                                20

<210> SEQ ID NO 1295
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1295
ucaaggaaga uggcauuucu                                                20

<210> SEQ ID NO 1296
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1296
gccaacuggg agcuggagcg caccaaccag                                          30

<210> SEQ ID NO 1297
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1297
ucaaggaaga uggcauuucu                                                     20

<210> SEQ ID NO 1298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1298
ucaaggaaga uggcauuucu                                                     20

<210> SEQ ID NO 1299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1299
ucaaggaaga uggcauuucu                                                     20

<210> SEQ ID NO 1300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1300
ucaaggaaga uggcauuucu                                                     20

<210> SEQ ID NO 1301
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1301
ccuucccuga agguuccucc                                                     20

<210> SEQ ID NO 1302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1302
```
ccuucccuga agguuccucc                                          20

<210> SEQ ID NO 1303
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1303
ccuucccuga agguuccucc                                          20

<210> SEQ ID NO 1304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1304
ccuucccuga agguuccucc                                          20

<210> SEQ ID NO 1305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1305
ccuucccuga agguuccucc                                          20

<210> SEQ ID NO 1306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1306
ccuucccuga agguuccucc                                          20

<210> SEQ ID NO 1307
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1307
ucaaggaaga uggcauuucu                                          20

<210> SEQ ID NO 1308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1308
ucaaggaaga uggcauuucu                                              20

<210> SEQ ID NO 1309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1309
ucaaggaaga uggcauuucu                                              20

<210> SEQ ID NO 1310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1310
ucaaggaaga uggcauuuc                                               19

<210> SEQ ID NO 1311
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1311
ucaaggaaga uggcauuu                                                18

<210> SEQ ID NO 1312
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1312
caaggaagau ggcauuucu                                               19

<210> SEQ ID NO 1313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1313
ggccaaaccu cggcuuaccu                                              20

<210> SEQ ID NO 1314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1314
ggccaaaccu cggcuuaccu                                              20

<210> SEQ ID NO 1315
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1315
uucuguaagg uuuuuaugug                                              20

<210> SEQ ID NO 1316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1316
auuucuguaa gguuuuaug                                               20

<210> SEQ ID NO 1317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1317
ccauuucugu aagguuuua                                               20

<210> SEQ ID NO 1318
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1318
auccauuucu guaagguuuu                                              20

<210> SEQ ID NO 1319
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1319
cauccauuuc uguaagguuu                                              20

<210> SEQ ID NO 1320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1320
ccauccauuu cuguaagguu                                              20

```
<210> SEQ ID NO 1321
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1321
gccauccauu ucuguaaggu                                                   20

<210> SEQ ID NO 1322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1322
agccauccau uucuguaagg                                                   20

<210> SEQ ID NO 1323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1323
cagccaucca uuucuguaag                                                   20

<210> SEQ ID NO 1324
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1324
ucagccaucc auuucuguaa                                                   20

<210> SEQ ID NO 1325
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1325
uucagccauc cauuucugua                                                   20

<210> SEQ ID NO 1326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1326
cuucagccau ccauuucugu                                                   20
```

```
<210> SEQ ID NO 1327
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1327
acuucagcca uccauuucug                                                     20

<210> SEQ ID NO 1328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1328
aacuucagcc auccauuucu                                                     20

<210> SEQ ID NO 1329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1329
caacuucagc cauccauuuc                                                     20

<210> SEQ ID NO 1330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1330
ucaacuucag ccauccauuu                                                     20

<210> SEQ ID NO 1331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1331
aucaacuuca gccauccauu                                                     20

<210> SEQ ID NO 1332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1332
caucaacuuc agccauccau                                                     20

<210> SEQ ID NO 1333
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1333
acaucaacuu cagccaucca                                                   20

<210> SEQ ID NO 1334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1334
aacaucaacu ucagccaucc                                                   20

<210> SEQ ID NO 1335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1335
gaaaacauca acuucagcca                                                   20

<210> SEQ ID NO 1336
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1336
caggaaaaca ucaacuucag                                                   20

<210> SEQ ID NO 1337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1337
uuucaggaaa acaucaacuu                                                   20

<210> SEQ ID NO 1338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1338
cucuuucagg aaaacaucaa                                                   20

<210> SEQ ID NO 1339
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1339
uuccucuuuc aggaaaacau                                               20

<210> SEQ ID NO 1340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1340
gccauuccuc uuucaggaaa                                               20

<210> SEQ ID NO 1341
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1341
ggccauuccu cuuucaggaa                                               20

<210> SEQ ID NO 1342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1342
aggccauucc ucuuucagga                                               20

<210> SEQ ID NO 1343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1343
caggccauuc cucuuucagg                                               20

<210> SEQ ID NO 1344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1344
gcaggccauu ccucuuucag                                               20

<210> SEQ ID NO 1345
<211> LENGTH: 20
<212> TYPE: RNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 1345
ggcaggccau uccucuuuca                                                20

<210> SEQ ID NO 1346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1346
gggcaggcca uccucuuuc                                                 20

<210> SEQ ID NO 1347
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1347
agggcaggcc auccucuuu                                                 20

<210> SEQ ID NO 1348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1348
cagggcaggc cauuccucuu                                                20

<210> SEQ ID NO 1349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1349
ccagggcagg ccauuccucu                                                20

<210> SEQ ID NO 1350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1350
cccagggcag gccauuccuc                                                20

<210> SEQ ID NO 1351
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1351
ccccagggca ggccauuccu                                                    20

<210> SEQ ID NO 1352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1352
cccccagggc aggccauucc                                                    20

<210> SEQ ID NO 1353
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1353
ucccccaggg caggccauuc                                                    20

<210> SEQ ID NO 1354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1354
aucccccagg gcaggccauu                                                    20

<210> SEQ ID NO 1355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1355
caucccccag ggcaggccau                                                    20

<210> SEQ ID NO 1356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1356 gcaucccccca gggcaggcca                                                   20

<210> SEQ ID NO 1357
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1357
agcauccccc agggcaggcc                                                  20

<210> SEQ ID NO 1358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1358 cagcauccccc cagggcaggc                                                 20

<210> SEQ ID NO 1359
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1359
ucagcauccc ccagggcagg                                                  20

<210> SEQ ID NO 1360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1360
uucagcaucc cccagggcag                                                  20

<210> SEQ ID NO 1361
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1361
uuucagcauc ccccagggca                                                  20

<210> SEQ ID NO 1362
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1362
auuucagcau cccccagggc                                                  20

<210> SEQ ID NO 1363
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1363
gauuucagca uccccccaggg				20

<210> SEQ ID NO 1364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1364
ggauuucagc auccccccagg				20

<210> SEQ ID NO 1365
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1365
aggauuucag cauccccccag				20

<210> SEQ ID NO 1366
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1366
caggauuuca gcauccccca				20

<210> SEQ ID NO 1367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1367
ucaggauuuc agcaucccccc				20

<210> SEQ ID NO 1368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1368
uucaggauuu cagcaucccc				20

<210> SEQ ID NO 1369
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1369
uuucaggauu ucagcauccc                                               20

<210> SEQ ID NO 1370
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1370
uuuucaggau uucagcaucc                                               20

<210> SEQ ID NO 1371
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1371
uuuuucagga uuucagcauc                                               20

<210> SEQ ID NO 1372
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1372
uuuuuucagg auuucagcau                                               20

<210> SEQ ID NO 1373
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1373 guuuuucag gauuucagca                                                20

<210> SEQ ID NO 1374
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1374
uguuuuuuca ggauuucagc                                               20

<210> SEQ ID NO 1375
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1375
cuguuuuuuc aggauuucag         20

<210> SEQ ID NO 1376
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1376
gcuguuuuuu caggauuuca         20

<210> SEQ ID NO 1377
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1377
agcuguuuuu ucaggauuuc         20

<210> SEQ ID NO 1378
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1378
gagcuguuuu uucaggauuu         20

<210> SEQ ID NO 1379
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1379
ugagcuguuu uuucaggauu         20

<210> SEQ ID NO 1380
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1380
uugagcuguu uuuucaggau         20

<210> SEQ ID NO 1381
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1381
uuugagcugu uuuuucagga                                          20

<210> SEQ ID NO 1382
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1382
guuugagcug uuuuuucagg                                          20

<210> SEQ ID NO 1383
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1383
uuguuugagc uguuuuuuca                                          20

<210> SEQ ID NO 1384
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1384
cauuguuuga gcuguuuuuu                                          20

<210> SEQ ID NO 1385
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1385
gcauuguuug agcuguuuuu                                          20

<210> SEQ ID NO 1386
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1386
ugcauuguuu gagcuguuuu                                          20

<210> SEQ ID NO 1387
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1387

-continued cugcauuguu ugagcuguuu                                                   20

<210> SEQ ID NO 1388
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1388
ucugcauugu uugagcuguu                                                   20

<210> SEQ ID NO 1389
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1389
cucugcauug uuugagcugu                                                   20

<210> SEQ ID NO 1390
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1390
acucugcauu guuugagcug                                                   20

<210> SEQ ID NO 1391
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1391
uacucugcau uguuugagcu                                                   20

<210> SEQ ID NO 1392
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1392
uuacucugca uuguuugagc                                                   20

<210> SEQ ID NO 1393
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1393
cuuacucugc auuguuugag                                                   20

<210> SEQ ID NO 1394
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1394
ucuuacucug cauuguuuga                                                   20

<210> SEQ ID NO 1395
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1395
aucuuacucu gcauuguuug                                                   20

<210> SEQ ID NO 1396
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1396
aaucuuacuc ugcauuguuu                                                   20

<210> SEQ ID NO 1397
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1397
caaaucuuac ucugcauugu                                                   20

<210> SEQ ID NO 1398
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1398
gauacaaauc uuacucugca                                                   20

<210> SEQ ID NO 1399
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1399

-continued gggucagctg ccaatgcuag                                    20

<210> SEQ ID NO 1400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1400
gggucagctg ccaatgcuag                                    20

<210> SEQ ID NO 1401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1401
gggucagctg ccaatgcuag                                    20

<210> SEQ ID NO 1402
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1402
gggucagctg ccaatgcuag                                    20

<210> SEQ ID NO 1403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1403
gggucagctg ccaatgctag                                    20

<210> SEQ ID NO 1404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1404
gggucagctg ccaatgctag        20

<210> SEQ ID NO 1405
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1405
gggtcagctg ccaatgcuag        20

<210> SEQ ID NO 1406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1406
gggtcagctg ccaatgcuag        20

<210> SEQ ID NO 1407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1407
gggucagctg ccaatgcuag        20

<210> SEQ ID NO 1408
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1408
gggucagctg ccaatgcuag        20

<210> SEQ ID NO 1409
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1409
gggtcagctg ccaatgctag                                              20

<210> SEQ ID NO 1410
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1410
gggtcagctg ccaatgctag                                              20

<210> SEQ ID NO 1411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1411
gggucagctg ccaatgcuag                                              20

<210> SEQ ID NO 1412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1412
gggucagctg ccaatgcuag                                              20

<210> SEQ ID NO 1413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1413
gggucagctg ccaatgcuag                                              20

<210> SEQ ID NO 1414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1414
gggucagctg ccaatgcuag                                              20

<210> SEQ ID NO 1415
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1415
gggucagctg ccaatgcuag                                               20

<210> SEQ ID NO 1416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1416
gggucagctg ccaatgcuag                                               20

<210> SEQ ID NO 1417
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1417
gggucagctg ccaatgcuag                                               20

<210> SEQ ID NO 1418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1418
gggucagctg ccaatgcuag                                               20

<210> SEQ ID NO 1419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1419
gggucagctg ccaatgcuag                                               20

<210> SEQ ID NO 1420
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1420
gggucagctg ccaatgcuag                                              20

<210> SEQ ID NO 1421
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1421
gggucagctg ccaatgcuag                                              20

<210> SEQ ID NO 1422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1422
gggucagctg ccaatgcuag                                              20

<210> SEQ ID NO 1423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1423
gggucagctg ccaatgcuag                                              20

<210> SEQ ID NO 1424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1424
gggucagctg ccaatgcuag                                                    20

<210> SEQ ID NO 1425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1425
gggucagctg ccaatgcuag                                                    20

<210> SEQ ID NO 1426
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1426
gggucagctg ccaatgcuag                                                    20

<210> SEQ ID NO 1427
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1427
gggucagctg ccaatgcuag                                                    20

<210> SEQ ID NO 1428
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1428
gggucagctg ccaatgcuag                                                    20

<210> SEQ ID NO 1429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1429
gggucagctg ccaatgcuag                                               20

<210> SEQ ID NO 1430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1430
gggucagctg ccaatgcuag                                               20

<210> SEQ ID NO 1431
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1431
gggucagctg ccaatgcuag                                               20

<210> SEQ ID NO 1432
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1432
gggucagctg ccaatgcuag                                               20

<210> SEQ ID NO 1433
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1433
gggucagctg ccaatgcuag                                               20

<210> SEQ ID NO 1434
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 1434 ggguucagctg ccaatgcuag                                              20

<210> SEQ ID NO 1435
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1435
gggucagctg ccaatgcuag                                               20

<210> SEQ ID NO 1436
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1436
gggucagctg ccaatgcuag                                               20

<210> SEQ ID NO 1437
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1437
gggucagctg ccaatgcuag                                               20

<210> SEQ ID NO 1438
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1438
gggucagctg ccaatgcuag                                               20

<210> SEQ ID NO 1439
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1439
cuagcauugg cagcugaccc                                               20

<210> SEQ ID NO 1440
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1440
gggtcagctg ccaatgctag                                               20

<210> SEQ ID NO 1441
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1441
gggucagctg ccaatgcuag                                               20

<210> SEQ ID NO 1442
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1442
gggucagctg ccaatgcuag                                               20

<210> SEQ ID NO 1443
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1443
gggtcagctg ccaatgctag                                               20

<210> SEQ ID NO 1444
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1444
gggtcagctg ccaatgctag                                               20

<210> SEQ ID NO 1445
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 1445
gggtcagctg ccaatgctag                                                    20

<210> SEQ ID NO 1446
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1446
gggtcagctg ccaatgctag                                                    20

<210> SEQ ID NO 1447
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1447
gggtcagctg ccaatgctag                                                    20

<210> SEQ ID NO 1448
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1448
gggtcagctg ccaatgctag                                                    20

<210> SEQ ID NO 1449
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1449
gggtcagctg ccaatgctag                                                    20

<210> SEQ ID NO 1450
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1450
gggtcagctg ccaatgctag                                                    20

<210> SEQ ID NO 1451
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1451
gggtcagctg ccaatgctag            20

<210> SEQ ID NO 1452
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1452
gggtcagctg ccaatgctag            20

<210> SEQ ID NO 1453
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1453
gggtcagctg ccaatgctag            20

<210> SEQ ID NO 1454
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1454
gggtcagctg ccaatgctag            20

<210> SEQ ID NO 1455
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1455
gggtcagctg ccaatgctag            20

<210> SEQ ID NO 1456
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1456
gggtcagctg ccaatgctag            20

<210> SEQ ID NO 1457
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1457
gggtcagctg ccaatgctag				20

<210> SEQ ID NO 1458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1458
gggtcagctg ccaatgctag				20

<210> SEQ ID NO 1459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1459
gggtcagctg ccaatgctag				20

<210> SEQ ID NO 1460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1460
gggtcagctg ccaatgctag				20

<210> SEQ ID NO 1461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1461
gggtcagctg ccaatgctag				20

<210> SEQ ID NO 1462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1462
gggtcagctg ccaatgctag				20

<210> SEQ ID NO 1463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 1463
gggtcagctg ccaatgctag                                               20

<210> SEQ ID NO 1464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1464
gggtcagctg ccaatgctag                                               20

<210> SEQ ID NO 1465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1465
uagcgcccac ctcaccccuc                                               20

<210> SEQ ID NO 1466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1466
uuagcgccca cctcaccccu                                               20

<210> SEQ ID NO 1467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1467
cuuagcgccc acctcacccc                                               20

<210> SEQ ID NO 1468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1468
accccgtcct ggaaaccagg                                               20

```
<210> SEQ ID NO 1469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1469
ccccgtcctg gaaaccagga                                                20

<210> SEQ ID NO 1470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1470
gcuuagcgcc cacctcaccc                                                20

<210> SEQ ID NO 1471
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1471
ggcuuagcgc ccaccucacc                                                20

<210> SEQ ID NO 1472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1472
cccgucctgg aaaccaggag                                                20

<210> SEQ ID NO 1473
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1473
ugaaccccgt cctggaaacc                                                20

<210> SEQ ID NO 1474
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1474
uuuccccucc ctcatcaaca                                          20

<210> SEQ ID NO 1475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1475
agcuccagtc cctgaaggug                                          20

<210> SEQ ID NO 1476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1476
aggcutagcg cccaccucac                                          20

<210> SEQ ID NO 1477
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1477
guuuccccuc cctcaucaac                                          20

<210> SEQ ID NO 1478
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1478 aacccgtcc tggaaaccag                                           20

<210> SEQ ID NO 1479
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 1479 gaacccgtc ctggaaacca                                              20

<210> SEQ ID NO 1480
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1480
gcuccagtcc ctgaaggugu                                             20

<210> SEQ ID NO 1481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1481
uugaaccccg tcctggaaac                                             20

<210> SEQ ID NO 1482
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1482 uuccctccc tcatcaacaa                                              20

<210> SEQ ID NO 1483
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1483
ccgucctgga aaccaggagu                                             20

<210> SEQ ID NO 1484
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 1484

```
gcagctccag tccctgaagg                                               20

<210> SEQ ID NO 1485
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1485
ugccaggctg gttatgacuc                                               20

<210> SEQ ID NO 1486
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1486
cgucctggaa accaggagug                                               20

<210> SEQ ID NO 1487
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1487
cagcuccagt ccctgaaggu                                               20

<210> SEQ ID NO 1488
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1488
cugccaggct ggttaugacu                                               20

<210> SEQ ID NO 1489
<211> LENGTH: 20
<212> TYPE: RNA
<213> ORGANISM: Artificial Sequence
<220> FEATURE:
<223> OTHER INFORMATION: Description of Artificial Sequence:
      Synthetic oligonucleotide

<400> SEQUENCE: 1489
uccuggaaac caggagugcc                                               20
```

<210> SEQ ID NO 1490
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1490
aaggcttagc gcccaccuca                                              20

<210> SEQ ID NO 1491
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1491
ccaggctggt tatgacucag                                              20

<210> SEQ ID NO 1492
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1492
ccuggaaacc aggagugcca                                              20

<210> SEQ ID NO 1493
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1493
gccaggctgg ttatgacuca                                              20

<210> SEQ ID NO 1494
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1494
aaaggcttag cgcccaccuc                                              20

<210> SEQ ID NO 1495
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1495
ggauugggag ttactugcca                                           20

<210> SEQ ID NO 1496
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1496
guccuggaaa ccaggagugc                                           20

<210> SEQ ID NO 1497
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1497
caggctggtt atgacucaga                                           20

<210> SEQ ID NO 1498
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1498
gggagttact tgccaacuug                                           20

<210> SEQ ID NO 1499
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1499
ugggagttac ttgccaacuu                                           20

<210> SEQ ID NO 1500
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1500
uugggagtta cttgccaacu                                               20

<210> SEQ ID NO 1501
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1501
auuucctcaa cactcagccu                                               20

<210> SEQ ID NO 1502
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1502
ccccuccctc atcaacaaaa                                               20

<210> SEQ ID NO 1503
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1503
acauutccac ttgccaguua                                               20

<210> SEQ ID NO 1504
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1504
aaaaggctta gcgcccaccu                                               20

<210> SEQ ID NO 1505
```

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1505
accugtctga ggcaaacgaa                                              20

<210> SEQ ID NO 1506
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1506
auugggagtt acttgccaac                                              20

<210> SEQ ID NO 1507
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1507
ucaacaaaag cccacccucu                                              20

<210> SEQ ID NO 1508
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1508
cuaagatgct agcttggcca                                              20

<210> SEQ ID NO 1509
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1509
gggtcagctg ccaatgctag                                              20

<210> SEQ ID NO 1510
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
     oligonucleotide

<400> SEQUENCE: 1510
gggtcagctg ccaatgctag                                            20

<210> SEQ ID NO 1511
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1511
gggtcagctg ccaatgctag                                            20

<210> SEQ ID NO 1512
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1512
gggtcagctg ccaatgctag                                            20

<210> SEQ ID NO 1513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1513
gggtcagctg ccaatgctag                                            20

<210> SEQ ID NO 1514
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1514
ucaaggaaga uggcauuucu                                            20

<210> SEQ ID NO 1515
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1515
ucaaggaaga uggcauuucu                                            20

<210> SEQ ID NO 1516
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 1516
ucaaggaaga uggcauuucu					20

<210> SEQ ID NO 1517
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1517
ucaaggaaga uggcauuucu					20

<210> SEQ ID NO 1518
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (8)..(10)
<223> OTHER INFORMATION: a, c, t, g, unknown or other

<400> SEQUENCE: 1518 nnndcgwnnn					10

<210> SEQ ID NO 1519
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1519
tttttttttg t					11

<210> SEQ ID NO 1520
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1520 tttttttttt					10

<210> SEQ ID NO 1521
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1521
ttcctgatgc t					11

<210> SEQ ID NO 1522
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1522
tttttttttt ttt                                                         13

<210> SEQ ID NO 1523
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (8)..(10)
<223> OTHER INFORMATION: a, c, t, g, unknown or other

<400> SEQUENCE: 1523 nnndcgwnnn                                                             10

<210> SEQ ID NO 1524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1524
gtcgcccctt ctccccgcag c                                                21

<210> SEQ ID NO 1525
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1525
gtcgcccctt                                                             10

<210> SEQ ID NO 1526
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1526 tcgcccttc tcc                                                          13

<210> SEQ ID NO 1527
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1527
ctccccgcag                                                              10

<210> SEQ ID NO 1528
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1528
ccttctcccc gcagc                                                        15

<210> SEQ ID NO 1529
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1529
tcgccccttc tc                                                           12

<210> SEQ ID NO 1530
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1530
ttctccccgc                                                              10

<210> SEQ ID NO 1531
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1531
gtcgcccctt ct                                                           12

<210> SEQ ID NO 1532
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1532
cccttctccc cgc                                                          13

<210> SEQ ID NO 1533
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1533 tctccccgca					10

<210> SEQ ID NO 1534
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1534
cttctccccg cag					13

<210> SEQ ID NO 1535
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1535 tcgcccctto tcccogca					18

<210> SEQ ID NO 1536
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1536 cgcccttct ccccg					15

<210> SEQ ID NO 1537
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1537 cttctccccg					10

<210> SEQ ID NO 1538
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1538
cccttctccc cg					12

<210> SEQ ID NO 1539
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1539 gtcgccccttc c					11

<210> SEQ ID NO 1540
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1540 gtcgccccttc ctccccgca					19

<210> SEQ ID NO 1541
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1541
tcgccccttc tccccg					16

<210> SEQ ID NO 1542
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1542 cgcccttct cc					12

<210> SEQ ID NO 1543
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1543
tcgccccttc tccccgcagc					20

<210> SEQ ID NO 1544
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1544
cgccccttct ccccgcag					18

<210> SEQ ID NO 1545
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1545

```
cgccccttct ccc                                            13
```

<210> SEQ ID NO 1546
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1546

```
gcccttctc cccg                                            14
```

<210> SEQ ID NO 1547
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1547

```
tctccccgca g                                              11
```

<210> SEQ ID NO 1548
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1548

```
cttctccccg cagc                                           14
```

<210> SEQ ID NO 1549
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1549

```
cgccccttct cccgca                                         17
```

<210> SEQ ID NO 1550
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1550

```
gcccttctc cccgca                                          16
```

<210> SEQ ID NO 1551
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1551

```
cgccccttct c                                                         11

<210> SEQ ID NO 1552
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1552
gtcgcccctt ctcc                                                      14

<210> SEQ ID NO 1553
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1553
gccccttctc cccgcagc                                                  18

<210> SEQ ID NO 1554
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1554 ttctcccgc a                                                          11

<210> SEQ ID NO 1555
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1555
cccttctccc cgcagc                                                    16

<210> SEQ ID NO 1556
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1556 tcgcccttc tccc                                                       14

<210> SEQ ID NO 1557
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1557
cgccccttct ccccgcagc                                                 19
```

<210> SEQ ID NO 1558
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1558 cccttctcc ccgc                                                      14

<210> SEQ ID NO 1559
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1559
cttctccccg c                                                        11

<210> SEQ ID NO 1560
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1560
ttctccccgc agc                                                      13

<210> SEQ ID NO 1561
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1561 gtcgccccett ctc                                                     13

<210> SEQ ID NO 1562
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1562
ccttctcccc gcag                                                     14

<210> SEQ ID NO 1563
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1563 gtcgccccett ctcccc                                                  16

<210> SEQ ID NO 1564
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1564
gtcgcccctt ctccc                                                    15

<210> SEQ ID NO 1565
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1565 gcccttctc cccgc                                                     15

<210> SEQ ID NO 1566
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1566 tcgcccttc tcccgc                                                    17

<210> SEQ ID NO 1567
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1567
gtcgcccctt ctccccgcag                                               20

<210> SEQ ID NO 1568
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1568
ccttctcccc gca                                                      13

<210> SEQ ID NO 1569
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1569 tcgcccttc t                                                         11

-continued

<210> SEQ ID NO 1570
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1570
cccttctccc cgcag                                                    15

<210> SEQ ID NO 1571
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1571
gtcgcccctt ctccccg                                                  17

<210> SEQ ID NO 1572
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1572
cgccccttct                                                          10

<210> SEQ ID NO 1573
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1573
cgccccttct cccc                                                     14

<210> SEQ ID NO 1574
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1574 cccttctcc ccgcagc                                                   17

<210> SEQ ID NO 1575
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1575
gccccttctc cccgcag                                                  17

<210> SEQ ID NO 1576

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1576 tcgcccttc tccccgcag                                                  19

<210> SEQ ID NO 1577
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1577
ttctccccgc ag                                                        12

<210> SEQ ID NO 1578
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1578
cttctccccg ca                                                        12

<210> SEQ ID NO 1579
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1579 cccttctcc ccg                                                        13

<210> SEQ ID NO 1580
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1580
tcgcccttc                                                            10

<210> SEQ ID NO 1581
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1581
tctccccgca gc                                                        12

<210> SEQ ID NO 1582
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1582
ccttctcccc g                                                          11

<210> SEQ ID NO 1583
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1583
ctccccgcag c                                                          11

<210> SEQ ID NO 1584
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1584
cccttctccc cgca                                                       14

<210> SEQ ID NO 1585
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1585
ccccttctcc ccgca                                                      15

<210> SEQ ID NO 1586
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1586
tcgcccsttc tcccc                                                      15

<210> SEQ ID NO 1587
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1587
ccccttctcc ccgcag                                                     16

<210> SEQ ID NO 1588
<211> LENGTH: 12
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1588
ccttctcccc gc                                                         12

<210> SEQ ID NO 1589
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1589
gtcgcccctt ctccccgc                                                   18

<210> SEQ ID NO 1590
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1590
tccccgcagc                                                            10

<210> SEQ ID NO 1591
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1591 cgcccttct ccccgc                                                      16

<210> SEQ ID NO 1592
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1592
tttgtcgttt tgtcg                                                      15

<210> SEQ ID NO 1593
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1593
ttgtcgtttt                                                            10

<210> SEQ ID NO 1594
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1594
gtcgttttgt cgtttt                                                     16

<210> SEQ ID NO 1595
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1595
tcgtcgtttt gtcgttttgt cgt                                             23

<210> SEQ ID NO 1596
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1596
tcgtcgtttt gtcgttttgt cg                                              22

<210> SEQ ID NO 1597
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1597
cgtcgttttg tcgttttgt                                                  19

<210> SEQ ID NO 1598
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1598
gtcgttttgt cgttttg                                                    17

<210> SEQ ID NO 1599
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1599
ttttgtcgtt tt                                                         12

<210> SEQ ID NO 1600
<211> LENGTH: 12
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 1600
tttgtcgttt tg                                                             12

<210> SEQ ID NO 1601
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1601
tgtcgttttg tc                                                             12

<210> SEQ ID NO 1602
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1602
ttttgtcgtt ttgtc                                                          15

<210> SEQ ID NO 1603
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1603
ttgtcgtttt gtcg                                                           14

<210> SEQ ID NO 1604
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1604
cgtcgttttg tcgttt                                                         16

<210> SEQ ID NO 1605
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1605
cgtcgttttg t                                                              11

<210> SEQ ID NO 1606
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1606
ttttgtcgtt t                                                            11

<210> SEQ ID NO 1607
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1607
tgtcgttttg tcgtt                                                        15

<210> SEQ ID NO 1608
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1608
cgtcgttttg tcgttttg                                                     18

<210> SEQ ID NO 1609
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1609
gttttgtcgt ttt                                                          13

<210> SEQ ID NO 1610
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1610
cgtcgttttg tcgt                                                         14

<210> SEQ ID NO 1611
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1611
tcgttttgtc gtt                                                          13

<210> SEQ ID NO 1612
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1612
cgtcgttttg tcgtt                                                    15

<210> SEQ ID NO 1613
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1613
cgtcgttttg tcg                                                      13

<210> SEQ ID NO 1614
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1614
cgtcgttttg tc                                                       12

<210> SEQ ID NO 1615
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1615
tcgttttgtc gttttgtc                                                 18

<210> SEQ ID NO 1616
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1616
tttgtcgttt t                                                        11

<210> SEQ ID NO 1617
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1617
tcgttttgtc gttttgtcg                                                19

<210> SEQ ID NO 1618
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 1618
gttttgtcgt tttgtc                                                              16

<210> SEQ ID NO 1619
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1619
cgtcgttttg                                                                     10

<210> SEQ ID NO 1620
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1620
cgtcgttttg tcgtttt                                                             17

<210> SEQ ID NO 1621
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1621
gttttgtcgt t                                                                   11

<210> SEQ ID NO 1622
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1622
tcgttttgtc                                                                     10

<210> SEQ ID NO 1623
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1623
ttttgtcgtt ttgtcgt                                                             17

<210> SEQ ID NO 1624
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1624

-continued cgttttgtcg ttttgtcgt         19

<210> SEQ ID NO 1625
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1625
ttttgtcgtt ttgtcgtt         18

<210> SEQ ID NO 1626
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1626
gttttgtcgt tttgtcgt         18

<210> SEQ ID NO 1627
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1627
cgtcgttttg tcgttttgtc gt         22

<210> SEQ ID NO 1628
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1628
tcgtcgtttt gtcgtttt         18

<210> SEQ ID NO 1629
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1629
tgtcgttttg tcg         13

<210> SEQ ID NO 1630
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1630
tcgttttgtc gttttgtcgt                    20

<210> SEQ ID NO 1631
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1631
cgttttgtcg ttttgtcgtt                    20

<210> SEQ ID NO 1632
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1632
tttgtcgttt tgt                    13

<210> SEQ ID NO 1633
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1633
gtcgttttgt cgt                    13

<210> SEQ ID NO 1634
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1634
cgttttgtcg tttt                    14

<210> SEQ ID NO 1635
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1635
ttgtcgtttt gtcgt                    15

<210> SEQ ID NO 1636
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1636
ttttgtcgtt                    10

<210> SEQ ID NO 1637
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1637
cgttttgtcg ttttg                                                    15

<210> SEQ ID NO 1638
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1638
gttttgtcgt tttgtcgtt                                                19

<210> SEQ ID NO 1639
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1639
tcgttttgtc gttt                                                     14

<210> SEQ ID NO 1640
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1640
tcgtcgtttt gtcgttt                                                  17

<210> SEQ ID NO 1641
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1641
tcgttttgtc gttttgtcgt t                                             21

<210> SEQ ID NO 1642
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1642
tgtcgttttg t                                                        11

<210> SEQ ID NO 1643
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1643
tcgtcgtttt gtcg                                                      14

<210> SEQ ID NO 1644
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1644
tgtcgttttg                                                           10

<210> SEQ ID NO 1645
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1645
tcgttttgtc gttttgt                                                   17

<210> SEQ ID NO 1646
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1646
gttttgtcgt                                                           10

<210> SEQ ID NO 1647
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1647
gttttgtcgt tt                                                        12

<210> SEQ ID NO 1648
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1648
tcgtcgtttt gtcgttttg                                                 19

```
<210> SEQ ID NO 1649
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1649
cgttttgtcg ttttgtc                                                  17

<210> SEQ ID NO 1650
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1650
cgttttgtcg                                                          10

<210> SEQ ID NO 1651
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1651
ttgtcgtttt gt                                                       12

<210> SEQ ID NO 1652
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1652
gtcgttttgt cgttttgtcg                                               20

<210> SEQ ID NO 1653
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1653
cgttttgtcg ttttgt                                                   16

<210> SEQ ID NO 1654
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1654
gtcgttttgt cgttttgtc                                                19

<210> SEQ ID NO 1655
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1655
gtcgttttgt cgttttgtcg t                                              21

<210> SEQ ID NO 1656
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1656
tcgtcgtttt gt                                                        12

<210> SEQ ID NO 1657
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1657
gtcgttttgt cgtt                                                      14

<210> SEQ ID NO 1658
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1658
gttttgtcgt tttg                                                      14

<210> SEQ ID NO 1659
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1659
cgtcgttttg tcgttttgtc g                                              21

<210> SEQ ID NO 1660
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1660
tcgtcgtttt gtcgtt                                                    16

<210> SEQ ID NO 1661
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1661
ttttgtcgtt ttgt                                                      14

<210> SEQ ID NO 1662
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1662
tgtcgttttg tcgt                                                      14

<210> SEQ ID NO 1663
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1663
tcgttttgtc gtttt                                                     15

<210> SEQ ID NO 1664
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1664
tcgttttgtc g                                                         11

<210> SEQ ID NO 1665
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1665
tcgtcgtttt g                                                         11

<210> SEQ ID NO 1666
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1666
tttgtcgttt tgtcgtt                                                   17

<210> SEQ ID NO 1667
<211> LENGTH: 17
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 1667
gttttgtcgt tttgtcg                                                  17

<210> SEQ ID NO 1668
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1668
gtcgttttgt cg                                                       12

<210> SEQ ID NO 1669
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1669
ttttgtcgtt ttgtcg                                                   16

<210> SEQ ID NO 1670
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1670
gtcgttttgt c                                                        11

<210> SEQ ID NO 1671
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1671
ttttgtcgtt ttg                                                      13

<210> SEQ ID NO 1672
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1672
cgttttgtcg ttt                                                      13

<210> SEQ ID NO 1673
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1673
cgttttgtcg ttttgtcg                                                      18

<210> SEQ ID NO 1674
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1674
tcgtcgtttt gtc                                                           13

<210> SEQ ID NO 1675
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1675
tcgtcgtttt gtcgttttgt c                                                  21

<210> SEQ ID NO 1676
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1676
ttgtcgtttt g                                                             11

<210> SEQ ID NO 1677
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1677
tttgtcgttt tgtcgt                                                        16

<210> SEQ ID NO 1678
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1678
gtcgttttgt cgttttgt                                                      18

<210> SEQ ID NO 1679
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1679
tttgtcgttt                                                              10

<210> SEQ ID NO 1680
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1680
ttgtcgtttt gtc                                                          13

<210> SEQ ID NO 1681
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1681
cgtcgttttg tcgttttgtc                                                   20

<210> SEQ ID NO 1682
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1682
tcgtcgtttt gtcgttttgt                                                   20

<210> SEQ ID NO 1683
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1683
gtcgttttgt                                                              10

<210> SEQ ID NO 1684
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1684
gtcgttttgt cgttt                                                        15

<210> SEQ ID NO 1685
<211> LENGTH: 16
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1685
tcgttttgtc gttttg                                          16

<210> SEQ ID NO 1686
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1686
cgttttgtcg tt                                              12

<210> SEQ ID NO 1687
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1687
tcgtcgtttt                                                 10

<210> SEQ ID NO 1688
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1688
cgtcgttttg tcgttttgtc gtt                                  23

<210> SEQ ID NO 1689
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1689
tcgttttgtc gt                                              12

<210> SEQ ID NO 1690
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1690
cgttttgtcg t                                               11

<210> SEQ ID NO 1691
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1691
tttgtcgttt tgtc                                                                14

<210> SEQ ID NO 1692
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1692
tcgtcgtttt gtcgt                                                               15

<210> SEQ ID NO 1693
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1693
gttttgtcgt tttgt                                                               15

<210> SEQ ID NO 1694
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1694
gtcgttttgt cgttttgtcg tt                                                       22

<210> SEQ ID NO 1695
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1695
ttgtcgtttt gtcgtt                                                              16

<210> SEQ ID NO 1696
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1696
ccgtcgccct tcagcacgca                                                          20

<210> SEQ ID NO 1697
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1697
cgcccttcag ca                                                              12

<210> SEQ ID NO 1698
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1698
tcgcccttca gcacg                                                           15

<210> SEQ ID NO 1699
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1699
tcgcccttca gcacgc                                                          16

<210> SEQ ID NO 1700
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1700
gtcgcccttc                                                                 10

<210> SEQ ID NO 1701
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1701
ccgtcgccct tca                                                             13

<210> SEQ ID NO 1702
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1702
cgtcgccctt cag                                                             13

<210> SEQ ID NO 1703
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1703
```

```
gtcgcccttc agcacgc                                                  17

<210> SEQ ID NO 1704
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1704
tcgcccttca gcac                                                     14

<210> SEQ ID NO 1705
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1705
cttcagcacg c                                                        11

<210> SEQ ID NO 1706
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1706
cgtcgccctt cagcacgc                                                 18

<210> SEQ ID NO 1707
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1707
cgtcgccctt cagcacgca                                                19

<210> SEQ ID NO 1708
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1708
tcagcacgca                                                          10

<210> SEQ ID NO 1709
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1709
```
cgcccttcag cacgc                                             15

<210> SEQ ID NO 1710
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1710
gcccttcagc acg                                               13

<210> SEQ ID NO 1711
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1711
cccttcagca cgca                                              14

<210> SEQ ID NO 1712
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1712
cccttcagca cg                                                12

<210> SEQ ID NO 1713
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1713
cgtcgccctt cagcacg                                           17

<210> SEQ ID NO 1714
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1714
gtcgcccttc agca                                              14

<210> SEQ ID NO 1715
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1715
tcgcccttca                                                   10

<210> SEQ ID NO 1716
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1716
ccttcagcac gc                                                             12

<210> SEQ ID NO 1717
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1717
ccgtcgccct tcagca                                                         16

<210> SEQ ID NO 1718
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1718 gtcgccctt c agc                                                           13

<210> SEQ ID NO 1719
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1719
ccgtcgccct tcagcacg                                                       18

<210> SEQ ID NO 1720
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1720
ccgtcgccct t                                                              11

<210> SEQ ID NO 1721
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1721
ccgtcgccct tcag                                                           14

```
<210> SEQ ID NO 1722
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1722
cttcagcacg                                                          10

<210> SEQ ID NO 1723
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1723
tcgcccttca gcacgca                                                  17

<210> SEQ ID NO 1724
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1724
gtcgcccttc ag                                                       12

<210> SEQ ID NO 1725
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1725
cgtcgccctt cagcac                                                   16

<210> SEQ ID NO 1726
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1726
tcgcccttca gc                                                       12

<210> SEQ ID NO 1727
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1727
gtcgcccttc a                                                        11
```

```
<210> SEQ ID NO 1728
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1728
cgcccttcag cacg                                                       14

<210> SEQ ID NO 1729
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1729 gtcgccttc agcacg                                                      16

<210> SEQ ID NO 1730
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1730
ccgtcgccct tcagcacgc                                                  19

<210> SEQ ID NO 1731
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1731
cgtcgccctt cagc                                                       14

<210> SEQ ID NO 1732
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1732
ccgtcgccct                                                            10

<210> SEQ ID NO 1733
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1733 gtcgccttc agcacgca                                                    18

<210> SEQ ID NO 1734
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1734
gcccttcagc acgca                                                          15

<210> SEQ ID NO 1735
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1735
cttcagcacg ca                                                             12

<210> SEQ ID NO 1736
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1736
gtcgcccttc agcac                                                          15

<210> SEQ ID NO 1737
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1737
ccgtcgccct tc                                                             12

<210> SEQ ID NO 1738
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1738
ccttcagcac g                                                              11

<210> SEQ ID NO 1739
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1739
cgtcgccctt cagca                                                          15

<210> SEQ ID NO 1740
<211> LENGTH: 13
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1740
cgcccttcag cac                                                        13

<210> SEQ ID NO 1741
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1741
cccttcagca cgc                                                        13

<210> SEQ ID NO 1742
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1742
cgtcgccctt ca                                                         12

<210> SEQ ID NO 1743
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1743
ttcagcacgc a                                                          11

<210> SEQ ID NO 1744
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1744
gcccttcagc acgc                                                       14

<210> SEQ ID NO 1745
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1745
cgcccttcag c                                                          11

<210> SEQ ID NO 1746
<211> LENGTH: 15
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 1746
ccgtcgccct tcagc                                                    15

<210> SEQ ID NO 1747
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1747
ccttcagcac gca                                                      13

<210> SEQ ID NO 1748
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1748
cgcccttcag                                                          10

<210> SEQ ID NO 1749
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1749
ccgtcgccct tcagcac                                                  17

<210> SEQ ID NO 1750
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1750
cgtcgccctt                                                          10

<210> SEQ ID NO 1751
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1751
cgcccttcag cacgca                                                   16

<210> SEQ ID NO 1752
<211> LENGTH: 13
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1752
tcgcccttca gca                                                          13

<210> SEQ ID NO 1753
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1753
ttcagcacgc                                                              10

<210> SEQ ID NO 1754
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1754
cgtcgccctt c                                                            11

<210> SEQ ID NO 1755
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1755
tcgcccttca g                                                            11

<210> SEQ ID NO 1756
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1756
gtcgcccctt ctccccgcag c                                                 21

<210> SEQ ID NO 1757
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1757
gtcgcccctt ctccccgcag c                                                 21

<210> SEQ ID NO 1758
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1758
gtcgccccct ctccccgcag c                                              21

<210> SEQ ID NO 1759
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1759
gtcgccccct ctccccgcag c                                              21

<210> SEQ ID NO 1760
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1760
gtcgccccct ctccccgcag c                                              21

<210> SEQ ID NO 1761
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1761
gtcgccccct ctccccgcag c                                              21

<210> SEQ ID NO 1762
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1762
gtcgccccct ctccccgcag c                                              21

<210> SEQ ID NO 1763
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1763
gtcgccccct ctccccgcag c                                              21

<210> SEQ ID NO 1764
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1764
gtcgcccctt ctccccgcag c                                              21

<210> SEQ ID NO 1765
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1765
gtcgcccctt ctccccgcag c                                              21

<210> SEQ ID NO 1766
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1766
gtcgcccctt ctccccgcag c                                              21

<210> SEQ ID NO 1767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1767
gtcgcccctt ctccccgcag c                                              21

<210> SEQ ID NO 1768
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1768
gtcgcccctt ctccccgcag c                                              21

<210> SEQ ID NO 1769
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1769
gtcgcccctt ctccccgcag c                                              21

<210> SEQ ID NO 1770
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1770
gtcgcccctt ctccccgcag c                                              21

<210> SEQ ID NO 1771
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1771
gtcgcccctt ctccccgcag c                                              21

<210> SEQ ID NO 1772
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1772
gtcgcccctt ctcccgcag c                                               21

<210> SEQ ID NO 1773
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1773
gucgcccctt ctcccgcag c                                               21

<210> SEQ ID NO 1774
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1774
gucgcccctt ctcccgcag c                                               21

<210> SEQ ID NO 1775
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1775
gtcgcccctt ctcccgcag c                                               21

<210> SEQ ID NO 1776
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1776
gtcgcccctt ctccccgcag c                                           21

<210> SEQ ID NO 1777
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1777
gtcgcccctt ctccccgcag c                                           21

<210> SEQ ID NO 1778
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1778
gtcgcccctt ctccccgcag c                                           21

<210> SEQ ID NO 1779
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1779
gtcgcccctt ctccccgcag c                                           21

<210> SEQ ID NO 1780
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1780
gtcgcccctt ctccccgcag c                                           21

<210> SEQ ID NO 1781
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1781
tcgtcgtttt gtcgttttgt cgtt                                        24

<210> SEQ ID NO 1782
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1782
tcgtcgtttt gtcgttttgt cgtt                                            24

<210> SEQ ID NO 1783
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1783
tcgtcgtttt gtcgttttgt cgtt                                            24

<210> SEQ ID NO 1784
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1784
tcgtcgtttt gtcgttttgt cgtt                                            24

<210> SEQ ID NO 1785
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1785
tcgtcgtttt gtcgttttgt cgtt                                            24

<210> SEQ ID NO 1786
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1786
tcgtcgtttt gtcgttttgt cgtt                                            24

<210> SEQ ID NO 1787
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1787
tcgtcgtttt gtcgttttgt cgtt                                            24

<210> SEQ ID NO 1788
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1788
tcgtcgtttt gtcgttttgt cgtt                                              24

<210> SEQ ID NO 1789
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1789
tttgtcgttt tgt                                                          13

<210> SEQ ID NO 1790
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1790
tttgtcgttt tgt                                                          13

<210> SEQ ID NO 1791
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1791
tttgtcgttt tgt                                                          13

<210> SEQ ID NO 1792
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1792
tttgtcgttt tgt                                                          13

<210> SEQ ID NO 1793
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1793
tttgtcgttt tgt                                                          13

<210> SEQ ID NO 1794
<211> LENGTH: 13
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 1794
tttgtcgttt tgt                                                              13

<210> SEQ ID NO 1795
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1795
tttgtcgttt tgt                                                              13

<210> SEQ ID NO 1796
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1796
ccgtcgccct tcagcacgca                                                       20

<210> SEQ ID NO 1797
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1797
ccgtcgccct tcagcacgca                                                       20

<210> SEQ ID NO 1798
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1798
ccgtcgccct tcagcacgca                                                       20

<210> SEQ ID NO 1799
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1799
ccgtcgccct tcagcacgca                                                       20

<210> SEQ ID NO 1800
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
        oligonucleotide

<400> SEQUENCE: 1800
ccgtcgccct tcagcacgca                                                   20

<210> SEQ ID NO 1801
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1801
ccgtcgccct tcagcacgca                                                   20

<210> SEQ ID NO 1802
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1802
ccgtcgccct tcagcacgca                                                   20

<210> SEQ ID NO 1803
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1803
ccgtcgccct tcagcacgca                                                   20

<210> SEQ ID NO 1804
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1804
ccgtcgccct tcagcacgca                                                   20

<210> SEQ ID NO 1805
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1805
ccgtcgccct tcagcacgca                                                   20

<210> SEQ ID NO 1806
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 1806
ccgtcgccct tcagcacgca                                           20

<210> SEQ ID NO 1807
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1807
ccgtcgccct tcagcacgca                                           20

<210> SEQ ID NO 1808
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1808
ccgtcgccct tcagcacgca                                           20

<210> SEQ ID NO 1809
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1809
ccgtcgccct tcagcacgca                                           20

<210> SEQ ID NO 1810
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1810
ccgtcgccct tcagcacgca                                           20

<210> SEQ ID NO 1811
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1811
ccgtcgccct tcagcacgca                                           20

<210> SEQ ID NO 1812
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1812
ccgtcgccct tcagcacgca                                                    20

<210> SEQ ID NO 1813
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1813
ccgtcgccct tcagcacgca                                                    20

<210> SEQ ID NO 1814
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1814
ccgtcgccct tcagcacgca                                                    20

<210> SEQ ID NO 1815
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1815
ccgtcgccct tcagcacgca                                                    20

<210> SEQ ID NO 1816
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1816
ccgtcgccct tcagcacgca                                                    20

<210> SEQ ID NO 1817
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1817
cagtcgccct tcagcacgca                                                    20

<210> SEQ ID NO 1818
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1818
```
ccgtagccct tcagcacgca                                           20

<210> SEQ ID NO 1819
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1819
tccatgacgt tcctgacgtt                                           20

<210> SEQ ID NO 1820
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1820
tccatgagct tcctgagctt                                           20

<210> SEQ ID NO 1821
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1821
tgctgctttt gtgcttttgt gctt                                      24

<210> SEQ ID NO 1822
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1822
gcctcagtct gcttcgcacc                                           20

<210> SEQ ID NO 1823
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1823
gcctcagtct gcttcgcacc                                           20

<210> SEQ ID NO 1824
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1824
gcctcagtct gcttcgcacc                                          20

<210> SEQ ID NO 1825
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1825
gtccctgaag atgtcaatgc                                          20

<210> SEQ ID NO 1826
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1826
gtccctgaag atgtcaatgc                                          20

<210> SEQ ID NO 1827
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1827
gtccctgaag atgtcaatgc                                          20

<210> SEQ ID NO 1828
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1828
gtccctgaag atgtcaatgc                                          20

<210> SEQ ID NO 1829
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1829
gtccctgaag atgtcaatgc                                          20

<210> SEQ ID NO 1830
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1830
gcctcagtct gcttcgcacc                                          20

<210> SEQ ID NO 1831
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1831
gcctcagtct gcttcgcacc                                                   20

<210> SEQ ID NO 1832
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1832
agaaatgcca                                                              10

<210> SEQ ID NO 1833
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1833
tcttccttga                                                              10

<210> SEQ ID NO 1834
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1834
ccgtcgccct tcagcacgca                                                   20